US009732155B2

(12) United States Patent
Spreter Von Kreudenstein et al.

(10) Patent No.: US 9,732,155 B2
(45) Date of Patent: Aug. 15, 2017

(54) CRYSTAL STRUCTURES OF HETERODIMERIC FC DOMAINS

(71) Applicant: ZYMEWORKS INC., Vancouver (CA)

(72) Inventors: Thomas Spreter Von Kreudenstein, Vancouver (CA); Surjit Bhimarao Dixit, Richmond (CA); Paula Irene Lario, Vancouver (CA); Eric Escobar-Cabrera, Burnaby (CA); Martin J. Boulanger, Victoria (CA); Michael D. L. Suits, Waterloo (CA)

(73) Assignee: ZYMEWORKS INC., Vancouver (CA)

( * ) Notice: Subject to any disclaimer, the term of this patent is extended or adjusted under 35 U.S.C. 154(b) by 0 days.

(21) Appl. No.: 14/439,532

(22) PCT Filed: Oct. 31, 2013

(86) PCT No.: PCT/CA2013/050832
§ 371 (c)(1),
(2) Date: Apr. 29, 2015

(87) PCT Pub. No.: WO2014/067011
PCT Pub. Date: May 8, 2014

(65) Prior Publication Data
US 2015/0284470 A1 Oct. 8, 2015

Related U.S. Application Data

(63) Continuation-in-part of application No. 13/668,098, filed on Nov. 2, 2012.

(60) Provisional application No. 61/813,084, filed on Apr. 17, 2013.

(51) Int. Cl.
C07K 16/32 (2006.01)
C07K 16/46 (2006.01)
C07K 16/28 (2006.01)
G06F 19/12 (2011.01)

(52) U.S. Cl.
CPC .......... *C07K 16/32* (2013.01); *C07K 16/2887* (2013.01); *C07K 16/46* (2013.01); *C07K 16/468* (2013.01); *G06F 19/12* (2013.01); *C07K 2316/52* (2013.01); *C07K 2317/52* (2013.01); *C07K 2317/524* (2013.01); *C07K 2317/526* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,880,935 A | 11/1989 | Thorpe |
| 5,122,368 A | 6/1992 | Greenfield et al. |
| 5,605,793 A | 2/1997 | Stemmer |
| 5,621,002 A | 4/1997 | Bosslet et al. |
| 5,622,929 A | 4/1997 | Willner et al. |
| 5,624,821 A | 4/1997 | Winter et al. |
| 5,731,168 A | 3/1998 | Carter et al. |
| 5,807,706 A | 9/1998 | Carter et al. |
| 5,821,333 A | 10/1998 | Carter et al. |
| 5,824,805 A | 10/1998 | King et al. |
| 5,830,721 A | 11/1998 | Stemmer et al. |
| 5,834,252 A | 11/1998 | Stemmer et al. |
| 5,837,458 A | 11/1998 | Minshull et al. |
| 5,885,573 A | 3/1999 | Bluestone et al. |
| 6,096,548 A | 8/2000 | Stemmer |
| 6,107,540 A | 8/2000 | Sawyer et al. |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,194,551 B1 | 2/2001 | Idusogie et al. |
| 6,214,345 B1 | 4/2001 | Firestone et al. |

(Continued)

FOREIGN PATENT DOCUMENTS

| | | |
|---|---|---|
| CA | 2548757 | 7/2005 |
| CN | 1176659 | 3/1998 |

(Continued)

OTHER PUBLICATIONS

McPherson, A. Current Approaches to Macromolecular Crystallization. European Journal of Biochemistry. 1990. vol. 189, pp. 1-23.*

(Continued)

*Primary Examiner* — Suzanne M Noakes
(74) *Attorney, Agent, or Firm* — Morgan, Lewis & Bockius LLP; Brett Lovejoy

(57) ABSTRACT

Disclosed are the atomic coordinates of compositions comprising Fc heterodimer proteins in crystalline form derived from high resolution x-ray diffraction. Further disclosed are systems and methods for using all or a portion of these atomic coordinates to identify and design improved Fc heterodimer proteins. Further disclosed are compositions comprising a mixture of (i) a solubilized Fc heterodimer protein and (ii) a mother liquor solution. The mother liquor solution comprises between 2% and 10% (v/v) ethylene glycol, between 10% and 25% (w/v) polyethylene glycol having an average molecular weight of between 2000 Daltons and 10000 Daltons, and between 0.05 M and 0.40 M ammonium iodide. Further disclosed are systems and methods of identifying a mutation which promotes heterodimeric Fc chain pair formation in which structure based modeling is performed to identify a candidate mutation to an Fc chain using all or a portion of the disclosed three-dimensional atomic coordinates.

15 Claims, 270 Drawing Sheets

(56) References Cited

U.S. PATENT DOCUMENTS

| | | |
|---|---|---|
| 6,218,519 B1 | 4/2001 | Kenten et al. |
| 6,331,415 B1 | 12/2001 | Cabilly et al. |
| 6,365,410 B1 | 4/2002 | Schellenberger et al. |
| 6,677,435 B2 | 1/2004 | Barbas, III et al. |
| 6,737,056 B1 | 5/2004 | Presta |
| 6,759,509 B1 | 7/2004 | King et al. |
| 6,809,185 B1 | 10/2004 | Schoonjans et al. |
| 6,835,807 B1 | 12/2004 | Susaki et al. |
| 7,183,076 B2 | 2/2007 | Arathoon et al. |
| 7,635,472 B2 | 12/2009 | Kufer et al. |
| 7,642,228 B2 | 1/2010 | Carter et al. |
| 7,695,936 B2 | 4/2010 | Carter et al. |
| 7,769,573 B2 | 8/2010 | Fejes et al. |
| 7,923,221 B1 | 4/2011 | Cabilly et al. |
| 7,951,917 B1 | 5/2011 | Arathoon et al. |
| 8,501,185 B2 | 8/2013 | Heitner et al. |
| 8,592,562 B2 | 11/2013 | Kannan et al. |
| 8,623,361 B2 | 1/2014 | Beirnaert et al. |
| 8,771,988 B2 | 7/2014 | Goepfert et al. |
| 2003/0096743 A1 | 5/2003 | Senter et al. |
| 2003/0130189 A1 | 7/2003 | Senter et al. |
| 2003/0190311 A1 | 10/2003 | Dall'acqua et al. |
| 2004/0018194 A1 | 1/2004 | Francisco et al. |
| 2004/0052793 A1 | 3/2004 | Carter et al. |
| 2004/0071696 A1 | 4/2004 | Adams et al. |
| 2004/0121940 A1 | 6/2004 | De Groot et al. |
| 2005/0069549 A1 | 3/2005 | Herman et al. |
| 2006/0074225 A1 | 4/2006 | Chamberlain |
| 2006/0106905 A1 | 5/2006 | Chren et al. |
| 2006/0160184 A1 | 7/2006 | Hoogenboom et al. |
| 2006/0263882 A1 | 11/2006 | Fazio et al. |
| 2007/0041987 A1 | 2/2007 | Carter et al. |
| 2007/0196363 A1 | 8/2007 | Arathoon et al. |
| 2007/0274985 A1 | 11/2007 | Dubel et al. |
| 2007/0276791 A1 | 11/2007 | Fejes et al. |
| 2007/0278170 A1 | 12/2007 | Wiebe et al. |
| 2008/0050370 A1 | 2/2008 | Glaser et al. |
| 2008/0147360 A1 | 6/2008 | Fejes et al. |
| 2009/0162360 A1 | 6/2009 | Klein et al. |
| 2009/0182127 A1 | 7/2009 | Kjaergaard et al. |
| 2009/0226466 A1 | 9/2009 | Fong et al. |
| 2009/0232811 A1 | 9/2009 | Klein et al. |
| 2009/0263392 A1 | 10/2009 | Igawa et al. |
| 2010/0104564 A1 | 4/2010 | Hansen et al. |
| 2010/0105874 A1 | 4/2010 | Schuurman et al. |
| 2010/0149876 A1 | 6/2010 | Mokhlesi |
| 2010/0166749 A1 | 7/2010 | Presta et al. |
| 2010/0196265 A1 | 8/2010 | Adams et al. |
| 2010/0256338 A1 | 10/2010 | Brinkmann et al. |
| 2010/0286374 A1 | 11/2010 | Kannan et al. |
| 2010/0322934 A1 | 12/2010 | Imhof-Jung et al. |
| 2010/0322935 A1 | 12/2010 | Croasdale et al. |
| 2010/0331527 A1 | 12/2010 | Davis et al. |
| 2011/0008345 A1 | 1/2011 | Ashman et al. |
| 2011/0044977 A1 | 2/2011 | Adler et al. |
| 2011/0053261 A1 | 3/2011 | Lario et al. |
| 2011/0059076 A1 | 3/2011 | McDonagh et al. |
| 2011/0200596 A1 | 8/2011 | Huang et al. |
| 2011/0274691 A1 | 11/2011 | Arvedson et al. |
| 2011/0275787 A1 | 11/2011 | Kufer et al. |
| 2011/0287009 A1 | 11/2011 | Scheer et al. |
| 2011/0293613 A1 | 12/2011 | Brinkmann et al. |
| 2012/0003221 A1 | 1/2012 | McDonagh |
| 2012/0076728 A1 | 3/2012 | Wu et al. |
| 2012/0143580 A1 | 6/2012 | Constantine et al. |
| 2012/0149876 A1 | 6/2012 | Spreter Von Kreudenstein et al. |
| 2012/0244577 A1 | 9/2012 | Dixit et al. |
| 2012/0244578 A1 | 9/2012 | Kannan et al. |
| 2012/0270801 A1 | 10/2012 | Frejd et al. |
| 2013/0078249 A1 | 3/2013 | Ast et al. |
| 2013/0195849 A1 | 8/2013 | Spreter Von Kreudenstein et al. |
| 2013/0238299 A1 | 9/2013 | Ohrn |
| 2013/0245963 A1 | 9/2013 | Ohrn et al. |
| 2013/0336973 A1 | 12/2013 | Spreter Von Kreudenstein et al. |
| 2014/0051835 A1 | 2/2014 | Dixit et al. |
| 2014/0066378 A1 | 3/2014 | Dixit et al. |
| 2014/0072581 A1 | 3/2014 | Dixit et al. |
| 2014/0154253 A1 | 6/2014 | Ng et al. |
| 2014/0199294 A1 | 7/2014 | Mimoto et al. |
| 2014/0200331 A1 | 7/2014 | Corper et al. |
| 2015/0051889 A1 | 2/2015 | Ohrn et al. |
| 2015/0125449 A1 | 5/2015 | Ng et al. |
| 2015/0142326 A1 | 5/2015 | Lakatos |
| 2015/0220681 A1 | 8/2015 | Dixit |
| 2015/0284470 A1 | 10/2015 | Spreter Von Kreudenstein et al. |
| 2015/0307594 A1 | 10/2015 | Corper et al. |
| 2016/0083480 A1 | 3/2016 | Ng et al. |
| 2016/0114057 A1 | 4/2016 | Dixit et al. |
| 2016/0257763 A1 | 9/2016 | Spreter Von Kreudenstein et al. |

FOREIGN PATENT DOCUMENTS

| | | |
|---|---|---|
| EP | 0368684 | 5/1990 |
| EP | 1870459 | 12/2007 |
| JP | 2011508604 A | 3/2011 |
| WO | WO 9308829 | 5/1993 |
| WO | WO 9404690 | 3/1994 |
| WO | WO 9627011 | 9/1996 |
| WO | WO 9734631 | 9/1997 |
| WO | WO 9813059 | 4/1998 |
| WO | WO 9816628 | 4/1998 |
| WO | WO 9958572 | 11/1999 |
| WO | WO 0042072 | 7/2000 |
| WO | WO 2003031464 | 4/2003 |
| WO | WO 2004029207 | 4/2004 |
| WO | WO 2004032828 | 4/2004 |
| WO | WO 2004068820 | 8/2004 |
| WO | WO 2005018629 | 3/2005 |
| WO | WO 2006003388 | 1/2006 |
| WO | WO 2006030220 | 3/2006 |
| WO | WO 2007110205 | 1/2007 |
| WO | WO 2008131242 | 10/2008 |
| WO | WO 2009089004 | 7/2009 |
| WO | WO 2010068722 | 6/2010 |
| WO | WO 2010085682 | 7/2010 |
| WO | WO 2010115553 | 10/2010 |
| WO | WO 2011028952 | 3/2011 |
| WO | WO 2011063348 | 5/2011 |
| WO | WO 2011/066655 A1 | 6/2011 |
| WO | WO 2012/040833 A1 | 9/2011 |
| WO | WO 2011120134 | 10/2011 |
| WO | WO 2011120135 | 10/2011 |
| WO | WO 2011143545 | 11/2011 |
| WO | WO 2011133886 | 12/2011 |
| WO | WO 2011147982 | 12/2011 |
| WO | WO 2012006635 | 1/2012 |
| WO | WO 2012/037659 A1 | 3/2012 |
| WO | WO 2012/058768 A1 | 5/2012 |
| WO | WO 2012116453 | 9/2012 |
| WO | WO 2012143523 | 10/2012 |
| WO | WO 2013002362 | 1/2013 |
| WO | WO 2013063702 | 5/2013 |
| WO | WO 2013166594 | 11/2013 |
| WO | WO 2013166604 | 11/2013 |
| WO | WO 2014004586 | 1/2014 |
| WO | WO 2014012082 | 1/2014 |
| WO | WO 2014012085 | 1/2014 |
| WO | WO 2014018572 | 1/2014 |
| WO | WO 2014067011 | 5/2014 |
| WO | WO 2014082179 | 6/2014 |
| WO | WO 2014182970 | 11/2014 |
| WO | WO 2014186905 | 11/2014 |
| WO | WO 2015006749 | 1/2015 |
| WO | WO 2015181805 | 12/2015 |

OTHER PUBLICATIONS

Cudney R. Protein Crystallization and Dumb Luck. The Rigaku Journal. 1999. vol. 16, No. 1, pp. 1-7.*

Atwell et al., "Stable Heterodimers from Remodeling the Domain Interface of a Homodimer using a Phage Display Library." J. Mol. Biol., vol. 270, pp. 26-35 (1997).

(56) References Cited

OTHER PUBLICATIONS

Beck et al., "Strategies and challenges for the next generation of therapeutic antibodies." Nature Reviews, Immunology, vol. 10, pp. 345-352 (2010).
Carter, P., "Introduction to current and future protein therapeutics: A protein engineering perspective." Experimental Cell Research, vol. 317, pp. 1261-1269 (2011).
Davis et al., "SEEDbodies: fusion proteins based on strand-exchange engineered domain (SEE) $C_H3$ heterodimers in an Fc analogue platform for asymmetric binders or immuonfusions and bispecific antibodies." Protein Engineering, Design & Selection, vol. 23, No. 4, pp. 195-202 (2010).
Demarest and Glaser, "Antibody therapeutics, antibody engineering, and the merits of protein stability." Current Opinion in Drug Discovery and Development, vol. 11, pp. 675-687 (2008).
Gunasekaran et al., "Enhancing Antibody Fc Heterodimer Formation through Electrostatic Steering Effects." Journal of Biological Chemistry, vol. 285, No. 25, pp. 19637-19646 (2010).
Jackman et al., "Development of a Two-part Strategy to Identify a Therapeutic Human Bispecific Antibody That Inhibits IgE Receptor Signaling." Journal of Bological Chemistry, vol. 285, No. 27, pp. 20850-20859 (2010).
Klein et al., "Progress in overcoming the chain association issue in bispecific heterodimeric IgG antibodies." mAbs, vol. 4, Issue 6, pp. 653-663 (2012).
Kontermann, R., "Dual targeting strategies with bispecific antibodies." mAbs, vol. 4, Issue 2, pp. 182-197 (2012).
Lindhofer et al., "Preferential Species-Restricted Heavy/Light Chain Pairing in Rat/Mouse Quadromas." The Journal of Immunology, vol. 155, pp. 219-225 (1995).
Merchant et al., "An efficient route to human bispecific IgG." Nature Biotechnology, vol. 16, pp. 677-681 (1998).
Milstein and Cuello, "Hybrid hybridomas and their use in immunohistochemistry." Nature, vol. 305, pp. 537-540 (1983).
Ridgway et al., "'Knobs-into-holes' engineering of antibody $C_H3$ domains for heavy chain heterodimerization." Protein Engineering, vol. 9, No. 7, pp. 617-621 (1996).
Segal et al.,"Introduction: bispecific antibodies." Journal of Immunological Methods, vol. 248, pp. 1-6 (2001).
Shields et al., "High Resolution Mapping of the Binding Site on Human IgG1 for FcγRI, FcγRII, FcγRIII, and FcRn and Design of IgG1 Variants with Improved Binding to the FcγR." The Journal of Biological Chemistry, vol. 276, No. 9, pp. 6591-6604 (2001).
Wang, W. "Protein aggregation and its inhibition in biopharmaceutics." International Journal of Pharmaceutics, vol. 289, pp. 1-30 (2005).
U.S. Appl. No. 13/289,934, "Restriction Requirement", dated Sep. 16, 2014, 6 pages.
U.S. Appl. No. 13/289,934, "Non-Final Office Action", dated Feb. 27, 2015, 15 pages.
U.S. Appl. No. 13/289,934, "Non-Final Office Action", dated May 13, 2015, 19 pages.
U.S. Appl. No. 13/289,934, "Final Office Action", dated Nov. 16, 2015, 19 pages.
U.S. Appl. No. 13/289,934, "Advisory Action", dated Feb. 5, 2016, 5 pages.
U.S. Appl. No. 13/668,098 "Restriction Requirement" dated Dec. 5, 2014.
U.S. Appl. No. 13/668,098 , "Non-Final Office Action", dated Apr. 3, 2015, 18 pages.
U.S. Appl. No. 13/668,098 , "Final Office Action", dated Nov. 17, 2015, 16 pages.
U.S. Appl. No. 13/892,198 , "Restriction Requirement", dated Jul. 10, 2015, 12 pages.
U.S. Appl. No. 13/892,198 , "Non-Final Office Action", dated Oct. 6, 2015, 23 pages.
U.S. Appl. No. 13/927,065 , "Restriction Requirement", dated Apr. 15, 2015, 9 pages.
U.S. Appl. No. 13/927,065 , "Non-Final Office Action", dated Oct. 7, 2015, 10 pages.
U.S. Appl. No. 13/927,065 , "Final Office Action", dated Feb. 22, 2016, 6 pages.
U.S. Appl. No. 13/927,065 , "Notice of Allowance", dated Aug. 26, 2016, 12 pages.
U.S. Appl. No. 13/941,449, "Restriction Requirement", dated Dec. 3, 2015, 10 pages.
U.S. Appl. No. 13/949,166, "Non-Final Office Action", dated Jan. 13, 2016, 11 pages.
U.S. Appl. No. 13/949,166, "Final Office Action", dated Aug. 21, 2015, 12 pages.
U.S. Appl. No. 13/949,166, "Restriction Requirement", dated Dec. 16, 2014, 9 pages.
U.S. Appl. No. 13/949,166 , "Non-Final Office Action", dated Apr. 14, 2015, 22 pages.
U.S. Appl. No. 13/949,166 , "Final Office Action", dated Jun. 16, 2016, 20 pages.
U.S. Appl. No. 13/941,449, "Non-Final Office Action", dated Apr. 13, 2016, 41 pages.
U.S. Appl. No. 14/092,804, "Restriction Requirement", dated May 12, 2016, 5 pages.
U.S. Appl. No. 14/092,804, "Non-Final Office Action", dated Sep. 10, 2015, 33 pages.
U.S. Appl. No. 14/399,789, "Restriction Requirement", dated Sep. 14, 2015, 11 pages.
U.S. Appl. No. 14/399,789 , "Non-Final Office Action", dated Dec. 17, 2015, 31 pages.
U.S. Appl. No. 14/648,222, "Restriction Requirement", dated May 9, 2016, 14 pages.
U.S. Appl. No. 14/893,706, "Restriction Requirement", dated Apr. 4, 2017, 7 pages.
U.S. Appl. No. 14/888,580 , "U.S. Patent Application", dated Nov. 2, 2015, Titled: Bispecific HER2 and HER3 Antigen Binding Constructs.
U.S. Appl. No. 14/893,706 , "U.S. Patent Application", dated Nov. 24, 2015, Titled: Modular Protein Drug Conjugate Therapeutic.
U.S. Appl. No. 14/903,184, "Bispecific CD3 and CD19 Antigen Binding Constructs", U.S. Patent Application dated Jan. 6, 2016.
U.S. Appl. No. 14/989,648, "Heteromultimer Constructs of Immunoglobulin Heavy Chains With Mutations in the FC Domain", U.S. Patent Application dated Jan. 6, 2016.
PCT/US2013/04 7725 , "International Preliminary Report on Patentability", dated Dec. 31, 2014, 7 pages.
PCT/US2013/047725, "International Search Report and Written Opinion", dated Nov. 22, 2013, 15 pages.
PCT/US2013/050408, "International Search Report and Written Opinion", dated Feb. 6, 2014, 14 pages.
Pot/US2013/051747, "International Search Report and Written Opinion", dated Feb. 3, 2014, 14 pages.
PCT/US2013/50411, "International Search Report and Written Opinion", dated Jan. 29, 2014, 19 pages.
PCT/US2014/037401, "International Search Report and Written Opinion", dated Oct. 7, 2014, 14 pages.
PCT/US2014/065571, "International Search Report and Written Opinion", dated Feb. 19, 2015, 13 pages.
PCT/US2014/46436, "International Search Report and Written Opinion", dated Jan. 2, 2015, 15 pages.
Aitman, et al. Copy number polymorphism in Fcgr3 predisposes to glomerulonephritis in rats and humans. Nature. Feb. 16, 2006;439(7078):851-5.
Alegre, et al. A non-activating "humanized" anti-CD3 monoclonal antibody retains immunosuppressive properties in vivo. Transplantation. Jun. 15, 1994;57(11): 1537-43.
Altintas et al., "Targeting epidermal growth factor receptor in tumors: from conventional monoclonal antibodies via heavy chain-only antibodies to nanobodies", Eur J Pharm Sci., vol. 45, No. 4, Oct. 28, 2011, pp. 399-407.
Arnold et al., "The impact of glycosylation on the biological function and structure of human immunoglobulins", Annu Rev Immunol., vol. 25, 2007, pp. 21-50.
Atwell, et al. Stable heterodimers from remodeling the domain interface of a homodimer using a phage display library. J Mol Biol. Jul. 4, 1997;270(1):26-35.

(56) References Cited

OTHER PUBLICATIONS

Barthelemy et al., "Comprehensive analysis of the factors contributing to the stability and solubility of autonomous human VH domains", J. Biol. Chem., vol. 283, No. 6, Feb. 2008, pp. 3639-3654.
Bell et al., "Differential tumor-targeting abilities of three single-domain antibody formats", Cancer Letters, vol. 289, 2009, pp. 81-90.
Bolon, et al. Specificity versus stability in computational protein design. Proc Natl Acad Sci US A. Sep. 6, 2005;102(36):12724-9. Epub Aug. 29, 2005.
Carter, et al. Humanization of an anti-pl 85HER2 antibody for human cancer therapy. Proc Natl Acad Sci US A. May 15, 1992;89(10):4285-9.
Chames et al., "Therapeutic antibodies: successes, limitations and hopes for the future", British Journal of Pharmacology, vol. 157, No. 2, 2009, pp. 220-223.
Cochlovius et al., "Treatment of human B cell lymphoma xenografts with a CD3 x CD19 diabody and T cells", Journal of Immunology, vol. 165, No. 2, 2000, pp. 888-895.
Colbere-Garapin et al., "A new dominant hybrid selective marker for higher eukaryotic cell", Journal of Molecular Biology, vol. 150, No. 1, Jul. 25, 1981, pp. 1-14.
Colman , "Effects of amino acid sequence changes on antibody-antigen interactions", Research in Immunology, vol. 145, No. 1, 1994, 33-36.
Coloma, et al. Design and production of novel tetravalent bispecific antibodies. Nat Biotechnol. Feb. 1997;15(2):159-63.
Dall'Acqua et al., Contribution of domain interface residues to the stability of antibody CH3 domain homodimers. Biochemistry, 37(26): 9266-9273 (1998).
Dekruif, et al. Leucine zipper dimerized bivalent and bispecific scFv antibodies from a semi-synthetic antibody phage display library. J Biol Chem. Mar. 29, 1996;271 (13):7630-4.
Demarest et al., "Optimization of the Antibody CH3 Domain by Residue Frequency Analysis of IgG Sequences", Journal of Molecular Biology, vol. 335, No. 1, Jan. 2, 2004, pp. 41-48.
Dockal et al., "Conformational Transitions of the Three Recombinant Domains of Human Serum Albumin Depending on pH", The Journal of Biological Chemistry, vol. 275, No. 5, Feb. 4, 2000, pp. 3042-3050.
Dockal et al., "Five recombinant fragments of human serum albumin-tools for the characterization of the warfarin binding site", Protein Science, vol. 9, No. 8, 2000, pp. 1455-1465.
Ducry et al. "Antibody-Drug Conjugates: Linking Cytotoxic Payloads to Monoclonal Antibodies", Bioconjugate Chem. 2010, vol. 21, pp. 5-13.
Duncan, et al. Localization of the binding site for the human high-affinity Fe receptor on IgG. Nature. 332(7)563-4 (1988).
Durocher et al., "High-level and high-throughput recombinant protein production by transient transfection of suspension-growing human HEK293-EBNA1 cells", Nucleic acids research, vol. 30, no. 2, Jan. 2002, p. e9.
Grabulovski et al., "A novel, non-immunogenic Fyn SH3-derived binding protein with tumor vascular targeting properties", J Biol Chem., vol. 282, No. 5, Feb. 2007, pp. 3196-3204.
Groot et al., "Identification by phage display of single-domain antibody fragments specific for the ODD domain in hypoxia-inducible factor 1 alpha", Lab Invest vol. 86, No. 4, Apr. 2006, pp. 345-356.
Guss et al., "Structure of the IgG-binding regions of streptococcal protein G", The EMBO Journal, vol. 5, No. 7, 1986, pp. 1567-1575.
Hardy et al., "Valency of Antibody Binding to Enveloped Virus Particles as Determined by Surface Plasmon Resonance", J Viral., vol. 77, No. 2, 2003, pp. 1649-1652.
Havnarek, et al. Automated design of specificity in molecular recognition. Nat Struct Biol. 10(1)5-52 (2003).
Hennecke et al., "Composition and arrangement of genes define the strength of IRES-driven translation in bicistronic mRNAs", Nucleic Acids Res., vol. 29, No. 16, Aug. 15, 2001, pp. 3327-3334.

Holt et al., "Domain antibodies: proteins for therapy", Trends in Biotechnology, Elsevier Publications, Cambridge, GB, vol. 21, No. 11, Nov. 2003, pp. 484-490.
Huang, et al. A de novo designed protein protein interface. Protein Sci. Dec. 2007;16(12):2770-4.
Hust et al., "Single chain Fab (scFab) fragment", BMC Biotechnology, vol. 7, No. 14. Available online at http://www.biomedcentral.com/14 72-6750/7 /14, 2007, pp. 1-15.
Hutchins, et al. Improved biodistribution, tumor targeting, and reduced immunogenicity in mice with a gamma 4 variant ofCampath-IH. Proc Natl Acad Sci U SA. Dec. 19, 1995;92(26): 11980-4.
Idusogie, et al. Engineered antibodies with increased activity to recruit complement. J Immunol. Feb. 15, 2001;166(4):2571-5.
Idusogie, et al. Mapping of the Clq binding site on rituxan, a chimeric antibody with a human IgGI Fe. J Immunol. Apr. 15, 2000;164(8):4178-84.
Igawa et al., "VH/VL interface engineering to promote selective expression and inhibit conformational isomerization of thrombopoietin receptor against single-chain diabody", Protein Engineering, Design & Selection, vol. 23, No. 8, Aug. 2010, pp. 667-677.
Janeway et al., "Structure of the Antibody Molecule and Immunoglobulin Genes", Immunology Third Edition, Garland Publishing Inc. Chapter 3, tructure of the Antibody Molecule and Immunoglobulin Genes, 1997, pp. 3:1-3:11.
Jefferis, et al. Interaction sites on human IgG-Fc for FcgammaR: current models. Immunol Lett. 82(1-2):57-65 (2002).
Jefferis, et al. Modulation ofFc(gamma)R and human complement activation by IgG3-core oligosaccharide interactions. Immunol Lett. 54(2-3):101-4 (1996).
Jefferis, et al. Recognition sites on human IgG for Fe gamma receptors: the role of glycosylation. Immunol Lett. 44(2-3): 111-7 (1995).
Jin et al., "MetMAb, the one-armed 5D5 anti-c-met antibody, inhibits orthotopic pancreatic tumor growth and improves survival", Cancer Res., vol. 68, No. 11, Jun. 1, 2008, pp. 4360-4368.
Kang et al., Engineering multivalent antibodies to target heregulin-induced HER3 signaling in breast cancer cells, MAbs, Bol. 6, pp. 340-353, 2013.
Kelley, Very large scale monoclonal antibody purification: the case for conventional unit operations. Biotechnol Prog. 23(5):995-1008 (2007).
Klein et al., "Progress in overcoming the chain association issue in bispecific heterodimeric IgG antibodies", MABS, vol. 4, No. 6, 2012, pp. 653-663.
Kontermann, "Dual targeting strategies with bispecific antibodies", MABS, vol. 4, No. 2, 2012, pp. 182-197.
Lewis et al. "Targeting HER2-Positive Breast Cancer with Trastuzumab-DM1, and Antibody-Cytotoxic Drug Conjugate" Cancer Res. 2008, vol. 68, pp. 9280-9290.
Li et al., "Bispecific antibody to ErbB2 overcomes trastuzumab resistance through comprehensive blockage of ErbB2 heterodimerization", 2013, pp. 6471-6483.
Lindhofer, et al. Preferential species-restricted heavy/light chain pairing in rat/mouse quadromas. Implications for a single-step purification ofbispecific antibodies. J Immunol. 155(1):219-25 (1995).
LoRusso et al. "Trastuzumab Emtansine: A Unique Antibody-Drug Conjugate in Development for Human Epidermal Growth Factor Receptor 2-Positive Cancer", Clin. Cancer Res. 2011, vol. 17, pp. 6437-6447.
Lu et al., "Fab-scFv fusion protein: an efficient approach to production of bispecific antibody fragments", Journal of Immunological Methods, vol. 267, No. 2, 2002, pp. 213-226.
Lund, et al. Human Fc gamma RI and Fc gamma RII interact with distinct but overlapping sites on human IgG. J Immunol. Oct. 15, 1991;147(8):2657-62.
Lund, et al. Multiple binding sites on the CH2 domain oflgG for mouse Fe gamma RII. Mol Immunol. 29(1):53-9 (1992).
Lund, et al. Multiple interactions oflgG with its core oligosaccharide can modulate recognition by complement and human Fe gamma

(56) References Cited

OTHER PUBLICATIONS receptor I and influence the synthesis of its oligosaccharide chains. J Immunol. 157(11):4963-9 (1996).
Lund, et al. Oligosaccharide-protein interactions in IgG can modulate recognition by Fc gamma receptors. FASEB J. Jan. 1995;9(1):115-9.
MacCallum et al., "Antibody-antigen interactions: Contact analysis and binding site topography", Journal of Molecular Biology, vol. 262 (5), Oct. 1996, pp. 732-745.
Marqusee et al., "Helix stabilization by Glu−. . . Lys+ salt bridges in short peptides of de nova design", Proc Natl Acad Sci US A vol. 84, No. 24, 1987, pp. 8898-8902.
McDonagh, et al., "Antitumor activity of a novel bispecific antibody that targets the ErbB2/ErbB3 oncogenic unit and inhibits heregulin-induced activation of ErbB3", Mol. Cancer Ther., vol. 11, No. 3, Jan. 2012, pp. 582-593.
Merchant, et al. An efficient route to human bispecific IgG. Nature Biotechnology. 1998; 16(7):677-81.
Milstein, et al. Hybrid hybridomas and their use in immunohistochemistry. Nature. 305(6):537-40 (1983).
Moore et al., "A novel bispecific antibody format enables simultaneous bivalent and monovalent co-engagement of distinct target antigens", MAbs, vol. 3, No. 6, 2011, pp. 546-557.
Moore et al., "Engineered Fc variant antibodies with enhanced ability to recruit complement and mediate effector functions", MABS, Landes Biosciences, vol. 2, No. 2, Mar. 2010, pp. 181-189.
Omidfar et al., "Studies of thermostability in Camelus bactrianus (Bactrian camel) single-domain antibody specific for the mutant epidermal-growth-factor receptor expressed by Pichia.", Biotechnol. Appl. Biochem., vol. 46, Jan. 2007, pp. 41-49.
Omidfar et al., "Single domain antibodies: A new concept for epidermal growth factor receptor and EGFRvIII targeting", vol. 31, No. 6, 2012.
Osborn et al., "Pharmacokinetic and Pharmacodynamics Studies of a Human Serum Albumin-Interferon-A Fusion Protein in Cynomolgus Monkeys", J. Pharamcology and Experimental Therapeutics, vol. 330, 2002, pp. 540-548.
Paul, "Protein and polypeptide antigenic determinants", Fundamental Immunology, 3d ed, 1993, p. 242.
Pham et al., "Large-scale transfection of mammalian cells for the fast production of recombinant protein", Molecular Biotechnology, vol. 34, No. 2, 2006, pp. 225-237.
Pluckthun, "Antibodies from *Escherichia coli*. In: The Pharmacology of Monoclonal Antibodies", Rosenburg and Moore eds, Springer-Verlag, vol. 113, chapter 11, 1994, pp. 269-315.
Portolano et al., "Lack of promiscuity in autoantigen-specific Hand L chain combinations as revealed by human Hand L chain "roulette".", J Immunol., vol. 150, No. 3, Feb. 1, 1993, pp. 880-887.
Presta, et al. Engineering therapeutic antibodies for improved function. Biochem Soc Trans. Aug. 2002;30(4):487-90.
Rakestraw et al., "Secretion-and-capture cell-surface display for selection of target-binding proteins", Protein Engineering, Design and Selection, vol. 24, No. 6, 2011, pp. 525-530.
Raymond et al., "A simplified polyethylenimine-mediated transfection process for large-scale and high-throughput applications", Methods, vol. 55, No. 1, 2011, pp. 44-51.
Reddy, et al. Elimination of Fc receptor-dependent effector functions of a modified IgG4 monoclonal antibody to human CD4. J Immunol. Feb. 15, 2000;164(4): 1925-33.
Ridgway, et al. 'Knobs-into-holes' engineering of antibody CH3 domains for heavy chain heterodimerization. Protein Eng. Jul. 1996;9(7):617-21.
Robinson et al., "Targeting ErbB2 and ErbB3 with a bispecific single-chain Fv enhances 1-5 targeting selectivity and induces a therapeutic effect in vitro", Br. J. Cancer, vol. 99, Oct. 7, 2008, 1415-1425.
Rudi Koff et al., "Single Amino Acid Substitution altering Antigen-binding Specificity", Proc. Natl Acad Sci., vol. 79, No. 6, 1982, pp. 1979-1983.
Segal, et al. Introduction: bispecific antibodies. J Immunol Methods. 248(1-2):1-6 (2001).
Shields, et al. High resolution mapping of the binding site on human IgGI for Fc gamma RI, Fc gamma RII, Fc gamma Riii, and FcRn and design ofIgGI variants with improved binding to the Fc gamma R. J Biol Chem. Mar. 2, 2001; 276(9):6591-604.
Stancovski et al., "Mechanistic Aspects of the Opposing effects of Monoclonal Antibodies to the ERBB2 receptor on Tumor Growth", Proceedings of the National Academy of Sciences, vol. 88, Nov. 1991, pp. 8691-8695.
Stanglmaier et al., "Bi20 (FBTA05), A Novel Trifunctional Bispecific Antibody (anti-CD20 3 anti-CD3), Mediates Efficient Killing Of B-cell Lymphoma Cells Even With Very Low CD20 Expression Levels", International Journal of Cancer, vol. 123, 2008, pp. 1181-1189.
Strohl et al., "Cell Line Development" Therapeutic Antibody Engineering, 2012, 154.
Strop et al., "Generating bispecific human IgG1 and IgG2 antibodies from any antibody pair.", Journal of Molecular Biology, vol. 420, No. 3, Jul. 13, 2012, pp. 204-219.
Suresh, et al. Bispecific monoclonal antibodies from hybrid hybridomas. Methods In Enzymol. 121:210-28 (1983).
Tamaskovic et al., "Designed ankyrin repeat proteins (DARPins): From reserach to therapy", Methods in Enzymology, vol. 503, 2012, pp. 101-134.
Traunecker, et al. Bispecific single chain molecules (Janusins) target cytotoxic lymphocytes on HIV infected cells. EMBO J. Dec. 1991;I0(12):3655-9.
Troise et al., "Differential binding of human immunoagents and Herceptin to the ErbB2 receptor", FEBS Journal, vol. 275, No. 20, 2008, pp. 4967-4979.
Verheesen et al., "Selection of phange display of single domain antibodies specifics to antigens in their native conformation", Methods Mo Bio., Chapter 6, vol. 911, 2012, pp. 81-104.
Vie et al., "Human fusion proteins between interleukin 2 and IgM heavy chain are cytotoxic for cells expressing the interleukin 2 receptor", Proc. Natl. Acad. Sci., vol. 89, 1992, pp. 11337-11341.
Vitetta et al., "Considering Therapeutic Antibodies", Immunology 313:303-309, 2006.
Von Kreudenstein et al., Protein engineering and the use of molecular modeling and simulation: The case ofheterodimeric Fc engineering. Methods, 65(1): 77-94 (2014).
Ward et al., "Binding activities of a repertoire of single immunoglobulin variable domains secreted from *Escherichia coli*", Nature, 334, 1989, pp. 544-546.
Wesolowski et al., "Single domain antibodies: promising experimental and therapeutic tools in infection and immunity", Med Microbiol Immunol., vol. 198, No. 3, 2009, pp. 157-174.
Wiens et al., "Mutation of a single conserved residue in VH complementarity-determining region 2 results in a severe Ig secretion defect.", J Immunology, vol. 167, No. 4, Aug. 2001, pp. 2179-2186.
Woods et al., LC-MS characterization and purity assessment of a prototype bispecific antibody. MABS 5(5): 711-722 (2013).
Wu et al., "Humanization of a Murine Monoclonal Antibody by Simultaneous Optimization of Framework and CDR Residues", Journal of Molecular Biology, vol. 294, Nov. 1999, pp. 151-162.
Wu et al. "Arming antibodies: prospects and challenges for immunoconjugates", Nature Biotech., 2005, vol. 23(9), pp. 1137-1146.
Xu, et al. In vitro characterization of five humanized OKT3 effector function variant antibodies. Cellimmunol. 200(1):16-26 (2000).
Zhu et al., "Remodeling domain interfaces to enhance heterodimer formation", Protein Science, vol. 6, No. 4, Apr. 1997, pp. 781-788.
Abécassis et al., "High efficiency family shuffling based on multi-step PCR and in vivo DNA recombination in yeast: statistical and functional analysis of a combinatorial library between human cytocrome P450 1A1 and 1A2." Nucleic Acids Research, vol. 28, No. 20, e88 (2000).
Akanuma et al., "Further improvement of the thermal stability of a partially stabilized *Bacillus subtilis* 3-isopropylmalate dehydrogenase variant by random and site-directed mutagenesis." Eur. J. Biochem., vol. 260, pp. 499-504 (1999).

(56) References Cited

OTHER PUBLICATIONS

Albanell et al., "Mechanism of Action of Anti-HER2 Monoclonal Antibodies: Scientific Update on TRASTUZUMAB and 2C4." New Trends in Cancer for the 21st Century, edited by Llombart-Bosch and Felipo, Kluwer Academic, p. 253-268 (2003).
Alley et al., "Controlling the location of drug attachment in antibody-drug conjugates." Proc. Amer. Assoc. Cancer Res., vol. 45 (2004).
Altschul et al., "Basic Local Alignment Search Tool." J. Mol. Biol., vol. 215, pp. 403-410 (1990).
Altschul et al., "Gapped BLAST and PSI-BLAST: a new generation of protein database search programs." Nucleic Acids Research, vol. 25, No. 17, pp. 3389-3402 (1997).
Baselga et al., "Recombinant Humanized Anti-HER2 Antibody (Herceptin™) Enhances the Antitumor Activity of Paclitaxel and Doxorubicin against HER2/neu Overexpressing Human Breast Cancer Xenografts." Cancer Research, vol. 58, pp. 2825-2831 (1998).
Bouizar et al., "Purification and characterization of calcitonin receptors in rat kidney membranes by covalent cross-linking techniques." Eur. J. Biochem., vol. 155, pp. 141-147 (1986).
Cadwell and Joyce, "Randomization of Genes by PCR Mutagenesis." PCR Methods and Applications, vol. 2, pp. 28-33 (1992).
Campbell and Marcus, "Monoclonal antibody therapy for lymphoma." Blood Reviews, vol. 17, pp. 143-152 (2003).
Carl et al., "A Novel Connector Linkage Applicable in Prodrug Design." Journal of Medicinal Chemistry, vol. 24, No. 5, Communications to the Editor (1981).
Chakravarty et al., "Plasmin-Activated Prodrugs for Cancer Chemotherapy. 2. Synthesis and Biological Activity of Peptidyl Derivatives of Doxorubicin." J. Med. Chem. vol. 26, No. 638-644 (1983).
Coco et al., "DNA shuffling method for generating highly recombined genes and evolved enzymes." Nature Biotechnology, vol. 19, pp. 354-359 (2001).
Coussens et al., "Tyrosine Kinase Receptor with Extensive Homology to EGF Receptor Shares Chromosomal Location with neu Oncogene." Science, vol. 230, pp. 1132-1139 (1985).
Cragg et al., "Complement-mediated lysis by anti-CD20 mAb correlates with segregation into lipid rafts." Blood, vol. 101, No. 3, pp. 1045-1051 (2003).
Crameri et al., "DNA shuffling of a family of genes from diverse species accelerates directed evolution." Nature, vol. 391, pp. 288-291 (1998).
Declerck et al., "Probing Structural Determinants Specifying High Thermostability in *Bacillus licheniformis* α-Amylase." J. Mol. Biol., vol. 301, pp. 1041-1057 (2000).
De Graaf et al., "Nonnatural Amino Acids for Site-Specific Protein Conjugation." Bioconjugate Chemistry, vol. 20, No. 7, (2009).
De Groot et al., "Synthesis and Biological Evaluation of Novel Prodrugs of Anthracyclines for Selective Activation by the Tumor-Associated Protease Plasmin." J. Med. Chem., vol. 42, pp. 5277-5283 (1999).
De Groot et al., "Elongated multiple Electronic Cascade and Cyclization Spacer Systems in Activatible Anticancer Prodrugs for Enhanced Drug Release." J. Org. Chem., vol. 66, pp. 8815-8830 (2001).
Del Mar Lorenzo and Blasco, "PCR-Based Method for the Introduction of Mutations in Genes Cloned and Expressed in Vaccinia Virus." BioTechniques, vol. 24, No. 2, pp. 308-313 (1998).
De Nardo et al., "Efficacy and Toxicity of $^{67}$Cu-2IT-BAT-Lym-1 Radio-immunoconjugate in Mice Implanted with Human Burkitt's Lymphoma (Raji)[1]." Clincial Cancer Research, vol. 3, pp. 71-79 (1997).
De Nardo et al., "Yttrium-90-DOTA-Peptide-Chimeric L6 Radioimmunconjugate: Efficacy and Toxicity in Mice Bearing P53 Mutant Human Breast Cancer Xenografts." The Journal of Nuclear Medicine, vol. 39, No. 5, pp. 842-849 (1998).
Delvin et al., "Random Peptide Libraries: A Source of Specific Protein Binding Molecules." Science, vol. 249, pp. 404-406 (1990).

Devy et al., "Plasmin-activated doxorubicin prodrugs containing a spacer reduce tumor growth and angiogenesis without systemic toxicity." The FASEB Journal, express article 10.1096 (2004).
Doronina et al., "Development of potent monoclonal antibody auristatin conjugates for cancer therapy." Nature Biotechnology, vol. 21, No. 7, pp. 778-784 (2003).
Dubowchik and Walker, "Receptor-mediated and enzyme-dependent targeting of cycotoxic anticancer drugs." Pharmacology & Therapeutics, vol. 83, pp. 67-123 (1999).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro anticancer Activity." Bioconjugate Chem., vol. 13, pp. 855-869 (2002).
Dubowchik et al., "Doxorubicin Immunoconjugates Containing Bivalent, Lysosomally-Cleavable Dipeptide Linkages." Bioorganic & Medicinal Chemistry Letters, vol. 12, pp. 1529-1532 (2002).
Francisco et al., "cAC10-vcMMAE, an anti-CD30-monomethyl auristatin E conjugate with potent and selective antitumor activity." Blood, vol. 102, No. 4, pp. 1458-1464 (2003).
Garnett, "Targeted drug conjugates: principles and progress." Advanced Drug Delivery Reviews, vol. 53, pp. 171-216 (2001).
Glockshuber et al., "A Comparison of Strategies to Stabilize Immunoglobulin $F_V$Fragments." Biochemistry, vol. 29, pp. 1362-1367 (1990).
Green and Lowenstein, "Autonomous Functional Domains of Chemically Synthesized Human Immunodeficiency Virus Tat Trans-Activator Protein." Cell, vol. 55, pp. 1179-1188 (1988).
Hamblett et al., "Effect of drug loading of the pharmacology, pharmacokinetics, and toxicity of an anti-CD30 antibody-drug conjugate." Proc. Amer. Assoc. Cancer. Res., vol. 45, Abstract (2004).
Hansson et al., "Evolution of Differential Substrate Specificities in Mu Class Glutathione Transferases Probed by DNA Shuffling." J. Mol. Biol., vol. 287, pp. 265-276 (1999).
Harayama, "Artificial evolution by DNA shuffling." Tibtech, vol. 16, pp. 76-81 (1998).
Hashimoto et al., "Significance of Cathepsin B Accumulation in Synovial Fluid of Rheumatoid Arthritis." Biochemical and Biophysical Research Communications, vol. 283, pp. 334-339 (2001).
Hay et al., "A 2-Nitroimidazole Carbamate Prodrug of 5-Amino-1-(Chloromethyl)-3-[(5,6,7-Trimethoxyindol-2-yl)Carbonyl]-1,2-Dihydro-3H-Benz[e]indole (Amino-SECO-CBI-TMI) for Use with ADEPT and GDEPT." Bioorganic & Medicinal Chemistry Letters, vol. 9, pp. 2237-2242 (1999).
Hudziak et al., "p185$^{HER2}$ Monoclonal Antibody Has Antiproliferative Effects In Vitro and Sensitizes Human Breast Tumor Cells to Tumor Necrosis Factor." Molecular and Cellular Biology, vol. 9, No. 3, pp. 1165-1172 (1989).
Igarashi et al., "Thermostabilization by Proline Substitution in an Alkaline, Liquefying α-Amylase from *Bacillus* sp. Strain KSM-1378." Biosci. Biotechno. Biochem., vol. 63, No. 9, pp. 1535-1540 (1999).
Johnson et al., "Anti-Tumor Activity of CC49-Doxorubicin Immunoconjugates." Anticancer Research, vol. 15, pp. 1387-1394 (1995).
Jung and Moroi, "Crosslinking of Platelet Glycoprotein 1b by N-Succinimidyl(4-Azidophenyldithio)Propionate and 3,3'-Dithiobis(Sulfosuccinimidyl Propionate." Biochimica et Biophsica Acta, vol. 761, pp. 152-162 (1983).
Karlin and Altshul, "Applications and statistics for multiple high-scoring segments in molecular sequences." PNAS USA, vol. 90, pp. 5873-5877 (1993).
Ke and Madison, "Rapid and efficient site-directed mutagenesis by single-tube 'mgaprimer' PCR method." Nucleic Acids Research, vol. 25, No. 16, pp. 3371-3372 (1997).
Kikuchi et al., "An effective family shuffling method using single-stranded DNA." Gene, vol. 243, pp. 133-137 (2000).
King et al., "Monoclonal Antibody Conjugates of Doxorubicin Prepared with Branched Peptide Linkers: Inhibition of Aggregation by Methoxytriethyleneglycol Chains." J. Med. Chem., vol. 45, pp. 4336-4343 (2002).

(56) References Cited

OTHER PUBLICATIONS

Klein et al., "Progression of metastatic human prostate cancer to andorgen independence in immunodficient SCID mice." Nature Medicine, vol. 3, No. 4, pp. 402-408 (1997).
Köhler and Milstein, "Continuous cultures of fused cells secreting antibody of predefined specificity." Nature, vol. 256, pp. 495-497 (1975).
Kreitman, "Toxin-Labeled Monoclonal Antibodies." Current Pharmaceutical Biotechnology, vol. 2, pp. 313-325 (2001).
Lamoyi and Nisonoff, "Preparation of F(ab')$_2$ Fragments from Mouse IgG of Various Subclasses." Journal of Immunological Methods, vol. 56, pp. 235-243 (1983).
Lau et al., "Conjugation of Doxorubicin to Monoclonal Anticarcinoembryonic Antigen Antibody via Novel Thiol-directed Cross-linking Reagents." Bioorganic & Medicinal Chemistry, vol. 3, No. 10, pp. 1299-1304 (1995).
Lau et al., "Novel Doxorubcin-Monoclonal Anti-carcinoembryonic Antigen Antibody Immunoconjugate Activity in vitro." Bioorganic & Medicinal Chemistry, vol. 3, No. 10, pp. 1305-1312 (1995).
Lewis et al., "Differential Responses of human tumor cell lines to anti-p185$^{HER2}$ monoclonal antibodies." Cancer Immunol Immunother, vol. 37, pp. 255-263 (1993).
Long-McGie et al., "Rapid In Vivo Evolution of a β-Lactamase Using Phagemids." Biotechnology and Bioengineering, vol. 68, No. 1, pp. 121-125 (2000).
Lutz et al., "Rapid generation of incremental truncation libraties for protein engineering using α-phosphothioate nucleotides." Nucleic Acids Research, vol. 29, No. 4 (2001).
Lutz and Benkovic, "Homology-independent protein engineering." Current Opinion in Biotechnology, vol. 11, pp. 319-324 (2000).
Matthew and Reichardt, "Development and Application of an Efficient Procedure for Converting Mouse IgM into Small, Active Fragments." Journal of Immunological Methods, vol. 50, pp. 239-253 (1982).
Merz et al., "Improving the Catlytic Activity of a Thermophilic Enzyme at Low Temperature." Biochemistry, vol. 39, pp. 880-889 (2000).
Mosmann, "Rapid Colorimetric Assay for Cellular Growth and Survival: Application to Proliferation and Cytotoxicity Assays." Journal of Immunological Methods, vol. 65, pp. 55-63 (1983).
Nakase et al., "Methodological and cellular aspects that govern the internalization mechanisms of arginine-rich cell-penetrating peptides." Advanced Drug Delivery Reviews, vol. 60, pp. 598-607 (2008).
Neuberger et al., "A hapten-specific chimaeric IgE antibody with human physiological effector fuction." Nature, vol. 314 (1995).
Neville, Jr., et al., "Enhancement of Immunotoxin Efficacy by Acid-cleavable Cross-linking Agents Utilizing Diphtheria Toxin and Toxin Mutants." The Journal of Biological Chemistry, vol. 264, No. 25, pp. 14653-14661 (1989).
Nicholson et al., "Radioimmunotherapy after chemotherapy compared to chemotherapy alone in the treatment of advanced ovarian cancer: A matched analysis." Oncology Reports, vol. 5, pp. 223-226 (1998).
Ostermeier et al., "A combinatorial approach to hybrid enzymes independent of DNA homology." Nature Biotechnology, vol. 17, pp. 1205-1209 (1999).
Parham et al., "Monoclonal Antibodies: Purification, Fragmentation and Application to Structural and Functional Studies of Class I MHC Antigens." Journal of Immunological Methods, vol. 53, pp. 133-173 (1982).
Parham, "On the Fragmentation of Monoclonal IgG1, IgG2a, and IgG2b from BALB/c Mice." J. Immunol., col. 131, pp. 2895-2902 (1983).
Pekrun et al., "Evolution of a Human Immunodeficiency Virus Type 1 Variant with Enhanced Replication in Pig-Tailed Macaque Cells by DNA Shuffling." Journal of Virology, vol. 76, No. 6, pp. 2924-2935 (2002).
Queen et al., "A humanized antibody that binds to the interleukin 2 receptor." PNAS USA, vol. 86, pp. 10029-10033 (1989).
Patten et al., "Applications of DNA shuffling to pharmaceuticals and vaccines." Current Opinion in Biotechnology, vol. 8, pp. 724-733 (1997).
Piazza et al., "Antineoplastic Drugs Sulindac Sulfide and Sulfone Inhibit Cell Growth by Inducing Apoptosis." Cancer Research, vol. 55, pp. 3110-3116 (1995).
Powell et al., "Breeding of retroviruses by DNA shuffling for improved stability and processing yields." Nature Biotechnology, vol. 18, pp. 1279-1282 (2000).
Press et al., "Radioimmunotherapy for Non-Hodgkin's Lymphomas: A Historical Perspective." Seminars in Oncology, vol. 30, No. 2, pp. 10-21 (2003).
Raillard et al., "Novel enzyme activities and functional plasticity revealed by recombining highly homologous enzymes." Chemistry & Biology, vol. 8, pp. 891-898 (2001).
Reff et al., "Future of Monoclonal Antibodies in the Treatment of Hematologic Malignancies." Cancer Control, vol. 9, No. 2, pp. 152-166 (2002).
Reidhaar-Olson et al., "Random Mutagenesis of Protein Sequences Using Oligonucleotide Cassettes." Methods in Enzymology, vol. 208, Academic Press, pp. 564-586 (1991).
Riechmann et al., "Reshaping human antibodies for therapy." Nature, vol. 332, pp. 323-327 (1988).
Rojkova et al., "Bacterial formate dehydrogenase. Increasing the enzyme thermal stability by hydrophobization of alpha-helices." FEBS Letters, vol. 445, pp. 183-188 (1999).
Scott and Smith, "Searching for Peptide Ligands with an Epitope Library." Science, New Series, vol. 249, No. 4967, pp. 386-390 (1990).
Selifonova et al., "Rapid Evolution of Novel Traits in Microorganisms." Applied and Environmental Microbiology, vol. 67, No. 8, pp. 3645-3649 (2001).
Shen and Ryser, "CIS-Aconityl Spacer Between Daunomycin and Macromoleular Carriers: A Model of pH-Sensitive Linkage Releasing Drug from a Lysosomotropic Conjugate." Biochemical and Biophysical Research Communications, vol. 102, No. 3, pp. 1048-1054 (1981).
Sieber et al., "Libraries of hybrid proteins from distantly related sequences." Nature Biotechnology, vol. 19, pp. 456-460 (2001).
Silverman et al., "Radiolabeled antibody therapy in non-Hodgkins lymphoma: radiation protection, isotope comparisons and quality of life issues." Cancer Treatment Reviews, vol. 30, pp. 165-172 (2004).
Sinha et al., "Plasma Membrane Associateion of Cathepsin B in Human Prostate Cancer: Biochemical and Immunogold Electron Microscopic Analysis." The Prostate, vol. 49, pp. 172-184 (2001).
Skehan et al., "New Colorimetric Cytotoxicity Assay for Anticancer-Drug Screening." Articles, vol. 82, No. 13, pp. 1107-1112 (1990).
Slamon et al., "Studies of the HER-2/neu Proto-oncogene in Human Breast and Ovarian Cancer." Science, vol. 244, pp. 707-712 (1989).
Stemmer, "Rapid evolution of a protein in vitro by DNA shuffling." Nature, vol. 370. pp. 389-391 (1994).
Stemmer, "DNA shuffling by random fragmentation and reassembly: In vitro recombination for molecular evolution." PNAS USA, vol. 91, pp. 10747-10751 (1994).
Urdal et al., "Lymphokine Purification by Reversed-Phase High-Performance Liquid Chromatography." Journal of Chromatography, vol. 296, pp. 171-179 (1984).
Walker et al., "Monoclonal antibody mediated intracellular targeting of tallysomycin $S_{10b}$." Bioorganic & Medicinal Chemistry Letters, vol. 14, pp. 4323-4327 (2004).
Ward et al., "Binding activities of a repertoire of single immunoglobulin variable domains secreted from *Esherichia coli*." Nature, vol. 341, pp. 544-546 (1989).
Winter and Milstein, "Man-made antibodies." Nature, vol. 349, pp. 293-299 (1991).
Witzig et al., "Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma." J. Clinical Oncology, vol. 20, No. 10, Abstract, (2002).

(56) References Cited

OTHER PUBLICATIONS

Zhao et al., "Molecular evolution by staggered extension process (StEP) in vitro recombination." Nature Biotechnology, vol. 16, pp. 258-261 (1998).
Zhang et al., "Directed evolution of a fucosidase from a galactosidase by DNA shuffling and screening." PNAS USA, vol. 94, pp. 4504-4509 (1997).
Zhu et al., "Increasing the thermostability of D-xylose imoerase by introduction of a proline into the turn of a random coil." Protein Engineering, vol. 12, No. 8, pp. 635-638 (1999).

* cited by examiner

| PDB | SG | cell dimensions (Å) | crystallization conditions | Crystal packing[3] | CH3CH3[2] backbone rmsd vs. AZ1 (Å) | CH3CH3[2] backbone rmsd vs. 3AVE (Å) |
|---|---|---|---|---|---|---|
| AZ1[1] | P212121 | 49.54,74.92,148.92 | 5% ethylene glycol, 18% PEG 3350, 0.15 M NH4I | 3 | - | 0.26 |
| 2WAH | P212121 | 49.39,74.98,149.2 | 20% PEG 6000, 0.1 M MES PH 6.0 | 3 | 0.31 | 0.36 |
| 3AVE | P212121 | 49.42,78.47,143.76 | H2O dialysis | 2 | 0.26 | - |
| 1H3X | P212121 | 49.69,80.2,138.96 | H2O dialysis | 2 | 0.39 | 0.31 |
| 4DZ8 | P212122 | 49.93,81.29,136.15 | Hepes pH 7.0, 1% Tryptone, 20% PEG 3350 | 2 | 0.31 | 0.32 |
| 3C2S | C2221 | 50.18,147.3,75.47 | 5% PEG 3350, 0.2 M Zn Acetate, 0.1 M Imidazole, pH 8.0 | 1 | 0.43 | 0.27 |
| 2QL1 | C2221 | 49.87,147.49,74.32 | 5% PEG 3350, 0.2 M Zn Acetate, 0.1 M Imidazole, pH 8.0 | 1 | 0.39 | 0.31 |

1   Rmsd (CH3CH3 backbone) AB vs. BA = 0.29
2   CH3CH3 domain defined as chains A and B, residues 345-440 (Eu numbering)
3   Classification of distinct crystal packing as described in detail in the text

Figure 8

| Variant | CD16a(F158) Kd [M] | CD32b(Y163) Kd [M] |
|---|---|---|
| Herceptin WT | 4.40E-07 | 1.70E-06 |
| AZ1 | 3.60E-07 | 9.90E-07 |
| AZ2 | 4.60E-07 | 1.20E-06 |

Figure 10

| Variant | Kd [M] – pH 6.0 | Kd [M] – pH 7.5 |
|---|---|---|
| Herceptin WT | 3.70E-06 | - |
| AZ1 | 3.90E-06 | - |
| AZ2 | 4.30E-06 | - |

Figure 14

Human IgG1 Fc germline sequence 231-447 (EU - numbering):

KTHTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHYTQKSLSLSPGK
(SEQ ID NO: 1)

AZ1 heterodimer:

Chain_A: Mutations T350V_T366L_K392L_T394W
KTHTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYVLPPSRDELTKNQVSLLCLVKGFYPSDI
AVEWESNGQPENNYLTWPPVLDSDGSFFLYSKLTVDKSRWQQGNVFSCSVMHEALHNHYTQKSLSLSPGK
(SEQ ID NO: 2)

Chain_B: Mutations T350V_L351Y_F405A_Y407V
KTHTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYVYPPSRDELTKNQVSLTCLVKGFYPSDI
AVEWESNGQPENNYKTTPPVLDSDGSFALVSKLTVDKSRWQQGNVFSCSVMHEALHNHYTQKSLSLSPGK
(SEQ ID NO: 3)

AZ2 heterodimer:

Chain_A: Mutations T350V_T366L_K392M_T394W
KTHTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYVLPPSRDELTKNQVSLLCLVKGFYPSDI
AVEWESNGQPENNYMTWPPVLDSDGSFFLYSKLTVDKSRWQQGNVFSCSVMHEALHNHYTQKSLSLSPGK
(SEQ ID NO: 4)

Chain_B: Mutations T350V_L351Y_F405A_Y407V
KTHTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYVYPPSRDELTKNQVSLTCLVKGFYPSDI
AVEWESNGQPENNYKTTPPVLDSDGSFALVSKLTVDKSRWQQGNVFSCSVMHEALHNHYTQKSLSLSPGK
(SEQ ID NO: 5)

Figure 16

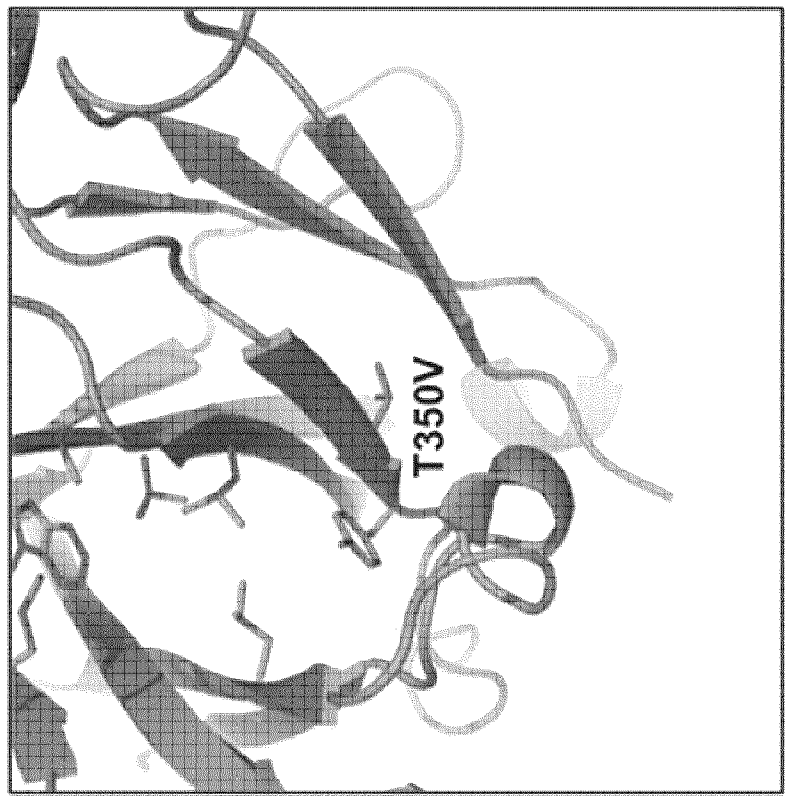
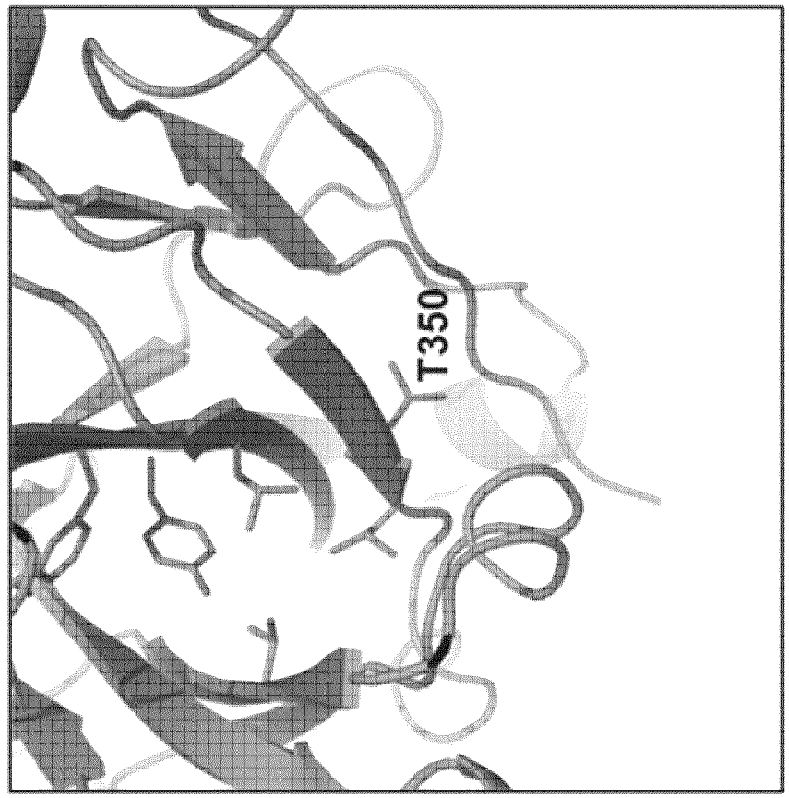
Figure 24

| CH2 Domain | | | | CH3 Domain | | | |
|---|---|---|---|---|---|---|---|
| EU No. | Amino Acid | EU No. | Amino Acid | EU No. | Amino Acid | EU No. | Amino Acid |
| 231 | A | 271 | P | 341 | G | 381 | W |
| 232 | P | 272 | E | 342 | Q | 382 | E |
| 233 | E | 273 | V | 343 | P | 383 | S |
| 234 | L | 274 | K | 344 | R | 384 | N |
| 235 | L | 275 | F | 345 | E | 385 | G |
| 236 | G | 276 | N | 346 | P | 386 | Q |
| 237 | G | 277 | W | 347 | Q | 387 | P |
| 238 | P | 278 | Y | 348 | V | 388 | E |
| 239 | S | 279 | V | 349 | Y | 389 | N |
| 240 | V | 280 | D | 350 | T | 390 | N |
| 241 | F | 281 | G | 351 | L | 391 | Y |
| 242 | L | 282 | V | 352 | P | 392 | K |
| 243 | F | 283 | E | 353 | P | 393 | T |
| 244 | P | 284 | V | 354 | S | 394 | T |
| 245 | P | 285 | H | 355 | R | 395 | P |
| 246 | K | 286 | N | 356 | D | 396 | P |
| 247 | P | 287 | A | 357 | E | 397 | V |
| 248 | K | 288 | K | 358 | L | 398 | L |
| 249 | D | 289 | T | 359 | T | 399 | D |
| 250 | T | 290 | K | 360 | K | 400 | S |
| 251 | L | 291 | P | 361 | N | 401 | D |
| 252 | M | 292 | R | 362 | Q | 402 | G |
| 253 | I | 293 | E | 363 | V | 403 | S |
| 254 | S | 294 | E | 364 | S | 404 | F |
| 255 | R | 295 | Q | 365 | L | 405 | F |
| 256 | T | 296 | Y | 366 | T | 406 | L |
| 257 | P | 297 | N | 367 | C | 407 | Y |
| 258 | E | 298 | S | 368 | L | 408 | S |
| 259 | V | 299 | T | 369 | V | 409 | K |
| 260 | T | 300 | Y | 370 | K | 410 | L |
| 261 | C | 301 | R | 371 | G | 411 | T |
| 262 | V | 302 | V | 372 | F | 412 | V |
| 263 | V | 303 | V | 373 | Y | 413 | D |
| 264 | V | 304 | S | 374 | P | 414 | K |
| 265 | D | 305 | V | 375 | S | 415 | S |
| 266 | V | 306 | L | 376 | D | 416 | R |
| 267 | S | 307 | T | 377 | I | 417 | W |
| 268 | H | 308 | V | 378 | A | 418 | Q |
| 269 | E | 309 | L | 379 | V | 419 | Q |
| 270 | D | 310 | H | 380 | E | 420 | G |
|  |  | 311 | Q |  |  | 421 | N |
|  |  | 312 | D |  |  | 422 | V |
|  |  | 313 | W |  |  | 423 | F |
|  |  | 314 | L |  |  | 424 | S |
|  |  | 315 | N |  |  | 425 | C |
|  |  | 316 | G |  |  | 426 | S |
|  |  | 317 | K |  |  | 427 | V |
|  |  | 318 | E |  |  | 428 | M |
|  |  | 319 | Y |  |  | 429 | H |
|  |  | 320 | K |  |  | 430 | E |
|  |  | 321 | C |  |  | 431 | A |
|  |  | 322 | K |  |  | 432 | L |
|  |  | 323 | V |  |  | 433 | H |
|  |  | 324 | S |  |  | 434 | N |
|  |  | 325 | N |  |  | 435 | H |
|  |  | 326 | K |  |  | 436 | Y |
|  |  | 327 | A |  |  | 437 | T |
|  |  | 328 | L |  |  | 438 | Q |
|  |  | 329 | P |  |  | 439 | K |
|  |  | 330 | A |  |  | 440 | S |
|  |  | 331 | P |  |  | 441 | L |
|  |  | 332 | I |  |  | 442 | S |
|  |  | 333 | E |  |  | 443 | L |
|  |  | 334 | K |  |  | 444 | S |
|  |  | 335 | T |  |  | 445 | P |
|  |  | 336 | I |  |  | 446 | G |
|  |  | 337 | S |  |  | 447 | K |
|  |  | 338 | K |  |  |  |  |
|  |  | 339 | A |  |  |  |  |
|  |  | 340 | K |  |  |  |  |

Structure coordinates for AZ2 (including SEQ ID NOS.: 4 and 5)

LEGEND

Column headings from left to right are (A) "Atom Number", (B) "Atom Type", (C) "Amino Acid", (D) "Chain Identifier", (E) "Amino Acid Number", (F) "X Coordinate", (G) "Y Coordinate", (H) "Z Coordinate", (I) "Occupancy" (OCC), (J) "B factor", and (K) atom type.

| | A | B | C | D | E | F | G | H | I | J | K |
|---|---|---|---|---|---|---|---|---|---|---|---|
| ATOM | 1 | N | GLY | A | 236 | -31.982 | -13.845 | 4.409 | 0.50 | 51.41 | N |
| ATOM | 2 | CA | GLY | A | 236 | -31.210 | -14.413 | 3.269 | 0.50 | 59.26 | C |
| ATOM | 3 | C | GLY | A | 236 | -32.018 | -15.445 | 2.501 | 0.50 | 56.57 | C |
| ATOM | 4 | O | GLY | A | 236 | -33.251 | -15.393 | 2.475 | 0.50 | 57.86 | O |
| ATOM | 5 | N | GLY | A | 237 | -31.326 | -16.378 | 1.856 | 0.50 | 54.03 | N |
| ATOM | 6 | CA | GLY | A | 237 | -32.010 | -17.466 | 1.150 | 0.50 | 54.83 | C |
| ATOM | 7 | C | GLY | A | 237 | -32.123 | -17.264 | -0.352 | 0.50 | 56.46 | C |
| ATOM | 8 | O | GLY | A | 237 | -31.452 | -16.407 | -0.919 | 0.50 | 55.59 | O |
| ATOM | 9 | N | PRO | A | 238 | -32.977 | -18.064 | -1.009 | 0.50 | 62.94 | N |
| ATOM | 10 | CA | PRO | A | 238 | -33.076 | -18.096 | -2.474 | 0.50 | 58.95 | C |
| ATOM | 11 | CB | PRO | A | 238 | -34.136 | -19.176 | -2.741 | 0.50 | 60.44 | C |
| ATOM | 12 | CG | PRO | A | 238 | -34.826 | -19.406 | -1.436 | 0.50 | 57.54 | C |
| ATOM | 13 | CD | PRO | A | 238 | -33.807 | -19.105 | -0.377 | 0.50 | 62.33 | C |
| ATOM | 14 | C | PRO | A | 238 | 33.491 | 16.769 | 3.111 | 0.50 | 57.49 | C |
| ATOM | 15 | O | PRO | A | 238 | -34.184 | -15.959 | -2.486 | 0.50 | 52.38 | O |
| ATOM | 16 | N | SER | A | 239 | -33.041 | -16.558 | -4.347 | 0.50 | 54.39 | N |
| ATOM | 17 | CA | SER | A | 239 | -33.485 | -15.435 | -5.173 | 0.50 | 53.22 | C |
| ATOM | 18 | CB | SER | A | 239 | -32.319 | -14.503 | -5.463 | 0.50 | 50.03 | C |
| ATOM | 19 | OG | SER | A | 239 | -32.328 | -13.434 | -4.541 | 0.50 | 55.78 | O |
| ATOM | 20 | C | SER | A | 239 | -34.084 | -15.925 | -6.493 | 0.50 | 54.30 | C |
| ATOM | 21 | O | SER | A | 239 | -33.698 | -16.979 | -7.008 | 0.50 | 46.28 | O |
| ATOM | 22 | N | VAL | A | 240 | -34.997 | -15.131 | -7.050 | 0.50 | 54.02 | N |
| ATOM | 23 | CA | VAL | A | 240 | -35.824 | -15.573 | -8.173 | 0.50 | 50.32 | C |
| ATOM | 24 | CB | VAL | A | 240 | -37.299 | -15.679 | -7.771 | 0.50 | 50.50 | C |
| ATOM | 25 | CG1 | VAL | A | 240 | -38.193 | -15.440 | -8.988 | 0.50 | 47.93 | C |
| ATOM | 26 | CG2 | VAL | A | 240 | -37.576 | -17.037 | -7.126 | 0.50 | 45.50 | C |
| ATOM | 27 | C | VAL | A | 240 | -35.721 | -14.662 | -9.399 | 0.50 | 51.35 | C |
| ATOM | 28 | O | VAL | A | 240 | -35.929 | -13.440 | -9.316 | 0.50 | 42.23 | O |
| ATOM | 29 | N | PHE | A | 241 | -35.401 | -15.269 | -10.536 | 0.50 | 44.27 | N |
| ATOM | 30 | CA | PHE | A | 241 | -35.333 | -14.520 | -11.793 | 0.50 | 45.77 | C |
| ATOM | 31 | CB | PHE | A | 241 | -33.880 | -14.431 | -12.294 | 0.50 | 46.55 | C |
| ATOM | 32 | CG | PHE | A | 241 | -32.959 | -13.701 | -11.343 | 0.50 | 48.84 | C |
| ATOM | 33 | CD1 | PHE | A | 241 | -32.827 | -12.314 | -11.402 | 0.50 | 50.02 | C |
| ATOM | 34 | CE1 | PHE | A | 241 | -32.004 | -11.636 | -10.511 | 0.50 | 48.04 | C |
| ATOM | 35 | CZ | PHE | A | 241 | -31.326 | -12.337 | -9.532 | 0.50 | 51.70 | C |
| ATOM | 36 | CE2 | PHE | A | 241 | -31.456 | -13.719 | -9.452 | 0.50 | 52.09 | C |
| ATOM | 37 | CD2 | PHE | A | 241 | -32.259 | -14.392 | -10.360 | 0.50 | 51.47 | C |
| ATOM | 38 | C | PHE | A | 241 | -36.282 | -15.136 | -12.830 | 0.50 | 43.04 | C |
| ATOM | 39 | O | PHE | A | 241 | -36.387 | -16.363 | -12.942 | 0.50 | 43.08 | O |
| ATOM | 40 | N | LEU | A | 242 | -37.008 | -14.275 | -13.535 | 0.50 | 41.52 | N |
| ATOM | 41 | CA | LEU | A | 242 | -38.111 | -14.676 | -14.419 | 0.50 | 41.74 | C |
| ATOM | 42 | CB | LEU | A | 242 | -39.425 | -14.030 | -13.971 | 0.50 | 41.05 | C |
| ATOM | 43 | CG | LEU | A | 242 | -40.740 | -14.454 | -14.638 | 0.50 | 41.58 | C |
| ATOM | 44 | CD1 | LEU | A | 242 | -40.918 | -15.956 | -14.533 | 0.50 | 41.88 | C |
| ATOM | 45 | CD2 | LEU | A | 242 | -41.923 | -13.740 | -14.008 | 0.50 | 36.94 | C |
| ATOM | 46 | C | LEU | A | 242 | -37.805 | -14.184 | -15.817 | 0.50 | 42.09 | C |
| ATOM | 47 | O | LEU | A | 242 | -37.618 | -12.976 | -16.032 | 0.50 | 39.76 | O |
| ATOM | 48 | N | PHE | A | 243 | -37.779 | -15.122 | -16.756 | 0.50 | 36.31 | N |
| ATOM | 49 | CA | PHE | A | 243 | -37.316 | -14.859 | -18.107 | 0.50 | 36.82 | C |
| ATOM | 50 | CB | PHE | A | 243 | -36.139 | -15.767 | -18.424 | 0.50 | 36.55 | C |

Figure 26 (Continued)

```
ATOM     51  CG  PHE A 243     -34.986 -15.613 -17.463  0.50 42.92           C
ATOM     52  CD1 PHE A 243     -34.082 -14.561 -17.599  0.50 42.58           C
ATOM     53  CE1 PHE A 243     -33.001 -14.428 -16.733  0.50 41.33           C
ATOM     54  CZ  PHE A 243     -32.830 -15.338 -15.699  0.50 46.42           C
ATOM     55  CE2 PHE A 243     -33.732 -16.387 -15.548  0.50 46.47           C
ATOM     56  CD2 PHE A 243     -34.808 -16.511 -16.420  0.50 41.81           C
ATOM     57  C   PHE A 243     -38.413 -15.064 -19.131  0.50 38.80           C
ATOM     58  O   PHE A 243     -39.222 -15.991 -19.004  0.50 41.08           O
ATOM     59  N   PRO A 244     -38.435 -14.213 -20.164  0.50 35.36           N
ATOM     60  CA  PRO A 244     -39.477 -14.234 -21.181  0.50 35.81           C
ATOM     61  CB  PRO A 244     -39.352 -12.832 -21.797  0.50 31.50           C
ATOM     62  CG  PRO A 244     -37.865 -12.606 -21.783  0.50 31.68           C
ATOM     63  CD  PRO A 244     -37.429 -13.164 -20.438  0.50 34.23           C
ATOM     64  C   PRO A 244     -39.184 -15.300 -22.263  0.50 35.91           C
ATOM     65  O   PRO A 244     -38.096 -15.871 -22.294  0.50 34.09           O
ATOM     66  N   PRO A 245     -40.163 -15.590 -23.130  0.50 37.42           N
ATOM     67  CA  PRO A 245     -39.870 -16.502 -24.259  0.50 35.23           C
ATOM     68  CB  PRO A 245     -41.241 -16.759 -24.886  0.50 36.43           C
ATOM     69  CG  PRO A 245     -42.146 -15.669 -24.360  0.50 39.72           C
ATOM     70  CD  PRO A 245     -41.589 -15.220 -23.034  0.50 34.86           C
ATOM     71  C   PRO A 245     -38.932 -15.869 -25.289  0.50 35.38           C
ATOM     72  O   PRO A 245     -38.785 -14.658 -25.333  0.50 34.17           O
ATOM     73  N   LYS A 246     -38.274 -16.686 -26.101  0.50 34.34           N
ATOM     74  CA  LYS A 246     -37.534 -16.170 -27.225  0.50 30.90           C
ATOM     75  CB  LYS A 246     -36.664 -17.286 -27.826  0.50 38.94           C
ATOM     76  CG  LYS A 246     -35.858 -18.043 -26.729  0.50 37.09           C
ATOM     77  CD  LYS A 246     -34.572 -17.311 -26.301  0.50 42.15           C
ATOM     78  CE  LYS A 246     -34.182 -17.556 -24.828  0.50 44.99           C
ATOM     79  NZ  LYS A 246     -34.484 -18.909 -24.267  0.50 53.05           N
ATOM     80  C   LYS A 246     -38.477 -15.536 -28.244  0.50 31.81           C
ATOM     81  O   LYS A 246     -39.562 -16.005 -28.471  0.50 33.43           O
ATOM     82  N   PRO A 247     -38.081 -14.408 -28.828  0.50 31.56           N
ATOM     83  CA  PRO A 247     -39.014 -13.757 -29.720  0.50 30.68           C
ATOM     84  CB  PRO A 247     -38.174 -12.611 -30.304  0.50 31.20           C
ATOM     85  CG  PRO A 247     -37.197 -12.274 -29.213  0.50 29.59           C
ATOM     86  CD  PRO A 247     -36.907 -13.566 -28.506  0.50 31.85           C
ATOM     87  C   PRO A 247     -39.471 -14.707 -30.845  0.50 30.45           C
ATOM     88  O   PRO A 247     -40.645 -14.717 -31.200  0.50 29.30           O
ATOM     89  N   LYS A 248     -38.534 -15.427 -31.458  0.50 29.03           N
ATOM     90  CA  LYS A 248     -38.865 -16.311 -32.583  0.50 28.48           C
ATOM     91  CB  LYS A 248     -37.613 -17.082 -33.030  0.50 32.17           C
ATOM     92  CG  LYS A 248     -37.716 -17.873 -34.324  0.50 31.34           C
ATOM     93  CD  LYS A 248     -36.303 -18.289 -34.759  0.50 33.01           C
ATOM     94  CE  LYS A 248     -36.293 -19.251 -35.936  0.50 32.92           C
ATOM     95  NZ  LYS A 248     -34.927 -19.838 -36.173  0.50 32.42           N
ATOM     96  C   LYS A 248     -39.912 -17.281 -32.130  0.50 29.63           C
ATOM     97  O   LYS A 248     -40.822 -17.628 -32.876  0.50 37.29           O
ATOM     98  N   ASP A 249     -39.834 -17.690 -30.876  0.50 30.62           N
ATOM     99  CA  ASP A 249     -40.843 -18.606 -30.360  0.50 32.82           C
ATOM    100  CB  ASP A 249     -40.399 -19.217 -29.032  0.50 31.91           C
ATOM    101  CG  ASP A 249     -39.221 -20.171 -29.192  0.50 33.82           C
ATOM    102  OD1 ASP A 249     -38.999 -20.684 -30.323  0.50 36.70           O
ATOM    103  OD2 ASP A 249     -38.497 -20.384 -28.195  0.50 35.24           O
ATOM    104  C   ASP A 249     -42.241 -18.005 -30.214  0.50 33.41           C
ATOM    105  O   ASP A 249     -43.221 -18.759 -30.269  0.50 30.66           O
ATOM    106  N   THR A 250     -42.367 -16.686 -29.984  0.50 28.29           N
ATOM    107  CA  THR A 250     -43.734 -16.112 -29.809  0.50 28.01           C
ATOM    108  CB  THR A 250     -43.736 -14.804 -28.962  0.50 31.82           C
ATOM    109  OG1 THR A 250     -43.020 -13.767 -29.667  0.50 30.51           O
ATOM    110  CG2 THR A 250     -43.083 -15.021 -27.594  0.50 27.15           C
ATOM    111  C   THR A 250     -44.322 -15.772 -31.169  0.50 26.70           C
ATOM    112  O   THR A 250     -45.528 -15.628 -31.333  0.50 28.66           O
ATOM    113  N   LEU A 251     -43.455 -15.589 -32.145  0.50 29.01           N
ATOM    114  CA  LEU A 251     -43.886 -15.117 -33.446  0.50 30.01           C
```

Figure 26 (Continued)

```
ATOM    115  CB  LEU A 251     -42.776 -14.273 -34.098  0.50 28.06           C
ATOM    116  CG  LEU A 251     -42.509 -12.981 -33.293  0.50 29.98           C
ATOM    117  CD1 LEU A 251     -41.246 -12.289 -33.773  0.50 29.16           C
ATOM    118  CD2 LEU A 251     -43.707 -12.033 -33.359  0.50 25.00           C
ATOM    119  C   LEU A 251     -44.260 -16.273 -34.348  0.50 34.84           C
ATOM    120  O   LEU A 251     -45.131 -16.137 -35.254  0.50 30.98           O
ATOM    121  N   MET A 252     -43.582 -17.405 -34.150  0.50 31.90           N
ATOM    122  CA  MET A 252     -43.749 -18.466 -35.141  0.50 34.84           C
ATOM    123  CB  MET A 252     -42.405 -18.938 -35.691  0.50 38.37           C
ATOM    124  CG  MET A 252     -41.491 -17.788 -36.096  0.50 39.53           C
ATOM    125  SD  MET A 252     -42.128 -16.647 -37.373  0.50 52.27           S
ATOM    126  CE  MET A 252     -41.751 -17.666 -38.790  0.50 40.00           C
ATOM    127  C   MET A 252     -44.621 -19.571 -34.547  0.50 34.16           C
ATOM    128  O   MET A 252     -44.320 -20.160 -33.482  0.50 28.60           O
ATOM    129  N   ILE A 253     -45.791 -19.736 -35.155  0.50 30.74           N
ATOM    130  CA  ILE A 253     -46.848 -20.462 -34.493  0.50 31.17           C
ATOM    131  CB  ILE A 253     -48.171 -20.362 -35.248  0.50 31.88           C
ATOM    132  CG1 ILE A 253     -49.307 -20.729 -34.332  0.50 33.94           C
ATOM    133  CD1 ILE A 253     -50.085 -21.875 -34.934  0.50 37.88           C
ATOM    134  CG2 ILE A 253     -48.200 -21.310 -36.452  0.50 34.97           C
ATOM    135  C   ILE A 253     -46.472 -21.933 -34.238  0.50 30.20           C
ATOM    136  O   ILE A 253     -46.865 -22.498 -33.229  0.50 31.90           O
ATOM    137  N   SER A 254     -45.696 -22.552 -35.111  0.50 30.34           N
ATOM    138  CA  SER A 254     -45.329 -23.961 -34.832  0.50 35.61           C
ATOM    139  CB  SER A 254     -44.773 -24.682 -36.064  0.50 32.84           C
ATOM    140  OG  SER A 254     -45.822 -24.893 -37.022  0.50 32.76           O
ATOM    141  C   SER A 254     -44.386 -24.103 -33.637  0.50 36.60           C
ATOM    142  O   SER A 254     -44.270 -25.173 -33.056  0.50 30.70           O
ATOM    143  N   ARG A 255     -43.702 -23.026 -33.266  0.50 31.02           N
ATOM    144  CA  ARG A 255     -42.698 -23.169 -32.224  0.50 31.34           C
ATOM    145  CB  ARG A 255     -41.596 -22.124 -32.414  0.50 33.06           C
ATOM    146  CG  ARG A 255     -40.796 -22.329 -33.691  0.50 30.16           C
ATOM    147  CD  ARG A 255     -39.713 -21.252 -33.860  0.50 35.01           C
ATOM    148  NE  ARG A 255     -38.569 -21.359 -32.946  0.50 33.89           N
ATOM    149  CZ  ARG A 255     -37.385 -21.856 -33.307  0.50 33.48           C
ATOM    150  NH1 ARG A 255     -37.215 -22.350 -34.529  0.50 32.85           N
ATOM    151  NH2 ARG A 255     -36.379 -21.897 -32.449  0.50 34.99           N
ATOM    152  C   ARG A 255     -43.411 -23.037 -30.896  0.50 30.02           C
ATOM    153  O   ARG A 255     -44.602 -22.777 -30.877  0.50 32.37           O
ATOM    154  N   THR A 256     -42.726 -23.270 -29.786  0.50 32.88           N
ATOM    155  CA  THR A 256     -43.418 -23.310 -28.513  0.50 33.64           C
ATOM    156  CB  THR A 256     -43.560 -24.760 -27.989  0.50 42.25           C
ATOM    157  OG1 THR A 256     -42.731 -25.668 -28.769  0.50 37.83           O
ATOM    158  CG2 THR A 256     -45.062 -25.204 -28.057  0.50 33.96           C
ATOM    159  C   THR A 256     -42.756 -22.382 -27.455  0.50 38.59           C
ATOM    160  O   THR A 256     -41.680 -22.661 -26.952  0.50 37.80           O
ATOM    161  N   PRO A 257     -43.374 -21.233 -27.172  0.50 38.88           N
ATOM    162  CA  PRO A 257     -42.770 -20.238 -26.264  0.50 38.64           C
ATOM    163  CB  PRO A 257     -43.547 -18.972 -26.578  0.50 36.09           C
ATOM    164  CG  PRO A 257     -44.901 -19.498 -26.981  0.50 38.72           C
ATOM    165  CD  PRO A 257     -44.620 -20.743 -27.776  0.50 39.22           C
ATOM    166  C   PRO A 257     -42.958 -20.596 -24.788  0.50 37.78           C
ATOM    167  O   PRO A 257     -44.011 -21.076 -24.400  0.50 39.70           O
ATOM    168  N   GLU A 258     -41.933 -20.352 -23.979  0.50 37.76           N
ATOM    169  CA  GLU A 258     -41.967 -20.702 -22.562  0.50 37.65           C
ATOM    170  CB  GLU A 258     -40.883 -21.765 -22.267  0.50 36.53           C
ATOM    171  CG  GLU A 258     -41.001 -23.011 -23.131  0.50 43.69           C
ATOM    172  CD  GLU A 258     -39.783 -23.914 -23.047  0.50 46.74           C
ATOM    173  OE1 GLU A 258     -38.672 -23.440 -22.694  0.50 48.86           O
ATOM    174  OE2 GLU A 258     -39.934 -25.104 -23.355  0.50 44.86           O
ATOM    175  C   GLU A 258     -41.592 -19.467 -21.774  0.50 34.80           C
ATOM    176  O   GLU A 258     -40.599 -18.807 -22.096  0.50 32.70           O
ATOM    177  N   VAL A 259     -42.291 -19.228 -20.676  0.50 34.23           N
ATOM    178  CA  VAL A 259     -41.734 -18.381 -19.619  0.50 37.86           C
```

Figure 26 (Continued)

```
ATOM    179  CB   VAL A 259     -42.818 -17.446 -19.034  0.50 40.70           C
ATOM    180  CG1  VAL A 259     -42.415 -16.883 -17.684  0.50 42.15           C
ATOM    181  CG2  VAL A 259     -43.093 -16.301 -20.011  0.50 37.75           C
ATOM    182  C    VAL A 259     -41.020 -19.257 -18.564  0.50 42.62           C
ATOM    183  O    VAL A 259     -41.481 -20.363 -18.226  0.50 42.78           O
ATOM    184  N    THR A 260     -39.860 -18.796 -18.098  0.50 38.58           N
ATOM    185  CA   THR A 260     -39.007 -19.592 -17.228  0.50 40.42           C
ATOM    186  CB   THR A 260     -37.674 -19.960 -17.931  0.50 38.60           C
ATOM    187  OG1  THR A 260     -37.969 -20.603 -19.173  0.50 38.29           O
ATOM    188  CG2  THR A 260     -36.845 -20.934 -17.099  0.50 34.11           C
ATOM    189  C    THR A 260     -38.766 -18.900 -15.883  0.50 39.88           C
ATOM    190  O    THR A 260     -38.402 -17.727 -15.819  0.50 38.76           O
ATOM    191  N    CYS A 261     -39.041 -19.612 -14.803  0.50 39.81           N
ATOM    192  CA   CYS A 261     -38.880 -19.041 -13.471  0.50 41.10           C
ATOM    193  CB   CYS A 261     -40.161 -19.198 -12.657  0.50 46.51           C
ATOM    194  SG   CYS A 261     -40.196 -18.279 -11.095  0.50 47.96           S
ATOM    195  C    CYS A 261     -37.715 -19.733 -12.795  0.50 42.36           C
ATOM    196  O    CYS A 261     -37.719 -20.959 -12.608  0.50 40.42           O
ATOM    197  N    VAL A 262     -36.676 -18.963 -12.492  0.50 41.55           N
ATOM    198  CA   VAL A 262     -35.459 -19.565 -11.967  0.50 44.02           C
ATOM    199  CB   VAL A 262     -34.239 -19.184 -12.820  0.50 44.22           C
ATOM    200  CG1  VAL A 262     -32.983 -19.876 -12.297  0.50 41.40           C
ATOM    201  CG2  VAL A 262     -34.504 -19.559 -14.272  0.50 39.43           C
ATOM    202  C    VAL A 262     -35.213 -19.178 -10.511  0.50 45.01           C
ATOM    203  O    VAL A 262     -35.238 -17.997 -10.167  0.50 43.13           O
ATOM    204  N    VAL A 263     -34.982 -20.186  -9.669  0.50 47.49           N
ATOM    205  CA   VAL A 263     -34.576 -19.971  -8.270  0.50 44.78           C
ATOM    206  CB   VAL A 263     -35.616 -20.530  -7.283  0.50 44.34           C
ATOM    207  CG1  VAL A 263     -35.215 -20.185  -5.853  0.50 46.13           C
ATOM    208  CG2  VAL A 263     -37.000 -19.983  -7.600  0.50 40.29           C
ATOM    209  C    VAL A 263     -33.197 -20.564  -7.939  0.50 43.17           C
ATOM    210  O    VAL A 263     -32.954 -21.769  -8.130  0.50 42.56           O
ATOM    211  N    VAL A 264     -32.296 -19.705  -7.459  0.50 38.91           N
ATOM    212  CA   VAL A 264     -30.982 -20.135  -6.992  0.50 41.51           C
ATOM    213  CB   VAL A 264     -29.831 -19.424  -7.753  0.50 38.67           C
ATOM    214  CG1  VAL A 264     -29.971 -19.613  -9.267  0.50 40.69           C
ATOM    215  CG2  VAL A 264     -29.801 -17.937  -7.412  0.50 41.36           C
ATOM    216  C    VAL A 264     -30.853 -19.871  -5.472  0.50 43.77           C
ATOM    217  O    VAL A 264     -31.770 -19.327  -4.846  0.50 39.85           O
ATOM    218  N    ASP A 265     -29.706 -20.232  -4.894  0.50 49.64           N
ATOM    219  CA   ASP A 265     -29.476 -20.086  -3.438  0.50 54.66           C
ATOM    220  CB   ASP A 265     -29.343 -18.618  -3.005  0.50 50.40           C
ATOM    221  CG   ASP A 265     -28.157 -17.941  -3.592  0.50 47.80           C
ATOM    222  OD1  ASP A 265     -27.279 -18.615  -4.185  0.50 51.70           O
ATOM    223  OD2  ASP A 265     -28.108 -16.712  -3.459  0.50 50.34           O
ATOM    224  C    ASP A 265     -30.644 -20.664  -2.675  0.50 51.86           C
ATOM    225  O    ASP A 265     -31.158 -20.031  -1.757  0.50 55.70           O
ATOM    226  N    VAL A 266     -31.106 -21.827  -3.103  0.50 55.01           N
ATOM    227  CA   VAL A 266     -32.037 -22.602  -2.315  0.50 61.45           C
ATOM    228  CB   VAL A 266     -32.875 -23.520  -3.209  0.50 58.88           C
ATOM    229  CG1  VAL A 266     -33.603 -24.550  -2.366  0.50 59.86           C
ATOM    230  CG2  VAL A 266     -33.853 -22.698  -4.034  0.50 61.16           C
ATOM    231  C    VAL A 266     -31.185 -23.453  -1.381  0.50 67.98           C
ATOM    232  O    VAL A 266     -30.156 -23.985  -1.814  0.50 65.28           O
ATOM    233  N    SER A 267     -31.601 -23.569  -0.116  0.50 73.73           N
ATOM    234  CA   SER A 267     -30.766 -24.192   0.930  0.50 77.66           C
ATOM    235  CB   SER A 267     -31.178 -23.736   2.344  0.50 70.88           C
ATOM    236  OG   SER A 267     -32.392 -24.343   2.772  0.50 70.05           O
ATOM    237  C    SER A 267     -30.719 -25.713   0.856  0.50 76.00           C
ATOM    238  O    SER A 267     -31.643 -26.364   0.350  0.50 73.49           O
ATOM    239  N    HIS A 268     -29.626 -26.272   1.361  0.50 79.36           N
ATOM    240  CA   HIS A 268     -29.459 -27.714   1.412  0.50 76.92           C
ATOM    241  CB   HIS A 268     -28.000 -28.070   1.672  0.50 79.47           C
ATOM    242  CG   HIS A 268     -27.347 -28.775   0.530  0.50 82.35           C
```

Figure 26 (Continued)

```
ATOM    243  ND1 HIS A 268     -26.652 -28.109  -0.455  0.50 81.13           N
ATOM    244  CE1 HIS A 268     -26.193 -28.984  -1.333  0.50 92.91           C
ATOM    245  NE2 HIS A 268     -26.570 -30.193  -0.953  0.50 98.02           N
ATOM    246  CD2 HIS A 268     -27.296 -30.090   0.208  0.50 89.23           C
ATOM    247  C   HIS A 268     -30.355 -28.379   2.450  0.50 70.03           C
ATOM    248  O   HIS A 268     -30.659 -29.567   2.338  0.50 73.11           O
ATOM    249  N   GLU A 269     -30.797 -27.609   3.440  0.50 69.04           N
ATOM    250  CA  GLU A 269     -31.562 -28.159   4.559  0.50 69.95           C
ATOM    251  CB  GLU A 269     -31.055 -27.612   5.901  0.50 68.17           C
ATOM    252  CG  GLU A 269     -29.671 -28.102   6.299  0.50 76.55           C
ATOM    253  CD  GLU A 269     -28.566 -27.137   5.902  0.50 83.93           C
ATOM    254  OE1 GLU A 269     -28.804 -25.905   5.935  0.50 91.65           O
ATOM    255  OE2 GLU A 269     -27.454 -27.608   5.571  0.50 80.26           O
ATOM    256  C   GLU A 269     -33.052 -27.881   4.399  0.50 70.06           C
ATOM    257  O   GLU A 269     -33.889 -28.518   5.041  0.50 63.36           O
ATOM    258  N   GLU A 270     -33.381 -26.932   3.533  0.50 69.01           N
ATOM    259  CA  GLU A 270     -34.774 -26.636   3.229  0.50 71.45           C
ATOM    260  CB  GLU A 270     -35.231 -25.379   3.964  0.50 69.02           C
ATOM    261  CG  GLU A 270     -35.040 -25.442   5.476  0.50 62.17           C
ATOM    262  CD  GLU A 270     -34.672 -24.091   6.053  0.50 59.80           C
ATOM    263  OE1 GLU A 270     -33.478 -23.883   6.349  0.50 64.45           O
ATOM    264  OE2 GLU A 270     -35.561 -23.217   6.157  0.50 55.95           O
ATOM    265  C   GLU A 270     -34.902 -26.457   1.728  0.50 75.98           C
ATOM    266  O   GLU A 270     -35.186 -25.358   1.250  0.50 75.16           O
ATOM    267  N   PRO A 271     -34.677 -27.553   0.985  0.50 77.00           N
ATOM    268  CA  PRO A 271     -34.496 -27.589  -0.459  0.50 76.25           C
ATOM    269  CB  PRO A 271     -33.719 -28.893  -0.670  0.50 77.84           C
ATOM    270  CG  PRO A 271     -34.221 -29.791   0.419  0.50 77.61           C
ATOM    271  CD  PRO A 271     -34.638 -28.906   1.573  0.50 75.73           C
ATOM    272  C   PRO A 271     -35.820 -27.650  -1.207  0.50 72.45           C
ATOM    273  O   PRO A 271     -35.847 -27.459  -2.422  0.50 72.18           O
ATOM    274  N   GLU A 272     -36.903 -27.933  -0.492  0.50 71.57           N
ATOM    275  CA  GLU A 272     -38.217 -27.981  -1.115  0.50 74.81           C
ATOM    276  CB  GLU A 272     -39.273 -28.532  -0.145  0.50 76.83           C
ATOM    277  CG  GLU A 272     -40.547 -29.024  -0.823  0.50 76.75           C
ATOM    278  CD  GLU A 272     -41.713 -29.227   0.139  0.50 80.74           C
ATOM    279  OE1 GLU A 272     -41.477 -29.563   1.322  0.50 73.20           O
ATOM    280  OE2 GLU A 272     -42.876 -29.061  -0.293  0.50 78.90           O
ATOM    281  C   GLU A 272     -38.595 -26.578  -1.569  0.50 76.00           C
ATOM    282  O   GLU A 272     -38.396 -25.600  -0.836  0.50 77.34           O
ATOM    283  N   VAL A 273     -39.112 -26.480  -2.792  0.50 68.10           N
ATOM    284  CA  VAL A 273     -39.614 -25.210  -3.300  0.50 64.19           C
ATOM    285  CB  VAL A 273     -38.653 -24.570  -4.316  0.50 61.87           C
ATOM    286  CG1 VAL A 273     -39.135 -23.172  -4.690  0.50 56.29           C
ATOM    287  CG2 VAL A 273     -37.243 -24.536  -3.758  0.50 55.66           C
ATOM    288  C   VAL A 273     -40.940 -25.415  -3.994  0.50 58.39           C
ATOM    289  O   VAL A 273     -41.076 -26.319  -4.820  0.50 58.20           O
ATOM    290  N   LYS A 274     -41.905 -24.559  -3.666  0.50 57.70           N
ATOM    291  CA  LYS A 274     -43.221 -24.604  -4.286  0.50 60.04           C
ATOM    292  CB  LYS A 274     -44.321 -24.646  -3.230  0.50 53.45           C
ATOM    293  CG  LYS A 274     -45.722 -24.580  -3.818  0.50 57.66           C
ATOM    294  CD  LYS A 274     -46.782 -24.574  -2.730  0.50 63.84           C
ATOM    295  CE  LYS A 274     -48.181 -24.695  -3.313  0.50 65.85           C
ATOM    296  NZ  LYS A 274     -49.212 -24.638  -2.237  0.50 66.38           N
ATOM    297  C   LYS A 274     -43.441 -23.398  -5.189  0.50 62.72           C
ATOM    298  O   LYS A 274     -43.177 -22.255  -4.779  0.50 61.82           O
ATOM    299  N   PHE A 275     -43.948 -23.668  -6.397  0.50 59.57           N
ATOM    300  CA  PHE A 275     -44.265 -22.632  -7.390  0.50 61.78           C
ATOM    301  CB  PHE A 275     -43.708 -23.016  -8.768  0.50 61.08           C
ATOM    302  CG  PHE A 275     -42.209 -23.072  -8.829  0.50 59.07           C
ATOM    303  CD1 PHE A 275     -41.538 -24.286  -8.697  0.50 60.89           C
ATOM    304  CE1 PHE A 275     -40.155 -24.338  -8.759  0.50 59.85           C
ATOM    305  CZ  PHE A 275     -39.435 -23.168  -8.941  0.50 55.44           C
ATOM    306  CE2 PHE A 275     -40.093 -21.959  -9.059  0.50 53.27           C
```

Figure 26 (Continued)

```
ATOM    307  CD2 PHE A 275     -41.469 -21.915  -9.026  0.50 54.86      C
ATOM    308  C   PHE A 275     -45.762 -22.442  -7.550  0.50 59.54      C
ATOM    309  O   PHE A 275     -46.475 -23.405  -7.805  0.50 58.48      O
ATOM    310  N   ASN A 276     -46.229 -21.195  -7.444  0.50 57.36      N
ATOM    311  CA  ASN A 276     -47.537 -20.822  -7.996  0.50 57.74      C
ATOM    312  CB  ASN A 276     -48.378 -20.071  -6.953  0.50 61.86      C
ATOM    313  CG  ASN A 276     -48.842 -20.963  -5.810  0.50 56.65      C
ATOM    314  OD1 ASN A 276     -48.217 -20.987  -4.758  0.50 49.61      O
ATOM    315  ND2 ASN A 276     -49.949 -21.695  -6.014  0.50 51.36      N
ATOM    316  C   ASN A 276     -47.429 -19.969  -9.280  0.50 56.67      C
ATOM    317  O   ASN A 276     -46.734 -18.949  -9.303  0.50 53.07      O
ATOM    318  N   TRP A 277     -48.161 -20.357 -10.312  0.50 56.93      N
ATOM    319  CA  TRP A 277     -48.153 -19.655 -11.574  0.50 54.23      C
ATOM    320  CB  TRP A 277     -47.814 -20.627 -12.673  0.50 53.21      C
ATOM    321  CG  TRP A 277     -46.350 -20.826 -12.913  0.50 52.69      C
ATOM    322  CD1 TRP A 277     -45.585 -21.931 -12.595  0.50 52.01      C
ATOM    323  NE1 TRP A 277     -44.300 -21.758 -12.995  0.50 53.94      N
ATOM    324  CE2 TRP A 277     -44.142 -20.569 -13.595  0.50 52.81      C
ATOM    325  CD2 TRP A 277     -45.432 -19.910 -13.584  0.50 53.26      C
ATOM    326  CE3 TRP A 277     -45.548 -18.658 -14.140  0.50 51.47      C
ATOM    327  CZ3 TRP A 277     -44.420 -18.075 -14.691  0.50 49.89      C
ATOM    328  CH2 TRP A 277     -43.197 -18.723 -14.699  0.50 51.14      C
ATOM    329  CZ2 TRP A 277     -43.033 -19.981 -14.146  0.50 54.07      C
ATOM    330  C   TRP A 277     -49.480 -19.026 -11.875  0.50 56.35      C
ATOM    331  O   TRP A 277     -50.523 -19.680 -11.768  0.50 57.98      O
ATOM    332  N   TYR A 278     -49.466 -17.758 -12.261  0.50 49.37      N
ATOM    333  CA  TYR A 278     -50.679 -17.032 -12.615  0.50 49.09      C
ATOM    334  CB  TYR A 278     -51.010 -16.011 -11.532  0.50 50.14      C
ATOM    335  CG  TYR A 278     -50.876 -16.573 -10.149  0.50 52.90      C
ATOM    336  CD1 TYR A 278     -51.978 -16.721  -9.331  0.50 51.24      C
ATOM    337  CE1 TYR A 278     -51.859 -17.248  -8.066  0.50 54.75      C
ATOM    338  CZ  TYR A 278     -50.635 -17.635  -7.615  0.50 53.42      C
ATOM    339  OH  TYR A 278     -50.510 -18.164  -6.363  0.50 50.19      O
ATOM    340  CE2 TYR A 278     -49.525 -17.507  -8.412  0.50 50.48      C
ATOM    341  CD2 TYR A 278     -49.653 -16.980  -9.670  0.50 56.34      C
ATOM    342  C   TYR A 278     -50.566 -16.324 -13.955  0.50 46.25      C
ATOM    343  O   TYR A 278     -49.503 -15.858 -14.319  0.50 44.85      O
ATOM    344  N   VAL A 279     -51.668 -16.268 -14.695  0.50 44.73      N
ATOM    345  CA  VAL A 279     -51.745 -15.482 -15.913  0.50 42.02      C
ATOM    346  CB  VAL A 279     -52.061 -16.374 -17.110  0.50 44.31      C
ATOM    347  CG1 VAL A 279     -52.154 -15.556 -18.376  0.50 42.32      C
ATOM    348  CG2 VAL A 279     -51.034 -17.471 -17.240  0.50 44.10      C
ATOM    349  C   VAL A 279     -52.879 -14.490 -15.761  0.50 44.78      C
ATOM    350  O   VAL A 279     -54.031 -14.874 -15.706  0.50 51.08      O
ATOM    351  N   ASP A 280     -52.555 -13.212 -15.740  0.50 44.62      N
ATOM    352  CA  ASP A 280     -53.518 -12.188 -15.386  0.50 48.24      C
ATOM    353  CB  ASP A 280     -54.464 -11.917 -16.553  0.50 45.79      C
ATOM    354  CG  ASP A 280     -53.795 -11.170 -17.695  0.50 48.73      C
ATOM    355  OD1 ASP A 280     -52.649 -10.681 -17.540  0.50 48.80      O
ATOM    356  OD2 ASP A 280     -54.428 -11.059 -18.762  0.50 47.92      O
ATOM    357  C   ASP A 280     -54.330 -12.684 -14.177  0.50 54.14      C
ATOM    358  O   ASP A 280     -55.553 -12.598 -14.169  0.50 53.74      O
ATOM    359  N   GLY A 281     -53.655 -13.235 -13.173  0.50 54.06      N
ATOM    360  CA  GLY A 281     -54.331 -13.576 -11.919  0.50 58.69      C
ATOM    361  C   GLY A 281     -54.862 -15.004 -11.844  0.50 56.72      C
ATOM    362  O   GLY A 281     -54.906 -15.625 -10.783  0.50 53.60      O
ATOM    363  N   VAL A 282     -55.260 -15.545 -12.976  0.50 52.63      N
ATOM    364  CA  VAL A 282     -55.785 -16.889 -12.977  0.50 53.54      C
ATOM    365  CB  VAL A 282     -56.463 -17.209 -14.316  0.50 53.34      C
ATOM    366  CG1 VAL A 282     -56.815 -18.692 -14.384  0.50 47.74      C
ATOM    367  CG2 VAL A 282     -57.673 -16.307 -14.529  0.50 49.87      C
ATOM    368  C   VAL A 282     -54.661 -17.888 -12.763  0.50 55.62      C
ATOM    369  O   VAL A 282     -53.618 -17.798 -13.408  0.50 53.91      O
ATOM    370  N   GLU A 283     -54.863 -18.849 -11.873  0.50 48.17      N
```

Figure 26 (Continued)

```
ATOM   371  CA   GLU A 283     -53.856 -19.867 -11.696  0.50 51.46           C
ATOM   372  CB   GLU A 283     -53.954 -20.538 -10.321  0.50 50.31           C
ATOM   373  CG   GLU A 283     -52.826 -21.525 -10.059  0.50 58.05           C
ATOM   374  CD   GLU A 283     -52.573 -21.781  -8.579  0.50 68.05           C
ATOM   375  OE1  GLU A 283     -53.223 -21.124  -7.734  0.50 65.03           O
ATOM   376  OE2  GLU A 283     -51.707 -22.635  -8.262  0.50 63.11           O
ATOM   377  C    GLU A 283     -53.931 -20.902 -12.807  0.50 51.23           C
ATOM   378  O    GLU A 283     -55.018 -21.284 -13.244  0.50 46.97           O
ATOM   379  N    VAL A 284     -52.770 -21.365 -13.258  0.50 45.96           N
ATOM   380  CA   VAL A 284     -52.722 -22.525 -14.138  0.50 44.58           C
ATOM   381  CB   VAL A 284     -52.132 -22.187 -15.526  0.50 44.10           C
ATOM   382  CG1  VAL A 284     -52.894 -21.016 -16.145  0.50 47.67           C
ATOM   383  CG2  VAL A 284     -50.650 -21.865 -15.422  0.50 34.07           C
ATOM   384  C    VAL A 284     -51.934 -23.660 -13.484  0.50 48.43           C
ATOM   385  O    VAL A 284     -51.320 -23.488 -12.434  0.50 51.25           O
ATOM   386  N    HIS A 285     -51.953 -24.832 -14.098  0.50 50.02           N
ATOM   387  CA   HIS A 285     -51.409 -25.987 -13.422  0.50 54.31           C
ATOM   388  CB   HIS A 285     -52.510 -26.726 -12.644  0.50 60.51           C
ATOM   389  CG   HIS A 285     -53.210 -25.872 -11.625  0.50 64.79           C
ATOM   390  ND1  HIS A 285     -54.299 -25.083 -11.937  0.50 68.72           N
ATOM   391  CE1  HIS A 285     -54.694 -24.429 -10.860  0.50 65.50           C
ATOM   392  NE2  HIS A 285     -53.898 -24.763  -9.858  0.50 73.35           N
ATOM   393  CD2  HIS A 285     -52.959 -25.662 -10.311  0.50 64.87           C
ATOM   394  C    HIS A 285     -50.760 -26.880 -14.441  0.50 53.42           C
ATOM   395  O    HIS A 285     -50.851 -28.102 -14.360  0.50 64.06           O
ATOM   396  N    ASN A 286     -50.092 -26.267 -15.407  0.50 53.20           N
ATOM   397  CA   ASN A 286     -49.470 -27.029 -16.483  0.50 51.27           C
ATOM   398  CB   ASN A 286     -50.119 -26.702 -17.837  0.50 54.76           C
ATOM   399  CG   ASN A 286     -50.353 -25.210 -18.038  0.50 52.27           C
ATOM   400  OD1  ASN A 286     -50.697 -24.478 -17.104  0.50 54.35           O
ATOM   401  ND2  ASN A 286     -50.195 -24.762 -19.269  0.50 53.17           N
ATOM   402  C    ASN A 286     -47.944 -26.902 -16.549  0.50 52.95           C
ATOM   403  O    ASN A 286     -47.288 -27.641 -17.291  0.50 51.16           O
ATOM   404  N    ALA A 287     -47.382 -25.994 -15.749  0.50 45.70           N
ATOM   405  CA   ALA A 287     -45.932 -25.864 -15.621  0.50 39.98           C
ATOM   406  CB   ALA A 287     -45.585 -24.822 -14.553  0.50 34.77           C
ATOM   407  C    ALA A 287     -45.303 -27.204 -15.259  0.50 42.24           C
ATOM   408  O    ALA A 287     -45.966 -28.081 -14.718  0.50 42.79           O
ATOM   409  N    LYS A 288     -44.012 -27.351 -15.532  0.50 40.97           N
ATOM   410  CA   LYS A 288     -43.291 -28.535 -15.092  0.50 49.88           C
ATOM   411  CB   LYS A 288     -43.103 -29.553 -16.223  0.50 51.51           C
ATOM   412  CG   LYS A 288     -44.398 -30.236 -16.666  0.50 57.70           C
ATOM   413  CD   LYS A 288     -45.043 -31.054 -15.550  0.50 62.12           C
ATOM   414  CE   LYS A 288     -46.558 -30.843 -15.471  0.50 67.68           C
ATOM   415  NZ   LYS A 288     -47.236 -30.577 -16.776  0.50 72.17           N
ATOM   416  C    LYS A 288     -41.953 -28.139 -14.497  0.50 52.01           C
ATOM   417  O    LYS A 288     -41.170 -27.393 -15.110  0.50 49.67           O
ATOM   418  N    THR A 289     -41.709 -28.627 -13.284  0.50 53.10           N
ATOM   419  CA   THR A 289     -40.518 -28.274 -12.535  0.50 54.61           C
ATOM   420  CB   THR A 289     -40.782 -28.339 -11.028  0.50 51.62           C
ATOM   421  OG1  THR A 289     -41.637 -27.256 -10.653  0.50 44.51           O
ATOM   422  CG2  THR A 289     -39.476 -28.247 -10.267  0.50 53.92           C
ATOM   423  C    THR A 289     -39.366 -29.192 -12.867  0.50 59.10           C
ATOM   424  O    THR A 289     -39.481 -30.405 -12.736  0.50 68.36           O
ATOM   425  N    LYS A 290     -38.251 -28.620 -13.307  0.50 66.56           N
ATOM   426  CA   LYS A 290     -37.023 -29.395 -13.433  0.50 68.83           C
ATOM   427  CB   LYS A 290     -35.889 -28.533 -13.988  0.50 70.93           C
ATOM   428  CG   LYS A 290     -36.201 -27.886 -15.328  0.50 71.27           C
ATOM   429  CD   LYS A 290     -35.008 -27.995 -16.263  0.50 71.91           C
ATOM   430  CE   LYS A 290     -35.214 -27.202 -17.546  0.50 70.85           C
ATOM   431  NZ   LYS A 290     -34.393 -27.753 -18.668  0.50 69.55           N
ATOM   432  C    LYS A 290     -36.627 -29.942 -12.063  0.50 66.00           C
ATOM   433  O    LYS A 290     -36.901 -29.319 -11.044  0.50 57.81           O
ATOM   434  N    PRO A 291     -35.997 -31.124 -12.031  0.50 69.53           N
```

Figure 26 (Continued)

```
ATOM    435  CA  PRO A 291     -35.475 -31.554 -10.739  0.50 68.99           C
ATOM    436  CB  PRO A 291     -35.094 -33.012 -10.988  0.50 68.27           C
ATOM    437  CG  PRO A 291     -34.786 -33.082 -12.453  0.50 68.31           C
ATOM    438  CD  PRO A 291     -35.563 -31.990 -13.139  0.50 64.80           C
ATOM    439  C   PRO A 291     -34.250 -30.707 -10.374  0.50 69.78           C
ATOM    440  O   PRO A 291     -33.363 -30.495 -11.217  0.50 64.69           O
ATOM    441  N   ARG A 292     -34.226 -30.208  -9.139  0.50 67.66           N
ATOM    442  CA  ARG A 292     -33.193 -29.275  -8.682  0.50 68.91           C
ATOM    443  CB  ARG A 292     -33.274 -29.097  -7.167  0.50 66.60           C
ATOM    444  CG  ARG A 292     -32.996 -30.371  -6.387  0.50 70.27           C
ATOM    445  CD  ARG A 292     -33.568 -30.305  -4.978  0.50 75.34           C
ATOM    446  NE  ARG A 292     -33.293 -31.525  -4.223  0.50 77.77           N
ATOM    447  CZ  ARG A 292     -33.905 -31.864  -3.092  0.50 76.77           C
ATOM    448  NH1 ARG A 292     -33.586 -32.997  -2.481  0.50 72.12           N
ATOM    449  NH2 ARG A 292     -34.841 -31.076  -2.578  0.50 71.51           N
ATOM    450  C   ARG A 292     -31.774 -29.691  -9.081  0.50 72.13           C
ATOM    451  O   ARG A 292     -31.511 -30.861  -9.391  0.50 64.11           O
ATOM    452  N   GLU A 293     -30.853 -28.731  -9.065  0.50 66.57           N
ATOM    453  CA  GLU A 293     -29.479 -29.005  -9.485  0.50 70.97           C
ATOM    454  CB  GLU A 293     -29.260 -28.613 -10.960  0.50 72.10           C
ATOM    455  CG  GLU A 293     -29.815 -29.611 -11.971  0.50 73.13           C
ATOM    456  CD  GLU A 293     -29.169 -29.489 -13.345  0.50 77.82           C
ATOM    457  OE1 GLU A 293     -28.038 -28.964 -13.439  0.50 78.62           O
ATOM    458  OE2 GLU A 293     -29.787 -29.925 -14.336  0.50 75.20           O
ATOM    459  C   GLU A 293     -28.439 -28.327  -8.588  0.50 67.79           C
ATOM    460  O   GLU A 293     -28.455 -27.107  -8.412  0.50 64.19           O
ATOM    461  N   GLU A 294     -27.535 -29.130  -8.029  0.50 67.17           N
ATOM    462  CA  GLU A 294     -26.456 -28.610  -7.197  0.50 57.56           C
ATOM    463  CB  GLU A 294     -25.662 -29.761  -6.574  0.50 59.02           C
ATOM    464  CG  GLU A 294     -24.474 -29.311  -5.725  0.50 61.09           C
ATOM    465  CD  GLU A 294     -24.905 -28.663  -4.418  0.50 62.80           C
ATOM    466  OE1 GLU A 294     -26.109 -28.336  -4.289  0.50 62.30           O
ATOM    467  OE2 GLU A 294     -24.050 -28.489  -3.516  0.50 58.57           O
ATOM    468  C   GLU A 294     -25.508 -27.729  -8.010  0.50 57.52           C
ATOM    469  O   GLU A 294     -24.960 -28.158  -9.033  0.50 53.78           O
ATOM    470  N   GLN A 295     -25.301 -26.501  -7.549  0.50 55.28           N
ATOM    471  CA  GLN A 295     -24.299 -25.633  -8.158  0.50 56.48           C
ATOM    472  CB  GLN A 295     -24.760 -24.173  -8.156  0.50 53.17           C
ATOM    473  CG  GLN A 295     -26.168 -23.970  -8.700  0.50 54.48           C
ATOM    474  CD  GLN A 295     -26.324 -24.499 -10.115  0.50 54.81           C
ATOM    475  OE1 GLN A 295     -25.729 -23.966 -11.056  0.50 54.70           O
ATOM    476  NE2 GLN A 295     -27.128 -25.553 -10.274  0.50 51.97           N
ATOM    477  C   GLN A 295     -22.986 -25.773  -7.403  0.50 61.52           C
ATOM    478  O   GLN A 295     -22.962 -26.147  -6.228  0.50 65.42           O
ATOM    479  N   TYR A 296     -21.887 -25.488  -8.082  0.50 63.24           N
ATOM    480  CA  TYR A 296     -20.583 -25.599  -7.451  0.50 66.04           C
ATOM    481  CB  TYR A 296     -19.499 -25.074  -8.388  0.50 69.47           C
ATOM    482  CG  TYR A 296     -19.398 -25.814  -9.709  0.50 71.32           C
ATOM    483  CD1 TYR A 296     -19.505 -25.131 -10.912  0.50 72.23           C
ATOM    484  CE1 TYR A 296     -19.391 -25.788 -12.124  0.50 75.05           C
ATOM    485  CZ  TYR A 296     -19.167 -27.151 -12.148  0.50 74.25           C
ATOM    486  OH  TYR A 296     -19.075 -27.785 -13.370  0.50 71.28           O
ATOM    487  CE2 TYR A 296     -19.061 -27.860 -10.965  0.50 72.59           C
ATOM    488  CD2 TYR A 296     -19.177 -27.190  -9.754  0.50 71.79           C
ATOM    489  C   TYR A 296     -20.528 -24.866  -6.101  0.50 70.29           C
ATOM    490  O   TYR A 296     -19.819 -25.296  -5.180  0.50 65.37           O
ATOM    491  N   ASN A 297     -21.286 -23.775  -5.976  0.50 63.59           N
ATOM    492  CA  ASN A 297     -21.142 -22.897  -4.818  0.50 58.23           C
ATOM    493  CB  ASN A 297     -21.447 -21.428  -5.171  0.50 57.05           C
ATOM    494  CG  ASN A 297     -22.883 -21.208  -5.618  0.50 53.68           C
ATOM    495  OD1 ASN A 297     -23.753 -22.038  -5.387  0.50 48.12           O
ATOM    496  ND2 ASN A 297     -23.138 -20.069  -6.249  0.50 60.40           N
ATOM    497  C   ASN A 297     -21.915 -23.331  -3.573  0.50 54.32           C
ATOM    498  O   ASN A 297     -22.098 -22.528  -2.659  0.50 49.83           O
```

Figure 26 (Continued)

```
ATOM    499  N    SER A 298     -22.381 -24.581  -3.560  0.50 52.00           N
ATOM    500  CA   SER A 298     -23.030 -25.177  -2.378  0.50 55.67           C
ATOM    501  CB   SER A 298     -22.325 -24.746  -1.088  0.50 53.07           C
ATOM    502  OG   SER A 298     -20.936 -25.057  -1.139  0.50 53.95           O
ATOM    503  C    SER A 298     -24.539 -24.950  -2.255  0.50 57.74           C
ATOM    504  O    SER A 298     -25.162 -25.368  -1.283  0.50 59.76           O
ATOM    505  N    THR A 299     -25.136 -24.326  -3.259  0.50 62.90           N
ATOM    506  CA   THR A 299     -26.552 -24.002  -3.205  0.50 58.77           C
ATOM    507  CB   THR A 299     -26.772 -22.497  -3.438  0.50 64.48           C
ATOM    508  OG1  THR A 299     -26.104 -22.110  -4.647  0.50 62.87           O
ATOM    509  CG2  THR A 299     -26.201 -21.675  -2.264  0.50 56.92           C
ATOM    510  C    THR A 299     -27.322 -24.783  -4.258  0.50 59.43           C
ATOM    511  O    THR A 299     -26.736 -25.358  -5.183  0.50 60.39           O
ATOM    512  N    TYR A 300     -28.640 -24.812  -4.115  0.50 62.54           N
ATOM    513  CA   TYR A 300     -29.489 -25.474  -5.100  0.50 64.61           C
ATOM    514  CB   TYR A 300     -30.589 -26.283  -4.412  0.50 73.04           C
ATOM    515  CG   TYR A 300     -30.116 -27.577  -3.781  0.50 79.54           C
ATOM    516  CD1  TYR A 300     -30.286 -27.815  -2.419  0.50 85.01           C
ATOM    517  CE1  TYR A 300     -29.876 -29.005  -1.836  0.50 88.94           C
ATOM    518  CZ   TYR A 300     -29.279 -29.976  -2.617  0.50 92.90           C
ATOM    519  OH   TYR A 300     -28.861 -31.162  -2.043  0.50 93.94           O
ATOM    520  CE2  TYR A 300     -29.097 -29.761  -3.973  0.50 95.85           C
ATOM    521  CD2  TYR A 300     -29.515 -28.567  -4.546  0.50 81.67           C
ATOM    522  C    TYR A 300     -30.108 -24.456  -6.055  0.50 61.30           C
ATOM    523  O    TYR A 300     -30.344 -23.306  -5.682  0.50 56.32           O
ATOM    524  N    ARG A 301     -30.347 -24.885  -7.291  0.50 57.29           N
ATOM    525  CA   ARG A 301     -31.006 -24.055  -8.290  0.50 56.31           C
ATOM    526  CB   ARG A 301     -30.036 -23.734  -9.434  0.50 63.31           C
ATOM    527  CG   ARG A 301     -30.651 -23.045 -10.648  0.50 60.88           C
ATOM    528  CD   ARG A 301     -29.560 -22.746 -11.664  0.50 57.71           C
ATOM    529  NE   ARG A 301     -30.001 -21.917 -12.782  0.50 57.09           N
ATOM    530  CZ   ARG A 301     -30.565 -22.406 -13.887  0.50 61.05           C
ATOM    531  NH1  ARG A 301     -30.799 -23.711 -13.990  0.50 57.42           N
ATOM    532  NH2  ARG A 301     -30.904 -21.596 -14.882  0.50 47.24           N
ATOM    533  C    ARG A 301     -32.199 -24.817  -8.824  0.50 54.53           C
ATOM    534  O    ARG A 301     -32.058 -25.950  -9.281  0.50 54.28           O
ATOM    535  N    VAL A 302     -33.370 -24.195  -8.763  0.50 49.96           N
ATOM    536  CA   VAL A 302     -34.604 -24.847  -9.185  0.50 49.79           C
ATOM    537  CB   VAL A 302     -35.566 -24.975  -7.993  0.50 50.06           C
ATOM    538  CG1  VAL A 302     -36.574 -26.089  -8.238  0.50 51.61           C
ATOM    539  CG2  VAL A 302     -34.782 -25.224  -6.713  0.50 55.55           C
ATOM    540  C    VAL A 302     -35.331 -24.067 -10.289  0.50 49.07           C
ATOM    541  O    VAL A 302     -35.577 -22.863 -10.146  0.50 46.31           O
ATOM    542  N    VAL A 303     -35.730 -24.772 -11.351  0.50 50.66           N
ATOM    543  CA   VAL A 303     -36.403 -24.162 -12.509  0.50 48.30           C
ATOM    544  CB   VAL A 303     -35.681 -24.525 -13.819  0.50 51.15           C
ATOM    545  CG1  VAL A 303     -36.205 -23.668 -14.966  0.50 51.33           C
ATOM    546  CG2  VAL A 303     -34.172 -24.427 -13.671  0.50 44.55           C
ATOM    547  C    VAL A 303     -37.857 -24.632 -12.676  0.50 47.22           C
ATOM    548  O    VAL A 303     -38.146 -25.829 -12.622  0.50 51.00           O
ATOM    549  N    SER A 304     -38.764 -23.685 -12.888  0.50 49.39           N
ATOM    550  CA   SER A 304     -40.152 -23.980 -13.279  0.50 48.75           C
ATOM    551  CB   SER A 304     -41.127 -23.474 -12.208  0.50 50.58           C
ATOM    552  OG   SER A 304     -42.476 -23.565 -12.645  0.50 52.53           O
ATOM    553  C    SER A 304     -40.469 -23.296 -14.618  0.50 53.43           C
ATOM    554  O    SER A 304     -40.343 -22.064 -14.734  0.50 49.73           O
ATOM    555  N    VAL A 305     -40.864 -24.101 -15.612  0.50 50.44           N
ATOM    556  CA   VAL A 305     -41.121 -23.653 -16.978  0.50 49.57           C
ATOM    557  CB   VAL A 305     -40.375 -24.539 -17.997  0.50 59.18           C
ATOM    558  CG1  VAL A 305     -40.688 -24.119 -19.433  0.50 51.55           C
ATOM    559  CG2  VAL A 305     -38.875 -24.511 -17.730  0.50 57.36           C
ATOM    560  C    VAL A 305     -42.613 -23.680 -17.306  0.50 54.85           C
ATOM    561  O    VAL A 305     -43.251 -24.731 -17.216  0.50 54.46           O
ATOM    562  N    LEU A 306     -43.167 -22.514 -17.660  0.50 45.24           N
```

Figure 26 (Continued)

```
ATOM    563  CA  LEU A 306     -44.551 -22.401 -18.082  0.50 43.34           C
ATOM    564  CB  LEU A 306     -45.234 -21.246 -17.333  0.50 37.93           C
ATOM    565  CG  LEU A 306     -46.699 -20.997 -17.721  0.50 42.67           C
ATOM    566  CD1 LEU A 306     -47.607 -22.160 -17.329  0.50 46.66           C
ATOM    567  CD2 LEU A 306     -47.258 -19.685 -17.180  0.50 41.11           C
ATOM    568  C   LEU A 306     -44.668 -22.186 -19.609  0.50 46.52           C
ATOM    569  O   LEU A 306     -44.138 -21.217 -20.163  0.50 48.58           O
ATOM    570  N   THR A 307     -45.394 -23.068 -20.276  0.50 46.15           N
ATOM    571  CA  THR A 307     -45.636 -22.947 -21.708  0.50 49.34           C
ATOM    572  CB  THR A 307     -46.167 -24.273 -22.286  0.50 48.71           C
ATOM    573  OG1 THR A 307     -45.064 -25.168 -22.462  0.50 53.93           O
ATOM    574  CG2 THR A 307     -46.867 -24.046 -23.630  0.50 45.84           C
ATOM    575  C   THR A 307     -46.669 -21.861 -21.910  0.50 45.44           C
ATOM    576  O   THR A 307     -47.656 -21.825 -21.189  0.50 48.63           O
ATOM    577  N   VAL A 308     -46.427 -20.929 -22.828  0.50 37.88           N
ATOM    578  CA  VAL A 308     -47.411 -19.853 -22.986  0.50 38.76           C
ATOM    579  CB  VAL A 308     -46.821 -18.451 -22.736  0.50 40.65           C
ATOM    580  CG1 VAL A 308     -46.099 -18.430 -21.397  0.50 41.49           C
ATOM    581  CG2 VAL A 308     -45.875 -18.054 -23.857  0.50 37.79           C
ATOM    582  C   VAL A 308     -48.074 -19.939 -24.344  0.50 34.48           C
ATOM    583  O   VAL A 308     -47.505 -20.509 -25.254  0.50 37.05           O
ATOM    584  N   LEU A 309     -49.288 -19.415 -24.464  0.50 33.12           N
ATOM    585  CA  LEU A 309     -49.955 -19.370 -25.742  0.50 35.48           C
ATOM    586  CB  LEU A 309     -51.465 -19.284 -25.551  0.50 40.77           C
ATOM    587  CG  LEU A 309     -52.145 -20.457 -24.836  0.50 44.43           C
ATOM    588  CD1 LEU A 309     -53.521 -20.038 -24.336  0.50 40.30           C
ATOM    589  CD2 LEU A 309     -52.247 -21.690 -25.745  0.50 41.95           C
ATOM    590  C   LEU A 309     -49.412 -18.160 -26.503  0.50 38.39           C
ATOM    591  O   LEU A 309     -49.205 -17.086 -25.909  0.50 37.34           O
ATOM    592  N   HIS A 310     -49.094 -18.358 -27.785  0.50 34.01           N
ATOM    593  CA  HIS A 310     -48.504 -17.287 -28.587  0.50 34.84           C
ATOM    594  CB  HIS A 310     -48.452 -17.676 -30.084  0.50 32.56           C
ATOM    595  CG  HIS A 310     -47.555 -18.834 -30.361  0.50 34.33           C
ATOM    596  ND1 HIS A 310     -47.915 -20.133 -30.065  0.50 32.05           N
ATOM    597  CE1 HIS A 310     -46.904 -20.942 -30.343  0.50 31.24           C
ATOM    598  NE2 HIS A 310     -45.897 -20.213 -30.791  0.50 33.56           N
ATOM    599  CD2 HIS A 310     -46.278 -18.888 -30.814  0.50 35.65           C
ATOM    600  C   HIS A 310     -49.315 -16.015 -28.432  0.50 35.28           C
ATOM    601  O   HIS A 310     -48.771 -14.934 -28.252  0.50 37.32           O
ATOM    602  N   GLN A 311     -50.624 -16.150 -28.550  0.50 36.78           N
ATOM    603  CA  GLN A 311     -51.484 -14.991 -28.665  0.50 42.44           C
ATOM    604  CB  GLN A 311     -52.832 -15.433 -29.249  0.50 43.19           C
ATOM    605  CG  GLN A 311     -53.467 -16.563 -28.453  0.50 58.68           C
ATOM    606  CD  GLN A 311     -53.313 -17.965 -29.057  0.50 61.61           C
ATOM    607  OE1 GLN A 311     -52.233 -18.372 -29.532  0.50 46.99           O
ATOM    608  NE2 GLN A 311     -54.403 -18.736 -28.988  0.50 59.80           N
ATOM    609  C   GLN A 311     -51.629 -14.274 -27.301  0.50 41.33           C
ATOM    610  O   GLN A 311     -51.694 -13.041 -27.239  0.50 38.97           O
ATOM    611  N   ASP A 312     -51.598 -15.041 -26.210  0.50 40.71           N
ATOM    612  CA  ASP A 312     -51.642 -14.446 -24.864  0.50 39.28           C
ATOM    613  CB  ASP A 312     -51.666 -15.517 -23.771  0.50 37.00           C
ATOM    614  CG  ASP A 312     -53.020 -16.189 -23.639  0.50 39.98           C
ATOM    615  OD1 ASP A 312     -53.959 -15.740 -24.322  0.50 37.52           O
ATOM    616  OD2 ASP A 312     -53.156 -17.134 -22.827  0.50 40.29           O
ATOM    617  C   ASP A 312     -50.425 -13.556 -24.682  0.50 37.30           C
ATOM    618  O   ASP A 312     -50.548 -12.407 -24.289  0.50 41.39           O
ATOM    619  N   TRP A 313     -49.246 -14.084 -24.997  0.50 38.74           N
ATOM    620  CA  TRP A 313     -48.011 -13.314 -24.830  0.50 35.62           C
ATOM    621  CB  TRP A 313     -46.764 -14.138 -25.217  0.50 33.10           C
ATOM    622  CG  TRP A 313     -45.490 -13.323 -25.052  0.50 30.27           C
ATOM    623  CD1 TRP A 313     -44.826 -12.636 -26.015  0.50 29.34           C
ATOM    624  NE1 TRP A 313     -43.736 -11.985 -25.467  0.50 29.25           N
ATOM    625  CE2 TRP A 313     -43.732 -12.195 -24.114  0.50 29.10           C
ATOM    626  CD2 TRP A 313     -44.814 -13.043 -23.818  0.50 30.82           C
```

Figure 26 (Continued)

```
ATOM    627  CE3 TRP A 313     -45.017 -13.446 -22.494  0.50 31.52           C
ATOM    628  CZ3 TRP A 313     -44.133 -12.960 -21.510  0.50 35.24           C
ATOM    629  CH2 TRP A 313     -43.059 -12.113 -21.851  0.50 29.06           C
ATOM    630  CZ2 TRP A 313     -42.834 -11.742 -23.141  0.50 31.14           C
ATOM    631  C   TRP A 313     -48.091 -12.051 -25.674  0.50 34.76           C
ATOM    632  O   TRP A 313     -47.885 -10.937 -25.180  0.50 36.08           O
ATOM    633  N   LEU A 314     -48.436 -12.230 -26.948  0.50 33.80           N
ATOM    634  CA  LEU A 314     -48.517 -11.114 -27.877  0.50 32.03           C
ATOM    635  CB  LEU A 314     -48.709 -11.616 -29.319  0.50 31.32           C
ATOM    636  CG  LEU A 314     -47.501 -12.347 -29.960  0.50 34.61           C
ATOM    637  CD1 LEU A 314     -47.814 -12.715 -31.399  0.50 34.23           C
ATOM    638  CD2 LEU A 314     -46.231 -11.506 -29.929  0.50 30.20           C
ATOM    639  C   LEU A 314     -49.594 -10.069 -27.489  0.50 35.81           C
ATOM    640  O   LEU A 314     -49.424  -8.880 -27.735  0.50 32.85           O
ATOM    641  N   ASN A 315     -50.697 -10.516 -26.902  0.50 36.74           N
ATOM    642  CA  ASN A 315     -51.712  -9.606 -26.394  0.50 42.02           C
ATOM    643  CB  ASN A 315     -53.061 -10.323 -26.256  0.50 38.60           C
ATOM    644  CG  ASN A 315     -53.702 -10.625 -27.594  0.50 37.30           C
ATOM    645  OD1 ASN A 315     -53.659  -9.823 -28.525  0.50 34.50           O
ATOM    646  ND2 ASN A 315     -54.307 -11.786 -27.688  0.50 36.27           N
ATOM    647  C   ASN A 315     -51.377  -8.984 -25.033  0.50 42.97           C
ATOM    648  O   ASN A 315     -52.225  -8.320 -24.439  0.50 44.28           O
ATOM    649  N   GLY A 316     -50.187  -9.243 -24.513  0.50 43.06           N
ATOM    650  CA  GLY A 316     -49.727  -8.556 -23.289  0.50 41.11           C
ATOM    651  C   GLY A 316     -50.186  -9.126 -21.954  0.50 41.05           C
ATOM    652  O   GLY A 316     -50.136  -8.452 -20.936  0.50 46.41           O
ATOM    653  N   LYS A 317     -50.643 -10.366 -21.927  0.50 38.50           N
ATOM    654  CA  LYS A 317     -50.964 -10.969 -20.639  0.50 38.06           C
ATOM    655  CB  LYS A 317     -51.509 -12.388 -20.819  0.50 37.73           C
ATOM    656  CG  LYS A 317     -52.729 -12.390 -21.727  0.50 38.79           C
ATOM    657  CD  LYS A 317     -53.871 -13.196 -21.147  0.50 37.24           C
ATOM    658  CE  LYS A 317     -55.141 -12.885 -21.921  0.50 39.85           C
ATOM    659  NZ  LYS A 317     -55.934 -14.118 -22.122  0.50 33.88           N
ATOM    660  C   LYS A 317     -49.736 -10.967 -19.754  0.50 39.92           C
ATOM    661  O   LYS A 317     -48.604 -11.087 -20.247  0.50 36.53           O
ATOM    662  N   GLU A 318     -49.949 -10.807 -18.448  0.50 43.15           N
ATOM    663  CA  GLU A 318     -48.831 -10.770 -17.499  0.50 42.74           C
ATOM    664  CB  GLU A 318     -49.066  -9.730 -16.401  0.50 45.58           C
ATOM    665  CG  GLU A 318     -49.398  -8.353 -16.939  0.50 50.35           C
ATOM    666  CD  GLU A 318     -49.593  -7.335 -15.831  0.50 58.29           C
ATOM    667  OE1 GLU A 318     -50.767  -7.067 -15.491  0.50 49.96           O
ATOM    668  OE2 GLU A 318     -48.571  -6.823 -15.294  0.50 58.99           O
ATOM    669  C   GLU A 318     -48.668 -12.130 -16.872  0.50 39.46           C
ATOM    670  O   GLU A 318     -49.646 -12.772 -16.508  0.50 35.61           O
ATOM    671  N   TYR A 319     -47.422 -12.567 -16.742  0.50 39.54           N
ATOM    672  CA  TYR A 319     -47.145 -13.882 -16.201  0.50 37.50           C
ATOM    673  CB  TYR A 319     -46.263 -14.683 -17.192  0.50 37.20           C
ATOM    674  CG  TYR A 319     -47.015 -14.951 -18.476  0.50 38.85           C
ATOM    675  CD1 TYR A 319     -47.179 -13.944 -19.433  0.50 37.26           C
ATOM    676  CE1 TYR A 319     -47.925 -14.163 -20.588  0.50 36.27           C
ATOM    677  CZ  TYR A 319     -48.532 -15.383 -20.782  0.50 38.59           C
ATOM    678  OH  TYR A 319     -49.274 -15.602 -21.928  0.50 44.67           O
ATOM    679  CE2 TYR A 319     -48.403 -16.396 -19.835  0.50 40.68           C
ATOM    680  CD2 TYR A 319     -47.659 -16.169 -18.684  0.50 37.33           C
ATOM    681  C   TYR A 319     -46.494 -13.699 -14.835  0.50 40.65           C
ATOM    682  O   TYR A 319     -45.461 -13.044 -14.722  0.50 37.53           O
ATOM    683  N   LYS A 320     -47.131 -14.240 -13.795  0.50 43.27           N
ATOM    684  CA  LYS A 320     -46.568 -14.175 -12.450  0.50 43.64           C
ATOM    685  CB  LYS A 320     -47.555 -13.556 -11.472  0.50 46.86           C
ATOM    686  CG  LYS A 320     -47.033 -13.517 -10.046  0.50 46.40           C
ATOM    687  CD  LYS A 320     -47.383 -12.196  -9.370  0.50 45.57           C
ATOM    688  CE  LYS A 320     -48.888 -12.017  -9.283  0.50 49.18           C
ATOM    689  NZ  LYS A 320     -49.259 -10.951  -8.313  0.50 49.80           N
ATOM    690  C   LYS A 320     -46.096 -15.516 -11.912  0.50 46.81           C
```

Figure 26 (Continued)

```
ATOM    691  O    LYS A 320     -46.839 -16.514 -11.905  0.50 46.26           O
ATOM    692  N    CYS A 321     -44.844 -15.533 -11.468  0.50 49.11           N
ATOM    693  CA   CYS A 321     -44.293 -16.679 -10.766  0.50 47.22           C
ATOM    694  CB   CYS A 321     -42.923 -17.032 -11.317  0.50 48.82           C
ATOM    695  SG   CYS A 321     -42.144 -18.449 -10.509  0.50 48.28           S
ATOM    696  C    CYS A 321     -44.165 -16.361  -9.285  0.50 51.94           C
ATOM    697  O    CYS A 321     -43.517 -15.374  -8.913  0.50 49.46           O
ATOM    698  N    LYS A 322     -44.805 -17.192  -8.454  0.50 56.06           N
ATOM    699  CA   LYS A 322     -44.673 -17.119  -6.994  0.50 50.02           C
ATOM    700  CB   LYS A 322     -46.032 -17.032  -6.306  0.50 54.49           C
ATOM    701  CG   LYS A 322     -45.935 -17.135  -4.783  0.50 61.46           C
ATOM    702  CD   LYS A 322     -47.199 -17.702  -4.141  0.50 62.68           C
ATOM    703  CE   LYS A 322     -48.328 -16.683  -4.141  0.50 64.92           C
ATOM    704  NZ   LYS A 322     -49.559 -17.213  -3.491  0.50 58.38           N
ATOM    705  C    LYS A 322     -43.936 -18.332  -6.460  0.50 47.94           C
ATOM    706  O    LYS A 322     -44.322 -19.488  -6.711  0.50 47.42           O
ATOM    707  N    VAL A 323     -42.886 -18.061  -5.693  0.50 48.19           N
ATOM    708  CA   VAL A 323     -41.987 -19.100  -5.226  0.50 47.81           C
ATOM    709  CB   VAL A 323     -40.555 -18.828  -5.736  0.50 45.00           C
ATOM    710  CG1  VAL A 323     -40.497 -18.892  -7.264  0.50 37.07           C
ATOM    711  CG2  VAL A 323     -40.086 -17.462  -5.269  0.50 48.43           C
ATOM    712  C    VAL A 323     -42.044 -19.153  -3.681  0.50 54.96           C
ATOM    713  O    VAL A 323     -42.029 -18.111  -3.007  0.50 57.07           O
ATOM    714  N    SER A 324     -42.161 -20.360  -3.133  0.50 55.29           N
ATOM    715  CA   SER A 324     -42.330 -20.545  -1.683  0.50 55.30           C
ATOM    716  CB   SER A 324     -43.686 -21.209  -1.376  0.50 50.43           C
ATOM    717  OG   SER A 324     -44.792 -20.336  -1.594  0.50 49.28           O
ATOM    718  C    SER A 324     -41.213 -21.440  -1.160  0.50 59.62           C
ATOM    719  O    SER A 324     -41.079 -22.584  -1.603  0.50 66.75           O
ATOM    720  N    ASN A 325     -40.401 -20.921  -0.243  0.50 57.70           N
ATOM    721  CA   ASN A 325     -39.389 -21.739   0.419  0.50 63.44           C
ATOM    722  CB   ASN A 325     -37.990 -21.343  -0.056  0.50 63.89           C
ATOM    723  CG   ASN A 325     -36.930 -22.364   0.318  0.50 64.16           C
ATOM    724  OD1  ASN A 325     -35.854 -22.013   0.831  0.50 63.77           O
ATOM    725  ND2  ASN A 325     -37.218 -23.638   0.051  0.50 63.14           N
ATOM    726  C    ASN A 325     -39.475 -21.571   1.935  0.50 64.65           C
ATOM    727  O    ASN A 325     -39.882 -20.508   2.419  0.50 53.16           O
ATOM    728  N    LYS A 326     -39.091 -22.617   2.669  0.50 68.10           N
ATOM    729  CA   LYS A 326     -38.977 -22.547   4.135  0.50 77.24           C
ATOM    730  CB   LYS A 326     -38.320 -23.814   4.686  0.50 86.46           C
ATOM    731  CG   LYS A 326     -39.265 -24.955   5.010  0.50 89.72           C
ATOM    732  CD   LYS A 326     -38.491 -26.104   5.645  0.50 92.50           C
ATOM    733  CE   LYS A 326     -39.162 -27.445   5.388  0.50 93.04           C
ATOM    734  NZ   LYS A 326     -40.532 -27.513   5.973  0.50 95.35           N
ATOM    735  C    LYS A 326     -38.156 -21.346   4.609  0.50 71.14           C
ATOM    736  O    LYS A 326     -38.430 -20.774   5.661  0.50 65.43           O
ATOM    737  N    ALA A 327     -37.130 -20.992   3.838  0.50 73.57           N
ATOM    738  CA   ALA A 327     -36.209 -19.927   4.223  0.50 69.94           C
ATOM    739  CB   ALA A 327     -34.843 -20.169   3.597  0.50 72.04           C
ATOM    740  C    ALA A 327     -36.753 -18.555   3.834  0.50 68.93           C
ATOM    741  O    ALA A 327     -36.098 -17.526   4.027  0.50 65.89           O
ATOM    742  N    LEU A 328     -37.961 -18.545   3.282  0.50 70.35           N
ATOM    743  CA   LEU A 328     -38.559 -17.309   2.794  0.50 70.44           C
ATOM    744  CB   LEU A 328     -39.138 -17.512   1.389  0.50 62.52           C
ATOM    745  CG   LEU A 328     -38.178 -17.473   0.194  0.50 67.17           C
ATOM    746  CD1  LEU A 328     -38.939 -17.714  -1.104  0.50 57.43           C
ATOM    747  CD2  LEU A 328     -37.397 -16.159   0.131  0.50 63.75           C
ATOM    748  C    LEU A 328     -39.655 -16.820   3.733  0.50 70.78           C
ATOM    749  O    LEU A 328     -40.779 -17.331   3.707  0.50 67.87           O
ATOM    750  N    PRO A 329     -39.357 -15.782   4.521  0.50 70.53           N
ATOM    751  CA   PRO A 329     -40.414 -15.336   5.428  0.50 73.91           C
ATOM    752  CB   PRO A 329     -39.923 -13.962   5.918  0.50 67.18           C
ATOM    753  CG   PRO A 329     -38.554 -13.767   5.347  0.50 69.02           C
ATOM    754  CD   PRO A 329     -38.400 -14.714   4.197  0.50 69.10           C
```

Figure 26 (Continued)

```
ATOM    755  C   PRO A 329     -41.706 -15.175   4.639  0.50 73.92           C
ATOM    756  O   PRO A 329     -42.807 -15.306   5.185  0.50 74.41           O
ATOM    757  N   ALA A 330     -41.545 -14.888   3.351  0.50 69.24           N
ATOM    758  CA  ALA A 330     -42.658 -14.695   2.425  0.50 68.74           C
ATOM    759  CB  ALA A 330     -43.010 -13.213   2.328  0.50 63.41           C
ATOM    760  C   ALA A 330     -42.280 -15.250   1.044  0.50 62.75           C
ATOM    761  O   ALA A 330     -41.128 -15.136   0.617  0.50 55.96           O
ATOM    762  N   PRO A 331     -43.230 -15.915   0.376  0.50 63.77           N
ATOM    763  CA  PRO A 331     -43.054 -16.269  -1.036  0.50 66.85           C
ATOM    764  CB  PRO A 331     -44.454 -16.737  -1.436  0.50 62.06           C
ATOM    765  CG  PRO A 331     -44.999 -17.356  -0.178  0.50 64.18           C
ATOM    766  CD  PRO A 331     -44.269 -16.748   1.007  0.50 46.01           C
ATOM    767  C   PRO A 331     -42.580 -15.108  -1.929  0.50 57.91           C
ATOM    768  O   PRO A 331     -43.022 -13.971  -1.757  0.50 54.66           O
ATOM    769  N   ILE A 332     -41.670 -15.403  -2.857  0.50 50.61           N
ATOM    770  CA  ILE A 332     -41.218 -14.403  -3.851  0.50 51.22           C
ATOM    771  CB  ILE A 332     -39.745 -14.633  -4.284  0.50 46.45           C
ATOM    772  CG1 ILE A 332     -38.820 -14.491  -3.067  0.50 46.01           C
ATOM    773  CD1 ILE A 332     -37.426 -15.039  -3.257  0.50 41.44           C
ATOM    774  CG2 ILE A 332     -39.325 -13.607  -5.328  0.50 45.54           C
ATOM    775  C   ILE A 332     -42.154 -14.267  -5.082  0.50 52.18           C
ATOM    776  O   ILE A 332     -42.610 -15.270  -5.662  0.50 48.28           O
ATOM    777  N   GLU A 333     -42.481 -13.025  -5.437  0.50 44.71           N
ATOM    778  CA  GLU A 333     -43.299 -12.767  -6.609  0.50 52.72           C
ATOM    779  CB  GLU A 333     -44.586 -12.033  -6.234  0.50 57.98           C
ATOM    780  CG  GLU A 333     -45.617 -12.925  -5.545  0.50 70.15           C
ATOM    781  CD  GLU A 333     -47.033 -12.385  -5.666  0.50 71.40           C
ATOM    782  OE1 GLU A 333     -47.193 -11.156  -5.825  0.50 64.21           O
ATOM    783  OE2 GLU A 333     -47.987 -13.192  -5.613  0.50 80.30           O
ATOM    784  C   GLU A 333     -42.546 -11.976  -7.685  0.50 56.32           C
ATOM    785  O   GLU A 333     -41.989 -10.908  -7.419  0.50 48.93           O
ATOM    786  N   LYS A 334     -42.543 -12.503  -8.905  0.50 49.01           N
ATOM    787  CA  LYS A 334     -42.063 -11.725 -10.030  0.50 46.12           C
ATOM    788  CB  LYS A 334     -40.720 -12.275 -10.523  0.50 45.25           C
ATOM    789  CG  LYS A 334     -39.654 -12.399  -9.433  0.50 45.15           C
ATOM    790  CD  LYS A 334     -38.902 -11.092  -9.231  0.50 37.12           C
ATOM    791  CE  LYS A 334     -37.924 -11.182  -8.065  0.50 34.04           C
ATOM    792  NZ  LYS A 334     -37.416  -9.826  -7.749  0.50 30.32           N
ATOM    793  C   LYS A 334     -43.110 -11.771 -11.127  0.50 44.25           C
ATOM    794  O   LYS A 334     -43.838 -12.771 -11.273  0.50 51.39           O
ATOM    795  N   THR A 335     -43.198 -10.694 -11.895  0.50 42.43           N
ATOM    796  CA  THR A 335     -44.147 -10.628 -13.007  0.50 45.61           C
ATOM    797  CB  THR A 335     -45.316  -9.674 -12.722  0.50 42.92           C
ATOM    798  OG1 THR A 335     -46.023 -10.139 -11.570  0.50 46.25           O
ATOM    799  CG2 THR A 335     -46.307  -9.706 -13.892  0.50 48.42           C
ATOM    800  C   THR A 335     -43.463 -10.215 -14.312  0.50 43.89           C
ATOM    801  O   THR A 335     -42.521  -9.438 -14.305  0.50 39.94           O
ATOM    802  N   ILE A 336     -43.936 -10.746 -15.428  0.50 40.70           N
ATOM    803  CA  ILE A 336     -43.345 -10.403 -16.714  0.50 42.02           C
ATOM    804  CB  ILE A 336     -42.137 -11.300 -17.071  0.50 45.17           C
ATOM    805  CG1 ILE A 336     -41.277 -10.617 -18.156  0.50 43.78           C
ATOM    806  CD1 ILE A 336     -39.958 -11.309 -18.453  0.50 46.50           C
ATOM    807  CG2 ILE A 336     -42.592 -12.703 -17.472  0.50 36.20           C
ATOM    808  C   ILE A 336     -44.401 -10.429 -17.807  0.50 40.48           C
ATOM    809  O   ILE A 336     -45.393 -11.147 -17.703  0.50 39.60           O
ATOM    810  N   SER A 337     -44.218  -9.570 -18.804  0.50 42.77           N
ATOM    811  CA  SER A 337     -45.073  -9.540 -19.991  0.50 40.74           C
ATOM    812  CB  SER A 337     -46.343  -8.730 -19.713  0.50 37.12           C
ATOM    813  OG  SER A 337     -46.008  -7.631 -18.904  0.50 39.18           O
ATOM    814  C   SER A 337     -44.269  -8.924 -21.138  0.50 36.21           C
ATOM    815  O   SER A 337     -43.143  -8.484 -20.946  0.50 36.03           O
ATOM    816  N   LYS A 338     -44.812  -8.948 -22.344  0.50 35.50           N
ATOM    817  CA  LYS A 338     -44.034  -8.519 -23.499  0.50 34.73           C
ATOM    818  CB  LYS A 338     -44.857  -8.759 -24.750  0.50 37.64           C
```

Figure 26 (Continued)

```
ATOM    819  CG  LYS A 338     -44.229  -8.348 -26.078  0.50 38.04           C
ATOM    820  CD  LYS A 338     -45.209  -8.644 -27.209  0.50 35.74           C
ATOM    821  CE  LYS A 338     -46.333  -7.621 -27.223  0.50 42.20           C
ATOM    822  NZ  LYS A 338     -45.841  -6.369 -27.867  0.50 35.02           N
ATOM    823  C   LYS A 338     -43.772  -7.020 -23.354  0.50 37.29           C
ATOM    824  O   LYS A 338     -44.506  -6.296 -22.696  0.50 39.73           O
ATOM    825  N   ALA A 339     -42.716  -6.553 -23.973  0.50 41.01           N
ATOM    826  CA  ALA A 339     -42.404  -5.142 -23.964  0.50 39.93           C
ATOM    827  CB  ALA A 339     -41.202  -4.876 -24.870  0.50 33.71           C
ATOM    828  C   ALA A 339     -43.622  -4.359 -24.430  0.50 39.16           C
ATOM    829  O   ALA A 339     -44.279  -4.744 -25.391  0.50 42.16           O
ATOM    830  N   LYS A 340     -43.895  -3.250 -23.748  0.50 39.68           N
ATOM    831  CA  LYS A 340     -45.020  -2.364 -24.028  0.50 42.03           C
ATOM    832  CB  LYS A 340     -45.318  -1.506 -22.795  0.50 42.50           C
ATOM    833  CG  LYS A 340     -46.409  -2.048 -21.884  0.50 50.19           C
ATOM    834  CD  LYS A 340     -46.363  -1.351 -20.533  0.50 50.81           C
ATOM    835  CE  LYS A 340     -47.682  -1.410 -19.777  0.50 49.05           C
ATOM    836  NZ  LYS A 340     -47.576  -0.579 -18.528  0.50 42.61           N
ATOM    837  C   LYS A 340     -44.672  -1.449 -25.194  0.50 40.04           C
ATOM    838  O   LYS A 340     -43.510  -1.297 -25.504  0.50 36.99           O
ATOM    839  N   GLY A 341     -45.678  -0.881 -25.860  0.50 37.47           N
ATOM    840  CA  GLY A 341     -45.443   0.067 -26.937  0.50 38.54           C
ATOM    841  C   GLY A 341     -46.304  -0.238 -28.139  0.50 40.02           C
ATOM    842  O   GLY A 341     -46.663  -1.381 -28.365  0.50 37.02           O
ATOM    843  N   GLN A 342     -46.656   0.798 -28.895  0.50 38.95           N
ATOM    844  CA  GLN A 342     -47.436   0.649 -30.131  0.50 38.35           C
ATOM    845  CB  GLN A 342     -47.817   2.053 -30.625  0.50 37.63           C
ATOM    846  CG  GLN A 342     -48.537   2.120 -31.961  0.50 45.30           C
ATOM    847  CD  GLN A 342     -49.970   2.614 -31.835  0.50 45.20           C
ATOM    848  OE1 GLN A 342     -50.728   2.145 -30.977  0.50 54.01           O
ATOM    849  NE2 GLN A 342     -50.353   3.551 -32.693  0.50 38.20           N
ATOM    850  C   GLN A 342     -46.551  -0.054 -31.173  0.50 37.32           C
ATOM    851  O   GLN A 342     -45.440   0.388 -31.436  0.50 36.71           O
ATOM    852  N   PRO A 343     -46.998  -1.193 -31.713  0.50 38.80           N
ATOM    853  CA  PRO A 343     -46.096  -1.810 -32.681  0.50 38.62           C
ATOM    854  CB  PRO A 343     -46.791  -3.154 -33.021  0.50 36.40           C
ATOM    855  CG  PRO A 343     -48.026  -3.215 -32.189  0.50 37.82           C
ATOM    856  CD  PRO A 343     -47.885  -2.195 -31.096  0.50 38.33           C
ATOM    857  C   PRO A 343     -45.935  -0.983 -33.936  0.50 37.36           C
ATOM    858  O   PRO A 343     -46.913  -0.473 -34.453  0.50 40.95           O
ATOM    859  N   ARG A 344     -44.716  -0.906 -34.462  0.50 33.77           N
ATOM    860  CA  ARG A 344     -44.486  -0.294 -35.759  0.50 34.32           C
ATOM    861  CB  ARG A 344     -43.608   0.991 -35.659  0.50 31.52           C
ATOM    862  CG  ARG A 344     -44.170   2.078 -34.722  0.50 37.59           C
ATOM    863  CD  ARG A 344     -43.313   3.367 -34.644  0.50 41.77           C
ATOM    864  NE  ARG A 344     -43.526   4.124 -33.383  0.50 46.44           N
ATOM    865  CZ  ARG A 344     -42.653   4.978 -32.820  0.50 42.32           C
ATOM    866  NH1 ARG A 344     -41.485   5.244 -33.409  0.50 34.41           N
ATOM    867  NH2 ARG A 344     -42.955   5.583 -31.662  0.50 36.29           N
ATOM    868  C   ARG A 344     -43.780  -1.337 -36.608  0.50 35.60           C
ATOM    869  O   ARG A 344     -42.911  -2.062 -36.114  0.50 37.85           O
ATOM    870  N   GLU A 345     -44.127  -1.384 -37.887  0.50 35.37           N
ATOM    871  CA  GLU A 345     -43.617  -2.406 -38.785  0.50 38.54           C
ATOM    872  CB  GLU A 345     -44.503  -2.477 -40.045  0.50 35.88           C
ATOM    873  CG  GLU A 345     -44.288  -3.728 -40.902  0.50 38.83           C
ATOM    874  CD  GLU A 345     -45.030  -3.649 -42.224  0.50 42.46           C
ATOM    875  OE1 GLU A 345     -45.416  -2.518 -42.593  0.50 40.29           O
ATOM    876  OE2 GLU A 345     -45.212  -4.699 -42.904  0.50 44.18           O
ATOM    877  C   GLU A 345     -42.188  -2.050 -39.158  0.50 37.37           C
ATOM    878  O   GLU A 345     -41.895  -0.883 -39.378  0.50 42.19           O
ATOM    879  N   PRO A 346     -41.286  -3.052 -39.190  0.50 34.58           N
ATOM    880  CA  PRO A 346     -39.924  -2.839 -39.647  0.50 30.98           C
ATOM    881  CB  PRO A 346     -39.190  -4.108 -39.231  0.50 32.71           C
ATOM    882  CG  PRO A 346     -40.234  -5.111 -38.889  0.50 28.05           C
```

Figure 26 (Continued)

```
ATOM    883  CD  PRO A 346     -41.552  -4.440 -38.764  0.50 28.68           C
ATOM    884  C   PRO A 346     -39.929  -2.784 -41.163  0.50 41.35           C
ATOM    885  O   PRO A 346     -40.762  -3.456 -41.801  0.50 34.38           O
ATOM    886  N   GLN A 347     -39.019  -1.974 -41.709  0.50 34.82           N
ATOM    887  CA  GLN A 347     -38.698  -1.950 -43.117  0.50 34.44           C
ATOM    888  CB  GLN A 347     -38.478  -0.497 -43.553  0.50 41.61           C
ATOM    889  CG  GLN A 347     -39.555   0.439 -43.021  0.50 41.54           C
ATOM    890  CD  GLN A 347     -40.926  -0.066 -43.397  0.50 49.02           C
ATOM    891  OE1 GLN A 347     -41.592  -0.749 -42.606  0.50 54.57           O
ATOM    892  NE2 GLN A 347     -41.334   0.203 -44.635  0.50 49.07           N
ATOM    893  C   GLN A 347     -37.376  -2.676 -43.203  0.50 33.00           C
ATOM    894  O   GLN A 347     -36.502  -2.497 -42.369  0.50 31.39           O
ATOM    895  N   VAL A 348     -37.228  -3.510 -44.209  0.50 33.22           N
ATOM    896  CA  VAL A 348     -36.087  -4.394 -44.277  0.50 32.64           C
ATOM    897  CB  VAL A 348     -36.585  -5.849 -44.266  0.50 33.46           C
ATOM    898  CG1 VAL A 348     -35.427  -6.850 -44.356  0.50 34.05           C
ATOM    899  CG2 VAL A 348     -37.433  -6.084 -43.023  0.50 33.93           C
ATOM    900  C   VAL A 348     -35.388  -4.066 -45.582  0.50 36.50           C
ATOM    901  O   VAL A 348     -36.030  -4.052 -46.619  0.50 35.84           O
ATOM    902  N   TYR A 349     -34.101  -3.732 -45.516  0.50 37.31           N
ATOM    903  CA  TYR A 349     -33.301  -3.490 -46.720  0.50 39.44           C
ATOM    904  CB  TYR A 349     -32.896  -2.011 -46.832  0.50 35.53           C
ATOM    905  CG  TYR A 349     -34.091  -1.109 -46.767  0.50 37.67           C
ATOM    906  CD1 TYR A 349     -35.076  -1.144 -47.769  0.50 35.51           C
ATOM    907  CE1 TYR A 349     -36.197  -0.347 -47.694  0.50 34.12           C
ATOM    908  CZ  TYR A 349     -36.358   0.494 -46.611  0.50 37.26           C
ATOM    909  OH  TYR A 349     -37.484   1.293 -46.512  0.50 37.38           O
ATOM    910  CE2 TYR A 349     -35.423   0.517 -45.593  0.50 38.93           C
ATOM    911  CD2 TYR A 349     -34.295  -0.285 -45.673  0.50 34.97           C
ATOM    912  C   TYR A 349     -32.065  -4.385 -46.722  0.50 39.01           C
ATOM    913  O   TYR A 349     -31.542  -4.762 -45.667  0.50 38.43           O
ATOM    914  N   VAL A 350     -31.611  -4.749 -47.908  0.50 35.80           N
ATOM    915  CA  VAL A 350     -30.418  -5.566 -48.022  0.50 37.65           C
ATOM    916  CB  VAL A 350     -30.766  -6.967 -48.533  0.50 41.49           C
ATOM    917  CG1 VAL A 350     -31.473  -7.728 -47.430  0.50 38.11           C
ATOM    918  CG2 VAL A 350     -31.639  -6.886 -49.789  0.50 39.76           C
ATOM    919  C   VAL A 350     -29.402  -4.928 -48.936  0.50 39.77           C
ATOM    920  O   VAL A 350     -29.721  -4.590 -50.073  0.50 39.90           O
ATOM    921  N   TYR A 351     -28.173  -4.809 -48.432  0.50 41.47           N
ATOM    922  CA  TYR A 351     -27.080  -4.081 -49.081  0.50 35.53           C
ATOM    923  CB  TYR A 351     -26.336  -3.235 -48.044  0.50 37.41           C
ATOM    924  CG  TYR A 351     -27.129  -2.051 -47.482  0.50 39.21           C
ATOM    925  CD1 TYR A 351     -26.817  -0.738 -47.856  0.50 43.48           C
ATOM    926  CE1 TYR A 351     -27.537   0.349 -47.368  0.50 37.37           C
ATOM    927  CZ  TYR A 351     -28.584   0.131 -46.501  0.50 37.24           C
ATOM    928  OH  TYR A 351     -29.282   1.218 -46.034  0.50 45.35           O
ATOM    929  CE2 TYR A 351     -28.924  -1.154 -46.111  0.50 32.80           C
ATOM    930  CD2 TYR A 351     -28.197  -2.238 -46.601  0.50 36.91           C
ATOM    931  C   TYR A 351     -26.082  -5.026 -49.718  0.50 39.55           C
ATOM    932  O   TYR A 351     -25.545  -5.913 -49.058  0.50 44.19           O
ATOM    933  N   PRO A 352     -25.801  -4.841 -51.011  0.50 42.22           N
ATOM    934  CA  PRO A 352     -24.745  -5.684 -51.563  0.50 39.94           C
ATOM    935  CB  PRO A 352     -24.891  -5.495 -53.088  0.50 41.19           C
ATOM    936  CG  PRO A 352     -25.631  -4.209 -53.260  0.50 41.12           C
ATOM    937  CD  PRO A 352     -26.505  -4.049 -52.039  0.50 43.23           C
ATOM    938  C   PRO A 352     -23.392  -5.225 -51.078  0.50 38.97           C
ATOM    939  O   PRO A 352     -23.280  -4.146 -50.492  0.50 33.67           O
ATOM    940  N   PRO A 353     -22.359  -6.047 -51.293  0.50 37.95           N
ATOM    941  CA  PRO A 353     -21.021  -5.679 -50.883  0.50 41.58           C
ATOM    942  CB  PRO A 353     -20.175  -6.878 -51.328  0.50 42.18           C
ATOM    943  CG  PRO A 353     -21.147  -8.020 -51.400  0.50 39.62           C
ATOM    944  CD  PRO A 353     -22.405  -7.383 -51.908  0.50 40.92           C
ATOM    945  C   PRO A 353     -20.538  -4.414 -51.585  0.50 43.41           C
ATOM    946  O   PRO A 353     -20.770  -4.236 -52.777  0.50 47.79           O
```

Figure 26 (Continued)

```
ATOM    947  N   SER A 354     -19.866  -3.557 -50.829  0.50 42.73           N
ATOM    948  CA  SER A 354     -19.048  -2.464 -51.361  0.50 43.22           C
ATOM    949  CB  SER A 354     -18.128  -1.971 -50.234  0.50 41.01           C
ATOM    950  OG  SER A 354     -17.140  -1.076 -50.712  0.50 54.35           O
ATOM    951  C   SER A 354     -18.167  -2.911 -52.514  0.50 43.01           C
ATOM    952  O   SER A 354     -17.464  -3.922 -52.403  0.50 39.27           O
ATOM    953  N   ARG A 355     -18.124  -2.122 -53.586  0.50 43.04           N
ATOM    954  CA  ARG A 355     -17.163  -2.398 -54.653  0.50 46.03           C
ATOM    955  CB  ARG A 355     -17.185  -1.299 -55.730  0.50 51.26           C
ATOM    956  CG  ARG A 355     -16.663  -1.760 -57.091  0.50 54.17           C
ATOM    957  CD  ARG A 355     -17.005  -0.786 -58.215  0.50 54.86           C
ATOM    958  NE  ARG A 355     -16.137   0.389 -58.195  0.50 59.58           N
ATOM    959  CZ  ARG A 355     -15.103   0.567 -59.013  0.50 62.73           C
ATOM    960  NH1 ARG A 355     -14.829  -0.344 -59.933  0.50 75.40           N
ATOM    961  NH2 ARG A 355     -14.343   1.653 -58.921  0.50 65.23           N
ATOM    962  C   ARG A 355     -15.748  -2.585 -54.095  0.50 41.50           C
ATOM    963  O   ARG A 355     -15.053  -3.517 -54.477  0.50 43.21           O
ATOM    964  N   ASP A 356     -15.343  -1.718 -53.163  0.50 42.76           N
ATOM    965  CA  ASP A 356     -14.028  -1.826 -52.517  0.50 43.06           C
ATOM    966  CB  ASP A 356     -13.864  -0.808 -51.375  0.50 44.22           C
ATOM    967  CG  ASP A 356     -13.561   0.594 -51.858  0.50 51.49           C
ATOM    968  OD1 ASP A 356     -12.961   1.366 -51.061  0.50 47.73           O
ATOM    969  OD2 ASP A 356     -13.958   0.935 -53.001  0.50 53.50           O
ATOM    970  C   ASP A 356     -13.762  -3.213 -51.946  0.50 40.28           C
ATOM    971  O   ASP A 356     -12.617  -3.637 -51.891  0.50 42.45           O
ATOM    972  N   GLU A 357     -14.797  -3.903 -51.461  0.50 40.24           N
ATOM    973  CA  GLU A 357     -14.567  -5.155 -50.702  0.50 40.19           C
ATOM    974  CB  GLU A 357     -15.749  -5.478 -49.772  0.50 41.51           C
ATOM    975  CG  GLU A 357     -15.446  -6.514 -48.687  0.50 36.70           C
ATOM    976  CD  GLU A 357     -16.630  -6.719 -47.767  0.50 37.72           C
ATOM    977  OE1 GLU A 357     -17.773  -6.456 -48.195  0.50 36.34           O
ATOM    978  OE2 GLU A 357     -16.437  -7.148 -46.615  0.50 39.57           O
ATOM    979  C   GLU A 357     -14.345  -6.314 -51.643  0.50 42.29           C
ATOM    980  O   GLU A 357     -13.769  -7.322 -51.259  0.50 42.91           O
ATOM    981  N   LEU A 358     -14.795  -6.154 -52.887  0.50 48.38           N
ATOM    982  CA  LEU A 358     -14.804  -7.256 -53.846  0.50 47.81           C
ATOM    983  CB  LEU A 358     -15.439  -6.829 -55.170  0.50 47.33           C
ATOM    984  CG  LEU A 358     -16.887  -6.331 -55.044  0.50 52.12           C
ATOM    985  CD1 LEU A 358     -17.376  -5.690 -56.339  0.50 50.61           C
ATOM    986  CD2 LEU A 358     -17.852  -7.434 -54.602  0.50 46.28           C
ATOM    987  C   LEU A 358     -13.423  -7.803 -54.064  0.50 46.44           C
ATOM    988  O   LEU A 358     -13.263  -8.973 -54.419  0.50 56.25           O
ATOM    989  N   THR A 359     -12.420  -6.978 -53.783  0.50 49.19           N
ATOM    990  CA  THR A 359     -11.022  -7.378 -53.914  0.50 51.11           C
ATOM    991  CB  THR A 359     -10.054  -6.171 -53.765  0.50 60.11           C
ATOM    992  OG1 THR A 359      -9.699  -6.000 -52.387  0.50 55.32           O
ATOM    993  CG2 THR A 359     -10.663  -4.865 -54.326  0.50 54.37           C
ATOM    994  C   THR A 359     -10.603  -8.425 -52.891  0.50 57.46           C
ATOM    995  O   THR A 359      -9.646  -9.166 -53.123  0.50 60.63           O
ATOM    996  N   LYS A 360     -11.279  -8.463 -51.740  0.50 55.33           N
ATOM    997  CA  LYS A 360     -10.916  -9.411 -50.682  0.50 50.24           C
ATOM    998  CB  LYS A 360     -11.450  -8.929 -49.333  0.50 50.08           C
ATOM    999  CG  LYS A 360     -11.171  -7.460 -49.048  0.50 48.38           C
ATOM   1000  CD  LYS A 360      -9.722  -7.234 -48.618  0.50 43.92           C
ATOM   1001  CE  LYS A 360      -9.609  -5.946 -47.810  0.50 47.53           C
ATOM   1002  NZ  LYS A 360      -8.203  -5.470 -47.652  0.50 47.01           N
ATOM   1003  C   LYS A 360     -11.489 -10.793 -51.017  0.50 46.74           C
ATOM   1004  O   LYS A 360     -12.237 -10.927 -51.983  0.50 47.32           O
ATOM   1005  N   ASN A 361     -11.152 -11.799 -50.215  0.50 43.25           N
ATOM   1006  CA  ASN A 361     -11.648 -13.162 -50.445  0.50 43.87           C
ATOM   1007  CB  ASN A 361     -10.737 -14.189 -49.765  0.50 43.60           C
ATOM   1008  CG  ASN A 361      -9.484 -14.479 -50.577  0.50 51.98           C
ATOM   1009  OD1 ASN A 361      -9.408 -14.162 -51.779  0.50 54.43           O
ATOM   1010  ND2 ASN A 361      -8.485 -15.076 -49.928  0.50 51.37           N
```

Figure 26 (Continued)

```
ATOM   1011  C    ASN A 361     -13.076 -13.318 -49.959  0.50 44.88           C
ATOM   1012  O    ASN A 361     -13.903 -13.955 -50.611  0.50 45.94           O
ATOM   1013  N    GLN A 362     -13.354 -12.709 -48.811  0.50 45.72           N
ATOM   1014  CA   GLN A 362     -14.689 -12.661 -48.235  0.50 41.75           C
ATOM   1015  CB   GLN A 362     -14.561 -12.883 -46.739  0.50 41.12           C
ATOM   1016  CG   GLN A 362     -13.798 -14.155 -46.424  0.50 47.71           C
ATOM   1017  CD   GLN A 362     -14.535 -15.034 -45.440  0.50 50.52           C
ATOM   1018  OE1  GLN A 362     -14.198 -15.066 -44.256  0.50 53.99           O
ATOM   1019  NE2  GLN A 362     -15.554 -15.752 -45.920  0.50 52.41           N
ATOM   1020  C    GLN A 362     -15.385 -11.329 -48.486  0.50 43.86           C
ATOM   1021  O    GLN A 362     -14.743 -10.272 -48.511  0.50 42.82           O
ATOM   1022  N    VAL A 363     -16.701 -11.363 -48.662  0.50 39.97           N
ATOM   1023  CA   VAL A 363     -17.430 -10.119 -48.774  0.50 35.47           C
ATOM   1024  CB   VAL A 363     -17.995  -9.885 -50.183  0.50 38.80           C
ATOM   1025  CG1  VAL A 363     -16.848  -9.763 -51.184  0.50 36.30           C
ATOM   1026  CG2  VAL A 363     -18.941 -11.010 -50.577  0.50 40.04           C
ATOM   1027  C    VAL A 363     -18.521 -10.078 -47.746  0.50 38.14           C
ATOM   1028  O    VAL A 363     -18.971 -11.150 -47.274  0.50 32.03           O
ATOM   1029  N    SER A 364     -18.958  -8.852 -47.412  0.50 32.63           N
ATOM   1030  CA   SER A 364     -20.069  -8.671 -46.471  0.50 31.37           C
ATOM   1031  CB   SER A 364     -19.714  -7.578 -45.440  0.50 30.42           C
ATOM   1032  OG   SER A 364     -18.435  -7.857 -44.846  0.50 28.85           O
ATOM   1033  C    SER A 364     -21.387  -8.333 -47.123  0.50 29.34           C
ATOM   1034  O    SER A 364     -21.493  -7.316 -47.810  0.50 41.31           O
ATOM   1035  N    LEU A 365     -22.430  -9.104 -46.816  0.50 28.57           N
ATOM   1036  CA   LEU A 365     -23.793  -8.703 -47.151  0.50 26.96           C
ATOM   1037  CB   LEU A 365     -24.600  -9.902 -47.674  0.50 27.97           C
ATOM   1038  CG   LEU A 365     -23.923 -10.624 -48.870  0.50 31.15           C
ATOM   1039  CD1  LEU A 365     -24.541 -12.000 -49.141  0.50 35.89           C
ATOM   1040  CD2  LEU A 365     -24.014  -9.751 -50.112  0.50 29.76           C
ATOM   1041  C    LEU A 365     -24.485  -8.108 -45.929  0.50 29.87           C
ATOM   1042  O    LEU A 365     -24.425  -8.671 -44.844  0.50 31.34           O
ATOM   1043  N    THR A 366     -25.221  -7.016 -46.133  0.50 29.58           N
ATOM   1044  CA   THR A 366     -25.765  -6.256 -45.020  0.50 28.30           C
ATOM   1045  CB   THR A 366     -25.199  -4.831 -45.033  0.50 27.43           C
ATOM   1046  OG1  THR A 366     -23.787  -4.920 -44.919  0.50 23.23           O
ATOM   1047  CG2  THR A 366     -25.737  -4.037 -43.861  0.50 25.29           C
ATOM   1048  C    THR A 366     -27.278  -6.171 -45.052  0.50 31.14           C
ATOM   1049  O    THR A 366     -27.876  -5.836 -46.088  0.50 31.44           O
ATOM   1050  N    CYS A 367     -27.896  -6.503 -43.921  0.50 29.46           N
ATOM   1051  CA   CYS A 367     -29.330  -6.363 -43.793  0.50 28.96           C
ATOM   1052  CB   CYS A 367     -29.946  -7.695 -43.360  0.50 29.49           C
ATOM   1053  SG   CYS A 367     -31.760  -7.758 -43.418  0.50 34.21           S
ATOM   1054  C    CYS A 367     -29.626  -5.308 -42.749  0.50 29.18           C
ATOM   1055  O    CYS A 367     -29.277  -5.506 -41.578  0.50 28.66           O
ATOM   1056  N    LEU A 368     -30.250  -4.203 -43.182  0.50 28.85           N
ATOM   1057  CA   LEU A 368     -30.733  -3.127 -42.304  0.50 30.73           C
ATOM   1058  CB   LEU A 368     -30.516  -1.739 -42.942  0.50 29.70           C
ATOM   1059  CG   LEU A 368     -31.225  -0.499 -42.391  0.50 33.10           C
ATOM   1060  CD1  LEU A 368     -30.854  -0.173 -40.948  0.50 30.00           C
ATOM   1061  CD2  LEU A 368     -30.941   0.731 -43.264  0.50 31.63           C
ATOM   1062  C    LEU A 368     -32.217  -3.337 -42.087  0.50 30.30           C
ATOM   1063  O    LEU A 368     -32.979  -3.575 -43.015  0.50 29.63           O
ATOM   1064  N    VAL A 369     -32.618  -3.250 -40.837  0.50 28.47           N
ATOM   1065  CA   VAL A 369     -33.991  -3.376 -40.482  0.50 27.69           C
ATOM   1066  CB   VAL A 369     -34.212  -4.686 -39.700  0.50 26.91           C
ATOM   1067  CG1  VAL A 369     -35.694  -4.975 -39.572  0.50 22.97           C
ATOM   1068  CG2  VAL A 369     -33.543  -5.847 -40.453  0.50 23.80           C
ATOM   1069  C    VAL A 369     -34.224  -2.168 -39.596  0.50 29.88           C
ATOM   1070  O    VAL A 369     -33.555  -1.997 -38.557  0.50 33.45           O
ATOM   1071  N    LYS A 370     -35.137  -1.298 -40.003  0.50 33.01           N
ATOM   1072  CA   LYS A 370     -35.356  -0.091 -39.194  0.50 33.20           C
ATOM   1073  CB   LYS A 370     -34.586   1.093 -39.798  0.50 33.30           C
ATOM   1074  CG   LYS A 370     -35.091   1.532 -41.153  0.50 30.51           C
```

Figure 26 (Continued)

```
ATOM   1075  CD   LYS A 370     -34.510    2.897 -41.539  0.50 32.10           C
ATOM   1076  CE   LYS A 370     -35.513    3.999 -41.289  0.50 30.89           C
ATOM   1077  NZ   LYS A 370     -34.867    5.338 -41.320  0.50 31.20           N
ATOM   1078  C    LYS A 370     -36.819    0.263 -38.950  0.50 34.00           C
ATOM   1079  O    LYS A 370     -37.715   -0.296 -39.554  0.50 33.26           O
ATOM   1080  N    GLY A 371     -37.059    1.166 -38.011  0.50 37.46           N
ATOM   1081  CA   GLY A 371     -38.400    1.683 -37.818  0.50 33.27           C
ATOM   1082  C    GLY A 371     -39.316    0.659 -37.159  0.50 34.06           C
ATOM   1083  O    GLY A 371     -40.524    0.726 -37.324  0.50 31.96           O
ATOM   1084  N    PHE A 372     -38.741   -0.257 -36.384  0.50 31.84           N
ATOM   1085  CA   PHE A 372     -39.551   -1.225 -35.670  0.50 31.83           C
ATOM   1086  CB   PHE A 372     -39.060   -2.677 -35.911  0.50 26.27           C
ATOM   1087  CG   PHE A 372     -37.708   -3.014 -35.310  0.50 24.15           C
ATOM   1088  CD1  PHE A 372     -36.565   -2.859 -36.042  0.50 22.74           C
ATOM   1089  CE1  PHE A 372     -35.329   -3.248 -35.548  0.50 23.21           C
ATOM   1090  CZ   PHE A 372     -35.224   -3.822 -34.290  0.50 21.85           C
ATOM   1091  CE2  PHE A 372     -36.359   -3.983 -33.532  0.50 21.96           C
ATOM   1092  CD2  PHE A 372     -37.605   -3.610 -34.057  0.50 24.00           C
ATOM   1093  C    PHE A 372     -39.762   -0.919 -34.201  0.50 30.16           C
ATOM   1094  O    PHE A 372     -38.966   -0.239 -33.589  0.50 28.59           O
ATOM   1095  N    TYR A 373     -40.882   -1.382 -33.661  0.50 27.76           N
ATOM   1096  CA   TYR A 373     -41.217   -1.181 -32.277  0.50 27.20           C
ATOM   1097  CB   TYR A 373     -41.933    0.156 -32.018  0.50 30.82           C
ATOM   1098  CG   TYR A 373     -41.707    0.642 -30.592  0.50 32.76           C
ATOM   1099  CD1  TYR A 373     -42.628    0.402 -29.593  0.50 40.08           C
ATOM   1100  CE1  TYR A 373     -42.397    0.835 -28.286  0.50 48.04           C
ATOM   1101  CZ   TYR A 373     -41.218    1.515 -27.992  0.50 42.88           C
ATOM   1102  OH   TYR A 373     -40.944    1.979 -26.727  0.50 50.00           O
ATOM   1103  CE2  TYR A 373     -40.293    1.740 -28.963  0.50 36.07           C
ATOM   1104  CD2  TYR A 373     -40.532    1.300 -30.251  0.50 36.67           C
ATOM   1105  C    TYR A 373     -42.087   -2.358 -31.865  0.50 28.28           C
ATOM   1106  O    TYR A 373     -43.010   -2.698 -32.609  0.50 23.11           O
ATOM   1107  N    PRO A 374     -42.069   -2.659 -30.565  0.50 30.36           N
ATOM   1108  CA   PRO A 374     -40.867   -2.914 -29.739  0.50 28.87           C
ATOM   1109  CB   PRO A 374     -41.398   -3.698 -28.549  0.50 30.34           C
ATOM   1110  CG   PRO A 374     -42.442   -4.561 -29.227  0.50 38.26           C
ATOM   1111  CD   PRO A 374     -43.121   -3.643 -30.236  0.50 30.02           C
ATOM   1112  C    PRO A 374     -39.720   -3.608 -30.366  0.50 27.94           C
ATOM   1113  O    PRO A 374     -39.766   -3.941 -31.529  0.50 29.75           O
ATOM   1114  N    SER A 375     -38.696   -3.824 -29.546  0.50 29.90           N
ATOM   1115  CA   SER A 375     -37.385   -4.161 -30.017  0.50 32.79           C
ATOM   1116  CB   SER A 375     -36.295   -3.601 -29.107  0.50 34.28           C
ATOM   1117  OG   SER A 375     -36.294   -4.273 -27.868  0.50 35.14           O
ATOM   1118  C    SER A 375     -37.209   -5.635 -30.140  0.50 27.21           C
ATOM   1119  O    SER A 375     -36.255   -6.052 -30.731  0.50 32.91           O
ATOM   1120  N    ASP A 376     -38.132   -6.418 -29.610  0.50 29.38           N
ATOM   1121  CA   ASP A 376     -38.064   -7.886 -29.766  0.50 28.22           C
ATOM   1122  CB   ASP A 376     -39.247   -8.534 -29.100  0.50 29.37           C
ATOM   1123  CG   ASP A 376     -39.403   -8.109 -27.667  0.50 32.66           C
ATOM   1124  OD1  ASP A 376     -38.513   -8.426 -26.857  0.50 28.01           O
ATOM   1125  OD2  ASP A 376     -40.437   -7.479 -27.370  0.50 36.99           O
ATOM   1126  C    ASP A 376     -38.161   -8.243 -31.244  0.50 30.06           C
ATOM   1127  O    ASP A 376     -39.165   -7.929 -31.909  0.50 30.90           O
ATOM   1128  N    ILE A 377     -37.164   -8.947 -31.745  0.50 28.92           N
ATOM   1129  CA   ILE A 377     -37.135   -9.257 -33.150  0.50 29.42           C
ATOM   1130  CB   ILE A 377     -36.613   -8.057 -33.944  0.50 28.33           C
ATOM   1131  CG1  ILE A 377     -36.844   -8.253 -35.449  0.50 28.41           C
ATOM   1132  CD1  ILE A 377     -36.807   -6.950 -36.219  0.50 34.40           C
ATOM   1133  CG2  ILE A 377     -35.149   -7.812 -33.597  0.50 28.39           C
ATOM   1134  C    ILE A 377     -36.187  -10.412 -33.352  0.50 30.69           C
ATOM   1135  O    ILE A 377     -35.384  -10.744 -32.456  0.50 32.06           O
ATOM   1136  N    ALA A 378     -36.309  -11.049 -34.516  0.50 28.98           N
ATOM   1137  CA   ALA A 378     -35.391  -12.134 -34.884  0.50 29.44           C
ATOM   1138  CB   ALA A 378     -36.029  -13.482 -34.643  0.50 26.89           C
```

Figure 26 (Continued)

| | | | | | | | | | | |
|---|---|---|---|---|---|---|---|---|---|---|
| ATOM | 1139 | C | ALA | A | 378 | -35.040 | -12.000 | -36.328 | 0.50 26.82 | C |
| ATOM | 1140 | O | ALA | A | 378 | -35.923 | -11.901 | -37.173 | 0.50 28.06 | O |
| ATOM | 1141 | N | VAL | A | 379 | -33.748 | -12.001 | -36.615 | 0.50 25.90 | N |
| ATOM | 1142 | CA | VAL | A | 379 | -33.267 | -11.763 | -37.952 | 0.50 27.95 | C |
| ATOM | 1143 | CB | VAL | A | 379 | -32.509 | -10.416 | -38.002 | 0.50 29.28 | C |
| ATOM | 1144 | CG1 | VAL | A | 379 | -31.978 | -10.193 | -39.406 | 0.50 31.17 | C |
| ATOM | 1145 | CG2 | VAL | A | 379 | -33.436 | -9.271 | -37.530 | 0.50 24.57 | C |
| ATOM | 1146 | C | VAL | A | 379 | -32.295 | -12.904 | -38.257 | 0.50 33.30 | C |
| ATOM | 1147 | O | VAL | A | 379 | -31.517 | -13.309 | -37.384 | 0.50 33.59 | O |
| ATOM | 1148 | N | GLU | A | 380 | -32.396 | -13.469 | -39.460 | 0.50 31.99 | N |
| ATOM | 1149 | CA | GLU | A | 380 | -31.671 | -14.701 | -39.812 | 0.50 33.31 | C |
| ATOM | 1150 | CB | GLU | A | 380 | -32.527 | -15.924 | -39.500 | 0.50 32.41 | C |
| ATOM | 1151 | CG | GLU | A | 380 | -32.365 | -16.382 | -38.072 | 0.50 42.01 | C |
| ATOM | 1152 | CD | GLU | A | 380 | -33.423 | -17.401 | -37.675 | 0.50 41.21 | C |
| ATOM | 1153 | OE1 | GLU | A | 380 | -33.720 | -17.470 | -36.453 | 0.50 48.63 | O |
| ATOM | 1154 | OE2 | GLU | A | 380 | -33.949 | -18.084 | -38.587 | 0.50 39.08 | O |
| ATOM | 1155 | C | GLU | A | 380 | -31.369 | -14.693 | -41.293 | 0.50 32.79 | C |
| ATOM | 1156 | O | GLU | A | 380 | -32.081 | -14.073 | -42.063 | 0.50 38.05 | O |
| ATOM | 1157 | N | TRP | A | 381 | -30.303 | -15.343 | -41.709 | 0.50 33.89 | N |
| ATOM | 1158 | CA | TRP | A | 381 | -29.984 | -15.303 | -43.123 | 0.50 34.57 | C |
| ATOM | 1159 | CB | TRP | A | 381 | -28.506 | -14.977 | -43.334 | 0.50 33.63 | C |
| ATOM | 1160 | CG | TRP | A | 381 | -28.149 | -13.520 | -43.186 | 0.50 35.84 | C |
| ATOM | 1161 | CD1 | TRP | A | 381 | -27.755 | -12.883 | -42.043 | 0.50 37.04 | C |
| ATOM | 1162 | NE1 | TRP | A | 381 | -27.510 | -11.545 | -42.307 | 0.50 40.87 | N |
| ATOM | 1163 | CE2 | TRP | A | 381 | -27.737 | -11.308 | -43.636 | 0.50 37.91 | C |
| ATOM | 1164 | CD2 | TRP | A | 381 | -28.171 | -12.526 | -44.217 | 0.50 35.56 | C |
| ATOM | 1165 | CE3 | TRP | A | 381 | -28.428 | -12.564 | -45.590 | 0.50 30.22 | C |
| ATOM | 1166 | CZ3 | TRP | A | 381 | -28.317 | -11.374 | -46.333 | 0.50 32.22 | C |
| ATOM | 1167 | CH2 | TRP | A | 381 | -27.909 | -10.180 | -45.718 | 0.50 33.96 | C |
| ATOM | 1168 | CZ2 | TRP | A | 381 | -27.600 | -10.129 | -44.378 | 0.50 33.47 | C |
| ATOM | 1169 | C | TRP | A | 381 | -30.254 | -16.695 | -43.685 | 0.50 37.60 | C |
| ATOM | 1170 | O | TRP | A | 381 | -30.046 | -17.691 | -42.995 | 0.50 30.65 | O |
| ATOM | 1171 | N | GLU | A | 382 | -30.645 | -16.763 | -44.953 | 0.50 34.96 | N |
| ATOM | 1172 | CA | GLU | A | 382 | -30.603 | -18.066 | -45.630 | 0.50 41.73 | C |
| ATOM | 1173 | CB | GLU | A | 382 | -31.973 | -18.743 | -45.523 | 0.50 35.58 | C |
| ATOM | 1174 | CG | GLU | A | 382 | -33.010 | -18.136 | -46.441 | 0.50 44.33 | C |
| ATOM | 1175 | CD | GLU | A | 382 | -34.421 | -18.627 | -46.137 | 0.50 48.72 | C |
| ATOM | 1176 | OE1 | GLU | A | 382 | -35.277 | -18.559 | -47.046 | 0.50 48.29 | O |
| ATOM | 1177 | OE2 | GLU | A | 382 | -34.679 | -19.078 | -44.994 | 0.50 50.15 | O |
| ATOM | 1178 | C | GLU | A | 382 | -30.130 | -17.956 | -47.103 | 0.50 39.58 | C |
| ATOM | 1179 | O | GLU | A | 382 | -30.053 | -16.844 | -47.670 | 0.50 36.31 | O |
| ATOM | 1180 | N | SER | A | 383 | -29.780 | -19.089 | -47.703 | 0.50 37.33 | N |
| ATOM | 1181 | CA | SER | A | 383 | -29.651 | -19.163 | -49.171 | 0.50 38.37 | C |
| ATOM | 1182 | CB | SER | A | 383 | -28.207 | -18.973 | -49.597 | 0.50 37.18 | C |
| ATOM | 1183 | OG | SER | A | 383 | -28.143 | -18.951 | -51.012 | 0.50 42.68 | O |
| ATOM | 1184 | C | SER | A | 383 | -30.136 | -20.507 | -49.761 | 0.50 37.74 | C |
| ATOM | 1185 | O | SER | A | 383 | -29.804 | -21.572 | -49.253 | 0.50 32.30 | O |
| ATOM | 1186 | N | ASN | A | 384 | -30.844 | -20.452 | -50.881 | 0.50 43.29 | N |
| ATOM | 1187 | CA | ASN | A | 384 | -31.386 | -21.673 | -51.452 | 0.50 50.75 | C |
| ATOM | 1188 | CB | ASN | A | 384 | -30.297 | -22.411 | -52.255 | 0.50 50.22 | C |
| ATOM | 1189 | CG | ASN | A | 384 | -30.863 | -23.536 | -53.120 | 0.50 59.51 | C |
| ATOM | 1190 | OD1 | ASN | A | 384 | -31.908 | -23.381 | -53.764 | 0.50 52.02 | O |
| ATOM | 1191 | ND2 | ASN | A | 384 | -30.169 | -24.675 | -53.144 | 0.50 55.09 | N |
| ATOM | 1192 | C | ASN | A | 384 | -31.950 | -22.564 | -50.320 | 0.50 54.19 | C |
| ATOM | 1193 | O | ASN | A | 384 | -31.682 | -23.769 | -50.263 | 0.50 50.01 | O |
| ATOM | 1194 | N | GLY | A | 385 | -32.645 | -21.928 | -49.370 | 0.50 55.19 | N |
| ATOM | 1195 | CA | GLY | A | 385 | -33.393 | -22.627 | -48.326 | 0.50 50.13 | C |
| ATOM | 1196 | C | GLY | A | 385 | -32.667 | -23.013 | -47.049 | 0.50 52.91 | C |
| ATOM | 1197 | O | GLY | A | 385 | -33.319 | -23.258 | -46.025 | 0.50 67.20 | O |
| ATOM | 1198 | N | GLN | A | 386 | -31.334 | -23.094 | -47.099 | 0.50 53.19 | N |
| ATOM | 1199 | CA | GLN | A | 386 | -30.517 | -23.499 | -45.930 | 0.50 53.49 | C |
| ATOM | 1200 | CB | GLN | A | 386 | -29.292 | -24.297 | -46.379 | 0.50 54.59 | C |
| ATOM | 1201 | CG | GLN | A | 386 | -29.597 | -25.622 | -47.045 | 0.50 70.16 | C |
| ATOM | 1202 | CD | GLN | A | 386 | -30.123 | -26.636 | -46.056 | 0.50 70.45 | C |

Figure 26 (Continued)

```
ATOM   1203  OE1 GLN A 386     -31.286 -27.029 -46.117  0.50 76.82           O
ATOM   1204  NE2 GLN A 386     -29.276 -27.046 -45.126  0.50 61.80           N
ATOM   1205  C   GLN A 386     -29.998 -22.305 -45.105  0.50 50.79           C
ATOM   1206  O   GLN A 386     -29.556 -21.302 -45.666  0.50 49.79           O
ATOM   1207  N   PRO A 387     -29.980 -22.448 -43.778  0.50 47.13           N
ATOM   1208  CA  PRO A 387     -29.470 -21.428 -42.878  0.50 51.71           C
ATOM   1209  CB  PRO A 387     -29.480 -22.129 -41.504  0.50 45.27           C
ATOM   1210  CG  PRO A 387     -29.664 -23.578 -41.810  0.50 44.72           C
ATOM   1211  CD  PRO A 387     -30.532 -23.578 -43.025  0.50 45.01           C
ATOM   1212  C   PRO A 387     -28.037 -21.086 -43.232  0.50 55.01           C
ATOM   1213  O   PRO A 387     -27.231 -21.987 -43.466  0.50 49.55           O
ATOM   1214  N   GLU A 388     -27.729 -19.791 -43.252  0.50 45.72           N
ATOM   1215  CA  GLU A 388     -26.365 -19.313 -43.476  0.50 44.10           C
ATOM   1216  CB  GLU A 388     -26.317 -18.318 -44.642  0.50 39.56           C
ATOM   1217  CG  GLU A 388     -26.651 -18.921 -45.982  0.50 41.46           C
ATOM   1218  CD  GLU A 388     -25.424 -19.430 -46.714  0.50 42.86           C
ATOM   1219  OE1 GLU A 388     -25.583 -20.116 -47.755  0.50 39.70           O
ATOM   1220  OE2 GLU A 388     -24.301 -19.145 -46.247  0.50 37.86           O
ATOM   1221  C   GLU A 388     -26.089 -18.581 -42.199  0.50 45.74           C
ATOM   1222  O   GLU A 388     -26.677 -17.520 -41.951  0.50 51.97           O
ATOM   1223  N   ASN A 389     -25.276 -19.169 -41.341  0.50 41.11           N
ATOM   1224  CA  ASN A 389     -25.235 -18.705 -39.978  0.50 43.97           C
ATOM   1225  CB  ASN A 389     -25.433 -19.896 -39.006  0.50 45.00           C
ATOM   1226  CG  ASN A 389     -26.815 -20.514 -39.102  0.50 42.32           C
ATOM   1227  OD1 ASN A 389     -27.683 -19.989 -39.798  0.50 46.72           O
ATOM   1228  ND2 ASN A 389     -27.032 -21.647 -38.406  0.50 38.81           N
ATOM   1229  C   ASN A 389     -23.923 -17.976 -39.694  0.50 42.52           C
ATOM   1230  O   ASN A 389     -23.584 -17.721 -38.536  0.50 44.76           O
ATOM   1231  N   ASN A 390     -23.138 -17.708 -40.743  0.50 42.71           N
ATOM   1232  CA  ASN A 390     -21.868 -17.014 -40.541  0.50 44.27           C
ATOM   1233  CB  ASN A 390     -20.872 -17.388 -41.611  0.50 41.72           C
ATOM   1234  CG  ASN A 390     -19.506 -16.836 -41.312  0.50 37.96           C
ATOM   1235  OD1 ASN A 390     -19.169 -16.609 -40.160  0.50 41.73           O
ATOM   1236  ND2 ASN A 390     -18.725 -16.590 -42.344  0.50 47.32           N
ATOM   1237  C   ASN A 390     -22.023 -15.471 -40.475  0.50 39.95           C
ATOM   1238  O   ASN A 390     -21.506 -14.712 -41.317  0.50 32.99           O
ATOM   1239  N   TYR A 391     -22.791 -15.028 -39.495  0.50 37.52           N
ATOM   1240  CA  TYR A 391     -23.210 -13.655 -39.468  0.50 36.43           C
ATOM   1241  CB  TYR A 391     -24.583 -13.511 -40.112  0.50 39.85           C
ATOM   1242  CG  TYR A 391     -25.745 -14.213 -39.392  0.50 47.31           C
ATOM   1243  CD1 TYR A 391     -26.403 -13.606 -38.325  0.50 50.39           C
ATOM   1244  CE1 TYR A 391     -27.488 -14.214 -37.709  0.50 54.34           C
ATOM   1245  CZ  TYR A 391     -27.952 -15.435 -38.189  0.50 54.07           C
ATOM   1246  OH  TYR A 391     -29.027 -16.054 -37.605  0.50 68.29           O
ATOM   1247  CE2 TYR A 391     -27.346 -16.038 -39.263  0.50 51.30           C
ATOM   1248  CD2 TYR A 391     -26.243 -15.433 -39.857  0.50 47.67           C
ATOM   1249  C   TYR A 391     -23.283 -13.240 -38.016  0.50 36.83           C
ATOM   1250  O   TYR A 391     -23.379 -14.098 -37.142  0.50 26.69           O
ATOM   1251  N   LYS A 392     -23.265 -11.923 -37.782  0.50 32.94           N
ATOM   1252  CA  LYS A 392     -23.528 -11.337 -36.471  0.50 28.13           C
ATOM   1253  CB  LYS A 392     -22.230 -10.791 -35.834  0.50 32.26           C
ATOM   1254  CG  LYS A 392     -21.063 -11.777 -35.717  0.50 33.24           C
ATOM   1255  CD  LYS A 392     -21.381 -12.911 -34.750  0.50 38.65           C
ATOM   1256  CE  LYS A 392     -20.185 -13.827 -34.544  0.50 36.42           C
ATOM   1257  NZ  LYS A 392     -19.240 -13.186 -33.590  0.50 36.97           N
ATOM   1258  C   LYS A 392     -24.494 -10.177 -36.683  0.50 29.02           C
ATOM   1259  O   LYS A 392     -24.503  -9.522 -37.746  0.50 27.41           O
ATOM   1260  N   THR A 393     -25.262  -9.904 -35.645  0.50 28.50           N
ATOM   1261  CA  THR A 393     -26.318  -8.932 -35.670  0.50 30.39           C
ATOM   1262  CB  THR A 393     -27.677  -9.657 -35.688  0.50 34.84           C
ATOM   1263  OG1 THR A 393     -27.677 -10.612 -36.766  0.50 34.86           O
ATOM   1264  CG2 THR A 393     -28.834  -8.687 -35.902  0.50 31.18           C
ATOM   1265  C   THR A 393     -26.176  -7.969 -34.486  0.50 36.06           C
ATOM   1266  O   THR A 393     -26.032  -8.374 -33.326  0.50 33.05           O
```

Figure 26 (Continued)

```
ATOM   1267  N    THR A 394     -26.133   -6.675  -34.772  0.50 32.66           N
ATOM   1268  CA   THR A 394     -26.018   -5.737  -33.687  0.50 28.59           C
ATOM   1269  CB   THR A 394     -26.003   -4.294  -34.187  0.50 30.23           C
ATOM   1270  OG1  THR A 394     -27.307   -3.966  -34.672  0.50 28.31           O
ATOM   1271  CG2  THR A 394     -24.987   -4.129  -35.311  0.50 31.50           C
ATOM   1272  C    THR A 394     -27.273   -5.862  -32.871  0.50 28.66           C
ATOM   1273  O    THR A 394     -28.343   -6.154  -33.413  0.50 30.89           O
ATOM   1274  N    PRO A 395     -27.158   -5.663  -31.558  0.50 30.96           N
ATOM   1275  CA   PRO A 395     -28.373   -5.542  -30.775  0.50 30.30           C
ATOM   1276  CB   PRO A 395     -27.855   -5.331  -29.335  0.50 32.67           C
ATOM   1277  CG   PRO A 395     -26.402   -4.948  -29.469  0.50 30.09           C
ATOM   1278  CD   PRO A 395     -25.920   -5.597  -30.735  0.50 28.60           C
ATOM   1279  C    PRO A 395     -29.145   -4.316  -31.280  0.50 34.92           C
ATOM   1280  O    PRO A 395     -28.557   -3.436  -31.899  0.50 34.48           O
ATOM   1281  N    PRO A 396     -30.473   -4.304  -31.106  0.50 32.98           N
ATOM   1282  CA   PRO A 396     -31.231   -3.102  -31.533  0.50 33.41           C
ATOM   1283  CB   PRO A 396     -32.707   -3.510  -31.314  0.50 30.47           C
ATOM   1284  CG   PRO A 396     -32.715   -5.021  -31.310  0.50 28.60           C
ATOM   1285  CD   PRO A 396     -31.322   -5.510  -30.977  0.50 31.18           C
ATOM   1286  C    PRO A 396     -30.908   -1.868  -30.665  0.50 34.14           C
ATOM   1287  O    PRO A 396     -30.681   -1.993  -29.463  0.50 33.95           O
ATOM   1288  N    VAL A 397     -30.900   -0.685  -31.264  0.50 32.82           N
ATOM   1289  CA   VAL A 397     -30.798    0.540  -30.472  0.50 31.24           C
ATOM   1290  CB   VAL A 397     -29.357    1.061  -30.425  0.50 35.50           C
ATOM   1291  CG1  VAL A 397     -28.463    0.131  -29.591  0.50 44.29           C
ATOM   1292  CG2  VAL A 397     -28.793    1.235  -31.822  0.50 36.69           C
ATOM   1293  C    VAL A 397     -31.750    1.619  -30.996  0.50 29.14           C
ATOM   1294  O    VAL A 397     -32.046    1.670  -32.193  0.50 28.83           O
ATOM   1295  N    LEU A 398     -32.226    2.486  -30.108  0.50 30.89           N
ATOM   1296  CA   LEU A 398     -33.199    3.524  -30.496  0.50 31.50           C
ATOM   1297  CB   LEU A 398     -33.521    4.427  -29.305  0.50 35.13           C
ATOM   1298  CG   LEU A 398     -34.974    4.795  -28.986  0.50 39.34           C
ATOM   1299  CD1  LEU A 398     -35.932    3.644  -29.266  0.50 41.93           C
ATOM   1300  CD2  LEU A 398     -35.112    5.240  -27.522  0.50 40.53           C
ATOM   1301  C    LEU A 398     -32.654    4.360  -31.632  0.50 33.99           C
ATOM   1302  O    LEU A 398     -31.473    4.703  -31.670  0.50 37.77           O
ATOM   1303  N    ASP A 399     -33.512    4.662  -32.585  0.50 36.33           N
ATOM   1304  CA   ASP A 399     -33.175    5.571  -33.650  0.50 37.08           C
ATOM   1305  CB   ASP A 399     -33.795    5.096  -34.954  0.50 36.42           C
ATOM   1306  CG   ASP A 399     -33.039    5.571  -36.147  0.50 37.85           C
ATOM   1307  OD1  ASP A 399     -32.408    6.640  -36.041  0.50 37.07           O
ATOM   1308  OD2  ASP A 399     -33.062    4.876  -37.188  0.50 42.35           O
ATOM   1309  C    ASP A 399     -33.776    6.922  -33.274  0.50 43.91           C
ATOM   1310  O    ASP A 399     -34.399    7.054  -32.222  0.50 37.82           O
ATOM   1311  N    SER A 400     -33.607    7.917  -34.144  0.50 39.62           N
ATOM   1312  CA   SER A 400     -33.890    9.278  -33.745  0.50 45.91           C
ATOM   1313  CB   SER A 400     -33.053   10.276  -34.553  0.50 40.44           C
ATOM   1314  OG   SER A 400     -33.425   10.267  -35.913  0.50 42.26           O
ATOM   1315  C    SER A 400     -35.378    9.606  -33.798  0.50 44.88           C
ATOM   1316  O    SER A 400     -35.748   10.772  -33.764  0.50 37.85           O
ATOM   1317  N    ASP A 401     -36.226    8.575  -33.845  0.50 41.02           N
ATOM   1318  CA   ASP A 401     -37.666    8.794  -33.817  0.50 40.03           C
ATOM   1319  CB   ASP A 401     -38.293    8.541  -35.188  0.50 40.61           C
ATOM   1320  CG   ASP A 401     -38.237    7.073  -35.607  0.50 43.95           C
ATOM   1321  OD1  ASP A 401     -37.757    6.212  -34.823  0.50 40.21           O
ATOM   1322  OD2  ASP A 401     -38.665    6.792  -36.743  0.50 41.75           O
ATOM   1323  C    ASP A 401     -38.369    7.971  -32.758  0.50 39.08           C
ATOM   1324  O    ASP A 401     -39.587    7.876  -32.743  0.50 37.30           O
ATOM   1325  N    GLY A 402     -37.605    7.371  -31.862  0.50 43.53           N
ATOM   1326  CA   GLY A 402     -38.207    6.487  -30.878  0.50 41.89           C
ATOM   1327  C    GLY A 402     -38.434    5.059  -31.356  0.50 41.67           C
ATOM   1328  O    GLY A 402     -38.769    4.181  -30.546  0.50 39.14           O
ATOM   1329  N    SER A 403     -38.235    4.802  -32.650  0.50 37.24           N
ATOM   1330  CA   SER A 403     -38.232    3.409  -33.145  0.50 35.93           C
```

Figure 26 (Continued)

```
ATOM   1331  CB  SER A 403     -38.710   3.347 -34.592  0.50 36.28           C
ATOM   1332  OG  SER A 403     -37.656   3.711 -35.452  0.50 38.39           O
ATOM   1333  C   SER A 403     -36.842   2.768 -33.070  0.50 38.82           C
ATOM   1334  O   SER A 403     -35.839   3.461 -32.899  0.50 35.14           O
ATOM   1335  N   PHE A 404     -36.770   1.451 -33.269  0.50 32.62           N
ATOM   1336  CA  PHE A 404     -35.472   0.759 -33.238  0.50 32.42           C
ATOM   1337  CB  PHE A 404     -35.585  -0.546 -32.474  0.50 29.74           C
ATOM   1338  CG  PHE A 404     -35.793  -0.355 -30.996  0.50 30.20           C
ATOM   1339  CD1 PHE A 404     -37.074  -0.384 -30.446  0.50 28.87           C
ATOM   1340  CE1 PHE A 404     -37.260  -0.230 -29.067  0.50 30.53           C
ATOM   1341  CZ  PHE A 404     -36.159  -0.021 -28.242  0.50 30.08           C
ATOM   1342  CE2 PHE A 404     -34.883   0.008 -28.793  0.50 31.97           C
ATOM   1343  CD2 PHE A 404     -34.706  -0.181 -30.156  0.50 27.16           C
ATOM   1344  C   PHE A 404     -34.909   0.487 -34.622  0.50 31.43           C
ATOM   1345  O   PHE A 404     -35.647   0.443 -35.596  0.50 32.48           O
ATOM   1346  N   ALA A 405     -33.587   0.349 -34.713  0.50 31.45           N
ATOM   1347  CA  ALA A 405     -32.974  -0.148 -35.939  0.50 29.79           C
ATOM   1348  CB  ALA A 405     -32.263   0.969 -36.697  0.50 32.79           C
ATOM   1349  C   ALA A 405     -31.996  -1.258 -35.623  0.50 31.65           C
ATOM   1350  O   ALA A 405     -31.476  -1.338 -34.531  0.50 32.73           O
ATOM   1351  N   LEU A 406     -31.702  -2.112 -36.589  0.50 33.11           N
ATOM   1352  CA  LEU A 406     -30.571  -2.986 -36.350  0.50 30.91           C
ATOM   1353  CB  LEU A 406     -31.038  -4.200 -35.522  0.50 30.26           C
ATOM   1354  CG  LEU A 406     -31.699  -5.396 -36.213  0.50 33.80           C
ATOM   1355  CD1 LEU A 406     -30.796  -6.002 -37.281  0.50 29.08           C
ATOM   1356  CD2 LEU A 406     -32.007  -6.479 -35.180  0.50 32.76           C
ATOM   1357  C   LEU A 406     -29.877  -3.350 -37.655  0.50 28.25           C
ATOM   1358  O   LEU A 406     -30.458  -3.232 -38.730  0.50 34.02           O
ATOM   1359  N   VAL A 407     -28.609  -3.718 -37.587  0.50 28.66           N
ATOM   1360  CA  VAL A 407     -27.943  -4.232 -38.779  0.50 27.73           C
ATOM   1361  CB  VAL A 407     -26.849  -3.281 -39.318  0.50 27.77           C
ATOM   1362  CG1 VAL A 407     -26.394  -3.769 -40.676  0.50 23.25           C
ATOM   1363  CG2 VAL A 407     -27.401  -1.855 -39.467  0.50 28.03           C
ATOM   1364  C   VAL A 407     -27.334  -5.618 -38.526  0.50 28.54           C
ATOM   1365  O   VAL A 407     -26.679  -5.842 -37.492  0.50 24.19           O
ATOM   1366  N   SER A 408     -27.575  -6.526 -39.478  0.50 28.21           N
ATOM   1367  CA  SER A 408     -26.992  -7.874 -39.495  0.50 26.92           C
ATOM   1368  CB  SER A 408     -28.121  -8.923 -39.617  0.50 28.30           C
ATOM   1369  OG  SER A 408     -27.659 -10.270 -39.435  0.50 28.48           O
ATOM   1370  C   SER A 408     -26.030  -7.976 -40.682  0.50 29.04           C
ATOM   1371  O   SER A 408     -26.336  -7.525 -41.798  0.50 30.96           O
ATOM   1372  N   LYS A 409     -24.869  -8.589 -40.454  0.50 25.43           N
ATOM   1373  CA  LYS A 409     -23.877  -8.720 -41.484  0.50 26.54           C
ATOM   1374  CB  LYS A 409     -22.554  -8.138 -40.984  0.50 24.50           C
ATOM   1375  CG  LYS A 409     -21.387  -8.315 -41.918  0.50 25.85           C
ATOM   1376  CD  LYS A 409     -20.175  -7.483 -41.503  0.50 25.66           C
ATOM   1377  CE  LYS A 409     -19.556  -7.981 -40.211  0.50 28.68           C
ATOM   1378  NZ  LYS A 409     -18.759  -9.248 -40.364  0.50 26.44           N
ATOM   1379  C   LYS A 409     -23.674 -10.204 -41.796  0.50 27.87           C
ATOM   1380  O   LYS A 409     -23.294 -10.964 -40.930  0.50 27.37           O
ATOM   1381  N   LEU A 410     -23.825 -10.597 -43.050  0.50 27.33           N
ATOM   1382  CA  LEU A 410     -23.429 -11.971 -43.394  0.50 31.28           C
ATOM   1383  CB  LEU A 410     -24.552 -12.716 -44.143  0.50 30.76           C
ATOM   1384  CG  LEU A 410     -24.165 -14.061 -44.810  0.50 31.81           C
ATOM   1385  CD1 LEU A 410     -24.236 -15.201 -43.806  0.50 25.71           C
ATOM   1386  CD2 LEU A 410     -25.093 -14.370 -45.990  0.50 30.79           C
ATOM   1387  C   LEU A 410     -22.159 -11.970 -44.206  0.50 27.93           C
ATOM   1388  O   LEU A 410     -22.019 -11.230 -45.186  0.50 28.58           O
ATOM   1389  N   THR A 411     -21.202 -12.762 -43.760  0.50 29.77           N
ATOM   1390  CA  THR A 411     -19.974 -12.897 -44.472  0.50 32.31           C
ATOM   1391  CB  THR A 411     -18.790 -12.963 -43.498  0.50 33.73           C
ATOM   1392  OG1 THR A 411     -18.835 -11.838 -42.619  0.50 32.33           O
ATOM   1393  CG2 THR A 411     -17.481 -12.934 -44.245  0.50 34.70           C
ATOM   1394  C   THR A 411     -20.005 -14.160 -45.325  0.50 36.07           C
```

Figure 26 (Continued)

| | | | | | | | | | | |
|---|---|---|---|---|---|---|---|---|---|---|
| ATOM | 1395 | O | THR | A | 411 | -20.247 | -15.253 | -44.806 | 0.50 35.03 | O |
| ATOM | 1396 | N | VAL | A | 412 | -19.757 | -13.995 | -46.625 | 0.50 38.50 | N |
| ATOM | 1397 | CA | VAL | A | 412 | -19.648 | -15.115 | -47.555 | 0.50 37.50 | C |
| ATOM | 1398 | CB | VAL | A | 412 | -20.887 | -15.209 | -48.484 | 0.50 42.77 | C |
| ATOM | 1399 | CG1 | VAL | A | 412 | -22.177 | -15.196 | -47.673 | 0.50 37.31 | C |
| ATOM | 1400 | CG2 | VAL | A | 412 | -20.905 | -14.095 | -49.528 | 0.50 41.48 | C |
| ATOM | 1401 | C | VAL | A | 412 | -18.362 | -15.018 | -48.393 | 0.50 42.46 | C |
| ATOM | 1402 | O | VAL | A | 412 | -17.894 | -13.916 | -48.728 | 0.50 36.85 | O |
| ATOM | 1403 | N | ASP | A | 413 | -17.756 | -16.170 | -48.680 | 0.50 44.71 | N |
| ATOM | 1404 | CA | ASP | A | 413 | -16.648 | -16.245 | -49.644 | 0.50 49.16 | C |
| ATOM | 1405 | CB | ASP | A | 413 | -16.357 | -17.703 | -50.024 | 0.50 53.53 | C |
| ATOM | 1406 | CG | ASP | A | 413 | -15.706 | -18.474 | -48.904 | 0.50 60.57 | C |
| ATOM | 1407 | OD1 | ASP | A | 413 | -15.389 | -17.853 | -47.867 | 0.50 60.24 | O |
| ATOM | 1408 | OD2 | ASP | A | 413 | -15.515 | -19.707 | -49.049 | 0.50 75.30 | O |
| ATOM | 1409 | C | ASP | A | 413 | -17.035 | -15.500 | -50.898 | 0.50 44.09 | C |
| ATOM | 1410 | O | ASP | A | 413 | -18.160 | -15.652 | -51.368 | 0.50 43.42 | O |
| ATOM | 1411 | N | LYS | A | 414 | -16.118 | -14.688 | -51.433 | 0.50 47.49 | N |
| ATOM | 1412 | CA | LYS | A | 414 | -16.387 | -13.925 | -52.659 | 0.50 47.82 | C |
| ATOM | 1413 | CB | LYS | A | 414 | -15.179 | -13.066 | -53.109 | 0.50 47.88 | C |
| ATOM | 1414 | CG | LYS | A | 414 | -15.464 | -12.290 | -54.407 | 0.50 47.98 | C |
| ATOM | 1415 | CD | LYS | A | 414 | -14.485 | -11.150 | -54.694 | 0.50 51.56 | C |
| ATOM | 1416 | CE | LYS | A | 414 | -13.263 | -11.612 | -55.474 | 0.50 43.79 | C |
| ATOM | 1417 | NZ | LYS | A | 414 | -12.227 | -10.542 | -55.569 | 0.50 48.16 | N |
| ATOM | 1418 | C | LYS | A | 414 | -16.842 | -14.834 | -53.799 | 0.50 50.47 | C |
| ATOM | 1419 | O | LYS | A | 414 | -17.623 | -14.411 | -54.661 | 0.50 49.88 | O |
| ATOM | 1420 | N | SER | A | 415 | -16.367 | -16.080 | -53.790 | 0.50 46.94 | N |
| ATOM | 1421 | CA | SER | A | 415 | -16.692 | -17.045 | -54.852 | 0.50 52.24 | C |
| ATOM | 1422 | CB | SER | A | 415 | -15.957 | -18.382 | -54.616 | 0.50 58.25 | C |
| ATOM | 1423 | OG | SER | A | 415 | -16.240 | -18.946 | -53.332 | 0.50 55.14 | O |
| ATOM | 1424 | C | SER | A | 415 | -18.191 | -17.286 | -54.973 | 0.50 50.33 | C |
| ATOM | 1425 | O | SER | A | 415 | -18.756 | -17.264 | -56.072 | 0.50 51.57 | O |
| ATOM | 1426 | N | ARG | A | 416 | -18.840 | -17.510 | -53.832 | 0.50 47.39 | N |
| ATOM | 1427 | CA | ARG | A | 416 | -20.284 | -17.750 | -53.805 | 0.50 43.16 | C |
| ATOM | 1428 | CB | ARG | A | 416 | -20.721 | -18.151 | -52.405 | 0.50 43.13 | C |
| ATOM | 1429 | CG | ARG | A | 416 | -19.927 | -19.333 | -51.847 | 0.50 42.97 | C |
| ATOM | 1430 | CD | ARG | A | 416 | -20.397 | -19.709 | -50.453 | 0.50 43.35 | C |
| ATOM | 1431 | NE | ARG | A | 416 | -21.824 | -20.025 | -50.477 | 0.50 45.56 | N |
| ATOM | 1432 | CZ | ARG | A | 416 | -22.625 | -19.944 | -49.424 | 0.50 45.47 | C |
| ATOM | 1433 | NH1 | ARG | A | 416 | -22.146 | -19.540 | -48.255 | 0.50 46.73 | N |
| ATOM | 1434 | NH2 | ARG | A | 416 | -23.904 | -20.258 | -49.542 | 0.50 45.15 | N |
| ATOM | 1435 | C | ARG | A | 416 | -21.061 | -16.539 | -54.284 | 0.50 45.12 | C |
| ATOM | 1436 | O | ARG | A | 416 | -22.021 | -16.660 | -55.030 | 0.50 46.39 | O |
| ATOM | 1437 | N | TRP | A | 417 | -20.627 | -15.351 | -53.887 | 0.50 43.26 | N |
| ATOM | 1438 | CA | TRP | A | 417 | -21.311 | -14.150 | -54.326 | 0.50 42.17 | C |
| ATOM | 1439 | CB | TRP | A | 417 | -20.697 | -12.931 | -53.652 | 0.50 39.38 | C |
| ATOM | 1440 | CG | TRP | A | 417 | -21.299 | -11.674 | -54.097 | 0.50 40.15 | C |
| ATOM | 1441 | CD1 | TRP | A | 417 | -20.686 | -10.680 | -54.793 | 0.50 41.37 | C |
| ATOM | 1442 | NE1 | TRP | A | 417 | -21.572 | -9.659 | -55.029 | 0.50 46.39 | N |
| ATOM | 1443 | CE2 | TRP | A | 417 | -22.788 | -9.984 | -54.484 | 0.50 40.67 | C |
| ATOM | 1444 | CD2 | TRP | A | 417 | -22.654 | -11.253 | -53.891 | 0.50 42.43 | C |
| ATOM | 1445 | CE3 | TRP | A | 417 | -23.758 | -11.818 | -53.238 | 0.50 41.23 | C |
| ATOM | 1446 | CZ3 | TRP | A | 417 | -24.935 | -11.113 | -53.211 | 0.50 37.07 | C |
| ATOM | 1447 | CH2 | TRP | A | 417 | -25.045 | -9.848 | -53.818 | 0.50 37.87 | C |
| ATOM | 1448 | CZ2 | TRP | A | 417 | -23.983 | -9.271 | -54.463 | 0.50 38.86 | C |
| ATOM | 1449 | C | TRP | A | 417 | -21.319 | -13.986 | -55.866 | 0.50 46.01 | C |
| ATOM | 1450 | O | TRP | A | 417 | -22.382 | -13.903 | -56.483 | 0.50 44.58 | O |
| ATOM | 1451 | N | GLN | A | 418 | -20.134 | -13.921 | -56.474 | 0.50 48.25 | N |
| ATOM | 1452 | CA | GLN | A | 418 | -19.997 | -13.705 | -57.926 | 0.50 52.19 | C |
| ATOM | 1453 | CB | GLN | A | 418 | -18.510 | -13.559 | -58.299 | 0.50 53.61 | C |
| ATOM | 1454 | CG | GLN | A | 418 | -17.670 | -12.807 | -57.269 | 0.50 50.36 | C |
| ATOM | 1455 | CD | GLN | A | 418 | -17.266 | -11.406 | -57.706 | 0.50 49.96 | C |
| ATOM | 1456 | OE1 | GLN | A | 418 | -16.092 | -11.157 | -57.969 | 0.50 63.35 | O |
| ATOM | 1457 | NE2 | GLN | A | 418 | -18.220 | -10.484 | -57.766 | 0.50 43.21 | N |
| ATOM | 1458 | C | GLN | A | 418 | -20.626 | -14.850 | -58.750 | 0.50 53.90 | C |

Figure 26 (Continued)

```
ATOM   1459  O    GLN A 418     -21.138 -14.623 -59.843  0.50 54.30           O
ATOM   1460  N    GLN A 419     -20.585 -16.070 -58.215  0.50 55.84           N
ATOM   1461  CA   GLN A 419     -21.292 -17.207 -58.817  0.50 56.86           C
ATOM   1462  CB   GLN A 419     -20.949 -18.511 -58.095  0.50 55.03           C
ATOM   1463  CG   GLN A 419     -19.712 -19.200 -58.640  0.50 61.22           C
ATOM   1464  CD   GLN A 419     -19.166 -20.241 -57.683  0.50 67.75           C
ATOM   1465  OE1  GLN A 419     -19.860 -20.688 -56.767  0.50 65.67           O
ATOM   1466  NE2  GLN A 419     -17.902 -20.618 -57.877  0.50 69.23           N
ATOM   1467  C    GLN A 419     -22.817 -17.040 -58.848  0.50 61.03           C
ATOM   1468  O    GLN A 419     -23.524 -17.890 -59.395  0.50 56.21           O
ATOM   1469  N    GLY A 420     -23.329 -15.976 -58.233  0.50 51.27           N
ATOM   1470  CA   GLY A 420     -24.739 -15.663 -58.367  0.50 49.04           C
ATOM   1471  C    GLY A 420     -25.670 -16.264 -57.329  0.50 43.79           C
ATOM   1472  O    GLY A 420     -26.855 -15.982 -57.332  0.50 52.07           O
ATOM   1473  N    ASN A 421     -25.165 -17.082 -56.426  0.50 45.74           N
ATOM   1474  CA   ASN A 421     -26.031 -17.556 -55.350  0.50 49.19           C
ATOM   1475  CB   ASN A 421     -25.217 -18.264 -54.273  0.50 50.78           C
ATOM   1476  CG   ASN A 421     -24.393 -19.411 -54.838  0.50 55.33           C
ATOM   1477  OD1  ASN A 421     -24.834 -20.564 -54.844  0.50 55.44           O
ATOM   1478  ND2  ASN A 421     -23.219 -19.091 -55.367  0.50 53.00           N
ATOM   1479  C    ASN A 421     -26.851 -16.409 -54.750  0.50 46.06           C
ATOM   1480  O    ASN A 421     -26.361 -15.278 -54.642  0.50 45.66           O
ATOM   1481  N    VAL A 422     -28.111 -16.700 -54.430  0.50 40.51           N
ATOM   1482  CA   VAL A 422     -29.028 -15.743 -53.848  0.50 37.04           C
ATOM   1483  CB   VAL A 422     -30.480 -15.947 -54.352  0.50 38.23           C
ATOM   1484  CG1  VAL A 422     -31.496 -15.248 -53.450  0.50 30.56           C
ATOM   1485  CG2  VAL A 422     -30.640 -15.488 -55.799  0.50 34.54           C
ATOM   1486  C    VAL A 422     -29.000 -15.885 -52.324  0.50 42.05           C
ATOM   1487  O    VAL A 422     -28.989 -16.990 -51.766  0.50 39.51           O
ATOM   1488  N    PHE A 423     -28.980 -14.749 -51.649  0.50 41.00           N
ATOM   1489  CA   PHE A 423     -28.939 -14.751 -50.199  0.50 36.33           C
ATOM   1490  CB   PHE A 423     -27.630 -14.139 -49.721  0.50 34.70           C
ATOM   1491  CG   PHE A 423     -26.428 -14.984 -50.027  0.50 36.95           C
ATOM   1492  CD1  PHE A 423     -25.742 -14.826 -51.229  0.50 39.54           C
ATOM   1493  CE1  PHE A 423     -24.648 -15.625 -51.536  0.50 35.40           C
ATOM   1494  CZ   PHE A 423     -24.236 -16.596 -50.642  0.50 35.01           C
ATOM   1495  CE2  PHE A 423     -24.908 -16.767 -49.450  0.50 39.31           C
ATOM   1496  CD2  PHE A 423     -26.009 -15.965 -49.145  0.50 37.71           C
ATOM   1497  C    PHE A 423     -30.128 -13.951 -49.704  0.50 37.63           C
ATOM   1498  O    PHE A 423     -30.481 -12.934 -50.296  0.50 41.03           O
ATOM   1499  N    SER A 424     -30.766 -14.409 -48.632  0.50 36.40           N
ATOM   1500  CA   SER A 424     -31.915 -13.672 -48.131  0.50 36.31           C
ATOM   1501  CB   SER A 424     -33.231 -14.323 -48.562  0.50 48.50           C
ATOM   1502  OG   SER A 424     -33.302 -14.423 -49.990  0.50 51.39           O
ATOM   1503  C    SER A 424     -31.889 -13.419 -46.630  0.50 37.13           C
ATOM   1504  O    SER A 424     -31.450 -14.225 -45.831  0.50 32.34           O
ATOM   1505  N    CYS A 425     -32.385 -12.255 -46.260  0.50 41.62           N
ATOM   1506  CA   CYS A 425     -32.478 -11.885 -44.880  0.50 35.93           C
ATOM   1507  CB   CYS A 425     -32.152 -10.402 -44.776  0.50 35.27           C
ATOM   1508  SG   CYS A 425     -32.095  -9.761 -43.090  0.50 38.70           S
ATOM   1509  C    CYS A 425     -33.923 -12.152 -44.449  0.50 38.14           C
ATOM   1510  O    CYS A 425     -34.848 -11.581 -45.009  0.50 31.32           O
ATOM   1511  N    SER A 426     -34.102 -13.044 -43.482  0.50 33.26           N
ATOM   1512  CA   SER A 426     -35.402 -13.332 -42.924  0.50 35.96           C
ATOM   1513  CB   SER A 426     -35.444 -14.799 -42.486  0.50 33.22           C
ATOM   1514  OG   SER A 426     -35.913 -15.621 -43.544  0.50 46.41           O
ATOM   1515  C    SER A 426     -35.605 -12.473 -41.698  0.50 31.78           C
ATOM   1516  O    SER A 426     -34.729 -12.426 -40.847  0.50 31.71           O
ATOM   1517  N    VAL A 427     -36.765 -11.850 -41.572  0.50 29.77           N
ATOM   1518  CA   VAL A 427     -37.007 -10.989 -40.428  0.50 32.41           C
ATOM   1519  CB   VAL A 427     -37.014  -9.487 -40.783  0.50 33.39           C
ATOM   1520  CG1  VAL A 427     -37.370  -8.659 -39.553  0.50 31.81           C
ATOM   1521  CG2  VAL A 427     -35.666  -9.062 -41.337  0.50 32.51           C
ATOM   1522  C    VAL A 427     -38.355 -11.324 -39.849  0.50 34.08           C
```

Figure 26 (Continued)

```
ATOM   1523  O    VAL A 427     -39.335 -11.480 -40.582  0.50 32.98           O
ATOM   1524  N    MET A 428     -38.384 -11.484 -38.528  0.50 32.80           N
ATOM   1525  CA   MET A 428     -39.582 -11.887 -37.850  0.50 30.44           C
ATOM   1526  CB   MET A 428     -39.385 -13.281 -37.302  0.50 29.96           C
ATOM   1527  CG   MET A 428     -39.237 -14.295 -38.431  0.50 31.97           C
ATOM   1528  SD   MET A 428     -38.386 -15.770 -37.859  0.50 33.06           S
ATOM   1529  CE   MET A 428     -36.659 -15.277 -37.897  0.50 30.36           C
ATOM   1530  C    MET A 428     -39.905 -10.900 -36.746  0.50 27.82           C
ATOM   1531  O    MET A 428     -39.062 -10.621 -35.919  0.50 28.55           O
ATOM   1532  N    HIS A 429     -41.129 -10.382 -36.758  0.50 27.97           N
ATOM   1533  CA   HIS A 429     -41.551  -9.319 -35.846  0.50 31.80           C
ATOM   1534  CB   HIS A 429     -41.006  -7.959 -36.317  0.50 33.37           C
ATOM   1535  CG   HIS A 429     -41.168  -6.855 -35.310  0.50 30.74           C
ATOM   1536  ND1  HIS A 429     -42.310  -6.086 -35.235  0.50 28.32           N
ATOM   1537  CE1  HIS A 429     -42.187  -5.204 -34.255  0.50 27.42           C
ATOM   1538  NE2  HIS A 429     -40.997  -5.360 -33.703  0.50 33.21           N
ATOM   1539  CD2  HIS A 429     -40.330  -6.378 -34.356  0.50 30.96           C
ATOM   1540  C    HIS A 429     -43.087  -9.296 -35.762  0.50 31.25           C
ATOM   1541  O    HIS A 429     -43.800  -9.568 -36.744  0.50 30.81           O
ATOM   1542  N    GLU A 430     -43.584  -9.014 -34.574  0.50 27.41           N
ATOM   1543  CA   GLU A 430     -45.027  -8.990 -34.319  0.50 28.58           C
ATOM   1544  CB   GLU A 430     -45.315  -8.689 -32.827  0.50 27.71           C
ATOM   1545  CG   GLU A 430     -44.525  -7.517 -32.261  0.50 30.58           C
ATOM   1546  CD   GLU A 430     -44.385  -7.547 -30.732  0.50 33.33           C
ATOM   1547  OE1  GLU A 430     -43.403  -8.171 -30.213  0.50 30.42           O
ATOM   1548  OE2  GLU A 430     -45.234  -6.928 -30.056  0.50 28.73           O
ATOM   1549  C    GLU A 430     -45.775  -7.998 -35.194  0.50 30.35           C
ATOM   1550  O    GLU A 430     -46.987  -8.170 -35.438  0.50 26.63           O
ATOM   1551  N    ALA A 431     -45.082  -6.971 -35.698  0.50 32.89           N
ATOM   1552  CA   ALA A 431     -45.799  -5.918 -36.447  0.50 33.90           C
ATOM   1553  CB   ALA A 431     -45.272  -4.538 -36.078  0.50 34.81           C
ATOM   1554  C    ALA A 431     -45.693  -6.153 -37.955  0.50 37.03           C
ATOM   1555  O    ALA A 431     -46.130  -5.331 -38.758  0.50 44.11           O
ATOM   1556  N    LEU A 432     -45.105  -7.270 -38.354  0.50 32.34           N
ATOM   1557  CA   LEU A 432     -45.116  -7.632 -39.768  0.50 30.97           C
ATOM   1558  CB   LEU A 432     -43.853  -8.422 -40.114  0.50 30.94           C
ATOM   1559  CG   LEU A 432     -42.500  -7.707 -40.195  0.50 31.64           C
ATOM   1560  CD1  LEU A 432     -41.409  -8.776 -40.146  0.50 29.81           C
ATOM   1561  CD2  LEU A 432     -42.369  -6.852 -41.476  0.50 29.05           C
ATOM   1562  C    LEU A 432     -46.333  -8.494 -40.095  0.50 34.12           C
ATOM   1563  O    LEU A 432     -46.888  -9.145 -39.229  0.50 33.43           O
ATOM   1564  N    HIS A 433     -46.697  -8.566 -41.370  0.50 36.80           N
ATOM   1565  CA   HIS A 433     -47.770  -9.462 -41.779  0.50 39.27           C
ATOM   1566  CB   HIS A 433     -48.178  -9.195 -43.235  0.50 38.12           C
ATOM   1567  CG   HIS A 433     -49.388  -9.967 -43.672  0.50 49.69           C
ATOM   1568  ND1  HIS A 433     -49.306 -11.151 -44.381  0.50 44.47           N
ATOM   1569  CE1  HIS A 433     -50.525 -11.597 -44.629  0.50 46.46           C
ATOM   1570  NE2  HIS A 433     -51.394 -10.765 -44.080  0.50 51.09           N
ATOM   1571  CD2  HIS A 433     -50.712  -9.734 -43.481  0.50 48.24           C
ATOM   1572  C    HIS A 433     -47.310 -10.915 -41.618  0.50 34.81           C
ATOM   1573  O    HIS A 433     -46.247 -11.286 -42.100  0.50 36.24           O
ATOM   1574  N    ASN A 434     -48.129 -11.749 -40.988  0.50 35.92           N
ATOM   1575  CA   ASN A 434     -47.716 -13.135 -40.670  0.50 36.88           C
ATOM   1576  CB   ASN A 434     -47.638 -13.984 -41.929  0.50 34.87           C
ATOM   1577  CG   ASN A 434     -49.014 -14.368 -42.447  0.50 40.33           C
ATOM   1578  OD1  ASN A 434     -50.008 -14.185 -41.751  0.50 38.71           O
ATOM   1579  ND2  ASN A 434     -49.079 -14.893 -43.676  0.50 42.08           N
ATOM   1580  C    ASN A 434     -46.392 -13.205 -39.911  0.50 35.92           C
ATOM   1581  O    ASN A 434     -45.735 -14.268 -39.884  0.50 31.41           O
ATOM   1582  N    HIS A 435     -45.985 -12.064 -39.338  0.50 30.22           N
ATOM   1583  CA   HIS A 435     -44.843 -12.029 -38.440  0.50 31.28           C
ATOM   1584  CB   HIS A 435     -45.013 -13.036 -37.295  0.50 32.21           C
ATOM   1585  CG   HIS A 435     -46.137 -12.702 -36.370  0.50 32.63           C
ATOM   1586  ND1  HIS A 435     -46.534 -13.530 -35.341  0.50 33.25           N
```

Figure 26 (Continued)

```
ATOM   1587  CE1 HIS A 435     -47.578 -12.999 -34.736  0.50 33.01           C
ATOM   1588  NE2 HIS A 435     -47.853 -11.846 -35.318  0.50 32.84           N
ATOM   1589  CD2 HIS A 435     -46.961 -11.633 -36.334  0.50 32.04           C
ATOM   1590  C   HIS A 435     -43.551 -12.350 -39.137  0.50 33.72           C
ATOM   1591  O   HIS A 435     -42.581 -12.803 -38.496  0.50 35.65           O
ATOM   1592  N   TYR A 436     -43.517 -12.137 -40.443  0.50 32.12           N
ATOM   1593  CA  TYR A 436     -42.400 -12.639 -41.203  0.50 36.70           C
ATOM   1594  CB  TYR A 436     -42.533 -14.159 -41.367  0.50 35.97           C
ATOM   1595  CG  TYR A 436     -41.489 -14.764 -42.289  0.50 37.67           C
ATOM   1596  CD1 TYR A 436     -41.708 -14.839 -43.656  0.50 35.57           C
ATOM   1597  CE1 TYR A 436     -40.762 -15.406 -44.514  0.50 40.70           C
ATOM   1598  CZ  TYR A 436     -39.576 -15.892 -44.009  0.50 40.93           C
ATOM   1599  OH  TYR A 436     -38.636 -16.417 -44.879  0.50 37.80           O
ATOM   1600  CE2 TYR A 436     -39.332 -15.829 -42.635  0.50 43.96           C
ATOM   1601  CD2 TYR A 436     -40.286 -15.261 -41.789  0.50 38.87           C
ATOM   1602  C   TYR A 436     -42.258 -11.965 -42.559  0.50 39.24           C
ATOM   1603  O   TYR A 436     -43.242 -11.755 -43.263  0.50 41.94           O
ATOM   1604  N   THR A 437     -41.029 -11.608 -42.915  0.50 37.06           N
ATOM   1605  CA  THR A 437     -40.740 -11.272 -44.294  0.50 36.26           C
ATOM   1606  CB  THR A 437     -40.956  -9.792 -44.622  0.50 35.47           C
ATOM   1607  OG1 THR A 437     -40.747  -9.616 -46.031  0.50 36.19           O
ATOM   1608  CG2 THR A 437     -39.978  -8.911 -43.851  0.50 36.06           C
ATOM   1609  C   THR A 437     -39.317 -11.650 -44.631  0.50 40.11           C
ATOM   1610  O   THR A 437     -38.503 -11.856 -43.738  0.50 41.12           O
ATOM   1611  N   GLN A 438     -39.025 -11.709 -45.925  0.50 38.84           N
ATOM   1612  CA  GLN A 438     -37.708 -12.056 -46.422  0.50 42.37           C
ATOM   1613  CB  GLN A 438     -37.669 -13.523 -46.817  0.50 43.22           C
ATOM   1614  CG  GLN A 438     -36.283 -14.029 -47.150  0.50 48.56           C
ATOM   1615  CD  GLN A 438     -36.303 -15.460 -47.669  0.50 48.69           C
ATOM   1616  OE1 GLN A 438     -36.615 -15.714 -48.836  0.50 47.58           O
ATOM   1617  NE2 GLN A 438     -35.953 -16.397 -46.808  0.50 47.21           N
ATOM   1618  C   GLN A 438     -37.359 -11.198 -47.639  0.50 46.66           C
ATOM   1619  O   GLN A 438     -38.174 -11.070 -48.581  0.50 37.43           O
ATOM   1620  N   LYS A 439     -36.166 -10.592 -47.594  0.50 43.63           N
ATOM   1621  CA  LYS A 439     -35.589  -9.852 -48.729  0.50 46.04           C
ATOM   1622  CB  LYS A 439     -35.241  -8.400 -48.324  0.50 47.97           C
ATOM   1623  CG  LYS A 439     -36.426  -7.443 -48.115  0.50 53.18           C
ATOM   1624  CD  LYS A 439     -36.634  -6.506 -49.312  0.50 52.22           C
ATOM   1625  CE  LYS A 439     -37.563  -5.330 -49.017  0.50 52.84           C
ATOM   1626  NZ  LYS A 439     -39.007  -5.690 -49.161  0.50 54.20           N
ATOM   1627  C   LYS A 439     -34.325 -10.583 -49.197  0.50 44.56           C
ATOM   1628  O   LYS A 439     -33.629 -11.205 -48.383  0.50 49.22           O
ATOM   1629  N   SER A 440     -34.003 -10.463 -50.489  0.50 42.37           N
ATOM   1630  CA  SER A 440     -32.952 -11.256 -51.130  0.50 41.33           C
ATOM   1631  CB  SER A 440     -33.611 -12.291 -52.048  0.50 39.71           C
ATOM   1632  OG  SER A 440     -34.411 -13.170 -51.301  0.50 37.49           O
ATOM   1633  C   SER A 440     -31.982 -10.414 -51.967  0.50 43.20           C
ATOM   1634  O   SER A 440     -32.373  -9.425 -52.563  0.50 46.82           O
ATOM   1635  N   LEU A 441     -30.716 -10.812 -52.030  0.50 45.44           N
ATOM   1636  CA  LEU A 441     -29.794 -10.202 -52.997  0.50 41.78           C
ATOM   1637  CB  LEU A 441     -28.970  -9.052 -52.398  0.50 45.20           C
ATOM   1638  CG  LEU A 441     -28.464  -9.087 -50.954  0.50 43.57           C
ATOM   1639  CD1 LEU A 441     -28.517 -10.479 -50.332  0.50 41.33           C
ATOM   1640  CD2 LEU A 441     -27.075  -8.482 -50.857  0.50 40.94           C
ATOM   1641  C   LEU A 441     -28.869 -11.211 -53.661  0.50 42.49           C
ATOM   1642  O   LEU A 441     -28.719 -12.327 -53.187  0.50 40.76           O
ATOM   1643  N   SER A 442     -28.247 -10.786 -54.758  0.50 43.68           N
ATOM   1644  CA  SER A 442     -27.392 -11.649 -55.569  0.50 44.60           C
ATOM   1645  CB  SER A 442     -28.239 -12.652 -56.338  0.50 47.01           C
ATOM   1646  OG  SER A 442     -28.896 -11.980 -57.400  0.50 38.28           O
ATOM   1647  C   SER A 442     -26.692 -10.778 -56.582  0.50 43.96           C
ATOM   1648  O   SER A 442     -27.162  -9.676 -56.880  0.50 42.00           O
ATOM   1649  N   LEU A 443     -25.573 -11.265 -57.105  0.50 46.91           N
ATOM   1650  CA  LEU A 443     -24.823 -10.552 -58.149  0.50 53.55           C
```

Figure 26 (Continued)

```
ATOM    1651  CB  LEU A 443     -23.357 -10.998 -58.171  0.50 49.13           C
ATOM    1652  CG  LEU A 443     -22.428 -10.131 -59.021  0.50 49.62           C
ATOM    1653  CD1 LEU A 443     -22.698  -8.652 -58.781  0.50 48.48           C
ATOM    1654  CD2 LEU A 443     -20.973 -10.470 -58.761  0.50 47.55           C
ATOM    1655  C   LEU A 443     -25.431 -10.777 -59.526  0.50 56.92           C
ATOM    1656  O   LEU A 443     -25.586 -11.921 -59.954  0.50 56.16           O
ATOM    1657  N   SER A 444     -25.757  -9.681 -60.212  0.50 64.10           N
ATOM    1658  CA  SER A 444     -26.331  -9.723 -61.573  0.50 71.73           C
ATOM    1659  CB  SER A 444     -26.470  -8.303 -62.161  0.50 72.56           C
ATOM    1660  OG  SER A 444     -25.331  -7.492 -61.886  0.50 62.22           O
ATOM    1661  C   SER A 444     -25.565 -10.612 -62.548  0.50 65.37           C
ATOM    1662  O   SER A 444     -24.350 -10.496 -62.686  0.50 76.28           O
ATOM    1663  N   PRO A 445     -26.283 -11.479 -63.264  0.50 65.58           N
ATOM    1664  CA  PRO A 445     -25.572 -12.446 -64.086  0.50 64.21           C
ATOM    1665  CB  PRO A 445     -26.590 -12.805 -65.179  0.50 55.25           C
ATOM    1666  CG  PRO A 445     -27.682 -11.784 -65.082  0.50 58.39           C
ATOM    1667  CD  PRO A 445     -27.695 -11.343 -63.654  0.50 65.90           C
ATOM    1668  C   PRO A 445     -24.324 -11.816 -64.699  0.50 62.89           C
ATOM    1669  O   PRO A 445     -24.438 -10.847 -65.451  0.50 61.48           O
HETATM  1670  C1  NAG A 500     -24.461 -19.813  -6.754  0.50 62.83           C
HETATM  1671  C2  NAG A 500     -24.662 -18.322  -6.543  0.50 63.58           C
HETATM  1672  N2  NAG A 500     -24.840 -18.068  -5.124  0.50 71.12           N
HETATM  1673  C7  NAG A 500     -23.854 -17.543  -4.394  0.50 68.26           C
HETATM  1674  O7  NAG A 500     -22.760 -17.246  -4.866  0.50 67.64           O
HETATM  1675  C8  NAG A 500     -24.134 -17.311  -2.940  0.50 60.65           C
HETATM  1676  C3  NAG A 500     -25.846 -17.790  -7.351  0.50 63.43           C
HETATM  1677  O3  NAG A 500     -25.880 -16.382  -7.234  0.50 55.90           O
HETATM  1678  C4  NAG A 500     -25.705 -18.221  -8.814  0.50 59.88           C
HETATM  1679  O4  NAG A 500     -26.812 -17.843  -9.603  0.50 53.90           O
HETATM  1680  C5  NAG A 500     -25.598 -19.737  -8.858  0.50 61.33           C
HETATM  1681  C6  NAG A 500     -25.458 -20.241 -10.292  0.50 60.65           C
HETATM  1682  O6  NAG A 500     -24.348 -19.606 -10.892  0.50 63.48           O
HETATM  1683  O5  NAG A 500     -24.463 -20.143  -8.130  0.50 62.87           O
HETATM  1684  C1  FUC A 501     -23.657 -20.513 -11.773  0.50 63.55           C
HETATM  1685  C2  FUC A 501     -22.686 -19.687 -12.587  0.50 68.04           C
HETATM  1686  O2  FUC A 501     -23.429 -18.761 -13.332  0.50 72.88           O
HETATM  1687  C3  FUC A 501     -21.765 -18.919 -11.650  0.50 70.70           C
HETATM  1688  O3  FUC A 501     -20.771 -18.285 -12.416  0.50 64.41           O
HETATM  1689  C4  FUC A 501     -21.146 -19.854 -10.609  0.50 75.41           C
HETATM  1690  O4  FUC A 501     -20.167 -20.654 -11.226  0.50 78.35           O
HETATM  1691  C5  FUC A 501     -22.211 -20.776 -10.011  0.50 81.15           C
HETATM  1692  C6  FUC A 501     -21.644 -21.773  -8.997  0.50 73.69           C
HETATM  1693  O5  FUC A 501     -22.886 -21.443 -11.065  0.50 74.01           O
HETATM  1694  C1  NAG A 502     -26.586 -16.605 -10.282  0.50 47.73           C
HETATM  1695  C2  NAG A 502     -27.365 -16.637 -11.598  0.50 51.43           C
HETATM  1696  N2  NAG A 502     -26.763 -17.613 -12.481  0.50 50.99           N
HETATM  1697  C7  NAG A 502     -27.360 -18.717 -12.935  0.50 55.71           C
HETATM  1698  O7  NAG A 502     -26.772 -19.502 -13.692  0.50 58.19           O
HETATM  1699  C8  NAG A 502     -28.780 -18.991 -12.527  0.50 40.95           C
HETATM  1700  C3  NAG A 502     -27.369 -15.264 -12.272  0.50 48.62           C
HETATM  1701  O3  NAG A 502     -28.215 -15.290 -13.403  0.50 56.84           O
HETATM  1702  C4  NAG A 502     -27.852 -14.223 -11.271  0.50 50.33           C
HETATM  1703  O4  NAG A 502     -27.755 -12.905 -11.743  0.50 49.29           O
HETATM  1704  C5  NAG A 502     -26.979 -14.271 -10.022  0.50 49.31           C
HETATM  1705  C6  NAG A 502     -27.538 -13.275  -9.011  0.50 51.05           C
HETATM  1706  O6  NAG A 502     -26.713 -13.278  -7.869  0.50 62.04           O
HETATM  1707  O5  NAG A 502     -27.045 -15.559  -9.460  0.50 49.87           O
HETATM  1708  C1  BMA A 503     -28.886 -12.467 -12.512  0.50 48.94           C
HETATM  1709  O5  BMA A 503     -28.680 -12.819 -13.886  0.50 42.62           O
HETATM  1710  C5  BMA A 503     -29.655 -12.325 -14.793  0.50 49.27           C
HETATM  1711  C6  BMA A 503     -29.288 -12.882 -16.173  0.50 45.57           C
HETATM  1712  O6  BMA A 503     -29.124 -14.306 -16.032  0.50 53.95           O
HETATM  1713  C4  BMA A 503     -29.691 -10.795 -14.745  0.50 49.04           C
HETATM  1714  O4  BMA A 503     -30.799 -10.332 -15.519  0.50 54.36           O
```

Figure 26 (Continued)

```
HETATM 1715  C3  BMA A 503     -29.943 -10.290 -13.330  0.50 50.76           C
HETATM 1716  O3  BMA A 503     -29.759  -8.873 -13.348  0.50 55.06           O
HETATM 1717  C2  BMA A 503     -28.989 -10.951 -12.332  0.50 45.59           C
HETATM 1718  O2  BMA A 503     -27.684 -10.429 -12.565  0.50 48.32           O
HETATM 1719  C1  MAN A 504     -29.239 -14.921 -17.324  0.50 48.29           C
HETATM 1720  C2  MAN A 504     -29.556 -16.397 -17.205  0.50 49.02           C
HETATM 1721  O2  MAN A 504     -29.518 -16.985 -18.497  0.50 48.42           O
HETATM 1722  C3  MAN A 504     -28.480 -17.104 -16.413  0.50 47.89           C
HETATM 1723  O3  MAN A 504     -28.688 -18.493 -16.538  0.50 43.37           O
HETATM 1724  C4  MAN A 504     -27.137 -16.816 -17.043  0.50 51.96           C
HETATM 1725  O4  MAN A 504     -26.125 -17.292 -16.188  0.50 56.91           O
HETATM 1726  C5  MAN A 504     -26.946 -15.332 -17.301  0.50 53.60           C
HETATM 1727  C6  MAN A 504     -25.677 -15.139 -18.116  0.50 55.05           C
HETATM 1728  O6  MAN A 504     -25.701 -13.828 -18.650  0.50 59.48           O
HETATM 1729  O5  MAN A 504     -28.039 -14.805 -18.032  0.50 54.19           O
HETATM 1730  C1  NAG A 505     -30.851 -17.014 -19.045  0.50 46.08           C
HETATM 1731  C2  NAG A 505     -30.778 -16.922 -20.566  0.50 47.56           C
HETATM 1732  N2  NAG A 505     -30.173 -15.665 -20.947  0.50 43.51           N
HETATM 1733  C7  NAG A 505     -28.891 -15.595 -21.273  0.50 48.83           C
HETATM 1734  O7  NAG A 505     -28.185 -16.579 -21.318  0.50 52.29           O
HETATM 1735  C8  NAG A 505     -28.355 -14.233 -21.575  0.50 47.40           C
HETATM 1736  C3  NAG A 505     -32.144 -17.030 -21.236  0.50 47.89           C
HETATM 1737  O3  NAG A 505     -31.960 -17.267 -22.633  0.50 43.04           O
HETATM 1738  C4  NAG A 505     -33.025 -18.116 -20.633  0.50 46.95           C
HETATM 1739  O4  NAG A 505     -34.376 -17.876 -21.041  0.50 52.51           O
HETATM 1740  C5  NAG A 505     -32.958 -18.087 -19.111  0.50 52.33           C
HETATM 1741  C6  NAG A 505     -33.770 -19.230 -18.520  0.50 49.28           C
HETATM 1742  O6  NAG A 505     -33.113 -20.469 -18.775  0.50 46.66           O
HETATM 1743  O5  NAG A 505     -31.606 -18.161 -18.664  0.50 49.77           O
HETATM 1744  C1  GAL A 506     -35.064 -19.115 -21.269  0.50 62.40           C
HETATM 1745  C2  GAL A 506     -36.412 -18.829 -21.946  0.50 67.86           C
HETATM 1746  O2  GAL A 506     -37.343 -18.288 -21.004  0.50 62.18           O
HETATM 1747  C3  GAL A 506     -37.039 -20.066 -22.580  0.50 71.45           C
HETATM 1748  O3  GAL A 506     -38.120 -19.691 -23.431  0.50 87.82           O
HETATM 1749  C4  GAL A 506     -35.995 -20.796 -23.394  0.50 73.92           C
HETATM 1750  O4  GAL A 506     -35.486 -19.907 -24.384  0.50 64.89           O
HETATM 1751  C5  GAL A 506     -34.865 -21.177 -22.460  0.50 72.91           C
HETATM 1752  C6  GAL A 506     -33.840 -22.056 -23.161  0.50 65.22           C
HETATM 1753  O6  GAL A 506     -32.551 -21.789 -22.607  0.50 59.70           O
HETATM 1754  O5  GAL A 506     -34.232 -19.977 -22.041  0.50 76.38           O
HETATM 1755  C1  MAN A 507     -30.731  -8.141 -12.956  0.50 65.77           C
HETATM 1756  C2  MAN A 507     -30.567  -6.642 -13.128  0.50 72.83           C
HETATM 1757  O2  MAN A 507     -31.650  -5.978 -12.485  0.50 87.61           O
HETATM 1758  C3  MAN A 507     -29.298  -6.204 -12.430  0.50 71.11           C
HETATM 1759  O3  MAN A 507     -29.157  -4.789 -12.538  0.50 75.86           O
HETATM 1760  C4  MAN A 507     -29.371  -6.601 -10.965  0.50 78.83           C
HETATM 1761  O4  MAN A 507     -28.102  -6.359 -10.354  0.50 84.00           O
HETATM 1762  C5  MAN A 507     -29.717  -8.077 -10.822  0.50 76.36           C
HETATM 1763  C6  MAN A 507     -29.914  -8.454  -9.359  0.50 74.38           C
HETATM 1764  O6  MAN A 507     -28.820  -9.266  -8.918  0.50 75.58           O
HETATM 1765  O5  MAN A 507     -30.897  -8.382 -11.563  0.50 79.47           O
HETATM 1766  C1  NAG A 508     -32.880  -6.356 -13.117  0.50101.11           C
HETATM 1767  C2  NAG A 508     -34.000  -6.318 -12.083  0.50101.78           C
HETATM 1768  N2  NAG A 508     -33.720  -7.247 -11.009  0.50103.51           N
HETATM 1769  C7  NAG A 508     -33.823  -6.893  -9.732  0.50100.48           C
HETATM 1770  O7  NAG A 508     -34.356  -7.610  -8.903  0.50103.02           O
HETATM 1771  C8  NAG A 508     -33.237  -5.558  -9.380  0.50 97.80           C
HETATM 1772  C3  NAG A 508     -35.332  -6.669 -12.725  0.50102.07           C
HETATM 1773  O3  NAG A 508     -36.395  -6.501 -11.782  0.50102.71           O
HETATM 1774  C4  NAG A 508     -35.552  -5.768 -13.928  0.50106.43           C
HETATM 1775  O4  NAG A 508     -36.777  -6.113 -14.577  0.50 97.11           O
HETATM 1776  C5  NAG A 508     -34.384  -5.932 -14.887  0.50106.48           C
HETATM 1777  C6  NAG A 508     -34.582  -5.114 -16.155  0.50114.45           C
HETATM 1778  O6  NAG A 508     -34.438  -5.968 -17.291  0.50111.34           O
```

Figure 26 (Continued)

```
HETATM 1779  O5  NAG A 508     -33.195   -5.514  -14.227  0.50100.86           O
ATOM   1780  N   GLY B 236     -19.747    6.370    6.102  0.50 76.91           N
ATOM   1781  CA  GLY B 236     -18.972    5.908    4.912  0.50 84.07           C
ATOM   1782  C   GLY B 236     -17.996    6.954    4.400  0.50 91.85           C
ATOM   1783  O   GLY B 236     -18.409    8.012    3.923  0.50 85.02           O
ATOM   1784  N   GLY B 237     -16.699    6.654    4.494  0.50 99.00           N
ATOM   1785  CA  GLY B 237     -15.642    7.570    4.042  0.50 90.88           C
ATOM   1786  C   GLY B 237     -15.812    8.068    2.611  0.50 83.45           C
ATOM   1787  O   GLY B 237     -16.867    7.882    2.001  0.50 83.54           O
ATOM   1788  N   PRO B 238     -14.777    8.730    2.074  0.50 76.61           N
ATOM   1789  CA  PRO B 238     -14.800    9.251    0.705  0.50 72.19           C
ATOM   1790  CB  PRO B 238     -13.627   10.232    0.683  0.50 73.86           C
ATOM   1791  CG  PRO B 238     -12.697    9.743    1.744  0.50 77.59           C
ATOM   1792  CD  PRO B 238     -13.549    9.104    2.801  0.50 71.96           C
ATOM   1793  C   PRO B 238     -14.562    8.157   -0.324  0.50 69.62           C
ATOM   1794  O   PRO B 238     -13.866    7.183   -0.036  0.50 65.63           O
ATOM   1795  N   SER B 239     -15.142    8.328   -1.512  0.50 67.42           N
ATOM   1796  CA  SER B 239     -14.943    7.395   -2.622  0.50 63.55           C
ATOM   1797  CB  SER B 239     -16.272    6.780   -3.058  0.50 58.49           C
ATOM   1798  OG  SER B 239     -16.550    5.632   -2.282  0.50 56.84           O
ATOM   1799  C   SER B 239     -14.254    8.046   -3.819  0.50 61.55           C
ATOM   1800  O   SER B 239     -14.326    9.266   -4.012  0.50 60.89           O
ATOM   1801  N   VAL B 240     -13.576    7.227   -4.617  0.50 57.35           N
ATOM   1802  CA  VAL B 240     -12.838    7.751   -5.768  0.50 54.98           C
ATOM   1803  CB  VAL B 240     -11.315    7.639   -5.577  0.50 57.00           C
ATOM   1804  CG1 VAL B 240     -10.598    8.292   -6.750  0.50 53.86           C
ATOM   1805  CG2 VAL B 240     -10.889    8.269   -4.243  0.50 58.49           C
ATOM   1806  C   VAL B 240     -13.205    7.045   -7.064  0.50 54.88           C
ATOM   1807  O   VAL B 240     -13.220    5.804   -7.138  0.50 50.17           O
ATOM   1808  N   PHE B 241     -13.466    7.843   -8.094  0.50 53.91           N
ATOM   1809  CA  PHE B 241     -13.728    7.303   -9.425  0.50 52.37           C
ATOM   1810  CB  PHE B 241     -15.173    7.562   -9.832  0.50 52.81           C
ATOM   1811  CG  PHE B 241     -16.169    6.915   -8.917  0.50 58.29           C
ATOM   1812  CD1 PHE B 241     -16.451    5.556   -9.022  0.50 60.69           C
ATOM   1813  CE1 PHE B 241     -17.347    4.951   -8.154  0.50 60.20           C
ATOM   1814  CZ  PHE B 241     -17.958    5.701   -7.158  0.50 66.06           C
ATOM   1815  CE2 PHE B 241     -17.677    7.052   -7.031  0.50 57.04           C
ATOM   1816  CD2 PHE B 241     -16.777    7.649   -7.898  0.50 62.84           C
ATOM   1817  C   PHE B 241     -12.759    7.876  -10.444  0.50 50.65           C
ATOM   1818  O   PHE B 241     -12.523    9.079  -10.479  0.50 45.38           O
ATOM   1819  N   LEU B 242     -12.208    6.996  -11.277  0.50 51.21           N
ATOM   1820  CA  LEU B 242     -11.128    7.352  -12.191  0.50 48.68           C
ATOM   1821  CB  LEU B 242      -9.914    6.459  -11.926  0.50 41.87           C
ATOM   1822  CG  LEU B 242      -8.598    6.779  -12.645  0.50 43.50           C
ATOM   1823  CD1 LEU B 242      -8.163    8.221  -12.438  0.50 40.49           C
ATOM   1824  CD2 LEU B 242      -7.507    5.815  -12.192  0.50 43.46           C
ATOM   1825  C   LEU B 242     -11.612    7.177  -13.633  0.50 47.83           C
ATOM   1826  O   LEU B 242     -12.082    6.113  -14.007  0.50 41.96           O
ATOM   1827  N   PHE B 243     -11.484    8.230  -14.428  0.50 44.78           N
ATOM   1828  CA  PHE B 243     -12.021    8.263  -15.784  0.50 45.56           C
ATOM   1829  CB  PHE B 243     -12.998    9.432  -15.925  0.50 48.25           C
ATOM   1830  CG  PHE B 243     -14.235    9.281  -15.083  0.50 50.80           C
ATOM   1831  CD1 PHE B 243     -15.436    8.848  -15.648  0.50 54.81           C
ATOM   1832  CE1 PHE B 243     -16.574    8.699  -14.866  0.50 51.62           C
ATOM   1833  CZ  PHE B 243     -16.511    8.954  -13.505  0.50 56.77           C
ATOM   1834  CE2 PHE B 243     -15.319    9.361  -12.925  0.50 54.88           C
ATOM   1835  CD2 PHE B 243     -14.189    9.520  -13.714  0.50 54.47           C
ATOM   1836  C   PHE B 243     -10.909    8.383  -16.825  0.50 46.12           C
ATOM   1837  O   PHE B 243      -9.924    9.090  -16.585  0.50 42.67           O
ATOM   1838  N   PRO B 244     -11.062    7.681  -17.977  0.50 41.92           N
ATOM   1839  CA  PRO B 244     -10.044    7.601  -19.031  0.50 38.39           C
ATOM   1840  CB  PRO B 244     -10.337    6.243  -19.680  0.50 36.96           C
ATOM   1841  CG  PRO B 244     -11.829    6.115  -19.564  0.50 38.26           C
ATOM   1842  CD  PRO B 244     -12.226    6.819  -18.282  0.50 39.68           C
```

Figure 26 (Continued)

```
ATOM   1843  C    PRO B 244     -10.179   8.706 -20.070  0.50 35.00           C
ATOM   1844  O    PRO B 244     -11.201   9.382 -20.127  0.50 30.04           O
ATOM   1845  N    PRO B 245      -9.138   8.905 -20.893  0.50 35.16           N
ATOM   1846  CA   PRO B 245      -9.344   9.842 -21.991  0.50 34.16           C
ATOM   1847  CB   PRO B 245      -8.006   9.849 -22.732  0.50 34.59           C
ATOM   1848  CG   PRO B 245      -7.079   8.947 -21.997  0.50 34.85           C
ATOM   1849  CD   PRO B 245      -7.868   8.162 -20.985  0.50 35.77           C
ATOM   1850  C    PRO B 245     -10.469   9.355 -22.901  0.50 33.02           C
ATOM   1851  O    PRO B 245     -10.840   8.181 -22.862  0.50 33.46           O
ATOM   1852  N    LYS B 246     -11.078  10.265 -23.641  0.50 33.69           N
ATOM   1853  CA   LYS B 246     -11.929   9.873 -24.757  0.50 38.19           C
ATOM   1854  CB   LYS B 246     -12.626  11.100 -25.354  0.50 37.98           C
ATOM   1855  CG   LYS B 246     -13.706  11.713 -24.478  0.50 40.04           C
ATOM   1856  CD   LYS B 246     -14.833  10.727 -24.245  0.50 46.58           C
ATOM   1857  CE   LYS B 246     -15.921  11.298 -23.317  0.50 49.98           C
ATOM   1858  NZ   LYS B 246     -15.472  11.497 -21.906  0.50 47.89           N
ATOM   1859  C    LYS B 246     -10.998   9.303 -25.811  0.50 33.89           C
ATOM   1860  O    LYS B 246      -9.999   9.926 -26.126  0.50 35.12           O
ATOM   1861  N    PRO B 247     -11.341   8.140 -26.383  0.50 33.37           N
ATOM   1862  CA   PRO B 247     -10.556   7.568 -27.491  0.50 32.94           C
ATOM   1863  CB   PRO B 247     -11.531   6.561 -28.138  0.50 34.31           C
ATOM   1864  CG   PRO B 247     -12.548   6.252 -27.065  0.50 37.66           C
ATOM   1865  CD   PRO B 247     -12.687   7.538 -26.279  0.50 36.45           C
ATOM   1866  C    PRO B 247     -10.155   8.614 -28.527  0.50 29.88           C
ATOM   1867  O    PRO B 247      -9.008   8.749 -28.851  0.50 35.80           O
ATOM   1868  N    LYS B 248     -11.119   9.336 -29.052  0.50 30.67           N
ATOM   1869  CA   LYS B 248     -10.861  10.372 -30.034  0.50 31.99           C
ATOM   1870  CB   LYS B 248     -12.173  11.125 -30.320  0.50 33.72           C
ATOM   1871  CG   LYS B 248     -12.058  12.276 -31.311  0.50 35.15           C
ATOM   1872  CD   LYS B 248     -13.374  13.040 -31.405  0.50 36.02           C
ATOM   1873  CE   LYS B 248     -13.248  14.299 -32.255  0.50 41.24           C
ATOM   1874  NZ   LYS B 248     -14.569  14.695 -32.833  0.50 36.12           N
ATOM   1875  C    LYS B 248      -9.798  11.361 -29.545  0.50 34.45           C
ATOM   1876  O    LYS B 248      -9.000  11.867 -30.354  0.50 33.34           O
ATOM   1877  N    ASP B 249      -9.732  11.609 -28.231  0.50 34.82           N
ATOM   1878  CA   ASP B 249      -8.758  12.623 -27.739  0.50 33.79           C
ATOM   1879  CB   ASP B 249      -9.034  13.048 -26.283  0.50 31.86           C
ATOM   1880  CG   ASP B 249     -10.345  13.853 -26.102  0.50 35.70           C
ATOM   1881  OD1  ASP B 249     -10.920  14.349 -27.085  0.50 30.81           O
ATOM   1882  OD2  ASP B 249     -10.807  13.942 -24.930  0.50 35.59           O
ATOM   1883  C    ASP B 249      -7.361  12.015 -27.780  0.50 33.78           C
ATOM   1884  O    ASP B 249      -6.370  12.730 -27.907  0.50 35.83           O
ATOM   1885  N    THR B 250      -7.269  10.696 -27.584  0.50 31.72           N
ATOM   1886  CA   THR B 250      -5.969  10.045 -27.606  0.50 31.46           C
ATOM   1887  CB   THR B 250      -6.000   8.654 -26.933  0.50 34.52           C
ATOM   1888  OG1  THR B 250      -6.793   7.753 -27.719  0.50 30.89           O
ATOM   1889  CG2  THR B 250      -6.623   8.742 -25.497  0.50 33.49           C
ATOM   1890  C    THR B 250      -5.436   9.915 -29.031  0.50 32.70           C
ATOM   1891  O    THR B 250      -4.229   9.762 -29.230  0.50 37.12           O
ATOM   1892  N    LEU B 251      -6.331   9.988 -30.014  0.50 29.53           N
ATOM   1893  CA   LEU B 251      -5.969   9.693 -31.431  0.50 29.33           C
ATOM   1894  CB   LEU B 251      -7.126   8.925 -32.113  0.50 28.29           C
ATOM   1895  CG   LEU B 251      -7.364   7.508 -31.514  0.50 30.49           C
ATOM   1896  CD1  LEU B 251      -8.644   6.903 -32.070  0.50 24.34           C
ATOM   1897  CD2  LEU B 251      -6.182   6.572 -31.769  0.50 24.38           C
ATOM   1898  C    LEU B 251      -5.608  10.891 -32.301  0.50 30.18           C
ATOM   1899  O    LEU B 251      -4.800  10.763 -33.225  0.50 34.46           O
ATOM   1900  N    MET B 252      -6.277  12.026 -32.068  0.50 30.03           N
ATOM   1901  CA   MET B 252      -6.020  13.257 -32.799  0.50 35.49           C
ATOM   1902  CB   MET B 252      -7.342  13.991 -33.046  0.50 32.28           C
ATOM   1903  CG   MET B 252      -8.421  13.151 -33.685  0.50 38.95           C
ATOM   1904  SD   MET B 252      -7.994  12.537 -35.326  0.50 46.66           S
ATOM   1905  CE   MET B 252      -7.225  11.033 -34.807  0.50 34.31           C
ATOM   1906  C    MET B 252      -5.070  14.182 -32.020  0.50 36.53           C
```

Figure 26 (Continued)

```
ATOM   1907  O    MET B 252      -5.404  14.642 -30.912  0.50 32.75           O
ATOM   1908  N    ILE B 253      -3.909  14.463 -32.604  0.50 36.43           N
ATOM   1909  CA   ILE B 253      -2.876  15.255 -31.930  0.50 39.17           C
ATOM   1910  CB   ILE B 253      -1.540  15.192 -32.719  0.50 38.97           C
ATOM   1911  CG1  ILE B 253      -0.392  15.858 -31.943  0.50 38.35           C
ATOM   1912  CD1  ILE B 253      -0.322  15.460 -30.495  0.50 33.94           C
ATOM   1913  CG2  ILE B 253      -1.685  15.832 -34.093  0.50 33.30           C
ATOM   1914  C    ILE B 253      -3.333  16.701 -31.545  0.50 40.65           C
ATOM   1915  O    ILE B 253      -2.790  17.317 -30.653  0.50 40.20           O
ATOM   1916  N    SER B 254      -4.438  17.162 -32.106  0.50 42.45           N
ATOM   1917  CA   SER B 254      -4.911  18.517 -31.867  0.50 38.38           C
ATOM   1918  CB   SER B 254      -5.774  18.960 -33.029  0.50 36.81           C
ATOM   1919  OG   SER B 254      -6.939  18.152 -33.086  0.50 36.18           O
ATOM   1920  C    SER B 254      -5.745  18.579 -30.619  0.50 40.33           C
ATOM   1921  O    SER B 254      -6.045  19.651 -30.124  0.50 39.19           O
ATOM   1922  N    ARG B 255      -6.164  17.426 -30.130  0.50 38.18           N
ATOM   1923  CA   ARG B 255      -6.971  17.374 -28.932  0.50 34.94           C
ATOM   1924  CB   ARG B 255      -8.091  16.361 -29.130  0.50 40.73           C
ATOM   1925  CG   ARG B 255      -8.875  16.633 -30.408  0.50 41.34           C
ATOM   1926  CD   ARG B 255     -10.018  15.669 -30.585  0.50 42.54           C
ATOM   1927  NE   ARG B 255     -10.901  15.690 -29.432  0.50 47.51           N
ATOM   1928  CZ   ARG B 255     -12.013  16.422 -29.354  0.50 53.50           C
ATOM   1929  NH1  ARG B 255     -12.373  17.208 -30.378  0.50 48.09           N
ATOM   1930  NH2  ARG B 255     -12.761  16.375 -28.246  0.50 48.81           N
ATOM   1931  C    ARG B 255      -6.117  17.014 -27.732  0.50 39.14           C
ATOM   1932  O    ARG B 255      -4.956  16.599 -27.889  0.50 37.99           O
ATOM   1933  N    THR B 256      -6.687  17.129 -26.535  0.50 37.42           N
ATOM   1934  CA   THR B 256      -5.918  16.931 -25.333  0.50 34.62           C
ATOM   1935  CB   THR B 256      -5.769  18.261 -24.569  0.50 45.73           C
ATOM   1936  OG1  THR B 256      -4.864  19.112 -25.287  0.50 38.37           O
ATOM   1937  CG2  THR B 256      -5.241  18.034 -23.151  0.50 45.76           C
ATOM   1938  C    THR B 256      -6.613  15.913 -24.454  0.50 37.95           C
ATOM   1939  O    THR B 256      -7.665  16.174 -23.913  0.50 38.81           O
ATOM   1940  N    PRO B 257      -6.059  14.697 -24.384  0.50 38.75           N
ATOM   1941  CA   PRO B 257      -6.645  13.625 -23.600  0.50 38.62           C
ATOM   1942  CB   PRO B 257      -5.837  12.405 -24.034  0.50 36.33           C
ATOM   1943  CG   PRO B 257      -4.550  12.962 -24.580  0.50 36.20           C
ATOM   1944  CD   PRO B 257      -4.990  14.217 -25.268  0.50 37.36           C
ATOM   1945  C    PRO B 257      -6.438  13.865 -22.103  0.50 34.97           C
ATOM   1946  O    PRO B 257      -5.390  14.346 -21.721  0.50 29.99           O
ATOM   1947  N    GLU B 258      -7.387  13.454 -21.269  0.50 32.86           N
ATOM   1948  CA   GLU B 258      -7.214  13.642 -19.828  0.50 36.99           C
ATOM   1949  CB   GLU B 258      -8.015  14.864 -19.342  0.50 36.85           C
ATOM   1950  CG   GLU B 258      -7.581  16.171 -20.012  0.50 39.72           C
ATOM   1951  CD   GLU B 258      -8.601  17.295 -19.868  0.50 41.47           C
ATOM   1952  OE1  GLU B 258      -9.640  17.079 -19.203  0.50 42.92           O
ATOM   1953  OE2  GLU B 258      -8.363  18.401 -20.423  0.50 41.83           O
ATOM   1954  C    GLU B 258      -7.667  12.443 -19.065  0.50 34.19           C
ATOM   1955  O    GLU B 258      -8.677  11.830 -19.403  0.50 32.52           O
ATOM   1956  N    VAL B 259      -6.949  12.126 -18.001  0.50 35.95           N
ATOM   1957  CA   VAL B 259      -7.443  11.163 -17.036  0.50 36.33           C
ATOM   1958  CB   VAL B 259      -6.349  10.166 -16.632  0.50 40.24           C
ATOM   1959  CG1  VAL B 259      -6.817   9.339 -15.453  0.50 40.30           C
ATOM   1960  CG2  VAL B 259      -6.006   9.232 -17.804  0.50 39.65           C
ATOM   1961  C    VAL B 259      -7.940  11.945 -15.801  0.50 43.11           C
ATOM   1962  O    VAL B 259      -7.207  12.764 -15.213  0.50 33.86           O
ATOM   1963  N    THR B 260      -9.181  11.677 -15.404  0.50 43.75           N
ATOM   1964  CA   THR B 260      -9.866  12.504 -14.419  0.50 41.71           C
ATOM   1965  CB   THR B 260     -11.156  13.050 -14.984  0.50 38.15           C
ATOM   1966  OG1  THR B 260     -10.836  13.751 -16.181  0.50 42.37           O
ATOM   1967  CG2  THR B 260     -11.819  14.011 -13.996  0.50 36.55           C
ATOM   1968  C    THR B 260     -10.160  11.732 -13.170  0.50 43.45           C
ATOM   1969  O    THR B 260     -10.758  10.660 -13.229  0.50 41.44           O
ATOM   1970  N    CYS B 261      -9.660  12.247 -12.050  0.50 42.51           N
```

Figure 26 (Continued)

```
ATOM   1971  CA   CYS B 261      -9.804  11.558 -10.767  0.50 44.48           C
ATOM   1972  CB   CYS B 261      -8.450  11.444 -10.079  0.50 40.22           C
ATOM   1973  SG   CYS B 261      -8.445  10.347  -8.645  0.50 47.10           S
ATOM   1974  C    CYS B 261     -10.806  12.339  -9.906  0.50 46.68           C
ATOM   1975  O    CYS B 261     -10.568  13.499  -9.566  0.50 45.88           O
ATOM   1976  N    VAL B 262     -11.944  11.709  -9.626  0.50 44.65           N
ATOM   1977  CA   VAL B 262     -13.049  12.333  -8.915  0.50 47.56           C
ATOM   1978  CB   VAL B 262     -14.372  12.163  -9.697  0.50 49.91           C
ATOM   1979  CG1  VAL B 262     -15.530  12.781  -8.932  0.50 49.97           C
ATOM   1980  CG2  VAL B 262     -14.262  12.809 -11.082  0.50 41.30           C
ATOM   1981  C    VAL B 262     -13.193  11.721  -7.522  0.50 52.78           C
ATOM   1982  O    VAL B 262     -13.200  10.486  -7.380  0.50 54.46           O
ATOM   1983  N    VAL B 263     -13.241  12.579  -6.496  0.50 50.42           N
ATOM   1984  CA   VAL B 263     -13.570  12.143  -5.120  0.50 49.82           C
ATOM   1985  CB   VAL B 263     -12.501  12.554  -4.087  0.50 51.81           C
ATOM   1986  CG1  VAL B 263     -12.775  11.874  -2.757  0.50 52.13           C
ATOM   1987  CG2  VAL B 263     -11.097  12.199  -4.567  0.50 52.81           C
ATOM   1988  C    VAL B 263     -14.924  12.707  -4.694  0.50 47.53           C
ATOM   1989  O    VAL B 263     -15.207  13.908  -4.859  0.50 48.13           O
ATOM   1990  N    VAL B 264     -15.800  11.819  -4.242  0.50 49.71           N
ATOM   1991  CA   VAL B 264     -17.086  12.225  -3.684  0.50 46.07           C
ATOM   1992  CB   VAL B 264     -18.282  11.700  -4.518  0.50 43.67           C
ATOM   1993  CG1  VAL B 264     -18.361  12.434  -5.863  0.50 43.05           C
ATOM   1994  CG2  VAL B 264     -18.233  10.182  -4.693  0.50 39.05           C
ATOM   1995  C    VAL B 264     -17.180  11.732  -2.243  0.50 49.79           C
ATOM   1996  O    VAL B 264     -16.304  10.991  -1.782  0.50 47.01           O
ATOM   1997  N    ASP B 265     -18.247  12.131  -1.543  0.50 54.18           N
ATOM   1998  CA   ASP B 265     -18.462  11.747  -0.140  0.50 47.53           C
ATOM   1999  CB   ASP B 265     -18.520  10.220   0.029  0.50 48.82           C
ATOM   2000  CG   ASP B 265     -19.806   9.606  -0.477  0.50 46.55           C
ATOM   2001  OD1  ASP B 265     -20.756  10.320  -0.864  0.50 48.90           O
ATOM   2002  OD2  ASP B 265     -19.861   8.367  -0.472  0.50 43.99           O
ATOM   2003  C    ASP B 265     -17.364  12.249   0.784  0.50 45.54           C
ATOM   2004  O    ASP B 265     -17.104  11.628   1.810  0.50 53.89           O
ATOM   2005  N    VAL B 266     -16.670  13.320   0.418  0.50 50.69           N
ATOM   2006  CA   VAL B 266     -15.742  13.909   1.372  0.50 57.33           C
ATOM   2007  CB   VAL B 266     -14.766  14.922   0.718  0.50 61.66           C
ATOM   2008  CG1  VAL B 266     -13.827  15.517   1.766  0.50 56.14           C
ATOM   2009  CG2  VAL B 266     -13.952  14.251  -0.385  0.50 64.05           C
ATOM   2010  C    VAL B 266     -16.590  14.567   2.484  0.50 55.03           C
ATOM   2011  O    VAL B 266     -17.740  14.961   2.246  0.50 45.25           O
ATOM   2012  N    SER B 267     -16.037  14.656   3.690  0.50 56.36           N
ATOM   2013  CA   SER B 267     -16.775  15.242   4.830  0.50 58.95           C
ATOM   2014  CB   SER B 267     -16.564  14.401   6.082  0.50 51.42           C
ATOM   2015  OG   SER B 267     -15.239  14.575   6.553  0.50 54.83           O
ATOM   2016  C    SER B 267     -16.380  16.686   5.137  0.50 59.54           C
ATOM   2017  O    SER B 267     -15.291  17.142   4.770  0.50 60.80           O
ATOM   2018  N    HIS B 268     -17.266  17.400   5.826  0.50 68.04           N
ATOM   2019  CA   HIS B 268     -16.942  18.730   6.347  0.50 70.83           C
ATOM   2020  CB   HIS B 268     -18.198  19.397   6.910  0.50 77.48           C
ATOM   2021  CG   HIS B 268     -19.089  19.992   5.867  0.50 84.73           C
ATOM   2022  ND1  HIS B 268     -19.084  21.338   5.565  0.50 89.88           N
ATOM   2023  CE1  HIS B 268     -19.969  21.576   4.613  0.50 88.16           C
ATOM   2024  NE2  HIS B 268     -20.548  20.434   4.286  0.50 86.02           N
ATOM   2025  CD2  HIS B 268     -20.016  19.428   5.057  0.50 85.99           C
ATOM   2026  C    HIS B 268     -15.863  18.646   7.436  0.50 67.89           C
ATOM   2027  O    HIS B 268     -15.095  19.585   7.645  0.50 68.25           O
ATOM   2028  N    GLU B 269     -15.814  17.506   8.118  0.50 73.60           N
ATOM   2029  CA   GLU B 269     -14.901  17.299   9.241  0.50 83.04           C
ATOM   2030  CB   GLU B 269     -15.474  16.256  10.208  0.50 81.62           C
ATOM   2031  CG   GLU B 269     -16.878  16.571  10.711  0.50 87.55           C
ATOM   2032  CD   GLU B 269     -17.961  16.323   9.668  0.50 95.81           C
ATOM   2033  OE1  GLU B 269     -17.627  16.045   8.493  0.50 88.41           O
ATOM   2034  OE2  GLU B 269     -19.158  16.410  10.029  0.50103.58           O
```

Figure 26 (Continued)

```
ATOM   2035  C    GLU B 269     -13.516  16.859   8.777  0.50 85.91           C
ATOM   2036  O    GLU B 269     -12.570  16.819   9.567  0.50 87.40           O
ATOM   2037  N    GLU B 270     -13.407  16.521   7.495  0.50 81.60           N
ATOM   2038  CA   GLU B 270     -12.148  16.058   6.923  0.50 79.43           C
ATOM   2039  CB   GLU B 270     -12.164  14.538   6.817  0.50 82.37           C
ATOM   2040  CG   GLU B 270     -12.978  13.861   7.902  0.50 91.54           C
ATOM   2041  CD   GLU B 270     -12.169  13.630   9.154  0.50 84.71           C
ATOM   2042  OE1  GLU B 270     -12.492  12.685   9.903  0.50 90.34           O
ATOM   2043  OE2  GLU B 270     -11.196  14.382   9.367  0.50 83.97           O
ATOM   2044  C    GLU B 270     -11.964  16.643   5.529  0.50 74.30           C
ATOM   2045  O    GLU B 270     -11.644  15.925   4.586  0.50 72.06           O
ATOM   2046  N    PRO B 271     -12.145  17.961   5.400  0.50 74.53           N
ATOM   2047  CA   PRO B 271     -12.363  18.565   4.085  0.50 69.10           C
ATOM   2048  CB   PRO B 271     -12.582  20.042   4.423  0.50 67.97           C
ATOM   2049  CG   PRO B 271     -11.757  20.254   5.656  0.50 63.25           C
ATOM   2050  CD   PRO B 271     -11.845  18.969   6.435  0.50 66.84           C
ATOM   2051  C    PRO B 271     -11.153  18.409   3.160  0.50 67.52           C
ATOM   2052  O    PRO B 271     -11.295  18.485   1.937  0.50 68.61           O
ATOM   2053  N    GLU B 272      -9.973  18.219   3.748  0.50 63.29           N
ATOM   2054  CA   GLU B 272      -8.726  18.223   2.992  0.50 59.41           C
ATOM   2055  CB   GLU B 272      -7.504  18.333   3.916  0.50 55.31           C
ATOM   2056  CG   GLU B 272      -7.223  19.729   4.472  0.50 59.64           C
ATOM   2057  CD   GLU B 272      -6.041  19.735   5.440  0.50 56.83           C
ATOM   2058  OE1  GLU B 272      -5.065  20.485   5.205  0.50 48.72           O
ATOM   2059  OE2  GLU B 272      -6.063  18.946   6.411  0.50 62.27           O
ATOM   2060  C    GLU B 272      -8.606  16.964   2.139  0.50 54.81           C
ATOM   2061  O    GLU B 272      -8.786  15.843   2.624  0.50 54.61           O
ATOM   2062  N    VAL B 273      -8.299  17.162   0.863  0.50 51.37           N
ATOM   2063  CA   VAL B 273      -7.981  16.048  -0.012  0.50 49.46           C
ATOM   2064  CB   VAL B 273      -9.199  15.681  -0.867  0.50 55.82           C
ATOM   2065  CG1  VAL B 273     -10.302  15.140   0.035  0.50 47.39           C
ATOM   2066  CG2  VAL B 273      -9.696  16.903  -1.637  0.50 51.11           C
ATOM   2067  C    VAL B 273      -6.782  16.378  -0.880  0.50 44.78           C
ATOM   2068  O    VAL B 273      -6.796  17.375  -1.611  0.50 44.88           O
ATOM   2069  N    LYS B 274      -5.735  15.561  -0.760  0.50 41.62           N
ATOM   2070  CA   LYS B 274      -4.541  15.691  -1.590  0.50 43.97           C
ATOM   2071  CB   LYS B 274      -3.284  15.632  -0.712  0.50 44.90           C
ATOM   2072  CG   LYS B 274      -1.975  16.028  -1.394  0.50 41.36           C
ATOM   2073  CD   LYS B 274      -0.750  15.633  -0.556  0.50 39.65           C
ATOM   2074  CE   LYS B 274      -0.767  14.144  -0.200  0.50 34.83           C
ATOM   2075  NZ   LYS B 274       0.510  13.647   0.368  0.50 32.94           N
ATOM   2076  C    LYS B 274      -4.489  14.579  -2.660  0.50 49.08           C
ATOM   2077  O    LYS B 274      -4.992  13.468  -2.439  0.50 52.15           O
ATOM   2078  N    PHE B 275      -3.856  14.881  -3.795  0.50 51.50           N
ATOM   2079  CA   PHE B 275      -3.666  13.912  -4.892  0.50 55.58           C
ATOM   2080  CB   PHE B 275      -4.235  14.487  -6.189  0.50 50.11           C
ATOM   2081  CG   PHE B 275      -5.726  14.561  -6.209  0.50 53.64           C
ATOM   2082  CD1  PHE B 275      -6.376  15.785  -6.089  0.50 54.47           C
ATOM   2083  CE1  PHE B 275      -7.755  15.852  -6.123  0.50 60.92           C
ATOM   2084  CZ   PHE B 275      -8.502  14.692  -6.276  0.50 65.14           C
ATOM   2085  CE2  PHE B 275      -7.867  13.469  -6.395  0.50 57.22           C
ATOM   2086  CD2  PHE B 275      -6.485  13.409  -6.368  0.50 55.34           C
ATOM   2087  C    PHE B 275      -2.198  13.573  -5.148  0.50 52.84           C
ATOM   2088  O    PHE B 275      -1.384  14.476  -5.287  0.50 56.24           O
ATOM   2089  N    ASN B 276      -1.860  12.284  -5.215  0.50 48.00           N
ATOM   2090  CA   ASN B 276      -0.601  11.856  -5.855  0.50 48.50           C
ATOM   2091  CB   ASN B 276       0.238  10.959  -4.923  0.50 39.91           C
ATOM   2092  CG   ASN B 276       0.630  11.649  -3.605  0.50 44.67           C
ATOM   2093  OD1  ASN B 276      -0.065  11.510  -2.594  0.50 41.80           O
ATOM   2094  ND2  ASN B 276       1.747  12.388  -3.611  0.50 39.94           N
ATOM   2095  C    ASN B 276      -0.871  11.124  -7.213  0.50 49.73           C
ATOM   2096  O    ASN B 276      -1.775  10.285  -7.311  0.50 48.44           O
ATOM   2097  N    TRP B 277      -0.078  11.426  -8.238  0.50 49.57           N
ATOM   2098  CA   TRP B 277      -0.294  10.838  -9.568  0.50 47.56           C
```

Figure 26 (Continued)

```
ATOM   2099  CB   TRP B 277      -0.623  11.924 -10.591  0.50 46.41           C
ATOM   2100  CG   TRP B 277      -2.081  12.401 -10.582  0.50 49.50           C
ATOM   2101  CD1  TRP B 277      -2.563  13.521  -9.982  0.50 49.91           C
ATOM   2102  NE1  TRP B 277      -3.917  13.638 -10.202  0.50 56.11           N
ATOM   2103  CE2  TRP B 277      -4.336  12.589 -10.976  0.50 51.79           C
ATOM   2104  CD2  TRP B 277      -3.210  11.783 -11.237  0.50 51.96           C
ATOM   2105  CE3  TRP B 277      -3.369  10.637 -12.029  0.50 51.05           C
ATOM   2106  CZ3  TRP B 277      -4.632  10.330 -12.508  0.50 48.27           C
ATOM   2107  CH2  TRP B 277      -5.736  11.159 -12.235  0.50 47.40           C
ATOM   2108  CZ2  TRP B 277      -5.604  12.288 -11.466  0.50 51.96           C
ATOM   2109  C    TRP B 277       0.944  10.082 -10.020  0.50 51.02           C
ATOM   2110  O    TRP B 277       2.056  10.603  -9.963  0.50 52.76           O
ATOM   2111  N    TYR B 278       0.756   8.841 -10.455  0.50 49.64           N
ATOM   2112  CA   TYR B 278       1.871   8.049 -10.969  0.50 50.31           C
ATOM   2113  CB   TYR B 278       2.102   6.812 -10.096  0.50 48.48           C
ATOM   2114  CG   TYR B 278       2.148   7.079  -8.601  0.50 58.96           C
ATOM   2115  CD1  TYR B 278       0.991   7.394  -7.897  0.50 54.46           C
ATOM   2116  CE1  TYR B 278       1.015   7.608  -6.537  0.50 56.21           C
ATOM   2117  CZ   TYR B 278       2.205   7.514  -5.850  0.50 59.66           C
ATOM   2118  OH   TYR B 278       2.210   7.730  -4.492  0.50 58.30           O
ATOM   2119  CE2  TYR B 278       3.374   7.198  -6.518  0.50 62.78           C
ATOM   2120  CD2  TYR B 278       3.341   6.974  -7.887  0.50 59.08           C
ATOM   2121  C    TYR B 278       1.654   7.605 -12.427  0.50 51.30           C
ATOM   2122  O    TYR B 278       0.554   7.191 -12.806  0.50 45.14           O
ATOM   2123  N    VAL B 279       2.707   7.675 -13.235  0.50 51.07           N
ATOM   2124  CA   VAL B 279       2.667   7.054 -14.550  0.50 47.19           C
ATOM   2125  CB   VAL B 279       2.864   8.089 -15.667  0.50 46.04           C
ATOM   2126  CG1  VAL B 279       2.627   7.444 -17.029  0.50 50.18           C
ATOM   2127  CG2  VAL B 279       1.918   9.271 -15.460  0.50 37.99           C
ATOM   2128  C    VAL B 279       3.678   5.909 -14.624  0.50 47.16           C
ATOM   2129  O    VAL B 279       4.878   6.109 -14.485  0.50 50.75           O
ATOM   2130  N    ASP B 280       3.182   4.690 -14.776  0.50 45.13           N
ATOM   2131  CA   ASP B 280       4.054   3.539 -14.692  0.50 48.58           C
ATOM   2132  CB   ASP B 280       4.980   3.504 -15.912  0.50 44.01           C
ATOM   2133  CG   ASP B 280       4.277   3.032 -17.165  0.50 45.19           C
ATOM   2134  OD1  ASP B 280       3.106   2.595 -17.070  0.50 43.16           O
ATOM   2135  OD2  ASP B 280       4.901   3.117 -18.248  0.50 48.09           O
ATOM   2136  C    ASP B 280       4.896   3.614 -13.408  0.50 49.35           C
ATOM   2137  O    ASP B 280       6.093   3.311 -13.424  0.50 48.56           O
ATOM   2138  N    GLY B 281       4.275   4.052 -12.314  0.50 52.22           N
ATOM   2139  CA   GLY B 281       4.940   4.086 -11.004  0.50 50.99           C
ATOM   2140  C    GLY B 281       5.703   5.362 -10.692  0.50 51.14           C
ATOM   2141  O    GLY B 281       6.011   5.637  -9.538  0.50 54.69           O
ATOM   2142  N    VAL B 282       6.004   6.155 -11.715  0.50 54.35           N
ATOM   2143  CA   VAL B 282       6.852   7.337 -11.544  0.50 47.56           C
ATOM   2144  CB   VAL B 282       7.786   7.538 -12.756  0.50 47.52           C
ATOM   2145  CG1  VAL B 282       8.669   8.776 -12.589  0.50 47.04           C
ATOM   2146  CG2  VAL B 282       8.648   6.292 -12.960  0.50 45.88           C
ATOM   2147  C    VAL B 282       5.987   8.569 -11.337  0.50 53.11           C
ATOM   2148  O    VAL B 282       5.138   8.895 -12.176  0.50 48.16           O
ATOM   2149  N    GLU B 283       6.198   9.237 -10.204  0.50 50.03           N
ATOM   2150  CA   GLU B 283       5.363  10.355  -9.793  0.50 46.94           C
ATOM   2151  CB   GLU B 283       5.765  10.855  -8.381  0.50 48.11           C
ATOM   2152  CG   GLU B 283       5.424  12.320  -8.131  0.50 46.52           C
ATOM   2153  CD   GLU B 283       5.137  12.644  -6.667  0.50 47.39           C
ATOM   2154  OE1  GLU B 283       4.509  13.693  -6.399  0.50 45.89           O
ATOM   2155  OE2  GLU B 283       5.497  11.836  -5.789  0.50 45.02           O
ATOM   2156  C    GLU B 283       5.463  11.487 -10.794  0.50 43.56           C
ATOM   2157  O    GLU B 283       6.547  11.826 -11.257  0.50 47.92           O
ATOM   2158  N    VAL B 284       4.327  12.087 -11.108  0.50 40.67           N
ATOM   2159  CA   VAL B 284       4.297  13.263 -11.946  0.50 41.13           C
ATOM   2160  CB   VAL B 284       3.662  12.931 -13.308  0.50 41.50           C
ATOM   2161  CG1  VAL B 284       4.597  11.993 -14.077  0.50 40.39           C
ATOM   2162  CG2  VAL B 284       2.304  12.260 -13.081  0.50 34.66           C
```

Figure 26 (Continued)

```
ATOM   2163  C    VAL B 284       3.499  14.344 -11.230  0.50 43.28           C
ATOM   2164  O    VAL B 284       2.658  14.052 -10.389  0.50 50.04           O
ATOM   2165  N    HIS B 285       3.750  15.596 -11.569  0.50 48.85           N
ATOM   2166  CA   HIS B 285       3.460  16.669 -10.635  0.50 54.75           C
ATOM   2167  CB   HIS B 285       4.771  17.272 -10.092  0.50 58.26           C
ATOM   2168  CG   HIS B 285       5.845  16.257  -9.815  0.50 59.17           C
ATOM   2169  ND1  HIS B 285       5.838  15.438  -8.702  0.50 48.81           N
ATOM   2170  CE1  HIS B 285       6.900  14.649  -8.727  0.50 49.28           C
ATOM   2171  NE2  HIS B 285       7.600  14.928  -9.815  0.50 58.39           N
ATOM   2172  CD2  HIS B 285       6.962  15.928 -10.515  0.50 60.96           C
ATOM   2173  C    HIS B 285       2.639  17.736 -11.303  0.50 51.61           C
ATOM   2174  O    HIS B 285       2.261  18.719 -10.674  0.50 52.89           O
ATOM   2175  N    ASN B 286       2.332  17.520 -12.575  0.50 53.99           N
ATOM   2176  CA   ASN B 286       1.803  18.580 -13.434  0.50 52.35           C
ATOM   2177  CB   ASN B 286       2.369  18.446 -14.857  0.50 57.47           C
ATOM   2178  CG   ASN B 286       1.784  17.256 -15.613  0.50 62.29           C
ATOM   2179  OD1  ASN B 286       2.104  16.100 -15.318  0.50 56.53           O
ATOM   2180  ND2  ASN B 286       0.917  17.536 -16.591  0.50 67.67           N
ATOM   2181  C    ASN B 286       0.292  18.612 -13.512  0.50 48.99           C
ATOM   2182  O    ASN B 286      -0.273  19.364 -14.309  0.50 52.19           O
ATOM   2183  N    ALA B 287      -0.367  17.789 -12.707  0.50 47.84           N
ATOM   2184  CA   ALA B 287      -1.825  17.686 -12.784  0.50 51.53           C
ATOM   2185  CB   ALA B 287      -2.341  16.591 -11.852  0.50 45.83           C
ATOM   2186  C    ALA B 287      -2.488  19.022 -12.470  0.50 54.94           C
ATOM   2187  O    ALA B 287      -1.814  20.022 -12.199  0.50 52.19           O
ATOM   2188  N    LYS B 288      -3.815  19.038 -12.488  0.50 48.78           N
ATOM   2189  CA   LYS B 288      -4.530  20.203 -12.015  0.50 49.53           C
ATOM   2190  CB   LYS B 288      -4.963  21.098 -13.178  0.50 56.45           C
ATOM   2191  CG   LYS B 288      -3.768  21.704 -13.910  0.50 64.28           C
ATOM   2192  CD   LYS B 288      -4.181  22.506 -15.137  0.50 67.91           C
ATOM   2193  CE   LYS B 288      -3.121  22.400 -16.227  0.50 74.71           C
ATOM   2194  NZ   LYS B 288      -3.456  23.181 -17.453  0.50 77.38           N
ATOM   2195  C    LYS B 288      -5.686  19.793 -11.117  0.50 49.08           C
ATOM   2196  O    LYS B 288      -6.532  18.981 -11.489  0.50 40.20           O
ATOM   2197  N    THR B 289      -5.687  20.313  -9.893  0.50 41.88           N
ATOM   2198  CA   THR B 289      -6.771  20.019  -8.989  0.50 47.47           C
ATOM   2199  CB   THR B 289      -6.224  19.502  -7.660  0.50 49.50           C
ATOM   2200  OG1  THR B 289      -5.342  18.403  -7.919  0.50 51.27           O
ATOM   2201  CG2  THR B 289      -7.363  19.057  -6.750  0.50 46.70           C
ATOM   2202  C    THR B 289      -7.651  21.243  -8.762  0.50 52.20           C
ATOM   2203  O    THR B 289      -7.168  22.282  -8.309  0.50 54.94           O
ATOM   2204  N    LYS B 290      -8.928  21.131  -9.106  0.50 52.93           N
ATOM   2205  CA   LYS B 290      -9.883  22.215  -8.864  0.50 62.86           C
ATOM   2206  CB   LYS B 290     -11.209  21.929  -9.580  0.50 69.20           C
ATOM   2207  CG   LYS B 290     -11.078  21.769 -11.091  0.50 70.95           C
ATOM   2208  CD   LYS B 290     -11.934  20.621 -11.617  0.50 67.17           C
ATOM   2209  CE   LYS B 290     -11.912  20.567 -13.142  0.50 68.18           C
ATOM   2210  NZ   LYS B 290     -10.558  20.854 -13.699  0.50 55.46           N
ATOM   2211  C    LYS B 290     -10.124  22.400  -7.364  0.50 64.59           C
ATOM   2212  O    LYS B 290      -9.649  21.604  -6.552  0.50 71.21           O
ATOM   2213  N    PRO B 291     -10.841  23.472  -6.988  0.50 66.27           N
ATOM   2214  CA   PRO B 291     -11.286  23.632  -5.609  0.50 61.01           C
ATOM   2215  CB   PRO B 291     -11.748  25.085  -5.567  0.50 59.28           C
ATOM   2216  CG   PRO B 291     -12.203  25.347  -6.959  0.50 62.47           C
ATOM   2217  CD   PRO B 291     -11.204  24.634  -7.819  0.50 62.24           C
ATOM   2218  C    PRO B 291     -12.467  22.723  -5.292  0.50 57.76           C
ATOM   2219  O    PRO B 291     -13.349  22.534  -6.140  0.50 60.21           O
ATOM   2220  N    ARG B 292     -12.471  22.177  -4.079  0.50 50.50           N
ATOM   2221  CA   ARG B 292     -13.604  21.446  -3.520  0.50 54.56           C
ATOM   2222  CB   ARG B 292     -13.447  21.319  -1.989  0.50 55.40           C
ATOM   2223  CG   ARG B 292     -13.705  22.616  -1.219  0.50 57.48           C
ATOM   2224  CD   ARG B 292     -13.373  22.511   0.277  0.50 64.95           C
ATOM   2225  NE   ARG B 292     -11.966  22.170   0.515  0.50 63.67           N
ATOM   2226  CZ   ARG B 292     -11.318  22.287   1.678  0.50 61.08           C
```

Figure 26 (Continued)

```
ATOM   2227  NH1 ARG B 292     -10.038  21.926   1.744  0.50 55.86           N
ATOM   2228  NH2 ARG B 292     -11.930  22.748   2.771  0.50 54.40           N
ATOM   2229  C   ARG B 292     -14.961  22.078  -3.853  0.50 56.11           C
ATOM   2230  O   ARG B 292     -15.088  23.299  -3.938  0.50 55.46           O
ATOM   2231  N   GLU B 293     -15.984  21.244  -4.031  0.50 53.76           N
ATOM   2232  CA  GLU B 293     -17.340  21.761  -4.180  0.50 55.23           C
ATOM   2233  CB  GLU B 293     -17.721  21.870  -5.655  0.50 55.03           C
ATOM   2234  CG  GLU B 293     -16.864  22.860  -6.421  0.50 57.16           C
ATOM   2235  CD  GLU B 293     -17.334  23.052  -7.843  0.50 64.09           C
ATOM   2236  OE1 GLU B 293     -16.512  23.484  -8.674  0.50 72.43           O
ATOM   2237  OE2 GLU B 293     -18.518  22.767  -8.134  0.50 70.74           O
ATOM   2238  C   GLU B 293     -18.384  20.961  -3.391  0.50 58.50           C
ATOM   2239  O   GLU B 293     -18.334  19.721  -3.324  0.50 53.46           O
ATOM   2240  N   GLU B 294     -19.332  21.680  -2.792  0.50 55.50           N
ATOM   2241  CA  GLU B 294     -20.320  21.052  -1.940  0.50 50.64           C
ATOM   2242  CB  GLU B 294     -20.818  22.020  -0.869  0.50 53.68           C
ATOM   2243  CG  GLU B 294     -22.035  21.493  -0.119  0.50 43.41           C
ATOM   2244  CD  GLU B 294     -22.404  22.364   1.078  0.50 48.07           C
ATOM   2245  OE1 GLU B 294     -22.407  21.833   2.209  0.50 44.95           O
ATOM   2246  OE2 GLU B 294     -22.683  23.571   0.884  0.50 39.17           O
ATOM   2247  C   GLU B 294     -21.511  20.557  -2.727  0.50 51.56           C
ATOM   2248  O   GLU B 294     -22.146  21.315  -3.448  0.50 52.87           O
ATOM   2249  N   GLN B 295     -21.847  19.286  -2.541  0.50 52.99           N
ATOM   2250  CA  GLN B 295     -23.009  18.710  -3.197  0.50 53.50           C
ATOM   2251  CB  GLN B 295     -22.792  17.214  -3.472  0.50 58.59           C
ATOM   2252  CG  GLN B 295     -21.497  16.913  -4.218  0.50 63.68           C
ATOM   2253  CD  GLN B 295     -21.315  17.805  -5.436  0.50 57.77           C
ATOM   2254  OE1 GLN B 295     -22.155  17.821  -6.331  0.50 63.37           O
ATOM   2255  NE2 GLN B 295     -20.221  18.560  -5.467  0.50 57.43           N
ATOM   2256  C   GLN B 295     -24.244  18.908  -2.332  0.50 58.11           C
ATOM   2257  O   GLN B 295     -24.157  18.998  -1.104  0.50 50.82           O
ATOM   2258  N   TYR B 296     -25.398  18.979  -2.980  0.50 55.24           N
ATOM   2259  CA  TYR B 296     -26.635  19.212  -2.276  0.50 59.51           C
ATOM   2260  CB  TYR B 296     -27.821  19.218  -3.245  0.50 54.48           C
ATOM   2261  CG  TYR B 296     -28.308  20.604  -3.585  0.50 55.09           C
ATOM   2262  CD1 TYR B 296     -27.524  21.476  -4.328  0.50 59.71           C
ATOM   2263  CE1 TYR B 296     -27.964  22.754  -4.625  0.50 64.06           C
ATOM   2264  CZ  TYR B 296     -29.208  23.176  -4.173  0.50 68.04           C
ATOM   2265  OH  TYR B 296     -29.665  24.446  -4.480  0.50 66.80           O
ATOM   2266  CE2 TYR B 296     -30.000  22.327  -3.423  0.50 55.78           C
ATOM   2267  CD2 TYR B 296     -29.544  21.054  -3.132  0.50 59.02           C
ATOM   2268  C   TYR B 296     -26.855  18.213  -1.138  0.50 65.25           C
ATOM   2269  O   TYR B 296     -27.826  18.330  -0.395  0.50 78.40           O
ATOM   2270  N   ASN B 297     -25.949  17.251  -0.982  0.50 61.61           N
ATOM   2271  CA  ASN B 297     -26.106  16.221   0.047  0.50 59.18           C
ATOM   2272  CB  ASN B 297     -26.006  14.803  -0.558  0.50 62.54           C
ATOM   2273  CG  ASN B 297     -24.694  14.565  -1.301  0.50 62.65           C
ATOM   2274  OD1 ASN B 297     -23.665  15.154  -0.968  0.50 55.78           O
ATOM   2275  ND2 ASN B 297     -24.726  13.690  -2.314  0.50 72.06           N
ATOM   2276  C   ASN B 297     -25.131  16.397   1.223  0.50 57.16           C
ATOM   2277  O   ASN B 297     -25.011  15.519   2.078  0.50 52.45           O
ATOM   2278  N   SER B 298     -24.422  17.523   1.233  0.50 54.01           N
ATOM   2279  CA  SER B 298     -23.558  17.906   2.354  0.50 61.37           C
ATOM   2280  CB  SER B 298     -24.270  17.693   3.700  0.50 56.44           C
ATOM   2281  OG  SER B 298     -24.979  18.863   4.070  0.50 51.41           O
ATOM   2282  C   SER B 298     -22.163  17.275   2.377  0.50 63.26           C
ATOM   2283  O   SER B 298     -21.543  17.165   3.443  0.50 56.32           O
ATOM   2284  N   THR B 299     -21.684  16.866   1.202  0.50 63.41           N
ATOM   2285  CA  THR B 299     -20.307  16.413   1.020  0.50 59.69           C
ATOM   2286  CB  THR B 299     -20.252  14.973   0.525  0.50 60.87           C
ATOM   2287  OG1 THR B 299     -21.147  14.846  -0.588  0.50 62.14           O
ATOM   2288  CG2 THR B 299     -20.650  14.008   1.647  0.50 62.82           C
ATOM   2289  C   THR B 299     -19.656  17.243  -0.056  0.50 54.45           C
ATOM   2290  O   THR B 299     -20.338  17.793  -0.921  0.50 52.27           O
```

Figure 26 (Continued)

```
ATOM   2291  N   TYR B 300     -18.333  17.344   0.004  0.50 56.55           N
ATOM   2292  CA  TYR B 300     -17.601  17.981  -1.074  0.50 61.69           C
ATOM   2293  CB  TYR B 300     -16.333  18.672  -0.570  0.50 65.56           C
ATOM   2294  CG  TYR B 300     -16.579  19.651   0.560  0.50 75.86           C
ATOM   2295  CD1 TYR B 300     -16.671  19.207   1.877  0.50 76.63           C
ATOM   2296  CE1 TYR B 300     -16.883  20.095   2.916  0.50 84.41           C
ATOM   2297  CZ  TYR B 300     -17.002  21.444   2.645  0.50 84.91           C
ATOM   2298  OH  TYR B 300     -17.213  22.323   3.681  0.50 91.46           O
ATOM   2299  CE2 TYR B 300     -16.910  21.912   1.347  0.50 80.63           C
ATOM   2300  CD2 TYR B 300     -16.699  21.018   0.315  0.50 74.05           C
ATOM   2301  C   TYR B 300     -17.267  16.961  -2.146  0.50 54.32           C
ATOM   2302  O   TYR B 300     -17.164  15.756  -1.882  0.50 51.85           O
ATOM   2303  N   ARG B 301     -17.134  17.459  -3.367  0.50 54.94           N
ATOM   2304  CA  ARG B 301     -16.668  16.659  -4.483  0.50 55.27           C
ATOM   2305  CB  ARG B 301     -17.752  16.562  -5.562  0.50 55.87           C
ATOM   2306  CG  ARG B 301     -17.303  15.971  -6.893  0.50 56.08           C
ATOM   2307  CD  ARG B 301     -18.468  15.976  -7.872  0.50 57.69           C
ATOM   2308  NE  ARG B 301     -18.134  15.399  -9.171  0.50 55.67           N
ATOM   2309  CZ  ARG B 301     -17.683  16.109 -10.200  0.50 53.31           C
ATOM   2310  NH1 ARG B 301     -17.500  17.410 -10.078  0.50 50.38           N
ATOM   2311  NH2 ARG B 301     -17.414  15.518 -11.351  0.50 54.26           N
ATOM   2312  C   ARG B 301     -15.446  17.386  -5.004  0.50 55.27           C
ATOM   2313  O   ARG B 301     -15.467  18.601  -5.194  0.50 54.13           O
ATOM   2314  N   VAL B 302     -14.358  16.654  -5.192  0.50 53.04           N
ATOM   2315  CA  VAL B 302     -13.118  17.297  -5.583  0.50 50.63           C
ATOM   2316  CB  VAL B 302     -12.180  17.480  -4.364  0.50 53.69           C
ATOM   2317  CG1 VAL B 302     -12.330  16.323  -3.392  0.50 52.44           C
ATOM   2318  CG2 VAL B 302     -10.729  17.710  -4.770  0.50 51.31           C
ATOM   2319  C   VAL B 302     -12.489  16.554  -6.761  0.50 49.57           C
ATOM   2320  O   VAL B 302     -12.415  15.314  -6.786  0.50 44.83           O
ATOM   2321  N   VAL B 303     -12.102  17.327  -7.766  0.50 47.57           N
ATOM   2322  CA  VAL B 303     -11.734  16.779  -9.052  0.50 53.13           C
ATOM   2323  CB  VAL B 303     -12.633  17.358 -10.158  0.50 54.98           C
ATOM   2324  CG1 VAL B 303     -12.089  16.972 -11.527  0.50 53.45           C
ATOM   2325  CG2 VAL B 303     -14.062  16.868  -9.970  0.50 54.66           C
ATOM   2326  C   VAL B 303     -10.308  17.125  -9.400  0.50 53.17           C
ATOM   2327  O   VAL B 303      -9.943  18.302  -9.427  0.50 58.21           O
ATOM   2328  N   SER B 304      -9.496  16.107  -9.668  0.50 51.20           N
ATOM   2329  CA  SER B 304      -8.178  16.366 -10.254  0.50 47.68           C
ATOM   2330  CB  SER B 304      -7.061  15.844  -9.369  0.50 45.73           C
ATOM   2331  OG  SER B 304      -5.823  16.313  -9.878  0.50 44.32           O
ATOM   2332  C   SER B 304      -8.052  15.792 -11.665  0.50 47.14           C
ATOM   2333  O   SER B 304      -8.579  14.722 -11.974  0.50 48.62           O
ATOM   2334  N   VAL B 305      -7.335  16.518 -12.509  0.50 52.24           N
ATOM   2335  CA  VAL B 305      -7.262  16.230 -13.927  0.50 47.91           C
ATOM   2336  CB  VAL B 305      -7.883  17.370 -14.754  0.50 49.23           C
ATOM   2337  CG1 VAL B 305      -7.603  17.163 -16.239  0.50 47.05           C
ATOM   2338  CG2 VAL B 305      -9.382  17.444 -14.502  0.50 49.71           C
ATOM   2339  C   VAL B 305      -5.801  16.132 -14.301  0.50 48.92           C
ATOM   2340  O   VAL B 305      -5.049  17.074 -14.089  0.50 46.96           O
ATOM   2341  N   LEU B 306      -5.392  14.983 -14.835  0.50 43.49           N
ATOM   2342  CA  LEU B 306      -4.045  14.851 -15.361  0.50 41.01           C
ATOM   2343  CB  LEU B 306      -3.375  13.579 -14.854  0.50 36.81           C
ATOM   2344  CG  LEU B 306      -1.938  13.405 -15.361  0.50 42.66           C
ATOM   2345  CD1 LEU B 306      -0.999  14.472 -14.802  0.50 40.42           C
ATOM   2346  CD2 LEU B 306      -1.393  12.008 -15.087  0.50 39.53           C
ATOM   2347  C   LEU B 306      -4.076  14.844 -16.889  0.50 42.51           C
ATOM   2348  O   LEU B 306      -4.836  14.080 -17.504  0.50 44.88           O
ATOM   2349  N   THR B 307      -3.209  15.651 -17.489  0.50 41.92           N
ATOM   2350  CA  THR B 307      -3.034  15.662 -18.933  0.50 43.71           C
ATOM   2351  CB  THR B 307      -2.427  16.986 -19.395  0.50 42.75           C
ATOM   2352  OG1 THR B 307      -3.465  17.958 -19.485  0.50 47.42           O
ATOM   2353  CG2 THR B 307      -1.774  16.826 -20.753  0.50 44.89           C
ATOM   2354  C   THR B 307      -2.118  14.517 -19.350  0.50 43.28           C
```

Figure 26 (Continued)

```
ATOM   2355  O    THR B 307      -1.052  14.345 -18.770  0.50 43.21           O
ATOM   2356  N    VAL B 308       2.548  13.696  20.311  0.50 38.72           N
ATOM   2357  CA   VAL B 308      -1.718  12.557 -20.709  0.50 36.44           C
ATOM   2358  CB   VAL B 308      -2.500  11.213 -20.694  0.50 40.69           C
ATOM   2359  CG1  VAL B 308      -3.645  11.267 -19.697  0.50 38.89           C
ATOM   2360  CG2  VAL B 308      -3.033  10.861 -22.083  0.50 36.18           C
ATOM   2361  C    VAL B 308      -1.127  12.826 -22.083  0.50 32.88           C
ATOM   2362  O    VAL B 308      -1.719  13.571 -22.874  0.50 34.26           O
ATOM   2363  N    LEU B 309       0.058  12.299 -22.373  0.50 31.88           N
ATOM   2364  CA   LEU B 309       0.544  12.428 -23.761  0.50 32.59           C
ATOM   2365  CB   LEU B 309       2.073  12.341 -23.880  0.50 32.48           C
ATOM   2366  CG   LEU B 309       2.948  13.399 -23.192  0.50 38.52           C
ATOM   2367  CD1  LEU B 309       4.420  13.290 -23.610  0.50 35.45           C
ATOM   2368  CD2  LEU B 309       2.375  14.799 -23.389  0.50 32.15           C
ATOM   2369  C    LEU B 309      -0.102  11.351 -24.625  0.50 33.16           C
ATOM   2370  O    LEU B 309      -0.216  10.200 -24.210  0.50 34.99           O
ATOM   2371  N    HIS B 310      -0.522  11.723 -25.826  0.50 34.69           N
ATOM   2372  CA   HIS B 310      -1.153  10.773 -26.728  0.50 34.33           C
ATOM   2373  CB   HIS B 310      -1.177  11.382 -28.120  0.50 34.26           C
ATOM   2374  CG   HIS B 310      -2.016  12.628 -28.202  0.50 38.86           C
ATOM   2375  ND1  HIS B 310      -1.635  13.824 -27.628  0.50 36.76           N
ATOM   2376  CE1  HIS B 310      -2.581  14.723 -27.810  0.50 37.69           C
ATOM   2377  NE2  HIS B 310      -3.569  14.155 -28.480  0.50 40.19           N
ATOM   2378  CD2  HIS B 310      -3.250  12.839 -28.714  0.50 36.52           C
ATOM   2379  C    HIS B 310      -0.439   9.411 -26.737  0.50 37.25           C
ATOM   2380  O    HIS B 310      -1.021   8.364 -26.393  0.50 34.45           O
ATOM   2381  N    GLN B 311       0.838   9.436 -27.073  0.50 37.13           N
ATOM   2382  CA   GLN B 311       1.555   8.210 -27.337  0.50 37.96           C
ATOM   2383  CB   GLN B 311       2.810   8.470 -28.180  0.50 39.00           C
ATOM   2384  CG   GLN B 311       3.343   7.216 -28.896  0.50 46.05           C
ATOM   2385  CD   GLN B 311       2.334   6.487 -29.806  0.50 40.56           C
ATOM   2386  OE1  GLN B 311       1.775   7.065 -30.763  0.50 34.08           O
ATOM   2387  NE2  GLN B 311       2.123   5.195 -29.527  0.50 36.58           N
ATOM   2388  C    GLN B 311       1.868   7.414 -26.066  0.50 38.45           C
ATOM   2389  O    GLN B 311       2.049   6.198 -26.143  0.50 35.72           O
ATOM   2390  N    ASP B 312       1.903   8.088 -24.913  0.50 37.84           N
ATOM   2391  CA   ASP B 312       1.989   7.391 -23.612  0.50 36.78           C
ATOM   2392  CB   ASP B 312       2.074   8.388 -22.449  0.50 37.83           C
ATOM   2393  CG   ASP B 312       3.497   8.829 -22.141  0.50 42.56           C
ATOM   2394  OD1  ASP B 312       4.453   8.206 -22.647  0.50 36.76           O
ATOM   2395  OD2  ASP B 312       3.649   9.811 -21.375  0.50 43.86           O
ATOM   2396  C    ASP B 312       0.743   6.557 -23.394  0.50 33.22           C
ATOM   2397  O    ASP B 312       0.804   5.426 -22.935  0.50 35.13           O
ATOM   2398  N    TRP B 313      -0.403   7.169 -23.632  0.50 32.00           N
ATOM   2399  CA   TRP B 313      -1.657   6.431 -23.491  0.50 35.60           C
ATOM   2400  CB   TRP B 313      -2.899   7.315 -23.718  0.50 32.19           C
ATOM   2401  CG   TRP B 313      -4.207   6.558 -23.534  0.50 32.77           C
ATOM   2402  CD1  TRP B 313      -5.032   6.063 -24.528  0.50 31.49           C
ATOM   2403  NE1  TRP B 313      -6.105   5.402 -23.964  0.50 29.79           N
ATOM   2404  CE2  TRP B 313      -5.989   5.459 -22.598  0.50 29.12           C
ATOM   2405  CD2  TRP B 313      -4.817   6.184 -22.292  0.50 30.31           C
ATOM   2406  CE3  TRP B 313      -4.471   6.369 -20.944  0.50 33.77           C
ATOM   2407  CZ3  TRP B 313      -5.298   5.857 -19.967  0.50 28.50           C
ATOM   2408  CH2  TRP B 313      -6.466   5.170 -20.296  0.50 29.45           C
ATOM   2409  CZ2  TRP B 313      -6.826   4.951 -21.607  0.50 31.03           C
ATOM   2410  C    TRP B 313      -1.652   5.272 -24.461  0.50 29.10           C
ATOM   2411  O    TRP B 313      -1.945   4.140 -24.076  0.50 31.31           O
ATOM   2412  N    LEU B 314      -1.351   5.565 -25.722  0.50 30.16           N
ATOM   2413  CA   LEU B 314      -1.378   4.553 -26.768  0.50 29.10           C
ATOM   2414  CB   LEU B 314      -1.175   5.174 -28.141  0.50 30.30           C
ATOM   2415  CG   LEU B 314      -2.305   6.077 -28.629  0.50 31.45           C
ATOM   2416  CD1  LEU B 314      -2.005   6.497 -30.065  0.50 34.34           C
ATOM   2417  CD2  LEU B 314      -3.633   5.351 -28.527  0.50 25.87           C
ATOM   2418  C    LEU B 314      -0.335   3.488 -26.557  0.50 32.08           C
```

Figure 26 (Continued)

```
ATOM   2419  O    LEU B 314      -0.548   2.323 -26.922  0.50 29.86           O
ATOM   2420  N    ASN B 315       0.781   3.878 -25.950  0.50 29.44           N
ATOM   2421  CA   ASN B 315       1.802   2.921 -25.575  0.50 32.25           C
ATOM   2422  CB   ASN B 315       3.191   3.579 -25.494  0.50 32.78           C
ATOM   2423  CG   ASN B 315       3.757   3.866 -26.872  0.50 35.88           C
ATOM   2424  OD1  ASN B 315       3.217   3.388 -27.880  0.50 32.85           O
ATOM   2425  ND2  ASN B 315       4.831   4.639 -26.934  0.50 36.56           N
ATOM   2426  C    ASN B 315       1.531   2.091 -24.337  0.50 34.72           C
ATOM   2427  O    ASN B 315       2.391   1.302 -23.927  0.50 35.84           O
ATOM   2428  N    GLY B 316       0.367   2.282 -23.731  0.50 32.51           N
ATOM   2429  CA   GLY B 316      -0.092   1.391 -22.659  0.50 35.31           C
ATOM   2430  C    GLY B 316       0.402   1.734 -21.257  0.50 38.97           C
ATOM   2431  O    GLY B 316       0.419   0.887 -20.356  0.50 38.76           O
ATOM   2432  N    LYS B 317       0.758   2.986 -21.044  0.50 36.70           N
ATOM   2433  CA   LYS B 317       1.186   3.388 -19.710  0.50 37.87           C
ATOM   2434  CB   LYS B 317       1.893   4.746 -19.758  0.50 32.77           C
ATOM   2435  CG   LYS B 317       3.215   4.692 -20.502  0.50 37.60           C
ATOM   2436  CD   LYS B 317       4.211   5.734 -20.029  0.50 38.48           C
ATOM   2437  CE   LYS B 317       5.534   5.568 -20.776  0.50 40.83           C
ATOM   2438  NZ   LYS B 317       6.480   6.690 -20.506  0.50 39.70           N
ATOM   2439  C    LYS B 317       0.003   3.398 -18.734  0.50 37.05           C
ATOM   2440  O    LYS B 317      -1.145   3.670 -19.130  0.50 35.56           O
ATOM   2441  N    GLU B 318       0.300   3.077 -17.469  0.50 38.52           N
ATOM   2442  CA   GLU B 318      -0.689   2.939 -16.392  0.50 37.32           C
ATOM   2443  CB   GLU B 318      -0.301   1.774 -15.492  0.50 38.94           C
ATOM   2444  CG   GLU B 318      -0.375   0.424 -16.195  0.50 44.29           C
ATOM   2445  CD   GLU B 318      -0.338  -0.752 -15.230  0.50 45.52           C
ATOM   2446  OE1  GLU B 318      -1.318  -1.534 -15.185  0.50 50.54           O
ATOM   2447  OE2  GLU B 318       0.671  -0.892 -14.509  0.50 51.37           O
ATOM   2448  C    GLU B 318      -0.767   4.205 -15.538  0.50 39.95           C
ATOM   2449  O    GLU B 318       0.239   4.661 -15.005  0.50 39.62           O
ATOM   2450  N    TYR B 319      -1.956   4.777 -15.413  0.50 39.60           N
ATOM   2451  CA   TYR B 319      -2.097   6.054 -14.720  0.50 39.68           C
ATOM   2452  CB   TYR B 319      -2.989   7.005 -15.522  0.50 34.75           C
ATOM   2453  CG   TYR B 319      -2.318   7.419 -16.804  0.50 39.04           C
ATOM   2454  CD1  TYR B 319      -2.265   6.549 -17.881  0.50 37.61           C
ATOM   2455  CE1  TYR B 319      -1.634   6.896 -19.051  0.50 36.56           C
ATOM   2456  CZ   TYR B 319      -1.013   8.107 -19.156  0.50 41.46           C
ATOM   2457  OH   TYR B 319      -0.370   8.425 -20.346  0.50 35.26           O
ATOM   2458  CE2  TYR B 319      -1.030   8.996 -18.084  0.50 36.70           C
ATOM   2459  CD2  TYR B 319      -1.673   8.639 -16.920  0.50 37.77           C
ATOM   2460  C    TYR B 319      -2.680   5.784 -13.350  0.50 41.35           C
ATOM   2461  O    TYR B 319      -3.703   5.107 -13.238  0.50 43.71           O
ATOM   2462  N    LYS B 320      -1.985   6.216 -12.301  0.50 39.96           N
ATOM   2463  CA   LYS B 320      -2.497   5.943 -10.960  0.50 41.69           C
ATOM   2464  CB   LYS B 320      -1.529   5.137 -10.114  0.50 42.13           C
ATOM   2465  CG   LYS B 320      -2.025   5.007  -8.675  0.50 45.00           C
ATOM   2466  CD   LYS B 320      -1.564   3.725  -8.016  0.50 42.64           C
ATOM   2467  CE   LYS B 320      -0.066   3.588  -8.088  0.50 40.93           C
ATOM   2468  NZ   LYS B 320       0.317   2.181  -7.826  0.50 38.36           N
ATOM   2469  C    LYS B 320      -2.905   7.209 -10.236  0.50 39.66           C
ATOM   2470  O    LYS B 320      -2.144   8.175 -10.181  0.50 41.58           O
ATOM   2471  N    CYS B 321      -4.137   7.224  -9.744  0.50 43.17           N
ATOM   2472  CA   CYS B 321      -4.578   8.286  -8.859  0.50 47.33           C
ATOM   2473  CB   CYS B 321      -5.992   8.718  -9.187  0.50 47.97           C
ATOM   2474  SG   CYS B 321      -6.490  10.168  -8.226  0.50 48.28           S
ATOM   2475  C    CYS B 321      -4.548   7.761  -7.428  0.50 49.35           C
ATOM   2476  O    CYS B 321      -5.157   6.733  -7.127  0.50 49.35           O
ATOM   2477  N    LYS B 322      -3.812   8.443  -6.561  0.50 47.89           N
ATOM   2478  CA   LYS B 322      -3.816   8.100  -5.140  0.50 50.97           C
ATOM   2479  CB   LYS B 322      -2.395   7.803  -4.648  0.50 53.54           C
ATOM   2480  CG   LYS B 322      -2.280   7.481  -3.161  0.50 57.68           C
ATOM   2481  CD   LYS B 322      -0.836   7.621  -2.685  0.50 59.20           C
ATOM   2482  CE   LYS B 322      -0.712   7.413  -1.178  0.50 63.14           C
```

Figure 26 (Continued)

```
ATOM   2483  NZ  LYS B 322       0.573   7.965  -0.651  0.50 60.17           N
ATOM   2484  C   LYS B 322      -4.425   9.286  -4.396  0.50 48.07           C
ATOM   2485  O   LYS B 322      -3.961  10.423  -4.527  0.50 46.64           O
ATOM   2486  N   VAL B 323      -5.523   9.019  -3.703  0.50 49.27           N
ATOM   2487  CA  VAL B 323      -6.267  10.052  -3.001  0.50 48.90           C
ATOM   2488  CB  VAL B 323      -7.735  10.122  -3.480  0.50 54.01           C
ATOM   2489  CG1 VAL B 323      -8.542  11.122  -2.634  0.50 44.61           C
ATOM   2490  CG2 VAL B 323      -7.798  10.485  -4.978  0.50 47.35           C
ATOM   2491  C   VAL B 323      -6.207   9.770  -1.499  0.50 54.61           C
ATOM   2492  O   VAL B 323      -6.575   8.676  -1.037  0.50 46.28           O
ATOM   2493  N   SER B 324      -5.676  10.735  -0.755  0.50 53.63           N
ATOM   2494  CA  SER B 324      -5.559  10.608   0.701  0.50 57.86           C
ATOM   2495  CB  SER B 324      -4.099  10.668   1.153  0.50 53.88           C
ATOM   2496  OG  SER B 324      -3.491   9.394   1.028  0.50 48.97           O
ATOM   2497  C   SER B 324      -6.374  11.669   1.418  0.50 57.28           C
ATOM   2498  O   SER B 324      -6.517  12.802   0.922  0.50 51.58           O
ATOM   2499  N   ASN B 325      -6.883  11.280   2.593  0.50 61.16           N
ATOM   2500  CA  ASN B 325      -7.820  12.077   3.390  0.50 58.72           C
ATOM   2501  CB  ASN B 325      -9.145  12.229   2.652  0.50 54.95           C
ATOM   2502  CG  ASN B 325     -10.293  12.604   3.576  0.50 55.05           C
ATOM   2503  OD1 ASN B 325     -10.563  11.911   4.556  0.50 48.72           O
ATOM   2504  ND2 ASN B 325     -10.993  13.694   3.250  0.50 47.39           N
ATOM   2505  C   ASN B 325      -8.056  11.463   4.784  0.50 67.25           C
ATOM   2506  O   ASN B 325      -8.298  10.256   4.914  0.50 65.33           O
ATOM   2507  N   LYS B 326      -8.007  12.302   5.819  0.50 66.97           N
ATOM   2508  CA  LYS B 326      -7.946  11.822   7.205  0.50 61.17           C
ATOM   2509  CB  LYS B 326      -7.705  12.991   8.173  0.50 59.43           C
ATOM   2510  CG  LYS B 326      -6.408  13.728   7.855  0.50 61.98           C
ATOM   2511  CD  LYS B 326      -6.204  14.998   8.665  0.50 65.50           C
ATOM   2512  CE  LYS B 326      -5.142  15.864   8.004  0.50 75.19           C
ATOM   2513  NZ  LYS B 326      -4.432  16.789   8.930  0.50 65.56           N
ATOM   2514  C   LYS B 326      -9.132  10.941   7.616  0.50 57.77           C
ATOM   2515  O   LYS B 326      -9.049  10.171   8.564  0.50 61.93           O
ATOM   2516  N   ALA B 327     -10.217  11.002   6.860  0.50 60.66           N
ATOM   2517  CA  ALA B 327     -11.350  10.127   7.111  0.50 59.72           C
ATOM   2518  CB  ALA B 327     -12.619  10.756   6.556  0.50 58.04           C
ATOM   2519  C   ALA B 327     -11.136   8.706   6.549  0.50 65.56           C
ATOM   2520  O   ALA B 327     -12.053   7.884   6.535  0.50 62.29           O
ATOM   2521  N   LEU B 328      -9.919   8.421   6.092  0.50 71.20           N
ATOM   2522  CA  LEU B 328      -9.595   7.112   5.524  0.50 66.94           C
ATOM   2523  CB  LEU B 328      -9.073   7.264   4.095  0.50 60.95           C
ATOM   2524  CG  LEU B 328      -9.827   8.215   3.162  0.50 65.00           C
ATOM   2525  CD1 LEU B 328      -8.902   8.683   2.049  0.50 64.20           C
ATOM   2526  CD2 LEU B 328     -11.087   7.572   2.590  0.50 64.90           C
ATOM   2527  C   LEU B 328      -8.536   6.400   6.354  0.50 70.63           C
ATOM   2528  O   LEU B 328      -7.541   7.010   6.758  0.50 68.59           O
ATOM   2529  N   PRO B 329      -8.734   5.095   6.589  0.50 70.38           N
ATOM   2530  CA  PRO B 329      -7.700   4.247   7.188  0.50 71.64           C
ATOM   2531  CB  PRO B 329      -8.291   2.829   7.082  0.50 68.27           C
ATOM   2532  CG  PRO B 329      -9.456   2.935   6.154  0.50 71.09           C
ATOM   2533  CD  PRO B 329      -9.955   4.344   6.258  0.50 67.99           C
ATOM   2534  C   PRO B 329      -6.367   4.351   6.420  0.50 75.98           C
ATOM   2535  O   PRO B 329      -5.327   4.629   7.019  0.50 66.63           O
ATOM   2536  N   ALA B 330      -6.409   4.147   5.102  0.50 76.05           N
ATOM   2537  CA  ALA B 330      -5.236   4.340   4.243  0.50 71.48           C
ATOM   2538  CB  ALA B 330      -4.522   3.019   3.988  0.50 70.19           C
ATOM   2539  C   ALA B 330      -5.620   4.995   2.920  0.50 70.68           C
ATOM   2540  O   ALA B 330      -6.784   4.958   2.510  0.50 68.15           O
ATOM   2541  N   PRO B 331      -4.636   5.597   2.240  0.50 69.01           N
ATOM   2542  CA  PRO B 331      -4.914   6.328   1.006  0.50 68.88           C
ATOM   2543  CB  PRO B 331      -3.561   6.977   0.662  0.50 65.86           C
ATOM   2544  CG  PRO B 331      -2.669   6.742   1.848  0.50 61.30           C
ATOM   2545  CD  PRO B 331      -3.193   5.503   2.506  0.50 64.66           C
ATOM   2546  C   PRO B 331      -5.368   5.375  -0.107  0.50 62.59           C
```

Figure 26 (Continued)

```
ATOM   2547  O    PRO B 331      -4.751   4.335  -0.315  0.50 58.45           O
ATOM   2548  N    ILE B 332      -6.462   5.715  -0.784  0.50 63.45           N
ATOM   2549  CA   ILE B 332      -6.998   4.868  -1.841  0.50 58.72           C
ATOM   2550  CB   ILE B 332      -8.499   5.095  -2.050  0.50 57.29           C
ATOM   2551  CG1  ILE B 332      -9.272   4.785  -0.762  0.50 60.71           C
ATOM   2552  CD1  ILE B 332     -10.670   5.377  -0.726  0.50 59.39           C
ATOM   2553  CG2  ILE B 332      -8.992   4.238  -3.208  0.50 55.78           C
ATOM   2554  C    ILE B 332      -6.285   5.126  -3.163  0.50 56.64           C
ATOM   2555  O    ILE B 332      -6.211   6.268  -3.628  0.50 58.55           O
ATOM   2556  N    GLU B 333      -5.768   4.060  -3.763  0.50 49.89           N
ATOM   2557  CA   GLU B 333      -5.128   4.148  -5.075  0.50 53.29           C
ATOM   2558  CB   GLU B 333      -3.804   3.372  -5.076  0.50 57.52           C
ATOM   2559  CG   GLU B 333      -2.636   4.111  -4.441  0.50 60.12           C
ATOM   2560  CD   GLU B 333      -1.362   3.294  -4.445  0.50 61.03           C
ATOM   2561  OE1  GLU B 333      -0.286   3.871  -4.188  0.50 65.24           O
ATOM   2562  OE2  GLU B 333      -1.435   2.072  -4.704  0.50 66.37           O
ATOM   2563  C    GLU B 333      -6.025   3.584  -6.176  0.50 49.93           C
ATOM   2564  O    GLU B 333      -6.554   2.485  -6.048  0.50 45.29           O
ATOM   2565  N    LYS B 334      -6.178   4.335  -7.260  0.50 52.25           N
ATOM   2566  CA   LYS B 334      -6.782   3.801  -8.481  0.50 53.19           C
ATOM   2567  CB   LYS B 334      -8.132   4.454  -8.766  0.50 57.80           C
ATOM   2568  CG   LYS B 334      -9.319   3.518  -8.576  0.50 66.22           C
ATOM   2569  CD   LYS B 334      -9.358   2.901  -7.184  0.50 66.27           C
ATOM   2570  CE   LYS B 334     -10.685   2.202  -6.939  0.50 72.94           C
ATOM   2571  NZ   LYS B 334     -11.826   2.931  -7.566  0.50 80.69           N
ATOM   2572  C    LYS B 334      -5.871   3.905  -9.701  0.50 51.66           C
ATOM   2573  O    LYS B 334      -5.058   4.826  -9.828  0.50 52.68           O
ATOM   2574  N    THR B 335      -6.056   2.970 -10.620  0.50 54.78           N
ATOM   2575  CA   THR B 335      -5.166   2.805 -11.763  0.50 52.56           C
ATOM   2576  CB   THR B 335      -4.208   1.616 -11.541  0.50 53.28           C
ATOM   2577  OG1  THR B 335      -3.181   2.001 -10.613  0.50 53.33           O
ATOM   2578  CG2  THR B 335      -3.551   1.186 -12.859  0.50 60.26           C
ATOM   2579  C    THR B 335      -5.996   2.561 -13.006  0.50 49.87           C
ATOM   2580  O    THR B 335      -6.968   1.804 -12.976  0.50 47.65           O
ATOM   2581  N    ILE B 336      -5.640   3.224 -14.099  0.50 49.06           N
ATOM   2582  CA   ILE B 336      -6.332   2.986 -15.366  0.50 46.17           C
ATOM   2583  CB   ILE B 336      -7.386   4.075 -15.624  0.50 45.89           C
ATOM   2584  CG1  ILE B 336      -8.431   3.603 -16.626  0.50 47.29           C
ATOM   2585  CD1  ILE B 336      -9.578   4.582 -16.785  0.50 43.50           C
ATOM   2586  CG2  ILE B 336      -6.744   5.354 -16.128  0.50 42.00           C
ATOM   2587  C    ILE B 336      -5.313   2.928 -16.508  0.50 44.54           C
ATOM   2588  O    ILE B 336      -4.196   3.416 -16.358  0.50 38.92           O
ATOM   2589  N    SER B 337      -5.688   2.301 -17.626  0.50 39.45           N
ATOM   2590  CA   SER B 337      -4.863   2.317 -18.840  0.50 38.07           C
ATOM   2591  CB   SER B 337      -3.582   1.523 -18.641  0.50 37.03           C
ATOM   2592  OG   SER B 337      -3.878   0.183 -18.274  0.50 44.98           O
ATOM   2593  C    SER B 337      -5.636   1.753 -20.041  0.50 37.04           C
ATOM   2594  O    SER B 337      -6.771   1.294 -19.899  0.50 35.95           O
ATOM   2595  N    LYS B 338      -5.023   1.808 -21.218  0.50 34.26           N
ATOM   2596  CA   LYS B 338      -5.736   1.496 -22.442  0.50 36.31           C
ATOM   2597  CB   LYS B 338      -4.883   1.870 -23.653  0.50 32.17           C
ATOM   2598  CG   LYS B 338      -5.612   1.824 -24.981  0.50 35.20           C
ATOM   2599  CD   LYS B 338      -4.778   2.408 -26.129  0.50 31.39           C
ATOM   2600  CE   LYS B 338      -3.576   1.512 -26.463  0.50 33.47           C
ATOM   2601  NZ   LYS B 338      -3.982   0.226 -27.063  0.50 30.00           N
ATOM   2602  C    LYS B 338      -6.044   0.008 -22.463  0.50 32.06           C
ATOM   2603  O    LYS B 338      -5.279  -0.774 -21.957  0.50 32.21           O
ATOM   2604  N    ALA B 339      -7.170  -0.385 -23.045  0.50 35.41           N
ATOM   2605  CA   ALA B 339      -7.430  -1.810 -23.265  0.50 40.25           C
ATOM   2606  CB   ALA B 339      -8.699  -1.988 -24.093  0.50 38.24           C
ATOM   2607  C    ALA B 339      -6.223  -2.529 -23.935  0.50 36.96           C
ATOM   2608  O    ALA B 339      -5.604  -1.990 -24.848  0.50 33.58           O
ATOM   2609  N    LYS B 340      -5.919  -3.736 -23.457  0.50 38.67           N
ATOM   2610  CA   LYS B 340      -4.840  -4.597 -23.981  0.50 38.03           C
```

Figure 26 (Continued)

```
ATOM   2611  CB  LYS B 340      -4.532  -5.697 -22.966  0.50 39.27           C
ATOM   2612  CG  LYS B 340      -4.214  -5.178 -21.559  0.50 47.72           C
ATOM   2613  CD  LYS B 340      -3.089  -5.987 -20.916  0.50 51.99           C
ATOM   2614  CE  LYS B 340      -2.354  -5.183 -19.860  0.50 54.40           C
ATOM   2615  NZ  LYS B 340      -2.108  -6.017 -18.654  0.50 61.57           N
ATOM   2616  C   LYS B 340      -5.211  -5.284 -25.291  0.50 36.68           C
ATOM   2617  O   LYS B 340      -6.377  -5.272 -25.674  0.50 36.40           O
ATOM   2618  N   GLY B 341      -4.238  -5.916 -25.959  0.50 33.10           N
ATOM   2619  CA  GLY B 341      -4.534  -6.730 -27.162  0.50 32.35           C
ATOM   2620  C   GLY B 341      -3.900  -6.166 -28.433  0.50 34.99           C
ATOM   2621  O   GLY B 341      -3.722  -4.955 -28.543  0.50 32.11           O
ATOM   2622  N   GLN B 342      -3.487  -7.034 -29.361  0.50 32.71           N
ATOM   2623  CA  GLN B 342      -2.735  -6.590 -30.561  0.50 33.01           C
ATOM   2624  CB  GLN B 342      -2.263  -7.806 -31.391  0.50 32.18           C
ATOM   2625  CG  GLN B 342      -0.905  -8.393 -31.017  0.50 42.14           C
ATOM   2626  CD  GLN B 342       0.169  -8.192 -32.096  0.50 51.45           C
ATOM   2627  OE1 GLN B 342       0.840  -7.140 -32.156  0.50 50.27           O
ATOM   2628  NE2 GLN B 342       0.369  -9.227 -32.933  0.50 42.93           N
ATOM   2629  C   GLN B 342      -3.636  -5.727 -31.441  0.50 30.24           C
ATOM   2630  O   GLN B 342      -4.730  -6.141 -31.760  0.50 27.79           O
ATOM   2631  N   PRO B 343      -3.161  -4.546 -31.869  0.50 30.14           N
ATOM   2632  CA  PRO B 343      -4.026  -3.710 -32.691  0.50 31.41           C
ATOM   2633  CB  PRO B 343      -3.191  -2.443 -32.919  0.50 32.93           C
ATOM   2634  CG  PRO B 343      -2.113  -2.482 -31.856  0.50 35.77           C
ATOM   2635  CD  PRO B 343      -1.825  -3.946 -31.690  0.50 32.07           C
ATOM   2636  C   PRO B 343      -4.306  -4.371 -34.041  0.50 34.68           C
ATOM   2637  O   PRO B 343      -3.436  -5.033 -34.597  0.50 35.73           O
ATOM   2638  N   ARG B 344      -5.521  -4.197 -34.541  0.50 30.31           N
ATOM   2639  CA  ARG B 344      -5.886  -4.611 -35.883  0.50 31.19           C
ATOM   2640  CB  ARG B 344      -6.908  -5.764 -35.828  0.50 30.03           C
ATOM   2641  CG  ARG B 344      -6.373  -7.028 -35.154  0.50 34.87           C
ATOM   2642  CD  ARG B 344      -7.474  -8.055 -34.881  0.50 42.94           C
ATOM   2643  NE  ARG B 344      -7.969  -8.625 -36.142  0.50 56.35           N
ATOM   2644  CZ  ARG B 344      -8.434  -9.870 -36.269  0.50 56.49           C
ATOM   2645  NH1 ARG B 344      -8.488 -10.661 -35.199  0.50 41.84           N
ATOM   2646  NH2 ARG B 344      -8.855 -10.312 -37.458  0.50 52.85           N
ATOM   2647  C   ARG B 344      -6.487  -3.411 -36.632  0.50 31.25           C
ATOM   2648  O   ARG B 344      -7.349  -2.706 -36.113  0.50 30.59           O
ATOM   2649  N   GLU B 345      -6.017  -3.194 -37.851  0.50 29.78           N
ATOM   2650  CA  GLU B 345      -6.516  -2.144 -38.705  0.50 31.58           C
ATOM   2651  CB  GLU B 345      -5.558  -1.969 -39.883  0.50 30.46           C
ATOM   2652  CG  GLU B 345      -5.981  -0.848 -40.795  0.50 37.31           C
ATOM   2653  CD  GLU B 345      -5.141  -0.771 -42.058  0.50 41.11           C
ATOM   2654  OE1 GLU B 345      -5.024   0.339 -42.620  0.50 43.40           O
ATOM   2655  OE2 GLU B 345      -4.607  -1.818 -42.484  0.50 41.74           O
ATOM   2656  C   GLU B 345      -7.943  -2.364 -39.234  0.50 34.81           C
ATOM   2657  O   GLU B 345      -8.228  -3.357 -39.895  0.50 39.13           O
ATOM   2658  N   PRO B 346      -8.840  -1.408 -38.987  0.50 30.69           N
ATOM   2659  CA  PRO B 346     -10.191  -1.498 -39.513  0.50 31.28           C
ATOM   2660  CB  PRO B 346     -10.896  -0.274 -38.920  0.50 33.82           C
ATOM   2661  CG  PRO B 346      -9.977   0.310 -37.911  0.50 33.57           C
ATOM   2662  CD  PRO B 346      -8.595  -0.203 -38.179  0.50 31.94           C
ATOM   2663  C   PRO B 346     -10.247  -1.406 -41.048  0.50 36.61           C
ATOM   2664  O   PRO B 346      -9.427  -0.709 -41.652  0.50 32.60           O
ATOM   2665  N   GLN B 347     -11.184  -2.135 -41.660  0.50 32.75           N
ATOM   2666  CA  GLN B 347     -11.549  -1.909 -43.058  0.50 33.83           C
ATOM   2667  CB  GLN B 347     -11.882  -3.225 -43.782  0.50 38.21           C
ATOM   2668  CG  GLN B 347     -10.819  -4.328 -43.771  0.50 44.40           C
ATOM   2669  CD  GLN B 347     -11.436  -5.718 -44.050  0.50 56.85           C
ATOM   2670  OE1 GLN B 347     -12.104  -5.945 -45.091  0.50 45.28           O
ATOM   2671  NE2 GLN B 347     -11.244  -6.649 -43.102  0.50 50.77           N
ATOM   2672  C   GLN B 347     -12.837  -1.116 -42.963  0.50 31.56           C
ATOM   2673  O   GLN B 347     -13.717  -1.474 -42.153  0.50 32.14           O
ATOM   2674  N   VAL B 348     -12.960  -0.089 -43.809  0.50 28.37           N
```

Figure 26 (Continued)

```
ATOM   2675  CA   VAL B 348     -14.098   0.836 -43.828  0.50 27.88           C
ATOM   2676  CB   VAL B 348     -13.573   2.281 -43.631  0.50 30.64           C
ATOM   2677  CG1  VAL B 348     -14.733   3.269 -43.597  0.50 28.89           C
ATOM   2678  CG2  VAL B 348     -12.713   2.365 -42.351  0.50 28.24           C
ATOM   2679  C    VAL B 348     -14.811   0.759 -45.180  0.50 30.62           C
ATOM   2680  O    VAL B 348     -14.163   0.950 -46.202  0.50 28.23           O
ATOM   2681  N    TYR B 349     -16.124   0.474 -45.196  0.50 29.18           N
ATOM   2682  CA   TYR B 349     -16.873   0.372 -46.454  0.50 34.42           C
ATOM   2683  CB   TYR B 349     -17.228  -1.084 -46.786  0.50 32.32           C
ATOM   2684  CG   TYR B 349     -16.014  -1.972 -46.882  0.50 33.93           C
ATOM   2685  CD1  TYR B 349     -15.075  -1.773 -47.882  0.50 37.89           C
ATOM   2686  CE1  TYR B 349     -13.955  -2.580 -47.985  0.50 35.98           C
ATOM   2687  CZ   TYR B 349     -13.752  -3.594 -47.067  0.50 35.34           C
ATOM   2688  OH   TYR B 349     -12.639  -4.390 -47.200  0.50 36.22           O
ATOM   2689  CE2  TYR B 349     -14.672  -3.823 -46.047  0.50 34.14           C
ATOM   2690  CD2  TYR B 349     -15.793  -3.012 -45.961  0.50 36.26           C
ATOM   2691  C    TYR B 349     -18.136   1.168 -46.283  0.50 37.31           C
ATOM   2692  O    TYR B 349     -18.748   1.127 -45.208  0.50 34.99           O
ATOM   2693  N    VAL B 350     -18.485   1.945 -47.310  0.50 30.99           N
ATOM   2694  CA   VAL B 350     -19.725   2.707 -47.299  0.50 30.96           C
ATOM   2695  CB   VAL B 350     -19.491   4.213 -47.580  0.50 32.32           C
ATOM   2696  CG1  VAL B 350     -18.916   4.875 -46.329  0.50 26.89           C
ATOM   2697  CG2  VAL B 350     -18.584   4.397 -48.804  0.50 30.47           C
ATOM   2698  C    VAL B 350     -20.673   2.134 -48.328  0.50 33.04           C
ATOM   2699  O    VAL B 350     -20.230   1.561 -49.309  0.50 32.07           O
ATOM   2700  N    LEU B 351     -21.970   2.238 -48.070  0.50 31.80           N
ATOM   2701  CA   LEU B 351     -22.954   1.597 -48.926  0.50 35.44           C
ATOM   2702  CB   LEU B 351     -23.485   0.320 -48.275  0.50 36.90           C
ATOM   2703  CG   LEU B 351     -22.504  -0.651 -47.615  0.50 37.76           C
ATOM   2704  CD1  LEU B 351     -22.275  -0.256 -46.177  0.50 42.19           C
ATOM   2705  CD2  LEU B 351     -21.206  -0.732 -48.380  0.50 37.11           C
ATOM   2706  C    LEU B 351     -24.122   2.513 -49.197  0.50 34.04           C
ATOM   2707  O    LEU B 351     -24.715   3.084 -48.277  0.50 34.79           O
ATOM   2708  N    PRO B 352     -24.495   2.632 -50.468  0.50 38.94           N
ATOM   2709  CA   PRO B 352     -25.596   3.547 -50.774  0.50 36.28           C
ATOM   2710  CB   PRO B 352     -25.560   3.649 -52.307  0.50 33.81           C
ATOM   2711  CG   PRO B 352     -24.843   2.422 -52.774  0.50 32.34           C
ATOM   2712  CD   PRO B 352     -23.860   2.071 -51.676  0.50 37.02           C
ATOM   2713  C    PRO B 352     -26.896   2.930 -50.299  0.50 41.44           C
ATOM   2714  O    PRO B 352     -26.930   1.742 -49.964  0.50 40.20           O
ATOM   2715  N    PRO B 353     -27.966   3.732 -50.273  0.50 41.21           N
ATOM   2716  CA   PRO B 353     -29.285   3.257 -49.891  0.50 43.93           C
ATOM   2717  CB   PRO B 353     -30.160   4.509 -50.039  0.50 43.62           C
ATOM   2718  CG   PRO B 353     -29.455   5.338 -51.064  0.50 41.45           C
ATOM   2719  CD   PRO B 353     -27.997   5.093 -50.838  0.50 43.97           C
ATOM   2720  C    PRO B 353     -29.766   2.156 -50.833  0.50 42.16           C
ATOM   2721  O    PRO B 353     -29.397   2.124 -52.004  0.50 40.71           O
ATOM   2722  N    SER B 354     -30.528   1.222 -50.292  0.50 41.59           N
ATOM   2723  CA   SER B 354     -31.193   0.200 -51.078  0.50 40.98           C
ATOM   2724  CB   SER B 354     -31.982  -0.699 -50.134  0.50 41.22           C
ATOM   2725  OG   SER B 354     -32.310  -1.931 -50.743  0.50 50.20           O
ATOM   2726  C    SER B 354     -32.182   0.874 -52.023  0.50 44.04           C
ATOM   2727  O    SER B 354     -32.796   1.885 -51.672  0.50 45.07           O
ATOM   2728  N    ARG B 355     -32.350   0.295 -53.205  0.50 46.96           N
ATOM   2729  CA   ARG B 355     -33.378   0.719 -54.154  0.50 50.62           C
ATOM   2730  CB   ARG B 355     -33.522  -0.344 -55.242  0.50 53.46           C
ATOM   2731  CG   ARG B 355     -34.264   0.120 -56.480  0.50 60.47           C
ATOM   2732  CD   ARG B 355     -34.637  -1.067 -57.357  0.50 60.09           C
ATOM   2733  NE   ARG B 355     -35.923  -0.865 -58.005  0.50 57.26           N
ATOM   2734  CZ   ARG B 355     -37.065  -0.704 -57.344  0.50 57.46           C
ATOM   2735  NH1  ARG B 355     -37.079  -0.718 -56.013  0.50 51.88           N
ATOM   2736  NH2  ARG B 355     -38.196  -0.524 -58.013  0.50 53.80           N
ATOM   2737  C    ARG B 355     -34.726   0.920 -53.468  0.50 50.46           C
ATOM   2738  O    ARG B 355     -35.386   1.945 -53.655  0.50 45.27           O
```

Figure 26 (Continued)

```
ATOM   2739  N    ASP B 356     -35.131   -0.070  -52.675  0.50 45.89           N
ATOM   2740  CA   ASP B 356     -36.436   -0.062  -52.041  0.50 43.82           C
ATOM   2741  CB   ASP B 356     -36.633   -1.343  -51.223  0.50 45.56           C
ATOM   2742  CG   ASP B 356     -36.862   -2.555  -52.088  0.50 50.48           C
ATOM   2743  OD1  ASP B 356     -37.300   -2.388  -53.259  0.50 43.36           O
ATOM   2744  OD2  ASP B 356     -36.614   -3.678  -51.586  0.50 50.93           O
ATOM   2745  C    ASP B 356     -36.614    1.129  -51.116  0.50 47.67           C
ATOM   2746  O    ASP B 356     -37.743    1.530  -50.827  0.50 47.86           O
ATOM   2747  N    GLU B 357     -35.514    1.657  -50.581  0.50 41.87           N
ATOM   2748  CA   GLU B 357     -35.641    2.822  -49.698  0.50 44.16           C
ATOM   2749  CB   GLU B 357     -34.446    2.955  -48.729  0.50 36.96           C
ATOM   2750  CG   GLU B 357     -34.818    3.707  -47.460  0.50 37.58           C
ATOM   2751  CD   GLU B 357     -33.663    3.861  -46.466  0.50 38.17           C
ATOM   2752  OE1  GLU B 357     -32.489    3.663  -46.836  0.50 38.75           O
ATOM   2753  OE2  GLU B 357     -33.932    4.245  -45.308  0.50 36.82           O
ATOM   2754  C    GLU B 357     -35.828    4.108  -50.511  0.50 41.21           C
ATOM   2755  O    GLU B 357     -36.376    5.099  -50.015  0.50 37.06           O
ATOM   2756  N    LEU B 358     -35.389    4.076  -51.766  0.50 45.71           N
ATOM   2757  CA   LEU B 358     -35.453    5.252  -52.627  0.50 50.06           C
ATOM   2758  CB   LEU B 358     -34.771    4.962  -53.970  0.50 52.61           C
ATOM   2759  CG   LEU B 358     -33.267    4.679  -53.862  0.50 55.24           C
ATOM   2760  CD1  LEU B 358     -32.633    4.283  -55.192  0.50 51.00           C
ATOM   2761  CD2  LEU B 358     -32.547    5.884  -53.263  0.50 56.72           C
ATOM   2762  C    LEU B 358     -36.901    5.721  -52.819  0.50 55.14           C
ATOM   2763  O    LEU B 358     -37.188    6.573  -53.657  0.50 55.50           O
ATOM   2764  N    THR B 359     -37.797    5.195  -51.985  0.50 56.81           N
ATOM   2765  CA   THR B 359     -39.205    5.541  -52.020  0.50 52.63           C
ATOM   2766  CB   THR B 359     -40.057    4.256  -52.041  0.50 62.91           C
ATOM   2767  OG1  THR B 359     -40.211    3.806  -53.397  0.50 62.66           O
ATOM   2768  CG2  THR B 359     -41.423    4.493  -51.404  0.50 58.07           C
ATOM   2769  C    THR B 359     -39.637    6.391  -50.819  0.50 56.38           C
ATOM   2770  O    THR B 359     -40.747    6.946  -50.816  0.50 51.14           O
ATOM   2771  N    LYS B 360     -38.784    6.482  -49.794  0.50 46.98           N
ATOM   2772  CA   LYS B 360     -39.180    7.136  -48.536  0.50 42.65           C
ATOM   2773  CB   LYS B 360     -38.574    6.414  -47.315  0.50 44.45           C
ATOM   2774  CG   LYS B 360     -38.953    4.936  -47.186  0.50 50.84           C
ATOM   2775  CD   LYS B 360     -40.357    4.776  -46.589  0.50 51.44           C
ATOM   2776  CE   LYS B 360     -40.836    3.333  -46.627  0.50 52.50           C
ATOM   2777  NZ   LYS B 360     -42.073    3.154  -45.806  0.50 49.49           N
ATOM   2778  C    LYS B 360     -38.808    8.630  -48.524  0.50 40.48           C
ATOM   2779  O    LYS B 360     -38.172    9.128  -49.440  0.50 42.74           O
ATOM   2780  N    ASN B 361     -39.217    9.346  -47.485  0.50 40.11           N
ATOM   2781  CA   ASN B 361     -38.840   10.746  -47.350  0.50 46.24           C
ATOM   2782  CB   ASN B 361     -39.728   11.439  -46.316  0.50 46.14           C
ATOM   2783  CG   ASN B 361     -41.137   11.695  -46.829  0.50 54.95           C
ATOM   2784  OD1  ASN B 361     -41.825   10.780  -47.320  0.50 45.55           O
ATOM   2785  ND2  ASN B 361     -41.592   12.939  -46.687  0.50 49.68           N
ATOM   2786  C    ASN B 361     -37.357   10.958  -46.976  0.50 47.72           C
ATOM   2787  O    ASN B 361     -36.750   11.984  -47.343  0.50 42.63           O
ATOM   2788  N    GLN B 362     -36.806   10.004  -46.221  0.50 42.84           N
ATOM   2789  CA   GLN B 362     -35.386    9.972  -45.867  0.50 43.81           C
ATOM   2790  CB   GLN B 362     -35.213   10.206  -44.369  0.50 46.97           C
ATOM   2791  CG   GLN B 362     -35.827   11.512  -43.892  0.50 51.99           C
ATOM   2792  CD   GLN B 362     -35.160   12.064  -42.642  0.50 56.17           C
ATOM   2793  OE1  GLN B 362     -35.700   11.959  -41.532  0.50 53.11           O
ATOM   2794  NE2  GLN B 362     -33.985   12.675  -42.815  0.50 55.85           N
ATOM   2795  C    GLN B 362     -34.788    8.625  -46.239  0.50 46.92           C
ATOM   2796  O    GLN B 362     -35.502    7.615  -46.290  0.50 39.41           O
ATOM   2797  N    VAL B 363     -33.478    8.610  -46.493  0.50 45.74           N
ATOM   2798  CA   VAL B 363     -32.782    7.380  -46.836  0.50 40.55           C
ATOM   2799  CB   VAL B 363     -32.347    7.341  -48.310  0.50 37.87           C
ATOM   2800  CG1  VAL B 363     -33.566    7.401  -49.223  0.50 37.21           C
ATOM   2801  CG2  VAL B 363     -31.373    8.476  -48.602  0.50 43.06           C
ATOM   2802  C    VAL B 363     -31.570    7.141  -45.942  0.50 42.17           C
```

Figure 26 (Continued)

```
ATOM   2803  O    VAL B 363     -31.158   8.036 -45.183  0.50 37.92           O
ATOM   2804  N    SER B 364     -31.023   5.923 -46.062  0.50 36.25           N
ATOM   2805  CA   SER B 364     -30.024   5.360 -45.168  0.50 34.66           C
ATOM   2806  CB   SER B 364     -30.538   4.016 -44.605  0.50 34.36           C
ATOM   2807  OG   SER B 364     -31.654   4.236 -43.747  0.50 36.40           O
ATOM   2808  C    SER B 364     -28.696   5.113 -45.866  0.50 31.33           C
ATOM   2809  O    SER B 364     -28.607   4.294 -46.780  0.50 32.10           O
ATOM   2810  N    LEU B 365     -27.663   5.820 -45.427  0.50 31.66           N
ATOM   2811  CA   LEU B 365     -26.309   5.554 -45.898  0.50 32.20           C
ATOM   2812  CB   LEU B 365     -25.570   6.878 -46.185  0.50 29.13           C
ATOM   2813  CG   LEU B 365     -26.425   7.991 -46.819  0.50 35.93           C
ATOM   2814  CD1  LEU B 365     -25.516   9.024 -47.489  0.50 37.52           C
ATOM   2815  CD2  LEU B 365     -27.364   7.417 -47.865  0.50 28.35           C
ATOM   2816  C    LEU B 365     -25.629   4.827 -44.750  0.50 31.18           C
ATOM   2817  O    LEU B 365     -25.725   5.278 -43.610  0.50 31.65           O
ATOM   2818  N    LEU B 366     -24.905   3.758 -45.069  0.50 33.01           N
ATOM   2819  CA   LEU B 366     -24.287   2.871 -44.069  0.50 33.12           C
ATOM   2820  CB   LEU B 366     -24.739   1.407 -44.278  0.50 31.97           C
ATOM   2821  CG   LEU B 366     -26.189   1.078 -43.951  0.50 33.03           C
ATOM   2822  CD1  LEU B 366     -26.496  -0.425 -43.974  0.50 31.91           C
ATOM   2823  CD2  LEU B 366     -26.507   1.646 -42.583  0.50 32.94           C
ATOM   2824  C    LEU B 366     -22.765   2.922 -44.151  0.50 31.69           C
ATOM   2825  O    LEU B 366     -22.192   2.954 -45.242  0.50 29.18           O
ATOM   2826  N    CYS B 367     -22.117   2.931 -42.987  0.50 28.50           N
ATOM   2827  CA   CYS B 367     -20.670   2.811 -42.927  0.50 29.62           C
ATOM   2828  CB   CYS B 367     -20.041   4.023 -42.241  0.50 28.33           C
ATOM   2829  SG   CYS B 367     -18.225   4.164 -42.350  0.50 30.38           S
ATOM   2830  C    CYS B 367     -20.371   1.608 -42.084  0.50 29.52           C
ATOM   2831  O    CYS B 367     -20.576   1.652 -40.881  0.50 28.61           O
ATOM   2832  N    LEU B 368     -19.900   0.532 -42.704  0.50 35.25           N
ATOM   2833  CA   LEU B 368     -19.497  -0.671 -41.952  0.50 30.86           C
ATOM   2834  CB   LEU B 368     -19.808  -1.932 -42.779  0.50 31.42           C
ATOM   2835  CG   LEU B 368     -18.920  -3.170 -42.617  0.50 29.93           C
ATOM   2836  CD1  LEU B 368     -19.128  -3.784 -41.243  0.50 28.15           C
ATOM   2837  CD2  LEU B 368     -19.202  -4.205 -43.696  0.50 30.33           C
ATOM   2838  C    LEU B 368     -18.003  -0.576 -41.714  0.50 29.53           C
ATOM   2839  O    LEU B 368     -17.234  -0.339 -42.652  0.50 26.07           O
ATOM   2840  N    VAL B 369     -17.606  -0.672 -40.447  0.50 24.84           N
ATOM   2841  CA   VAL B 369     -16.207  -0.682 -40.086  0.50 24.19           C
ATOM   2842  CB   VAL B 369     -15.869   0.444 -39.077  0.50 25.08           C
ATOM   2843  CG1  VAL B 369     -14.365   0.559 -38.901  0.50 22.25           C
ATOM   2844  CG2  VAL B 369     -16.466   1.803 -39.531  0.50 22.97           C
ATOM   2845  C    VAL B 369     -15.944  -2.058 -39.436  0.50 26.26           C
ATOM   2846  O    VAL B 369     -16.578  -2.430 -38.445  0.50 26.52           O
ATOM   2847  N    LYS B 370     -15.006  -2.806 -39.971  0.50 26.78           N
ATOM   2848  CA   LYS B 370     -14.840  -4.171 -39.471  0.50 30.42           C
ATOM   2849  CB   LYS B 370     -15.562  -5.181 -40.406  0.50 32.35           C
ATOM   2850  CG   LYS B 370     -14.827  -5.439 -41.735  0.50 30.83           C
ATOM   2851  CD   LYS B 370     -15.389  -6.687 -42.453  0.50 33.43           C
ATOM   2852  CE   LYS B 370     -14.631  -7.963 -42.071  0.50 34.39           C
ATOM   2853  NZ   LYS B 370     -15.102  -9.210 -42.754  0.50 30.65           N
ATOM   2854  C    LYS B 370     -13.386  -4.554 -39.343  0.50 27.26           C
ATOM   2855  O    LYS B 370     -12.507  -3.965 -39.988  0.50 28.12           O
ATOM   2856  N    GLY B 371     -13.129  -5.608 -38.581  0.50 24.90           N
ATOM   2857  CA   GLY B 371     -11.779  -6.108 -38.495  0.50 23.65           C
ATOM   2858  C    GLY B 371     -10.868  -5.306 -37.581  0.50 23.88           C
ATOM   2859  O    GLY B 371      -9.660  -5.391 -37.715  0.50 24.04           O
ATOM   2860  N    PHE B 372     -11.424  -4.530 -36.651  0.50 25.33           N
ATOM   2861  CA   PHE B 372     -10.568  -3.657 -35.834  0.50 24.34           C
ATOM   2862  CB   PHE B 372     -11.037  -2.160 -35.859  0.50 23.80           C
ATOM   2863  CG   PHE B 372     -12.427  -1.914 -35.299  0.50 23.46           C
ATOM   2864  CD1  PHE B 372     -13.541  -2.077 -36.091  0.50 23.05           C
ATOM   2865  CE1  PHE B 372     -14.814  -1.861 -35.589  0.50 22.49           C
ATOM   2866  CZ   PHE B 372     -14.981  -1.435 -34.281  0.50 24.83           C
```

Figure 26 (Continued)

```
ATOM   2867  CE2 PHE B 372     -13.874  -1.246 -33.473  0.50 22.23           C
ATOM   2868  CD2 PHE B 372     -12.605  -1.486 -33.988  0.50 22.94           C
ATOM   2869  C   PHE B 372     -10.355  -4.178 -34.409  0.50 23.85           C
ATOM   2870  O   PHE B 372     -11.122  -4.984 -33.905  0.50 20.18           O
ATOM   2871  N   TYR B 373      -9.252  -3.759 -33.806  0.50 22.65           N
ATOM   2872  CA  TYR B 373      -8.928  -4.119 -32.449  0.50 24.80           C
ATOM   2873  CB  TYR B 373      -8.205  -5.465 -32.339  0.50 27.03           C
ATOM   2874  CG  TYR B 373      -8.469  -6.043 -30.975  0.50 27.59           C
ATOM   2875  CD1 TYR B 373      -7.745  -5.610 -29.882  0.50 30.37           C
ATOM   2876  CE1 TYR B 373      -7.994  -6.117 -28.602  0.50 34.41           C
ATOM   2877  CZ  TYR B 373      -9.031  -7.020 -28.412  0.50 32.60           C
ATOM   2878  OH  TYR B 373      -9.241  -7.505 -27.143  0.50 38.49           O
ATOM   2879  CE2 TYR B 373      -9.771  -7.478 -29.488  0.50 31.16           C
ATOM   2880  CD2 TYR B 373      -9.520  -6.947 -30.763  0.50 29.02           C
ATOM   2881  C   TYR B 373      -8.013  -3.040 -31.925  0.50 23.39           C
ATOM   2882  O   TYR B 373      -7.044  -2.750 -32.605  0.50 19.61           O
ATOM   2883  N   PRO B 374      -7.999  -2.889 -30.609  0.50 24.63           N
ATOM   2884  CA  PRO B 374      -9.164  -2.827 -29.752  0.50 24.65           C
ATOM   2885  CB  PRO B 374      -8.591  -2.426 -28.378  0.50 28.20           C
ATOM   2886  CG  PRO B 374      -7.229  -1.847 -28.668  0.50 31.21           C
ATOM   2887  CD  PRO B 374      -6.954  -1.957 -30.157  0.50 24.62           C
ATOM   2888  C   PRO B 374     -10.403  -2.053 -30.193  0.50 27.03           C
ATOM   2889  O   PRO B 374     -10.481  -1.564 -31.310  0.50 27.84           O
ATOM   2890  N   SER B 375     -11.408  -2.059 -29.337  0.50 25.31           N
ATOM   2891  CA  SER B 375     -12.709  -1.695 -29.759  0.50 28.97           C
ATOM   2892  CB  SER B 375     -13.774  -2.411 -28.930  0.50 28.65           C
ATOM   2893  OG  SER B 375     -13.830  -1.834 -27.639  0.50 32.13           O
ATOM   2894  C   SER B 375     -12.877  -0.184 -29.660  0.50 28.08           C
ATOM   2895  O   SER B 375     -13.878   0.311 -30.053  0.50 27.09           O
ATOM   2896  N   ASP B 376     -11.883   0.529 -29.140  0.50 30.55           N
ATOM   2897  CA  ASP B 376     -11.988   1.987 -28.994  0.50 30.30           C
ATOM   2898  CB  ASP B 376     -10.859   2.507 -28.126  0.50 31.42           C
ATOM   2899  CG  ASP B 376     -10.892   1.898 -26.731  0.50 34.23           C
ATOM   2900  OD1 ASP B 376     -11.812   2.227 -25.941  0.50 35.89           O
ATOM   2901  OD2 ASP B 376     -10.036   1.056 -26.447  0.50 34.90           O
ATOM   2902  C   ASP B 376     -11.893   2.630 -30.352  0.50 27.97           C
ATOM   2903  O   ASP B 376     -10.938   2.409 -31.075  0.50 24.63           O
ATOM   2904  N   ILE B 377     -12.886   3.429 -30.705  0.50 25.46           N
ATOM   2905  CA  ILE B 377     -12.939   3.943 -32.053  0.50 27.40           C
ATOM   2906  CB  ILE B 377     -13.498   2.863 -33.004  0.50 25.95           C
ATOM   2907  CG1 ILE B 377     -13.307   3.247 -34.479  0.50 23.68           C
ATOM   2908  CD1 ILE B 377     -13.154   2.036 -35.379  0.50 26.79           C
ATOM   2909  CG2 ILE B 377     -14.943   2.519 -32.656  0.50 25.14           C
ATOM   2910  C   ILE B 377     -13.862   5.165 -32.033  0.50 27.93           C
ATOM   2911  O   ILE B 377     -14.687   5.293 -31.141  0.50 27.99           O
ATOM   2912  N   ALA B 378     -13.684   6.066 -32.993  0.50 26.54           N
ATOM   2913  CA  ALA B 378     -14.649   7.157 -33.223  0.50 27.71           C
ATOM   2914  CB  ALA B 378     -13.996   8.509 -32.907  0.50 28.39           C
ATOM   2915  C   ALA B 378     -15.080   7.149 -34.682  0.50 27.30           C
ATOM   2916  O   ALA B 378     -14.263   6.987 -35.556  0.50 30.77           O
ATOM   2917  N   VAL B 379     -16.356   7.381 -34.939  0.50 23.99           N
ATOM   2918  CA  VAL B 379     -16.863   7.312 -36.266  0.50 28.70           C
ATOM   2919  CB  VAL B 379     -17.660   5.994 -36.428  0.50 27.10           C
ATOM   2920  CG1 VAL B 379     -18.565   6.050 -37.624  0.50 25.02           C
ATOM   2921  CG2 VAL B 379     -16.659   4.832 -36.504  0.50 23.02           C
ATOM   2922  C   VAL B 379     -17.780   8.530 -36.411  0.50 33.44           C
ATOM   2923  O   VAL B 379     -18.599   8.804 -35.535  0.50 33.43           O
ATOM   2924  N   GLU B 380     -17.604   9.282 -37.493  0.50 32.43           N
ATOM   2925  CA  GLU B 380     -18.274  10.590 -37.634  0.50 29.88           C
ATOM   2926  CB  GLU B 380     -17.304  11.746 -37.298  0.50 31.16           C
ATOM   2927  CG  GLU B 380     -17.079  11.992 -35.808  0.50 32.69           C
ATOM   2928  CD  GLU B 380     -16.023  13.052 -35.538  0.50 35.83           C
ATOM   2929  OE1 GLU B 380     -15.701  13.842 -36.453  0.50 36.04           O
ATOM   2930  OE2 GLU B 380     -15.505  13.108 -34.406  0.50 35.42           O
```

Figure 26 (Continued)

```
ATOM   2931  C    GLU B 380     -18.725  10.686 -39.064  0.50 29.87           C
ATOM   2932  O    GLU B 380     -18.130  10.050 -39.936  0.50 30.07           O
ATOM   2933  N    TRP B 381     -19.753  11.494 -39.319  0.50 30.23           N
ATOM   2934  CA   TRP B 381     -20.177  11.772 -40.688  0.50 30.62           C
ATOM   2935  CB   TRP B 381     -21.598  11.288 -40.910  0.50 31.00           C
ATOM   2936  CG   TRP B 381     -21.800   9.804 -40.944  0.50 31.91           C
ATOM   2937  CD1  TRP B 381     -21.982   8.968 -39.861  0.50 33.75           C
ATOM   2938  NE1  TRP B 381     -22.201   7.673 -40.295  0.50 31.92           N
ATOM   2939  CE2  TRP B 381     -22.131   7.646 -41.667  0.50 30.21           C
ATOM   2940  CD2  TRP B 381     -21.877   8.967 -42.111  0.50 29.31           C
ATOM   2941  CE3  TRP B 381     -21.775   9.208 -43.485  0.50 30.00           C
ATOM   2942  CZ3  TRP B 381     -21.909   8.138 -44.369  0.50 30.30           C
ATOM   2943  CH2  TRP B 381     -22.195   6.840 -43.904  0.50 31.55           C
ATOM   2944  CZ2  TRP B 381     -22.301   6.573 -42.557  0.50 31.87           C
ATOM   2945  C    TRP B 381     -20.151  13.289 -40.989  0.50 34.60           C
ATOM   2946  O    TRP B 381     -20.341  14.135 -40.091  0.50 30.38           O
ATOM   2947  N    GLU B 382     -20.012  13.621 -42.271  0.50 32.31           N
ATOM   2948  CA   GLU B 382     -19.946  15.032 -42.689  0.50 35.36           C
ATOM   2949  CB   GLU B 382     -18.569  15.648 -42.392  0.50 33.62           C
ATOM   2950  CG   GLU B 382     -17.394  15.013 -43.135  0.50 33.03           C
ATOM   2951  CD   GLU B 382     -16.400  14.250 -42.220  0.50 39.68           C
ATOM   2952  OE1  GLU B 382     -16.587  14.189 -40.968  0.50 34.62           O
ATOM   2953  OE2  GLU B 382     -15.403  13.702 -42.763  0.50 40.23           O
ATOM   2954  C    GLU B 382     -20.244  15.151 -44.157  0.50 34.14           C
ATOM   2955  O    GLU B 382     -20.244  14.164 -44.880  0.50 29.53           O
ATOM   2956  N    SER B 383     -20.453  16.384 -44.600  0.50 37.70           N
ATOM   2957  CA   SER B 383     -20.855  16.641 -45.974  0.50 38.50           C
ATOM   2958  CB   SER B 383     -22.352  16.377 -46.150  0.50 34.52           C
ATOM   2959  OG   SER B 383     -22.685  16.395 -47.529  0.50 42.86           O
ATOM   2960  C    SER B 383     -20.617  18.114 -46.208  0.50 42.27           C
ATOM   2961  O    SER B 383     -20.987  18.937 -45.360  0.50 38.43           O
ATOM   2962  N    ASN B 384     -19.990  18.447 -47.329  0.50 42.21           N
ATOM   2963  CA   ASN B 384     -19.836  19.854 -47.697  0.50 44.57           C
ATOM   2964  CB   ASN B 384     -21.215  20.471 -47.959  0.50 47.93           C
ATOM   2965  CG   ASN B 384     -21.815  20.015 -49.267  0.50 55.35           C
ATOM   2966  OD1  ASN B 384     -21.093  19.732 -50.224  0.50 63.97           O
ATOM   2967  ND2  ASN B 384     -23.145  19.926 -49.316  0.50 63.83           N
ATOM   2968  C    ASN B 384     -19.145  20.663 -46.607  0.50 48.47           C
ATOM   2969  O    ASN B 384     -19.556  21.800 -46.315  0.50 42.38           O
ATOM   2970  N    GLY B 385     -18.136  20.080 -45.964  0.50 43.94           N
ATOM   2971  CA   GLY B 385     -17.401  20.825 -44.930  0.50 42.82           C
ATOM   2972  C    GLY B 385     -18.127  21.047 -43.608  0.50 38.03           C
ATOM   2973  O    GLY B 385     -17.689  21.827 -42.777  0.50 45.23           O
ATOM   2974  N    GLN B 386     -19.227  20.343 -43.405  0.50 39.75           N
ATOM   2975  CA   GLN B 386     -20.009  20.450 -42.170  0.50 42.56           C
ATOM   2976  CB   GLN B 386     -21.280  21.327 -42.386  0.50 44.16           C
ATOM   2977  CG   GLN B 386     -22.585  20.831 -41.716  0.50 52.20           C
ATOM   2978  CD   GLN B 386     -23.002  21.596 -40.441  0.50 55.78           C
ATOM   2979  OE1  GLN B 386     -22.987  22.838 -40.395  0.50 66.44           O
ATOM   2980  NE2  GLN B 386     -23.412  20.860 -39.421  0.50 45.43           N
ATOM   2981  C    GLN B 386     -20.395  19.041 -41.713  0.50 39.78           C
ATOM   2982  O    GLN B 386     -20.667  18.169 -42.540  0.50 42.93           O
ATOM   2983  N    PRO B 387     -20.408  18.818 -40.395  0.50 38.10           N
ATOM   2984  CA   PRO B 387     -20.806  17.516 -39.876  0.50 40.47           C
ATOM   2985  CB   PRO B 387     -20.719  17.695 -38.358  0.50 38.68           C
ATOM   2986  CG   PRO B 387     -19.766  18.821 -38.140  0.50 42.30           C
ATOM   2987  CD   PRO B 387     -19.687  19.636 -39.402  0.50 38.09           C
ATOM   2988  C    PRO B 387     -22.246  17.234 -40.251  0.50 43.92           C
ATOM   2989  O    PRO B 387     -23.045  18.159 -40.354  0.50 43.65           O
ATOM   2990  N    GLU B 388     -22.575  15.957 -40.406  0.50 41.61           N
ATOM   2991  CA   GLU B 388     -23.956  15.481 -40.337  0.50 39.46           C
ATOM   2992  CB   GLU B 388     -24.083  14.227 -41.191  0.50 39.93           C
ATOM   2993  CG   GLU B 388     -23.873  14.573 -42.652  0.50 37.87           C
ATOM   2994  CD   GLU B 388     -25.020  15.424 -43.144  0.50 47.19           C
```

Figure 26 (Continued)

```
ATOM   2995  OE1 GLU B 388     -26.088  15.322 -42.506  0.50 45.00           O
ATOM   2996  OE2 GLU B 388     -24.856  16.208 -44.116  0.50 55.07           O
ATOM   2997  C   GLU B 388     -24.529  15.255 -38.921  0.50 42.14           C
ATOM   2998  O   GLU B 388     -23.858  14.750 -38.034  0.50 53.09           O
ATOM   2999  N   ASN B 389     -25.781  15.638 -38.712  0.50 44.60           N
ATOM   3000  CA  ASN B 389     -26.370  15.484 -37.395  0.50 50.20           C
ATOM   3001  CB  ASN B 389     -27.576  16.415 -37.186  0.50 40.74           C
ATOM   3002  CG  ASN B 389     -28.018  16.451 -35.738  0.50 43.63           C
ATOM   3003  OD1 ASN B 389     -27.222  16.787 -34.860  0.50 40.96           O
ATOM   3004  ND2 ASN B 389     -29.280  16.065 -35.470  0.50 43.07           N
ATOM   3005  C   ASN B 389     -26.844  14.060 -37.205  0.50 48.69           C
ATOM   3006  O   ASN B 389     -26.352  13.343 -36.327  0.50 49.72           O
ATOM   3007  N   ASN B 390     -27.824  13.685 -38.026  0.50 42.02           N
ATOM   3008  CA  ASN B 390     -28.720  12.605 -37.677  0.50 42.48           C
ATOM   3009  CB  ASN B 390     -30.128  12.828 -38.281  0.50 43.84           C
ATOM   3010  CG  ASN B 390     -31.091  11.698 -37.934  0.50 51.08           C
ATOM   3011  OD1 ASN B 390     -30.997  11.095 -36.857  0.50 60.30           O
ATOM   3012  ND2 ASN B 390     -32.005  11.397 -38.837  0.50 50.44           N
ATOM   3013  C   ASN B 390     -28.138  11.241 -38.052  0.50 34.66           C
ATOM   3014  O   ASN B 390     -28.602  10.573 -38.970  0.50 35.40           O
ATOM   3015  N   TYR B 391     -27.098  10.832 -37.341  0.50 37.08           N
ATOM   3016  CA  TYR B 391     -26.576   9.482 -37.531  0.50 35.26           C
ATOM   3017  CB  TYR B 391     -25.156   9.430 -38.160  0.50 32.65           C
ATOM   3018  CG  TYR B 391     -24.029  10.067 -37.353  0.50 35.83           C
ATOM   3019  CD1 TYR B 391     -23.273   9.317 -36.454  0.50 31.39           C
ATOM   3020  CE1 TYR B 391     -22.234   9.892 -35.737  0.50 32.49           C
ATOM   3021  CZ  TYR B 391     -21.910  11.234 -35.967  0.50 35.64           C
ATOM   3022  OH  TYR B 391     -20.892  11.826 -35.270  0.50 34.29           O
ATOM   3023  CE2 TYR B 391     -22.629  11.994 -36.871  0.50 30.57           C
ATOM   3024  CD2 TYR B 391     -23.666  11.410 -37.564  0.50 31.63           C
ATOM   3025  C   TYR B 391     -26.630   8.724 -36.242  0.50 34.80           C
ATOM   3026  O   TYR B 391     -26.638   9.316 -35.157  0.50 33.59           O
ATOM   3027  N   LEU B 392     -26.686   7.403 -36.352  0.50 34.50           N
ATOM   3028  CA  LEU B 392     -26.495   6.591 -35.163  0.50 33.52           C
ATOM   3029  CB  LEU B 392     -27.824   6.151 -34.563  0.50 40.97           C
ATOM   3030  CG  LEU B 392     -28.621   5.075 -35.295  0.50 45.79           C
ATOM   3031  CD1 LEU B 392     -27.938   3.720 -35.176  0.50 51.97           C
ATOM   3032  CD2 LEU B 392     -28.861   5.450 -36.752  0.50 49.53           C
ATOM   3033  C   LEU B 392     -25.579   5.405 -35.455  0.50 32.91           C
ATOM   3034  O   LEU B 392     -25.554   4.817 -36.558  0.50 34.13           O
ATOM   3035  N   THR B 393     -24.765   5.095 -34.477  0.50 30.81           N
ATOM   3036  CA  THR B 393     -23.675   4.180 -34.710  0.50 32.46           C
ATOM   3037  CB  THR B 393     -22.322   4.924 -34.656  0.50 33.09           C
ATOM   3038  OG1 THR B 393     -22.292   5.954 -35.663  0.50 34.67           O
ATOM   3039  CG2 THR B 393     -21.155   3.953 -34.889  0.50 32.20           C
ATOM   3040  C   THR B 393     -23.763   3.179 -33.594  0.50 34.06           C
ATOM   3041  O   THR B 393     -23.599   3.533 -32.438  0.50 30.47           O
ATOM   3042  N   TRP B 394     -24.038   1.929 -33.937  0.50 35.43           N
ATOM   3043  CA  TRP B 394     -24.153   0.895 -32.934  0.50 31.43           C
ATOM   3044  CB  TRP B 394     -24.745  -0.355 -33.556  0.50 29.76           C
ATOM   3045  CG  TRP B 394     -26.181  -0.195 -33.982  0.50 27.93           C
ATOM   3046  CD1 TRP B 394     -27.299  -0.550 -33.269  0.50 29.13           C
ATOM   3047  NE1 TRP B 394     -28.424  -0.314 -34.007  0.50 28.97           N
ATOM   3048  CE2 TRP B 394     -28.052   0.189 -35.233  0.50 31.09           C
ATOM   3049  CD2 TRP B 394     -26.650   0.266 -35.254  0.50 29.54           C
ATOM   3050  CE3 TRP B 394     -26.019   0.771 -36.397  0.50 29.96           C
ATOM   3051  CZ3 TRP B 394     -26.807   1.188 -37.459  0.50 33.14           C
ATOM   3052  CH2 TRP B 394     -28.204   1.059 -37.419  0.50 28.58           C
ATOM   3053  CZ2 TRP B 394     -28.839   0.596 -36.316  0.50 31.42           C
ATOM   3054  C   TRP B 394     -22.806   0.565 -32.313  0.50 31.71           C
ATOM   3055  O   TRP B 394     -21.786   0.756 -32.939  0.50 31.87           O
ATOM   3056  N   PRO B 395     -22.816   0.031 -31.076  0.50 32.70           N
ATOM   3057  CA  PRO B 395     -21.612  -0.342 -30.358  0.50 33.85           C
ATOM   3058  CB  PRO B 395     -22.152  -0.931 -29.042  0.50 36.28           C
```

Figure 26 (Continued)

```
ATOM   3059  CG   PRO B 395     -23.512   -0.320  -28.878  0.50 39.80           C
ATOM   3060  CD   PRO B 395     -24.041   -0.241  -30.286  0.50 36.34           C
ATOM   3061  C    PRO B 395     -20.823   -1.417  -31.124  0.50 31.62           C
ATOM   3062  O    PRO B 395     -21.396   -2.190  -31.910  0.50 31.35           O
ATOM   3063  N    PRO B 396     -19.513   -1.447  -30.922  0.50 25.27           N
ATOM   3064  CA   PRO B 396     -18.729   -2.451  -31.623  0.50 29.66           C
ATOM   3065  CB   PRO B 396     -17.336   -2.245  -31.058  0.50 26.23           C
ATOM   3066  CG   PRO B 396     -17.278   -0.755  -30.840  0.50 22.66           C
ATOM   3067  CD   PRO B 396     -18.662   -0.414  -30.305  0.50 25.44           C
ATOM   3068  C    PRO B 396     -19.256   -3.845  -31.290  0.50 33.81           C
ATOM   3069  O    PRO B 396     -19.800   -4.042  -30.208  0.50 31.54           O
ATOM   3070  N    VAL B 397     -19.193   -4.921  -31.693  0.50 29.99           N
ATOM   3071  CA   VAL B 397     -19.323   -6.305  -31.269  0.50 32.55           C
ATOM   3072  CB   VAL B 397     -20.695   -6.904  -31.646  0.50 31.77           C
ATOM   3073  CG1  VAL B 397     -21.799   -6.176  -30.911  0.50 37.92           C
ATOM   3074  CG2  VAL B 397     -20.913   -6.840  -33.150  0.50 34.13           C
ATOM   3075  C    VAL B 397     -18.214   -7.098  -31.916  0.50 30.13           C
ATOM   3076  O    VAL B 397     -17.893   -6.900  -33.089  0.50 30.24           O
ATOM   3077  N    LEU B 398     -18.117   -7.967  -31.322  0.50 31.64           N
ATOM   3078  CA   LEU B 398     -17.068   -8.945  -31.442  0.50 32.20           C
ATOM   3079  CB   LEU B 398     -17.030   -9.745  -30.138  0.50 37.53           C
ATOM   3080  CG   LEU B 398     -15.740  -10.387  -29.671  0.50 43.01           C
ATOM   3081  CD1  LEU B 398     -14.551   -9.462  -29.899  0.50 42.13           C
ATOM   3082  CD2  LEU B 398     -15.872  -10.791  -28.200  0.50 40.85           C
ATOM   3083  C    LEU B 398     -17.413   -9.845  -32.613  0.50 30.83           C
ATOM   3084  O    LEU B 398     -18.460  -10.467  -32.644  0.50 35.28           O
ATOM   3085  N    ASP B 399     -16.557   -9.875  -33.613  0.50 32.85           N
ATOM   3086  CA   ASP B 399     -16.814  -10.685  -34.807  0.50 33.66           C
ATOM   3087  CB   ASP B 399     -16.276   -9.925  -36.008  0.50 32.43           C
ATOM   3088  CG   ASP B 399     -16.966  -10.285  -37.315  0.50 36.92           C
ATOM   3089  OD1  ASP B 399     -17.662  -11.324  -37.372  0.50 37.71           O
ATOM   3090  OD2  ASP B 399     -16.791   -9.512  -38.295  0.50 34.54           O
ATOM   3091  C    ASP B 399     -16.136  -12.079  -34.657  0.50 35.09           C
ATOM   3092  O    ASP B 399     -15.184  -12.244  -33.890  0.50 32.00           O
ATOM   3093  N    SER B 400     -16.624  -13.072  -35.389  0.50 39.44           N
ATOM   3094  CA   SER B 400     -16.218  -14.461  -35.159  0.50 43.37           C
ATOM   3095  CB   SER B 400     -16.849  -15.367  -36.219  0.50 44.12           C
ATOM   3096  OG   SER B 400     -16.513  -14.899  -37.519  0.50 46.56           O
ATOM   3097  C    SER B 400     -14.701  -14.621  -35.161  0.50 45.94           C
ATOM   3098  O    SER B 400     -14.170  -15.419  -34.400  0.50 48.46           O
ATOM   3099  N    ASP B 401     -13.999  -13.815  -35.967  0.50 43.10           N
ATOM   3100  CA   ASP B 401     -12.552  -13.959  -36.132  0.50 36.73           C
ATOM   3101  CB   ASP B 401     -12.103  -13.435  -37.495  0.50 35.71           C
ATOM   3102  CG   ASP B 401     -12.049  -11.893  -37.553  0.50 38.71           C
ATOM   3103  OD1  ASP B 401     -12.779  -11.210  -36.794  0.50 35.37           O
ATOM   3104  OD2  ASP B 401     -11.253  -11.370  -38.356  0.50 37.43           O
ATOM   3105  C    ASP B 401     -11.707  -13.293  -35.051  0.50 35.88           C
ATOM   3106  O    ASP B 401     -10.480  -13.260  -35.169  0.50 37.87           O
ATOM   3107  N    GLY B 402     -12.333  -12.804  -33.988  0.50 32.47           N
ATOM   3108  CA   GLY B 402     -11.564  -12.211  -32.885  0.50 28.41           C
ATOM   3109  C    GLY B 402     -11.506  -10.670  -32.925  0.50 31.19           C
ATOM   3110  O    GLY B 402     -11.113  -10.044  -31.947  0.50 29.88           O
ATOM   3111  N    SER B 403     -11.966  -10.052  -34.013  0.50 26.09           N
ATOM   3112  CA   SER B 403     -11.934   -8.557  -34.116  0.50 25.22           C
ATOM   3113  CB   SER B 403     -11.364   -8.141  -35.475  0.50 29.22           C
ATOM   3114  OG   SER B 403     -12.262   -8.547  -36.486  0.50 27.60           O
ATOM   3115  C    SER B 403     -13.332   -7.955  -33.940  0.50 27.65           C
ATOM   3116  O    SER B 403     -14.339   -8.694  -33.794  0.50 27.81           O
ATOM   3117  N    PHE B 404     -13.420   -6.622  -33.906  0.50 25.31           N
ATOM   3118  CA   PHE B 404     -14.735   -5.974  -33.729  0.50 25.36           C
ATOM   3119  CB   PHE B 404     -14.646   -4.806  -32.723  0.50 27.09           C
ATOM   3120  CG   PHE B 404     -14.408   -5.246  -31.307  0.50 24.26           C
ATOM   3121  CD1  PHE B 404     -13.111   -5.308  -30.783  0.50 29.08           C
ATOM   3122  CE1  PHE B 404     -12.895   -5.678  -29.430  0.50 25.65           C
```

Figure 26 (Continued)

```
ATOM   3123  CZ   PHE B 404     -13.989  -6.012 -28.639  0.50 25.98           C
ATOM   3124  CE2  PHE B 404      15.286   5.981  29.166  0.50 27.32           C
ATOM   3125  CD2  PHE B 404     -15.485  -5.579 -30.492  0.50 25.08           C
ATOM   3126  C    PHE B 404     -15.245  -5.409 -35.026  0.50 25.26           C
ATOM   3127  O    PHE B 404     -14.466  -5.100 -35.917  0.50 27.02           O
ATOM   3128  N    PHE B 405     -16.557  -5.237 -35.121  0.50 24.80           N
ATOM   3129  CA   PHE B 405     -17.105  -4.508 -36.240  0.50 28.01           C
ATOM   3130  CB   PHE B 405     -17.616  -5.411 -37.356  0.50 23.90           C
ATOM   3131  CG   PHE B 405     -18.968  -6.001 -37.105  0.50 26.22           C
ATOM   3132  CD1  PHE B 405     -20.118  -5.271 -37.366  0.50 23.11           C
ATOM   3133  CE1  PHE B 405     -21.365  -5.822 -37.153  0.50 23.89           C
ATOM   3134  CZ   PHE B 405     -21.475  -7.151 -36.753  0.50 27.22           C
ATOM   3135  CE2  PHE B 405     -20.330  -7.912 -36.541  0.50 25.07           C
ATOM   3136  CD2  PHE B 405     -19.090  -7.336 -36.722  0.50 26.34           C
ATOM   3137  C    PHE B 405     -18.194  -3.646 -35.705  0.50 27.28           C
ATOM   3138  O    PHE B 405     -18.638  -3.833 -34.584  0.50 27.06           O
ATOM   3139  N    LEU B 406     -18.580  -2.655 -36.491  0.50 31.71           N
ATOM   3140  CA   LEU B 406     -19.774  -1.892 -36.175  0.50 30.29           C
ATOM   3141  CB   LEU B 406     -19.428  -0.731 -35.259  0.50 34.24           C
ATOM   3142  CG   LEU B 406     -18.558   0.471 -35.642  0.50 36.18           C
ATOM   3143  CD1  LEU B 406     -19.172   1.310 -36.770  0.50 28.68           C
ATOM   3144  CD2  LEU B 406     -18.387   1.337 -34.384  0.50 30.68           C
ATOM   3145  C    LEU B 406     -20.323  -1.366 -37.455  0.50 29.14           C
ATOM   3146  O    LEU B 406     -19.660  -1.425 -38.462  0.50 33.32           O
ATOM   3147  N    TYR B 407     -21.501  -0.772 -37.402  0.50 30.15           N
ATOM   3148  CA   TYR B 407     -21.926   0.048 -38.514  0.50 29.18           C
ATOM   3149  CB   TYR B 407     -23.203  -0.500 -39.139  0.50 29.73           C
ATOM   3150  CG   TYR B 407     -23.029  -1.697 -40.008  0.50 24.76           C
ATOM   3151  CD1  TYR B 407     -23.085  -1.572 -41.391  0.50 23.39           C
ATOM   3152  CE1  TYR B 407     -22.993  -2.687 -42.211  0.50 25.49           C
ATOM   3153  CZ   TYR B 407     -22.916  -3.953 -41.640  0.50 25.71           C
ATOM   3154  OH   TYR B 407     -22.780  -5.076 -42.463  0.50 24.95           O
ATOM   3155  CE2  TYR B 407     -22.893  -4.085 -40.256  0.50 23.38           C
ATOM   3156  CD2  TYR B 407     -22.971  -2.967 -39.459  0.50 23.68           C
ATOM   3157  C    TYR B 407     -22.242   1.429 -37.963  0.50 27.83           C
ATOM   3158  O    TYR B 407     -22.345   1.612 -36.752  0.50 26.01           O
ATOM   3159  N    SER B 408     -22.402   2.392 -38.871  0.50 29.18           N
ATOM   3160  CA   SER B 408     -23.035   3.663 -38.536  0.50 29.07           C
ATOM   3161  CB   SER B 408     -22.013   4.823 -38.510  0.50 27.72           C
ATOM   3162  OG   SER B 408     -22.500   5.937 -37.757  0.50 28.75           O
ATOM   3163  C    SER B 408     -24.064   3.898 -39.626  0.50 30.18           C
ATOM   3164  O    SER B 408     -23.783   3.661 -40.816  0.50 29.25           O
ATOM   3165  N    LYS B 409     -25.236   4.399 -39.234  0.50 29.35           N
ATOM   3166  CA   LYS B 409     -26.273   4.707 -40.208  0.50 31.09           C
ATOM   3167  CB   LYS B 409     -27.618   4.103 -39.813  0.50 32.78           C
ATOM   3168  CG   LYS B 409     -28.721   4.405 -40.840  0.50 35.24           C
ATOM   3169  CD   LYS B 409     -29.992   3.564 -40.642  0.50 32.14           C
ATOM   3170  CE   LYS B 409     -30.595   3.726 -39.256  0.50 35.09           C
ATOM   3171  NZ   LYS B 409     -31.517   4.908 -39.102  0.50 32.96           N
ATOM   3172  C    LYS B 409     -26.423   6.214 -40.267  0.50 33.53           C
ATOM   3173  O    LYS B 409     -26.704   6.873 -39.231  0.50 29.80           O
ATOM   3174  N    LEU B 410     -26.243   6.749 -41.473  0.50 29.20           N
ATOM   3175  CA   LEU B 410     -26.616   8.142 -41.743  0.50 34.76           C
ATOM   3176  CB   LEU B 410     -25.542   8.864 -42.579  0.50 32.13           C
ATOM   3177  CG   LEU B 410     -25.829  10.341 -42.923  0.50 37.83           C
ATOM   3178  CD1  LEU B 410     -25.716  11.289 -41.724  0.50 31.95           C
ATOM   3179  CD2  LEU B 410     -24.916  10.802 -44.049  0.50 30.19           C
ATOM   3180  C    LEU B 410     -27.965   8.237 -42.453  0.50 35.95           C
ATOM   3181  O    LEU B 410     -28.179   7.666 -43.530  0.50 30.60           O
ATOM   3182  N    THR B 411     -28.892   8.979 -41.867  0.50 37.81           N
ATOM   3183  CA   THR B 411     -30.124   9.236 -42.582  0.50 34.75           C
ATOM   3184  CB   THR B 411     -31.313   9.071 -41.631  0.50 37.01           C
ATOM   3185  OG1  THR B 411     -31.291   7.727 -41.113  0.50 36.95           O
ATOM   3186  CG2  THR B 411     -32.647   9.315 -42.355  0.50 32.21           C
```

Figure 26 (Continued)

```
ATOM   3187  C   THR B 411     -30.094  10.610 -43.264  0.50 36.03           C
ATOM   3188  O   THR B 411     -29.786  11.628 -42.639  0.50 38.54           O
ATOM   3189  N   VAL B 412     -30.376  10.637 -44.560  0.50 39.72           N
ATOM   3190  CA  VAL B 412     -30.413  11.915 -45.309  0.50 41.68           C
ATOM   3191  CB  VAL B 412     -29.254  12.016 -46.334  0.50 41.92           C
ATOM   3192  CG1 VAL B 412     -27.940  11.575 -45.710  0.50 38.84           C
ATOM   3193  CG2 VAL B 412     -29.569  11.205 -47.582  0.50 37.49           C
ATOM   3194  C   VAL B 412     -31.703  12.014 -46.101  0.50 43.25           C
ATOM   3195  O   VAL B 412     -32.065  11.037 -46.759  0.50 38.82           O
ATOM   3196  N   ASP B 413     -32.361  13.186 -46.093  0.50 43.47           N
ATOM   3197  CA  ASP B 413     -33.612  13.361 -46.853  0.50 43.18           C
ATOM   3198  CB  ASP B 413     -34.147  14.805 -46.804  0.50 48.55           C
ATOM   3199  CG  ASP B 413     -34.402  15.302 -45.399  0.50 50.40           C
ATOM   3200  OD1 ASP B 413     -35.054  14.589 -44.596  0.50 53.86           O
ATOM   3201  OD2 ASP B 413     -33.968  16.435 -45.103  0.50 53.22           O
ATOM   3202  C   ASP B 413     -33.266  13.018 -48.280  0.50 42.94           C
ATOM   3203  O   ASP B 413     -32.195  13.374 -48.765  0.50 42.68           O
ATOM   3204  N   LYS B 414     -34.158  12.309 -48.951  0.50 43.04           N
ATOM   3205  CA  LYS B 414     -33.845  11.766 -50.264  0.50 39.93           C
ATOM   3206  CB  LYS B 414     -35.035  10.983 -50.823  0.50 42.22           C
ATOM   3207  CG  LYS B 414     -34.825  10.565 -52.274  0.50 44.03           C
ATOM   3208  CD  LYS B 414     -35.900   9.626 -52.789  0.50 49.93           C
ATOM   3209  CE  LYS B 414     -37.208  10.341 -53.128  0.50 50.81           C
ATOM   3210  NZ  LYS B 414     -38.363   9.397 -52.959  0.50 53.80           N
ATOM   3211  C   LYS B 414     -33.420  12.823 -51.274  0.50 43.73           C
ATOM   3212  O   LYS B 414     -32.715  12.512 -52.241  0.50 44.47           O
ATOM   3213  N   SER B 415     -33.883  14.057 -51.080  0.50 43.03           N
ATOM   3214  CA  SER B 415     -33.561  15.144 -52.008  0.50 44.48           C
ATOM   3215  CB  SER B 415     -34.359  16.421 -51.668  0.50 43.52           C
ATOM   3216  OG  SER B 415     -33.919  17.040 -50.460  0.50 40.66           O
ATOM   3217  C   SER B 415     -32.053  15.415 -52.050  0.50 46.72           C
ATOM   3218  O   SER B 415     -31.420  15.232 -53.097  0.50 47.85           O
ATOM   3219  N   ARG B 416     -31.479  15.789 -50.899  0.50 45.80           N
ATOM   3220  CA  ARG B 416     -30.027  15.927 -50.756  0.50 42.81           C
ATOM   3221  CB  ARG B 416     -29.623  16.034 -49.288  0.50 47.81           C
ATOM   3222  CG  ARG B 416     -30.193  17.254 -48.589  0.50 48.57           C
ATOM   3223  CD  ARG B 416     -29.784  17.278 -47.134  0.50 51.67           C
ATOM   3224  NE  ARG B 416     -28.351  17.510 -47.005  0.50 51.08           N
ATOM   3225  CZ  ARG B 416     -27.646  17.269 -45.901  0.50 45.73           C
ATOM   3226  NH1 ARG B 416     -28.236  16.776 -44.819  0.50 45.60           N
ATOM   3227  NH2 ARG B 416     -26.344  17.520 -45.884  0.50 41.74           N
ATOM   3228  C   ARG B 416     -29.279  14.791 -51.428  0.50 43.73           C
ATOM   3229  O   ARG B 416     -28.349  15.042 -52.200  0.50 47.95           O
ATOM   3230  N   TRP B 417     -29.688  13.546 -51.159  0.50 43.62           N
ATOM   3231  CA  TRP B 417     -29.082  12.372 -51.831  0.50 40.09           C
ATOM   3232  CB  TRP B 417     -29.652  11.049 -51.306  0.50 37.23           C
ATOM   3233  CG  TRP B 417     -29.080   9.838 -52.010  0.50 38.04           C
ATOM   3234  CD1 TRP B 417     -29.727   9.027 -52.888  0.50 40.77           C
ATOM   3235  NE1 TRP B 417     -28.887   8.045 -53.349  0.50 38.77           N
ATOM   3236  CE2 TRP B 417     -27.671   8.185 -52.739  0.50 37.63           C
ATOM   3237  CD2 TRP B 417     -27.751   9.303 -51.889  0.50 41.62           C
ATOM   3238  CE3 TRP B 417     -26.518   9.674 -51.164  0.50 36.80           C
ATOM   3239  CZ3 TRP B 417     -25.490   8.913 -51.280  0.50 33.49           C
ATOM   3240  CH2 TRP B 417     -25.438   7.825 -52.137  0.50 37.08           C
ATOM   3241  CZ2 TRP B 417     -26.526   7.429 -52.860  0.50 39.49           C
ATOM   3242  C   TRP B 417     -29.268  12.438 -53.332  0.50 40.71           C
ATOM   3243  O   TRP B 417     -28.292  12.361 -54.090  0.50 41.32           O
ATOM   3244  N   GLN B 418     -30.522  12.577 -53.760  0.50 43.82           N
ATOM   3245  CA  GLN B 418     -30.861  12.712 -55.188  0.50 49.66           C
ATOM   3246  CB  GLN B 418     -32.385  12.834 -55.359  0.50 49.19           C
ATOM   3247  CG  GLN B 418     -33.130  11.520 -55.127  0.50 62.69           C
ATOM   3248  CD  GLN B 418     -32.640  10.415 -56.053  0.50 70.92           C
ATOM   3249  OE1 GLN B 418     -32.020  10.691 -57.083  0.50 84.72           O
ATOM   3250  NE2 GLN B 418     -32.908   9.162 -55.695  0.50 63.53           N
```

Figure 26 (Continued)

```
ATOM   3251  C    GLN B 418     -30.164  13.904 -55.862  0.50 45.16           C
ATOM   3252  O    GLN B 418     -29.809  13.849 -57.043  0.50 43.96           O
ATOM   3253  N    GLN B 419     -29.984  14.986 -55.116  0.50 44.41           N
ATOM   3254  CA   GLN B 419     -29.303  16.161 -55.657  0.50 49.57           C
ATOM   3255  CB   GLN B 419     -29.593  17.385 -54.811  0.50 46.54           C
ATOM   3256  CG   GLN B 419     -31.050  17.805 -54.854  0.50 46.84           C
ATOM   3257  CD   GLN B 419     -31.272  19.051 -54.037  0.50 50.24           C
ATOM   3258  OE1  GLN B 419     -31.062  19.062 -52.817  0.50 44.11           O
ATOM   3259  NE2  GLN B 419     -31.663  20.127 -54.711  0.50 59.78           N
ATOM   3260  C    GLN B 419     -27.795  15.984 -55.822  0.50 52.09           C
ATOM   3261  O    GLN B 419     -27.122  16.802 -56.447  0.50 48.85           O
ATOM   3262  N    GLY B 420     -27.246  14.906 -55.291  0.50 51.04           N
ATOM   3263  CA   GLY B 420     -25.853  14.612 -55.620  0.50 46.57           C
ATOM   3264  C    GLY B 420     -24.888  15.054 -54.547  0.50 39.93           C
ATOM   3265  O    GLY B 420     -23.692  15.077 -54.771  0.50 37.77           O
ATOM   3266  N    ASN B 421     -25.405  15.410 -53.377  0.50 38.56           N
ATOM   3267  CA   ASN B 421     -24.539  15.679 -52.241  0.50 38.64           C
ATOM   3268  CB   ASN B 421     -25.372  16.172 -51.067  0.50 39.70           C
ATOM   3269  CG   ASN B 421     -25.860  17.595 -51.279  0.50 46.82           C
ATOM   3270  OD1  ASN B 421     -25.069  18.544 -51.230  0.50 43.57           O
ATOM   3271  ND2  ASN B 421     -27.160  17.747 -51.565  0.50 43.17           N
ATOM   3272  C    ASN B 421     -23.696  14.457 -51.843  0.50 39.44           C
ATOM   3273  O    ASN B 421     -24.238  13.364 -51.688  0.50 36.76           O
ATOM   3274  N    VAL B 422     -22.379  14.665 -51.740  0.50 35.40           N
ATOM   3275  CA   VAL B 422     -21.428  13.683 -51.270  0.50 37.60           C
ATOM   3276  CB   VAL B 422     -20.003  14.015 -51.732  0.50 37.13           C
ATOM   3277  CG1  VAL B 422     -19.023  12.997 -51.146  0.50 33.91           C
ATOM   3278  CG2  VAL B 422     -19.915  14.027 -53.270  0.50 33.03           C
ATOM   3279  C    VAL B 422     -21.416  13.621 -49.748  0.50 38.30           C
ATOM   3280  O    VAL B 422     -21.456  14.654 -49.068  0.50 41.83           O
ATOM   3281  N    PHE B 423     -21.406  12.402 -49.225  0.50 37.24           N
ATOM   3282  CA   PHE B 423     -21.419  12.153 -47.781  0.50 33.74           C
ATOM   3283  CB   PHE B 423     -22.725  11.448 -47.385  0.50 34.26           C
ATOM   3284  CG   PHE B 423     -23.949  12.301 -47.602  0.50 34.52           C
ATOM   3285  CD1  PHE B 423     -24.613  12.282 -48.816  0.50 33.52           C
ATOM   3286  CE1  PHE B 423     -25.698  13.096 -49.039  0.50 34.74           C
ATOM   3287  CZ   PHE B 423     -26.118  13.969 -48.065  0.50 34.12           C
ATOM   3288  CE2  PHE B 423     -25.453  14.022 -46.859  0.50 37.21           C
ATOM   3289  CD2  PHE B 423     -24.364  13.191 -46.636  0.50 34.86           C
ATOM   3290  C    PHE B 423     -20.208  11.306 -47.414  0.50 34.75           C
ATOM   3291  O    PHE B 423     -19.818  10.412 -48.160  0.50 34.47           O
ATOM   3292  N    SER B 424     -19.609  11.592 -46.270  0.50 32.88           N
ATOM   3293  CA   SER B 424     -18.337  10.977 -45.938  0.50 34.40           C
ATOM   3294  CB   SER B 424     -17.240  12.043 -46.006  0.50 30.88           C
ATOM   3295  OG   SER B 424     -17.050  12.449 -47.346  0.50 34.33           O
ATOM   3296  C    SER B 424     -18.352  10.398 -44.542  0.50 32.88           C
ATOM   3297  O    SER B 424     -18.801  11.039 -43.601  0.50 29.56           O
ATOM   3298  N    CYS B 425     -17.822   9.194 -44.399  0.50 33.39           N
ATOM   3299  CA   CYS B 425     -17.786   8.573 -43.093  0.50 28.91           C
ATOM   3300  CB   CYS B 425     -18.287   7.119 -43.204  0.50 27.79           C
ATOM   3301  SG   CYS B 425     -17.957   6.136 -41.730  0.50 31.97           S
ATOM   3302  C    CYS B 425     -16.324   8.628 -42.707  0.50 27.37           C
ATOM   3303  O    CYS B 425     -15.493   8.170 -43.450  0.50 26.02           O
ATOM   3304  N    SER B 426     -16.017   9.193 -41.547  0.50 28.14           N
ATOM   3305  CA   SER B 426     -14.647   9.345 -41.092  0.50 28.11           C
ATOM   3306  CB   SER B 426     -14.440  10.770 -40.570  0.50 29.84           C
ATOM   3307  OG   SER B 426     -14.202  11.655 -41.642  0.50 33.19           O
ATOM   3308  C    SER B 426     -14.421   8.380 -39.932  0.50 28.79           C
ATOM   3309  O    SER B 426     -15.209   8.346 -38.991  0.50 28.56           O
ATOM   3310  N    VAL B 427     -13.315   7.654 -39.954  0.50 28.46           N
ATOM   3311  CA   VAL B 427     -13.062   6.683 -38.894  0.50 28.83           C
ATOM   3312  CB   VAL B 427     -13.060   5.256 -39.469  0.50 30.85           C
ATOM   3313  CG1  VAL B 427     -12.877   4.220 -38.333  0.50 27.78           C
ATOM   3314  CG2  VAL B 427     -14.367   5.025 -40.243  0.50 27.45           C
```

Figure 26 (Continued)

```
ATOM   3315  C   VAL B 427     -11.741    6.982  -38.213  0.50 28.42           C
ATOM   3316  O   VAL B 427      10.738    7.192   38.864  0.50 25.38           O
ATOM   3317  N   MET B 428     -11.726    6.983  -36.893  0.50 27.27           N
ATOM   3318  CA  MET B 428     -10.476    7.218  -36.213  0.50 28.77           C
ATOM   3319  CB  MET B 428     -10.538    8.532  -35.402  0.50 28.06           C
ATOM   3320  CG  MET B 428     -10.524    9.797  -36.273  0.50 31.21           C
ATOM   3321  SD  MET B 428     -11.442   11.212  -35.558  0.50 35.96           S
ATOM   3322  CE  MET B 428     -13.121   10.662  -35.810  0.50 31.32           C
ATOM   3323  C   MET B 428     -10.173    6.060  -35.298  0.50 24.81           C
ATOM   3324  O   MET B 428     -11.001    5.691  -34.502  0.50 24.22           O
ATOM   3325  N   HIS B 429      -8.949    5.541  -35.368  0.50 27.02           N
ATOM   3326  CA  HIS B 429      -8.618    4.291  -34.680  0.50 25.58           C
ATOM   3327  CB  HIS B 429      -9.195    3.062  -35.415  0.50 23.65           C
ATOM   3328  CG  HIS B 429      -9.060    1.791  -34.619  0.50 21.01           C
ATOM   3329  ND1 HIS B 429      -7.900    1.052  -34.603  0.50 22.63           N
ATOM   3330  CE1 HIS B 429      -8.035    0.015  -33.788  0.50 20.74           C
ATOM   3331  NE2 HIS B 429      -9.233    0.086  -33.232  0.50 25.73           N
ATOM   3332  CD2 HIS B 429      -9.895    1.194  -33.738  0.50 20.12           C
ATOM   3333  C   HIS B 429      -7.121    4.195  -34.682  0.50 26.30           C
ATOM   3334  O   HIS B 429      -6.480    4.598  -35.644  0.50 29.07           O
ATOM   3335  N   GLU B 430      -6.553    3.697  -33.594  0.50 26.80           N
ATOM   3336  CA  GLU B 430      -5.103    3.707  -33.430  0.50 26.90           C
ATOM   3337  CB  GLU B 430      -4.706    3.131  -32.064  0.50 28.42           C
ATOM   3338  CG  GLU B 430      -5.131    1.686  -31.895  0.50 29.74           C
ATOM   3339  CD  GLU B 430      -4.769    1.164  -30.523  0.50 33.18           C
ATOM   3340  OE1 GLU B 430      -5.628    1.241  -29.625  0.50 29.42           O
ATOM   3341  OE2 GLU B 430      -3.613    0.721  -30.336  0.50 38.55           O
ATOM   3342  C   GLU B 430      -4.380    2.885  -34.472  0.50 25.91           C
ATOM   3343  O   GLU B 430      -3.182    3.081  -34.676  0.50 26.97           O
ATOM   3344  N   ALA B 431      -5.062    1.942  -35.109  0.50 24.74           N
ATOM   3345  CA  ALA B 431      -4.349    1.090  -36.061  0.50 27.47           C
ATOM   3346  CB  ALA B 431      -4.799   -0.370  -35.917  0.50 24.73           C
ATOM   3347  C   ALA B 431      -4.584    1.598  -37.490  0.50 28.91           C
ATOM   3348  O   ALA B 431      -4.232    0.924  -38.451  0.50 28.08           O
ATOM   3349  N   LEU B 432      -5.205    2.767  -37.647  0.50 25.37           N
ATOM   3350  CA  LEU B 432      -5.164    3.397  -38.953  0.50 27.84           C
ATOM   3351  CB  LEU B 432      -6.411    4.247  -39.207  0.50 27.52           C
ATOM   3352  CG  LEU B 432      -7.667    3.382  -39.313  0.50 28.18           C
ATOM   3353  CD1 LEU B 432      -8.916    4.236  -39.153  0.50 25.15           C
ATOM   3354  CD2 LEU B 432      -7.672    2.601  -40.637  0.50 27.53           C
ATOM   3355  C   LEU B 432      -3.902    4.232  -39.121  0.50 31.56           C
ATOM   3356  O   LEU B 432      -3.398    4.846  -38.165  0.50 29.15           O
ATOM   3357  N   HIS B 433      -3.366    4.243  -40.331  0.50 31.20           N
ATOM   3358  CA  HIS B 433      -2.315    5.210  -40.645  0.50 36.30           C
ATOM   3359  CB  HIS B 433      -1.972    5.141  -42.144  0.50 40.49           C
ATOM   3360  CG  HIS B 433      -0.785    5.973  -42.540  0.50 45.98           C
ATOM   3361  ND1 HIS B 433      -0.873    7.013  -43.439  0.50 46.38           N
ATOM   3362  CE1 HIS B 433       0.321    7.558  -43.602  0.50 51.14           C
ATOM   3363  NE2 HIS B 433       1.185    6.909  -42.840  0.50 53.97           N
ATOM   3364  CD2 HIS B 433       0.520    5.910  -42.167  0.50 52.97           C
ATOM   3365  C   HIS B 433      -2.859    6.607  -40.340  0.50 37.25           C
ATOM   3366  O   HIS B 433      -3.956    6.936  -40.777  0.50 33.15           O
ATOM   3367  N   ASN B 434      -2.092    7.427  -39.622  0.50 35.63           N
ATOM   3368  CA  ASN B 434      -2.534    8.787  -39.249  0.50 35.89           C
ATOM   3369  CB  ASN B 434      -2.903    9.602  -40.496  0.50 36.52           C
ATOM   3370  CG  ASN B 434      -1.820    9.576  -41.555  0.50 40.34           C
ATOM   3371  OD1 ASN B 434      -1.998    8.993  -42.617  0.50 43.36           O
ATOM   3372  ND2 ASN B 434      -0.700   10.231  -41.279  0.50 43.20           N
ATOM   3373  C   ASN B 434      -3.719    8.796  -38.292  0.50 32.64           C
ATOM   3374  O   ASN B 434      -4.297    9.858  -38.030  0.50 31.31           O
ATOM   3375  N   HIS B 435      -4.106    7.603  -37.847  0.50 28.73           N
ATOM   3376  CA  HIS B 435      -5.254    7.340  -36.979  0.50 26.18           C
ATOM   3377  CB  HIS B 435      -5.130    7.963  -35.588  0.50 29.16           C
ATOM   3378  CG  HIS B 435      -3.908    7.549  -34.833  0.50 29.07           C
```

Figure 26 (Continued)

```
ATOM   3379  ND1  HIS B 435      -3.424    8.267  -33.761  0.50 29.22           N
ATOM   3380  CE1  HIS B 435      -2.319    7.692  -33.310  0.50 29.31           C
ATOM   3381  NE2  HIS B 435      -2.072    6.629  -34.053  0.50 29.53           N
ATOM   3382  CD2  HIS B 435      -3.055    6.509  -35.007  0.50 28.72           C
ATOM   3383  C    HIS B 435      -6.573    7.763  -37.546  0.50 27.03           C
ATOM   3384  O    HIS B 435      -7.528    7.992  -36.783  0.50 27.87           O
ATOM   3385  N    TYR B 436      -6.582    7.785  -38.865  0.50 25.94           N
ATOM   3386  CA   TYR B 436      -7.862    8.352  -39.461  0.50 25.89           C
ATOM   3387  CB   TYR B 436      -7.670    9.858  -39.577  0.50 27.11           C
ATOM   3388  CG   TYR B 436      -8.809   10.573  -40.299  0.50 27.85           C
ATOM   3389  CD1  TYR B 436      -8.797   10.743  -41.668  0.50 24.66           C
ATOM   3390  CE1  TYR B 436      -9.846   11.384  -42.314  0.50 27.93           C
ATOM   3391  CZ   TYR B 436     -10.989   11.893  -41.573  0.50 30.59           C
ATOM   3392  OH   TYR B 436     -11.943   12.560  -42.161  0.50 31.73           O
ATOM   3393  CE2  TYR B 436     -10.934   11.707  -40.214  0.50 27.59           C
ATOM   3394  CD2  TYR B 436      -9.897   11.039  -39.588  0.50 28.70           C
ATOM   3395  C    TYR B 436      -7.971    7.829  -40.866  0.50 26.62           C
ATOM   3396  O    TYR B 436      -6.965    7.713  -41.524  0.50 28.32           O
ATOM   3397  N    THR B 437      -9.183    7.498  -41.305  0.50 27.19           N
ATOM   3398  CA   THR B 437      -9.448    7.299  -42.714  0.50 31.61           C
ATOM   3399  CB   THR B 437      -9.308    5.839  -43.156  0.50 31.20           C
ATOM   3400  OG1  THR B 437      -9.506    5.812  -44.565  0.50 32.50           O
ATOM   3401  CG2  THR B 437     -10.386    5.004  -42.535  0.50 29.99           C
ATOM   3402  C    THR B 437     -10.866    7.750  -43.009  0.50 29.02           C
ATOM   3403  O    THR B 437     -11.622    7.978  -42.097  0.50 31.68           O
ATOM   3404  N    GLN B 438     -11.228    7.871  -44.273  0.50 28.63           N
ATOM   3405  CA   GLN B 438     -12.531    8.432  -44.633  0.50 31.42           C
ATOM   3406  CB   GLN B 438     -12.424    9.969  -44.857  0.50 31.36           C
ATOM   3407  CG   GLN B 438     -13.772   10.698  -44.954  0.50 31.33           C
ATOM   3408  CD   GLN B 438     -13.631   12.159  -45.453  0.50 33.48           C
ATOM   3409  OE1  GLN B 438     -13.113   12.406  -46.530  0.50 33.48           O
ATOM   3410  NE2  GLN B 438     -14.114   13.109  -44.665  0.50 30.66           N
ATOM   3411  C    GLN B 438     -12.981    7.776  -45.926  0.50 33.16           C
ATOM   3412  O    GLN B 438     -12.172    7.514  -46.802  0.50 33.55           O
ATOM   3413  N    LYS B 439     -14.271    7.522  -46.060  0.50 32.39           N
ATOM   3414  CA   LYS B 439     -14.774    6.970  -47.316  0.50 36.73           C
ATOM   3415  CB   LYS B 439     -15.122    5.482  -47.179  0.50 33.29           C
ATOM   3416  CG   LYS B 439     -13.907    4.568  -46.995  0.50 38.06           C
ATOM   3417  CD   LYS B 439     -13.233    4.247  -48.326  0.50 37.39           C
ATOM   3418  CE   LYS B 439     -12.674    2.810  -48.304  0.50 44.85           C
ATOM   3419  NZ   LYS B 439     -13.511    1.702  -48.731  0.50 32.62           N
ATOM   3420  C    LYS B 439     -16.006    7.730  -47.721  0.50 34.52           C
ATOM   3421  O    LYS B 439     -16.848    8.023  -46.883  0.50 36.34           O
ATOM   3422  N    SER B 440     -16.126    8.008  -49.012  0.50 35.34           N
ATOM   3423  CA   SER B 440     -17.183    8.878  -49.488  0.50 39.33           C
ATOM   3424  CB   SER B 440     -16.584   10.162  -50.104  0.50 38.40           C
ATOM   3425  OG   SER B 440     -15.974   10.956  -49.089  0.50 36.97           O
ATOM   3426  C    SER B 440     -18.091    8.175  -50.489  0.50 42.02           C
ATOM   3427  O    SER B 440     -17.703    7.202  -51.119  0.50 42.45           O
ATOM   3428  N    LEU B 441     -19.324    8.647  -50.597  0.50 39.64           N
ATOM   3429  CA   LEU B 441     -20.196    8.135  -51.623  0.50 40.39           C
ATOM   3430  CB   LEU B 441     -20.862    6.820  -51.180  0.50 41.26           C
ATOM   3431  CG   LEU B 441     -22.062    6.884  -50.230  0.50 37.72           C
ATOM   3432  CD1  LEU B 441     -21.701    7.613  -48.963  0.50 38.41           C
ATOM   3433  CD2  LEU B 441     -22.554    5.463  -49.935  0.50 37.80           C
ATOM   3434  C    LEU B 441     -21.219    9.198  -51.969  0.50 36.76           C
ATOM   3435  O    LEU B 441     -21.460   10.123  -51.189  0.50 38.24           O
ATOM   3436  N    SER B 442     -21.796    9.067  -53.153  0.50 38.37           N
ATOM   3437  CA   SER B 442     -22.827    9.980  -53.631  0.50 38.22           C
ATOM   3438  CB   SER B 442     -22.175   11.195  -54.274  0.50 37.45           C
ATOM   3439  OG   SER B 442     -21.303   10.759  -55.312  0.50 36.36           O
ATOM   3440  C    SER B 442     -23.669    9.253  -54.690  0.50 42.56           C
ATOM   3441  O    SER B 442     -23.294    8.169  -55.175  0.50 35.47           O
ATOM   3442  N    LEU B 443     -24.816    9.831  -55.041  0.50 41.48           N
```

Figure 26 (Continued)

```
ATOM   3443  CA   LEU B 443     -25.678    9.136  -55.979  0.50  49.30           C
ATOM   3444  CB   LEU B 443     -26.949    9.932  -56.300  0.50  47.40           C
ATOM   3445  CG   LEU B 443     -28.164    9.022  -56.547  0.50  51.38           C
ATOM   3446  CD1  LEU B 443     -29.411    9.814  -56.895  0.50  42.75           C
ATOM   3447  CD2  LEU B 443     -27.865    7.971  -57.617  0.50  49.08           C
ATOM   3448  C    LEU B 443     -24.872    8.818  -57.229  0.50  48.79           C
ATOM   3449  O    LEU B 443     -24.069    9.628  -57.692  0.50  50.46           O
ATOM   3450  N    SER B 444     -25.013    7.597  -57.711  0.50  48.57           N
ATOM   3451  CA   SER B 444     -24.592    7.279  -59.059  0.50  60.93           C
ATOM   3452  CB   SER B 444     -23.853    5.946  -59.070  0.50  56.78           C
ATOM   3453  OG   SER B 444     -24.136    5.218  -57.891  0.50  49.58           O
ATOM   3454  C    SER B 444     -25.830    7.253  -59.975  0.50  69.04           C
ATOM   3455  O    SER B 444     -26.744    6.435  -59.791  0.50  64.36           O
ATOM   3456  N    PRO B 445     -25.886    8.195  -60.932  0.50  75.22           N
ATOM   3457  CA   PRO B 445     -27.025    8.410  -61.839  0.50  78.43           C
ATOM   3458  CB   PRO B 445     -26.430    9.292  -62.935  0.50  77.33           C
ATOM   3459  CG   PRO B 445     -25.371   10.075  -62.233  0.50  80.35           C
ATOM   3460  CD   PRO B 445     -24.825    9.197  -61.133  0.50  78.38           C
ATOM   3461  C    PRO B 445     -27.588    7.125  -62.449  0.50  70.64           C
ATOM   3462  O    PRO B 445     -26.827    6.221  -62.779  0.50  76.83           O
HETATM 3463  C1   NAG B 500     -23.567   13.193   -2.900  0.50  71.15           C
HETATM 3464  C2   NAG B 500     -23.589   11.671   -2.911  0.50  73.13           C
HETATM 3465  N2   NAG B 500     -23.325   11.166   -1.583  0.50  74.36           N
HETATM 3466  C7   NAG B 500     -24.285   10.623   -0.847  0.50  75.86           C
HETATM 3467  O7   NAG B 500     -25.424   10.498   -1.252  0.50  70.18           O
HETATM 3468  C8   NAG B 500     -23.872   10.175    0.519  0.50  70.97           C
HETATM 3469  C3   NAG B 500     -22.566   11.103   -3.884  0.50  74.04           C
HETATM 3470  O3   NAG B 500     -22.759    9.694   -4.011  0.50  69.91           O
HETATM 3471  C4   NAG B 500     -22.710   11.766   -5.242  0.50  71.68           C
HETATM 3472  O4   NAG B 500     -21.696   11.290   -6.135  0.50  76.88           O
HETATM 3473  C5   NAG B 500     -22.604   13.268   -5.054  0.50  71.01           C
HETATM 3474  C6   NAG B 500     -22.686   13.994   -6.385  0.50  76.88           C
HETATM 3475  O6   NAG B 500     -23.992   13.809   -6.928  0.50  80.95           O
HETATM 3476  O5   NAG B 500     -23.675   13.699   -4.224  0.50  70.18           O
HETATM 3477  C1   FUC B 501     -24.417   15.035   -7.539  0.50  78.32           C
HETATM 3478  C2   FUC B 501     -25.425   14.701   -8.629  0.50  74.96           C
HETATM 3479  O2   FUC B 501     -24.860   13.718   -9.499  0.50  72.93           O
HETATM 3480  C3   FUC B 501     -26.733   14.163   -8.058  0.50  67.56           C
HETATM 3481  O3   FUC B 501     -27.739   14.260   -9.068  0.50  57.14           O
HETATM 3482  C4   FUC B 501     -27.200   14.939   -6.830  0.50  66.11           C
HETATM 3483  O4   FUC B 501     -27.781   16.181   -7.237  0.50  62.93           O
HETATM 3484  C5   FUC B 501     -26.047   15.218   -5.879  0.50  71.01           C
HETATM 3485  C6   FUC B 501     -26.505   16.065   -4.703  0.50  61.08           C
HETATM 3486  O5   FUC B 501     -25.027   15.903   -6.593  0.50  79.82           O
HETATM 3487  C1   NAG B 502     -21.911   10.430   -6.992  0.50  71.29           C
HETATM 3488  C2   NAG B 502     -21.229   10.565   -8.355  0.50  70.80           C
HETATM 3489  N2   NAG B 502     -21.514   11.811   -9.048  0.50  72.82           N
HETATM 3490  C7   NAG B 502     -20.552   12.627   -9.514  0.50  74.21           C
HETATM 3491  O7   NAG B 502     -20.775   13.679  -10.116  0.50  71.42           O
HETATM 3492  C8   NAG B 502     -19.127   12.243   -9.265  0.50  67.14           C
HETATM 3493  C3   NAG B 502     -21.697    9.415   -9.232  0.50  71.28           C
HETATM 3494  O3   NAG B 502     -21.162    9.531  -10.532  0.50  72.63           O
HETATM 3495  C4   NAG B 502     -21.302    8.109   -8.565  0.50  69.74           C
HETATM 3496  O4   NAG B 502     -21.757    7.030   -9.338  0.50  65.18           O
HETATM 3497  C5   NAG B 502     -21.975    8.053   -7.196  0.50  72.85           C
HETATM 3498  C6   NAG B 502     -21.562    6.794   -6.451  0.50  66.49           C
HETATM 3499  O6   NAG B 502     -22.036    6.909   -5.130  0.50  69.75           O
HETATM 3500  O5   NAG B 502     -21.624    9.174   -6.409  0.50  68.32           O
HETATM 3501  C1   BMA B 503     -20.647    6.510  -10.074  0.50  68.19           C
HETATM 3502  O5   BMA B 503     -20.741    6.971  -11.411  0.50  66.90           O
HETATM 3503  C5   BMA B 503     -19.726    6.467  -12.260  0.50  68.91           C
HETATM 3504  C6   BMA B 503     -19.877    7.166  -13.601  0.50  64.52           C
HETATM 3505  O6   BMA B 503     -20.155    8.545  -13.345  0.50  62.32           O
HETATM 3506  C4   BMA B 503     -19.885    4.958  -12.363  0.50  74.09           C
```

Figure 26 (Continued)

```
HETATM 3507  O4  BMA B 503     -18.889    4.419 -13.230  0.50 75.20           O
HETATM 3508  C3  BMA B 503     -19.729    4.350 -10.981  0.50 71.45           C
HETATM 3509  O3  BMA B 503     -19.952    2.939 -11.038  0.50 76.70           O
HETATM 3510  C2  BMA B 503     -20.728    4.991 -10.032  0.50 68.83           C
HETATM 3511  O2  BMA B 503     -22.052    4.601 -10.400  0.50 59.32           O
HETATM 3512  C1  MAN B 504     -20.050    9.283 -14.567  0.50 64.98           C
HETATM 3513  C2  MAN B 504     -19.576   10.694 -14.277  0.50 64.22           C
HETATM 3514  O2  MAN B 504     -19.548   11.422 -15.501  0.50 66.09           O
HETATM 3515  C3  MAN B 504     -20.550   11.399 -13.353  0.50 60.26           C
HETATM 3516  O3  MAN B 504     -20.153   12.766 -13.229  0.50 51.27           O
HETATM 3517  C4  MAN B 504     -21.953   11.327 -13.940  0.50 58.15           C
HETATM 3518  O4  MAN B 504     -22.905   11.802 -12.984  0.50 54.21           O
HETATM 3519  C5  MAN B 504     -22.303    9.900 -14.344  0.50 63.32           C
HETATM 3520  C6  MAN B 504     -23.637    9.850 -15.070  0.50 58.67           C
HETATM 3521  O6  MAN B 504     -24.029    8.484 -15.215  0.50 51.56           O
HETATM 3522  O5  MAN B 504     -21.307    9.381 -15.215  0.50 65.22           O
HETATM 3523  C1  NAG B 505     -18.264   11.225 -16.122  0.50 76.57           C
HETATM 3524  C2  NAG B 505     -18.397   11.382 -17.632  0.50 79.78           C
HETATM 3525  N2  NAG B 505     -19.363   10.431 -18.146  0.50 85.29           N
HETATM 3526  C7  NAG B 505     -20.635   10.767 -18.338  0.50 96.03           C
HETATM 3527  O7  NAG B 505     -21.014   11.926 -18.298  0.50 95.56           O
HETATM 3528  C8  NAG B 505     -21.574    9.628 -18.607  0.50 92.74           C
HETATM 3529  C3  NAG B 505     -17.052   11.184 -18.320  0.50 86.13           C
HETATM 3530  O3  NAG B 505     -17.161   11.559 -19.698  0.50 83.09           O
HETATM 3531  C4  NAG B 505     -15.966   12.019 -17.651  0.50 85.04           C
HETATM 3532  O4  NAG B 505     -14.686   11.633 -18.164  0.50 85.29           O
HETATM 3533  C5  NAG B 505     -15.983   11.831 -16.139  0.50 84.57           C
HETATM 3534  C6  NAG B 505     -14.953   12.731 -15.466  0.50 84.58           C
HETATM 3535  O6  NAG B 505     -15.445   14.075 -15.430  0.50 78.83           O
HETATM 3536  O5  NAG B 505     -17.282   12.137 -15.635  0.50 76.77           O
HETATM 3537  C1  GAL B 506     -14.031   12.799 -18.696  0.50 89.75           C
HETATM 3538  C2  GAL B 506     -12.739   12.383 -19.390  0.50 90.04           C
HETATM 3539  O2  GAL B 506     -11.879   11.733 -18.447  0.50104.40           O
HETATM 3540  C3  GAL B 506     -12.023   13.591 -19.981  0.50 84.31           C
HETATM 3541  O3  GAL B 506     -10.945   13.147 -20.813  0.50 86.65           O
HETATM 3542  C4  GAL B 506     -12.980   14.445 -20.804  0.50 85.89           C
HETATM 3543  O4  GAL B 506     -13.309   13.760 -22.018  0.50 81.34           O
HETATM 3544  C5  GAL B 506     -14.257   14.738 -20.025  0.50 87.90           C
HETATM 3545  C6  GAL B 506     -15.246   15.528 -20.874  0.50 94.96           C
HETATM 3546  O6  GAL B 506     -16.105   16.291 -20.020  0.50 85.89           O
HETATM 3547  O5  GAL B 506     -14.856   13.511 -19.616  0.50 96.54           O
HETATM 3548  C1  MAN B 507     -18.683    1.387 -11.484  0.50 82.78           C
HETATM 3549  C2  MAN B 507     -19.409    0.122 -11.927  0.50 86.94           C
HETATM 3550  O2  MAN B 507     -18.578   -1.017 -11.679  0.50100.13           O
HETATM 3551  C3  MAN B 507     -20.730   -0.039 -11.184  0.50 86.07           C
HETATM 3552  O3  MAN B 507     -21.272   -1.337 -11.451  0.50 85.90           O
HETATM 3553  C4  MAN B 507     -20.535    0.131  -9.682  0.50 81.63           C
HETATM 3554  O4  MAN B 507     -21.814    0.201  -9.040  0.50 65.14           O
HETATM 3555  C5  MAN B 507     -19.742    1.395  -9.373  0.50 80.40           C
HETATM 3556  C6  MAN B 507     -19.482    1.524  -7.877  0.50 83.66           C
HETATM 3557  O6  MAN B 507     -20.854    1.858  -7.252  0.50 83.21           O
HETATM 3558  O5  MAN B 507     -18.498    1.357 -10.070  0.50 82.21           O
HETATM 3559  C1  NAG B 508     -17.396   -1.414 -11.956  0.50111.14           C
HETATM 3560  C2  NAG B 508     -17.479   -1.063 -13.432  0.50115.14           C
HETATM 3561  N2  NAG B 508     -18.287   -2.053 -14.103  0.50108.02           N
HETATM 3562  C7  NAG B 508     -19.057   -1.676 -15.099  0.50105.55           C
HETATM 3563  O7  NAG B 508     -20.268   -1.793 -15.072  0.50101.67           O
HETATM 3564  C8  NAG B 508     -18.306   -1.076 -16.242  0.50107.60           C
HETATM 3565  C3  NAG B 508     -16.105   -1.028 -14.072  0.50119.44           C
HETATM 3566  O3  NAG B 508     -16.201   -0.551 -15.419  0.50124.34           O
HETATM 3567  C4  NAG B 508     -15.207   -0.130 -13.243  0.50122.61           C
HETATM 3568  O4  NAG B 508     -13.896   -0.102 -13.807  0.50123.02           O
HETATM 3569  C5  NAG B 508     -15.164   -0.678 -11.826  0.50118.67           C
HETATM 3570  C6  NAG B 508     -14.274    0.136 -10.906  0.50121.26           C
```

Figure 26 (Continued)

| | | | | | | | | | |
|---|---|---|---|---|---|---|---|---|---|
| HETATM | 3571 | O6 | NAG B 508 | -15.104 | 1.104 | -10.255 | 0.50 | 117.24 | O |
| HETATM | 3572 | O5 | NAG B 508 | -16.471 | -0.568 | -11.298 | 0.50 | 116.86 | O |
| ATOM | 3573 | N | GLY b 236 | -18.389 | 24.786 | -78.278 | 0.50 | 53.03 | N |
| ATOM | 3574 | CA | GLY b 236 | -18.736 | 24.819 | -76.825 | 0.50 | 54.62 | C |
| ATOM | 3575 | C | GLY b 236 | -18.485 | 23.484 | -76.148 | 0.50 | 57.56 | C |
| ATOM | 3576 | O | GLY b 236 | -19.310 | 23.008 | -75.369 | 0.50 | 59.01 | O |
| ATOM | 3577 | N | GLY b 237 | -17.338 | 22.880 | -76.446 | 0.50 | 61.24 | N |
| ATOM | 3578 | CA | GLY b 237 | -17.012 | 21.529 | -75.968 | 0.50 | 59.08 | C |
| ATOM | 3579 | C | GLY b 237 | -17.099 | 21.369 | -74.456 | 0.50 | 58.07 | C |
| ATOM | 3580 | O | GLY b 237 | -17.760 | 22.158 | -73.788 | 0.50 | 57.52 | O |
| ATOM | 3581 | N | PRO b 238 | -16.440 | 20.329 | -73.916 | 0.50 | 53.37 | N |
| ATOM | 3582 | CA | PRO b 238 | -16.395 | 19.984 | -72.489 | 0.50 | 54.92 | C |
| ATOM | 3583 | CB | PRO b 238 | -15.199 | 19.033 | -72.400 | 0.50 | 53.53 | C |
| ATOM | 3584 | CG | PRO b 238 | -15.134 | 18.380 | -73.745 | 0.50 | 54.68 | C |
| ATOM | 3585 | CD | PRO b 238 | -15.845 | 19.265 | -74.747 | 0.50 | 55.65 | C |
| ATOM | 3586 | C | PRO b 238 | -16.185 | 21.163 | -71.540 | 0.50 | 50.71 | C |
| ATOM | 3587 | O | PRO b 238 | -15.785 | 22.245 | -71.970 | 0.50 | 46.12 | O |
| ATOM | 3588 | N | SER b 239 | -16.451 | 20.928 | -70.255 | 0.50 | 50.68 | N |
| ATOM | 3589 | CA | SER b 239 | -16.310 | 21.942 | -69.206 | 0.50 | 50.30 | C |
| ATOM | 3590 | CB | SER b 239 | -17.685 | 22.479 | -68.820 | 0.50 | 45.74 | C |
| ATOM | 3591 | OG | SER b 239 | -17.946 | 23.688 | -69.498 | 0.50 | 58.34 | O |
| ATOM | 3592 | C | SER b 239 | -15.628 | 21.381 | -67.949 | 0.50 | 50.80 | C |
| ATOM | 3593 | O | SER b 239 | -15.936 | 20.269 | -67.504 | 0.50 | 44.57 | O |
| ATOM | 3594 | N | VAL b 240 | -14.746 | 22.187 | -67.360 | 0.50 | 49.23 | N |
| ATOM | 3595 | CA | VAL b 240 | -13.931 | 21.763 | -66.223 | 0.50 | 45.14 | C |
| ATOM | 3596 | CB | VAL b 240 | -12.430 | 21.858 | -66.540 | 0.50 | 43.55 | C |
| ATOM | 3597 | CG1 | VAL b 240 | -11.625 | 21.168 | -65.444 | 0.50 | 40.75 | C |
| ATOM | 3598 | CG2 | VAL b 240 | -12.107 | 21.263 | -67.909 | 0.50 | 37.60 | C |
| ATOM | 3599 | C | VAL b 240 | -14.180 | 22.656 | -65.001 | 0.50 | 46.64 | C |
| ATOM | 3600 | O | VAL b 240 | -14.204 | 23.891 | -65.106 | 0.50 | 38.15 | O |
| ATOM | 3601 | N | PHE b 241 | -14.353 | 22.032 | -63.843 | 0.50 | 41.08 | N |
| ATOM | 3602 | CA | PHE b 241 | -14.375 | 22.795 | -62.588 | 0.50 | 43.53 | C |
| ATOM | 3603 | CB | PHE b 241 | -15.801 | 22.883 | -62.018 | 0.50 | 44.10 | C |
| ATOM | 3604 | CG | PHE b 241 | -16.772 | 23.596 | -62.929 | 0.50 | 46.02 | C |
| ATOM | 3605 | CD1 | PHE b 241 | -16.809 | 24.990 | -62.981 | 0.50 | 48.26 | C |
| ATOM | 3606 | CE1 | PHE b 241 | -17.685 | 25.650 | -63.834 | 0.50 | 47.96 | C |
| ATOM | 3607 | CZ | PHE b 241 | -18.521 | 24.920 | -64.654 | 0.50 | 53.65 | C |
| ATOM | 3608 | CE2 | PHE b 241 | -18.492 | 23.530 | -64.615 | 0.50 | 53.03 | C |
| ATOM | 3609 | CD2 | PHE b 241 | -17.630 | 22.878 | -63.748 | 0.50 | 46.80 | C |
| ATOM | 3610 | C | PHE b 241 | -13.383 | 22.193 | -61.587 | 0.50 | 41.47 | C |
| ATOM | 3611 | O | PHE b 241 | -13.276 | 20.967 | -61.466 | 0.50 | 41.72 | O |
| ATOM | 3612 | N | LEU b 242 | -12.620 | 23.058 | -60.926 | 0.50 | 40.86 | N |
| ATOM | 3613 | CA | LEU b 242 | -11.508 | 22.651 | -60.055 | 0.50 | 41.24 | C |
| ATOM | 3614 | CB | LEU b 242 | -10.192 | 23.277 | -60.520 | 0.50 | 41.04 | C |
| ATOM | 3615 | CG | LEU b 242 | -8.888 | 22.887 | -59.810 | 0.50 | 40.97 | C |
| ATOM | 3616 | CD1 | LEU b 242 | -8.691 | 21.383 | -59.847 | 0.50 | 41.43 | C |
| ATOM | 3617 | CD2 | LEU b 242 | -7.700 | 23.587 | -60.442 | 0.50 | 36.23 | C |
| ATOM | 3618 | C | LEU b 242 | -11.786 | 23.136 | -58.651 | 0.50 | 41.76 | C |
| ATOM | 3619 | O | LEU b 242 | -11.874 | 24.350 | -58.408 | 0.50 | 40.55 | O |
| ATOM | 3620 | N | PHE b 243 | -11.905 | 22.183 | -57.737 | 0.50 | 35.64 | N |
| ATOM | 3621 | CA | PHE b 243 | -12.368 | 22.450 | -56.388 | 0.50 | 35.62 | C |
| ATOM | 3622 | CB | PHE b 243 | -13.552 | 21.552 | -56.079 | 0.50 | 35.68 | C |
| ATOM | 3623 | CG | PHE b 243 | -14.680 | 21.686 | -57.073 | 0.50 | 41.50 | C |
| ATOM | 3624 | CD1 | PHE b 243 | -15.549 | 22.775 | -57.019 | 0.50 | 41.49 | C |
| ATOM | 3625 | CE1 | PHE b 243 | -16.604 | 22.892 | -57.918 | 0.50 | 41.42 | C |
| ATOM | 3626 | CZ | PHE b 243 | -16.783 | 21.930 | -58.905 | 0.50 | 45.22 | C |
| ATOM | 3627 | CE2 | PHE b 243 | -15.917 | 20.843 | -58.974 | 0.50 | 43.80 | C |
| ATOM | 3628 | CD2 | PHE b 243 | -14.865 | 20.738 | -58.070 | 0.50 | 40.66 | C |
| ATOM | 3629 | C | PHE b 243 | -11.269 | 22.224 | -55.373 | 0.50 | 37.13 | C |
| ATOM | 3630 | O | PHE b 243 | -10.512 | 21.251 | -55.480 | 0.50 | 37.64 | O |
| ATOM | 3631 | N | PRO b 244 | -11.187 | 23.114 | -54.374 | 0.50 | 33.61 | N |
| ATOM | 3632 | CA | PRO b 244 | -10.122 | 23.100 | -53.383 | 0.50 | 33.17 | C |
| ATOM | 3633 | CB | PRO b 244 | -10.240 | 24.506 | -52.769 | 0.50 | 29.90 | C |
| ATOM | 3634 | CG | PRO b 244 | -11.730 | 24.721 | -52.742 | 0.50 | 31.23 | C |

Figure 26 (Continued)

```
ATOM   3635  CD   PRO b 244     -12.199  24.150 -54.072  0.50 32.87           C
ATOM   3636  C    PRO b 244      10.412  22.029  52.300  0.50 34.26           C
ATOM   3637  O    PRO b 244     -11.496  21.443 -52.284  0.50 32.29           O
ATOM   3638  N    PRO b 245      -9.446  21.770 -51.405  0.50 35.20           N
ATOM   3639  CA   PRO b 245      -9.742  20.850 -50.277  0.50 34.22           C
ATOM   3640  CB   PRO b 245      -8.379  20.605 -49.629  0.50 35.46           C
ATOM   3641  CG   PRO b 245      -7.428  21.623 -50.219  0.50 37.40           C
ATOM   3642  CD   PRO b 245      -8.099  22.370 -51.343  0.50 32.45           C
ATOM   3643  C    PRO b 245     -10.706  21.471 -49.264  0.50 34.21           C
ATOM   3644  O    PRO b 245     -11.000  22.653 -49.336  0.50 33.13           O
ATOM   3645  N    LYS b 246     -11.225  20.668 -48.341  0.50 34.82           N
ATOM   3646  CA   LYS b 246     -12.030  21.190 -47.262  0.50 29.63           C
ATOM   3647  CB   LYS b 246     -12.945  20.082 -46.714  0.50 37.70           C
ATOM   3648  CG   LYS b 246     -13.776  19.386 -47.834  0.50 32.39           C
ATOM   3649  CD   LYS b 246     -15.115  20.097 -48.114  0.50 35.56           C
ATOM   3650  CE   LYS b 246     -15.685  19.808 -49.517  0.50 36.27           C
ATOM   3651  NZ   LYS b 246     -15.023  18.696 -50.261  0.50 39.86           N
ATOM   3652  C    LYS b 246     -11.147  21.816 -46.183  0.50 31.13           C
ATOM   3653  O    LYS b 246     -10.114  21.302 -45.829  0.50 33.48           O
ATOM   3654  N    PRO b 247     -11.531  22.979 -45.674  0.50 30.99           N
ATOM   3655  CA   PRO b 247     -10.587  23.583 -44.766  0.50 29.82           C
ATOM   3656  CB   PRO b 247     -11.374  24.776 -44.212  0.50 30.94           C
ATOM   3657  CG   PRO b 247     -12.299  25.162 -45.332  0.50 29.54           C
ATOM   3658  CD   PRO b 247     -12.614  23.902 -46.083  0.50 31.07           C
ATOM   3659  C    PRO b 247     -10.176  22.630 -43.621  0.50 29.90           C
ATOM   3660  O    PRO b 247      -9.019  22.637 -43.213  0.50 28.86           O
ATOM   3661  N    LYS b 248     -11.120  21.892 -43.042  0.50 28.93           N
ATOM   3662  CA   LYS b 248     -10.778  21.044 -41.890  0.50 28.29           C
ATOM   3663  CB   LYS b 248     -12.010  20.306 -41.348  0.50 31.57           C
ATOM   3664  CG   LYS b 248     -11.774  19.581 -40.033  0.50 29.42           C
ATOM   3665  CD   LYS b 248     -13.086  19.066 -39.435  0.50 31.29           C
ATOM   3666  CE   LYS b 248     -12.802  18.085 -38.313  0.50 29.63           C
ATOM   3667  NZ   LYS b 248     -14.002  17.729 -37.492  0.50 30.06           N
ATOM   3668  C    LYS b 248      -9.743  20.049 -42.315  0.50 30.03           C
ATOM   3669  O    LYS b 248      -8.826  19.727 -41.565  0.50 38.28           O
ATOM   3670  N    ASP b 249      -9.842  19.581 -43.547  0.50 30.97           N
ATOM   3671  CA   ASP b 249      -8.828  18.662 -44.046  0.50 32.91           C
ATOM   3672  CB   ASP b 249      -9.252  18.061 -45.382  0.50 32.14           C
ATOM   3673  CG   ASP b 249     -10.468  17.156 -45.257  0.50 33.70           C
ATOM   3674  OD1  ASP b 249     -10.784  16.701 -44.123  0.50 36.10           O
ATOM   3675  OD2  ASP b 249     -11.128  16.922 -46.291  0.50 35.29           O
ATOM   3676  C    ASP b 249      -7.458  19.304 -44.199  0.50 33.63           C
ATOM   3677  O    ASP b 249      -6.448  18.594 -44.129  0.50 30.81           O
ATOM   3678  N    THR b 250      -7.396  20.618 -44.464  0.50 30.50           N
ATOM   3679  CA   THR b 250      -6.079  21.246 -44.708  0.50 29.54           C
ATOM   3680  CB   THR b 250      -6.219  22.575 -45.501  0.50 33.77           C
ATOM   3681  OG1  THR b 250      -6.977  23.521 -44.723  0.50 30.81           O
ATOM   3682  CG2  THR b 250      -6.942  22.353 -46.820  0.50 27.61           C
ATOM   3683  C    THR b 250      -5.429  21.559 -43.372  0.50 27.62           C
ATOM   3684  O    THR b 250      -4.217  21.698 -43.261  0.50 30.11           O
ATOM   3685  N    LEU b 251      -6.259  21.708 -42.356  0.50 29.28           N
ATOM   3686  CA   LEU b 251      -5.816  22.200 -41.066  0.50 29.87           C
ATOM   3687  CB   LEU b 251      -6.917  23.083 -40.443  0.50 27.98           C
ATOM   3688  CG   LEU b 251      -7.116  24.378 -41.267  0.50 29.03           C
ATOM   3689  CD1  LEU b 251      -8.410  25.091 -40.918  0.50 28.05           C
ATOM   3690  CD2  LEU b 251      -5.922  25.317 -41.107  0.50 24.33           C
ATOM   3691  C    LEU b 251      -5.449  21.075 -40.116  0.50 34.46           C
ATOM   3692  O    LEU b 251      -4.572  21.243 -39.220  0.50 31.08           O
ATOM   3693  N    MET b 252      -6.135  19.939 -40.248  0.50 31.19           N
ATOM   3694  CA   MET b 252      -5.940  18.925 -39.203  0.50 33.06           C
ATOM   3695  CB   MET b 252      -7.265  18.455 -38.594  0.50 36.78           C
ATOM   3696  CG   MET b 252      -8.141  19.583 -38.057  0.50 40.41           C
ATOM   3697  SD   MET b 252      -7.430  20.681 -36.776  0.50 48.73           S
ATOM   3698  CE   MET b 252      -7.545  19.556 -35.401  0.50 43.54           C
```

Figure 26 (Continued)

```
ATOM   3699  C    MET b 252     -5.052  17.797 -39.739  0.50 31.91           C
ATOM   3700  O    MET b 252     -5.301  17.217 -40.824  0.50 27.99           O
ATOM   3701  N    ILE b 253     -3.919  17.607 -39.065  0.50 27.94           N
ATOM   3702  CA   ILE b 253     -2.834  16.847 -39.666  0.50 28.07           C
ATOM   3703  CB   ILE b 253     -1.513  17.001 -38.893  0.50 29.41           C
ATOM   3704  CG1  ILE b 253     -0.338  16.785 -39.820  0.50 29.43           C
ATOM   3705  CD1  ILE b 253      0.968  16.745 -39.063  0.50 30.80           C
ATOM   3706  CG2  ILE b 253     -1.441  16.112 -37.635  0.50 28.07           C
ATOM   3707  C    ILE b 253     -3.202  15.372 -39.925  0.50 26.65           C
ATOM   3708  O    ILE b 253     -2.718  14.775 -40.873  0.50 27.97           O
ATOM   3709  N    SER b 254     -4.115  14.811 -39.150  0.50 28.31           N
ATOM   3710  CA   SER b 254     -4.547  13.416 -39.417  0.50 33.47           C
ATOM   3711  CB   SER b 254     -5.343  12.847 -38.243  0.50 32.33           C
ATOM   3712  OG   SER b 254     -4.656  13.047 -36.994  0.50 36.59           O
ATOM   3713  C    SER b 254     -5.356  13.276 -40.714  0.50 35.04           C
ATOM   3714  O    SER b 254     -5.539  12.179 -41.237  0.50 28.21           O
ATOM   3715  N    ARG b 255     -5.875  14.385 -41.225  0.50 29.71           N
ATOM   3716  CA   ARG b 255     -6.385  14.254 -42.264  0.50 31.31           C
ATOM   3717  CB   ARG b 255     -7.991  15.295 -42.063  0.50 33.03           C
ATOM   3718  CG   ARG b 255     -8.896  14.999 -40.875  0.50 30.18           C
ATOM   3719  CD   ARG b 255     -9.965  16.090 -40.701  0.50 35.13           C
ATOM   3720  NE   ARG b 255    -11.155  15.965 -41.555  0.50 33.62           N
ATOM   3721  CZ   ARG b 255    -12.317  15.470 -41.125  0.50 33.21           C
ATOM   3722  NH1  ARG b 255    -12.418  14.992 -39.890  0.50 32.77           N
ATOM   3723  NH2  ARG b 255    -13.371  15.412 -41.926  0.50 34.32           N
ATOM   3724  C    ARG b 255     -6.261  14.329 -43.646  0.50 31.00           C
ATOM   3725  O    ARG b 255     -5.062  14.508 -43.774  0.50 33.61           O
ATOM   3726  N    THR b 256     -7.063  14.159 -44.685  0.50 34.64           N
ATOM   3727  CA   THR b 256     -6.536  14.045 -46.034  0.50 37.76           C
ATOM   3728  CB   THR b 256     -6.917  12.688 -46.638  0.50 44.25           C
ATOM   3729  OG1  THR b 256     -8.159  12.271 -46.064  0.50 40.87           O
ATOM   3730  CG2  THR b 256     -5.847  11.633 -46.318  0.50 54.27           C
ATOM   3731  C    THR b 256     -7.146  15.126 -46.942  0.50 40.15           C
ATOM   3732  O    THR b 256     -8.314  15.052 -47.307  0.50 37.66           O
ATOM   3733  N    PRO b 257     -6.383  16.172 -47.256  0.50 39.95           N
ATOM   3734  CA   PRO b 257     -6.954  17.180 -48.166  0.50 39.05           C
ATOM   3735  CB   PRO b 257     -6.197  18.447 -47.803  0.50 36.64           C
ATOM   3736  CG   PRO b 257     -4.878  17.939 -47.285  0.50 40.58           C
ATOM   3737  CD   PRO b 257     -5.179  16.654 -46.567  0.50 40.21           C
ATOM   3738  C    PRO b 257     -6.715  16.822 -49.635  0.50 38.08           C
ATOM   3739  O    PRO b 257     -5.661  16.313 -49.980  0.50 39.75           O
ATOM   3740  N    GLU b 258     -7.708  17.064 -50.484  0.50 37.86           N
ATOM   3741  CA   GLU b 258     -7.593  16.732 -51.901  0.50 36.86           C
ATOM   3742  CB   GLU b 258     -8.526  15.550 -52.243  0.50 38.05           C
ATOM   3743  CG   GLU b 258     -7.959  14.181 -51.884  0.50 42.56           C
ATOM   3744  CD   GLU b 258     -8.939  13.048 -52.141  0.50 43.90           C
ATOM   3745  OE1  GLU b 258    -10.024  13.300 -52.702  0.50 49.08           O
ATOM   3746  OE2  GLU b 258     -8.627  11.902 -51.767  0.50 50.92           O
ATOM   3747  C    GLU b 258     -8.057  17.914 -52.717  0.50 34.65           C
ATOM   3748  O    GLU b 258     -9.077  18.537 -52.396  0.50 32.26           O
ATOM   3749  N    VAL b 259     -7.385  18.152 -53.832  0.50 34.49           N
ATOM   3750  CA   VAL b 259     -7.947  18.989 -54.892  0.50 38.20           C
ATOM   3751  CB   VAL b 259     -6.850  19.896 -55.500  0.50 40.91           C
ATOM   3752  CG1  VAL b 259     -7.316  20.577 -56.773  0.50 42.33           C
ATOM   3753  CG2  VAL b 259     -6.435  20.955 -54.477  0.50 39.39           C
ATOM   3754  C    VAL b 259     -8.668  18.096 -55.934  0.50 42.79           C
ATOM   3755  O    VAL b 259     -8.185  17.005 -56.290  0.50 42.98           O
ATOM   3756  N    THR b 260     -9.852  18.527 -56.369  0.50 38.31           N
ATOM   3757  CA   THR b 260    -10.716  17.700 -57.202  0.50 40.54           C
ATOM   3758  CB   THR b 260    -12.030  17.336 -56.465  0.50 38.24           C
ATOM   3759  OG1  THR b 260    -11.705  16.688 -55.233  0.50 38.09           O
ATOM   3760  CG2  THR b 260    -12.881  16.371 -57.284  0.50 33.14           C
ATOM   3761  C    THR b 260    -11.025  18.360 -58.544  0.50 39.57           C
ATOM   3762  O    THR b 260    -11.599  19.438 -58.604  0.50 39.72           O
```

Figure 26 (Continued)

```
ATOM   3763  N    CYS b 261     -10.596  17.724 -59.620  0.50 39.57           N
ATOM   3764  CA   CYS b 261     -10.788  18.283 -60.951  0.50 40.47           C
ATOM   3765  CB   CYS b 261      -9.515  18.134 -61.775  0.50 45.66           C
ATOM   3766  SG   CYS b 261      -9.545  18.974 -63.376  0.50 46.41           S
ATOM   3767  C    CYS b 261     -11.952  17.576 -61.619  0.50 41.72           C
ATOM   3768  O    CYS b 261     -11.934  16.350 -61.808  0.50 39.61           O
ATOM   3769  N    VAL b 262     -13.001  18.333 -61.921  0.50 41.26           N
ATOM   3770  CA   VAL b 262     -14.203  17.716 -62.463  0.50 43.38           C
ATOM   3771  CB   VAL b 262     -15.442  18.101 -61.639  0.50 43.91           C
ATOM   3772  CG1  VAL b 262     -16.679  17.376 -62.162  0.50 40.82           C
ATOM   3773  CG2  VAL b 262     -15.194  17.773 -60.172  0.50 39.06           C
ATOM   3774  C    VAL b 262     -14.412  18.098 -63.926  0.50 44.81           C
ATOM   3775  O    VAL b 262     -14.395  19.279 -64.270  0.50 42.43           O
ATOM   3776  N    VAL b 263     -14.603  17.087 -64.775  0.50 47.42           N
ATOM   3777  CA   VAL b 263     -14.936  17.303 -66.193  0.50 45.73           C
ATOM   3778  CB   VAL b 263     -13.995  16.524 -67.126  0.50 45.45           C
ATOM   3779  CG1  VAL b 263     -13.868  17.249 -68.463  0.50 49.12           C
ATOM   3780  CG2  VAL b 263     -12.630  16.344 -66.478  0.50 40.97           C
ATOM   3781  C    VAL b 263     -16.395  16.972 -66.543  0.50 44.46           C
ATOM   3782  O    VAL b 263     -16.882  15.857 -66.287  0.50 44.43           O
ATOM   3783  N    VAL b 264     -17.078  17.955 -67.129  0.50 40.94           N
ATOM   3784  CA   VAL b 264     -18.488  17.840 -67.464  0.50 44.98           C
ATOM   3785  CB   VAL b 264     -19.305  18.931 -66.737  0.50 45.61           C
ATOM   3786  CG1  VAL b 264     -19.287  18.705 -65.222  0.50 43.75           C
ATOM   3787  CG2  VAL b 264     -18.740  20.305 -67.065  0.50 41.39           C
ATOM   3788  C    VAL b 264     -18.698  17.955 -68.994  0.50 46.63           C
ATOM   3789  O    VAL b 264     -17.787  18.353 -69.724  0.50 41.95           O
ATOM   3790  N    ASP b 265     -19.896  17.602 -69.465  0.50 52.29           N
ATOM   3791  CA   ASP b 265     -20.230  17.624 -70.910  0.50 57.10           C
ATOM   3792  CB   ASP b 265     -20.338  19.050 -71.454  0.50 49.61           C
ATOM   3793  CG   ASP b 265     -21.453  19.817 -70.859  0.50 48.46           C
ATOM   3794  OD1  ASP b 265     -22.412  19.221 -70.314  0.50 52.81           O
ATOM   3795  OD2  ASP b 265     -21.363  21.047 -70.946  0.50 53.82           O
ATOM   3796  C    ASP b 265     -19.157  16.962 -71.736  0.50 52.74           C
ATOM   3797  O    ASP b 265     -18.651  17.575 -72.671  0.50 51.41           O
ATOM   3798  N    VAL b 266     -18.773  15.750 -71.368  0.50 55.68           N
ATOM   3799  CA   VAL b 266     -17.914  14.960 -72.220  0.50 65.08           C
ATOM   3800  CB   VAL b 266     -17.002  14.040 -71.397  0.50 61.34           C
ATOM   3801  CG1  VAL b 266     -16.416  12.955 -72.282  0.50 62.26           C
ATOM   3802  CG2  VAL b 266     -15.899  14.853 -70.739  0.50 64.94           C
ATOM   3803  C    VAL b 266     -18.828  14.131 -73.116  0.50 71.60           C
ATOM   3804  O    VAL b 266     -19.608  13.316 -72.615  0.50 71.17           O
ATOM   3805  N    SER b 267     -18.750  14.375 -74.427  0.50 78.25           N
ATOM   3806  CA   SER b 267     -19.645  13.748 -75.420  0.50 78.70           C
ATOM   3807  CB   SER b 267     -19.481  14.407 -76.795  0.50 66.83           C
ATOM   3808  OG   SER b 267     -18.345  13.905 -77.476  0.50 68.99           O
ATOM   3809  C    SER b 267     -19.460  12.238 -75.568  0.50 76.32           C
ATOM   3810  O    SER b 267     -18.340  11.745 -75.723  0.50 83.44           O
ATOM   3811  N    HIS b 268     -20.573  11.513 -75.539  0.50 77.61           N
ATOM   3812  CA   HIS b 268     -20.556  10.088 -75.827  0.50 78.23           C
ATOM   3813  CB   HIS b 268     -21.978   9.574 -76.023  0.50 79.51           C
ATOM   3814  CG   HIS b 268     -22.457   8.702 -74.910  0.50 84.32           C
ATOM   3815  ND1  HIS b 268     -23.195   9.186 -73.853  0.50 85.06           N
ATOM   3816  CE1  HIS b 268     -23.478   8.193 -73.027  0.50 96.32           C
ATOM   3817  NE2  HIS b 268     -22.948   7.083 -73.511  0.50100.72            N
ATOM   3818  CD2  HIS b 268     -22.302   7.374 -74.689  0.50 91.68           C
ATOM   3819  C    HIS b 268     -19.714   9.774 -77.062  0.50 73.60           C
ATOM   3820  O    HIS b 268     -19.086   8.723 -77.141  0.50 70.17           O
ATOM   3821  N    GLU b 269     -19.696  10.701 -78.015  0.50 80.19           N
ATOM   3822  CA   GLU b 269     -19.046  10.473 -79.307  0.50 82.33           C
ATOM   3823  CB   GLU b 269     -19.514  11.507 -80.340  0.50 76.35           C
ATOM   3824  CG   GLU b 269     -20.980  11.389 -80.748  0.50 74.21           C
ATOM   3825  CD   GLU b 269     -21.946  11.987 -79.731  0.50 72.60           C
ATOM   3826  OE1  GLU b 269     -21.675  13.104 -79.239  0.50 59.70           O
```

Figure 26 (Continued)

```
ATOM   3827  OE2 GLU b 269     -22.986  11.345 -79.442  0.50 65.48           O
ATOM   3828  C   GLU b 269     -17.521  10.480 -79.190  0.50 83.78           C
ATOM   3829  O   GLU b 269     -16.828   9.813 -79.958  0.50 83.63           O
ATOM   3830  N   GLU b 270     -17.005  11.241 -78.231  0.50 83.13           N
ATOM   3831  CA  GLU b 270     -15.575  11.260 -77.959  0.50 80.41           C
ATOM   3832  CB  GLU b 270     -14.896  12.411 -78.696  0.50 80.05           C
ATOM   3833  CG  GLU b 270     -15.436  12.670 -80.093  0.50 71.34           C
ATOM   3834  CD  GLU b 270     -16.388  13.854 -80.135  0.50 70.34           C
ATOM   3835  OE1 GLU b 270     -17.527  13.732 -79.631  0.50 56.61           O
ATOM   3836  OE2 GLU b 270     -15.993  14.913 -80.676  0.50 71.95           O
ATOM   3837  C   GLU b 270     -15.345  11.388 -76.463  0.50 83.19           C
ATOM   3838  O   GLU b 270     -15.310  12.500 -75.927  0.50 74.50           O
ATOM   3839  N   PRO b 271     -15.205  10.240 -75.782  0.50 85.01           N
ATOM   3840  CA  PRO b 271     -15.211  10.173 -74.333  0.50 84.07           C
ATOM   3841  CB  PRO b 271     -16.041   8.912 -74.061  0.50 89.02           C
ATOM   3842  CG  PRO b 271     -15.794   8.034 -75.256  0.50 89.63           C
ATOM   3843  CD  PRO b 271     -15.270   8.896 -76.382  0.50 85.03           C
ATOM   3844  C   PRO b 271     -13.826  10.029 -73.702  0.50 80.22           C
ATOM   3845  O   PRO b 271     -13.733   9.724 -72.514  0.50 81.09           O
ATOM   3846  N   GLU b 272     -12.760  10.240 -74.470  0.50 79.59           N
ATOM   3847  CA  GLU b 272     -11.427  10.110 -73.891  0.50 81.97           C
ATOM   3848  CB  GLU b 272     -10.380   9.612 -74.895  0.50 85.17           C
ATOM   3849  CG  GLU b 272      -9.454   8.558 -74.288  0.50 92.01           C
ATOM   3850  CD  GLU b 272      -7.998   8.680 -74.726  0.50 98.22           C
ATOM   3851  OE1 GLU b 272      -7.734   8.814 -75.943  0.50 95.84           O
ATOM   3852  OE2 GLU b 272      -7.106   8.613 -73.850  0.50 99.13           O
ATOM   3853  C   GLU b 272     -10.970  11.400 -73.232  0.50 81.73           C
ATOM   3854  O   GLU b 272     -10.938  12.464 -73.857  0.50 79.72           O
ATOM   3855  N   VAL b 273     -10.619  11.289 -71.956  0.50 76.00           N
ATOM   3856  CA  VAL b 273     -10.172  12.430 -71.181  0.50 69.16           C
ATOM   3857  CB  VAL b 273     -11.121  12.711 -70.007  0.50 65.47           C
ATOM   3858  CG1 VAL b 273     -10.512  13.748 -69.073  0.50 56.80           C
ATOM   3859  CG2 VAL b 273     -12.482  13.149 -70.520  0.50 61.29           C
ATOM   3860  C   VAL b 273      -8.816  12.126 -70.590  0.50 61.85           C
ATOM   3861  O   VAL b 273      -8.662  11.136 -69.876  0.50 60.67           O
ATOM   3862  N   LYS b 274      -7.843  12.980 -70.886  0.50 60.62           N
ATOM   3863  CA  LYS b 274      -6.530  12.869 -70.275  0.50 60.96           C
ATOM   3864  CB  LYS b 274      -5.425  12.937 -71.320  0.50 54.34           C
ATOM   3865  CG  LYS b 274      -4.030  12.892 -70.716  0.50 57.65           C
ATOM   3866  CD  LYS b 274      -2.954  12.940 -71.787  0.50 63.65           C
ATOM   3867  CE  LYS b 274      -1.575  12.692 -71.197  0.50 64.89           C
ATOM   3868  NZ  LYS b 274      -0.521  12.750 -72.252  0.50 64.93           N
ATOM   3869  C   LYS b 274      -6.331  13.981 -69.260  0.50 63.20           C
ATOM   3870  O   LYS b 274      -6.550  15.160 -69.576  0.50 64.11           O
ATOM   3871  N   PHE b 275      -5.904  13.589 -68.055  0.50 58.01           N
ATOM   3872  CA  PHE b 275      -5.596  14.527 -66.970  0.50 61.08           C
ATOM   3873  CB  PHE b 275      -6.148  14.013 -65.637  0.50 59.69           C
ATOM   3874  CG  PHE b 275      -7.634  14.135 -65.511  0.50 57.71           C
ATOM   3875  CD1 PHE b 275      -8.445  13.004 -65.570  0.50 60.20           C
ATOM   3876  CE1 PHE b 275      -9.818  13.118 -65.451  0.50 57.05           C
ATOM   3877  CZ  PHE b 275     -10.388  14.369 -65.301  0.50 53.35           C
ATOM   3878  CE2 PHE b 275      -9.590  15.497 -65.261  0.50 52.09           C
ATOM   3879  CD2 PHE b 275      -8.223  15.377 -65.345  0.50 52.71           C
ATOM   3880  C   PHE b 275      -4.108  14.705 -66.796  0.50 56.02           C
ATOM   3881  O   PHE b 275      -3.402  13.732 -66.579  0.50 54.51           O
ATOM   3882  N   ASN b 276      -3.643  15.952 -66.842  0.50 58.07           N
ATOM   3883  CA  ASN b 276      -2.309  16.276 -66.337  0.50 53.75           C
ATOM   3884  CB  ASN b 276      -1.422  16.795 -67.469  0.50 58.31           C
ATOM   3885  CG  ASN b 276      -1.178  15.744 -68.542  0.50 50.23           C
ATOM   3886  OD1 ASN b 276      -2.116  15.272 -69.167  0.50 43.88           O
ATOM   3887  ND2 ASN b 276       0.080  15.341 -68.718  0.50 44.95           N
ATOM   3888  C   ASN b 276      -2.308  17.244 -65.133  0.50 52.97           C
ATOM   3889  O   ASN b 276      -2.970  18.287 -65.148  0.50 49.59           O
ATOM   3890  N   TRP b 277      -1.547  16.895 -64.098  0.50 53.26           N
```

Figure 26 (Continued)

```
ATOM   3891  CA   TRP b 277      -1.540  17.654 -62.849  0.50 51.29           C
ATOM   3892  CB   TRP b 277      -1.879  16.731 -61.697  0.50 51.20           C
ATOM   3893  CG   TRP b 277      -3.321  16.555 -61.447  0.50 50.90           C
ATOM   3894  CD1  TRP b 277      -4.074  15.449 -61.714  0.50 50.49           C
ATOM   3895  NE1  TRP b 277      -5.364  15.645 -61.275  0.50 52.01           N
ATOM   3896  CE2  TRP b 277      -5.455  16.890 -60.702  0.50 47.86           C
ATOM   3897  CD2  TRP b 277      -4.190  17.490 -60.792  0.50 51.42           C
ATOM   3898  CE3  TRP b 277      -4.012  18.777 -60.271  0.50 46.86           C
ATOM   3899  CZ3  TRP b 277      -5.096  19.411 -59.694  0.50 49.32           C
ATOM   3900  CH2  TRP b 277      -6.342  18.794 -59.619  0.50 45.47           C
ATOM   3901  CZ2  TRP b 277      -6.547  17.537 -60.122  0.50 50.68           C
ATOM   3902  C    TRP b 277      -0.206  18.328 -62.552  0.50 53.09           C
ATOM   3903  O    TRP b 277       0.843  17.669 -62.510  0.50 54.66           O
ATOM   3904  N    TYR b 278      -0.250  19.640 -62.330  0.50 45.55           N
ATOM   3905  CA   TYR b 278       0.942  20.399 -61.944  0.50 45.45           C
ATOM   3906  CB   TYR b 278       1.108  21.625 -62.847  0.50 45.37           C
ATOM   3907  CG   TYR b 278       1.173  21.276 -64.305  0.50 51.98           C
ATOM   3908  CD1  TYR b 278       2.343  21.478 -65.043  0.50 56.64           C
ATOM   3909  CE1  TYR b 278       2.405  21.147 -66.386  0.50 53.00           C
ATOM   3910  CZ   TYR b 278       1.300  20.589 -66.990  0.50 53.67           C
ATOM   3911  OH   TYR b 278       1.339  20.247 -68.316  0.50 65.63           O
ATOM   3912  CE2  TYR b 278       0.139  20.367 -66.274  0.50 59.35           C
ATOM   3913  CD2  TYR b 278       0.082  20.710 -64.942  0.50 50.23           C
ATOM   3914  C    TYR b 278       0.808  20.882 -60.512  0.50 42.00           C
ATOM   3915  O    TYR b 278      -0.317  21.003 -60.003  0.50 36.05           O
ATOM   3916  N    VAL b 279       1.951  21.186 -59.892  0.50 42.36           N
ATOM   3917  CA   VAL b 279       2.019  21.839 -58.576  0.50 41.37           C
ATOM   3918  CB   VAL b 279       2.417  20.837 -57.484  0.50 43.45           C
ATOM   3919  CG1  VAL b 279       2.631  21.551 -56.153  0.50 42.36           C
ATOM   3920  CG2  VAL b 279       1.364  19.753 -57.363  0.50 43.46           C
ATOM   3921  C    VAL b 279       3.071  22.949 -58.611  0.50 44.72           C
ATOM   3922  O    VAL b 279       4.267  22.674 -58.521  0.50 51.23           O
ATOM   3923  N    ASP b 280       2.630  24.196 -58.761  0.50 45.66           N
ATOM   3924  CA   ASP b 280       3.542  25.288 -59.074  0.50 49.43           C
ATOM   3925  CB   ASP b 280       4.613  25.421 -57.999  0.50 47.28           C
ATOM   3926  CG   ASP b 280       4.131  26.189 -56.790  0.50 50.08           C
ATOM   3927  OD1  ASP b 280       2.984  26.702 -56.796  0.50 50.00           O
ATOM   3928  OD2  ASP b 280       4.910  26.292 -55.826  0.50 49.13           O
ATOM   3929  C    ASP b 280       4.213  25.056 -60.432  0.50 57.72           C
ATOM   3930  O    ASP b 280       5.331  25.517 -60.664  0.50 60.23           O
ATOM   3931  N    GLY b 281       3.540  24.329 -61.320  0.50 55.62           N
ATOM   3932  CA   GLY b 281       4.044  24.154 -62.677  0.50 60.77           C
ATOM   3933  C    GLY b 281       4.977  22.962 -62.850  0.50 67.34           C
ATOM   3934  O    GLY b 281       5.450  22.692 -63.955  0.50 69.28           O
ATOM   3935  N    VAL b 282       5.243  22.244 -61.768  0.50 56.11           N
ATOM   3936  CA   VAL b 282       6.013  21.022 -61.867  0.50 52.25           C
ATOM   3937  CB   VAL b 282       6.919  20.840 -60.631  0.50 53.58           C
ATOM   3938  CG1  VAL b 282       7.804  19.612 -60.796  0.50 53.85           C
ATOM   3939  CG2  VAL b 282       7.754  22.091 -60.388  0.50 48.57           C
ATOM   3940  C    VAL b 282       5.047  19.850 -61.963  0.50 55.61           C
ATOM   3941  O    VAL b 282       4.381  19.510 -60.984  0.50 54.95           O
ATOM   3942  N    GLU b 283       4.939  19.241 -63.139  0.50 49.64           N
ATOM   3943  CA   GLU b 283       3.918  18.214 -63.324  0.50 52.96           C
ATOM   3944  CB   GLU b 283       4.037  17.530 -64.690  0.50 48.08           C
ATOM   3945  CG   GLU b 283       2.801  16.729 -65.064  0.50 51.22           C
ATOM   3946  CD   GLU b 283       2.923  16.007 -66.402  0.50 59.22           C
ATOM   3947  OE1  GLU b 283       3.580  16.552 -67.314  0.50 55.35           O
ATOM   3948  OE2  GLU b 283       2.342  14.903 -66.549  0.50 56.64           O
ATOM   3949  C    GLU b 283       3.988  17.188 -62.202  0.50 51.97           C
ATOM   3950  O    GLU b 283       5.031  17.028 -61.588  0.50 50.55           O
ATOM   3951  N    VAL b 284       2.881  16.485 -61.950  0.50 49.70           N
ATOM   3952  CA   VAL b 284       2.839  15.495 -60.873  0.50 50.63           C
ATOM   3953  CB   VAL b 284       2.441  16.134 -59.515  0.50 51.97           C
ATOM   3954  CG1  VAL b 284       1.256  17.094 -59.655  0.50 42.75           C
```

Figure 26 (Continued)

```
ATOM   3955  CG2 VAL b 284       3.624  16.886 -58.921  0.50 51.14           C
ATOM   3956  C   VAL b 284       1.965  14.279 -61.232  0.50 56.12           C
ATOM   3957  O   VAL b 284       0.928  14.409 -61.890  0.50 62.86           O
ATOM   3958  N   HIS b 285       2.376  13.092 -60.797  0.50 57.30           N
ATOM   3959  CA  HIS b 285       1.873  11.875 -61.425  0.50 58.02           C
ATOM   3960  CB  HIS b 285       3.030  11.039 -61.981  0.50 60.81           C
ATOM   3961  CG  HIS b 285       3.807  11.751 -63.042  0.50 61.53           C
ATOM   3962  ND1 HIS b 285       3.471  11.682 -64.378  0.50 58.06           N
ATOM   3963  CE1 HIS b 285       4.295  12.450 -65.072  0.50 62.98           C
ATOM   3964  NE2 HIS b 285       5.133  13.036 -64.232  0.50 59.73           N
ATOM   3965  CD2 HIS b 285       4.839  12.627 -62.955  0.50 60.37           C
ATOM   3966  C   HIS b 285       0.950  11.044 -60.567  0.50 52.03           C
ATOM   3967  O   HIS b 285       0.308  10.127 -61.067  0.50 58.40           O
ATOM   3968  N   ASN b 286       0.840  11.382 -59.292  0.50 52.80           N
ATOM   3969  CA  ASN b 286      -0.090  10.663 -58.426  0.50 57.22           C
ATOM   3970  CB  ASN b 286       0.414  10.608 -56.973  0.50 58.80           C
ATOM   3971  CG  ASN b 286       0.764  11.979 -56.422  0.50 54.59           C
ATOM   3972  OD1 ASN b 286       0.582  12.995 -57.090  0.50 53.97           O
ATOM   3973  ND2 ASN b 286       1.281  12.011 -55.202  0.50 53.06           N
ATOM   3974  C   ASN b 286      -1.540  11.164 -58.496  0.50 62.07           C
ATOM   3975  O   ASN b 286      -2.292  11.056 -57.527  0.50 66.70           O
ATOM   3976  N   ALA b 287      -1.962  11.662 -59.653  0.50 61.86           N
ATOM   3977  CA  ALA b 287      -3.382  11.943 -59.825  0.50 64.69           C
ATOM   3978  CB  ALA b 287      -3.608  12.860 -61.009  0.50 57.59           C
ATOM   3979  C   ALA b 287      -4.135  10.625 -60.000  0.50 68.51           C
ATOM   3980  O   ALA b 287      -3.634   9.712 -60.649  0.50 67.13           O
ATOM   3981  N   LYS b 288      -5.316  10.520 -59.395  0.50 67.46           N
ATOM   3982  CA  LYS b 288      -6.120   9.307 -59.493  0.50 70.19           C
ATOM   3983  CB  LYS b 288      -6.290   8.648 -58.119  0.50 74.76           C
ATOM   3984  CG  LYS b 288      -5.101   8.795 -57.168  0.50 76.15           C
ATOM   3985  CD  LYS b 288      -3.927   7.907 -57.560  0.50 70.87           C
ATOM   3986  CE  LYS b 288      -2.870   7.850 -56.464  0.50 67.50           C
ATOM   3987  NZ  LYS b 288      -3.047   6.694 -55.535  0.50 62.92           N
ATOM   3988  C   LYS b 288      -7.493   9.641 -60.072  0.50 73.90           C
ATOM   3989  O   LYS b 288      -8.312  10.289 -59.414  0.50 70.12           O
ATOM   3990  N   THR b 289      -7.746   9.187 -61.298  0.50 73.67           N
ATOM   3991  CA  THR b 289      -8.974   9.535 -62.017  0.50 73.31           C
ATOM   3992  CB  THR b 289      -8.701   9.649 -63.521  0.50 66.86           C
ATOM   3993  OG1 THR b 289      -7.511  10.417 -63.716  0.50 61.95           O
ATOM   3994  CG2 THR b 289      -9.858  10.325 -64.220  0.50 71.91           C
ATOM   3995  C   THR b 289     -10.090   8.527 -61.805  0.50 69.76           C
ATOM   3996  O   THR b 289      -9.959   7.375 -62.196  0.50 76.84           O
ATOM   3997  N   LYS b 290     -11.189   8.966 -61.194  0.50 74.74           N
ATOM   3998  CA  LYS b 290     -12.358   8.106 -60.999  0.50 75.70           C
ATOM   3999  CB  LYS b 290     -13.495   8.877 -60.323  0.50 76.86           C
ATOM   4000  CG  LYS b 290     -13.188   9.342 -58.905  0.50 72.84           C
ATOM   4001  CD  LYS b 290     -14.466   9.703 -58.165  0.50 70.85           C
ATOM   4002  CE  LYS b 290     -14.194  10.501 -56.897  0.50 65.15           C
ATOM   4003  NZ  LYS b 290     -13.925   9.638 -55.706  0.50 63.40           N
ATOM   4004  C   LYS b 290     -12.831   7.546 -62.342  0.50 74.23           C
ATOM   4005  O   LYS b 290     -12.423   8.034 -63.393  0.50 65.64           O
ATOM   4006  N   PRO b 291     -13.685   6.509 -62.313  0.50 77.98           N
ATOM   4007  CA  PRO b 291     -14.117   5.924 -63.580  0.50 78.41           C
ATOM   4008  CB  PRO b 291     -14.629   4.548 -63.158  0.50 78.03           C
ATOM   4009  CG  PRO b 291     -15.140   4.755 -61.763  0.50 78.01           C
ATOM   4010  CD  PRO b 291     -14.382   5.911 -61.158  0.50 72.52           C
ATOM   4011  C   PRO b 291     -15.236   6.745 -64.231  0.50 77.61           C
ATOM   4012  O   PRO b 291     -16.201   7.129 -63.558  0.50 74.59           O
ATOM   4013  N   ARG b 292     -15.093   7.026 -65.523  0.50 75.82           N
ATOM   4014  CA  ARG b 292     -16.115   7.744 -66.288  0.50 75.62           C
ATOM   4015  CB  ARG b 292     -15.992   7.385 -67.769  0.50 76.97           C
ATOM   4016  CG  ARG b 292     -17.174   7.799 -68.628  0.50 77.34           C
ATOM   4017  CD  ARG b 292     -16.997   7.333 -70.068  0.50 78.22           C
ATOM   4018  NE  ARG b 292     -16.795   5.888 -70.150  0.50 79.21           N
```

Figure 26 (Continued)

```
ATOM   4019  CZ   ARG b 292     -15.625    5.305  -70.401  0.50  79.39           C
ATOM   4020  NH1  ARG b 292     -14.541    6.041  -70.617  0.50  70.14           N
ATOM   4021  NH2  ARG b 292     -15.545    3.979  -70.449  0.50  78.23           N
ATOM   4022  C    ARG b 292     -17.525    7.425  -65.787  0.50  76.79           C
ATOM   4023  O    ARG b 292     -17.857    6.261  -65.555  0.50  72.27           O
ATOM   4024  N    GLU b 293     -18.354    8.455  -65.614  0.50  72.14           N
ATOM   4025  CA   GLU b 293     -19.706    8.255  -65.077  0.50  72.54           C
ATOM   4026  CB   GLU b 293     -19.782    8.677  -63.594  0.50  74.60           C
ATOM   4027  CG   GLU b 293     -21.159    8.538  -62.953  0.50  73.92           C
ATOM   4028  CD   GLU b 293     -21.105    8.001  -61.528  0.50  77.20           C
ATOM   4029  OE1  GLU b 293     -21.772    8.577  -60.639  0.50  72.61           O
ATOM   4030  OE2  GLU b 293     -20.402    6.995  -61.297  0.50  71.78           O
ATOM   4031  C    GLU b 293     -20.780    8.959  -65.917  0.50  70.71           C
ATOM   4032  O    GLU b 293     -20.646   10.134  -66.257  0.50  66.13           O
ATOM   4033  N    GLU b 294     -21.843    8.227  -66.246  0.50  73.95           N
ATOM   4034  CA   GLU b 294     -22.868    8.714  -67.170  0.50  67.46           C
ATOM   4035  CB   GLU b 294     -23.526    7.532  -67.886  0.50  70.94           C
ATOM   4036  CG   GLU b 294     -24.625    7.918  -68.866  0.50  76.91           C
ATOM   4037  CD   GLU b 294     -24.600    7.089  -70.142  0.50  78.72           C
ATOM   4038  OE1  GLU b 294     -24.101    5.936  -70.114  0.50  72.73           O
ATOM   4039  OE2  GLU b 294     -25.080    7.598  -71.181  0.50  76.09           O
ATOM   4040  C    GLU b 294     -23.926    9.570  -66.468  0.50  68.77           C
ATOM   4041  O    GLU b 294     -24.472    9.180  -65.428  0.50  65.57           O
ATOM   4042  N    GLN b 295     -24.217   10.735  -67.042  0.50  67.23           N
ATOM   4043  CA   GLN b 295     -25.214   11.641  -66.466  0.50  70.03           C
ATOM   4044  CB   GLN b 295     -24.769   13.103  -66.592  0.50  68.64           C
ATOM   4045  CG   GLN b 295     -23.354   13.374  -66.098  0.50  67.74           C
ATOM   4046  CD   GLN b 295     -23.206   13.124  -64.612  0.50  70.18           C
ATOM   4047  OE1  GLN b 295     -23.857   13.782  -63.794  0.50  69.63           O
ATOM   4048  NE2  GLN b 295     -22.353   12.162  -64.251  0.50  66.89           N
ATOM   4049  C    GLN b 295     -26.568   11.456  -67.137  0.50  74.82           C
ATOM   4050  O    GLN b 295     -26.669   10.871  -68.219  0.50  77.62           O
ATOM   4051  N    TYR b 296     -27.610   11.959  -66.494  0.50  75.22           N
ATOM   4052  CA   TYR b 296     -28.948   11.851  -67.049  0.50  76.97           C
ATOM   4053  CB   TYR b 296     -29.986   12.299  -66.023  0.50  81.85           C
ATOM   4054  CG   TYR b 296     -30.092   11.369  -64.832  0.50  87.25           C
ATOM   4055  CD1  TYR b 296     -30.011   11.856  -63.536  0.50  90.84           C
ATOM   4056  CE1  TYR b 296     -30.117   11.010  -62.446  0.50 100.12           C
ATOM   4057  CZ   TYR b 296     -30.295    9.654  -62.647  0.50  98.02           C
ATOM   4058  OH   TYR b 296     -30.391    8.809  -61.567  0.50 102.46           O
ATOM   4059  CE2  TYR b 296     -30.369    9.143  -63.926  0.50  93.96           C
ATOM   4060  CD2  TYR b 296     -30.266    9.998  -65.008  0.50  87.88           C
ATOM   4061  C    TYR b 296     -29.090   12.620  -68.370  0.50  78.22           C
ATOM   4062  O    TYR b 296     -29.961   12.304  -69.190  0.50  71.45           O
ATOM   4063  N    ASN b 297     -28.225   13.613  -68.585  0.50  68.32           N
ATOM   4064  CA   ASN b 297     -28.209   14.322  -69.863  0.50  64.13           C
ATOM   4065  CB   ASN b 297     -27.884   15.825  -69.695  0.50  59.91           C
ATOM   4066  CG   ASN b 297     -26.526   16.081  -69.050  0.50  52.33           C
ATOM   4067  OD1  ASN b 297     -25.606   15.284  -69.178  0.50  48.58           O
ATOM   4068  ND2  ASN b 297     -26.395   17.220  -68.378  0.50  56.11           N
ATOM   4069  C    ASN b 297     -27.316   13.627  -70.905  0.50  62.14           C
ATOM   4070  O    ASN b 297     -26.786   14.264  -71.818  0.50  60.25           O
ATOM   4071  N    SER b 298     -27.143   12.318  -70.735  0.50  59.59           N
ATOM   4072  CA   SER b 298     -26.456   11.461  -71.719  0.50  63.19           C
ATOM   4073  CB   SER b 298     -27.287   11.335  -73.001  0.50  64.30           C
ATOM   4074  OG   SER b 298     -28.665   11.215  -72.681  0.50  63.42           O
ATOM   4075  C    SER b 298     -25.013   11.864  -72.046  0.50  63.78           C
ATOM   4076  O    SER b 298     -24.391   11.306  -72.953  0.50  63.60           O
ATOM   4077  N    THR b 299     -24.485   12.816  -71.285  0.50  62.73           N
ATOM   4078  CA   THR b 299     -23.079   13.184  -71.346  0.50  55.22           C
ATOM   4079  CB   THR b 299     -22.895   14.683  -71.058  0.50  59.40           C
ATOM   4080  OG1  THR b 299     -23.302   14.945  -69.709  0.50  51.89           O
ATOM   4081  CG2  THR b 299     -23.736   15.554  -72.030  0.50  53.16           C
ATOM   4082  C    THR b 299     -22.313   12.433  -70.264  0.50  57.20           C
```

Figure 26 (Continued)

```
ATOM   4083  O    THR b 299     -22.905  11.862 -69.342  0.50 59.29           O
ATOM   4084  N    TYR b 300     -20.990  12.449 -70.357  0.50 59.20           N
ATOM   4085  CA   TYR b 300     -20.159  11.819 -69.332  0.50 59.67           C
ATOM   4086  CB   TYR b 300     -18.994  11.056 -69.968  0.50 64.47           C
ATOM   4087  CG   TYR b 300     -19.301   9.624 -70.372  0.50 66.38           C
ATOM   4088  CD1  TYR b 300     -18.920   9.136 -71.626  0.50 73.47           C
ATOM   4089  CE1  TYR b 300     -19.167   7.820 -72.000  0.50 69.15           C
ATOM   4090  CZ   TYR b 300     -19.810   6.971 -71.118  0.50 72.42           C
ATOM   4091  OH   TYR b 300     -20.064   5.661 -71.483  0.50 67.05           O
ATOM   4092  CE2  TYR b 300     -20.196   7.433 -69.865  0.50 73.40           C
ATOM   4093  CD2  TYR b 300     -19.941   8.752 -69.502  0.50 64.58           C
ATOM   4094  C    TYR b 300     -19.623  12.854 -68.342  0.50 57.77           C
ATOM   4095  O    TYR b 300     -19.424  14.019 -68.695  0.50 53.59           O
ATOM   4096  N    ARG b 301     -19.418  12.423 -67.100  0.50 54.53           N
ATOM   4097  CA   ARG b 301     -18.759  13.239 -66.086  0.50 54.40           C
ATOM   4098  CB   ARG b 301     -19.690  13.459 -64.885  0.50 60.31           C
ATOM   4099  CG   ARG b 301     -19.052  14.140 -63.676  0.50 57.45           C
ATOM   4100  CD   ARG b 301     -20.129  14.519 -62.673  0.50 54.12           C
ATOM   4101  NE   ARG b 301     -19.670  15.412 -61.610  0.50 54.17           N
ATOM   4102  CZ   ARG b 301     -19.177  14.983 -60.447  0.50 56.58           C
ATOM   4103  NH1  ARG b 301     -19.038  13.680 -60.227  0.50 52.41           N
ATOM   4104  NH2  ARG b 301     -18.815  15.847 -59.508  0.50 43.49           N
ATOM   4105  C    ARG b 301     -17.515  12.510 -65.632  0.50 52.88           C
ATOM   4106  O    ARG b 301     -17.597  11.374 -65.168  0.50 53.12           O
ATOM   4107  N    VAL b 302     -16.366  13.162 -65.765  0.50 48.18           N
ATOM   4108  CA   VAL b 302     -15.095  12.547 -65.393  0.50 48.92           C
ATOM   4109  CB   VAL b 302     -14.168  12.463 -66.616  0.50 48.58           C
ATOM   4110  CG1  VAL b 302     -12.946  11.606 -66.312  0.50 48.38           C
ATOM   4111  CG2  VAL b 302     -14.933  11.904 -67.810  0.50 52.54           C
ATOM   4112  C    VAL b 302     -14.365  13.328 -64.293  0.50 49.95           C
ATOM   4113  O    VAL b 302     -14.167  14.544 -64.408  0.50 47.24           O
ATOM   4114  N    VAL b 303     -13.912  12.617 -63.262  0.50 51.44           N
ATOM   4115  CA   VAL b 303     -13.261  13.252 -62.111  0.50 49.62           C
ATOM   4116  CB   VAL b 303     -14.117  13.109 -60.850  0.50 50.67           C
ATOM   4117  CG1  VAL b 303     -13.436  13.807 -59.678  0.50 52.78           C
ATOM   4118  CG2  VAL b 303     -15.514  13.645 -61.093  0.50 48.26           C
ATOM   4119  C    VAL b 303     -11.877  12.680 -61.799  0.50 47.71           C
ATOM   4120  O    VAL b 303     -11.678  11.463 -61.778  0.50 51.69           O
ATOM   4121  N    SER b 304     -10.924  13.573 -61.568  0.50 47.95           N
ATOM   4122  CA   SER b 304      -9.610  13.206 -61.043  0.50 46.51           C
ATOM   4123  CB   SER b 304      -8.512  13.556 -62.046  0.50 49.65           C
ATOM   4124  OG   SER b 304      -7.230  13.367 -61.471  0.50 50.09           O
ATOM   4125  C    SER b 304      -9.356  13.946 -59.722  0.50 51.13           C
ATOM   4126  O    SER b 304      -9.598  15.168 -59.626  0.50 46.99           O
ATOM   4127  N    VAL b 305      -8.890  13.187 -58.722  0.50 46.89           N
ATOM   4128  CA   VAL b 305      -8.609  13.656 -57.373  0.50 46.30           C
ATOM   4129  CB   VAL b 305      -9.303  12.753 -56.331  0.50 55.72           C
ATOM   4130  CG1  VAL b 305      -9.042  13.238 -54.905  0.50 47.27           C
ATOM   4131  CG2  VAL b 305     -10.798  12.656 -56.616  0.50 53.07           C
ATOM   4132  C    VAL b 305      -7.106  13.637 -57.097  0.50 51.31           C
ATOM   4133  O    VAL b 305      -6.453  12.609 -57.288  0.50 50.74           O
ATOM   4134  N    LEU b 306      -6.560  14.785 -56.678  0.50 43.00           N
ATOM   4135  CA   LEU b 306      -5.169  14.891 -56.282  0.50 40.52           C
ATOM   4136  CB   LEU b 306      -4.494  16.044 -57.047  0.50 36.17           C
ATOM   4137  CG   LEU b 306      -3.053  16.323 -56.597  0.50 40.56           C
ATOM   4138  CD1  LEU b 306      -2.182  15.074 -56.705  0.50 45.11           C
ATOM   4139  CD2  LEU b 306      -2.390  17.503 -57.302  0.50 39.51           C
ATOM   4140  C    LEU b 306      -5.014  15.100 -54.753  0.50 42.70           C
ATOM   4141  O    LEU b 306      -5.448  16.113 -54.197  0.50 43.94           O
ATOM   4142  N    THR b 307      -4.374  14.150 -54.091  0.50 44.24           N
ATOM   4143  CA   THR b 307      -3.986  14.283 -52.689  0.50 47.30           C
ATOM   4144  CB   THR b 307      -3.246  13.014 -52.213  0.50 44.55           C
ATOM   4145  OG1  THR b 307      -4.139  11.897 -52.289  0.50 51.17           O
ATOM   4146  CG2  THR b 307      -2.744  13.176 -50.776  0.50 42.23           C
```

Figure 26 (Continued)

```
ATOM   4147  C    THR b 307     -3.022  15.451 -52.600  0.50 44.22           C
ATOM   4148  O    THR b 307     -2.161  15.576 -53.460  0.50 47.15           O
ATOM   4149  N    VAL b 308     -3.177  16.331 -51.611  0.50 38.01           N
ATOM   4150  CA   VAL b 308     -2.178  17.404 -51.467  0.50 39.33           C
ATOM   4151  CB   VAL b 308     -2.739  18.803 -51.788  0.50 40.86           C
ATOM   4152  CG1  VAL b 308     -3.275  18.824 -53.214  0.50 41.09           C
ATOM   4153  CG2  VAL b 308     -3.825  19.188 -50.793  0.50 38.45           C
ATOM   4154  C    VAL b 308     -1.539  17.384 -50.090  0.50 35.10           C
ATOM   4155  O    VAL b 308     -2.131  16.865 -49.164  0.50 37.99           O
ATOM   4156  N    LEU b 309     -0.325  17.918 -49.968  0.50 34.14           N
ATOM   4157  CA   LEU b 309      0.345  17.988 -48.685  0.50 36.86           C
ATOM   4158  CB   LEU b 309      1.858  18.096 -48.864  0.50 42.80           C
ATOM   4159  CG   LEU b 309      2.684  16.906 -49.365  0.50 48.21           C
ATOM   4160  CD1  LEU b 309      4.133  17.056 -48.889  0.50 40.93           C
ATOM   4161  CD2  LEU b 309      2.084  15.565 -48.926  0.50 43.65           C
ATOM   4162  C    LEU b 309     -0.180  19.206 -47.930  0.50 39.46           C
ATOM   4163  O    LEU b 309     -0.241  20.312 -48.492  0.50 39.29           O
ATOM   4164  N    HIS b 310     -0.599  18.999 -46.679  0.50 34.66           N
ATOM   4165  CA   HIS b 310     -1.166  20.089 -45.886  0.50 34.87           C
ATOM   4166  CB   HIS b 310     -1.212  19.715 -44.386  0.50 33.03           C
ATOM   4167  CG   HIS b 310     -2.084  18.541 -44.099  0.50 34.77           C
ATOM   4168  ND1  HIS b 310     -1.723  17.254 -44.441  0.50 32.45           N
ATOM   4169  CE1  HIS b 310     -2.712  16.427 -44.141  0.50 32.25           C
ATOM   4170  NE2  HIS b 310     -3.706  17.132 -43.630  0.50 34.43           N
ATOM   4171  CD2  HIS b 310     -3.338  18.461 -43.592  0.50 36.21           C
ATOM   4172  C    HIS b 310     -0.337  21.347 -46.062  0.50 34.97           C
ATOM   4173  O    HIS b 310     -0.865  22.433 -46.260  0.50 37.14           O
ATOM   4174  N    GLN b 311      0.971  21.194 -45.947  0.50 36.38           N
ATOM   4175  CA   GLN b 311      1.851  22.342 -45.856  0.50 42.04           C
ATOM   4176  CB   GLN b 311      3.187  21.892 -45.258  0.50 42.88           C
ATOM   4177  CG   GLN b 311      3.879  20.848 -46.121  0.50 58.77           C
ATOM   4178  CD   GLN b 311      3.636  19.393 -45.708  0.50 62.07           C
ATOM   4179  OE1  GLN b 311      2.542  19.004 -45.240  0.50 50.84           O
ATOM   4180  NE2  GLN b 311      4.669  18.563 -45.914  0.50 57.38           N
ATOM   4181  C    GLN b 311      2.029  23.033 -47.231  0.50 39.97           C
ATOM   4182  O    GLN b 311      2.221  24.250 -47.306  0.50 37.44           O
ATOM   4183  N    ASP b 312      1.900  22.268 -48.318  0.50 40.38           N
ATOM   4184  CA   ASP b 312      1.954  22.870 -49.661  0.50 39.08           C
ATOM   4185  CB   ASP b 312      1.889  21.812 -50.763  0.50 37.65           C
ATOM   4186  CG   ASP b 312      3.174  21.008 -50.899  0.50 40.81           C
ATOM   4187  OD1  ASP b 312      4.244  21.485 -50.461  0.50 40.34           O
ATOM   4188  OD2  ASP b 312      3.113  19.915 -51.506  0.50 40.32           O
ATOM   4189  C    ASP b 312      0.759  23.794 -49.808  0.50 37.30           C
ATOM   4190  O    ASP b 312      0.908  24.950 -50.168  0.50 41.56           O
ATOM   4191  N    TRP b 313     -0.430  23.278 -49.510  0.50 38.74           N
ATOM   4192  CA   TRP b 313     -1.665  24.052 -49.681  0.50 35.41           C
ATOM   4193  CB   TRP b 313     -2.911  23.220 -49.304  0.50 33.03           C
ATOM   4194  CG   TRP b 313     -4.193  24.039 -49.419  0.50 30.46           C
ATOM   4195  CD1  TRP b 313     -4.843  24.689 -48.422  0.50 29.40           C
ATOM   4196  NE1  TRP b 313     -5.947  25.351 -48.928  0.50 29.38           N
ATOM   4197  CE2  TRP b 313     -5.978  25.182 -50.286  0.50 29.39           C
ATOM   4198  CD2  TRP b 313     -4.895  24.354 -50.630  0.50 30.94           C
ATOM   4199  CE3  TRP b 313     -4.715  23.996 -51.968  0.50 32.62           C
ATOM   4200  CZ3  TRP b 313     -5.619  24.506 -52.920  0.50 35.10           C
ATOM   4201  CH2  TRP b 313     -6.691  25.329 -52.535  0.50 28.50           C
ATOM   4202  CZ2  TRP b 313     -6.897  25.659 -51.229  0.50 31.26           C
ATOM   4203  C    TRP b 313     -1.609  25.312 -48.835  0.50 34.55           C
ATOM   4204  O    TRP b 313     -1.818  26.426 -49.328  0.50 35.93           O
ATOM   4205  N    LEU b 314     -1.299  25.132 -47.554  0.50 34.24           N
ATOM   4206  CA   LEU b 314     -1.260  26.249 -46.628  0.50 32.32           C
ATOM   4207  CB   LEU b 314     -1.157  25.741 -45.182  0.50 32.01           C
ATOM   4208  CG   LEU b 314     -2.447  25.058 -44.653  0.50 33.30           C
ATOM   4209  CD1  LEU b 314     -2.224  24.443 -43.287  0.50 32.27           C
ATOM   4210  CD2  LEU b 314     -3.600  26.044 -44.564  0.50 29.57           C
```

Figure 26 (Continued)

```
ATOM   4211  C    LEU  b  314    -0.148   27.266  -46.971  0.50  36.97           C
ATOM   4212  O    LEU  b  314    -0.255   28.446  -46.649  0.50  33.58           O
ATOM   4213  N    ASN  b  315     0.907   26.810  -47.631  0.50  38.90           N
ATOM   4214  CA   ASN  b  315     1.960   27.701  -48.078  0.50  43.98           C
ATOM   4215  CB   ASN  b  315     3.294   26.955  -48.151  0.50  40.66           C
ATOM   4216  CG   ASN  b  315     3.962   26.834  -46.799  0.50  39.02           C
ATOM   4217  OD1  ASN  b  315     3.632   27.555  -45.856  0.50  36.31           O
ATOM   4218  ND2  ASN  b  315     4.904   25.923  -46.702  0.50  37.81           N
ATOM   4219  C    ASN  b  315     1.692   28.360  -49.433  0.50  44.71           C
ATOM   4220  O    ASN  b  315     2.538   29.099  -49.935  0.50  47.62           O
ATOM   4221  N    GLY  b  316     0.557   28.061  -50.044  0.50  44.61           N
ATOM   4222  CA   GLY  b  316     0.142   28.775  -51.269  0.50  41.17           C
ATOM   4223  C    GLY  b  316     0.602   28.178  -52.591  0.50  41.47           C
ATOM   4224  O    GLY  b  316     0.611   28.849  -53.615  0.50  45.19           O
ATOM   4225  N    LYS  b  317     0.992   26.916  -52.598  0.50  38.54           N
ATOM   4226  CA   LYS  b  317     1.305   26.272  -53.869  0.50  37.80           C
ATOM   4227  CB   LYS  b  317     1.831   24.849  -53.647  0.50  36.92           C
ATOM   4228  CG   LYS  b  317     3.109   24.836  -52.812  0.50  39.15           C
ATOM   4229  CD   LYS  b  317     4.047   23.723  -53.241  0.50  37.79           C
ATOM   4230  CE   LYS  b  317     5.395   23.823  -52.538  0.50  40.70           C
ATOM   4231  NZ   LYS  b  317     6.463   23.154  -53.332  0.50  36.92           N
ATOM   4232  C    LYS  b  317     0.079   26.271  -54.765  0.50  39.45           C
ATOM   4233  O    LYS  b  317    -1.056   26.127  -54.282  0.50  36.30           O
ATOM   4234  N    GLU  b  318     0.296   26.462  -56.067  0.50  42.01           N
ATOM   4235  CA   GLU  b  318    -0.820   26.513  -57.024  0.50  42.14           C
ATOM   4236  CB   GLU  b  318    -0.568   27.539  -58.139  0.50  45.01           C
ATOM   4237  CG   GLU  b  318    -0.444   28.964  -57.637  0.50  50.84           C
ATOM   4238  CD   GLU  b  318    -0.534   29.998  -58.753  0.50  60.55           C
ATOM   4239  OE1  GLU  b  318    -0.012   31.126  -58.539  0.50  49.57           O
ATOM   4240  OE2  GLU  b  318    -1.131   29.687  -59.825  0.50  55.03           O
ATOM   4241  C    GLU  b  318    -1.012   25.149  -57.632  0.50  39.21           C
ATOM   4242  O    GLU  b  318    -0.048   24.483  -57.988  0.50  35.88           O
ATOM   4243  N    TYR  b  319    -2.266   24.731  -57.756  0.50  38.95           N
ATOM   4244  CA   TYR  b  319    -2.560   23.411  -58.273  0.50  37.05           C
ATOM   4245  CB   TYR  b  319    -3.447   22.633  -57.270  0.50  36.54           C
ATOM   4246  CG   TYR  b  319    -2.683   22.365  -55.992  0.50  38.31           C
ATOM   4247  CD1  TYR  b  319    -2.539   23.362  -55.021  0.50  37.04           C
ATOM   4248  CE1  TYR  b  319    -1.780   23.146  -53.875  0.50  36.33           C
ATOM   4249  CZ   TYR  b  319    -1.138   21.939  -53.701  0.50  38.79           C
ATOM   4250  OH   TYR  b  319    -0.384   21.721  -52.564  0.50  44.72           O
ATOM   4251  CE2  TYR  b  319    -1.247   20.937  -54.662  0.50  40.16           C
ATOM   4252  CD2  TYR  b  319    -2.004   21.162  -55.806  0.50  36.67           C
ATOM   4253  C    TYR  b  319    -3.186   23.554  -59.658  0.50  40.08           C
ATOM   4254  O    TYR  b  319    -4.187   24.253  -59.821  0.50  37.54           O
ATOM   4255  N    LYS  b  320    -2.553   22.928  -60.654  0.50  40.83           N
ATOM   4256  CA   LYS  b  320    -3.025   22.976  -62.037  0.50  39.33           C
ATOM   4257  CB   LYS  b  320    -1.885   23.350  -62.971  0.50  39.44           C
ATOM   4258  CG   LYS  b  320    -2.259   23.345  -64.440  0.50  36.81           C
ATOM   4259  CD   LYS  b  320    -1.617   24.517  -65.189  0.50  41.41           C
ATOM   4260  CE   LYS  b  320    -0.193   24.214  -65.632  0.50  42.44           C
ATOM   4261  NZ   LYS  b  320     0.383   25.304  -66.485  0.50  41.61           N
ATOM   4262  C    LYS  b  320    -3.640   21.667  -62.519  0.50  42.67           C
ATOM   4263  O    LYS  b  320    -3.005   20.595  -62.485  0.50  41.15           O
ATOM   4264  N    CYS  b  321    -4.885   21.756  -62.971  0.50  45.67           N
ATOM   4265  CA   CYS  b  321    -5.487   20.671  -63.721  0.50  44.45           C
ATOM   4266  CB   CYS  b  321    -6.914   20.426  -63.279  0.50  46.65           C
ATOM   4267  SG   CYS  b  321    -7.595   18.897  -63.961  0.50  46.94           S
ATOM   4268  C    CYS  b  321    -5.491   21.024  -65.196  0.50  48.70           C
ATOM   4269  O    CYS  b  321    -5.833   22.156  -65.561  0.50  45.98           O
ATOM   4270  N    LYS  b  322    -5.094   20.052  -66.027  0.50  51.81           N
ATOM   4271  CA   LYS  b  322    -5.155   20.172  -67.486  0.50  46.04           C
ATOM   4272  CB   LYS  b  322    -3.759   20.229  -68.100  0.50  50.47           C
ATOM   4273  CG   LYS  b  322    -3.775   20.410  -69.616  0.50  57.81           C
ATOM   4274  CD   LYS  b  322    -2.373   20.404  -70.214  0.50  61.07           C
```

Figure 26 (Continued)

```
ATOM   4275  CE   LYS b 322      -1.555  21.582 -69.704  0.50 57.53           C
ATOM   4276  NZ   LYS b 322      -0.153  21.587 -70.225  0.50 65.42           N
ATOM   4277  C    LYS b 322      -5.926  19.007 -68.083  0.50 45.35           C
ATOM   4278  O    LYS b 322      -5.596  17.825 -67.862  0.50 42.91           O
ATOM   4279  N    VAL b 323      -6.970  19.342 -68.837  0.50 45.60           N
ATOM   4280  CA   VAL b 323      -7.856  18.321 -69.376  0.50 48.49           C
ATOM   4281  CB   VAL b 323      -9.271  18.431 -68.771  0.50 47.07           C
ATOM   4282  CG1  VAL b 323      -9.666  19.892 -68.597  0.50 47.20           C
ATOM   4283  CG2  VAL b 323     -10.288  17.631 -69.585  0.50 44.02           C
ATOM   4284  C    VAL b 323      -7.861  18.346 -70.916  0.50 51.73           C
ATOM   4285  O    VAL b 323      -8.129  19.377 -71.555  0.50 55.23           O
ATOM   4286  N    SER b 324      -7.487  17.215 -71.496  0.50 49.53           N
ATOM   4287  CA   SER b 324      -7.358  17.092 -72.941  0.50 46.70           C
ATOM   4288  CB   SER b 324      -5.932  16.681 -73.319  0.50 42.95           C
ATOM   4289  OG   SER b 324      -5.005  17.747 -73.115  0.50 36.46           O
ATOM   4290  C    SER b 324      -8.346  16.039 -73.406  0.50 53.38           C
ATOM   4291  O    SER b 324      -8.537  15.012 -72.745  0.50 58.91           O
ATOM   4292  N    ASN b 325      -8.977  16.312 -74.540  0.50 56.47           N
ATOM   4293  CA   ASN b 325     -10.052  15.490 -75.054  0.50 59.71           C
ATOM   4294  CB   ASN b 325     -11.301  15.755 -74.215  0.50 57.49           C
ATOM   4295  CG   ASN b 325     -12.575  15.281 -74.875  0.50 58.17           C
ATOM   4296  OD1  ASN b 325     -13.378  16.089 -75.367  0.50 55.06           O
ATOM   4297  ND2  ASN b 325     -12.797  13.969 -74.850  0.50 58.92           N
ATOM   4298  C    ASN b 325     -10.264  15.901 -76.516  0.50 59.13           C
ATOM   4299  O    ASN b 325     -10.110  17.085 -76.856  0.50 50.09           O
ATOM   4300  N    LYS b 326     -10.571  14.930 -77.380  0.50 63.59           N
ATOM   4301  CA   LYS b 326     -10.726  15.203 -78.828  0.50 65.20           C
ATOM   4302  CB   LYS b 326     -11.236  13.970 -79.582  0.50 68.38           C
ATOM   4303  CG   LYS b 326     -10.201  12.896 -79.858  0.50 67.39           C
ATOM   4304  CD   LYS b 326     -10.839  11.733 -80.609  0.50 72.39           C
ATOM   4305  CE   LYS b 326     -10.097  10.423 -80.364  0.50 77.18           C
ATOM   4306  NZ   LYS b 326      -8.681  10.461 -80.839  0.50 75.69           N
ATOM   4307  C    LYS b 326     -11.669  16.371 -79.114  0.50 64.25           C
ATOM   4308  O    LYS b 326     -11.405  17.199 -79.988  0.50 62.61           O
ATOM   4309  N    ALA b 327     -12.773  16.429 -78.373  0.50 66.42           N
ATOM   4310  CA   ALA b 327     -13.816  17.418 -78.625  0.50 62.26           C
ATOM   4311  CB   ALA b 327     -15.074  17.059 -77.844  0.50 65.43           C
ATOM   4312  C    ALA b 327     -13.348  18.835 -78.296  0.50 61.05           C
ATOM   4313  O    ALA b 327     -14.116  19.796 -78.371  0.50 56.42           O
ATOM   4314  N    LEU b 328     -12.079  18.960 -77.926  0.50 65.76           N
ATOM   4315  CA   LEU b 328     -11.528  20.248 -77.522  0.50 65.05           C
ATOM   4316  CB   LEU b 328     -11.244  20.261 -76.017  0.50 62.91           C
ATOM   4317  CG   LEU b 328     -12.316  20.704 -75.010  0.50 63.64           C
ATOM   4318  CD1  LEU b 328     -11.751  20.553 -73.606  0.50 57.46           C
ATOM   4319  CD2  LEU b 328     -12.775  22.137 -75.245  0.50 55.73           C
ATOM   4320  C    LEU b 328     -10.222  20.486 -78.254  0.50 68.25           C
ATOM   4321  O    LEU b 328      -9.309  19.662 -78.185  0.50 72.61           O
ATOM   4322  N    PRO b 329     -10.101  21.640 -78.912  0.50 69.39           N
ATOM   4323  CA   PRO b 329      -8.845  21.958 -79.585  0.50 72.36           C
ATOM   4324  CB   PRO b 329      -9.136  23.306 -80.277  0.50 65.51           C
ATOM   4325  CG   PRO b 329     -10.604  23.551 -80.116  0.50 65.70           C
ATOM   4326  CD   PRO b 329     -11.033  22.777 -78.906  0.50 67.03           C
ATOM   4327  C    PRO b 329      -7.707  22.124 -78.579  0.50 73.98           C
ATOM   4328  O    PRO b 329      -6.794  21.292 -78.522  0.50 82.41           O
ATOM   4329  N    ALA b 330      -7.771  23.201 -77.796  0.50 70.18           N
ATOM   4330  CA   ALA b 330      -6.719  23.541 -76.834  0.50 66.14           C
ATOM   4331  CB   ALA b 330      -6.382  25.026 -76.924  0.50 56.43           C
ATOM   4332  C    ALA b 330      -7.082  23.163 -75.392  0.50 64.81           C
ATOM   4333  O    ALA b 330      -7.858  23.860 -74.737  0.50 65.65           O
ATOM   4334  N    PRO b 331      -6.518  22.054 -74.891  0.50 65.43           N
ATOM   4335  CA   PRO b 331      -6.729  21.702 -73.498  0.50 71.82           C
ATOM   4336  CB   PRO b 331      -5.365  21.135 -73.095  0.50 66.94           C
ATOM   4337  CG   PRO b 331      -4.830  20.526 -74.370  0.50 72.18           C
ATOM   4338  CD   PRO b 331      -5.619  21.086 -75.541  0.50 67.85           C
```

Figure 26 (Continued)

```
ATOM   4339  C    PRO b 331      -7.098  22.903 -72.630  0.50 62.32           C
ATOM   4340  O    PRO b 331      -6.426  23.930 -72.687  0.50 63.30           O
ATOM   4341  N    ILE b 332      -8.172  22.778 -71.852  0.50 58.54           N
ATOM   4342  CA   ILE b 332      -8.490  23.786 -70.827  0.50 57.97           C
ATOM   4343  CB   ILE b 332     -10.007  23.900 -70.554  0.50 58.54           C
ATOM   4344  CG1  ILE b 332     -10.710  24.581 -71.731  0.50 53.61           C
ATOM   4345  CD1  ILE b 332     -12.207  24.374 -71.744  0.50 49.44           C
ATOM   4346  CG2  ILE b 332     -10.265  24.694 -69.278  0.50 52.78           C
ATOM   4347  C    ILE b 332      -7.738  23.509 -69.517  0.50 58.65           C
ATOM   4348  O    ILE b 332      -7.777  22.394 -68.974  0.50 63.24           O
ATOM   4349  N    GLU b 333      -7.014  24.516 -69.044  0.50 48.03           N
ATOM   4350  CA   GLU b 333      -6.237  24.377 -67.832  0.50 53.45           C
ATOM   4351  CB   GLU b 333      -4.772  24.713 -68.092  0.50 57.72           C
ATOM   4352  CG   GLU b 333      -4.179  24.036 -69.325  0.50 59.26           C
ATOM   4353  CD   GLU b 333      -2.698  24.317 -69.476  0.50 59.36           C
ATOM   4354  OE1  GLU b 333      -2.256  25.435 -69.105  0.50 52.62           O
ATOM   4355  OE2  GLU b 333      -1.972  23.409 -69.944  0.50 63.71           O
ATOM   4356  C    GLU b 333      -6.795  25.305 -66.755  0.50 60.19           C
ATOM   4357  O    GLU b 333      -6.990  26.506 -66.996  0.50 53.08           O
ATOM   4358  N    LYS b 334      -7.034  24.761 -65.571  0.50 51.40           N
ATOM   4359  CA   LYS b 334      -7.536  25.538 -64.456  0.50 49.76           C
ATOM   4360  CB   LYS b 334      -8.894  25.014 -64.012  0.50 50.91           C
ATOM   4361  CG   LYS b 334     -10.016  25.277 -64.993  0.50 52.58           C
ATOM   4362  CD   LYS b 334     -10.475  26.713 -64.926  0.50 45.55           C
ATOM   4363  CE   LYS b 334     -11.960  26.829 -65.196  0.50 46.98           C
ATOM   4364  NZ   LYS b 334     -12.238  27.165 -66.610  0.50 44.08           N
ATOM   4365  C    LYS b 334      -6.556  25.478 -63.301  0.50 46.84           C
ATOM   4366  O    LYS b 334      -5.895  24.471 -63.103  0.50 50.92           O
ATOM   4367  N    THR b 335      -6.463  26.569 -62.554  0.50 42.99           N
ATOM   4368  CA   THR b 335      -5.543  26.666 -61.420  0.50 45.52           C
ATOM   4369  CB   THR b 335      -4.393  27.644 -61.699  0.50 42.53           C
ATOM   4370  OG1  THR b 335      -3.782  27.292 -62.941  0.50 46.54           O
ATOM   4371  CG2  THR b 335      -3.316  27.509 -60.610  0.50 46.03           C
ATOM   4372  C    THR b 335      -6.263  27.099 -60.140  0.50 43.62           C
ATOM   4373  O    THR b 335      -7.220  27.858 -60.185  0.50 39.11           O
ATOM   4374  N    ILE b 336      -5.802  26.608 -59.001  0.50 40.54           N
ATOM   4375  CA   ILE b 336      -6.423  26.973 -57.736  0.50 41.50           C
ATOM   4376  CB   ILE b 336      -7.626  26.066 -57.384  0.50 44.51           C
ATOM   4377  CG1  ILE b 336      -8.498  26.742 -56.304  0.50 42.77           C
ATOM   4378  CD1  ILE b 336      -9.812  26.037 -56.012  0.50 45.34           C
ATOM   4379  CG2  ILE b 336      -7.163  24.667 -56.975  0.50 35.74           C
ATOM   4380  C    ILE b 336      -5.381  26.976 -56.628  0.50 40.22           C
ATOM   4381  O    ILE b 336      -4.415  26.220 -56.681  0.50 39.04           O
ATOM   4382  N    SER b 337      -5.541  27.904 -55.688  0.50 42.55           N
ATOM   4383  CA   SER b 337      -4.660  28.015 -54.524  0.50 41.23           C
ATOM   4384  CB   SER b 337      -3.565  29.049 -54.780  0.50 37.96           C
ATOM   4385  OG   SER b 337      -4.100  30.340 -54.539  0.50 39.96           O
ATOM   4386  C    SER b 337      -5.483  28.457 -53.315  0.50 36.41           C
ATOM   4387  O    SER b 337      -6.643  28.824 -53.448  0.50 36.26           O
ATOM   4388  N    LYS b 338      -4.896  28.408 -52.129  0.50 35.61           N
ATOM   4389  CA   LYS b 338      -5.619  28.849 -50.945  0.50 34.98           C
ATOM   4390  CB   LYS b 338      -4.720  28.673 -49.733  0.50 37.64           C
ATOM   4391  CG   LYS b 338      -5.352  28.957 -48.371  0.50 38.36           C
ATOM   4392  CD   LYS b 338      -4.340  28.660 -47.268  0.50 35.27           C
ATOM   4393  CE   LYS b 338      -3.262  29.734 -47.230  0.50 41.39           C
ATOM   4394  NZ   LYS b 338      -3.819  30.962 -46.589  0.50 34.63           N
ATOM   4395  C    LYS b 338      -5.878  30.342 -51.144  0.50 37.21           C
ATOM   4396  O    LYS b 338      -5.100  31.050 -51.768  0.50 40.04           O
ATOM   4397  N    ALA b 339      -6.982  30.822 -50.631  0.50 39.49           N
ATOM   4398  CA   ALA b 339      -7.246  32.243 -50.652  0.50 37.96           C
ATOM   4399  CB   ALA b 339      -8.514  32.551 -49.855  0.50 33.10           C
ATOM   4400  C    ALA b 339      -6.043  32.948 -50.048  0.50 38.00           C
ATOM   4401  O    ALA b 339      -5.509  32.507 -49.036  0.50 41.07           O
ATOM   4402  N    LYS b 340      -5.641  34.053 -50.667  0.50 38.81           N
```

Figure 26 (Continued)

```
ATOM   4403  CA   LYS b 340     -4.459  34.813 -50.276  0.50 41.38           C
ATOM   4404  CB   LYS b 340     -3.816  35.456 -51.510  0.50 43.32           C
ATOM   4405  CG   LYS b 340     -3.746  34.541 -52.729  0.50 46.34           C
ATOM   4406  CD   LYS b 340     -2.614  34.965 -53.671  0.50 49.31           C
ATOM   4407  CE   LYS b 340     -2.826  34.429 -55.081  0.50 52.85           C
ATOM   4408  NZ   LYS b 340     -1.544  34.372 -55.849  0.50 57.13           N
ATOM   4409  C    LYS b 340     -4.870  35.904 -49.289  0.50 40.34           C
ATOM   4410  O    LYS b 340     -6.044  36.172 -49.154  0.50 35.58           O
ATOM   4411  N    GLY b 341     -3.902  36.496 -48.586  0.50 37.71           N
ATOM   4412  CA   GLY b 341     -4.176  37.517 -47.585  0.50 39.76           C
ATOM   4413  C    GLY b 341     -3.466  37.160 -46.300  0.50 41.17           C
ATOM   4414  O    GLY b 341     -3.351  35.988 -45.968  0.50 38.48           O
ATOM   4415  N    GLN b 342     -2.969  38.168 -45.588  0.50 40.51           N
ATOM   4416  CA   GLN b 342     -2.223  37.947 -44.342  0.50 40.33           C
ATOM   4417  CB   GLN b 342     -1.723  39.298 -43.813  0.50 41.49           C
ATOM   4418  CG   GLN b 342     -1.102  39.257 -42.426  0.50 51.95           C
ATOM   4419  CD   GLN b 342      0.419  39.279 -42.450  0.50 55.28           C
ATOM   4420  OE1  GLN b 342      1.043  39.137 -43.513  0.50 64.33           O
ATOM   4421  NE2  GLN b 342      1.027  39.447 -41.275  0.50 52.21           N
ATOM   4422  C    GLN b 342     -3.144  37.270 -43.310  0.50 38.87           C
ATOM   4423  O    GLN b 342     -4.253  37.736 -43.075  0.50 37.84           O
ATOM   4424  N    PRO b 343     -2.725  36.128 -42.755  0.50 40.06           N
ATOM   4425  CA   PRO b 343     -3.600  35.478 -41.782  0.50 39.68           C
ATOM   4426  CB   PRO b 343     -2.808  34.213 -41.391  0.50 37.13           C
ATOM   4427  CG   PRO b 343     -1.891  33.945 -42.535  0.50 39.42           C
ATOM   4428  CD   PRO b 343     -1.854  35.150 -43.438  0.50 39.11           C
ATOM   4429  C    PRO b 343     -3.853  36.319 -40.546  0.50 38.02           C
ATOM   4430  O    PRO b 343     -2.937  36.937 -40.034  0.50 40.11           O
ATOM   4431  N    ARG b 344     -5.072  36.282 -40.019  0.50 34.40           N
ATOM   4432  CA   ARG b 344     -5.340  36.918 -38.740  0.50 35.81           C
ATOM   4433  CB   ARG b 344     -6.164  38.213 -38.909  0.50 33.75           C
ATOM   4434  CG   ARG b 344     -5.755  38.992 -40.161  0.50 41.02           C
ATOM   4435  CD   ARG b 344     -6.065  40.483 -40.073  0.50 49.87           C
ATOM   4436  NE   ARG b 344     -6.963  40.943 -41.149  0.50 54.38           N
ATOM   4437  CZ   ARG b 344     -6.701  40.905 -42.459  0.50 46.79           C
ATOM   4438  NH1  ARG b 344     -5.546  40.418 -42.935  0.50 39.31           N
ATOM   4439  NH2  ARG b 344     -7.609  41.374 -43.296  0.50 44.51           N
ATOM   4440  C    ARG b 344     -6.058  35.943 -37.824  0.50 36.99           C
ATOM   4441  O    ARG b 344     -6.931  35.189 -38.258  0.50 38.95           O
ATOM   4442  N    GLU b 345     -5.720  36.018 -36.545  0.50 35.94           N
ATOM   4443  CA   GLU b 345     -6.091  35.013 -35.571  0.50 39.46           C
ATOM   4444  CB   GLU b 345     -5.069  35.043 -34.425  0.50 35.46           C
ATOM   4445  CG   GLU b 345     -5.331  34.013 -33.339  0.50 40.39           C
ATOM   4446  CD   GLU b 345     -4.242  34.015 -32.286  0.50 44.37           C
ATOM   4447  OE1  GLU b 345     -4.511  33.548 -31.158  0.50 49.50           O
ATOM   4448  OE2  GLU b 345     -3.118  34.488 -32.582  0.50 43.57           O
ATOM   4449  C    GLU b 345     -7.499  35.248 -35.033  0.50 38.76           C
ATOM   4450  O    GLU b 345     -7.770  36.290 -34.449  0.50 43.20           O
ATOM   4451  N    PRO b 346     -8.400  34.265 -35.212  0.50 36.53           N
ATOM   4452  CA   PRO b 346     -9.773  34.438 -34.776  0.50 34.02           C
ATOM   4453  CB   PRO b 346    -10.415  33.080 -35.046  0.50 34.57           C
ATOM   4454  CG   PRO b 346     -9.452  32.313 -35.885  0.50 30.27           C
ATOM   4455  CD   PRO b 346     -8.105  32.889 -35.649  0.50 30.53           C
ATOM   4456  C    PRO b 346     -9.778  34.637 -33.274  0.50 46.16           C
ATOM   4457  O    PRO b 346     -8.950  34.032 -32.573  0.50 40.82           O
ATOM   4458  N    GLN b 347    -10.695  35.479 -32.800  0.50 40.53           N
ATOM   4459  CA   GLN b 347    -11.074  35.526 -31.407  0.50 41.46           C
ATOM   4460  CB   GLN b 347    -11.392  36.970 -31.010  0.50 48.23           C
ATOM   4461  CG   GLN b 347    -10.499  37.991 -31.699  0.50 52.76           C
ATOM   4462  CD   GLN b 347     -9.042  37.767 -31.375  0.50 59.40           C
ATOM   4463  OE1  GLN b 347     -8.173  37.893 -32.244  0.50 75.62           O
ATOM   4464  NE2  GLN b 347     -8.765  37.404 -30.122  0.50 63.53           N
ATOM   4465  C    GLN b 347    -12.349  34.710 -31.339  0.50 37.88           C
ATOM   4466  O    GLN b 347    -13.191  34.789 -32.225  0.50 37.50           O
```

Figure 26 (Continued)

```
ATOM   4467  N    VAL b 348    -12.500  33.934 -30.287  0.50 36.07           N
ATOM   4468  CA   VAL b 348    -13.634  33.043 -30.167  0.50 33.96           C
ATOM   4469  CB   VAL b 348    -13.129  31.590 -30.128  0.50 34.65           C
ATOM   4470  CG1  VAL b 348    -14.289  30.589 -30.105  0.50 35.83           C
ATOM   4471  CG2  VAL b 348    -12.204  31.341 -31.310  0.50 34.96           C
ATOM   4472  C    VAL b 348    -14.316  33.424 -28.861  0.50 36.42           C
ATOM   4473  O    VAL b 348    -13.664  33.444 -27.832  0.50 34.88           O
ATOM   4474  N    TYR b 349    -15.591  33.806 -28.925  0.50 36.71           N
ATOM   4475  CA   TYR b 349    -16.381  34.122 -27.725  0.50 38.98           C
ATOM   4476  CB   TYR b 349    -16.727  35.611 -27.665  0.50 34.77           C
ATOM   4477  CG   TYR b 349    -15.521  36.482 -27.780  0.50 38.28           C
ATOM   4478  CD1  TYR b 349    -14.527  36.467 -26.793  0.50 36.99           C
ATOM   4479  CE1  TYR b 349    -13.404  37.252 -26.907  0.50 36.17           C
ATOM   4480  CZ   TYR b 349    -13.252  38.062 -28.018  0.50 39.51           C
ATOM   4481  OH   TYR b 349    -12.125  38.846 -28.161  0.50 38.17           O
ATOM   4482  CE2  TYR b 349    -14.205  38.074 -29.018  0.50 40.38           C
ATOM   4483  CD2  TYR b 349    -15.335  37.278 -28.895  0.50 36.82           C
ATOM   4484  C    TYR b 349    -17.684  33.349 -27.765  0.50 38.20           C
ATOM   4485  O    TYR b 349    -18.453  33.491 -28.723  0.50 39.53           O
ATOM   4486  N    VAL b 350    -17.929  32.538 -26.740  0.50 34.29           N
ATOM   4487  CA   VAL b 350    -19.216  31.866 -26.611  0.50 35.38           C
ATOM   4488  CB   VAL b 350    -19.052  30.433 -26.086  0.50 38.16           C
ATOM   4489  CG1  VAL b 350    -18.496  29.552 -27.191  0.50 35.37           C
ATOM   4490  CG2  VAL b 350    -18.156  30.402 -24.843  0.50 40.43           C
ATOM   4491  C    VAL b 350    -20.141  32.649 -25.703  0.50 35.80           C
ATOM   4492  O    VAL b 350    -19.691  33.451 -24.894  0.50 35.22           O
ATOM   4493  N    LEU b 351    -21.442  32.417 -25.833  0.50 39.15           N
ATOM   4494  CA   LEU b 351    -22.417  33.166 -25.048  0.50 34.50           C
ATOM   4495  CB   LEU b 351    -22.929  34.360 -25.835  0.50 38.23           C
ATOM   4496  CG   LEU b 351    -21.818  35.099 -26.588  0.50 42.92           C
ATOM   4497  CD1  LEU b 351    -21.468  34.311 -27.841  0.50 39.53           C
ATOM   4498  CD2  LEU b 351    -22.250  36.507 -26.973  0.50 52.13           C
ATOM   4499  C    LEU b 351    -23.585  32.323 -24.614  0.50 38.78           C
ATOM   4500  O    LEU b 351    -24.218  31.664 -25.427  0.50 42.42           O
ATOM   4501  N    PRO b 352    -23.891  32.347 -23.314  0.50 41.43           N
ATOM   4502  CA   PRO b 352    -25.007  31.542 -22.832  0.50 39.22           C
ATOM   4503  CB   PRO b 352    -24.919  31.683 -21.297  0.50 39.79           C
ATOM   4504  CG   PRO b 352    -24.084  32.897 -21.048  0.50 38.81           C
ATOM   4505  CD   PRO b 352    -23.148  33.010 -22.225  0.50 42.97           C
ATOM   4506  C    PRO b 352    -26.314  32.079 -23.351  0.50 38.29           C
ATOM   4507  O    PRO b 352    -26.355  33.177 -23.909  0.50 33.56           O
ATOM   4508  N    PRO b 353    -27.386  31.298 -23.193  0.50 36.84           N
ATOM   4509  CA   PRO b 353    -28.703  31.734 -23.598  0.50 40.44           C
ATOM   4510  CB   PRO b 353    -29.604  30.580 -23.141  0.50 40.12           C
ATOM   4511  CG   PRO b 353    -28.693  29.383 -23.139  0.50 39.45           C
ATOM   4512  CD   PRO b 353    -27.396  29.935 -22.635  0.50 40.17           C
ATOM   4513  C    PRO b 353    -29.111  33.033 -22.904  0.50 41.39           C
ATOM   4514  O    PRO b 353    -28.651  33.328 -21.807  0.50 44.63           O
ATOM   4515  N    SER b 354    -29.977  33.790 -23.562  0.50 42.75           N
ATOM   4516  CA   SER b 354    -30.718  34.893 -22.948  0.50 42.63           C
ATOM   4517  CB   SER b 354    -31.535  35.585 -24.049  0.50 43.01           C
ATOM   4518  OG   SER b 354    -32.123  36.795 -23.586  0.50 55.57           O
ATOM   4519  C    SER b 354    -31.693  34.373 -21.897  0.50 43.02           C
ATOM   4520  O    SER b 354    -32.422  33.409 -22.155  0.50 37.28           O
ATOM   4521  N    ARG b 355    -31.766  35.035 -20.741  0.50 43.10           N
ATOM   4522  CA   ARG b 355    -32.806  34.695 -19.760  0.50 43.74           C
ATOM   4523  CB   ARG b 355    -32.916  35.768 -18.668  0.50 51.08           C
ATOM   4524  CG   ARG b 355    -34.066  35.517 -17.696  0.50 51.08           C
ATOM   4525  CD   ARG b 355    -34.504  36.777 -16.951  0.50 61.85           C
ATOM   4526  NE   ARG b 355    -35.214  36.453 -15.709  0.50 58.70           N
ATOM   4527  CZ   ARG b 355    -36.535  36.510 -15.533  0.50 50.81           C
ATOM   4528  NH1  ARG b 355    -37.336  36.907 -16.503  0.50 53.85           N
ATOM   4529  NH2  ARG b 355    -37.061  36.170 -14.366  0.50 48.71           N
ATOM   4530  C    ARG b 355    -34.161  34.560 -20.436  0.50 41.30           C
```

Figure 26 (Continued)

```
ATOM   4531  O    ARG b 355     -34.881  33.574 -20.240  0.50 43.92           O
ATOM   4532  N    ASP b 356     -34.501  35.556 -21.249  0.50 40.95           N
ATOM   4533  CA   ASP b 356     -35.754  35.549 -21.996  0.50 40.43           C
ATOM   4534  CB   ASP b 356     -35.792  36.680 -23.034  0.50 39.97           C
ATOM   4535  CG   ASP b 356     -36.015  38.043 -22.414  0.50 45.69           C
ATOM   4536  OD1  ASP b 356     -35.470  39.050 -22.945  0.50 38.45           O
ATOM   4537  OD2  ASP b 356     -36.753  38.102 -21.403  0.50 45.76           O
ATOM   4538  C    ASP b 356     -36.020  34.218 -22.685  0.50 37.94           C
ATOM   4539  O    ASP b 356     -37.172  33.851 -22.866  0.50 39.14           O
ATOM   4540  N    GLU b 357     -34.975  33.502 -23.109  0.50 39.20           N
ATOM   4541  CA   GLU b 357     -35.201  32.239 -23.848  0.50 38.54           C
ATOM   4542  CB   GLU b 357     -34.027  31.892 -24.781  0.50 40.50           C
ATOM   4543  CG   GLU b 357     -34.353  30.793 -25.798  0.50 34.38           C
ATOM   4544  CD   GLU b 357     -33.222  30.539 -26.771  0.50 35.66           C
ATOM   4545  OE1  GLU b 357     -32.040  30.769 -26.428  0.50 33.47           O
ATOM   4546  OE2  GLU b 357     -33.505  30.060 -27.884  0.50 38.40           O
ATOM   4547  C    GLU b 357     -35.401  31.114 -22.867  0.50 41.04           C
ATOM   4548  O    GLU b 357     -35.897  30.057 -23.222  0.50 41.69           O
ATOM   4549  N    LEU b 358     -35.019  31.364 -21.615  0.50 48.36           N
ATOM   4550  CA   LEU b 358     -35.005  30.321 -20.602  0.50 49.12           C
ATOM   4551  CB   LEU b 358     -34.247  30.778 -19.356  0.50 51.56           C
ATOM   4552  CG   LEU b 358     -32.771  30.391 -19.426  0.50 59.26           C
ATOM   4553  CD1  LEU b 358     -31.992  30.841 -18.197  0.50 58.59           C
ATOM   4554  CD2  LEU b 358     -32.668  28.885 -19.617  0.50 56.90           C
ATOM   4555  C    LEU b 358     -36.377  29.857 -20.226  0.50 46.14           C
ATOM   4556  O    LEU b 358     -36.519  29.134 -19.256  0.50 57.83           O
ATOM   4557  N    THR b 359     -37.382  30.259 -21.001  0.50 50.34           N
ATOM   4558  CA   THR b 359     -38.757  29.782 -20.829  0.50 49.65           C
ATOM   4559  CB   THR b 359     -39.745  30.954 -20.583  0.50 62.13           C
ATOM   4560  OG1  THR b 359     -40.269  31.426 -21.832  0.50 55.29           O
ATOM   4561  CG2  THR b 359     -39.070  32.120 -19.820  0.50 61.00           C
ATOM   4562  C    THR b 359     -39.231  28.977 -22.055  0.50 57.24           C
ATOM   4563  O    THR b 359     -40.390  28.529 -22.129  0.50 49.36           O
ATOM   4564  N    LYS b 360     -38.343  28.797 -23.031  0.50 50.98           N
ATOM   4565  CA   LYS b 360     -38.654  27.897 -24.141  0.50 48.87           C
ATOM   4566  CB   LYS b 360     -37.950  28.354 -25.421  0.50 48.44           C
ATOM   4567  CG   LYS b 360     -38.519  29.629 -26.027  0.50 50.19           C
ATOM   4568  CD   LYS b 360     -39.862  29.375 -26.700  0.50 46.85           C
ATOM   4569  CE   LYS b 360     -40.174  30.437 -27.738  0.50 50.65           C
ATOM   4570  NZ   LYS b 360     -41.256  31.365 -27.297  0.50 51.03           N
ATOM   4571  C    LYS b 360     -38.236  26.468 -23.773  0.50 44.93           C
ATOM   4572  O    LYS b 360     -37.668  26.246 -22.711  0.50 43.67           O
ATOM   4573  N    ASN b 361     -38.514  25.515 -24.657  0.50 41.57           N
ATOM   4574  CA   ASN b 361     -38.167  24.106 -24.421  0.50 41.99           C
ATOM   4575  CB   ASN b 361     -39.244  23.213 -25.024  0.50 39.52           C
ATOM   4576  CG   ASN b 361     -40.646  23.661 -24.635  0.50 45.62           C
ATOM   4577  OD1  ASN b 361     -40.899  24.050 -23.479  0.50 48.72           O
ATOM   4578  ND2  ASN b 361     -41.571  23.618 -25.597  0.50 46.43           N
ATOM   4579  C    ASN b 361     -36.795  23.746 -24.981  0.50 43.35           C
ATOM   4580  O    ASN b 361     -36.293  22.627 -24.801  0.50 44.02           O
ATOM   4581  N    GLN b 362     -36.193  24.722 -25.651  0.50 46.07           N
ATOM   4582  CA   GLN b 362     -34.836  24.623 -26.155  0.50 43.23           C
ATOM   4583  CB   GLN b 362     -34.890  24.078 -27.573  0.50 48.41           C
ATOM   4584  CG   GLN b 362     -35.235  22.588 -27.607  0.50 46.13           C
ATOM   4585  CD   GLN b 362     -35.300  22.064 -29.018  0.50 51.65           C
ATOM   4586  OE1  GLN b 362     -35.923  22.687 -29.881  0.50 48.91           O
ATOM   4587  NE2  GLN b 362     -34.663  20.911 -29.268  0.50 50.74           N
ATOM   4588  C    GLN b 362     -34.157  25.989 -26.127  0.50 45.67           C
ATOM   4589  O    GLN b 362     -34.800  27.015 -26.385  0.50 44.43           O
ATOM   4590  N    VAL b 363     -32.870  26.020 -25.789  0.50 40.80           N
ATOM   4591  CA   VAL b 363     -32.180  27.293 -25.700  0.50 36.89           C
ATOM   4592  CB   VAL b 363     -31.640  27.581 -24.287  0.50 39.66           C
ATOM   4593  CG1  VAL b 363     -32.789  27.573 -23.280  0.50 37.85           C
ATOM   4594  CG2  VAL b 363     -30.564  26.575 -23.897  0.50 40.67           C
```

Figure 26 (Continued)

```
ATOM   4595  C   VAL b 363     -31.076  27.369 -26.721  0.50 40.90           C
ATOM   4596  O   VAL b 363     -30.677  26.319  27.278  0.50 36.34           O
ATOM   4597  N   SER b 364     -30.566  28.593 -26.944  0.50 33.79           N
ATOM   4598  CA  SER b 364     -29.500  28.816 -27.926  0.50 31.42           C
ATOM   4599  CB  SER b 364     -29.956  29.855 -28.970  0.50 30.87           C
ATOM   4600  OG  SER b 364     -31.263  29.522 -29.466  0.50 30.01           O
ATOM   4601  C   SER b 364     -28.153  29.233 -27.376  0.50 31.36           C
ATOM   4602  O   SER b 364     -27.985  30.382 -26.920  0.50 38.22           O
ATOM   4603  N   LEU b 365     -27.148  28.376 -27.562  0.50 28.41           N
ATOM   4604  CA  LEU b 365     -25.768  28.748 -27.288  0.50 26.50           C
ATOM   4605  CB  LEU b 365     -24.982  27.525 -26.783  0.50 25.67           C
ATOM   4606  CG  LEU b 365     -25.796  26.512 -25.929  0.50 29.29           C
ATOM   4607  CD1 LEU b 365     -24.847  25.629 -25.105  0.50 30.98           C
ATOM   4608  CD2 LEU b 365     -26.765  27.230 -25.015  0.50 25.43           C
ATOM   4609  C   LEU b 365     -25.087  29.314 -28.544  0.50 29.95           C
ATOM   4610  O   LEU b 365     -25.097  28.681 -29.595  0.50 30.54           O
ATOM   4611  N   LEU b 366     -24.418  30.460 -28.405  0.50 30.22           N
ATOM   4612  CA  LEU b 366     -23.756  31.103 -29.538  0.50 30.09           C
ATOM   4613  CB  LEU b 366     -24.139  32.579 -29.595  0.50 31.25           C
ATOM   4614  CG  LEU b 366     -25.592  32.809 -29.950  0.50 28.21           C
ATOM   4615  CD1 LEU b 366     -25.820  34.236 -30.419  0.50 29.03           C
ATOM   4616  CD2 LEU b 366     -26.030  31.830 -31.019  0.50 27.42           C
ATOM   4617  C   LEU b 366     -22.242  31.020 -29.461  0.50 32.60           C
ATOM   4618  O   LEU b 366     -21.654  31.137 -28.377  0.50 31.80           O
ATOM   4619  N   CYS b 367     -21.606  30.842 -30.615  0.50 29.82           N
ATOM   4620  CA  CYS b 367     -20.165  30.972 -30.691  0.50 29.93           C
ATOM   4621  CB  CYS b 367     -19.552  29.642 -31.130  0.50 29.57           C
ATOM   4622  SG  CYS b 367     -17.734  29.517 -31.117  0.50 33.45           S
ATOM   4623  C   CYS b 367     -19.838  32.038 -31.716  0.50 30.37           C
ATOM   4624  O   CYS b 367     -20.135  31.848 -32.902  0.50 30.66           O
ATOM   4625  N   LEU b 368     -19.242  33.144 -31.255  0.50 29.26           N
ATOM   4626  CA  LEU b 368     -18.824  34.256 -32.113  0.50 31.47           C
ATOM   4627  CB  LEU b 368     -19.025  35.614 -31.409  0.50 29.59           C
ATOM   4628  CG  LEU b 368     -18.373  36.885 -31.963  0.50 32.94           C
ATOM   4629  CD1 LEU b 368     -18.712  37.179 -33.422  0.50 29.68           C
ATOM   4630  CD2 LEU b 368     -18.738  38.107 -31.108  0.50 30.83           C
ATOM   4631  C   LEU b 368     -17.354  34.065 -32.421  0.50 30.82           C
ATOM   4632  O   LEU b 368     -16.532  33.851 -31.537  0.50 29.81           O
ATOM   4633  N   VAL b 369     -17.039  34.106 -33.699  0.50 29.54           N
ATOM   4634  CA  VAL b 369     -15.682  34.012 -34.135  0.50 29.47           C
ATOM   4635  CB  VAL b 369     -15.468  32.770 -35.014  0.50 27.31           C
ATOM   4636  CG1 VAL b 369     -14.018  32.713 -35.460  0.50 27.64           C
ATOM   4637  CG2 VAL b 369     -15.802  31.513 -34.200  0.50 27.05           C
ATOM   4638  C   VAL b 369     -15.432  35.252 -34.959  0.50 31.27           C
ATOM   4639  O   VAL b 369     -16.033  35.445 -36.035  0.50 33.30           O
ATOM   4640  N   LYS b 370     -14.545  36.105 -34.471  0.50 35.06           N
ATOM   4641  CA  LYS b 370     -14.309  37.357 -35.188  0.50 35.74           C
ATOM   4642  CB  LYS b 370     -14.962  38.508 -34.422  0.50 35.95           C
ATOM   4643  CG  LYS b 370     -14.357  38.701 -33.056  0.50 35.31           C
ATOM   4644  CD  LYS b 370     -14.812  39.995 -32.398  0.50 40.09           C
ATOM   4645  CE  LYS b 370     -14.216  41.196 -33.084  0.50 37.51           C
ATOM   4646  NZ  LYS b 370     -14.141  42.277 -32.077  0.50 41.69           N
ATOM   4647  C   LYS b 370     -12.837  37.644 -35.435  0.50 36.04           C
ATOM   4648  O   LYS b 370     -11.966  37.056 -34.822  0.50 36.04           O
ATOM   4649  N   GLY b 371     -12.564  38.536 -36.375  0.50 39.36           N
ATOM   4650  CA  GLY b 371     -11.218  39.039 -36.545  0.50 34.45           C
ATOM   4651  C   GLY b 371     -10.301  38.030 -37.219  0.50 35.25           C
ATOM   4652  O   GLY b 371      -9.091  38.135 -37.104  0.50 32.80           O
ATOM   4653  N   PHE b 372     -10.876  37.079 -37.949  0.50 33.76           N
ATOM   4654  CA  PHE b 372     -10.067  36.111 -38.664  0.50 35.20           C
ATOM   4655  CB  PHE b 372     -10.574  34.672 -38.424  0.50 28.17           C
ATOM   4656  CG  PHE b 372     -11.915  34.353 -39.049  0.50 25.76           C
ATOM   4657  CD1 PHE b 372     -13.071  34.561 -38.351  0.50 24.11           C
ATOM   4658  CE1 PHE b 372     -14.301  34.199 -38.870  0.50 24.67           C
```

Figure 26 (Continued)

```
ATOM   4659  CZ   PHE b 372     -14.389  33.596 -40.113  0.50 23.68           C
ATOM   4660  CE2  PHE b 372     -13.243  33.386 -40.839  0.50 23.83           C
ATOM   4661  CD2  PHE b 372     -12.002  33.738 -40.294  0.50 25.43           C
ATOM   4662  C    PHE b 372      -9.926  36.415 -40.139  0.50 35.13           C
ATOM   4663  O    PHE b 372     -10.798  37.015 -40.733  0.50 32.58           O
ATOM   4664  N    TYR b 373      -8.803  36.014 -40.720  0.50 36.49           N
ATOM   4665  CA   TYR b 373      -8.595  36.186 -42.134  0.50 40.00           C
ATOM   4666  CB   TYR b 373      -7.715  37.403 -42.457  0.50 42.65           C
ATOM   4667  CG   TYR b 373      -7.959  37.938 -43.860  0.50 41.79           C
ATOM   4668  CD1  TYR b 373      -7.031  37.763 -44.868  0.50 49.21           C
ATOM   4669  CE1  TYR b 373      -7.271  38.243 -46.152  0.50 55.98           C
ATOM   4670  CZ   TYR b 373      -8.459  38.909 -46.420  0.50 50.21           C
ATOM   4671  OH   TYR b 373      -8.733  39.412 -47.669  0.50 57.19           O
ATOM   4672  CE2  TYR b 373      -9.391  39.078 -45.440  0.50 43.37           C
ATOM   4673  CD2  TYR b 373      -9.144  38.591 -44.171  0.50 45.27           C
ATOM   4674  C    TYR b 373      -8.021  34.901 -42.710  0.50 49.12           C
ATOM   4675  O    TYR b 373      -7.620  34.018 -41.957  0.50 59.93           O
ATOM   4676  N    PRO b 374      -7.765  34.904 -44.019  0.50 53.56           N
ATOM   4677  CA   PRO b 374      -8.768  34.367 -44.943  0.50 46.72           C
ATOM   4678  CB   PRO b 374      -8.005  33.337 -45.779  0.50 54.68           C
ATOM   4679  CG   PRO b 374      -6.675  33.173 -45.092  0.50 59.48           C
ATOM   4680  CD   PRO b 374      -6.412  34.498 -44.432  0.50 54.22           C
ATOM   4681  C    PRO b 374      -9.924  33.744 -44.231  0.50 41.21           C
ATOM   4682  O    PRO b 374      -9.845  33.476 -43.042  0.50 40.97           O
ATOM   4683  N    SER b 375     -10.986  33.506 -44.992  0.50 38.53           N
ATOM   4684  CA   SER b 375     -12.276  33.193 -44.442  0.50 37.72           C
ATOM   4685  CB   SER b 375     -13.395  33.755 -45.312  0.50 38.54           C
ATOM   4686  OG   SER b 375     -13.412  33.102 -46.561  0.50 38.14           O
ATOM   4687  C    SER b 375     -12.476  31.721 -44.296  0.50 30.07           C
ATOM   4688  O    SER b 375     -13.413  31.326 -43.655  0.50 35.22           O
ATOM   4689  N    ASP b 376     -11.602  30.917 -44.882  0.50 31.18           N
ATOM   4690  CA   ASP b 376     -11.678  29.448 -44.731  0.50 28.76           C
ATOM   4691  CB   ASP b 376     -10.532  28.776 -45.468  0.50 31.75           C
ATOM   4692  CG   ASP b 376     -10.653  28.883 -46.992  0.50 33.74           C
ATOM   4693  OD1  ASP b 376     -11.775  29.129 -47.497  0.50 33.15           O
ATOM   4694  OD2  ASP b 376      -9.620  28.710 -47.681  0.50 42.13           O
ATOM   4695  C    ASP b 376     -11.535  29.094 -43.246  0.50 30.78           C
ATOM   4696  O    ASP b 376     -10.520  29.425 -42.608  0.50 31.40           O
ATOM   4697  N    ILE b 377     -12.517  28.394 -42.705  0.50 29.26           N
ATOM   4698  CA   ILE b 377     -12.503  28.081 -41.296  0.50 29.68           C
ATOM   4699  CB   ILE b 377     -13.049  29.258 -40.484  0.50 28.51           C
ATOM   4700  CG1  ILE b 377     -12.803  29.052 -38.982  0.50 28.48           C
ATOM   4701  CD1  ILE b 377     -12.921  30.333 -38.186  0.50 34.74           C
ATOM   4702  CG2  ILE b 377     -14.523  29.456 -40.811  0.50 28.59           C
ATOM   4703  C    ILE b 377     -13.422  26.903 -41.084  0.50 31.09           C
ATOM   4704  O    ILE b 377     -14.217  26.552 -41.982  0.50 32.51           O
ATOM   4705  N    ALA b 378     -13.302  26.282 -39.910  0.50 29.35           N
ATOM   4706  CA   ALA b 378     -14.226  25.204 -39.530  0.50 30.41           C
ATOM   4707  CB   ALA b 378     -13.594  23.852 -39.756  0.50 27.66           C
ATOM   4708  C    ALA b 378     -14.599  25.347 -38.090  0.50 27.86           C
ATOM   4709  O    ALA b 378     -13.729  25.440 -37.231  0.50 29.41           O
ATOM   4710  N    VAL b 379     -15.896  25.352 -37.826  0.50 26.99           N
ATOM   4711  CA   VAL b 379     -16.406  25.594 -36.499  0.50 29.09           C
ATOM   4712  CB   VAL b 379     -17.201  26.919 -36.488  0.50 30.41           C
ATOM   4713  CG1  VAL b 379     -17.798  27.139 -35.112  0.50 32.51           C
ATOM   4714  CG2  VAL b 379     -16.283  28.082 -36.930  0.50 25.88           C
ATOM   4715  C    VAL b 379     -17.340  24.416 -36.194  0.50 34.65           C
ATOM   4716  O    VAL b 379     -18.100  23.982 -37.070  0.50 34.94           O
ATOM   4717  N    GLU b 380     -17.229  23.862 -34.986  0.50 32.91           N
ATOM   4718  CA   GLU b 380     -17.917  22.611 -34.624  0.50 34.30           C
ATOM   4719  CB   GLU b 380     -16.971  21.424 -34.782  0.50 32.11           C
ATOM   4720  CG   GLU b 380     -16.847  20.914 -36.194  0.50 42.34           C
ATOM   4721  CD   GLU b 380     -15.933  19.702 -36.261  0.50 38.01           C
ATOM   4722  OE1  GLU b 380     -15.610  19.267 -37.383  0.50 46.66           O
```

Figure 26 (Continued)

```
ATOM   4723  OE2 GLU b 380     -15.532  19.214 -35.176  0.50 38.12           O
ATOM   4724  C   GLU b 380     -18.316  22.675 -33.165  0.50 33.57           C
ATOM   4725  O   GLU b 380     -17.668  23.344 -32.377  0.50 38.76           O
ATOM   4726  N   TRP b 381     -19.377  21.991 -32.789  0.50 34.56           N
ATOM   4727  CA  TRP b 381     -19.729  21.973 -31.382  0.50 36.23           C
ATOM   4728  CB  TRP b 381     -21.181  22.392 -31.175  0.50 34.56           C
ATOM   4729  CG  TRP b 381     -21.450  23.861 -31.349  0.50 36.78           C
ATOM   4730  CD1 TRP b 381     -21.733  24.510 -32.519  0.50 38.32           C
ATOM   4731  NE1 TRP b 381     -21.925  25.859 -32.274  0.50 41.66           N
ATOM   4732  CE2 TRP b 381     -21.774  26.092 -30.933  0.50 37.25           C
ATOM   4733  CD2 TRP b 381     -21.440  24.859 -30.322  0.50 35.41           C
ATOM   4734  CE3 TRP b 381     -21.278  24.816 -28.933  0.50 30.19           C
ATOM   4735  CZ3 TRP b 381     -21.379  26.013 -28.202  0.50 32.89           C
ATOM   4736  CH2 TRP b 381     -21.684  27.225 -28.846  0.50 34.43           C
ATOM   4737  CZ2 TRP b 381     -21.899  27.282 -30.203  0.50 34.11           C
ATOM   4738  C   TRP b 381     -19.587  20.528 -30.914  0.50 38.30           C
ATOM   4739  O   TRP b 381     -19.760  19.608 -31.700  0.50 32.42           O
ATOM   4740  N   GLU b 382     -19.335  20.347 -29.625  0.50 37.90           N
ATOM   4741  CA  GLU b 382     -19.460  19.017 -29.030  0.50 37.21           C
ATOM   4742  CB  GLU b 382     -18.134  18.274 -29.236  0.50 34.34           C
ATOM   4743  CG  GLU b 382     -16.932  19.106 -28.858  0.50 34.07           C
ATOM   4744  CD  GLU b 382     -15.606  18.404 -29.077  0.50 42.66           C
ATOM   4745  OE1 GLU b 382     -15.069  17.866 -28.081  0.50 49.35           O
ATOM   4746  OE2 GLU b 382     -15.084  18.416 -30.224  0.50 46.18           O
ATOM   4747  C   GLU b 382     -19.838  19.122 -27.523  0.50 37.42           C
ATOM   4748  O   GLU b 382     -19.742  20.206 -26.908  0.50 38.07           O
ATOM   4749  N   SER b 383     -20.297  18.015 -26.950  0.50 35.86           N
ATOM   4750  CA  SER b 383     -20.364  17.871 -25.482  0.50 42.99           C
ATOM   4751  CB  SER b 383     -21.769  18.149 -24.978  0.50 37.76           C
ATOM   4752  OG  SER b 383     -21.764  18.218 -23.562  0.50 44.87           O
ATOM   4753  C   SER b 383     -19.978  16.439 -25.048  0.50 42.25           C
ATOM   4754  O   SER b 383     -20.448  15.470 -25.650  0.50 44.43           O
ATOM   4755  N   ASN b 384     -19.164  16.314 -24.003  0.50 44.07           N
ATOM   4756  CA  ASN b 384     -18.651  14.998 -23.579  0.50 55.94           C
ATOM   4757  CB  ASN b 384     -19.795  14.033 -23.229  0.50 50.40           C
ATOM   4758  CG  ASN b 384     -19.326  12.840 -22.404  0.50 65.59           C
ATOM   4759  OD1 ASN b 384     -18.694  13.000 -21.351  0.50 62.31           O
ATOM   4760  ND2 ASN b 384     -19.637  11.629 -22.876  0.50 65.74           N
ATOM   4761  C   ASN b 384     -17.743  14.371 -24.646  0.50 54.94           C
ATOM   4762  O   ASN b 384     -17.990  13.239 -25.108  0.50 51.48           O
ATOM   4763  N   GLY b 385     -16.722  15.138 -25.046  0.50 52.60           N
ATOM   4764  CA  GLY b 385     -15.762  14.737 -26.073  0.50 43.58           C
ATOM   4765  C   GLY b 385     -16.425  14.439 -27.397  0.50 43.24           C
ATOM   4766  O   GLY b 385     -15.727  14.207 -28.416  0.50 42.50           O
ATOM   4767  N   GLN b 386     -17.762  14.490 -27.378  0.50 41.38           N
ATOM   4768  CA  GLN b 386     -18.640  14.033 -28.477  0.50 47.65           C
ATOM   4769  CB  GLN b 386     -19.851  13.308 -27.887  0.50 49.57           C
ATOM   4770  CG  GLN b 386     -19.490  12.190 -26.937  0.50 64.91           C
ATOM   4771  CD  GLN b 386     -18.621  11.169 -27.623  0.50 67.35           C
ATOM   4772  OE1 GLN b 386     -17.405  11.334 -27.700  0.50 66.29           O
ATOM   4773  NE2 GLN b 386     -19.245  10.118 -28.153  0.50 69.46           N
ATOM   4774  C   GLN b 386     -19.189  15.177 -29.342  0.50 47.27           C
ATOM   4775  O   GLN b 386     -19.434  16.270 -28.845  0.50 50.26           O
ATOM   4776  N   PRO b 387     -19.438  14.896 -30.624  0.50 46.74           N
ATOM   4777  CA  PRO b 387     -20.053  15.811 -31.577  0.50 50.72           C
ATOM   4778  CB  PRO b 387     -20.113  14.974 -32.856  0.50 44.25           C
ATOM   4779  CG  PRO b 387     -18.909  14.098 -32.756  0.50 40.24           C
ATOM   4780  CD  PRO b 387     -18.617  13.877 -31.302  0.50 42.23           C
ATOM   4781  C   PRO b 387     -21.469  16.233 -31.195  0.50 56.13           C
ATOM   4782  O   PRO b 387     -22.325  15.376 -30.964  0.50 51.64           O
ATOM   4783  N   GLU b 388     -21.707  17.548 -31.167  0.50 47.23           N
ATOM   4784  CA  GLU b 388     -23.053  18.102 -30.979  0.50 47.41           C
ATOM   4785  CB  GLU b 388     -23.074  19.167 -29.872  0.50 41.22           C
ATOM   4786  CG  GLU b 388     -22.985  18.609 -28.483  0.50 43.06           C
```

Figure 26 (Continued)

```
ATOM   4787  CD   GLU b 388     -24.076  17.605 -28.196  0.50 43.96           C
ATOM   4788  OE1  GLU b 388     -23.734  16.451 -27.853  0.50 41.95           O
ATOM   4789  OE2  GLU b 388     -25.267  17.978 -28.298  0.50 40.30           O
ATOM   4790  C    GLU b 388     -23.349  18.774 -32.288  0.50 49.00           C
ATOM   4791  O    GLU b 388     -22.723  19.791 -32.624  0.50 53.49           O
ATOM   4792  N    ASN b 389     -24.255  18.203 -33.059  0.50 42.64           N
ATOM   4793  CA   ASN b 389     -24.337  18.591 -34.441  0.50 44.17           C
ATOM   4794  CB   ASN b 389     -24.181  17.345 -35.351  0.50 43.47           C
ATOM   4795  CG   ASN b 389     -22.747  16.858 -35.450  0.50 42.13           C
ATOM   4796  OD1  ASN b 389     -21.833  17.489 -34.914  0.50 45.58           O
ATOM   4797  ND2  ASN b 389     -22.535  15.712 -36.128  0.50 37.01           N
ATOM   4798  C    ASN b 389     -25.641  19.327 -34.740  0.50 41.69           C
ATOM   4799  O    ASN b 389     -25.946  19.600 -35.900  0.50 43.97           O
ATOM   4800  N    ASN b 390     -26.458  19.577 -33.712  0.50 42.63           N
ATOM   4801  CA   ASN b 390     -27.739  20.240 -33.947  0.50 43.25           C
ATOM   4802  CB   ASN b 390     -28.743  19.876 -32.883  0.50 40.99           C
ATOM   4803  CG   ASN b 390     -30.091  20.485 -33.162  0.50 37.03           C
ATOM   4804  OD1  ASN b 390     -30.424  20.757 -34.306  0.50 41.18           O
ATOM   4805  ND2  ASN b 390     -30.860  20.728 -32.122  0.50 45.62           N
ATOM   4806  C    ASN b 390     -27.578  21.779 -34.020  0.50 40.26           C
ATOM   4807  O    ASN b 390     -28.215  22.558 -33.285  0.50 34.12           O
ATOM   4808  N    TYR b 391     -26.647  22.195 -34.859  0.50 36.71           N
ATOM   4809  CA   TYR b 391     -26.197  23.547 -34.807  0.50 33.76           C
ATOM   4810  CB   TYR b 391     -24.744  23.650 -34.315  0.50 37.68           C
ATOM   4811  CG   TYR b 391     -23.566  23.121 -35.182  0.50 37.02           C
ATOM   4812  CD1  TYR b 391     -23.060  23.877 -36.237  0.50 39.45           C
ATOM   4813  CE1  TYR b 391     -21.941  23.471 -36.951  0.50 37.07           C
ATOM   4814  CZ   TYR b 391     -21.253  22.312 -36.572  0.50 37.98           C
ATOM   4815  OH   TYR b 391     -20.121  21.965 -37.290  0.50 40.99           O
ATOM   4816  CE2  TYR b 391     -21.671  21.575 -35.474  0.50 30.73           C
ATOM   4817  CD2  TYR b 391     -22.820  21.990 -34.781  0.50 37.39           C
ATOM   4818  C    TYR b 391     -26.390  24.133 -36.177  0.50 36.74           C
ATOM   4819  O    TYR b 391     -26.688  23.397 -37.131  0.50 26.80           O
ATOM   4820  N    LEU b 392     -26.241  25.459 -36.244  0.50 32.32           N
ATOM   4821  CA   LEU b 392     -26.457  26.222 -37.456  0.50 31.64           C
ATOM   4822  CB   LEU b 392     -27.807  26.964 -37.365  0.50 31.92           C
ATOM   4823  CG   LEU b 392     -28.500  27.422 -38.663  0.50 30.33           C
ATOM   4824  CD1  LEU b 392     -29.219  28.765 -38.563  0.50 27.95           C
ATOM   4825  CD2  LEU b 392     -27.566  27.407 -39.833  0.50 27.58           C
ATOM   4826  C    LEU b 392     -25.344  27.251 -37.459  0.50 30.68           C
ATOM   4827  O    LEU b 392     -25.164  27.986 -36.483  0.50 27.44           O
ATOM   4828  N    THR b 393     -24.587  27.275 -38.538  0.50 27.61           N
ATOM   4829  CA   THR b 393     -23.494  28.195 -38.668  0.50 29.15           C
ATOM   4830  CB   THR b 393     -22.170  27.435 -38.771  0.50 32.76           C
ATOM   4831  OG1  THR b 393     -21.916  26.772 -37.515  0.50 31.82           O
ATOM   4832  CG2  THR b 393     -21.019  28.397 -39.102  0.50 29.76           C
ATOM   4833  C    THR b 393     -23.717  29.087 -39.870  0.50 34.06           C
ATOM   4834  O    THR b 393     -24.045  28.612 -40.956  0.50 35.21           O
ATOM   4835  N    TRP b 394     -23.643  30.390 -39.668  0.50 31.96           N
ATOM   4836  CA   TRP b 394     -23.809  31.290 -40.790  0.50 25.48           C
ATOM   4837  CB   TRP b 394     -24.348  32.633 -40.332  0.50 25.87           C
ATOM   4838  CG   TRP b 394     -25.737  32.569 -39.819  0.50 21.34           C
ATOM   4839  CD1  TRP b 394     -26.881  32.896 -40.496  0.50 19.91           C
ATOM   4840  NE1  TRP b 394     -27.973  32.703 -39.674  0.50 21.64           N
ATOM   4841  CE2  TRP b 394     -27.541  32.271 -38.441  0.50 22.16           C
ATOM   4842  CD2  TRP b 394     -26.142  32.184 -38.489  0.50 22.49           C
ATOM   4843  CE3  TRP b 394     -25.447  31.775 -37.337  0.50 24.03           C
ATOM   4844  CZ3  TRP b 394     -26.170  31.454 -36.204  0.50 22.79           C
ATOM   4845  CH2  TRP b 394     -27.565  31.558 -36.192  0.50 24.00           C
ATOM   4846  CZ2  TRP b 394     -28.267  31.968 -37.292  0.50 21.73           C
ATOM   4847  C    TRP b 394     -22.455  31.473 -41.443  0.50 27.76           C
ATOM   4848  O    TRP b 394     -21.423  31.296 -40.790  0.50 29.92           O
ATOM   4849  N    PRO b 395     -22.446  31.732 -42.755  0.50 30.48           N
ATOM   4850  CA   PRO b 395     -21.188  31.901 -43.458  0.50 31.36           C
```

Figure 26 (Continued)

```
ATOM   4851  CB   PRO b 395     -21.624  31.981 -44.931  0.50 34.69           C
ATOM   4852  CG   PRO b 395     -22.879  31.153 -44.980  0.50 32.74           C
ATOM   4853  CD   PRO b 395     -23.581  31.516 -43.690  0.50 31.80           C
ATOM   4854  C    PRO b 395     -20.463  33.175 -42.990  0.50 34.83           C
ATOM   4855  O    PRO b 395     -21.069  34.040 -42.372  0.50 33.88           O
ATOM   4856  N    PRO b 396     -19.149  33.249 -43.226  0.50 33.05           N
ATOM   4857  CA   PRO b 396     -18.321  34.330 -42.635  0.50 30.28           C
ATOM   4858  CB   PRO b 396     -16.904  34.066 -43.211  0.50 28.12           C
ATOM   4859  CG   PRO b 396     -16.994  32.832 -44.083  0.50 28.81           C
ATOM   4860  CD   PRO b 396     -18.356  32.206 -43.913  0.50 32.18           C
ATOM   4861  C    PRO b 396     -18.803  35.720 -43.071  0.50 31.95           C
ATOM   4862  O    PRO b 396     -19.215  35.906 -44.216  0.50 28.97           O
ATOM   4863  N    VAL b 397     -18.768  36.712 -42.238  0.50 26.97           N
ATOM   4864  CA   VAL b 397     -19.136  37.953 -42.849  0.50 34.73           C
ATOM   4865  CB   VAL b 397     -20.571  38.425 -42.463  0.50 35.21           C
ATOM   4866  CG1  VAL b 397     -21.229  37.494 -41.447  0.50 38.25           C
ATOM   4867  CG2  VAL b 397     -20.587  39.858 -42.006  0.50 30.78           C
ATOM   4868  C    VAL b 397     -18.009  38.968 -42.749  0.50 32.04           C
ATOM   4869  O    VAL b 397     -17.467  39.227 -41.713  0.50 30.17           O
ATOM   4870  N    LEU b 398     -17.651  39.479 -43.900  0.50 32.13           N
ATOM   4871  CA   LEU b 398     -16.719  40.591 -44.083  0.50 36.09           C
ATOM   4872  CB   LEU b 398     -16.787  41.064 -45.533  0.50 39.34           C
ATOM   4873  CG   LEU b 398     -15.494  41.600 -46.137  0.50 39.91           C
ATOM   4874  CD1  LEU b 398     -14.378  40.553 -46.062  0.50 43.96           C
ATOM   4875  CD2  LEU b 398     -15.699  42.071 -47.570  0.50 36.24           C
ATOM   4876  C    LEU b 398     -17.075  41.740 -43.172  0.50 37.39           C
ATOM   4877  O    LEU b 398     -18.014  42.486 -43.439  0.50 45.79           O
ATOM   4878  N    ASP b 399     -16.339  41.857 -42.079  0.50 37.80           N
ATOM   4879  CA   ASP b 399     -16.556  42.873 -41.067  0.50 38.17           C
ATOM   4880  CB   ASP b 399     -15.832  42.452 -39.795  0.50 36.45           C
ATOM   4881  CG   ASP b 399     -16.580  42.815 -38.560  0.50 35.30           C
ATOM   4882  OD1  ASP b 399     -17.419  43.732 -38.632  0.50 34.67           O
ATOM   4883  OD2  ASP b 399     -16.334  42.169 -37.518  0.50 39.00           O
ATOM   4884  C    ASP b 399     -15.953  44.199 -41.541  0.50 45.07           C
ATOM   4885  O    ASP b 399     -15.286  44.243 -42.565  0.50 41.41           O
ATOM   4886  N    SER b 400     -16.147  45.264 -40.761  0.50 45.28           N
ATOM   4887  CA   SER b 400     -15.735  46.596 -41.184  0.50 49.68           C
ATOM   4888  CB   SER b 400     -16.296  47.661 -40.233  0.50 46.51           C
ATOM   4889  OG   SER b 400     -15.731  47.526 -38.943  0.50 45.47           O
ATOM   4890  C    SER b 400     -14.219  46.716 -41.252  0.50 48.62           C
ATOM   4891  O    SER b 400     -13.688  47.506 -42.019  0.50 41.15           O
ATOM   4892  N    ASP b 401     -13.515  45.940 -40.437  0.50 42.68           N
ATOM   4893  CA   ASP b 401     -12.086  46.143 -40.354  0.50 40.41           C
ATOM   4894  CB   ASP b 401     -11.567  45.888 -38.938  0.50 39.70           C
ATOM   4895  CG   ASP b 401     -11.797  44.454 -38.466  0.50 41.15           C
ATOM   4896  OD1  ASP b 401     -12.666  43.740 -39.020  0.50 35.21           O
ATOM   4897  OD2  ASP b 401     -11.098  44.052 -37.518  0.50 39.78           O
ATOM   4898  C    ASP b 401     -11.333  45.340 -41.391  0.50 39.05           C
ATOM   4899  O    ASP b 401     -10.122  45.225 -41.325  0.50 38.20           O
ATOM   4900  N    GLY b 402     -12.047  44.797 -42.366  0.50 43.22           N
ATOM   4901  CA   GLY b 402     -11.397  43.974 -43.380  0.50 40.57           C
ATOM   4902  C    GLY b 402     -11.234  42.500 -43.025  0.50 40.19           C
ATOM   4903  O    GLY b 402     -10.889  41.684 -43.897  0.50 38.02           O
ATOM   4904  N    SER b 403     -11.495  42.134 -41.770  0.50 36.28           N
ATOM   4905  CA   SER b 403     -11.513  40.703 -41.397  0.50 34.61           C
ATOM   4906  CB   SER b 403     -10.990  40.510 -39.977  0.50 35.34           C
ATOM   4907  OG   SER b 403     -11.894  41.069 -39.055  0.50 36.96           O
ATOM   4908  C    SER b 403     -12.915  40.078 -41.499  0.50 37.38           C
ATOM   4909  O    SER b 403     -13.900  40.779 -41.701  0.50 33.96           O
ATOM   4910  N    PHE b 404     -13.012  38.765 -41.290  0.50 31.70           N
ATOM   4911  CA   PHE b 404     -14.325  38.100 -41.255  0.50 31.18           C
ATOM   4912  CB   PHE b 404     -14.266  36.792 -42.016  0.50 28.86           C
ATOM   4913  CG   PHE b 404     -14.009  36.971 -43.488  0.50 29.41           C
ATOM   4914  CD1  PHE b 404     -12.709  36.948 -43.999  0.50 28.49           C
```

Figure 26 (Continued)

```
ATOM   4915  CE1  PHE  b  404     -12.481  37.091  -45.372  0.50  30.09           C
ATOM   4916  CZ   PHE  b  404     -13.556  37.286  -46.232  0.50  29.63           C
ATOM   4917  CE2  PHE  b  404     -14.851  37.308  -45.722  0.50  31.65           C
ATOM   4918  CD2  PHE  b  404     -15.069  37.131  -44.362  0.50  26.68           C
ATOM   4919  C    PHE  b  404     -14.810  37.831  -39.841  0.50  30.32           C
ATOM   4920  O    PHE  b  404     -14.017  37.784  -38.914  0.50  31.21           O
ATOM   4921  N    PHE  b  405     -16.123  37.689  -39.664  0.50  29.85           N
ATOM   4922  CA   PHE  b  405     -16.628  37.108  -38.427  0.50  28.60           C
ATOM   4923  CB   PHE  b  405     -17.196  38.170  -37.473  0.50  30.21           C
ATOM   4924  CG   PHE  b  405     -18.561  38.668  -37.860  0.50  28.51           C
ATOM   4925  CD1  PHE  b  405     -19.699  38.069  -37.342  0.50  31.55           C
ATOM   4926  CE1  PHE  b  405     -20.953  38.538  -37.663  0.50  29.91           C
ATOM   4927  CZ   PHE  b  405     -21.074  39.635  -38.517  0.50  33.49           C
ATOM   4928  CE2  PHE  b  405     -19.946  40.258  -39.026  0.50  28.13           C
ATOM   4929  CD2  PHE  b  405     -18.700  39.776  -38.681  0.50  32.08           C
ATOM   4930  C    PHE  b  405     -17.688  36.072  -38.720  0.50  30.51           C
ATOM   4931  O    PHE  b  405     -18.267  36.049  -39.785  0.50  30.23           O
ATOM   4932  N    LEU  b  406     -17.989  35.218  -37.757  0.50  32.16           N
ATOM   4933  CA   LEU  b  406     -19.146  34.388  -38.002  0.50  30.24           C
ATOM   4934  CB   LEU  b  406     -18.724  33.181  -38.857  0.50  31.50           C
ATOM   4935  CG   LEU  b  406     -17.963  32.033  -38.189  0.50  34.32           C
ATOM   4936  CD1  LEU  b  406     -18.790  31.390  -37.082  0.50  30.19           C
ATOM   4937  CD2  LEU  b  406     -17.643  30.963  -39.230  0.50  34.59           C
ATOM   4938  C    LEU  b  406     -19.844  34.012  -36.709  0.50  27.74           C
ATOM   4939  O    LEU  b  406     -19.316  34.192  -35.615  0.50  31.60           O
ATOM   4940  N    TYR  b  407     -21.066  33.541  -36.803  0.50  28.58           N
ATOM   4941  CA   TYR  b  407     -21.668  32.976  -35.617  0.50  27.96           C
ATOM   4942  CB   TYR  b  407     -22.966  33.711  -35.271  0.50  26.72           C
ATOM   4943  CG   TYR  b  407     -22.784  35.035  -34.533  0.50  28.68           C
ATOM   4944  CD1  TYR  b  407     -22.722  35.071  -33.150  0.50  24.63           C
ATOM   4945  CE1  TYR  b  407     -22.592  36.273  -32.472  0.50  26.51           C
ATOM   4946  CZ   TYR  b  407     -22.537  37.450  -33.173  0.50  24.77           C
ATOM   4947  OH   TYR  b  407     -22.426  38.634  -32.486  0.50  27.21           O
ATOM   4948  CE2  TYR  b  407     -22.547  37.449  -34.551  0.50  25.66           C
ATOM   4949  CD2  TYR  b  407     -22.687  36.247  -35.227  0.50  25.76           C
ATOM   4950  C    TYR  b  407     -21.946  31.492  -35.868  0.50  27.08           C
ATOM   4951  O    TYR  b  407     -22.064  31.062  -37.007  0.50  23.71           O
ATOM   4952  N    SER  b  408     -22.086  30.727  -34.791  0.50  27.41           N
ATOM   4953  CA   SER  b  408     -22.672  29.390  -34.868  0.50  26.07           C
ATOM   4954  CB   SER  b  408     -21.564  28.318  -34.807  0.50  27.82           C
ATOM   4955  OG   SER  b  408     -22.090  26.990  -34.938  0.50  26.91           O
ATOM   4956  C    SER  b  408     -23.648  29.239  -33.706  0.50  28.66           C
ATOM   4957  O    SER  b  408     -23.322  29.562  -32.553  0.50  29.24           O
ATOM   4958  N    LYS  b  409     -24.848  28.741  -34.000  0.50  24.71           N
ATOM   4959  CA   LYS  b  409     -25.861  28.597  -32.994  0.50  26.32           C
ATOM   4960  CB   LYS  b  409     -27.187  29.152  -33.514  0.50  23.64           C
ATOM   4961  CG   LYS  b  409     -28.326  29.076  -32.533  0.50  25.08           C
ATOM   4962  CD   LYS  b  409     -29.521  29.932  -32.947  0.50  24.73           C
ATOM   4963  CE   LYS  b  409     -30.176  29.433  -34.222  0.50  27.60           C
ATOM   4964  NZ   LYS  b  409     -31.018  28.198  -34.042  0.50  25.45           N
ATOM   4965  C    LYS  b  409     -26.051  27.116  -32.670  0.50  27.51           C
ATOM   4966  O    LYS  b  409     -26.481  26.353  -33.512  0.50  27.52           O
ATOM   4967  N    LEU  b  410     -25.843  26.732  -31.423  0.50  27.16           N
ATOM   4968  CA   LEU  b  410     -26.216  25.361  -31.056  0.50  30.76           C
ATOM   4969  CB   LEU  b  410     -25.068  24.640  -30.314  0.50  29.50           C
ATOM   4970  CG   LEU  b  410     -25.353  23.248  -29.690  0.50  31.04           C
ATOM   4971  CD1  LEU  b  410     -25.378  22.158  -30.745  0.50  24.71           C
ATOM   4972  CD2  LEU  b  410     -24.294  22.899  -28.638  0.50  27.49           C
ATOM   4973  C    LEU  b  410     -27.492  25.359  -30.246  0.50  27.23           C
ATOM   4974  O    LEU  b  410     -27.645  26.103  -29.270  0.50  28.09           O
ATOM   4975  N    THR  b  411     -28.445  24.576  -30.712  0.50  29.16           N
ATOM   4976  CA   THR  b  411     -29.683  24.416  -30.027  0.50  31.01           C
ATOM   4977  CB   THR  b  411     -30.822  24.268  -31.050  0.50  32.46           C
ATOM   4978  OG1  THR  b  411     -30.972  25.497  -31.770  0.50  31.03           O
```

Figure 26 (Continued)

```
ATOM   4979  CG2 THR b 411     -32.140  23.936 -30.380  0.50 31.89           C
ATOM   4980  C   THR b 411     -29.596  23.182 -29.129  0.50 34.69           C
ATOM   4981  O   THR b 411     -29.207  22.106 -29.591  0.50 33.12           O
ATOM   4982  N   VAL b 412     -29.933  23.356 -27.849  0.50 37.60           N
ATOM   4983  CA  VAL b 412     -30.004  22.248 -26.898  0.50 36.93           C
ATOM   4984  CB  VAL b 412     -28.745  22.171 -25.992  0.50 42.15           C
ATOM   4985  CG1 VAL b 412     -27.469  22.204 -26.820  0.50 36.94           C
ATOM   4986  CG2 VAL b 412     -28.730  23.275 -24.936  0.50 40.84           C
ATOM   4987  C   VAL b 412     -31.265  22.314 -26.023  0.50 41.90           C
ATOM   4988  O   VAL b 412     -31.840  23.394 -25.789  0.50 36.77           O
ATOM   4989  N   ASP b 413     -31.714  21.147 -25.571  0.50 44.90           N
ATOM   4990  CA  ASP b 413     -32.821  21.055 -24.614  0.50 48.58           C
ATOM   4991  CB  ASP b 413     -33.057  19.603 -24.196  0.50 52.06           C
ATOM   4992  CG  ASP b 413     -33.564  18.766 -25.329  0.50 58.09           C
ATOM   4993  OD1 ASP b 413     -34.016  19.363 -26.331  0.50 58.12           O
ATOM   4994  OD2 ASP b 413     -33.507  17.515 -25.231  0.50 72.55           O
ATOM   4995  C   ASP b 413     -32.523  21.868 -23.386  0.50 44.31           C
ATOM   4996  O   ASP b 413     -31.390  21.865 -22.901  0.50 44.56           O
ATOM   4997  N   LYS b 414     -33.539  22.570 -22.883  0.50 46.56           N
ATOM   4998  CA  LYS b 414     -33.381  23.415 -21.703  0.50 45.00           C
ATOM   4999  CB  LYS b 414     -34.709  24.089 -21.293  0.50 43.48           C
ATOM   5000  CG  LYS b 414     -34.529  25.117 -20.170  0.50 45.36           C
ATOM   5001  CD  LYS b 414     -35.809  25.342 -19.362  0.50 43.94           C
ATOM   5002  CE  LYS b 414     -37.032  24.920 -20.169  0.50 39.42           C
ATOM   5003  NZ  LYS b 414     -38.136  25.921 -20.078  0.50 43.30           N
ATOM   5004  C   LYS b 414     -32.774  22.658 -20.519  0.50 46.12           C
ATOM   5005  O   LYS b 414     -31.914  23.202 -19.813  0.50 42.47           O
ATOM   5006  N   SER b 415     -33.202  21.408 -20.316  0.50 43.84           N
ATOM   5007  CA  SER b 415     -32.762  20.610 -19.155  0.50 43.75           C
ATOM   5008  CB  SER b 415     -33.676  19.390 -18.927  0.50 47.97           C
ATOM   5009  OG  SER b 415     -33.796  18.543 -20.076  0.50 55.73           O
ATOM   5010  C   SER b 415     -31.302  20.177 -19.248  0.50 46.42           C
ATOM   5011  O   SER b 415     -30.578  20.138 -18.238  0.50 43.83           O
ATOM   5012  N   ARG b 416     -30.850  19.868 -20.462  0.50 45.51           N
ATOM   5013  CA  ARG b 416     -29.428  19.592 -20.667  0.50 42.75           C
ATOM   5014  CB  ARG b 416     -29.149  19.280 -22.128  0.50 42.87           C
ATOM   5015  CG  ARG b 416     -29.938  18.076 -22.645  0.50 43.20           C
ATOM   5016  CD  ARG b 416     -29.400  17.610 -23.984  0.50 42.80           C
ATOM   5017  NE  ARG b 416     -27.957  17.398 -23.882  0.50 46.53           N
ATOM   5018  CZ  ARG b 416     -27.118  17.461 -24.905  0.50 46.05           C
ATOM   5019  NH1 ARG b 416     -27.572  17.742 -26.120  0.50 47.72           N
ATOM   5020  NH2 ARG b 416     -25.828  17.254 -24.707  0.50 45.55           N
ATOM   5021  C   ARG b 416     -28.619  20.783 -20.211  0.50 44.73           C
ATOM   5022  O   ARG b 416     -27.637  20.645 -19.498  0.50 47.02           O
ATOM   5023  N   TRP b 417     -29.058  21.977 -20.581  0.50 43.24           N
ATOM   5024  CA  TRP b 417     -28.412  23.162 -20.065  0.50 41.65           C
ATOM   5025  CB  TRP b 417     -28.869  24.388 -20.843  0.50 40.20           C
ATOM   5026  CG  TRP b 417     -28.254  25.637 -20.366  0.50 41.57           C
ATOM   5027  CD1 TRP b 417     -28.854  26.610 -19.632  0.50 43.20           C
ATOM   5028  NE1 TRP b 417     -27.966  27.627 -19.384  0.50 48.67           N
ATOM   5029  CE2 TRP b 417     -26.761  27.321 -19.961  0.50 41.78           C
ATOM   5030  CD2 TRP b 417     -26.904  26.070 -20.589  0.50 44.08           C
ATOM   5031  CE3 TRP b 417     -25.812  25.528 -21.278  0.50 41.37           C
ATOM   5032  CZ3 TRP b 417     -24.637  26.235 -21.305  0.50 38.35           C
ATOM   5033  CH2 TRP b 417     -24.517  27.482 -20.663  0.50 38.70           C
ATOM   5034  CZ2 TRP b 417     -25.569  28.040 -19.987  0.50 40.69           C
ATOM   5035  C   TRP b 417     -28.688  23.342 -18.558  0.50 44.74           C
ATOM   5036  O   TRP b 417     -27.832  23.807 -17.805  0.50 37.32           O
ATOM   5037  N   GLN b 418     -29.883  22.989 -18.103  0.50 46.96           N
ATOM   5038  CA  GLN b 418     -30.214  23.344 -16.717  0.50 56.37           C
ATOM   5039  CB  GLN b 418     -31.720  23.570 -16.502  0.50 49.20           C
ATOM   5040  CG  GLN b 418     -32.025  25.057 -16.671  0.50 50.82           C
ATOM   5041  CD  GLN b 418     -33.492  25.412 -16.610  0.50 51.98           C
ATOM   5042  OE1 GLN b 418     -34.353  24.557 -16.377  0.50 44.04           O
```

Figure 26 (Continued)

```
ATOM   5043  NE2 GLN b 418    -33.787  26.702 -16.804  0.50 56.90           N
ATOM   5044  C   GLN b 418    -29.525  22.519 -15.627  0.50 54.83           C
ATOM   5045  O   GLN b 418    -29.061  23.063 -14.627  0.50 60.60           O
ATOM   5046  N   GLN b 419    -29.387  21.223 -15.879  0.50 55.66           N
ATOM   5047  CA  GLN b 419    -28.520  20.364 -15.083  0.50 55.81           C
ATOM   5048  CB  GLN b 419    -28.415  18.987 -15.734  0.50 55.51           C
ATOM   5049  CG  GLN b 419    -29.743  18.292 -15.946  0.50 61.54           C
ATOM   5050  CD  GLN b 419    -29.607  17.159 -16.936  0.50 65.06           C
ATOM   5051  OE1 GLN b 419    -28.494  16.805 -17.317  0.50 68.87           O
ATOM   5052  NE2 GLN b 419    -30.732  16.597 -17.372  0.50 71.12           N
ATOM   5053  C   GLN b 419    -27.105  20.935 -14.897  0.50 60.08           C
ATOM   5054  O   GLN b 419    -26.589  20.984 -13.775  0.50 57.94           O
ATOM   5055  N   GLY b 420    -26.458  21.322 -15.997  0.50 55.14           N
ATOM   5056  CA  GLY b 420    -25.079  21.780 -15.925  0.50 51.00           C
ATOM   5057  C   GLY b 420    -24.128  21.118 -16.908  0.50 48.18           C
ATOM   5058  O   GLY b 420    -22.920  21.228 -16.771  0.50 56.93           O
ATOM   5059  N   ASN b 421    -24.658  20.437 -17.907  0.50 47.86           N
ATOM   5060  CA  ASN b 421    -23.806  19.911 -18.966  0.50 52.90           C
ATOM   5061  CB  ASN b 421    -24.647  19.200 -20.021  0.50 54.82           C
ATOM   5062  CG  ASN b 421    -25.407  18.016 -19.448  0.50 58.28           C
ATOM   5063  OD1 ASN b 421    -24.821  16.968 -19.157  0.50 59.40           O
ATOM   5064  ND2 ASN b 421    -26.712  18.181 -19.265  0.50 57.29           N
ATOM   5065  C   ASN b 421    -22.926  20.986 -19.608  0.50 50.08           C
ATOM   5066  O   ASN b 421    -23.264  22.178 -19.604  0.50 47.81           O
ATOM   5067  N   VAL b 422    -21.722  20.820 -20.188  0.50 45.38           N
ATOM   5068  CA  VAL b 422    -20.722  21.655 -20.807  0.50 41.56           C
ATOM   5069  CB  VAL b 422    -19.319  21.373 -20.239  0.50 44.25           C
ATOM   5070  CG1 VAL b 422    -18.267  22.180 -20.997  0.50 44.68           C
ATOM   5071  CG2 VAL b 422    -19.269  21.667 -18.737  0.50 37.51           C
ATOM   5072  C   VAL b 422    -20.707  21.392 -22.309  0.50 45.10           C
ATOM   5073  O   VAL b 422    -20.699  20.245 -22.766  0.50 41.74           O
ATOM   5074  N   PHE b 423    -20.768  22.524 -22.822  0.50 43.61           N
ATOM   5075  CA  PHE b 423    -20.803  22.565 -24.271  0.50 37.66           C
ATOM   5076  CB  PHE b 423    -22.108  23.189 -24.742  0.50 36.58           C
ATOM   5077  CG  PHE b 423    -23.303  22.311 -24.509  0.50 38.54           C
ATOM   5078  CD1 PHE b 423    -24.040  22.426 -23.336  0.50 41.53           C
ATOM   5079  CE1 PHE b 423    -25.119  21.594 -23.085  0.50 37.27           C
ATOM   5080  CZ  PHE b 423    -25.474  20.632 -24.014  0.50 36.57           C
ATOM   5081  CE2 PHE b 423    -24.749  20.500 -25.183  0.50 42.48           C
ATOM   5082  CD2 PHE b 423    -23.655  21.331 -25.425  0.50 39.81           C
ATOM   5083  C   PHE b 423    -19.593  23.318 -24.794  0.50 38.70           C
ATOM   5084  O   PHE b 423    -19.147  24.292 -24.189  0.50 40.99           O
ATOM   5085  N   SER b 424    -19.048  22.853 -25.914  0.50 36.50           N
ATOM   5086  CA  SER b 424    -17.808  23.425 -26.416  0.50 37.71           C
ATOM   5087  CB  SER b 424    -16.651  22.453 -26.175  0.50 47.27           C
ATOM   5088  OG  SER b 424    -16.442  22.281 -24.767  0.50 56.80           O
ATOM   5089  C   SER b 424    -17.890  23.786 -27.893  0.50 36.75           C
ATOM   5090  O   SER b 424    -18.324  23.007 -28.720  0.50 34.51           O
ATOM   5091  N   CYS b 425    -17.456  24.989 -28.216  0.50 41.96           N
ATOM   5092  CA  CYS b 425    -17.319  25.382 -29.592  0.50 35.46           C
ATOM   5093  CB  CYS b 425    -17.718  26.843 -29.729  0.50 35.75           C
ATOM   5094  SG  CYS b 425    -17.534  27.492 -31.407  0.50 37.39           S
ATOM   5095  C   CYS b 425    -15.854  25.208 -29.981  0.50 38.40           C
ATOM   5096  O   CYS b 425    -14.967  25.780 -29.354  0.50 30.66           O
ATOM   5097  N   SER b 426    -15.617  24.407 -31.011  0.50 33.53           N
ATOM   5098  CA  SER b 426    -14.290  24.142 -31.493  0.50 35.72           C
ATOM   5099  CB  SER b 426    -14.148  22.639 -31.714  0.50 35.90           C
ATOM   5100  OG  SER b 426    -14.086  21.988 -30.452  0.50 47.27           O
ATOM   5101  C   SER b 426    -14.089  24.852 -32.811  0.50 31.74           C
ATOM   5102  O   SER b 426    -14.940  24.765 -33.695  0.50 30.25           O
ATOM   5103  N   VAL b 427    -12.952  25.507 -32.963  0.50 29.64           N
ATOM   5104  CA  VAL b 427    -12.737  26.346 -34.122  0.50 32.39           C
ATOM   5105  CB  VAL b 427    -12.758  27.850 -33.776  0.50 34.01           C
ATOM   5106  CG1 VAL b 427    -12.357  28.680 -34.991  0.50 31.96           C
```

Figure 26 (Continued)

```
ATOM   5107  CG2 VAL b 427     -14.125  28.262 -33.271  0.50 33.09           C
ATOM   5108  C   VAL b 427     -11.371  26.034 -34.670  0.50 34.47           C
ATOM   5109  O   VAL b 427     -10.394  25.978 -33.919  0.50 32.74           O
ATOM   5110  N   MET b 428     -11.320  25.767 -35.973  0.50 33.01           N
ATOM   5111  CA  MET b 428     -10.075  25.443 -36.612  0.50 31.42           C
ATOM   5112  CB  MET b 428     -10.158  24.054 -37.198  0.50 31.55           C
ATOM   5113  CG  MET b 428     -10.076  22.985 -36.120  0.50 34.12           C
ATOM   5114  SD  MET b 428     -10.944  21.528 -36.687  0.50 36.64           S
ATOM   5115  CE  MET b 428     -12.674  21.917 -36.402  0.50 32.42           C
ATOM   5116  C   MET b 428      -9.754  26.458 -37.688  0.50 28.71           C
ATOM   5117  O   MET b 428     -10.599  26.764 -38.503  0.50 29.48           O
ATOM   5118  N   HIS b 429      -8.523  26.957 -37.680  0.50 28.84           N
ATOM   5119  CA  HIS b 429      -8.102  28.022 -38.584  0.50 32.69           C
ATOM   5120  CB  HIS b 429      -8.659  29.375 -38.113  0.50 34.19           C
ATOM   5121  CG  HIS b 429      -8.533  30.474 -39.129  0.50 31.61           C
ATOM   5122  ND1 HIS b 429      -7.421  31.283 -39.207  0.50 29.19           N
ATOM   5123  CE1 HIS b 429      -7.571  32.152 -40.195  0.50 28.36           C
ATOM   5124  NE2 HIS b 429      -8.752  31.946 -40.752  0.50 34.94           N
ATOM   5125  CD2 HIS b 429      -9.383  30.909 -40.093  0.50 31.43           C
ATOM   5126  C   HIS b 429      -6.567  28.060 -38.677  0.50 32.05           C
ATOM   5127  O   HIS b 429      -5.845  27.787 -37.704  0.50 31.35           O
ATOM   5128  N   GLU b 430      -6.085  28.357 -39.867  0.50 28.29           N
ATOM   5129  CA  GLU b 430      -4.648  28.388 -40.147  0.50 29.63           C
ATOM   5130  CB  GLU b 430      -4.396  28.785 -41.616  0.50 28.40           C
ATOM   5131  CG  GLU b 430      -4.587  30.272 -41.892  0.50 31.04           C
ATOM   5132  CD  GLU b 430      -4.737  30.572 -43.377  0.50 32.13           C
ATOM   5133  OE1 GLU b 430      -5.864  30.505 -43.922  0.50 32.89           O
ATOM   5134  OE2 GLU b 430      -3.724  30.860 -44.007  0.50 34.33           O
ATOM   5135  C   GLU b 430      -3.877  29.345 -39.260  0.50 31.38           C
ATOM   5136  O   GLU b 430      -2.668  29.149 -39.036  0.50 27.77           O
ATOM   5137  N   ALA b 431      -4.536  30.392 -38.757  0.50 34.37           N
ATOM   5138  CA  ALA b 431      -3.782  31.413 -38.001  0.50 34.35           C
ATOM   5139  CB  ALA b 431      -4.364  32.799 -38.233  0.50 35.83           C
ATOM   5140  C   ALA b 431      -3.773  31.058 -36.509  0.50 38.13           C
ATOM   5141  O   ALA b 431      -3.039  31.645 -35.713  0.50 43.66           O
ATOM   5142  N   LEU b 432      -4.577  30.084 -36.118  0.50 33.27           N
ATOM   5143  CA  LEU b 432      -4.532  29.631 -34.733  0.50 32.57           C
ATOM   5144  CB  LEU b 432      -5.821  28.889 -34.382  0.50 32.07           C
ATOM   5145  CG  LEU b 432      -7.147  29.648 -34.283  0.50 32.79           C
ATOM   5146  CD1 LEU b 432      -8.269  28.612 -34.320  0.50 31.09           C
ATOM   5147  CD2 LEU b 432      -7.236  30.498 -32.997  0.50 31.15           C
ATOM   5148  C   LEU b 432      -3.356  28.684 -34.497  0.50 35.72           C
ATOM   5149  O   LEU b 432      -3.110  27.782 -35.286  0.50 35.53           O
ATOM   5150  N   HIS b 433      -2.686  28.838 -33.364  0.50 38.77           N
ATOM   5151  CA  HIS b 433      -1.666  27.890 -32.947  0.50 40.76           C
ATOM   5152  CB  HIS b 433      -1.101  28.293 -31.573  0.50 42.54           C
ATOM   5153  CG  HIS b 433       0.137  27.542 -31.192  0.50 51.94           C
ATOM   5154  ND1 HIS b 433       0.185  26.664 -30.125  0.50 52.46           N
ATOM   5155  CE1 HIS b 433       1.396  26.140 -30.045  0.50 51.46           C
ATOM   5156  NE2 HIS b 433       2.130  26.633 -31.030  0.50 47.84           N
ATOM   5157  CD2 HIS b 433       1.365  27.504 -31.765  0.50 47.00           C
ATOM   5158  C   HIS b 433      -2.266  26.475 -32.888  0.50 36.10           C
ATOM   5159  O   HIS b 433      -3.368  26.288 -32.392  0.50 37.53           O
ATOM   5160  N   ASN b 434      -1.524  25.476 -33.355  0.50 36.69           N
ATOM   5161  CA  ASN b 434      -2.071  24.110 -33.501  0.50 35.77           C
ATOM   5162  CB  ASN b 434      -2.408  23.514 -32.136  0.50 35.00           C
ATOM   5163  CG  ASN b 434      -1.225  23.574 -31.161  0.50 45.25           C
ATOM   5164  OD1 ASN b 434      -0.079  23.269 -31.534  0.50 37.14           O
ATOM   5165  ND2 ASN b 434      -1.495  23.977 -29.906  0.50 37.88           N
ATOM   5166  C   ASN b 434      -3.302  24.075 -34.428  0.50 35.41           C
ATOM   5167  O   ASN b 434      -3.945  23.016 -34.583  0.50 31.00           O
ATOM   5168  N   HIS b 435      -3.639  25.236 -35.015  0.50 30.25           N
ATOM   5169  CA  HIS b 435      -4.771  25.334 -35.929  0.50 30.78           C
ATOM   5170  CB  HIS b 435      -4.630  24.351 -37.101  0.50 31.91           C
```

Figure 26 (Continued)

```
ATOM   5171  CG   HIS b 435      -3.519  24.692 -38.039  0.50 32.20           C
ATOM   5172  ND1  HIS b 435      -3.132  23.866 -39.074  0.50 32.89           N
ATOM   5173  CE1  HIS b 435      -2.096  24.399 -39.690  0.50 32.64           C
ATOM   5174  NE2  HIS b 435      -1.821  25.554 -39.115  0.50 32.63           N
ATOM   5175  CD2  HIS b 435      -2.700  25.764 -38.086  0.50 31.85           C
ATOM   5176  C    HIS b 435      -6.077  25.023 -35.245  0.50 33.04           C
ATOM   5177  O    HIS b 435      -7.039  24.572 -35.898  0.50 35.78           O
ATOM   5178  N    TYR b 436      -6.126  25.240 -33.939  0.50 31.67           N
ATOM   5179  CA   TYR b 436      -7.221  24.705 -33.161  0.50 36.70           C
ATOM   5180  CB   TYR b 436      -7.016  23.192 -32.978  0.50 35.75           C
ATOM   5181  CG   TYR b 436      -8.153  22.462 -32.269  0.50 37.61           C
ATOM   5182  CD1  TYR b 436      -8.088  22.190 -30.909  0.50 36.49           C
ATOM   5183  CE1  TYR b 436      -9.109  21.490 -30.258  0.50 39.01           C
ATOM   5184  CZ   TYR b 436     -10.211  21.051 -30.979  0.50 43.16           C
ATOM   5185  OH   TYR b 436     -11.248  20.394 -30.340  0.50 41.29           O
ATOM   5186  CE2  TYR b 436     -10.291  21.296 -32.343  0.50 40.79           C
ATOM   5187  CD2  TYR b 436      -9.266  21.998 -32.977  0.50 37.88           C
ATOM   5188  C    TYR b 436      -7.333  25.407 -31.815  0.50 39.51           C
ATOM   5189  O    TYR b 436      -6.350  25.534 -31.093  0.50 42.61           O
ATOM   5190  N    THR b 437      -8.527  25.889 -31.483  0.50 38.07           N
ATOM   5191  CA   THR b 437      -8.766  26.366 -30.135  0.50 37.03           C
ATOM   5192  CB   THR b 437      -8.584  27.888 -29.983  0.50 36.62           C
ATOM   5193  OG1  THR b 437      -8.664  28.227 -28.588  0.50 40.89           O
ATOM   5194  CG2  THR b 437      -9.674  28.642 -30.735  0.50 37.08           C
ATOM   5195  C    THR b 437     -10.164  25.979 -29.731  0.50 40.88           C
ATOM   5196  O    THR b 437     -10.938  25.492 -30.553  0.50 41.76           O
ATOM   5197  N    GLN b 438     -10.491  26.204 -28.465  0.50 39.50           N
ATOM   5198  CA   GLN b 438     -11.771  25.777 -27.933  0.50 43.18           C
ATOM   5199  CB   GLN b 438     -11.617  24.448 -27.190  0.50 43.14           C
ATOM   5200  CG   GLN b 438     -12.823  23.542 -27.273  0.50 48.18           C
ATOM   5201  CD   GLN b 438     -12.695  22.349 -26.337  0.50 54.22           C
ATOM   5202  OE1  GLN b 438     -12.621  22.511 -25.111  0.50 52.65           O
ATOM   5203  NE2  GLN b 438     -12.667  21.149 -26.903  0.50 43.33           N
ATOM   5204  C    GLN b 438     -12.310  26.833 -26.972  0.50 45.20           C
ATOM   5205  O    GLN b 438     -11.545  27.553 -26.314  0.50 39.46           O
ATOM   5206  N    LYS b 439     -13.633  26.910 -26.880  0.50 41.62           N
ATOM   5207  CA   LYS b 439     -14.258  27.640 -25.786  0.50 43.07           C
ATOM   5208  CB   LYS b 439     -14.571  29.092 -26.194  0.50 41.67           C
ATOM   5209  CG   LYS b 439     -13.341  29.916 -26.597  0.50 44.46           C
ATOM   5210  CD   LYS b 439     -12.285  29.947 -25.484  0.50 42.04           C
ATOM   5211  CE   LYS b 439     -11.171  30.955 -25.752  0.50 46.78           C
ATOM   5212  NZ   LYS b 439      -9.865  30.327 -26.127  0.50 46.05           N
ATOM   5213  C    LYS b 439     -15.506  26.890 -25.343  0.50 43.00           C
ATOM   5214  O    LYS b 439     -16.322  26.470 -26.178  0.50 43.86           O
ATOM   5215  N    SER b 440     -15.646  26.729 -24.027  0.50 42.19           N
ATOM   5216  CA   SER b 440     -16.696  25.925 -23.429  0.50 42.91           C
ATOM   5217  CB   SER b 440     -16.056  24.784 -22.628  0.50 41.46           C
ATOM   5218  OG   SER b 440     -15.994  23.603 -23.410  0.50 42.46           O
ATOM   5219  C    SER b 440     -17.546  26.777 -22.498  0.50 45.08           C
ATOM   5220  O    SER b 440     -17.073  27.759 -21.952  0.50 48.58           O
ATOM   5221  N    LEU b 441     -18.805  26.406 -22.315  0.50 48.30           N
ATOM   5222  CA   LEU b 441     -19.603  27.035 -21.267  0.50 46.03           C
ATOM   5223  CB   LEU b 441     -20.174  28.388 -21.705  0.50 50.85           C
ATOM   5224  CG   LEU b 441     -20.870  28.467 -23.064  0.50 49.04           C
ATOM   5225  CD1  LEU b 441     -21.960  27.418 -23.166  0.50 48.12           C
ATOM   5226  CD2  LEU b 441     -21.402  29.865 -23.331  0.50 43.75           C
ATOM   5227  C    LEU b 441     -20.698  26.125 -20.730  0.50 46.05           C
ATOM   5228  O    LEU b 441     -21.034  25.117 -21.334  0.50 43.51           O
ATOM   5229  N    SER b 442     -21.219  26.499 -19.567  0.50 47.75           N
ATOM   5230  CA   SER b 442     -22.243  25.748 -18.853  0.50 48.12           C
ATOM   5231  CB   SER b 442     -21.642  24.514 -18.162  0.50 53.12           C
ATOM   5232  OG   SER b 442     -20.294  24.743 -17.754  0.50 49.99           O
ATOM   5233  C    SER b 442     -22.792  26.722 -17.831  0.50 45.30           C
ATOM   5234  O    SER b 442     -22.200  27.779 -17.615  0.50 41.46           O
```

Figure 26 (Continued)

```
ATOM    5235  N   LEU b 443     -23.947  26.408 -17.258  0.50 44.85           N
ATOM    5236  CA  LEU b 443     -24.595  27.279 -16.261  0.50 48.43           C
ATOM    5237  CB  LEU b 443     -25.820  26.561 -15.683  0.50 48.52           C
ATOM    5238  CG  LEU b 443     -26.750  27.324 -14.742  0.50 54.19           C
ATOM    5239  CD1 LEU b 443     -27.005  28.738 -15.249  0.50 52.59           C
ATOM    5240  CD2 LEU b 443     -28.049  26.550 -14.604  0.50 51.64           C
ATOM    5241  C   LEU b 443     -23.635  27.670 -15.133  0.50 46.56           C
ATOM    5242  O   LEU b 443     -23.008  26.810 -14.535  0.50 45.00           O
ATOM    5243  N   SER b 444     -23.525  28.958 -14.821  0.50 52.59           N
ATOM    5244  CA  SER b 444     -22.542  29.394 -13.805  0.50 69.19           C
ATOM    5245  CB  SER b 444     -22.513  30.928 -13.678  0.50 70.22           C
ATOM    5246  OG  SER b 444     -23.571  31.409 -12.859  0.50 71.13           O
ATOM    5247  C   SER b 444     -22.670  28.714 -12.411  0.50 77.84           C
ATOM    5248  O   SER b 444     -23.742  28.732 -11.787  0.50 78.26           O
ATOM    5249  N   PRO b 445     -21.569  28.102 -11.923  0.50 76.83           N
ATOM    5250  CA  PRO b 445     -21.555  27.451 -10.611  0.50 78.86           C
ATOM    5251  CB  PRO b 445     -20.059  27.204 -10.344  0.50 77.86           C
ATOM    5252  CG  PRO b 445     -19.316  27.964 -11.396  0.50 74.32           C
ATOM    5253  CD  PRO b 445     -20.247  28.053 -12.569  0.50 77.72           C
ATOM    5254  C   PRO b 445     -22.144  28.332  -9.510  0.50 83.96           C
ATOM    5255  O   PRO b 445     -23.358  28.309  -9.290  0.50 83.15           O
HETATM  5256  C1  NAG b 500     -25.216  17.455 -67.719  0.50 57.19           C
HETATM  5257  C2  NAG b 500     -25.047  18.944 -67.978  0.50 56.31           C
HETATM  5258  N2  NAG b 500     -24.894  19.187 -69.396  0.50 63.05           N
HETATM  5259  C7  NAG b 500     -25.798  19.886 -70.072  0.50 58.91           C
HETATM  5260  O7  NAG b 500     -26.833  20.267 -69.563  0.50 55.72           O
HETATM  5261  C8  NAG b 500     -25.466  20.176 -71.502  0.50 51.67           C
HETATM  5262  C3  NAG b 500     -23.855  19.499 -67.210  0.50 56.33           C
HETATM  5263  O3  NAG b 500     -23.827  20.920 -67.348  0.50 46.67           O
HETATM  5264  C4  NAG b 500     -23.966  19.123 -65.740  0.50 53.75           C
HETATM  5265  O4  NAG b 500     -22.822  19.575 -65.007  0.50 48.53           O
HETATM  5266  C5  NAG b 500     -24.127  17.614 -65.620  0.50 56.97           C
HETATM  5267  C6  NAG b 500     -24.256  17.184 -64.168  0.50 59.36           C
HETATM  5268  O6  NAG b 500     -25.337  17.902 -63.575  0.50 71.23           O
HETATM  5269  O5  NAG b 500     -25.303  17.224 -66.317  0.50 57.07           O
HETATM  5270  C1  FUC b 501     -26.035  17.045 -62.662  0.50 71.90           C
HETATM  5271  C2  FUC b 501     -26.973  17.904 -61.835  0.50 71.40           C
HETATM  5272  O2  FUC b 501     -26.214  18.956 -61.246  0.50 73.90           O
HETATM  5273  C3  FUC b 501     -28.053  18.510 -62.712  0.50 71.47           C
HETATM  5274  O3  FUC b 501     -29.013  19.178 -61.893  0.50 64.20           O
HETATM  5275  C4  FUC b 501     -28.731  17.407 -63.502  0.50 76.61           C
HETATM  5276  O4  FUC b 501     -29.372  16.525 -62.584  0.50 79.46           O
HETATM  5277  C5  FUC b 501     -27.688  16.620 -64.275  0.50 83.01           C
HETATM  5278  C6  FUC b 501     -28.323  15.527 -65.124  0.50 77.31           C
HETATM  5279  O5  FUC b 501     -26.787  16.044 -63.337  0.50 85.25           O
HETATM  5280  C1  NAG b 502     -22.741  20.686 -64.249  0.50 43.37           C
HETATM  5281  C2  NAG b 502     -21.907  20.591 -62.972  0.50 44.64           C
HETATM  5282  N2  NAG b 502     -22.421  19.548 -62.103  0.50 43.12           N
HETATM  5283  C7  NAG b 502     -21.724  18.461 -61.748  0.50 47.59           C
HETATM  5284  O7  NAG b 502     -22.166  17.578 -61.008  0.50 57.28           O
HETATM  5285  C8  NAG b 502     -20.338  18.306 -62.267  0.50 41.97           C
HETATM  5286  C3  NAG b 502     -21.813  21.940 -62.248  0.50 43.05           C
HETATM  5287  O3  NAG b 502     -20.827  21.848 -61.239  0.50 46.42           O
HETATM  5288  C4  NAG b 502     -21.431  23.051 -63.229  0.50 44.86           C
HETATM  5289  O4  NAG b 502     -21.689  24.344 -62.741  0.50 43.74           O
HETATM  5290  C5  NAG b 502     -22.245  22.941 -64.520  0.50 47.19           C
HETATM  5291  C6  NAG b 502     -21.739  23.992 -65.508  0.50 44.77           C
HETATM  5292  O6  NAG b 502     -22.685  24.108 -66.541  0.50 56.71           O
HETATM  5293  O5  NAG b 502     -22.104  21.640 -65.059  0.50 42.09           O
HETATM  5294  C1  BMA b 503     -20.657  24.827 -61.874  0.50 46.38           C
HETATM  5295  O5  BMA b 503     -20.943  24.486 -60.526  0.50 40.50           O
HETATM  5296  C5  BMA b 503     -19.940  24.935 -59.632  0.50 47.34           C
HETATM  5297  C6  BMA b 503     -20.215  24.336 -58.260  0.50 43.57           C
HETATM  5298  O6  BMA b 503     -20.409  22.926 -58.395  0.50 50.32           O
```

Figure 26 (Continued)

```
HETATM 5299  C4  BMA b 503     -19.964  26.454 -59.601  0.50 47.73
HETATM 5300  O4  BMA b 503     -18.928  26.940 -58.747  0.50 53.37
HETATM 5301  C3  BMA b 503     -19.743  27.024 -60.992  0.50 49.11
HETATM 5302  O3  BMA b 503     -20.065  28.412 -60.962  0.50 54.31
HETATM 5303  C2  BMA b 503     -20.623  26.343 -62.028  0.50 43.90
HETATM 5304  O2  BMA b 503     -21.949  26.861 -61.914  0.50 45.60
HETATM 5305  C1  MAN b 504     -20.364  22.329 -57.092  0.50 44.93
HETATM 5306  C2  MAN b 504     -20.052  20.851 -57.219  0.50 46.91
HETATM 5307  O2  MAN b 504     -20.047  20.254 -55.925  0.50 46.31
HETATM 5308  C3  MAN b 504     -21.137  20.162 -58.017  0.50 45.56
HETATM 5309  O3  MAN b 504     -20.894  18.757 -57.997  0.50 41.56
HETATM 5310  C4  MAN b 504     -22.488  20.446 -57.384  0.50 48.28
HETATM 5311  O4  MAN b 504     -23.524  19.967 -58.242  0.50 52.56
HETATM 5312  C5  MAN b 504     -22.687  21.936 -57.152  0.50 49.56
HETATM 5313  C6  MAN b 504     -23.976  22.174 -56.381  0.50 49.94
HETATM 5314  O6  MAN b 504     -24.035  23.537 -55.955  0.50 51.75
HETATM 5315  O5  MAN b 504     -21.598  22.468 -56.408  0.50 48.59
HETATM 5316  C1  NAG b 505     -18.708  20.305 -55.401  0.50 44.95
HETATM 5317  C2  NAG b 505     -18.759  20.393 -53.880  0.50 46.14
HETATM 5318  N2  NAG b 505     -19.508  21.567 -53.476  0.50 45.74
HETATM 5319  C7  NAG b 505     -20.819  21.515 -53.261  0.50 50.45
HETATM 5320  O7  NAG b 505     -21.432  20.460 -53.237  0.50 53.95
HETATM 5321  C8  NAG b 505     -21.496  22.837 -53.051  0.50 50.94
HETATM 5322  C3  NAG b 505     -17.355  20.441 -53.290  0.50 45.58
HETATM 5323  O3  NAG b 505     -17.430  20.294 -51.868  0.50 45.04
HETATM 5324  C4  NAG b 505     -16.479  19.336 -53.869  0.50 42.23
HETATM 5325  O4  NAG b 505     -15.119  19.551 -53.476  0.50 41.90
HETATM 5326  C5  NAG b 505     -16.568  19.308 -55.391  0.50 48.29
HETATM 5327  C6  NAG b 505     -15.757  18.151 -55.963  0.50 46.12
HETATM 5328  O6  NAG b 505     -16.509  16.938 -55.850  0.50 43.17
HETATM 5329  O5  NAG b 505     -17.932  19.172 -55.785  0.50 47.49
HETATM 5330  C1  GAL b 506     -14.521  18.278 -53.168  0.50 49.87
HETATM 5331  C2  GAL b 506     -13.176  18.501 -52.488  0.50 57.11
HETATM 5332  O2  GAL b 506     -12.316  19.242 -53.361  0.50 65.35
HETATM 5333  C3  GAL b 506     -12.517  17.174 -52.132  0.50 50.44
HETATM 5334  O3  GAL b 506     -11.377  17.414 -51.300  0.50 56.58
HETATM 5335  C4  GAL b 506     -13.493  16.257 -51.404  0.50 49.97
HETATM 5336  O4  GAL b 506     -13.722  16.757 -50.082  0.50 52.34
HETATM 5337  C5  GAL b 506     -14.819  16.168 -52.150  0.50 54.54
HETATM 5338  C6  GAL b 506     -15.821  15.313 -51.383  0.50 52.48
HETATM 5339  O6  GAL b 506     -17.149  15.774 -51.655  0.50 40.05
HETATM 5340  O5  GAL b 506     -15.352  17.479 -52.329  0.50 46.40
HETATM 5341  C1  MAN b 507     -18.941  29.220 -61.510  0.50 64.32
HETATM 5342  C2  MAN b 507     -19.105  30.718 -61.338  0.50 71.01
HETATM 5343  O2  MAN b 507     -18.022  31.382 -61.980  0.50 78.15
HETATM 5344  C3  MAN b 507     -20.374  31.155 -62.036  0.50 73.47
HETATM 5345  O3  MAN b 507     -20.516  32.571 -61.927  0.50 77.64
HETATM 5346  C4  MAN b 507     -20.301  30.759 -63.501  0.50 77.56
HETATM 5347  O4  MAN b 507     -21.569  31.000 -64.112  0.50 80.67
HETATM 5348  C5  MAN b 507     -19.954  29.283 -63.643  0.50 75.16
HETATM 5349  C6  MAN b 507     -19.757  28.906 -65.107  0.50 72.99
HETATM 5350  O6  MAN b 507     -20.851  28.094 -65.548  0.50 76.20
HETATM 5351  O5  MAN b 507     -18.774  28.979 -62.902  0.50 77.26
HETATM 5352  C1  NAG b 508     -16.792  31.004 -61.348  0.50 94.79
HETATM 5353  C2  NAG b 508     -15.672  31.042 -62.382  0.50 99.86
HETATM 5354  N2  NAG b 508     -15.952  30.114 -63.456  0.50101.09
HETATM 5355  C7  NAG b 508     -15.848  30.467 -64.733  0.50 97.42
HETATM 5356  O7  NAG b 508     -15.314  29.750 -65.561  0.50 94.18
HETATM 5357  C8  NAG b 508     -16.433  31.803 -65.085  0.50 95.21
HETATM 5358  C3  NAG b 508     -14.340  30.692 -61.740  0.50101.65
HETATM 5359  O3  NAG b 508     -13.277  30.859 -62.682  0.50103.73
HETATM 5360  C4  NAG b 508     -14.120  31.592 -60.537  0.50105.50
HETATM 5361  O4  NAG b 508     -12.895  31.247 -59.888  0.50 99.87
HETATM 5362  C5  NAG b 508     -15.288  31.428 -59.578  0.50108.16
```

Figure 26 (Continued)

```
HETATM 5363  C6  NAG b 508     -15.091  32.247 -58.310  0.50115.27           C
HETATM 5364  O6  NAG b 508     -15.230  31.392 -57.174  0.50130.60           O
HETATM 5365  O5  NAG b 508     -16.478  31.846 -60.238  0.50 96.93           O
ATOM   5366  N   GLY a 236     -33.727  41.070 -79.327  0.50 52.50           N
ATOM   5367  CA  GLY a 236     -32.566  41.870 -79.783  0.50 51.60           C
ATOM   5368  C   GLY a 236     -32.736  43.279 -79.262  0.50 62.76           C
ATOM   5369  O   GLY a 236     -31.745  43.979 -79.015  0.50 71.86           O
ATOM   5370  N   GLY a 237     -33.999  43.680 -79.076  0.50 61.29           N
ATOM   5371  CA  GLY a 237     -34.363  45.019 -78.590  0.50 61.23           C
ATOM   5372  C   GLY a 237     -34.024  45.329 -77.129  0.50 58.75           C
ATOM   5373  O   GLY a 237     -32.970  44.932 -76.629  0.50 61.42           O
ATOM   5374  N   PRO a 238     -34.900  46.095 -76.455  0.50 56.56           N
ATOM   5375  CA  PRO a 238     -34.733  46.517 -75.056  0.50 56.48           C
ATOM   5376  CB  PRO a 238     -35.863  47.532 -74.848  0.50 54.46           C
ATOM   5377  CG  PRO a 238     -36.867  47.225 -75.913  0.50 61.03           C
ATOM   5378  CD  PRO a 238     -36.093  46.694 -77.084  0.50 52.58           C
ATOM   5379  C   PRO a 238     -34.919  45.374 -74.070  0.50 59.14           C
ATOM   5380  O   PRO a 238     -35.515  44.352 -74.413  0.50 56.14           O
ATOM   5381  N   SER a 239     -34.416  45.568 -72.851  0.50 60.67           N
ATOM   5382  CA  SER a 239     -34.580  44.607 -71.760  0.50 60.49           C
ATOM   5383  CB  SER a 239     -33.224  44.057 -71.324  0.50 56.98           C
ATOM   5384  OG  SER a 239     -32.759  43.100 -72.254  0.50 60.42           O
ATOM   5385  C   SER a 239     -35.290  45.233 -70.562  0.50 58.48           C
ATOM   5386  O   SER a 239     -35.116  46.423 -70.274  0.50 59.69           O
ATOM   5387  N   VAL a 240     -36.092  44.430 -69.869  0.50 54.30           N
ATOM   5388  CA  VAL a 240     -36.895  44.945 -68.753  0.50 53.55           C
ATOM   5389  CB  VAL a 240     -38.402  44.722 -68.987  0.50 54.83           C
ATOM   5390  CG1 VAL a 240     -39.199  45.304 -67.831  0.50 52.10           C
ATOM   5391  CG2 VAL a 240     -38.841  45.324 -70.330  0.50 55.40           C
ATOM   5392  C   VAL a 240     -36.531  44.295 -67.424  0.50 53.19           C
ATOM   5393  O   VAL a 240     -36.487  43.058 -67.312  0.50 47.43           O
ATOM   5394  N   PHE a 241     -36.317  45.127 -66.408  0.50 51.41           N
ATOM   5395  CA  PHE a 241     -36.064  44.621 -65.059  0.50 49.40           C
ATOM   5396  CB  PHE a 241     -34.622  44.899 -64.646  0.50 48.66           C
ATOM   5397  CG  PHE a 241     -33.616  44.288 -65.577  0.50 53.57           C
ATOM   5398  CD1 PHE a 241     -33.337  42.925 -65.523  0.50 55.24           C
ATOM   5399  CE1 PHE a 241     -32.437  42.352 -66.410  0.50 53.58           C
ATOM   5400  CZ  PHE a 241     -31.823  43.139 -67.377  0.50 58.57           C
ATOM   5401  CE2 PHE a 241     -32.100  44.495 -67.452  0.50 50.11           C
ATOM   5402  CD2 PHE a 241     -33.005  45.060 -66.569  0.50 56.97           C
ATOM   5403  C   PHE a 241     -37.053  45.187 -64.051  0.50 46.74           C
ATOM   5404  O   PHE a 241     -37.250  46.394 -63.982  0.50 42.19           O
ATOM   5405  N   LEU a 242     -37.659  44.294 -63.267  0.50 47.00           N
ATOM   5406  CA  LEU a 242     -38.763  44.640 -62.371  0.50 43.26           C
ATOM   5407  CB  LEU a 242     -39.989  43.798 -62.698  0.50 39.64           C
ATOM   5408  CG  LEU a 242     -41.258  44.087 -61.887  0.50 40.76           C
ATOM   5409  CD1 LEU a 242     -41.686  45.544 -61.982  0.50 37.47           C
ATOM   5410  CD2 LEU a 242     -42.387  43.165 -62.333  0.50 40.77           C
ATOM   5411  C   LEU a 242     -38.363  44.377 -60.925  0.50 44.57           C
ATOM   5412  O   LEU a 242     -38.182  43.233 -60.529  0.50 34.36           O
ATOM   5413  N   PHE a 243     -38.275  45.442 -60.143  0.50 40.15           N
ATOM   5414  CA  PHE a 243     -37.757  45.371 -58.791  0.50 40.50           C
ATOM   5415  CB  PHE a 243     -36.658  46.423 -58.630  0.50 42.22           C
ATOM   5416  CG  PHE a 243     -35.507  46.204 -59.570  0.50 40.37           C
ATOM   5417  CD1 PHE a 243     -34.485  45.312 -59.240  0.50 38.11           C
ATOM   5418  CE1 PHE a 243     -33.452  45.070 -60.121  0.50 36.12           C
ATOM   5419  CZ  PHE a 243     -33.444  45.688 -61.371  0.50 39.47           C
ATOM   5420  CE2 PHE a 243     -34.467  46.550 -61.728  0.50 40.47           C
ATOM   5421  CD2 PHE a 243     -35.500  46.794 -60.831  0.50 42.44           C
ATOM   5422  C   PHE a 243     -38.865  45.541 -57.746  0.50 43.07           C
ATOM   5423  O   PHE a 243     -39.768  46.363 -57.936  0.50 39.65           O
ATOM   5424  N   PRO a 244     -38.801  44.741 -56.654  0.50 40.07           N
ATOM   5425  CA  PRO a 244     -39.712  44.777 -55.499  0.50 38.67           C
ATOM   5426  CB  PRO a 244     -39.410  43.450 -54.799  0.50 35.84           C
```

Figure 26 (Continued)

```
ATOM   5427  CG   PRO a 244    -37.933  43.289 -55.016  0.50 37.74           C
ATOM   5428  CD   PRO a 244    -37.692  43.786 -56.430  0.50 39.16           C
ATOM   5429  C    PRO a 244    -39.365  45.928 -54.560  0.50 35.49           C
ATOM   5430  O    PRO a 244    -38.296  46.507 -54.685  0.50 33.53           O
ATOM   5431  N    PRO a 245    -40.271  46.266 -53.626  0.50 36.38           N
ATOM   5432  CA   PRO a 245    -39.971  47.270 -52.603  0.50 35.64           C
ATOM   5433  CB   PRO a 245    -41.337  47.568 -51.994  0.50 34.06           C
ATOM   5434  CG   PRO a 245    -42.135  46.336 -52.222  0.50 33.74           C
ATOM   5435  CD   PRO a 245    -41.659  45.778 -53.537  0.50 35.88           C
ATOM   5436  C    PRO a 245    -39.009  46.739 -51.545  0.50 34.39           C
ATOM   5437  O    PRO a 245    -38.715  45.545 -51.512  0.50 34.08           O
ATOM   5438  N    LYS a 246    -38.444  47.632 -50.750  0.50 35.45           N
ATOM   5439  CA   LYS a 246    -37.672  47.221 -49.583  0.50 40.43           C
ATOM   5440  CB   LYS a 246    -36.947  48.421 -48.975  0.50 39.86           C
ATOM   5441  CG   LYS a 246    -36.166  49.262 -49.968  0.50 41.98           C
ATOM   5442  CD   LYS a 246    -34.732  48.791 -50.063  0.50 48.03           C
ATOM   5443  CE   LYS a 246    -33.983  49.474 -51.209  0.50 49.03           C
ATOM   5444  NZ   LYS a 246    -34.365  48.981 -52.568  0.50 47.94           N
ATOM   5445  C    LYS a 246    -38.652  46.694 -48.550  0.50 36.17           C
ATOM   5446  O    LYS a 246    -39.599  47.390 -48.209  0.50 38.38           O
ATOM   5447  N    PRO a 247    -38.414  45.486 -48.021  0.50 34.96           N
ATOM   5448  CA   PRO a 247    -39.211  44.976 -46.898  0.50 33.77           C
ATOM   5449  CB   PRO a 247    -38.323  43.860 -46.321  0.50 35.57           C
ATOM   5450  CG   PRO a 247    -37.576  43.349 -47.526  0.50 39.46           C
ATOM   5451  CD   PRO a 247    -37.287  44.590 -48.350  0.50 39.25           C
ATOM   5452  C    PRO a 247    -39.535  46.018 -45.823  0.50 30.18           C
ATOM   5453  O    PRO a 247    -40.657  46.138 -45.420  0.50 35.80           O
ATOM   5454  N    LYS a 248    -38.566  46.762 -45.339  0.50 31.21           N
ATOM   5455  CA   LYS a 248    -38.880  47.761 -44.330  0.50 32.14           C
ATOM   5456  CB   LYS a 248    -37.633  48.570 -43.952  0.50 34.71           C
ATOM   5457  CG   LYS a 248    -37.917  49.599 -42.867  0.50 35.28           C
ATOM   5458  CD   LYS a 248    -36.670  50.355 -42.442  0.50 37.08           C
ATOM   5459  CE   LYS a 248    -36.985  51.336 -41.310  0.50 37.77           C
ATOM   5460  NZ   LYS a 248    -35.918  52.369 -41.131  0.50 35.82           N
ATOM   5461  C    LYS a 248    -39.973  48.723 -44.808  0.50 34.95           C
ATOM   5462  O    LYS a 248    -40.842  49.135 -44.013  0.50 32.49           O
ATOM   5463  N    ASP a 249    -39.981  49.054 -46.103  0.50 36.38           N
ATOM   5464  CA   ASP a 249    -40.959  50.064 -46.580  0.50 33.43           C
ATOM   5465  CB   ASP a 249    -40.651  50.550 -48.009  0.50 32.93           C
ATOM   5466  CG   ASP a 249    -39.342  51.355 -48.113  0.50 35.75           C
ATOM   5467  OD1  ASP a 249    -38.874  51.871 -47.095  0.50 35.94           O
ATOM   5468  OD2  ASP a 249    -38.769  51.428 -49.229  0.50 37.13           O
ATOM   5469  C    ASP a 249    -42.343  49.438 -46.577  0.50 33.70           C
ATOM   5470  O    ASP a 249    -43.338  50.135 -46.417  0.50 36.91           O
ATOM   5471  N    THR a 250    -42.418  48.123 -46.815  0.50 32.02           N
ATOM   5472  CA   THR a 250    -43.709  47.453 -46.806  0.50 30.96           C
ATOM   5473  CB   THR a 250    -43.654  46.077 -47.507  0.50 34.01           C
ATOM   5474  OG1  THR a 250    -42.841  45.175 -46.744  0.50 29.60           O
ATOM   5475  CG2  THR a 250    -43.034  46.213 -48.944  0.50 32.90           C
ATOM   5476  C    THR a 250    -44.242  47.296 -45.383  0.50 32.19           C
ATOM   5477  O    THR a 250    -45.451  47.154 -45.183  0.50 36.54           O
ATOM   5478  N    LEU a 251    -43.345  47.340 -44.401  0.50 29.11           N
ATOM   5479  CA   LEU a 251    -43.708  47.030 -42.987  0.50 28.62           C
ATOM   5480  CB   LEU a 251    -42.537  46.282 -42.306  0.50 27.28           C
ATOM   5481  CG   LEU a 251    -42.280  44.876 -42.926  0.50 29.59           C
ATOM   5482  CD1  LEU a 251    -40.986  44.278 -42.393  0.50 23.56           C
ATOM   5483  CD2  LEU a 251    -43.449  43.920 -42.678  0.50 23.75           C
ATOM   5484  C    LEU a 251    -44.092  48.216 -42.116  0.50 29.52           C
ATOM   5485  O    LEU a 251    -44.895  48.073 -41.188  0.50 33.69           O
ATOM   5486  N    MET a 252    -43.453  49.364 -42.352  0.50 29.68           N
ATOM   5487  CA   MET a 252    -43.709  50.564 -41.580  0.50 35.09           C
ATOM   5488  CB   MET a 252    -42.376  51.222 -41.224  0.50 31.81           C
ATOM   5489  CG   MET a 252    -41.406  50.261 -40.564  0.50 38.52           C
ATOM   5490  SD   MET a 252    -41.674  50.017 -38.789  0.50 45.33           S
```

Figure 26 (Continued)

```
ATOM   5491  CE  MET a 252     -42.584  48.494 -38.786  0.50 34.75           C
ATOM   5492  C   MET a 252     -44.618  51.537 -42.346  0.50 36.44           C
ATOM   5493  O   MET a 252     -44.271  52.014 -43.444  0.50 33.16           O
ATOM   5494  N   ILE a 253     -45.778  51.821 -41.763  0.50 36.67           N
ATOM   5495  CA  ILE a 253     -46.819  52.583 -42.448  0.50 39.56           C
ATOM   5496  CB  ILE a 253     -48.144  52.522 -41.643  0.50 39.62           C
ATOM   5497  CG1 ILE a 253     -49.351  52.901 -42.516  0.50 39.97           C
ATOM   5498  CD1 ILE a 253     -50.032  51.704 -43.137  0.50 39.15           C
ATOM   5499  CG2 ILE a 253     -48.055  53.334 -40.355  0.50 33.17           C
ATOM   5500  C   ILE a 253     -46.365  54.014 -42.892  0.50 41.53           C
ATOM   5501  O   ILE a 253     -46.730  54.495 -43.952  0.50 38.99           O
ATOM   5502  N   SER a 254     -45.434  54.610 -42.171  0.50 44.48           N
ATOM   5503  CA  SER a 254     -44.888  55.908 -42.559  0.50 39.88           C
ATOM   5504  CB  SER a 254     -43.961  56.424 -41.475  0.50 37.25           C
ATOM   5505  OG  SER a 254     -42.900  55.510 -41.265  0.50 35.60           O
ATOM   5506  C   SER a 254     -44.145  55.905 -43.880  0.50 41.64           C
ATOM   5507  O   SER a 254     -44.041  56.935 -44.524  0.50 42.23           O
ATOM   5508  N   ARG a 255     -43.597  54.767 -44.278  0.50 39.26           N
ATOM   5509  CA  ARG a 255     -42.800  54.707 -45.500  0.50 35.20           C
ATOM   5510  CB  ARG a 255     -41.677  53.691 -45.329  0.50 40.44           C
ATOM   5511  CG  ARG a 255     -40.828  53.969 -44.095  0.50 40.81           C
ATOM   5512  CD  ARG a 255     -39.659  53.024 -43.996  0.50 41.63           C
ATOM   5513  NE  ARG a 255     -38.839  53.068 -45.196  0.50 46.38           N
ATOM   5514  CZ  ARG a 255     -37.710  53.771 -45.304  0.50 52.39           C
ATOM   5515  NH1 ARG a 255     -37.276  54.500 -44.267  0.50 49.41           N
ATOM   5516  NH2 ARG a 255     -37.018  53.756 -46.452  0.50 45.51           N
ATOM   5517  C   ARG a 255     -43.616  54.392 -46.752  0.50 39.44           C
ATOM   5518  O   ARG a 255     -44.784  53.979 -46.655  0.50 38.01           O
ATOM   5519  N   THR a 256     -42.969  54.504 -47.916  0.50 37.30           N
ATOM   5520  CA  THR a 256     -43.629  54.436 -49.204  0.50 35.05           C
ATOM   5521  CB  THR a 256     -43.284  55.702 -50.044  0.50 41.90           C
ATOM   5522  OG1 THR a 256     -43.477  56.887 -49.255  0.50 39.57           O
ATOM   5523  CG2 THR a 256     -44.148  55.785 -51.302  0.50 42.45           C
ATOM   5524  C   THR a 256     -43.075  53.275 -50.002  0.50 37.87           C
ATOM   5525  O   THR a 256     -42.042  53.399 -50.618  0.50 38.11           O
ATOM   5526  N   PRO a 257     -43.738  52.112 -49.977  0.50 39.39           N
ATOM   5527  CA  PRO a 257     -43.144  51.052 -50.769  0.50 38.88           C
ATOM   5528  CB  PRO a 257     -43.898  49.815 -50.303  0.50 37.12           C
ATOM   5529  CG  PRO a 257     -45.224  50.336 -49.826  0.50 36.47           C
ATOM   5530  CD  PRO a 257     -44.873  51.642 -49.169  0.50 38.29           C
ATOM   5531  C   PRO a 257     -43.400  51.279 -52.261  0.50 36.21           C
ATOM   5532  O   PRO a 257     -44.477  51.723 -52.617  0.50 32.28           O
ATOM   5533  N   GLU a 258     -42.458  50.911 -53.122  0.50 34.55           N
ATOM   5534  CA  GLU a 258     -42.722  51.017 -54.553  0.50 38.40           C
ATOM   5535  CB  GLU a 258     -42.080  52.274 -55.145  0.50 40.12           C
ATOM   5536  CG  GLU a 258     -42.181  53.517 -54.277  0.50 42.89           C
ATOM   5537  CD  GLU a 258     -41.162  54.561 -54.688  0.50 44.99           C
ATOM   5538  OE1 GLU a 258     -39.963  54.220 -54.751  0.50 46.20           O
ATOM   5539  OE2 GLU a 258     -41.566  55.708 -54.974  0.50 46.62           O
ATOM   5540  C   GLU a 258     -42.140  49.861 -55.280  0.50 35.77           C
ATOM   5541  O   GLU a 258     -41.087  49.348 -54.912  0.50 35.86           O
ATOM   5542  N   VAL a 259     -42.787  49.497 -56.370  0.50 38.23           N
ATOM   5543  CA  VAL a 259     -42.177  48.598 -57.315  0.50 39.68           C
ATOM   5544  CB  VAL a 259     -43.226  47.652 -57.903  0.50 42.61           C
ATOM   5545  CG1 VAL a 259     -42.568  46.731 -58.910  0.50 43.50           C
ATOM   5546  CG2 VAL a 259     -43.873  46.826 -56.786  0.50 47.60           C
ATOM   5547  C   VAL a 259     -41.581  49.486 -58.416  0.50 46.59           C
ATOM   5548  O   VAL a 259     -42.033  50.620 -58.618  0.50 43.92           O
ATOM   5549  N   THR a 260     -40.589  48.968 -59.139  0.50 45.49           N
ATOM   5550  CA  THR a 260     -39.856  49.781 -60.105  0.50 42.41           C
ATOM   5551  CB  THR a 260     -38.588  50.333 -59.493  0.50 37.58           C
ATOM   5552  OG1 THR a 260     -38.959  51.025 -58.306  0.50 40.49           O
ATOM   5553  CG2 THR a 260     -37.898  51.307 -60.451  0.50 36.59           C
ATOM   5554  C   THR a 260     -39.534  49.001 -61.345  0.50 43.89           C
```

Figure 26 (Continued)

```
ATOM   5555  O    THR a 260     -38.911  47.945 -61.271  0.50 41.90           O
ATOM   5556  N    CYS a 261     -40.050  49.486 -62.472  0.50 42.59           N
ATOM   5557  CA   CYS a 261     -39.897  48.792 -63.754  0.50 41.82           C
ATOM   5558  CB   CYS a 261     -41.252  48.675 -64.444  0.50 38.44           C
ATOM   5559  SG   CYS a 261     -41.279  47.599 -65.900  0.50 42.47           S
ATOM   5560  C    CYS a 261     -38.902  49.595 -64.605  0.50 45.08           C
ATOM   5561  O    CYS a 261     -39.174  50.740 -64.969  0.50 44.61           O
ATOM   5562  N    VAL a 262     -37.732  49.007 -64.841  0.50 43.79           N
ATOM   5563  CA   VAL a 262     -36.644  49.654 -65.561  0.50 46.92           C
ATOM   5564  CB   VAL a 262     -35.312  49.514 -64.788  0.50 49.33           C
ATOM   5565  CG1  VAL a 262     -34.189  50.235 -65.515  0.50 49.39           C
ATOM   5566  CG2  VAL a 262     -35.454  50.084 -63.372  0.50 41.82           C
ATOM   5567  C    VAL a 262     -36.506  49.033 -66.952  0.50 52.14           C
ATOM   5568  O    VAL a 262     -36.410  47.801 -67.077  0.50 53.82           O
ATOM   5569  N    VAL a 263     -36.571  49.874 -67.992  0.50 49.27           N
ATOM   5570  CA   VAL a 263     -36.264  49.443 -69.376  0.50 47.60           C
ATOM   5571  CB   VAL a 263     -37.345  49.874 -70.392  0.50 49.23           C
ATOM   5572  CG1  VAL a 263     -37.077  49.244 -71.749  0.50 47.55           C
ATOM   5573  CG2  VAL a 263     -38.743  49.488 -69.921  0.50 48.60           C
ATOM   5574  C    VAL a 263     -34.922  50.023 -69.806  0.50 45.06           C
ATOM   5575  O    VAL a 263     -34.650  51.222 -69.622  0.50 48.06           O
ATOM   5576  N    VAL a 264     -34.041  49.156 -70.280  0.50 48.92           N
ATOM   5577  CA   VAL a 264     -32.741  49.596 -70.778  0.50 46.61           C
ATOM   5578  CB   VAL a 264     -31.568  48.987 -69.975  0.50 44.94           C
ATOM   5579  CG1  VAL a 264     -31.496  49.620 -68.585  0.50 47.22           C
ATOM   5580  CG2  VAL a 264     -31.663  47.466 -69.901  0.50 41.65           C
ATOM   5581  C    VAL a 264     -32.630  49.220 -72.248  0.50 48.17           C
ATOM   5582  O    VAL a 264     -33.455  48.452 -72.754  0.50 46.11           O
ATOM   5583  N    ASP a 265     -31.601  49.742 -72.921  0.50 53.61           N
ATOM   5584  CA   ASP a 265     -31.379  49.468 -74.346  0.50 44.90           C
ATOM   5585  CB   ASP a 265     -30.927  48.011 -74.571  0.50 49.00           C
ATOM   5586  CG   ASP a 265     -29.663  47.666 -73.784  0.50 47.70           C
ATOM   5587  OD1  ASP a 265     -29.172  48.550 -73.049  0.50 55.54           O
ATOM   5588  OD2  ASP a 265     -29.146  46.533 -73.898  0.50 43.14           O
ATOM   5589  C    ASP a 265     -32.614  49.829 -75.175  0.50 43.88           C
ATOM   5590  O    ASP a 265     -33.029  49.089 -76.067  0.50 47.74           O
ATOM   5591  N    VAL a 266     -33.225  50.963 -74.840  0.50 47.05           N
ATOM   5592  CA   VAL a 266     -34.176  51.601 -75.742  0.50 56.44           C
ATOM   5593  CB   VAL a 266     -35.161  52.539 -74.992  0.50 57.97           C
ATOM   5594  CG1  VAL a 266     -36.090  53.239 -75.977  0.50 50.85           C
ATOM   5595  CG2  VAL a 266     -35.979  51.759 -73.963  0.50 56.75           C
ATOM   5596  C    VAL a 266     -33.378  52.393 -76.805  0.50 56.62           C
ATOM   5597  O    VAL a 266     -32.577  53.280 -76.466  0.50 49.64           O
ATOM   5598  N    SER a 267     -33.578  52.043 -78.075  0.50 56.22           N
ATOM   5599  CA   SER a 267     -32.805  52.637 -79.189  0.50 57.37           C
ATOM   5600  CB   SER a 267     -32.934  51.770 -80.436  0.50 49.25           C
ATOM   5601  OG   SER a 267     -34.259  51.855 -80.930  0.50 52.80           O
ATOM   5602  C    SER a 267     -33.224  54.063 -79.546  0.50 56.90           C
ATOM   5603  O    SER a 267     -34.316  54.520 -79.184  0.50 58.47           O
ATOM   5604  N    HIS a 268     -32.356  54.755 -80.279  0.50 63.84           N
ATOM   5605  CA   HIS a 268     -32.674  56.083 -80.810  0.50 65.25           C
ATOM   5606  CB   HIS a 268     -31.421  56.710 -81.426  0.50 70.31           C
ATOM   5607  CG   HIS a 268     -30.427  57.194 -80.419  0.50 75.28           C
ATOM   5608  ND1  HIS a 268     -29.973  58.497 -80.388  0.50 79.25           N
ATOM   5609  CE1  HIS a 268     -29.114  58.637 -79.393  0.50 80.51           C
ATOM   5610  NE2  HIS a 268     -28.996  57.474 -78.778  0.50 77.55           N
ATOM   5611  CD2  HIS a 268     -29.806  56.554 -79.400  0.50 76.10           C
ATOM   5612  C    HIS a 268     -33.795  56.024 -81.860  0.50 63.33           C
ATOM   5613  O    HIS a 268     -34.579  56.962 -82.007  0.50 64.89           O
ATOM   5614  N    GLU a 269     -33.859  54.912 -82.583  0.50 69.20           N
ATOM   5615  CA   GLU a 269     -34.813  54.744 -83.679  0.50 78.71           C
ATOM   5616  CB   GLU a 269     -34.326  53.656 -84.644  0.50 78.46           C
ATOM   5617  CG   GLU a 269     -32.911  53.872 -85.167  0.50 85.60           C
ATOM   5618  CD   GLU a 269     -31.837  53.638 -84.112  0.50 94.89           C
```

Figure 26 (Continued)

```
ATOM   5619  OE1 GLU a 269     -32.179  53.255 -82.971  0.50 89.27           O
ATOM   5620  OE2 GLU a 269     -30.641  53.836 -84.430  0.50104.36           O
ATOM   5621  C   GLU a 269     -36.201  54.392 -83.159  0.50 81.31           C
ATOM   5622  O   GLU a 269     -37.208  54.632 -83.828  0.50 82.09           O
ATOM   5623  N   GLU a 270     -36.245  53.826 -81.956  0.50 75.84           N
ATOM   5624  CA  GLU a 270     -37.493  53.391 -81.348  0.50 73.66           C
ATOM   5625  CB  GLU a 270     -37.533  51.873 -81.325  0.50 74.39           C
ATOM   5626  CG  GLU a 270     -36.686  51.233 -82.404  0.50 81.56           C
ATOM   5627  CD  GLU a 270     -37.527  50.754 -83.557  0.50 72.39           C
ATOM   5628  OE1 GLU a 270     -37.232  49.662 -84.087  0.50 73.06           O
ATOM   5629  OE2 GLU a 270     -38.502  51.454 -83.896  0.50 71.65           O
ATOM   5630  C   GLU a 270     -37.556  53.883 -79.913  0.50 69.78           C
ATOM   5631  O   GLU a 270     -37.614  53.083 -78.987  0.50 67.91           O
ATOM   5632  N   PRO a 271     -37.534  55.204 -79.719  0.50 70.45           N
ATOM   5633  CA  PRO a 271     -37.300  55.707 -78.371  0.50 64.33           C
ATOM   5634  CB  PRO a 271     -36.881  57.159 -78.622  0.50 62.28           C
ATOM   5635  CG  PRO a 271     -37.589  57.540 -79.896  0.50 62.39           C
ATOM   5636  CD  PRO a 271     -37.905  56.277 -80.661  0.50 63.77           C
ATOM   5637  C   PRO a 271     -38.566  55.650 -77.506  0.50 64.29           C
ATOM   5638  O   PRO a 271     -38.547  56.088 -76.351  0.50 66.36           O
ATOM   5639  N   GLU a 272     -39.649  55.109 -78.063  0.50 62.45           N
ATOM   5640  CA  GLU a 272     -40.975  55.239 -77.447  0.50 64.96           C
ATOM   5641  CB  GLU a 272     -42.049  55.532 -78.498  0.50 61.07           C
ATOM   5642  CG  GLU a 272     -41.865  56.837 -79.265  0.50 64.53           C
ATOM   5643  CD  GLU a 272     -43.022  57.103 -80.210  0.50 61.59           C
ATOM   5644  OE1 GLU a 272     -43.523  58.243 -80.222  0.50 62.54           O
ATOM   5645  OE2 GLU a 272     -43.458  56.158 -80.908  0.50 68.49           O
ATOM   5646  C   GLU a 272     -41.392  54.012 -76.638  0.50 60.88           C
ATOM   5647  O   GLU a 272     -41.585  52.926 -77.192  0.50 61.72           O
ATOM   5648  N   VAL a 273     -41.581  54.209 -75.335  0.50 61.27           N
ATOM   5649  CA  VAL a 273     -41.928  53.116 -74.430  0.50 57.42           C
ATOM   5650  CB  VAL a 273     -40.909  53.037 -73.293  0.50 68.16           C
ATOM   5651  CG1 VAL a 273     -39.494  53.058 -73.867  0.50 66.87           C
ATOM   5652  CG2 VAL a 273     -41.119  54.214 -72.345  0.50 67.71           C
ATOM   5653  C   VAL a 273     -43.304  53.305 -73.812  0.50 50.13           C
ATOM   5654  O   VAL a 273     -43.603  54.356 -73.231  0.50 47.94           O
ATOM   5655  N   LYS a 274     -44.146  52.286 -73.930  0.50 47.06           N
ATOM   5656  CA  LYS a 274     -45.419  52.291 -73.215  0.50 47.45           C
ATOM   5657  CB  LYS a 274     -46.583  51.975 -74.150  0.50 45.33           C
ATOM   5658  CG  LYS a 274     -47.936  52.167 -73.465  0.50 45.31           C
ATOM   5659  CD  LYS a 274     -49.078  51.563 -74.268  0.50 40.17           C
ATOM   5660  CE  LYS a 274     -48.599  50.320 -74.984  0.50 40.19           C
ATOM   5661  NZ  LYS a 274     -49.748  49.412 -75.223  0.50 43.48           N
ATOM   5662  C   LYS a 274     -45.470  51.318 -72.025  0.50 48.96           C
ATOM   5663  O   LYS a 274     -45.431  50.096 -72.214  0.50 46.05           O
ATOM   5664  N   PHE a 275     -45.598  51.868 -70.816  0.50 47.44           N
ATOM   5665  CA  PHE a 275     -45.860  51.067 -69.605  0.50 50.35           C
ATOM   5666  CB  PHE a 275     -45.198  51.714 -68.394  0.50 44.67           C
ATOM   5667  CG  PHE a 275     -43.721  51.676 -68.456  0.50 44.07           C
ATOM   5668  CD1 PHE a 275     -43.013  52.736 -69.000  0.50 45.81           C
ATOM   5669  CE1 PHE a 275     -41.638  52.679 -69.099  0.50 48.41           C
ATOM   5670  CZ  PHE a 275     -40.958  51.559 -68.636  0.50 50.46           C
ATOM   5671  CE2 PHE a 275     -41.657  50.501 -68.089  0.50 44.95           C
ATOM   5672  CD2 PHE a 275     -43.034  50.559 -68.010  0.50 45.12           C
ATOM   5673  C   PHE a 275     -47.334  50.940 -69.289  0.50 49.38           C
ATOM   5674  O   PHE a 275     -48.022  51.949 -69.188  0.50 47.09           O
ATOM   5675  N   ASN a 276     -47.800  49.705 -69.127  0.50 48.27           N
ATOM   5676  CA  ASN a 276     -49.058  49.439 -68.425  0.50 51.82           C
ATOM   5677  CB  ASN a 276     -50.065  48.754 -69.358  0.50 47.26           C
ATOM   5678  CG  ASN a 276     -50.457  49.638 -70.546  0.50 56.74           C
ATOM   5679  OD1 ASN a 276     -49.596  50.104 -71.301  0.50 54.43           O
ATOM   5680  ND2 ASN a 276     -51.758  49.885 -70.704  0.50 47.12           N
ATOM   5681  C   ASN a 276     -48.835  48.605 -67.129  0.50 51.15           C
ATOM   5682  O   ASN a 276     -48.085  47.622 -67.121  0.50 49.31           O
```

Figure 26 (Continued)

```
ATOM   5683  N   TRP a 277     -49.495  48.998 -66.046  0.50 51.79           N
ATOM   5684  CA  TRP a 277     -49.294  48.352 -64.749  0.50 47.40           C
ATOM   5685  CB  TRP a 277     -48.975  49.394 -63.682  0.50 46.30           C
ATOM   5686  CG  TRP a 277     -47.531  49.908 -63.668  0.50 46.68           C
ATOM   5687  CD1 TRP a 277     -47.077  51.060 -64.232  0.50 46.69           C
ATOM   5688  NE1 TRP a 277     -45.729  51.213 -63.989  0.50 52.23           N
ATOM   5689  CE2 TRP a 277     -45.287  50.160 -63.232  0.50 46.63           C
ATOM   5690  CD2 TRP a 277     -46.391  49.312 -63.005  0.50 47.68           C
ATOM   5691  CE3 TRP a 277     -46.206  48.152 -62.239  0.50 45.63           C
ATOM   5692  CZ3 TRP a 277     -44.935  47.871 -61.751  0.50 42.37           C
ATOM   5693  CH2 TRP a 277     -43.853  48.736 -61.992  0.50 38.31           C
ATOM   5694  CZ2 TRP a 277     -44.015  49.886 -62.734  0.50 44.40           C
ATOM   5695  C   TRP a 277     -50.560  47.624 -64.353  0.50 50.93           C
ATOM   5696  O   TRP a 277     -51.657  48.158 -64.499  0.50 54.20           O
ATOM   5697  N   TYR a 278     -50.418  46.404 -63.856  0.50 50.36           N
ATOM   5698  CA  TYR a 278     -51.574  45.667 -63.358  0.50 50.20           C
ATOM   5699  CB  TYR a 278     -51.937  44.548 -64.333  0.50 49.00           C
ATOM   5700  CG  TYR a 278     -51.976  45.018 -65.774  0.50 53.61           C
ATOM   5701  CD1 TYR a 278     -50.803  45.322 -66.452  0.50 48.16           C
ATOM   5702  CE1 TYR a 278     -50.821  45.740 -67.763  0.50 52.61           C
ATOM   5703  CZ  TYR a 278     -52.026  45.875 -68.421  0.50 54.42           C
ATOM   5704  OH  TYR a 278     -52.026  46.303 -69.732  0.50 55.41           O
ATOM   5705  CE2 TYR a 278     -53.214  45.591 -67.771  0.50 54.82           C
ATOM   5706  CD2 TYR a 278     -53.185  45.162 -66.452  0.50 53.58           C
ATOM   5707  C   TYR a 278     -51.347  45.103 -61.950  0.50 51.84           C
ATOM   5708  O   TYR a 278     -50.232  44.705 -61.593  0.50 46.34           O
ATOM   5709  N   VAL a 279     -52.410  45.074 -61.152  0.50 51.33           N
ATOM   5710  CA  VAL a 279     -52.344  44.414 -59.861  0.50 47.58           C
ATOM   5711  CB  VAL a 279     -52.557  45.414 -58.716  0.50 46.77           C
ATOM   5712  CG1 VAL a 279     -52.281  44.744 -57.373  0.50 50.19           C
ATOM   5713  CG2 VAL a 279     -51.651  46.629 -58.911  0.50 38.73           C
ATOM   5714  C   VAL a 279     -53.323  43.243 -59.809  0.50 47.50           C
ATOM   5715  O   VAL a 279     -54.531  43.411 -59.928  0.50 50.61           O
ATOM   5716  N   ASP a 280     -52.785  42.036 -59.699  0.50 45.54           N
ATOM   5717  CA  ASP a 280     -53.509  40.853 -59.814  0.50 48.20           C
ATOM   5718  CB  ASP a 280     -54.563  40.766 -58.619  0.50 44.46           C
ATOM   5719  CG  ASP a 280     -53.384  40.243 -57.376  0.50 44.43           C
ATOM   5720  OD1 ASP a 280     -52.750  39.721 -57.495  0.50 43.07           O
ATOM   5721  OD2 ASP a 280     -54.482  40.367 -56.283  0.50 47.11           O
ATOM   5722  C   ASP a 280     -54.404  40.892 -61.127  0.50 49.45           C
ATOM   5723  O   ASP a 280     -55.580  40.529 -61.161  0.50 49.62           O
ATOM   5724  N   GLY a 281     -53.765  41.368 -62.192  0.50 52.25           N
ATOM   5725  CA  GLY a 281     -54.374  41.348 -63.526  0.50 51.22           C
ATOM   5726  C   GLY a 281     -55.293  42.510 -63.844  0.50 50.02           C
ATOM   5727  O   GLY a 281     -55.824  42.591 -64.946  0.50 52.63           O
ATOM   5728  N   VAL a 282     -55.479  43.418 -62.889  0.50 54.62           N
ATOM   5729  CA  VAL a 282     -56.331  44.588 -63.097  0.50 50.58           C
ATOM   5730  CB  VAL a 282     -57.273  44.829 -61.901  0.50 50.28           C
ATOM   5731  CG1 VAL a 282     -58.051  46.130 -62.068  0.50 55.29           C
ATOM   5732  CG2 VAL a 282     -58.227  43.648 -61.734  0.50 51.64           C
ATOM   5733  C   VAL a 282     -55.444  45.801 -63.280  0.50 55.93           C
ATOM   5734  O   VAL a 282     -54.651  46.141 -62.392  0.50 50.80           O
ATOM   5735  N   GLU a 283     -55.565  46.440 -64.441  0.50 53.05           N
ATOM   5736  CA  GLU a 283     -54.728  47.583 -64.767  0.50 48.24           C
ATOM   5737  CB  GLU a 283     -54.951  48.051 -66.230  0.50 49.45           C
ATOM   5738  CG  GLU a 283     -54.031  49.199 -66.636  0.50 45.27           C
ATOM   5739  CD  GLU a 283     -53.842  49.349 -68.148  0.50 49.00           C
ATOM   5740  OE1 GLU a 283     -53.077  50.256 -68.546  0.50 42.65           O
ATOM   5741  OE2 GLU a 283     -54.441  48.582 -68.934  0.50 44.35           O
ATOM   5742  C   GLU a 283     -54.976  48.721 -63.791  0.50 44.38           C
ATOM   5743  O   GLU a 283     -56.107  48.979 -63.389  0.50 48.35           O
ATOM   5744  N   VAL a 284     -53.902  49.403 -63.423  0.50 42.37           N
ATOM   5745  CA  VAL a 284     -53.968  50.562 -62.558  0.50 42.15           C
ATOM   5746  CB  VAL a 284     -53.345  50.225 -61.188  0.50 43.16           C
```

Figure 26 (Continued)

```
ATOM   5747  CG1 VAL a 284      -54.192  49.151 -60.496  0.50 40.96           C
ATOM   5748  CG2 VAL a 284      -51.911  49.726 -61.385  0.50 35.98           C
ATOM   5749  C   VAL a 284      -53.186  51.682 -63.242  0.50 44.82           C
ATOM   5750  O   VAL a 284      -52.365  51.422 -64.113  0.50 51.66           O
ATOM   5751  N   HIS a 285      -53.431  52.927 -62.865  0.50 50.87           N
ATOM   5752  CA  HIS a 285      -53.006  54.022 -63.725  0.50 57.26           C
ATOM   5753  CB  HIS a 285      -54.165  54.536 -64.600  0.50 62.90           C
ATOM   5754  CG  HIS a 285      -55.438  53.751 -64.470  0.50 65.51           C
ATOM   5755  ND1 HIS a 285      -55.847  52.831 -65.416  0.50 60.26           N
ATOM   5756  CE1 HIS a 285      -57.001  52.303 -65.042  0.50 65.71           C
ATOM   5757  NE2 HIS a 285      -57.361  52.854 -63.893  0.50 62.90           N
ATOM   5758  CD2 HIS a 285      -56.405  53.769 -63.516  0.50 61.76           C
ATOM   5759  C   HIS a 285      -52.445  55.187 -62.962  0.50 54.76           C
ATOM   5760  O   HIS a 285      -52.605  56.325 -63.396  0.50 63.29           O
ATOM   5761  N   ASN a 286      -51.789  54.928 -61.837  0.50 53.89           N
ATOM   5762  CA  ASN a 286      -51.199  56.022 -61.067  0.50 47.59           C
ATOM   5763  CB  ASN a 286      -51.877  56.218 -59.690  0.50 50.41           C
ATOM   5764  CG  ASN a 286      -51.883  54.960 -58.818  0.50 51.44           C
ATOM   5765  OD1 ASN a 286      -51.553  53.852 -59.258  0.50 47.95           O
ATOM   5766  ND2 ASN a 286      -52.263  55.143 -57.551  0.50 49.27           N
ATOM   5767  C   ASN a 286      -49.683  55.982 -60.962  0.50 47.49           C
ATOM   5768  O   ASN a 286      -49.083  56.694 -60.154  0.50 50.72           O
ATOM   5769  N   ALA a 287      -49.064  55.179 -61.819  0.50 48.01           N
ATOM   5770  CA  ALA a 287      -47.605  55.058 -61.834  0.50 51.50           C
ATOM   5771  CB  ALA a 287      -47.177  53.822 -62.617  0.50 46.15           C
ATOM   5772  C   ALA a 287      -46.953  56.318 -62.404  0.50 56.80           C
ATOM   5773  O   ALA a 287      -47.447  56.903 -63.380  0.50 50.40           O
ATOM   5774  N   LYS a 288      -45.846  56.735 -61.794  0.50 52.03           N
ATOM   5775  CA  LYS a 288      -45.185  57.975 -62.180  0.50 54.74           C
ATOM   5776  CB  LYS a 288      -44.847  58.814 -60.949  0.50 58.17           C
ATOM   5777  CG  LYS a 288      -46.070  59.235 -60.143  0.50 60.85           C
ATOM   5778  CD  LYS a 288      -45.669  60.067 -58.931  0.50 59.41           C
ATOM   5779  CE  LYS a 288      -46.418  59.618 -57.679  0.50 61.55           C
ATOM   5780  NZ  LYS a 288      -46.250  60.553 -56.524  0.50 58.56           N
ATOM   5781  C   LYS a 288      -43.931  57.707 -62.996  0.50 55.32           C
ATOM   5782  O   LYS a 288      -42.835  57.566 -62.445  0.50 55.19           O
ATOM   5783  N   THR a 289      -44.093  57.651 -64.317  0.50 50.84           N
ATOM   5784  CA  THR a 289      -42.977  57.377 -65.197  0.50 51.31           C
ATOM   5785  CB  THR a 289      -43.477  56.910 -66.567  0.50 51.85           C
ATOM   5786  OG1 THR a 289      -44.325  55.770 -66.388  0.50 52.06           O
ATOM   5787  CG2 THR a 289      -42.302  56.549 -67.477  0.50 49.59           C
ATOM   5788  C   THR a 289      -42.067  58.597 -65.345  0.50 56.12           C
ATOM   5789  O   THR a 289      -42.516  59.740 -65.210  0.50 59.32           O
ATOM   5790  N   LYS a 290      -40.786  58.353 -65.595  0.50 56.15           N
ATOM   5791  CA  LYS a 290      -39.838  59.433 -65.879  0.50 65.49           C
ATOM   5792  CB  LYS a 290      -38.616  59.330 -64.959  0.50 73.09           C
ATOM   5793  CG  LYS a 290      -38.942  58.929 -63.524  0.50 78.28           C
ATOM   5794  CD  LYS a 290      -37.746  58.295 -62.821  0.50 76.46           C
ATOM   5795  CE  LYS a 290      -38.076  57.960 -61.369  0.50 76.65           C
ATOM   5796  NZ  LYS a 290      -36.866  57.764 -60.518  0.50 63.84           N
ATOM   5797  C   LYS a 290      -39.383  59.388 -67.341  0.50 66.63           C
ATOM   5798  O   LYS a 290      -38.878  58.356 -67.802  0.50 68.61           O
ATOM   5799  N   PRO a 291      -39.545  60.509 -68.072  0.50 66.83           N
ATOM   5800  CA  PRO a 291      -39.036  60.565 -69.442  0.50 67.96           C
ATOM   5801  CB  PRO a 291      -39.016  62.067 -69.748  0.50 69.02           C
ATOM   5802  CG  PRO a 291      -40.080  62.637 -68.874  0.50 71.75           C
ATOM   5803  CD  PRO a 291      -40.059  61.814 -67.615  0.50 68.20           C
ATOM   5804  C   PRO a 291      -37.621  60.000 -69.513  0.50 66.42           C
ATOM   5805  O   PRO a 291      -36.857  60.121 -68.552  0.50 72.08           O
ATOM   5806  N   ARG a 292      -37.284  59.402 -70.651  0.50 68.39           N
ATOM   5807  CA  ARG a 292      -35.999  58.737 -70.869  0.50 73.38           C
ATOM   5808  CB  ARG a 292      -35.864  58.352 -72.346  0.50 78.90           C
ATOM   5809  CG  ARG a 292      -36.091  59.513 -73.301  0.50 88.52           C
ATOM   5810  CD  ARG a 292      -36.020  59.051 -74.748  0.50 98.98           C
```

Figure 26 (Continued)

```
ATOM   5811  NE   ARG a 292     -37.264  59.319 -75.466  0.50105.36           N
ATOM   5812  CZ   ARG a 292     -38.427  58.732 -75.189  0.50109.22           C
ATOM   5813  NH1  ARG a 292     -38.513  57.850 -74.193  0.50107.14           N
ATOM   5814  NH2  ARG a 292     -39.509  59.032 -75.900  0.50102.62           N
ATOM   5815  C    ARG a 292     -34.761  59.532 -70.435  0.50 73.13           C
ATOM   5816  O    ARG a 292     -34.773  60.762 -70.396  0.50 74.83           O
ATOM   5817  N    GLU a 293     -33.683  58.812 -70.132  0.50 68.40           N
ATOM   5818  CA   GLU a 293     -32.395  59.431 -69.828  0.50 65.36           C
ATOM   5819  CB   GLU a 293     -32.153  59.423 -68.317  0.50 63.29           C
ATOM   5820  CG   GLU a 293     -30.698  59.250 -67.898  0.50 64.39           C
ATOM   5821  CD   GLU a 293     -30.555  58.534 -66.558  0.50 68.12           C
ATOM   5822  OE1  GLU a 293     -31.410  58.742 -65.663  0.50 66.20           O
ATOM   5823  OE2  GLU a 293     -29.597  57.749 -66.396  0.50 63.76           O
ATOM   5824  C    GLU a 293     -31.273  58.693 -70.560  0.50 67.66           C
ATOM   5825  O    GLU a 293     -30.309  57.643 -70.104  0.50 69.71           O
ATOM   5826  N    GLU a 294     -30.348  59.234 -71.703  0.50 62.16           N
ATOM   5827  CA   GLU a 294     -29.874  58.550 -72.546  0.50 51.92           C
ATOM   5828  CB   GLU a 294     -29.485  59.404 -73.756  0.50 54.46           C
ATOM   5829  CG   GLU a 294     -28.518  58.699 -74.708  0.50 47.51           C
ATOM   5830  CD   GLU a 294     -28.085  59.590 -75.871  0.50 49.23           C
ATOM   5831  OE1  GLU a 294     -27.676  59.032 -76.904  0.50 48.95           O
ATOM   5832  OE2  GLU a 294     -28.134  60.836 -75.751  0.50 43.46           O
ATOM   5833  C    GLU a 294     -28.643  58.237 -71.739  0.50 46.71           C
ATOM   5834  O    GLU a 294     -28.265  59.019 -70.883  0.50 44.81           O
ATOM   5835  N    GLN a 295     -28.015  57.099 -72.031  0.50 52.68           N
ATOM   5836  CA   GLN a 295     -26.855  56.624 -71.284  0.50 51.54           C
ATOM   5837  CB   GLN a 295     -27.041  55.143 -70.930  0.50 59.51           C
ATOM   5838  CG   GLN a 295     -28.375  54.843 -70.254  0.50 61.63           C
ATOM   5839  CD   GLN a 295     -28.477  55.500 -68.890  0.50 56.72           C
ATOM   5840  OE1  GLN a 295     -27.691  55.203 -67.995  0.50 63.25           O
ATOM   5841  NE2  GLN a 295     -29.433  56.413 -68.731  0.50 54.80           N
ATOM   5842  C    GLN a 295     -25.561  56.808 -72.074  0.50 60.36           C
ATOM   5843  O    GLN a 295     -25.577  57.146 -73.264  0.50 53.92           O
ATOM   5844  N    TYR a 296     -24.436  56.568 -71.408  0.50 58.71           N
ATOM   5845  CA   TYR a 296     -23.143  56.714 -72.045  0.50 60.35           C
ATOM   5846  CB   TYR a 296     -22.011  56.706 -71.015  0.50 55.12           C
ATOM   5847  CG   TYR a 296     -21.434  58.074 -70.742  0.50 55.66           C
ATOM   5848  CD1  TYR a 296     -22.148  59.021 -70.019  0.50 60.40           C
ATOM   5849  CE1  TYR a 296     -21.622  60.281 -69.778  0.50 64.42           C
ATOM   5850  CZ   TYR a 296     -20.360  60.605 -70.267  0.50 68.01           C
ATOM   5851  OH   TYR a 296     -19.810  61.852 -70.022  0.50 64.87           O
ATOM   5852  CE2  TYR a 296     -19.639  59.679 -70.995  0.50 56.05           C
ATOM   5853  CD2  TYR a 296     -20.179  58.427 -71.228  0.50 59.06           C
ATOM   5854  C    TYR a 296     -22.884  55.703 -73.170  0.50 65.67           C
ATOM   5855  O    TYR a 296     -22.006  55.930 -73.998  0.50 77.92           O
ATOM   5856  N    ASN a 297     -23.642  54.607 -73.216  0.50 62.29           N
ATOM   5857  CA   ASN a 297     -23.506  53.642 -74.315  0.50 56.18           C
ATOM   5858  CB   ASN a 297     -23.634  52.173 -73.835  0.50 58.06           C
ATOM   5859  CG   ASN a 297     -24.966  51.878 -73.146  0.50 55.65           C
ATOM   5860  OD1  ASN a 297     -25.963  52.561 -73.382  0.50 50.94           O
ATOM   5861  ND2  ASN a 297     -24.985  50.840 -72.293  0.50 60.85           N
ATOM   5862  C    ASN a 297     -24.472  53.957 -75.465  0.50 55.76           C
ATOM   5863  O    ASN a 297     -24.664  53.149 -76.376  0.50 49.80           O
ATOM   5864  N    SER a 298     -25.094  55.131 -75.390  0.50 53.88           N
ATOM   5865  CA   SER a 298     -25.915  55.665 -76.477  0.50 58.49           C
ATOM   5866  CB   SER a 298     -25.267  55.376 -77.846  0.50 58.42           C
ATOM   5867  OG   SER a 298     -24.403  56.437 -78.216  0.50 49.28           O
ATOM   5868  C    SER a 298     -27.387  55.240 -76.474  0.50 59.04           C
ATOM   5869  O    SER a 298     -28.150  55.629 -77.364  0.50 58.09           O
ATOM   5870  N    THR a 299     -27.776  54.433 -75.486  0.50 60.20           N
ATOM   5871  CA   THR a 299     -29.160  53.974 -75.352  0.50 56.06           C
ATOM   5872  CB   THR a 299     -29.237  52.510 -74.930  0.50 57.84           C
ATOM   5873  OG1  THR a 299     -28.335  52.308 -73.834  0.50 56.88           O
ATOM   5874  CG2  THR a 299     -28.875  51.593 -76.108  0.50 59.27           C
```

Figure 26 (Continued)

```
ATOM   5875  C    THR a 299     -29.894  54.748 -74.291  0.50 51.33           C
ATOM   5876  O    THR a 299     -29.284  55.388 -73.436  0.50 50.10           O
ATOM   5877  N    TYR a 300     -31.218  54.694 -74.361  0.50 53.18           N
ATOM   5878  CA   TYR a 300     -32.030  55.274 -73.314  0.50 58.06           C
ATOM   5879  CB   TYR a 300     -33.284  55.940 -73.878  0.50 61.37           C
ATOM   5880  CG   TYR a 300     -32.994  56.926 -74.992  0.50 70.26           C
ATOM   5881  CD1  TYR a 300     -32.886  56.496 -76.312  0.50 70.34           C
ATOM   5882  CE1  TYR a 300     -32.631  57.391 -77.335  0.50 78.34           C
ATOM   5883  CZ   TYR a 300     -32.484  58.734 -77.044  0.50 78.52           C
ATOM   5884  OH   TYR a 300     -32.232  59.620 -78.065  0.50 85.49           O
ATOM   5885  CE2  TYR a 300     -32.589  59.188 -75.742  0.50 74.36           C
ATOM   5886  CD2  TYR a 300     -32.842  58.286 -74.726  0.50 68.29           C
ATOM   5887  C    TYR a 300     -32.391  54.222 -72.284  0.50 51.22           C
ATOM   5888  O    TYR a 300     -32.479  53.023 -72.583  0.50 48.90           O
ATOM   5889  N    ARG a 301     -32.561  54.688 -71.056  0.50 52.93           N
ATOM   5890  CA   ARG a 301     -33.051  53.860 -69.973  0.50 52.30           C
ATOM   5891  CB   ARG a 301     -31.960  53.678 -68.911  0.50 53.02           C
ATOM   5892  CG   ARG a 301     -32.426  53.195 -67.540  0.50 52.73           C
ATOM   5893  CD   ARG a 301     -31.275  53.320 -66.553  0.50 54.84           C
ATOM   5894  NE   ARG a 301     -31.561  52.755 -65.237  0.50 53.03           N
ATOM   5895  CZ   ARG a 301     -32.009  53.466 -64.208  0.50 50.93           C
ATOM   5896  NH1  ARG a 301     -32.239  54.758 -64.343  0.50 48.08           N
ATOM   5897  NH2  ARG a 301     -32.228  52.885 -63.041  0.50 51.64           N
ATOM   5898  C    ARG a 301     -34.239  54.629 -69.431  0.50 52.62           C
ATOM   5899  O    ARG a 301     -34.185  55.849 -69.283  0.50 50.17           O
ATOM   5900  N    VAL a 302     -35.338  53.927 -69.196  0.50 50.07           N
ATOM   5901  CA   VAL a 302     -36.559  54.601 -68.791  0.50 48.21           C
ATOM   5902  CB   VAL a 302     -37.524  54.766 -69.989  0.50 50.85           C
ATOM   5903  CG1  VAL a 302     -38.138  53.431 -70.378  0.50 50.66           C
ATOM   5904  CG2  VAL a 302     -38.599  55.813 -69.702  0.50 48.39           C
ATOM   5905  C    VAL a 302     -37.202  53.830 -67.641  0.50 47.28           C
ATOM   5906  O    VAL a 302     -37.240  52.589 -67.640  0.50 42.35           O
ATOM   5907  N    VAL a 303     -37.667  54.569 -66.643  0.50 45.85           N
ATOM   5908  CA   VAL a 303     -38.159  53.952 -65.428  0.50 50.26           C
ATOM   5909  CB   VAL a 303     -37.333  54.400 -64.215  0.50 56.22           C
ATOM   5910  CG1  VAL a 303     -37.819  53.674 -62.971  0.50 49.83           C
ATOM   5911  CG2  VAL a 303     -35.854  54.127 -64.469  0.50 54.67           C
ATOM   5912  C    VAL a 303     -39.615  54.287 -65.177  0.50 50.55           C
ATOM   5913  O    VAL a 303     -40.022  55.449 -65.289  0.50 54.27           O
ATOM   5914  N    SER a 304     -40.405  53.260 -64.870  0.50 47.06           N
ATOM   5915  CA   SER a 304     -41.778  53.467 -64.388  0.50 43.11           C
ATOM   5916  CB   SER a 304     -42.762  52.678 -65.258  0.50 40.83           C
ATOM   5917  OG   SER a 304     -44.106  52.968 -64.868  0.50 41.84           O
ATOM   5918  C    SER a 304     -41.891  53.040 -62.912  0.50 42.71           C
ATOM   5919  O    SER a 304     -41.523  51.928 -62.547  0.50 43.42           O
ATOM   5920  N    VAL a 305     -42.382  53.933 -62.065  0.50 49.57           N
ATOM   5921  CA   VAL a 305     -42.437  53.673 -60.631  0.50 46.39           C
ATOM   5922  CB   VAL a 305     -41.818  54.820 -59.813  0.50 47.17           C
ATOM   5923  CG1  VAL a 305     -42.124  54.633 -58.330  0.50 47.15           C
ATOM   5924  CG2  VAL a 305     -40.313  54.863 -60.034  0.50 48.49           C
ATOM   5925  C    VAL a 305     -43.876  53.506 -60.202  0.50 47.38           C
ATOM   5926  O    VAL a 305     -44.677  54.413 -60.373  0.50 46.15           O
ATOM   5927  N    LEU a 306     -44.208  52.337 -59.655  0.50 42.70           N
ATOM   5928  CA   LEU a 306     -45.530  52.135 -59.094  0.50 40.17           C
ATOM   5929  CB   LEU a 306     -46.178  50.870 -59.644  0.50 36.60           C
ATOM   5930  CG   LEU a 306     -47.567  50.579 -59.070  0.50 42.00           C
ATOM   5931  CD1  LEU a 306     -48.600  51.630 -59.480  0.50 40.69           C
ATOM   5932  CD2  LEU a 306     -48.042  49.183 -59.441  0.50 39.88           C
ATOM   5933  C    LEU a 306     -45.459  52.063 -57.567  0.50 41.74           C
ATOM   5934  O    LEU a 306     -44.867  51.129 -56.991  0.50 40.81           O
ATOM   5935  N    THR a 307     -46.098  53.026 -56.926  0.50 41.35           N
ATOM   5936  CA   THR a 307     -46.296  53.012 -55.488  0.50 42.98           C
ATOM   5937  CB   THR a 307     -46.774  54.379 -55.014  0.50 41.49           C
ATOM   5938  OG1  THR a 307     -45.738  55.322 -55.277  0.50 44.59           O
```

Figure 26 (Continued)

```
ATOM   5939  CG2 THR a 307     -47.061  54.361 -53.533  0.50 42.53           C
ATOM   5940  C   THR a 307     -47.338  51.957 -55.128  0.50 42.88           C
ATOM   5941  O   THR a 307     -48.384  51.895 -55.766  0.50 41.33           O
ATOM   5942  N   VAL a 308     -47.031  51.086 -54.161  0.50 37.89           N
ATOM   5943  CA  VAL a 308     -47.995  50.049 -53.791  0.50 35.22           C
ATOM   5944  CB  VAL a 308     -47.440  48.608 -53.906  0.50 37.90           C
ATOM   5945  CG1 VAL a 308     -47.182  48.239 -55.353  0.50 33.73           C
ATOM   5946  CG2 VAL a 308     -46.200  48.422 -53.030  0.50 35.77           C
ATOM   5947  C   VAL a 308     -48.522  50.255 -52.389  0.50 32.92           C
ATOM   5948  O   VAL a 308     -47.927  50.981 -51.583  0.50 34.45           O
ATOM   5949  N   LEU a 309     -49.659  49.644 -52.102  0.50 31.94           N
ATOM   5950  CA  LEU a 309     -50.247  49.785 -50.772  0.50 33.47           C
ATOM   5951  CB  LEU a 309     -51.768  49.655 -50.880  0.50 34.92           C
ATOM   5952  CG  LEU a 309     -52.334  50.325 -52.161  0.50 40.70           C
ATOM   5953  CD1 LEU a 309     -53.809  50.010 -52.404  0.50 37.82           C
ATOM   5954  CD2 LEU a 309     -52.105  51.843 -52.131  0.50 37.25           C
ATOM   5955  C   LEU a 309     -49.648  48.725 -49.835  0.50 33.60           C
ATOM   5956  O   LEU a 309     -49.518  47.564 -50.218  0.50 34.83           O
ATOM   5957  N   HIS a 310     -49.249  49.122 -48.630  0.50 34.74           N
ATOM   5958  CA  HIS a 310     -48.605  48.184 -47.711  0.50 34.83           C
ATOM   5959  CB  HIS a 310     -48.524  48.808 -46.327  0.50 34.26           C
ATOM   5960  CG  HIS a 310     -47.635  50.022 -46.275  0.50 37.82           C
ATOM   5961  ND1 HIS a 310     -47.999  51.236 -46.819  0.50 35.24           N
ATOM   5962  CE1 HIS a 310     -47.014  52.101 -46.672  0.50 36.46           C
ATOM   5963  NE2 HIS a 310     -46.020  51.492 -46.050  0.50 38.56           N
ATOM   5964  CD2 HIS a 310     -46.373  50.185 -45.814  0.50 35.22           C
ATOM   5965  C   HIS a 310     -49.337  46.833 -47.662  0.50 38.14           C
ATOM   5966  O   HIS a 310     -48.743  45.763 -47.888  0.50 36.65           O
ATOM   5967  N   GLN a 311     -50.640  46.894 -47.436  0.50 38.75           N
ATOM   5968  CA  GLN a 311     -51.419  45.688 -47.228  0.50 39.86           C
ATOM   5969  CB  GLN a 311     -52.830  45.989 -46.712  0.50 38.12           C
ATOM   5970  CG  GLN a 311     -53.541  44.710 -46.250  0.50 47.64           C
ATOM   5971  CD  GLN a 311     -53.037  44.179 -44.893  0.50 49.74           C
ATOM   5972  OE1 GLN a 311     -52.876  44.946 -43.937  0.50 45.61           O
ATOM   5973  NE2 GLN a 311     -52.791  42.865 -44.809  0.50 46.10           N
ATOM   5974  C   GLN a 311     -51.503  44.834 -48.483  0.50 39.65           C
ATOM   5975  O   GLN a 311     -51.519  43.606 -48.385  0.50 37.50           O
ATOM   5976  N   ASP a 312     -51.576  45.482 -49.646  0.50 38.64           N
ATOM   5977  CA  ASP a 312     -51.601  44.764 -50.933  0.50 36.65           C
ATOM   5978  CB  ASP a 312     -51.555  45.745 -52.104  0.50 36.40           C
ATOM   5979  CG  ASP a 312     -52.892  46.359 -52.414  0.50 41.13           C
ATOM   5980  OD1 ASP a 312     -53.875  46.058 -51.691  0.50 36.38           O
ATOM   5981  OD2 ASP a 312     -52.930  47.159 -53.384  0.50 36.03           O
ATOM   5982  C   ASP a 312     -50.368  43.912 -51.056  0.50 33.21           C
ATOM   5983  O   ASP a 312     -50.425  42.756 -51.447  0.50 35.14           O
ATOM   5984  N   TRP a 313     -49.227  44.537 -50.832  0.50 32.25           N
ATOM   5985  CA  TRP a 313     -47.972  43.802 -50.949  0.50 35.73           C
ATOM   5986  CB  TRP a 313     -46.741  44.688 -50.693  0.50 32.27           C
ATOM   5987  CG  TRP a 313     -45.439  43.934 -50.880  0.50 32.90           C
ATOM   5988  CD1 TRP a 313     -44.616  43.434 -49.887  0.50 31.47           C
ATOM   5989  NE1 TRP a 313     -43.547  42.769 -50.455  0.50 29.88           N
ATOM   5990  CE2 TRP a 313     -43.666  42.828 -51.821  0.50 29.37           C
ATOM   5991  CD2 TRP a 313     -44.835  43.556 -52.123  0.50 30.40           C
ATOM   5992  CE3 TRP a 313     -45.185  43.744 -53.469  0.50 34.10           C
ATOM   5993  CZ3 TRP a 313     -44.362  43.230 -54.449  0.50 28.77           C
ATOM   5994  CH2 TRP a 313     -43.195  42.540 -54.124  0.50 29.77           C
ATOM   5995  CZ2 TRP a 313     -42.832  42.318 -52.814  0.50 31.27           C
ATOM   5996  C   TRP a 313     -47.994  42.637 -49.988  0.50 29.28           C
ATOM   5997  O   TRP a 313     -47.695  41.507 -50.376  0.50 31.37           O
ATOM   5998  N   LEU a 314     -48.317  42.921 -48.731  0.50 30.21           N
ATOM   5999  CA  LEU a 314     -48.296  41.903 -47.689  0.50 29.12           C
ATOM   6000  CB  LEU a 314     -48.490  42.521 -46.313  0.50 30.23           C
ATOM   6001  CG  LEU a 314     -47.351  43.420 -45.835  0.50 31.21           C
ATOM   6002  CD1 LEU a 314     -47.674  43.906 -44.425  0.50 34.11           C
```

Figure 26 (Continued)

```
ATOM   6003  CD2 LEU a 314     -46.038  42.661 -45.877  0.50 25.86           C
ATOM   6004  C   LEU a 314     -49.345  40.842 -47.902  0.50 32.25           C
ATOM   6005  O   LEU a 314     -49.144  39.681 -47.520  0.50 30.33           O
ATOM   6006  N   ASN a 315     -50.449  41.229 -48.534  0.50 29.56           N
ATOM   6007  CA  ASN a 315     -51.466  40.273 -48.920  0.50 31.94           C
ATOM   6008  CB  ASN a 315     -52.846  40.938 -49.044  0.50 32.55           C
ATOM   6009  CG  ASN a 315     -53.462  41.222 -47.690  0.50 36.09           C
ATOM   6010  OD1 ASN a 315     -52.972  40.735 -46.658  0.50 34.46           O
ATOM   6011  ND2 ASN a 315     -54.529  42.002 -47.675  0.50 37.28           N
ATOM   6012  C   ASN a 315     -51.183  39.438 -50.152  0.50 34.17           C
ATOM   6013  O   ASN a 315     -52.047  38.662 -50.578  0.50 35.23           O
ATOM   6014  N   GLY a 316     -50.013  39.621 -50.746  0.50 32.00           N
ATOM   6015  CA  GLY a 316     -49.554  38.736 -51.824  0.50 34.27           C
ATOM   6016  C   GLY a 316     -50.059  39.067 -53.228  0.50 37.72           C
ATOM   6017  O   GLY a 316     -49.994  38.238 -54.145  0.50 37.15           O
ATOM   6018  N   LYS a 317     -50.521  40.288 -53.422  0.50 35.22           N
ATOM   6019  CA  LYS a 317     -50.945  40.694 -54.758  0.50 36.47           C
ATOM   6020  CB  LYS a 317     -51.665  42.047 -54.713  0.50 31.40           C
ATOM   6021  CG  LYS a 317     -52.923  42.051 -53.862  0.50 35.82           C
ATOM   6022  CD  LYS a 317     -54.066  42.793 -54.531  0.50 36.43           C
ATOM   6023  CE  LYS a 317     -55.334  42.699 -53.681  0.50 37.45           C
ATOM   6024  NZ  LYS a 317     -55.613  43.952 -52.924  0.50 40.04           N
ATOM   6025  C   LYS a 317     -49.743  40.742 -55.715  0.50 36.36           C
ATOM   6026  O   LYS a 317     -48.610  41.041 -55.295  0.50 34.94           O
ATOM   6027  N   GLU a 318     -50.011  40.443 -56.993  0.50 38.99           N
ATOM   6028  CA  GLU a 318     -49.000  40.348 -58.060  0.50 39.06           C
ATOM   6029  CB  GLU a 318     -49.358  39.209 -59.004  0.50 42.69           C
ATOM   6030  CG  GLU a 318     -48.965  37.838 -58.479  0.50 53.57           C
ATOM   6031  CD  GLU a 318     -48.866  36.798 -59.584  0.50 59.34           C
ATOM   6032  OE1 GLU a 318     -47.810  36.129 -59.700  0.50 63.84           O
ATOM   6033  OE2 GLU a 318     -49.842  36.658 -60.348  0.50 66.95           O
ATOM   6034  C   GLU a 318     -48.897  41.630 -58.888  0.50 41.09           C
ATOM   6035  O   GLU a 318     -49.902  42.164 -59.348  0.50 40.01           O
ATOM   6036  N   TYR a 319     -47.684  42.122 -59.094  0.50 40.07           N
ATOM   6037  CA  TYR a 319     -47.514  43.404 -59.773  0.50 41.06           C
ATOM   6038  CB  TYR a 319     -46.670  44.358 -58.925  0.50 35.23           C
ATOM   6039  CG  TYR a 319     -47.407  44.727 -57.669  0.50 39.29           C
ATOM   6040  CD1 TYR a 319     -47.391  43.881 -56.574  0.50 37.42           C
ATOM   6041  CE1 TYR a 319     -48.086  44.179 -55.429  0.50 35.60           C
ATOM   6042  CZ  TYR a 319     -48.852  45.305 -55.371  0.50 39.19           C
ATOM   6043  OH  TYR a 319     -49.553  45.568 -54.202  0.50 31.67           O
ATOM   6044  CE2 TYR a 319     -48.905  46.173 -56.461  0.50 36.47           C
ATOM   6045  CD2 TYR a 319     -48.199  45.862 -57.604  0.50 38.19           C
ATOM   6046  C   TYR a 319     -46.889  43.169 -61.130  0.50 42.74           C
ATOM   6047  O   TYR a 319     -45.751  42.713 -61.208  0.50 47.22           O
ATOM   6048  N   LYS a 320     -47.662  43.403 -62.191  0.50 42.79           N
ATOM   6049  CA  LYS a 320     -47.187  43.095 -63.538  0.50 42.59           C
ATOM   6050  CB  LYS a 320     -48.233  42.329 -64.337  0.50 45.95           C
ATOM   6051  CG  LYS a 320     -47.704  41.815 -65.674  0.50 49.75           C
ATOM   6052  CD  LYS a 320     -48.682  40.863 -66.353  0.50 49.72           C
ATOM   6053  CE  LYS a 320     -49.705  41.627 -67.179  0.50 56.11           C
ATOM   6054  NZ  LYS a 320     -50.474  40.742 -68.108  0.50 63.79           N
ATOM   6055  C   LYS a 320     -46.812  44.383 -64.248  0.50 40.70           C
ATOM   6056  O   LYS a 320     -47.609  45.317 -64.306  0.50 42.41           O
ATOM   6057  N   CYS a 321     -45.574  44.460 -64.719  0.50 43.13           N
ATOM   6058  CA  CYS a 321     -45.168  45.579 -65.555  0.50 46.68           C
ATOM   6059  CB  CYS a 321     -43.737  45.989 -65.270  0.50 45.24           C
ATOM   6060  SG  CYS a 321     -43.243  47.407 -66.282  0.50 45.42           S
ATOM   6061  C   CYS a 321     -45.272  45.160 -67.018  0.50 48.34           C
ATOM   6062  O   CYS a 321     -44.696  44.147 -67.415  0.50 48.47           O
ATOM   6063  N   LYS a 322     -46.027  45.917 -67.804  0.50 46.35           N
ATOM   6064  CA  LYS a 322     -46.119  45.649 -69.239  0.50 50.38           C
ATOM   6065  CB  LYS a 322     -47.582  45.545 -69.680  0.50 49.62           C
ATOM   6066  CG  LYS a 322     -47.771  45.290 -71.173  0.50 52.09           C
```

Figure 26 (Continued)

```
ATOM   6067  CD   LYS a 322    -49.245  45.228 -71.557  0.50 47.31           C
ATOM   6068  CE   LYS a 322    -49.415  44.600 -72.937  0.50 55.40           C
ATOM   6069  NZ   LYS a 322    -50.842  44.540 -73.357  0.50 45.28           N
ATOM   6070  C    LYS a 322    -45.411  46.781 -69.979  0.50 47.16           C
ATOM   6071  O    LYS a 322    -45.758  47.958 -69.808  0.50 45.10           O
ATOM   6072  N    VAL a 323    -44.381  46.416 -70.734  0.50 48.31           N
ATOM   6073  CA   VAL a 323    -43.540  47.379 -71.430  0.50 49.84           C
ATOM   6074  CB   VAL a 323    -42.057  47.229 -71.035  0.50 53.10           C
ATOM   6075  CG1  VAL a 323    -41.183  48.152 -71.895  0.50 50.38           C
ATOM   6076  CG2  VAL a 323    -41.869  47.530 -69.537  0.50 52.32           C
ATOM   6077  C    VAL a 323    -43.678  47.209 -72.947  0.50 55.33           C
ATOM   6078  O    VAL a 323    -43.515  46.101 -73.487  0.50 46.51           O
ATOM   6079  N    SER a 324    -44.002  48.310 -73.620  0.50 55.39           N
ATOM   6080  CA   SER a 324    -44.185  48.304 -75.076  0.50 61.80           C
ATOM   6081  CB   SER a 324    -45.588  48.790 -75.454  0.50 57.25           C
ATOM   6082  OG   SER a 324    -46.582  47.889 -74.988  0.50 58.88           O
ATOM   6083  C    SER a 324    -43.133  49.146 -75.787  0.50 60.88           C
ATOM   6084  O    SER a 324    -42.755  50.226 -75.305  0.50 57.32           O
ATOM   6085  N    ASN a 325    -42.589  48.638 -76.942  0.50 63.64           N
ATOM   6086  CA   ASN a 325    -41.594  49.287 -77.800  0.50 59.13           C
ATOM   6087  CB   ASN a 325    -40.285  48.884 -77.365  0.50 53.67           C
ATOM   6088  CG   ASN a 325    -39.202  49.771 -77.968  0.50 55.39           C
ATOM   6089  OD1  ASN a 325    -38.291  49.284 -78.649  0.50 48.21           O
ATOM   6090  ND2  ASN a 325    -39.276  51.078 -77.691  0.50 50.42           N
ATOM   6091  C    ASN a 325    -41.923  48.882 -79.270  0.50 68.60           C
ATOM   6092  O    ASN a 325    -42.308  47.742 -79.556  0.50 65.74           O
ATOM   6093  N    LYS a 326    -41.688  49.809 -80.200  0.50 69.89           N
ATOM   6094  CA   LYS a 326    -41.907  49.523 -81.622  0.50 65.76           C
ATOM   6095  CB   LYS a 326    -42.040  50.814 -82.445  0.50 63.50           C
ATOM   6096  CG   LYS a 326    -43.284  51.622 -82.088  0.50 65.06           C
ATOM   6097  CD   LYS a 326    -43.313  52.999 -82.741  0.50 66.19           C
ATOM   6098  CE   LYS a 326    -44.109  53.985 -81.887  0.50 75.21           C
ATOM   6099  NZ   LYS a 326    -44.820  55.062 -82.649  0.50 63.37           N
ATOM   6100  C    LYS a 326    -40.835  48.590 -82.184  0.50 61.93           C
ATOM   6101  O    LYS a 326    -41.019  47.984 -83.230  0.50 72.59           O
ATOM   6102  N    ALA a 327    -39.730  48.446 -81.466  0.50 64.05           N
ATOM   6103  CA   ALA a 327    -38.689  47.513 -81.866  0.50 62.01           C
ATOM   6104  CB   ALA a 327    -37.364  47.904 -81.228  0.50 60.28           C
ATOM   6105  C    ALA a 327    -39.062  46.063 -81.530  0.50 67.65           C
ATOM   6106  O    ALA a 327    -38.936  45.169 -82.366  0.50 71.56           O
ATOM   6107  N    LEU a 328    -39.544  45.841 -80.310  0.50 70.01           N
ATOM   6108  CA   LEU a 328    -39.930  44.506 -79.852  0.50 64.03           C
ATOM   6109  CB   LEU a 328    -40.674  44.601 -78.522  0.50 56.17           C
ATOM   6110  CG   LEU a 328    -39.755  44.635 -77.308  0.50 61.36           C
ATOM   6111  CD1  LEU a 328    -40.576  44.724 -76.030  0.50 58.77           C
ATOM   6112  CD2  LEU a 328    -38.848  43.410 -77.313  0.50 54.62           C
ATOM   6113  C    LEU a 328    -40.799  43.738 -80.832  0.50 66.27           C
ATOM   6114  O    LEU a 328    -41.690  44.308 -81.466  0.50 67.34           O
ATOM   6115  N    PRO a 329    -40.573  42.421 -80.915  0.50 65.31           N
ATOM   6116  CA   PRO a 329    -41.466  41.479 -81.593  0.50 67.68           C
ATOM   6117  CB   PRO a 329    -40.675  40.169 -81.558  0.50 62.85           C
ATOM   6118  CG   PRO a 329    -39.813  40.291 -80.347  0.50 68.43           C
ATOM   6119  CD   PRO a 329    -39.443  41.746 -80.254  0.50 63.77           C
ATOM   6120  C    PRO a 329    -42.789  41.325 -80.827  0.50 73.97           C
ATOM   6121  O    PRO a 329    -43.755  40.762 -81.350  0.50 66.26           O
ATOM   6122  N    ALA a 330    -42.814  41.830 -79.592  0.50 74.81           N
ATOM   6123  CA   ALA a 330    -44.002  41.807 -78.736  0.50 70.70           C
ATOM   6124  CB   ALA a 330    -44.546  40.391 -78.598  0.50 72.27           C
ATOM   6125  C    ALA a 330    -43.646  42.378 -77.364  0.50 68.93           C
ATOM   6126  O    ALA a 330    -42.487  42.325 -76.942  0.50 65.35           O
ATOM   6127  N    PRO a 331    -44.641  42.938 -76.664  0.50 65.25           N
ATOM   6128  CA   PRO a 331    -44.359  43.611 -75.395  0.50 63.84           C
ATOM   6129  CB   PRO a 331    -45.747  44.068 -74.922  0.50 61.23           C
ATOM   6130  CG   PRO a 331    -46.585  44.108 -76.167  0.50 59.38           C
```

Figure 26 (Continued)

```
ATOM   6131  CD   PRO a 331     -46.075  42.970 -77.002  0.50 62.75           C
ATOM   6132  C    PRO a 331     -43.688  42.683 -74.365  0.50 56.76           C
ATOM   6133  O    PRO a 331     -43.928  41.474 -74.354  0.50 43.93           O
ATOM   6134  N    ILE a 332     -42.806  43.244 -73.543  0.50 55.88           N
ATOM   6135  CA   ILE a 332     -42.147  42.454 -72.521  0.50 51.45           C
ATOM   6136  CB   ILE a 332     -40.745  42.974 -72.209  0.50 51.85           C
ATOM   6137  CG1  ILE a 332     -39.881  42.972 -73.477  0.50 52.23           C
ATOM   6138  CD1  ILE a 332     -39.442  41.586 -73.916  0.50 49.41           C
ATOM   6139  CG2  ILE a 332     -40.115  42.116 -71.118  0.50 50.97           C
ATOM   6140  C    ILE a 332     -42.959  42.505 -71.244  0.50 54.27           C
ATOM   6141  O    ILE a 332     -43.331  43.588 -70.780  0.50 55.03           O
ATOM   6142  N    GLU a 333     -43.231  41.335 -70.677  0.50 49.78           N
ATOM   6143  CA   GLU a 333     -43.929  41.266 -69.403  0.50 53.83           C
ATOM   6144  CB   GLU a 333     -45.158  40.353 -69.508  0.50 56.04           C
ATOM   6145  CG   GLU a 333     -46.149  40.837 -70.560  0.50 57.21           C
ATOM   6146  CD   GLU a 333     -47.482  40.136 -70.482  0.50 55.54           C
ATOM   6147  OE1  GLU a 333     -48.486  40.732 -70.940  0.50 49.18           O
ATOM   6148  OE2  GLU a 333     -47.510  38.991 -69.972  0.50 52.28           O
ATOM   6149  C    GLU a 333     -43.004  40.824 -68.268  0.50 46.83           C
ATOM   6150  O    GLU a 333     -42.139  39.966 -68.444  0.50 47.55           O
ATOM   6151  N    LYS a 334     -43.165  41.461 -67.118  0.50 46.41           N
ATOM   6152  CA   LYS a 334     -42.520  41.017 -65.889  0.50 43.67           C
ATOM   6153  CB   LYS a 334     -41.268  41.854 -65.581  0.50 43.88           C
ATOM   6154  CG   LYS a 334     -40.081  41.686 -66.546  0.50 42.20           C
ATOM   6155  CD   LYS a 334     -39.615  40.239 -66.722  0.50 42.45           C
ATOM   6156  CE   LYS a 334     -38.363  40.153 -67.601  0.50 42.57           C
ATOM   6157  NZ   LYS a 334     -37.066  40.102 -66.838  0.50 43.80           N
ATOM   6158  C    LYS a 334     -43.517  41.120 -64.740  0.50 45.11           C
ATOM   6159  O    LYS a 334     -44.264  42.094 -64.617  0.50 47.31           O
ATOM   6160  N    THR a 335     -43.494  40.117 -63.877  0.50 49.81           N
ATOM   6161  CA   THR a 335     -44.453  40.003 -62.783  0.50 48.91           C
ATOM   6162  CB   THR a 335     -45.401  38.807 -63.011  0.50 47.80           C
ATOM   6163  OG1  THR a 335     -46.545  39.248 -63.763  0.50 48.44           O
ATOM   6164  CG2  THR a 335     -45.875  38.221 -61.680  0.50 56.10           C
ATOM   6165  C    THR a 335     -43.680  39.812 -61.498  0.50 46.66           C
ATOM   6166  O    THR a 335     -42.683  39.089 -61.471  0.50 44.52           O
ATOM   6167  N    ILE a 336     -44.097  40.482 -60.431  0.50 46.94           N
ATOM   6168  CA   ILE a 336     -43.409  40.284 -59.152  0.50 45.42           C
ATOM   6169  CB   ILE a 336     -42.350  41.367 -58.915  0.50 44.97           C
ATOM   6170  CG1  ILE a 336     -41.266  40.850 -57.976  0.50 47.07           C
ATOM   6171  CD1  ILE a 336     -40.031  40.341 -58.693  0.50 41.90           C
ATOM   6172  CG2  ILE a 336     -42.981  42.631 -58.359  0.50 41.93           C
ATOM   6173  C    ILE a 336     -44.387  40.235 -57.977  0.50 43.53           C
ATOM   6174  O    ILE a 336     -45.500  40.746 -58.078  0.50 38.56           O
ATOM   6175  N    SER a 337     -43.959  39.622 -56.870  0.50 38.69           N
ATOM   6176  CA   SER a 337     -44.792  39.511 -55.674  0.50 37.05           C
ATOM   6177  CB   SER a 337     -45.885  38.493 -55.902  0.50 37.06           C
ATOM   6178  OG   SER a 337     -45.316  37.318 -56.469  0.50 39.59           O
ATOM   6179  C    SER a 337     -43.965  39.056 -54.471  0.50 36.62           C
ATOM   6180  O    SER a 337     -42.824  38.611 -54.620  0.50 34.90           O
ATOM   6181  N    LYS a 338     -44.556  39.169 -53.289  0.50 34.27           N
ATOM   6182  CA   LYS a 338     -43.842  38.911 -52.060  0.50 36.50           C
ATOM   6183  CB   LYS a 338     -44.678  39.402 -50.879  0.50 32.62           C
ATOM   6184  CG   LYS a 338     -44.047  39.198 -49.520  0.50 36.17           C
ATOM   6185  CD   LYS a 338     -44.976  39.633 -48.381  0.50 34.01           C
ATOM   6186  CE   LYS a 338     -45.984  38.525 -48.039  0.50 34.45           C
ATOM   6187  NZ   LYS a 338     -45.256  37.251 -47.820  0.50 32.91           N
ATOM   6188  C    LYS a 338     -43.615  37.412 -51.947  0.50 32.68           C
ATOM   6189  O    LYS a 338     -44.461  36.644 -52.338  0.50 32.55           O
ATOM   6190  N    ALA a 339     -42.469  37.001 -51.419  0.50 35.91           N
ATOM   6191  CA   ALA a 339     -42.239  35.584 -51.124  0.50 41.15           C
ATOM   6192  CB   ALA a 339     -40.979  35.429 -50.278  0.50 39.06           C
ATOM   6193  C    ALA a 339     -43.461  34.943 -50.413  0.50 37.75           C
ATOM   6194  O    ALA a 339     -44.030  35.538 -49.504  0.50 34.29           O
```

Figure 26 (Continued)

```
ATOM   6195  N    LYS a 340     -43.844  33.743 -50.842  0.50 39.25           N
ATOM   6196  CA   LYS a 340     -44.961  32.999 -50.243  0.50 38.17           C
ATOM   6197  CB   LYS a 340     -45.651  32.151 -51.300  0.50 41.16           C
ATOM   6198  CG   LYS a 340     -46.385  32.946 -52.371  0.50 42.14           C
ATOM   6199  CD   LYS a 340     -46.308  32.169 -53.681  0.50 41.22           C
ATOM   6200  CE   LYS a 340     -47.095  32.820 -54.800  0.50 41.04           C
ATOM   6201  NZ   LYS a 340     -46.285  32.715 -56.041  0.50 30.96           N
ATOM   6202  C    LYS a 340     -44.512  32.056 -49.132  0.50 37.61           C
ATOM   6203  O    LYS a 340     -43.317  31.843 -48.941  0.50 37.12           O
ATOM   6204  N    GLY a 341     -45.473  31.451 -48.430  0.50 33.96           N
ATOM   6205  CA   GLY a 341     -45.151  30.594 -47.275  0.50 33.58           C
ATOM   6206  C    GLY a 341     -45.760  31.172 -46.003  0.50 36.54           C
ATOM   6207  O    GLY a 341     -45.922  32.387 -45.896  0.50 33.61           O
ATOM   6208  N    GLN a 342     -46.179  30.315 -45.074  0.50 34.49           N
ATOM   6209  CA   GLN a 342     -46.924  30.785 -43.891  0.50 35.26           C
ATOM   6210  CB   GLN a 342     -47.470  29.591 -43.084  0.50 34.00           C
ATOM   6211  CG   GLN a 342     -48.759  28.998 -43.633  0.50 44.24           C
ATOM   6212  CD   GLN a 342     -49.963  29.902 -43.384  0.50 53.19           C
ATOM   6213  OE1  GLN a 342     -50.030  30.604 -42.369  0.50 53.37           O
ATOM   6214  NE2  GLN a 342     -50.920  29.888 -44.312  0.50 51.95           N
ATOM   6215  C    GLN a 342     -46.010  31.625 -43.004  0.50 32.24           C
ATOM   6216  O    GLN a 342     -44.950  31.165 -42.629  0.50 30.11           O
ATOM   6217  N    PRO a 343     -46.426  32.848 -42.648  0.50 32.06           N
ATOM   6218  CA   PRO a 343     -45.514  33.665 -41.868  0.50 32.34           C
ATOM   6219  CB   PRO a 343     -46.223  35.025 -41.788  0.50 34.00           C
ATOM   6220  CG   PRO a 343     -47.320  34.970 -42.828  0.50 36.86           C
ATOM   6221  CD   PRO a 343     -47.721  33.519 -42.851  0.50 35.03           C
ATOM   6222  C    PRO a 343     -45.361  33.080 -40.466  0.50 36.14           C
ATOM   6223  O    PRO a 343     -46.331  32.590 -39.897  0.50 37.54           O
ATOM   6224  N    ARG a 344     -44.144  33.108 -39.940  0.50 31.36           N
ATOM   6225  CA   ARG a 344     -43.894  32.748 -38.557  0.50 31.81           C
ATOM   6226  CB   ARG a 344     -43.041  31.466 -38.465  0.50 32.59           C
ATOM   6227  CG   ARG a 344     -43.868  30.193 -38.653  0.50 34.72           C
ATOM   6228  CD   ARG a 344     -43.031  28.919 -38.796  0.50 47.51           C
ATOM   6229  NE   ARG a 344     -42.337  28.489 -37.560  0.50 45.26           N
ATOM   6230  CZ   ARG a 344     -41.495  27.447 -37.511  0.50 47.02           C
ATOM   6231  NH1  ARG a 344     -41.224  26.744 -38.624  0.50 37.96           N
ATOM   6232  NH2  ARG a 344     -40.886  27.131 -36.367  0.50 43.57           N
ATOM   6233  C    ARG a 344     -43.226  33.912 -37.808  0.50 32.08           C
ATOM   6234  O    ARG a 344     -42.305  34.560 -38.307  0.50 31.30           O
ATOM   6235  N    GLU a 345     -43.721  34.164 -36.608  0.50 30.07           N
ATOM   6236  CA   GLU a 345     -43.215  35.205 -35.755  0.50 31.65           C
ATOM   6237  CB   GLU a 345     -44.154  35.340 -34.556  0.50 30.45           C
ATOM   6238  CG   GLU a 345     -43.816  36.515 -33.682  0.50 37.38           C
ATOM   6239  CD   GLU a 345     -44.860  36.769 -32.607  0.50 42.07           C
ATOM   6240  OE1  GLU a 345     -44.609  37.645 -31.755  0.50 43.55           O
ATOM   6241  OE2  GLU a 345     -45.925  36.109 -32.620  0.50 43.99           O
ATOM   6242  C    GLU a 345     -41.772  34.982 -35.275  0.50 34.59           C
ATOM   6243  O    GLU a 345     -41.441  33.939 -34.720  0.50 39.10           O
ATOM   6244  N    PRO a 346     -40.903  35.976 -35.466  0.50 30.71           N
ATOM   6245  CA   PRO a 346     -39.572  35.858 -34.909  0.50 30.80           C
ATOM   6246  CB   PRO a 346     -38.815  37.022 -35.552  0.50 33.34           C
ATOM   6247  CG   PRO a 346     -39.857  37.992 -35.983  0.50 33.03           C
ATOM   6248  CD   PRO a 346     -41.081  37.175 -36.303  0.50 31.51           C
ATOM   6249  C    PRO a 346     -39.558  36.001 -33.374  0.50 36.24           C
ATOM   6250  O    PRO a 346     -40.452  36.639 -32.804  0.50 32.18           O
ATOM   6251  N    GLN a 347     -38.594  35.340 -32.726  0.50 32.89           N
ATOM   6252  CA   GLN a 347     -38.260  35.602 -31.328  0.50 33.06           C
ATOM   6253  CB   GLN a 347     -38.052  34.296 -30.544  0.50 39.47           C
ATOM   6254  CG   GLN a 347     -39.147  33.237 -30.701  0.50 43.33           C
ATOM   6255  CD   GLN a 347     -38.578  31.813 -30.683  0.50 59.42           C
ATOM   6256  OE1  GLN a 347     -38.739  31.058 -31.656  0.50 53.82           O
ATOM   6257  NE2  GLN a 347     -37.880  31.445 -29.581  0.50 54.08           N
ATOM   6258  C    GLN a 347     -36.924  36.330 -31.416  0.50 31.38           C
```

Figure 26 (Continued)

```
ATOM   6259  O    GLN a 347     -36.070  35.940 -32.233  0.50 32.91           O
ATOM   6260  N    VAL a 348     -36.735  37.337 -30.559  0.50 28.10           N
ATOM   6261  CA   VAL a 348     -35.556  38.210 -30.565  0.50 27.43           C
ATOM   6262  CB   VAL a 348     -36.022  39.671 -30.770  0.50 30.21           C
ATOM   6263  CG1  VAL a 348     -34.826  40.612 -30.797  0.50 28.54           C
ATOM   6264  CG2  VAL a 348     -36.879  39.784 -32.050  0.50 28.57           C
ATOM   6265  C    VAL a 348     -34.832  38.117 -29.218  0.50 30.06           C
ATOM   6266  O    VAL a 348     -35.471  38.310 -28.192  0.50 27.68           O
ATOM   6267  N    TYR a 349     -33.521  37.816 -29.206  0.50 28.32           N
ATOM   6268  CA   TYR a 349     -32.775  37.692 -27.944  0.50 33.72           C
ATOM   6269  CB   TYR a 349     -32.429  36.231 -27.625  0.50 31.21           C
ATOM   6270  CG   TYR a 349     -33.645  35.345 -27.520  0.50 33.13           C
ATOM   6271  CD1  TYR a 349     -34.545  35.503 -26.475  0.50 37.19           C
ATOM   6272  CE1  TYR a 349     -35.665  34.696 -26.365  0.50 35.55           C
ATOM   6273  CZ   TYR a 349     -35.904  33.720 -27.315  0.50 34.82           C
ATOM   6274  OH   TYR a 349     -37.012  32.920 -27.170  0.50 35.27           O
ATOM   6275  CE2  TYR a 349     -35.020  33.527 -28.374  0.50 33.58           C
ATOM   6276  CD2  TYR a 349     -33.900  34.338 -28.469  0.50 35.49           C
ATOM   6277  C    TYR a 349     -31.501  38.477 -28.101  0.50 36.55           C
ATOM   6278  O    TYR a 349     -30.864  38.407 -29.160  0.50 35.12           O
ATOM   6279  N    VAL a 350     -31.160  39.263 -27.079  0.50 30.45           N
ATOM   6280  CA   VAL a 350     -29.935  40.049 -27.107  0.50 30.53           C
ATOM   6281  CB   VAL a 350     -30.191  41.540 -26.782  0.50 32.02           C
ATOM   6282  CG1  VAL a 350     -30.931  42.182 -27.953  0.50 27.28           C
ATOM   6283  CG2  VAL a 350     -30.959  41.673 -25.460  0.50 29.25           C
ATOM   6284  C    VAL a 350     -28.917  39.483 -26.141  0.50 32.82           C
ATOM   6285  O    VAL a 350     -29.286  38.919 -25.128  0.50 31.74           O
ATOM   6286  N    TYR a 351     -27.642  39.591 -26.490  0.50 31.52           N
ATOM   6287  CA   TYR a 351     -26.588  38.933 -25.728  0.50 35.81           C
ATOM   6288  CB   TYR a 351     -25.928  37.844 -26.577  0.50 35.45           C
ATOM   6289  CG   TYR a 351     -26.745  36.585 -26.786  0.50 39.49           C
ATOM   6290  CD1  TYR a 351     -26.440  35.410 -26.099  0.50 40.23           C
ATOM   6291  CE1  TYR a 351     -27.154  34.252 -26.306  0.50 34.48           C
ATOM   6292  CZ   TYR a 351     -28.186  34.268 -27.214  0.50 38.58           C
ATOM   6293  OH   TYR a 351     -28.915  33.144 -27.447  0.50 37.63           O
ATOM   6294  CE2  TYR a 351     -28.494  35.413 -27.915  0.50 36.11           C
ATOM   6295  CD2  TYR a 351     -27.773  36.556 -27.695  0.50 34.86           C
ATOM   6296  C    TYR a 351     -25.509  39.916 -25.322  0.50 34.20           C
ATOM   6297  O    TYR a 351     -24.915  40.590 -26.167  0.50 34.84           O
ATOM   6298  N    PRO a 352     -25.194  39.968 -24.029  0.50 38.87           N
ATOM   6299  CA   PRO a 352     -24.097  40.880 -23.679  0.50 36.54           C
ATOM   6300  CB   PRO a 352     -24.169  40.954 -22.146  0.50 34.14           C
ATOM   6301  CG   PRO a 352     -24.875  39.707 -21.719  0.50 33.44           C
ATOM   6302  CD   PRO a 352     -25.822  39.342 -22.850  0.50 37.03           C
ATOM   6303  C    PRO a 352     -22.789  40.260 -24.136  0.50 41.18           C
ATOM   6304  O    PRO a 352     -22.763  39.074 -24.480  0.50 39.90           O
ATOM   6305  N    PRO a 353     -21.704  41.048 -24.138  0.50 40.62           N
ATOM   6306  CA   PRO a 353     -20.424  40.518 -24.571  0.50 42.69           C
ATOM   6307  CB   PRO a 353     -19.495  41.753 -24.541  0.50 43.09           C
ATOM   6308  CG   PRO a 353     -20.373  42.936 -24.244  0.50 40.08           C
ATOM   6309  CD   PRO a 353     -21.560  42.375 -23.519  0.50 42.76           C
ATOM   6310  C    PRO a 353     -19.915  39.444 -23.610  0.50 40.90           C
ATOM   6311  O    PRO a 353     -20.275  39.423 -22.437  0.50 39.47           O
ATOM   6312  N    SER a 354     -19.142  38.518 -24.147  0.50 39.82           N
ATOM   6313  CA   SER a 354     -18.434  37.513 -23.375  0.50 38.64           C
ATOM   6314  CB   SER a 354     -17.546  36.737 -24.338  0.50 35.98           C
ATOM   6315  OG   SER a 354     -16.628  35.923 -23.649  0.50 41.37           O
ATOM   6316  C    SER a 354     -17.532  38.174 -22.332  0.50 42.58           C
ATOM   6317  O    SER a 354     -16.922  39.208 -22.600  0.50 44.38           O
ATOM   6318  N    ARG a 355     -17.427  37.554 -21.159  0.50 47.14           N
ATOM   6319  CA   ARG a 355     -16.430  37.944 -20.160  0.50 52.57           C
ATOM   6320  CB   ARG a 355     -16.284  36.838 -19.104  0.50 55.08           C
ATOM   6321  CG   ARG a 355     -16.302  37.335 -17.660  0.50 61.99           C
ATOM   6322  CD   ARG a 355     -15.661  36.342 -16.685  0.50 65.23           C
```

Figure 26 (Continued)

```
ATOM   6323  NE   ARG a 355     -16.423  35.100 -16.536  0.50 62.88           N
ATOM   6324  CZ   ARG a 355     -16.154  33.969 -17.189  0.50 59.55           C
ATOM   6325  NH1  ARG a 355     -15.144  33.914 -18.046  0.50 60.73           N
ATOM   6326  NH2  ARG a 355     -16.897  32.893 -16.992  0.50 58.92           N
ATOM   6327  C    ARG a 355     -15.095  38.159 -20.855  0.50 51.70           C
ATOM   6328  O    ARG a 355     -14.435  39.187 -20.674  0.50 47.41           O
ATOM   6329  N    ASP a 356     -14.717  37.175 -21.671  0.50 48.23           N
ATOM   6330  CA   ASP a 356     -13.443  37.170 -22.367  0.50 45.68           C
ATOM   6331  CB   ASP a 356     -13.350  35.934 -23.272  0.50 48.04           C
ATOM   6332  CG   ASP a 356     -13.089  34.665 -22.502  0.50 53.94           C
ATOM   6333  OD1  ASP a 356     -13.429  34.619 -21.293  0.50 54.22           O
ATOM   6334  OD2  ASP a 356     -12.526  33.718 -23.104  0.50 53.50           O
ATOM   6335  C    ASP a 356     -13.216  38.408 -23.220  0.50 48.07           C
ATOM   6336  O    ASP a 356     -12.069  38.777 -23.471  0.50 46.90           O
ATOM   6337  N    GLU a 357     -14.292  39.008 -23.732  0.50 41.57           N
ATOM   6338  CA   GLU a 357     -14.138  40.136 -24.674  0.50 45.38           C
ATOM   6339  CB   GLU a 357     -15.380  40.300 -25.583  0.50 36.80           C
ATOM   6340  CG   GLU a 357     -15.026  40.813 -26.973  0.50 37.59           C
ATOM   6341  CD   GLU a 357     -16.237  41.063 -27.882  0.50 36.62           C
ATOM   6342  OE1  GLU a 357     -17.387  41.016 -27.412  0.50 40.32           O
ATOM   6343  OE2  GLU a 357     -16.040  41.388 -29.071  0.50 35.44           O
ATOM   6344  C    GLU a 357     -13.760  41.477 -24.007  0.50 42.74           C
ATOM   6345  O    GLU a 357     -13.109  42.332 -24.621  0.50 40.37           O
ATOM   6346  N    LEU a 358     -14.165  41.661 -22.754  0.50 47.35           N
ATOM   6347  CA   LEU a 358     -13.853  42.895 -22.025  0.50 50.71           C
ATOM   6348  CB   LEU a 358     -14.160  42.696 -20.546  0.50 51.66           C
ATOM   6349  CG   LEU a 358     -15.669  42.607 -20.329  0.50 46.56           C
ATOM   6350  CD1  LEU a 358     -16.019  42.420 -18.866  0.50 48.18           C
ATOM   6351  CD2  LEU a 358     -16.328  43.856 -20.900  0.50 44.55           C
ATOM   6352  C    LEU a 358     -12.389  43.329 -22.216  0.50 60.60           C
ATOM   6353  O    LEU a 358     -12.077  44.517 -22.416  0.50 61.38           O
ATOM   6354  N    THR a 359     -11.506  42.340 -22.160  0.50 57.63           N
ATOM   6355  CA   THR a 359     -10.090  42.502 -22.430  0.50 58.30           C
ATOM   6356  CB   THR a 359      -9.471  41.118 -22.738  0.50 60.24           C
ATOM   6357  OG1  THR a 359      -9.567  40.284 -21.571  0.50 62.99           O
ATOM   6358  CG2  THR a 359      -8.016  41.239 -23.185  0.50 56.38           C
ATOM   6359  C    THR a 359      -9.764  43.419 -23.603  0.50 62.04           C
ATOM   6360  O    THR a 359      -8.584  43.657 -23.882  0.50 54.31           O
ATOM   6361  N    LYS a 360     -10.784  43.919 -24.303  0.50 56.17           N
ATOM   6362  CA   LYS a 360     -10.548  44.572 -25.596  0.50 54.20           C
ATOM   6363  CB   LYS a 360     -11.210  43.769 -26.723  0.50 58.01           C
ATOM   6364  CG   LYS a 360     -10.833  42.291 -26.748  0.50 61.86           C
ATOM   6365  CD   LYS a 360      -9.656  42.058 -27.691  0.50 67.95           C
ATOM   6366  CE   LYS a 360      -8.928  40.752 -27.412  0.50 64.00           C
ATOM   6367  NZ   LYS a 360      -7.806  40.572 -28.383  0.50 62.47           N
ATOM   6368  C    LYS a 360     -10.994  46.043 -25.632  0.50 51.95           C
ATOM   6369  O    LYS a 360     -11.770  46.484 -24.790  0.50 56.64           O
ATOM   6370  N    ASN a 361     -10.482  46.801 -26.596  0.50 51.53           N
ATOM   6371  CA   ASN a 361     -10.872  48.195 -26.744  0.50 58.33           C
ATOM   6372  CB   ASN a 361     -10.179  48.831 -27.962  0.50 64.09           C
ATOM   6373  CG   ASN a 361      -8.667  48.849 -27.837  0.50 76.92           C
ATOM   6374  OD1  ASN a 361      -8.117  48.474 -26.797  0.50 81.10           O
ATOM   6375  ND2  ASN a 361      -7.981  49.290 -28.903  0.50 67.34           N
ATOM   6376  C    ASN a 361     -12.379  48.273 -26.949  0.50 59.14           C
ATOM   6377  O    ASN a 361     -13.005  49.329 -26.747  0.50 53.57           O
ATOM   6378  N    GLN a 362     -12.950  47.142 -27.359  0.50 50.08           N
ATOM   6379  CA   GLN a 362     -14.257  47.122 -27.994  0.50 50.89           C
ATOM   6380  CB   GLN a 362     -14.120  47.299 -29.503  0.50 53.83           C
ATOM   6381  CG   GLN a 362     -13.840  48.726 -29.929  0.50 58.08           C
ATOM   6382  CD   GLN a 362     -13.958  48.893 -31.425  0.50 60.93           C
ATOM   6383  OE1  GLN a 362     -13.702  47.956 -32.181  0.50 57.63           O
ATOM   6384  NE2  GLN a 362     -14.364  50.082 -31.863  0.50 67.94           N
ATOM   6385  C    GLN a 362     -14.950  45.811 -27.722  0.50 53.02           C
ATOM   6386  O    GLN a 362     -14.310  44.770 -27.580  0.50 45.81           O
```

Figure 26 (Continued)

```
ATOM   6387  N    VAL a 363     -16.275  45.859 -27.688  0.50 49.39           N
ATOM   6388  CA   VAL a 363     -17.035  44.669 -27.431  0.50 43.21           C
ATOM   6389  CB   VAL a 363     -17.541  44.632 -25.986  0.50 41.06           C
ATOM   6390  CG1  VAL a 363     -16.357  44.683 -25.030  0.50 41.18           C
ATOM   6391  CG2  VAL a 363     -18.490  45.798 -25.740  0.50 45.07           C
ATOM   6392  C    VAL a 363     -18.180  44.514 -28.420  0.50 43.71           C
ATOM   6393  O    VAL a 363     -18.474  45.429 -29.211  0.50 38.24           O
ATOM   6394  N    SER a 364     -18.785  43.325 -28.367  0.50 37.50           N
ATOM   6395  CA   SER a 364     -19.718  42.834 -29.353  0.50 35.57           C
ATOM   6396  CB   SER a 364     -19.145  41.551 -29.998  0.50 37.57           C
ATOM   6397  OG   SER a 364     -17.924  41.841 -30.680  0.50 37.88           O
ATOM   6398  C    SER a 364     -21.048  42.523 -28.687  0.50 32.01           C
ATOM   6399  O    SER a 364     -21.143  41.630 -27.848  0.50 32.76           O
ATOM   6400  N    LEU a 365     -22.074  43.286 -29.040  0.50 31.79           N
ATOM   6401  CA   LEU a 365     -23.416  43.003 -28.546  0.50 32.04           C
ATOM   6402  CB   LEU a 365     -24.211  44.302 -28.328  0.50 28.84           C
ATOM   6403  CG   LEU a 365     -23.604  45.238 -27.280  0.50 38.44           C
ATOM   6404  CD1  LEU a 365     -24.355  46.567 -27.245  0.50 37.20           C
ATOM   6405  CD2  LEU a 365     -23.626  44.576 -25.911  0.50 29.03           C
ATOM   6406  C    LEU a 365     -24.072  42.180 -29.633  0.50 30.07           C
ATOM   6407  O    LEU a 365     -23.899  42.483 -30.804  0.50 31.30           O
ATOM   6408  N    THR a 366     -24.889  41.214 -29.234  0.50 29.76           N
ATOM   6409  CA   THR a 366     -25.382  40.183 -30.152  0.50 28.89           C
ATOM   6410  CB   THR a 366     -24.792  38.799 -29.767  0.50 25.73           C
ATOM   6411  OG1  THR a 366     -23.376  38.845 -29.912  0.50 23.57           O
ATOM   6412  CG2  THR a 366     -25.356  37.665 -30.603  0.50 22.79           C
ATOM   6413  C    THR a 366     -26.900  40.135 -30.111  0.50 28.61           C
ATOM   6414  O    THR a 366     -27.487  40.053 -29.032  0.50 28.41           O
ATOM   6415  N    CYS a 367     -27.524  40.246 -31.288  0.50 27.34           N
ATOM   6416  CA   CYS a 367     -28.974  40.180 -31.398  0.50 28.66           C
ATOM   6417  CB   CYS a 367     -29.538  41.384 -32.157  0.50 28.18           C
ATOM   6418  SG   CYS a 367     -31.355  41.528 -32.144  0.50 31.29           S
ATOM   6419  C    CYS a 367     -29.342  38.942 -32.168  0.50 28.81           C
ATOM   6420  O    CYS a 367     -28.989  38.828 -33.337  0.50 28.12           O
ATOM   6421  N    LEU a 368     -30.077  38.038 -31.519  0.50 33.34           N
ATOM   6422  CA   LEU a 368     -30.479  36.764 -32.138  0.50 32.50           C
ATOM   6423  CB   LEU a 368     -30.384  35.625 -31.114  0.50 29.68           C
ATOM   6424  CG   LEU a 368     -30.787  34.243 -31.632  0.50 29.12           C
ATOM   6425  CD1  LEU a 368     -30.132  33.948 -32.974  0.50 27.69           C
ATOM   6426  CD2  LEU a 368     -30.433  33.164 -30.620  0.50 29.29           C
ATOM   6427  C    LEU a 368     -31.915  36.853 -32.590  0.50 30.21           C
ATOM   6428  O    LEU a 368     -32.798  37.090 -31.774  0.50 26.91           O
ATOM   6429  N    VAL a 369     -32.163  36.697 -33.888  0.50 25.59           N
ATOM   6430  CA   VAL a 369     -33.530  36.675 -34.356  0.50 24.93           C
ATOM   6431  CB   VAL a 369     -33.821  37.804 -35.375  0.50 25.83           C
ATOM   6432  CG1  VAL a 369     -35.316  37.909 -35.625  0.50 23.23           C
ATOM   6433  CG2  VAL a 369     -33.259  39.161 -34.881  0.50 23.76           C
ATOM   6434  C    VAL a 369     -33.783  35.297 -34.999  0.50 26.84           C
ATOM   6435  O    VAL a 369     -33.134  34.912 -35.973  0.50 26.90           O
ATOM   6436  N    LYS a 370     -34.742  34.565 -34.474  0.50 27.52           N
ATOM   6437  CA   LYS a 370     -34.909  33.191 -34.941  0.50 31.25           C
ATOM   6438  CB   LYS a 370     -34.233  32.213 -33.948  0.50 34.20           C
ATOM   6439  CG   LYS a 370     -34.975  32.110 -32.606  0.50 30.60           C
ATOM   6440  CD   LYS a 370     -34.489  30.909 -31.776  0.50 36.51           C
ATOM   6441  CE   LYS a 370     -35.313  29.653 -32.057  0.50 37.23           C
ATOM   6442  NZ   LYS a 370     -35.323  28.714 -30.906  0.50 33.02           N
ATOM   6443  C    LYS a 370     -36.359  32.807 -35.078  0.50 28.62           C
ATOM   6444  O    LYS a 370     -37.240  33.380 -34.420  0.50 28.83           O
ATOM   6445  N    GLY a 371     -36.609  31.759 -35.852  0.50 26.28           N
ATOM   6446  CA   GLY a 371     -37.952  31.248 -35.946  0.50 25.51           C
ATOM   6447  C    GLY a 371     -38.875  32.049 -36.849  0.50 26.19           C
ATOM   6448  O    GLY a 371     -40.080  31.965 -36.695  0.50 26.25           O
ATOM   6449  N    PHE a 372     -38.333  32.821 -37.790  0.50 28.65           N
ATOM   6450  CA   PHE a 372     -39.195  33.664 -38.630  0.50 28.49           C
```

Figure 26 (Continued)

```
ATOM   6451  CB   PHE a 372     -38.762  35.163 -38.612  0.50 27.70           C
ATOM   6452  CG   PHE a 372     -37.406  35.440 -39.227  0.50 26.81           C
ATOM   6453  CD1  PHE a 372     -36.267  35.368 -38.457  0.50 25.71           C
ATOM   6454  CE1  PHE a 372     -35.023  35.616 -39.001  0.50 25.76           C
ATOM   6455  CZ   PHE a 372     -34.904  35.986 -40.330  0.50 27.88           C
ATOM   6456  CE2  PHE a 372     -36.031  36.085 -41.118  0.50 25.02           C
ATOM   6457  CD2  PHE a 372     -37.281  35.805 -40.565  0.50 25.95           C
ATOM   6458  C    PHE a 372     -39.311  33.140 -40.060  0.50 30.04           C
ATOM   6459  O    PHE a 372     -38.474  32.387 -40.529  0.50 25.43           O
ATOM   6460  N    TYR a 373     -40.388  33.529 -40.722  0.50 31.81           N
ATOM   6461  CA   TYR a 373     -40.637  33.160 -42.093  0.50 38.30           C
ATOM   6462  CB   TYR a 373     -41.447  31.864 -42.195  0.50 39.80           C
ATOM   6463  CG   TYR a 373     -41.194  31.187 -43.513  0.50 38.93           C
ATOM   6464  CD1  TYR a 373     -42.057  31.370 -44.577  0.50 42.55           C
ATOM   6465  CE1  TYR a 373     -41.817  30.771 -45.808  0.50 44.01           C
ATOM   6466  CZ   TYR a 373     -40.679  29.991 -45.981  0.50 43.63           C
ATOM   6467  OH   TYR a 373     -40.453  29.392 -47.202  0.50 49.58           O
ATOM   6468  CE2  TYR a 373     -39.812  29.776 -44.933  0.50 39.92           C
ATOM   6469  CD2  TYR a 373     -40.054  30.400 -43.709  0.50 39.72           C
ATOM   6470  C    TYR a 373     -41.432  34.305 -42.685  0.50 41.65           C
ATOM   6471  O    TYR a 373     -42.279  34.844 -41.987  0.50 44.81           O
ATOM   6472  N    PRO a 374     -41.491  34.362 -44.010  0.50 43.01           N
ATOM   6473  CA   PRO a 374     -40.448  34.756 -44.935  0.50 41.42           C
ATOM   6474  CB   PRO a 374     -41.133  35.768 -45.865  0.50 50.32           C
ATOM   6475  CG   PRO a 374     -42.232  36.322 -45.038  0.50 49.26           C
ATOM   6476  CD   PRO a 374     -42.733  35.109 -44.295  0.50 43.12           C
ATOM   6477  C    PRO a 374     -39.190  35.333 -44.327  0.50 40.13           C
ATOM   6478  O    PRO a 374     -39.182  35.825 -43.203  0.50 41.31           O
ATOM   6479  N    SER a 375     -38.129  35.259 -45.106  0.50 32.91           N
ATOM   6480  CA   SER a 375     -36.859  35.708 -44.669  0.50 34.74           C
ATOM   6481  CB   SER a 375     -35.753  35.044 -45.487  0.50 32.89           C
ATOM   6482  OG   SER a 375     -35.845  35.474 -46.832  0.50 35.35           O
ATOM   6483  C    SER a 375     -36.779  37.231 -44.780  0.50 31.53           C
ATOM   6484  O    SER a 375     -35.839  37.788 -44.323  0.50 31.00           O
ATOM   6485  N    ASP a 376     -37.771  37.887 -45.381  0.50 32.93           N
ATOM   6486  CA   ASP a 376     -37.769  39.361 -45.488  0.50 31.45           C
ATOM   6487  CB   ASP a 376     -39.019  39.848 -46.217  0.50 31.84           C
ATOM   6488  CG   ASP a 376     -39.008  39.497 -47.708  0.50 35.47           C
ATOM   6489  OD1  ASP a 376     -37.903  39.348 -48.289  0.50 38.63           O
ATOM   6490  OD2  ASP a 376     -40.101  39.411 -48.297  0.50 35.86           O
ATOM   6491  C    ASP a 376     -37.802  39.956 -44.098  0.50 29.05           C
ATOM   6492  O    ASP a 376     -38.733  39.706 -43.355  0.50 25.56           O
ATOM   6493  N    ILE a 377     -36.814  40.765 -43.745  0.50 26.49           N
ATOM   6494  CA   ILE a 377     -36.767  41.284 -42.391  0.50 28.40           C
ATOM   6495  CB   ILE a 377     -36.198  40.211 -41.435  0.50 26.87           C
ATOM   6496  CG1  ILE a 377     -36.416  40.568 -39.958  0.50 24.42           C
ATOM   6497  CD1  ILE a 377     -36.166  39.385 -39.039  0.50 27.74           C
ATOM   6498  CG2  ILE a 377     -34.740  39.903 -41.755  0.50 26.03           C
ATOM   6499  C    ILE a 377     -35.863  42.525 -42.416  0.50 29.42           C
ATOM   6500  O    ILE a 377     -35.095  42.697 -43.351  0.50 29.46           O
ATOM   6501  N    ALA a 378     -35.987  43.390 -41.416  0.50 28.33           N
ATOM   6502  CA   ALA a 378     -35.015  44.479 -41.211  0.50 29.61           C
ATOM   6503  CB   ALA a 378     -35.652  45.827 -41.568  0.50 31.11           C
ATOM   6504  C    ALA a 378     -34.577  44.506 -39.752  0.50 29.24           C
ATOM   6505  O    ALA a 378     -35.395  44.432 -38.866  0.50 32.82           O
ATOM   6506  N    VAL a 379     -33.291  44.664 -39.501  0.50 25.56           N
ATOM   6507  CA   VAL a 379     -32.833  44.666 -38.153  0.50 30.12           C
ATOM   6508  CB   VAL a 379     -32.066  43.348 -37.864  0.50 28.87           C
ATOM   6509  CG1  VAL a 379     -31.483  43.356 -36.475  0.50 28.27           C
ATOM   6510  CG2  VAL a 379     -33.056  42.185 -38.027  0.50 24.18           C
ATOM   6511  C    VAL a 379     -31.955  45.917 -38.064  0.50 34.26           C
ATOM   6512  O    VAL a 379     -31.308  46.291 -39.040  0.50 33.26           O
ATOM   6513  N    GLU a 380     -32.013  46.604 -36.928  0.50 32.97           N
ATOM   6514  CA   GLU a 380     -31.368  47.924 -36.793  0.50 30.09           C
```

Figure 26 (Continued)

```
ATOM   6515  CB   GLU a 380     -32.351  49.062 -37.142  0.50 31.23           C
ATOM   6516  CG   GLU a 380     -32.432  49.418 -38.622  0.50 31.91           C
ATOM   6517  CD   GLU a 380     -33.575  50.366 -38.926  0.50 35.66           C
ATOM   6518  OE1  GLU a 380     -34.078  51.032 -37.991  0.50 36.67           O
ATOM   6519  OE2  GLU a 380     -33.976  50.454 -40.101  0.50 35.45           O
ATOM   6520  C    GLU a 380     -30.957  48.028 -35.355  0.50 30.18           C
ATOM   6521  O    GLU a 380     -31.579  47.403 -34.493  0.50 30.28           O
ATOM   6522  N    TRP a 381     -29.938  48.839 -35.083  0.50 30.57           N
ATOM   6523  CA   TRP a 381     -29.543  49.122 -33.710  0.50 30.89           C
ATOM   6524  CB   TRP a 381     -28.124  48.640 -33.467  0.50 30.87           C
ATOM   6525  CG   TRP a 381     -27.917  47.154 -33.424  0.50 31.08           C
ATOM   6526  CD1  TRP a 381     -27.717  46.310 -34.501  0.50 33.12           C
ATOM   6527  NE1  TRP a 381     -27.496  45.020 -34.054  0.50 31.12           N
ATOM   6528  CE2  TRP a 381     -27.585  45.004 -32.682  0.50 29.09           C
ATOM   6529  CD2  TRP a 381     -27.849  46.328 -32.252  0.50 28.19           C
ATOM   6530  CE3  TRP a 381     -27.970  46.580 -30.882  0.50 28.79           C
ATOM   6531  CZ3  TRP a 381     -27.843  45.520 -29.987  0.50 28.68           C
ATOM   6532  CH2  TRP a 381     -27.546  44.218 -30.437  0.50 30.30           C
ATOM   6533  CZ2  TRP a 381     -27.419  43.940 -31.780  0.50 31.00           C
ATOM   6534  C    TRP a 381     -29.573  50.646 -33.429  0.50 35.59           C
ATOM   6535  O    TRP a 381     -29.344  51.477 -34.330  0.50 31.31           O
ATOM   6536  N    GLU a 382     -29.769  50.998 -32.159  0.50 34.75           N
ATOM   6537  CA   GLU a 382     -29.720  52.412 -31.738  0.50 37.93           C
ATOM   6538  CB   GLU a 382     -31.012  53.168 -32.090  0.50 36.70           C
ATOM   6539  CG   GLU a 382     -32.251  52.760 -31.289  0.50 36.27           C
ATOM   6540  CD   GLU a 382     -33.241  51.936 -32.114  0.50 46.39           C
ATOM   6541  OE1  GLU a 382     -33.895  52.502 -33.022  0.50 44.82           O
ATOM   6542  OE2  GLU a 382     -33.357  50.710 -31.861  0.50 43.13           O
ATOM   6543  C    GLU a 382     -29.472  52.526 -30.258  0.50 36.66           C
ATOM   6544  O    GLU a 382     -29.629  51.565 -29.513  0.50 31.39           O
ATOM   6545  N    SER a 383     -29.116  53.730 -29.834  0.50 40.35           N
ATOM   6546  CA   SER a 383     -28.893  54.005 -28.423  0.50 40.95           C
ATOM   6547  CB   SER a 383     -27.453  53.679 -28.022  0.50 38.52           C
ATOM   6548  OG   SER a 383     -27.363  53.556 -26.602  0.50 43.78           O
ATOM   6549  C    SER a 383     -29.116  55.491 -28.248  0.50 44.55           C
ATOM   6550  O    SER a 383     -28.681  56.288 -29.091  0.50 40.30           O
ATOM   6551  N    ASN a 384     -29.820  55.855 -27.184  0.50 44.20           N
ATOM   6552  CA   ASN a 384     -29.969  57.265 -26.830  0.50 46.03           C
ATOM   6553  CB   ASN a 384     -28.599  57.859 -26.492  0.50 49.48           C
ATOM   6554  CG   ASN a 384     -28.090  57.398 -25.151  0.50 55.24           C
ATOM   6555  OD1  ASN a 384     -28.874  56.999 -24.286  0.50 61.17           O
ATOM   6556  ND2  ASN a 384     -26.772  57.429 -24.971  0.50 63.54           N
ATOM   6557  C    ASN a 384     -30.605  58.094 -27.936  0.50 51.06           C
ATOM   6558  O    ASN a 384     -30.185  59.235 -28.187  0.50 44.21           O
ATOM   6559  N    GLY a 385     -31.584  57.525 -28.630  0.50 47.24           N
ATOM   6560  CA   GLY a 385     -32.303  58.303 -29.643  0.50 43.84           C
ATOM   6561  C    GLY a 385     -31.604  58.491 -30.981  0.50 39.56           C
ATOM   6562  O    GLY a 385     -32.001  59.326 -31.780  0.50 48.55           O
ATOM   6563  N    GLN a 386     -30.570  57.711 -31.238  0.50 39.55           N
ATOM   6564  CA   GLN a 386     -29.895  57.757 -32.530  0.50 41.62           C
ATOM   6565  CB   GLN a 386     -28.797  58.849 -32.570  0.50 46.44           C
ATOM   6566  CG   GLN a 386     -27.883  58.767 -33.808  0.50 52.33           C
ATOM   6567  CD   GLN a 386     -26.995  60.006 -34.000  0.50 59.49           C
ATOM   6568  OE1  GLN a 386     -27.129  61.004 -33.278  0.50 45.03           O
ATOM   6569  NE2  GLN a 386     -26.077  59.937 -34.966  0.50 53.22           N
ATOM   6570  C    GLN a 386     -29.297  56.403 -32.929  0.50 39.46           C
ATOM   6571  O    GLN a 386     -28.822  55.635 -32.087  0.50 43.19           O
ATOM   6572  N    PRO a 387     -29.299  56.132 -34.235  0.50 38.37           N
ATOM   6573  CA   PRO a 387     -28.849  54.886 -34.859  0.50 38.95           C
ATOM   6574  CB   PRO a 387     -29.192  55.088 -36.335  0.50 38.12           C
ATOM   6575  CG   PRO a 387     -30.296  56.093 -36.348  0.50 42.33           C
ATOM   6576  CD   PRO a 387     -30.091  56.974 -35.150  0.50 37.62           C
ATOM   6577  C    PRO a 387     -27.348  54.673 -34.725  0.50 41.06           C
ATOM   6578  O    PRO a 387     -26.561  55.622 -34.828  0.50 35.19           O
```

Figure 26 (Continued)

```
ATOM   6579  N    GLU a 388     -26.954  53.418 -34.535  0.50 40.08           N
ATOM   6580  CA   GLU a 388     -25.546  53.050 -34.474  0.50 34.25           C
ATOM   6581  CB   GLU a 388     -25.348  51.936 -33.432  0.50 36.86           C
ATOM   6582  CG   GLU a 388     -25.775  52.403 -32.028  0.50 34.66           C
ATOM   6583  CD   GLU a 388     -24.748  53.365 -31.404  0.50 41.62           C
ATOM   6584  OE1  GLU a 388     -23.622  52.895 -31.155  0.50 39.11           O
ATOM   6585  OE2  GLU a 388     -25.042  54.583 -31.149  0.50 39.01           O
ATOM   6586  C    GLU a 388     -24.835  52.813 -35.850  0.50 34.87           C
ATOM   6587  O    GLU a 388     -25.438  52.465 -36.850  0.50 34.84           O
ATOM   6588  N    ASN a 389     -23.548  53.111 -35.928  0.50 41.91           N
ATOM   6589  CA   ASN a 389     -22.885  53.020 -37.238  0.50 48.78           C
ATOM   6590  CB   ASN a 389     -21.840  54.114 -37.425  0.50 42.27           C
ATOM   6591  CG   ASN a 389     -21.488  54.330 -38.892  0.50 47.58           C
ATOM   6592  OD1  ASN a 389     -22.339  54.153 -39.773  0.50 46.65           O
ATOM   6593  ND2  ASN a 389     -20.235  54.716 -39.162  0.50 44.89           N
ATOM   6594  C    ASN a 389     -22.216  51.670 -37.406  0.50 48.53           C
ATOM   6595  O    ASN a 389     -21.851  51.255 -38.516  0.50 45.93           O
ATOM   6596  N    ASN a 390     -22.055  50.983 -36.286  0.50 40.98           N
ATOM   6597  CA   ASN a 390     -21.091  49.934 -36.265  0.50 42.82           C
ATOM   6598  CB   ASN a 390     -20.049  50.227 -35.178  0.50 45.79           C
ATOM   6599  CG   ASN a 390     -18.655  49.853 -35.604  0.50 47.84           C
ATOM   6600  OD1  ASN a 390     -18.368  49.745 -36.795  0.50 58.06           O
ATOM   6601  ND2  ASN a 390     -17.771  49.667 -34.632  0.50 55.57           N
ATOM   6602  C    ASN a 390     -21.726  48.561 -36.092  0.50 34.38           C
ATOM   6603  O    ASN a 390     -21.490  47.891 -35.101  0.50 34.32           O
ATOM   6604  N    TYR a 391     -22.538  48.134 -37.054  0.50 36.59           N
ATOM   6605  CA   TYR a 391     -23.138  46.795 -36.950  0.50 33.95           C
ATOM   6606  CB   TYR a 391     -24.548  46.771 -36.292  0.50 31.91           C
ATOM   6607  CG   TYR a 391     -25.689  47.380 -37.101  0.50 35.26           C
ATOM   6608  CD1  TYR a 391     -26.389  46.631 -38.045  0.50 31.28           C
ATOM   6609  CE1  TYR a 391     -27.439  47.184 -38.764  0.50 31.91           C
ATOM   6610  CZ   TYR a 391     -27.830  48.499 -38.493  0.50 35.50           C
ATOM   6611  OH   TYR a 391     -28.861  49.073 -39.186  0.50 34.49           O
ATOM   6612  CE2  TYR a 391     -27.168  49.255 -37.545  0.50 31.00           C
ATOM   6613  CD2  TYR a 391     -26.118  48.696 -36.852  0.50 31.68           C
ATOM   6614  C    TYR a 391     -23.118  45.994 -38.221  0.50 33.24           C
ATOM   6615  O    TYR a 391     -23.157  46.542 -39.333  0.50 32.31           O
ATOM   6616  N    LYS a 392     -23.070  44.674 -38.044  0.50 29.99           N
ATOM   6617  CA   LYS a 392     -23.132  43.768 -39.184  0.50 28.03           C
ATOM   6618  CB   LYS a 392     -21.743  43.218 -39.506  0.50 29.06           C
ATOM   6619  CG   LYS a 392     -20.738  44.284 -39.957  0.50 31.20           C
ATOM   6620  CD   LYS a 392     -20.909  44.676 -41.420  0.50 32.48           C
ATOM   6621  CE   LYS a 392     -19.818  45.654 -41.829  0.50 30.90           C
ATOM   6622  NZ   LYS a 392     -19.331  45.196 -43.149  0.50 40.31           N
ATOM   6623  C    LYS a 392     -24.138  42.624 -38.943  0.50 26.99           C
ATOM   6624  O    LYS a 392     -24.344  42.117 -37.803  0.50 26.79           O
ATOM   6625  N    THR a 393     -24.801  42.240 -40.011  0.50 26.26           N
ATOM   6626  CA   THR a 393     -25.850  41.243 -39.895  0.50 27.95           C
ATOM   6627  CB   THR a 393     -27.244  41.827 -40.248  0.50 28.47           C
ATOM   6628  OG1  THR a 393     -27.377  43.162 -39.759  0.50 28.38           O
ATOM   6629  CG2  THR a 393     -28.357  40.982 -39.633  0.50 28.51           C
ATOM   6630  C    THR a 393     -25.555  40.137 -40.878  0.50 30.69           C
ATOM   6631  O    THR a 393     -25.239  40.397 -42.035  0.50 32.19           O
ATOM   6632  N    THR a 394     -25.726  38.898 -40.437  0.50 31.38           N
ATOM   6633  CA   THR a 394     -25.650  37.778 -41.336  0.50 28.36           C
ATOM   6634  CB   THR a 394     -25.563  36.470 -40.543  0.50 23.41           C
ATOM   6635  OG1  THR a 394     -26.865  36.095 -40.105  0.50 23.25           O
ATOM   6636  CG2  THR a 394     -24.727  36.677 -39.329  0.50 27.21           C
ATOM   6637  C    THR a 394     -26.924  37.767 -42.165  0.50 28.73           C
ATOM   6638  O    THR a 394     -27.982  38.058 -41.650  0.50 29.21           O
ATOM   6639  N    PRO a 395     -26.825  37.443 -43.465  0.50 29.78           N
ATOM   6640  CA   PRO a 395     -28.071  37.236 -44.160  0.50 30.76           C
ATOM   6641  CB   PRO a 395     -27.630  36.843 -45.580  0.50 32.93           C
ATOM   6642  CG   PRO a 395     -26.224  37.368 -45.716  0.50 34.51           C
```

Figure 26 (Continued)

```
ATOM   6643  CD  PRO a 395     -25.637  37.251 -44.331  0.50 32.53           C
ATOM   6644  C   PRO a 395     -28.781  36.066 -43.459  0.50 32.36           C
ATOM   6645  O   PRO a 395     -28.135  35.251 -42.787  0.50 33.69           O
ATOM   6646  N   PRO a 396     -30.101  36.019 -43.562  0.50 26.55           N
ATOM   6647  CA  PRO a 396     -30.926  35.014 -42.903  0.50 31.49           C
ATOM   6648  CB  PRO a 396     -32.345  35.472 -43.206  0.50 29.47           C
ATOM   6649  CG  PRO a 396     -32.218  36.218 -44.494  0.50 28.45           C
ATOM   6650  CD  PRO a 396     -30.890  36.925 -44.406  0.50 27.62           C
ATOM   6651  C   PRO a 396     -30.676  33.669 -43.553  0.50 33.98           C
ATOM   6652  O   PRO a 396     -30.528  33.613 -44.770  0.50 29.53           O
ATOM   6653  N   VAL a 397     -30.467  32.448 -42.756  0.50 36.84           N
ATOM   6654  CA  VAL a 397     -30.389  31.071 -43.236  0.50 35.94           C
ATOM   6655  CB  VAL a 397     -29.023  30.454 -42.910  0.50 37.71           C
ATOM   6656  CG1 VAL a 397     -27.933  31.197 -43.652  0.50 41.54           C
ATOM   6657  CG2 VAL a 397     -28.772  30.422 -41.403  0.50 38.47           C
ATOM   6658  C   VAL a 397     -31.453  30.251 -42.523  0.50 33.84           C
ATOM   6659  O   VAL a 397     -31.756  30.481 -41.356  0.50 33.87           O
ATOM   6660  N   LEU a 398     -31.666  29.284 -43.359  0.50 34.36           N
ATOM   6661  CA  LEU a 398     -32.650  28.292 -42.978  0.50 34.60           C
ATOM   6662  CB  LEU a 398     -32.786  27.314 -44.147  0.50 41.75           C
ATOM   6663  CG  LEU a 398     -34.142  26.749 -44.536  0.50 48.94           C
ATOM   6664  CD1 LEU a 398     -35.244  27.773 -44.303  0.50 46.57           C
ATOM   6665  CD2 LEU a 398     -34.084  26.311 -46.001  0.50 48.41           C
ATOM   6666  C   LEU a 398     -32.198  27.536 -41.745  0.50 31.88           C
ATOM   6667  O   LEU a 398     -31.097  27.012 -41.693  0.50 35.24           O
ATOM   6668  N   ASP a 399     -33.038  27.483 -40.730  0.50 33.28           N
ATOM   6669  CA  ASP a 399     -32.722  26.675 -39.551  0.50 32.83           C
ATOM   6670  CB  ASP a 399     -33.391  27.296 -38.338  0.50 32.77           C
ATOM   6671  CG  ASP a 399     -32.593  27.115 -37.057  0.50 37.07           C
ATOM   6672  OD1 ASP a 399     -31.750  26.196 -37.001  0.50 37.38           O
ATOM   6673  OD2 ASP a 399     -32.819  27.901 -36.102  0.50 34.87           O
ATOM   6674  C   ASP a 399     -33.214  25.227 -39.800  0.50 34.37           C
ATOM   6675  O   ASP a 399     -33.493  24.863 -40.932  0.50 30.51           O
ATOM   6676  N   SER a 400     -33.325  24.412 -38.755  0.50 36.87           N
ATOM   6677  CA  SER a 400     -33.644  22.985 -39.944  0.50 41.92           C
ATOM   6678  CB  SER a 400     -32.937  22.149 -37.882  0.50 42.71           C
ATOM   6679  OG  SER a 400     -33.564  22.364 -36.624  0.50 40.65           O
ATOM   6680  C   SER a 400     -35.144  22.701 -38.876  0.50 43.11           C
ATOM   6681  O   SER a 400     -35.579  21.593 -39.144  0.50 43.42           O
ATOM   6682  N   ASP a 401     -35.945  23.698 -38.505  0.50 39.30           N
ATOM   6683  CA  ASP a 401     -37.387  23.544 -38.619  0.50 35.43           C
ATOM   6684  CB  ASP a 401     -38.118  24.085 -37.388  0.50 33.16           C
ATOM   6685  CG  ASP a 401     -37.830  25.566 -37.133  0.50 37.14           C
ATOM   6686  OD1 ASP a 401     -37.210  26.237 -37.993  0.50 34.79           O
ATOM   6687  OD2 ASP a 401     -38.239  26.057 -36.065  0.50 35.56           O
ATOM   6688  C   ASP a 401     -37.904  24.182 -39.913  0.50 34.60           C
ATOM   6689  O   ASP a 401     -39.103  24.163 -40.206  0.50 35.42           O
ATOM   6690  N   GLY a 402     -36.992  24.660 -40.745  0.50 33.92           N
ATOM   6691  CA  GLY a 402     -37.409  25.317 -41.991  0.50 29.87           C
ATOM   6692  C   GLY a 402     -37.828  26.781 -41.750  0.50 33.47           C
ATOM   6693  O   GLY a 402     -38.352  27.416 -42.649  0.50 30.88           O
ATOM   6694  N   SER a 403     -37.528  27.312 -40.539  0.50 27.11           N
ATOM   6695  CA  SER a 403     -37.770  28.785 -40.321  0.50 26.09           C
ATOM   6696  CB  SER a 403     -38.235  29.066 -38.889  0.50 29.94           C
ATOM   6697  OG  SER a 403     -37.151  28.808 -38.017  0.50 28.11           O
ATOM   6698  C   SER a 403     -36.399  29.421 -40.524  0.50 28.37           C
ATOM   6699  O   SER a 403     -35.385  28.704 -40.706  0.50 29.29           O
ATOM   6700  N   PHE a 404     -36.330  30.754 -40.525  0.50 25.99           N
ATOM   6701  CA  PHE a 404     -35.018  31.410 -40.684  0.50 26.53           C
ATOM   6702  CB  PHE a 404     -35.092  32.573 -41.694  0.50 28.30           C
ATOM   6703  CG  PHE a 404     -35.302  32.123 -43.112  0.50 25.39           C
ATOM   6704  CD1 PHE a 404     -36.588  32.053 -43.657  0.50 30.34           C
ATOM   6705  CE1 PHE a 404     -36.779  31.666 -45.007  0.50 26.91           C
ATOM   6706  CZ  PHE a 404     -35.672  31.317 -45.773  0.50 27.37           C
```

Figure 26 (Continued)

```
ATOM   6707  CE2 PHE a 404     -34.386  31.355 -45.225  0.50 28.61           C
ATOM   6708  CD2 PHE a 404     -34.210  31.773 -43.902  0.50 26.06           C
ATOM   6709  C   PHE a 404     -34.504  31.949 -39.375  0.50 26.25           C
ATOM   6710  O   PHE a 404     -35.283  32.236 -38.474  0.50 28.68           O
ATOM   6711  N   ALA a 405     -33.189  32.107 -39.283  0.50 25.64           N
ATOM   6712  CA  ALA a 405     -32.585  32.666 -38.091  0.50 27.99           C
ATOM   6713  CB  ALA a 405     -31.945  31.595 -37.236  0.50 24.12           C
ATOM   6714  C   ALA a 405     -31.551  33.607 -38.605  0.50 27.27           C
ATOM   6715  O   ALA a 405     -31.089  33.459 -39.728  0.50 26.83           O
ATOM   6716  N   LEU a 406     -31.201  34.593 -37.796  0.50 30.18           N
ATOM   6717  CA  LEU a 406     -30.131  35.494 -38.199  0.50 29.59           C
ATOM   6718  CB  LEU a 406     -30.725  36.601 -39.055  0.50 29.45           C
ATOM   6719  CG  LEU a 406     -31.416  37.896 -38.634  0.50 33.10           C
ATOM   6720  CD1 LEU a 406     -30.585  38.708 -37.631  0.50 26.36           C
ATOM   6721  CD2 LEU a 406     -31.659  38.733 -39.906  0.50 29.77           C
ATOM   6722  C   LEU a 406     -29.403  36.036 -36.992  0.50 28.91           C
ATOM   6723  O   LEU a 406     -29.970  36.074 -35.928  0.50 34.34           O
ATOM   6724  N   VAL a 407     -28.172  36.503 -37.157  0.50 29.66           N
ATOM   6725  CA  VAL a 407     -27.492  37.132 -36.028  0.50 29.34           C
ATOM   6726  CB  VAL a 407     -26.288  36.296 -35.512  0.50 28.65           C
ATOM   6727  CG1 VAL a 407     -25.801  36.875 -34.187  0.50 25.28           C
ATOM   6728  CG2 VAL a 407     -26.636  34.823 -35.393  0.50 25.56           C
ATOM   6729  C   VAL a 407     -26.943  38.502 -36.436  0.50 25.97           C
ATOM   6730  O   VAL a 407     -26.260  38.620 -37.440  0.50 22.43           O
ATOM   6731  N   SER a 408     -27.211  39.532 -35.634  0.50 28.68           N
ATOM   6732  CA  SER a 408     -26.649  40.846 -35.923  0.50 28.29           C
ATOM   6733  CB  SER a 408     -27.744  41.927 -35.990  0.50 27.33           C
ATOM   6734  OG  SER a 408     -27.197  43.206 -35.732  0.50 27.49           O
ATOM   6735  C   SER a 408     -25.639  41.186 -34.845  0.50 29.69           C
ATOM   6736  O   SER a 408     -25.918  41.000 -33.648  0.50 29.19           O
ATOM   6737  N   LYS a 409     -24.496  41.736 -35.267  0.50 29.17           N
ATOM   6738  CA  LYS a 409     -23.437  42.095 -34.331  0.50 31.19           C
ATOM   6739  CB  LYS a 409     -22.121  41.398 -34.661  0.50 32.91           C
ATOM   6740  CG  LYS a 409     -21.019  41.714 -33.637  0.50 36.10           C
ATOM   6741  CD  LYS a 409     -19.722  40.928 -33.882  0.50 33.14           C
ATOM   6742  CE  LYS a 409     -19.229  41.066 -35.315  0.50 35.63           C
ATOM   6743  NZ  LYS a 409     -18.339  42.253 -35.567  0.50 36.04           N
ATOM   6744  C   LYS a 409     -23.215  43.597 -34.399  0.50 32.91           C
ATOM   6745  O   LYS a 409     -22.851  44.155 -35.470  0.50 26.73           O
ATOM   6746  N   LEU a 410     -23.405  44.236 -33.247  0.50 29.17           N
ATOM   6747  CA  LEU a 410     -23.072  45.651 -33.106  0.50 31.73           C
ATOM   6748  CB  LEU a 410     -24.223  46.438 -32.423  0.50 30.18           C
ATOM   6749  CG  LEU a 410     -23.928  47.881 -31.949  0.50 35.72           C
ATOM   6750  CD1 LEU a 410     -23.604  48.840 -33.091  0.50 30.07           C
ATOM   6751  CD2 LEU a 410     -25.071  48.434 -31.106  0.50 30.65           C
ATOM   6752  C   LEU a 410     -21.740  45.821 -32.360  0.50 33.73           C
ATOM   6753  O   LEU a 410     -21.537  45.329 -31.226  0.50 29.40           O
ATOM   6754  N   THR a 411     -20.825  46.530 -33.016  0.50 32.00           N
ATOM   6755  CA  THR a 411     -19.515  46.824 -32.452  0.50 31.46           C
ATOM   6756  CB  THR a 411     -18.494  46.825 -33.594  0.50 30.53           C
ATOM   6757  OG1 THR a 411     -18.443  45.502 -34.166  0.50 36.46           O
ATOM   6758  CG2 THR a 411     -17.093  47.257 -33.114  0.50 29.09           C
ATOM   6759  C   THR a 411     -19.503  48.199 -31.767  0.50 34.35           C
ATOM   6760  O   THR a 411     -19.807  49.217 -32.405  0.50 34.81           O
ATOM   6761  N   VAL a 412     -19.152  48.251 -30.488  0.50 36.09           N
ATOM   6762  CA  VAL a 412     -19.031  49.566 -29.809  0.50 35.41           C
ATOM   6763  CB  VAL a 412     -20.205  49.818 -28.843  0.50 39.52           C
ATOM   6764  CG1 VAL a 412     -21.506  49.958 -29.633  0.50 36.92           C
ATOM   6765  CG2 VAL a 412     -20.314  48.692 -27.810  0.50 34.07           C
ATOM   6766  C   VAL a 412     -17.714  49.674 -29.051  0.50 37.43           C
ATOM   6767  O   VAL a 412     -17.085  48.659 -28.768  0.50 31.80           O
ATOM   6768  N   ASP a 413     -17.294  50.898 -28.714  0.50 39.39           N
ATOM   6769  CA  ASP a 413     -16.096  51.074 -27.889  0.50 41.56           C
ATOM   6770  CB  ASP a 413     -15.706  52.559 -27.775  0.50 47.01           C
```

Figure 26 (Continued)

```
ATOM   6771  CG   ASP a 413     -14.743  53.003 -28.859  0.50 52.74           C
ATOM   6772  OD1  ASP a 413     -14.638  52.335 -29.917  0.50 57.75           O
ATOM   6773  OD2  ASP a 413     -14.074  54.038 -28.654  0.50 60.43           O
ATOM   6774  C    ASP a 413     -16.462  50.517 -26.533  0.50 39.45           C
ATOM   6775  O    ASP a 413     -17.615  50.644 -26.111  0.50 35.88           O
ATOM   6776  N    LYS a 414     -15.514  49.859 -25.876  0.50 38.84           N
ATOM   6777  CA   LYS a 414     -15.804  49.217 -24.589  0.50 39.42           C
ATOM   6778  CB   LYS a 414     -14.569  48.513 -24.020  0.50 40.43           C
ATOM   6779  CG   LYS a 414     -14.739  48.189 -22.540  0.50 44.32           C
ATOM   6780  CD   LYS a 414     -13.524  47.524 -21.923  0.50 48.73           C
ATOM   6781  CE   LYS a 414     -12.209  48.067 -22.470  0.50 49.21           C
ATOM   6782  NZ   LYS a 414     -11.191  46.973 -22.532  0.50 49.59           N
ATOM   6783  C    LYS a 414     -16.291  50.208 -23.558  0.50 43.79           C
ATOM   6784  O    LYS a 414     -17.129  49.877 -22.720  0.50 47.77           O
ATOM   6785  N    SER a 415     -15.709  51.405 -23.577  0.50 45.16           N
ATOM   6786  CA   SER a 415     -16.024  52.406 -22.565  0.50 48.19           C
ATOM   6787  CB   SER a 415     -15.048  53.598 -22.633  0.50 47.82           C
ATOM   6788  OG   SER a 415     -14.778  53.993 -23.967  0.50 49.75           O
ATOM   6789  C    SER a 415     -17.487  52.860 -22.644  0.50 50.41           C
ATOM   6790  O    SER a 415     -18.129  53.036 -21.611  0.50 51.93           O
ATOM   6791  N    ARG a 416     -18.022  52.994 -23.863  0.50 47.88           N
ATOM   6792  CA   ARG a 416     -19.458  53.227 -24.037  0.50 45.13           C
ATOM   6793  CB   ARG a 416     -19.835  53.332 -25.516  0.50 49.12           C
ATOM   6794  CG   ARG a 416     -19.116  54.444 -26.256  0.50 51.21           C
ATOM   6795  CD   ARG a 416     -19.554  54.512 -27.708  0.50 52.34           C
ATOM   6796  NE   ARG a 416     -20.971  54.852 -27.821  0.50 50.93           N
ATOM   6797  CZ   ARG a 416     -21.755  54.476 -28.831  0.50 44.01           C
ATOM   6798  NH1  ARG a 416     -21.262  53.733 -29.816  0.50 46.58           N
ATOM   6799  NH2  ARG a 416     -23.035  54.830 -28.848  0.50 39.89           N
ATOM   6800  C    ARG a 416     -20.291  52.157 -23.348  0.50 43.86           C
ATOM   6801  O    ARG a 416     -21.299  52.485 -22.729  0.50 47.54           O
ATOM   6802  N    TRP a 417     -19.855  50.891 -23.430  0.50 43.84           N
ATOM   6803  CA   TRP a 417     -20.504  49.767 -22.696  0.50 42.50           C
ATOM   6804  CB   TRP a 417     -19.993  48.398 -23.174  0.50 38.89           C
ATOM   6805  CG   TRP a 417     -20.576  47.205 -22.419  0.50 39.69           C
ATOM   6806  CD1  TRP a 417     -19.927  46.410 -21.526  0.50 42.73           C
ATOM   6807  NE1  TRP a 417     -20.768  45.438 -21.039  0.50 40.22           N
ATOM   6808  CE2  TRP a 417     -21.984  45.565 -21.649  0.50 39.08           C
ATOM   6809  CD2  TRP a 417     -21.905  46.661 -22.529  0.50 43.16           C
ATOM   6810  CE3  TRP a 417     -23.039  47.013 -23.262  0.50 38.36           C
ATOM   6811  CZ3  TRP a 417     -24.169  46.256 -23.121  0.50 34.67           C
ATOM   6812  CH2  TRP a 417     -24.221  45.189 -22.236  0.50 38.37           C
ATOM   6813  CZ2  TRP a 417     -23.132  44.812 -21.506  0.50 40.77           C
ATOM   6814  C    TRP a 417     -20.324  49.868 -21.194  0.50 43.00           C
ATOM   6815  O    TRP a 417     -21.296  49.759 -20.440  0.50 46.12           O
ATOM   6816  N    GLN a 418     -19.078  50.055 -20.758  0.50 46.26           N
ATOM   6817  CA   GLN a 418     -18.769  50.212 -19.327  0.50 52.67           C
ATOM   6818  CB   GLN a 418     -17.251  50.337 -19.114  0.50 50.32           C
ATOM   6819  CG   GLN a 418     -16.503  49.019 -19.297  0.50 64.69           C
ATOM   6820  CD   GLN a 418     -17.041  47.926 -18.385  0.50 73.52           C
ATOM   6821  OE1  GLN a 418     -17.680  48.218 -17.370  0.50 85.87           O
ATOM   6822  NE2  GLN a 418     -16.796  46.666 -18.741  0.50 64.49           N
ATOM   6823  C    GLN a 418     -19.497  51.407 -18.697  0.50 47.09           C
ATOM   6824  O    GLN a 418     -19.952  51.345 -17.551  0.50 46.04           O
ATOM   6825  N    GLN a 419     -19.607  52.494 -19.449  0.50 47.19           N
ATOM   6826  CA   GLN a 419     -20.315  53.674 -18.955  0.50 51.78           C
ATOM   6827  CB   GLN a 419     -19.954  54.908 -19.760  0.50 53.52           C
ATOM   6828  CG   GLN a 419     -18.477  55.256 -19.728  0.50 56.67           C
ATOM   6829  CD   GLN a 419     -18.194  56.458 -20.597  0.50 65.98           C
ATOM   6830  OE1  GLN a 419     -17.380  56.402 -21.524  0.50 68.90           O
ATOM   6831  NE2  GLN a 419     -18.905  57.550 -20.329  0.50 72.78           N
ATOM   6832  C    GLN a 419     -21.832  53.530 -18.905  0.50 51.48           C
ATOM   6833  O    GLN a 419     -22.536  54.471 -18.560  0.50 49.58           O
ATOM   6834  N    GLY a 420     -22.353  52.357 -19.228  0.50 49.25           N
```

Figure 26 (Continued)

```
ATOM   6835  CA   GLY a 420    -23.750  52.096 -18.871  0.50 45.10           C
ATOM   6836  C    GLY a 420    -24.740  52.462 -19.952  0.50 38.71           C
ATOM   6837  O    GLY a 420    -25.933  52.463 -19.718  0.50 35.66           O
ATOM   6838  N    ASN a 421    -24.250  52.777 -21.143  0.50 37.43           N
ATOM   6839  CA   ASN a 421    -25.152  53.017 -22.257  0.50 38.07           C
ATOM   6840  CB   ASN a 421    -24.350  53.484 -23.471  0.50 38.07           C
ATOM   6841  CG   ASN a 421    -23.566  54.760 -23.171  0.50 45.12           C
ATOM   6842  OD1  ASN a 421    -22.979  55.393 -24.065  0.50 42.04           O
ATOM   6843  ND2  ASN a 421    -23.572  55.157 -21.890  0.50 39.02           N
ATOM   6844  C    ASN a 421    -26.081  51.811 -22.556  0.50 39.28           C
ATOM   6845  O    ASN a 421    -25.685  50.657 -22.395  0.50 38.50           O
ATOM   6846  N    VAL a 422    -27.342  52.102 -22.877  0.50 35.36           N
ATOM   6847  CA   VAL a 422    -28.304  51.099 -23.273  0.50 37.23           C
ATOM   6848  CB   VAL a 422    -29.713  51.430 -22.775  0.50 36.17           C
ATOM   6849  CG1  VAL a 422    -30.690  50.354 -23.254  0.50 33.32           C
ATOM   6850  CG2  VAL a 422    -29.733  51.526 -21.239  0.50 33.41           C
ATOM   6851  C    VAL a 422    -28.343  51.009 -24.789  0.50 37.35           C
ATOM   6852  O    VAL a 422    -28.406  52.036 -25.480  0.50 41.12           O
ATOM   6853  N    PHE a 423    -28.225  49.791 -25.301  0.50 36.53           N
ATOM   6854  CA   PHE a 423    -28.226  49.535 -26.746  0.50 32.59           C
ATOM   6855  CB   PHE a 423    -26.916  48.840 -27.157  0.50 33.44           C
ATOM   6856  CG   PHE a 423    -25.693  49.687 -26.916  0.50 33.17           C
ATOM   6857  CD1  PHE a 423    -25.039  49.645 -25.696  0.50 32.43           C
ATOM   6858  CE1  PHE a 423    -23.957  50.455 -25.448  0.50 33.51           C
ATOM   6859  CZ   PHE a 423    -23.530  51.349 -26.401  0.50 33.17           C
ATOM   6860  CE2  PHE a 423    -24.187  51.428 -27.610  0.50 35.96           C
ATOM   6861  CD2  PHE a 423    -25.275  50.602 -27.857  0.50 34.12           C
ATOM   6862  C    PHE a 423    -29.437  48.683 -27.102  0.50 34.16           C
ATOM   6863  O    PHE a 423    -29.807  47.775 -26.362  0.50 33.69           O
ATOM   6864  N    SER a 424    -30.060  48.982 -28.229  0.50 32.61           N
ATOM   6865  CA   SER a 424    -31.329  48.353 -28.548  0.50 34.66           C
ATOM   6866  CB   SER a 424    -32.435  49.409 -28.474  0.50 30.96           C
ATOM   6867  OG   SER a 424    -32.548  49.881 -27.149  0.50 34.67           O
ATOM   6868  C    SER a 424    -31.319  47.771 -29.942  0.50 32.95           C
ATOM   6869  O    SER a 424    -30.872  48.409 -30.883  0.50 29.78           O
ATOM   6870  N    CYS a 425    -31.842  46.564 -30.081  0.50 33.75           N
ATOM   6871  CA   CYS a 425    -31.875  45.938 -31.386  0.50 28.98           C
ATOM   6872  CB   CYS a 425    -31.365  44.485 -31.273  0.50 27.98           C
ATOM   6873  SG   CYS a 425    -31.614  43.504 -32.768  0.50 31.83           S
ATOM   6874  C    CYS a 425    -33.337  45.978 -31.769  0.50 27.97           C
ATOM   6875  O    CYS a 425    -34.168  45.523 -31.021  0.50 26.22           O
ATOM   6876  N    SER a 426    -33.644  46.547 -32.927  0.50 28.95           N
ATOM   6877  CA   SER a 426    -35.014  46.702 -33.381  0.50 29.27           C
ATOM   6878  CB   SER a 426    -35.213  48.119 -33.924  0.50 30.63           C
ATOM   6879  OG   SER a 426    -35.372  49.028 -32.863  0.50 34.29           O
ATOM   6880  C    SER a 426    -35.245  45.732 -34.531  0.50 29.87           C
ATOM   6881  O    SER a 426    -34.477  45.709 -35.489  0.50 29.97           O
ATOM   6882  N    VAL a 427    -36.337  44.987 -34.480  0.50 29.62           N
ATOM   6883  CA   VAL a 427    -36.601  44.014 -35.533  0.50 29.79           C
ATOM   6884  CB   VAL a 427    -36.614  42.590 -34.951  0.50 31.99           C
ATOM   6885  CG1  VAL a 427    -36.793  41.549 -36.080  0.50 28.92           C
ATOM   6886  CG2  VAL a 427    -35.311  42.358 -34.171  0.50 28.41           C
ATOM   6887  C    VAL a 427    -37.923  44.324 -36.210  0.50 29.21           C
ATOM   6888  O    VAL a 427    -38.920  44.547 -35.554  0.50 26.24           O
ATOM   6889  N    MET a 428    -37.943  44.325 -37.531  0.50 27.62           N
ATOM   6890  CA   MET a 428    -39.190  44.583 -38.209  0.50 28.75           C
ATOM   6891  CB   MET a 428    -39.089  45.880 -39.044  0.50 27.88           C
ATOM   6892  CG   MET a 428    -39.083  47.161 -38.200  0.50 31.35           C
ATOM   6893  SD   MET a 428    -38.195  48.559 -38.985  0.50 34.42           S
ATOM   6894  CE   MET a 428    -36.511  48.115 -38.607  0.50 30.89           C
ATOM   6895  C    MET a 428    -39.542  43.424 -39.105  0.50 24.75           C
ATOM   6896  O    MET a 428    -38.740  43.029 -39.917  0.50 23.72           O
ATOM   6897  N    HIS a 429    -40.779  42.935 -39.008  0.50 26.59           N
ATOM   6898  CA   HIS a 429    -41.140  41.681 -39.679  0.50 25.77           C
```

Figure 26 (Continued)

```
ATOM   6899  CB   HIS a 429     -40.568  40.453 -38.936  0.50 23.60           C
ATOM   6900  CG   HIS a 429     -40.700  39.180 -39.725  0.50 21.83           C
ATOM   6901  ND1  HIS a 429     -41.851  38.426 -39.721  0.50 23.55           N
ATOM   6902  CE1  HIS a 429     -41.710  37.384 -40.528  0.50 21.76           C
ATOM   6903  NE2  HIS a 429     -40.519  37.462 -41.093  0.50 26.93           N
ATOM   6904  CD2  HIS a 429     -39.866  38.583 -40.608  0.50 20.59           C
ATOM   6905  C    HIS a 429     -42.641  41.575 -39.727  0.50 26.42           C
ATOM   6906  O    HIS a 429     -43.323  41.960 -38.783  0.50 29.40           O
ATOM   6907  N    GLU a 430     -43.167  41.086 -40.841  0.50 26.68           N
ATOM   6908  CA   GLU a 430     -44.611  41.076 -41.052  0.50 26.69           C
ATOM   6909  CB   GLU a 430     -44.978  40.514 -42.442  0.50 28.00           C
ATOM   6910  CG   GLU a 430     -44.482  39.099 -42.693  0.50 29.84           C
ATOM   6911  CD   GLU a 430     -45.290  38.405 -43.780  0.50 33.13           C
ATOM   6912  OE1  GLU a 430     -44.896  38.460 -44.972  0.50 28.88           O
ATOM   6913  OE2  GLU a 430     -46.354  37.829 -43.443  0.50 36.84           O
ATOM   6914  C    GLU a 430     -45.360  40.266 -40.019  0.50 25.52           C
ATOM   6915  O    GLU a 430     -46.558  40.485 -39.828  0.50 26.07           O
ATOM   6916  N    ALA a 431     -44.697  39.326 -39.359  0.50 24.42           N
ATOM   6917  CA   ALA a 431     -45.447  38.472 -38.437  0.50 26.41           C
ATOM   6918  CB   ALA a 431     -44.930  37.027 -38.497  0.50 24.56           C
ATOM   6919  C    ALA a 431     -45.364  39.034 -37.015  0.50 28.55           C
ATOM   6920  O    ALA a 431     -46.033  38.520 -36.129  0.50 28.50           O
ATOM   6921  N    LEU a 432     -44.543  40.067 -36.781  0.50 25.58           N
ATOM   6922  CA   LEU a 432     -44.581  40.731 -35.483  0.50 27.67           C
ATOM   6923  CB   LEU a 432     -43.320  41.571 -35.246  0.50 27.79           C
ATOM   6924  CG   LEU a 432     -42.047  40.730 -35.136  0.50 28.48           C
ATOM   6925  CD1  LEU a 432     -40.807  41.608 -35.256  0.50 25.58           C
ATOM   6926  CD2  LEU a 432     -42.053  39.928 -33.826  0.50 27.87           C
ATOM   6927  C    LEU a 432     -45.828  41.601 -35.348  0.50 31.24           C
ATOM   6928  O    LEU a 432     -46.288  42.220 -36.319  0.50 28.59           O
ATOM   6929  N    HIS a 433     -46.404  41.640 -34.156  0.50 30.76           N
ATOM   6930  CA   HIS a 433     -47.483  42.603 -33.917  0.50 33.59           C
ATOM   6931  CB   HIS a 433     -47.961  42.512 -32.453  0.50 38.89           C
ATOM   6932  CG   HIS a 433     -49.129  43.407 -32.130  0.50 41.43           C
ATOM   6933  ND1  HIS a 433     -50.369  43.277 -32.735  0.50 44.41           N
ATOM   6934  CE1  HIS a 433     -51.197  44.184 -32.244  0.50 42.58           C
ATOM   6935  NE2  HIS a 433     -50.544  44.895 -31.338  0.50 43.20           N
ATOM   6936  CD2  HIS a 433     -49.255  44.420 -31.238  0.50 41.68           C
ATOM   6937  C    HIS a 433     -46.925  44.007 -34.183  0.50 35.05           C
ATOM   6938  O    HIS a 433     -45.838  44.333 -33.710  0.50 31.01           O
ATOM   6939  N    ASN a 434     -47.665  44.829 -34.926  0.50 33.00           N
ATOM   6940  CA   ASN a 434     -47.204  46.184 -35.309  0.50 32.69           C
ATOM   6941  CB   ASN a 434     -46.929  47.040 -34.070  0.50 32.81           C
ATOM   6942  CG   ASN a 434     -48.198  47.506 -33.401  0.50 36.35           C
ATOM   6943  OD1  ASN a 434     -49.297  47.274 -33.908  0.50 38.43           O
ATOM   6944  ND2  ASN a 434     -48.058  48.166 -32.254  0.50 32.99           N
ATOM   6945  C    ASN a 434     -45.965  46.179 -36.181  0.50 30.41           C
ATOM   6946  O    ASN a 434     -45.340  47.231 -36.383  0.50 28.87           O
ATOM   6947  N    HIS a 435     -45.585  44.980 -36.612  0.50 27.44           N
ATOM   6948  CA   HIS a 435     -44.421  44.697 -37.441  0.50 25.49           C
ATOM   6949  CB   HIS a 435     -44.521  45.283 -38.852  0.50 28.36           C
ATOM   6950  CG   HIS a 435     -45.778  44.924 -39.581  0.50 28.37           C
ATOM   6951  ND1  HIS a 435     -46.197  45.593 -40.711  0.50 28.27           N
ATOM   6952  CE1  HIS a 435     -47.348  45.081 -41.124  0.50 28.65           C
ATOM   6953  NE2  HIS a 435     -47.691  44.109 -40.297  0.50 28.32           N
ATOM   6954  CD2  HIS a 435     -46.718  43.976 -39.334  0.50 28.35           C
ATOM   6955  C    HIS a 435     -43.120  45.128 -36.837  0.50 26.67           C
ATOM   6956  O    HIS a 435     -42.145  45.357 -37.572  0.50 28.19           O
ATOM   6957  N    TYR a 436     -43.050  45.151 -35.514  0.50 25.89           N
ATOM   6958  CA   TYR a 436     -41.895  45.738 -34.882  0.50 26.67           C
ATOM   6959  CB   TYR a 436     -42.132  47.235 -34.710  0.50 26.91           C
ATOM   6960  CG   TYR a 436     -41.059  47.914 -33.868  0.50 27.48           C
ATOM   6961  CD1  TYR a 436     -41.183  48.006 -32.500  0.50 24.97           C
ATOM   6962  CE1  TYR a 436     -40.192  48.607 -31.739  0.50 29.47           C
```

Figure 26 (Continued)

```
ATOM   6963  CZ   TYR a 436     -39.090  49.130 -32.362  0.50 29.56           C
ATOM   6964  OH   TYR a 436     -38.123  49.761 -31.626  0.50 34.06           O
ATOM   6965  CE2  TYR a 436     -38.948  49.043 -33.728  0.50 28.72           C
ATOM   6966  CD2  TYR a 436     -39.924  48.420 -34.463  0.50 27.78           C
ATOM   6967  C    TYR a 436     -41.718  45.175 -33.492  0.50 27.26           C
ATOM   6968  O    TYR a 436     -42.684  45.063 -32.774  0.50 30.93           O
ATOM   6969  N    THR a 437     -40.489  44.846 -33.109  0.50 27.82           N
ATOM   6970  CA   THR a 437     -40.201  44.603 -31.711  0.50 32.15           C
ATOM   6971  CB   THR a 437     -40.385  43.135 -31.307  0.50 31.99           C
ATOM   6972  OG1  THR a 437     -40.347  43.077 -29.886  0.50 35.10           O
ATOM   6973  CG2  THR a 437     -39.253  42.311 -31.829  0.50 30.63           C
ATOM   6974  C    THR a 437     -38.782  45.038 -31.398  0.50 29.15           C
ATOM   6975  O    THR a 437     -38.000  45.236 -32.294  0.50 31.17           O
ATOM   6976  N    GLN a 438     -38.449  45.188 -30.132  0.50 28.64           N
ATOM   6977  CA   GLN a 438     -37.159  45.762 -29.762  0.50 31.33           C
ATOM   6978  CB   GLN a 438     -37.292  47.300 -29.584  0.50 31.16           C
ATOM   6979  CG   GLN a 438     -35.969  48.066 -29.481  0.50 31.18           C
ATOM   6980  CD   GLN a 438     -36.163  49.457 -28.833  0.50 32.59           C
ATOM   6981  OE1  GLN a 438     -36.863  49.580 -27.840  0.50 34.12           O
ATOM   6982  NE2  GLN a 438     -35.534  50.479 -29.386  0.50 28.07           N
ATOM   6983  C    GLN a 438     -36.768  45.148 -28.434  0.50 32.88           C
ATOM   6984  O    GLN a 438     -37.592  45.042 -27.542  0.50 33.53           O
ATOM   6985  N    LYS a 439     -35.514  44.751 -28.297  0.50 32.23           N
ATOM   6986  CA   LYS a 439     -35.007  44.309 -26.999  0.50 34.92           C
ATOM   6987  CB   LYS a 439     -34.644  42.811 -27.021  0.50 31.09           C
ATOM   6988  CG   LYS a 439     -35.764  41.907 -27.565  0.50 34.25           C
ATOM   6989  CD   LYS a 439     -37.006  41.963 -26.683  0.50 34.01           C
ATOM   6990  CE   LYS a 439     -37.940  40.777 -26.932  0.50 34.78           C
ATOM   6991  NZ   LYS a 439     -37.774  39.714 -25.888  0.50 42.92           N
ATOM   6992  C    LYS a 439     -33.774  45.143 -26.735  0.50 32.61           C
ATOM   6993  O    LYS a 439     -33.109  45.552 -27.681  0.50 33.89           O
ATOM   6994  N    SER a 440     -33.469  45.394 -25.466  0.50 33.44           N
ATOM   6995  CA   SER a 440     -32.361  46.280 -25.125  0.50 36.14           C
ATOM   6996  CB   SER a 440     -32.881  47.638 -24.590  0.50 37.22           C
ATOM   6997  OG   SER a 440     -33.411  48.445 -25.641  0.50 34.01           O
ATOM   6998  C    SER a 440     -31.410  45.654 -24.105  0.50 40.23           C
ATOM   6999  O    SER a 440     -31.761  44.715 -23.393  0.50 38.19           O
ATOM   7000  N    LEU a 441     -30.191  46.171 -24.037  0.50 36.17           N
ATOM   7001  CA   LEU a 441     -29.281  45.645 -23.044  0.50 38.78           C
ATOM   7002  CB   LEU a 441     -28.591  44.373 -23.554  0.50 39.21           C
ATOM   7003  CG   LEU a 441     -27.577  44.533 -24.680  0.50 33.33           C
ATOM   7004  CD1  LEU a 441     -28.291  45.057 -25.907  0.50 41.04           C
ATOM   7005  CD2  LEU a 441     -26.955  43.166 -24.967  0.50 39.22           C
ATOM   7006  C    LEU a 441     -28.262  46.675 -22.620  0.50 36.33           C
ATOM   7007  O    LEU a 441     -27.940  47.596 -23.373  0.50 37.78           O
ATOM   7008  N    SER a 442     -27.759  46.505 -21.405  0.50 38.10           N
ATOM   7009  CA   SER a 442     -26.736  47.379 -20.848  0.50 38.19           C
ATOM   7010  CB   SER a 442     -27.397  48.601 -20.226  0.50 37.43           C
ATOM   7011  OG   SER a 442     -28.296  48.169 -19.210  0.50 37.30           O
ATOM   7012  C    SER a 442     -25.951  46.627 -19.750  0.50 43.08           C
ATOM   7013  O    SER a 442     -26.401  45.584 -19.238  0.50 36.59           O
ATOM   7014  N    LEU a 443     -24.775  47.152 -19.403  0.50 42.23           N
ATOM   7015  CA   LEU a 443     -23.926  46.495 -18.408  0.50 50.41           C
ATOM   7016  CB   LEU a 443     -22.668  47.338 -18.120  0.50 48.50           C
ATOM   7017  CG   LEU a 443     -21.593  46.839 -17.132  0.50 52.91           C
ATOM   7018  CD1  LEU a 443     -21.069  45.445 -17.465  0.50 47.79           C
ATOM   7019  CD2  LEU a 443     -22.115  46.869 -15.705  0.50 48.35           C
ATOM   7020  C    LEU a 443     -24.748  46.264 -17.147  0.50 50.78           C
ATOM   7021  O    LEU a 443     -25.336  47.197 -16.610  0.50 54.21           O
ATOM   7022  N    SER a 444     -24.857  45.013 -16.722  0.50 50.18           N
ATOM   7023  CA   SER a 444     -25.450  44.719 -15.423  0.50 64.44           C
ATOM   7024  CB   SER a 444     -26.246  43.421 -15.476  0.50 65.62           C
ATOM   7025  OG   SER a 444     -26.425  42.912 -14.164  0.50 73.37           O
ATOM   7026  C    SER a 444     -24.383  44.626 -14.321  0.50 73.00           C
```

Figure 26 (Continued)

```
ATOM    7027  O   SER a 444     -23.950  43.525 -13.958  0.50 74.31           O
ATOM    7028  N   PRO a 445     -23.998  45.785 -13.756  0.50 76.48           N
ATOM    7029  CA  PRO a 445     -22.872  46.001 -12.842  0.50 80.30           C
ATOM    7030  CB  PRO a 445     -23.492  46.870 -11.745  0.50 80.88           C
ATOM    7031  CG  PRO a 445     -24.604  47.612 -12.433  0.50 82.08           C
ATOM    7032  CD  PRO a 445     -24.896  46.949 -13.762  0.50 78.64           C
ATOM    7033  C   PRO a 445     -22.277  44.727 -12.239  0.50 75.24           C
ATOM    7034  O   PRO a 445     -22.939  44.048 -11.460  0.50 70.94           O
HETATM  7035  C1  NAG a 500     -26.173  50.470 -71.555  0.50 54.03           C
HETATM  7036  C2  NAG a 500     -26.101  48.954 -71.508  0.50 53.43           C
HETATM  7037  N2  NAG a 500     -26.436  48.334 -72.782  0.50 49.87           N
HETATM  7038  C7  NAG a 500     -25.518  47.796 -73.605  0.50 48.44           C
HETATM  7039  O7  NAG a 500     -24.306  47.815 -73.410  0.50 44.72           O
HETATM  7040  C8  NAG a 500     -26.029  47.188 -74.873  0.50 44.15           C
HETATM  7041  C3  NAG a 500     -27.125  48.426 -70.514  0.50 52.39           C
HETATM  7042  O3  NAG a 500     -26.994  47.027 -70.465  0.50 44.11           O
HETATM  7043  C4  NAG a 500     -26.945  49.004 -69.123  0.50 51.85           C
HETATM  7044  O4  NAG a 500     -28.095  48.706 -68.342  0.50 52.61           O
HETATM  7045  C5  NAG a 500     -26.779  50.518 -69.135  0.50 55.83           C
HETATM  7046  C6  NAG a 500     -25.935  50.877 -67.905  0.50 61.42           C
HETATM  7047  O6  NAG a 500     -26.256  52.177 -67.442  0.50 72.47           O
HETATM  7048  O5  NAG a 500     -26.125  51.072 -70.270  0.50 52.48           O
HETATM  7049  C1  FUC a 501     -25.112  52.898 -66.930  0.50 72.01           C
HETATM  7050  C2  FUC a 501     -24.198  52.031 -66.052  0.50 76.22           C
HETATM  7051  O2  FUC a 501     -24.917  51.200 -65.165  0.50 75.57           O
HETATM  7052  C3  FUC a 501     -23.247  51.160 -66.858  0.50 72.40           C
HETATM  7053  O3  FUC a 501     -22.269  50.699 -65.961  0.50 68.99           O
HETATM  7054  C4  FUC a 501     -22.622  51.955 -68.008  0.50 74.24           C
HETATM  7055  O4  FUC a 501     -21.789  52.978 -67.506  0.50 71.21           O
HETATM  7056  C5  FUC a 501     -23.738  52.609 -68.808  0.50 75.64           C
HETATM  7057  C6  FUC a 501     -23.204  53.318 -70.046  0.50 67.49           C
HETATM  7058  O5  FUC a 501     -24.380  53.541 -67.957  0.50 78.40           O
HETATM  7059  C1  NAG a 502     -27.935  47.499 -67.569  0.50 45.88           C
HETATM  7060  C2  NAG a 502     -28.740  47.639 -66.277  0.50 44.65           C
HETATM  7061  N2  NAG a 502     -28.272  48.800 -65.541  0.50 43.19           N
HETATM  7062  C7  NAG a 502     -29.004  49.878 -65.207  0.50 44.42           C
HETATM  7063  O7  NAG a 502     -28.540  50.833 -64.566  0.50 46.05           O
HETATM  7064  C8  NAG a 502     -30.435  49.942 -65.630  0.50 34.85           C
HETATM  7065  C3  NAG a 502     -28.564  46.371 -65.433  0.50 43.51           C
HETATM  7066  O3  NAG a 502     -29.292  46.413 -64.228  0.50 44.26           O
HETATM  7067  C4  NAG a 502     -28.948  45.130 -66.220  0.50 46.10           C
HETATM  7068  O4  NAG a 502     -28.518  44.001 -65.501  0.50 48.19           O
HETATM  7069  C5  NAG a 502     -28.175  45.132 -67.546  0.50 50.09           C
HETATM  7070  C6  NAG a 502     -28.613  43.969 -68.410  0.50 49.65           C
HETATM  7071  O6  NAG a 502     -27.772  43.932 -69.539  0.50 55.04           O
HETATM  7072  O5  NAG a 502     -28.324  46.336 -68.281  0.50 44.27           O
HETATM  7073  C1  BMA a 503     -29.511  43.528 -64.562  0.50 48.00           C
HETATM  7074  O5  BMA a 503     -29.256  44.073 -63.269  0.50 42.99           O
HETATM  7075  C5  BMA a 503     -30.108  43.598 -62.240  0.50 51.90           C
HETATM  7076  C6  BMA a 503     -29.758  44.324 -60.948  0.50 49.57           C
HETATM  7077  O6  BMA a 503     -29.672  45.713 -61.267  0.50 53.48           O
HETATM  7078  C4  BMA a 503     -29.887  42.098 -62.072  0.50 51.81           C
HETATM  7079  O4  BMA a 503     -30.789  41.606 -61.092  0.50 52.54           O
HETATM  7080  C3  BMA a 503     -30.225  41.378 -63.354  0.50 48.58           C
HETATM  7081  O3  BMA a 503     -29.818  40.024 -63.148  0.50 53.85           O
HETATM  7082  C2  BMA a 503     -29.478  41.997 -64.541  0.50 49.11           C
HETATM  7083  O2  BMA a 503     -28.110  41.550 -64.550  0.50 45.54           O
HETATM  7084  C1  MAN a 504     -29.605  46.489 -60.074  0.50 46.14           C
HETATM  7085  C2  MAN a 504     -30.033  47.923 -60.377  0.50 48.38           C
HETATM  7086  O2  MAN a 504     -30.004  48.689 -59.178  0.50 46.06           O
HETATM  7087  C3  MAN a 504     -29.095  48.520 -61.423  0.50 49.96           C
HETATM  7088  O3  MAN a 504     -29.376  49.889 -61.593  0.50 53.52           O
HETATM  7089  C4  MAN a 504     -27.640  48.368 -60.985  0.50 52.27           C
HETATM  7090  O4  MAN a 504     -26.737  48.725 -62.014  0.50 58.75           O
```

Figure 26 (Continued)

```
HETATM 7091  C5  MAN a 504     -27.349  46.940 -60.563  0.50 47.72           C
HETATM 7092  C6  MAN a 504     -25.979  46.891 -59.911  0.50 46.12           C
HETATM 7093  O6  MAN a 504     -25.674  45.538 -59.689  0.50 49.47           O
HETATM 7094  O5  MAN a 504     -28.286  46.491 -59.603  0.50 48.24           O
HETATM 7095  C1  NAG a 505     -31.284  48.582 -58.520  0.50 47.59           C
HETATM 7096  C2  NAG a 505     -31.140  48.719 -57.012  0.50 46.68           C
HETATM 7097  N2  NAG a 505     -30.204  47.741 -56.508  0.50 46.47           N
HETATM 7098  C7  NAG a 505     -28.986  48.100 -56.123  0.50 48.64           C
HETATM 7099  O7  NAG a 505     -28.619  49.261 -56.111  0.50 42.65           O
HETATM 7100  C8  NAG a 505     -28.089  46.975 -55.708  0.50 47.71           C
HETATM 7101  C3  NAG a 505     -32.487  48.537 -56.324  0.50 51.68           C
HETATM 7102  O3  NAG a 505     -32.364  48.831 -54.933  0.50 50.79           O
HETATM 7103  C4  NAG a 505     -33.555  49.434 -56.935  0.50 52.11           C
HETATM 7104  O4  NAG a 505     -34.836  49.027 -56.442  0.50 55.74           O
HETATM 7105  C5  NAG a 505     -33.534  49.323 -58.455  0.50 48.79           C
HETATM 7106  C6  NAG a 505     -34.497  50.318 -59.092  0.50 45.23           C
HETATM 7107  O6  NAG a 505     -34.147  51.646 -58.697  0.50 38.27           O
HETATM 7108  O5  NAG a 505     -32.220  49.562 -58.951  0.50 46.46           O
HETATM 7109  C1  GAL a 506     -35.556  50.158 -55.919  0.50 68.38           C
HETATM 7110  C2  GAL a 506     -36.850  49.703 -55.229  0.50 69.16           C
HETATM 7111  O2  GAL a 506     -37.758  49.117 -56.172  0.50 89.97           O
HETATM 7112  C3  GAL a 506     -37.552  50.866 -54.545  0.50 69.20           C
HETATM 7113  O3  GAL a 506     -38.628  50.397 -53.734  0.50 68.63           O
HETATM 7114  C4  GAL a 506     -36.563  51.613 -53.674  0.50 70.10           C
HETATM 7115  O4  GAL a 506     -36.051  50.718 -52.688  0.50 67.11           O
HETATM 7116  C5  GAL a 506     -35.413  52.089 -54.538  0.50 67.88           C
HETATM 7117  C6  GAL a 506     -34.453  52.951 -53.728  0.50 62.76           C
HETATM 7118  O6  GAL a 506     -33.704  53.800 -54.602  0.50 52.70           O
HETATM 7119  O5  GAL a 506     -34.743  50.939 -55.045  0.50 77.78           O
HETATM 7120  C1  MAN a 507     -30.950  38.707 -62.981  0.50 61.55           C
HETATM 7121  C2  MAN a 507     -30.333  37.360 -62.654  0.50 69.27           C
HETATM 7122  O2  MAN a 507     -31.101  36.303 -63.232  0.50 88.22           O
HETATM 7123  C3  MAN a 507     -28.978  37.304 -63.313  0.50 66.72           C
HETATM 7124  O3  MAN a 507     -28.357  36.054 -63.006  0.50 76.15           O
HETATM 7125  C4  MAN a 507     -29.194  37.417 -64.812  0.50 62.66           C
HETATM 7126  O4  MAN a 507     -27.921  37.428 -65.466  0.50 63.68           O
HETATM 7127  C5  MAN a 507     -29.975  38.681 -65.164  0.50 58.85           C
HETATM 7128  C6  MAN a 507     -30.392  38.662 -66.629  0.50 56.53           C
HETATM 7129  O6  MAN a 507     -29.537  39.500 -67.411  0.50 50.95           O
HETATM 7130  O5  MAN a 507     -31.162  38.787 -64.386  0.50 61.86           O
HETATM 7131  C1  NAG a 508     -32.365  36.168 -62.563  0.50 98.37           C
HETATM 7132  C2  NAG a 508     -32.221  36.476 -61.079  0.50100.89           C
HETATM 7133  N2  NAG a 508     -31.350  35.484 -60.484  0.50100.61           N
HETATM 7134  C7  NAG a 508     -30.638  35.750 -59.401  0.50 95.22           C
HETATM 7135  O7  NAG a 508     -29.427  35.621 -59.373  0.50 92.72           O
HETATM 7136  C8  NAG a 508     -31.429  36.222 -58.220  0.50 85.38           C
HETATM 7137  C3  NAG a 508     -33.569  36.455 -60.370  0.50102.54           C
HETATM 7138  O3  NAG a 508     -33.437  36.983 -59.045  0.50103.62           O
HETATM 7139  C4  NAG a 508     -34.593  37.266 -61.151  0.50103.44           C
HETATM 7140  O4  NAG a 508     -35.883  37.133 -60.549  0.50102.61           O
HETATM 7141  C5  NAG a 508     -34.640  36.772 -62.588  0.50101.78           C
HETATM 7142  C6  NAG a 508     -35.653  37.541 -63.419  0.50101.69           C
HETATM 7143  O6  NAG a 508     -34.955  38.564 -64.137  0.50 95.82           O
HETATM 7144  O5  NAG a 508     -33.360  36.988 -63.159  0.50103.17           O
HETATM 7145  O2  EDO E   2     -18.171   7.364 -32.497  0.50 41.32           O
HETATM 7146  C2  EDO E   2     -17.621   6.091 -32.852  0.50 47.03           C
HETATM 7147  C1  EDO E   2     -18.101   5.061 -31.845  0.50 42.88           C
HETATM 7148  O1  EDO E   2     -19.456   5.429 -31.540  0.50 52.46           O
HETATM 7149  O2  EDO E   3     -51.326 -15.674 -32.709  0.50 32.77           O
HETATM 7150  C2  EDO E   3     -49.926 -15.494 -32.982  0.50 30.46           C
HETATM 7151  C1  EDO E   3     -49.412 -16.778 -33.609  0.50 27.59           C
HETATM 7152  O1  EDO E   3     -48.014 -16.713 -33.865  0.50 26.03           O
HETATM 7153  O2  EDO E   4     -15.782   4.171 -12.973  0.50 64.17           O
HETATM 7154  C2  EDO E   4     -15.034   3.409 -12.019  0.50 64.25           C
```

Figure 26 (Continued)

```
HETATM 7155  C1  EDO E   4     -13.915    4.250  -11.407  0.50 55.47           C
HETATM 7156  O1  EDO E   4     -12.982    3.424  -10.727  0.50 42.87           O
HETATM 7157  O2  EDO E   5     -18.527   26.905  -41.282  0.50 38.37           O
HETATM 7158  C2  EDO E   5     -17.764   25.692  -41.267  0.50 30.54           C
HETATM 7159  C1  EDO E   5     -17.866   25.031  -39.919  0.50 25.05           C
HETATM 7160  O1  EDO E   5     -19.195   25.299  -39.387  0.50 38.19           O
HETATM 7161  O2  EDO E   6     -31.481  -12.670  -20.323  0.50 52.99           O
HETATM 7162  C2  EDO E   6     -31.912  -13.741  -21.178  0.50 45.51           C
HETATM 7163  C1  EDO E   6     -33.309  -13.410  -21.716  0.50 50.64           C
HETATM 7164  O1  EDO E   6     -34.123  -14.589  -21.753  0.50 53.47           O
HETATM 7165  O2  EDO E   7     -14.753    3.621  -28.284  0.50 35.18           O
HETATM 7166  C2  EDO E   7     -15.173    2.493  -29.073  0.50 36.20           C
HETATM 7167  C1  EDO E   7     -16.608    2.118  -28.699  0.50 36.99           C
HETATM 7168  O1  EDO E   7     -17.536    2.990  -29.364  0.50 34.45           O
HETATM 7169  I   IOD I   1     -44.087   53.482  -38.712  0.50 31.55           I
HETATM 7170  I   IOD I   2     -34.826  -18.910  -31.029  0.50 48.08           I
HETATM 7171  O   HOH S   1     -14.178    9.208  -28.537  0.50 41.43           O
HETATM 7172  O   HOH S   2     -10.338    5.768  -23.720  0.50 32.65           O
HETATM 7173  O   HOH S   3     -46.745  -17.856  -37.423  0.50 43.56           O
HETATM 7174  O   HOH S   4      -6.269   -8.796  -31.648  0.50 34.37           O
HETATM 7175  O   HOH S   5     -39.117  -23.012  -37.159  0.50 43.37           O
HETATM 7176  O   HOH S   6     -17.280   15.361  -47.306  0.50 32.82           O
HETATM 7177  O   HOH S   7     -14.812   -7.875  -38.073  0.50 28.70           O
HETATM 7178  O   HOH S   9     -29.594    7.089  -38.706  0.50 38.01           O
HETATM 7179  O   HOH S  10     -29.869  -18.397  -40.390  0.50 35.66           O
HETATM 7180  O   HOH S  11       1.776   10.554  -20.293  0.50 32.41           O
HETATM 7181  O   HOH S  12     -46.505  -24.255  -39.716  0.50 33.55           O
HETATM 7182  O   HOH S  13     -16.438   11.247  -32.331  0.50 33.51           O
HETATM 7183  O   HOH S  14     -34.331  -13.537  -31.534  0.50 32.18           O
HETATM 7184  O   HOH S  15     -19.490  -12.933  -38.278  0.50 26.34           O
HETATM 7185  O   HOH S  16     -17.578   -9.564  -43.026  0.50 32.11           O
HETATM 7186  O   HOH S  17     -35.372    3.295  -37.062  0.50 39.81           O
HETATM 7187  O   HOH S  18      -2.886    3.033  -21.457  0.50 28.47           O
HETATM 7188  O   HOH S  19      -7.237    2.785  -28.792  0.50 48.35           O
HETATM 7189  O   HOH S  20     -20.108  -11.206  -40.339  0.50 33.27           O
HETATM 7190  O   HOH S  21     -47.399  -10.214  -22.547  0.50 37.77           O
HETATM 7191  O   HOH S  22     -11.269   -3.797  -26.648  0.50 33.66           O
HETATM 7192  O   HOH S  23     -28.457  -21.929   -6.787  0.50 49.33           O
HETATM 7193  O   HOH S  24     -24.441  -13.797  -56.013  0.50 37.22           O
HETATM 7194  O   HOH S  25     -10.764   13.863  -44.455  0.50 31.54           O
HETATM 7195  O   HOH S  26     -54.308   -8.994  -23.113  0.50 44.60           O
HETATM 7196  O   HOH S  27     -49.585   -0.247  -34.626  0.50 67.38           O
HETATM 7197  O   HOH S  28     -36.651  -11.258  -12.655  0.50 27.14           O
HETATM 7198  O   HOH S  29     -14.775   13.538  -39.056  0.50 34.92           O
HETATM 7199  O   HOH S  30     -32.465    5.663  -41.484  0.50 32.05           O
HETATM 7200  O   HOH S  31      -2.187   10.033  -31.287  0.50 16.39           O
HETATM 7201  O   HOH S  32     -19.910   14.141  -37.270  0.50 40.25           O
HETATM 7202  O   HOH S  33     -41.652   -8.664  -32.119  0.50 32.13           O
HETATM 7203  O   HOH S  34      -8.399    3.315  -31.367  0.50 37.46           O
HETATM 7204  O   HOH S  35     -20.696    6.868  -34.235  0.50 33.92           O
HETATM 7205  O   HOH S  36     -35.482  -12.477   -5.846  0.50 45.18           O
HETATM 7206  O   HOH S  37     -50.521  -18.104  -22.218  0.50 39.91           O
HETATM 7207  O   HOH S  38     -25.979   12.204  -53.483  0.50 28.39           O
HETATM 7208  O   HOH S  39     -36.100  -21.549  -28.584  0.50 19.94           O
HETATM 7209  O   HOH S  40      -9.014    1.499  -23.670  0.50 30.92           O
HETATM 7210  O   HOH S  41     -17.340   17.333  -45.826  0.50 32.83           O
HETATM 7211  O   HOH S  42      -7.369    4.953  -27.151  0.50 32.66           O
HETATM 7212  O   HOH S  43     -49.900   -6.187  -27.034  0.50 32.33           O
HETATM 7213  O   HOH S  44     -26.563   -0.248  -50.781  0.50 27.45           O
HETATM 7214  O   HOH S  45     -15.221    6.896  -28.994  0.50 37.19           O
HETATM 7215  O   HOH S  46     -24.069   -1.605  -51.192  0.50 37.71           O
HETATM 7216  O   HOH S  47       1.877   13.598   -7.921  0.50 44.95           O
HETATM 7217  O   HOH S  49      -3.825    2.798  -42.258  0.50 32.74           O
HETATM 7218  O   HOH S  50      -4.763   -0.341  -15.306  0.50 37.32           O
```

Figure 26 (Continued)

```
HETATM 7219  O   HOH S  51       1.281    4.943 -12.601  0.50 29.04           O
HETATM 7220  O   HOH S  52     -16.893   18.834 -40.864  0.50 38.19           O
HETATM 7221  O   HOH S  53     -24.689   25.348 -41.148  0.50 34.63           O
HETATM 7222  O   HOH S  54     -31.621 -19.905 -39.795  0.50 37.87           O
HETATM 7223  O   HOH S  55     -10.282    0.785 -45.281  0.50 39.35           O
HETATM 7224  O   HOH S  56     -31.182    1.879 -47.657  0.50 26.74           O
HETATM 7225  O   HOH S  57     -33.653   -3.829 -50.215  0.50 40.02           O
HETATM 7226  O   HOH S  58     -14.154   -8.383 -45.940  0.50 40.96           O
HETATM 7227  O   HOH S  59     -19.216   16.198 -49.325  0.50 40.07           O
HETATM 7228  O   HOH S  60     -26.971 -15.150  -4.898  0.50 50.35           O
HETATM 7229  O   HOH S  61     -38.765   -2.554 -27.137  0.50 46.43           O
HETATM 7230  O   HOH S  62     -38.056    3.026 -43.868  0.50 43.06           O
HETATM 7231  O   HOH S  63     -42.569   -7.518 -17.942  0.50 40.19           O
HETATM 7232  O   HOH S  64       4.803    1.887 -22.414  0.50 45.08           O
HETATM 7233  O   HOH S  65      -6.143   20.817 -27.790  0.50 32.32           O
HETATM 7234  O   HOH S  66     -16.435    1.461 -49.809  0.50 40.31           O
HETATM 7235  O   HOH S  67      -4.267   21.563 -29.839  0.50 37.53           O
HETATM 7236  O   HOH S  68     -54.460   -8.701 -20.635  0.50 35.52           O
HETATM 7237  O   HOH S  69      -1.997   17.824 -16.410  0.50 25.02           O
HETATM 7238  O   HOH S  70     -22.248   -4.620 -47.158  0.50 39.89           O
HETATM 7239  O   HOH S  71      -5.617    5.553 -42.993  0.50 40.58           O
HETATM 7240  O   HOH S  72      -8.286   -6.307 -40.394  0.50 38.45           O
HETATM 7241  O   HOH S  73     -31.301   15.350 -44.489  0.50 42.66           O
HETATM 7242  O   HOH S  74     -28.816 -20.312 -18.435  0.50 48.86           O
HETATM 7243  O   HOH S  75      -8.956    4.703 -25.529  0.50 38.89           O
HETATM 7244  O   HOH S  76     -54.737 -14.150 -25.840  0.50 48.12           O
HETATM 7245  O   HOH S  78      -7.759    0.585 -43.794  0.50 42.24           O
HETATM 7246  O   HOH S  79       0.050    6.773 -37.835  0.50 35.78           O
HETATM 7247  O   HOH S  81     -29.137 -19.467 -54.884  0.50 37.83           O
HETATM 7248  O   HOH S  82      -1.641   15.828 -23.973  0.50 44.31           O
HETATM 7249  O   HOH S  84      -7.132   -4.743 -21.395  0.50 38.88           O
HETATM 7250  O   HOH S  85     -25.959    3.534 -30.108  0.50 43.49           O
HETATM 7251  O   HOH S  86     -13.386   10.315 -48.901  0.50 44.44           O
HETATM 7252  O   HOH S  87     -18.795 -18.511 -48.018  0.50 37.88           O
HETATM 7253  O   HOH S  88     -39.406   -3.344 -46.065  0.50 34.29           O
HETATM 7254  O   HOH S  89     -47.087 -17.048 -39.399  0.50 28.33           O
HETATM 7255  O   HOH S  90     -21.617   17.272 -51.559  0.50 39.14           O
HETATM 7256  O   HOH S  91      -3.695   18.786 -16.635  0.50 31.52           O
HETATM 7257  O   HOH S  92     -31.096 -17.022 -12.918  0.50 38.66           O
HETATM 7258  O   HOH S  93     -44.819 -13.206 -45.385  0.50 36.26           O
HETATM 7259  O   HOH S  97     -23.874   21.943    4.209  0.50 57.77           O
HETATM 7260  O   HOH S  98     -24.600   -8.882 -30.957  0.50 38.12           O
HETATM 7261  O   HOH S  99     -19.325    0.289 -53.907  0.50 55.85           O
HETATM 7262  O   HOH S 100      -3.995   -5.083 -39.208  0.50 43.74           O
HETATM 7263  O   HOH S 101      -2.121   11.213   -2.033  0.50 43.20           O
HETATM 7264  O   HOH S 102     -24.865   18.302 -55.187  0.50 42.67           O
HETATM 7265  O   HOH S 103     -18.438    6.944   -0.224  0.50 48.22           O
HETATM 7266  O   HOH S 104     -54.340 -24.123 -15.687  0.50 55.16           O
HETATM 7267  O   HOH S 105     -36.781   -9.812   -5.201  0.50 40.28           O
HETATM 7268  O   HOH S 106     -34.965   -9.196 -29.679  0.50 29.56           O
HETATM 7269  O   HOH S 108     -50.498 -10.909 -39.312  0.50 45.14           O
HETATM 7270  O   HOH S 109      -1.512   -5.284 -25.139  0.50 29.91           O
HETATM 7271  O   HOH S 110     -45.969   -6.726 -43.114  0.50 43.62           O
HETATM 7272  O   HOH S 111     -24.638    7.352 -32.249  0.50 28.48           O
HETATM 7273  O   HOH S 112     -39.850 -27.879   -6.420  0.50 40.67           O
HETATM 7274  O   HOH S 113       0.112   -0.357 -26.685  0.50 44.14           O
HETATM 7275  O   HOH S 114     -20.777 -17.731 -44.634  0.50 52.74           O
HETATM 7276  O   HOH S 115     -10.320 -12.502 -40.294  0.50 51.61           O
HETATM 7277  O   HOH S 116     -11.861   -1.721 -24.919  0.50 47.01           O
HETATM 7278  O   HOH S 118      -6.522    6.695 -45.405  0.50 56.37           O
HETATM 7279  O   HOH S 121     -49.616 -21.146 -29.332  0.50 54.35           O
HETATM 7280  O   HOH S 122     -14.156    7.053 -50.599  0.50 40.53           O
HETATM 7281  O   HOH S 123     -40.122   -0.820 -47.804  0.50 34.77           O
HETATM 7282  O   HOH S 124     -31.246 -19.827 -23.151  0.50 42.22           O
```

Figure 26 (Continued)

```
HETATM 7283  O   HOH S 125       5.799   6.458 -24.451  0.50 52.88           O
HETATM 7284  O   HOH S 126     -37.903   5.288 -38.395  0.50 46.89           O
HETATM 7285  O   HOH S 127     -21.080 -11.153 -30.712  0.50 36.05           O
HETATM 7286  O   HOH S 130     -50.520 -13.612 -13.607  0.50 48.19           O
HETATM 7287  O   HOH S 131     -21.318 -18.850  -6.308  0.50 47.18           O
HETATM 7288  O   HOH S 132     -36.234 -10.218 -52.242  0.50 46.20           O
HETATM 7289  O   HOH S 133     -17.774  15.624 -36.400  0.50 39.94           O
HETATM 7290  O   HOH S 134       2.439  12.260 -27.693  0.50 40.19           O
HETATM 7291  O   HOH S 135      -2.493  18.706  -7.479  0.50 63.72           O
HETATM 7292  O   HOH S 138     -50.389  -1.117 -28.754  0.50 39.34           O
HETATM 7293  O   HOH S 139     -33.951   9.380 -37.996  0.50 52.77           O
HETATM 7294  O   HOH S 141     -23.368  21.079   7.133  0.50 96.27           O
HETATM 7295  O   HOH S 142      -3.184  21.845  -9.390  0.50 52.45           O
HETATM 7296  O   HOH S 143      -0.929  16.623  -7.919  0.50 53.08           O
HETATM 7297  O   HOH S 146     -14.026 -16.877 -52.273  0.50 46.56           O
HETATM 7298  O   HOH S 148     -44.771  -9.493 -44.143  0.50 37.63           O
HETATM 7299  O   HOH S 149     -38.698   4.703 -27.313  0.50 57.90           O
HETATM 7300  O   HOH S 150     -32.855  18.864 -50.332  0.50 38.29           O
HETATM 7301  O   HOH S 151     -51.074 -12.815 -34.177  0.50 37.75           O
HETATM 7302  O   HOH S 153       6.885   6.804 -18.409  0.50 43.69           O
HETATM 7303  O   HOH S 154      -7.783   0.160 -17.198  0.50 56.78           O
HETATM 7304  O   HOH S 155     -38.762   8.253 -44.137  0.50 51.23           O
HETATM 7305  O   HOH S 156     -23.613  -3.624 -31.173  0.50 42.34           O
HETATM 7306  O   HOH S 158     -21.700   3.785 -54.231  0.50 51.80           O
HETATM 7307  O   HOH S 159      -0.819   2.878 -36.578  0.50 46.29           O
HETATM 7308  O   HOH S 160     -42.096 -10.474  -4.171  0.50 48.96           O
HETATM 7309  O   HOH S 161     -39.217 -19.717 -25.890  0.50 30.89           O
HETATM 7310  O   HOH S 162     -35.806 -15.629 -30.940  0.50 30.40           O
HETATM 7311  O   HOH S 163     -16.707  16.540 -39.920  0.50 33.88           O
HETATM 7312  O   HOH S 164     -25.343  11.861 -33.131  0.50 59.73           O
HETATM 7313  O   HOH S 165     -13.264   3.793  -3.796  0.50 52.35           O
HETATM 7314  O   HOH S 166     -14.168   2.694 -25.428  0.50 61.79           O
HETATM 7315  O   HOH S 167     -18.857  21.373 -50.409  0.50 36.30           O
HETATM 7316  O   HOH S 168     -26.180  -2.354 -30.957  0.50 45.88           O
HETATM 7317  O   HOH S 169     -40.384 -21.474 -37.708  0.50 25.96           O
HETATM 7318  O   HOH S 170     -49.538  -4.645 -28.470  0.50 27.08           O
HETATM 7319  O   HOH S 171     -10.022  12.851 -22.725  0.50 21.50           O
HETATM 7320  O   HOH S 172     -41.676   1.617 -39.886  0.50 45.91           O
HETATM 7321  O   HOH S 173      -6.819 -10.913 -30.961  0.50 42.36           O
HETATM 7322  O   HOH S 174     -46.605   0.763 -38.320  0.50 45.09           O
HETATM 7323  O   HOH S 175     -10.232  -0.810 -47.615  0.50 62.65           O
HETATM 7324  O   HOH S 176     -17.164 -15.670 -41.743  0.50 50.08           O
HETATM 7325  O   HOH S 180      -0.098   2.330 -38.728  0.50 40.98           O
HETATM 7326  O   HOH S 183     -44.131 -26.480  -7.193  0.50 39.39           O
HETATM 7327  O   HOH S 184     -22.969 -11.111 -31.498  0.50 36.90           O
HETATM 7328  O   HOH S 186     -26.768   5.498 -30.313  0.50 38.07           O
HETATM 7329  O   HOH S 187     -21.993  15.014 -56.519  0.50 43.92           O
HETATM 7330  O   HOH S 188      -5.482   8.300 -43.786  0.50 38.36           O
HETATM 7331  O   HOH S 191     -49.928 -13.713 -37.938  0.50 37.28           O
HETATM 7332  O   HOH S 193     -14.470   6.981 -22.500  0.50 51.17           O
HETATM 7333  O   HOH S 196     -33.300 -12.422 -28.970  0.50 28.68           O
HETATM 7334  O   HOH S 198     -12.801   4.357 -22.702  0.50 57.06           O
HETATM 7335  O   HOH S 199     -43.864 -26.773 -19.750  0.50 39.18           O
HETATM 7336  O   HOH S 202     -42.413 -11.375 -27.766  0.50 37.32           O
HETATM 7337  O   HOH S 206     -41.262 -27.951 -28.913  0.50 43.45           O
HETATM 7338  O   HOH S 208     -13.023  19.891  -7.434  0.50 52.85           O
HETATM 7339  O   HOH S 209     -33.968 -12.679 -26.780  0.50 40.91           O
HETATM 7340  O   HOH S 211       0.669  -2.123 -24.570  0.50 63.47           O
HETATM 7341  O   HOH S 212       7.214   4.802 -18.192  0.50 39.97           O
HETATM 7343  O   HOH S 214     -10.140   2.790 -22.116  0.50 37.47           O
HETATM 7344  O   HOH S 215      -8.200  20.902 -21.149  0.50 43.87           O
HETATM 7345  O   HOH S 216     -12.843   1.772  -3.233  0.50 36.73           O
HETATM 7346  O   HOH S 217     -33.220 -19.347 -48.850  0.50 47.57           O
HETATM 7347  O   HOH S 220      -1.796  -2.197 -40.962  0.50 47.79           O
```

Figure 26 (Continued)

```
HETATM 7348  O   HOH S 222      2.025  16.446  -6.684  0.50 52.15           O
HETATM 7349  O   HOH S 223    -18.176   9.950 -53.918  0.50 36.09           O
HETATM 7350  O   HOH S 224    -18.713   7.766 -18.030  0.50 29.09           O
HETATM 7351  O   HOH S 225    -33.871 -10.310 -14.561  0.50 42.81           O
HETATM 7352  O   HOH S 226    -25.029  49.125 -41.069  0.50 59.99           O
HETATM 7353  O   HOH S 227    -32.355 -11.797 -55.712  0.50 42.78           O
HETATM 7354  O   HOH S 228    -38.250  26.251 -28.816  0.50 29.53           O
HETATM 7355  O   HOH S 229    -31.930 -23.973 -17.282  0.50 36.39           O
HETATM 7356  O   HOH S 230    -24.900 -25.559 -40.904  0.50 63.97           O
HETATM 7357  O   HOH S 231    -31.678  47.409 -20.363  0.50 39.54           O
HETATM 7358  O   HOH S 232    -31.380  43.856 -57.097  0.50 29.62           O
HETATM 7359  O   HOH S 233    -15.829  26.988 -59.885  0.50 43.97           O
HETATM 7360  O   HOH S 234    -13.434  26.430 -61.862  0.50 51.81           O
HETATM 7361  O   HOH S 235    -32.281  50.940 -17.459  0.50 41.16           O
HETATM 7362  O2  EDO F   2    -31.574  44.693 -42.047  0.50 45.89           O
HETATM 7363  C2  EDO F   2    -31.790  43.294 -41.816  0.50 47.37           C
HETATM 7364  C1  EDO F   2    -31.157  42.444 -42.910  0.50 48.51           C
HETATM 7365  O1  EDO F   2    -31.122  43.149 -44.168  0.50 41.03           O
HETATM 7366  O2  EDO F   3     -1.876  21.537 -41.185  0.50 32.62           O
HETATM 7367  C2  EDO F   3     -1.143  20.488 -40.558  0.50 31.39           C
HETATM 7368  C1  EDO F   3     -0.265  21.072 -39.464  0.50 35.43           C
HETATM 7369  O1  EDO F   3     -1.076  21.276 -38.308  0.50 39.78           O
HETATM 7370  O2  EDO F   4    -33.916  41.646 -61.267  0.50 51.42           O
HETATM 7371  C2  EDO F   4    -34.849  40.792 -61.969  0.50 53.09           C
HETATM 7372  C1  EDO F   4    -35.515  41.594 -63.107  0.50 43.29           C
HETATM 7373  O1  EDO F   4    -36.718  40.976 -63.601  0.50 37.63           O
HETATM 7374  O2  EDO F   6    -18.149  25.078 -54.663  0.50 52.85           O
HETATM 7375  C2  EDO F   6    -17.691  24.147 -53.660  0.50 52.22           C
HETATM 7376  C1  EDO F   6    -16.318  24.599 -53.156  0.50 57.50           C
HETATM 7377  O1  EDO F   6    -15.529  23.498 -52.693  0.50 52.12           O
HETATM 7378  O2  EDO F   7    -35.005  41.423 -47.866  0.50 48.69           O
HETATM 7379  C2  EDO F   7    -34.842  40.953 -46.521  0.50 43.63           C
HETATM 7380  C1  EDO F   7    -34.038  39.651 -46.518  0.50 43.92           C
HETATM 7381  O1  EDO F   7    -33.953  39.150 -45.168  0.50 34.20           O
HETATM 7382  I   IOD i   1     -5.247  16.102 -36.102  0.50 37.67           I
HETATM 7383  I   IOD i   2    -14.822  18.417 -43.463  0.50 48.58           I
HETATM 7384  O   HOH H   1    -35.967  46.390 -45.898  0.50 46.41           O
HETATM 7385  O   HOH H   2    -39.078  42.275 -51.700  0.50 32.64           O
HETATM 7386  O   HOH H   3     -2.735  19.578 -37.203  0.50 38.26           O
HETATM 7387  O   HOH H   4    -43.067  28.390 -43.065  0.50 35.97           O
HETATM 7388  O   HOH H   5    -13.634  15.427 -36.021  0.50 24.56           O
HETATM 7389  O   HOH H   6    -32.176  52.632 -26.824  0.50 35.48           O
HETATM 7390  O   HOH H   7    -34.914  29.467 -36.376  0.50 27.58           O
HETATM 7391  O   HOH H   9    -20.179  44.385 -35.808  0.50 37.99           O
HETATM 7392  O   HOH H  10    -19.823  18.965 -34.007  0.50 33.26           O
HETATM 7393  O   HOH H  11    -50.634  48.152 -54.349  0.50 40.01           O
HETATM 7394  O   HOH H  12     -3.066  12.643 -34.886  0.50 39.63           O
HETATM 7395  O   HOH H  13    -32.633  48.676 -42.482  0.50 33.06           O
HETATM 7396  O   HOH H  14    -15.986  24.120 -43.255  0.50 40.92           O
HETATM 7397  O   HOH H  15    -11.082  14.332 -37.330  0.50 41.62           O
HETATM 7398  O   HOH H  16     -7.473  26.298 -45.042  0.50 28.85           O
HETATM 7399  O   HOH H  17    -29.819  24.036 -35.137  0.50 29.30           O
HETATM 7400  O   HOH H  18    -32.016  27.829 -31.414  0.50 32.93           O
HETATM 7401  O   HOH H  19    -14.336  40.666 -37.427  0.50 39.66           O
HETATM 7402  O   HOH H  20    -47.539  40.868 -52.830  0.50 29.40           O
HETATM 7403  O   HOH H  21    -42.766  40.029 -45.673  0.50 37.54           O
HETATM 7404  O   HOH H  22    -29.104  25.912 -33.985  0.50 34.47           O
HETATM 7405  O   HOH H  23     -2.266  27.095 -51.989  0.50 33.95           O
HETATM 7406  O   HOH H  24    -38.501  33.447 -47.870  0.50 34.29           O
HETATM 7407  O   HOH H  25    -21.687  16.229 -67.690  0.50 47.66           O
HETATM 7408  O   HOH H  26    -24.405  23.922 -18.041  0.50 45.23           O
HETATM 7409  O   HOH H  27    -39.128  51.195 -29.915  0.50 27.67           O
HETATM 7410  O   HOH H  28      4.977  28.168 -51.344  0.50 40.65           O
HETATM 7411  O   HOH H  29      0.075  36.439 -40.418  0.50 49.85           O
```

Figure 26 (Continued)

```
HETATM 7412  O   HOH H  30     -34.999  50.921 -35.669  0.50 33.82        O
HETATM 7413  O   HOH H  31     -17.251  43.031 -32.862  0.50 33.44        O
HETATM 7414  O   HOH H  32     -29.813  51.492 -36.749  0.50 34.80        O
HETATM 7415  O   HOH H  33      -7.715  28.480 -42.277  0.50 38.82        O
HETATM 7416  O   HOH H  34     -41.148  40.529 -43.381  0.50 32.87        O
HETATM 7417  O   HOH H  35     -29.294  44.663 -40.619  0.50 33.64        O
HETATM 7418  O   HOH H  36     -14.205  25.614 -68.741  0.50 44.68        O
HETATM 7419  O   HOH H  37       1.011  19.254 -52.178  0.50 39.53        O
HETATM 7420  O   HOH H  38     -24.208  49.125 -20.551  0.50 36.16        O
HETATM 7421  O   HOH H  39     -32.381  54.670 -28.489  0.50 33.96        O
HETATM 7422  O   HOH H  40     -42.242  42.354 -47.041  0.50 38.03        O
HETATM 7423  O   HOH H  41       0.650  30.873 -47.171  0.50 39.15        O
HETATM 7424  O   HOH H  42     -23.723  36.436 -23.101  0.50 28.31        O
HETATM 7425  O   HOH H  43      -8.813   9.095 -46.595  0.50 36.03        O
HETATM 7426  O   HOH H  44     -34.020  44.513 -45.172  0.50 35.76        O
HETATM 7427  O   HOH H  45     -13.315  51.356 -20.128  0.50 27.96        O
HETATM 7428  O   HOH H  46     -25.842  35.648 -23.202  0.50 38.13        O
HETATM 7429  O   HOH H  47     -19.559  45.843 -37.494  0.50 28.25        O
HETATM 7430  O   HOH H  48     -51.490  50.814 -66.631  0.50 46.00        O
HETATM 7431  O   HOH H  49     -45.062  40.226 -31.793  0.50 28.57        O
HETATM 7432  O   HOH H  50     -45.755  37.046 -58.831  0.50 41.80        O
HETATM 7433  O   HOH H  51      -8.146  26.670 -47.330  0.50 33.15        O
HETATM 7434  O   HOH H  52     -51.083  41.423 -62.232  0.50 36.99        O
HETATM 7435  O   HOH H  53     -32.453  56.413 -33.994  0.50 40.92        O
HETATM 7436  O   HOH H  54     -25.050  62.411 -33.952  0.50 40.41        O
HETATM 7437  O   HOH H  55     -17.762  17.500 -35.149  0.50 36.84        O
HETATM 7438  O   HOH H  56     -38.973  37.877 -28.703  0.50 37.43        O
HETATM 7439  O   HOH H  58     -16.137  33.326 -24.020  0.50 45.25        O
HETATM 7440  O   HOH H  59     -35.274  29.103 -28.515  0.50 33.10        O
HETATM 7441  O   HOH H  60     -30.502  54.204 -25.701  0.50 39.02        O
HETATM 7442  O   HOH H  61     -23.799  21.705 -69.785  0.50 52.53        O
HETATM 7443  O   HOH H  62     -10.799  35.137 -47.817  0.50 42.19        O
HETATM 7444  O   HOH H  63     -12.103  39.946 -29.488  0.50 37.92        O
HETATM 7445  O   HOH H  64      -8.271  29.815 -56.254  0.50 34.85        O
HETATM 7446  O   HOH H  65     -54.021  39.141 -52.088  0.50 37.62        O
HETATM 7447  O   HOH H  66     -42.138  57.659 -47.268  0.50 31.67        O
HETATM 7448  O   HOH H  67     -33.431  39.189 -24.732  0.50 38.18        O
HETATM 7449  O   HOH H  68     -45.002  59.122 -43.970  0.50 33.89        O
HETATM 7450  O   HOH H  69       4.563  28.543 -54.781  0.50 42.47        O
HETATM 7451  O   HOH H  70     -30.635  33.174 -26.194  0.50 26.21        O
HETATM 7452  O   HOH H  71     -44.204  43.051 -31.663  0.50 51.33        O
HETATM 7453  O   HOH H  72     -41.142  29.904 -35.327  0.50 28.45        O
HETATM 7454  O   HOH H  73     -18.373  52.766 -30.584  0.50 40.87        O
HETATM 7455  O   HOH H  74     -20.200  17.440 -55.812  0.50 42.69        O
HETATM 7456  O   HOH H  75     -40.756  41.998 -48.929  0.50 40.01        O
HETATM 7457  O   HOH H  76       5.489  23.081 -49.133  0.50 46.58        O
HETATM 7458  O   HOH H  78     -40.915  38.090 -30.296  0.50 42.74        O
HETATM 7459  O   HOH H  79     -50.905  49.916 -56.305  0.50 25.91        O
HETATM 7460  O   HOH H  80     -50.306  44.413 -35.593  0.50 39.57        O
HETATM 7461  O   HOH H  82     -48.540  53.238 -49.968  0.50 39.35        O
HETATM 7462  O   HOH H  85     -41.542  32.405 -52.547  0.50 37.17        O
HETATM 7463  O   HOH H  86     -24.077  40.611 -44.156  0.50 35.47        O
HETATM 7464  O   HOH H  88     -36.016  47.788 -26.391  0.50 40.31        O
HETATM 7465  O   HOH H  89     -29.806  18.609 -26.967  0.50 34.79        O
HETATM 7466  O   HOH H  90     -10.523  35.050 -27.362  0.50 58.53        O
HETATM 7467  O   HOH H  91      -3.508  20.709 -34.000  0.50 30.09        O
HETATM 7468  O   HOH H  92     -28.735  54.926 -22.661  0.50 39.88        O
HETATM 7469  O   HOH H  93     -18.888  20.501 -61.343  0.50 37.12        O
HETATM 7470  O   HOH H  94     -36.365  57.088 -66.968  0.50 53.95        O
HETATM 7471  O   HOH H  95      -4.608  24.261 -29.922  0.50 35.45        O
HETATM 7472  O   HOH H  97     -33.560  21.153 -32.486  0.50 43.11        O
HETATM 7473  O   HOH H 100     -25.814  59.173 -78.694  0.50 58.85        O
HETATM 7474  O   HOH H 101     -25.605  28.134 -43.528  0.50 42.03        O
HETATM 7475  O   HOH H 102     -30.579  36.818 -20.206  0.50 40.88        O
```

Figure 26 (Continued)

```
HETATM 7476  O  HOH H 103   -46.024  32.369 -35.227  0.50 43.05      O
HETATM 7477  O  HOH H 104   -46.572  48.336 -72.873  0.50 47.41      O
HETATM 7478  O  HOH H 105   -24.854  55.607 -19.501  0.50 40.28      O
HETATM 7479  O  HOH H 106   -31.749  45.033 -74.685  0.50 60.97      O
HETATM 7480  O  HOH H 107     4.382  12.338 -58.826  0.50 46.75      O
HETATM 7481  O  HOH H 109     6.171  21.944 -57.471  0.50 30.28      O
HETATM 7482  O  HOH H 110     0.816  25.413 -34.807  0.50 43.62      O
HETATM 7483  O  HOH H 111   -40.288  56.209 -47.352  0.50 31.79      O
HETATM 7484  O  HOH H 112    -3.659  30.533 -31.316  0.50 40.28      O
HETATM 7485  O  HOH H 113   -24.361  43.756 -42.651  0.50 37.33      O
HETATM 7486  O  HOH H 114   -10.918   8.716 -68.005  0.50 42.67      O
HETATM 7487  O  HOH H 115   -50.333  37.326 -47.763  0.50 47.62      O
HETATM 7488  O  HOH H 116   -29.159  19.499 -29.604  0.50 50.47      O
HETATM 7489  O  HOH H 117   -38.277  36.103 -48.761  0.50 42.97      O
HETATM 7490  O  HOH H 119   -43.130  43.542 -29.222  0.50 45.11      O
HETATM 7491  O  HOH H 122     0.786  15.991 -45.774  0.50 40.97      O
HETATM 7492  O  HOH H 123   -35.800  44.608 -23.637  0.50 45.43      O
HETATM 7493  O  HOH H 124    -9.887  35.177 -25.419  0.50 40.43      O
HETATM 7494  O  HOH H 125   -18.643  17.333 -51.292  0.50 45.43      O
HETATM 7495  O  HOH H 126   -54.672  44.279 -49.518  0.50 35.91      O
HETATM 7496  O  HOH H 127   -12.225  42.411 -35.977  0.50 52.21      O
HETATM 7497  O  HOH H 128   -29.709  26.512 -43.282  0.50 44.27      O
HETATM 7498  O  HOH H 131     0.906  24.459 -61.016  0.50 41.11      O
HETATM 7499  O  HOH H 132   -29.175  19.274 -67.173  0.50 38.76      O
HETATM 7500  O  HOH H 133   -13.539  28.068 -21.958  0.50 39.66      O
HETATM 7501  O  HOH H 134     5.244  19.741 -53.212  0.50 41.18      O
HETATM 7502  O  HOH H 135   -55.773  46.538 -55.051  0.50 40.55      O
HETATM 7503  O  HOH H 136   -32.084  52.899 -36.886  0.50 34.03      O
HETATM 7504  O  HOH H 137   -51.969  49.169 -47.233  0.50 36.45      O
HETATM 7505  O  HOH H 138   -47.487  54.849 -67.520  0.50 36.65      O
HETATM 7506  O  HOH H 141     0.661  35.335 -46.253  0.50 34.91      O
HETATM 7507  O  HOH H 142   -14.668  46.262 -36.194  0.50 43.83      O
HETATM 7508  O  HOH H 143   -26.870  58.519 -81.185  0.50 80.48      O
HETATM 7509  O  HOH H 144   -37.435  46.730 -24.800  0.50 34.65      O
HETATM 7510  O  HOH H 145   -46.159  58.882 -66.023  0.50 50.85      O
HETATM 7511  O  HOH H 146   -48.518  53.421 -66.561  0.50 45.15      O
HETATM 7512  O  HOH H 149   -36.367  21.028 -21.804  0.50 52.31      O
HETATM 7513  O  HOH H 152    -4.879  27.393 -30.117  0.50 44.14      O
HETATM 7514  O  HOH H 153   -17.974  56.216 -23.514  0.50 33.93      O
HETATM 7515  O  HOH H 154   -55.071  48.227 -56.213  0.50 46.32      O
HETATM 7516  O  HOH H 155   -56.222  44.460 -57.834  0.50 31.53      O
HETATM 7517  O  HOH H 156   -41.638  37.256 -57.357  0.50 40.26      O
HETATM 7518  O  HOH H 158   -11.003  45.515 -30.542  0.50 38.86      O
HETATM 7519  O  HOH H 159   -51.871  51.321 -57.656  0.50 30.68      O
HETATM 7520  O  HOH H 160   -13.187  26.172 -49.155  0.50 33.65      O
HETATM 7521  O  HOH H 161   -25.431  34.183 -43.705  0.50 34.18      O
HETATM 7522  O  HOH H 163   -28.577  41.427 -20.746  0.50 49.06      O
HETATM 7523  O  HOH H 164   -48.824  40.100 -38.242  0.50 35.68      O
HETATM 7524  O  HOH H 165    -7.683  26.485 -70.134  0.50 47.12      O
HETATM 7525  O  HOH H 166   -10.340  18.044 -48.551  0.50 37.44      O
HETATM 7526  O  HOH H 167   -13.989  21.578 -43.516  0.50 27.68      O
HETATM 7527  O  HOH H 168   -33.323  54.033 -35.097  0.50 38.23      O
HETATM 7528  O  HOH H 170   -36.634  41.160 -70.725  0.50 49.10      O
HETATM 7529  O  HOH H 171   -36.178  40.391 -48.978  0.50 37.95      O
HETATM 7530  O  HOH H 172   -30.144  59.400 -24.731  0.50 42.13      O
HETATM 7531  O  HOH H 173   -31.101  40.835 -44.138  0.50 42.99      O
HETATM 7532  O  HOH H 175    -9.650  16.193 -35.562  0.50 36.97      O
HETATM 7533  O  HOH H 176    -0.237  32.817 -45.424  0.50 42.11      O
HETATM 7534  O  HOH H 177     1.154  24.494 -41.640  0.50 34.61      O
HETATM 7535  O  HOH H 178   -42.233  27.060 -44.454  0.50 41.39      O
HETATM 7536  O  HOH H 179     0.793  22.652 -42.228  0.50 32.75      O
HETATM 7537  O  HOH H 181   -38.977  37.061 -27.387  0.50 45.37      O
HETATM 7538  O  HOH H 182   -25.388  26.212 -42.826  0.50 36.80      O
HETATM 7539  O  HOH H 183   -39.381  24.626 -34.426  0.50 56.41      O
```

Figure 26 (Continued)

```
HETATM 7540  O    HOH H 186      -8.077  39.646 -35.280  0.50 39.63           O
HETATM 7541  O    HOH H 187     -55.951  43.092 -45.414  0.50 44.02           O
HETATM 7542  O    HOH H 188     -21.032  10.258 -30.926  0.50 51.08           O
HETATM 7543  O    HOH H 190     -27.343  51.780 -17.586  0.50 52.87           O
HETATM 7544  O    HOH H 192     -30.537  55.227 -88.035  0.50 33.78           O
HETATM 7545  O    HOH H 193     -23.452  35.013 -43.527  0.50 50.62           O
HETATM 7546  O    HOH H 195     -34.636  24.982 -35.209  0.50 40.24           O
HETATM 7547  O    HOH H 198      -3.845  37.991 -35.116  0.50 37.63           O
HETATM 7548  O    HOH H 199     -12.890  51.652 -24.937  0.50 34.25           O
HETATM 7549  O    HOH H 200     -35.688  44.474 -51.021  0.50 43.10           O
HETATM 7550  O    HOH H 202      -4.758  11.602 -68.111  0.50 41.39           O
HETATM 7551  O    HOH H 203     -34.711  25.712 -33.755  0.50 39.38           O
HETATM 7552  O    HOH H 206      -8.853  27.446 -25.285  0.50 45.78           O
HETATM 7553  O    HOH H 207     -48.007  36.173 -36.128  0.50 39.48           O
HETATM 7554  O    HOH H 208     -36.750  42.294 -51.138  0.50 43.56           O
HETATM 7555  O    HOH H 209     -40.598  57.737 -52.643  0.50 40.98           O
HETATM 7556  O    HOH H 210     -40.347  38.932 -50.824  0.50 39.25           O
HETATM 7557  O    HOH H 212     -11.135   8.367 -69.811  0.50 34.86           O
HETATM 7558  O    HOH H 213     -38.553  37.224 -25.499  0.50 41.22           O
HETATM 7559  O    HOH H 214     -39.751  35.252 -25.877  0.50 46.79           O
HETATM 7560  O    HOH H 215     -50.721  35.177 -49.283  0.50 43.60           O
HETATM 7561  O    HOH H 216     -11.089  42.651 -46.370  0.50 66.67           O
HETATM 7562  O    HOH H 217     -46.873  33.703 -33.155  0.50 40.59           O
HETATM 7563  O    HOH H 218     -37.264  32.067 -49.272  0.50 48.66           O
HETATM 7564  O    HOH H 219     -15.474  18.140 -24.692  0.50 45.66           O
```

Figure 27

Structure coordinates for AZ1 (including SEQ ID NOS.: 2 and 3)

LEGEND

Column headings from left to right are (A) "Atom Number", (B) "Atom Type", (C) "Amino Acid", (D) "Chain Identifier", (E) "Amino Acid Number", (F) "X Coordinate", (G) "Y Coordinate", (H) "Z Coordinate", (I) "Occupancy" (OCC), (J) "B factor", and (K) atom type.

```
         A    B    C   D E      F        G        H       I    J       K
ATOM     1    N    GLY A 236   -30.650  -12.405   2.256  0.50 37.65   N
ATOM     2    CA   GLY A 236   -30.251  -13.832   2.056  0.50 39.33   C
ATOM     3    C    GLY A 236   -31.430  -14.747   1.765  0.50 38.64   C
ATOM     4    O    GLY A 236   -32.576  -14.293   1.644  0.50 40.00   O
ATOM     5    N    GLY A 237   -31.156  -16.046   1.682  0.50 34.61   N
ATOM     6    CA   GLY A 237   -32.164  -17.010   1.257  0.50 29.84   C
ATOM     7    C    GLY A 237   -32.112  -17.098  -0.256  0.50 27.99   C
ATOM     8    O    GLY A 237   -31.231  -16.498  -0.877  0.50 25.43   O
ATOM     9    N    PRO A 238   -33.063  -17.824  -0.856  0.50 27.62   N
ATOM    10    CA   PRO A 238   -33.015  -18.154  -2.275  0.50 28.71   C
ATOM    11    CB   PRO A 238   -34.087  -19.250  -2.420  0.50 29.32   C
ATOM    12    CG   PRO A 238   -34.670  -19.448  -1.040  0.50 29.51   C
ATOM    13    CD   PRO A 238   -34.365  -18.189  -0.287  0.50 30.49   C
ATOM    14    C    PRO A 238   -33.422  -16.933  -3.062  0.50 27.28   C
ATOM    15    O    PRO A 238   -34.127  -16.069  -2.524  0.50 24.20   O
ATOM    16    N    SER A 239   -32.965  -16.866  -4.316  0.50 25.89   N
ATOM    17    CA   SER A 239   -33.279  -15.757  -5.207  0.50 27.65   C
ATOM    18    CB   SER A 239   -32.003  -15.028  -5.642  0.50 27.04   C
ATOM    19    OG   SER A 239   -31.509  -14.171  -4.627  0.50 31.07   O
ATOM    20    C    SER A 239   -34.006  -16.303  -6.431  0.50 24.63   C
ATOM    21    O    SER A 239   -33.903  -17.492  -6.750  0.50 23.41   O
ATOM    22    N    VAL A 240   -34.748  -15.438  -7.107  0.50 23.49   N
ATOM    23    CA   VAL A 240   -35.525  -15.868  -8.263  0.50 22.83   C
ATOM    24    CB   VAL A 240   -37.008  -16.023  -7.913  0.50 23.77   C
ATOM    25    CG1  VAL A 240   -37.795  -16.527  -9.114  0.50 22.07   C
ATOM    26    CG2  VAL A 240   -37.159  -16.959  -6.735  0.50 22.83   C
ATOM    27    C    VAL A 240   -35.380  -14.903  -9.419  0.50 23.75   C
ATOM    28    O    VAL A 240   -35.435  -13.680  -9.244  0.50 24.25   O
ATOM    29    N    PHE A 241   -35.185  -15.464 -10.607  0.50 23.11   N
ATOM    30    CA   PHE A 241   -35.109  -14.650 -11.810  0.50 22.66   C
ATOM    31    CB   PHE A 241   -33.687  -14.684 -12.380  0.50 23.86   C
ATOM    32    CG   PHE A 241   -32.672  -14.043 -11.466  0.50 23.25   C
ATOM    33    CD1  PHE A 241   -32.517  -12.663 -11.441  0.50 24.99   C
ATOM    34    CE1  PHE A 241   -31.605  -12.061 -10.588  0.50 24.85   C
ATOM    35    CZ   PHE A 241   -30.850  -12.845  -9.732  0.50 25.95   C
ATOM    36    CE2  PHE A 241   -31.011  -14.219  -9.731  0.50 25.06   C
ATOM    37    CD2  PHE A 241   -31.923  -14.813 -10.597  0.50 24.63   C
ATOM    38    C    PHE A 241   -36.155  -15.139 -12.810  0.50 21.03   C
ATOM    39    O    PHE A 241   -36.422  -16.335 -12.888  0.50 20.03   O
ATOM    40    N    LEU A 242   -36.775  -14.204 -13.530  0.50 21.72   N
ATOM    41    CA   LEU A 242   -37.912  -14.532 -14.397  0.50 20.34   C
ATOM    42    CB   LEU A 242   -39.182  -13.854 -13.876  0.50 18.98   C
ATOM    43    CG   LEU A 242   -40.483  -14.036 -14.667  0.50 17.74   C
ATOM    44    CD1  LEU A 242   -40.859  -15.501 -14.723  0.50 18.11   C
ATOM    45    CD2  LEU A 242   -41.614  -13.234 -14.029  0.50 17.28   C
ATOM    46    C    LEU A 242   -37.620  -14.091 -15.828  0.50 20.11   C
ATOM    47    O    LEU A 242   -37.379  -12.902 -16.088  0.50 19.70   O
ATOM    48    N    PHE A 243   -37.640  -15.048 -16.748  0.50 19.93   N
ATOM    49    CA   PHE A 243   -37.193  -14.803 -18.117  0.50 19.99   C
ATOM    50    CB   PHE A 243   -36.036  -15.741 -18.441  0.50 20.65   C
```

Figure 27 (Continued)

```
ATOM     51  CG  PHE A 243     -34.871 -15.609 -17.496  0.50 21.73           C
ATOM     52  CD1 PHE A 243     -33.967 -14.551 -17.624  0.50 22.87           C
ATOM     53  CE1 PHE A 243     -32.886 -14.433 -16.777  0.50 23.66           C
ATOM     54  CZ  PHE A 243     -32.694 -15.369 -15.772  0.50 23.49           C
ATOM     55  CE2 PHE A 243     -33.581 -16.423 -15.629  0.50 23.20           C
ATOM     56  CD2 PHE A 243     -34.661 -16.544 -16.496  0.50 23.03           C
ATOM     57  C   PHE A 243     -38.287 -15.007 -19.140  0.50 19.58           C
ATOM     58  O   PHE A 243     -39.058 -15.972 -19.046  0.50 19.60           O
ATOM     59  N   PRO A 244     -38.330 -14.126 -20.153  0.50 18.95           N
ATOM     60  CA  PRO A 244     -39.340 -14.171 -21.210  0.50 18.08           C
ATOM     61  CB  PRO A 244     -39.208 -12.784 -21.848  0.50 18.57           C
ATOM     62  CG  PRO A 244     -37.747 -12.487 -21.722  0.50 18.38           C
ATOM     63  CD  PRO A 244     -37.388 -13.011 -20.347  0.50 19.58           C
ATOM     64  C   PRO A 244     -38.991 -15.249 -22.239  0.50 17.74           C
ATOM     65  O   PRO A 244     -37.860 -15.739 -22.266  0.50 18.69           O
ATOM     66  N   PRO A 245     -39.956 -15.597 -23.087  0.50 16.75           N
ATOM     67  CA  PRO A 245     -39.713 -16.504 -24.208  0.50 17.35           C
ATOM     68  CB  PRO A 245     -41.090 -16.650 -24.867  0.50 17.04           C
ATOM     69  CG  PRO A 245     -42.080 -16.059 -23.898  0.50 17.24           C
ATOM     70  CD  PRO A 245     -41.335 -15.086 -23.042  0.50 17.10           C
ATOM     71  C   PRO A 245     -38.756 -15.841 -25.184  0.50 16.94           C
ATOM     72  O   PRO A 245     -38.508 -14.623 -25.115  0.50 16.61           O
ATOM     73  N   LYS A 246     -38.211 -16.602 -26.113  0.50 16.07           N
ATOM     74  CA  LYS A 246     -37.446 -16.033 -27.197  0.50 16.37           C
ATOM     75  CB  LYS A 246     -36.588 -17.093 -27.851  0.50 16.63           C
ATOM     76  CG  LYS A 246     -35.629 -17.758 -26.885  0.50 17.58           C
ATOM     77  CD  LYS A 246     -34.375 -16.941 -26.715  0.50 20.73           C
ATOM     78  CE  LYS A 246     -33.432 -17.596 -25.724  0.50 23.85           C
ATOM     79  NZ  LYS A 246     -34.078 -17.861 -24.421  0.50 23.53           N
ATOM     80  C   LYS A 246     -38.372 -15.416 -28.229  0.50 16.28           C
ATOM     81  O   LYS A 246     -39.386 -15.955 -28.534  0.50 16.37           O
ATOM     82  N   PRO A 247     -38.001 -14.289 -28.784  0.50 15.38           N
ATOM     83  CA  PRO A 247     -38.951 -13.662 -29.681  0.50 16.01           C
ATOM     84  CB  PRO A 247     -38.246 -12.359 -30.084  0.50 16.51           C
ATOM     85  CG  PRO A 247     -37.394 -12.034 -28.894  0.50 15.29           C
ATOM     86  CD  PRO A 247     -36.938 -13.362 -28.341  0.50 16.14           C
ATOM     87  C   PRO A 247     -39.344 -14.535 -30.897  0.50 15.21           C
ATOM     88  O   PRO A 247     -40.517 -14.555 -31.280  0.50 16.27           O
ATOM     89  N   LYS A 248     -38.402 -15.288 -31.479  0.50 15.52           N
ATOM     90  CA  LYS A 248     -38.768 -16.205 -32.569  0.50 15.27           C
ATOM     91  CB  LYS A 248     -37.538 -16.933 -33.132  0.50 16.05           C
ATOM     92  CG  LYS A 248     -37.786 -17.623 -34.483  0.50 16.27           C
ATOM     93  CD  LYS A 248     -36.458 -18.115 -35.031  0.50 17.20           C
ATOM     94  CE  LYS A 248     -36.643 -19.160 -36.129  0.50 18.48           C
ATOM     95  NZ  LYS A 248     -35.306 -19.671 -36.548  0.50 18.83           N
ATOM     96  C   LYS A 248     -39.833 -17.206 -32.124  0.50 15.61           C
ATOM     97  O   LYS A 248     -40.747 -17.554 -32.899  0.50 15.55           O
ATOM     98  N   ASP A 249     -39.734 -17.670 -30.881  0.50 15.21           N
ATOM     99  CA  ASP A 249     -40.704 -18.637 -30.371  0.50 15.49           C
ATOM    100  CB  ASP A 249     -40.267 -19.226 -29.021  0.50 15.14           C
ATOM    101  CG  ASP A 249     -39.118 -20.197 -29.143  0.50 15.56           C
ATOM    102  OD1 ASP A 249     -38.893 -20.745 -30.244  0.50 16.02           O
ATOM    103  OD2 ASP A 249     -38.445 -20.423 -28.118  0.50 16.50           O
ATOM    104  C   ASP A 249     -42.095 -18.037 -30.211  0.50 16.08           C
ATOM    105  O   ASP A 249     -43.101 -18.746 -30.307  0.50 14.99           O
ATOM    106  N   THR A 250     -42.180 -16.747 -29.902  0.50 15.96           N
ATOM    107  CA  THR A 250     -43.518 -16.156 -29.755  0.50 16.75           C
ATOM    108  CB  THR A 250     -43.526 -14.859 -28.914  0.50 17.65           C
ATOM    109  OG1 THR A 250     -42.819 -13.834 -29.617  0.50 18.26           O
ATOM    110  CG2 THR A 250     -42.906 -15.093 -27.544  0.50 18.32           C
ATOM    111  C   THR A 250     -44.130 -15.816 -31.106  0.50 16.53           C
ATOM    112  O   THR A 250     -45.372 -15.715 -31.233  0.50 16.88           O
ATOM    113  N   LEU A 251     -43.284 -15.623 -32.117  0.50 15.64           N
ATOM    114  CA  LEU A 251     -43.747 -15.059 -33.376  0.50 14.73           C
```

Figure 27 (Continued)

```
ATOM    115  CB   LEU A 251     -42.659 -14.174 -33.975  0.50 14.40          C
ATOM    116  CG   LEU A 251     -42.435 -12.826 -33.278  0.50 14.04          C
ATOM    117  CD1  LEU A 251     -41.088 -12.254 -33.719  0.50 14.43          C
ATOM    118  CD2  LEU A 251     -43.602 -11.890 -33.615  0.50 14.07          C
ATOM    119  C    LEU A 251     -44.126 -16.149 -34.363  0.50 15.15          C
ATOM    120  O    LEU A 251     -45.019 -15.966 -35.214  0.50 15.34          O
ATOM    121  N    MET A 252     -43.480 -17.308 -34.210  0.50 14.14          N
ATOM    122  CA   MET A 252     -43.629 -18.351 -35.215  0.50 14.26          C
ATOM    123  CB   MET A 252     -42.228 -18.795 -35.661  0.50 15.10          C
ATOM    124  CG   MET A 252     -41.352 -17.586 -36.001  0.50 16.82          C
ATOM    125  SD   MET A 252     -42.052 -16.322 -37.103  0.50 20.59          S
ATOM    126  CE   MET A 252     -42.176 -17.334 -38.591  0.50 16.78          C
ATOM    127  C    MET A 252     -44.480 -19.478 -34.624  0.50 13.39          C
ATOM    128  O    MET A 252     -44.139 -20.050 -33.592  0.50 13.59          O
ATOM    129  N    ILE A 253     -45.627 -19.716 -35.251  0.50 13.80          N
ATOM    130  CA   ILE A 253     -46.720 -20.474 -34.657  0.50 15.03          C
ATOM    131  CB   ILE A 253     -48.025 -20.338 -35.491  0.50 14.76          C
ATOM    132  CG1  ILE A 253     -49.201 -20.921 -34.711  0.50 16.30          C
ATOM    133  CD1  ILE A 253     -50.551 -20.559 -35.283  0.50 17.65          C
ATOM    134  CG2  ILE A 253     -47.868 -20.987 -36.875  0.50 16.53          C
ATOM    135  C    ILE A 253     -46.377 -21.945 -34.421  0.50 15.99          C
ATOM    136  O    ILE A 253     -46.953 -22.603 -33.540  0.50 16.19          O
ATOM    137  N    SER A 254     -45.423 -22.464 -35.173  0.50 15.19          N
ATOM    138  CA   SER A 254     -45.037 -23.855 -34.880  0.50 15.59          C
ATOM    139  CB   SER A 254     -44.434 -24.525 -36.109  0.50 16.73          C
ATOM    140  OG   SER A 254     -45.491 -25.074 -36.891  0.50 18.07          O
ATOM    141  C    SER A 254     -44.125 -23.995 -33.678  0.50 16.09          C
ATOM    142  O    SER A 254     -43.969 -25.089 -33.147  0.50 16.70          O
ATOM    143  N    ARG A 255     -43.478 -22.904 -33.270  0.50 15.50          N
ATOM    144  CA   ARG A 255     -42.461 -23.001 -32.217  0.50 17.47          C
ATOM    145  CB   ARG A 255     -41.331 -21.965 -32.421  0.50 17.37          C
ATOM    146  CG   ARG A 255     -40.599 -22.160 -33.749  0.50 17.85          C
ATOM    147  CD   ARG A 255     -39.574 -21.065 -34.018  0.50 18.95          C
ATOM    148  NE   ARG A 255     -38.417 -21.139 -33.134  0.50 18.47          N
ATOM    149  CZ   ARG A 255     -37.308 -21.808 -33.436  0.50 19.07          C
ATOM    150  NH1  ARG A 255     -37.236 -22.455 -34.590  0.50 18.90          N
ATOM    151  NH2  ARG A 255     -36.284 -21.825 -32.596  0.50 18.77          N
ATOM    152  C    ARG A 255     -43.086 -22.914 -30.840  0.50 17.67          C
ATOM    153  O    ARG A 255     -44.274 -22.676 -30.707  0.50 18.60          O
ATOM    154  N    THR A 256     -42.266 -23.116 -29.814  0.50 20.56          N
ATOM    155  CA   THR A 256     -42.755 -23.359 -28.475  0.50 21.38          C
ATOM    156  CB   THR A 256     -42.217 -24.727 -28.003  0.50 24.55          C
ATOM    157  OG1  THR A 256     -42.525 -25.733 -28.984  0.50 26.48          O
ATOM    158  CG2  THR A 256     -42.804 -25.102 -26.680  0.50 25.53          C
ATOM    159  C    THR A 256     -42.241 -22.290 -27.485  0.50 21.16          C
ATOM    160  O    THR A 256     -41.168 -22.440 -26.920  0.50 22.01          O
ATOM    161  N    PRO A 257     -43.006 -21.205 -27.278  0.50 20.26          N
ATOM    162  CA   PRO A 257     -42.570 -20.161 -26.337  0.50 19.27          C
ATOM    163  CB   PRO A 257     -43.452 -18.967 -26.714  0.50 18.99          C
ATOM    164  CG   PRO A 257     -44.710 -19.611 -27.251  0.50 19.70          C
ATOM    165  CD   PRO A 257     -44.264 -20.859 -27.953  0.50 21.35          C
ATOM    166  C    PRO A 257     -42.806 -20.570 -24.881  0.50 19.93          C
ATOM    167  O    PRO A 257     -43.877 -21.119 -24.543  0.50 20.98          O
ATOM    168  N    GLU A 258     -41.802 -20.322 -24.035  0.50 20.44          N
ATOM    169  CA   GLU A 258     -41.855 -20.654 -22.614  0.50 21.31          C
ATOM    170  CB   GLU A 258     -40.886 -21.805 -22.286  0.50 23.63          C
ATOM    171  CG   GLU A 258     -41.005 -23.020 -23.193  0.50 27.24          C
ATOM    172  CD   GLU A 258     -39.781 -23.929 -23.132  0.50 28.67          C
ATOM    173  OE1  GLU A 258     -38.674 -23.461 -22.772  0.50 30.75          O
ATOM    174  OE2  GLU A 258     -39.928 -25.125 -23.445  0.50 28.05          O
ATOM    175  C    GLU A 258     -41.416 -19.451 -21.791  0.50 19.28          C
ATOM    176  O    GLU A 258     -40.501 -18.715 -22.178  0.50 18.85          O
ATOM    177  N    VAL A 259     -42.009 -19.302 -20.617  0.50 18.85          N
ATOM    178  CA   VAL A 259     -41.480 -18.363 -19.639  0.50 20.14          C
```

Figure 27 (Continued)

```
ATOM    179  CB   VAL A 259     -42.589 -17.518 -19.004  0.50 21.13           C
ATOM    180  CG1  VAL A 259     -42.050 -16.706 -17.840  0.50 22.02           C
ATOM    181  CG2  VAL A 259     -43.194 -16.583 -20.045  0.50 21.33           C
ATOM    182  C    VAL A 259     -40.745 -19.216 -18.601  0.50 19.89           C
ATOM    183  O    VAL A 259     -41.153 -20.340 -18.316  0.50 18.76           O
ATOM    184  N    THR A 260     -39.643 -18.698 -18.071  0.50 20.69           N
ATOM    185  CA   THR A 260     -38.752 -19.522 -17.273  0.50 21.86           C
ATOM    186  CB   THR A 260     -37.406 -19.708 -17.996  0.50 21.56           C
ATOM    187  OG1  THR A 260     -37.647 -20.336 -19.267  0.50 22.10           O
ATOM    188  CG2  THR A 260     -36.468 -20.586 -17.177  0.50 19.83           C
ATOM    189  C    THR A 260     -38.529 -18.886 -15.913  0.50 22.40           C
ATOM    190  O    THR A 260     -38.129 -17.723 -15.820  0.50 22.29           O
ATOM    191  N    CYS A 261     -38.819 -19.637 -14.858  0.50 22.41           N
ATOM    192  CA   CYS A 261     -38.686 -19.105 -13.511  0.50 22.58           C
ATOM    193  CB   CYS A 261     -39.991 -19.320 -12.748  0.50 22.60           C
ATOM    194  SG   CYS A 261     -40.028 -18.550 -11.120  0.50 26.41           S
ATOM    195  C    CYS A 261     -37.534 -19.825 -12.830  0.50 22.63           C
ATOM    196  O    CYS A 261     -37.577 -21.038 -12.655  0.50 23.16           O
ATOM    197  N    VAL A 262     -36.484 -19.076 -12.506  0.50 22.96           N
ATOM    198  CA   VAL A 262     -35.238 -19.653 -12.015  0.50 23.01           C
ATOM    199  CB   VAL A 262     -34.024 -19.058 -12.764  0.50 22.88           C
ATOM    200  CG1  VAL A 262     -32.723 -19.601 -12.194  0.50 22.17           C
ATOM    201  CG2  VAL A 262     -34.118 -19.386 -14.256  0.50 22.32           C
ATOM    202  C    VAL A 262     -35.106 -19.382 -10.520  0.50 22.64           C
ATOM    203  O    VAL A 262     -35.268 -18.249 -10.076  0.50 22.11           O
ATOM    204  N    VAL A 263     -34.835 -20.440  -9.755  0.50 23.54           N
ATOM    205  CA   VAL A 263     -34.571 -20.310  -8.328  0.50 23.53           C
ATOM    206  CB   VAL A 263     -35.548 -21.167  -7.494  0.50 22.68           C
ATOM    207  CG1  VAL A 263     -35.452 -20.770  -6.029  0.50 20.76           C
ATOM    208  CG2  VAL A 263     -36.981 -20.989  -7.983  0.50 21.37           C
ATOM    209  C    VAL A 263     -33.122 -20.711  -8.007  0.50 23.50           C
ATOM    210  O    VAL A 263     -32.698 -21.831  -8.306  0.50 24.46           O
ATOM    211  N    VAL A 264     -32.368 -19.783  -7.416  0.50 24.60           N
ATOM    212  CA   VAL A 264     -30.965 -20.010  -7.059  0.50 25.17           C
ATOM    213  CB   VAL A 264     -30.009 -19.129  -7.890  0.50 25.18           C
ATOM    214  CG1  VAL A 264     -30.281 -19.306  -9.378  0.50 24.81           C
ATOM    215  CG2  VAL A 264     -30.165 -17.665  -7.505  0.50 24.58           C
ATOM    216  C    VAL A 264     -30.708 -19.708  -5.574  0.50 26.71           C
ATOM    217  O    VAL A 264     -31.397 -18.879  -4.962  0.50 25.69           O
ATOM    218  N    ASP A 265     -29.680 -20.352  -5.026  0.50 27.17           N
ATOM    219  CA   ASP A 265     -29.382 -20.264  -3.599  0.50 28.86           C
ATOM    220  CB   ASP A 265     -29.360 -18.812  -3.131  0.50 29.71           C
ATOM    221  CG   ASP A 265     -28.152 -18.080  -3.618  0.50 29.20           C
ATOM    222  OD1  ASP A 265     -27.265 -18.746  -4.198  0.50 30.78           O
ATOM    223  OD2  ASP A 265     -28.088 -16.850  -3.424  0.50 30.12           O
ATOM    224  C    ASP A 265     -30.401 -21.039  -2.794  0.50 29.03           C
ATOM    225  O    ASP A 265     -30.804 -20.608  -1.718  0.50 27.25           O
ATOM    226  N    VAL A 266     -30.829 -22.175  -3.328  0.50 28.37           N
ATOM    227  CA   VAL A 266     -31.693 -23.067  -2.578  0.50 30.17           C
ATOM    228  CB   VAL A 266     -32.533 -23.967  -3.495  0.50 29.42           C
ATOM    229  CG1  VAL A 266     -33.347 -24.945  -2.666  0.50 29.33           C
ATOM    230  CG2  VAL A 266     -33.450 -23.125  -4.370  0.50 29.11           C
ATOM    231  C    VAL A 266     -30.776 -23.939  -1.744  0.50 31.24           C
ATOM    232  O    VAL A 266     -29.766 -24.438  -2.248  0.50 31.00           O
ATOM    233  N    SER A 267     -31.115 -24.106  -0.472  0.50 33.00           N
ATOM    234  CA   SER A 267     -30.213 -24.780   0.466  0.50 34.17           C
ATOM    235  CB   SER A 267     -30.373 -24.202   1.864  0.50 33.95           C
ATOM    236  OG   SER A 267     -31.575 -24.647   2.488  0.50 34.39           O
ATOM    237  C    SER A 267     -30.393 -26.298   0.494  0.50 35.76           C
ATOM    238  O    SER A 267     -31.463 -26.824   0.162  0.50 33.40           O
ATOM    239  N    HIS A 268     -29.329 -26.991   0.893  0.50 38.29           N
ATOM    240  CA   HIS A 268     -29.402 -28.411   1.205  0.50 41.15           C
ATOM    241  CB   HIS A 268     -28.009 -28.954   1.520  0.50 43.80           C
ATOM    242  CG   HIS A 268     -26.931 -28.423   0.627  0.50 45.71           C
```

Figure 27 (Continued)

```
ATOM    243  ND1 HIS A 268     -26.185 -29.233  -0.202  0.50 47.15           N
ATOM    244  CE1 HIS A 268     -25.309 -28.497  -0.862  0.50 47.60           C
ATOM    245  NE2 HIS A 268     -25.460 -27.238  -0.491  0.50 47.18           N
ATOM    246  CD2 HIS A 268     -26.467 -27.164   0.440  0.50 46.52           C
ATOM    247  C   HIS A 268     -30.297 -28.601   2.431  0.50 40.22           C
ATOM    248  O   HIS A 268     -31.107 -29.523   2.489  0.50 37.58           O
ATOM    249  N   GLU A 269     -30.148 -27.712   3.407  0.50 40.94           N
ATOM    250  CA  GLU A 269     -30.881 -27.830   4.666  0.50 43.57           C
ATOM    251  CB  GLU A 269     -30.219 -26.989   5.770  0.50 44.84           C
ATOM    252  CG  GLU A 269     -28.767 -27.361   6.058  0.50 44.97           C
ATOM    253  CD  GLU A 269     -27.761 -26.404   5.431  0.50 46.99           C
ATOM    254  OE1 GLU A 269     -28.130 -25.239   5.160  0.50 49.60           O
ATOM    255  OE2 GLU A 269     -26.591 -26.805   5.222  0.50 45.31           O
ATOM    256  C   GLU A 269     -32.363 -27.471   4.510  0.50 44.59           C
ATOM    257  O   GLU A 269     -33.217 -28.009   5.217  0.50 42.03           O
ATOM    258  N   GLU A 270     -32.663 -26.570   3.575  0.50 45.20           N
ATOM    259  CA  GLU A 270     -34.045 -26.202   3.269  0.50 44.70           C
ATOM    260  CB  GLU A 270     -34.402 -24.863   3.904  0.50 45.39           C
ATOM    261  CG  GLU A 270     -34.079 -24.760   5.383  0.50 46.57           C
ATOM    262  CD  GLU A 270     -33.719 -23.348   5.782  0.50 47.57           C
ATOM    263  OE1 GLU A 270     -32.605 -22.896   5.426  0.50 50.41           O
ATOM    264  OE2 GLU A 270     -34.552 -22.688   6.440  0.50 47.21           O
ATOM    265  C   GLU A 270     -34.220 -26.103   1.762  0.50 45.20           C
ATOM    266  O   GLU A 270     -34.343 -25.003   1.220  0.50 42.22           O
ATOM    267  N   PRO A 271     -34.225 -27.259   1.084  0.50 44.05           N
ATOM    268  CA  PRO A 271     -34.272 -27.349  -0.368  0.50 44.12           C
ATOM    269  CB  PRO A 271     -33.710 -28.745  -0.637  0.50 43.37           C
ATOM    270  CG  PRO A 271     -34.143 -29.542   0.555  0.50 45.46           C
ATOM    271  CD  PRO A 271     -34.171 -28.589   1.721  0.50 44.75           C
ATOM    272  C   PRO A 271     -35.690 -27.253  -0.923  0.50 43.06           C
ATOM    273  O   PRO A 271     -35.868 -27.227  -2.135  0.50 45.38           O
ATOM    274  N   GLU A 272     -36.687 -27.203  -0.048  0.50 42.73           N
ATOM    275  CA  GLU A 272     -38.082 -27.245  -0.483  0.50 44.31           C
ATOM    276  CB  GLU A 272     -39.022 -27.492   0.702  0.50 47.09           C
ATOM    277  CG  GLU A 272     -38.743 -28.777   1.465  0.50 50.02           C
ATOM    278  CD  GLU A 272     -38.873 -30.012   0.596  0.50 53.41           C
ATOM    279  OE1 GLU A 272     -39.770 -30.033  -0.277  0.50 54.52           O
ATOM    280  OE2 GLU A 272     -38.080 -30.962   0.791  0.50 54.64           O
ATOM    281  C   GLU A 272     -38.504 -25.976  -1.221  0.50 40.96           C
ATOM    282  O   GLU A 272     -38.563 -24.891  -0.637  0.50 40.55           O
ATOM    283  N   VAL A 273     -38.803 -26.127  -2.509  0.50 39.20           N
ATOM    284  CA  VAL A 273     -39.290 -25.020  -3.324  0.50 35.93           C
ATOM    285  CB  VAL A 273     -38.260 -24.590  -4.389  0.50 35.26           C
ATOM    286  CG1 VAL A 273     -38.795 -23.413  -5.193  0.50 33.59           C
ATOM    287  CG2 VAL A 273     -36.923 -24.239  -3.752  0.50 34.68           C
ATOM    288  C   VAL A 273     -40.574 -25.428  -4.032  0.50 33.53           C
ATOM    289  O   VAL A 273     -40.599 -26.416  -4.772  0.50 31.99           O
ATOM    290  N   LYS A 274     -41.644 -24.671  -3.795  0.50 32.66           N
ATOM    291  CA  LYS A 274     -42.905 -24.881  -4.496  0.50 32.03           C
ATOM    292  CB  LYS A 274     -44.069 -24.934  -3.498  0.50 33.27           C
ATOM    293  CG  LYS A 274     -45.460 -24.890  -4.120  0.50 35.77           C
ATOM    294  CD  LYS A 274     -46.527 -24.726  -3.044  0.50 38.77           C
ATOM    295  CE  LYS A 274     -47.899 -24.431  -3.629  0.50 41.84           C
ATOM    296  NZ  LYS A 274     -48.843 -23.984  -2.565  0.50 44.13           N
ATOM    297  C   LYS A 274     -43.111 -23.743  -5.489  0.50 29.68           C
ATOM    298  O   LYS A 274     -42.783 -22.596  -5.194  0.50 29.18           O
ATOM    299  N   PHE A 275     -43.626 -24.070  -6.670  0.50 28.22           N
ATOM    300  CA  PHE A 275     -43.958 -23.057  -7.669  0.50 27.32           C
ATOM    301  CB  PHE A 275     -43.381 -23.439  -9.036  0.50 26.59           C
ATOM    302  CG  PHE A 275     -41.889 -23.368  -9.125  0.50 25.55           C
ATOM    303  CD1 PHE A 275     -41.118 -24.507  -8.954  0.50 25.30           C
ATOM    304  CE1 PHE A 275     -39.743 -24.452  -9.065  0.50 24.23           C
ATOM    305  CZ  PHE A 275     -39.119 -23.252  -9.356  0.50 23.20           C
ATOM    306  CE2 PHE A 275     -39.880 -22.106  -9.525  0.50 24.44           C
```

Figure 27 (Continued)

```
ATOM    307  CD2 PHE A 275     -41.253 -22.170  -9.423  0.50 24.42           C
ATOM    308  C   PHE A 275     -45.462 -22.926  -7.844  0.50 26.76           C
ATOM    309  O   PHE A 275     -46.156 -23.931  -8.013  0.50 23.52           O
ATOM    310  N   ASN A 276     -45.965 -21.692  -7.841  0.50 24.84           N
ATOM    311  CA  ASN A 276     -47.286 -21.413  -8.403  0.50 25.11           C
ATOM    312  CB  ASN A 276     -48.277 -20.894  -7.347  0.50 26.64           C
ATOM    313  CG  ASN A 276     -48.436 -21.841  -6.164  0.50 26.85           C
ATOM    314  OD1 ASN A 276     -47.541 -21.955  -5.335  0.50 27.07           O
ATOM    315  ND2 ASN A 276     -49.595 -22.500  -6.067  0.50 25.98           N
ATOM    316  C   ASN A 276     -47.166 -20.411  -9.559  0.50 25.46           C
ATOM    317  O   ASN A 276     -46.355 -19.487  -9.506  0.50 25.80           O
ATOM    318  N   TRP A 277     -47.969 -20.610 -10.604  0.50 26.26           N
ATOM    319  CA  TRP A 277     -47.976 -19.728 -11.774  0.50 27.57           C
ATOM    320  CB  TRP A 277     -47.637 -20.538 -13.004  0.50 27.23           C
ATOM    321  CG  TRP A 277     -46.195 -20.868 -13.146  0.50 27.36           C
ATOM    322  CD1 TRP A 277     -45.565 -22.004 -12.736  0.50 27.80           C
ATOM    323  NE1 TRP A 277     -44.235 -21.948 -13.062  0.50 27.31           N
ATOM    324  CE2 TRP A 277     -43.985 -20.754 -13.692  0.50 26.12           C
ATOM    325  CD2 TRP A 277     -45.196 -20.052 -13.765  0.50 26.43           C
ATOM    326  CE3 TRP A 277     -45.213 -18.793 -14.368  0.50 25.23           C
ATOM    327  CZ3 TRP A 277     -44.034 -18.295 -14.888  0.50 25.67           C
ATOM    328  CH2 TRP A 277     -42.848 -19.020 -14.810  0.50 25.03           C
ATOM    329  CZ2 TRP A 277     -42.803 -20.255 -14.227  0.50 26.57           C
ATOM    330  C   TRP A 277     -49.342 -19.094 -12.006  0.50 29.17           C
ATOM    331  O   TRP A 277     -50.372 -19.739 -11.785  0.50 31.08           O
ATOM    332  N   TYR A 278     -49.355 -17.856 -12.496  0.50 28.72           N
ATOM    333  CA  TYR A 278     -50.605 -17.154 -12.794  0.50 27.51           C
ATOM    334  CB  TYR A 278     -51.032 -16.281 -11.612  0.50 27.80           C
ATOM    335  CG  TYR A 278     -50.904 -16.932 -10.257  0.50 26.83           C
ATOM    336  CD1 TYR A 278     -49.672 -17.034  -9.637  0.50 26.23           C
ATOM    337  CE1 TYR A 278     -49.548 -17.604  -8.384  0.50 26.52           C
ATOM    338  CZ  TYR A 278     -50.670 -18.070  -7.731  0.50 26.37           C
ATOM    339  OH  TYR A 278     -50.515 -18.638  -6.493  0.50 24.24           O
ATOM    340  CE2 TYR A 278     -51.912 -17.986  -8.325  0.50 26.60           C
ATOM    341  CD2 TYR A 278     -52.026 -17.418  -9.579  0.50 25.82           C
ATOM    342  C   TYR A 278     -50.517 -16.264 -14.034  0.50 27.37           C
ATOM    343  O   TYR A 278     -49.509 -15.585 -14.268  0.50 26.13           O
ATOM    344  N   VAL A 279     -51.605 -16.234 -14.797  0.50 25.51           N
ATOM    345  CA  VAL A 279     -51.647 -15.504 -16.057  0.50 26.09           C
ATOM    346  CB  VAL A 279     -51.967 -16.469 -17.215  0.50 25.76           C
ATOM    347  CG1 VAL A 279     -51.635 -15.844 -18.559  0.50 25.47           C
ATOM    348  CG2 VAL A 279     -51.203 -17.777 -17.043  0.50 24.99           C
ATOM    349  C   VAL A 279     -52.697 -14.398 -15.932  0.50 28.95           C
ATOM    350  O   VAL A 279     -53.904 -14.666 -15.945  0.50 30.93           O
ATOM    351  N   ASP A 280     -52.240 -13.163 -15.754  0.50 29.30           N
ATOM    352  CA  ASP A 280     -53.134 -12.046 -15.416  0.50 32.32           C
ATOM    353  CB  ASP A 280     -54.199 -11.849 -16.499  0.50 31.49           C
ATOM    354  CG  ASP A 280     -53.664 -11.144 -17.728  0.50 31.35           C
ATOM    355  OD1 ASP A 280     -52.603 -10.476 -17.633  0.50 31.83           O
ATOM    356  OD2 ASP A 280     -54.311 -11.255 -18.795  0.50 33.15           O
ATOM    357  C   ASP A 280     -53.822 -12.259 -14.066  0.50 33.42           C
ATOM    358  O   ASP A 280     -54.918 -11.742 -13.833  0.50 35.86           O
ATOM    359  N   GLY A 281     -53.198 -13.034 -13.187  0.50 34.43           N
ATOM    360  CA  GLY A 281     -53.725 -13.213 -11.837  0.50 32.25           C
ATOM    361  C   GLY A 281     -54.560 -14.462 -11.617  0.50 31.95           C
ATOM    362  O   GLY A 281     -55.064 -14.681 -10.509  0.50 32.27           O
ATOM    363  N   VAL A 282     -54.705 -15.283 -12.658  0.50 31.28           N
ATOM    364  CA  VAL A 282     -55.391 -16.573 -12.551  0.50 30.09           C
ATOM    365  CB  VAL A 282     -56.418 -16.740 -13.690  0.50 30.96           C
ATOM    366  CG1 VAL A 282     -57.331 -17.929 -13.418  0.50 30.48           C
ATOM    367  CG2 VAL A 282     -57.217 -15.457 -13.874  0.50 30.03           C
ATOM    368  C   VAL A 282     -54.388 -17.728 -12.618  0.50 31.80           C
ATOM    369  O   VAL A 282     -53.432 -17.660 -13.390  0.50 29.43           O
ATOM    370  N   GLU A 283     -54.608 -18.791 -11.834  0.50 30.00           N
```

Figure 27 (Continued)

```
ATOM   371  CA  GLU A 283     -53.608 -19.867 -11.714  0.50 30.69           C
ATOM   372  CB  GLU A 283     -53.706 -20.571 -10.353  0.50 29.84           C
ATOM   373  CG  GLU A 283     -52.599 -21.587 -10.102  0.50 31.20           C
ATOM   374  CD  GLU A 283     -52.510 -22.052  -8.656  0.50 32.09           C
ATOM   375  OE1 GLU A 283     -53.435 -21.764  -7.861  0.50 34.24           O
ATOM   376  OE2 GLU A 283     -51.514 -22.721  -8.317  0.50 32.43           O
ATOM   377  C   GLU A 283     -53.668 -20.905 -12.837  0.50 32.00           C
ATOM   378  O   GLU A 283     -54.752 -21.289 -13.272  0.50 30.12           O
ATOM   379  N   VAL A 284     -52.498 -21.348 -13.302  0.50 30.54           N
ATOM   380  CA  VAL A 284     -52.403 -22.456 -14.263  0.50 29.18           C
ATOM   381  CB  VAL A 284     -51.779 -22.044 -15.623  0.50 27.56           C
ATOM   382  CG1 VAL A 284     -52.697 -21.099 -16.376  0.50 27.02           C
ATOM   383  CG2 VAL A 284     -50.390 -21.432 -15.443  0.50 25.51           C
ATOM   384  C   VAL A 284     -51.579 -23.585 -13.656  0.50 31.38           C
ATOM   385  O   VAL A 284     -50.814 -23.365 -12.712  0.50 32.08           O
ATOM   386  N   HIS A 285     -51.724 -24.784 -14.209  0.50 32.68           N
ATOM   387  CA  HIS A 285     -51.078 -25.966 -13.644  0.50 34.58           C
ATOM   388  CB  HIS A 285     -52.117 -26.852 -12.930  0.50 34.93           C
ATOM   389  CG  HIS A 285     -52.844 -26.155 -11.816  0.50 35.02           C
ATOM   390  ND1 HIS A 285     -52.311 -26.011 -10.552  0.50 35.80           N
ATOM   391  CE1 HIS A 285     -53.164 -25.354  -9.786  0.50 35.01           C
ATOM   392  NE2 HIS A 285     -54.226 -25.054 -10.512  0.50 37.25           N
ATOM   393  CD2 HIS A 285     -54.054 -25.548 -11.783  0.50 35.30           C
ATOM   394  C   HIS A 285     -50.293 -26.769 -14.686  0.50 34.42           C
ATOM   395  O   HIS A 285     -49.895 -27.908 -14.431  0.50 37.70           O
ATOM   396  N   ASN A 286     -50.055 -26.175 -15.852  0.50 33.94           N
ATOM   397  CA  ASN A 286     -49.341 -26.872 -16.921  0.50 33.50           C
ATOM   398  CB  ASN A 286     -49.853 -26.447 -18.305  0.50 35.32           C
ATOM   399  CG  ASN A 286     -49.823 -24.941 -18.513  0.50 36.91           C
ATOM   400  OD1 ASN A 286     -50.511 -24.189 -17.823  0.50 38.00           O
ATOM   401  ND2 ASN A 286     -49.044 -24.498 -19.492  0.50 39.21           N
ATOM   402  C   ASN A 286     -47.817 -26.735 -16.857  0.50 31.41           C
ATOM   403  O   ASN A 286     -47.103 -27.300 -17.687  0.50 28.94           O
ATOM   404  N   ALA A 287     -47.319 -25.994 -15.874  0.50 28.65           N
ATOM   405  CA  ALA A 287     -45.884 -25.791 -15.768  0.50 27.80           C
ATOM   406  CB  ALA A 287     -45.566 -24.726 -14.723  0.50 26.02           C
ATOM   407  C   ALA A 287     -45.177 -27.093 -15.430  0.50 29.11           C
ATOM   408  O   ALA A 287     -45.796 -28.074 -14.999  0.50 28.03           O
ATOM   409  N   LYS A 288     -43.869 -27.095 -15.618  0.50 29.71           N
ATOM   410  CA  LYS A 288     -43.077 -28.247 -15.260  0.50 32.72           C
ATOM   411  CB  LYS A 288     -42.672 -29.040 -16.501  0.50 33.89           C
ATOM   412  CG  LYS A 288     -43.865 -29.604 -17.266  0.50 34.71           C
ATOM   413  CD  LYS A 288     -44.852 -30.302 -16.337  0.50 38.33           C
ATOM   414  CE  LYS A 288     -46.247 -30.336 -16.953  0.50 38.98           C
ATOM   415  NZ  LYS A 288     -47.187 -31.256 -16.252  0.50 40.61           N
ATOM   416  C   LYS A 288     -41.868 -27.790 -14.467  0.50 33.80           C
ATOM   417  O   LYS A 288     -41.116 -26.909 -14.903  0.50 31.72           O
ATOM   418  N   THR A 289     -41.700 -28.374 -13.285  0.50 34.27           N
ATOM   419  CA  THR A 289     -40.596 -28.003 -12.418  0.50 37.57           C
ATOM   420  CB  THR A 289     -41.044 -27.887 -10.952  0.50 37.96           C
ATOM   421  OG1 THR A 289     -42.000 -26.827 -10.825  0.50 39.53           O
ATOM   422  CG2 THR A 289     -39.847 -27.607 -10.061  0.50 37.88           C
ATOM   423  C   THR A 289     -39.496 -29.038 -12.510  0.50 39.38           C
ATOM   424  O   THR A 289     -39.748 -30.226 -12.332  0.50 39.39           O
ATOM   425  N   LYS A 290     -38.280 -28.582 -12.797  0.50 43.03           N
ATOM   426  CA  LYS A 290     -37.124 -29.469 -12.870  0.50 46.59           C
ATOM   427  CB  LYS A 290     -35.985 -28.809 -13.654  0.50 47.50           C
ATOM   428  CG  LYS A 290     -36.382 -28.326 -15.039  0.50 48.49           C
ATOM   429  CD  LYS A 290     -35.165 -27.914 -15.852  0.50 50.13           C
ATOM   430  CE  LYS A 290     -35.575 -27.289 -17.178  0.50 50.09           C
ATOM   431  NZ  LYS A 290     -34.397 -26.863 -17.982  0.50 49.73           N
ATOM   432  C   LYS A 290     -36.644 -29.837 -11.472  0.50 45.59           C
ATOM   433  O   LYS A 290     -36.828 -29.070 -10.527  0.50 46.01           O
ATOM   434  N   PRO A 291     -36.034 -31.023 -11.332  0.50 46.46           N
```

Figure 27 (Continued)

```
ATOM    435  CA  PRO A 291     -35.473 -31.398 -10.040  0.50 44.44           C
ATOM    436  CB  PRO A 291     -34.907 -32.799 -10.289  0.50 44.90           C
ATOM    437  CG  PRO A 291     -35.619 -33.301 -11.503  0.50 45.87           C
ATOM    438  CD  PRO A 291     -35.885 -32.087 -12.339  0.50 45.05           C
ATOM    439  C   PRO A 291     -34.355 -30.437  -9.655  0.50 44.66           C
ATOM    440  O   PRO A 291     -33.507 -29.973 -10.522  0.50 43.24           O
ATOM    441  N   ARG A 292     -34.256 -30.132  -8.367  0.50 42.98           N
ATOM    442  CA  ARG A 292     -33.188 -29.281  -7.851  0.50 42.50           C
ATOM    443  CB  ARG A 292     -33.179 -29.322  -6.325  0.50 43.84           C
ATOM    444  CG  ARG A 292     -33.038 -30.722  -5.753  0.50 44.55           C
ATOM    445  CD  ARG A 292     -32.807 -30.686  -4.249  0.50 47.57           C
ATOM    446  NE  ARG A 292     -33.238 -31.924  -3.609  0.50 48.19           N
ATOM    447  CZ  ARG A 292     -32.551 -33.060  -3.644  0.50 48.44           C
ATOM    448  NH1 ARG A 292     -31.394 -33.121  -4.289  0.50 49.14           N
ATOM    449  NH2 ARG A 292     -33.023 -34.139  -3.036  0.50 49.92           N
ATOM    450  C   ARG A 292     -31.826 -29.724  -8.366  0.50 41.85           C
ATOM    451  O   ARG A 292     -31.556 -30.923  -8.488  0.50 40.96           O
ATOM    452  N   GLU A 293     -30.959 -28.752  -8.641  0.50 42.09           N
ATOM    453  CA  GLU A 293     -29.525 -29.040  -9.164  0.50 40.74           C
ATOM    454  CB  GLU A 293     -29.559 -28.697 -10.658  0.50 43.52           C
ATOM    455  CG  GLU A 293     -28.440 -29.392 -11.413  0.50 46.26           C
ATOM    456  CD  GLU A 293     -28.731 -29.509 -12.898  0.50 48.86           C
ATOM    457  OE1 GLU A 293     -29.363 -28.585 -13.458  0.50 50.65           O
ATOM    458  OE2 GLU A 293     -28.334 -30.529 -13.500  0.50 49.82           O
ATOM    459  C   GLU A 293     -28.527 -28.303  -8.391  0.50 39.45           C
ATOM    460  O   GLU A 293     -28.564 -27.082  -8.252  0.50 38.43           O
ATOM    461  N   GLU A 294     -27.545 -29.058  -7.901  0.50 38.05           N
ATOM    462  CA  GLU A 294     -26.428 -28.509  -7.134  0.50 36.54           C
ATOM    463  CB  GLU A 294     -25.686 -29.649  -6.429  0.50 37.85           C
ATOM    464  CG  GLU A 294     -24.463 -29.219  -5.634  0.50 38.34           C
ATOM    465  CD  GLU A 294     -24.821 -28.521  -4.337  0.50 39.42           C
ATOM    466  OE1 GLU A 294     -25.814 -27.761  -4.330  0.50 39.80           O
ATOM    467  OE2 GLU A 294     -24.107 -28.722  -3.325  0.50 39.49           O
ATOM    468  C   GLU A 294     -25.442 -27.691  -7.985  0.50 34.75           C
ATOM    469  O   GLU A 294     -25.060 -28.106  -9.082  0.50 35.81           O
ATOM    470  N   GLN A 295     -25.098 -26.534  -7.481  0.50 33.74           N
ATOM    471  CA  GLN A 295     -24.183 -25.658  -8.146  0.50 32.36           C
ATOM    472  CB  GLN A 295     -24.658 -24.227  -8.011  0.50 31.53           C
ATOM    473  CG  GLN A 295     -26.062 -24.024  -8.534  0.50 31.05           C
ATOM    474  CD  GLN A 295     -26.164 -24.409  -9.980  0.50 30.91           C
ATOM    475  OE1 GLN A 295     -25.508 -23.753 -10.824  0.50 32.58           O
ATOM    476  NE2 GLN A 295     -26.851 -25.489 -10.260  0.50 29.61           N
ATOM    477  C   GLN A 295     -22.832 -25.855  -7.510  0.50 32.86           C
ATOM    478  O   GLN A 295     -22.730 -26.402  -6.432  0.50 32.91           O
ATOM    479  N   TYR A 296     -21.798 -25.402  -8.183  0.50 33.02           N
ATOM    480  CA  TYR A 296     -20.454 -25.604  -7.701  0.50 35.16           C
ATOM    481  CB  TYR A 296     -19.431 -25.146  -8.725  0.50 37.96           C
ATOM    482  CG  TYR A 296     -19.307 -26.079  -9.903  0.50 39.87           C
ATOM    483  CD1 TYR A 296     -19.384 -25.602 -11.196  0.50 41.69           C
ATOM    484  CE1 TYR A 296     -19.265 -26.446 -12.280  0.50 43.66           C
ATOM    485  CZ  TYR A 296     -19.079 -27.787 -12.079  0.50 44.48           C
ATOM    486  OH  TYR A 296     -18.972 -28.626 -13.164  0.50 46.15           O
ATOM    487  CE2 TYR A 296     -18.998 -28.287 -10.799  0.50 43.79           C
ATOM    488  CD2 TYR A 296     -19.115 -27.433  -9.724  0.50 42.03           C
ATOM    489  C   TYR A 296     -20.302 -24.880  -6.369  0.50 33.92           C
ATOM    490  O   TYR A 296     -19.427 -25.196  -5.588  0.50 34.15           O
ATOM    491  N   ASN A 297     -21.169 -23.910  -6.124  0.50 31.19           N
ATOM    492  CA  ASN A 297     -21.122 -23.115  -4.911  0.50 30.72           C
ATOM    493  CB  ASN A 297     -21.459 -21.637  -5.170  0.50 27.77           C
ATOM    494  CG  ASN A 297     -22.914 -21.414  -5.551  0.50 29.30           C
ATOM    495  OD1 ASN A 297     -23.750 -22.257  -5.323  0.50 27.16           O
ATOM    496  ND2 ASN A 297     -23.206 -20.255  -6.113  0.50 27.02           N
ATOM    497  C   ASN A 297     -21.949 -23.701  -3.784  0.50 29.09           C
ATOM    498  O   ASN A 297     -22.183 -23.056  -2.789  0.50 29.63           O
```

Figure 27 (Continued)

```
ATOM    499  N   SER A 298     -22.420 -24.922  -3.957  0.50 30.37           N
ATOM    500  CA  SER A 298     -23.015 -25.639  -2.847  0.50 28.91           C
ATOM    501  CB  SER A 298     -22.212 -25.360  -1.589  0.50 30.35           C
ATOM    502  OG  SER A 298     -21.152 -26.273  -1.474  0.50 30.41           O
ATOM    503  C   SER A 298     -24.472 -25.311  -2.584  0.50 30.43           C
ATOM    504  O   SER A 298     -25.051 -25.723  -1.598  0.50 28.83           O
ATOM    505  N   THR A 299     -25.057 -24.554  -3.482  0.50 29.53           N
ATOM    506  CA  THR A 299     -26.460 -24.259  -3.399  0.50 30.63           C
ATOM    507  CB  THR A 299     -26.739 -22.786  -3.586  0.50 31.79           C
ATOM    508  OG1 THR A 299     -26.297 -22.412  -4.881  0.50 31.72           O
ATOM    509  CG2 THR A 299     -26.002 -21.982  -2.553  0.50 33.59           C
ATOM    510  C   THR A 299     -27.075 -24.979  -4.549  0.50 28.35           C
ATOM    511  O   THR A 299     -26.405 -25.454  -5.437  0.50 27.37           O
ATOM    512  N   TYR A 300     -28.368 -25.103  -4.510  0.50 29.79           N
ATOM    513  CA  TYR A 300     -29.063 -25.770  -5.606  0.50 28.57           C
ATOM    514  CB  TYR A 300     -30.155 -26.702  -5.073  0.50 31.60           C
ATOM    515  CG  TYR A 300     -29.654 -27.937  -4.362  0.50 33.49           C
ATOM    516  CD1 TYR A 300     -29.651 -28.008  -2.974  0.50 36.61           C
ATOM    517  CE1 TYR A 300     -29.212 -29.145  -2.317  0.50 38.19           C
ATOM    518  CZ  TYR A 300     -28.767 -30.227  -3.047  0.50 38.58           C
ATOM    519  OH  TYR A 300     -28.326 -31.359  -2.389  0.50 39.87           O
ATOM    520  CE2 TYR A 300     -28.761 -30.184  -4.430  0.50 36.52           C
ATOM    521  CD2 TYR A 300     -29.201 -29.041  -5.078  0.50 36.40           C
ATOM    522  C   TYR A 300     -29.712 -24.724  -6.503  0.50 27.21           C
ATOM    523  O   TYR A 300     -29.900 -23.587  -6.089  0.50 25.39           O
ATOM    524  N   ARG A 301     -30.070 -25.132  -7.719  0.50 28.73           N
ATOM    525  CA  ARG A 301     -30.810 -24.276  -8.658  0.50 28.49           C
ATOM    526  CB  ARG A 301     -30.002 -24.055  -9.935  0.50 29.02           C
ATOM    527  CG  ARG A 301     -30.592 -23.022 -10.887  0.50 28.33           C
ATOM    528  CD  ARG A 301     -29.534 -22.554 -11.870  0.50 30.57           C
ATOM    529  NE  ARG A 301     -30.096 -21.824 -13.008  0.50 29.97           N
ATOM    530  CZ  ARG A 301     -30.718 -22.404 -14.033  0.50 30.50           C
ATOM    531  NH1 ARG A 301     -30.883 -23.717 -14.053  0.50 30.69           N
ATOM    532  NH2 ARG A 301     -31.184 -21.669 -15.031  0.50 30.52           N
ATOM    533  C   ARG A 301     -32.131 -24.941  -9.003  0.50 29.01           C
ATOM    534  O   ARG A 301     -32.162 -26.118  -9.353  0.50 29.93           O
ATOM    535  N   VAL A 302     -33.222 -24.189  -8.901  0.50 28.46           N
ATOM    536  CA  VAL A 302     -34.538 -24.753  -9.155  0.50 28.20           C
ATOM    537  CB  VAL A 302     -35.407 -24.716  -7.889  0.50 28.08           C
ATOM    538  CG1 VAL A 302     -36.704 -25.475  -8.123  0.50 29.65           C
ATOM    539  CG2 VAL A 302     -34.652 -25.317  -6.709  0.50 30.06           C
ATOM    540  C   VAL A 302     -35.255 -23.977 -10.258  0.50 27.81           C
ATOM    541  O   VAL A 302     -35.260 -22.742 -10.239  0.50 28.95           O
ATOM    542  N   VAL A 303     -35.877 -24.706 -11.186  0.50 25.94           N
ATOM    543  CA  VAL A 303     -36.533 -24.087 -12.347  0.50 25.20           C
ATOM    544  CB  VAL A 303     -35.706 -24.287 -13.621  0.50 24.87           C
ATOM    545  CG1 VAL A 303     -36.330 -23.521 -14.790  0.50 24.38           C
ATOM    546  CG2 VAL A 303     -34.266 -23.873 -13.390  0.50 25.58           C
ATOM    547  C   VAL A 303     -37.924 -24.649 -12.630  0.50 26.17           C
ATOM    548  O   VAL A 303     -38.167 -25.859 -12.545  0.50 26.61           O
ATOM    549  N   SER A 304     -38.835 -23.763 -12.998  0.50 27.64           N
ATOM    550  CA  SER A 304     -40.120 -24.187 -13.545  0.50 26.21           C
ATOM    551  CB  SER A 304     -41.263 -23.793 -12.620  0.50 27.77           C
ATOM    552  OG  SER A 304     -42.512 -24.205 -13.155  0.50 26.17           O
ATOM    553  C   SER A 304     -40.308 -23.508 -14.894  0.50 26.72           C
ATOM    554  O   SER A 304     -40.151 -22.288 -14.991  0.50 25.56           O
ATOM    555  N   VAL A 305     -40.633 -24.306 -15.913  0.50 25.86           N
ATOM    556  CA  VAL A 305     -40.847 -23.813 -17.277  0.50 24.63           C
ATOM    557  CB  VAL A 305     -40.031 -24.629 -18.308  0.50 26.60           C
ATOM    558  CG1 VAL A 305     -40.230 -24.083 -19.721  0.50 24.08           C
ATOM    559  CG2 VAL A 305     -38.545 -24.650 -17.946  0.50 26.10           C
ATOM    560  C   VAL A 305     -42.333 -23.889 -17.624  0.50 25.12           C
ATOM    561  O   VAL A 305     -42.943 -24.957 -17.550  0.50 23.86           O
ATOM    562  N   LEU A 306     -42.912 -22.742 -17.979  0.50 23.38           N
```

Figure 27 (Continued)

```
ATOM    563  CA  LEU A 306     -44.337 -22.638 -18.294  0.50 24.10           C
ATOM    564  CB  LEU A 306     -45.019 -21.598 -17.398  0.50 24.01           C
ATOM    565  CG  LEU A 306     -46.483 -21.288 -17.765  0.50 23.88           C
ATOM    566  CD1 LEU A 306     -47.467 -22.216 -17.050  0.50 25.07           C
ATOM    567  CD2 LEU A 306     -46.838 -19.829 -17.496  0.50 24.46           C
ATOM    568  C   LEU A 306     -44.526 -22.215 -19.745  0.50 22.92           C
ATOM    569  O   LEU A 306     -44.336 -21.044 -20.082  0.50 21.20           O
ATOM    570  N   THR A 307     -44.914 -23.168 -20.587  0.50 21.97           N
ATOM    571  CA  THR A 307     -45.147 -22.907 -22.006  0.50 21.79           C
ATOM    572  CB  THR A 307     -45.498 -24.204 -22.756  0.50 21.91           C
ATOM    573  OG1 THR A 307     -44.430 -25.158 -22.621  0.50 24.59           O
ATOM    574  CG2 THR A 307     -45.733 -23.913 -24.219  0.50 21.29           C
ATOM    575  C   THR A 307     -46.328 -21.963 -22.107  0.50 22.21           C
ATOM    576  O   THR A 307     -47.295 -22.121 -21.369  0.50 23.23           O
ATOM    577  N   VAL A 308     -46.252 -20.962 -22.984  0.50 20.91           N
ATOM    578  CA  VAL A 308     -47.364 -20.017 -23.099  0.50 20.23           C
ATOM    579  CB  VAL A 308     -46.972 -18.557 -22.766  0.50 19.77           C
ATOM    580  CG1 VAL A 308     -46.395 -18.457 -21.354  0.50 21.49           C
ATOM    581  CG2 VAL A 308     -46.009 -18.004 -23.813  0.50 19.69           C
ATOM    582  C   VAL A 308     -47.991 -20.098 -24.482  0.50 18.81           C
ATOM    583  O   VAL A 308     -47.385 -20.631 -25.425  0.50 19.20           O
ATOM    584  N   LEU A 309     -49.213 -19.586 -24.585  0.50 18.97           N
ATOM    585  CA  LEU A 309     -49.849 -19.367 -25.882  0.50 18.38           C
ATOM    586  CB  LEU A 309     -51.361 -19.217 -25.709  0.50 20.21           C
ATOM    587  CG  LEU A 309     -52.115 -20.454 -25.211  0.50 20.65           C
ATOM    588  CD1 LEU A 309     -53.614 -20.159 -25.234  0.50 21.99           C
ATOM    589  CD2 LEU A 309     -51.760 -21.707 -26.017  0.50 21.76           C
ATOM    590  C   LEU A 309     -49.279 -18.106 -26.538  0.50 18.58           C
ATOM    591  O   LEU A 309     -49.190 -17.052 -25.900  0.50 17.74           O
ATOM    592  N   HIS A 310     -48.902 -18.229 -27.814  0.50 16.92           N
ATOM    593  CA  HIS A 310     -48.300 -17.133 -28.569  0.50 18.68           C
ATOM    594  CB  HIS A 310     -48.174 -17.488 -30.064  0.50 18.14           C
ATOM    595  CG  HIS A 310     -47.361 -18.717 -30.341  0.50 18.47           C
ATOM    596  ND1 HIS A 310     -47.805 -19.983 -30.030  0.50 18.51           N
ATOM    597  CE1 HIS A 310     -46.887 -20.869 -30.377  0.50 18.50           C
ATOM    598  NE2 HIS A 310     -45.872 -20.226 -30.923  0.50 18.60           N
ATOM    599  CD2 HIS A 310     -46.139 -18.874 -30.908  0.50 18.59           C
ATOM    600  C   HIS A 310     -49.190 -15.912 -28.436  0.50 18.49           C
ATOM    601  O   HIS A 310     -48.719 -14.791 -28.223  0.50 18.32           O
ATOM    602  N   GLN A 311     -50.491 -16.137 -28.596  0.50 20.70           N
ATOM    603  CA  GLN A 311     -51.453 -15.037 -28.564  0.50 21.50           C
ATOM    604  CB  GLN A 311     -52.865 -15.530 -28.850  0.50 22.79           C
ATOM    605  CG  GLN A 311     -53.327 -16.630 -27.903  0.50 25.72           C
ATOM    606  CD  GLN A 311     -53.173 -18.036 -28.471  0.50 26.26           C
ATOM    607  OE1 GLN A 311     -52.115 -18.414 -29.031  0.50 24.84           O
ATOM    608  NE2 GLN A 311     -54.233 -18.828 -28.326  0.50 23.84           N
ATOM    609  C   GLN A 311     -51.423 -14.298 -27.224  0.50 20.25           C
ATOM    610  O   GLN A 311     -51.382 -13.073 -27.208  0.50 21.01           O
ATOM    611  N   ASP A 312     -51.418 -15.038 -26.116  0.50 20.34           N
ATOM    612  CA  ASP A 312     -51.425 -14.423 -24.776  0.50 19.32           C
ATOM    613  CB  ASP A 312     -51.482 -15.478 -23.674  0.50 21.17           C
ATOM    614  CG  ASP A 312     -52.812 -16.217 -23.619  0.50 24.01           C
ATOM    615  OD1 ASP A 312     -53.812 -15.753 -24.217  0.50 24.44           O
ATOM    616  OD2 ASP A 312     -52.854 -17.269 -22.948  0.50 24.22           O
ATOM    617  C   ASP A 312     -50.190 -13.544 -24.561  0.50 19.00           C
ATOM    618  O   ASP A 312     -50.300 -12.392 -24.114  0.50 17.93           O
ATOM    619  N   TRP A 313     -49.014 -14.063 -24.904  0.50 17.32           N
ATOM    620  CA  TRP A 313     -47.792 -13.250 -24.801  0.50 17.20           C
ATOM    621  CB  TRP A 313      46.527  14.041  25.202  0.50 16.73           C
ATOM    622  CG  TRP A 313     -45.255 -13.194 -25.120  0.50 16.40           C
ATOM    623  CD1 TRP A 313     -44.607 -12.589 -26.162  0.50 15.98           C
ATOM    624  NE1 TRP A 313     -43.507 -11.897 -25.698  0.50 16.69           N
ATOM    625  CE2 TRP A 313     -43.426 -12.046 -24.337  0.50 15.97           C
ATOM    626  CD2 TRP A 313     -44.508 -12.860 -23.935  0.50 15.80           C
```

Figure 27 (Continued)

```
ATOM    627  CE3 TRP A 313     -44.657 -13.163 -22.578  0.50 16.04           C
ATOM    628  CZ3 TRP A 313     -43.729 -12.653 -21.669  0.50 16.06           C
ATOM    629  CH2 TRP A 313     -42.650 -11.850 -22.099  0.50 16.21           C
ATOM    630  CZ2 TRP A 313     -42.491 -11.522 -23.425  0.50 15.36           C
ATOM    631  C   TRP A 313     -47.877 -11.989 -25.661  0.50 17.51           C
ATOM    632  O   TRP A 313     -47.597 -10.890 -25.183  0.50 16.51           O
ATOM    633  N   LEU A 314     -48.216 -12.165 -26.944  0.50 16.59           N
ATOM    634  CA  LEU A 314     -48.342 -11.032 -27.858  0.50 16.49           C
ATOM    635  CB  LEU A 314     -48.532 -11.495 -29.299  0.50 16.62           C
ATOM    636  CG  LEU A 314     -47.247 -12.127 -29.850  0.50 15.63           C
ATOM    637  CD1 LEU A 314     -47.565 -13.061 -31.022  0.50 15.99           C
ATOM    638  CD2 LEU A 314     -46.213 -11.087 -30.254  0.50 16.37           C
ATOM    639  C   LEU A 314     -49.460 -10.044 -27.489  0.50 17.28           C
ATOM    640  O   LEU A 314     -49.420  -8.890 -27.897  0.50 17.77           O
ATOM    641  N   ASN A 315     -50.435 -10.494 -26.720  0.50 18.23           N
ATOM    642  CA  ASN A 315     -51.508  -9.590 -26.307  0.50 18.72           C
ATOM    643  CB  ASN A 315     -52.814 -10.352 -26.118  0.50 19.84           C
ATOM    644  CG  ASN A 315     -53.534 -10.607 -27.420  0.50 20.94           C
ATOM    645  OD1 ASN A 315     -53.430  -9.836 -28.382  0.50 22.44           O
ATOM    646  ND2 ASN A 315     -54.289 -11.686 -27.453  0.50 21.70           N
ATOM    647  C   ASN A 315     -51.170  -8.849 -25.024  0.50 19.41           C
ATOM    648  O   ASN A 315     -51.908  -7.945 -24.603  0.50 18.07           O
ATOM    649  N   GLY A 316     -50.063  -9.218 -24.388  0.50 18.08           N
ATOM    650  CA  GLY A 316     -49.643  -8.503 -23.169  0.50 19.27           C
ATOM    651  C   GLY A 316     -50.119  -9.120 -21.869  0.50 20.37           C
ATOM    652  O   GLY A 316     -50.150  -8.459 -20.821  0.50 21.04           O
ATOM    653  N   LYS A 317     -50.476 -10.395 -21.901  0.50 19.01           N
ATOM    654  CA  LYS A 317     -50.870 -11.051 -20.667  0.50 19.73           C
ATOM    655  CB  LYS A 317     -51.530 -12.391 -20.966  0.50 20.14           C
ATOM    656  CG  LYS A 317     -52.791 -12.219 -21.804  0.50 18.82           C
ATOM    657  CD  LYS A 317     -53.687 -13.428 -21.672  0.50 21.03           C
ATOM    658  CE  LYS A 317     -54.934 -13.291 -22.530  0.50 21.67           C
ATOM    659  NZ  LYS A 317     -56.059 -14.063 -21.942  0.50 24.52           N
ATOM    660  C   LYS A 317     -49.709 -11.180 -19.679  0.50 18.95           C
ATOM    661  O   LYS A 317     -48.550 -11.353 -20.069  0.50 18.08           O
ATOM    662  N   GLU A 318     -50.026 -11.068 -18.390  0.50 19.41           N
ATOM    663  CA  GLU A 318     -49.006 -11.010 -17.344  0.50 20.34           C
ATOM    664  CB  GLU A 318     -49.409 -10.004 -16.245  0.50 22.40           C
ATOM    665  CG  GLU A 318     -49.479  -8.559 -16.735  0.50 23.95           C
ATOM    666  CD  GLU A 318     -49.760  -7.559 -15.619  0.50 27.70           C
ATOM    667  OE1 GLU A 318     -50.489  -7.917 -14.678  0.50 27.87           O
ATOM    668  OE2 GLU A 318     -49.258  -6.408 -15.687  0.50 29.28           O
ATOM    669  C   GLU A 318     -48.721 -12.373 -16.743  0.50 20.12           C
ATOM    670  O   GLU A 318     -49.644 -13.131 -16.408  0.50 21.12           O
ATOM    671  N   TYR A 319     -47.439 -12.694 -16.624  0.50 20.38           N
ATOM    672  CA  TYR A 319     -47.026 -13.998 -16.119  0.50 20.29           C
ATOM    673  CB  TYR A 319     -46.164 -14.730 -17.162  0.50 20.78           C
ATOM    674  CG  TYR A 319     -46.939 -15.018 -18.426  0.50 20.64           C
ATOM    675  CD1 TYR A 319     -47.065 -14.051 -19.416  0.50 20.86           C
ATOM    676  CE1 TYR A 319     -47.821 -14.283 -20.556  0.50 20.08           C
ATOM    677  CZ  TYR A 319     -48.440 -15.503 -20.724  0.50 20.62           C
ATOM    678  OH  TYR A 319     -49.171 -15.744 -21.875  0.50 20.50           O
ATOM    679  CE2 TYR A 319     -48.335 -16.484 -19.755  0.50 20.76           C
ATOM    680  CD2 TYR A 319     -47.589 -16.235 -18.610  0.50 20.29           C
ATOM    681  C   TYR A 319     -46.276 -13.806 -14.815  0.50 21.74           C
ATOM    682  O   TYR A 319     -45.210 -13.195 -14.787  0.50 21.65           O
ATOM    683  N   LYS A 320     -46.871 -14.302 -13.736  0.50 23.06           N
ATOM    684  CA  LYS A 320     -46.267 -14.247 -12.411  0.50 23.51           C
ATOM    685  CB  LYS A 320     -47.194 -13.510 -11.421  0.50 24.66           C
ATOM    686  CG  LYS A 320     -46.588 -13.337 -10.035  0.50 23.82           C
ATOM    687  CD  LYS A 320     -47.205 -12.173  -9.265  0.50 26.17           C
ATOM    688  CE  LYS A 320     -48.711 -12.297  -9.182  0.50 25.90           C
ATOM    689  NZ  LYS A 320     -49.228 -11.641  -7.937  0.50 26.84           N
ATOM    690  C   LYS A 320     -45.935 -15.650 -11.913  0.50 24.29           C
```

Figure 27 (Continued)

```
ATOM    691  O   LYS A 320     -46.778 -16.556 -11.951  0.50 26.21           O
ATOM    692  N   CYS A 321     -44.680 -15.823 -11.487  0.50 23.34           N
ATOM    693  CA  CYS A 321     -44.182 -17.057 -10.878  0.50 24.65           C
ATOM    694  CB  CYS A 321     -42.825 -17.430 -11.476  0.50 24.04           C
ATOM    695  SG  CYS A 321     -41.972 -18.762 -10.596  0.50 25.20           S
ATOM    696  C   CYS A 321     -43.993 -16.827  -9.392  0.50 24.79           C
ATOM    697  O   CYS A 321     -43.274 -15.894  -8.998  0.50 24.54           O
ATOM    698  N   LYS A 322     -44.614 -17.678  -8.571  0.50 22.72           N
ATOM    699  CA  LYS A 322     -44.530 -17.524  -7.119  0.50 24.34           C
ATOM    700  CB  LYS A 322     -45.916 -17.569  -6.461  0.50 24.66           C
ATOM    701  CG  LYS A 322     -45.845 -17.505  -4.934  0.50 27.43           C
ATOM    702  CD  LYS A 322     -47.164 -17.129  -4.276  0.50 29.34           C
ATOM    703  CE  LYS A 322     -48.130 -18.301  -4.194  0.50 29.85           C
ATOM    704  NZ  LYS A 322     -49.185 -18.057  -3.160  0.50 30.64           N
ATOM    705  C   LYS A 322     -43.628 -18.583  -6.516  0.50 23.92           C
ATOM    706  O   LYS A 322     -43.837 -19.785  -6.736  0.50 24.73           O
ATOM    707  N   VAL A 323     -42.639 -18.119  -5.750  0.50 25.57           N
ATOM    708  CA  VAL A 323     -41.646 -18.990  -5.115  0.50 24.09           C
ATOM    709  CB  VAL A 323     -40.223 -18.636  -5.544  0.50 22.19           C
ATOM    710  CG1 VAL A 323     -39.239 -19.656  -4.978  0.50 20.81           C
ATOM    711  CG2 VAL A 323     -40.137 -18.583  -7.063  0.50 22.67           C
ATOM    712  C   VAL A 323     -41.685 -18.883  -3.594  0.50 25.33           C
ATOM    713  O   VAL A 323     -41.369 -17.841  -3.006  0.50 26.53           O
ATOM    714  N   SER A 324     -42.093 -19.974  -2.979  0.50 29.16           N
ATOM    715  CA  SER A 324     -42.185 -20.047  -1.535  0.50 30.13           C
ATOM    716  CB  SER A 324     -43.597 -20.467  -1.137  0.50 29.13           C
ATOM    717  OG  SER A 324     -44.519 -19.405  -1.327  0.50 29.22           O
ATOM    718  C   SER A 324     -41.169 -21.071  -1.062  0.50 32.35           C
ATOM    719  O   SER A 324     -41.061 -22.158  -1.633  0.50 34.46           O
ATOM    720  N   ASN A 325     -40.412 -20.717  -0.030  0.50 34.46           N
ATOM    721  CA  ASN A 325     -39.372 -21.598   0.489  0.50 38.23           C
ATOM    722  CB  ASN A 325     -38.056 -21.355  -0.248  0.50 36.82           C
ATOM    723  CG  ASN A 325     -36.959 -22.313   0.180  0.50 37.28           C
ATOM    724  OD1 ASN A 325     -36.011 -21.922   0.861  0.50 39.06           O
ATOM    725  ND2 ASN A 325     -37.081 -23.572  -0.224  0.50 37.23           N
ATOM    726  C   ASN A 325     -39.177 -21.360   1.983  0.50 39.56           C
ATOM    727  O   ASN A 325     -39.218 -20.212   2.438  0.50 39.62           O
ATOM    728  N   LYS A 326     -38.966 -22.439   2.739  0.50 43.56           N
ATOM    729  CA  LYS A 326     -38.787 -22.332   4.194  0.50 44.81           C
ATOM    730  CB  LYS A 326     -38.148 -23.602   4.773  0.50 47.49           C
ATOM    731  CG  LYS A 326     -39.129 -24.724   5.091  0.50 52.23           C
ATOM    732  CD  LYS A 326     -38.514 -25.738   6.051  0.50 54.52           C
ATOM    733  CE  LYS A 326     -39.314 -27.032   6.103  0.50 56.24           C
ATOM    734  NZ  LYS A 326     -40.743 -26.806   6.457  0.50 57.54           N
ATOM    735  C   LYS A 326     -37.957 -21.109   4.573  0.50 44.03           C
ATOM    736  O   LYS A 326     -38.325 -20.351   5.474  0.50 44.65           O
ATOM    737  N   ALA A 327     -36.843 -20.911   3.876  0.50 42.32           N
ATOM    738  CA  ALA A 327     -35.943 -19.803   4.178  0.50 41.00           C
ATOM    739  CB  ALA A 327     -34.614 -19.981   3.463  0.50 40.20           C
ATOM    740  C   ALA A 327     -36.573 -18.476   3.800  0.50 39.18           C
ATOM    741  O   ALA A 327     -35.973 -17.416   3.969  0.50 40.41           O
ATOM    742  N   LEU A 328     -37.784 -18.541   3.263  0.50 39.13           N
ATOM    743  CA  LEU A 328     -38.466 -17.340   2.802  0.50 37.39           C
ATOM    744  CB  LEU A 328     -38.834 -17.478   1.327  0.50 36.65           C
ATOM    745  CG  LEU A 328     -37.654 -17.624   0.365  0.50 35.58           C
ATOM    746  CD1 LEU A 328     -38.172 -18.024  -1.008  0.50 36.75           C
ATOM    747  CD2 LEU A 328     -36.876 -16.321   0.295  0.50 36.30           C
ATOM    748  C   LEU A 328     -39.715 -17.067   3.626  0.50 36.80           C
ATOM    749  O   LEU A 328     -40.771 -17.647   3.373  0.50 36.32           O
ATOM    750  N   PRO A 329     -39.593 -16.167   4.609  0.50 36.52           N
ATOM    751  CA  PRO A 329     -40.693 -15.689   5.451  0.50 35.87           C
ATOM    752  CB  PRO A 329     -40.090 -14.469   6.153  0.50 35.63           C
ATOM    753  CG  PRO A 329     -38.620 -14.707   6.160  0.50 34.57           C
ATOM    754  CD  PRO A 329     -38.302 -15.541   4.950  0.50 36.94           C
```

Figure 27 (Continued)

```
ATOM    755  C   PRO A 329     -41.893 -15.236   4.611  0.50 34.63           C
ATOM    756  O   PRO A 329     -43.030 -15.253   5.080  0.50 34.71           O
ATOM    757  N   ALA A 330     -41.622 -14.820   3.378  0.50 33.09           N
ATOM    758  CA  ALA A 330     -42.651 -14.321   2.476  0.50 30.11           C
ATOM    759  CB  ALA A 330     -42.730 -12.806   2.552  0.50 29.79           C
ATOM    760  C   ALA A 330     -42.300 -14.760   1.057  0.50 29.87           C
ATOM    761  O   ALA A 330     -41.127 -14.760   0.691  0.50 30.30           O
ATOM    762  N   PRO A 331     -43.309 -15.169   0.273  0.50 29.84           N
ATOM    763  CA  PRO A 331     -43.061 -15.560  -1.120  0.50 28.47           C
ATOM    764  CB  PRO A 331     -44.454 -15.933  -1.636  0.50 30.14           C
ATOM    765  CG  PRO A 331     -45.258 -16.235  -0.415  0.50 30.87           C
ATOM    766  CD  PRO A 331     -44.716 -15.336   0.659  0.50 30.40           C
ATOM    767  C   PRO A 331     -42.506 -14.392  -1.924  0.50 30.58           C
ATOM    768  O   PRO A 331     -42.973 -13.263  -1.764  0.50 28.42           O
ATOM    769  N   ILE A 332     -41.505 -14.651  -2.765  0.50 28.65           N
ATOM    770  CA  ILE A 332     -41.057 -13.648  -3.725  0.50 29.59           C
ATOM    771  CB  ILE A 332     -39.564 -13.793  -4.082  0.50 29.02           C
ATOM    772  CG1 ILE A 332     -38.681 -13.549  -2.859  0.50 30.05           C
ATOM    773  CD1 ILE A 332     -37.245 -13.981  -3.065  0.50 29.39           C
ATOM    774  CG2 ILE A 332     -39.189 -12.818  -5.192  0.50 28.82           C
ATOM    775  C   ILE A 332     -41.849 -13.872  -5.002  0.50 28.32           C
ATOM    776  O   ILE A 332     -41.949 -15.001  -5.487  0.50 25.88           O
ATOM    777  N   GLU A 333     -42.428 -12.797  -5.521  0.50 28.78           N
ATOM    778  CA  GLU A 333     -43.181 -12.851  -6.762  0.50 30.09           C
ATOM    779  CB  GLU A 333     -44.613 -12.395  -6.532  0.50 33.24           C
ATOM    780  CG  GLU A 333     -45.390 -13.305  -5.600  0.50 36.72           C
ATOM    781  CD  GLU A 333     -46.806 -12.826  -5.378  0.50 39.85           C
ATOM    782  OE1 GLU A 333     -47.100 -11.658  -5.716  0.50 42.34           O
ATOM    783  OE2 GLU A 333     -47.615 -13.622  -4.856  0.50 43.79           O
ATOM    784  C   GLU A 333     -42.528 -11.939  -7.782  0.50 29.77           C
ATOM    785  O   GLU A 333     -42.326 -10.757  -7.519  0.50 27.56           O
ATOM    786  N   LYS A 334     -42.175 -12.509  -8.935  0.50 29.37           N
ATOM    787  CA  LYS A 334     -41.737 -11.728 -10.074  0.50 27.44           C
ATOM    788  CB  LYS A 334     -40.443 -12.287 -10.674  0.50 27.04           C
ATOM    789  CG  LYS A 334     -39.210 -12.181  -9.791  0.50 28.68           C
ATOM    790  CD  LYS A 334     -38.791 -10.741  -9.576  0.50 27.19           C
ATOM    791  CE  LYS A 334     -37.471 -10.677  -8.821  0.50 29.13           C
ATOM    792  NZ  LYS A 334     -37.328  -9.390  -8.086  0.50 28.51           N
ATOM    793  C   LYS A 334     -42.824 -11.849 -11.119  0.50 25.31           C
ATOM    794  O   LYS A 334     -43.437 -12.906 -11.269  0.50 25.51           O
ATOM    795  N   THR A 335     -43.047 -10.760 -11.836  0.50 24.32           N
ATOM    796  CA  THR A 335     -43.970 -10.760 -12.962  0.50 25.08           C
ATOM    797  CB  THR A 335     -45.139  -9.783 -12.724  0.50 25.76           C
ATOM    798  OG1 THR A 335     -45.669  -9.990 -11.409  0.50 27.09           O
ATOM    799  CG2 THR A 335     -46.257 -10.005 -13.744  0.50 25.84           C
ATOM    800  C   THR A 335     -43.211 -10.361 -14.224  0.50 24.11           C
ATOM    801  O   THR A 335     -42.204  -9.643 -14.174  0.50 23.04           O
ATOM    802  N   ILE A 336     -43.682 -10.847 -15.359  0.50 24.52           N
ATOM    803  CA  ILE A 336     -43.127 -10.421 -16.628  0.50 24.02           C
ATOM    804  CB  ILE A 336     -41.924 -11.287 -17.048  0.50 24.96           C
ATOM    805  CG1 ILE A 336     -41.090 -10.565 -18.113  0.50 26.48           C
ATOM    806  CD1 ILE A 336     -39.719 -11.167 -18.343  0.50 26.36           C
ATOM    807  CG2 ILE A 336     -42.389 -12.671 -17.508  0.50 24.72           C
ATOM    808  C   ILE A 336     -44.196 -10.466 -17.711  0.50 24.35           C
ATOM    809  O   ILE A 336     -45.147 -11.239 -17.638  0.50 22.84           O
ATOM    810  N   SER A 337     -44.009  -9.621 -18.712  0.50 22.99           N
ATOM    811  CA  SER A 337     -44.866  -9.576 -19.879  0.50 24.24           C
ATOM    812  CB  SER A 337     -46.108  -8.730 -19.618  0.50 24.68           C
ATOM    813  OG  SER A 337     -45.773  -7.364 -19.745  0.50 27.61           O
ATOM    814  C   SER A 337     -44.063  -8.962 -21.015  0.50 21.54           C
ATOM    815  O   SER A 337     -42.932  -8.472 -20.827  0.50 23.71           O
ATOM    816  N   LYS A 338     -44.647  -9.009 -22.203  0.50 19.43           N
ATOM    817  CA  LYS A 338     -44.028  -8.481 -23.394  0.50 20.04           C
ATOM    818  CB  LYS A 338     -45.024  -8.547 -24.546  0.50 18.49           C
```

Figure 27 (Continued)

| ATOM | 819 | CG | LYS | A | 338 | -44.400 | -8.546 | -25.935 | 0.50 | 20.04 | C |
|---|---|---|---|---|---|---|---|---|---|---|---|
| ATOM | 820 | CD | LYS | A | 338 | -45.486 | -8.719 | -26.979 | 0.50 | 20.29 | C |
| ATOM | 821 | CE | LYS | A | 338 | -46.373 | -7.486 | -27.026 | 0.50 | 19.80 | C |
| ATOM | 822 | NZ | LYS | A | 338 | -45.557 | -6.258 | -27.238 | 0.50 | 19.73 | N |
| ATOM | 823 | C | LYS | A | 338 | -43.596 | -7.031 | -23.204 | 0.50 | 20.94 | C |
| ATOM | 824 | O | LYS | A | 338 | -44.149 | -6.307 | -22.368 | 0.50 | 20.71 | O |
| ATOM | 825 | N | ALA | A | 339 | -42.657 | -6.598 | -24.036 | 0.50 | 20.05 | N |
| ATOM | 826 | CA | ALA | A | 339 | -42.248 | -5.200 | -24.083 | 0.50 | 21.43 | C |
| ATOM | 827 | CB | ALA | A | 339 | -41.093 | -5.007 | -25.063 | 0.50 | 21.82 | C |
| ATOM | 828 | C | ALA | A | 339 | -43.415 | -4.322 | -24.475 | 0.50 | 21.52 | C |
| ATOM | 829 | O | ALA | A | 339 | -44.131 | -4.632 | -25.413 | 0.50 | 22.45 | O |
| ATOM | 830 | N | LYS | A | 340 | -43.582 | -3.201 | -23.778 | 0.50 | 21.15 | N |
| ATOM | 831 | CA | LYS | A | 340 | -44.719 | -2.327 | -24.026 | 0.50 | 21.95 | C |
| ATOM | 832 | CB | LYS | A | 340 | -45.072 | -1.544 | -22.756 | 0.50 | 22.32 | C |
| ATOM | 833 | CG | LYS | A | 340 | -45.627 | -2.401 | -21.637 | 0.50 | 26.13 | C |
| ATOM | 834 | CD | LYS | A | 340 | -46.420 | -1.540 | -20.667 | 0.50 | 26.73 | C |
| ATOM | 835 | CE | LYS | A | 340 | -47.304 | -2.395 | -19.790 | 0.50 | 31.49 | C |
| ATOM | 836 | NZ | LYS | A | 340 | -46.532 | -3.501 | -19.170 | 0.50 | 30.55 | N |
| ATOM | 837 | C | LYS | A | 340 | -44.495 | -1.371 | -25.202 | 0.50 | 21.82 | C |
| ATOM | 838 | O | LYS | A | 340 | -43.356 | -1.067 | -25.567 | 0.50 | 21.81 | O |
| ATOM | 839 | N | GLY | A | 341 | -45.596 | -0.911 | -25.802 | 0.50 | 21.67 | N |
| ATOM | 840 | CA | GLY | A | 341 | -45.539 | 0.095 | -26.852 | 0.50 | 20.65 | C |
| ATOM | 841 | C | GLY | A | 341 | -46.420 | -0.268 | -28.023 | 0.50 | 20.89 | C |
| ATOM | 842 | O | GLY | A | 341 | -46.779 | -1.444 | -28.210 | 0.50 | 19.39 | O |
| ATOM | 843 | N | GLN | A | 342 | -46.794 | 0.753 | -28.793 | 0.50 | 21.38 | N |
| ATOM | 844 | CA | GLN | A | 342 | -47.584 | 0.583 | -30.007 | 0.50 | 22.22 | C |
| ATOM | 845 | CB | GLN | A | 342 | -48.119 | 1.946 | -30.454 | 0.50 | 26.71 | C |
| ATOM | 846 | CG | GLN | A | 342 | -49.399 | 1.915 | -31.277 | 0.50 | 31.50 | C |
| ATOM | 847 | CD | GLN | A | 342 | -49.745 | 3.298 | -31.802 | 0.50 | 36.68 | C |
| ATOM | 848 | OE1 | GLN | A | 342 | -49.313 | 4.306 | -31.233 | 0.50 | 36.99 | O |
| ATOM | 849 | NE2 | GLN | A | 342 | -50.490 | 3.359 | -32.906 | 0.50 | 37.45 | N |
| ATOM | 850 | C | GLN | A | 342 | -46.673 | -0.004 | -31.094 | 0.50 | 20.99 | C |
| ATOM | 851 | O | GLN | A | 342 | -45.563 | 0.454 | -31.260 | 0.50 | 19.24 | O |
| ATOM | 852 | N | PRO | A | 343 | -47.133 | -1.049 | -31.804 | 0.50 | 20.51 | N |
| ATOM | 853 | CA | PRO | A | 343 | -46.206 | -1.689 | -32.750 | 0.50 | 20.36 | C |
| ATOM | 854 | CB | PRO | A | 343 | -46.958 | -2.949 | -33.195 | 0.50 | 20.55 | C |
| ATOM | 855 | CG | PRO | A | 343 | -47.900 | -3.250 | -32.088 | 0.50 | 21.58 | C |
| ATOM | 856 | CD | PRO | A | 343 | -48.234 | -1.943 | -31.407 | 0.50 | 20.02 | C |
| ATOM | 857 | C | PRO | A | 343 | -45.870 | -0.818 | -33.953 | 0.50 | 20.85 | C |
| ATOM | 858 | O | PRO | A | 343 | -46.706 | -0.063 | -34.460 | 0.50 | 18.89 | O |
| ATOM | 859 | N | ARG | A | 344 | -44.643 | -0.945 | -34.427 | 0.50 | 19.66 | N |
| ATOM | 860 | CA | ARG | A | 344 | -44.251 | -0.280 | -35.639 | 0.50 | 19.73 | C |
| ATOM | 861 | CB | ARG | A | 344 | -43.326 | 0.902 | -35.359 | 0.50 | 20.59 | C |
| ATOM | 862 | CG | ARG | A | 344 | -44.052 | 2.226 | -35.229 | 0.50 | 23.62 | C |
| ATOM | 863 | CD | ARG | A | 344 | -43.095 | 3.400 | -35.314 | 0.50 | 23.12 | C |
| ATOM | 864 | NE | ARG | A | 344 | -42.643 | 3.682 | -36.675 | 0.50 | 27.08 | N |
| ATOM | 865 | CZ | ARG | A | 344 | -41.895 | 4.733 | -36.990 | 0.50 | 28.84 | C |
| ATOM | 866 | NH1 | ARG | A | 344 | -41.527 | 5.586 | -36.032 | 0.50 | 28.98 | N |
| ATOM | 867 | NH2 | ARG | A | 344 | -41.518 | 4.933 | -38.250 | 0.50 | 30.27 | N |
| ATOM | 868 | C | ARG | A | 344 | -43.545 | -1.282 | -36.511 | 0.50 | 20.52 | C |
| ATOM | 869 | O | ARG | A | 344 | -42.617 | -1.963 | -36.074 | 0.50 | 18.30 | O |
| ATOM | 870 | N | GLU | A | 345 | -44.010 | -1.356 | -37.747 | 0.50 | 21.16 | N |
| ATOM | 871 | CA | GLU | A | 345 | -43.529 | -2.314 | -38.718 | 0.50 | 21.75 | C |
| ATOM | 872 | CB | GLU | A | 345 | -44.464 | -2.238 | -39.931 | 0.50 | 24.29 | C |
| ATOM | 873 | CG | GLU | A | 345 | -44.184 | -3.242 | -41.025 | 0.50 | 25.44 | C |
| ATOM | 874 | CD | GLU | A | 345 | -45.253 | -3.236 | -42.103 | 0.50 | 27.75 | C |
| ATOM | 875 | OE1 | GLU | A | 345 | -45.004 | -3.805 | -43.185 | 0.50 | 28.40 | O |
| ATOM | 876 | OE2 | GLU | A | 345 | -46.329 | -2.645 | -41.883 | 0.50 | 29.28 | O |
| ATOM | 877 | C | GLU | A | 345 | -42.098 | -2.001 | -39.168 | 0.50 | 21.81 | C |
| ATOM | 878 | O | GLU | A | 345 | -41.842 | -0.945 | -39.731 | 0.50 | 23.92 | O |
| ATOM | 879 | N | PRO | A | 346 | -41.174 | -2.939 | -38.952 | 0.50 | 21.10 | N |
| ATOM | 880 | CA | PRO | A | 346 | -39.812 | -2.727 | -39.422 | 0.50 | 22.06 | C |
| ATOM | 881 | CB | PRO | A | 346 | -39.114 | -4.041 | -39.066 | 0.50 | 22.27 | C |
| ATOM | 882 | CG | PRO | A | 346 | -40.214 | -5.054 | -39.075 | 0.50 | 20.45 | C |

Figure 27 (Continued)

```
ATOM    883  CD   PRO A 346     -41.415  -4.330 -38.535  0.50 20.41           C
ATOM    884  C    PRO A 346     -39.796  -2.515 -40.931  0.50 23.17           C
ATOM    885  O    PRO A 346     -40.657  -3.050 -41.663  0.50 22.69           O
ATOM    886  N    GLN A 347     -38.824  -1.734 -41.396  0.50 22.39           N
ATOM    887  CA   GLN A 347     -38.569  -1.583 -42.811  0.50 22.49           C
ATOM    888  CB   GLN A 347     -38.381  -0.102 -43.147  0.50 24.66           C
ATOM    889  CG   GLN A 347     -39.391   0.793 -42.441  0.50 27.68           C
ATOM    890  CD   GLN A 347     -40.782   0.663 -43.027  0.50 32.07           C
ATOM    891  OE1  GLN A 347     -41.775   0.531 -42.301  0.50 38.34           O
ATOM    892  NE2  GLN A 347     -40.865   0.703 -44.351  0.50 32.51           N
ATOM    893  C    GLN A 347     -37.273  -2.345 -43.027  0.50 20.90           C
ATOM    894  O    GLN A 347     -36.330  -2.209 -42.238  0.50 21.00           O
ATOM    895  N    VAL A 348     -37.228  -3.169 -44.057  0.50 19.56           N
ATOM    896  CA   VAL A 348     -36.087  -4.070 -44.235  0.50 18.54           C
ATOM    897  CB   VAL A 348     -36.514  -5.553 -44.230  0.50 18.46           C
ATOM    898  CG1  VAL A 348     -35.303  -6.479 -44.353  0.50 19.48           C
ATOM    899  CG2  VAL A 348     -37.263  -5.870 -42.958  0.50 18.66           C
ATOM    900  C    VAL A 348     -35.445  -3.778 -45.571  0.50 18.68           C
ATOM    901  O    VAL A 348     -36.126  -3.711 -46.606  0.50 19.35           O
ATOM    902  N    TYR A 349     -34.130  -3.606 -45.533  0.50 18.67           N
ATOM    903  CA   TYR A 349     -33.359  -3.322 -46.716  0.50 19.48           C
ATOM    904  CB   TYR A 349     -32.982  -1.842 -46.780  0.50 19.05           C
ATOM    905  CG   TYR A 349     -34.176  -0.933 -46.752  0.50 20.19           C
ATOM    906  CD1  TYR A 349     -35.137  -0.983 -47.761  0.50 18.95           C
ATOM    907  CE1  TYR A 349     -36.241  -0.154 -47.731  0.50 20.76           C
ATOM    908  CZ   TYR A 349     -36.396   0.736 -46.699  0.50 20.73           C
ATOM    909  OH   TYR A 349     -37.495   1.562 -46.662  0.50 23.47           O
ATOM    910  CE2  TYR A 349     -35.466   0.802 -45.685  0.50 21.21           C
ATOM    911  CD2  TYR A 349     -34.358  -0.029 -45.718  0.50 19.63           C
ATOM    912  C    TYR A 349     -32.121  -4.173 -46.715  0.50 19.38           C
ATOM    913  O    TYR A 349     -31.529  -4.470 -45.661  0.50 19.17           O
ATOM    914  N    VAL A 350     -31.734  -4.609 -47.893  0.50 18.08           N
ATOM    915  CA   VAL A 350     -30.464  -5.284 -48.003  0.50 19.05           C
ATOM    916  CB   VAL A 350     -30.612  -6.752 -48.461  0.50 19.12           C
ATOM    917  CG1  VAL A 350     -31.455  -7.547 -47.462  0.50 18.60           C
ATOM    918  CG2  VAL A 350     -31.245  -6.837 -49.838  0.50 17.97           C
ATOM    919  C    VAL A 350     -29.512  -4.445 -48.861  0.50 19.68           C
ATOM    920  O    VAL A 350     -29.934  -3.645 -49.734  0.50 19.33           O
ATOM    921  N    TYR A 351     -28.230  -4.602 -48.562  0.50 20.10           N
ATOM    922  CA   TYR A 351     -27.152  -3.843 -49.176  0.50 20.16           C
ATOM    923  CB   TYR A 351     -26.467  -2.967 -48.124  0.50 20.71           C
ATOM    924  CG   TYR A 351     -27.250  -1.787 -47.591  0.50 20.76           C
ATOM    925  CD1  TYR A 351     -26.841  -0.472 -47.871  0.50 21.72           C
ATOM    926  CE1  TYR A 351     -27.536   0.623 -47.380  0.50 21.37           C
ATOM    927  CZ   TYR A 351     -28.631   0.415 -46.568  0.50 24.08           C
ATOM    928  OH   TYR A 351     -29.316   1.496 -46.057  0.50 25.93           O
ATOM    929  CE2  TYR A 351     -29.029  -0.875 -46.243  0.50 21.57           C
ATOM    930  CD2  TYR A 351     -28.338  -1.964 -46.760  0.50 21.11           C
ATOM    931  C    TYR A 351     -26.103  -4.816 -49.672  0.50 20.17           C
ATOM    932  O    TYR A 351     -25.557  -5.593 -48.895  0.50 20.75           O
ATOM    933  N    PRO A 352     -25.752  -4.737 -50.958  0.50 21.03           N
ATOM    934  CA   PRO A 352     -24.656  -5.557 -51.465  0.50 20.90           C
ATOM    935  CB   PRO A 352     -24.769  -5.383 -52.983  0.50 21.55           C
ATOM    936  CG   PRO A 352     -25.445  -4.067 -53.161  0.50 21.80           C
ATOM    937  CD   PRO A 352     -26.415  -3.961 -52.021  0.50 22.31           C
ATOM    938  C    PRO A 352     -23.292  -5.105 -50.940  0.50 20.90           C
ATOM    939  O    PRO A 352     -23.216  -4.120 -50.207  0.50 21.52           O
ATOM    940  N    PRO A 353     -22.227  -5.849 -51.263  0.50 21.64           N
ATOM    941  CA   PRO A 353     -20.876  -5.478 -50.848  0.50 22.04           C
ATOM    942  CB   PRO A 353     -20.017  -6.665 -51.299  0.50 23.01           C
ATOM    943  CG   PRO A 353     -20.976  -7.771 -51.667  0.50 21.76           C
ATOM    944  CD   PRO A 353     -22.249  -7.093 -52.058  0.50 22.19           C
ATOM    945  C    PRO A 353     -20.367  -4.212 -51.533  0.50 22.05           C
ATOM    946  O    PRO A 353     -20.641  -3.984 -52.712  0.50 23.77           O
```

Figure 27 (Continued)

```
ATOM    947  N    SER A 354     -19.604   -3.424  -50.793  0.50 21.21           N
ATOM    948  CA   SER A 354     -18.847   -2.307  -51.362  0.50 21.73           C
ATOM    949  CB   SER A 354     -17.886   -1.738  -50.304  0.50 18.11           C
ATOM    950  OG   SER A 354     -16.877   -0.933  -50.910  0.50 20.17           O
ATOM    951  C    SER A 354     -18.027   -2.755  -52.583  0.50 22.15           C
ATOM    952  O    SER A 354     -17.466   -3.843  -52.596  0.50 22.81           O
ATOM    953  N    ARG A 355     -17.932   -1.899  -53.598  0.50 26.71           N
ATOM    954  CA   ARG A 355     -16.930   -2.107  -54.648  0.50 28.65           C
ATOM    955  CB   ARG A 355     -16.881   -0.897  -55.602  0.50 31.53           C
ATOM    956  CG   ARG A 355     -15.829   -0.998  -56.699  0.50 37.55           C
ATOM    957  CD   ARG A 355     -16.438   -1.194  -58.086  0.50 41.38           C
ATOM    958  NE   ARG A 355     -17.414   -2.289  -58.136  0.50 44.04           N
ATOM    959  CZ   ARG A 355     -17.768   -2.932  -59.246  0.50 43.26           C
ATOM    960  NH1  ARG A 355     -18.669   -3.909  -59.195  0.50 41.58           N
ATOM    961  NH2  ARG A 355     -17.216   -2.605  -60.408  0.50 44.52           N
ATOM    962  C    ARG A 355     -15.538   -2.375  -54.036  0.50 27.94           C
ATOM    963  O    ARG A 355     -14.841   -3.331  -54.417  0.50 26.69           O
ATOM    964  N    ASP A 356     -15.144   -1.533  -53.081  0.50 25.77           N
ATOM    965  CA   ASP A 356     -13.857   -1.662  -52.397  0.50 24.54           C
ATOM    966  CB   ASP A 356     -13.701   -0.595  -51.296  0.50 24.46           C
ATOM    967  CG   ASP A 356     -13.668    0.835  -51.835  0.50 26.85           C
ATOM    968  OD1  ASP A 356     -13.404    1.748  -51.010  0.50 24.43           O
ATOM    969  OD2  ASP A 356     -13.914    1.066  -53.051  0.50 26.29           O
ATOM    970  C    ASP A 356     -13.614   -3.041  -51.767  0.50 23.59           C
ATOM    971  O    ASP A 356     -12.471   -3.489  -51.675  0.50 24.24           O
ATOM    972  N    GLU A 357     -14.678   -3.709  -51.307  0.50 22.81           N
ATOM    973  CA   GLU A 357     -14.511   -4.932  -50.520  0.50 21.72           C
ATOM    974  CB   GLU A 357     -15.731   -5.203  -49.610  0.50 21.02           C
ATOM    975  CG   GLU A 357     -15.480   -6.276  -48.557  0.50 19.35           C
ATOM    976  CD   GLU A 357     -16.681   -6.504  -47.657  0.50 18.24           C
ATOM    977  OE1  GLU A 357     -17.816   -6.263  -48.124  0.50 19.16           O
ATOM    978  OE2  GLU A 357     -16.488   -6.925  -46.500  0.50 19.01           O
ATOM    979  C    GLU A 357     -14.232   -6.147  -51.408  0.50 23.23           C
ATOM    980  O    GLU A 357     -13.799   -7.192  -50.928  0.50 22.28           O
ATOM    981  N    LEU A 358     -14.457   -5.996  -52.708  0.50 25.74           N
ATOM    982  CA   LEU A 358     -14.350   -7.136  -53.623  0.50 28.45           C
ATOM    983  CB   LEU A 358     -14.941   -6.785  -54.990  0.50 28.65           C
ATOM    984  CG   LEU A 358     -16.415   -6.365  -54.996  0.50 29.33           C
ATOM    985  CD1  LEU A 358     -16.845   -5.954  -56.394  0.50 31.29           C
ATOM    986  CD2  LEU A 358     -17.308   -7.481  -54.469  0.50 29.82           C
ATOM    987  C    LEU A 358     -12.916   -7.624  -53.778  0.50 30.27           C
ATOM    988  O    LEU A 358     -12.680   -8.674  -54.360  0.50 32.64           O
ATOM    989  N    THR A 359     -11.968   -6.850  -53.261  0.50 31.75           N
ATOM    990  CA   THR A 359     -10.549   -7.202  -53.309  0.50 31.60           C
ATOM    991  CB   THR A 359      -9.676   -5.968  -53.019  0.50 33.06           C
ATOM    992  OG1  THR A 359     -10.002   -5.448  -51.723  0.50 34.95           O
ATOM    993  CG2  THR A 359      -9.930   -4.879  -54.061  0.50 33.82           C
ATOM    994  C    THR A 359     -10.223   -8.291  -52.287  0.50 32.42           C
ATOM    995  O    THR A 359      -9.148   -8.902  -52.321  0.50 30.64           O
ATOM    996  N    LYS A 360     -11.174   -8.562  -51.404  0.50 29.45           N
ATOM    997  CA   LYS A 360     -10.940   -9.478  -50.293  0.50 28.92           C
ATOM    998  CB   LYS A 360     -11.563   -8.906  -49.018  0.50 30.62           C
ATOM    999  CG   LYS A 360     -11.238   -7.432  -48.823  0.50 33.14           C
ATOM   1000  CD   LYS A 360      -9.732   -7.213  -48.694  0.50 32.74           C
ATOM   1001  CE   LYS A 360      -9.388   -5.731  -48.581  0.50 33.89           C
ATOM   1002  NZ   LYS A 360      -8.027   -5.510  -48.014  0.50 36.48           N
ATOM   1003  C    LYS A 360     -11.472  -10.882  -50.576  0.50 28.90           C
ATOM   1004  O    LYS A 360     -12.235  -11.088  -51.516  0.50 28.24           O
ATOM   1005  N    ASN A 361     -11.043  -11.853  -49.775  0.50 28.41           N
ATOM   1006  CA   ASN A 361     -11.493  -13.226  -49.963  0.50 29.41           C
ATOM   1007  CB   ASN A 361     -10.612  -14.196  -49.185  0.50 31.04           C
ATOM   1008  CG   ASN A 361      -9.239  -14.341  -49.798  0.50 34.88           C
ATOM   1009  OD1  ASN A 361      -9.078  -14.249  -51.025  0.50 36.45           O
ATOM   1010  ND2  ASN A 361      -8.236  -14.556  -48.956  0.50 32.50           N
```

Figure 27 (Continued)

```
ATOM   1011  C    ASN A 361     -12.950 -13.415 -49.567  0.50 28.52           C
ATOM   1012  O    ASN A 361     -13.592 -14.390 -49.968  0.50 26.48           O
ATOM   1013  N    GLN A 362     -13.466 -12.462 -48.795  0.50 26.69           N
ATOM   1014  CA   GLN A 362     -14.848 -12.514 -48.322  0.50 25.71           C
ATOM   1015  CB   GLN A 362     -14.872 -12.934 -46.853  0.50 27.30           C
ATOM   1016  CG   GLN A 362     -14.337 -14.348 -46.677  0.50 30.82           C
ATOM   1017  CD   GLN A 362     -14.109 -14.743 -45.236  0.50 33.70           C
ATOM   1018  OE1  GLN A 362     -13.565 -13.975 -44.442  0.50 37.45           O
ATOM   1019  NE2  GLN A 362     -14.504 -15.967 -44.895  0.50 35.73           N
ATOM   1020  C    GLN A 362     -15.550 -11.180 -48.533  0.50 23.97           C
ATOM   1021  O    GLN A 362     -14.906 -10.146 -48.717  0.50 22.28           O
ATOM   1022  N    VAL A 363     -16.878 -11.197 -48.530  0.50 21.35           N
ATOM   1023  CA   VAL A 363     -17.600  -9.965 -48.757  0.50 20.09           C
ATOM   1024  CB   VAL A 363     -18.162  -9.887 -50.183  0.50 20.95           C
ATOM   1025  CG1  VAL A 363     -17.026  -9.886 -51.205  0.50 22.11           C
ATOM   1026  CG2  VAL A 363     -19.125 -11.043 -50.423  0.50 19.64           C
ATOM   1027  C    VAL A 363     -18.714  -9.849 -47.730  0.50 18.96           C
ATOM   1028  O    VAL A 363     -19.098 -10.841 -47.112  0.50 18.53           O
ATOM   1029  N    SER A 364     -19.203  -8.634 -47.524  0.50 17.62           N
ATOM   1030  CA   SER A 364     -20.127  -8.363 -46.433  0.50 17.39           C
ATOM   1031  CB   SER A 364     -19.604  -7.214 -45.561  0.50 17.12           C
ATOM   1032  OG   SER A 364     -18.378  -7.557 -44.938  0.50 16.98           O
ATOM   1033  C    SER A 364     -21.505  -7.999 -46.953  0.50 17.58           C
ATOM   1034  O    SER A 364     -21.702  -6.932 -47.551  0.50 18.12           O
ATOM   1035  N    LEU A 365     -22.463  -8.887 -46.711  0.50 16.04           N
ATOM   1036  CA   LEU A 365     -23.835  -8.590 -47.050  0.50 15.01           C
ATOM   1037  CB   LEU A 365     -24.589  -9.840 -47.517  0.50 14.64           C
ATOM   1038  CG   LEU A 365     -24.109 -10.414 -48.867  0.50 13.73           C
ATOM   1039  CD1  LEU A 365     -25.099 -11.450 -49.394  0.50 14.05           C
ATOM   1040  CD2  LEU A 365     -23.856  -9.357 -49.924  0.50 14.96           C
ATOM   1041  C    LEU A 365     -24.482  -8.016 -45.816  0.50 14.56           C
ATOM   1042  O    LEU A 365     -24.376  -8.569 -44.723  0.50 16.10           O
ATOM   1043  N    THR A 366     -25.186  -6.925 -46.018  0.50 14.23           N
ATOM   1044  CA   THR A 366     -25.680  -6.103 -44.930  0.50 14.14           C
ATOM   1045  CB   THR A 366     -25.115  -4.678 -45.071  0.50 13.67           C
ATOM   1046  OG1  THR A 366     -23.681  -4.701 -44.999  0.50 13.59           O
ATOM   1047  CG2  THR A 366     -25.676  -3.781 -43.990  0.50 13.02           C
ATOM   1048  C    THR A 366     -27.209  -6.053 -44.990  0.50 14.59           C
ATOM   1049  O    THR A 366     -27.794  -5.811 -46.056  0.50 16.13           O
ATOM   1050  N    CYS A 367     -27.865  -6.269 -43.845  0.50 14.84           N
ATOM   1051  CA   CYS A 367     -29.314  -6.112 -43.747  0.50 15.97           C
ATOM   1052  CB   CYS A 367     -29.938  -7.468 -43.397  0.50 17.05           C
ATOM   1053  SG   CYS A 367     -31.740  -7.577 -43.320  0.50 19.16           S
ATOM   1054  C    CYS A 367     -29.636  -5.073 -42.665  0.50 16.47           C
ATOM   1055  O    CYS A 367     -29.354  -5.293 -41.476  0.50 16.71           O
ATOM   1056  N    LEU A 368     -30.185  -3.943 -43.104  0.50 16.42           N
ATOM   1057  CA   LEU A 368     -30.689  -2.880 -42.225  0.50 16.20           C
ATOM   1058  CB   LEU A 368     -30.527  -1.503 -42.887  0.50 16.41           C
ATOM   1059  CG   LEU A 368     -31.153  -0.301 -42.158  0.50 16.03           C
ATOM   1060  CD1  LEU A 368     -30.427  -0.032 -40.849  0.50 15.42           C
ATOM   1061  CD2  LEU A 368     -31.103   0.958 -43.034  0.50 16.64           C
ATOM   1062  C    LEU A 368     -32.166  -3.128 -41.932  0.50 16.03           C
ATOM   1063  O    LEU A 368     -32.967  -3.334 -42.843  0.50 17.65           O
ATOM   1064  N    VAL A 369     -32.514  -3.139 -40.657  0.50 16.18           N
ATOM   1065  CA   VAL A 369     -33.911  -3.218 -40.220  0.50 15.84           C
ATOM   1066  CB   VAL A 369     -34.155  -4.525 -39.442  0.50 15.57           C
ATOM   1067  CG1  VAL A 369     -35.649  -4.792 -39.309  0.50 16.61           C
ATOM   1068  CG2  VAL A 369     -33.446  -5.684 -40.148  0.50 15.78           C
ATOM   1069  C    VAL A 369     -34.132  -2.004 -39.316  0.50 16.42           C
ATOM   1070  O    VAL A 369     -33.405  -1.826 -38.332  0.50 19.13           O
ATOM   1071  N    LYS A 370     -35.051  -1.122 -39.692  0.50 17.12           N
ATOM   1072  CA   LYS A 370     -35.281   0.103 -38.924  0.50 17.49           C
ATOM   1073  CB   LYS A 370     -34.618   1.316 -39.598  0.50 17.80           C
ATOM   1074  CG   LYS A 370     -35.371   1.798 -40.839  0.50 17.60           C
```

Figure 27 (Continued)

```
ATOM   1075  CD  LYS A 370     -34.891    3.165  -41.316  0.50 17.64           C
ATOM   1076  CE  LYS A 370     -35.427    4.272  -40.435  0.50 18.10           C
ATOM   1077  NZ  LYS A 370     -35.453    5.590  -41.114  0.50 17.60           N
ATOM   1078  C   LYS A 370     -36.769    0.393  -38.785  0.50 17.38           C
ATOM   1079  O   LYS A 370     -37.610   -0.254  -39.411  0.50 18.33           O
ATOM   1080  N   GLY A 371     -37.069    1.388  -37.967  0.50 16.57           N
ATOM   1081  CA  GLY A 371     -38.446    1.848  -37.772  0.50 16.92           C
ATOM   1082  C   GLY A 371     -39.305    0.939  -36.908  0.50 16.58           C
ATOM   1083  O   GLY A 371     -40.501    1.181  -36.764  0.50 16.06           O
ATOM   1084  N   PHE A 372     -38.701   -0.088  -36.317  0.50 15.97           N
ATOM   1085  CA  PHE A 372     -39.505   -1.065  -35.549  0.50 16.07           C
ATOM   1086  CB  PHE A 372     -39.031   -2.510  -35.801  0.50 15.87           C
ATOM   1087  CG  PHE A 372     -37.648   -2.831  -35.267  0.50 16.09           C
ATOM   1088  CD1 PHE A 372     -36.523   -2.631  -36.050  0.50 16.26           C
ATOM   1089  CE1 PHE A 372     -35.258   -2.964  -35.591  0.50 16.51           C
ATOM   1090  CZ  PHE A 372     -35.103   -3.527  -34.329  0.50 16.42           C
ATOM   1091  CE2 PHE A 372     -36.219   -3.765  -33.545  0.50 16.52           C
ATOM   1092  CD2 PHE A 372     -37.489   -3.420  -34.009  0.50 16.41           C
ATOM   1093  C   PHE A 372     -39.723   -0.770  -34.067  0.50 16.81           C
ATOM   1094  O   PHE A 372     -38.922   -0.103  -33.411  0.50 16.71           O
ATOM   1095  N   TYR A 373     -40.867   -1.221  -33.553  0.50 16.38           N
ATOM   1096  CA  TYR A 373     -41.159   -1.070  -32.146  0.50 17.38           C
ATOM   1097  CB  TYR A 373     -41.805    0.271  -31.834  0.50 18.91           C
ATOM   1098  CG  TYR A 373     -41.497    0.729  -30.432  0.50 21.98           C
ATOM   1099  CD1 TYR A 373     -42.271    0.311  -29.362  0.50 22.75           C
ATOM   1100  CE1 TYR A 373     -41.986    0.723  -28.071  0.50 25.55           C
ATOM   1101  CZ  TYR A 373     -40.900    1.565  -27.848  0.50 25.93           C
ATOM   1102  OH  TYR A 373     -40.588    2.000  -26.576  0.50 27.98           O
ATOM   1103  CE2 TYR A 373     -40.117    1.987  -28.897  0.50 23.99           C
ATOM   1104  CD2 TYR A 373     -40.404    1.553  -30.177  0.50 22.64           C
ATOM   1105  C   TYR A 373     -42.034   -2.229  -31.727  0.50 17.08           C
ATOM   1106  O   TYR A 373     -42.933   -2.563  -32.508  0.50 16.77           O
ATOM   1107  N   PRO A 374     -42.066   -2.458  -30.415  0.50 17.52           N
ATOM   1108  CA  PRO A 374     -40.852   -2.675  -29.600  0.50 16.77           C
ATOM   1109  CB  PRO A 374     -41.375   -3.358  -28.316  0.50 16.72           C
ATOM   1110  CG  PRO A 374     -42.874   -3.255  -28.412  0.50 18.28           C
ATOM   1111  CD  PRO A 374     -43.153   -3.300  -29.896  0.50 18.13           C
ATOM   1112  C   PRO A 374     -39.657   -3.408  -30.214  0.50 16.90           C
ATOM   1113  O   PRO A 374     -39.679   -3.789  -31.379  0.50 17.37           O
ATOM   1114  N   SER A 375     -38.599   -3.548  -29.415  0.50 17.45           N
ATOM   1115  CA  SER A 375     -37.304   -3.961  -29.927  0.50 17.71           C
ATOM   1116  CB  SER A 375     -36.163   -3.459  -29.019  0.50 18.57           C
ATOM   1117  OG  SER A 375     -36.244   -4.075  -27.748  0.50 20.67           O
ATOM   1118  C   SER A 375     -37.167   -5.470  -30.095  0.50 18.18           C
ATOM   1119  O   SER A 375     -36.200   -5.934  -30.687  0.50 18.77           O
ATOM   1120  N   ASP A 376     -38.131   -6.237  -29.583  0.50 18.92           N
ATOM   1121  CA  ASP A 376     -38.024   -7.701  -29.667  0.50 19.09           C
ATOM   1122  CB  ASP A 376     -39.129   -8.393  -28.863  0.50 21.16           C
ATOM   1123  CG  ASP A 376     -38.857   -8.430  -27.367  0.50 22.78           C
ATOM   1124  OD1 ASP A 376     -37.707   -8.217  -26.931  0.50 24.83           O
ATOM   1125  OD2 ASP A 376     -39.816   -8.687  -26.616  0.50 26.69           O
ATOM   1126  C   ASP A 376     -38.149   -8.135  -31.128  0.50 18.75           C
ATOM   1127  O   ASP A 376     -39.097   -7.754  -31.824  0.50 19.06           O
ATOM   1128  N   ILE A 377     -37.190   -8.921  -31.607  0.50 17.14           N
ATOM   1129  CA  ILE A 377     -37.066   -9.131  -33.035  0.50 16.65           C
ATOM   1130  CB  ILE A 377     -36.555   -7.847  -33.749  0.50 16.39           C
ATOM   1131  CG1 ILE A 377     -36.744   -7.940  -35.266  0.50 17.32           C
ATOM   1132  CD1 ILE A 377     -36.779   -6.578  -35.948  0.50 16.98           C
ATOM   1133  CG2 ILE A 377     -35.096   -7.584  -33.383  0.50 17.17           C
ATOM   1134  C   ILE A 377     -36.115  -10.287  -33.278  0.50 16.53           C
ATOM   1135  O   ILE A 377     -35.251  -10.558  -32.448  0.50 18.43           O
ATOM   1136  N   ALA A 378     -36.303  -10.983  -34.394  0.50 15.64           N
ATOM   1137  CA  ALA A 378     -35.368  -12.042  -34.793  0.50 15.60           C
ATOM   1138  CB  ALA A 378     -36.019  -13.412  -34.629  0.50 16.26           C
```

Figure 27 (Continued)

```
ATOM   1139  C    ALA A 378     -34.951 -11.816 -36.236  0.50 15.39           C
ATOM   1140  O    ALA A 378     -35.793 -11.589 -37.110  0.50 15.65           O
ATOM   1141  N    VAL A 379     -33.650 -11.881 -36.498  0.50 15.44           N
ATOM   1142  CA   VAL A 379     -33.124 -11.659 -37.833  0.50 14.74           C
ATOM   1143  CB   VAL A 379     -32.430 -10.278 -37.925  0.50 15.00           C
ATOM   1144  CG1  VAL A 379     -31.850 -10.064 -39.312  0.50 14.76           C
ATOM   1145  CG2  VAL A 379     -33.427  -9.174 -37.572  0.50 14.62           C
ATOM   1146  C    VAL A 379     -32.125 -12.772 -38.168  0.50 15.81           C
ATOM   1147  O    VAL A 379     -31.182 -13.037 -37.400  0.50 15.24           O
ATOM   1148  N    GLU A 380     -32.326 -13.428 -39.304  0.50 15.91           N
ATOM   1149  CA   GLU A 380     -31.522 -14.606 -39.658  0.50 16.45           C
ATOM   1150  CB   GLU A 380     -32.260 -15.902 -39.259  0.50 17.05           C
ATOM   1151  CG   GLU A 380     -32.718 -15.935 -37.815  0.50 19.89           C
ATOM   1152  CD   GLU A 380     -33.420 -17.242 -37.466  0.50 19.79           C
ATOM   1153  OE1  GLU A 380     -33.536 -17.554 -36.261  0.50 24.50           O
ATOM   1154  OE2  GLU A 380     -33.860 -17.951 -38.384  0.50 20.98           O
ATOM   1155  C    GLU A 380     -31.284 -14.613 -41.147  0.50 16.39           C
ATOM   1156  O    GLU A 380     -32.054 -14.001 -41.895  0.50 18.86           O
ATOM   1157  N    TRP A 381     -30.223 -15.283 -41.587  0.50 17.08           N
ATOM   1158  CA   TRP A 381     -29.927 -15.393 -42.998  0.50 17.52           C
ATOM   1159  CB   TRP A 381     -28.534 -14.857 -43.321  0.50 17.69           C
ATOM   1160  CG   TRP A 381     -28.276 -13.381 -43.051  0.50 17.06           C
ATOM   1161  CD1  TRP A 381     -27.992 -12.812 -41.850  0.50 16.62           C
ATOM   1162  NE1  TRP A 381     -27.778 -11.447 -42.011  0.50 16.73           N
ATOM   1163  CE2  TRP A 381     -27.902 -11.132 -43.335  0.50 16.85           C
ATOM   1164  CD2  TRP A 381     -28.238 -12.322 -44.025  0.50 16.68           C
ATOM   1165  CE3  TRP A 381     -28.421 -12.272 -45.418  0.50 16.44           C
ATOM   1166  CZ3  TRP A 381     -28.307 -11.042 -46.063  0.50 17.32           C
ATOM   1167  CH2  TRP A 381     -27.977  -9.872 -45.336  0.50 16.80           C
ATOM   1168  CZ2  TRP A 381     -27.773  -9.904 -43.984  0.50 16.09           C
ATOM   1169  C    TRP A 381     -29.938 -16.845 -43.484  0.50 19.50           C
ATOM   1170  O    TRP A 381     -29.678 -17.775 -42.715  0.50 19.96           O
ATOM   1171  N    GLU A 382     -30.127 -17.008 -44.789  0.50 20.92           N
ATOM   1172  CA   GLU A 382     -30.056 -18.327 -45.411  0.50 21.14           C
ATOM   1173  CB   GLU A 382     -31.386 -19.070 -45.179  0.50 22.00           C
ATOM   1174  CG   GLU A 382     -32.609 -18.245 -45.525  0.50 24.96           C
ATOM   1175  CD   GLU A 382     -33.913 -19.013 -45.409  0.50 26.66           C
ATOM   1176  OE1  GLU A 382     -34.453 -19.401 -46.472  0.50 27.44           O
ATOM   1177  OE2  GLU A 382     -34.397 -19.204 -44.263  0.50 26.12           O
ATOM   1178  C    GLU A 382     -29.744 -18.199 -46.905  0.50 21.62           C
ATOM   1179  O    GLU A 382     -29.806 -17.101 -47.487  0.50 21.37           O
ATOM   1180  N    SER A 383     -29.402 -19.321 -47.528  0.50 21.17           N
ATOM   1181  CA   SER A 383     -29.209 -19.383 -48.971  0.50 22.66           C
ATOM   1182  CB   SER A 383     -27.751 -19.111 -49.337  0.50 22.13           C
ATOM   1183  OG   SER A 383     -27.489 -19.514 -50.670  0.50 22.82           O
ATOM   1184  C    SER A 383     -29.597 -20.792 -49.410  0.50 23.54           C
ATOM   1185  O    SER A 383     -29.206 -21.760 -48.766  0.50 22.03           O
ATOM   1186  N    ASN A 384     -30.409 -20.891 -50.459  0.50 27.25           N
ATOM   1187  CA   ASN A 384     -30.892 -22.184 -50.948  0.50 30.50           C
ATOM   1188  CB   ASN A 384     -29.734 -22.996 -51.535  0.50 33.04           C
ATOM   1189  CG   ASN A 384     -30.206 -24.085 -52.484  0.50 37.37           C
ATOM   1190  OD1  ASN A 384     -30.749 -23.798 -53.559  0.50 39.05           O
ATOM   1191  ND2  ASN A 384     -30.001 -25.341 -52.095  0.50 35.70           N
ATOM   1192  C    ASN A 384     -31.617 -22.992 -49.873  0.50 31.74           C
ATOM   1193  O    ASN A 384     -31.460 -24.211 -49.798  0.50 31.21           O
ATOM   1194  N    GLY A 385     -32.399 -22.298 -49.044  0.50 32.50           N
ATOM   1195  CA   GLY A 385     -33.226 -22.920 -48.008  0.50 32.86           C
ATOM   1196  C    GLY A 385     -32.471 -23.260 -46.734  0.50 35.06           C
ATOM   1197  O    GLY A 385     -33.072 -23.613 -45.719  0.50 36.18           O
ATOM   1198  N    GLN A 386     -31.151 -23.151 -46.792  0.50 31.82           N
ATOM   1199  CA   GLN A 386     -30.290 -23.608 -45.708  0.50 32.14           C
ATOM   1200  CB   GLN A 386     -29.070 -24.327 -46.287  0.50 31.99           C
ATOM   1201  CG   GLN A 386     -29.412 -25.626 -47.006  0.50 34.70           C
ATOM   1202  CD   GLN A 386     -30.079 -26.624 -46.082  0.50 36.14           C
```

Figure 27 (Continued)

```
ATCM   1203  OE1  GLN A 386     -29.504 -27.028 -45.074  0.50 38.25           O
ATCM   1204  NE2  GLN A 386     -31.297 -27.033 -46.426  0.50 37.96           N
ATCM   1205  C    GLN A 386     -29.845 -22.404 -44.883  0.50 29.04           C
ATCM   1206  O    GLN A 386     -29.519 -21.358 -45.445  0.50 27.79           O
ATCM   1207  N    PRO A 387     -29.846 -22.546 -43.551  0.50 28.52           N
ATCM   1208  CA   PRO A 387     -29.386 -21.450 -42.707  0.50 26.87           C
ATCM   1209  CB   PRO A 387     -29.339 -22.080 -41.316  0.50 27.27           C
ATCM   1210  CG   PRO A 387     -30.405 -23.124 -41.356  0.50 28.21           C
ATCM   1211  CD   PRO A 387     -30.397 -23.661 -42.761  0.50 28.43           C
ATCM   1212  C    PRO A 387     -27.985 -21.052 -43.108  0.50 27.13           C
ATCM   1213  O    PRO A 387     -27.118 -21.913 -43.297  0.50 22.91           O
ATCM   1214  N    GLU A 388     -27.776 -19.743 -43.250  0.50 26.80           N
ATCM   1215  CA   GLU A 388     -26.466 -19.188 -43.526  0.50 25.52           C
ATCM   1216  CB   GLU A 388     -26.548 -18.210 -44.700  0.50 28.26           C
ATCM   1217  CG   GLU A 388     -26.828 -18.878 -46.029  0.50 28.90           C
ATCM   1218  CD   GLU A 388     -25.611 -19.606 -46.546  0.50 30.36           C
ATCM   1219  OE1  GLU A 388     -25.747 -20.781 -46.971  0.50 30.62           O
ATCM   1220  OE2  GLU A 388     -24.518 -18.997 -46.506  0.50 30.18           O
ATCM   1221  C    GLU A 388     -26.183 -18.429 -42.265  0.50 26.63           C
ATCM   1222  O    GLU A 388     -26.718 -17.326 -42.071  0.50 24.64           O
ATCM   1223  N    ASN A 389     -25.389 -19.041 -41.392  0.50 20.60           N
ATCM   1224  CA   ASN A 389     -25.359 -18.622 -40.023  0.50 22.00           C
ATCM   1225  CB   ASN A 389     -25.524 -19.828 -39.098  0.50 22.33           C
ATCM   1226  CG   ASN A 389     -26.938 -20.364 -39.108  0.50 20.30           C
ATCM   1227  OD1  ASN A 389     -27.844 -19.709 -39.622  0.50 23.35           O
ATCM   1228  ND2  ASN A 389     -27.146 -21.563 -38.536  0.50 20.93           N
ATCM   1229  C    ASN A 389     -24.076 -17.883 -39.738  0.50 21.70           C
ATCM   1230  O    ASN A 389     -23.741 -17.614 -38.586  0.50 23.18           O
ATCM   1231  N    ASN A 390     -23.359 -17.564 -40.807  0.50 22.42           N
ATCM   1232  CA   ASN A 390     -22.087 -16.892 -40.657  0.50 22.95           C
ATCM   1233  CB   ASN A 390     -21.158 -17.258 -41.787  0.50 22.17           C
ATCM   1234  CG   ASN A 390     -19.768 -16.748 -41.535  0.50 22.82           C
ATCM   1235  OD1  ASN A 390     -19.419 -16.503 -40.395  0.50 23.09           O
ATCM   1236  ND2  ASN A 390     -18.978 -16.590 -42.576  0.50 25.20           N
ATCM   1237  C    ASN A 390     -22.251 -15.367 -40.561  0.50 21.50           C
ATCM   1238  O    ASN A 390     -21.753 -14.599 -41.418  0.50 19.57           O
ATCM   1239  N    TYR A 391     -22.966 -14.952 -39.522  0.50 19.78           N
ATCM   1240  CA   TYR A 391     -23.428 -13.582 -39.415  0.50 19.90           C
ATCM   1241  CB   TYR A 391     -24.826 -13.417 -40.048  0.50 20.24           C
ATCM   1242  CG   TYR A 391     -26.047 -13.924 -39.256  0.50 21.05           C
ATCM   1243  CD1  TYR A 391     -26.690 -13.112 -38.328  0.50 21.80           C
ATCM   1244  CE1  TYR A 391     -27.840 -13.533 -37.661  0.50 22.52           C
ATCM   1245  CZ   TYR A 391     -28.366 -14.786 -37.941  0.50 22.86           C
ATCM   1246  OH   TYR A 391     -29.516 -15.227 -37.278  0.50 24.09           O
ATCM   1247  CE2  TYR A 391     -27.764 -15.593 -38.884  0.50 20.07           C
ATCM   1248  CD2  TYR A 391     -26.624 -15.158 -39.544  0.50 22.75           C
ATCM   1249  C    TYR A 391     -23.433 -13.083 -37.986  0.50 18.06           C
ATCM   1250  O    TYR A 391     -23.537 -13.873 -37.038  0.50 15.84           O
ATCM   1251  N    LYS A 392     -23.289 -11.763 -37.830  0.50 16.93           N
ATCM   1252  CA   LYS A 392     -23.474 -11.130 -36.535  0.50 16.81           C
ATCM   1253  CB   LYS A 392     -22.160 -10.492 -36.029  0.50 18.21           C
ATCM   1254  CG   LYS A 392     -21.004 -11.467 -35.948  0.50 20.33           C
ATCM   1255  CD   LYS A 392     -21.286 -12.485 -34.867  0.50 23.37           C
ATCM   1256  CE   LYS A 392     -20.011 -13.126 -34.362  0.50 25.30           C
ATCM   1257  NZ   LYS A 392     -20.381 -14.027 -33.235  0.50 28.74           N
ATCM   1258  C    LYS A 392     -24.493 -10.024 -36.698  0.50 16.55           C
ATCM   1259  O    LYS A 392     -24.683  -9.496 -37.807  0.50 16.36           O
ATCM   1260  N    THR A 393     -25.130  -9.667 -35.592  0.50 16.17           N
ATCM   1261  CA   THR A 393     -26.138  -8.611 -35.602  0.50 15.00           C
ATCM   1262  CB   THR A 393     -27.541  -9.238 -35.568  0.50 16.11           C
ATCM   1263  OG1  THR A 393     -27.587 -10.360 -36.464  0.50 15.25           O
ATCM   1264  CG2  THR A 393     -28.610  -8.225 -35.975  0.50 16.55           C
ATCM   1265  C    THR A 393     -25.958  -7.618 -34.444  0.50 15.64           C
ATCM   1266  O    THR A 393     -25.754  -8.021 -33.287  0.50 15.17           O
```

Figure 27 (Continued)

```
ATOM   1267  N    THR A 394     -26.043  -6.317 -34.737  0.50 14.19           N
ATOM   1268  CA   THR A 394     -26.055  -5.331 -33.662  0.50 14.79           C
ATOM   1269  CB   THR A 394     -26.101  -3.873 -34.202  0.50 13.53           C
ATOM   1270  OG1  THR A 394     -27.397  -3.604 -34.779  0.50 13.42           O
ATOM   1271  CG2  THR A 394     -25.027  -3.645 -35.271  0.50 14.60           C
ATOM   1272  C    THR A 394     -27.316  -5.573 -32.824  0.50 15.06           C
ATOM   1273  O    THR A 394     -28.386  -5.819 -33.367  0.50 15.91           O
ATOM   1274  N    PRO A 395     -27.202  -5.529 -31.492  0.50 16.46           N
ATOM   1275  CA   PRO A 395     -28.480  -5.421 -30.793  0.50 16.29           C
ATOM   1276  CB   PRO A 395     -28.076  -5.353 -29.313  0.50 15.65           C
ATOM   1277  CG   PRO A 395     -26.711  -5.980 -29.240  0.50 16.08           C
ATOM   1278  CD   PRO A 395     -26.071  -5.865 -30.605  0.50 16.27           C
ATOM   1279  C    PRO A 395     -29.182  -4.125 -31.230  0.50 16.40           C
ATOM   1280  O    PRO A 395     -28.511  -3.159 -31.597  0.50 17.13           O
ATOM   1281  N    PRO A 396     -30.533  -4.107 -31.212  0.50 15.42           N
ATOM   1282  CA   PRO A 396     -31.272  -2.909 -31.595  0.50 16.64           C
ATOM   1283  CB   PRO A 396     -32.745  -3.315 -31.365  0.50 15.95           C
ATOM   1284  CG   PRO A 396     -32.750  -4.795 -31.546  0.50 15.23           C
ATOM   1285  CD   PRO A 396     -31.427  -5.263 -30.984  0.50 15.32           C
ATOM   1286  C    PRO A 396     -30.919  -1.708 -30.716  0.50 17.18           C
ATOM   1287  O    PRO A 396     -30.676  -1.862 -29.522  0.50 17.61           O
ATOM   1288  N    VAL A 397     -30.922  -0.530 -31.313  0.50 18.64           N
ATOM   1289  CA   VAL A 397     -30.671   0.714 -30.587  0.50 19.08           C
ATOM   1290  CB   VAL A 397     -29.216   1.110 -30.810  0.50 19.77           C
ATOM   1291  CG1  VAL A 397     -28.850   0.840 -32.268  0.50 23.46           C
ATOM   1292  CG2  VAL A 397     -28.322   0.288 -29.885  0.50 20.58           C
ATOM   1293  C    VAL A 397     -31.618   1.813 -31.095  0.50 18.45           C
ATOM   1294  O    VAL A 397     -32.060   1.764 -32.237  0.50 17.27           O
ATOM   1295  N    LEU A 398     -31.946   2.788 -30.251  0.50 19.09           N
ATOM   1296  CA   LEU A 398     -32.959   3.804 -30.610  0.50 18.06           C
ATOM   1297  CB   LEU A 398     -33.412   4.569 -29.341  0.50 18.27           C
ATOM   1298  CG   LEU A 398     -34.231   3.721 -28.341  0.50 19.10           C
ATOM   1299  CD1  LEU A 398     -34.308   4.306 -26.939  0.50 19.05           C
ATOM   1300  CD2  LEU A 398     -35.627   3.436 -28.866  0.50 18.11           C
ATOM   1301  C    LEU A 398     -32.499   4.759 -31.734  0.50 19.12           C
ATOM   1302  O    LEU A 398     -31.368   5.269 -31.724  0.50 19.63           O
ATOM   1303  N    ASP A 399     -33.378   4.987 -32.704  0.50 19.52           N
ATOM   1304  CA   ASP A 399     -33.105   5.901 -33.805  0.50 20.65           C
ATOM   1305  CB   ASP A 399     -33.751   5.376 -35.085  0.50 20.76           C
ATOM   1306  CG   ASP A 399     -33.112   5.922 -36.355  0.50 21.34           C
ATOM   1307  OD1  ASP A 399     -32.557   7.041 -36.345  0.50 20.58           O
ATOM   1308  OD2  ASP A 399     -33.192   5.233 -37.395  0.50 20.70           O
ATOM   1309  C    ASP A 399     -33.683   7.272 -33.433  0.50 22.41           C
ATOM   1310  O    ASP A 399     -34.264   7.435 -32.360  0.50 23.27           O
ATOM   1311  N    SER A 400     -33.553   8.242 -34.331  0.50 24.16           N
ATOM   1312  CA   SER A 400     -33.870   9.619 -33.982  0.50 25.80           C
ATOM   1313  CB   SER A 400     -33.042  10.602 -34.822  0.50 24.61           C
ATOM   1314  OG   SER A 400     -33.198  10.367 -36.209  0.50 24.71           O
ATOM   1315  C    SER A 400     -35.364   9.937 -34.022  0.50 26.94           C
ATOM   1316  O    SER A 400     -35.772  11.042 -33.685  0.50 28.97           O
ATOM   1317  N    ASP A 401     -36.176   8.948 -34.394  0.50 26.19           N
ATOM   1318  CA   ASP A 401     -37.623   9.112 -34.469  0.50 25.17           C
ATOM   1319  CB   ASP A 401     -38.115   8.758 -35.874  0.50 25.42           C
ATOM   1320  CG   ASP A 401     -37.860   7.313 -36.221  0.50 24.48           C
ATOM   1321  OD1  ASP A 401     -37.131   6.626 -35.465  0.50 24.27           O
ATOM   1322  OD2  ASP A 401     -38.406   6.865 -37.239  0.50 25.20           O
ATOM   1323  C    ASP A 401     -38.326   8.243 -33.435  0.50 25.37           C
ATOM   1324  O    ASP A 401     -39.539   8.016 -33.510  0.50 25.52           O
ATOM   1325  N    GLY A 402     -37.555   7.749 -32.470  0.50 24.11           N
ATOM   1326  CA   GLY A 402     -38.117   6.982 -31.366  0.50 23.80           C
ATOM   1327  C    GLY A 402     -38.388   5.520 -31.637  0.50 22.94           C
ATOM   1328  O    GLY A 402     -38.898   4.809 -30.765  0.50 24.78           O
ATOM   1329  N    SER A 403     -38.060   5.054 -32.837  0.50 20.65           N
ATOM   1330  CA   SER A 403     -38.158   3.625 -33.129  0.50 20.01           C
```

Figure 27 (Continued)

```
ATOM   1331  CB   SER A 403     -38.609   3.398 -34.571  0.50 20.62           C
ATOM   1332  OG   SER A 403     -37.690   3.972 -35.491  0.50 22.13           O
ATOM   1333  C    SER A 403     -36.792   2.970 -32.919  0.50 18.72           C
ATOM   1334  O    SER A 403     -35.847   3.628 -32.481  0.50 17.23           O
ATOM   1335  N    PHE A 404     -36.691   1.681 -33.238  0.50 17.87           N
ATOM   1336  CA   PHE A 404     -35.402   1.000 -33.149  0.50 18.11           C
ATOM   1337  CB   PHE A 404     -35.543  -0.303 -32.377  0.50 17.27           C
ATOM   1338  CG   PHE A 404     -35.703  -0.103 -30.921  0.50 17.61           C
ATOM   1339  CD1  PHE A 404     -36.967  -0.164 -30.343  0.50 17.35           C
ATOM   1340  CE1  PHE A 404     -37.129   0.020 -28.979  0.50 18.46           C
ATOM   1341  CZ   PHE A 404     -36.025   0.293 -28.191  0.50 18.67           C
ATOM   1342  CE2  PHE A 404     -34.768   0.398 -28.767  0.50 19.34           C
ATOM   1343  CD2  PHE A 404     -34.610   0.190 -30.128  0.50 18.49           C
ATOM   1344  C    PHE A 404     -34.872   0.686 -34.516  0.50 18.21           C
ATOM   1345  O    PHE A 404     -35.639   0.584 -35.481  0.50 18.10           O
ATOM   1346  N    ALA A 405     -33.550   0.545 -34.600  0.50 17.16           N
ATOM   1347  CA   ALA A 405     -32.934   0.006 -35.798  0.50 16.50           C
ATOM   1348  CB   ALA A 405     -32.416   1.118 -36.714  0.50 17.63           C
ATOM   1349  C    ALA A 405     -31.809  -0.933 -35.414  0.50 15.90           C
ATOM   1350  O    ALA A 405     -31.278  -0.867 -34.304  0.50 16.30           O
ATOM   1351  N    LEU A 406     -31.447  -1.807 -36.343  0.50 16.14           N
ATOM   1352  CA   LEU A 406     -30.308  -2.675 -36.151  0.50 16.29           C
ATOM   1353  CB   LEU A 406     -30.711  -3.913 -35.335  0.50 17.49           C
ATOM   1354  CG   LEU A 406     -31.790  -4.808 -35.964  0.50 16.77           C
ATOM   1355  CD1  LEU A 406     -31.187  -5.621 -37.103  0.50 16.31           C
ATOM   1356  CD2  LEU A 406     -32.258  -5.784 -34.885  0.50 16.59           C
ATOM   1357  C    LEU A 406     -29.788  -3.060 -37.521  0.50 15.61           C
ATOM   1358  O    LEU A 406     -30.453  -2.828 -38.530  0.50 15.80           O
ATOM   1359  N    VAL A 407     -28.590  -3.619 -37.556  0.50 14.85           N
ATOM   1360  CA   VAL A 407     -27.963  -4.058 -38.806  0.50 14.12           C
ATOM   1361  CB   VAL A 407     -26.835  -3.090 -39.219  0.50 14.03           C
ATOM   1362  CG1  VAL A 407     -26.371  -3.396 -40.641  0.50 12.80           C
ATOM   1363  CG2  VAL A 407     -27.359  -1.665 -39.121  0.50 13.58           C
ATOM   1364  C    VAL A 407     -27.358  -5.439 -38.576  0.50 14.10           C
ATOM   1365  O    VAL A 407     -26.656  -5.655 -37.578  0.50 14.16           O
ATOM   1366  N    SER A 408     -27.643  -6.359 -39.504  0.50 14.89           N
ATOM   1367  CA   SER A 408     -27.069  -7.689 -39.511  0.50 14.63           C
ATOM   1368  CB   SER A 408     -28.185  -8.750 -39.648  0.50 14.84           C
ATOM   1369  OG   SER A 408     -27.640 -10.040 -39.386  0.50 15.45           O
ATOM   1370  C    SER A 408     -26.071  -7.812 -40.669  0.50 14.47           C
ATOM   1371  O    SER A 408     -26.336  -7.383 -41.793  0.50 14.33           O
ATOM   1372  N    LYS A 409     -24.927  -8.414 -40.388  0.50 13.99           N
ATOM   1373  CA   LYS A 409     -23.878  -8.591 -41.370  0.50 14.04           C
ATOM   1374  CB   LYS A 409     -22.572  -8.001 -40.825  0.50 13.42           C
ATOM   1375  CG   LYS A 409     -21.392  -8.125 -41.783  0.50 13.62           C
ATOM   1376  CD   LYS A 409     -20.217  -7.227 -41.371  0.50 14.09           C
ATOM   1377  CE   LYS A 409     -19.583  -7.697 -40.067  0.50 13.59           C
ATOM   1378  NZ   LYS A 409     -18.875  -9.016 -40.185  0.50 13.24           N
ATOM   1379  C    LYS A 409     -23.635 -10.079 -41.578  0.50 14.38           C
ATOM   1380  O    LYS A 409     -23.255 -10.757 -40.645  0.50 14.34           O
ATOM   1381  N    LEU A 410     -23.838 -10.564 -42.795  0.50 14.54           N
ATOM   1382  CA   LEU A 410     -23.441 -11.919 -43.163  0.50 15.53           C
ATOM   1383  CB   LEU A 410     -24.575 -12.632 -43.948  0.50 15.61           C
ATOM   1384  CG   LEU A 410     -24.066 -13.864 -44.733  0.50 16.25           C
ATOM   1385  CD1  LEU A 410     -23.899 -15.074 -43.818  0.50 15.80           C
ATOM   1386  CD2  LEU A 410     -25.024 -14.172 -45.884  0.50 16.37           C
ATOM   1387  C    LEU A 410     -22.172 -11.864 -44.013  0.50 15.46           C
ATOM   1388  O    LEU A 410     -22.089 -11.092 -44.970  0.50 17.24           O
ATOM   1389  N    THR A 411     -21.189 -12.670 -43.650  0.50 15.47           N
ATOM   1390  CA   THR A 411     -19.951 -12.755 -44.407  0.50 16.35           C
ATOM   1391  CB   THR A 411     -18.745 -12.927 -43.467  0.50 16.95           C
ATOM   1392  OG1  THR A 411     -18.821 -11.970 -42.397  0.50 15.86           O
ATOM   1393  CG2  THR A 411     -17.443 -12.706 -44.242  0.50 17.23           C
ATOM   1394  C    THR A 411     -20.046 -13.953 -45.370  0.50 17.59           C
```

Figure 27 (Continued)

```
ATOM   1395  O    THR A 411     -20.417 -15.053 -44.958  0.50 17.64           O
ATOM   1396  N    VAL A 412     -19.750 -13.721 -46.643  0.50 18.74           N
ATOM   1397  CA   VAL A 412     -19.799 -14.791 -47.637  0.50 21.29           C
ATOM   1398  CB   VAL A 412     -21.088 -14.712 -48.482  0.50 21.69           C
ATOM   1399  CG1  VAL A 412     -22.299 -14.534 -47.579  0.50 20.95           C
ATOM   1400  CG2  VAL A 412     -20.995 -13.563 -49.476  0.50 20.96           C
ATOM   1401  C    VAL A 412     -18.574 -14.766 -48.557  0.50 23.06           C
ATOM   1402  O    VAL A 412     -17.956 -13.726 -48.770  0.50 23.03           O
ATOM   1403  N    ASP A 413     -18.198 -15.926 -49.080  0.50 24.06           N
ATOM   1404  CA   ASP A 413     -17.098 -15.986 -50.029  0.50 25.03           C
ATOM   1405  CB   ASP A 413     -16.840 -17.426 -50.475  0.50 28.23           C
ATOM   1406  CG   ASP A 413     -16.024 -18.203 -49.466  0.50 31.82           C
ATOM   1407  OD1  ASP A 413     -15.519 -17.583 -48.504  0.50 34.48           O
ATOM   1408  OD2  ASP A 413     -15.874 -19.430 -49.641  0.50 34.59           O
ATOM   1409  C    ASP A 413     -17.408 -15.131 -51.238  0.50 23.78           C
ATOM   1410  O    ASP A 413     -18.493 -15.226 -51.808  0.50 23.37           O
ATOM   1411  N    LYS A 414     -16.463 -14.284 -51.632  0.50 24.55           N
ATOM   1412  CA   LYS A 414     -16.671 -13.464 -52.822  0.50 24.03           C
ATOM   1413  CB   LYS A 414     -15.402 -12.666 -53.183  0.50 25.05           C
ATOM   1414  CG   LYS A 414     -15.484 -11.935 -54.521  0.50 24.66           C
ATOM   1415  CD   LYS A 414     -14.367 -10.913 -54.693  0.50 25.56           C
ATOM   1416  CE   LYS A 414     -13.029 -11.537 -55.058  0.50 24.07           C
ATOM   1417  NZ   LYS A 414     -11.957 -10.497 -55.138  0.50 24.00           N
ATOM   1418  C    LYS A 414     -17.095 -14.364 -53.978  0.50 24.97           C
ATOM   1419  O    LYS A 414     -17.985 -14.016 -54.752  0.50 25.12           O
ATOM   1420  N    SER A 415     -16.464 -15.527 -54.086  0.50 26.39           N
ATOM   1421  CA   SER A 415     -16.812 -16.461 -55.149  0.50 28.14           C
ATOM   1422  CB   SER A 415     -15.973 -17.734 -55.056  0.50 29.50           C
ATOM   1423  OG   SER A 415     -16.244 -18.417 -53.844  0.50 31.48           O
ATOM   1424  C    SER A 415     -18.292 -16.822 -55.105  0.50 28.54           C
ATOM   1425  O    SER A 415     -18.971 -16.785 -56.135  0.50 30.30           O
ATOM   1426  N    ARG A 416     -18.785 -17.203 -53.922  0.50 28.96           N
ATOM   1427  CA   ARG A 416     -20.197 -17.559 -53.792  0.50 28.05           C
ATOM   1428  CB   ARG A 416     -20.560 -17.920 -52.354  0.50 28.00           C
ATOM   1429  CG   ARG A 416     -19.881 -19.167 -51.822  0.50 28.66           C
ATOM   1430  CD   ARG A 416     -20.456 -19.541 -50.466  0.50 29.09           C
ATOM   1431  NE   ARG A 416     -21.884 -19.853 -50.548  0.50 28.75           N
ATOM   1432  CZ   ARG A 416     -22.728 -19.773 -49.522  0.50 30.07           C
ATOM   1433  NH1  ARG A 416     -22.296 -19.363 -48.333  0.50 30.15           N
ATOM   1434  NH2  ARG A 416     -24.006 -20.083 -49.690  0.50 29.69           N
ATOM   1435  C    ARG A 416     -21.021 -16.384 -54.253  0.50 27.04           C
ATOM   1436  O    ARG A 416     -21.950 -16.539 -55.041  0.50 28.72           O
ATOM   1437  N    TRP A 417     -20.660 -15.192 -53.784  0.50 25.79           N
ATOM   1438  CA   TRP A 417     -21.271 -13.980 -54.298  0.50 24.91           C
ATOM   1439  CB   TRP A 417     -20.674 -12.749 -53.607  0.50 24.19           C
ATOM   1440  CG   TRP A 417     -21.296 -11.479 -54.044  0.50 24.98           C
ATOM   1441  CD1  TRP A 417     -20.702 -10.485 -54.771  0.50 25.16           C
ATOM   1442  NE1  TRP A 417     -21.594  -9.467 -54.992  0.50 26.24           N
ATOM   1443  CE2  TRP A 417     -22.792  -9.790 -54.411  0.50 24.65           C
ATOM   1444  CD2  TRP A 417     -22.640 -11.049 -53.799  0.50 24.29           C
ATOM   1445  CE3  TRP A 417     -23.736 -11.607 -53.115  0.50 23.47           C
ATOM   1446  CZ3  TRP A 417     -24.911 -10.907 -53.078  0.50 23.17           C
ATOM   1447  CH2  TRP A 417     -25.038  -9.649 -53.692  0.50 23.07           C
ATOM   1448  CZ2  TRP A 417     -23.991  -9.074 -54.364  0.50 23.71           C
ATOM   1449  C    TRP A 417     -21.056 -13.898 -55.811  0.50 25.81           C
ATOM   1450  O    TRP A 417     -21.937 -13.480 -56.563  0.50 25.17           O
ATOM   1451  N    GLN A 418     -19.868 -14.292 -56.253  0.50 26.48           N
ATOM   1452  CA   GLN A 418     -19.528 -14.193 -57.671  0.50 29.28           C
ATOM   1453  CB   GLN A 418     -18.025 -14.355 -57.855  0.50 29.81           C
ATOM   1454  CG   GLN A 418     -17.230 -13.378 -57.016  0.50 32.56           C
ATOM   1455  CD   GLN A 418     -16.889 -12.102 -57.757  0.50 33.66           C
ATOM   1456  OE1  GLN A 418     -17.768 -11.281 -58.064  0.50 34.78           O
ATOM   1457  NE2  GLN A 418     -15.598 -11.913 -58.026  0.50 33.45           N
ATOM   1458  C    GLN A 418     -20.269 -15.252 -58.467  0.50 30.98           C
```

Figure 27 (Continued)

```
ATOM   1459  O    GLN A 418     -20.647 -15.034 -59.619  0.50 30.34           O
ATOM   1460  N    GLN A 419     -20.493 -16.394 -57.830  0.50 34.07           N
ATOM   1461  CA   GLN A 419     -21.196 -17.504 -58.461  0.50 35.63           C
ATOM   1462  CB   GLN A 419     -21.045 -18.777 -57.620  0.50 38.69           C
ATOM   1463  CG   GLN A 419     -19.689 -19.452 -57.752  0.50 42.90           C
ATOM   1464  CD   GLN A 419     -19.432 -20.483 -56.664  0.50 45.27           C
ATOM   1465  OE1  GLN A 419     -20.286 -20.736 -55.813  0.50 47.09           O
ATOM   1466  NE2  GLN A 419     -18.248 -21.084 -56.689  0.50 47.95           N
ATOM   1467  C    GLN A 419     -22.672 -17.189 -58.696  0.50 36.48           C
ATOM   1468  O    GLN A 419     -23.395 -17.988 -59.294  0.50 35.86           O
ATOM   1469  N    GLY A 420     -23.122 -16.031 -58.217  0.50 34.95           N
ATOM   1470  CA   GLY A 420     -24.475 -15.561 -58.503  0.50 31.79           C
ATOM   1471  C    GLY A 420     -25.527 -16.014 -57.507  0.50 30.18           C
ATOM   1472  O    GLY A 420     -26.715 -15.731 -57.671  0.50 30.28           O
ATOM   1473  N    ASN A 421     -25.088 -16.718 -56.473  0.50 29.93           N
ATOM   1474  CA   ASN A 421     -25.980 -17.203 -55.440  0.50 29.11           C
ATOM   1475  CB   ASN A 421     -25.188 -17.936 -54.362  0.50 29.89           C
ATOM   1476  CG   ASN A 421     -24.511 -19.177 -54.892  0.50 31.57           C
ATOM   1477  OD1  ASN A 421     -25.175 -20.085 -55.394  0.50 30.67           O
ATOM   1478  ND2  ASN A 421     -23.187 -19.233 -54.775  0.50 29.37           N
ATOM   1479  C    ASN A 421     -26.813 -16.104 -54.806  0.50 28.08           C
ATOM   1480  O    ASN A 421     -26.340 -14.979 -54.623  0.50 27.89           O
ATOM   1481  N    VAL A 422     -28.046 -16.457 -54.453  0.50 25.78           N
ATOM   1482  CA   VAL A 422     -28.960 -15.534 -53.821  0.50 24.78           C
ATOM   1483  CB   VAL A 422     -30.417 -15.714 -54.330  0.50 25.28           C
ATOM   1484  CG1  VAL A 422     -31.374 -14.787 -53.598  0.50 23.93           C
ATOM   1485  CG2  VAL A 422     -30.492 -15.460 -55.827  0.50 26.55           C
ATOM   1486  C    VAL A 422     -28.879 -15.725 -52.310  0.50 23.36           C
ATOM   1487  O    VAL A 422     -28.752 -16.853 -51.795  0.50 22.97           O
ATOM   1488  N    PHE A 423     -28.905 -14.600 -51.605  0.50 20.49           N
ATOM   1489  CA   PHE A 423     -28.909 -14.613 -50.163  0.50 18.95           C
ATOM   1490  CB   PHE A 423     -27.592 -14.013 -49.668  0.50 18.98           C
ATOM   1491  CG   PHE A 423     -26.391 -14.788 -50.116  0.50 18.47           C
ATOM   1492  CD1  PHE A 423     -25.754 -14.490 -51.311  0.50 19.58           C
ATOM   1493  CE1  PHE A 423     -24.663 -15.234 -51.740  0.50 18.12           C
ATOM   1494  CZ   PHE A 423     -24.199 -16.276 -50.965  0.50 18.98           C
ATOM   1495  CE2  PHE A 423     -24.850 -16.591 -49.788  0.50 18.36           C
ATOM   1496  CD2  PHE A 423     -25.933 -15.850 -49.368  0.50 18.75           C
ATOM   1497  C    PHE A 423     -30.082 -13.776 -49.692  0.50 18.17           C
ATOM   1498  O    PHE A 423     -30.339 -12.728 -50.251  0.50 19.17           O
ATOM   1499  N    SER A 424     -30.788 -14.229 -48.657  0.50 17.17           N
ATOM   1500  CA   SER A 424     -31.950 -13.497 -48.192  0.50 16.70           C
ATOM   1501  CB   SER A 424     -33.241 -14.286 -48.439  0.50 16.26           C
ATOM   1502  OG   SER A 424     -33.453 -14.449 -49.828  0.50 17.77           O
ATOM   1503  C    SER A 424     -31.848 -13.213 -46.719  0.50 16.02           C
ATOM   1504  O    SER A 424     -31.388 -14.044 -45.949  0.50 15.48           O
ATOM   1505  N    CYS A 425     -32.313 -12.030 -46.339  0.50 16.85           N
ATOM   1506  CA   CYS A 425     -32.394 -11.659 -44.940  0.50 16.38           C
ATOM   1507  CB   CYS A 425     -32.086 -10.164 -44.802  0.50 17.22           C
ATOM   1508  SG   CYS A 425     -32.060  -9.579 -43.089  0.50 19.88           S
ATOM   1509  C    CYS A 425     -33.820 -11.969 -44.449  0.50 16.84           C
ATOM   1510  O    CYS A 425     -34.796 -11.563 -45.082  0.50 16.49           O
ATOM   1511  N    SER A 426     -33.938 -12.707 -43.339  0.50 15.91           N
ATOM   1512  CA   SER A 426     -35.234 -13.033 -42.752  0.50 16.19           C
ATOM   1513  CB   SER A 426     -35.304 -14.522 -42.373  0.50 16.57           C
ATOM   1514  OG   SER A 426     -35.098 -15.318 -43.521  0.50 19.32           O
ATOM   1515  C    SER A 426     -35.472 -12.210 -41.513  0.50 15.72           C
ATOM   1516  O    SER A 426     -34.619 -12.162 -40.625  0.50 15.75           O
ATOM   1517  N    VAL A 427     -36.631 -11.570 -41.451  0.50 15.01           N
ATOM   1518  CA   VAL A 427     -36.974 -10.711 -40.321  0.50 15.02           C
ATOM   1519  CB   VAL A 427     -37.003  -9.238 -40.773  0.50 14.86           C
ATOM   1520  CG1  VAL A 427     -37.371  -8.328 -39.617  0.50 14.54           C
ATOM   1521  CG2  VAL A 427     -35.661  -8.875 -41.405  0.50 15.21           C
ATOM   1522  C    VAL A 427     -38.306 -11.126 -39.738  0.50 15.39           C
```

Figure 27 (Continued)

```
ATOM   1523  O    VAL A 427     -39.299 -11.251 -40.465  0.50 16.97           O
ATOM   1524  N    MET A 428     -38.330 -11.355 -38.426  0.50 14.91           N
ATOM   1525  CA   MET A 428     -39.557 -11.752 -37.740  0.50 14.70           C
ATOM   1526  CB   MET A 428     -39.349 -13.134 -37.133  0.50 16.53           C
ATOM   1527  CG   MET A 428     -39.307 -14.192 -38.228  0.50 17.40           C
ATOM   1528  SD   MET A 428     -38.446 -15.697 -37.747  0.50 19.92           S
ATOM   1529  CE   MET A 428     -36.736 -15.217 -37.969  0.50 20.80           C
ATOM   1530  C    MET A 428     -39.837 -10.719 -36.667  0.50 15.09           C
ATOM   1531  O    MET A 428     -38.975 -10.436 -35.850  0.50 14.45           O
ATOM   1532  N    HIS A 429     -41.039 -10.149 -36.683  0.50 14.66           N
ATOM   1533  CA   HIS A 429     -41.418  -9.094 -35.734  0.50 16.38           C
ATOM   1534  CB   HIS A 429     -40.875  -7.731 -36.193  0.50 15.85           C
ATOM   1535  CG   HIS A 429     -41.070  -6.627 -35.194  0.50 15.96           C
ATOM   1536  ND1  HIS A 429     -42.209  -5.850 -35.162  0.50 17.65           N
ATOM   1537  CE1  HIS A 429     -42.102  -4.950 -34.197  0.50 17.64           C
ATOM   1538  NE2  HIS A 429     -40.921  -5.100 -33.615  0.50 17.03           N
ATOM   1539  CD2  HIS A 429     -40.246  -6.126 -34.234  0.50 16.57           C
ATOM   1540  C    HIS A 429     -42.942  -9.040 -35.638  0.50 15.83           C
ATOM   1541  O    HIS A 429     -43.633  -9.313 -36.616  0.50 17.51           O
ATOM   1542  N    GLU A 430     -43.450  -8.740 -34.453  0.50 16.15           N
ATOM   1543  CA   GLU A 430     -44.898  -8.736 -34.220  0.50 17.61           C
ATOM   1544  CB   GLU A 430     -45.203  -8.388 -32.764  0.50 19.27           C
ATOM   1545  CG   GLU A 430     -44.670  -7.021 -32.360  0.50 19.96           C
ATOM   1546  CD   GLU A 430     -44.656  -6.828 -30.851  0.50 21.63           C
ATOM   1547  OE1  GLU A 430     -43.733  -7.324 -30.172  0.50 22.66           O
ATOM   1548  OE2  GLU A 430     -45.572  -6.163 -30.352  0.50 23.34           O
ATOM   1549  C    GLU A 430     -45.658  -7.792 -35.166  0.50 18.62           C
ATOM   1550  O    GLU A 430     -46.832  -8.043 -35.487  0.50 18.52           O
ATOM   1551  N    ALA A 431     -45.005  -6.720 -35.614  0.50 18.09           N
ATOM   1552  CA   ALA A 431     -45.674  -5.718 -36.457  0.50 20.63           C
ATOM   1553  CB   ALA A 431     -44.959  -4.371 -36.362  0.50 19.91           C
ATOM   1554  C    ALA A 431     -45.812  -6.140 -37.917  0.50 21.21           C
ATOM   1555  O    ALA A 431     -46.633  -5.580 -38.671  0.50 20.97           O
ATOM   1556  N    LEU A 432     -45.013  -7.109 -38.342  0.50 20.16           N
ATOM   1557  CA   LEU A 432     -45.075  -7.546 -39.724  0.50 19.18           C
ATOM   1558  CB   LEU A 432     -43.820  -8.345 -40.111  0.50 19.47           C
ATOM   1559  CG   LEU A 432     -42.497  -7.585 -40.222  0.50 19.08           C
ATOM   1560  CD1  LEU A 432     -41.341  -8.580 -40.287  0.50 18.70           C
ATOM   1561  CD2  LEU A 432     -42.556  -6.691 -41.467  0.50 20.12           C
ATOM   1562  C    LEU A 432     -46.307  -8.414 -39.934  0.50 20.51           C
ATOM   1563  O    LEU A 432     -46.722  -9.137 -39.041  0.50 18.34           O
ATOM   1564  N    HIS A 433     -46.895  -8.335 -41.119  0.50 21.60           N
ATOM   1565  CA   HIS A 433     -47.943  -9.264 -41.456  0.50 21.82           C
ATOM   1566  CB   HIS A 433     -48.618  -8.899 -42.778  0.50 23.06           C
ATOM   1567  CG   HIS A 433     -49.875  -9.671 -43.020  0.50 25.52           C
ATOM   1568  ND1  HIS A 433     -49.956 -10.698 -43.936  0.50 26.14           N
ATOM   1569  CE1  HIS A 433     -51.170 -11.218 -43.906  0.50 26.34           C
ATOM   1570  NE2  HIS A 433     -51.874 -10.575 -42.994  0.50 27.52           N
ATOM   1571  CD2  HIS A 433     -51.083  -9.614 -42.413  0.50 26.47           C
ATOM   1572  C    HIS A 433     -47.371 -10.692 -41.493  0.50 20.81           C
ATOM   1573  O    HIS A 433     -46.251 -10.921 -41.948  0.50 20.84           O
ATOM   1574  N    ASN A 434     -48.133 -11.655 -41.001  0.50 20.70           N
ATOM   1575  CA   ASN A 434     -47.611 -13.015 -40.806  0.50 19.54           C
ATOM   1576  CB   ASN A 434     -47.275 -13.694 -42.147  0.50 22.81           C
ATOM   1577  CG   ASN A 434     -48.381 -13.556 -43.190  0.50 24.41           C
ATOM   1578  OD1  ASN A 434     -49.573 -13.698 -42.891  0.50 24.39           O
ATOM   1579  ND2  ASN A 434     -47.978 -13.306 -44.443  0.50 24.97           N
ATOM   1580  C    ASN A 434     -46.363 -13.074 -39.896  0.50 19.82           C
ATOM   1581  O    ASN A 434     -45.704 -14.127 -39.794  0.50 18.53           O
ATOM   1582  N    HIS A 435     -46.019 -11.939 -39.279  0.50 17.16           N
ATOM   1583  CA   HIS A 435     -44.824 -11.836 -38.436  0.50 18.42           C
ATOM   1584  CB   HIS A 435     -44.914 -12.790 -37.236  0.50 17.68           C
ATOM   1585  CG   HIS A 435     -46.114 -12.553 -36.368  0.50 18.49           C
ATOM   1586  ND1  HIS A 435     -46.557 -13.478 -35.443  0.50 18.81           N
```

Figure 27 (Continued)

```
ATOM   1587  CE1 HIS A 435     -47.618 -12.997 -34.814  0.50 19.24           C
ATOM   1588  NE2 HIS A 435     -47.880 -11.793 -35.300  0.50 18.93           N
ATOM   1589  CD2 HIS A 435     -46.946 -11.488 -36.264  0.50 18.89           C
ATOM   1590  C   HIS A 435     -43.518 -12.074 -39.180  0.50 18.16           C
ATOM   1591  O   HIS A 435     -42.503 -12.412 -38.562  0.50 18.46           O
ATOM   1592  N   TYR A 436     -43.528 -11.920 -40.498  0.50 18.68           N
ATOM   1593  CA  TYR A 436     -42.388 -12.393 -41.277  0.50 20.57           C
ATOM   1594  CB  TYR A 436     -42.550 -13.896 -41.554  0.50 22.81           C
ATOM   1595  CG  TYR A 436     -41.447 -14.520 -42.377  0.50 24.50           C
ATOM   1596  CD1 TYR A 436     -41.638 -14.812 -43.722  0.50 25.00           C
ATOM   1597  CE1 TYR A 436     -40.639 -15.393 -44.476  0.50 27.34           C
ATOM   1598  CZ  TYR A 436     -39.430 -15.682 -43.898  0.50 25.84           C
ATOM   1599  OH  TYR A 436     -38.446 -16.254 -44.658  0.50 25.28           O
ATOM   1600  CE2 TYR A 436     -39.211 -15.411 -42.560  0.50 26.96           C
ATOM   1601  CD2 TYR A 436     -40.217 -14.831 -41.810  0.50 25.15           C
ATOM   1602  C   TYR A 436     -42.224 -11.639 -42.583  0.50 20.97           C
ATOM   1603  O   TYR A 436     -43.195 -11.365 -43.284  0.50 20.43           O
ATOM   1604  N   THR A 437     -40.984 -11.297 -42.911  0.50 20.28           N
ATOM   1605  CA  THR A 437     -40.672 -10.851 -44.269  0.50 20.36           C
ATOM   1606  CB  THR A 437     -40.908  -9.340 -44.483  0.50 22.24           C
ATOM   1607  OG1 THR A 437     -40.855  -9.027 -45.884  0.50 22.87           O
ATOM   1608  CG2 THR A 437     -39.869  -8.511 -43.750  0.50 21.87           C
ATOM   1609  C   THR A 437     -39.233 -11.212 -44.568  0.50 20.75           C
ATOM   1610  O   THR A 437     -38.388 -11.221 -43.673  0.50 19.59           O
ATOM   1611  N   GLN A 438     -38.967 -11.525 -45.833  0.50 20.09           N
ATOM   1612  CA  GLN A 438     -37.635 -11.882 -46.289  0.50 20.99           C
ATOM   1613  CB  GLN A 438     -37.540 -13.395 -46.555  0.50 22.39           C
ATOM   1614  CG  GLN A 438     -36.203 -13.857 -47.149  0.50 24.45           C
ATOM   1615  CD  GLN A 438     -36.253 -15.275 -47.699  0.50 25.93           C
ATOM   1616  OE1 GLN A 438     -36.591 -15.497 -48.871  0.50 27.04           O
ATOM   1617  NE2 GLN A 438     -35.903 -16.243 -46.864  0.50 26.58           N
ATOM   1618  C   GLN A 438     -37.263 -11.085 -47.536  0.50 21.54           C
ATOM   1619  O   GLN A 438     -38.052 -10.951 -48.489  0.50 19.70           O
ATOM   1620  N   LYS A 439     -36.049 -10.550 -47.533  0.50 21.14           N
ATOM   1621  CA  LYS A 439     -35.582  -9.743 -48.643  0.50 21.47           C
ATOM   1622  CB  LYS A 439     -35.376  -8.291 -48.201  0.50 22.43           C
ATOM   1623  CG  LYS A 439     -36.642  -7.624 -47.673  0.50 25.18           C
ATOM   1624  CD  LYS A 439     -37.670  -7.469 -48.792  0.50 25.17           C
ATOM   1625  CE  LYS A 439     -38.580  -6.260 -48.599  0.50 27.96           C
ATOM   1626  NZ  LYS A 439     -40.021  -6.622 -48.439  0.50 27.30           N
ATOM   1627  C   LYS A 439     -34.285 -10.339 -49.170  0.50 21.12           C
ATOM   1628  O   LYS A 439     -33.451 -10.798 -48.404  0.50 19.72           O
ATOM   1629  N   SER A 440     -34.116 -10.330 -50.486  0.50 21.71           N
ATOM   1630  CA  SER A 440     -33.038 -11.075 -51.112  0.50 22.35           C
ATOM   1631  CB  SER A 440     -33.615 -12.133 -52.051  0.50 22.73           C
ATOM   1632  OG  SER A 440     -34.633 -12.855 -51.400  0.50 22.31           O
ATOM   1633  C   SER A 440     -32.125 -10.172 -51.922  0.50 22.53           C
ATOM   1634  O   SER A 440     -32.518  -9.079 -52.338  0.50 24.82           O
ATOM   1635  N   LEU A 441     -30.906 -10.637 -52.135  0.50 22.88           N
ATOM   1636  CA  LEU A 441     -29.990  -9.973 -53.061  0.50 22.94           C
ATOM   1637  CB  LEU A 441     -29.252  -8.825 -52.377  0.50 24.45           C
ATOM   1638  CG  LEU A 441     -28.059  -9.180 -51.488  0.50 24.17           C
ATOM   1639  CD1 LEU A 441     -27.325  -7.892 -51.131  0.50 24.42           C
ATOM   1640  CD2 LEU A 441     -28.486  -9.929 -50.226  0.50 24.16           C
ATOM   1641  C   LEU A 441     -28.993 -10.951 -53.663  0.50 22.78           C
ATOM   1642  O   LEU A 441     -28.704 -11.998 -53.101  0.50 21.27           O
ATOM   1643  N   SER A 442     -28.469 -10.593 -54.827  0.50 23.66           N
ATOM   1644  CA  SER A 442     -27.507 -11.437 -55.507  0.50 26.56           C
ATOM   1645  CB  SER A 442     -28.212 -12.605 -56.202  0.50 27.64           C
ATOM   1646  OG  SER A 442     -29.121 -12.122 -57.176  0.50 29.23           O
ATOM   1647  C   SER A 442     -26.805 -10.593 -56.532  0.50 27.96           C
ATOM   1648  O   SER A 442     -27.203  -9.457 -56.773  0.50 27.90           O
ATOM   1649  N   LEU A 443     -25.756 -11.150 -57.124  0.50 30.05           N
ATOM   1650  CA  LEU A 443     -25.065 -10.505 -58.230  0.50 35.18           C
```

Figure 27 (Continued)

```
ATOM    1651  CB  LEU A 443     -23.601 -10.944 -58.254  0.50 33.46           C
ATOM    1652  CG  LEU A 443     -22.695 -10.271 -59.286  0.50 33.94           C
ATOM    1653  CD1 LEU A 443     -22.877  -8.757 -59.279  0.50 34.85           C
ATOM    1654  CD2 LEU A 443     -21.251 -10.637 -59.000  0.50 34.35           C
ATOM    1655  C   LEU A 443     -25.734 -10.860 -59.559  0.50 38.93           C
ATOM    1656  O   LEU A 443     -25.752 -12.025 -59.960  0.50 38.68           O
ATOM    1657  N   SER A 444     -26.291  -9.854 -60.229  0.50 42.79           N
ATOM    1658  CA  SER A 444     -26.889 -10.040 -61.556  0.50 46.43           C
ATOM    1659  CB  SER A 444     -27.437  -8.707 -62.084  0.50 48.32           C
ATOM    1660  OG  SER A 444     -26.580  -7.625 -61.742  0.50 46.11           O
ATOM    1661  C   SER A 444     -25.897 -10.653 -62.555  0.50 49.13           C
ATOM    1662  O   SER A 444     -24.739 -10.241 -62.617  0.50 48.80           O
ATOM    1663  N   PRO A 445     -26.358 -11.640 -63.343  0.50 51.54           N
ATOM    1664  CA  PRO A 445     -25.509 -12.439 -64.223  0.50 53.33           C
ATOM    1665  CB  PRO A 445     -26.481 -12.892 -65.311  0.50 52.42           C
ATOM    1666  CG  PRO A 445     -27.780 -13.024 -64.592  0.50 52.70           C
ATOM    1667  CD  PRO A 445     -27.785 -11.977 -63.505  0.50 53.45           C
ATOM    1668  C   PRO A 445     -24.367 -11.635 -64.835  0.50 53.35           C
ATOM    1669  O   PRO A 445     -23.505 -12.206 -65.507  0.50 54.48           O
HETATM  1670  C1  NAG A 500     -24.302 -19.775  -6.697  0.50 26.72           C
HETATM  1671  C2  NAG A 500     -24.482 -18.281  -6.539  0.50 27.02           C
HETATM  1672  N2  NAG A 500     -24.672 -17.975  -5.148  0.50 26.10           N
HETATM  1673  C7  NAG A 500     -23.745 -17.382  -4.410  0.50 27.56           C
HETATM  1674  O7  NAG A 500     -22.656 -17.089  -4.841  0.50 28.03           O
HETATM  1675  C8  NAG A 500     -24.143 -17.078  -2.995  0.50 24.75           C
HETATM  1676  C3  NAG A 500     -25.685 -17.801  -7.341  0.50 25.91           C
HETATM  1677  O3  NAG A 500     -25.752 -16.397  -7.266  0.50 26.14           O
HETATM  1678  C4  NAG A 500     -25.536 -18.206  -8.797  0.50 27.79           C
HETATM  1679  O4  NAG A 500     -26.594 -17.678  -9.623  0.50 25.95           O
HETATM  1680  C5  NAG A 500     -25.401 -19.719  -8.821  0.50 29.08           C
HETATM  1681  C6  NAG A 500     -25.215 -20.235 -10.232  0.50 28.78           C
HETATM  1682  O6  NAG A 500     -24.230 -19.411 -10.827  0.50 30.97           O
HETATM  1683  O5  NAG A 500     -24.251 -20.097  -8.074  0.50 29.20           O
HETATM  1684  C1  FUC A 501     -23.626 -20.111 -11.907  0.50 70.02           C
HETATM  1685  C2  FUC A 501     -22.813 -19.105 -12.703  0.50 68.96           C
HETATM  1686  O2  FUC A 501     -23.621 -17.939 -12.944  0.50 70.11           O
HETATM  1687  C3  FUC A 501     -21.540 -18.691 -11.968  0.50 68.27           C
HETATM  1688  O3  FUC A 501     -20.524 -18.503 -12.928  0.50 65.41           O
HETATM  1689  C4  FUC A 501     -20.991 -19.707 -10.977  0.50 69.34           C
HETATM  1690  O4  FUC A 501     -20.134 -20.584 -11.684  0.50 68.06           O
HETATM  1691  C5  FUC A 501     -22.058 -20.565 -10.334  0.50 71.04           C
HETATM  1692  C6  FUC A 501     -21.469 -21.636  -9.415  0.50 68.12           C
HETATM  1693  O5  FUC A 501     -22.786 -21.122 -11.407  0.50 72.10           O
HETATM  1694  C1  NAG A 502     -26.873 -16.961 -10.200  0.50 25.98           C
HETATM  1695  C2  NAG A 502     -27.706 -16.954 -11.476  0.50 26.29           C
HETATM  1696  N2  NAG A 502     -27.152 -17.968 -12.367  0.50 26.21           N
HETATM  1697  C7  NAG A 502     -27.805 -19.078 -12.757  0.50 26.98           C
HETATM  1698  O7  NAG A 502     -27.303 -19.939 -13.509  0.50 28.00           O
HETATM  1699  C8  NAG A 502     -29.202 -19.259 -12.269  0.50 25.45           C
HETATM  1700  C3  NAG A 502     -27.690 -15.568 -12.108  0.50 26.99           C
HETATM  1701  O3  NAG A 502     -28.632 -15.556 -13.161  0.50 26.25           O
HETATM  1702  C4  NAG A 502     -28.018 -14.491 -11.062  0.50 26.81           C
HETATM  1703  O4  NAG A 502     -27.743 -13.190 -11.531  0.50 28.54           O
HETATM  1704  C5  NAG A 502     -27.237 -14.706  -9.765  0.50 27.83           C
HETATM  1705  C6  NAG A 502     -27.728 -13.765  -8.672  0.50 29.73           C
HETATM  1706  O6  NAG A 502     -26.896 -13.946  -7.544  0.50 30.84           O
HETATM  1707  O5  NAG A 502     -27.420 -16.023  -9.303  0.50 26.38           O
HETATM  1708  C1  BMA A 503     -28.842 -12.565 -12.417  0.50 22.27           C
HETATM  1709  O5  BMA A 503     -28.494 -12.858 -13.765  0.50 21.51           O
HETATM  1710  C5  BMA A 503     -29.473 -12.343 -14.652  0.50 21.32           C
HETATM  1711  C6  BMA A 503     -29.273 -12.971 -16.033  0.50 20.48           C
HETATM  1712  O6  BMA A 503     -29.373 -14.388 -15.836  0.50 20.72           O
HETATM  1713  C4  BMA A 503     -29.381 -10.819 -14.647  0.50 21.48           C
HETATM  1714  O4  BMA A 503     -30.441 -10.335 -15.462  0.50 22.88           O
```

Figure 27 (Continued)

```
HETATM 1715  C3  BMA A 503     -29.622 -10.311 -13.228  0.50 22.64           C
HETATM 1716  O3  BMA A 503     -29.231  -8.935 -13.192  0.50 24.78           O
HETATM 1717  C2  BMA A 503     -28.753 -11.061 -12.231  0.50 22.69           C
HETATM 1718  O2  BMA A 503     -27.416 -10.627 -12.462  0.50 21.63           O
HETATM 1719  C1  MAN A 504     -29.179 -14.861 -17.260  0.50 21.37           C
HETATM 1720  C2  MAN A 504     -29.477 -16.348 -17.097  0.50 21.84           C
HETATM 1721  O2  MAN A 504     -29.519 -16.984 -18.357  0.50 21.52           O
HETATM 1722  C3  MAN A 504     -28.383 -17.023 -16.310  0.50 21.88           C
HETATM 1723  O3  MAN A 504     -28.638 -18.410 -16.287  0.50 23.49           O
HETATM 1724  C4  MAN A 504     -27.087 -16.768 -17.049  0.50 23.27           C
HETATM 1725  O4  MAN A 504     -26.064 -17.316 -16.264  0.50 20.90           O
HETATM 1726  C5  MAN A 504     -26.825 -15.282 -17.265  0.50 22.65           C
HETATM 1727  C6  MAN A 504     -25.602 -15.139 -18.172  0.50 25.45           C
HETATM 1728  O6  MAN A 504     -25.362 -13.774 -18.397  0.50 25.71           O
HETATM 1729  O5  MAN A 504     -27.931 -14.628 -17.880  0.50 23.58           O
HETATM 1730  C1  NAG A 505     -30.741 -16.831 -19.105  0.50 22.58           C
HETATM 1731  C2  NAG A 505     -30.604 -16.856 -20.622  0.50 23.78           C
HETATM 1732  N2  NAG A 505     -29.921 -15.669 -21.070  0.50 22.92           N
HETATM 1733  C7  NAG A 505     -28.602 -15.627 -21.304  0.50 24.90           C
HETATM 1734  O7  NAG A 505     -27.842 -16.581 -21.157  0.50 26.60           O
HETATM 1735  C8  NAG A 505     -28.030 -14.311 -21.759  0.50 25.34           C
HETATM 1736  C3  NAG A 505     -31.959 -16.963 -21.314  0.50 23.20           C
HETATM 1737  O3  NAG A 505     -31.744 -17.258 -22.679  0.50 24.61           O
HETATM 1738  C4  NAG A 505     -32.827 -18.027 -20.647  0.50 23.57           C
HETATM 1739  O4  NAG A 505     -34.147 -17.869 -21.118  0.50 23.19           O
HETATM 1740  C5  NAG A 505     -32.824 -17.872 -19.132  0.50 23.38           C
HETATM 1741  C6  NAG A 505     -33.668 -18.937 -18.420  0.50 26.53           C
HETATM 1742  O6  NAG A 505     -33.327 -20.239 -18.845  0.50 27.14           O
HETATM 1743  O5  NAG A 505     -31.494 -17.934 -18.675  0.50 24.44           O
HETATM 1744  C1  GAL A 506     -35.147 -18.873 -21.527  0.50103.12           C
HETATM 1745  C2  GAL A 506     -36.503 -18.844 -22.228  0.50100.43           C
HETATM 1746  O2  GAL A 506     -37.503 -18.453 -21.312  0.50 94.91           O
HETATM 1747  C3  GAL A 506     -36.849 -20.214 -22.799  0.50100.12           C
HETATM 1748  O3  GAL A 506     -37.991 -20.114 -23.621  0.50 99.08           O
HETATM 1749  C4  GAL A 506     -35.679 -20.775 -23.600  0.50102.38           C
HETATM 1750  O4  GAL A 506     -35.528 -20.038 -24.794  0.50103.02           O
HETATM 1751  C5  GAL A 506     -34.391 -20.698 -22.785  0.50102.83           C
HETATM 1752  C6  GAL A 506     -33.195 -21.222 -23.573  0.50 99.48           C
HETATM 1753  O6  GAL A 506     -32.016 -20.615 -23.093  0.50 92.85           O
HETATM 1754  O5  GAL A 506     -34.156 -19.358 -22.409  0.50104.66           O
HETATM 1755  C1  MAN A 507     -30.921  -8.353 -12.666  0.50 34.32           C
HETATM 1756  C2  MAN A 507     -30.866  -6.878 -13.018  0.50 35.39           C
HETATM 1757  O2  MAN A 507     -32.026  -6.251 -12.525  0.50 37.27           O
HETATM 1758  C3  MAN A 507     -29.671  -6.233 -12.351  0.50 34.97           C
HETATM 1759  O3  MAN A 507     -29.706  -4.856 -12.586  0.50 36.77           O
HETATM 1760  C4  MAN A 507     -29.768  -6.476 -10.856  0.50 34.81           C
HETATM 1761  O4  MAN A 507     -28.643  -5.891 -10.233  0.50 35.21           O
HETATM 1762  C5  MAN A 507     -29.831  -7.982 -10.604  0.50 34.82           C
HETATM 1763  C6  MAN A 507     -29.942  -8.297  -9.119  0.50 36.08           C
HETATM 1764  O6  MAN A 507     -29.175  -9.446  -8.820  0.50 36.84           O
HETATM 1765  O5  MAN A 507     -30.960  -8.517 -11.266  0.50 35.35           O
HETATM 1766  C1  NAG A 508     -32.977  -5.853 -12.937  0.50106.57           C
HETATM 1767  C2  NAG A 508     -33.007  -5.903 -14.457  0.50105.91           C
HETATM 1768  N2  NAG A 508     -31.899  -5.161 -15.027  0.50104.87           N
HETATM 1769  C7  NAG A 508     -31.669  -5.169 -16.337  0.50102.07           C
HETATM 1770  O7  NAG A 508     -30.739  -4.555 -16.856  0.50101.25           O
HETATM 1771  C8  NAG A 508     -32.614  -5.975 -17.179  0.50100.31           C
HETATM 1772  C3  NAG A 508     -34.336  -5.353 -14.946  0.50106.12           C
HETATM 1773  O3  NAG A 508     -34.416  -5.482 -16.349  0.50105.63           O
HETATM 1774  C4  NAG A 508     -35.481  -6.114 -14.286  0.50106.31           C
HETATM 1775  O4  NAG A 508     -36.693  -5.441 -14.547  0.50104.66           O
HETATM 1776  C5  NAG A 508     -35.297  -6.261 -12.773  0.50106.56           C
HETATM 1777  C6  NAG A 508     -36.294  -7.267 -12.206  0.50104.37           C
HETATM 1778  O6  NAG A 508     -37.426  -6.599 -11.697  0.50102.00           O
```

Figure 27 (Continued)

```
HETATM 1779  O5   NAG A 508     -33.993   -6.701  -12.449  0.50106.10           O
ATOM   1780  N    GLY B 236     -16.300    4.560    7.650  0.50 44.33           N
ATOM   1781  CA   GLY B 236     -16.863    5.501    6.633  0.50 44.72           C
ATOM   1782  C    GLY B 236     -16.069    5.512    5.340  0.50 45.04           C
ATOM   1783  O    GLY B 236     -15.901    4.472    4.703  0.50 44.94           O
ATOM   1784  N    GLY B 237     -15.586    6.692    4.952  0.50 43.31           N
ATOM   1785  CA   GLY B 237     -14.720    6.834    3.783  0.50 42.37           C
ATOM   1786  C    GLY B 237     -15.344    7.522    2.574  0.50 39.99           C
ATOM   1787  O    GLY B 237     -16.426    7.147    2.125  0.50 40.17           O
ATOM   1788  N    PRO B 238     -14.677    8.564    2.062  0.50 38.08           N
ATOM   1789  CA   PRO B 238     -14.962    9.076    0.721  0.50 36.21           C
ATOM   1790  CB   PRO B 238     -14.083   10.327    0.629  0.50 36.27           C
ATOM   1791  CG   PRO B 238     -13.837   10.726    2.049  0.50 36.52           C
ATOM   1792  CD   PRO B 238     -13.741    9.430    2.796  0.50 37.51           C
ATOM   1793  C    PRO B 238     -14.498    8.049   -0.307  0.50 34.55           C
ATOM   1794  O    PRO B 238     -13.658    7.202    0.010  0.50 32.83           O
ATOM   1795  N    SER B 239     -15.044    8.125   -1.519  0.50 32.79           N
ATOM   1796  CA   SER B 239     -14.714    7.179   -2.591  0.50 30.35           C
ATOM   1797  CB   SER B 239     -15.959    6.387   -3.012  0.50 30.30           C
ATOM   1798  OG   SER B 239     -16.408    5.538   -1.969  0.50 32.75           O
ATOM   1799  C    SER B 239     -14.149    7.890   -3.814  0.50 30.66           C
ATOM   1800  O    SER B 239     -14.498    9.039   -4.101  0.50 29.57           O
ATOM   1801  N    VAL B 240     -13.291    7.186   -4.549  0.50 29.23           N
ATOM   1802  CA   VAL B 240     -12.678    7.742   -5.754  0.50 27.11           C
ATOM   1803  CB   VAL B 240     -11.145    7.749   -5.651  0.50 28.04           C
ATOM   1804  CG1  VAL B 240     -10.533    8.426   -6.865  0.50 29.27           C
ATOM   1805  CG2  VAL B 240     -10.703    8.434   -4.362  0.50 26.57           C
ATOM   1806  C    VAL B 240     -13.076    6.961   -7.010  0.50 25.36           C
ATOM   1807  O    VAL B 240     -13.208    5.721   -6.986  0.50 23.82           O
ATOM   1808  N    PHE B 241     -13.273    7.703   -8.092  0.50 23.45           N
ATOM   1809  CA   PHE B 241     -13.518    7.104   -9.409  0.50 23.77           C
ATOM   1810  CB   PHE B 241     -14.981    7.265   -9.801  0.50 23.77           C
ATOM   1811  CG   PHE B 241     -15.929    6.721   -8.772  0.50 24.03           C
ATOM   1812  CD1  PHE B 241     -16.337    5.397   -8.820  0.50 24.26           C
ATOM   1813  CE1  PHE B 241     -17.181    4.876   -7.859  0.50 24.48           C
ATOM   1814  CZ   PHE B 241     -17.627    5.686   -6.828  0.50 23.88           C
ATOM   1815  CE2  PHE B 241     -17.220    7.003   -6.757  0.50 23.61           C
ATOM   1816  CD2  PHE B 241     -16.366    7.517   -7.718  0.50 24.68           C
ATOM   1817  C    PHE B 241     -12.579    7.739  -10.420  0.50 23.07           C
ATOM   1818  O    PHE B 241     -12.430    8.958  -10.467  0.50 23.74           O
ATOM   1819  N    LEU B 242     -11.932    6.904  -11.230  0.50 21.12           N
ATOM   1820  CA   LEU B 242     -10.880    7.382  -12.122  0.50 20.83           C
ATOM   1821  CB   LEU B 242      -9.582    6.630  -11.848  0.50 20.00           C
ATOM   1822  CG   LEU B 242      -8.376    7.031  -12.695  0.50 19.75           C
ATOM   1823  CD1  LEU B 242      -8.124    8.529  -12.556  0.50 20.32           C
ATOM   1824  CD2  LEU B 242      -7.129    6.246  -12.298  0.50 19.55           C
ATOM   1825  C    LEU B 242     -11.312    7.102  -13.542  0.50 19.62           C
ATOM   1826  O    LEU B 242     -11.570    5.945  -13.892  0.50 21.23           O
ATOM   1827  N    PHE B 243     -11.408    8.155  -14.344  0.50 18.78           N
ATOM   1828  CA   PHE B 243     -11.960    8.061  -15.682  0.50 18.57           C
ATOM   1829  CB   PHE B 243     -13.078    9.100  -15.852  0.50 18.77           C
ATOM   1830  CG   PHE B 243     -14.233    8.901  -14.890  0.50 19.90           C
ATOM   1831  CD1  PHE B 243     -15.300    8.083  -15.222  0.50 19.85           C
ATOM   1832  CE1  PHE B 243     -16.349    7.891  -14.340  0.50 20.46           C
ATOM   1833  CZ   PHE B 243     -16.340    8.503  -13.094  0.50 20.68           C
ATOM   1834  CE2  PHE B 243     -15.273    9.306  -12.739  0.50 19.26           C
ATOM   1835  CD2  PHE B 243     -14.222    9.497  -13.626  0.50 19.08           C
ATOM   1836  C    PHE B 243     -10.857    8.227  -16.732  0.50 17.36           C
ATOM   1837  O    PHE B 243      -9.925    9.012  -16.558  0.50 17.55           O
ATOM   1838  N    PRO B 244     -10.949    7.470  -17.836  0.50 17.38           N
ATOM   1839  CA   PRO B 244      -9.941    7.625  -18.877  0.50 18.03           C
ATOM   1840  CB   PRO B 244      -9.976    6.257  -19.578  0.50 17.17           C
ATOM   1841  CG   PRO B 244     -11.396    5.838  -19.459  0.50 17.54           C
ATOM   1842  CD   PRO B 244     -11.912    6.393  -18.140  0.50 18.24           C
```

Figure 27 (Continued)

```
ATOM   1843  C    PRO B 244     -10.291    8.750  -19.864  0.50 17.06           C
ATOM   1844  O    PRO B 244     -11.392    9.312  -19.792  0.50 19.28           O
ATOM   1845  N    PRO B 245      -9.364    9.080  -20.778  0.50 17.36           N
ATOM   1846  CA   PRO B 245      -9.570   10.078  -21.821  0.50 17.35           C
ATOM   1847  CB   PRO B 245      -8.176   10.232  -22.439  0.50 18.47           C
ATOM   1848  CG   PRO B 245      -7.519    8.920  -22.201  0.50 17.92           C
ATOM   1849  CD   PRO B 245      -8.029    8.455  -20.869  0.50 17.62           C
ATOM   1850  C    PRO B 245     -10.521    9.511  -22.861  0.50 17.75           C
ATOM   1851  O    PRO B 245     -10.703    8.286  -22.951  0.50 17.70           O
ATOM   1852  N    LYS B 246     -11.149   10.383  -23.633  0.50 17.47           N
ATOM   1853  CA   LYS B 246     -11.956    9.959  -24.762  0.50 18.29           C
ATOM   1854  CB   LYS B 246     -12.766   11.123  -25.316  0.50 19.81           C
ATOM   1855  CG   LYS B 246     -13.681   11.776  -24.316  0.50 21.70           C
ATOM   1856  CD   LYS B 246     -14.717   10.802  -23.819  0.50 24.53           C
ATOM   1857  CE   LYS B 246     -15.713   11.472  -22.881  0.50 25.69           C
ATOM   1858  NZ   LYS B 246     -15.103   11.869  -21.592  0.50 26.03           N
ATOM   1859  C    LYS B 246     -11.049    9.434  -25.863  0.50 17.88           C
ATOM   1860  O    LYS B 246     -10.075   10.075  -26.190  0.50 17.21           O
ATOM   1861  N    PRO B 247     -11.386    8.292  -26.460  0.50 16.98           N
ATOM   1862  CA   PRO B 247     -10.504    7.815  -27.528  0.50 16.77           C
ATOM   1863  CB   PRO B 247     -11.327    6.695  -28.173  0.50 17.05           C
ATOM   1864  CG   PRO B 247     -12.103    6.130  -27.016  0.50 16.70           C
ATOM   1865  CD   PRO B 247     -12.483    7.345  -26.182  0.50 17.24           C
ATOM   1866  C    PRO B 247     -10.141    8.875  -28.575  0.50 15.63           C
ATOM   1867  O    PRO B 247      -8.986    8.978  -28.958  0.50 16.04           O
ATOM   1868  N    LYS B 248     -11.109    9.643  -29.053  0.50 15.91           N
ATOM   1869  CA   LYS B 248     -10.804   10.649  -30.060  0.50 16.08           C
ATOM   1870  CB   LYS B 248     -12.054   11.464  -30.387  0.50 16.89           C
ATOM   1871  CG   LYS B 248     -11.872   12.469  -31.506  0.50 17.60           C
ATOM   1872  CD   LYS B 248     -13.195   13.189  -31.775  0.50 17.69           C
ATOM   1873  CE   LYS B 248     -12.998   14.585  -32.357  0.50 20.15           C
ATOM   1874  NZ   LYS B 248     -14.297   15.051  -32.929  0.50 18.78           N
ATOM   1875  C    LYS B 248      -9.698   11.587  -29.599  0.50 15.41           C
ATOM   1876  O    LYS B 248      -8.832   11.986  -30.381  0.50 15.08           O
ATOM   1877  N    ASP B 249      -9.740   11.949  -28.323  0.50 15.36           N
ATOM   1878  CA   ASP B 249      -8.742   12.876  -27.796  0.50 15.74           C
ATOM   1879  CB   ASP B 249      -9.103   13.294  -26.378  0.50 15.41           C
ATOM   1880  CG   ASP B 249     -10.471   13.966  -26.271  0.50 15.95           C
ATOM   1881  OD1  ASP B 249     -11.085   14.341  -27.293  0.50 15.44           O
ATOM   1882  OD2  ASP B 249     -10.906   14.152  -25.114  0.50 16.03           O
ATOM   1883  C    ASP B 249      -7.344   12.259  -27.778  0.50 16.14           C
ATOM   1884  O    ASP B 249      -6.336   12.984  -27.866  0.50 16.21           O
ATOM   1885  N    THR B 250      -7.269   10.938  -27.630  0.50 15.72           N
ATOM   1886  CA   THR B 250      -5.971   10.269  -27.624  0.50 15.53           C
ATOM   1887  CB   THR B 250      -6.044    8.870  -26.960  0.50 16.10           C
ATOM   1888  OG1  THR B 250      -6.850    8.001  -27.763  0.50 16.40           O
ATOM   1889  CG2  THR B 250      -6.678    8.958  -25.562  0.50 16.01           C
ATOM   1890  C    THR B 250      -5.431   10.062  -29.033  0.50 15.22           C
ATOM   1891  O    THR B 250      -4.242    9.801  -29.199  0.50 15.63           O
ATOM   1892  N    LEU B 251      -6.312   10.131  -30.027  0.50 14.66           N
ATOM   1893  CA   LEU B 251      -5.946    9.839  -31.420  0.50 14.94           C
ATOM   1894  CB   LEU B 251      -7.092    9.074  -32.100  0.50 14.95           C
ATOM   1895  CG   LEU B 251      -7.418    7.691  -31.512  0.50 14.74           C
ATOM   1896  CD1  LEU B 251      -8.734    7.127  -32.045  0.50 13.99           C
ATOM   1897  CD2  LEU B 251      -6.281    6.713  -31.802  0.50 14.74           C
ATOM   1898  C    LEU B 251      -5.578   11.043  -32.272  0.50 16.11           C
ATOM   1899  O    LEU B 251      -4.727   10.943  -33.162  0.50 15.52           O
ATOM   1900  N    MET B 252      -6.260   12.167  -32.038  0.50 15.72           N
ATOM   1901  CA   MET B 252      -6.007   13.386  -32.800  0.50 16.18           C
ATOM   1902  CB   MET B 252      -7.308   14.173  -33.049  0.50 16.23           C
ATOM   1903  CG   MET B 252      -8.443   13.510  -33.807  0.50 16.47           C
ATOM   1904  SD   MET B 252      -8.003   12.851  -35.432  0.50 22.07           S
ATOM   1905  CE   MET B 252      -7.781   11.238  -34.777  0.50 12.72           C
ATOM   1906  C    MET B 252      -5.076   14.298  -31.993  0.50 15.64           C
```

Figure 27 (Continued)

```
ATOM   1907  O    MET B 252      -5.402  14.687 -30.855  0.50 15.09           O
ATOM   1908  N    ILE B 253      -3.913  14.599 -32.563  0.50 15.68           N
ATOM   1909  CA   ILE B 253      -2.873  15.382 -31.889  0.50 17.84           C
ATOM   1910  CB   ILE B 253      -1.624  15.472 -32.820  0.50 17.43           C
ATOM   1911  CG1  ILE B 253      -0.334  15.790 -32.031  0.50 19.25           C
ATOM   1912  CD1  ILE B 253       0.062  14.646 -31.130  0.50 19.27           C
ATOM   1913  CG2  ILE B 253      -1.888  16.397 -34.004  0.50 19.24           C
ATOM   1914  C    ILE B 253      -3.387  16.789 -31.470  0.50 17.18           C
ATOM   1915  O    ILE B 253      -2.920  17.365 -30.477  0.50 17.42           O
ATOM   1916  N    SER B 254      -4.361  17.316 -32.213  0.50 18.14           N
ATOM   1917  CA   SER B 254      -4.945  18.642 -31.930  0.50 18.00           C
ATOM   1918  CB   SER B 254      -5.834  19.083 -33.103  0.50 18.79           C
ATOM   1919  OG   SER B 254      -6.901  18.159 -33.315  0.50 21.18           O
ATOM   1920  C    SER B 254      -5.796  18.640 -30.673  0.50 18.20           C
ATOM   1921  O    SER B 254      -6.166  19.700 -30.140  0.50 17.09           O
ATOM   1922  N    ARG B 255      -6.135  17.449 -30.196  0.50 17.64           N
ATOM   1923  CA   ARG B 255      -6.991  17.333 -29.022  0.50 17.88           C
ATOM   1924  CB   ARG B 255      -8.043  16.238 -29.260  0.50 17.82           C
ATOM   1925  CG   ARG B 255      -8.927  16.532 -30.479  0.50 19.97           C
ATOM   1926  CD   ARG B 255     -10.003  15.473 -30.692  0.50 21.06           C
ATOM   1927  NE   ARG B 255     -10.979  15.496 -29.610  0.50 22.65           N
ATOM   1928  CZ   ARG B 255     -12.038  16.299 -29.556  0.50 23.32           C
ATOM   1929  NH1  ARG B 255     -12.284  17.164 -30.545  0.50 24.26           N
ATOM   1930  NH2  ARG B 255     -12.842  16.243 -28.496  0.50 23.21           N
ATOM   1931  C    ARG B 255      -6.231  17.076 -27.725  0.50 17.98           C
ATOM   1932  O    ARG B 255      -5.061  16.682 -27.732  0.50 17.71           O
ATOM   1933  N    THR B 256      -6.896  17.335 -26.602  0.50 16.91           N
ATOM   1934  CA   THR B 256      -6.281  17.167 -25.310  0.50 15.89           C
ATOM   1935  CB   THR B 256      -6.365  18.456 -24.487  0.50 17.67           C
ATOM   1936  OG1  THR B 256      -5.845  19.554 -25.254  0.50 15.29           O
ATOM   1937  CG2  THR B 256      -5.540  18.304 -23.229  0.50 17.36           C
ATOM   1938  C    THR B 256      -6.889  16.007 -24.525  0.50 16.13           C
ATOM   1939  O    THR B 256      -7.989  16.116 -23.983  0.50 15.69           O
ATOM   1940  N    PRO B 257      -6.167  14.880 -24.455  0.50 16.02           N
ATOM   1941  CA   PRO B 257      -6.675  13.752 -23.675  0.50 16.60           C
ATOM   1942  CB   PRO B 257      -5.921  12.559 -24.281  0.50 15.63           C
ATOM   1943  CG   PRO B 257      -4.621  13.135 -24.743  0.50 16.07           C
ATOM   1944  CD   PRO B 257      -4.887  14.574 -25.120  0.50 16.65           C
ATOM   1945  C    PRO B 257      -6.404  13.891 -22.165  0.50 17.04           C
ATOM   1946  O    PRO B 257      -5.316  14.304 -21.766  0.50 17.09           O
ATOM   1947  N    GLU B 258      -7.400  13.566 -21.340  0.50 17.28           N
ATOM   1948  CA   GLU B 258      -7.269  13.795 -19.899  0.50 18.97           C
ATOM   1949  CB   GLU B 258      -8.067  15.059 -19.512  0.50 20.05           C
ATOM   1950  CG   GLU B 258      -7.342  16.357 -19.892  0.50 23.68           C
ATOM   1951  CD   GLU B 258      -8.172  17.618 -19.657  0.50 24.97           C
ATOM   1952  OE1  GLU B 258      -9.398  17.510 -19.414  0.50 26.64           O
ATOM   1953  OE2  GLU B 258      -7.598  18.731 -19.769  0.50 28.32           O
ATOM   1954  C    GLU B 258      -7.699  12.584 -19.088  0.50 18.05           C
ATOM   1955  O    GLU B 258      -8.691  11.914 -19.434  0.50 17.41           O
ATOM   1956  N    VAL B 259      -6.961  12.309 -18.013  0.50 17.53           N
ATOM   1957  CA   VAL B 259      -7.346  11.330 -17.024  0.50 18.66           C
ATOM   1958  CB   VAL B 259      -6.149  10.463 -16.594  0.50 19.41           C
ATOM   1959  CG1  VAL B 259      -6.550   9.550 -15.451  0.50 20.63           C
ATOM   1960  CG2  VAL B 259      -5.666   9.617 -17.777  0.50 19.36           C
ATOM   1961  C    VAL B 259      -7.861  12.128 -15.829  0.50 18.73           C
ATOM   1962  O    VAL B 259      -7.188  13.059 -15.370  0.50 18.69           O
ATOM   1963  N    THR B 260      -9.041  11.754 -15.350  0.50 19.41           N
ATOM   1964  CA   THR B 260      -9.775  12.557 -14.357  0.50 19.30           C
ATOM   1965  CB   THR B 260     -11.086  13.086 -14.949  0.50 19.22           C
ATOM   1966  OG1  THR B 260     -10.804  13.787 -16.167  0.50 20.37           O
ATOM   1967  CG2  THR B 260     -11.820  14.014 -13.969  0.50 20.38           C
ATOM   1968  C    THR B 260     -10.090  11.750 -13.125  0.50 20.57           C
ATOM   1969  O    THR B 260     -10.764  10.730 -13.205  0.50 19.98           O
ATOM   1970  N    CYS B 261      -9.603  12.219 -11.972  0.50 20.53           N
```

Figure 27 (Continued)

```
ATOM   1971  CA   CYS B 261      -9.793  11.506 -10.708  0.50 21.18           C
ATOM   1972  CB   CYS B 261      -8.471  11.457  -9.945  0.50 22.09           C
ATOM   1973  SG   CYS B 261      -8.358  10.280  -8.580  0.50 22.79           S
ATOM   1974  C    CYS B 261     -10.823  12.281  -9.898  0.50 21.81           C
ATOM   1975  O    CYS B 261     -10.623  13.459  -9.619  0.50 21.49           O
ATOM   1976  N    VAL B 262     -11.930  11.624  -9.565  0.50 22.04           N
ATOM   1977  CA   VAL B 262     -13.089  12.298  -8.947  0.50 23.69           C
ATOM   1978  CB   VAL B 262     -14.361  12.215  -9.826  0.50 22.86           C
ATOM   1979  CG1  VAL B 262     -15.556  12.819  -9.091  0.50 22.40           C
ATOM   1980  CG2  VAL B 262     -14.156  12.976 -11.136  0.50 21.85           C
ATOM   1981  C    VAL B 262     -13.360  11.704  -7.574  0.50 23.47           C
ATOM   1982  O    VAL B 262     -13.731  10.535  -7.455  0.50 22.48           O
ATOM   1983  N    VAL B 263     -13.142  12.510  -6.525  0.50 25.33           N
ATOM   1984  CA   VAL B 263     -13.373  12.073  -5.148  0.50 24.75           C
ATOM   1985  CB   VAL B 263     -12.233  12.501  -4.197  0.50 25.89           C
ATOM   1986  CG1  VAL B 263     -12.648  12.307  -2.749  0.50 27.26           C
ATOM   1987  CG2  VAL B 263     -10.940  11.745  -4.501  0.50 26.20           C
ATOM   1988  C    VAL B 263     -14.663  12.724  -4.663  0.50 23.90           C
ATOM   1989  O    VAL B 263     -14.818  13.934  -4.753  0.50 23.42           O
ATOM   1990  N    VAL B 264     -15.596  11.903  -4.211  0.50 24.56           N
ATOM   1991  CA   VAL B 264     -16.896  12.368  -3.727  0.50 26.25           C
ATOM   1992  CB   VAL B 264     -18.047  11.716  -4.518  0.50 26.06           C
ATOM   1993  CG1  VAL B 264     -18.138  12.305  -5.920  0.50 27.23           C
ATOM   1994  CG2  VAL B 264     -17.879  10.201  -4.562  0.50 27.88           C
ATOM   1995  C    VAL B 264     -17.028  11.984  -2.255  0.50 26.60           C
ATOM   1996  O    VAL B 264     -16.093  11.420  -1.676  0.50 25.08           O
ATOM   1997  N    ASP B 265     -18.193  12.278  -1.671  0.50 27.43           N
ATOM   1998  CA   ASP B 265     -18.524  11.874  -0.293  0.50 27.53           C
ATOM   1999  CB   ASP B 265     -18.861  10.381  -0.220  0.50 28.49           C
ATOM   2000  CG   ASP B 265     -20.255  10.066  -0.741  0.50 28.00           C
ATOM   2001  OD1  ASP B 265     -21.002  11.012  -1.058  0.50 30.89           O
ATOM   2002  OD2  ASP B 265     -20.609   8.875  -0.854  0.50 27.66           O
ATOM   2003  C    ASP B 265     -17.447  12.227   0.737  0.50 27.22           C
ATOM   2004  O    ASP B 265     -17.306  11.546   1.752  0.50 28.40           O
ATOM   2005  N    VAL B 266     -16.687  13.287   0.476  0.50 26.63           N
ATOM   2006  CA   VAL B 266     -15.793  13.844   1.483  0.50 26.52           C
ATOM   2007  CB   VAL B 266     -14.698  14.740   0.855  0.50 25.51           C
ATOM   2008  CG1  VAL B 266     -13.713  15.218   1.911  0.50 26.20           C
ATOM   2009  CG2  VAL B 266     -13.952  13.988  -0.248  0.50 25.25           C
ATOM   2010  C    VAL B 266     -16.652  14.660   2.470  0.50 27.57           C
ATOM   2011  O    VAL B 266     -17.672  15.224   2.086  0.50 25.45           O
ATOM   2012  N    SER B 267     -16.233  14.731   3.728  0.50 31.16           N
ATOM   2013  CA   SER B 267     -17.016  15.453   4.749  0.50 31.37           C
ATOM   2014  CB   SER B 267     -17.162  14.582   6.001  0.50 31.20           C
ATOM   2015  OG   SER B 267     -15.915  14.049   6.402  0.50 32.94           O
ATOM   2016  C    SER B 267     -16.467  16.845   5.121  0.50 31.91           C
ATOM   2017  O    SER B 267     -15.335  17.183   4.774  0.50 31.94           O
ATOM   2018  N    HIS B 268     -17.276  17.646   5.829  0.50 31.74           N
ATOM   2019  CA   HIS B 268     -16.872  18.997   6.272  0.50 29.74           C
ATOM   2020  CB   HIS B 268     -18.073  19.778   6.840  0.50 32.21           C
ATOM   2021  CG   HIS B 268     -19.103  20.164   5.823  0.50 34.23           C
ATOM   2022  ND1  HIS B 268     -19.448  21.476   5.576  0.50 35.31           N
ATOM   2023  CE1  HIS B 268     -20.378  21.517   4.637  0.50 34.08           C
ATOM   2024  NE2  HIS B 268     -20.657  20.277   4.275  0.50 33.45           N
ATOM   2025  CD2  HIS B 268     -19.881  19.411   5.009  0.50 33.69           C
ATOM   2026  C    HIS B 268     -15.783  18.943   7.351  0.50 28.45           C
ATOM   2027  O    HIS B 268     -14.992  19.880   7.506  0.50 25.69           O
ATOM   2028  N    GLU B 269     -15.772  17.858   8.118  0.50 28.97           N
ATOM   2029  CA   GLU B 269     -14.855  17.711   9.249  0.50 30.64           C
ATOM   2030  CB   GLU B 269     -15.362  16.634  10.221  0.50 33.79           C
ATOM   2031  CG   GLU B 269     -16.663  16.995  10.929  0.50 36.61           C
ATOM   2032  CD   GLU B 269     -17.883  16.863  10.037  0.50 39.27           C
ATOM   2033  OE1  GLU B 269     -17.742  16.376   8.891  0.50 39.61           O
ATOM   2034  OE2  GLU B 269     -18.990  17.243  10.489  0.50 39.74           O
```

Figure 27 (Continued)

```
ATOM   2035  C    GLU B 269     -13.425  17.386   8.818  0.50 29.99           C
ATOM   2036  O    GLU B 269     -12.472  17.755   9.494  0.50 29.18           O
ATOM   2037  N    GLU B 270     -13.282  16.695   7.687  0.50 28.96           N
ATOM   2038  CA   GLU B 270     -11.973  16.276   7.185  0.50 28.66           C
ATOM   2039  CB   GLU B 270     -11.784  14.763   7.368  0.50 31.13           C
ATOM   2040  CG   GLU B 270     -11.746  14.269   8.809  0.50 34.00           C
ATOM   2041  CD   GLU B 270     -10.489  14.720   9.517  0.50 36.80           C
ATOM   2042  OE1  GLU B 270     -10.191  15.934   9.470  0.50 38.91           O
ATOM   2043  OE2  GLU B 270      -9.796  13.863  10.113  0.50 42.90           O
ATOM   2044  C    GLU B 270     -11.894  16.603   5.696  0.50 27.79           C
ATOM   2045  O    GLU B 270     -11.974  15.704   4.862  0.50 29.26           O
ATOM   2046  N    PRO B 271     -11.742  17.891   5.356  0.50 28.36           N
ATOM   2047  CA   PRO B 271     -11.964  18.343   3.985  0.50 27.89           C
ATOM   2048  CB   PRO B 271     -12.454  19.776   4.186  0.50 27.40           C
ATOM   2049  CG   PRO B 271     -11.700  20.234   5.402  0.50 26.88           C
ATOM   2050  CD   PRO B 271     -11.511  19.022   6.276  0.50 27.31           C
ATOM   2051  C    PRO B 271     -10.715  18.346   3.096  0.50 29.58           C
ATOM   2052  O    PRO B 271     -10.833  18.412   1.874  0.50 30.20           O
ATOM   2053  N    GLU B 272      -9.532  18.328   3.695  0.50 27.79           N
ATOM   2054  CA   GLU B 272      -8.304  18.313   2.914  0.50 27.88           C
ATOM   2055  CB   GLU B 272      -7.074  18.435   3.823  0.50 27.33           C
ATOM   2056  CG   GLU B 272      -6.840  19.844   4.346  0.50 31.13           C
ATOM   2057  CD   GLU B 272      -5.779  19.889   5.428  0.50 30.65           C
ATOM   2058  OE1  GLU B 272      -4.838  20.697   5.301  0.50 31.93           O
ATOM   2059  OE2  GLU B 272      -5.885  19.109   6.394  0.50 33.43           O
ATOM   2060  C    GLU B 272      -8.212  17.037   2.072  0.50 26.03           C
ATOM   2061  O    GLU B 272      -8.296  15.924   2.595  0.50 24.16           O
ATOM   2062  N    VAL B 273      -8.045  17.220   0.766  0.50 25.16           N
ATOM   2063  CA   VAL B 273      -7.777  16.107  -0.133  0.50 24.33           C
ATOM   2064  CB   VAL B 273      -8.903  15.922  -1.168  0.50 24.05           C
ATOM   2065  CG1  VAL B 273      -8.462  14.948  -2.259  0.50 23.78           C
ATOM   2066  CG2  VAL B 273     -10.170  15.422  -0.488  0.50 24.01           C
ATOM   2067  C    VAL B 273      -6.486  16.401  -0.855  0.50 23.18           C
ATOM   2068  O    VAL B 273      -6.303  17.502  -1.386  0.50 24.36           O
ATOM   2069  N    LYS B 274      -5.578  15.436  -0.834  0.50 23.03           N
ATOM   2070  CA   LYS B 274      -4.346  15.531  -1.596  0.50 24.22           C
ATOM   2071  CB   LYS B 274      -3.125  15.486  -0.683  0.50 25.79           C
ATOM   2072  CG   LYS B 274      -1.828  15.797  -1.417  0.50 26.37           C
ATOM   2073  CD   LYS B 274      -0.599  15.404  -0.619  0.50 24.72           C
ATOM   2074  CE   LYS B 274      -0.650  13.953  -0.162  0.50 25.63           C
ATOM   2075  NZ   LYS B 274       0.627  13.578   0.494  0.50 23.80           N
ATOM   2076  C    LYS B 274      -4.254  14.394  -2.614  0.50 24.70           C
ATOM   2077  O    LYS B 274      -4.527  13.238  -2.297  0.50 25.04           O
ATOM   2078  N    PHE B 275      -3.845  14.736  -3.828  0.50 24.76           N
ATOM   2079  CA   PHE B 275      -3.644  13.735  -4.865  0.50 24.34           C
ATOM   2080  CB   PHE B 275      -4.264  14.212  -6.185  0.50 24.34           C
ATOM   2081  CG   PHE B 275      -5.745  14.459  -6.114  0.50 23.64           C
ATOM   2082  CD1  PHE B 275      -6.251  15.656  -5.606  0.50 23.35           C
ATOM   2083  CE1  PHE B 275      -7.611  15.883  -5.553  0.50 22.12           C
ATOM   2084  CZ   PHE B 275      -8.493  14.920  -6.029  0.50 24.81           C
ATOM   2085  CE2  PHE B 275      -8.005  13.734  -6.535  0.50 22.93           C
ATOM   2086  CD2  PHE B 275      -6.640  13.508  -6.573  0.50 23.08           C
ATOM   2087  C    PHE B 275      -2.168  13.433  -5.068  0.50 23.73           C
ATOM   2088  O    PHE B 275      -1.332  14.333  -5.031  0.50 23.76           O
ATOM   2089  N    ASN B 276      -1.851  12.159  -5.275  0.50 22.48           N
ATOM   2090  CA   ASN B 276      -0.568  11.793  -5.845  0.50 22.52           C
ATOM   2091  CB   ASN B 276       0.327  11.077  -4.840  0.50 24.31           C
ATOM   2092  CG   ASN B 276       0.763  12.001  -3.703  0.50 25.95           C
ATOM   2093  OD1  ASN B 276      -0.072  12.481  -2.935  0.50 25.94           O
ATOM   2094  ND2  ASN B 276       2.068  12.282  -3.618  0.50 23.60           N
ATOM   2095  C    ASN B 276      -0.798  10.964  -7.110  0.50 20.66           C
ATOM   2096  O    ASN B 276      -1.572  10.020  -7.102  0.50 19.59           O
ATOM   2097  N    TRP B 277      -0.147  11.370  -8.184  0.50 21.64           N
ATOM   2098  CA   TRP B 277      -0.373  10.770  -9.490  0.50 21.63           C
```

Figure 27 (Continued)

```
ATOM   2099  CB  TRP B 277      -0.709  11.850 -10.510  0.50 20.48           C
ATOM   2100  CG  TRP B 277      -2.130  12.365 -10.483  0.50 20.12           C
ATOM   2101  CD1 TRP B 277      -2.601  13.453  -9.797  0.50 19.84           C
ATOM   2102  NE1 TRP B 277      -3.938  13.626 -10.048  0.50 20.13           N
ATOM   2103  CE2 TRP B 277      -4.360  12.648 -10.914  0.50 20.01           C
ATOM   2104  CD2 TRP B 277      -3.247  11.835 -11.209  0.50 20.24           C
ATOM   2105  CE3 TRP B 277      -3.411  10.754 -12.090  0.50 21.11           C
ATOM   2106  CZ3 TRP B 277      -4.657  10.518 -12.618  0.50 20.74           C
ATOM   2107  CH2 TRP B 277      -5.745  11.350 -12.320  0.50 19.80           C
ATOM   2108  CZ2 TRP B 277      -5.612  12.427 -11.473  0.50 20.44           C
ATOM   2109  C   TRP B 277       0.904  10.078  -9.929  0.50 22.54           C
ATOM   2110  O   TRP B 277       2.018  10.624  -9.792  0.50 22.95           O
ATOM   2111  N   TYR B 278       0.746   8.890 -10.496  0.50 22.77           N
ATOM   2112  CA  TYR B 278       1.877   8.098 -10.932  0.50 21.48           C
ATOM   2113  CB  TYR B 278       2.041   6.873 -10.035  0.50 21.92           C
ATOM   2114  CG  TYR B 278       2.051   7.196  -8.551  0.50 21.52           C
ATOM   2115  CD1 TYR B 278       0.870   7.434  -7.867  0.50 21.17           C
ATOM   2116  CE1 TYR B 278       0.868   7.733  -6.511  0.50 23.01           C
ATOM   2117  CZ  TYR B 278       2.074   7.784  -5.822  0.50 24.25           C
ATOM   2118  OH  TYR B 278       2.101   8.062  -4.463  0.50 24.20           O
ATOM   2119  CE2 TYR B 278       3.259   7.555  -6.483  0.50 23.35           C
ATOM   2120  CD2 TYR B 278       3.248   7.253  -7.839  0.50 22.71           C
ATOM   2121  C   TYR B 278       1.591   7.644 -12.349  0.50 20.89           C
ATOM   2122  O   TYR B 278       0.457   7.366 -12.676  0.50 20.14           O
ATOM   2123  N   VAL B 279       2.609   7.633 -13.193  0.50 20.60           N
ATOM   2124  CA  VAL B 279       2.457   7.078 -14.538  0.50 21.93           C
ATOM   2125  CB  VAL B 279       2.635   8.132 -15.634  0.50 20.95           C
ATOM   2126  CG1 VAL B 279       2.370   7.521 -17.019  0.50 20.85           C
ATOM   2127  CG2 VAL B 279       1.708   9.306 -15.398  0.50 20.34           C
ATOM   2128  C   VAL B 279       3.539   6.029 -14.658  0.50 23.36           C
ATOM   2129  O   VAL B 279       4.737   6.341 -14.596  0.50 25.47           O
ATOM   2130  N   ASP B 280       3.119   4.780 -14.774  0.50 24.31           N
ATOM   2131  CA  ASP B 280       4.048   3.670 -14.625  0.50 25.17           C
ATOM   2132  CB  ASP B 280       4.877   3.501 -15.889  0.50 25.74           C
ATOM   2133  CG  ASP B 280       4.117   2.783 -16.982  0.50 25.00           C
ATOM   2134  OD1 ASP B 280       2.977   2.314 -16.718  0.50 23.56           O
ATOM   2135  OD2 ASP B 280       4.666   2.677 -18.094  0.50 26.24           O
ATOM   2136  C   ASP B 280       4.941   3.915 -13.405  0.50 25.64           C
ATOM   2137  O   ASP B 280       6.159   3.755 -13.465  0.50 23.67           O
ATOM   2138  N   GLY B 281       4.315   4.304 -12.305  0.50 26.35           N
ATOM   2139  CA  GLY B 281       4.989   4.368 -11.001  0.50 27.93           C
ATOM   2140  C   GLY B 281       5.844   5.596 -10.739  0.50 28.37           C
ATOM   2141  O   GLY B 281       6.293   5.816  -9.608  0.50 30.06           O
ATOM   2142  N   VAL B 282       6.061   6.384 -11.755  0.50 29.58           N
ATOM   2143  CA  VAL B 282       6.841   7.552 -11.546  0.50 27.95           C
ATOM   2144  CB  VAL B 282       7.716   7.846 -12.758  0.50 30.18           C
ATOM   2145  CG1 VAL B 282       8.648   8.999 -12.471  0.50 30.87           C
ATOM   2146  CG2 VAL B 282       8.521   6.617 -13.098  0.50 31.83           C
ATOM   2147  C   VAL B 282       5.875   8.674 -11.257  0.50 27.97           C
ATOM   2148  O   VAL B 282       5.012   8.971 -12.046  0.50 25.34           O
ATOM   2149  N   GLU B 283       6.034   9.294 -10.098  0.50 24.92           N
ATOM   2150  CA  GLU B 283       5.148  10.373  -9.730  0.50 24.00           C
ATOM   2151  CB  GLU B 283       5.422  10.891  -8.309  0.50 23.73           C
ATOM   2152  CG  GLU B 283       4.562  12.082  -7.934  0.50 23.19           C
ATOM   2153  CD  GLU B 283       4.497  12.330  -6.438  0.50 24.20           C
ATOM   2154  OE1 GLU B 283       3.601  13.042  -5.982  0.50 24.91           O
ATOM   2155  OE2 GLU B 283       5.340  11.791  -5.722  0.50 24.58           O
ATOM   2156  C   GLU B 283       5.311  11.490 -10.718  0.50 23.57           C
ATOM   2157  O   GLU B 283       6.403  11.781 -11.163  0.50 22.34           O
ATOM   2158  N   VAL B 284       4.199  12.112 -11.052  0.50 22.11           N
ATOM   2159  CA  VAL B 284       4.194  13.258 -11.921  0.50 23.58           C
ATOM   2160  CB  VAL B 284       3.563  12.953 -13.286  0.50 22.99           C
ATOM   2161  CG1 VAL B 284       4.360  11.869 -13.978  0.50 23.70           C
ATOM   2162  CG2 VAL B 284       2.116  12.546 -13.130  0.50 23.26           C
```

Figure 27 (Continued)

```
ATOM   2163  C    VAL B 284       3.469  14.392 -11.226  0.50 24.25           C
ATOM   2164  O    VAL B 284       2.641  14.168 -10.384  0.50 27.89           O
ATOM   2165  N    HIS B 285       3.854  15.608 -11.555  0.50 28.13           N
ATOM   2166  CA   HIS B 285       3.506  16.758 -10.766  0.50 27.48           C
ATOM   2167  CB   HIS B 285       4.796  17.395 -10.247  0.50 29.76           C
ATOM   2168  CG   HIS B 285       5.851  16.382  -9.854  0.50 29.55           C
ATOM   2169  ND1  HIS B 285       5.735  15.608  -8.774  0.50 29.92           N
ATOM   2170  CE1  HIS B 285       6.780  14.793  -8.691  0.50 26.78           C
ATOM   2171  NE2  HIS B 285       7.580  15.041  -9.725  0.50 31.04           N
ATOM   2172  CD2  HIS B 285       7.040  16.017 -10.464  0.50 30.61           C
ATOM   2173  C    HIS B 285       2.650  17.782 -11.431  0.50 29.37           C
ATOM   2174  O    HIS B 285       2.408  18.829 -10.853  0.50 30.70           O
ATOM   2175  N    ASN B 286       2.186  17.518 -12.645  0.50 26.83           N
ATOM   2176  CA   ASN B 286       1.534  18.543 -13.448  0.50 26.39           C
ATOM   2177  CB   ASN B 286       2.122  18.592 -14.858  0.50 28.49           C
ATOM   2178  CG   ASN B 286       1.972  17.295 -15.595  0.50 29.39           C
ATOM   2179  OD1  ASN B 286       2.044  16.238 -15.021  0.50 30.63           O
ATOM   2180  ND2  ASN B 286       1.767  17.382 -16.883  0.50 30.84           N
ATOM   2181  C    ASN B 286       0.015  18.573 -13.528  0.50 24.85           C
ATOM   2182  O    ASN B 286      -0.520  19.287 -14.337  0.50 26.75           O
ATOM   2183  N    ALA B 287      -0.666  17.806 -12.695  0.50 22.54           N
ATOM   2184  CA   ALA B 287      -2.128  17.749 -12.703  0.50 21.44           C
ATOM   2185  CB   ALA B 287      -2.600  16.648 -11.781  0.50 20.95           C
ATOM   2186  C    ALA B 287      -2.768  19.086 -12.289  0.50 23.37           C
ATOM   2187  O    ALA B 287      -2.104  19.876 -11.636  0.50 23.15           O
ATOM   2188  N    LYS B 288      -4.012  19.340 -12.711  0.50 22.55           N
ATOM   2189  CA   LYS B 288      -4.761  20.519 -12.301  0.50 24.02           C
ATOM   2190  CB   LYS B 288      -5.322  21.264 -13.522  0.50 25.11           C
ATOM   2191  CG   LYS B 288      -4.229  21.787 -14.465  0.50 27.52           C
ATOM   2192  CD   LYS B 288      -4.736  22.198 -15.844  0.50 30.85           C
ATOM   2193  CE   LYS B 288      -3.554  22.448 -16.783  0.50 30.68           C
ATOM   2194  NZ   LYS B 288      -3.922  23.081 -18.083  0.50 33.13           N
ATOM   2195  C    LYS B 288      -5.864  20.095 -11.342  0.50 24.21           C
ATOM   2196  O    LYS B 288      -6.745  19.288 -11.665  0.50 20.67           O
ATOM   2197  N    THR B 289      -5.821  20.619 -10.128  0.50 24.31           N
ATOM   2198  CA   THR B 289      -6.844  20.265  -9.175  0.50 25.71           C
ATOM   2199  CB   THR B 289      -6.218  19.881  -7.831  0.50 26.20           C
ATOM   2200  OG1  THR B 289      -5.254  18.850  -8.066  0.50 29.00           O
ATOM   2201  CG2  THR B 289      -7.282  19.360  -6.887  0.50 27.65           C
ATOM   2202  C    THR B 289      -7.849  21.403  -9.021  0.50 28.21           C
ATOM   2203  O    THR B 289      -7.488  22.578  -9.046  0.50 28.10           O
ATOM   2204  N    LYS B 290      -9.117  21.052  -8.898  0.50 28.25           N
ATOM   2205  CA   LYS B 290     -10.149  22.067  -8.769  0.50 31.57           C
ATOM   2206  CB   LYS B 290     -11.371  21.682  -9.598  0.50 32.81           C
ATOM   2207  CG   LYS B 290     -11.048  21.153 -10.995  0.50 35.04           C
ATOM   2208  CD   LYS B 290     -10.156  22.115 -11.769  0.50 35.63           C
ATOM   2209  CE   LYS B 290      -9.903  21.644 -13.202  0.50 35.68           C
ATOM   2210  NZ   LYS B 290      -8.772  20.677 -13.321  0.50 30.77           N
ATOM   2211  C    LYS B 290     -10.524  22.233  -7.299  0.50 30.24           C
ATOM   2212  O    LYS B 290     -10.464  21.278  -6.532  0.50 28.50           O
ATOM   2213  N    PRO B 291     -10.879  23.460  -6.890  0.50 31.74           N
ATOM   2214  CA   PRO B 291     -11.397  23.677  -5.536  0.50 32.73           C
ATOM   2215  CB   PRO B 291     -11.937  25.105  -5.603  0.50 31.07           C
ATOM   2216  CG   PRO B 291     -11.091  25.776  -6.638  0.50 33.01           C
ATOM   2217  CD   PRO B 291     -10.729  24.717  -7.645  0.50 32.12           C
ATOM   2218  C    PRO B 291     -12.540  22.708  -5.201  0.50 32.26           C
ATOM   2219  O    PRO B 291     -13.372  22.420  -6.061  0.50 32.72           O
ATOM   2220  N    ARG B 292     -12.600  22.222  -3.966  0.50 33.44           N
ATOM   2221  CA   ARG B 292     -13.739  21.402  -3.566  0.50 35.03           C
ATOM   2222  CB   ARG B 292     -13.606  20.906  -2.120  0.50 38.95           C
ATOM   2223  CG   ARG B 292     -13.776  21.957  -1.027  0.50 42.50           C
ATOM   2224  CD   ARG B 292     -13.718  21.277   0.337  0.50 45.07           C
ATOM   2225  NE   ARG B 292     -13.640  22.210   1.458  0.50 49.52           N
ATOM   2226  CZ   ARG B 292     -12.544  22.418   2.186  0.50 50.33           C
```

Figure 27 (Continued)

```
ATOM   2227  NH1 ARG B 292     -11.423  21.763   1.910  0.50 52.64           N
ATOM   2228  NH2 ARG B 292     -12.569  23.283   3.192  0.50 48.86           N
ATOM   2229  C   ARG B 292     -15.041  22.170  -3.797  0.50 36.41           C
ATOM   2230  O   ARG B 292     -15.053  23.404  -3.748  0.50 37.54           O
ATOM   2231  N   GLU B 293     -16.122  21.448  -4.096  0.50 35.50           N
ATOM   2232  CA  GLU B 293     -17.430  22.073  -4.331  0.50 36.20           C
ATOM   2233  CB  GLU B 293     -17.734  22.134  -5.828  0.50 39.65           C
ATOM   2234  CG  GLU B 293     -16.668  22.858  -6.634  0.50 42.20           C
ATOM   2235  CD  GLU B 293     -17.038  23.017  -8.093  0.50 46.84           C
ATOM   2236  OE1 GLU B 293     -16.115  23.149  -8.929  0.50 49.13           O
ATOM   2237  OE2 GLU B 293     -18.250  23.006  -8.403  0.50 50.07           O
ATOM   2238  C   GLU B 293     -18.540  21.319  -3.601  0.50 34.31           C
ATOM   2239  O   GLU B 293     -18.602  20.086  -3.653  0.50 31.17           O
ATOM   2240  N   GLU B 294     -19.421  22.043  -2.908  0.50 30.96           N
ATOM   2241  CA  GLU B 294     -20.366  21.347  -2.041  0.50 27.58           C
ATOM   2242  CB  GLU B 294     -20.864  22.214  -0.866  0.50 27.32           C
ATOM   2243  CG  GLU B 294     -21.668  21.391   0.142  0.50 27.99           C
ATOM   2244  CD  GLU B 294     -21.988  22.141   1.430  0.50 27.75           C
ATOM   2245  OE1 GLU B 294     -22.253  21.476   2.456  0.50 30.16           O
ATOM   2246  OE2 GLU B 294     -21.959  23.382   1.418  0.50 28.73           O
ATOM   2247  C   GLU B 294     -21.544  20.774  -2.810  0.50 26.72           C
ATOM   2248  O   GLU B 294     -22.169  21.454  -3.611  0.50 25.66           O
ATOM   2249  N   GLN B 295     -21.844  19.513  -2.541  0.50 28.49           N
ATOM   2250  CA  GLN B 295     -22.969  18.843  -3.169  0.50 29.40           C
ATOM   2251  CB  GLN B 295     -22.639  17.365  -3.398  0.50 30.35           C
ATOM   2252  CG  GLN B 295     -21.251  17.130  -3.982  0.50 31.59           C
ATOM   2253  CD  GLN B 295     -21.056  17.822  -5.316  0.50 30.34           C
ATOM   2254  OE1 GLN B 295     -21.752  17.514  -6.279  0.50 31.65           O
ATOM   2255  NE2 GLN B 295     -20.106  18.759  -5.380  0.50 29.28           N
ATOM   2256  C   GLN B 295     -24.199  18.989  -2.281  0.50 28.71           C
ATOM   2257  O   GLN B 295     -24.083  19.309  -1.090  0.50 28.87           O
ATOM   2258  N   TYR B 296     -25.370  18.731  -2.849  0.50 26.62           N
ATOM   2259  CA  TYR B 296     -26.622  18.960  -2.128  0.50 28.54           C
ATOM   2260  CB  TYR B 296     -27.814  19.105  -3.099  0.50 27.97           C
ATOM   2261  CG  TYR B 296     -28.189  20.538  -3.436  0.50 28.27           C
ATOM   2262  CD1 TYR B 296     -27.331  21.356  -4.173  0.50 28.22           C
ATOM   2263  CE1 TYR B 296     -27.674  22.665  -4.477  0.50 28.22           C
ATOM   2264  CZ  TYR B 296     -28.892  23.177  -4.042  0.50 28.93           C
ATOM   2265  OH  TYR B 296     -29.250  24.477  -4.358  0.50 28.88           O
ATOM   2266  CE2 TYR B 296     -29.761  22.381  -3.323  0.50 27.69           C
ATOM   2267  CD2 TYR B 296     -29.407  21.079  -3.016  0.50 28.32           C
ATOM   2268  C   TYR B 296     -26.888  17.907  -1.043  0.50 28.37           C
ATOM   2269  O   TYR B 296     -27.915  17.933  -0.370  0.50 31.25           O
ATOM   2270  N   ASN B 297     -25.929  17.036  -0.850  0.50 27.48           N
ATOM   2271  CA  ASN B 297     -25.985  16.067   0.199  0.50 26.79           C
ATOM   2272  CB  ASN B 297     -25.662  14.684  -0.356  0.50 26.25           C
ATOM   2273  CG  ASN B 297     -24.477  14.692  -1.292  0.50 26.49           C
ATOM   2274  OD1 ASN B 297     -23.591  15.504  -1.154  0.50 24.80           O
ATOM   2275  ND2 ASN B 297     -24.467  13.780  -2.255  0.50 24.76           N
ATOM   2276  C   ASN B 297     -25.043  16.500   1.329  0.50 27.45           C
ATOM   2277  O   ASN B 297     -24.673  15.735   2.174  0.50 28.78           O
ATOM   2278  N   SER B 298     -24.664  17.760   1.285  0.50 27.47           N
ATOM   2279  CA  SER B 298     -23.646  18.376   2.138  0.50 27.39           C
ATOM   2280  CB  SER B 298     -24.220  18.697   3.532  0.50 27.58           C
ATOM   2281  OG  SER B 298     -25.183  19.740   3.444  0.50 25.06           O
ATOM   2282  C   SER B 298     -22.349  17.567   2.237  0.50 27.24           C
ATOM   2283  O   SER B 298     -21.857  17.290   3.331  0.50 25.88           O
ATOM   2284  N   THR B 299     -21.797  17.208   1.076  0.50 26.81           N
ATOM   2285  CA  THR B 299     -20.468  16.598   0.992  0.50 26.68           C
ATOM   2286  CB  THR B 299     -20.551  15.146   0.496  0.50 27.27           C
ATOM   2287  OG1 THR B 299     -21.020  15.143  -0.854  0.50 28.09           O
ATOM   2288  CG2 THR B 299     -21.518  14.319   1.356  0.50 26.30           C
ATOM   2289  C   THR B 299     -19.594  17.372  -0.006  0.50 24.67           C
ATOM   2290  O   THR B 299     -20.106  18.167  -0.801  0.50 23.15           O
```

Figure 27 (Continued)

```
ATOM   2291  N   TYR B 300     -18.276  17.137   0.017  0.50 24.52           N
ATOM   2292  CA  TYR B 300     -17.400  17.785  -0.960  0.50 23.90           C
ATOM   2293  CB  TYR B 300     -16.087  18.261  -0.347  0.50 24.81           C
ATOM   2294  CG  TYR B 300     -16.257  19.445   0.585  0.50 26.89           C
ATOM   2295  CD1 TYR B 300     -16.343  19.252   1.951  0.50 27.70           C
ATOM   2296  CE1 TYR B 300     -16.510  20.319   2.810  0.50 29.80           C
ATOM   2297  CZ  TYR B 300     -16.600  21.595   2.306  0.50 29.40           C
ATOM   2298  OH  TYR B 300     -16.766  22.643   3.191  0.50 30.41           O
ATOM   2299  CE2 TYR B 300     -16.516  21.820   0.944  0.50 31.11           C
ATOM   2300  CD2 TYR B 300     -16.353  20.741   0.089  0.50 27.96           C
ATOM   2301  C   TYR B 300     -17.091  16.881  -2.134  0.50 22.27           C
ATOM   2302  O   TYR B 300     -16.852  15.676  -1.958  0.50 22.06           O
ATOM   2303  N   ARG B 301     -17.111  17.484  -3.320  0.50 23.78           N
ATOM   2304  CA  ARG B 301     -16.623  16.845  -4.554  0.50 24.22           C
ATOM   2305  CB  ARG B 301     -17.643  17.006  -5.697  0.50 25.16           C
ATOM   2306  CG  ARG B 301     -17.298  16.249  -6.981  0.50 26.16           C
ATOM   2307  CD  ARG B 301     -18.459  16.302  -7.961  0.50 26.45           C
ATOM   2308  NE  ARG B 301     -18.196  15.531  -9.175  0.50 29.13           N
ATOM   2309  CZ  ARG B 301     -17.576  16.033 -10.235  0.50 30.57           C
ATOM   2310  NH1 ARG B 301     -17.153  17.288 -10.213  0.50 29.54           N
ATOM   2311  NH2 ARG B 301     -17.372  15.280 -11.308  0.50 32.38           N
ATOM   2312  C   ARG B 301     -15.317  17.518  -4.931  0.50 24.62           C
ATOM   2313  O   ARG B 301     -15.220  18.756  -4.975  0.50 24.11           O
ATOM   2314  N   VAL B 302     -14.303  16.705  -5.206  0.50 24.22           N
ATOM   2315  CA  VAL B 302     -12.990  17.244  -5.499  0.50 24.16           C
ATOM   2316  CB  VAL B 302     -12.097  17.240  -4.241  0.50 25.28           C
ATOM   2317  CG1 VAL B 302     -12.162  15.883  -3.564  0.50 28.18           C
ATOM   2318  CG2 VAL B 302     -10.668  17.656  -4.568  0.50 25.33           C
ATOM   2319  C   VAL B 302     -12.369  16.484  -6.673  0.50 22.13           C
ATOM   2320  O   VAL B 302     -12.128  15.280  -6.583  0.50 20.38           O
ATOM   2321  N   VAL B 303     -12.166  17.208  -7.767  0.50 20.85           N
ATOM   2322  CA  VAL B 303     -11.719  16.631  -9.051  0.50 21.45           C
ATOM   2323  CB  VAL B 303     -12.688  16.991 -10.192  0.50 21.39           C
ATOM   2324  CG1 VAL B 303     -12.253  16.314 -11.487  0.50 21.07           C
ATOM   2325  CG2 VAL B 303     -14.113  16.593  -9.850  0.50 22.16           C
ATOM   2326  C   VAL B 303     -10.341  17.122  -9.464  0.50 21.03           C
ATOM   2327  O   VAL B 303     -10.100  18.349  -9.551  0.50 19.91           O
ATOM   2328  N   SER B 304      -9.471  16.160  -9.794  0.50 20.50           N
ATOM   2329  CA  SER B 304      -8.097  16.399 -10.235  0.50 20.16           C
ATOM   2330  CB  SER B 304      -7.132  15.624  -9.322  0.50 20.71           C
ATOM   2331  OG  SER B 304      -5.772  15.830  -9.662  0.50 20.96           O
ATOM   2332  C   SER B 304      -7.971  15.893 -11.679  0.50 21.32           C
ATOM   2333  O   SER B 304      -8.333  14.753 -11.957  0.50 22.57           O
ATOM   2334  N   VAL B 305      -7.485  16.750 -12.570  0.50 20.78           N
ATOM   2335  CA  VAL B 305      -7.378  16.432 -14.006  0.50 20.15           C
ATOM   2336  CB  VAL B 305      -8.092  17.507 -14.851  0.50 20.27           C
ATOM   2337  CG1 VAL B 305      -8.142  17.083 -16.320  0.50 20.59           C
ATOM   2338  CG2 VAL B 305      -9.494  17.768 -14.313  0.50 20.21           C
ATOM   2339  C   VAL B 305      -5.915  16.343 -14.447  0.50 19.91           C
ATOM   2340  O   VAL B 305      -5.165  17.325 -14.363  0.50 20.51           O
ATOM   2341  N   LEU B 306      -5.519  15.166 -14.940  0.50 19.54           N
ATOM   2342  CA  LEU B 306      -4.151  14.938 -15.402  0.50 19.27           C
ATOM   2343  CB  LEU B 306      -3.587  13.635 -14.811  0.50 19.19           C
ATOM   2344  CG  LEU B 306      -2.123  13.324 -15.172  0.50 18.84           C
ATOM   2345  CD1 LEU B 306      -1.114  14.204 -14.423  0.50 19.04           C
ATOM   2346  CD2 LEU B 306      -1.834  11.863 -14.893  0.50 18.87           C
ATOM   2347  C   LEU B 306      -4.142  14.850 -16.916  0.50 20.23           C
ATOM   2348  O   LEU B 306      -4.791  13.963 -17.487  0.50 21.10           O
ATOM   2349  N   THR B 307      -3.420  15.772 -17.550  0.50 20.54           N
ATOM   2350  CA  THR B 307      -3.247  15.768 -18.995  0.50 20.92           C
ATOM   2351  CB  THR B 307      -2.644  17.091 -19.496  0.50 22.79           C
ATOM   2352  OG1 THR B 307      -3.690  18.070 -19.618  0.50 20.78           O
ATOM   2353  CG2 THR B 307      -1.954  16.890 -20.853  0.50 23.89           C
ATOM   2354  C   THR B 307      -2.326  14.606 -19.331  0.50 20.28           C
```

Figure 27 (Continued)

```
ATOM   2355  O    THR B 307      -1.300  14.420 -18.689  0.50 21.33           O
ATOM   2356  N    VAL B 308      -2.721  13.784 -20.298  0.50 19.55           N
ATOM   2357  CA   VAL B 308      -1.847  12.694 -20.740  0.50 18.84           C
ATOM   2358  CB   VAL B 308      -2.546  11.300 -20.678  0.50 19.29           C
ATOM   2359  CG1  VAL B 308      -3.658  11.294 -19.637  0.50 19.10           C
ATOM   2360  CG2  VAL B 308      -3.090  10.888 -22.041  0.50 17.19           C
ATOM   2361  C    VAL B 308      -1.263  12.983 -22.127  0.50 18.66           C
ATOM   2362  O    VAL B 308      -1.835  13.751 -22.914  0.50 19.53           O
ATOM   2363  N    LEU B 309      -0.066  12.456 -22.383  0.50 18.15           N
ATOM   2364  CA   LEU B 309       0.537  12.569 -23.704  0.50 17.55           C
ATOM   2365  CB   LEU B 309       2.045  12.349 -23.654  0.50 19.04           C
ATOM   2366  CG   LEU B 309       2.848  13.335 -22.793  0.50 19.55           C
ATOM   2367  CD1  LEU B 309       4.332  13.268 -23.155  0.50 20.50           C
ATOM   2368  CD2  LEU B 309       2.282  14.745 -22.912  0.50 18.96           C
ATOM   2369  C    LEU B 309      -0.091  11.479 -24.558  0.50 16.39           C
ATOM   2370  O    LEU B 309      -0.192  10.337 -24.126  0.50 17.42           O
ATOM   2371  N    HIS B 310      -0.509  11.835 -25.761  0.50 16.13           N
ATOM   2372  CA   HIS B 310      -1.213  10.879 -26.614  0.50 16.11           C
ATOM   2373  CB   HIS B 310      -1.333  11.467 -28.017  0.50 15.86           C
ATOM   2374  CG   HIS B 310      -2.094  12.753 -28.065  0.50 16.36           C
ATOM   2375  ND1  HIS B 310      -1.688  13.883 -27.387  0.50 16.34           N
ATOM   2376  CE1  HIS B 310      -2.550  14.858 -27.603  0.50 15.97           C
ATOM   2377  NE2  HIS B 310      -3.498  14.406 -28.404  0.50 16.12           N
ATOM   2378  CD2  HIS B 310      -3.241  13.088 -28.703  0.50 15.91           C
ATOM   2379  C    HIS B 310      -0.476   9.538 -26.688  0.50 16.11           C
ATOM   2380  O    HIS B 310      -1.069   8.446 -26.537  0.50 15.70           O
ATOM   2381  N    GLN B 311       0.823   9.600 -26.960  0.50 17.12           N
ATOM   2382  CA   GLN B 311       1.526   8.366 -27.219  0.50 17.99           C
ATOM   2383  CB   GLN B 311       2.810   8.580 -28.027  0.50 18.72           C
ATOM   2384  CG   GLN B 311       3.352   7.264 -28.587  0.50 19.82           C
ATOM   2385  CD   GLN B 311       2.456   6.671 -29.676  0.50 19.35           C
ATOM   2386  OE1  GLN B 311       1.870   7.414 -30.489  0.50 20.73           O
ATOM   2387  NE2  GLN B 311       2.357   5.327 -29.716  0.50 18.79           N
ATOM   2388  C    GLN B 311       1.802   7.565 -25.957  0.50 17.93           C
ATOM   2389  O    GLN B 311       2.007   6.355 -26.031  0.50 18.46           O
ATOM   2390  N    ASP B 312       1.825   8.220 -24.800  0.50 17.77           N
ATOM   2391  CA   ASP B 312       1.929   7.474 -23.551  0.50 18.37           C
ATOM   2392  CB   ASP B 312       1.924   8.407 -22.345  0.50 19.01           C
ATOM   2393  CG   ASP B 312       3.314   8.917 -21.953  0.50 19.92           C
ATOM   2394  OD1  ASP B 312       4.364   8.461 -22.484  0.50 20.64           O
ATOM   2395  OD2  ASP B 312       3.334   9.827 -21.097  0.50 21.03           O
ATOM   2396  C    ASP B 312       0.706   6.575 -23.423  0.50 16.86           C
ATOM   2397  O    ASP B 312       0.809   5.409 -23.062  0.50 16.62           O
ATOM   2398  N    TRP B 313      -0.462   7.155 -23.673  0.50 16.69           N
ATOM   2399  CA   TRP B 313      -1.704   6.430 -23.509  0.50 16.61           C
ATOM   2400  CB   TRP B 313      -2.912   7.352 -23.748  0.50 16.46           C
ATOM   2401  CG   TRP B 313      -4.214   6.610 -23.576  0.50 16.59           C
ATOM   2402  CD1  TRP B 313      -5.025   6.104 -24.568  0.50 16.29           C
ATOM   2403  NE1  TRP B 313      -6.109   5.453 -24.001  0.50 15.82           N
ATOM   2404  CE2  TRP B 313      -6.020   5.549 -22.637  0.50 16.43           C
ATOM   2405  CD2  TRP B 313      -4.825   6.243 -22.333  0.50 16.50           C
ATOM   2406  CE3  TRP B 313      -4.508   6.482 -20.990  0.50 16.72           C
ATOM   2407  CZ3  TRP B 313      -5.358   5.973 -19.993  0.50 16.84           C
ATOM   2408  CH2  TRP B 313      -6.527   5.273 -20.330  0.50 17.53           C
ATOM   2409  CZ2  TRP B 313      -6.868   5.038 -21.638  0.50 16.48           C
ATOM   2410  C    TRP B 313      -1.719   5.284 -24.520  0.50 15.61           C
ATOM   2411  O    TRP B 313      -2.062   4.145 -24.189  0.50 17.42           O
ATOM   2412  N    LEU B 314      -1.386   5.606 -25.761  0.50 15.91           N
ATOM   2413  CA   LEU B 314      -1.414   4.599 -26.813  0.50 16.34           C
ATOM   2414  CB   LEU B 314      -1.305   5.239 -28.183  0.50 16.87           C
ATOM   2415  CG   LEU B 314      -2.540   6.107 -28.470  0.50 15.68           C
ATOM   2416  CD1  LEU B 314      -2.427   6.787 -29.834  0.50 17.77           C
ATOM   2417  CD2  LEU B 314      -3.808   5.264 -28.392  0.50 16.78           C
ATOM   2418  C    LEU B 314      -0.369   3.500 -26.598  0.50 17.55           C
```

Figure 27 (Continued)

```
ATOM   2419  O    LEU B 314      -0.571   2.354 -27.027  0.50 19.48           O
ATOM   2420  N    ASN B 315       0.700   3.844 -25.887  0.50 16.90           N
ATOM   2421  CA   ASN B 315       1.743   2.877 -25.541  0.50 17.67           C
ATOM   2422  CB   ASN B 315       3.100   3.584 -25.382  0.50 18.96           C
ATOM   2423  CG   ASN B 315       3.746   3.897 -26.708  0.50 19.45           C
ATOM   2424  OD1  ASN B 315       3.314   3.392 -27.748  0.50 21.02           O
ATOM   2425  ND2  ASN B 315       4.769   4.756 -26.692  0.50 20.37           N
ATOM   2426  C    ASN B 315       1.460   2.052 -24.299  0.50 18.52           C
ATOM   2427  O    ASN B 315       2.309   1.248 -23.885  0.50 19.01           O
ATOM   2428  N    GLY B 316       0.282   2.241 -23.712  0.50 17.78           N
ATOM   2429  CA   GLY B 316      -0.179   1.400 -22.619  0.50 18.52           C
ATOM   2430  C    GLY B 316       0.322   1.795 -21.243  0.50 19.43           C
ATOM   2431  O    GLY B 316       0.321   0.974 -20.326  0.50 19.19           O
ATOM   2432  N    LYS B 317       0.743   3.042 -21.082  0.50 18.79           N
ATOM   2433  CA   LYS B 317       1.150   3.485 -19.754  0.50 18.57           C
ATOM   2434  CB   LYS B 317       1.780   4.879 -19.781  0.50 18.39           C
ATOM   2435  CG   LYS B 317       3.278   4.824 -20.073  0.50 19.38           C
ATOM   2436  CD   LYS B 317       3.960   6.187 -20.068  0.50 21.85           C
ATOM   2437  CE   LYS B 317       5.309   6.107 -20.775  0.50 22.74           C
ATOM   2438  NZ   LYS B 317       6.325   7.127 -20.347  0.50 25.40           N
ATOM   2439  C    LYS B 317      -0.002   3.403 -18.762  0.50 18.88           C
ATOM   2440  O    LYS B 317      -1.171   3.529 -19.134  0.50 18.92           O
ATOM   2441  N    GLU B 318       0.351   3.179 -17.493  0.50 18.94           N
ATOM   2442  CA   GLU B 318      -0.629   2.994 -16.429  0.50 20.16           C
ATOM   2443  CB   GLU B 318      -0.224   1.801 -15.564  0.50 22.36           C
ATOM   2444  CG   GLU B 318      -0.282   0.468 -16.290  0.50 24.60           C
ATOM   2445  CD   GLU B 318      -0.120  -0.710 -15.342  0.50 25.83           C
ATOM   2446  OE1  GLU B 318       0.802  -0.674 -14.500  0.50 28.08           O
ATOM   2447  OE2  GLU B 318      -0.922  -1.660 -15.421  0.50 28.96           O
ATOM   2448  C    GLU B 318      -0.673   4.244 -15.560  0.50 19.29           C
ATOM   2449  O    GLU B 318       0.352   4.646 -15.006  0.50 19.12           O
ATOM   2450  N    TYR B 319      -1.851   4.858 -15.460  0.50 19.48           N
ATOM   2451  CA   TYR B 319      -2.030   6.093 -14.706  0.50 19.57           C
ATOM   2452  CB   TYR B 319      -2.891   7.069 -15.515  0.50 18.55           C
ATOM   2453  CG   TYR B 319      -2.194   7.445 -16.779  0.50 18.71           C
ATOM   2454  CD1  TYR B 319      -2.227   6.595 -17.884  0.50 18.93           C
ATOM   2455  CE1  TYR B 319      -1.564   6.913 -19.046  0.50 18.58           C
ATOM   2456  CZ   TYR B 319      -0.844   8.094 -19.124  0.50 18.90           C
ATOM   2457  OH   TYR B 319      -0.161   8.391 -20.278  0.50 19.42           O
ATOM   2458  CE2  TYR B 319      -0.771   8.940 -18.035  0.50 19.31           C
ATOM   2459  CD2  TYR B 319      -1.445   8.617 -16.873  0.50 18.03           C
ATOM   2460  C    TYR B 319      -2.688   5.764 -13.382  0.50 19.36           C
ATOM   2461  O    TYR B 319      -3.792   5.219 -13.365  0.50 20.89           O
ATOM   2462  N    LYS B 320      -2.009   6.092 -12.282  0.50 19.62           N
ATOM   2463  CA   LYS B 320      -2.570   5.860 -10.953  0.50 19.10           C
ATOM   2464  CB   LYS B 320      -1.673   4.954 -10.111  0.50 20.35           C
ATOM   2465  CG   LYS B 320      -2.244   4.686  -8.723  0.50 19.12           C
ATOM   2466  CD   LYS B 320      -1.230   3.976  -7.831  0.50 20.92           C
ATOM   2467  CE   LYS B 320      -0.906   2.598  -8.339  0.50 23.63           C
ATOM   2468  NZ   LYS B 320       0.071   1.917  -7.432  0.50 24.40           N
ATOM   2469  C    LYS B 320      -2.803   7.182 -10.256  0.50 18.74           C
ATOM   2470  O    LYS B 320      -1.957   8.074 -10.287  0.50 18.60           O
ATOM   2471  N    CYS B 321      -4.007   7.328  -9.726  0.50 20.58           N
ATOM   2472  CA   CYS B 321      -4.345   8.462  -8.896  0.50 21.99           C
ATOM   2473  CB   CYS B 321      -5.670   9.072  -9.353  0.50 23.19           C
ATOM   2474  SG   CYS B 321      -6.369  10.253  -8.171  0.50 24.95           S
ATOM   2475  C    CYS B 321      -4.444   7.942  -7.468  0.50 22.66           C
ATOM   2476  O    CYS B 321      -5.093   6.930  -7.206  0.50 22.45           O
ATOM   2477  N    LYS B 322      -3.763   8.621  -6.556  0.50 22.69           N
ATOM   2478  CA   LYS B 322      -3.812   8.273  -5.145  0.50 23.42           C
ATOM   2479  CB   LYS B 322      -2.403   8.055  -4.598  0.50 23.56           C
ATOM   2480  CG   LYS B 322      -2.321   8.198  -3.079  0.50 24.22           C
ATOM   2481  CD   LYS B 322      -0.919   8.601  -2.638  0.50 27.40           C
ATOM   2482  CE   LYS B 322      -0.123   7.373  -2.238  0.50 29.49           C
```

Figure 27 (Continued)

```
ATOM   2483  NZ   LYS B 322       0.725   7.648  -1.044  0.50 32.14           N
ATOM   2484  C    LYS B 322       4.464   9.440   4.419  0.50 23.20           C
ATOM   2485  O    LYS B 322      -4.114  10.594  -4.662  0.50 23.65           O
ATOM   2486  N    VAL B 323      -5.420   9.132  -3.548  0.50 23.92           N
ATOM   2487  CA   VAL B 323      -6.181  10.161  -2.844  0.50 24.26           C
ATOM   2488  CB   VAL B 323      -7.639  10.202  -3.305  0.50 24.63           C
ATOM   2489  CG1  VAL B 323      -8.437  11.235  -2.509  0.50 22.36           C
ATOM   2490  CG2  VAL B 323      -7.719  10.478  -4.796  0.50 22.78           C
ATOM   2491  C    VAL B 323      -6.196   9.850  -1.352  0.50 24.68           C
ATOM   2492  O    VAL B 323      -6.659   8.794  -0.926  0.50 23.97           O
ATOM   2493  N    SER B 324      -5.710  10.804  -0.573  0.50 27.11           N
ATOM   2494  CA   SER B 324      -5.645  10.653   0.879  0.50 25.03           C
ATOM   2495  CB   SER B 324      -4.272  11.103   1.392  0.50 25.55           C
ATOM   2496  OG   SER B 324      -3.214  10.388   0.777  0.50 28.69           O
ATOM   2497  C    SER B 324      -6.719  11.541   1.477  0.50 24.68           C
ATOM   2498  O    SER B 324      -7.008  12.617   0.952  0.50 24.18           O
ATOM   2499  N    ASN B 325      -7.303  11.092   2.585  0.50 25.01           N
ATOM   2500  CA   ASN B 325      -8.306  11.863   3.310  0.50 24.94           C
ATOM   2501  CB   ASN B 325      -9.663  11.802   2.591  0.50 23.98           C
ATOM   2502  CG   ASN B 325     -10.798  12.430   3.394  0.50 24.36           C
ATOM   2503  OD1  ASN B 325     -11.513  11.727   4.096  0.50 23.82           O
ATOM   2504  ND2  ASN B 325     -10.983  13.743   3.269  0.50 22.79           N
ATOM   2505  C    ASN B 325      -8.380  11.283   4.722  0.50 25.58           C
ATOM   2506  O    ASN B 325      -8.089  10.105   4.930  0.50 24.80           O
ATOM   2507  N    LYS B 326      -8.722  12.105   5.703  0.50 28.31           N
ATOM   2508  CA   LYS B 326      -8.592  11.654   7.088  0.50 29.99           C
ATOM   2509  CB   LYS B 326      -8.507  12.844   8.048  0.50 31.01           C
ATOM   2510  CG   LYS B 326      -7.392  13.815   7.696  0.50 32.81           C
ATOM   2511  CD   LYS B 326      -7.104  14.786   8.825  0.50 36.15           C
ATOM   2512  CE   LYS B 326      -6.289  15.969   8.339  0.50 38.16           C
ATOM   2513  NZ   LYS B 326      -5.791  16.782   9.481  0.50 38.62           N
ATOM   2514  C    LYS B 326      -9.675  10.649   7.497  0.50 30.68           C
ATOM   2515  O    LYS B 326      -9.480   9.867   8.422  0.50 32.31           O
ATOM   2516  N    ALA B 327     -10.806  10.660   6.796  0.50 32.74           N
ATOM   2517  CA   ALA B 327     -11.858   9.661   7.019  0.50 33.92           C
ATOM   2518  CB   ALA B 327     -13.204  10.215   6.594  0.50 34.26           C
ATOM   2519  C    ALA B 327     -11.599   8.303   6.347  0.50 35.28           C
ATOM   2520  O    ALA B 327     -12.461   7.412   6.358  0.50 36.34           O
ATOM   2521  N    LEU B 328     -10.415   8.145   5.766  0.50 36.77           N
ATOM   2522  CA   LEU B 328     -10.003   6.870   5.187  0.50 36.41           C
ATOM   2523  CB   LEU B 328      -9.324   7.103   3.837  0.50 37.58           C
ATOM   2524  CG   LEU B 328     -10.183   7.780   2.771  0.50 39.32           C
ATOM   2525  CD1  LEU B 328      -9.337   8.098   1.547  0.50 38.24           C
ATOM   2526  CD2  LEU B 328     -11.366   6.896   2.405  0.50 40.82           C
ATOM   2527  C    LEU B 328      -9.047   6.113   6.106  0.50 37.58           C
ATOM   2528  O    LEU B 328      -8.223   6.722   6.788  0.50 36.29           O
ATOM   2529  N    PRO B 329      -9.149   4.774   6.121  0.50 38.47           N
ATOM   2530  CA   PRO B 329      -8.194   3.960   6.871  0.50 39.62           C
ATOM   2531  CB   PRO B 329      -8.734   2.534   6.702  0.50 40.07           C
ATOM   2532  CG   PRO B 329      -9.560   2.580   5.459  0.50 40.92           C
ATOM   2533  CD   PRO B 329     -10.167   3.954   5.441  0.50 38.88           C
ATOM   2534  C    PRO B 329      -6.797   4.072   6.268  0.50 39.57           C
ATOM   2535  O    PRO B 329      -5.827   3.590   6.854  0.50 39.52           O
ATOM   2536  N    ALA B 330      -6.709   4.716   5.103  0.50 38.77           N
ATOM   2537  CA   ALA B 330      -5.444   4.891   4.384  0.50 36.23           C
ATOM   2538  CB   ALA B 330      -4.661   3.588   4.333  0.50 37.10           C
ATOM   2539  C    ALA B 330      -5.751   5.379   2.968  0.50 34.66           C
ATOM   2540  O    ALA B 330      -6.907   5.366   2.543  0.50 36.82           O
ATOM   2541  N    PRO B 331      -4.722   5.815   2.234  0.50 32.80           N
ATOM   2542  CA   PRO B 331      -5.034   6.299   0.899  0.50 31.44           C
ATOM   2543  CB   PRO B 331      -3.655   6.623   0.324  0.50 32.06           C
ATOM   2544  CG   PRO B 331      -2.876   7.070   1.522  0.50 34.44           C
ATOM   2545  CD   PRO B 331      -3.353   6.176   2.641  0.50 32.72           C
ATOM   2546  C    PRO B 331      -5.796   5.291   0.026  0.50 29.93           C
```

Figure 27 (Continued)

```
ATOM   2547  O    PRO B 331      -5.760   4.078   0.253  0.50 28.27           O
ATOM   2548  N    ILE B 332      -6.523   5.819  -0.947  0.50 29.03           N
ATOM   2549  CA   ILE B 332      -7.185   4.996  -1.939  0.50 28.69           C
ATOM   2550  CB   ILE B 332      -8.614   5.501  -2.191  0.50 27.78           C
ATOM   2551  CG1  ILE B 332      -9.469   5.309  -0.930  0.50 27.13           C
ATOM   2552  CD1  ILE B 332     -10.791   6.050  -0.966  0.50 26.87           C
ATOM   2553  CG2  ILE B 332      -9.244   4.782  -3.373  0.50 28.41           C
ATOM   2554  C    ILE B 332      -6.351   5.121  -3.206  0.50 27.83           C
ATOM   2555  O    ILE B 332      -5.925   6.225  -3.559  0.50 25.69           O
ATOM   2556  N    GLU B 333      -6.072   3.993  -3.854  0.50 26.86           N
ATOM   2557  CA   GLU B 333      -5.408   4.029  -5.158  0.50 27.60           C
ATOM   2558  CB   GLU B 333      -4.031   3.342  -5.118  0.50 28.04           C
ATOM   2559  CG   GLU B 333      -2.973   4.160  -4.379  0.50 30.23           C
ATOM   2560  CD   GLU B 333      -1.570   3.569  -4.418  0.50 33.28           C
ATOM   2561  OE1  GLU B 333      -1.384   2.429  -4.898  0.50 33.08           O
ATOM   2562  OE2  GLU B 333      -0.638   4.259  -3.957  0.50 36.77           O
ATOM   2563  C    GLU B 333      -6.314   3.487  -6.274  0.50 25.50           C
ATOM   2564  O    GLU B 333      -7.167   2.616  -6.052  0.50 25.89           O
ATOM   2565  N    LYS B 334      -6.154   4.057  -7.465  0.50 23.18           N
ATOM   2566  CA   LYS B 334      -6.891   3.628  -8.650  0.50 23.12           C
ATOM   2567  CB   LYS B 334      -8.158   4.471  -8.848  0.50 22.23           C
ATOM   2568  CG   LYS B 334      -9.148   4.424  -7.681  0.50 23.25           C
ATOM   2569  CD   LYS B 334      -9.651   3.016  -7.399  0.50 22.24           C
ATOM   2570  CE   LYS B 334     -10.654   3.000  -6.252  0.50 23.20           C
ATOM   2571  NZ   LYS B 334     -11.405   1.721  -6.240  0.50 25.29           N
ATOM   2572  C    LYS B 334      -5.947   3.813  -9.825  0.50 22.91           C
ATOM   2573  O    LYS B 334      -5.257   4.833  -9.936  0.50 23.32           O
ATOM   2574  N    THR B 335      -5.875   2.800 -10.678  0.50 23.30           N
ATOM   2575  CA   THR B 335      -5.007   2.855 -11.847  0.50 21.70           C
ATOM   2576  CB   THR B 335      -3.803   1.892 -11.693  0.50 22.41           C
ATOM   2577  OG1  THR B 335      -3.045   2.226 -10.514  0.50 23.23           O
ATOM   2578  CG2  THR B 335      -2.876   1.960 -12.919  0.50 22.98           C
ATOM   2579  C    THR B 335      -5.853   2.447 -13.048  0.50 22.02           C
ATOM   2580  O    THR B 335      -6.662   1.526 -12.955  0.50 20.19           O
ATOM   2581  N    ILE B 336      -5.689   3.162 -14.160  0.50 21.84           N
ATOM   2582  CA   ILE B 336      -6.390   2.829 -15.399  0.50 21.77           C
ATOM   2583  CB   ILE B 336      -7.462   3.880 -15.756  0.50 21.87           C
ATOM   2584  CG1  ILE B 336      -6.866   5.288 -15.683  0.50 23.57           C
ATOM   2585  CD1  ILE B 336      -7.716   6.337 -16.366  0.50 23.30           C
ATOM   2586  CG2  ILE B 336      -8.655   3.775 -14.819  0.50 22.87           C
ATOM   2587  C    ILE B 336      -5.358   2.830 -16.498  0.50 20.14           C
ATOM   2588  O    ILE B 336      -4.313   3.444 -16.365  0.50 21.70           O
ATOM   2589  N    SER B 337      -5.659   2.146 -17.597  0.50 20.19           N
ATOM   2590  CA   SER B 337      -4.787   2.160 -18.761  0.50 19.12           C
ATOM   2591  CB   SER B 337      -3.584   1.222 -18.570  0.50 20.96           C
ATOM   2592  OG   SER B 337      -3.995  -0.065 -18.120  0.50 22.78           O
ATOM   2593  C    SER B 337      -5.621   1.731 -19.967  0.50 17.66           C
ATOM   2594  O    SER B 337      -6.783   1.318 -19.825  0.50 16.41           O
ATOM   2595  N    LYS B 338      -5.036   1.858 -21.148  0.50 17.53           N
ATOM   2596  CA   LYS B 338      -5.754   1.571 -22.380  0.50 17.48           C
ATOM   2597  CB   LYS B 338      -4.901   1.987 -23.584  0.50 18.10           C
ATOM   2598  CG   LYS B 338      -5.634   1.853 -24.921  0.50 17.93           C
ATOM   2599  CD   LYS B 338      -4.749   2.297 -26.087  0.50 20.28           C
ATOM   2600  CE   LYS B 338      -3.643   1.293 -26.356  0.50 19.27           C
ATOM   2601  NZ   LYS B 338      -4.127   0.177 -27.219  0.50 19.68           N
ATOM   2602  C    LYS B 338      -6.096   0.090 -22.467  0.50 17.78           C
ATOM   2603  O    LYS B 338      -5.394  -0.763 -21.903  0.50 18.43           O
ATOM   2604  N    ALA B 339      -7.169  -0.225 -23.184  0.50 16.87           N
ATOM   2605  CA   ALA B 339      -7.471  -1.629 -23.486  0.50 18.08           C
ATOM   2606  CB   ALA B 339      -8.636  -1.731 -24.467  0.50 18.09           C
ATOM   2607  C    ALA B 339      -6.247  -2.359 -24.036  0.50 18.02           C
ATOM   2608  O    ALA B 339      -5.503  -1.817 -24.844  0.50 19.56           O
ATOM   2609  N    LYS B 340      -6.059  -3.604 -23.610  0.50 18.03           N
ATOM   2610  CA   LYS B 340      -4.925  -4.419 -24.087  0.50 18.65           C
```

Figure 27 (Continued)

```
ATOM   2611  CB  LYS B 340      -4.518  -5.446 -23.020  0.50 20.04           C
ATOM   2612  CG  LYS B 340      -4.161  -4.841 -21.664  0.50 22.46           C
ATOM   2613  CD  LYS B 340      -3.086  -5.653 -20.956  0.50 24.24           C
ATOM   2614  CE  LYS B 340      -2.121  -4.750 -20.202  0.50 26.02           C
ATOM   2615  NZ  LYS B 340      -1.535  -5.440 -19.020  0.50 29.58           N
ATOM   2616  C   LYS B 340      -5.242  -5.136 -25.411  0.50 18.12           C
ATOM   2617  O   LYS B 340      -6.384  -5.100 -25.889  0.50 17.98           O
ATOM   2618  N   GLY B 341      -4.224  -5.792 -25.989  0.50 18.07           N
ATOM   2619  CA  GLY B 341      -4.406  -6.631 -27.190  0.50 18.53           C
ATOM   2620  C   GLY B 341      -3.740  -6.069 -28.442  0.50 19.01           C
ATOM   2621  O   GLY B 341      -3.611  -4.854 -28.589  0.50 18.95           O
ATOM   2622  N   GLN B 342      -3.273  -6.942 -29.345  0.50 20.02           N
ATOM   2623  CA  GLN B 342      -2.653  -6.465 -30.584  0.50 20.11           C
ATOM   2624  CB  GLN B 342      -2.133  -7.614 -31.465  0.50 22.87           C
ATOM   2625  CG  GLN B 342      -0.756  -8.164 -31.083  0.50 26.06           C
ATOM   2626  CD  GLN B 342       0.432  -7.287 -31.504  0.50 28.45           C
ATOM   2627  OE1 GLN B 342       0.623  -6.976 -32.687  0.50 28.48           O
ATOM   2628  NE2 GLN B 342       1.266  -6.925 -30.529  0.50 28.57           N
ATOM   2629  C   GLN B 342      -3.679  -5.664 -31.391  0.50 17.72           C
ATOM   2630  O   GLN B 342      -4.753  -6.159 -31.695  0.50 16.22           O
ATOM   2631  N   PRO B 343      -3.328  -4.424 -31.740  0.50 17.57           N
ATOM   2632  CA  PRO B 343      -4.244  -3.646 -32.558  0.50 17.28           C
ATOM   2633  CB  PRO B 343      -3.608  -2.249 -32.555  0.50 17.14           C
ATOM   2634  CG  PRO B 343      -2.800  -2.211 -31.270  0.50 17.86           C
ATOM   2635  CD  PRO B 343      -2.241  -3.599 -31.178  0.50 18.26           C
ATOM   2636  C   PRO B 343      -4.378  -4.217 -33.977  0.50 16.31           C
ATOM   2637  O   PRO B 343      -3.420  -4.810 -34.513  0.50 18.53           O
ATOM   2638  N   ARG B 344      -5.570  -4.067 -34.564  0.50 15.87           N
ATOM   2639  CA  ARG B 344      -5.839  -4.531 -35.903  0.50 15.98           C
ATOM   2640  CB  ARG B 344      -6.790  -5.743 -35.873  0.50 17.69           C
ATOM   2641  CG  ARG B 344      -6.357  -6.843 -34.898  0.50 20.75           C
ATOM   2642  CD  ARG B 344      -7.426  -7.909 -34.659  0.50 27.00           C
ATOM   2643  NE  ARG B 344      -7.622  -8.750 -35.839  0.50 31.06           N
ATOM   2644  CZ  ARG B 344      -8.011 -10.028 -35.818  0.50 31.83           C
ATOM   2645  NH1 ARG B 344      -8.268 -10.649 -34.670  0.50 30.77           N
ATOM   2646  NH2 ARG B 344      -8.157 -10.677 -36.967  0.50 31.56           N
ATOM   2647  C   ARG B 344      -6.503  -3.371 -36.628  0.50 15.21           C
ATOM   2648  O   ARG B 344      -7.326  -2.673 -36.039  0.50 13.27           O
ATOM   2649  N   GLU B 345      -6.164  -3.202 -37.897  0.50 14.49           N
ATOM   2650  CA  GLU B 345      -6.595  -2.042 -38.690  0.50 15.68           C
ATOM   2651  CB  GLU B 345      -5.671  -1.936 -39.926  0.50 16.14           C
ATOM   2652  CG  GLU B 345      -5.739  -0.580 -40.637  0.50 18.12           C
ATOM   2653  CD  GLU B 345      -4.757  -0.397 -41.790  0.50 19.81           C
ATOM   2654  OE1 GLU B 345      -5.016   0.508 -42.609  0.50 22.99           O
ATOM   2655  OE2 GLU B 345      -3.756  -1.153 -41.928  0.50 20.78           O
ATOM   2656  C   GLU B 345      -8.088  -2.074 -39.130  0.50 15.14           C
ATOM   2657  O   GLU B 345      -8.550  -3.032 -39.724  0.50 15.53           O
ATOM   2658  N   PRO B 346      -8.853  -1.013 -38.833  0.50 14.32           N
ATOM   2659  CA  PRO B 346     -10.209  -0.981 -39.371  0.50 16.39           C
ATOM   2660  CB  PRO B 346     -10.756   0.369 -38.871  0.50 16.10           C
ATOM   2661  CG  PRO B 346      -9.925   0.692 -37.663  0.50 16.52           C
ATOM   2662  CD  PRO B 346      -8.558   0.125 -37.947  0.50 15.31           C
ATOM   2663  C   PRO B 346     -10.248  -1.057 -40.906  0.50 17.13           C
ATOM   2664  O   PRO B 346      -9.315  -0.583 -41.617  0.50 17.14           O
ATOM   2665  N   GLN B 347     -11.303  -1.686 -41.430  0.50 16.72           N
ATOM   2666  CA  GLN B 347     -11.530  -1.686 -42.859  0.50 17.09           C
ATOM   2667  CB  GLN B 347     -11.702  -3.127 -43.372  0.50 18.85           C
ATOM   2668  CG  GLN B 347     -10.490  -3.996 -43.063  0.50 20.46           C
ATOM   2669  CD  GLN B 347      -9.217  -3.454 -43.684  0.50 22.92           C
ATOM   2670  OE1 GLN B 347      -9.168  -3.210 -44.891  0.50 24.64           O
ATOM   2671  NE2 GLN B 347      -8.186  -3.222 -42.853  0.50 23.86           N
ATOM   2672  C   GLN B 347     -12.826  -0.919 -42.986  0.50 15.41           C
ATOM   2673  O   GLN B 347     -13.793  -1.246 -42.286  0.50 16.29           O
ATOM   2674  N   VAL B 348     -12.873   0.097 -43.848  0.50 15.36           N
```

Figure 27 (Continued)

```
ATOM   2675  CA   VAL B 348     -14.034    0.996 -43.862  0.50 15.08           C
ATOM   2676  CB   VAL B 348     -13.607    2.457 -43.596  0.50 15.42           C
ATOM   2677  CG1  VAL B 348     -14.850    3.348 -43.475  0.50 15.63           C
ATOM   2678  CG2  VAL B 348     -12.719    2.519 -42.346  0.50 14.86           C
ATOM   2679  C    VAL B 348     -14.741    0.962 -45.206  0.50 15.01           C
ATOM   2680  O    VAL B 348     -14.106    1.164 -46.248  0.50 16.45           O
ATOM   2681  N    TYR B 349     -16.044    0.682 -45.178  0.50 14.90           N
ATOM   2682  CA   TYR B 349     -16.848    0.599 -46.389  0.50 15.95           C
ATOM   2683  CB   TYR B 349     -17.255   -0.862 -46.658  0.50 16.46           C
ATOM   2684  CG   TYR B 349     -16.047   -1.750 -46.842  0.50 16.98           C
ATOM   2685  CD1  TYR B 349     -15.194   -1.565 -47.937  0.50 17.35           C
ATOM   2686  CE1  TYR B 349     -14.083   -2.364 -48.118  0.50 18.30           C
ATOM   2687  CZ   TYR B 349     -13.813   -3.375 -47.215  0.50 17.34           C
ATOM   2688  OH   TYR B 349     -12.702   -4.157 -47.395  0.50 18.81           O
ATOM   2689  CE2  TYR B 349     -14.639   -3.585 -46.127  0.50 17.41           C
ATOM   2690  CD2  TYR B 349     -15.745   -2.763 -45.939  0.50 17.42           C
ATOM   2691  C    TYR B 349     -18.045    1.505 -46.278  0.50 16.09           C
ATOM   2692  O    TYR B 349     -18.606    1.694 -45.192  0.50 14.86           O
ATOM   2693  N    VAL B 350     -18.441    2.091 -47.403  0.50 16.18           N
ATOM   2694  CA   VAL B 350     -19.653    2.879 -47.415  0.50 17.19           C
ATOM   2695  CB   VAL B 350     -19.365    4.396 -47.624  0.50 17.99           C
ATOM   2696  CG1  VAL B 350     -18.821    5.026 -46.332  0.50 18.17           C
ATOM   2697  CG2  VAL B 350     -18.387    4.600 -48.779  0.50 17.87           C
ATOM   2698  C    VAL B 350     -20.632    2.292 -48.437  0.50 17.36           C
ATOM   2699  O    VAL B 350     -20.229    1.880 -49.541  0.50 17.78           O
ATOM   2700  N    LEU B 351     -21.905    2.230 -48.057  0.50 16.26           N
ATOM   2701  CA   LEU B 351     -22.943    1.619 -48.901  0.50 16.15           C
ATOM   2702  CB   LEU B 351     -23.495    0.342 -48.251  0.50 16.90           C
ATOM   2703  CG   LEU B 351     -22.518   -0.477 -47.416  0.50 17.38           C
ATOM   2704  CD1  LEU B 351     -21.900    0.431 -46.391  0.50 18.99           C
ATOM   2705  CD2  LEU B 351     -21.467   -1.176 -48.254  0.50 17.31           C
ATOM   2706  C    LEU B 351     -24.078    2.594 -49.089  0.50 16.48           C
ATOM   2707  O    LEU B 351     -24.610    3.139 -48.124  0.50 17.40           O
ATOM   2708  N    PRO B 352     -24.457    2.835 -50.338  0.50 18.63           N
ATOM   2709  CA   PRO B 352     -25.563    3.747 -50.617  0.50 19.61           C
ATOM   2710  CB   PRO B 352     -25.491    3.916 -52.139  0.50 19.63           C
ATOM   2711  CG   PRO B 352     -24.890    2.636 -52.620  0.50 20.22           C
ATOM   2712  CD   PRO B 352     -23.900    2.232 -51.557  0.50 19.08           C
ATOM   2713  C    PRO B 352     -26.898    3.123 -50.221  0.50 21.91           C
ATOM   2714  O    PRO B 352     -26.963    1.909 -49.989  0.50 20.95           O
ATOM   2715  N    PRO B 353     -27.959    3.940 -50.151  0.50 21.80           N
ATOM   2716  CA   PRO B 353     -29.230    3.341 -49.791  0.50 23.33           C
ATOM   2717  CB   PRO B 353     -30.181    4.540 -49.678  0.50 23.16           C
ATOM   2718  CG   PRO B 353     -29.435    5.729 -50.202  0.50 22.78           C
ATOM   2719  CD   PRO B 353     -28.128    5.272 -50.756  0.50 24.05           C
ATOM   2720  C    PRO B 353     -29.704    2.367 -50.861  0.50 23.08           C
ATOM   2721  O    PRO B 353     -29.478    2.576 -52.057  0.50 24.51           O
ATOM   2722  N    SER B 354     -30.323    1.291 -50.407  0.50 24.35           N
ATOM   2723  CA   SER B 354     -30.964    0.332 -51.281  0.50 23.74           C
ATOM   2724  CB   SER B 354     -31.631   -0.751 -50.433  0.50 25.87           C
ATOM   2725  OG   SER B 354     -32.446   -1.588 -51.234  0.50 29.14           O
ATOM   2726  C    SER B 354     -32.031    1.040 -52.122  0.50 23.72           C
ATOM   2727  O    SER B 354     -32.752    1.911 -51.624  0.50 21.62           O
ATOM   2728  N    ARG B 355     -32.124    0.646 -53.390  0.50 25.02           N
ATOM   2729  CA   ARG B 355     -33.128    1.173 -54.313  0.50 26.77           C
ATOM   2730  CB   ARG B 355     -33.101    0.388 -55.623  0.50 29.07           C
ATOM   2731  CG   ARG B 355     -34.121    0.856 -56.649  0.50 34.14           C
ATOM   2732  CD   ARG B 355     -34.781   -0.326 -57.342  0.50 38.88           C
ATOM   2733  NE   ARG B 355     -33.823   -1.345 -57.760  0.50 42.13           N
ATOM   2734  CZ   ARG B 355     -33.459   -1.548 -59.023  0.50 45.48           C
ATOM   2735  NH1  ARG B 355     -33.973   -0.797 -59.986  0.50 46.14           N
ATOM   2736  NH2  ARG B 355     -32.582   -2.497 -59.324  0.50 46.87           N
ATOM   2737  C    ARG B 355     -34.521    1.101 -53.705  0.50 25.91           C
ATOM   2738  O    ARG B 355     -35.360    1.971 -53.931  0.50 25.48           O
```

Figure 27 (Continued)

```
ATOM   2739  N   ASP B 356     -34.773   0.045 -52.937  0.50 24.35           N
ATOM   2740  CA  ASP B 356     -36.040  -0.077 -52.225  0.50 24.36           C
ATOM   2741  CB  ASP B 356     -36.087  -1.374 -51.411  0.50 24.96           C
ATOM   2742  CG  ASP B 356     -36.657  -2.545 -52.198  0.50 28.63           C
ATOM   2743  OD1 ASP B 356     -37.403  -2.321 -53.184  0.50 26.53           O
ATOM   2744  OD2 ASP B 356     -36.373  -3.695 -51.810  0.50 27.57           O
ATOM   2745  C   ASP B 356     -36.361   1.106 -51.315  0.50 23.04           C
ATOM   2746  O   ASP B 356     -37.524   1.319 -50.997  0.50 23.87           O
ATOM   2747  N   GLU B 357     -35.354   1.853 -50.845  0.50 22.16           N
ATOM   2748  CA  GLU B 357     -35.609   2.880 -49.815  0.50 21.96           C
ATOM   2749  CB  GLU B 357     -34.426   3.026 -48.827  0.50 19.86           C
ATOM   2750  CG  GLU B 357     -34.800   3.828 -47.583  0.50 20.38           C
ATOM   2751  CD  GLU B 357     -33.643   4.022 -46.597  0.50 19.43           C
ATOM   2752  OE1 GLU B 357     -32.487   3.860 -47.020  0.50 21.25           O
ATOM   2753  OE2 GLU B 357     -33.896   4.350 -45.416  0.50 21.31           O
ATOM   2754  C   GLU B 357     -35.946   4.265 -50.385  0.50 23.20           C
ATOM   2755  O   GLU B 357     -36.431   5.141 -49.668  0.50 22.86           O
ATOM   2756  N   LEU B 358     -35.630   4.464 -51.658  0.50 26.77           N
ATOM   2757  CA  LEU B 358     -35.722   5.782 -52.279  0.50 30.39           C
ATOM   2758  CB  LEU B 358     -35.129   5.747 -53.687  0.50 30.31           C
ATOM   2759  CG  LEU B 358     -33.729   5.154 -53.824  0.50 32.94           C
ATOM   2760  CD1 LEU B 358     -33.342   4.969 -55.284  0.50 34.31           C
ATOM   2761  CD2 LEU B 358     -32.710   6.020 -53.092  0.50 34.11           C
ATOM   2762  C   LEU B 358     -37.158   6.302 -52.338  0.50 32.14           C
ATOM   2763  O   LEU B 358     -37.393   7.456 -52.680  0.50 32.85           O
ATOM   2764  N   THR B 359     -38.108   5.444 -51.995  0.50 35.12           N
ATOM   2765  CA  THR B 359     -39.515   5.796 -52.058  0.50 36.25           C
ATOM   2766  CB  THR B 359     -40.380   4.572 -52.436  0.50 38.25           C
ATOM   2767  OG1 THR B 359     -40.015   3.447 -51.624  0.50 36.03           O
ATOM   2768  CG2 THR B 359     -40.174   4.202 -53.900  0.50 35.93           C
ATOM   2769  C   THR B 359     -39.972   6.384 -50.725  0.50 35.74           C
ATOM   2770  O   THR B 359     -41.169   6.434 -50.445  0.50 35.31           O
ATOM   2771  N   LYS B 360     -39.008   6.848 -49.921  0.50 31.24           N
ATOM   2772  CA  LYS B 360     -39.283   7.373 -48.572  0.50 28.37           C
ATOM   2773  CB  LYS B 360     -38.599   6.495 -47.518  0.50 30.06           C
ATOM   2774  CG  LYS B 360     -38.900   5.011 -47.675  0.50 31.97           C
ATOM   2775  CD  LYS B 360     -40.344   4.725 -47.288  0.50 32.95           C
ATOM   2776  CE  LYS B 360     -40.718   3.265 -47.454  0.50 31.50           C
ATOM   2777  NZ  LYS B 360     -42.121   3.059 -46.990  0.50 32.85           N
ATOM   2778  C   LYS B 360     -38.840   8.834 -48.419  0.50 26.08           C
ATOM   2779  O   LYS B 360     -38.152   9.367 -49.280  0.50 25.00           O
ATOM   2780  N   ASN B 361     -39.235   9.490 -47.326  0.50 25.21           N
ATOM   2781  CA  ASN B 361     -38.889  10.901 -47.140  0.50 25.73           C
ATOM   2782  CB  ASN B 361     -39.832  11.588 -46.147  0.50 29.21           C
ATOM   2783  CG  ASN B 361     -40.999  12.287 -46.826  0.50 32.26           C
ATOM   2784  OD1 ASN B 361     -41.031  12.433 -48.051  0.50 34.78           O
ATOM   2785  ND2 ASN B 361     -41.972  12.715 -46.027  0.50 34.52           N
ATOM   2786  C   ASN B 361     -37.434  11.103 -46.698  0.50 23.25           C
ATOM   2787  O   ASN B 361     -36.836  12.157 -46.938  0.50 22.95           O
ATOM   2788  N   GLN B 362     -36.882  10.085 -46.050  0.50 22.02           N
ATOM   2789  CA  GLN B 362     -35.499  10.120 -45.583  0.50 20.63           C
ATOM   2790  CB  GLN B 362     -35.457  10.220 -44.068  0.50 21.74           C
ATOM   2791  CG  GLN B 362     -35.912  11.574 -43.555  0.50 26.12           C
ATOM   2792  CD  GLN B 362     -35.048  12.078 -42.419  0.50 27.55           C
ATOM   2793  OE1 GLN B 362     -35.342  11.831 -41.250  0.50 29.47           O
ATOM   2794  NE2 GLN B 362     -33.957  12.775 -42.761  0.50 30.25           N
ATOM   2795  C   GLN B 362     -34.832   8.840 -45.996  0.50 18.94           C
ATOM   2796  O   GLN B 362     -35.502   7.817 -46.136  0.50 17.77           O
ATOM   2797  N   VAL B 363     -33.515   8.873 -46.187  0.50 17.29           N
ATOM   2798  CA  VAL B 363     -32.824   7.660 -46.608  0.50 16.85           C
ATOM   2799  CB  VAL B 363     -32.393   7.685 -48.104  0.50 17.53           C
ATOM   2800  CG1 VAL B 363     -33.626   7.764 -49.008  0.50 17.83           C
ATOM   2801  CG2 VAL B 363     -31.441   8.835 -48.398  0.50 17.73           C
ATOM   2802  C   VAL B 363     -31.645   7.400 -45.679  0.50 16.81           C
```

Figure 27 (Continued)

```
ATOM   2803  O    VAL B 363     -31.300   8.250 -44.853  0.50 16.03           O
ATOM   2804  N    SER B 364     -31.081   6.197 -45.802  0.50 16.27           N
ATOM   2805  CA   SER B 364     -29.968   5.725 -44.984  0.50 16.57           C
ATOM   2806  CB   SER B 364     -30.400   4.454 -44.216  0.50 16.37           C
ATOM   2807  OG   SER B 364     -31.635   4.667 -43.544  0.50 17.10           O
ATOM   2808  C    SER B 364     -28.724   5.435 -45.840  0.50 15.78           C
ATOM   2809  O    SER B 364     -28.773   4.722 -46.861  0.50 16.96           O
ATOM   2810  N    LEU B 365     -27.592   6.001 -45.440  0.50 16.57           N
ATOM   2811  CA   LEU B 365     -26.306   5.628 -46.011  0.50 15.09           C
ATOM   2812  CB   LEU B 365     -25.502   6.874 -46.416  0.50 16.80           C
ATOM   2813  CG   LEU B 365     -26.328   7.973 -47.087  0.50 17.97           C
ATOM   2814  CD1  LEU B 365     -25.367   9.008 -47.676  0.50 18.05           C
ATOM   2815  CD2  LEU B 365     -27.276   7.414 -48.132  0.50 18.54           C
ATOM   2816  C    LEU B 365     -25.567   4.914 -44.886  0.50 14.76           C
ATOM   2817  O    LEU B 365     -25.594   5.377 -43.760  0.50 14.36           O
ATOM   2818  N    LEU B 366     -24.935   3.787 -45.173  0.50 15.25           N
ATOM   2819  CA   LEU B 366     -24.247   3.041 -44.100  0.50 15.84           C
ATOM   2820  CB   LEU B 366     -24.642   1.569 -44.119  0.50 15.43           C
ATOM   2821  CG   LEU B 366     -26.126   1.304 -43.926  0.50 15.20           C
ATOM   2822  CD1  LEU B 366     -26.483  -0.158 -44.161  0.50 16.10           C
ATOM   2823  CD2  LEU B 366     -26.530   1.777 -42.539  0.50 15.70           C
ATOM   2824  C    LEU B 366     -22.735   3.141 -44.196  0.50 15.19           C
ATOM   2825  O    LEU B 366     -22.161   3.201 -45.287  0.50 16.29           O
ATOM   2826  N    CYS B 367     -22.092   3.096 -43.039  0.50 15.48           N
ATOM   2827  CA   CYS B 367     -20.643   3.040 -42.971  0.50 14.99           C
ATOM   2828  CB   CYS B 367     -20.109   4.252 -42.240  0.50 16.28           C
ATOM   2829  SG   CYS B 367     -18.301   4.385 -42.314  0.50 16.57           S
ATOM   2830  C    CYS B 367     -20.300   1.799 -42.175  0.50 14.89           C
ATOM   2831  O    CYS B 367     -20.647   1.707 -41.012  0.50 14.82           O
ATOM   2832  N    LEU B 368     -19.663   0.839 -42.831  0.50 14.08           N
ATOM   2833  CA   LEU B 368     -19.274  -0.411 -42.168  0.50 14.39           C
ATOM   2834  CB   LEU B 368     -19.424  -1.581 -43.138  0.50 13.75           C
ATOM   2835  CG   LEU B 368     -19.035  -2.955 -42.561  0.50 13.57           C
ATOM   2836  CD1  LEU B 368     -19.690  -3.279 -41.227  0.50 13.03           C
ATOM   2837  CD2  LEU B 368     -19.352  -4.039 -43.582  0.50 13.90           C
ATOM   2838  C    LEU B 368     -17.821  -0.319 -41.793  0.50 13.64           C
ATOM   2839  O    LEU B 368     -16.974  -0.097 -42.655  0.50 15.26           O
ATOM   2840  N    VAL B 369     -17.526  -0.507 -40.513  0.50 13.93           N
ATOM   2841  CA   VAL B 369     -16.155  -0.532 -40.057  0.50 13.62           C
ATOM   2842  CB   VAL B 369     -15.850   0.588 -39.054  0.50 13.10           C
ATOM   2843  CG1  VAL B 369     -14.350   0.594 -38.732  0.50 13.86           C
ATOM   2844  CG2  VAL B 369     -16.281   1.949 -39.626  0.50 14.26           C
ATOM   2845  C    VAL B 369     -15.962  -1.880 -39.381  0.50 13.83           C
ATOM   2846  O    VAL B 369     -16.648  -2.192 -38.404  0.50 14.01           O
ATOM   2847  N    LYS B 370     -15.068  -2.677 -39.919  0.50 14.64           N
ATOM   2848  CA   LYS B 370     -14.869  -4.013 -39.373  0.50 14.25           C
ATOM   2849  CB   LYS B 370     -15.548  -5.089 -40.256  0.50 16.14           C
ATOM   2850  CG   LYS B 370     -14.902  -5.271 -41.641  0.50 14.98           C
ATOM   2851  CD   LYS B 370     -15.301  -6.555 -42.364  0.50 18.91           C
ATOM   2852  CE   LYS B 370     -14.216  -7.625 -42.291  0.50 19.37           C
ATOM   2853  NZ   LYS B 370     -14.693  -9.011 -42.604  0.50 18.59           N
ATOM   2854  C    LYS B 370     -13.376  -4.326 -39.209  0.50 13.78           C
ATOM   2855  O    LYS B 370     -12.493  -3.526 -39.558  0.50 12.43           O
ATOM   2856  N    GLY B 371     -13.126  -5.490 -38.628  0.50 12.59           N
ATOM   2857  CA   GLY B 371     -11.787  -5.997 -38.388  0.50 13.17           C
ATOM   2858  C    GLY B 371     -10.885  -5.170 -37.484  0.50 13.08           C
ATOM   2859  O    GLY B 371      -9.658  -5.316 -37.539  0.50 13.56           O
ATOM   2860  N    PHE B 372     -11.452  -4.300 -36.648  0.50 13.21           N
ATOM   2861  CA   PHE B 372     -10.596  -3.502 -35.757  0.50 13.40           C
ATOM   2862  CB   PHE B 372     -11.038  -2.008 -35.728  0.50 13.39           C
ATOM   2863  CG   PHE B 372     -12.450  -1.765 -35.211  0.50 12.79           C
ATOM   2864  CD1  PHE B 372     -13.550  -1.820 -36.071  0.50 12.40           C
ATOM   2865  CE1  PHE B 372     -14.837  -1.540 -35.614  0.50 11.97           C
ATOM   2866  CZ   PHE B 372     -15.045  -1.194 -34.283  0.50 12.61           C
```

Figure 27 (Continued)

```
ATOM   2867  CE2 PHE B 372     -13.969  -1.106 -33.424  0.50 12.78           C
ATOM   2868  CD2 PHE B 372     -12.676  -1.386 -33.880  0.50 13.09           C
ATOM   2869  C   PHE B 372     -10.375  -4.048 -34.350  0.50 13.76           C
ATOM   2870  O   PHE B 372     -11.202  -4.781 -33.798  0.50 13.62           O
ATOM   2871  N   TYR B 373      -9.268  -3.618 -33.758  0.50 13.56           N
ATOM   2872  CA  TYR B 373      -8.928  -4.012 -32.401  0.50 15.35           C
ATOM   2873  CB  TYR B 373      -8.275  -5.387 -32.345  0.50 15.56           C
ATOM   2874  CG  TYR B 373      -8.536  -5.998 -30.998  0.50 17.40           C
ATOM   2875  CD1 TYR B 373      -7.673  -5.788 -29.935  0.50 17.95           C
ATOM   2876  CE1 TYR B 373      -7.959  -6.327 -28.684  0.50 21.29           C
ATOM   2877  CZ  TYR B 373      -9.127  -7.051 -28.505  0.50 20.89           C
ATOM   2878  OH  TYR B 373      -9.442  -7.629 -27.282  0.50 26.52           O
ATOM   2879  CE2 TYR B 373      -9.994  -7.251 -29.544  0.50 20.67           C
ATOM   2880  CD2 TYR B 373      -9.704  -6.719 -30.778  0.50 17.14           C
ATOM   2881  C   TYR B 373      -8.019  -2.938 -31.873  0.50 14.66           C
ATOM   2882  O   TYR B 373      -7.102  -2.542 -32.581  0.50 14.35           O
ATOM   2883  N   PRO B 374      -8.017  -2.821 -30.553  0.50 15.35           N
ATOM   2884  CA  PRO B 374      -9.172  -2.721 -29.669  0.50 14.71           C
ATOM   2885  CB  PRO B 374      -8.577  -2.270 -28.325  0.50 15.36           C
ATOM   2886  CG  PRO B 374      -7.082  -2.291 -28.529  0.50 15.46           C
ATOM   2887  CD  PRO B 374      -6.885  -2.072 -29.993  0.50 16.59           C
ATOM   2888  C   PRO B 374     -10.422  -1.948 -30.099  0.50 14.70           C
ATOM   2889  O   PRO B 374     -10.459  -1.389 -31.191  0.50 14.76           O
ATOM   2890  N   SER B 375     -11.454  -1.992 -29.269  0.50 14.34           N
ATOM   2891  CA  SER B 375     -12.759  -1.518 -29.709  0.50 14.60           C
ATOM   2892  CB  SER B 375     -13.883  -2.141 -28.889  0.50 15.43           C
ATOM   2893  OG  SER B 375     -13.829  -1.685 -27.543  0.50 16.07           O
ATOM   2894  C   SER B 375     -12.867   0.006 -29.665  0.50 14.07           C
ATOM   2895  O   SER B 375     -13.812   0.577 -30.217  0.50 14.15           O
ATOM   2896  N   ASP B 376     -11.909   0.663 -29.026  0.50 14.71           N
ATOM   2897  CA  ASP B 376     -11.926   2.120 -28.935  0.50 15.11           C
ATOM   2898  CB  ASP B 376     -10.710   2.617 -28.152  0.50 16.26           C
ATOM   2899  CG  ASP B 376     -10.770   2.247 -26.682  0.50 17.63           C
ATOM   2900  OD1 ASP B 376     -11.877   1.924 -26.165  0.50 20.09           O
ATOM   2901  OD2 ASP B 376      -9.711   2.393 -26.035  0.50 19.59           O
ATOM   2902  C   ASP B 376     -11.876   2.732 -30.331  0.50 14.82           C
ATOM   2903  O   ASP B 376     -10.985   2.410 -31.115  0.50 15.37           O
ATOM   2904  N   ILE B 377     -12.813   3.616 -30.644  0.50 13.79           N
ATOM   2905  CA  ILE B 377     -12.933   4.094 -32.021  0.50 13.04           C
ATOM   2906  CB  ILE B 377     -13.579   3.009 -32.939  0.50 12.24           C
ATOM   2907  CG1 ILE B 377     -13.428   3.377 -34.430  0.50 12.35           C
ATOM   2908  CD1 ILE B 377     -13.763   2.248 -35.397  0.50 11.61           C
ATOM   2909  CG2 ILE B 377     -15.043   2.796 -32.602  0.50 13.36           C
ATOM   2910  C   ILE B 377     -13.826   5.318 -31.977  0.50 13.85           C
ATOM   2911  O   ILE B 377     -14.642   5.448 -31.052  0.50 14.22           O
ATOM   2912  N   ALA B 378     -13.668   6.201 -32.962  0.50 13.07           N
ATOM   2913  CA  ALA B 378     -14.574   7.347 -33.115  0.50 12.71           C
ATOM   2914  CB  ALA B 378     -13.852   8.624 -32.745  0.50 13.83           C
ATOM   2915  C   ALA B 378     -15.012   7.382 -34.580  0.50 12.89           C
ATOM   2916  O   ALA B 378     -14.175   7.285 -35.470  0.50 13.79           O
ATOM   2917  N   VAL B 379     -16.312   7.498 -34.821  0.50 13.84           N
ATOM   2918  CA  VAL B 379     -16.853   7.576 -36.175  0.50 13.12           C
ATOM   2919  CB  VAL B 379     -17.668   6.307 -36.543  0.50 13.51           C
ATOM   2920  CG1 VAL B 379     -18.190   6.406 -37.978  0.50 13.56           C
ATOM   2921  CG2 VAL B 379     -16.807   5.064 -36.368  0.50 12.46           C
ATOM   2922  C   VAL B 379     -17.755   8.813 -36.250  0.50 14.13           C
ATOM   2923  O   VAL B 379     -18.469   9.149 -35.280  0.50 13.99           O
ATOM   2924  N   GLU B 380     -17.665   9.509 -37.380  0.50 14.38           N
ATOM   2925  CA  GLU B 380     -18.348  10.802 -37.583  0.50 14.10           C
ATOM   2926  CB  GLU B 380     -17.399  11.972 -37.258  0.50 14.43           C
ATOM   2927  CG  GLU B 380     -17.073  12.081 -35.769  0.50 15.63           C
ATOM   2928  CD  GLU B 380     -16.085  13.181 -35.448  0.50 16.50           C
ATOM   2929  OE1 GLU B 380     -15.750  13.984 -36.358  0.50 16.77           O
ATOM   2930  OE2 GLU B 380     -15.646  13.231 -34.282  0.50 17.57           O
```

Figure 27 (Continued)

```
ATOM   2931  C    GLU B 380     -18.802  10.874 -39.035  0.50 14.01           C
ATOM   2932  O    GLU B 380     -18.262  10.182 -39.905  0.50 14.77           O
ATOM   2933  N    TRP B 381     -19.797  11.717 -39.317  0.50 13.80           N
ATOM   2934  CA   TRP B 381     -20.149  12.003 -40.713  0.50 13.94           C
ATOM   2935  CB   TRP B 381     -21.535  11.492 -41.076  0.50 14.51           C
ATOM   2936  CG   TRP B 381     -21.775   9.971 -41.082  0.50 14.24           C
ATOM   2937  CD1  TRP B 381     -22.042   9.174 -39.991  0.50 15.32           C
ATOM   2938  NE1  TRP B 381     -22.296   7.883 -40.407  0.50 15.18           N
ATOM   2939  CE2  TRP B 381     -22.191   7.823 -41.771  0.50 14.24           C
ATOM   2940  CD2  TRP B 381     -21.901   9.132 -42.232  0.50 14.72           C
ATOM   2941  CE3  TRP B 381     -21.740   9.342 -43.615  0.50 14.43           C
ATOM   2942  CZ3  TRP B 381     -21.914   8.289 -44.477  0.50 16.23           C
ATOM   2943  CH2  TRP B 381     -22.219   6.984 -43.984  0.50 15.24           C
ATOM   2944  CZ2  TRP B 381     -22.361   6.750 -42.643  0.50 15.24           C
ATOM   2945  C    TRP B 381     -20.221  13.512 -40.921  0.50 14.79           C
ATOM   2946  O    TRP B 381     -20.693  14.248 -40.038  0.50 15.15           O
ATOM   2947  N    GLU B 382     -19.827  13.935 -42.118  0.50 15.78           N
ATOM   2948  CA   GLU B 382     -19.924  15.333 -42.533  0.50 16.82           C
ATOM   2949  CB   GLU B 382     -18.568  16.030 -42.352  0.50 17.64           C
ATOM   2950  CG   GLU B 382     -17.406  15.281 -42.990  0.50 19.45           C
ATOM   2951  CD   GLU B 382     -16.631  14.406 -42.017  0.50 21.06           C
ATOM   2952  OE1  GLU B 382     -17.037  14.282 -40.840  0.50 22.43           O
ATOM   2953  OE2  GLU B 382     -15.583  13.863 -42.424  0.50 22.33           O
ATOM   2954  C    GLU B 382     -20.331  15.397 -43.995  0.50 16.44           C
ATOM   2955  O    GLU B 382     -20.343  14.384 -44.704  0.50 15.61           O
ATOM   2956  N    SER B 383     -20.670  16.608 -44.440  0.50 16.12           N
ATOM   2957  CA   SER B 383     -20.883  16.880 -45.859  0.50 17.36           C
ATOM   2958  CB   SER B 383     -22.275  16.425 -46.321  0.50 18.30           C
ATOM   2959  OG   SER B 383     -22.459  16.672 -47.725  0.50 20.51           O
ATOM   2960  C    SER B 383     -20.768  18.402 -46.026  0.50 17.34           C
ATOM   2961  O    SER B 383     -21.252  19.162 -45.178  0.50 18.09           O
ATOM   2962  N    ASN B 384     -20.100  18.817 -47.097  0.50 19.30           N
ATOM   2963  CA   ASN B 384     -20.048  20.232 -47.487  0.50 20.77           C
ATOM   2964  CB   ASN B 384     -21.454  20.754 -47.750  0.50 21.52           C
ATOM   2965  CG   ASN B 384     -22.030  20.160 -48.999  0.50 20.89           C
ATOM   2966  OD1  ASN B 384     -21.272  19.877 -49.926  0.50 22.23           O
ATOM   2967  ND2  ASN B 384     -23.350  19.924 -49.035  0.50 22.05           N
ATOM   2968  C    ASN B 384     -19.288  21.077 -46.486  0.50 22.88           C
ATOM   2969  O    ASN B 384     -19.488  22.290 -46.376  0.50 23.51           O
ATOM   2970  N    GLY B 385     -18.412  20.413 -45.741  0.50 23.16           N
ATOM   2971  CA   GLY B 385     -17.630  21.092 -44.713  0.50 25.50           C
ATOM   2972  C    GLY B 385     -18.350  21.318 -43.396  0.50 25.44           C
ATOM   2973  O    GLY B 385     -17.916  22.118 -42.577  0.50 30.26           O
ATOM   2974  N    GLN B 386     -19.475  20.651 -43.198  0.50 25.08           N
ATOM   2975  CA   GLN B 386     -20.177  20.722 -41.934  0.50 25.99           C
ATOM   2976  CB   GLN B 386     -21.587  21.339 -42.106  0.50 27.46           C
ATOM   2977  CG   GLN B 386     -22.391  21.449 -40.804  0.50 30.47           C
ATOM   2978  CD   GLN B 386     -23.283  22.678 -40.718  0.50 31.04           C
ATOM   2979  OE1  GLN B 386     -23.158  23.628 -41.507  0.50 28.70           O
ATOM   2980  NE2  GLN B 386     -24.188  22.673 -39.739  0.50 30.63           N
ATOM   2981  C    GLN B 386     -20.245  19.278 -41.463  0.50 23.16           C
ATOM   2982  O    GLN B 386     -20.311  18.379 -42.285  0.50 20.33           O
ATOM   2983  N    PRO B 387     -20.182  19.050 -40.148  0.50 22.25           N
ATOM   2984  CA   PRO B 387     -20.547  17.707 -39.719  0.50 21.51           C
ATOM   2985  CB   PRO B 387     -20.269  17.734 -38.215  0.50 22.36           C
ATOM   2986  CG   PRO B 387     -19.222  18.807 -38.047  0.50 22.30           C
ATOM   2987  CD   PRO B 387     -19.596  19.853 -39.060  0.50 22.31           C
ATOM   2988  C    PRO B 387     -22.029  17.477 -39.985  0.50 21.58           C
ATOM   2989  O    PRO B 387     -22.761  18.450 -40.180  0.50 22.31           O
ATOM   2990  N    GLU B 388     -22.458  16.207 -40.014  0.50 21.20           N
ATOM   2991  CA   GLU B 388     -23.883  15.810 -40.059  0.50 24.45           C
ATOM   2992  CB   GLU B 388     -24.056  14.572 -40.943  0.50 25.52           C
ATOM   2993  CG   GLU B 388     -24.245  14.895 -42.404  0.50 25.53           C
ATOM   2994  CD   GLU B 388     -25.461  15.773 -42.623  0.50 25.89           C
```

Figure 27 (Continued)

```
ATOM   2995  OE1 GLU B 388     -26.585  15.327 -42.305  0.50 26.74           O
ATOM   2996  OE2 GLU B 388     -25.278  16.915 -43.082  0.50 26.30           O
ATOM   2997  C   GLU B 388     -24.553  15.536 -38.700  0.50 24.77           C
ATOM   2998  O   GLU B 388     -23.980  14.909 -37.826  0.50 31.70           O
ATOM   2999  N   ASN B 389     -25.800  15.974 -38.548  0.50 27.78           N
ATOM   3000  CA  ASN B 389     -26.514  15.853 -37.272  0.50 27.46           C
ATOM   3001  CB  ASN B 389     -27.432  17.072 -37.070  0.50 27.63           C
ATOM   3002  CG  ASN B 389     -27.953  17.180 -35.656  0.50 25.87           C
ATOM   3003  OD1 ASN B 389     -27.275  16.798 -34.697  0.50 29.57           O
ATOM   3004  ND2 ASN B 389     -29.168  17.705 -35.510  0.50 28.60           N
ATOM   3005  C   ASN B 389     -27.342  14.581 -37.130  0.50 28.76           C
ATOM   3006  O   ASN B 389     -27.870  14.272 -36.049  0.50 27.86           O
ATOM   3007  N   ASN B 390     -27.489  13.847 -38.219  0.50 25.74           N
ATOM   3008  CA  ASN B 390     -28.531  12.857 -38.213  0.50 23.89           C
ATOM   3009  CB  ASN B 390     -29.603  13.161 -39.243  0.50 26.89           C
ATOM   3010  CG  ASN B 390     -30.965  12.841 -38.725  0.50 27.73           C
ATOM   3011  OD1 ASN B 390     -31.181  12.888 -37.512  0.50 33.60           O
ATOM   3012  ND2 ASN B 390     -31.894  12.512 -39.615  0.50 30.21           N
ATOM   3013  C   ASN B 390     -28.055  11.437 -38.354  0.50 20.54           C
ATOM   3014  O   ASN B 390     -28.574  10.697 -39.168  0.50 20.74           O
ATOM   3015  N   TYR B 391     -27.095  11.056 -37.530  0.50 19.36           N
ATOM   3016  CA  TYR B 391     -26.616   9.663 -37.544  0.50 17.22           C
ATOM   3017  CB  TYR B 391     -25.201   9.565 -38.165  0.50 16.87           C
ATOM   3018  CG  TYR B 391     -24.065  10.321 -37.489  0.50 17.18           C
ATOM   3019  CD1 TYR B 391     -23.295   9.728 -36.480  0.50 16.53           C
ATOM   3020  CE1 TYR B 391     -22.229  10.402 -35.891  0.50 17.33           C
ATOM   3021  CZ  TYR B 391     -21.908  11.672 -36.333  0.50 15.93           C
ATOM   3022  OH  TYR B 391     -20.830  12.359 -35.792  0.50 17.03           O
ATOM   3023  CE2 TYR B 391     -22.625  12.265 -37.356  0.50 16.25           C
ATOM   3024  CD2 TYR B 391     -23.702  11.600 -37.927  0.50 17.08           C
ATOM   3025  C   TYR B 391     -26.671   8.968 -36.195  0.50 16.49           C
ATOM   3026  O   TYR B 391     -26.810   9.608 -35.153  0.50 17.40           O
ATOM   3027  N   MET B 392     -26.553   7.637 -36.220  0.50 15.52           N
ATOM   3028  CA  MET B 392     -26.498   6.859 -34.997  0.50 14.88           C
ATOM   3029  CB  MET B 392     -27.853   6.240 -34.653  0.50 16.22           C
ATOM   3030  CG  MET B 392     -28.376   5.327 -35.745  0.50 15.58           C
ATOM   3031  SD  MET B 392     -29.966   4.536 -35.361  0.50 18.52           S
ATOM   3032  CE  MET B 392     -29.541   3.682 -33.861  0.50 17.01           C
ATOM   3033  C   MET B 392     -25.524   5.750 -35.295  0.50 14.98           C
ATOM   3034  O   MET B 392     -25.428   5.295 -36.434  0.50 16.00           O
ATOM   3035  N   THR B 393     -24.791   5.341 -34.281  0.50 16.05           N
ATOM   3036  CA  THR B 393     -23.735   4.365 -34.478  0.50 15.45           C
ATOM   3037  CB  THR B 393     -22.370   5.050 -34.347  0.50 15.73           C
ATOM   3038  OG1 THR B 393     -22.248   5.990 -35.417  0.50 16.29           O
ATOM   3039  CG2 THR B 393     -21.245   4.035 -34.445  0.50 15.80           C
ATOM   3040  C   THR B 393     -23.854   3.319 -33.409  0.50 16.18           C
ATOM   3041  O   THR B 393     -23.833   3.636 -32.217  0.50 16.90           O
ATOM   3042  N   TRP B 394     -23.978   2.064 -33.832  0.50 14.36           N
ATOM   3043  CA  TRP B 394     -24.149   0.947 -32.892  0.50 14.59           C
ATOM   3044  CB  TRP B 394     -24.615  -0.294 -33.641  0.50 13.75           C
ATOM   3045  CG  TRP B 394     -26.024  -0.182 -34.131  0.50 13.80           C
ATOM   3046  CD1 TRP B 394     -27.152  -0.605 -33.472  0.50 14.13           C
ATOM   3047  NE1 TRP B 394     -28.260  -0.332 -34.224  0.50 14.79           N
ATOM   3048  CE2 TRP B 394     -27.877   0.320 -35.370  0.50 14.10           C
ATOM   3049  CD2 TRP B 394     -26.473   0.421 -35.348  0.50 14.18           C
ATOM   3050  CE3 TRP B 394     -25.829   1.036 -36.422  0.50 13.69           C
ATOM   3051  CZ3 TRP B 394     -26.592   1.509 -37.468  0.50 14.80           C
ATOM   3052  CH2 TRP B 394     -27.987   1.396 -37.460  0.50 14.12           C
ATOM   3053  CZ2 TRP B 394     -28.642   0.797 -36.434  0.50 14.54           C
ATOM   3054  C   TRP B 394     -22.821   0.635 -32.236  0.50 14.12           C
ATOM   3055  O   TRP B 394     -21.773   0.875 -32.811  0.50 15.68           O
ATOM   3056  N   PRO B 395     -22.869   0.023 -31.055  0.50 15.26           N
ATOM   3057  CA  PRO B 395     -21.668  -0.351 -30.322  0.50 15.29           C
ATOM   3058  CB  PRO B 395     -22.224  -1.045 -29.065  0.50 16.32           C
```

Figure 27 (Continued)

```
ATOM   3059  CG   PRO B 395     -23.658   -0.646  -28.982  0.50 17.09           C
ATOM   3060  CD   PRO B 395     -24.101   -0.474  -30.407  0.50 15.05           C
ATOM   3061  C    PRO B 395     -20.789   -1.307  -31.137  0.50 15.22           C
ATOM   3062  O    PRO B 395     -21.275   -1.990  -32.067  0.50 14.18           O
ATOM   3063  N    PRO B 396     -19.494   -1.363  -30.820  0.50 14.49           N
ATOM   3064  CA   PRO B 396     -18.689   -2.326  -31.547  0.50 13.78           C
ATOM   3065  CB   PRO B 396     -17.265   -2.109  -30.964  0.50 14.10           C
ATOM   3066  CG   PRO B 396     -17.286   -0.689  -30.496  0.50 15.08           C
ATOM   3067  CD   PRO B 396     -18.676   -0.449  -29.993  0.50 14.58           C
ATOM   3068  C    PRO B 396     -19.195   -3.735  -31.238  0.50 13.91           C
ATOM   3069  O    PRO B 396     -19.537   -4.013  -30.092  0.50 14.99           O
ATOM   3070  N    VAL B 397     -19.231   -4.601  -32.252  0.50 13.04           N
ATOM   3071  CA   VAL B 397     -19.644   -5.994  -32.069  0.50 14.38           C
ATOM   3072  CB   VAL B 397     -20.788   -6.369  -33.016  0.50 15.44           C
ATOM   3073  CG1  VAL B 397     -21.271   -7.771  -32.665  0.50 15.81           C
ATOM   3074  CG2  VAL B 397     -21.924   -5.339  -32.898  0.50 15.40           C
ATOM   3075  C    VAL B 397     -18.474   -6.938  -32.285  0.50 13.99           C
ATOM   3076  O    VAL B 397     -17.716   -6.809  -33.237  0.50 13.37           O
ATOM   3077  N    LEU B 398     -18.297   -7.893  -31.378  0.50 16.64           N
ATOM   3078  CA   LEU B 398     -17.200   -8.835  -31.527  0.50 17.54           C
ATOM   3079  CB   LEU B 398     -17.002   -9.679  -30.250  0.50 18.78           C
ATOM   3080  CG   LEU B 398     -15.593   -9.768  -29.642  0.50 21.33           C
ATOM   3081  CD1  LEU B 398     -14.458   -9.465  -30.605  0.50 21.69           C
ATOM   3082  CD2  LEU B 398     -15.338  -11.075  -28.885  0.50 20.78           C
ATOM   3083  C    LEU B 398     -17.571   -9.753  -32.664  0.50 17.74           C
ATOM   3084  O    LEU B 398     -18.661  -10.381  -32.656  0.50 18.54           O
ATOM   3085  N    ASP B 399     -16.685   -9.811  -33.651  0.50 17.94           N
ATOM   3086  CA   ASP B 399     -16.864  -10.663  -34.820  0.50 19.16           C
ATOM   3087  CB   ASP B 399     -16.232  -10.008  -36.052  0.50 18.97           C
ATOM   3088  CG   ASP B 399     -17.079  -10.158  -37.313  0.50 19.04           C
ATOM   3089  OD1  ASP B 399     -17.834  -11.142  -37.417  0.50 20.17           O
ATOM   3090  OD2  ASP B 399     -16.965   -9.308  -38.226  0.50 17.49           O
ATOM   3091  C    ASP B 399     -16.200  -12.010  -34.507  0.50 20.94           C
ATOM   3092  O    ASP B 399     -15.435  -12.145  -33.531  0.50 18.10           O
ATOM   3093  N    SER B 400     -16.521  -13.002  -35.322  0.50 22.05           N
ATOM   3094  CA   SER B 400     -16.079  -14.380  -35.089  0.50 23.63           C
ATOM   3095  CB   SER B 400     -16.621  -15.274  -36.205  0.50 24.13           C
ATOM   3096  OG   SER B 400     -16.077  -14.894  -37.460  0.50 26.00           O
ATOM   3097  C    SER B 400     -14.569  -14.531  -34.984  0.50 23.53           C
ATOM   3098  O    SER B 400     -14.081  -15.442  -34.320  0.50 23.56           O
ATOM   3099  N    ASP B 401     -13.829  -13.627  -35.626  0.50 23.20           N
ATOM   3100  CA   ASP B 401     -12.383  -13.771  -35.781  0.50 22.39           C
ATOM   3101  CB   ASP B 401     -11.956  -13.340  -37.187  0.50 21.66           C
ATOM   3102  CG   ASP B 401     -11.827  -11.827  -37.320  0.50 20.86           C
ATOM   3103  OD1  ASP B 401     -12.547  -11.111  -36.586  0.50 20.56           O
ATOM   3104  OD2  ASP B 401     -11.012  -11.366  -38.145  0.50 21.76           O
ATOM   3105  C    ASP B 401     -11.630  -12.984  -34.714  0.50 22.41           C
ATOM   3106  O    ASP B 401     -10.412  -12.768  -34.824  0.50 25.60           O
ATOM   3107  N    GLY B 402     -12.361  -12.592  -33.676  0.50 20.43           N
ATOM   3108  CA   GLY B 402     -11.814  -11.905  -32.511  0.50 20.19           C
ATOM   3109  C    GLY B 402     -11.767  -10.385  -32.621  0.50 18.24           C
ATOM   3110  O    GLY B 402     -11.586   -9.684  -31.621  0.50 18.09           O
ATOM   3111  N    SER B 403     -11.901   -9.882  -33.842  0.50 18.17           N
ATOM   3112  CA   SER B 403     -11.905   -8.430  -34.072  0.50 16.58           C
ATOM   3113  CB   SER B 403     -11.536   -8.113  -35.531  0.50 16.51           C
ATOM   3114  OG   SER B 403     -12.580   -8.516  -36.414  0.50 17.43           O
ATOM   3115  C    SER B 403     -13.288   -7.843  -33.785  0.50 15.96           C
ATOM   3116  O    SER B 403     -14.266   -8.555  -33.532  0.50 14.59           O
ATOM   3117  N    PHE B 404     -13.376   -6.527  -33.884  0.50 14.41           N
ATOM   3118  CA   PHE B 404     -14.671   -5.851  -33.805  0.50 14.20           C
ATOM   3119  CB   PHE B 404     -14.593   -4.664  -32.840  0.50 14.65           C
ATOM   3120  CG   PHE B 404     -14.426   -5.076  -31.424  0.50 15.17           C
ATOM   3121  CD1  PHE B 404     -13.150   -5.223  -30.882  0.50 15.75           C
ATOM   3122  CE1  PHE B 404     -12.990   -5.651  -29.572  0.50 16.05           C
```

Figure 27 (Continued)

```
ATOM   3123  CZ   PHE B 404     -14.109   -5.920  -28.797  0.50 15.32           C
ATOM   3124  CE2  PHE B 404     -15.381   -5.768  -29.328  0.50 15.02           C
ATOM   3125  CD2  PHE B 404     -15.531   -5.339  -30.640  0.50 15.78           C
ATOM   3126  C    PHE B 404     -15.095   -5.329  -35.158  0.50 13.84           C
ATOM   3127  O    PHE B 404     -14.258   -5.002  -36.010  0.50 13.71           O
ATOM   3128  N    PHE B 405     -16.409   -5.252  -35.346  0.50 14.28           N
ATOM   3129  CA   PHE B 405     -16.962   -4.429  -36.406  0.50 15.47           C
ATOM   3130  CB   PHE B 405     -17.522   -5.280  -37.548  0.50 15.55           C
ATOM   3131  CG   PHE B 405     -18.865   -5.895  -37.238  0.50 15.47           C
ATOM   3132  CD1  PHE B 405     -20.037   -5.270  -37.629  0.50 15.72           C
ATOM   3133  CE1  PHE B 405     -21.266   -5.820  -37.336  0.50 16.79           C
ATOM   3134  CZ   PHE B 405     -21.351   -7.025  -36.674  0.50 16.59           C
ATOM   3135  CE2  PHE B 405     -20.185   -7.670  -36.280  0.50 16.13           C
ATOM   3136  CD2  PHE B 405     -18.947   -7.095  -36.567  0.50 16.38           C
ATOM   3137  C    PHE B 405     -18.035   -3.523  -35.828  0.50 15.04           C
ATOM   3138  O    PHE B 405     -18.470   -3.685  -34.696  0.50 15.77           O
ATOM   3139  N    LEU B 406     -18.459   -2.546  -36.617  0.50 14.47           N
ATOM   3140  CA   LEU B 406     -19.596   -1.742  -36.224  0.50 14.87           C
ATOM   3141  CB   LEU B 406     -19.198   -0.686  -35.191  0.50 17.20           C
ATOM   3142  CG   LEU B 406     -18.264    0.444  -35.613  0.50 16.01           C
ATOM   3143  CD1  LEU B 406     -18.917    1.416  -36.609  0.50 16.49           C
ATOM   3144  CD2  LEU B 406     -17.805    1.235  -34.379  0.50 15.72           C
ATOM   3145  C    LEU B 406     -20.185   -1.118  -37.464  0.50 13.75           C
ATOM   3146  O    LEU B 406     -19.562   -1.130  -38.533  0.50 14.39           O
ATOM   3147  N    TYR B 407     -21.389   -0.594  -37.338  0.50 13.34           N
ATOM   3148  CA   TYR B 407     -21.983    0.175  -38.430  0.50 12.63           C
ATOM   3149  CB   TYR B 407     -23.251   -0.526  -38.925  0.50 12.79           C
ATOM   3150  CG   TYR B 407     -23.046   -1.678  -39.873  0.50 12.01           C
ATOM   3151  CD1  TYR B 407     -23.055   -1.488  -41.244  0.50 12.37           C
ATOM   3152  CE1  TYR B 407     -22.911   -2.573  -42.127  0.50 12.24           C
ATOM   3153  CZ   TYR B 407     -22.761   -3.864  -41.610  0.50 12.67           C
ATOM   3154  OH   TYR B 407     -22.608   -4.951  -42.436  0.50 13.01           O
ATOM   3155  CE2  TYR B 407     -22.725   -4.061  -40.246  0.50 11.95           C
ATOM   3156  CD2  TYR B 407     -22.883   -2.983  -39.387  0.50 13.00           C
ATOM   3157  C    TYR B 407     -22.376    1.543  -37.865  0.50 12.53           C
ATOM   3158  O    TYR B 407     -22.662    1.679  -36.655  0.50 12.53           O
ATOM   3159  N    SER B 408     -22.431    2.532  -38.752  0.50 13.19           N
ATOM   3160  CA   SER B 408     -23.072    3.807  -38.442  0.50 13.59           C
ATOM   3161  CB   SER B 408     -22.013    4.913  -38.422  0.50 12.83           C
ATOM   3162  OG   SER B 408     -22.507    6.120  -37.848  0.50 13.01           O
ATOM   3163  C    SER B 408     -24.048    4.093  -39.568  0.50 13.31           C
ATOM   3164  O    SER B 408     -23.752    3.811  -40.736  0.50 14.44           O
ATOM   3165  N    LYS B 409     -25.195    4.665  -39.218  0.50 13.99           N
ATOM   3166  CA   LYS B 409     -26.241    4.977  -40.190  0.50 14.78           C
ATOM   3167  CB   LYS B 409     -27.537    4.232  -39.825  0.50 14.97           C
ATOM   3168  CG   LYS B 409     -28.699    4.517  -40.790  0.50 15.07           C
ATOM   3169  CD   LYS B 409     -29.981    3.752  -40.416  0.50 15.49           C
ATOM   3170  CE   LYS B 409     -30.413    3.941  -38.956  0.50 15.31           C
ATOM   3171  NZ   LYS B 409     -31.152    5.239  -38.695  0.50 14.26           N
ATOM   3172  C    LYS B 409     -26.505    6.486  -40.230  0.50 15.09           C
ATOM   3173  O    LYS B 409     -26.882    7.082  -39.224  0.50 15.99           O
ATOM   3174  N    LEU B 410     -26.270    7.089  -41.390  0.50 15.68           N
ATOM   3175  CA   LEU B 410     -26.567    8.509  -41.603  0.50 16.39           C
ATOM   3176  CB   LEU B 410     -25.423    9.170  -42.393  0.50 16.24           C
ATOM   3177  CG   LEU B 410     -25.835   10.496  -43.056  0.50 16.42           C
ATOM   3178  CD1  LEU B 410     -25.994   11.584  -41.997  0.50 16.50           C
ATOM   3179  CD2  LEU B 410     -24.843   10.905  -44.138  0.50 16.06           C
ATOM   3180  C    LEU B 410     -27.862    8.626  -42.400  0.50 17.56           C
ATOM   3181  O    LEU B 410     -27.957    8.106  -43.502  0.50 18.30           O
ATOM   3182  N    THR B 411     -28.860    9.298  -41.829  0.50 17.78           N
ATOM   3183  CA   THR B 411     -30.117    9.505  -42.537  0.50 17.97           C
ATOM   3184  CB   THR B 411     -31.308    9.456  -41.586  0.50 18.77           C
ATOM   3185  OG1  THR B 411     -31.273    8.217  -40.877  0.50 18.51           O
ATOM   3186  CG2  THR B 411     -32.640    9.570  -42.357  0.50 17.09           C
```

Figure 27 (Continued)

```
ATOM   3187  C   THR B 411     -30.093  10.853 -43.231  0.50 19.31           C
ATOM   3188  O   THR B 411     -29.751  11.864 -42.618  0.50 17.48           O
ATOM   3189  N   VAL B 412     -30.446  10.849 -44.514  0.50 20.39           N
ATOM   3190  CA  VAL B 412     -30.531  12.094 -45.273  0.50 21.22           C
ATOM   3191  CB  VAL B 412     -29.274  12.359 -46.136  0.50 21.06           C
ATOM   3192  CG1 VAL B 412     -28.001  12.207 -45.293  0.50 21.17           C
ATOM   3193  CG2 VAL B 412     -29.249  11.444 -47.347  0.50 20.09           C
ATOM   3194  C   VAL B 412     -31.814  12.165 -46.118  0.50 21.89           C
ATOM   3195  O   VAL B 412     -32.277  11.161 -46.676  0.50 21.37           O
ATOM   3196  N   ASP B 413     -32.411  13.348 -46.167  0.50 25.56           N
ATOM   3197  CA  ASP B 413     -33.556  13.571 -47.037  0.50 25.74           C
ATOM   3198  CB  ASP B 413     -33.961  15.046 -47.032  0.50 30.87           C
ATOM   3199  CG  ASP B 413     -34.919  15.383 -45.907  0.50 32.90           C
ATOM   3200  OD1 ASP B 413     -35.028  14.587 -44.949  0.50 35.07           O
ATOM   3201  OD2 ASP B 413     -35.578  16.447 -45.985  0.50 36.73           O
ATOM   3202  C   ASP B 413     -33.204  13.125 -48.449  0.50 25.27           C
ATOM   3203  O   ASP B 413     -32.130  13.433 -48.958  0.50 22.61           O
ATOM   3204  N   LYS B 414     -34.108  12.392 -49.084  0.50 24.76           N
ATOM   3205  CA  LYS B 414     -33.829  11.893 -50.420  0.50 26.46           C
ATOM   3206  CB  LYS B 414     -35.028  11.142 -51.010  0.50 28.79           C
ATOM   3207  CG  LYS B 414     -34.731  10.597 -52.404  0.50 30.12           C
ATOM   3208  CD  LYS B 414     -35.950   9.996 -53.079  0.50 34.35           C
ATOM   3209  CE  LYS B 414     -37.166  10.891 -52.913  0.50 37.01           C
ATOM   3210  NZ  LYS B 414     -38.445  10.133 -53.020  0.50 40.27           N
ATOM   3211  C   LYS B 414     -33.418  13.022 -51.367  0.50 28.08           C
ATOM   3212  O   LYS B 414     -32.599  12.818 -52.256  0.50 28.27           O
ATOM   3213  N   SER B 415     -33.999  14.206 -51.200  0.50 27.83           N
ATOM   3214  CA  SER B 415     -33.682  15.295 -52.108  0.50 30.26           C
ATOM   3215  CB  SER B 415     -34.468  16.574 -51.773  0.50 31.51           C
ATOM   3216  OG  SER B 415     -34.171  17.051 -50.469  0.50 33.69           O
ATOM   3217  C   SER B 415     -32.177  15.553 -52.093  0.50 29.99           C
ATOM   3218  O   SER B 415     -31.554  15.632 -53.146  0.50 30.88           O
ATOM   3219  N   ARG B 416     -31.594  15.652 -50.897  0.50 29.43           N
ATOM   3220  CA  ARG B 416     -30.157  15.899 -50.785  0.50 26.90           C
ATOM   3221  CB  ARG B 416     -29.711  16.027 -49.320  0.50 25.76           C
ATOM   3222  CG  ARG B 416     -30.535  16.979 -48.457  0.50 26.55           C
ATOM   3223  CD  ARG B 416     -30.173  16.860 -46.976  0.50 25.75           C
ATOM   3224  NE  ARG B 416     -28.848  17.417 -46.671  0.50 25.69           N
ATOM   3225  CZ  ARG B 416     -28.153  17.168 -45.560  0.50 24.74           C
ATOM   3226  NH1 ARG B 416     -28.647  16.374 -44.618  0.50 25.87           N
ATOM   3227  NH2 ARG B 416     -26.950  17.722 -45.386  0.50 22.69           N
ATOM   3228  C   ARG B 416     -29.386  14.784 -51.492  0.50 25.77           C
ATOM   3229  O   ARG B 416     -28.464  15.046 -52.265  0.50 23.64           O
ATOM   3230  N   TRP B 417     -29.796  13.555 -51.234  0.50 23.65           N
ATOM   3231  CA  TRP B 417     -29.156  12.463 -51.893  0.50 23.76           C
ATOM   3232  CB  TRP B 417     -29.712  11.138 -51.389  0.50 23.38           C
ATOM   3233  CG  TRP B 417     -29.095   9.970 -52.071  0.50 23.71           C
ATOM   3234  CD1 TRP B 417     -29.673   9.131 -52.990  0.50 24.26           C
ATOM   3235  NE1 TRP B 417     -28.799   8.191 -53.404  0.50 25.97           N
ATOM   3236  CE2 TRP B 417     -27.620   8.341 -52.804  0.50 23.40           C
ATOM   3237  CD2 TRP B 417     -27.737   9.479 -51.919  0.50 24.10           C
ATOM   3238  CE3 TRP B 417     -26.650   9.857 -51.171  0.50 22.45           C
ATOM   3239  CZ3 TRP B 417     -25.488   9.126 -51.292  0.50 21.48           C
ATOM   3240  CH2 TRP B 417     -25.392   8.045 -52.149  0.50 21.72           C
ATOM   3241  CZ2 TRP B 417     -26.458   7.625 -52.913  0.50 24.18           C
ATOM   3242  C   TRP B 417     -29.346  12.572 -53.375  0.50 24.38           C
ATOM   3243  O   TRP B 417     -28.393  12.464 -54.139  0.50 24.14           O
ATOM   3244  N   GLN B 418     -30.567  12.843 -53.810  0.50 26.61           N
ATOM   3245  CA  GLN B 418     -30.812  12.881 -55.243  0.50 27.18           C
ATOM   3246  CB  GLN B 418     -32.261  12.504 -55.633  0.50 27.64           C
ATOM   3247  CG  GLN B 418     -32.329  11.314 -56.625  0.50 31.71           C
ATOM   3248  CD  GLN B 418     -32.613   9.934 -56.010  0.50 34.33           C
ATOM   3249  OE1 GLN B 418     -33.299   9.830 -55.031  0.50 39.59           O
ATOM   3250  NE2 GLN B 418     -32.122   8.881 -56.633  0.50 32.50           N
```

Figure 27 (Continued)

```
ATOM   3251  C    GLN B 418     -30.195  14.123 -55.918  0.50 27.22           C
ATOM   3252  O    GLN B 418     -29.897  14.123 -57.081  0.50 26.25           O
ATOM   3253  N    GLN B 419     -29.961  15.151 -55.124  0.50 27.70           N
ATOM   3254  CA   GLN B 419     -29.274  16.361 -55.563  0.50 27.27           C
ATOM   3255  CB   GLN B 419     -29.561  17.531 -54.632  0.50 28.44           C
ATOM   3256  CG   GLN B 419     -30.320  18.276 -55.010  0.50 31.79           C
ATOM   3257  CD   GLN B 419     -31.512  18.930 -53.850  0.50 34.94           C
ATOM   3258  OE1  GLN B 419     -30.899  19.308 -52.873  0.50 36.62           O
ATOM   3259  NE2  GLN B 419     -32.813  19.067 -53.959  0.50 36.82           N
ATOM   3260  C    GLN B 419     -27.759  16.188 -55.791  0.50 25.82           C
ATOM   3261  O    GLN B 419     -27.117  17.089 -56.272  0.50 25.54           O
ATOM   3262  N    GLY B 420     -27.199  15.041 -55.430  0.50 24.26           N
ATOM   3263  CA   GLY B 420     -25.818  14.736 -55.786  0.50 22.55           C
ATOM   3264  C    GLY B 420     -24.789  15.104 -54.746  0.50 23.03           C
ATOM   3265  O    GLY B 420     -23.611  15.120 -54.938  0.50 23.19           O
ATOM   3266  N    ASN B 421     -25.309  15.433 -53.610  0.50 21.74           N
ATOM   3267  CA   ASN B 421     -24.508  15.839 -52.443  0.50 21.18           C
ATOM   3268  CB   ASN B 421     -25.416  16.302 -51.296  0.50 22.74           C
ATOM   3269  CG   ASN B 421     -25.902  17.742 -51.454  0.50 24.42           C
ATOM   3270  OD1  ASN B 421     -25.108  18.677 -51.486  0.50 23.37           O
ATOM   3271  ND2  ASN B 421     -27.227  17.922 -51.522  0.50 24.09           N
ATOM   3272  C    ASN B 421     -23.641  14.674 -51.953  0.50 20.76           C
ATOM   3273  O    ASN B 421     -24.059  13.508 -51.998  0.50 19.96           O
ATOM   3274  N    VAL B 422     -22.441  15.003 -51.476  0.50 18.69           N
ATOM   3275  CA   VAL B 422     -21.472  13.993 -51.079  0.50 18.37           C
ATOM   3276  CB   VAL B 422     -20.050  14.389 -51.479  0.50 18.61           C
ATOM   3277  CG1  VAL B 422     -19.068  13.265 -51.141  0.50 19.19           C
ATOM   3278  CG2  VAL B 422     -20.022  14.755 -52.958  0.50 18.72           C
ATOM   3279  C    VAL B 422     -21.512  13.867 -49.578  0.50 17.46           C
ATOM   3280  O    VAL B 422     -21.543  14.869 -48.855  0.50 17.27           O
ATOM   3281  N    PHE B 423     -21.455  12.618 -49.125  0.50 16.67           N
ATOM   3282  CA   PHE B 423     -21.519  12.324 -47.707  0.50 16.86           C
ATOM   3283  CB   PHE B 423     -22.847  11.613 -47.413  0.50 17.33           C
ATOM   3284  CG   PHE B 423     -24.039  12.500 -47.686  0.50 17.39           C
ATOM   3285  CD1  PHE B 423     -24.673  12.483 -48.928  0.50 17.82           C
ATOM   3286  CE1  PHE B 423     -25.730  13.342 -49.174  0.50 18.22           C
ATOM   3287  CZ   PHE B 423     -26.145  14.234 -48.206  0.50 18.38           C
ATOM   3288  CE2  PHE B 423     -25.504  14.286 -46.991  0.50 18.59           C
ATOM   3289  CD2  PHE B 423     -24.450  13.421 -46.742  0.50 18.35           C
ATOM   3290  C    PHE B 423     -20.288  11.506 -47.350  0.50 16.12           C
ATOM   3291  O    PHE B 423     -19.858  10.676 -48.139  0.50 16.05           O
ATOM   3292  N    SER B 424     -19.696  11.789 -46.190  0.50 14.80           N
ATOM   3293  CA   SER B 424     -18.400  11.193 -45.844  0.50 14.36           C
ATOM   3294  CB   SER B 424     -17.286  12.250 -45.907  0.50 14.77           C
ATOM   3295  OG   SER B 424     -17.400  12.969 -47.109  0.50 14.98           O
ATOM   3296  C    SER B 424     -18.445  10.633 -44.439  0.50 13.60           C
ATOM   3297  O    SER B 424     -18.941  11.271 -43.510  0.50 14.44           O
ATOM   3298  N    CYS B 425     -17.931   9.419 -44.313  0.50 13.38           N
ATOM   3299  CA   CYS B 425     -17.787   8.749 -43.029  0.50 14.00           C
ATOM   3300  CB   CYS B 425     -18.238   7.296 -43.184  0.50 14.71           C
ATOM   3301  SG   CYS B 425     -18.006   6.338 -41.699  0.50 16.90           S
ATOM   3302  C    CYS B 425     -16.311   8.829 -42.655  0.50 13.78           C
ATOM   3303  O    CYS B 425     -15.444   8.413 -43.432  0.50 15.03           O
ATOM   3304  N    SER B 426     -16.031   9.398 -41.489  0.50 14.25           N
ATOM   3305  CA   SER B 426     -14.659   9.568 -41.000  0.50 13.68           C
ATOM   3306  CB   SER B 426     -14.388  11.017 -40.586  0.50 14.21           C
ATOM   3307  OG   SER B 426     -14.431  11.903 -41.704  0.50 15.24           O
ATOM   3308  C    SER B 426     -14.495   8.663 -39.784  0.50 12.98           C
ATOM   3309  O    SER B 426     -15.264   8.750 -38.829  0.50 13.48           O
ATOM   3310  N    VAL B 427     -13.475   7.821 -39.819  0.50 12.08           N
ATOM   3311  CA   VAL B 427     -13.221   6.841 -38.759  0.50 11.86           C
ATOM   3312  CB   VAL B 427     -13.344   5.414 -39.336  0.50 11.90           C
ATOM   3313  CG1  VAL B 427     -13.104   4.352 -38.275  0.50 12.01           C
ATOM   3314  CG2  VAL B 427     -14.741   5.249 -39.964  0.50 11.70           C
```

Figure 27 (Continued)

```
ATOM   3315  C    VAL B 427     -11.837   7.112 -38.172  0.50 11.41           C
ATOM   3316  O    VAL B 427     -10.860   7.247 -38.911  0.50 12.35           O
ATOM   3317  N    MET B 428     -11.772   7.175 -36.845  0.50 12.44           N
ATOM   3318  CA   MET B 428     -10.509   7.411 -36.145  0.50 12.46           C
ATOM   3319  CB   MET B 428     -10.617   8.735 -35.356  0.50 14.00           C
ATOM   3320  CG   MET B 428     -10.722   9.916 -36.316  0.50 14.59           C
ATOM   3321  SD   MET B 428     -11.448  11.391 -35.531  0.50 17.28           S
ATOM   3322  CE   MET B 428     -13.180  10.952 -35.639  0.50 15.62           C
ATOM   3323  C    MET B 428     -10.231   6.225 -35.254  0.50 11.66           C
ATOM   3324  O    MET B 428     -11.097   5.806 -34.488  0.50 10.20           O
ATOM   3325  N    HIS B 429      -9.032   5.656 -35.394  0.50 11.27           N
ATOM   3326  CA   HIS B 429      -8.649   4.444 -34.672  0.50 12.64           C
ATOM   3327  CB   HIS B 429      -9.258   3.194 -35.363  0.50 12.48           C
ATOM   3328  CG   HIS B 429      -9.063   1.922 -34.588  0.50 12.57           C
ATOM   3329  ND1  HIS B 429      -7.929   1.150 -34.720  0.50 12.66           N
ATOM   3330  CE1  HIS B 429      -7.999   0.119 -33.902  0.50 12.87           C
ATOM   3331  NE2  HIS B 429      -9.152   0.182 -33.251  0.50 13.05           N
ATOM   3332  CD2  HIS B 429      -9.826   1.317 -33.645  0.50 13.00           C
ATOM   3333  C    HIS B 429      -7.131   4.385 -34.681  0.50 12.63           C
ATOM   3334  O    HIS B 429      -6.502   4.786 -35.664  0.50 13.52           O
ATOM   3335  N    GLU B 430      -6.546   3.830 -33.623  0.50 13.39           N
ATOM   3336  CA   GLU B 430      -5.101   3.872 -33.444  0.50 13.58           C
ATOM   3337  CB   GLU B 430      -4.732   3.395 -32.034  0.50 14.86           C
ATOM   3338  CG   GLU B 430      -5.004   1.926 -31.785  0.50 14.70           C
ATOM   3339  CD   GLU B 430      -4.197   1.395 -30.613  0.50 15.39           C
ATOM   3340  OE1  GLU B 430      -4.695   1.412 -29.475  0.50 14.91           O
ATOM   3341  OE2  GLU B 430      -3.076   0.927 -30.839  0.50 15.81           O
ATOM   3342  C    GLU B 430      -4.357   3.059 -34.490  0.50 14.71           C
ATOM   3343  O    GLU B 430      -3.185   3.326 -34.744  0.50 13.65           O
ATOM   3344  N    ALA B 431      -5.034   2.090 -35.114  0.50 13.75           N
ATOM   3345  CA   ALA B 431      -4.346   1.240 -36.073  0.50 15.01           C
ATOM   3346  CB   ALA B 431      -4.795  -0.215 -35.925  0.50 13.98           C
ATOM   3347  C    ALA B 431      -4.437   1.705 -37.516  0.50 15.11           C
ATOM   3348  O    ALA B 431      -3.883   1.057 -38.406  0.50 17.24           O
ATOM   3349  N    LEU B 432      -5.109   2.828 -37.752  0.50 14.66           N
ATOM   3350  CA   LEU B 432      -5.059   3.466 -39.049  0.50 14.88           C
ATOM   3351  CB   LEU B 432      -6.323   4.298 -39.267  0.50 14.74           C
ATOM   3352  CG   LEU B 432      -7.659   3.540 -39.297  0.50 14.89           C
ATOM   3353  CD1  LEU B 432      -8.813   4.501 -39.014  0.50 15.12           C
ATOM   3354  CD2  LEU B 432      -7.856   2.893 -40.673  0.50 16.56           C
ATOM   3355  C    LEU B 432      -3.837   4.389 -39.134  0.50 14.95           C
ATOM   3356  O    LEU B 432      -3.496   5.097 -38.163  0.50 15.05           O
ATOM   3357  N    HIS B 433      -3.207   4.411 -40.304  0.50 16.54           N
ATOM   3358  CA   HIS B 433      -2.168   5.409 -40.583  0.50 18.52           C
ATOM   3359  CB   HIS B 433      -1.656   5.256 -42.022  0.50 21.26           C
ATOM   3360  CG   HIS B 433      -0.417   6.050 -42.313  0.50 24.49           C
ATOM   3361  ND1  HIS B 433      -0.318   6.914 -43.386  0.50 27.12           N
ATOM   3362  CE1  HIS B 433       0.878   7.478 -43.386  0.50 28.41           C
ATOM   3363  NE2  HIS B 433       1.563   7.003 -42.360  0.50 27.18           N
ATOM   3364  CD2  HIS B 433       0.773   6.114 -41.669  0.50 25.97           C
ATOM   3365  C    HIS B 433      -2.782   6.780 -40.392  0.50 17.68           C
ATOM   3366  O    HIS B 433      -3.896   7.028 -40.874  0.50 16.84           O
ATOM   3367  N    ASN B 434      -2.074   7.656 -39.671  0.50 17.17           N
ATOM   3368  CA   ASN B 434      -2.564   8.991 -39.329  0.50 16.78           C
ATOM   3369  CB   ASN B 434      -3.008   9.780 -40.586  0.50 18.64           C
ATOM   3370  CG   ASN B 434      -1.998   9.720 -41.726  0.50 19.72           C
ATOM   3371  OD1  ASN B 434      -2.276   9.145 -42.801  0.50 21.96           O
ATOM   3372  ND2  ASN B 434      -0.829  10.337 -41.525  0.50 19.69           N
ATOM   3373  C    ASN B 434      -3.727   8.967 -38.309  0.50 15.85           C
ATOM   3374  O    ASN B 434      -4.323  10.007 -38.024  0.50 15.23           O
ATOM   3375  N    HIS B 435      -4.063   7.772 -37.802  0.50 13.75           N
ATOM   3376  CA   HIS B 435      -5.231   7.540 -36.920  0.50 13.51           C
ATOM   3377  CB   HIS B 435      -5.115   8.247 -35.561  0.50 14.78           C
ATOM   3378  CG   HIS B 435      -4.004   7.719 -34.709  0.50 15.16           C
```

Figure 27 (Continued)

```
ATOM   3379  ND1 HIS B 435      -3.462   8.434 -33.662  0.50 16.39           N
ATOM   3380  CE1 HIS B 435      -2.496   7.723 -33.105  0.50 16.98           C
ATOM   3381  NE2 HIS B 435      -2.367   6.595 -33.775  0.50 15.71           N
ATOM   3382  CD2 HIS B 435      -3.315   6.554 -34.768  0.50 17.00           C
ATOM   3383  C   HIS B 435      -6.561   7.897 -37.559  0.50 12.86           C
ATOM   3384  O   HIS B 435      -7.562   8.107 -36.845  0.50 12.78           O
ATOM   3385  N   TYR B 436      -6.586   7.923 -38.888  0.50 13.25           N
ATOM   3386  CA  TYR B 436      -7.750   8.500 -39.582  0.50 13.07           C
ATOM   3387  CB  TYR B 436      -7.615  10.046 -39.601  0.50 13.64           C
ATOM   3388  CG  TYR B 436      -8.707  10.738 -40.374  0.50 13.91           C
ATOM   3389  CD1 TYR B 436      -8.609  10.904 -41.752  0.50 14.78           C
ATOM   3390  CE1 TYR B 436      -9.623  11.536 -42.467  0.50 14.94           C
ATOM   3391  CZ  TYR B 436     -10.748  11.987 -41.809  0.50 14.56           C
ATOM   3392  OH  TYR B 436     -11.769  12.600 -42.519  0.50 16.87           O
ATOM   3393  CE2 TYR B 436     -10.871  11.835 -40.440  0.50 14.96           C
ATOM   3394  CD2 TYR B 436      -9.849  11.219 -39.726  0.50 14.11           C
ATOM   3395  C   TYR B 436      -7.929   7.994 -40.998  0.50 12.47           C
ATOM   3396  O   TYR B 436      -6.956   7.913 -41.770  0.50 12.87           O
ATOM   3397  N   THR B 437      -9.165   7.652 -41.355  0.50 13.45           N
ATOM   3398  CA  THR B 437      -9.506   7.434 -42.758  0.50 14.26           C
ATOM   3399  CB  THR B 437      -9.428   5.954 -43.170  0.50 15.93           C
ATOM   3400  OG1 THR B 437      -9.778   5.836 -44.562  0.50 17.75           O
ATOM   3401  CG2 THR B 437     -10.389   5.173 -42.335  0.50 15.87           C
ATOM   3402  C   THR B 437     -10.910   7.962 -43.024  0.50 14.69           C
ATOM   3403  O   THR B 437     -11.709   8.118 -42.118  0.50 14.08           O
ATOM   3404  N   GLN B 438     -11.209   8.233 -44.281  0.50 14.67           N
ATOM   3405  CA  GLN B 438     -12.514   8.735 -44.643  0.50 15.35           C
ATOM   3406  CB  GLN B 438     -12.468  10.259 -44.854  0.50 15.70           C
ATOM   3407  CG  GLN B 438     -13.844  10.894 -45.023  0.50 16.20           C
ATOM   3408  CD  GLN B 438     -13.745  12.345 -45.442  0.50 17.60           C
ATOM   3409  OE1 GLN B 438     -13.199  12.662 -46.509  0.50 17.79           O
ATOM   3410  NE2 GLN B 438     -14.268  13.239 -44.608  0.50 16.74           N
ATOM   3411  C   GLN B 438     -12.913   8.049 -45.934  0.50 16.51           C
ATOM   3412  O   GLN B 438     -12.060   7.762 -46.791  0.50 17.25           O
ATOM   3413  N   LYS B 439     -14.190   7.722 -46.042  0.50 15.62           N
ATOM   3414  CA  LYS B 439     -14.734   7.185 -47.290  0.50 16.76           C
ATOM   3415  CB  LYS B 439     -15.153   5.722 -47.132  0.50 18.22           C
ATOM   3416  CG  LYS B 439     -14.006   4.723 -46.985  0.50 20.06           C
ATOM   3417  CD  LYS B 439     -13.428   4.344 -48.338  0.50 21.56           C
ATOM   3418  CE  LYS B 439     -12.689   3.005 -48.303  0.50 23.14           C
ATOM   3419  NZ  LYS B 439     -13.524   1.816 -48.683  0.50 22.78           N
ATOM   3420  C   LYS B 439     -15.954   8.005 -47.647  0.50 16.37           C
ATOM   3421  O   LYS B 439     -16.742   8.357 -46.769  0.50 16.38           O
ATOM   3422  N   SER B 440     -16.129   8.283 -48.939  0.50 16.10           N
ATOM   3423  CA  SER B 440     -17.202   9.159 -49.386  0.50 16.74           C
ATOM   3424  CB  SER B 440     -16.640  10.436 -50.037  0.50 16.73           C
ATOM   3425  OG  SER B 440     -15.730  11.078 -49.171  0.50 16.28           O
ATOM   3426  C   SER B 440     -18.066   8.437 -50.401  0.50 16.46           C
ATOM   3427  O   SER B 440     -17.593   7.538 -51.114  0.50 15.47           O
ATOM   3428  N   LEU B 441     -19.326   8.831 -50.464  0.50 17.07           N
ATOM   3429  CA  LEU B 441     -20.212   8.363 -51.523  0.50 18.33           C
ATOM   3430  CB  LEU B 441     -20.974   7.124 -51.079  0.50 19.18           C
ATOM   3431  CG  LEU B 441     -22.206   7.297 -50.182  0.50 18.39           C
ATOM   3432  CD1 LEU B 441     -21.883   7.875 -48.809  0.50 19.69           C
ATOM   3433  CD2 LEU B 441     -22.829   5.915 -50.039  0.50 20.69           C
ATOM   3434  C   LEU B 441     -21.195   9.455 -51.948  0.50 17.70           C
ATOM   3435  O   LEU B 441     -21.412  10.445 -51.238  0.50 17.31           O
ATOM   3436  N   SER B 442     -21.755   9.283 -53.143  0.50 17.91           N
ATOM   3437  CA  SER B 442     -22.790  10.190 -53.640  0.50 19.11           C
ATOM   3438  CB  SER B 442     -22.171  11.363 -54.415  0.50 18.87           C
ATOM   3439  OG  SER B 442     -21.169  10.900 -55.307  0.50 19.96           O
ATOM   3440  C   SER B 442     -23.714   9.419 -54.561  0.50 20.37           C
ATOM   3441  O   SER B 442     -23.357   8.339 -55.037  0.50 20.55           O
ATOM   3442  N   LEU B 443     -24.887   9.990 -54.825  0.50 22.98           N
```

Figure 27 (Continued)

```
ATOM    3443  CA  LEU B 443     -25.831   9.378 -55.756  0.50 25.10           C
ATOM    3444  CB  LEU B 443     -27.103  10.224 -55.826  0.50 25.78           C
ATOM    3445  CG  LEU B 443     -28.189  10.010 -56.886  0.50 28.62           C
ATOM    3446  CD1 LEU B 443     -28.417   8.525 -57.137  0.50 27.32           C
ATOM    3447  CD2 LEU B 443     -27.865  10.767 -58.174  0.50 27.65           C
ATOM    3448  C   LEU B 443     -25.185   9.225 -57.137  0.50 26.31           C
ATOM    3449  O   LEU B 443     -24.631  10.180 -57.690  0.50 26.18           O
ATOM    3450  N   SER B 444     -25.236   8.010 -57.674  0.50 27.34           N
ATOM    3451  CA  SER B 444     -24.843   7.752 -59.058  0.50 29.64           C
ATOM    3452  CB  SER B 444     -24.060   6.438 -59.134  0.50 31.83           C
ATOM    3453  OG  SER B 444     -23.762   6.087 -60.479  0.50 34.74           O
ATOM    3454  C   SER B 444     -26.098   7.648 -59.935  0.50 28.33           C
ATOM    3455  O   SER B 444     -26.902   6.745 -59.746  0.50 28.71           O
ATOM    3456  N   PRO B 445     -26.256   8.570 -60.903  0.50 29.59           N
ATOM    3457  CA  PRO B 445     -27.466   8.682 -61.724  0.50 32.05           C
ATOM    3458  CB  PRO B 445     -27.148   9.853 -62.666  0.50 32.03           C
ATOM    3459  CG  PRO B 445     -26.014  10.584 -62.016  0.50 31.69           C
ATOM    3460  CD  PRO B 445     -25.215   9.510 -61.344  0.50 31.06           C
ATOM    3461  C   PRO B 445     -27.752   7.415 -62.533  0.50 33.39           C
ATOM    3462  O   PRO B 445     -26.823   6.768 -63.018  0.50 32.54           O
HETATM  3463  C1  NAG B 500     -23.608  13.312  -2.889  0.50 32.58           C
HETATM  3464  C2  NAG B 500     -23.574  11.797  -2.953  0.50 34.15           C
HETATM  3465  N2  NAG B 500     -23.264  11.262  -1.661  0.50 34.79           N
HETATM  3466  C7  NAG B 500     -24.207  10.718  -0.915  0.50 37.82           C
HETATM  3467  O7  NAG B 500     -25.376  10.755  -1.207  0.50 36.02           O
HETATM  3468  C8  NAG B 500     -23.742  10.050   0.339  0.50 37.72           C
HETATM  3469  C3  NAG B 500     -22.541  11.268  -3.946  0.50 34.53           C
HETATM  3470  O3  NAG B 500     -22.652   9.859  -4.086  0.50 33.50           O
HETATM  3471  C4  NAG B 500     -22.687  11.949  -5.281  0.50 33.90           C
HETATM  3472  O4  NAG B 500     -21.669  11.438  -6.140  0.50 35.17           O
HETATM  3473  C5  NAG B 500     -22.571  13.442  -5.029  0.50 33.90           C
HETATM  3474  C6  NAG B 500     -22.632  14.248  -6.308  0.50 34.53           C
HETATM  3475  O6  NAG B 500     -23.845  13.944  -6.972  0.50 33.93           O
HETATM  3476  O5  NAG B 500     -23.632  13.866  -4.186  0.50 33.67           O
HETATM  3477  C1  FUC B 501     -24.460  15.141  -7.417  0.50 56.37           C
HETATM  3478  C2  FUC B 501     -25.532  14.787  -8.430  0.50 54.92           C
HETATM  3479  O2  FUC B 501     -24.998  13.893  -9.395  0.50 52.69           O
HETATM  3480  C3  FUC B 501     -26.732  14.119  -7.795  0.50 54.93           C
HETATM  3481  O3  FUC B 501     -27.784  14.088  -8.749  0.50 53.02           O
HETATM  3482  C4  FUC B 501     -27.201  14.881  -6.566  0.50 55.81           C
HETATM  3483  O4  FUC B 501     -27.793  16.109  -6.979  0.50 54.33           O
HETATM  3484  C5  FUC B 501     -26.018  15.135  -5.646  0.50 56.84           C
HETATM  3485  C6  FUC B 501     -26.457  15.909  -4.417  0.50 56.54           C
HETATM  3486  O5  FUC B 501     -25.042  15.875  -6.349  0.50 58.13           O
HETATM  3487  C1  NAG B 502     -21.757  10.448  -6.846  0.50 27.01           C
HETATM  3488  C2  NAG B 502     -21.056  10.584  -8.185  0.50 26.90           C
HETATM  3489  N2  NAG B 502     -21.530  11.754  -8.866  0.50 25.88           N
HETATM  3490  C7  NAG B 502     -20.749  12.740  -9.269  0.50 26.70           C
HETATM  3491  O7  NAG B 502     -21.169  13.687  -9.888  0.50 27.00           O
HETATM  3492  C8  NAG B 502     -19.311  12.641  -8.916  0.50 24.81           C
HETATM  3493  C3  NAG B 502     -21.236   9.347  -9.056  0.50 26.92           C
HETATM  3494  O3  NAG B 502     -20.387   9.490 -10.180  0.50 28.02           O
HETATM  3495  C4  NAG B 502     -20.887   8.084  -8.299  0.50 27.07           C
HETATM  3496  O4  NAG B 502     -21.336   6.922  -8.980  0.50 29.91           O
HETATM  3497  C5  NAG B 502     -21.613   8.087  -6.967  0.50 26.79           C
HETATM  3498  C6  NAG B 502     -21.168   6.874  -6.183  0.50 27.32           C
HETATM  3499  O6  NAG B 502     -21.796   6.881  -4.916  0.50 28.31           O
HETATM  3500  O5  NAG B 502     -21.326   9.258  -6.231  0.50 27.41           O
HETATM  3501  C1  BMA B 503     -20.363   6.368  -9.865  0.50 43.04           C
HETATM  3502  O5  BMA B 503     -20.597   6.901 -11.141  0.50 42.16           O
HETATM  3503  C5  BMA B 503     -19.738   6.398 -12.154  0.50 43.10           C
HETATM  3504  C6  BMA B 503     -20.037   7.117 -13.458  0.50 43.47           C
HETATM  3505  O6  BMA B 503     -20.052   8.514 -13.204  0.50 43.57           O
HETATM  3506  C4  BMA B 503     -19.906   4.894 -12.305  0.50 42.93           C
```

Figure 27 (Continued)

```
HETATM 3507  O4  BMA B 503     -18.966    4.447 -13.271  0.50 45.75           O
HETATM 3508  C3  BMA B 503     -19.638    4.253 -10.967  0.50 43.60           C
HETATM 3509  O3  BMA B 503     -19.739    2.830 -11.026  0.50 43.02           O
HETATM 3510  C2  BMA B 503     -20.604    4.873  -9.960  0.50 42.89           C
HETATM 3511  O2  BMA B 503     -21.950    4.726 -10.393  0.50 41.10           O
HETATM 3512  C1  MAN B 504     -19.969    9.238 -14.415  0.50 30.94           C
HETATM 3513  C2  MAN B 504     -19.530   10.666 -14.183  0.50 30.87           C
HETATM 3514  O2  MAN B 504     -19.497   11.321 -15.423  0.50 29.28           O
HETATM 3515  C3  MAN B 504     -20.549   11.424 -13.360  0.50 31.92           C
HETATM 3516  O3  MAN B 504     -20.171   12.787 -13.309  0.50 31.98           O
HETATM 3517  C4  MAN B 504     -21.888   11.342 -14.059  0.50 33.10           C
HETATM 3518  O4  MAN B 504     -22.878   11.913 -13.216  0.50 35.03           O
HETATM 3519  C5  MAN B 504     -22.237    9.899 -14.395  0.50 32.56           C
HETATM 3520  C6  MAN B 504     -23.493    9.821 -15.252  0.50 33.80           C
HETATM 3521  O6  MAN B 504     -23.788    8.441 -15.411  0.50 32.27           O
HETATM 3522  O5  MAN B 504     -21.189    9.270 -15.113  0.50 33.54           O
HETATM 3523  C1  NAG B 505     -18.213   11.152 -16.026  0.50 37.48           C
HETATM 3524  C2  NAG B 505     -18.429   11.374 -17.522  0.50 38.99           C
HETATM 3525  N2  NAG B 505     -19.309   10.368 -18.061  0.50 39.23           N
HETATM 3526  C7  NAG B 505     -20.565   10.652 -18.382  0.50 43.77           C
HETATM 3527  O7  NAG B 505     -21.033   11.766 -18.313  0.50 42.63           O
HETATM 3528  C8  NAG B 505     -21.388    9.484 -18.829  0.50 43.85           C
HETATM 3529  C3  NAG B 505     -17.102   11.367 -18.283  0.50 37.34           C
HETATM 3530  O3  NAG B 505     -17.259   11.687 -19.666  0.50 38.79           O
HETATM 3531  C4  NAG B 505     -16.091   12.323 -17.680  0.50 37.00           C
HETATM 3532  O4  NAG B 505     -14.838   11.935 -18.185  0.50 34.86           O
HETATM 3533  C5  NAG B 505     -16.039   12.083 -16.190  0.50 37.33           C
HETATM 3534  C6  NAG B 505     -15.064   13.029 -15.503  0.50 38.42           C
HETATM 3535  O6  NAG B 505     -15.507   14.367 -15.605  0.50 37.39           O
HETATM 3536  O5  NAG B 505     -17.333   12.185 -15.625  0.50 38.62           O
HETATM 3537  C1  GAL B 506     -14.057   13.021 -18.653  0.50239.17           C
HETATM 3538  C2  GAL B 506     -12.740   12.522 -19.286  0.50237.03           C
HETATM 3539  O2  GAL B 506     -11.823   11.934 -18.351  0.50235.87           O
HETATM 3540  C3  GAL B 506     -11.975   13.672 -19.909  0.50236.04           C
HETATM 3541  O3  GAL B 506     -10.844   13.175 -20.585  0.50231.04           O
HETATM 3542  C4  GAL B 506     -12.857   14.446 -20.856  0.50236.60           C
HETATM 3543  O4  GAL B 506     -13.375   13.567 -21.840  0.50236.97           O
HETATM 3544  C5  GAL B 506     -14.025   14.957 -20.030  0.50237.03           C
HETATM 3545  C6  GAL B 506     -14.888   15.891 -20.868  0.50233.66           C
HETATM 3546  O6  GAL B 506     -16.043   16.226 -20.109  0.50230.19           O
HETATM 3547  O5  GAL B 506     -14.784   13.844 -19.558  0.50238.95           O
HETATM 3548  C1  MAN B 507     -18.889    2.158 -10.838  0.50110.52           C
HETATM 3549  C2  MAN B 507     -19.036    0.859 -11.620  0.50111.52           C
HETATM 3550  O2  MAN B 507     -17.823    0.142 -11.562  0.50115.52           O
HETATM 3551  C3  MAN B 507     -20.146   -0.002 -11.036  0.50110.07           C
HETATM 3552  O3  MAN B 507     -20.097   -1.279 -11.626  0.50109.48           O
HETATM 3553  C4  MAN B 507     -19.987   -0.132  -9.525  0.50109.74           C
HETATM 3554  O4  MAN B 507     -21.150   -0.714  -8.979  0.50109.72           O
HETATM 3555  C5  MAN B 507     -19.743    1.226  -8.875  0.50109.13           C
HETATM 3556  C6  MAN B 507     -19.478    1.076  -7.382  0.50107.81           C
HETATM 3557  O6  MAN B 507     -20.024    2.176  -6.690  0.50106.57           O
HETATM 3558  O5  MAN B 507     -18.637    1.855  -9.485  0.50108.84           O
HETATM 3559  C1  NAG B 508     -16.976   -1.052 -11.686  0.50112.56           C
HETATM 3560  C2  NAG B 508     -17.155   -0.757 -13.171  0.50112.36           C
HETATM 3561  N2  NAG B 508     -18.226   -1.566 -13.722  0.50111.27           N
HETATM 3562  C7  NAG B 508     -18.727   -1.331 -14.932  0.50110.25           C
HETATM 3563  O7  NAG B 508     -19.636   -2.003 -15.415  0.50109.61           O
HETATM 3564  C8  NAG B 508     -18.127   -0.192 -15.705  0.50109.31           C
HETATM 3565  C3  NAG B 508     -15.855   -1.005 -13.928  0.50111.94           C
HETATM 3566  O3  NAG B 508     -15.979   -0.549 -15.257  0.50112.28           O
HETATM 3567  C4  NAG B 508     -14.711   -0.273 -13.241  0.50111.72           C
HETATM 3568  O4  NAG B 508     -13.489   -0.650 -13.833  0.50110.73           O
HETATM 3569  C5  NAG B 508     -14.686   -0.596 -11.750  0.50112.19           C
HETATM 3570  C6  NAG B 508     -13.576    0.172 -11.043  0.50113.53           C
```

Figure 27 (Continued)

| | | | | | | | | | |
|---|---|---|---|---|---|---|---|---|---|
| HETATM | 3571 | O6 | NAG | B | 508 | -12.842 | -0.710 | -10.222 | 0.50113.64 | O |
| HETATM | 3572 | O5 | NAG | B | 508 | -15.928 | -0.259 | -11.173 | 0.50111.10 | O |
| ATOM | 3573 | N | GLY | b | 236 | -18.219 | 25.893 | -78.068 | 0.50 55.70 | N |
| ATOM | 3574 | CA | GLY | b | 236 | -18.966 | 24.630 | -77.797 | 0.50 56.94 | C |
| ATOM | 3575 | C | GLY | b | 236 | -18.042 | 23.477 | -77.452 | 0.50 55.39 | C |
| ATOM | 3576 | O | GLY | b | 236 | -17.257 | 23.032 | -78.289 | 0.50 57.42 | O |
| ATOM | 3577 | N | GLY | b | 237 | -18.138 | 22.992 | -76.215 | 0.50 53.08 | N |
| ATOM | 3578 | CA | GLY | b | 237 | -17.300 | 21.888 | -75.748 | 0.50 45.26 | C |
| ATOM | 3579 | C | GLY | b | 237 | -17.443 | 21.650 | -74.253 | 0.50 39.53 | C |
| ATOM | 3580 | O | GLY | b | 237 | -18.282 | 22.266 | -73.599 | 0.50 39.91 | O |
| ATOM | 3581 | N | PRO | b | 238 | -16.629 | 20.742 | -73.702 | 0.50 34.58 | N |
| ATOM | 3582 | CA | PRO | b | 238 | -16.674 | 20.469 | -72.268 | 0.50 33.13 | C |
| ATOM | 3583 | CB | PRO | b | 238 | -15.719 | 19.278 | -72.094 | 0.50 32.83 | C |
| ATOM | 3584 | CG | PRO | b | 238 | -15.565 | 18.699 | -73.466 | 0.50 33.03 | C |
| ATOM | 3585 | CD | PRO | b | 238 | -15.656 | 19.885 | -74.391 | 0.50 34.19 | C |
| ATOM | 3586 | C | PRO | b | 238 | -16.157 | 21.639 | -71.461 | 0.50 31.59 | C |
| ATOM | 3587 | O | PRO | b | 238 | -15.506 | 22.535 | -71.999 | 0.50 29.07 | O |
| ATOM | 3588 | N | SER | b | 239 | -16.433 | 21.603 | -70.163 | 0.50 30.87 | N |
| ATOM | 3589 | CA | SER | b | 239 | -15.996 | 22.643 | -69.249 | 0.50 27.88 | C |
| ATOM | 3590 | CB | SER | b | 239 | -17.167 | 23.559 | -68.898 | 0.50 28.99 | C |
| ATOM | 3591 | OG | SER | b | 239 | -17.481 | 24.403 | -69.999 | 0.50 32.70 | O |
| ATOM | 3592 | C | SER | b | 239 | -15.425 | 22.009 | -67.985 | 0.50 25.87 | C |
| ATOM | 3593 | O | SER | b | 239 | -15.847 | 20.929 | -67.576 | 0.50 25.88 | O |
| ATOM | 3594 | N | VAL | b | 240 | -14.469 | 22.697 | -67.373 | 0.50 24.48 | N |
| ATOM | 3595 | CA | VAL | b | 240 | -13.720 | 22.148 | -66.246 | 0.50 23.20 | C |
| ATOM | 3596 | CB | VAL | b | 240 | -12.201 | 22.156 | -66.539 | 0.50 23.56 | C |
| ATOM | 3597 | CG1 | VAL | b | 240 | -11.410 | 21.668 | -65.334 | 0.50 21.64 | C |
| ATOM | 3598 | CG2 | VAL | b | 240 | -11.911 | 21.282 | -67.748 | 0.50 22.99 | C |
| ATOM | 3599 | C | VAL | b | 240 | -14.012 | 22.980 | -65.015 | 0.50 23.88 | C |
| ATOM | 3600 | O | VAL | b | 240 | -14.106 | 24.210 | -65.082 | 0.50 23.10 | O |
| ATOM | 3601 | N | PHE | b | 241 | -14.197 | 22.307 | -63.889 | 0.50 23.67 | N |
| ATOM | 3602 | CA | PHE | b | 241 | -14.358 | 23.019 | -62.637 | 0.50 22.47 | C |
| ATOM | 3603 | CB | PHE | b | 241 | -15.829 | 23.060 | -62.222 | 0.50 24.22 | C |
| ATOM | 3604 | CG | PHE | b | 241 | -16.696 | 23.758 | -63.227 | 0.50 22.64 | C |
| ATOM | 3605 | CD1 | PHE | b | 241 | -16.836 | 25.137 | -63.201 | 0.50 24.65 | C |
| ATOM | 3606 | CE1 | PHE | b | 241 | -17.610 | 25.789 | -64.145 | 0.50 23.38 | C |
| ATOM | 3607 | CZ | PHE | b | 241 | -18.216 | 25.061 | -65.152 | 0.50 24.72 | C |
| ATOM | 3608 | CE2 | PHE | b | 241 | -18.065 | 23.689 | -65.201 | 0.50 22.44 | C |
| ATOM | 3609 | CD2 | PHE | b | 241 | -17.303 | 23.043 | -64.244 | 0.50 24.58 | C |
| ATOM | 3610 | C | PHE | b | 241 | -13.488 | 22.354 | -61.590 | 0.50 20.98 | C |
| ATOM | 3611 | O | PHE | b | 241 | -13.583 | 21.150 | -61.376 | 0.50 20.03 | O |
| ATOM | 3612 | N | LEU | b | 242 | -12.623 | 23.160 | -60.977 | 0.50 21.61 | N |
| ATOM | 3613 | CA | LEU | b | 242 | -11.602 | 22.680 | -60.051 | 0.50 19.64 | C |
| ATOM | 3614 | CB | LEU | b | 242 | -10.230 | 23.159 | -60.522 | 0.50 18.95 | C |
| ATOM | 3615 | CG | LEU | b | 242 | -9.016 | 22.772 | -59.677 | 0.50 17.52 | C |
| ATOM | 3616 | CD1 | LEU | b | 242 | -8.895 | 21.259 | -59.602 | 0.50 19.05 | C |
| ATOM | 3617 | CD2 | LEU | b | 242 | -7.738 | 23.371 | -60.250 | 0.50 17.74 | C |
| ATOM | 3618 | C | LEU | b | 242 | -11.893 | 23.229 | -58.658 | 0.50 19.35 | C |
| ATOM | 3619 | O | LEU | b | 242 | -12.083 | 24.444 | -58.478 | 0.50 19.62 | O |
| ATOM | 3620 | N | PHE | b | 243 | -11.928 | 22.339 | -57.677 | 0.50 18.98 | N |
| ATOM | 3621 | CA | PHE | b | 243 | -12.344 | 22.715 | -56.332 | 0.50 18.56 | C |
| ATOM | 3622 | CB | PHE | b | 243 | -13.610 | 21.943 | -55.970 | 0.50 19.23 | C |
| ATOM | 3623 | CG | PHE | b | 243 | -14.740 | 22.134 | -56.954 | 0.50 20.03 | C |
| ATOM | 3624 | CD1 | PHE | b | 243 | -15.736 | 23.088 | -56.722 | 0.50 20.26 | C |
| ATOM | 3625 | CE1 | PHE | b | 243 | -16.787 | 23.256 | -57.600 | 0.50 20.90 | C |
| ATOM | 3626 | CZ | PHE | b | 243 | -16.857 | 22.476 | -58.746 | 0.50 21.41 | C |
| ATOM | 3627 | CE2 | PHE | b | 243 | -15.879 | 21.527 | -58.991 | 0.50 20.87 | C |
| ATOM | 3628 | CD2 | PHE | b | 243 | -14.830 | 21.358 | -58.092 | 0.50 20.65 | C |
| ATOM | 3629 | C | PHE | b | 243 | -11.263 | 22.434 | -55.310 | 0.50 18.14 | C |
| ATOM | 3630 | O | PHE | b | 243 | -10.498 | 21.472 | -55.457 | 0.50 18.15 | O |
| ATOM | 3631 | N | PRO | b | 244 | -11.221 | 23.249 | -54.243 | 0.50 17.39 | N |
| ATOM | 3632 | CA | PRO | b | 244 | -10.184 | 23.218 | -53.206 | 0.50 16.35 | C |
| ATOM | 3633 | CB | PRO | b | 244 | -10.313 | 24.612 | -52.581 | 0.50 16.97 | C |
| ATOM | 3634 | CG | PRO | b | 244 | -11.785 | 24.896 | -52.664 | 0.50 16.75 | C |

Figure 27 (Continued)

```
ATOM   3635  CD   PRO b 244     -12.279  24.223 -53.931  0.50 17.95           C
ATOM   3636  C    PRO b 244     -10.489  22.134 -52.153  0.50 15.75           C
ATOM   3637  O    PRO b 244     -11.578  21.564 -52.157  0.50 16.86           O
ATOM   3638  N    PRO b 245      -9.536  21.872 -51.254  0.50 14.98           N
ATOM   3639  CA   PRO b 245      -9.771  21.026 -50.070  0.50 15.40           C
ATOM   3640  CB   PRO b 245      -8.394  20.956 -49.406  0.50 14.99           C
ATOM   3641  CG   PRO b 245      -7.648  22.170 -49.930  0.50 14.83           C
ATOM   3642  CD   PRO b 245      -8.141  22.334 -51.343  0.50 15.13           C
ATOM   3643  C    PRO b 245     -10.715  21.722 -49.106  0.50 15.52           C
ATOM   3644  O    PRO b 245     -10.764  22.960 -49.062  0.50 14.78           O
ATOM   3645  N    LYS b 246     -11.421  20.950 -48.286  0.50 14.41           N
ATOM   3646  CA   LYS b 246     -12.203  21.535 -47.215  0.50 14.91           C
ATOM   3647  CB   LYS b 246     -13.050  20.454 -46.533  0.50 14.35           C
ATOM   3648  CG   LYS b 246     -14.086  19.818 -47.458  0.50 15.22           C
ATOM   3649  CD   LYS b 246     -15.369  20.652 -47.461  0.50 15.39           C
ATOM   3650  CE   LYS b 246     -16.434  20.010 -48.354  0.50 16.94           C
ATOM   3651  NZ   LYS b 246     -15.919  19.921 -49.761  0.50 19.59           N
ATOM   3652  C    LYS b 246     -11.263  22.149 -46.179  0.50 15.09           C
ATOM   3653  O    LYS b 246     -10.202  21.597 -45.911  0.50 15.30           O
ATOM   3654  N    PRO b 247     -11.661  23.270 -45.569  0.50 14.92           N
ATOM   3655  CA   PRO b 247     -10.724  23.905 -44.658  0.50 15.81           C
ATOM   3656  CB   PRO b 247     -11.531  25.072 -44.068  0.50 16.67           C
ATOM   3657  CG   PRO b 247     -12.568  25.369 -45.103  0.50 15.45           C
ATOM   3658  CD   PRO b 247     -12.908  24.043 -45.733  0.50 15.91           C
ATOM   3659  C    PRO b 247     -10.252  22.961 -43.551  0.50 15.04           C
ATOM   3660  O    PRO b 247      -9.054  22.889 -43.273  0.50 16.26           O
ATOM   3661  N    LYS b 248     -11.183  22.220 -42.941  0.50 15.38           N
ATOM   3662  CA   LYS b 248     -10.828  21.302 -41.858  0.50 15.22           C
ATOM   3663  CB   LYS b 248     -12.070  20.577 -41.322  0.50 15.82           C
ATOM   3664  CG   LYS b 248     -11.783  19.707 -40.092  0.50 16.02           C
ATOM   3665  CD   LYS b 248     -13.076  19.079 -39.610  0.50 17.00           C
ATOM   3666  CE   LYS b 248     -12.832  18.090 -38.475  0.50 17.88           C
ATOM   3667  NZ   LYS b 248     -14.125  17.754 -37.814  0.50 18.56           N
ATOM   3668  C    LYS b 248      -9.766  20.296 -42.279  0.50 15.56           C
ATOM   3669  O    LYS b 248      -8.856  19.963 -41.493  0.50 15.74           O
ATOM   3670  N    ASP b 249      -9.863  19.799 -43.508  0.50 15.16           N
ATOM   3671  CA   ASP b 249      -8.889  18.817 -43.970  0.50 15.33           C
ATOM   3672  CB   ASP b 249      -9.301  18.190 -45.318  0.50 15.01           C
ATOM   3673  CG   ASP b 249     -10.594  17.369 -45.238  0.50 15.35           C
ATOM   3674  OD1  ASP b 249     -11.093  17.051 -44.130  0.50 15.31           O
ATOM   3675  OD2  ASP b 249     -11.117  17.041 -46.319  0.50 16.43           O
ATOM   3676  C    ASP b 249      -7.499  19.450 -44.081  0.50 15.78           C
ATOM   3677  O    ASP b 249      -6.475  18.803 -43.809  0.50 14.95           O
ATOM   3678  N    THR b 250      -7.442  20.705 -44.516  0.50 15.73           N
ATOM   3679  CA   THR b 250      -6.133  21.349 -44.689  0.50 16.72           C
ATOM   3680  CB   THR b 250      -6.230  22.671 -45.491  0.50 17.51           C
ATOM   3681  OG1  THR b 250      -6.889  23.662 -44.697  0.50 18.42           O
ATOM   3682  CG2  THR b 250      -7.012  22.465 -46.784  0.50 18.34           C
ATOM   3683  C    THR b 250      -5.483  21.666 -43.345  0.50 16.38           C
ATOM   3684  O    THR b 250      -4.240  21.814 -43.257  0.50 17.03           O
ATOM   3685  N    LEU b 251      -6.297  21.781 -42.295  0.50 15.48           N
ATOM   3686  CA   LEU b 251      -5.817  22.347 -41.041  0.50 14.86           C
ATOM   3687  CB   LEU b 251      -6.847  23.330 -40.494  0.50 14.22           C
ATOM   3688  CG   LEU b 251      -7.107  24.557 -41.383  0.50 13.39           C
ATOM   3689  CD1  LEU b 251      -8.330  25.293 -40.837  0.50 14.29           C
ATOM   3690  CD2  LEU b 251      -5.868  25.462 -41.394  0.50 13.68           C
ATOM   3691  C    LEU b 251      -5.477  21.285 -39.997  0.50 15.64           C
ATOM   3692  O    LEU b 251      -4.560  21.476 -39.172  0.50 15.96           O
ATOM   3693  N    MET b 252      -6.116  20.143 -40.127  0.50 15.37           N
ATOM   3694  CA   MET b 252      -5.866  19.077 -39.199  0.50 15.76           C
ATOM   3695  CB   MET b 252      -7.204  18.491 -38.802  0.50 17.90           C
ATOM   3696  CG   MET b 252      -8.188  19.518 -38.280  0.50 21.42           C
ATOM   3697  SD   MET b 252      -7.530  20.737 -37.110  0.50 29.03           S
ATOM   3698  CE   MET b 252      -7.684  19.825 -35.631  0.50 29.18           C
```

Figure 27 (Continued)

```
ATOM   3699  C    MET b 252      -4.969  18.017 -39.844  0.50 14.43           C
ATOM   3700  O    MET b 252      -5.326  17.464 -40.830  0.50 14.44           O
ATOM   3701  N    ILE b 253      -3.798  17.760 -39.273  0.50 14.38           N
ATOM   3702  CA   ILE b 253      -2.776  16.960 -39.948  0.50 15.22           C
ATOM   3703  CB   ILE b 253      -1.390  17.006 -39.232  0.50 14.87           C
ATOM   3704  CG1  ILE b 253      -0.292  16.610 -40.219  0.50 15.80           C
ATOM   3705  CD1  ILE b 253      -0.142  17.567 -41.376  0.50 16.93           C
ATOM   3706  CG2  ILE b 253      -1.340  16.080 -38.018  0.50 16.44           C
ATOM   3707  C    ILE b 253      -3.242  15.520 -40.170  0.50 16.23           C
ATOM   3708  O    ILE b 253      -2.840  14.862 -41.142  0.50 16.16           O
ATOM   3709  N    SER b 254      -4.111  15.044 -39.289  0.50 15.28           N
ATOM   3710  CA   SER b 254      -4.609  13.668 -39.456  0.50 15.96           C
ATOM   3711  CB   SER b 254      -5.384  13.241 -38.215  0.50 16.82           C
ATOM   3712  OG   SER b 254      -4.481  13.013 -37.136  0.50 20.32           O
ATOM   3713  C    SER b 254      -5.486  13.494 -40.686  0.50 16.10           C
ATOM   3714  O    SER b 254      -5.715  12.369 -41.131  0.50 15.94           O
ATOM   3715  N    ARG b 255      -6.052  14.590 -41.189  0.50 15.24           N
ATOM   3716  CA   ARG b 255      -7.075  14.481 -42.235  0.50 17.10           C
ATOM   3717  CB   ARG b 255      -8.209  15.512 -42.034  0.50 16.95           C
ATOM   3718  CG   ARG b 255      -8.948  15.309 -40.711  0.50 17.45           C
ATOM   3719  CD   ARG b 255      -9.977  16.400 -40.442  0.50 18.50           C
ATOM   3720  NE   ARG b 255     -11.132  16.325 -41.327  0.50 18.05           N
ATOM   3721  CZ   ARG b 255     -12.241  15.653 -41.025  0.50 18.64           C
ATOM   3722  NH1  ARG b 255     -12.311  15.005 -39.873  0.50 18.51           N
ATOM   3723  NH2  ARG b 255     -13.264  15.634 -41.866  0.50 18.35           N
ATOM   3724  C    ARG b 255      -6.471  14.550 -43.619  0.50 17.19           C
ATOM   3725  O    ARG b 255      -5.280  14.756 -43.773  0.50 18.04           O
ATOM   3726  N    THR b 256      -7.318  14.385 -44.630  0.50 19.90           N
ATOM   3727  CA   THR b 256      -6.868  14.106 -45.974  0.50 20.57           C
ATOM   3728  CB   THR b 256      -7.496  12.766 -46.417  0.50 23.48           C
ATOM   3729  OG1  THR b 256      -7.282  11.771 -45.401  0.50 25.15           O
ATOM   3730  CG2  THR b 256      -6.911  12.311 -47.717  0.50 23.66           C
ATOM   3731  C    THR b 256      -7.347  15.173 -46.979  0.50 20.32           C
ATOM   3732  O    THR b 256      -8.396  15.018 -47.581  0.50 21.28           O
ATOM   3733  N    PRO b 257      -6.578  16.262 -47.161  0.50 19.54           N
ATOM   3734  CA   PRO b 257      -7.003  17.316 -48.098  0.50 18.64           C
ATOM   3735  CB   PRO b 257      -6.113  18.501 -47.707  0.50 18.27           C
ATOM   3736  CG   PRO b 257      -4.860  17.841 -47.175  0.50 19.00           C
ATOM   3737  CD   PRO b 257      -5.321  16.594 -46.479  0.50 20.59           C
ATOM   3738  C    PRO b 257      -6.766  16.923 -49.559  0.50 19.37           C
ATOM   3739  O    PRO b 257      -5.707  16.352 -49.895  0.50 20.74           O
ATOM   3740  N    GLU b 258      -7.753  17.210 -50.415  0.50 19.99           N
ATOM   3741  CA   GLU b 258      -7.687  16.886 -51.840  0.50 20.94           C
ATOM   3742  CB   GLU b 258      -8.586  15.680 -52.172  0.50 23.46           C
ATOM   3743  CG   GLU b 258      -8.492  14.533 -51.178  0.50 26.75           C
ATOM   3744  CD   GLU b 258      -9.294  13.310 -51.598  0.50 28.02           C
ATOM   3745  OE1  GLU b 258     -10.489  13.446 -51.966  0.50 30.55           O
ATOM   3746  OE2  GLU b 258      -8.722  12.208 -51.537  0.50 28.42           O
ATOM   3747  C    GLU b 258      -8.154  18.061 -52.691  0.50 18.94           C
ATOM   3748  O    GLU b 258      -9.109  18.767 -52.335  0.50 18.26           O
ATOM   3749  N    VAL b 259      -7.520  18.228 -53.845  0.50 18.71           N
ATOM   3750  CA   VAL b 259      -8.012  19.165 -54.854  0.50 19.80           C
ATOM   3751  CB   VAL b 259      -6.887  20.055 -55.413  0.50 20.80           C
ATOM   3752  CG1  VAL b 259      -7.240  20.600 -56.788  0.50 21.56           C
ATOM   3753  CG2  VAL b 259      -6.608  21.217 -54.467  0.50 19.96           C
ATOM   3754  C    VAL b 259      -8.637  18.291 -55.942  0.50 19.90           C
ATOM   3755  O    VAL b 259      -8.089  17.250 -56.295  0.50 19.43           O
ATOM   3756  N    THR b 260      -9.803  18.691 -56.438  0.50 20.75           N
ATOM   3757  CA   THR b 260     -10.589  17.803 -57.276  0.50 21.34           C
ATOM   3758  CB   THR b 260     -11.906  17.445 -56.575  0.50 21.68           C
ATOM   3759  OG1  THR b 260     -11.617  16.959 -55.252  0.50 20.97           O
ATOM   3760  CG2  THR b 260     -12.690  16.388 -57.374  0.50 20.25           C
ATOM   3761  C    THR b 260     -10.906  18.479 -58.592  0.50 22.11           C
ATOM   3762  O    THR b 260     -11.467  19.574 -58.619  0.50 21.89           O
```

Figure 27 (Continued)

```
ATOM   3763  N    CYS b 261     -10.544  17.828 -59.690  0.50 22.03           N
ATOM   3764  CA   CYS b 261     -10.758  18.425 -60.999  0.50 22.65           C
ATOM   3765  CB   CYS b 261      -9.487  18.318 -61.840  0.50 22.97           C
ATOM   3766  SG   CYS b 261      -9.534  19.318 -63.349  0.50 27.11           S
ATOM   3767  C    CYS b 261     -11.910  17.701 -61.670  0.50 22.71           C
ATOM   3768  O    CYS b 261     -11.841  16.495 -61.884  0.50 23.22           O
ATOM   3769  N    VAL b 262     -12.982  18.438 -61.944  0.50 23.30           N
ATOM   3770  CA   VAL b 262     -14.205  17.861 -62.482  0.50 23.53           C
ATOM   3771  CB   VAL b 262     -15.411  18.145 -61.570  0.50 23.97           C
ATOM   3772  CG1  VAL b 262     -16.682  17.559 -62.167  0.50 22.94           C
ATOM   3773  CG2  VAL b 262     -15.166  17.571 -60.177  0.50 22.54           C
ATOM   3774  C    VAL b 262     -14.480  18.432 -63.866  0.50 22.51           C
ATOM   3775  O    VAL b 262     -14.518  19.646 -64.063  0.50 22.15           O
ATOM   3776  N    VAL b 263     -14.655  17.530 -64.820  0.50 24.19           N
ATOM   3777  CA   VAL b 263     -14.937  17.890 -66.189  0.50 24.53           C
ATOM   3778  CB   VAL b 263     -13.968  17.161 -67.123  0.50 25.20           C
ATOM   3779  CG1  VAL b 263     -14.113  17.690 -68.534  0.50 24.06           C
ATOM   3780  CG2  VAL b 263     -12.534  17.242 -66.606  0.50 25.52           C
ATOM   3781  C    VAL b 263     -16.358  17.435 -66.540  0.50 25.03           C
ATOM   3782  O    VAL b 263     -16.703  16.272 -66.352  0.50 24.60           O
ATOM   3783  N    VAL b 264     -17.192  18.356 -67.015  0.50 25.23           N
ATOM   3784  CA   VAL b 264     -18.547  17.987 -67.415  0.50 25.92           C
ATOM   3785  CB   VAL b 264     -19.624  18.845 -66.716  0.50 25.28           C
ATOM   3786  CG1  VAL b 264     -19.852  18.355 -65.288  0.50 25.12           C
ATOM   3787  CG2  VAL b 264     -19.217  20.312 -66.716  0.50 24.42           C
ATOM   3788  C    VAL b 264     -18.691  18.072 -68.936  0.50 27.44           C
ATOM   3789  O    VAL b 264     -17.696  18.259 -69.644  0.50 25.65           O
ATOM   3790  N    ASP b 265     -19.920  17.900 -69.421  0.50 28.28           N
ATOM   3791  CA   ASP b 265     -20.243  18.043 -70.852  0.50 31.50           C
ATOM   3792  CB   ASP b 265     -20.393  19.520 -71.229  0.50 30.80           C
ATOM   3793  CG   ASP b 265     -21.668  20.130 -70.682  0.50 32.30           C
ATOM   3794  OD1  ASP b 265     -22.513  19.382 -70.152  0.50 33.50           O
ATOM   3795  OD2  ASP b 265     -21.835  21.359 -70.783  0.50 33.77           O
ATOM   3796  C    ASP b 265     -19.262  17.346 -71.800  0.50 31.85           C
ATOM   3797  O    ASP b 265     -18.960  17.857 -72.880  0.50 32.42           O
ATOM   3798  N    VAL b 266     -18.775  16.178 -71.397  0.50 34.02           N
ATOM   3799  CA   VAL b 266     -17.972  15.356 -72.284  0.50 34.50           C
ATOM   3800  CB   VAL b 266     -16.980  14.482 -71.502  0.50 36.04           C
ATOM   3801  CG1  VAL b 266     -16.161  13.627 -72.451  0.50 34.93           C
ATOM   3802  CG2  VAL b 266     -16.071  15.353 -70.643  0.50 35.63           C
ATOM   3803  C    VAL b 266     -18.919  14.474 -73.097  0.50 36.46           C
ATOM   3804  O    VAL b 266     -19.859  13.889 -72.550  0.50 34.88           O
ATOM   3805  N    SER b 267     -18.682  14.385 -74.401  0.50 38.19           N
ATOM   3806  CA   SER b 267     -19.623  13.698 -75.296  0.50 40.42           C
ATOM   3807  CB   SER b 267     -19.506  14.254 -76.716  0.50 36.93           C
ATOM   3808  OG   SER b 267     -18.214  14.018 -77.248  0.50 37.76           O
ATOM   3809  C    SER b 267     -19.435  12.179 -75.321  0.50 43.47           C
ATOM   3810  O    SER b 267     -18.315  11.681 -75.199  0.50 43.96           O
ATOM   3811  N    HIS b 268     -20.535  11.452 -75.501  0.50 46.97           N
ATOM   3812  CA   HIS b 268     -20.491   9.991 -75.568  0.50 49.88           C
ATOM   3813  CB   HIS b 268     -21.900   9.414 -75.731  0.50 50.92           C
ATOM   3814  CG   HIS b 268     -22.375   8.622 -74.550  0.50 52.18           C
ATOM   3815  ND1  HIS b 268     -22.412   7.243 -74.545  0.50 53.35           N
ATOM   3816  CE1  HIS b 268     -22.880   6.820 -73.384  0.50 54.13           C
ATOM   3817  NE2  HIS b 268     -23.145   7.874 -72.633  0.50 53.63           N
ATOM   3818  CD2  HIS b 268     -22.839   9.013 -73.339  0.50 52.71           C
ATOM   3819  C    HIS b 268     -19.578   9.463 -76.682  0.50 51.97           C
ATOM   3820  O    HIS b 268     -19.312   8.263 -76.752  0.50 50.36           O
ATOM   3821  N    GLU b 269     -19.097  10.356 -77.542  0.50 53.40           N
ATOM   3822  CA   GLU b 269     -18.238   9.951 -78.657  0.50 57.50           C
ATOM   3823  CB   GLU b 269     -18.293  10.978 -79.794  0.50 59.31           C
ATOM   3824  CG   GLU b 269     -19.634  11.042 -80.514  0.50 61.28           C
ATOM   3825  CD   GLU b 269     -20.771  11.462 -79.600  0.50 64.38           C
ATOM   3826  OE1  GLU b 269     -20.489  12.011 -78.512  0.50 65.26           O
```

Figure 27 (Continued)

```
ATOM   3827  OE2 GLU b 269     -21.947   11.247  -79.968  0.50 66.94           O
ATOM   3828  C   GLU b 269     -16.792    9.705  -78.215  0.50 58.12           C
ATOM   3829  O   GLU b 269     -16.314    8.570  -78.235  0.50 59.80           O
ATOM   3830  N   GLU b 270     -16.095   10.771  -77.832  0.50 57.41           N
ATOM   3831  CA  GLU b 270     -14.763   10.638  -77.249  0.50 55.66           C
ATOM   3832  CB  GLU b 270     -13.834   11.755  -77.729  0.50 55.58           C
ATOM   3833  CG  GLU b 270     -13.380   11.624  -79.173  0.50 56.94           C
ATOM   3834  CD  GLU b 270     -14.299   12.344  -80.134  0.50 54.81           C
ATOM   3835  OE1 GLU b 270     -15.484   11.965  -80.218  0.50 55.67           O
ATOM   3836  OE2 GLU b 270     -13.836   13.296  -80.795  0.50 55.70           O
ATOM   3837  C   GLU b 270     -14.873   10.673  -75.730  0.50 54.64           C
ATOM   3838  O   GLU b 270     -14.847   11.745  -75.127  0.50 54.24           O
ATOM   3839  N   PRO b 271     -14.996    9.492  -75.108  0.50 53.91           N
ATOM   3840  CA  PRO b 271     -15.288    9.391  -73.683  0.50 51.84           C
ATOM   3841  CB  PRO b 271     -15.859    7.980  -73.557  0.50 51.66           C
ATOM   3842  CG  PRO b 271     -15.120    7.207  -74.601  0.50 52.44           C
ATOM   3843  CD  PRO b 271     -14.850    8.165  -75.735  0.50 51.59           C
ATOM   3844  C   PRO b 271     -14.040    9.509  -72.820  0.50 50.69           C
ATOM   3845  O   PRO b 271     -14.132    9.884  -71.650  0.50 53.44           O
ATOM   3846  N   GLU b 272     -12.887    9.175  -73.389  0.50 47.69           N
ATOM   3847  CA  GLU b 272     -11.659    9.097  -72.612  0.50 44.82           C
ATOM   3848  CB  GLU b 272     -10.635    8.194  -73.305  0.50 45.93           C
ATOM   3849  CG  GLU b 272     -11.238    6.973  -73.992  0.50 48.14           C
ATOM   3850  CD  GLU b 272     -11.687    5.884  -73.030  0.50 48.47           C
ATOM   3851  OE1 GLU b 272     -10.875    4.992  -72.705  0.50 48.92           O
ATOM   3852  OE2 GLU b 272     -12.865    5.897  -72.624  0.50 49.90           O
ATOM   3853  C   GLU b 272     -11.089   10.491  -72.358  0.50 43.10           C
ATOM   3854  O   GLU b 272     -11.300   11.413  -73.153  0.50 41.38           O
ATOM   3855  N   VAL b 273     -10.371   10.643  -71.248  0.50 38.99           N
ATOM   3856  CA  VAL b 273      -9.906   11.962  -70.817  0.50 38.38           C
ATOM   3857  CB  VAL b 273     -10.799   12.520  -69.692  0.50 38.33           C
ATOM   3858  CG1 VAL b 273     -10.345   13.915  -69.287  0.50 37.45           C
ATOM   3859  CG2 VAL b 273     -12.254   12.535  -70.131  0.50 37.66           C
ATOM   3860  C   VAL b 273      -8.459   11.950  -70.339  0.50 38.27           C
ATOM   3861  O   VAL b 273      -8.029   11.011  -69.670  0.50 36.54           O
ATOM   3862  N   LYS b 274      -7.714   13.000  -70.678  0.50 38.44           N
ATOM   3863  CA  LYS b 274      -6.311   13.095  -70.282  0.50 40.18           C
ATOM   3864  CB  LYS b 274      -5.407   13.078  -71.527  0.50 40.75           C
ATOM   3865  CG  LYS b 274      -5.745   11.947  -72.500  0.50 42.56           C
ATOM   3866  CD  LYS b 274      -4.802   11.838  -73.700  0.50 41.38           C
ATOM   3867  CE  LYS b 274      -4.959   12.987  -74.692  0.50 41.47           C
ATOM   3868  NZ  LYS b 274      -6.335   13.152  -75.239  0.50 39.72           N
ATOM   3869  C   LYS b 274      -6.047   14.323  -69.395  0.50 39.50           C
ATOM   3870  O   LYS b 274      -6.227   15.463  -69.830  0.50 40.15           O
ATOM   3871  N   PHE b 275      -5.643   14.073  -68.147  0.50 38.92           N
ATOM   3872  CA  PHE b 275      -5.333   15.132  -67.177  0.50 36.76           C
ATOM   3873  CB  PHE b 275      -5.902   14.790  -65.793  0.50 36.60           C
ATOM   3874  CG  PHE b 275      -7.398   14.819  -65.711  0.50 35.21           C
ATOM   3875  CD1 PHE b 275      -8.141   13.684  -65.995  0.50 36.55           C
ATOM   3876  CE1 PHE b 275      -9.517   13.700  -65.906  0.50 34.91           C
ATOM   3877  CZ  PHE b 275     -10.170   14.855  -65.518  0.50 35.67           C
ATOM   3878  CE2 PHE b 275      -9.442   15.991  -65.219  0.50 34.26           C
ATOM   3879  CD2 PHE b 275      -8.063   15.969  -65.306  0.50 34.39           C
ATOM   3880  C   PHE b 275      -3.835   15.339  -66.993  0.50 36.68           C
ATOM   3881  O   PHE b 275      -3.086   14.378  -66.809  0.50 40.02           O
ATOM   3882  N   ASN b 276      -3.407   16.596  -67.002  0.50 35.34           N
ATOM   3883  CA  ASN b 276      -2.084   16.957  -66.500  0.50 32.94           C
ATOM   3884  CB  ASN b 276      -1.253   17.677  -67.570  0.50 31.48           C
ATOM   3885  CG  ASN b 276      -0.914   16.783  -68.747  0.50 31.77           C
ATOM   3886  OD1 ASN b 276      -1.628   16.775  -69.746  0.50 29.88           O
ATOM   3887  ND2 ASN b 276       0.175   16.021  -68.631  0.50 30.03           N
ATOM   3888  C   ASN b 276      -2.188   17.832  -65.253  0.50 31.77           C
ATOM   3889  O   ASN b 276      -2.729   18.942  -65.295  0.50 29.21           O
ATOM   3890  N   TRP b 277      -1.660   17.318  -64.149  0.50 31.52           N
```

Figure 27 (Continued)

```
ATOM   3891  CA   TRP b 277     -1.684  18.010 -62.870  0.50 31.33           C
ATOM   3892  CB   TRP b 277     -1.963  17.002 -61.776  0.50 28.62           C
ATOM   3893  CG   TRP b 277     -3.402  16.659 -61.573  0.50 27.76           C
ATOM   3894  CD1  TRP b 277     -4.060  15.551 -62.024  0.50 27.45           C
ATOM   3895  NE1  TRP b 277     -5.367  15.577 -61.605  0.50 26.73           N
ATOM   3896  CE2  TRP b 277     -5.570  16.718 -60.870  0.50 25.48           C
ATOM   3897  CD2  TRP b 277     -4.356  17.417 -60.825  0.50 26.11           C
ATOM   3898  CE3  TRP b 277     -4.297  18.627 -60.130  0.50 24.54           C
ATOM   3899  CZ3  TRP b 277     -5.438  19.080 -59.498  0.50 24.78           C
ATOM   3900  CH2  TRP b 277     -6.626  18.359 -59.553  0.50 23.82           C
ATOM   3901  CZ2  TRP b 277     -6.713  17.173 -60.221  0.50 25.54           C
ATOM   3902  C    TRP b 277     -0.340  18.649 -62.572  0.50 32.73           C
ATOM   3903  O    TRP b 277      0.691  17.968 -62.593  0.50 36.44           O
ATOM   3904  N    TYR b 278     -0.343  19.943 -62.270  0.50 33.07           N
ATOM   3905  CA   TYR b 278      0.881  20.630 -61.862  0.50 31.77           C
ATOM   3906  CB   TYR b 278      1.173  21.810 -62.800  0.50 32.64           C
ATOM   3907  CG   TYR b 278      1.154  21.411 -64.255  0.50 33.22           C
ATOM   3908  CD1  TYR b 278     -0.032  21.402 -64.970  0.50 34.88           C
ATOM   3909  CE1  TYR b 278     -0.064  21.013 -66.298  0.50 34.79           C
ATOM   3910  CZ   TYR b 278      1.098  20.617 -66.924  0.50 34.52           C
ATOM   3911  OH   TYR b 278      1.055  20.232 -68.242  0.50 35.78           O
ATOM   3912  CE2  TYR b 278      2.290  20.605 -66.235  0.50 34.27           C
ATOM   3913  CD2  TYR b 278      2.315  20.994 -64.905  0.50 35.89           C
ATOM   3914  C    TYR b 278      0.791  21.117 -60.424  0.50 29.99           C
ATOM   3915  O    TYR b 278     -0.291  21.452 -59.950  0.50 29.12           O
ATOM   3916  N    VAL b 279      1.927  21.130 -59.729  0.50 26.55           N
ATOM   3917  CA   VAL b 279      2.047  21.851 -58.463  0.50 25.24           C
ATOM   3918  CB   VAL b 279      2.312  20.919 -57.267  0.50 25.20           C
ATOM   3919  CG1  VAL b 279      2.767  21.729 -56.056  0.50 25.65           C
ATOM   3920  CG2  VAL b 279      1.073  20.096 -56.933  0.50 24.37           C
ATOM   3921  C    VAL b 279      3.217  22.798 -58.644  0.50 26.73           C
ATOM   3922  O    VAL b 279      4.330  22.358 -58.947  0.50 25.01           O
ATOM   3923  N    ASP b 280      2.964  24.091 -58.486  0.50 24.80           N
ATOM   3924  CA   ASP b 280      3.928  25.119 -58.891  0.50 27.82           C
ATOM   3925  CB   ASP b 280      4.864  25.487 -57.736  0.50 26.18           C
ATOM   3926  CG   ASP b 280      4.187  26.365 -56.699  0.50 26.07           C
ATOM   3927  OD1  ASP b 280      3.036  26.803 -56.942  0.50 26.73           O
ATOM   3928  OD2  ASP b 280      4.800  26.617 -55.634  0.50 27.32           O
ATOM   3929  C    ASP b 280      4.719  24.720 -60.140  0.50 27.70           C
ATOM   3930  O    ASP b 280      5.929  24.943 -60.228  0.50 25.88           O
ATOM   3931  N    GLY b 281      4.029  24.139 -61.112  0.50 29.75           N
ATOM   3932  CA   GLY b 281      4.639  23.873 -62.409  0.50 30.02           C
ATOM   3933  C    GLY b 281      5.301  22.517 -62.498  0.50 32.26           C
ATOM   3934  O    GLY b 281      5.519  21.990 -63.588  0.50 33.94           O
ATOM   3935  N    VAL b 282      5.626  21.932 -61.357  0.50 31.97           N
ATOM   3936  CA   VAL b 282      6.200  20.602 -61.385  0.50 33.29           C
ATOM   3937  CB   VAL b 282      6.836  20.212 -60.038  0.50 33.88           C
ATOM   3938  CG1  VAL b 282      7.249  18.745 -60.062  0.50 33.90           C
ATOM   3939  CG2  VAL b 282      8.024  21.109 -59.731  0.50 33.39           C
ATOM   3940  C    VAL b 282      5.115  19.603 -61.741  0.50 34.80           C
ATOM   3941  O    VAL b 282      4.436  19.063 -60.855  0.50 32.74           O
ATOM   3942  N    GLU b 283      4.910  19.356 -63.031  0.50 34.01           N
ATOM   3943  CA   GLU b 283      3.892  18.384 -63.339  0.50 34.59           C
ATOM   3944  CB   GLU b 283      4.034  17.803 -64.743  0.50 35.64           C
ATOM   3945  CG   GLU b 283      3.077  16.647 -64.974  0.50 36.15           C
ATOM   3946  CD   GLU b 283      2.827  16.355 -66.438  0.50 37.92           C
ATOM   3947  OE1  GLU b 283      3.649  16.766 -67.290  0.50 39.05           O
ATOM   3948  OE2  GLU b 283      1.804  15.703 -66.730  0.50 37.66           O
ATOM   3949  C    GLU b 283      4.094  17.314 -62.280  0.50 34.54           C
ATOM   3950  O    GLU b 283      5.232  16.915 -62.007  0.50 32.42           O
ATOM   3951  N    VAL b 284      3.006  16.910 -61.632  0.50 33.45           N
ATOM   3952  CA   VAL b 284      3.057  15.844 -60.630  0.50 33.35           C
ATOM   3953  CB   VAL b 284      2.491  16.298 -59.259  0.50 32.01           C
ATOM   3954  CG1  VAL b 284      3.331  17.425 -58.671  0.50 30.10           C
```

Figure 27 (Continued)

```
ATOM   3955  CG2 VAL b 284      1.040  16.746 -59.391  0.50 30.09           C
ATOM   3956  C   VAL b 284      2.292  14.646 -61.195  0.50 34.97           C
ATOM   3957  O   VAL b 284      1.511  14.802 -62.137  0.50 34.93           O
ATOM   3958  N   HIS b 285      2.521  13.454 -60.650  0.50 35.15           N
ATOM   3959  CA  HIS b 285      2.038  12.240 -61.311  0.50 37.36           C
ATOM   3960  CB  HIS b 285      3.223  11.437 -61.877  0.50 38.55           C
ATOM   3961  CG  HIS b 285      4.176  12.261 -62.687  0.50 39.03           C
ATOM   3962  ND1 HIS b 285      3.811  12.874 -63.867  0.50 39.55           N
ATOM   3963  CE1 HIS b 285      4.843  13.541 -64.353  0.50 38.04           C
ATOM   3964  NE2 HIS b 285      5.867  13.377 -63.535  0.50 40.44           N
ATOM   3965  CD2 HIS b 285      5.477  12.580 -62.485  0.50 39.49           C
ATOM   3966  C   HIS b 285      1.143  11.325 -60.469  0.50 37.65           C
ATOM   3967  O   HIS b 285      0.812  10.225 -60.906  0.50 40.19           O
ATOM   3968  N   ASN b 286      0.731  11.771 -59.287  0.50 37.79           N
ATOM   3969  CA  ASN b 286     -0.012  10.891 -58.380  0.50 36.59           C
ATOM   3970  CB  ASN b 286      0.642  10.873 -56.993  0.50 37.40           C
ATOM   3971  CG  ASN b 286      0.758  12.258 -56.382  0.50 38.38           C
ATOM   3972  OD1 ASN b 286      0.944  13.247 -57.091  0.50 39.57           O
ATOM   3973  ND2 ASN b 286      0.666  12.332 -55.057  0.50 36.25           N
ATOM   3974  C   ASN b 286     -1.532  11.111 -58.251  0.50 36.74           C
ATOM   3975  O   ASN b 286     -2.150  10.639 -57.292  0.50 34.77           O
ATOM   3976  N   ALA b 287     -2.143  11.790 -59.216  0.50 35.87           N
ATOM   3977  CA  ALA b 287     -3.597  11.964 -59.202  0.50 36.94           C
ATOM   3978  CB  ALA b 287     -4.011  13.036 -60.197  0.50 34.98           C
ATOM   3979  C   ALA b 287     -4.331  10.649 -59.482  0.50 37.92           C
ATOM   3980  O   ALA b 287     -3.817   9.789 -60.197  0.50 37.96           O
ATOM   3981  N   LYS b 288     -5.524  10.497 -58.912  0.50 35.98           N
ATOM   3982  CA  LYS b 288     -6.296   9.261 -59.046  0.50 36.80           C
ATOM   3983  CB  LYS b 288     -6.460   8.568 -57.692  0.50 40.25           C
ATOM   3984  CG  LYS b 288     -5.291   8.741 -56.731  0.50 43.55           C
ATOM   3985  CD  LYS b 288     -3.996   8.165 -57.277  0.50 45.01           C
ATOM   3986  CE  LYS b 288     -2.928   8.095 -56.196  0.50 46.76           C
ATOM   3987  NZ  LYS b 288     -1.649   7.539 -56.720  0.50 49.45           N
ATOM   3988  C   LYS b 288     -7.676   9.518 -59.652  0.50 35.29           C
ATOM   3989  O   LYS b 288     -8.449  10.330 -59.129  0.50 32.20           O
ATOM   3990  N   THR b 289     -7.988   8.806 -60.737  0.50 32.49           N
ATOM   3991  CA  THR b 289     -9.251   8.997 -61.458  0.50 31.84           C
ATOM   3992  CB  THR b 289     -9.072   8.789 -62.974  0.50 32.52           C
ATOM   3993  OG1 THR b 289     -8.024   9.640 -63.463  0.50 32.73           O
ATOM   3994  CG2 THR b 289    -10.368   9.104 -63.711  0.50 32.25           C
ATOM   3995  C   THR b 289    -10.371   8.073 -60.976  0.50 33.11           C
ATOM   3996  O   THR b 289    -10.212   6.855 -60.937  0.50 33.37           O
ATOM   3997  N   LYS b 290    -11.510   8.659 -60.619  0.50 33.64           N
ATOM   3998  CA  LYS b 290    -12.680   7.882 -60.235  0.50 36.31           C
ATOM   3999  CB  LYS b 290    -13.697   8.759 -59.502  0.50 36.95           C
ATOM   4000  CG  LYS b 290    -13.157   9.556 -58.325  0.50 38.82           C
ATOM   4001  CD  LYS b 290    -14.317  10.143 -57.531  0.50 39.84           C
ATOM   4002  CE  LYS b 290    -13.940  11.432 -56.825  0.50 38.99           C
ATOM   4003  NZ  LYS b 290    -15.135  12.252 -56.472  0.50 41.74           N
ATOM   4004  C   LYS b 290    -13.345   7.297 -61.477  0.50 37.07           C
ATOM   4005  O   LYS b 290    -13.113   7.765 -62.595  0.50 36.34           O
ATOM   4006  N   PRO b 291    -14.207   6.294 -61.282  0.50 39.78           N
ATOM   4007  CA  PRO b 291    -14.902   5.688 -62.415  0.50 41.67           C
ATOM   4008  CB  PRO b 291    -15.761   4.591 -61.768  0.50 41.25           C
ATOM   4009  CG  PRO b 291    -15.289   4.465 -60.354  0.50 41.63           C
ATOM   4010  CD  PRO b 291    -14.698   5.793 -59.990  0.50 39.83           C
ATOM   4011  C   PRO b 291    -15.795   6.710 -63.109  0.50 43.07           C
ATOM   4012  O   PRO b 291    -16.530   7.443 -62.438  0.50 41.07           O
ATOM   4013  N   ARG b 292    -15.729   6.757 -64.439  0.50 46.55           N
ATOM   4014  CA  ARG b 292    -16.565   7.667 -65.224  0.50 48.80           C
ATOM   4015  CB  ARG b 292    -16.389   7.433 -66.732  0.50 52.05           C
ATOM   4016  CG  ARG b 292    -14.966   7.615 -67.245  0.50 55.94           C
ATOM   4017  CD  ARG b 292    -14.935   8.170 -68.667  0.50 59.09           C
ATOM   4018  NE  ARG b 292    -15.441   7.228 -69.666  0.50 58.82           N
```

Figure 27 (Continued)

```
ATOM   4019  CZ   ARG b 292    -14.698    6.681  -70.625  0.50  57.98           C
ATOM   4020  NH1  ARG b 292    -13.411    6.983  -70.725  0.50  57.28           N
ATOM   4021  NH2  ARG b 292    -15.244    5.836  -71.489  0.50  57.57           N
ATOM   4022  C    ARG b 292    -18.030    7.500  -64.831  0.50  47.06           C
ATOM   4023  O    ARG b 292    -18.480    6.396  -64.518  0.50  44.47           O
ATOM   4024  N    GLU b 293    -18.775    8.598  -64.858  0.50  47.60           N
ATOM   4025  CA   GLU b 293    -20.146    8.581  -64.367  0.50  47.57           C
ATOM   4026  CB   GLU b 293    -20.277    9.478  -63.134  0.50  47.06           C
ATOM   4027  CG   GLU b 293    -21.521    9.215  -62.307  0.50  49.41           C
ATOM   4028  CD   GLU b 293    -21.358    9.638  -60.862  0.50  49.98           C
ATOM   4029  OE1  GLU b 293    -22.153    9.184  -60.013  0.50  50.77           O
ATOM   4030  OE2  GLU b 293    -20.424   10.416  -60.571  0.50  51.61           O
ATOM   4031  C    GLU b 293    -21.151    8.995  -65.437  0.50  46.63           C
ATOM   4032  O    GLU b 293    -21.245   10.169  -65.796  0.50  44.91           O
ATOM   4033  N    GLU b 294    -21.905    8.021  -65.939  0.50  47.02           N
ATOM   4034  CA   GLU b 294    -22.962    8.298  -66.898  0.50  44.09           C
ATOM   4035  CB   GLU b 294    -23.662    7.000  -67.307  0.50  45.01           C
ATOM   4036  CG   GLU b 294    -24.935    7.204  -68.112  0.50  48.33           C
ATOM   4037  CD   GLU b 294    -24.659    7.574  -69.556  0.50  48.55           C
ATOM   4038  OE1  GLU b 294    -23.470    7.665  -69.930  0.50  49.73           O
ATOM   4039  OE2  GLU b 294    -25.631    7.773  -70.317  0.50  50.98           O
ATOM   4040  C    GLU b 294    -23.971    9.263  -66.287  0.50  41.70           C
ATOM   4041  O    GLU b 294    -24.605    8.953  -65.277  0.50  41.99           O
ATOM   4042  N    GLN b 295    -24.106   10.440  -66.887  0.50  38.68           N
ATOM   4043  CA   GLN b 295    -25.099   11.407  -66.432  0.50  37.86           C
ATOM   4044  CB   GLN b 295    -24.670   12.839  -66.766  0.50  36.56           C
ATOM   4045  CG   GLN b 295    -23.312   13.224  -66.194  0.50  35.48           C
ATOM   4046  CD   GLN b 295    -23.173   12.816  -64.744  0.50  35.25           C
ATOM   4047  OE1  GLN b 295    -23.791   13.408  -63.864  0.50  33.94           O
ATOM   4048  NE2  GLN b 295    -22.376   11.786  -64.492  0.50  33.74           N
ATOM   4049  C    GLN b 295    -26.445   11.105  -67.071  0.50  39.12           C
ATOM   4050  O    GLN b 295    -26.518   10.433  -68.108  0.50  39.26           O
ATOM   4051  N    TYR b 296    -27.510   11.605  -66.456  0.50  38.70           N
ATOM   4052  CA   TYR b 296    -28.845   11.385  -66.996  0.50  38.14           C
ATOM   4053  CB   TYR b 296    -29.921   11.833  -66.008  0.50  40.81           C
ATOM   4054  CG   TYR b 296    -30.085   10.884  -64.847  0.50  43.43           C
ATOM   4055  CD1  TYR b 296    -30.011   11.336  -63.534  0.50  45.74           C
ATOM   4056  CE1  TYR b 296    -30.155   10.463  -62.468  0.50  47.82           C
ATOM   4057  CZ   TYR b 296    -30.363    9.117  -62.709  0.50  48.50           C
ATOM   4058  OH   TYR b 296    -30.502    8.240  -61.656  0.50  49.08           O
ATOM   4059  CE2  TYR b 296    -30.431    8.648  -64.003  0.50  46.34           C
ATOM   4060  CD2  TYR b 296    -30.287    9.526  -65.062  0.50  45.32           C
ATOM   4061  C    TYR b 296    -29.003   12.085  -68.338  0.50  35.73           C
ATOM   4062  O    TYR b 296    -29.879   11.731  -69.124  0.50  34.30           O
ATOM   4063  N    ASN b 297    -28.144   13.069  -68.598  0.50  33.70           N
ATOM   4064  CA   ASN b 297    -28.139   13.754  -69.887  0.50  31.70           C
ATOM   4065  CB   ASN b 297    -27.936   15.255  -69.724  0.50  33.15           C
ATOM   4066  CG   ASN b 297    -26.492   15.527  -69.060  0.50  32.38           C
ATOM   4067  OD1  ASN b 297    -25.527   14.791  -69.250  0.50  30.64           O
ATOM   4068  ND2  ASN b 297    -26.421   16.621  -68.306  0.50  33.18           N
ATOM   4069  C    ASN b 297    -27.250   13.086  -70.943  0.50  34.00           C
ATOM   4070  O    ASN b 297    -26.858   13.712  -71.934  0.50  30.32           O
ATOM   4071  N    SER b 298    -26.962   11.802  -70.729  0.50  34.11           N
ATOM   4072  CA   SER b 298    -26.231   10.976  -71.693  0.50  36.21           C
ATOM   4073  CB   SER b 298    -27.001   10.866  -73.016  0.50  37.80           C
ATOM   4074  OG   SER b 298    -27.926    9.794  -72.977  0.50  40.30           O
ATOM   4075  C    SER b 298    -24.808   11.459  -71.953  0.50  35.87           C
ATOM   4076  O    SER b 298    -24.231   11.188  -73.000  0.50  35.75           O
ATOM   4077  N    THR b 299    -24.246   12.181  -70.994  0.50  34.92           N
ATOM   4078  CA   THR b 299    -22.891   12.694  -71.133  0.50  33.37           C
ATOM   4079  CB   THR b 299    -22.843   14.217  -70.930  0.50  33.24           C
ATOM   4080  OG1  THR b 299    -23.231   14.532  -69.582  0.50  30.92           O
ATOM   4081  CG2  THR b 299    -23.784   14.906  -71.900  0.50  33.28           C
ATOM   4082  C    THR b 299    -22.016   12.058  -70.078  0.50  32.70           C
```

Figure 27 (Continued)

```
ATOM   4083  O    THR b 299     -22.502  11.328 -69.208  0.50 32.26           O
ATOM   4084  N    TYR b 300     -20.722  12.339 -70.159  0.50 34.17           N
ATOM   4085  CA   TYR b 300     -19.780  11.830 -69.189  0.50 34.19           C
ATOM   4086  CB   TYR b 300     -18.601  11.154 -69.893  0.50 35.91           C
ATOM   4087  CG   TYR b 300     -18.898   9.748 -70.385  0.50 38.39           C
ATOM   4088  CD1  TYR b 300     -18.909   9.448 -71.747  0.50 39.53           C
ATOM   4089  CE1  TYR b 300     -19.174   8.163 -72.197  0.50 39.63           C
ATOM   4090  CZ   TYR b 300     -19.436   7.158 -71.287  0.50 40.46           C
ATOM   4091  OH   TYR b 300     -19.705   5.876 -71.726  0.50 39.99           O
ATOM   4092  CE2  TYR b 300     -19.429   7.431 -69.932  0.50 42.22           C
ATOM   4093  CD2  TYR b 300     -19.161   8.718 -69.490  0.50 39.86           C
ATOM   4094  C    TYR b 300     -19.295  12.950 -68.273  0.50 31.14           C
ATOM   4095  O    TYR b 300     -18.876  14.006 -68.742  0.50 30.41           O
ATOM   4096  N    ARG b 301     -19.404  12.714 -66.968  0.50 30.94           N
ATOM   4097  CA   ARG b 301     -18.737  13.523 -65.938  0.50 28.16           C
ATOM   4098  CB   ARG b 301     -19.715  13.874 -64.813  0.50 28.53           C
ATOM   4099  CG   ARG b 301     -19.139  14.693 -63.655  0.50 25.92           C
ATOM   4100  CD   ARG b 301     -20.232  14.972 -62.629  0.50 26.82           C
ATOM   4101  NE   ARG b 301     -19.829  15.875 -61.542  0.50 25.41           N
ATOM   4102  CZ   ARG b 301     -19.407  15.468 -60.346  0.50 26.11           C
ATOM   4103  NH1  ARG b 301     -19.321  14.173 -60.075  0.50 24.82           N
ATOM   4104  NH2  ARG b 301     -19.086  16.358 -59.418  0.50 24.06           N
ATOM   4105  C    ARG b 301     -17.624  12.655 -65.383  0.50 27.91           C
ATOM   4106  O    ARG b 301     -17.878  11.554 -64.897  0.50 28.58           O
ATOM   4107  N    VAL b 302     -16.391  13.143 -65.472  0.50 26.66           N
ATOM   4108  CA   VAL b 302     -15.238  12.380 -65.028  0.50 24.82           C
ATOM   4109  CB   VAL b 302     -14.313  12.034 -66.217  0.50 26.21           C
ATOM   4110  CG1  VAL b 302     -13.160  11.147 -65.774  0.50 26.99           C
ATOM   4111  CG2  VAL b 302     -15.104  11.348 -67.329  0.50 26.34           C
ATOM   4112  C    VAL b 302     -14.466  13.221 -64.014  0.50 24.49           C
ATOM   4113  O    VAL b 302     -14.100  14.362 -64.297  0.50 25.39           O
ATOM   4114  N    VAL b 303     -14.204  12.643 -62.848  0.50 22.68           N
ATOM   4115  CA   VAL b 303     -13.566  13.380 -61.756  0.50 21.43           C
ATOM   4116  CB   VAL b 303     -14.370  13.247 -60.452  0.50 22.39           C
ATOM   4117  CG1  VAL b 303     -13.678  14.034 -59.341  0.50 21.67           C
ATOM   4118  CG2  VAL b 303     -15.800  13.736 -60.638  0.50 22.67           C
ATOM   4119  C    VAL b 303     -12.153  12.876 -61.505  0.50 22.31           C
ATOM   4120  O    VAL b 303     -11.946  11.666 -61.332  0.50 21.67           O
ATOM   4121  N    SER b 304     -11.192  13.800 -61.489  0.50 22.58           N
ATOM   4122  CA   SER b 304      -9.790  13.511 -61.111  0.50 24.10           C
ATOM   4123  CB   SER b 304      -8.825  14.139 -62.122  0.50 24.07           C
ATOM   4124  OG   SER b 304      -7.467  13.784 -61.861  0.50 26.09           O
ATOM   4125  C    SER b 304      -9.504  14.127 -59.743  0.50 25.09           C
ATOM   4126  O    SER b 304      -9.931  15.257 -59.477  0.50 23.01           O
ATOM   4127  N    VAL b 305      -8.757  13.404 -58.907  0.50 25.91           N
ATOM   4128  CA   VAL b 305      -8.423  13.879 -57.565  0.50 26.62           C
ATOM   4129  CB   VAL b 305      -9.175  13.087 -56.484  0.50 28.30           C
ATOM   4130  CG1  VAL b 305      -8.734  13.527 -55.091  0.50 28.13           C
ATOM   4131  CG2  VAL b 305     -10.684  13.248 -56.653  0.50 29.69           C
ATOM   4132  C    VAL b 305      -6.924  13.848 -57.259  0.50 26.83           C
ATOM   4133  O    VAL b 305      -6.220  12.866 -57.532  0.50 26.58           O
ATOM   4134  N    LEU b 306      -6.447  14.936 -56.671  0.50 24.77           N
ATOM   4135  CA   LEU b 306      -5.057  15.030 -56.260  0.50 24.02           C
ATOM   4136  CB   LEU b 306      -4.383  16.239 -56.917  0.50 23.52           C
ATOM   4137  CG   LEU b 306      -2.894  16.405 -56.586  0.50 23.38           C
ATOM   4138  CD1  LEU b 306      -2.148  15.085 -56.724  0.50 24.07           C
ATOM   4139  CD2  LEU b 306      -2.228  17.489 -57.429  0.50 23.56           C
ATOM   4140  C    LEU b 306      -4.971  15.134 -54.737  0.50 22.65           C
ATOM   4141  O    LEU b 306      -5.746  15.865 -54.107  0.50 19.36           O
ATOM   4142  N    THR b 307      -4.049  14.382 -54.144  0.50 21.61           N
ATOM   4143  CA   THR b 307      -3.745  14.580 -52.736  0.50 23.77           C
ATOM   4144  CB   THR b 307      -2.967  13.411 -52.135  0.50 24.93           C
ATOM   4145  OG1  THR b 307      -3.772  12.231 -52.204  0.50 29.17           O
ATOM   4146  CG2  THR b 307      -2.631  13.707 -50.673  0.50 26.33           C
```

Figure 27 (Continued)

```
ATOM   4147  C    THR b 307      -2.889  15.821 -52.634  0.50 22.91           C
ATOM   4148  O    THR b 307      -2.021  16.051 -53.472  0.50 25.32           O
ATOM   4149  N    VAL b 308      -3.144  16.629 -51.615  0.50 21.06           N
ATOM   4150  CA   VAL b 308      -2.325  17.798 -51.387  0.50 18.96           C
ATOM   4151  CB   VAL b 308      -3.168  19.086 -51.393  0.50 18.01           C
ATOM   4152  CG1  VAL b 308      -3.780  19.334 -52.761  0.50 18.22           C
ATOM   4153  CG2  VAL b 308      -4.262  18.980 -50.366  0.50 17.33           C
ATOM   4154  C    VAL b 308      -1.664  17.606 -50.032  0.50 18.56           C
ATOM   4155  O    VAL b 308      -2.271  17.051 -49.106  0.50 18.94           O
ATOM   4156  N    LEU b 309      -0.407  18.030 -49.941  0.50 19.04           N
ATOM   4157  CA   LEU b 309       0.277  18.162 -48.659  0.50 18.73           C
ATOM   4158  CB   LEU b 309       1.785  18.278 -48.900  0.50 20.71           C
ATOM   4159  CG   LEU b 309       2.355  17.149 -49.774  0.50 21.75           C
ATOM   4160  CD1  LEU b 309       3.853  17.358 -49.984  0.50 23.10           C
ATOM   4161  CD2  LEU b 309       2.043  15.774 -49.189  0.50 22.55           C
ATOM   4162  C    LEU b 309      -0.254  19.404 -47.928  0.50 18.77           C
ATOM   4163  O    LEU b 309      -0.348  20.482 -48.522  0.50 18.06           O
ATOM   4164  N    HIS b 310      -0.605  19.232 -46.649  0.50 17.02           N
ATOM   4165  CA   HIS b 310      -1.239  20.280 -45.840  0.50 18.77           C
ATOM   4166  CB   HIS b 310      -1.293  19.881 -44.354  0.50 18.00           C
ATOM   4167  CG   HIS b 310      -2.181  18.712 -44.059  0.50 18.18           C
ATOM   4168  ND1  HIS b 310      -1.830  17.420 -44.379  0.50 18.36           N
ATOM   4169  CE1  HIS b 310      -2.797  16.598 -44.013  0.50 18.08           C
ATOM   4170  NE2  HIS b 310      -3.753  17.305 -43.441  0.50 18.47           N
ATOM   4171  CD2  HIS b 310      -3.398  18.637 -43.464  0.50 18.18           C
ATOM   4172  C    HIS b 310      -0.453  21.572 -45.938  0.50 18.72           C
ATOM   4173  O    HIS b 310      -1.002  22.644 -46.210  0.50 18.71           O
ATOM   4174  N    GLN b 311       0.840  21.470 -45.656  0.50 21.06           N
ATOM   4175  CA   GLN b 311       1.695  22.651 -45.646  0.50 21.67           C
ATOM   4176  CB   GLN b 311       3.043  22.355 -44.977  0.50 23.75           C
ATOM   4177  CG   GLN b 311       3.841  21.225 -45.607  0.50 27.78           C
ATOM   4178  CD   GLN b 311       3.628  19.871 -44.936  0.50 29.64           C
ATOM   4179  OE1  GLN b 311       2.493  19.443 -44.667  0.50 27.61           O
ATOM   4180  NE2  GLN b 311       4.730  19.164 -44.701  0.50 30.34           N
ATOM   4181  C    GLN b 311       1.880  23.275 -47.047  0.50 21.01           C
ATOM   4182  O    GLN b 311       1.961  24.492 -47.154  0.50 21.41           O
ATOM   4183  N    ASP b 312       1.908  22.457 -48.100  0.50 20.53           N
ATOM   4184  CA   ASP b 312       1.962  22.980 -49.487  0.50 20.00           C
ATOM   4185  CB   ASP b 312       1.937  21.843 -50.512  0.50 21.65           C
ATOM   4186  CG   ASP b 312       3.297  21.189 -50.734  0.50 24.12           C
ATOM   4187  OD1  ASP b 312       4.305  21.574 -50.091  0.50 24.23           O
ATOM   4188  OD2  ASP b 312       3.350  20.280 -51.589  0.50 24.33           O
ATOM   4189  C    ASP b 312       0.751  23.878 -49.744  0.50 19.93           C
ATOM   4190  O    ASP b 312       0.877  25.031 -50.192  0.50 19.21           O
ATOM   4191  N    TRP b 313      -0.431  23.362 -49.434  0.50 17.95           N
ATOM   4192  CA   TRP b 313      -1.650  24.146 -49.616  0.50 17.80           C
ATOM   4193  CB   TRP b 313      -2.901  23.324 -49.273  0.50 17.46           C
ATOM   4194  CG   TRP b 313      -4.154  24.107 -49.514  0.50 17.12           C
ATOM   4195  CD1  TRP b 313      -4.901  24.755 -48.576  0.50 16.94           C
ATOM   4196  NE1  TRP b 313      -5.960  25.390 -49.175  0.50 17.67           N
ATOM   4197  CE2  TRP b 313      -5.922  25.149 -50.523  0.50 16.89           C
ATOM   4198  CD2  TRP b 313      -4.786  24.353 -50.779  0.50 16.66           C
ATOM   4199  CE3  TRP b 313      -4.504  23.971 -52.101  0.50 16.15           C
ATOM   4200  CZ3  TRP b 313      -5.371  24.414 -53.123  0.50 16.52           C
ATOM   4201  CH2  TRP b 313      -6.499  25.204 -52.822  0.50 17.62           C
ATOM   4202  CZ2  TRP b 313      -6.775  25.598 -51.536  0.50 17.91           C
ATOM   4203  C    TRP b 313      -1.655  25.441 -48.789  0.50 17.94           C
ATOM   4204  O    TRP b 313      -1.936  26.518 -49.319  0.50 16.84           O
ATOM   4205  N    LEU b 314      -1.389  25.323 -47.482  0.50 16.72           N
ATOM   4206  CA   LEU b 314      -1.364  26.498 -46.611  0.50 16.33           C
ATOM   4207  CB   LEU b 314      -1.138  26.110 -45.147  0.50 16.76           C
ATOM   4208  CG   LEU b 314      -2.335  25.333 -44.579  0.50 15.81           C
ATOM   4209  CD1  LEU b 314      -2.205  25.045 -43.076  0.50 16.30           C
ATOM   4210  CD2  LEU b 314      -3.646  26.035 -44.874  0.50 16.24           C
```

Figure 27 (Continued)

```
ATOM   4211  C    LEU b 314      -0.328  27.551 -47.033  0.50 17.27           C
ATOM   4212  O    LEU b 314      -0.553  28.748 -46.843  0.50 16.46           O
ATOM   4213  N    ASN b 315       0.773  27.089 -47.609  0.50 17.12           N
ATOM   4214  CA   ASN b 315       1.880  27.966 -48.017  0.50 17.40           C
ATOM   4215  CB   ASN b 315       3.203  27.212 -47.943  0.50 17.71           C
ATOM   4216  CG   ASN b 315       3.728  27.077 -46.538  0.50 18.53           C
ATOM   4217  OD1  ASN b 315       3.297  27.764 -45.620  0.50 18.20           O
ATOM   4218  ND2  ASN b 315       4.688  26.188 -46.369  0.50 18.66           N
ATOM   4219  C    ASN b 315       1.712  28.492 -49.436  0.50 18.36           C
ATOM   4220  O    ASN b 315       2.670  29.033 -50.037  0.50 17.42           O
ATOM   4221  N    GLY b 316       0.508  28.338 -49.980  0.50 17.75           N
ATOM   4222  CA   GLY b 316       0.128  29.088 -51.184  0.50 19.71           C
ATOM   4223  C    GLY b 316       0.538  28.502 -52.516  0.50 21.04           C
ATOM   4224  O    GLY b 316       0.438  29.180 -53.549  0.50 21.94           O
ATOM   4225  N    LYS b 317       0.983  27.247 -52.528  0.50 20.45           N
ATOM   4226  CA   LYS b 317       1.254  26.598 -53.801  0.50 21.58           C
ATOM   4227  CB   LYS b 317       1.781  25.168 -53.602  0.50 21.93           C
ATOM   4228  CG   LYS b 317       3.158  25.100 -52.926  0.50 21.36           C
ATOM   4229  CD   LYS b 317       3.984  23.956 -53.501  0.50 22.86           C
ATOM   4230  CE   LYS b 317       5.284  23.729 -52.738  0.50 24.46           C
ATOM   4231  NZ   LYS b 317       6.241  22.870 -53.501  0.50 25.98           N
ATOM   4232  C    LYS b 317       0.005  26.639 -54.694  0.50 21.02           C
ATOM   4233  O    LYS b 317      -1.133  26.625 -54.206  0.50 20.20           O
ATOM   4234  N    GLU b 318       0.219  26.727 -56.005  0.50 21.87           N
ATOM   4235  CA   GLU b 318      -0.886  26.753 -56.964  0.50 22.97           C
ATOM   4236  CB   GLU b 318      -0.687  27.856 -58.019  0.50 25.71           C
ATOM   4237  CG   GLU b 318      -0.777  29.265 -57.470  0.50 28.08           C
ATOM   4238  CD   GLU b 318      -0.465  30.325 -58.512  0.50 32.80           C
ATOM   4239  OE1  GLU b 318       0.572  31.014 -58.359  0.50 31.83           O
ATOM   4240  OE2  GLU b 318      -1.247  30.465 -59.484  0.50 33.63           O
ATOM   4241  C    GLU b 318      -1.000  25.411 -57.655  0.50 21.85           C
ATOM   4242  O    GLU b 318      -0.001  24.843 -58.106  0.50 24.29           O
ATOM   4243  N    TYR b 319      -2.222  24.898 -57.731  0.50 21.69           N
ATOM   4244  CA   TYR b 319      -2.456  23.565 -58.274  0.50 21.42           C
ATOM   4245  CB   TYR b 319      -3.339  22.754 -57.313  0.50 21.73           C
ATOM   4246  CG   TYR b 319      -2.617  22.462 -56.021  0.50 21.44           C
ATOM   4247  CD1  TYR b 319      -2.482  23.444 -55.046  0.50 21.64           C
ATOM   4248  CE1  TYR b 319      -1.770  23.208 -53.880  0.50 20.84           C
ATOM   4249  CZ   TYR b 319      -1.208  21.967 -53.670  0.50 21.26           C
ATOM   4250  OH   TYR b 319      -0.523  21.718 -52.494  0.50 21.02           O
ATOM   4251  CE2  TYR b 319      -1.321  20.972 -54.625  0.50 21.47           C
ATOM   4252  CD2  TYR b 319      -2.021  21.225 -55.796  0.50 20.94           C
ATOM   4253  C    TYR b 319      -3.095  23.703 -59.637  0.50 22.64           C
ATOM   4254  O    TYR b 319      -4.116  24.370 -59.777  0.50 22.72           O
ATOM   4255  N    LYS b 320      -2.464  23.099 -60.640  0.50 23.28           N
ATOM   4256  CA   LYS b 320      -2.942  23.188 -62.013  0.50 23.93           C
ATOM   4257  CB   LYS b 320      -1.821  23.601 -62.979  0.50 22.54           C
ATOM   4258  CG   LYS b 320      -2.303  23.679 -64.421  0.50 22.34           C
ATOM   4259  CD   LYS b 320      -1.448  24.627 -65.255  0.50 23.38           C
ATOM   4260  CE   LYS b 320      -0.349  23.893 -65.998  0.50 25.87           C
ATOM   4261  NZ   LYS b 320       0.424  24.851 -66.852  0.50 26.45           N
ATOM   4262  C    LYS b 320      -3.566  21.911 -62.504  0.50 24.40           C
ATOM   4263  O    LYS b 320      -2.947  20.837 -62.477  0.50 27.36           O
ATOM   4264  N    CYS b 321      -4.811  22.039 -62.954  0.50 24.53           N
ATOM   4265  CA   CYS b 321      -5.455  20.996 -63.706  0.50 25.19           C
ATOM   4266  CB   CYS b 321      -6.857  20.719 -63.169  0.50 24.93           C
ATOM   4267  SG   CYS b 321      -7.602  19.296 -63.973  0.50 26.33           S
ATOM   4268  C    CYS b 321      -5.528  21.433 -65.159  0.50 24.34           C
ATOM   4269  O    CYS b 321      -6.124  22.470 -65.480  0.50 21.39           O
ATOM   4270  N    LYS b 322      -4.893  20.637 -66.017  0.50 24.78           N
ATOM   4271  CA   LYS b 322      -5.017  20.749 -67.463  0.50 24.95           C
ATOM   4272  CB   LYS b 322      -3.629  20.930 -68.073  0.50 26.31           C
ATOM   4273  CG   LYS b 322      -3.612  21.294 -69.545  0.50 26.63           C
ATOM   4274  CD   LYS b 322      -2.183  21.567 -70.019  0.50 28.93           C
```

Figure 27 (Continued)

```
ATOM   4275  CE   LYS b 322      -1.429  20.276 -70.308  0.50 31.70           C
ATOM   4276  NZ   LYS b 322      -0.056  20.514 -70.837  0.50 33.47           N
ATOM   4277  C    LYS b 322      -5.637  19.435 -67.945  0.50 24.97           C
ATOM   4278  O    LYS b 322      -5.167  18.346 -67.596  0.50 25.00           O
ATOM   4279  N    VAL b 323      -6.697  19.535 -68.741  0.50 26.62           N
ATOM   4280  CA   VAL b 323      -7.423  18.337 -69.189  0.50 26.07           C
ATOM   4281  CB   VAL b 323      -8.893  18.401 -68.765  0.50 25.40           C
ATOM   4282  CG1  VAL b 323      -9.018  18.175 -67.261  0.50 23.36           C
ATOM   4283  CG2  VAL b 323      -9.472  19.746 -69.145  0.50 26.63           C
ATOM   4284  C    VAL b 323      -7.392  18.194 -70.705  0.50 28.03           C
ATOM   4285  O    VAL b 323      -7.372  19.194 -71.424  0.50 28.81           O
ATOM   4286  N    SER b 324      -7.399  16.945 -71.166  0.50 29.27           N
ATOM   4287  CA   SER b 324      -7.311  16.657 -72.601  0.50 31.00           C
ATOM   4288  CB   SER b 324      -5.955  16.046 -72.956  0.50 27.03           C
ATOM   4289  OG   SER b 324      -4.904  16.976 -72.739  0.50 27.08           O
ATOM   4290  C    SER b 324      -8.446  15.768 -73.081  0.50 33.15           C
ATOM   4291  O    SER b 324      -8.849  14.804 -72.415  0.50 34.54           O
ATOM   4292  N    ASN b 325      -8.949  16.096 -74.262  0.50 36.35           N
ATOM   4293  CA   ASN b 325     -10.076  15.398 -74.838  0.50 37.46           C
ATOM   4294  CB   ASN b 325     -11.372  15.934 -74.234  0.50 36.65           C
ATOM   4295  CG   ASN b 325     -12.601  15.223 -74.759  0.50 36.50           C
ATOM   4296  OD1  ASN b 325     -13.373  15.789 -75.535  0.50 37.72           O
ATOM   4297  ND2  ASN b 325     -12.796  13.981 -74.332  0.50 35.78           N
ATOM   4298  C    ASN b 325     -10.052  15.671 -76.334  0.50 40.10           C
ATOM   4299  O    ASN b 325      -9.716  16.782 -76.757  0.50 38.42           O
ATOM   4300  N    LYS b 326     -10.396  14.660 -77.126  0.50 43.60           N
ATOM   4301  CA   LYS b 326     -10.428  14.811 -78.580  0.50 47.47           C
ATOM   4302  CB   LYS b 326     -10.838  13.496 -79.245  0.50 49.49           C
ATOM   4303  CG   LYS b 326      -9.929  12.321 -78.913  0.50 52.79           C
ATOM   4304  CD   LYS b 326     -10.470  11.026 -79.499  0.50 54.51           C
ATOM   4305  CE   LYS b 326      -9.684   9.817 -79.016  0.50 54.70           C
ATOM   4306  NZ   LYS b 326      -8.281   9.827 -79.517  0.50 55.06           N
ATOM   4307  C    LYS b 326     -11.374  15.931 -79.008  0.50 46.97           C
ATOM   4308  O    LYS b 326     -11.124  16.622 -79.996  0.50 49.00           O
ATOM   4309  N    ALA b 327     -12.451  16.118 -78.249  0.50 47.29           N
ATOM   4310  CA   ALA b 327     -13.472  17.103 -78.602  0.50 46.41           C
ATOM   4311  CB   ALA b 327     -14.799  16.755 -77.942  0.50 46.80           C
ATOM   4312  C    ALA b 327     -13.058  18.529 -78.256  0.50 44.80           C
ATOM   4313  O    ALA b 327     -13.761  19.483 -78.577  0.50 45.13           O
ATOM   4314  N    LEU b 328     -11.922  18.669 -77.586  0.50 44.72           N
ATOM   4315  CA   LEU b 328     -11.426  19.988 -77.213  0.50 44.51           C
ATOM   4316  CB   LEU b 328     -10.808  19.948 -75.816  0.50 43.53           C
ATOM   4317  CG   LEU b 328     -11.762  20.001 -74.624  0.50 42.74           C
ATOM   4318  CD1  LEU b 328     -10.945  20.141 -73.348  0.50 41.47           C
ATOM   4319  CD2  LEU b 328     -12.720  21.170 -74.775  0.50 42.89           C
ATOM   4320  C    LEU b 328     -10.377  20.455 -78.203  0.50 43.93           C
ATOM   4321  O    LEU b 328      -9.397  19.754 -78.440  0.50 45.01           O
ATOM   4322  N    PRO b 329     -10.566  21.650 -78.775  0.50 43.88           N
ATOM   4323  CA   PRO b 329      -9.516  22.171 -79.644  0.50 44.08           C
ATOM   4324  CB   PRO b 329      -9.896  23.649 -79.829  0.50 43.76           C
ATOM   4325  CG   PRO b 329     -11.044  23.911 -78.900  0.50 42.50           C
ATOM   4326  CD   PRO b 329     -11.688  22.589 -78.622  0.50 44.37           C
ATOM   4327  C    PRO b 329      -8.151  22.029 -78.961  0.50 43.77           C
ATOM   4328  O    PRO b 329      -7.280  21.304 -79.449  0.50 43.60           O
ATOM   4329  N    ALA b 330      -7.987  22.708 -77.829  0.50 40.26           N
ATOM   4330  CA   ALA b 330      -6.803  22.559 -76.987  0.50 36.08           C
ATOM   4331  CB   ALA b 330      -6.097  23.899 -76.841  0.50 35.00           C
ATOM   4332  C    ALA b 330      -7.236  22.034 -75.615  0.50 33.87           C
ATOM   4333  O    ALA b 330      -8.402  22.167 -75.243  0.50 33.88           O
ATOM   4334  N    PRO b 331      -6.309  21.424 -74.862  0.50 32.90           N
ATOM   4335  CA   PRO b 331      -6.704  21.039 -73.507  0.50 32.07           C
ATOM   4336  CB   PRO b 331      -5.388  20.576 -72.892  0.50 32.19           C
ATOM   4337  CG   PRO b 331      -4.666  19.975 -74.047  0.50 32.44           C
ATOM   4338  CD   PRO b 331      -5.047  20.787 -75.261  0.50 31.84           C
```

Figure 27 (Continued)

```
ATOM   4339  C    PRO b 331      -7.278  22.208 -72.717  0.50 30.48           C
ATOM   4340  O    PRO b 331      -7.045  23.366 -73.076  0.50 31.31           O
ATOM   4341  N    ILE b 332      -8.034  21.898 -71.659  0.50 27.56           N
ATOM   4342  CA   ILE b 332      -8.497  22.903 -70.703  0.50 27.77           C
ATOM   4343  CB   ILE b 332      -9.944  22.637 -70.240  0.50 26.30           C
ATOM   4344  CG1  ILE b 332     -10.935  22.865 -71.384  0.50 26.60           C
ATOM   4345  CD1  ILE b 332     -12.269  22.168 -71.215  0.50 25.53           C
ATOM   4346  CG2  ILE b 332     -10.296  23.526 -69.053  0.50 26.03           C
ATOM   4347  C    ILE b 332      -7.592  22.906 -69.472  0.50 26.44           C
ATOM   4348  O    ILE b 332      -7.218  21.843 -68.974  0.50 25.54           O
ATOM   4349  N    GLU b 333      -7.207  24.099 -69.021  0.50 26.38           N
ATOM   4350  CA   GLU b 333      -6.382  24.256 -67.825  0.50 26.99           C
ATOM   4351  CB   GLU b 333      -5.078  24.971 -68.157  0.50 31.09           C
ATOM   4352  CG   GLU b 333      -4.074  24.112 -68.904  0.50 34.07           C
ATOM   4353  CD   GLU b 333      -2.827  24.886 -69.269  0.50 37.71           C
ATOM   4354  OE1  GLU b 333      -2.628  25.990 -68.713  0.50 39.52           O
ATOM   4355  OE2  GLU b 333      -2.055  24.396 -70.122  0.50 41.02           O
ATOM   4356  C    GLU b 333      -7.113  25.063 -66.765  0.50 26.81           C
ATOM   4357  O    GLU b 333      -7.780  26.060 -67.063  0.50 22.49           O
ATOM   4358  N    LYS b 334      -6.965  24.634 -65.515  0.50 25.52           N
ATOM   4359  CA   LYS b 334      -7.537  25.363 -64.409  0.50 24.92           C
ATOM   4360  CB   LYS b 334      -8.826  24.681 -63.937  0.50 23.90           C
ATOM   4361  CG   LYS b 334      -9.898  24.589 -65.021  0.50 25.17           C
ATOM   4362  CD   LYS b 334     -10.475  25.957 -65.365  0.50 25.14           C
ATOM   4363  CE   LYS b 334     -11.553  25.812 -66.429  0.50 24.76           C
ATOM   4364  NZ   LYS b 334     -12.121  27.132 -66.806  0.50 27.44           N
ATOM   4365  C    LYS b 334      -6.508  25.409 -63.290  0.50 23.48           C
ATOM   4366  O    LYS b 334      -5.780  24.441 -63.080  0.50 25.20           O
ATOM   4367  N    THR b 335      -6.444  26.537 -62.595  0.50 23.13           N
ATOM   4368  CA   THR b 335      -5.488  26.703 -61.484  0.50 24.10           C
ATOM   4369  CB   THR b 335      -4.267  27.550 -61.903  0.50 24.52           C
ATOM   4370  OG1  THR b 335      -3.526  26.858 -62.918  0.50 25.06           O
ATOM   4371  CG2  THR b 335      -3.346  27.811 -60.713  0.50 24.83           C
ATOM   4372  C    THR b 335      -6.121  27.284 -60.208  0.50 23.87           C
ATOM   4373  O    THR b 335      -6.779  28.338 -60.224  0.50 24.02           O
ATOM   4374  N    ILE b 336      -5.910  26.584 -59.101  0.50 24.09           N
ATOM   4375  CA   ILE b 336      -6.453  26.993 -57.812  0.50 23.49           C
ATOM   4376  CB   ILE b 336      -7.574  26.034 -57.368  0.50 24.62           C
ATOM   4377  CG1  ILE b 336      -8.328  26.576 -56.149  0.50 26.15           C
ATOM   4378  CD1  ILE b 336      -9.593  25.795 -55.843  0.50 26.27           C
ATOM   4379  CG2  ILE b 336      -7.017  24.634 -57.104  0.50 23.72           C
ATOM   4380  C    ILE b 336      -5.364  27.024 -56.737  0.50 23.63           C
ATOM   4381  O    ILE b 336      -4.386  26.284 -56.803  0.50 22.40           O
ATOM   4382  N    SER b 337      -5.569  27.886 -55.748  0.50 21.83           N
ATOM   4383  CA   SER b 337      -4.700  28.008 -54.580  0.50 22.33           C
ATOM   4384  CB   SER b 337      -3.489  28.905 -54.872  0.50 22.08           C
ATOM   4385  OG   SER b 337      -3.875  30.048 -55.620  0.50 21.53           O
ATOM   4386  C    SER b 337      -5.520  28.552 -53.413  0.50 20.56           C
ATOM   4387  O    SER b 337      -6.682  28.976 -53.585  0.50 22.45           O
ATOM   4388  N    LYS b 338      -4.943  28.514 -52.218  0.50 18.92           N
ATOM   4389  CA   LYS b 338      -5.614  29.063 -51.058  0.50 20.09           C
ATOM   4390  CB   LYS b 338      -4.789  28.881 -49.788  0.50 19.40           C
ATOM   4391  CG   LYS b 338      -5.519  29.393 -48.540  0.50 20.88           C
ATOM   4392  CD   LYS b 338      -4.770  29.126 -47.241  0.50 21.25           C
ATOM   4393  CE   LYS b 338      -3.499  29.962 -47.146  0.50 22.05           C
ATOM   4394  NZ   LYS b 338      -3.842  31.377 -46.838  0.50 22.14           N
ATOM   4395  C    LYS b 338      -5.870  30.549 -51.239  0.50 20.85           C
ATOM   4396  O    LYS b 338      -5.009  31.282 -51.753  0.50 18.76           O
ATOM   4397  N    ALA b 339      -7.020  31.008 -50.761  0.50 19.91           N
ATOM   4398  CA   ALA b 339      -7.306  32.437 -50.768  0.50 22.00           C
ATOM   4399  CB   ALA b 339      -8.552  32.772 -49.945  0.50 21.41           C
ATOM   4400  C    ALA b 339      -6.098  33.176 -50.229  0.50 22.12           C
ATOM   4401  O    ALA b 339      -5.574  32.834 -49.180  0.50 22.07           O
ATOM   4402  N    LYS b 340      -5.667  34.202 -50.958  0.50 21.64           N
```

Figure 27 (Continued)

```
ATOM   4403  CA   LYS b 340      -4.512  34.987 -50.559  0.50 22.70           C
ATOM   4404  CB   LYS b 340      -3.916  35.719 -51.762  0.50 23.39           C
ATOM   4405  CG   LYS b 340      -3.108  34.855 -52.721  0.50 28.60           C
ATOM   4406  CD   LYS b 340      -2.134  35.732 -53.497  0.50 30.28           C
ATOM   4407  CE   LYS b 340      -1.864  35.225 -54.911  0.50 37.02           C
ATOM   4408  NZ   LYS b 340      -1.258  33.862 -54.973  0.50 37.73           N
ATOM   4409  C    LYS b 340      -4.907  36.009 -49.503  0.50 21.89           C
ATOM   4410  O    LYS b 340      -6.075  36.399 -49.410  0.50 22.77           O
ATOM   4411  N    GLY b 341      -3.924  36.450 -48.716  0.50 21.23           N
ATOM   4412  CA   GLY b 341      -4.143  37.496 -47.732  0.50 19.47           C
ATOM   4413  C    GLY b 341      -3.426  37.210 -46.438  0.50 18.25           C
ATOM   4414  O    GLY b 341      -3.295  36.055 -46.002  0.50 18.74           O
ATOM   4415  N    GLN b 342      -2.905  38.257 -45.823  0.50 17.49           N
ATOM   4416  CA   GLN b 342      -2.186  38.047 -44.595  0.50 16.83           C
ATOM   4417  CB   GLN b 342      -1.804  39.359 -43.982  0.50 18.35           C
ATOM   4418  CG   GLN b 342      -1.093  39.116 -42.686  0.50 19.30           C
ATOM   4419  CD   GLN b 342      -0.384  40.345 -42.269  0.50 21.00           C
ATOM   4420  OE1  GLN b 342      -0.902  41.445 -42.492  0.50 19.66           O
ATOM   4421  NE2  GLN b 342       0.844  40.195 -41.755  0.50 20.69           N
ATOM   4422  C    GLN b 342      -3.076  37.351 -43.575  0.50 16.13           C
ATOM   4423  O    GLN b 342      -4.048  37.920 -43.156  0.50 15.36           O
ATOM   4424  N    PRO b 343      -2.699  36.145 -43.128  0.50 16.54           N
ATOM   4425  CA   PRO b 343      -3.543  35.488 -42.110  0.50 16.79           C
ATOM   4426  CB   PRO b 343      -2.799  34.169 -41.852  0.50 16.20           C
ATOM   4427  CG   PRO b 343      -2.047  33.909 -43.142  0.50 15.65           C
ATOM   4428  CD   PRO b 343      -1.588  35.287 -43.571  0.50 15.17           C
ATOM   4429  C    PRO b 343      -3.649  36.315 -40.825  0.50 18.52           C
ATOM   4430  O    PRO b 343      -2.637  36.849 -40.355  0.50 18.90           O
ATOM   4431  N    ARG b 344      -4.857  36.441 -40.270  0.50 19.28           N
ATOM   4432  CA   ARG b 344      -5.062  37.085 -38.969  0.50 19.62           C
ATOM   4433  CB   ARG b 344      -5.826  38.412 -39.089  0.50 22.03           C
ATOM   4434  CG   ARG b 344      -5.855  38.982 -40.491  0.50 25.31           C
ATOM   4435  CD   ARG b 344      -5.494  40.456 -40.549  0.50 28.75           C
ATOM   4436  NE   ARG b 344      -6.609  41.365 -40.287  0.50 32.27           N
ATOM   4437  CZ   ARG b 344      -7.135  42.202 -41.184  0.50 31.72           C
ATOM   4438  NH1  ARG b 344      -6.676  42.235 -42.432  0.50 34.44           N
ATOM   4439  NH2  ARG b 344      -8.123  43.015 -40.832  0.50 29.28           N
ATOM   4440  C    ARG b 344      -5.858  36.155 -38.079  0.50 20.93           C
ATOM   4441  O    ARG b 344      -6.825  35.529 -38.525  0.50 18.16           O
ATOM   4442  N    GLU b 345      -5.475  36.114 -36.812  0.50 21.81           N
ATOM   4443  CA   GLU b 345      -6.007  35.145 -35.870  0.50 23.06           C
ATOM   4444  CB   GLU b 345      -5.077  35.108 -34.657  0.50 27.31           C
ATOM   4445  CG   GLU b 345      -5.494  34.135 -33.580  0.50 29.94           C
ATOM   4446  CD   GLU b 345      -4.548  34.153 -32.401  0.50 33.77           C
ATOM   4447  OE1  GLU b 345      -4.374  35.236 -31.798  0.50 35.20           O
ATOM   4448  OE2  GLU b 345      -3.996  33.085 -32.072  0.50 35.94           O
ATOM   4449  C    GLU b 345      -7.428  35.464 -35.396  0.50 23.01           C
ATOM   4450  O    GLU b 345      -7.724  36.590 -35.035  0.50 25.05           O
ATOM   4451  N    PRO b 346      -8.297  34.451 -35.377  0.50 22.18           N
ATOM   4452  CA   PRO b 346      -9.647  34.523 -34.826  0.50 22.62           C
ATOM   4453  CB   PRO b 346     -10.188  33.106 -35.056  0.50 22.96           C
ATOM   4454  CG   PRO b 346      -9.377  32.562 -36.191  0.50 21.39           C
ATOM   4455  CD   PRO b 346      -8.009  33.137 -35.973  0.50 21.04           C
ATOM   4456  C    PRO b 346      -9.654  34.828 -33.325  0.50 23.62           C
ATOM   4457  O    PRO b 346      -8.813  34.305 -32.568  0.50 21.25           O
ATOM   4458  N    GLN b 347     -10.606  35.656 -32.889  0.50 22.01           N
ATOM   4459  CA   GLN b 347     -10.919  35.763 -31.474  0.50 21.63           C
ATOM   4460  CB   GLN b 347     -11.005  37.230 -31.058  0.50 23.09           C
ATOM   4461  CG   GLN b 347      -9.765  37.999 -31.489  0.50 25.81           C
ATOM   4462  CD   GLN b 347      -8.486  37.345 -30.982  0.50 26.93           C
ATOM   4463  OE1  GLN b 347      -8.315  37.160 -29.777  0.50 31.76           O
ATOM   4464  NE2  GLN b 347      -7.581  36.991 -31.899  0.50 27.87           N
ATOM   4465  C    GLN b 347     -12.254  35.050 -31.313  0.50 19.99           C
ATOM   4466  O    GLN b 347     -13.156  35.218 -32.142  0.50 20.71           O
```

Figure 27 (Continued)

```
ATOM   4467  N    VAL b 348     -12.372  34.227 -30.288  0.50 19.55           N
ATOM   4468  CA   VAL b 348     -13.548  33.362 -30.166  0.50 18.44           C
ATOM   4469  CB   VAL b 348     -13.159  31.870 -30.186  0.50 18.27           C
ATOM   4470  CG1  VAL b 348     -14.400  30.976 -30.151  0.50 18.99           C
ATOM   4471  CG2  VAL b 348     -12.353  31.558 -31.424  0.50 18.13           C
ATOM   4472  C    VAL b 348     -14.242  33.649 -28.848  0.50 18.98           C
ATOM   4473  O    VAL b 348     -13.654  33.457 -27.773  0.50 20.39           O
ATOM   4474  N    TYR b 349     -15.488  34.110 -28.942  0.50 19.23           N
ATOM   4475  CA   TYR b 349     -16.276  34.486 -27.771  0.50 19.64           C
ATOM   4476  CB   TYR b 349     -16.529  35.996 -27.731  0.50 18.81           C
ATOM   4477  CG   TYR b 349     -15.287  36.839 -27.916  0.50 19.39           C
ATOM   4478  CD1  TYR b 349     -14.283  36.859 -26.949  0.50 18.38           C
ATOM   4479  CE1  TYR b 349     -13.150  37.635 -27.113  0.50 19.06           C
ATOM   4480  CZ   TYR b 349     -12.994  38.378 -28.260  0.50 19.48           C
ATOM   4481  OH   TYR b 349     -11.859  39.139 -28.433  0.50 20.50           O
ATOM   4482  CE2  TYR b 349     -13.972  38.383 -29.231  0.50 19.47           C
ATOM   4483  CD2  TYR b 349     -15.114  37.605 -29.055  0.50 19.00           C
ATOM   4484  C    TYR b 349     -17.595  33.737 -27.747  0.50 19.51           C
ATOM   4485  O    TYR b 349     -18.410  33.853 -28.682  0.50 19.73           O
ATOM   4486  N    VAL b 350     -17.801  32.954 -26.690  0.50 18.75           N
ATOM   4487  CA   VAL b 350     -19.031  32.163 -26.525  0.50 20.57           C
ATOM   4488  CB   VAL b 350     -18.734  30.704 -26.129  0.50 20.80           C
ATOM   4489  CG1  VAL b 350     -18.334  29.861 -27.336  0.50 20.97           C
ATOM   4490  CG2  VAL b 350     -17.653  30.650 -25.065  0.50 20.07           C
ATOM   4491  C    VAL b 350     -20.017  32.767 -25.510  0.50 21.40           C
ATOM   4492  O    VAL b 350     -19.649  33.156 -24.376  0.50 21.54           O
ATOM   4493  N    LEU b 351     -21.280  32.815 -25.919  0.50 22.07           N
ATOM   4494  CA   LEU b 351     -22.335  33.517 -25.190  0.50 22.20           C
ATOM   4495  CB   LEU b 351     -22.950  34.590 -26.095  0.50 23.50           C
ATOM   4496  CG   LEU b 351     -22.044  35.711 -26.611  0.50 24.48           C
ATOM   4497  CD1  LEU b 351     -22.310  36.049 -28.071  0.50 25.02           C
ATOM   4498  CD2  LEU b 351     -22.260  36.954 -25.749  0.50 27.49           C
ATOM   4499  C    LEU b 351     -23.439  32.570 -24.737  0.50 21.80           C
ATOM   4500  O    LEU b 351     -24.009  31.835 -25.539  0.50 22.11           O
ATOM   4501  N    PRO b 352     -23.796  32.627 -23.449  0.50 22.39           N
ATOM   4502  CA   PRO b 352     -24.879  31.814 -22.922  0.50 22.22           C
ATOM   4503  CB   PRO b 352     -24.665  31.919 -21.413  0.50 22.51           C
ATOM   4504  CG   PRO b 352     -24.130  33.298 -21.238  0.50 22.91           C
ATOM   4505  CD   PRO b 352     -23.236  33.531 -22.427  0.50 23.53           C
ATOM   4506  C    PRO b 352     -26.200  32.436 -23.322  0.50 22.02           C
ATOM   4507  O    PRO b 352     -26.224  33.621 -23.643  0.50 23.12           O
ATOM   4508  N    PRO b 353     -27.289  31.652 -23.316  0.50 22.31           N
ATOM   4509  CA   PRO b 353     -28.601  32.160 -23.711  0.50 23.14           C
ATOM   4510  CB   PRO b 353     -29.565  31.061 -23.251  0.50 22.97           C
ATOM   4511  CG   PRO b 353     -28.725  29.815 -23.137  0.50 24.23           C
ATOM   4512  CD   PRO b 353     -27.358  30.288 -22.753  0.50 23.24           C
ATOM   4513  C    PRO b 353     -28.958  33.475 -23.019  0.50 22.78           C
ATOM   4514  O    PRO b 353     -28.580  33.704 -21.868  0.50 25.29           O
ATOM   4515  N    SER b 354     -29.691  34.323 -23.719  0.50 23.55           N
ATOM   4516  CA   SER b 354     -30.315  35.487 -23.092  0.50 23.26           C
ATOM   4517  CB   SER b 354     -31.097  36.279 -24.149  0.50 23.01           C
ATOM   4518  OG   SER b 354     -31.899  37.294 -23.548  0.50 26.46           O
ATOM   4519  C    SER b 354     -31.283  34.965 -22.018  0.50 25.05           C
ATOM   4520  O    SER b 354     -31.976  33.978 -22.237  0.50 24.27           O
ATOM   4521  N    ARG b 355     -31.344  35.632 -20.868  0.50 28.01           N
ATOM   4522  CA   ARG b 355     -32.322  35.247 -19.845  0.50 30.51           C
ATOM   4523  CB   ARG b 355     -32.290  36.227 -18.657  0.50 33.58           C
ATOM   4524  CG   ARG b 355     -33.076  35.748 -17.443  0.50 39.35           C
ATOM   4525  CD   ARG b 355     -32.400  36.128 -16.123  0.50 43.93           C
ATOM   4526  NE   ARG b 355     -31.120  35.438 -15.933  0.50 45.06           N
ATOM   4527  CZ   ARG b 355     -30.568  35.172 -14.749  0.50 45.34           C
ATOM   4528  NH1  ARG b 355     -31.180  35.523 -13.624  0.50 45.92           N
ATOM   4529  NH2  ARG b 355     -29.399  34.549 -14.690  0.50 44.22           N
ATOM   4530  C    ARG b 355     -33.748  35.102 -20.416  0.50 30.28           C
```

Figure 27 (Continued)

```
ATOM   4531  O    ARG b 355     -34.501  34.197 -20.024  0.50 30.63           O
ATOM   4532  N    ASP b 356     -34.110  35.990 -21.342  0.50 28.81           N
ATOM   4533  CA   ASP b 356     -35.414  35.937 -22.010  0.50 27.22           C
ATOM   4534  CB   ASP b 356     -35.523  37.013 -23.099  0.50 28.28           C
ATOM   4535  CG   ASP b 356     -35.840  38.382 -22.545  0.50 31.68           C
ATOM   4536  OD1  ASP b 356     -35.516  39.381 -23.234  0.50 31.04           O
ATOM   4537  OD2  ASP b 356     -36.409  38.457 -21.430  0.50 30.41           O
ATOM   4538  C    ASP b 356     -35.699  34.593 -22.663  0.50 25.99           C
ATOM   4539  O    ASP b 356     -36.847  34.163 -22.717  0.50 26.31           O
ATOM   4540  N    GLU b 357     -34.664  33.945 -23.205  0.50 24.69           N
ATOM   4541  CA   GLU b 357     -34.868  32.681 -23.910  0.50 22.59           C
ATOM   4542  CB   GLU b 357     -33.738  32.376 -24.928  0.50 21.32           C
ATOM   4543  CG   GLU b 357     -34.119  31.272 -25.917  0.50 19.42           C
ATOM   4544  CD   GLU b 357     -32.985  30.848 -26.840  0.50 18.13           C
ATOM   4545  OE1  GLU b 357     -31.812  31.012 -26.449  0.50 18.76           O
ATOM   4546  OE2  GLU b 357     -33.274  30.323 -27.939  0.50 18.78           O
ATOM   4547  C    GLU b 357     -34.993  31.544 -22.902  0.50 24.43           C
ATOM   4548  O    GLU b 357     -35.575  30.502 -23.206  0.50 23.51           O
ATOM   4549  N    LEU b 358     -34.475  31.773 -21.695  0.50 27.19           N
ATOM   4550  CA   LEU b 358     -34.402  30.723 -20.671  0.50 31.58           C
ATOM   4551  CB   LEU b 358     -33.602  31.199 -19.456  0.50 31.57           C
ATOM   4552  CG   LEU b 358     -32.082  31.188 -19.625  0.50 32.51           C
ATOM   4553  CD1  LEU b 358     -31.388  31.712 -18.376  0.50 34.39           C
ATOM   4554  CD2  LEU b 358     -31.586  29.793 -19.974  0.50 31.39           C
ATOM   4555  C    LEU b 358     -35.779  30.237 -20.239  0.50 32.94           C
ATOM   4556  O    LEU b 358     -35.898  29.321 -19.430  0.50 33.86           O
ATOM   4557  N    THR b 359     -36.820  30.853 -20.784  0.50 34.89           N
ATOM   4558  CA   THR b 359     -38.183  30.450 -20.476  0.50 36.81           C
ATOM   4559  CB   THR b 359     -39.124  31.673 -20.403  0.50 39.39           C
ATOM   4560  OG1  THR b 359     -39.253  32.264 -21.702  0.50 38.42           O
ATOM   4561  CG2  THR b 359     -38.567  32.713 -19.437  0.50 39.22           C
ATOM   4562  C    THR b 359     -38.711  29.444 -21.493  0.50 36.43           C
ATOM   4563  O    THR b 359     -39.737  28.794 -21.257  0.50 38.40           O
ATOM   4564  N    LYS b 360     -38.006  29.314 -22.618  0.50 31.90           N
ATOM   4565  CA   LYS b 360     -38.377  28.366 -23.674  0.50 31.52           C
ATOM   4566  CB   LYS b 360     -37.790  28.815 -25.018  0.50 32.19           C
ATOM   4567  CG   LYS b 360     -38.272  30.177 -25.498  0.50 33.26           C
ATOM   4568  CD   LYS b 360     -39.499  30.057 -26.401  0.50 32.33           C
ATOM   4569  CE   LYS b 360     -39.773  31.368 -27.127  0.50 32.41           C
ATOM   4570  NZ   LYS b 360     -41.177  31.512 -27.610  0.50 33.51           N
ATOM   4571  C    LYS b 360     -37.859  26.970 -23.331  0.50 30.82           C
ATOM   4572  O    LYS b 360     -37.168  26.794 -22.329  0.50 30.23           O
ATOM   4573  N    ASN b 361     -38.197  25.986 -24.162  0.50 30.89           N
ATOM   4574  CA   ASN b 361     -37.776  24.608 -23.941  0.50 30.89           C
ATOM   4575  CB   ASN b 361     -38.880  23.634 -24.374  0.50 34.20           C
ATOM   4576  CG   ASN b 361     -40.267  24.081 -23.924  0.50 37.58           C
ATOM   4577  OD1  ASN b 361     -41.194  24.171 -24.734  0.50 39.26           O
ATOM   4578  ND2  ASN b 361     -40.414  24.363 -22.631  0.50 38.21           N
ATOM   4579  C    ASN b 361     -36.444  24.252 -24.631  0.50 29.36           C
ATOM   4580  O    ASN b 361     -35.745  23.335 -24.190  0.50 27.54           O
ATOM   4581  N    GLN b 362     -36.122  24.957 -25.720  0.50 26.16           N
ATOM   4582  CA   GLN b 362     -34.793  24.871 -26.359  0.50 24.20           C
ATOM   4583  CB   GLN b 362     -34.910  24.435 -27.818  0.50 24.78           C
ATOM   4584  CG   GLN b 362     -35.388  23.006 -27.982  0.50 26.32           C
ATOM   4585  CD   GLN b 362     -34.659  22.275 -29.085  0.50 27.42           C
ATOM   4586  OE1  GLN b 362     -34.855  22.560 -30.274  0.50 27.05           O
ATOM   4587  NE2  GLN b 362     -33.814  21.318 -28.703  0.50 30.04           N
ATOM   4588  C    GLN b 362     -34.121  26.224 -26.320  0.50 22.26           C
ATOM   4589  O    GLN b 362     -34.768  27.232 -26.618  0.50 20.32           O
ATOM   4590  N    VAL b 363     -32.830  26.250 -25.969  0.50 20.69           N
ATOM   4591  CA   VAL b 363     -32.100  27.510 -25.890  0.50 19.42           C
ATOM   4592  CB   VAL b 363     -31.569  27.810 -24.472  0.50 19.68           C
ATOM   4593  CG1  VAL b 363     -32.722  28.072 -23.503  0.50 20.49           C
ATOM   4594  CG2  VAL b 363     -30.639  26.696 -23.983  0.50 19.53           C
```

Figure 27 (Continued)

```
ATOM   4595  C    VAL b 363     -30.950  27.550 -26.890  0.50 18.64           C
ATOM   4596  O    VAL b 363     -30.580  26.529 -27.465  0.50 18.29           O
ATOM   4597  N    SER b 364     -30.409  28.740 -27.121  0.50 17.29           N
ATOM   4598  CA   SER b 364     -29.386  28.919 -28.139  0.50 16.89           C
ATOM   4599  CB   SER b 364     -29.780  30.052 -29.098  0.50 16.78           C
ATOM   4600  OG   SER b 364     -31.129  29.917 -29.522  0.50 16.68           O
ATOM   4601  C    SER b 364     -28.093  29.295 -27.455  0.50 17.60           C
ATOM   4602  O    SER b 364     -28.084  30.145 -26.571  0.50 17.00           O
ATOM   4603  N    LEU b 365     -27.002  28.662 -27.868  0.50 16.81           N
ATOM   4604  CA   LEU b 365     -25.692  29.038 -27.385  0.50 16.83           C
ATOM   4605  CB   LEU b 365     -24.959  27.823 -26.801  0.50 17.58           C
ATOM   4606  CG   LEU b 365     -25.822  26.879 -25.942  0.50 17.65           C
ATOM   4607  CD1  LEU b 365     -24.999  25.679 -25.478  0.50 18.99           C
ATOM   4608  CD2  LEU b 365     -26.475  27.575 -24.760  0.50 18.31           C
ATOM   4609  C    LEU b 365     -24.945  29.587 -28.589  0.50 16.29           C
ATOM   4610  O    LEU b 365     -24.961  28.987 -29.664  0.50 17.94           O
ATOM   4611  N    LEU b 366     -24.297  30.724 -28.413  0.50 16.61           N
ATOM   4612  CA   LEU b 366     -23.638  31.392 -29.534  0.50 16.21           C
ATOM   4613  CB   LEU b 366     -24.046  32.857 -29.606  0.50 16.31           C
ATOM   4614  CG   LEU b 366     -25.498  33.127 -29.957  0.50 15.72           C
ATOM   4615  CD1  LEU b 366     -25.723  34.634 -30.042  0.50 16.85           C
ATOM   4616  CD2  LEU b 366     -25.880  32.432 -31.250  0.50 15.40           C
ATOM   4617  C    LEU b 366     -22.128  31.323 -29.473  0.50 16.56           C
ATOM   4618  O    LEU b 366     -21.505  31.513 -28.415  0.50 17.56           O
ATOM   4619  N    CYS b 367     -21.530  31.109 -30.639  0.50 16.04           N
ATOM   4620  CA   CYS b 367     -20.096  31.242 -30.767  0.50 17.07           C
ATOM   4621  CB   CYS b 367     -19.506  29.916 -31.217  0.50 17.90           C
ATOM   4622  SG   CYS b 367     -17.712  29.818 -31.158  0.50 19.68           S
ATOM   4623  C    CYS b 367     -19.797  32.324 -31.792  0.50 17.59           C
ATOM   4624  O    CYS b 367     -20.153  32.205 -32.973  0.50 17.90           O
ATOM   4625  N    LEU b 368     -19.155  33.377 -31.312  0.50 17.30           N
ATOM   4626  CA   LEU b 368     -18.738  34.500 -32.132  0.50 16.85           C
ATOM   4627  CB   LEU b 368     -18.960  35.801 -31.361  0.50 16.57           C
ATOM   4628  CG   LEU b 368     -18.147  37.016 -31.807  0.50 16.14           C
ATOM   4629  CD1  LEU b 368     -18.405  37.388 -33.262  0.50 15.48           C
ATOM   4630  CD2  LEU b 368     -18.456  38.188 -30.865  0.50 16.09           C
ATOM   4631  C    LEU b 368     -17.258  34.321 -32.442  0.50 16.62           C
ATOM   4632  O    LEU b 368     -16.437  34.218 -31.534  0.50 18.39           O
ATOM   4633  N    VAL b 369     -16.927  34.214 -33.718  0.50 16.56           N
ATOM   4634  CA   VAL b 369     -15.528  34.196 -34.160  0.50 16.00           C
ATOM   4635  CB   VAL b 369     -15.237  32.975 -35.054  0.50 15.63           C
ATOM   4636  CG1  VAL b 369     -13.797  33.034 -35.570  0.50 15.48           C
ATOM   4637  CG2  VAL b 369     -15.497  31.690 -34.276  0.50 16.18           C
ATOM   4638  C    VAL b 369     -15.267  35.472 -34.945  0.50 16.75           C
ATOM   4639  O    VAL b 369     -15.880  35.700 -35.986  0.50 19.73           O
ATOM   4640  N    LYS b 370     -14.429  36.355 -34.413  0.50 17.85           N
ATOM   4641  CA   LYS b 370     -14.230  37.628 -35.080  0.50 18.82           C
ATOM   4642  CB   LYS b 370     -14.956  38.763 -34.343  0.50 19.71           C
ATOM   4643  CG   LYS b 370     -14.525  38.939 -32.898  0.50 18.81           C
ATOM   4644  CD   LYS b 370     -14.935  40.306 -32.338  0.50 19.36           C
ATOM   4645  CE   LYS b 370     -13.994  41.391 -32.819  0.50 18.52           C
ATOM   4646  NZ   LYS b 370     -14.291  42.687 -32.177  0.50 18.96           N
ATOM   4647  C    LYS b 370     -12.761  37.956 -35.296  0.50 18.47           C
ATOM   4648  O    LYS b 370     -11.878  37.446 -34.589  0.50 19.28           O
ATOM   4649  N    GLY b 371     -12.521  38.787 -36.300  0.50 16.81           N
ATOM   4650  CA   GLY b 371     -11.176  39.266 -36.613  0.50 17.42           C
ATOM   4651  C    GLY b 371     -10.262  38.229 -37.239  0.50 16.87           C
ATOM   4652  O    GLY b 371      -9.071  38.199 -36.920  0.50 16.04           O
ATOM   4653  N    PHE b 372     -10.814  37.396 -38.124  0.50 16.19           N
ATOM   4654  CA   PHE b 372      -9.991  36.418 -38.879  0.50 16.35           C
ATOM   4655  CB   PHE b 372     -10.466  34.970 -38.631  0.50 16.05           C
ATOM   4656  CG   PHE b 372     -11.854  34.651 -39.162  0.50 16.29           C
ATOM   4657  CD1  PHE b 372     -12.976  34.850 -38.373  0.50 16.46           C
ATOM   4658  CE1  PHE b 372     -14.243  34.520 -38.828  0.50 16.68           C
```

Figure 27 (Continued)

```
ATOM   4659  CZ   PHE b 372     -14.403  33.955 -40.089  0.50 16.72           C
ATOM   4660  CE2  PHE b 372     -13.292  33.716 -40.877  0.50 16.80           C
ATOM   4661  CD2  PHE b 372     -12.020  34.059 -40.418  0.50 16.60           C
ATOM   4662  C    PHE b 372      -9.795  36.725 -40.367  0.50 17.17           C
ATOM   4663  O    PHE b 372     -10.597  37.416 -40.995  0.50 17.00           O
ATOM   4664  N    TYR b 373      -8.684  36.241 -40.925  0.50 16.91           N
ATOM   4665  CA   TYR b 373      -8.397  36.451 -42.332  0.50 18.30           C
ATOM   4666  CB   TYR b 373      -7.715  37.800 -42.562  0.50 18.89           C
ATOM   4667  CG   TYR b 373      -7.914  38.392 -43.947  0.50 20.86           C
ATOM   4668  CD1  TYR b 373      -6.834  38.575 -44.801  0.50 21.56           C
ATOM   4669  CE1  TYR b 373      -6.997  39.135 -46.062  0.50 22.39           C
ATOM   4670  CZ   TYR b 373      -8.252  39.524 -46.476  0.50 23.45           C
ATOM   4671  OH   TYR b 373      -8.412  40.075 -47.728  0.50 24.79           O
ATOM   4672  CE2  TYR b 373      -9.343  39.366 -45.644  0.50 21.87           C
ATOM   4673  CD2  TYR b 373      -9.174  38.796 -44.388  0.50 20.96           C
ATOM   4674  C    TYR b 373      -7.527  35.292 -42.777  0.50 19.39           C
ATOM   4675  O    TYR b 373      -6.619  34.927 -42.021  0.50 18.23           O
ATOM   4676  N    PRO b 374      -7.557  35.044 -44.088  0.50 21.64           N
ATOM   4677  CA   PRO b 374      -8.525  34.333 -44.931  0.50 22.05           C
ATOM   4678  CB   PRO b 374      -7.732  33.142 -45.466  0.50 23.50           C
ATOM   4679  CG   PRO b 374      -6.375  33.733 -45.645  0.50 25.07           C
ATOM   4680  CD   PRO b 374      -6.181  34.678 -44.477  0.50 24.48           C
ATOM   4681  C    PRO b 374      -9.840  33.938 -44.252  0.50 19.95           C
ATOM   4682  O    PRO b 374      -9.885  33.742 -43.041  0.50 19.67           O
ATOM   4683  N    SER b 375     -10.911  33.867 -45.044  0.50 19.40           N
ATOM   4684  CA   SER b 375     -12.217  33.503 -44.522  0.50 18.82           C
ATOM   4685  CB   SER b 375     -13.351  34.019 -45.431  0.50 19.64           C
ATOM   4686  OG   SER b 375     -13.296  33.389 -46.696  0.50 21.59           O
ATOM   4687  C    SER b 375     -12.364  31.993 -44.346  0.50 18.90           C
ATOM   4688  O    SER b 375     -13.340  31.538 -43.760  0.50 19.29           O
ATOM   4689  N    ASP b 376     -11.396  31.214 -44.839  0.50 19.19           N
ATOM   4690  CA   ASP b 376     -11.502  29.750 -44.712  0.50 19.08           C
ATOM   4691  CB   ASP b 376     -10.347  29.011 -45.402  0.50 20.50           C
ATOM   4692  CG   ASP b 376     -10.137  29.414 -46.848  0.50 21.53           C
ATOM   4693  OD1  ASP b 376     -11.117  29.683 -47.563  0.50 22.72           O
ATOM   4694  OD2  ASP b 376      -8.961  29.391 -47.290  0.50 23.16           O
ATOM   4695  C    ASP b 376     -11.439  29.363 -43.236  0.50 18.93           C
ATOM   4696  O    ASP b 376     -10.476  29.694 -42.537  0.50 19.09           O
ATOM   4697  N    ILE b 377     -12.455  28.662 -42.747  0.50 17.16           N
ATOM   4698  CA   ILE b 377     -12.513  28.350 -41.335  0.50 16.53           C
ATOM   4699  CB   ILE b 377     -13.075  29.525 -40.482  0.50 15.92           C
ATOM   4700  CG1  ILE b 377     -12.808  29.298 -38.987  0.50 16.61           C
ATOM   4701  CD1  ILE b 377     -12.992  30.549 -38.145  0.50 17.10           C
ATOM   4702  CG2  ILE b 377     -14.581  29.656 -40.692  0.50 16.34           C
ATOM   4703  C    ILE b 377     -13.412  27.148 -41.183  0.50 16.48           C
ATOM   4704  O    ILE b 377     -14.205  26.853 -42.075  0.50 18.23           O
ATOM   4705  N    ALA b 378     -13.252  26.446 -40.070  0.50 15.81           N
ATOM   4706  CA   ALA b 378     -14.201  25.404 -39.687  0.50 15.85           C
ATOM   4707  CB   ALA b 378     -13.580  24.025 -39.881  0.50 16.57           C
ATOM   4708  C    ALA b 378     -14.570  25.634 -38.232  0.50 15.80           C
ATOM   4709  O    ALA b 378     -13.701  25.857 -37.386  0.50 16.17           O
ATOM   4710  N    VAL b 379     -15.861  25.590 -37.929  0.50 16.04           N
ATOM   4711  CA   VAL b 379     -16.339  25.809 -36.576  0.50 15.48           C
ATOM   4712  CB   VAL b 379     -17.122  27.143 -36.495  0.50 15.81           C
ATOM   4713  CG1  VAL b 379     -17.704  27.348 -35.109  0.50 15.63           C
ATOM   4714  CG2  VAL b 379     -16.198  28.299 -36.875  0.50 15.51           C
ATOM   4715  C    VAL b 379     -17.241  24.623 -36.222  0.50 16.62           C
ATOM   4716  O    VAL b 379     -17.992  24.151 -37.080  0.50 16.89           O
ATOM   4717  N    GLU b 380     -17.151  24.134 -34.984  0.50 16.99           N
ATOM   4718  CA   GLU b 380     -17.909  22.947 -34.528  0.50 17.40           C
ATOM   4719  CB   GLU b 380     -17.029  21.683 -34.593  0.50 19.10           C
ATOM   4720  CG   GLU b 380     -16.507  21.380 -35.957  0.50 20.88           C
ATOM   4721  CD   GLU b 380     -15.698  20.096 -36.000  0.50 20.70           C
ATOM   4722  OE1  GLU b 380     -15.270  19.752 -37.094  0.50 22.78           O
```

Figure 27 (Continued)

```
ATOM   4723  OE2 GLU b 380     -15.512  19.420 -34.956  0.50 22.08           O
ATOM   4724  C   GLU b 380     -18.332  23.112 -33.093  0.50 17.66           C
ATOM   4725  O   GLU b 380     -17.844  24.008 -32.399  0.50 19.18           O
ATOM   4726  N   TRP b 381     -19.225  22.248 -32.631  0.50 17.02           N
ATOM   4727  CA  TRP b 381     -19.574  22.218 -31.238  0.50 17.75           C
ATOM   4728  CB  TRP b 381     -21.047  22.576 -31.040  0.50 17.75           C
ATOM   4729  CG  TRP b 381     -21.386  24.038 -31.312  0.50 17.45           C
ATOM   4730  CD1 TRP b 381     -21.685  24.596 -32.516  0.50 17.12           C
ATOM   4731  NE1 TRP b 381     -21.942  25.955 -32.358  0.50 17.26           N
ATOM   4732  CE2 TRP b 381     -21.819  26.276 -31.034  0.50 17.18           C
ATOM   4733  CD2 TRP b 381     -21.441  25.098 -30.345  0.50 17.21           C
ATOM   4734  CE3 TRP b 381     -21.240  25.158 -28.954  0.50 16.82           C
ATOM   4735  CZ3 TRP b 381     -21.394  26.385 -28.311  0.50 17.78           C
ATOM   4736  CH2 TRP b 381     -21.767  27.543 -29.039  0.50 17.03           C
ATOM   4737  CZ2 TRP b 381     -21.976  27.500 -30.389  0.50 16.08           C
ATOM   4738  C   TRP b 381     -19.326  20.824 -30.666  0.50 18.88           C
ATOM   4739  O   TRP b 381     -19.474  19.829 -31.367  0.50 19.12           O
ATOM   4740  N   GLU b 382     -19.138  20.699 -29.385  0.50 18.66           N
ATOM   4741  CA  GLU b 382     -19.177  19.374 -28.827  0.50 20.14           C
ATOM   4742  CB  GLU b 382     -17.839  18.680 -29.038  0.50 19.76           C
ATOM   4743  CG  GLU b 382     -16.704  19.393 -28.360  0.50 21.21           C
ATOM   4744  CD  GLU b 382     -15.360  18.748 -28.595  0.50 23.37           C
ATOM   4745  OE1 GLU b 382     -14.654  18.533 -27.605  0.50 23.39           O
ATOM   4746  OE2 GLU b 382     -15.021  18.480 -29.756  0.50 24.15           O
ATOM   4747  C   GLU b 382     -19.552  19.443 -27.356  0.50 19.99           C
ATOM   4748  O   GLU b 382     -19.552  20.497 -26.768  0.50 18.10           O
ATOM   4749  N   SER b 383     -19.933  18.314 -26.788  0.50 18.17           N
ATOM   4750  CA  SER b 383     -20.090  18.220 -25.358  0.50 18.23           C
ATOM   4751  CB  SER b 383     -21.542  18.403 -24.964  0.50 17.68           C
ATOM   4752  OG  SER b 383     -21.668  18.436 -23.574  0.50 17.35           O
ATOM   4753  C   SER b 383     -19.593  16.861 -24.898  0.50 19.41           C
ATOM   4754  O   SER b 383     -19.928  15.871 -25.488  0.50 17.17           O
ATOM   4755  N   ASN b 384     -18.817  16.849 -23.827  0.50 20.71           N
ATOM   4756  CA  ASN b 384     -18.249  15.617 -23.297  0.50 22.88           C
ATOM   4757  CB  ASN b 384     -19.321  14.753 -22.652  0.50 22.99           C
ATOM   4758  CG  ASN b 384     -18.745  13.775 -21.645  0.50 24.94           C
ATOM   4759  OD1 ASN b 384     -17.790  14.082 -20.947  0.50 24.43           O
ATOM   4760  ND2 ASN b 384     -19.314  12.590 -21.590  0.50 27.21           N
ATOM   4761  C   ASN b 384     -17.438  14.813 -24.313  0.50 22.68           C
ATOM   4762  O   ASN b 384     -17.577  13.614 -24.399  0.50 25.25           O
ATOM   4763  N   GLY b 385     -16.619  15.514 -25.090  0.50 22.27           N
ATOM   4764  CA  GLY b 385     -15.667  14.930 -26.021  0.50 22.87           C
ATOM   4765  C   GLY b 385     -16.326  14.584 -27.319  0.50 23.01           C
ATOM   4766  O   GLY b 385     -15.740  14.112 -28.283  0.50 22.93           O
ATOM   4767  N   GLN b 386     -17.596  14.875 -27.349  0.50 22.73           N
ATOM   4768  CA  GLN b 386     -18.438  14.344 -28.409  0.50 23.19           C
ATOM   4769  CB  GLN b 386     -19.576  13.519 -27.788  0.50 25.43           C
ATOM   4770  CG  GLN b 386     -19.105  12.438 -26.811  0.50 28.97           C
ATOM   4771  CD  GLN b 386     -18.294  11.339 -27.485  0.50 31.72           C
ATOM   4772  OE1 GLN b 386     -18.266  11.235 -28.718  0.50 34.00           O
ATOM   4773  NE2 GLN b 386     -17.647  10.491 -26.674  0.50 32.58           N
ATOM   4774  C   GLN b 386     -19.045  15.461 -29.277  0.50 21.60           C
ATOM   4775  O   GLN b 386     -19.424  16.487 -28.756  0.50 19.32           O
ATOM   4776  N   PRO b 387     -19.161  15.237 -30.589  0.50 21.62           N
ATOM   4777  CA  PRO b 387     -19.776  16.267 -31.444  0.50 20.19           C
ATOM   4778  CB  PRO b 387     -19.763  15.626 -32.833  0.50 22.00           C
ATOM   4779  CG  PRO b 387     -18.647  14.620 -32.785  0.50 21.85           C
ATOM   4780  CD  PRO b 387     -18.552  14.143 -31.370  0.50 21.70           C
ATOM   4781  C   PRO b 387     -21.217  16.558 -31.028  0.50 21.36           C
ATOM   4782  O   PRO b 387     -21.977  15.637 -30.682  0.50 18.59           O
ATOM   4783  N   GLU b 388     -21.592  17.842 -31.056  0.50 21.86           N
ATOM   4784  CA  GLU b 388     -22.999  18.242 -30.909  0.50 21.70           C
ATOM   4785  CB  GLU b 388     -23.180  19.238 -29.752  0.50 23.80           C
ATOM   4786  CG  GLU b 388     -22.928  18.678 -28.366  0.50 24.08           C
```

Figure 27 (Continued)

```
ATOM   4787  CD   GLU b 388     -24.143  17.973 -27.801  0.50 24.76           C
ATOM   4788  OE1  GLU b 388     -24.015  17.340 -26.723  0.50 24.59           O
ATOM   4789  OE2  GLU b 388     -25.217  18.042 -28.445  0.50 25.62           O
ATOM   4790  C    GLU b 388     -23.313  18.948 -32.200  0.50 23.54           C
ATOM   4791  O    GLU b 388     -22.724  20.011 -32.478  0.50 21.94           O
ATOM   4792  N    ASN b 389     -24.215  18.371 -32.990  0.50 18.77           N
ATOM   4793  CA   ASN b 389     -24.290  18.746 -34.373  0.50 20.74           C
ATOM   4794  CB   ASN b 389     -24.146  17.518 -35.273  0.50 21.30           C
ATOM   4795  CG   ASN b 389     -22.706  17.064 -35.385  0.50 19.64           C
ATOM   4796  OD1  ASN b 389     -21.812  17.742 -34.898  0.50 22.53           O
ATOM   4797  ND2  ASN b 389     -22.470  15.906 -36.029  0.50 20.56           N
ATOM   4798  C    ASN b 389     -25.537  19.536 -34.713  0.50 21.05           C
ATOM   4799  O    ASN b 389     -25.771  19.861 -35.876  0.50 22.68           O
ATOM   4800  N    ASN b 390     -26.339  19.836 -33.699  0.50 22.48           N
ATOM   4801  CA   ASN b 390     -27.596  20.519 -33.962  0.50 22.85           C
ATOM   4802  CB   ASN b 390     -28.623  20.179 -32.920  0.50 22.74           C
ATOM   4803  CG   ASN b 390     -29.971  20.722 -33.295  0.50 22.65           C
ATOM   4804  OD1  ASN b 390     -30.330  20.686 -34.459  0.50 24.72           O
ATOM   4805  ND2  ASN b 390     -30.697  21.262 -32.341  0.50 23.13           N
ATOM   4806  C    ASN b 390     -27.444  22.040 -34.032  0.50 21.44           C
ATOM   4807  O    ASN b 390     -28.125  22.799 -33.313  0.50 20.17           O
ATOM   4808  N    TYR b 391     -26.510  22.471 -34.858  0.50 19.85           N
ATOM   4809  CA   TYR b 391     -26.161  23.864 -34.909  0.50 19.87           C
ATOM   4810  CB   TYR b 391     -24.738  24.107 -34.364  0.50 20.58           C
ATOM   4811  CG   TYR b 391     -23.553  23.523 -35.152  0.50 22.28           C
ATOM   4812  CD1  TYR b 391     -22.940  24.250 -36.165  0.50 22.98           C
ATOM   4813  CE1  TYR b 391     -21.824  23.764 -36.839  0.50 24.96           C
ATOM   4814  CZ   TYR b 391     -21.299  22.530 -36.484  0.50 24.76           C
ATOM   4815  OH   TYR b 391     -20.185  22.027 -37.154  0.50 27.46           O
ATOM   4816  CE2  TYR b 391     -21.868  21.805 -35.462  0.50 22.05           C
ATOM   4817  CD2  TYR b 391     -22.981  22.302 -34.793  0.50 24.18           C
ATOM   4818  C    TYR b 391     -26.289  24.326 -36.334  0.50 17.54           C
ATOM   4819  O    TYR b 391     -26.468  23.503 -37.243  0.50 15.56           O
ATOM   4820  N    MET b 392     -26.248  25.646 -36.517  0.50 16.27           N
ATOM   4821  CA   MET b 392     -26.111  26.232 -37.832  0.50 15.48           C
ATOM   4822  CB   MET b 392     -27.438  26.881 -38.275  0.50 17.04           C
ATOM   4823  CG   MET b 392     -27.973  27.892 -37.269  0.50 17.94           C
ATOM   4824  SD   MET b 392     -29.560  28.576 -37.785  0.50 21.06           S
ATOM   4825  CE   MET b 392     -29.092  29.277 -39.346  0.50 18.73           C
ATOM   4826  C    MET b 392     -25.070  27.329 -37.699  0.50 15.70           C
ATOM   4827  O    MET b 392     -25.005  28.010 -36.663  0.50 15.09           O
ATOM   4828  N    THR b 393     -24.247  27.471 -38.727  0.50 15.08           N
ATOM   4829  CA   THR b 393     -23.228  28.517 -38.773  0.50 15.35           C
ATOM   4830  CB   THR b 393     -21.830  27.869 -38.814  0.50 15.94           C
ATOM   4831  OG1  THR b 393     -21.622  27.164 -37.584  0.50 15.91           O
ATOM   4832  CG2  THR b 393     -20.687  28.907 -39.028  0.50 15.42           C
ATOM   4833  C    THR b 393     -23.475  29.419 -39.980  0.50 16.51           C
ATOM   4834  O    THR b 393     -23.679  28.935 -41.108  0.50 17.93           O
ATOM   4835  N    TRP b 394     -23.466  30.736 -39.772  0.50 15.87           N
ATOM   4836  CA   TRP b 394     -23.664  31.633 -40.899  0.50 15.30           C
ATOM   4837  CB   TRP b 394     -24.200  32.981 -40.428  0.50 14.32           C
ATOM   4838  CG   TRP b 394     -25.587  32.944 -39.892  0.50 13.47           C
ATOM   4839  CD1  TRP b 394     -26.722  33.341 -40.540  0.50 14.01           C
ATOM   4840  NE1  TRP b 394     -27.802  33.211 -39.721  0.50 13.31           N
ATOM   4841  CE2  TRP b 394     -27.389  32.716 -38.511  0.50 13.00           C
ATOM   4842  CD2  TRP b 394     -25.997  32.526 -38.586  0.50 12.75           C
ATOM   4843  CE3  TRP b 394     -25.321  32.051 -37.459  0.50 12.04           C
ATOM   4844  CZ3  TRP b 394     -26.042  31.736 -36.332  0.50 12.10           C
ATOM   4845  CH2  TRP b 394     -27.437  31.905 -36.291  0.50 12.61           C
ATOM   4846  CZ2  TRP b 394     -28.126  32.402 -37.372  0.50 12.51           C
ATOM   4847  C    TRP b 394     -22.336  31.852 -41.634  0.50 16.49           C
ATOM   4848  O    TRP b 394     -21.263  31.686 -41.060  0.50 17.12           O
ATOM   4849  N    PRO b 395     -22.412  32.236 -42.913  0.50 18.77           N
ATOM   4850  CA   PRO b 395     -21.251  32.588 -43.724  0.50 18.73           C
```

Figure 27 (Continued)

```
ATOM   4851  CB   PRO b 395     -21.879  33.189 -44.993  0.50 19.43           C
ATOM   4852  CG   PRO b 395     -23.238  32.592 -45.074  0.50 19.78           C
ATOM   4853  CD   PRO b 395     -23.656  32.136 -43.701  0.50 19.28           C
ATOM   4854  C    PRO b 395     -20.349  33.631 -43.053  0.50 18.35           C
ATOM   4855  O    PRO b 395     -20.829  34.438 -42.251  0.50 17.71           O
ATOM   4856  N    PRO b 396     -19.034  33.613 -43.370  0.50 17.10           N
ATOM   4857  CA   PRO b 396     -18.205  34.714 -42.881  0.50 18.36           C
ATOM   4858  CB   PRO b 396     -16.848  34.464 -43.574  0.50 17.48           C
ATOM   4859  CG   PRO b 396     -16.816  32.994 -43.853  0.50 18.51           C
ATOM   4860  CD   PRO b 396     -18.252  32.609 -44.130  0.50 17.80           C
ATOM   4861  C    PRO b 396     -18.759  36.063 -43.343  0.50 17.94           C
ATOM   4862  O    PRO b 396     -19.103  36.203 -44.502  0.50 18.65           O
ATOM   4863  N    VAL b 397     -18.811  37.055 -42.468  0.50 20.31           N
ATOM   4864  CA   VAL b 397     -19.147  38.401 -42.925  0.50 21.64           C
ATOM   4865  CB   VAL b 397     -20.287  39.021 -42.113  0.50 24.55           C
ATOM   4866  CG1  VAL b 397     -21.606  38.358 -42.498  0.50 26.48           C
ATOM   4867  CG2  VAL b 397     -20.011  38.879 -40.630  0.50 27.48           C
ATOM   4868  C    VAL b 397     -17.933  39.325 -42.901  0.50 21.71           C
ATOM   4869  O    VAL b 397     -17.242  39.423 -41.884  0.50 20.77           O
ATOM   4870  N    LEU b 398     -17.672  39.984 -44.030  0.50 23.11           N
ATOM   4871  CA   LEU b 398     -16.598  40.973 -44.099  0.50 23.13           C
ATOM   4872  CB   LEU b 398     -16.401  41.503 -45.523  0.50 24.61           C
ATOM   4873  CG   LEU b 398     -15.181  42.427 -45.607  0.50 26.95           C
ATOM   4874  CD1  LEU b 398     -13.913  41.664 -45.246  0.50 26.95           C
ATOM   4875  CD2  LEU b 398     -15.025  43.098 -46.964  0.50 27.67           C
ATOM   4876  C    LEU b 398     -16.966  42.126 -43.204  0.50 22.75           C
ATOM   4877  O    LEU b 398     -17.962  42.816 -43.449  0.50 23.37           O
ATOM   4878  N    ASP b 399     -16.150  42.346 -42.186  0.50 21.25           N
ATOM   4879  CA   ASP b 399     -16.397  43.360 -41.192  0.50 20.29           C
ATOM   4880  CB   ASP b 399     -15.699  42.950 -39.902  0.50 19.87           C
ATOM   4881  CG   ASP b 399     -16.492  43.279 -38.668  0.50 19.90           C
ATOM   4882  OD1  ASP b 399     -17.351  44.183 -38.726  0.50 19.53           O
ATOM   4883  OD2  ASP b 399     -16.229  42.648 -37.616  0.50 19.70           O
ATOM   4884  C    ASP b 399     -15.819  44.694 -41.683  0.50 19.88           C
ATOM   4885  O    ASP b 399     -15.128  44.753 -42.714  0.50 18.89           O
ATOM   4886  N    SER b 400     -16.047  45.736 -40.894  0.50 20.06           N
ATOM   4887  CA   SER b 400     -15.634  47.103 -41.231  0.50 21.74           C
ATOM   4888  CB   SER b 400     -16.206  48.089 -40.202  0.50 21.74           C
ATOM   4889  OG   SER b 400     -15.511  48.003 -38.966  0.50 23.41           O
ATOM   4890  C    SER b 400     -14.123  47.317 -41.374  0.50 21.04           C
ATOM   4891  O    SER b 400     -13.702  48.275 -42.022  0.50 20.67           O
ATOM   4892  N    ASP b 401     -13.310  46.473 -40.734  0.50 21.38           N
ATOM   4893  CA   ASP b 401     -11.854  46.578 -40.832  0.50 21.31           C
ATOM   4894  CB   ASP b 401     -11.170  46.374 -39.479  0.50 22.59           C
ATOM   4895  CG   ASP b 401     -11.324  44.952 -38.932  0.50 23.22           C
ATOM   4896  OD1  ASP b 401     -12.082  44.131 -39.511  0.50 23.05           O
ATOM   4897  OD2  ASP b 401     -10.671  44.664 -37.902  0.50 21.63           O
ATOM   4898  C    ASP b 401     -11.283  45.625 -41.870  0.50 21.06           C
ATOM   4899  O    ASP b 401     -10.071  45.446 -41.976  0.50 18.08           O
ATOM   4900  N    GLY b 402     -12.172  45.019 -42.644  0.50 20.47           N
ATOM   4901  CA   GLY b 402     -11.755  44.094 -43.679  0.50 21.49           C
ATOM   4902  C    GLY b 402     -11.395  42.699 -43.207  0.50 21.33           C
ATOM   4903  O    GLY b 402     -10.982  41.866 -44.021  0.50 21.64           O
ATOM   4904  N    SER b 403     -11.540  42.436 -41.907  0.50 19.61           N
ATOM   4905  CA   SER b 403     -11.409  41.072 -41.378  0.50 19.46           C
ATOM   4906  CB   SER b 403     -10.829  41.088 -39.963  0.50 20.37           C
ATOM   4907  OG   SER b 403     -11.808  41.492 -39.011  0.50 21.67           O
ATOM   4908  C    SER b 403     -12.801  40.435 -41.323  0.50 18.29           C
ATOM   4909  O    SER b 403     -13.797  41.148 -41.337  0.50 17.18           O
ATOM   4910  N    PHE b 404     -12.868  39.105 -41.245  0.50 17.63           N
ATOM   4911  CA   PHE b 404     -14.168  38.415 -41.245  0.50 17.92           C
ATOM   4912  CB   PHE b 404     -14.053  37.093 -42.003  0.50 17.23           C
ATOM   4913  CG   PHE b 404     -13.908  37.253 -43.477  0.50 17.46           C
ATOM   4914  CD1  PHE b 404     -12.641  37.391 -44.048  0.50 17.26           C
```

Figure 27 (Continued)

```
ATOM   4915  CE1 PHE b 404     -12.495  37.520 -45.422  0.50 18.60           C
ATOM   4916  CZ  PHE b 404     -13.615  37.510 -46.236  0.50 18.58           C
ATOM   4917  CE2 PHE b 404     -14.879  37.386 -45.676  0.50 20.05           C
ATOM   4918  CD2 PHE b 404     -15.018  37.243 -44.302  0.50 18.51           C
ATOM   4919  C   PHE b 404     -14.637  38.120 -39.833  0.50 18.23           C
ATOM   4920  O   PHE b 404     -13.818  38.020 -38.915  0.50 17.75           O
ATOM   4921  N   PHE b 405     -15.958  37.998 -39.656  0.50 17.39           N
ATOM   4922  CA  PHE b 405     -16.519  37.389 -38.444  0.50 16.90           C
ATOM   4923  CB  PHE b 405     -17.069  38.446 -37.454  0.50 17.36           C
ATOM   4924  CG  PHE b 405     -18.372  39.063 -37.896  0.50 17.83           C
ATOM   4925  CD1 PHE b 405     -19.581  38.545 -37.445  0.50 17.74           C
ATOM   4926  CE1 PHE b 405     -20.783  39.105 -37.843  0.50 18.01           C
ATOM   4927  CZ  PHE b 405     -20.796  40.175 -38.734  0.50 19.00           C
ATOM   4928  CE2 PHE b 405     -19.597  40.708 -39.178  0.50 17.59           C
ATOM   4929  CD2 PHE b 405     -18.393  40.165 -38.749  0.50 18.85           C
ATOM   4930  C   PHE b 405     -17.629  36.411 -38.843  0.50 16.15           C
ATOM   4931  O   PHE b 405     -18.141  36.482 -39.956  0.50 16.56           O
ATOM   4932  N   LEU b 406     -17.975  35.487 -37.943  0.50 16.23           N
ATOM   4933  CA  LEU b 406     -19.186  34.678 -38.108  0.50 16.45           C
ATOM   4934  CB  LEU b 406     -18.934  33.358 -38.875  0.50 17.53           C
ATOM   4935  CG  LEU b 406     -18.085  32.213 -38.279  0.50 17.07           C
ATOM   4936  CD1 LEU b 406     -18.655  31.520 -37.053  0.50 15.41           C
ATOM   4937  CD2 LEU b 406     -17.916  31.159 -39.347  0.50 15.43           C
ATOM   4938  C   LEU b 406     -19.790  34.374 -36.763  0.50 15.86           C
ATOM   4939  O   LEU b 406     -19.179  34.606 -35.731  0.50 16.06           O
ATOM   4940  N   TYR b 407     -21.007  33.872 -36.788  0.50 15.24           N
ATOM   4941  CA  TYR b 407     -21.616  33.279 -35.609  0.50 14.34           C
ATOM   4942  CB  TYR b 407     -22.919  34.007 -35.269  0.50 14.71           C
ATOM   4943  CG  TYR b 407     -22.683  35.315 -34.540  0.50 14.93           C
ATOM   4944  CD1 TYR b 407     -22.606  35.360 -33.150  0.50 15.67           C
ATOM   4945  CE1 TYR b 407     -22.428  36.570 -32.482  0.50 14.73           C
ATOM   4946  CZ  TYR b 407     -22.293  37.723 -33.216  0.50 15.27           C
ATOM   4947  OH  TYR b 407     -22.088  38.933 -32.603  0.50 15.29           O
ATOM   4948  CE2 TYR b 407     -22.323  37.698 -34.588  0.50 14.71           C
ATOM   4949  CD2 TYR b 407     -22.540  36.507 -35.244  0.50 15.12           C
ATOM   4950  C   TYR b 407     -21.918  31.824 -35.942  0.50 13.74           C
ATOM   4951  O   TYR b 407     -22.103  31.471 -37.123  0.50 12.93           O
ATOM   4952  N   SER b 408     -21.953  31.005 -34.886  0.50 14.25           N
ATOM   4953  CA  SER b 408     -22.547  29.691 -34.912  0.50 14.17           C
ATOM   4954  CB  SER b 408     -21.461  28.608 -34.766  0.50 14.66           C
ATOM   4955  OG  SER b 408     -22.045  27.345 -35.050  0.50 14.85           O
ATOM   4956  C   SER b 408     -23.533  29.614 -33.741  0.50 14.07           C
ATOM   4957  O   SER b 408     -23.229  30.037 -32.628  0.50 13.92           O
ATOM   4958  N   LYS b 409     -24.714  29.076 -33.994  0.50 13.74           N
ATOM   4959  CA  LYS b 409     -25.719  28.918 -32.957  0.50 13.89           C
ATOM   4960  CB  LYS b 409     -27.043  29.574 -33.371  0.50 13.40           C
ATOM   4961  CG  LYS b 409     -28.146  29.399 -32.327  0.50 12.98           C
ATOM   4962  CD  LYS b 409     -29.430  30.186 -32.607  0.50 13.07           C
ATOM   4963  CE  LYS b 409     -30.074  29.786 -33.930  0.50 12.99           C
ATOM   4964  NZ  LYS b 409     -30.757  28.454 -33.907  0.50 12.90           N
ATOM   4965  C   LYS b 409     -25.991  27.439 -32.709  0.50 14.35           C
ATOM   4966  O   LYS b 409     -26.450  26.730 -33.595  0.50 14.17           O
ATOM   4967  N   LEU b 410     -25.725  26.997 -31.494  0.50 14.78           N
ATOM   4968  CA  LEU b 410     -26.041  25.642 -31.108  0.50 16.09           C
ATOM   4969  CB  LEU b 410     -24.858  25.012 -30.329  0.50 15.79           C
ATOM   4970  CG  LEU b 410     -25.043  23.528 -29.958  0.50 17.59           C
ATOM   4971  CD1 LEU b 410     -24.898  22.606 -31.164  0.50 17.00           C
ATOM   4972  CD2 LEU b 410     -24.028  23.179 -28.878  0.50 17.24           C
ATOM   4973  C   LEU b 410     -27.334  25.638 -30.297  0.50 16.01           C
ATOM   4974  O   LEU b 410     -27.481  26.394 -29.334  0.50 17.60           O
ATOM   4975  N   THR b 411     -28.270  24.801 -30.710  0.50 15.87           N
ATOM   4976  CA  THR b 411     -29.548  24.677 -30.039  0.50 16.97           C
ATOM   4977  CB  THR b 411     -30.692  24.688 -31.051  0.50 17.68           C
ATOM   4978  OG1 THR b 411     -30.780  26.004 -31.602  0.50 16.68           O
```

Figure 27 (Continued)

```
ATOM   4979  CG2 THR b 411     -32.035  24.304 -30.377  0.50 18.48           C
ATOM   4980  C   THR b 411     -29.579  23.374 -29.261  0.50 18.10           C
ATOM   4981  O   THR b 411     -29.335  22.302 -29.820  0.50 17.77           O
ATOM   4982  N   VAL b 412     -29.856  23.484 -27.973  0.50 19.09           N
ATOM   4983  CA  VAL b 412     -29.991  22.306 -27.141  0.50 20.64           C
ATOM   4984  CB  VAL b 412     -28.789  22.152 -26.187  0.50 21.47           C
ATOM   4985  CG1 VAL b 412     -27.491  22.011 -26.976  0.50 21.41           C
ATOM   4986  CG2 VAL b 412     -28.723  23.335 -25.225  0.50 22.18           C
ATOM   4987  C   VAL b 412     -31.276  22.390 -26.324  0.50 22.13           C
ATOM   4988  O   VAL b 412     -31.766  23.476 -25.996  0.50 21.52           O
ATOM   4989  N   ASP b 413     -31.834  21.232 -26.002  0.50 22.14           N
ATOM   4990  CA  ASP b 413     -32.953  21.188 -25.083  0.50 23.51           C
ATOM   4991  CB  ASP b 413     -33.292  19.739 -24.755  0.50 27.81           C
ATOM   4992  CG  ASP b 413     -33.698  18.948 -25.983  0.50 30.59           C
ATOM   4993  OD1 ASP b 413     -34.216  19.564 -26.940  0.50 34.43           O
ATOM   4994  OD2 ASP b 413     -33.522  17.712 -25.984  0.50 36.94           O
ATOM   4995  C   ASP b 413     -32.606  21.957 -23.807  0.50 22.38           C
ATOM   4996  O   ASP b 413     -31.503  21.841 -23.291  0.50 21.25           O
ATOM   4997  N   LYS b 414     -33.559  22.729 -23.296  0.50 22.87           N
ATOM   4998  CA  LYS b 414     -33.318  23.538 -22.100  0.50 25.76           C
ATOM   4999  CB  LYS b 414     -34.578  24.328 -21.710  0.50 27.36           C
ATOM   5000  CG  LYS b 414     -34.446  25.072 -20.383  0.50 29.81           C
ATOM   5001  CD  LYS b 414     -35.668  25.928 -20.077  0.50 31.32           C
ATOM   5002  CE  LYS b 414     -36.951  25.117 -20.155  0.50 31.66           C
ATOM   5003  NZ  LYS b 414     -38.119  26.009 -20.385  0.50 32.86           N
ATOM   5004  C   LYS b 414     -32.824  22.716 -20.907  0.50 25.24           C
ATOM   5005  O   LYS b 414     -31.984  23.168 -20.135  0.50 24.08           O
ATOM   5006  N   SER b 415     -33.334  21.505 -20.748  0.50 26.37           N
ATOM   5007  CA  SER b 415     -32.968  20.736 -19.561  0.50 28.62           C
ATOM   5008  CB  SER b 415     -33.810  19.464 -19.435  0.50 30.21           C
ATOM   5009  OG  SER b 415     -34.023  18.866 -20.703  0.50 32.03           O
ATOM   5010  C   SER b 415     -31.473  20.420 -19.496  0.50 29.06           C
ATOM   5011  O   SER b 415     -30.923  20.255 -18.408  0.50 28.89           O
ATOM   5012  N   ARG b 416     -30.812  20.335 -20.654  0.50 28.38           N
ATOM   5013  CA  ARG b 416     -29.372  20.046 -20.665  0.50 27.79           C
ATOM   5014  CB  ARG b 416     -28.902  19.603 -22.051  0.50 27.87           C
ATOM   5015  CG  ARG b 416     -29.603  18.366 -22.578  0.50 28.32           C
ATOM   5016  CD  ARG b 416     -29.083  18.000 -23.958  0.50 28.84           C
ATOM   5017  NE  ARG b 416     -27.664  17.642 -23.926  0.50 28.53           N
ATOM   5018  CZ  ARG b 416     -26.858  17.696 -24.984  0.50 29.84           C
ATOM   5019  NH1 ARG b 416     -27.324  18.117 -26.155  0.50 29.82           N
ATOM   5020  NH2 ARG b 416     -25.584  17.347 -24.866  0.50 29.38           N
ATOM   5021  C   ARG b 416     -28.533  21.215 -20.168  0.50 27.19           C
ATOM   5022  O   ARG b 416     -27.536  21.010 -19.479  0.50 28.79           O
ATOM   5023  N   TRP b 417     -28.940  22.442 -20.495  0.50 25.49           N
ATOM   5024  CA  TRP b 417     -28.229  23.630 -20.010  0.50 24.85           C
ATOM   5025  CB  TRP b 417     -28.678  24.881 -20.785  0.50 23.46           C
ATOM   5026  CG  TRP b 417     -28.059  26.167 -20.299  0.50 23.73           C
ATOM   5027  CD1 TRP b 417     -28.670  27.126 -19.538  0.50 23.98           C
ATOM   5028  NE1 TRP b 417     -27.799  28.158 -19.283  0.50 24.64           N
ATOM   5029  CE2 TRP b 417     -26.600  27.887 -19.891  0.50 23.18           C
ATOM   5030  CD2 TRP b 417     -26.728  26.646 -20.549  0.50 22.67           C
ATOM   5031  CE3 TRP b 417     -25.621  26.141 -21.260  0.50 21.26           C
ATOM   5032  CZ3 TRP b 417     -24.461  26.880 -21.285  0.50 21.74           C
ATOM   5033  CH2 TRP b 417     -24.366  28.116 -20.631  0.50 21.18           C
ATOM   5034  CZ2 TRP b 417     -25.425  28.640 -19.932  0.50 21.52           C
ATOM   5035  C   TRP b 417     -28.358  23.865 -18.492  0.50 25.96           C
ATOM   5036  O   TRP b 417     -27.356  24.020 -17.791  0.50 25.96           O
ATOM   5037  N   GLN b 418     -29.589  23.917 -17.988  0.50 27.48           N
ATOM   5038  CA  GLN b 418     -29.806  24.294 -16.593  0.50 28.18           C
ATOM   5039  CB  GLN b 418     -31.312  24.474 -16.288  0.50 27.82           C
ATOM   5040  CG  GLN b 418     -32.072  25.365 -17.274  0.50 29.40           C
ATOM   5041  CD  GLN b 418     -32.402  26.776 -16.768  0.50 28.41           C
ATOM   5042  OE1 GLN b 418     -31.525  27.619 -16.581  0.50 25.34           O
```

Figure 27 (Continued)

```
ATOM   5043  NE2 GLN b 418     -33.692  27.044 -16.590  0.50 29.98           N
ATOM   5044  C   GLN b 418     -29.145  23.292 -15.636  0.50 29.06           C
ATOM   5045  O   GLN b 418     -28.774  23.646 -14.512  0.50 28.13           O
ATOM   5046  N   GLN b 419     -28.958  22.058 -16.105  0.50 29.83           N
ATOM   5047  CA  GLN b 419     -28.324  21.002 -15.305  0.50 30.01           C
ATOM   5048  CB  GLN b 419     -28.778  19.620 -15.776  0.50 30.49           C
ATOM   5049  CG  GLN b 419     -30.222  19.269 -15.452  0.50 31.57           C
ATOM   5050  CD  GLN b 419     -30.614  17.927 -16.033  0.50 35.73           C
ATOM   5051  OE1 GLN b 419     -30.015  17.464 -17.002  0.50 38.61           O
ATOM   5052  NE2 GLN b 419     -31.622  17.293 -15.443  0.50 37.94           N
ATOM   5053  C   GLN b 419     -26.793  21.056 -15.292  0.50 30.50           C
ATOM   5054  O   GLN b 419     -26.148  20.326 -14.532  0.50 30.29           O
ATOM   5055  N   GLY b 420     -26.208  21.892 -16.146  0.50 28.74           N
ATOM   5056  CA  GLY b 420     -24.764  22.087 -16.145  0.50 29.21           C
ATOM   5057  C   GLY b 420     -23.907  21.277 -17.109  0.50 28.44           C
ATOM   5058  O   GLY b 420     -22.710  21.153 -16.898  0.50 29.93           O
ATOM   5059  N   ASN b 421     -24.489  20.723 -18.165  0.50 29.63           N
ATOM   5060  CA  ASN b 421     -23.667  20.142 -19.218  0.50 29.91           C
ATOM   5061  CB  ASN b 421     -24.526  19.551 -20.334  0.50 31.85           C
ATOM   5062  CG  ASN b 421     -25.412  18.421 -19.853  0.50 33.79           C
ATOM   5063  OD1 ASN b 421     -25.596  17.426 -20.557  0.50 36.50           O
ATOM   5064  ND2 ASN b 421     -25.954  18.559 -18.650  0.50 31.37           N
ATOM   5065  C   ASN b 421     -22.746  21.213 -19.789  0.50 29.10           C
ATOM   5066  O   ASN b 421     -23.149  22.373 -19.907  0.50 28.65           O
ATOM   5067  N   VAL b 422     -21.521  20.827 -20.144  0.50 26.43           N
ATOM   5068  CA  VAL b 422     -20.554  21.780 -20.674  0.50 26.00           C
ATOM   5069  CB  VAL b 422     -19.138  21.610 -20.065  0.50 26.57           C
ATOM   5070  CG1 VAL b 422     -18.117  22.439 -20.833  0.50 25.27           C
ATOM   5071  CG2 VAL b 422     -19.141  22.012 -18.599  0.50 27.80           C
ATOM   5072  C   VAL b 422     -20.493  21.695 -22.193  0.50 24.67           C
ATOM   5073  O   VAL b 422     -20.253  20.630 -22.778  0.50 25.01           O
ATOM   5074  N   PHE b 423     -20.733  22.826 -22.842  0.50 21.67           N
ATOM   5075  CA  PHE b 423     -20.731  22.828 -24.285  0.50 20.20           C
ATOM   5076  CB  PHE b 423     -22.038  23.427 -24.805  0.50 20.21           C
ATOM   5077  CG  PHE b 423     -23.219  22.524 -24.589  0.50 19.84           C
ATOM   5078  CD1 PHE b 423     -23.958  22.599 -23.422  0.50 20.92           C
ATOM   5079  CE1 PHE b 423     -25.029  21.755 -23.195  0.50 19.71           C
ATOM   5080  CZ  PHE b 423     -25.368  20.798 -24.140  0.50 20.30           C
ATOM   5081  CE2 PHE b 423     -24.626  20.705 -25.313  0.50 20.00           C
ATOM   5082  CD2 PHE b 423     -23.550  21.559 -25.527  0.50 19.89           C
ATOM   5083  C   PHE b 423     -19.502  23.516 -24.845  0.50 19.44           C
ATOM   5084  O   PHE b 423     -18.949  24.406 -24.223  0.50 19.44           O
ATOM   5085  N   SER b 424     -18.971  23.083 -25.966  0.50 18.46           N
ATOM   5086  CA  SER b 424     -17.754  23.710 -26.427  0.50 17.88           C
ATOM   5087  CB  SER b 424     -16.553  22.813 -26.171  0.50 17.86           C
ATOM   5088  OG  SER b 424     -16.349  22.647 -24.791  0.50 18.87           O
ATOM   5089  C   SER b 424     -17.799  24.068 -27.887  0.50 17.31           C
ATOM   5090  O   SER b 424     -18.240  23.300 -28.673  0.50 17.38           O
ATOM   5091  N   CYS b 425     -17.287  25.241 -28.216  0.50 18.32           N
ATOM   5092  CA  CYS b 425     -17.170  25.669 -29.591  0.50 16.73           C
ATOM   5093  CB  CYS b 425     -17.583  27.135 -29.723  0.50 18.03           C
ATOM   5094  SG  CYS b 425     -17.484  27.833 -31.384  0.50 20.20           S
ATOM   5095  C   CYS b 425     -15.717  25.515 -30.010  0.50 16.92           C
ATOM   5096  O   CYS b 425     -14.851  26.082 -29.411  0.50 16.55           O
ATOM   5097  N   SER b 426     -15.497  24.743 -31.060  0.50 15.58           N
ATOM   5098  CA  SER b 426     -14.184  24.469 -31.581  0.50 15.57           C
ATOM   5099  CB  SER b 426     -14.001  22.973 -31.829  0.50 15.86           C
ATOM   5100  OG  SER b 426     -14.022  22.262 -30.628  0.50 19.82           O
ATOM   5101  C   SER b 426     -14.013  25.193 -32.896  0.50 15.06           C
ATOM   5102  O   SER b 426     -14.840  25.096 -33.754  0.50 15.03           O
ATOM   5103  N   VAL b 427     -12.916  25.915 -33.014  0.50 14.57           N
ATOM   5104  CA  VAL b 427     -12.623  26.702 -34.186  0.50 14.84           C
ATOM   5105  CB  VAL b 427     -12.614  28.185 -33.816  0.50 14.85           C
ATOM   5106  CG1 VAL b 427     -12.291  29.037 -35.011  0.50 15.27           C
```

Figure 27 (Continued)

```
ATOM   5107  CG2 VAL b 427     -13.941  28.551 -33.210  0.50 15.65           C
ATOM   5108  C   VAL b 427     -11.275  26.301 -34.766  0.50 15.08           C
ATOM   5109  O   VAL b 427     -10.320  26.197 -34.036  0.50 16.64           O
ATOM   5110  N   MET b 428     -11.221  26.091 -36.075  0.50 14.46           N
ATOM   5111  CA  MET b 428      -9.982  25.687 -36.729  0.50 14.26           C
ATOM   5112  CB  MET b 428     -10.188  24.310 -37.346  0.50 15.82           C
ATOM   5113  CG  MET b 428     -10.295  23.250 -36.261  0.50 16.49           C
ATOM   5114  SD  MET b 428     -11.262  21.823 -36.785  0.50 18.58           S
ATOM   5115  CE  MET b 428     -12.906  22.536 -36.875  0.50 18.95           C
ATOM   5116  C   MET b 428      -9.686  26.715 -37.794  0.50 14.74           C
ATOM   5117  O   MET b 428     -10.529  26.989 -38.634  0.50 14.12           O
ATOM   5118  N   HIS b 429      -8.490  27.293 -37.748  0.50 14.40           N
ATOM   5119  CA  HIS b 429      -8.111  28.360 -38.674  0.50 16.18           C
ATOM   5120  CB  HIS b 429      -8.649  29.713 -38.185  0.50 15.60           C
ATOM   5121  CG  HIS b 429      -8.467  30.831 -39.168  0.50 15.77           C
ATOM   5122  ND1 HIS b 429      -7.350  31.640 -39.169  0.50 17.30           N
ATOM   5123  CE1 HIS b 429      -7.464  32.546 -40.126  0.50 17.41           C
ATOM   5124  NE2 HIS b 429      -8.629  32.370 -40.734  0.50 17.02           N
ATOM   5125  CD2 HIS b 429      -9.286  31.319 -40.139  0.50 16.63           C
ATOM   5126  C   HIS b 429      -6.589  28.416 -38.793  0.50 15.67           C
ATOM   5127  O   HIS b 429      -5.883  28.132 -37.828  0.50 17.36           O
ATOM   5128  N   GLU b 430      -6.102  28.722 -39.986  0.50 15.98           N
ATOM   5129  CA  GLU b 430      -4.661  28.700 -40.257  0.50 17.41           C
ATOM   5130  CB  GLU b 430      -4.385  29.004 -41.729  0.50 19.02           C
ATOM   5131  CG  GLU b 430      -4.708  30.441 -42.120  0.50 19.81           C
ATOM   5132  CD  GLU b 430      -5.021  30.567 -43.605  0.50 21.41           C
ATOM   5133  OE1 GLU b 430      -6.187  30.369 -43.991  0.50 23.02           O
ATOM   5134  OE2 GLU b 430      -4.105  30.856 -44.387  0.50 22.31           O
ATOM   5135  C   GLU b 430      -3.862  29.655 -39.363  0.50 18.40           C
ATOM   5136  O   GLU b 430      -2.653  29.448 -39.158  0.50 18.21           O
ATOM   5137  N   ALA b 431      -4.513  30.688 -38.833  0.50 17.80           N
ATOM   5138  CA  ALA b 431      -3.806  31.675 -38.013  0.50 20.05           C
ATOM   5139  CB  ALA b 431      -4.198  33.093 -38.426  0.50 18.85           C
ATOM   5140  C   ALA b 431      -3.987  31.466 -36.503  0.50 20.56           C
ATOM   5141  O   ALA b 431      -3.711  32.375 -35.690  0.50 20.88           O
ATOM   5142  N   LEU b 432      -4.386  30.257 -36.112  0.50 19.65           N
ATOM   5143  CA  LEU b 432      -4.448  29.897 -34.700  0.50 18.85           C
ATOM   5144  CB  LEU b 432      -5.764  29.179 -34.376  0.50 19.27           C
ATOM   5145  CG  LEU b 432      -7.066  29.962 -34.543  0.50 18.36           C
ATOM   5146  CD1 LEU b 432      -8.229  28.982 -34.597  0.50 18.25           C
ATOM   5147  CD2 LEU b 432      -7.195  30.943 -33.379  0.50 20.62           C
ATOM   5148  C   LEU b 432      -3.294  28.977 -34.306  0.50 20.15           C
ATOM   5149  O   LEU b 432      -2.903  28.101 -35.060  0.50 17.44           O
ATOM   5150  N   HIS b 433      -2.769  29.164 -33.102  0.50 21.68           N
ATOM   5151  CA  HIS b 433      -1.771  28.248 -32.590  0.50 21.88           C
ATOM   5152  CB  HIS b 433      -1.453  28.570 -31.124  0.50 23.94           C
ATOM   5153  CG  HIS b 433      -0.318  27.775 -30.558  0.50 27.14           C
ATOM   5154  ND1 HIS b 433      -0.507  26.674 -29.749  0.50 28.73           N
ATOM   5155  CE1 HIS b 433       0.669  26.179 -29.402  0.50 29.66           C
ATOM   5156  NE2 HIS b 433       1.612  26.917 -29.960  0.50 28.67           N
ATOM   5157  CD2 HIS b 433       1.023  27.920 -30.688  0.50 27.91           C
ATOM   5158  C   HIS b 433      -2.275  26.805 -32.766  0.50 20.87           C
ATOM   5159  O   HIS b 433      -3.358  26.446 -32.305  0.50 21.33           O
ATOM   5160  N   ASN b 434      -1.505  25.977 -33.460  0.50 19.83           N
ATOM   5161  CA  ASN b 434      -1.935  24.591 -33.724  0.50 18.61           C
ATOM   5162  CB  ASN b 434      -2.032  23.796 -32.422  0.50 21.51           C
ATOM   5163  CG  ASN b 434      -0.675  23.439 -31.856  0.50 22.31           C
ATOM   5164  OD1 ASN b 434       0.350  23.658 -32.499  0.50 22.30           O
ATOM   5165  ND2 ASN b 434      -0.659  22.907 -30.633  0.50 23.97           N
ATOM   5166  C   ASN b 434      -3.262  24.470 -34.493  0.50 19.02           C
ATOM   5167  O   ASN b 434      -3.946  23.427 -34.418  0.50 17.73           O
ATOM   5168  N   HIS b 435      -3.634  25.541 -35.198  0.50 16.40           N
ATOM   5169  CA  HIS b 435      -4.847  25.547 -36.022  0.50 17.28           C
ATOM   5170  CB  HIS b 435      -4.706  24.571 -37.201  0.50 16.39           C
```

Figure 27 (Continued)

```
ATOM   5171  CG   HIS b 435      -3.611  24.928 -38.162  0.50 17.33           C
ATOM   5172  ND1  HIS b 435      -3.113  24.027 -39.084  0.50 17.35           N
ATOM   5173  CE1  HIS b 435      -2.181  24.619 -39.817  0.50 17.80           C
ATOM   5174  NE2  HIS b 435      -2.058  25.871 -39.403  0.50 17.33           N
ATOM   5175  CD2  HIS b 435      -2.946  26.090 -38.373  0.50 17.14           C
ATOM   5176  C    HIS b 435      -6.139  25.236 -35.275  0.50 17.49           C
ATOM   5177  O    HIS b 435      -7.130  24.848 -35.896  0.50 17.42           O
ATOM   5178  N    TYR b 436      -6.112  25.356 -33.963  0.50 18.08           N
ATOM   5179  CA   TYR b 436      -7.238  24.913 -33.183  0.50 19.24           C
ATOM   5180  CB   TYR b 436      -7.048  23.428 -32.891  0.50 20.22           C
ATOM   5181  CG   TYR b 436      -8.171  22.747 -32.170  0.50 20.78           C
ATOM   5182  CD1  TYR b 436      -8.135  22.585 -30.815  0.50 20.90           C
ATOM   5183  CE1  TYR b 436      -9.145  21.955 -30.147  0.50 22.11           C
ATOM   5184  CZ   TYR b 436     -10.207  21.471 -30.832  0.50 21.94           C
ATOM   5185  OH   TYR b 436     -11.200  20.850 -30.156  0.50 23.06           O
ATOM   5186  CE2  TYR b 436     -10.268  21.598 -32.191  0.50 21.50           C
ATOM   5187  CD2  TYR b 436      -9.248  22.235 -32.851  0.50 21.11           C
ATOM   5188  C    TYR b 436      -7.364  25.706 -31.905  0.50 19.94           C
ATOM   5189  O    TYR b 436      -6.387  25.987 -31.264  0.50 19.45           O
ATOM   5190  N    THR b 437      -8.585  26.061 -31.549  0.50 19.51           N
ATOM   5191  CA   THR b 437      -8.867  26.595 -30.239  0.50 20.19           C
ATOM   5192  CB   THR b 437      -8.657  28.112 -30.141  0.50 21.56           C
ATOM   5193  OG1  THR b 437      -8.596  28.487 -28.769  0.50 21.03           O
ATOM   5194  CG2  THR b 437      -9.766  28.859 -30.810  0.50 21.31           C
ATOM   5195  C    THR b 437     -10.271  26.201 -29.859  0.50 21.28           C
ATOM   5196  O    THR b 437     -11.072  25.920 -30.704  0.50 20.78           O
ATOM   5197  N    GLN b 438     -10.536  26.153 -28.571  0.50 21.34           N
ATOM   5198  CA   GLN b 438     -11.852  25.819 -28.076  0.50 22.05           C
ATOM   5199  CB   GLN b 438     -11.857  24.376 -27.594  0.50 25.29           C
ATOM   5200  CG   GLN b 438     -13.216  23.791 -27.291  0.50 29.20           C
ATOM   5201  CD   GLN b 438     -13.146  22.305 -27.044  0.50 29.94           C
ATOM   5202  OE1  GLN b 438     -12.783  21.861 -25.972  0.50 33.28           O
ATOM   5203  NE2  GLN b 438     -13.491  21.535 -28.043  0.50 30.93           N
ATOM   5204  C    GLN b 438     -12.232  26.744 -26.939  0.50 22.36           C
ATOM   5205  O    GLN b 438     -11.408  27.080 -26.123  0.50 21.39           O
ATOM   5206  N    LYS b 439     -13.492  27.146 -26.901  0.50 22.09           N
ATOM   5207  CA   LYS b 439     -14.052  27.887 -25.789  0.50 22.43           C
ATOM   5208  CB   LYS b 439     -14.387  29.319 -26.175  0.50 22.27           C
ATOM   5209  CG   LYS b 439     -13.214  30.117 -26.681  0.50 24.73           C
ATOM   5210  CD   LYS b 439     -12.326  30.571 -25.538  0.50 25.70           C
ATOM   5211  CE   LYS b 439     -11.351  31.648 -25.980  0.50 27.87           C
ATOM   5212  NZ   LYS b 439      -9.998  31.095 -26.234  0.50 29.57           N
ATOM   5213  C    LYS b 439     -15.307  27.164 -25.327  0.50 22.06           C
ATOM   5214  O    LYS b 439     -16.057  26.667 -26.123  0.50 20.59           O
ATOM   5215  N    SER b 440     -15.509  27.125 -24.021  0.50 22.86           N
ATOM   5216  CA   SER b 440     -16.551  26.316 -23.421  0.50 23.61           C
ATOM   5217  CB   SER b 440     -15.935  25.248 -22.538  0.50 24.18           C
ATOM   5218  OG   SER b 440     -15.189  24.359 -23.298  0.50 23.47           O
ATOM   5219  C    SER b 440     -17.482  27.129 -22.569  0.50 24.33           C
ATOM   5220  O    SER b 440     -17.134  28.194 -22.121  0.50 27.33           O
ATOM   5221  N    LEU b 441     -18.674  26.611 -22.352  0.50 25.36           N
ATOM   5222  CA   LEU b 441     -19.553  27.255 -21.378  0.50 25.41           C
ATOM   5223  CB   LEU b 441     -20.138  28.559 -21.924  0.50 27.04           C
ATOM   5224  CG   LEU b 441     -21.133  28.520 -23.086  0.50 27.32           C
ATOM   5225  CD1  LEU b 441     -20.639  27.707 -24.279  0.50 27.75           C
ATOM   5226  CD2  LEU b 441     -21.442  29.950 -23.499  0.50 27.05           C
ATOM   5227  C    LEU b 441     -20.640  26.375 -20.784  0.50 24.82           C
ATOM   5228  O    LEU b 441     -21.015  25.344 -21.331  0.50 23.01           O
ATOM   5229  N    SER b 442     -21.129  26.802 -19.629  0.50 25.55           N
ATOM   5230  CA   SER b 442     -22.116  26.043 -18.895  0.50 28.15           C
ATOM   5231  CB   SER b 442     -21.442  24.932 -18.094  0.50 29.05           C
ATOM   5232  OG   SER b 442     -20.528  25.492 -17.166  0.50 30.19           O
ATOM   5233  C    SER b 442     -22.772  27.004 -17.948  0.50 29.76           C
ATOM   5234  O    SER b 442     -22.267  28.103 -17.730  0.50 29.46           O
```

Figure 27 (Continued)

```
ATOM   5235  N   LEU b 443     -23.897  26.583 -17.388  0.50 32.51           N
ATOM   5236  CA  LEU b 443     -24.573  27.355 -16.360  0.50 37.71           C
ATOM   5237  CB  LEU b 443     -25.847  26.625 -15.934  0.50 36.44           C
ATOM   5238  CG  LEU b 443     -26.823  27.345 -15.007  0.50 36.60           C
ATOM   5239  CD1 LEU b 443     -26.961  28.817 -15.379  0.50 36.70           C
ATOM   5240  CD2 LEU b 443     -28.167  26.644 -15.068  0.50 36.69           C
ATOM   5241  C   LEU b 443     -23.629  27.523 -15.177  0.50 41.82           C
ATOM   5242  O   LEU b 443     -23.120  26.541 -14.633  0.50 43.13           O
ATOM   5243  N   SER b 444     -23.382  28.766 -14.785  0.50 47.83           N
ATOM   5244  CA  SER b 444     -22.440  29.037 -13.699  0.50 55.11           C
ATOM   5245  CB  SER b 444     -22.117  30.533 -13.642  0.50 55.59           C
ATOM   5246  OG  SER b 444     -23.054  31.273 -14.405  0.50 53.97           O
ATOM   5247  C   SER b 444     -22.920  28.518 -12.334  0.50 59.93           C
ATOM   5248  O   SER b 444     -24.097  28.646 -11.988  0.50 56.75           O
ATOM   5249  N   PRO b 445     -21.999  27.918 -11.559  0.50 64.76           N
ATOM   5250  CA  PRO b 445     -22.321  27.367 -10.249  0.50 66.82           C
ATOM   5251  CB  PRO b 445     -20.983  27.439  -9.501  0.50 65.72           C
ATOM   5252  CG  PRO b 445     -19.923  27.571 -10.557  0.50 64.46           C
ATOM   5253  CD  PRO b 445     -20.583  27.710 -11.903  0.50 64.79           C
ATOM   5254  C   PRO b 445     -23.374  28.201  -9.523  0.50 67.53           C
ATOM   5255  O   PRO b 445     -24.474  27.712  -9.259  0.50 68.26           O
HETATM 5256  C1  NAG b 500     -25.319  17.655 -67.831  0.50 29.08           C
HETATM 5257  C2  NAG b 500     -25.106  19.147 -67.968  0.50 29.01           C
HETATM 5258  N2  NAG b 500     -24.896  19.468 -69.349  0.50 29.90           N
HETATM 5259  C7  NAG b 500     -25.813  20.083 -70.074  0.50 30.01           C
HETATM 5260  O7  NAG b 500     -26.894  20.387 -69.630  0.50 30.33           O
HETATM 5261  C8  NAG b 500     -25.410  20.396 -71.485  0.50 30.17           C
HETATM 5262  C3  NAG b 500     -23.885  19.582 -67.180  0.50 28.75           C
HETATM 5263  O3  NAG b 500     -23.805  20.993 -67.173  0.50 29.19           O
HETATM 5264  C4  NAG b 500     -23.974  19.086 -65.755  0.50 28.88           C
HETATM 5265  O4  NAG b 500     -22.708  19.231 -65.159  0.50 27.14           O
HETATM 5266  C5  NAG b 500     -24.244  17.606 -65.729  0.50 29.55           C
HETATM 5267  C6  NAG b 500     -24.398  17.136 -64.293  0.50 30.62           C
HETATM 5268  O6  NAG b 500     -25.283  18.036 -63.650  0.50 30.77           O
HETATM 5269  O5  NAG b 500     -25.418  17.325 -66.459  0.50 29.94           O
HETATM 5270  C1  FUC b 501     -25.897  17.367 -62.555  0.50 42.54           C
HETATM 5271  C2  FUC b 501     -26.705  18.387 -61.770  0.50 42.40           C
HETATM 5272  O2  FUC b 501     -25.897  19.558 -61.546  0.50 44.92           O
HETATM 5273  C3  FUC b 501     -27.988  18.784 -62.497  0.50 42.04           C
HETATM 5274  O3  FUC b 501     -29.003  18.950 -61.532  0.50 38.58           O
HETATM 5275  C4  FUC b 501     -28.535  17.764 -63.487  0.50 41.72           C
HETATM 5276  O4  FUC b 501     -29.400  16.896 -62.778  0.50 43.12           O
HETATM 5277  C5  FUC b 501     -27.467  16.897 -64.117  0.50 43.77           C
HETATM 5278  C6  FUC b 501     -28.054  15.820 -65.032  0.50 42.71           C
HETATM 5279  O5  FUC b 501     -26.744  16.352 -63.034  0.50 42.39           O
HETATM 5280  C1  NAG b 502     -22.981  21.138 -63.954  0.50 24.93           C
HETATM 5281  C2  NAG b 502     -22.008  20.876 -62.837  0.50 25.98           C
HETATM 5282  N2  NAG b 502     -22.524  19.811 -61.987  0.50 26.10           N
HETATM 5283  C7  NAG b 502     -21.908  18.669 -61.652  0.50 30.02           C
HETATM 5284  O7  NAG b 502     -22.435  17.794 -60.984  0.50 31.47           O
HETATM 5285  C8  NAG b 502     -20.516  18.473 -62.121  0.50 24.89           C
HETATM 5286  C3  NAG b 502     -21.906  22.227 -62.147  0.50 25.68           C
HETATM 5287  O3  NAG b 502     -20.968  22.126 -61.098  0.50 26.50           O
HETATM 5288  C4  NAG b 502     -21.546  23.349 -63.150  0.50 24.81           C
HETATM 5289  O4  NAG b 502     -21.723  24.684 -62.663  0.50 25.76           O
HETATM 5290  C5  NAG b 502     -22.417  23.249 -64.404  0.50 25.37           C
HETATM 5291  C6  NAG b 502     -22.043  24.275 -65.466  0.50 25.26           C
HETATM 5292  O6  NAG b 502     -22.847  24.043 -66.622  0.50 28.11           O
HETATM 5293  O5  NAG b 502     -22.359  21.943 -64.927  0.50 23.86           O
HETATM 5294  C1  BMA b 503     -20.650  25.087 -61.876  0.50 35.25           C
HETATM 5295  O5  BMA b 503     -20.929  24.704 -60.555  0.50 34.34           O
HETATM 5296  C5  BMA b 503     -19.941  25.167 -59.681  0.50 35.27           C
HETATM 5297  C6  BMA b 503     -20.200  24.577 -58.308  0.50 33.14           C
HETATM 5298  O6  BMA b 503     -20.236  23.176 -58.464  0.50 34.77           O
```

Figure 27 (Continued)

```
HETATM 5299  C4  BMA b 503     -19.968  26.684 -59.659  0.50 36.07           C
HETATM 5300  O4  BMA b 503     -18.878  27.149 -58.896  0.50 37.94           O
HETATM 5301  C3  BMA b 503     -19.808  27.272 -61.047  0.50 36.67           C
HETATM 5302  O3  BMA b 503     -20.198  28.627 -61.013  0.50 38.77           O
HETATM 5303  C2  BMA b 503     -20.736  26.589 -62.012  0.50 36.64           C
HETATM 5304  O2  BMA b 503     -22.065  27.005 -61.730  0.50 34.82           O
HETATM 5305  C1  MAN b 504     -20.287  22.580 -57.173  0.50 33.67           C
HETATM 5306  C2  MAN b 504     -20.054  21.083 -57.270  0.50 34.57           C
HETATM 5307  O2  MAN b 504     -20.074  20.488 -55.983  0.50 34.42           O
HETATM 5308  C3  MAN b 504     -21.168  20.456 -58.062  0.50 34.88           C
HETATM 5309  O3  MAN b 504     -20.984  19.053 -58.100  0.50 36.74           O
HETATM 5310  C4  MAN b 504     -22.463  20.763 -57.349  0.50 35.84           C
HETATM 5311  O4  MAN b 504     -23.547  20.282 -58.112  0.50 34.58           O
HETATM 5312  C5  MAN b 504     -22.635  22.252 -57.143  0.50 35.96           C
HETATM 5313  C6  MAN b 504     -23.867  22.495 -56.284  0.50 38.27           C
HETATM 5314  O6  MAN b 504     -23.981  23.877 -56.029  0.50 40.10           O
HETATM 5315  O5  MAN b 504     -21.506  22.836 -56.516  0.50 35.25           O
HETATM 5316  C1  NAG b 505     -18.776  20.509 -55.395  0.50 40.06           C
HETATM 5317  C2  NAG b 505     -18.898  20.526 -53.875  0.50 41.37           C
HETATM 5318  N2  NAG b 505     -19.543  21.732 -53.435  0.50 39.73           N
HETATM 5319  C7  NAG b 505     -20.844  21.819 -53.193  0.50 43.08           C
HETATM 5320  O7  NAG b 505     -21.597  20.888 -53.267  0.50 44.58           O
HETATM 5321  C8  NAG b 505     -21.346  23.178 -52.829  0.50 43.19           C
HETATM 5322  C3  NAG b 505     -17.545  20.389 -53.182  0.50 40.54           C
HETATM 5323  O3  NAG b 505     -17.728  20.061 -51.814  0.50 40.97           O
HETATM 5324  C4  NAG b 505     -16.655  19.334 -53.828  0.50 41.00           C
HETATM 5325  O4  NAG b 505     -15.327  19.593 -53.405  0.50 41.44           O
HETATM 5326  C5  NAG b 505     -16.702  19.419 -55.344  0.50 41.31           C
HETATM 5327  C6  NAG b 505     -15.911  18.300 -56.016  0.50 43.14           C
HETATM 5328  O6  NAG b 505     -16.379  17.017 -55.651  0.50 43.08           O
HETATM 5329  O5  NAG b 505     -18.036  19.383 -55.801  0.50 42.08           O
HETATM 5330  C1  GAL b 506     -14.667  18.395 -53.006  0.50 26.68           C
HETATM 5331  C2  GAL b 506     -13.296  18.712 -52.378  0.50 26.17           C
HETATM 5332  O2  GAL b 506     -12.312  19.034 -53.357  0.50 25.26           O
HETATM 5333  C3  GAL b 506     -12.754  17.536 -51.569  0.50 25.59           C
HETATM 5334  O3  GAL b 506     -11.586  17.917 -50.883  0.50 25.22           O
HETATM 5335  C4  GAL b 506     -13.806  17.009 -50.623  0.50 25.70           C
HETATM 5336  O4  GAL b 506     -14.344  18.055 -49.819  0.50 26.36           O
HETATM 5337  C5  GAL b 506     -14.893  16.536 -51.565  0.50 25.58           C
HETATM 5338  C6  GAL b 506     -15.961  15.664 -50.930  0.50 23.79           C
HETATM 5339  O6  GAL b 506     -17.047  15.581 -51.845  0.50 23.01           O
HETATM 5340  O5  GAL b 506     -15.498  17.700 -52.094  0.50 24.97           O
HETATM 5341  C1  MAN b 507     -18.168  29.277 -61.853  0.50136.50           C
HETATM 5342  C2  MAN b 507     -18.452  30.691 -61.400  0.50135.97           C
HETATM 5343  O2  MAN b 507     -17.464  31.555 -61.924  0.50138.75           O
HETATM 5344  C3  MAN b 507     -19.755  31.185 -61.970  0.50134.60           C
HETATM 5345  O3  MAN b 507     -19.888  32.565 -61.719  0.50133.51           O
HETATM 5346  C4  MAN b 507     -19.709  31.016 -63.464  0.50135.04           C
HETATM 5347  O4  MAN b 507     -20.869  31.618 -64.036  0.50137.33           O
HETATM 5348  C5  MAN b 507     -19.680  29.531 -63.756  0.50135.47           C
HETATM 5349  C6  MAN b 507     -19.656  29.271 -65.251  0.50134.05           C
HETATM 5350  O6  MAN b 507     -20.551  28.212 -65.602  0.50133.73           O
HETATM 5351  O5  MAN b 507     -18.501  28.974 -63.201  0.50136.89           O
HETATM 5352  C1  NAG b 508     -16.199  31.619 -61.230  0.50118.20           C
HETATM 5353  C2  NAG b 508     -16.107  31.549 -59.713  0.50117.22           C
HETATM 5354  N2  NAG b 508     -17.139  32.347 -59.081  0.50116.02           N
HETATM 5355  C7  NAG b 508     -17.291  32.343 -57.760  0.50113.09           C
HETATM 5356  O7  NAG b 508     -18.153  33.001 -57.182  0.50113.33           O
HETATM 5357  C8  NAG b 508     -16.342  31.481 -56.982  0.50111.38           C
HETATM 5358  C3  NAG b 508     -14.728  32.012 -59.272  0.50117.32           C
HETATM 5359  O3  NAG b 508     -14.602  31.858 -57.876  0.50115.67           O
HETATM 5360  C4  NAG b 508     -13.658  31.195 -59.989  0.50117.79           C
HETATM 5361  O4  NAG b 508     -12.397  31.781 -59.758  0.50116.88           O
HETATM 5362  C5  NAG b 508     -13.910  31.108 -61.495  0.50118.68           C
```

Figure 27 (Continued)

```
HETATM 5363  C6   NAG b 508    -12.977  30.085 -62.139  0.50116.97           C
HETATM 5364  O6   NAG b 508    -11.790  30.713 -62.569  0.50114.81           O
HETATM 5365  O5   NAG b 508    -15.245  30.731 -61.771  0.50119.12           O
ATOM   5366  N    GLY a 236    -31.521  43.301 -80.930  0.50 42.62           N
ATOM   5367  CA   GLY a 236    -31.015  43.748 -79.598  0.50 42.48           C
ATOM   5368  C    GLY a 236    -31.906  44.762 -78.901  0.50 40.83           C
ATOM   5369  O    GLY a 236    -31.412  45.632 -78.187  0.50 42.32           O
ATOM   5370  N    GLY a 237    -33.219  44.636 -79.093  0.50 39.14           N
ATOM   5371  CA   GLY a 237    -34.196  45.570 -78.526  0.50 34.52           C
ATOM   5372  C    GLY a 237    -34.015  45.800 -77.035  0.50 31.82           C
ATOM   5373  O    GLY a 237    -33.005  45.399 -76.463  0.50 32.06           O
ATOM   5374  N    PRO a 238    -35.011  46.430 -76.393  0.50 31.31           N
ATOM   5375  CA   PRO a 238    -34.921  46.793 -74.973  0.50 28.78           C
ATOM   5376  CB   PRO a 238    -36.205  47.603 -74.722  0.50 28.05           C
ATOM   5377  CG   PRO a 238    -36.824  47.858 -76.058  0.50 28.86           C
ATOM   5378  CD   PRO a 238    -36.318  46.779 -76.975  0.50 29.82           C
ATOM   5379  C    PRO a 238    -34.862  45.581 -74.030  0.50 28.69           C
ATOM   5380  O    PRO a 238    -35.210  44.457 -74.422  0.50 27.35           O
ATOM   5381  N    SER a 239    -34.388  45.821 -72.807  0.50 28.11           N
ATOM   5382  CA   SER a 239    -34.460  44.839 -71.713  0.50 27.35           C
ATOM   5383  CB   SER a 239    -33.064  44.376 -71.284  0.50 26.24           C
ATOM   5384  OG   SER a 239    -32.433  43.575 -72.271  0.50 29.17           O
ATOM   5385  C    SER a 239    -35.154  45.477 -70.516  0.50 26.84           C
ATOM   5386  O    SER a 239    -35.122  46.694 -70.336  0.50 26.01           O
ATOM   5387  N    VAL a 240    -35.761  44.644 -69.677  0.50 25.55           N
ATOM   5388  CA   VAL a 240    -36.648  45.139 -68.625  0.50 24.23           C
ATOM   5389  CB   VAL a 240    -38.114  44.762 -68.937  0.50 24.17           C
ATOM   5390  CG1  VAL a 240    -39.037  45.118 -67.784  0.50 23.21           C
ATOM   5391  CG2  VAL a 240    -38.580  45.436 -70.230  0.50 23.38           C
ATOM   5392  C    VAL a 240    -36.227  44.521 -67.290  0.50 22.67           C
ATOM   5393  O    VAL a 240    -36.001  43.307 -67.210  0.50 22.56           O
ATOM   5394  N    PHE a 241    -36.095  45.363 -66.268  0.50 22.59           N
ATOM   5395  CA   PHE a 241    -35.762  44.887 -64.909  0.50 22.96           C
ATOM   5396  CB   PHE a 241    -34.347  45.300 -64.502  0.50 24.44           C
ATOM   5397  CG   PHE a 241    -33.278  44.726 -65.385  0.50 25.59           C
ATOM   5398  CD1  PHE a 241    -32.830  43.430 -65.200  0.50 25.95           C
ATOM   5399  CE1  PHE a 241    -31.858  42.891 -66.021  0.50 28.52           C
ATOM   5400  CZ   PHE a 241    -31.331  43.646 -67.052  0.50 26.39           C
ATOM   5401  CE2  PHE a 241    -31.768  44.941 -67.254  0.50 26.94           C
ATOM   5402  CD2  PHE a 241    -32.739  45.477 -66.426  0.50 26.61           C
ATOM   5403  C    PHE a 241    -36.780  45.412 -63.918  0.50 22.78           C
ATOM   5404  O    PHE a 241    -37.057  46.610 -63.869  0.50 23.40           O
ATOM   5405  N    LEU a 242    -37.332  44.511 -63.108  0.50 20.75           N
ATOM   5406  CA   LEU a 242    -38.416  44.879 -62.214  0.50 20.43           C
ATOM   5407  CB   LEU a 242    -39.637  43.996 -62.489  0.50 19.53           C
ATOM   5408  CG   LEU a 242    -40.954  44.330 -61.791  0.50 18.99           C
ATOM   5409  CD1  LEU a 242    -41.354  45.785 -62.033  0.50 20.32           C
ATOM   5410  CD2  LEU a 242    -42.051  43.384 -62.271  0.50 19.47           C
ATOM   5411  C    LEU a 242    -37.906  44.648 -60.806  0.50 19.43           C
ATOM   5412  O    LEU a 242    -37.398  43.551 -60.498  0.50 20.25           O
ATOM   5413  N    PHE a 243    -38.005  45.690 -59.985  0.50 18.86           N
ATOM   5414  CA   PHE a 243    -37.441  45.710 -58.643  0.50 18.85           C
ATOM   5415  CB   PHE a 243    -36.462  46.878 -58.493  0.50 19.10           C
ATOM   5416  CG   PHE a 243    -35.287  46.798 -59.425  0.50 21.16           C
ATOM   5417  CD1  PHE a 243    -34.165  46.060 -59.086  0.50 21.99           C
ATOM   5418  CE1  PHE a 243    -33.079  45.981 -59.943  0.50 22.08           C
ATOM   5419  CZ   PHE a 243    -33.125  46.608 -61.178  0.50 22.43           C
ATOM   5420  CE2  PHE a 243    -34.249  47.323 -61.540  0.50 21.39           C
ATOM   5421  CD2  PHE a 243    -35.329  47.417 -60.668  0.50 20.55           C
ATOM   5422  C    PHE a 243    -38.536  45.849 -57.598  0.50 17.77           C
ATOM   5423  O    PHE a 243    -39.442  46.655 -57.740  0.50 17.66           O
ATOM   5424  N    PRO a 244    -38.414  45.099 -56.497  0.50 17.53           N
ATOM   5425  CA   PRO a 244    -39.412  45.131 -55.449  0.50 17.89           C
ATOM   5426  CB   PRO a 244    -39.131  43.817 -54.714  0.50 17.03           C
```

Figure 27 (Continued)

```
ATOM   5427  CG   PRO a 244     -37.646  43.746 -54.761  0.50 17.95           C
ATOM   5428  CD   PRO a 244     -37.266  44.245 -56.135  0.50 17.77           C
ATOM   5429  C    PRO a 244     -39.225  46.316 -54.487  0.50 16.65           C
ATOM   5430  O    PRO a 244     -38.189  46.988 -54.520  0.50 18.14           O
ATOM   5431  N    PRO a 245     -40.214  46.574 -53.625  0.50 16.90           N
ATOM   5432  CA   PRO a 245     -40.024  47.576 -52.586  0.50 16.82           C
ATOM   5433  CB   PRO a 245     -41.410  47.683 -51.937  0.50 17.83           C
ATOM   5434  CG   PRO a 245     -42.059  46.375 -52.211  0.50 17.39           C
ATOM   5435  CD   PRO a 245     -41.534  45.920 -53.539  0.50 17.08           C
ATOM   5436  C    PRO a 245     -39.034  47.017 -51.578  0.50 17.26           C
ATOM   5437  O    PRO a 245     -38.789  45.798 -51.542  0.50 17.26           O
ATOM   5438  N    LYS a 246     -38.431  47.906 -50.803  0.50 17.08           N
ATOM   5439  CA   LYS a 246     -37.589  47.481 -49.677  0.50 17.89           C
ATOM   5440  CB   LYS a 246     -36.764  48.649 -49.143  0.50 19.51           C
ATOM   5441  CG   LYS a 246     -35.899  49.314 -50.198  0.50 21.40           C
ATOM   5442  CD   LYS a 246     -34.693  48.455 -50.517  0.50 24.36           C
ATOM   5443  CE   LYS a 246     -33.764  49.173 -51.498  0.50 25.13           C
ATOM   5444  NZ   LYS a 246     -34.525  49.722 -52.656  0.50 24.95           N
ATOM   5445  C    LYS a 246     -38.484  46.939 -48.572  0.50 17.43           C
ATOM   5446  O    LYS a 246     -39.547  47.500 -48.305  0.50 16.78           O
ATOM   5447  N    PRO a 247     -38.078  45.820 -47.933  0.50 16.56           N
ATOM   5448  CA   PRO a 247     -38.931  45.332 -46.849  0.50 16.27           C
ATOM   5449  CB   PRO a 247     -38.051  44.273 -46.177  0.50 16.46           C
ATOM   5450  CG   PRO a 247     -37.280  43.694 -47.333  0.50 16.56           C
ATOM   5451  CD   PRO a 247     -36.966  44.891 -48.222  0.50 16.81           C
ATOM   5452  C    PRO a 247     -39.352  46.384 -45.822  0.50 14.93           C
ATOM   5453  O    PRO a 247     -40.514  46.444 -45.459  0.50 15.22           O
ATOM   5454  N    LYS a 248     -38.427  47.191 -45.327  0.50 15.11           N
ATOM   5455  CA   LYS a 248     -38.810  48.147 -44.300  0.50 15.32           C
ATOM   5456  CB   LYS a 248     -37.595  48.942 -43.830  0.50 15.72           C
ATOM   5457  CG   LYS a 248     -37.905  49.954 -42.755  0.50 16.17           C
ATOM   5458  CD   LYS a 248     -36.707  50.873 -42.543  0.50 16.66           C
ATOM   5459  CE   LYS a 248     -36.980  51.900 -41.442  0.50 17.44           C
ATOM   5460  NZ   LYS a 248     -35.719  52.607 -41.046  0.50 16.93           N
ATOM   5461  C    LYS a 248     -39.892  49.101 -44.788  0.50 14.90           C
ATOM   5462  O    LYS a 248     -40.733  49.547 -44.008  0.50 14.54           O
ATOM   5463  N    ASP a 249     -39.858  49.414 -46.078  0.50 15.48           N
ATOM   5464  CA   ASP a 249     -40.857  50.312 -46.659  0.50 16.09           C
ATOM   5465  CB   ASP a 249     -40.492  50.631 -48.101  0.50 16.39           C
ATOM   5466  CG   ASP a 249     -39.353  51.629 -48.223  0.50 17.71           C
ATOM   5467  OD1  ASP a 249     -38.975  52.280 -47.220  0.50 17.78           O
ATOM   5468  OD2  ASP a 249     -38.860  51.776 -49.361  0.50 17.23           O
ATOM   5469  C    ASP a 249     -42.259  49.711 -46.643  0.50 16.46           C
ATOM   5470  O    ASP a 249     -43.259  50.439 -46.512  0.50 16.36           O
ATOM   5471  N    THR a 250     -42.344  48.395 -46.819  0.50 15.80           N
ATOM   5472  CA   THR a 250     -43.640  47.734 -46.832  0.50 15.45           C
ATOM   5473  CB   THR a 250     -43.551  46.331 -47.478  0.50 15.85           C
ATOM   5474  OG1  THR a 250     -42.763  45.480 -46.640  0.50 16.17           O
ATOM   5475  CG2  THR a 250     -42.871  46.410 -48.860  0.50 15.86           C
ATOM   5476  C    THR a 250     -44.167  47.532 -45.419  0.50 15.17           C
ATOM   5477  O    THR a 250     -45.358  47.298 -45.236  0.50 15.68           O
ATOM   5478  N    LEU a 251     -43.274  47.579 -44.436  0.50 14.61           N
ATOM   5479  CA   LEU a 251     -43.633  47.261 -43.050  0.50 14.92           C
ATOM   5480  CB   LEU a 251     -42.463  46.530 -42.378  0.50 14.88           C
ATOM   5481  CG   LEU a 251     -42.173  45.133 -42.944  0.50 14.67           C
ATOM   5482  CD1  LEU a 251     -40.906  44.516 -42.360  0.50 13.95           C
ATOM   5483  CD2  LEU a 251     -43.367  44.218 -42.679  0.50 14.64           C
ATOM   5484  C    LEU a 251     -44.029  48.441 -42.191  0.50 16.00           C
ATOM   5485  O    LEU a 251     -44.843  48.309 -41.271  0.50 15.46           O
ATOM   5486  N    MET a 252     -43.405  49.589 -42.449  0.50 16.00           N
ATOM   5487  CA   MET a 252     -43.609  50.752 -41.605  0.50 16.42           C
ATOM   5488  CB   MET a 252     -42.248  51.385 -41.237  0.50 16.80           C
ATOM   5489  CG   MET a 252     -41.249  50.484 -40.514  0.50 19.02           C
ATOM   5490  SD   MET a 252     -41.692  50.269 -38.758  0.50 24.22           S
```

Figure 27 (Continued)

```
ATOM   5491  CE   MET a 252     -42.409  48.652 -38.871  0.50 19.32           C
ATOM   5492  C    MET a 252     -44.488  51.754 -42.376  0.50 15.77           C
ATOM   5493  O    MET a 252     -44.138  52.184 -43.492  0.50 15.56           O
ATOM   5494  N    ILE a 253     -45.660  52.053 -41.817  0.50 15.55           N
ATOM   5495  CA   ILE a 253     -46.705  52.799 -42.533  0.50 17.50           C
ATOM   5496  CB   ILE a 253     -48.056  52.735 -41.752  0.50 16.33           C
ATOM   5497  CG1  ILE a 253     -49.244  53.178 -42.635  0.50 16.86           C
ATOM   5498  CD1  ILE a 253     -49.118  52.693 -44.057  0.50 15.89           C
ATOM   5499  CG2  ILE a 253     -48.002  53.556 -40.476  0.50 18.23           C
ATOM   5500  C    ILE a 253     -46.264  54.254 -42.840  0.50 17.59           C
ATOM   5501  O    ILE a 253     -46.842  54.920 -43.701  0.50 18.52           O
ATOM   5502  N    SER a 254     -45.220  54.724 -42.160  0.50 18.78           N
ATOM   5503  CA   SER a 254     -44.674  56.061 -42.437  0.50 19.44           C
ATOM   5504  CB   SER a 254     -43.645  56.452 -41.367  0.50 19.74           C
ATOM   5505  OG   SER a 254     -42.564  55.521 -41.326  0.50 21.31           O
ATOM   5506  C    SER a 254     -44.004  56.121 -43.794  0.50 20.21           C
ATOM   5507  O    SER a 254     -43.948  57.184 -44.422  0.50 20.24           O
ATOM   5508  N    ARG a 255     -43.469  54.989 -44.244  0.50 20.30           N
ATOM   5509  CA   ARG a 255     -42.718  54.936 -45.500  0.50 20.58           C
ATOM   5510  CB   ARG a 255     -41.593  53.899 -45.366  0.50 21.68           C
ATOM   5511  CG   ARG a 255     -40.767  54.156 -44.102  0.50 24.64           C
ATOM   5512  CD   ARG a 255     -39.559  53.248 -43.977  0.50 26.90           C
ATOM   5513  NE   ARG a 255     -38.709  53.317 -45.159  0.50 29.18           N
ATOM   5514  CZ   ARG a 255     -37.694  54.165 -45.318  0.50 29.96           C
ATOM   5515  NH1  ARG a 255     -37.377  55.041 -44.362  0.50 30.50           N
ATOM   5516  NH2  ARG a 255     -36.986  54.126 -46.437  0.50 29.05           N
ATOM   5517  C    ARG a 255     -43.612  54.645 -46.706  0.50 21.64           C
ATOM   5518  O    ARG a 255     -44.777  54.281 -46.541  0.50 20.37           O
ATOM   5519  N    THR a 256     -43.091  54.859 -47.917  0.50 20.67           N
ATOM   5520  CA   THR a 256     -43.878  54.621 -49.118  0.50 21.08           C
ATOM   5521  CB   THR a 256     -44.203  55.936 -49.869  0.50 23.80           C
ATOM   5522  OG1  THR a 256     -43.001  56.495 -50.427  0.50 27.63           O
ATOM   5523  CG2  THR a 256     -44.818  56.931 -48.912  0.50 20.81           C
ATOM   5524  C    THR a 256     -43.218  53.599 -50.035  0.50 20.15           C
ATOM   5525  O    THR a 256     -42.333  53.930 -50.821  0.50 20.40           O
ATOM   5526  N    PRO a 257     -43.668  52.341 -49.953  0.50 18.89           N
ATOM   5527  CA   PRO a 257     -43.107  51.295 -50.801  0.50 18.68           C
ATOM   5528  CB   PRO a 257     -43.740  50.018 -50.233  0.50 17.82           C
ATOM   5529  CG   PRO a 257     -45.052  50.471 -49.677  0.50 18.25           C
ATOM   5530  CD   PRO a 257     -44.832  51.874 -49.174  0.50 19.29           C
ATOM   5531  C    PRO a 257     -43.446  51.494 -52.291  0.50 18.44           C
ATOM   5532  O    PRO a 257     -44.517  51.998 -52.611  0.50 18.48           O
ATOM   5533  N    GLU a 258     -42.515  51.129 -53.175  0.50 18.48           N
ATOM   5534  CA   GLU a 258     -42.697  51.268 -54.633  0.50 18.79           C
ATOM   5535  CB   GLU a 258     -41.971  52.524 -55.138  0.50 21.49           C
ATOM   5536  CG   GLU a 258     -41.724  53.623 -54.113  0.50 24.16           C
ATOM   5537  CD   GLU a 258     -40.737  54.685 -54.600  0.50 25.31           C
ATOM   5538  OE1  GLU a 258     -39.610  54.344 -55.040  0.50 26.36           O
ATOM   5539  OE2  GLU a 258     -41.082  55.884 -54.525  0.50 26.34           O
ATOM   5540  C    GLU a 258     -42.093  50.072 -55.347  0.50 17.31           C
ATOM   5541  O    GLU a 258     -41.076  49.520 -54.889  0.50 17.74           O
ATOM   5542  N    VAL a 259     -42.662  49.696 -56.494  0.50 16.61           N
ATOM   5543  CA   VAL a 259     -42.013  48.758 -57.383  0.50 17.67           C
ATOM   5544  CB   VAL a 259     -42.973  47.654 -57.859  0.50 18.02           C
ATOM   5545  CG1  VAL a 259     -42.351  46.823 -58.955  0.50 19.78           C
ATOM   5546  CG2  VAL a 259     -43.362  46.756 -56.689  0.50 17.51           C
ATOM   5547  C    VAL a 259     -41.509  49.581 -58.562  0.50 17.79           C
ATOM   5548  O    VAL a 259     -42.166  50.538 -58.984  0.50 18.33           O
ATOM   5549  N    THR a 260     -40.335  49.220 -59.053  0.50 18.83           N
ATOM   5550  CA   THR a 260     -39.632  50.043 -60.046  0.50 18.36           C
ATOM   5551  CB   THR a 260     -38.268  50.486 -59.512  0.50 18.59           C
ATOM   5552  OG1  THR a 260     -38.443  51.159 -58.258  0.50 19.43           O
ATOM   5553  CG2  THR a 260     -37.536  51.403 -60.505  0.50 19.11           C
ATOM   5554  C    THR a 260     -39.419  49.249 -61.297  0.50 19.51           C
```

Figure 27 (Continued)

```
ATOM   5555  O    THR a 260     -38.759  48.219 -61.266  0.50 18.92           O
ATOM   5556  N    CYS a 261     -39.974  49.723 -62.417  0.50 19.51           N
ATOM   5557  CA   CYS a 261     -39.821  49.000 -63.676  0.50 20.26           C
ATOM   5558  CB   CYS a 261     -41.172  48.829 -64.360  0.50 21.84           C
ATOM   5559  SG   CYS a 261     -41.108  47.818 -65.848  0.50 23.07           S
ATOM   5560  C    CYS a 261     -38.884  49.779 -64.580  0.50 20.38           C
ATOM   5561  O    CYS a 261     -39.177  50.919 -64.929  0.50 19.82           O
ATOM   5562  N    VAL a 262     -37.758  49.157 -64.921  0.50 19.75           N
ATOM   5563  CA   VAL a 262     -36.641  49.824 -65.617  0.50 21.50           C
ATOM   5564  CB   VAL a 262     -35.303  49.676 -64.855  0.50 21.02           C
ATOM   5565  CG1  VAL a 262     -34.192  50.446 -65.568  0.50 21.13           C
ATOM   5566  CG2  VAL a 262     -35.433  50.213 -63.431  0.50 20.95           C
ATOM   5567  C    VAL a 262     -36.506  49.217 -67.002  0.50 20.48           C
ATOM   5568  O    VAL a 262     -36.612  47.999 -67.170  0.50 16.94           O
ATOM   5569  N    VAL a 263     -36.286  50.069 -68.012  0.50 21.37           N
ATOM   5570  CA   VAL a 263     -36.111  49.589 -69.378  0.50 22.32           C
ATOM   5571  CB   VAL a 263     -37.214  50.116 -70.329  0.50 22.76           C
ATOM   5572  CG1  VAL a 263     -37.220  49.335 -71.634  0.50 23.70           C
ATOM   5573  CG2  VAL a 263     -38.591  50.042 -69.662  0.50 23.19           C
ATOM   5574  C    VAL a 263     -34.737  50.083 -69.827  0.50 21.95           C
ATOM   5575  O    VAL a 263     -34.372  51.223 -69.575  0.50 22.30           O
ATOM   5576  N    VAL a 264     -33.942  49.190 -70.389  0.50 24.12           N
ATOM   5577  CA   VAL a 264     -32.624  49.575 -70.895  0.50 26.19           C
ATOM   5578  CB   VAL a 264     -31.465  49.121 -69.973  0.50 25.87           C
ATOM   5579  CG1  VAL a 264     -31.614  49.736 -68.586  0.50 27.08           C
ATOM   5580  CG2  VAL a 264     -31.359  47.601 -69.898  0.50 27.47           C
ATOM   5581  C    VAL a 264     -32.469  49.065 -72.325  0.50 26.59           C
ATOM   5582  O    VAL a 264     -33.229  48.199 -72.767  0.50 27.26           O
ATOM   5583  N    ASP a 265     -31.508  49.631 -73.052  0.50 26.79           N
ATOM   5584  CA   ASP a 265     -31.347  49.338 -74.477  0.50 24.94           C
ATOM   5585  CB   ASP a 265     -31.248  47.829 -74.719  0.50 25.33           C
ATOM   5586  CG   ASP a 265     -29.922  47.239 -74.239  0.50 25.08           C
ATOM   5587  OD1  ASP a 265     -29.000  48.005 -73.916  0.50 25.07           O
ATOM   5588  OD2  ASP a 265     -29.806  45.999 -74.173  0.50 29.25           O
ATOM   5589  C    ASP a 265     -32.492  49.944 -75.304  0.50 23.70           C
ATOM   5590  O    ASP a 265     -32.955  49.334 -76.277  0.50 24.26           O
ATOM   5591  N    VAL a 266     -32.953  51.135 -74.916  0.50 22.15           N
ATOM   5592  CA   VAL a 266     -33.948  51.862 -75.701  0.50 21.11           C
ATOM   5593  CB   VAL a 266     -34.801  52.836 -74.856  0.50 19.77           C
ATOM   5594  CG1  VAL a 266     -35.665  53.713 -75.747  0.50 18.42           C
ATOM   5595  CG2  VAL a 266     -35.692  52.051 -73.891  0.50 20.26           C
ATOM   5596  C    VAL a 266     -33.223  52.620 -76.824  0.50 22.40           C
ATOM   5597  O    VAL a 266     -32.409  53.507 -76.565  0.50 19.64           O
ATOM   5598  N    SER a 267     -33.519  52.236 -78.060  0.50 25.58           N
ATOM   5599  CA   SER a 267     -32.777  52.745 -79.219  0.50 27.91           C
ATOM   5600  CB   SER a 267     -33.040  51.868 -80.442  0.50 26.42           C
ATOM   5601  OG   SER a 267     -34.335  52.135 -80.975  0.50 27.22           O
ATOM   5602  C    SER a 267     -33.107  54.182 -79.585  0.50 29.58           C
ATOM   5603  O    SER a 267     -34.105  54.752 -79.134  0.50 29.94           O
ATOM   5604  N    HIS a 268     -32.250  54.758 -80.427  0.50 31.89           N
ATOM   5605  CA   HIS a 268     -32.566  55.998 -81.115  0.50 32.31           C
ATOM   5606  CB   HIS a 268     -31.290  56.610 -81.712  0.50 34.51           C
ATOM   5607  CG   HIS a 268     -30.411  57.287 -80.704  0.50 32.86           C
ATOM   5608  ND1  HIS a 268     -29.942  58.575 -80.864  0.50 31.77           N
ATOM   5609  CE1  HIS a 268     -29.208  58.909 -79.815  0.50 33.21           C
ATOM   5610  NE2  HIS a 268     -29.189  57.886 -78.977  0.50 32.48           N
ATOM   5611  CD2  HIS a 268     -29.928  56.857 -79.513  0.50 33.00           C
ATOM   5612  C    HIS a 268     -33.591  55.681 -82.211  0.50 31.92           C
ATOM   5613  O    HIS a 268     -34.545  56.433 -82.425  0.50 29.18           O
ATOM   5614  N    GLU a 269     -33.404  54.538 -82.873  0.50 33.93           N
ATOM   5615  CA   GLU a 269     -34.306  54.085 -83.943  0.50 36.30           C
ATOM   5616  CB   GLU a 269     -33.780  52.812 -84.611  0.50 38.06           C
ATOM   5617  CG   GLU a 269     -32.534  52.998 -85.455  0.50 41.82           C
ATOM   5618  CD   GLU a 269     -31.255  52.926 -84.643  0.50 40.35           C
```

Figure 27 (Continued)

```
ATOM   5619  OE1 GLU a 269     -31.327  52.745 -83.408  0.50 40.27           O
ATOM   5620  OE2 GLU a 269     -30.174  53.055 -85.251  0.50 40.34           O
ATOM   5621  C   GLU a 269     -35.715  53.813 -83.442  0.50 35.32           C
ATOM   5622  O   GLU a 269     -36.692  54.021 -84.162  0.50 32.66           O
ATOM   5623  N   GLU a 270     -35.802  53.324 -82.209  0.50 34.48           N
ATOM   5624  CA  GLU a 270     -37.077  53.033 -81.563  0.50 35.11           C
ATOM   5625  CB  GLU a 270     -37.311  51.517 -81.533  0.50 34.72           C
ATOM   5626  CG  GLU a 270     -36.990  50.810 -82.840  0.50 35.98           C
ATOM   5627  CD  GLU a 270     -37.909  51.237 -83.945  0.50 34.95           C
ATOM   5628  OE1 GLU a 270     -37.987  50.519 -84.962  0.50 43.63           O
ATOM   5629  OE2 GLU a 270     -38.566  52.287 -83.793  0.50 33.19           O
ATOM   5630  C   GLU a 270     -37.038  53.550 -80.125  0.50 35.12           C
ATOM   5631  O   GLU a 270     -36.864  52.764 -79.200  0.50 37.51           O
ATOM   5632  N   PRO a 271     -37.202  54.868 -79.933  0.50 34.92           N
ATOM   5633  CA  PRO a 271     -36.944  55.482 -78.626  0.50 34.34           C
ATOM   5634  CB  PRO a 271     -36.443  56.880 -78.998  0.50 34.55           C
ATOM   5635  CG  PRO a 271     -37.068  57.173 -80.329  0.50 33.57           C
ATOM   5636  CD  PRO a 271     -37.469  55.875 -80.977  0.50 35.09           C
ATOM   5637  C   PRO a 271     -38.153  55.595 -77.701  0.50 34.74           C
ATOM   5638  O   PRO a 271     -37.992  55.922 -76.518  0.50 33.47           O
ATOM   5639  N   GLU a 272     -39.348  55.362 -78.237  0.50 33.50           N
ATOM   5640  CA  GLU a 272     -40.573  55.488 -77.458  0.50 31.61           C
ATOM   5641  CB  GLU a 272     -41.776  55.775 -78.376  0.50 33.06           C
ATOM   5642  CG  GLU a 272     -41.702  57.093 -79.144  0.50 34.18           C
ATOM   5643  CD  GLU a 272     -42.742  57.181 -80.252  0.50 33.58           C
ATOM   5644  OE1 GLU a 272     -43.572  58.109 -80.219  0.50 33.04           O
ATOM   5645  OE2 GLU a 272     -42.739  56.312 -81.152  0.50 33.36           O
ATOM   5646  C   GLU a 272     -40.826  54.201 -76.670  0.50 28.20           C
ATOM   5647  O   GLU a 272     -40.576  53.108 -77.169  0.50 27.16           O
ATOM   5648  N   VAL a 273     -41.353  54.341 -75.455  0.50 28.24           N
ATOM   5649  CA  VAL a 273     -41.663  53.187 -74.605  0.50 25.84           C
ATOM   5650  CB  VAL a 273     -40.566  52.974 -73.535  0.50 26.07           C
ATOM   5651  CG1 VAL a 273     -40.850  51.725 -72.701  0.50 24.97           C
ATOM   5652  CG2 VAL a 273     -39.188  52.888 -74.182  0.50 26.06           C
ATOM   5653  C   VAL a 273     -43.008  53.392 -73.913  0.50 23.66           C
ATOM   5654  O   VAL a 273     -43.272  54.452 -73.355  0.50 25.89           O
ATOM   5655  N   LYS a 274     -43.884  52.397 -73.987  0.50 23.62           N
ATOM   5656  CA  LYS a 274     -45.143  52.488 -73.260  0.50 23.60           C
ATOM   5657  CB  LYS a 274     -46.331  52.084 -74.141  0.50 25.23           C
ATOM   5658  CG  LYS a 274     -47.680  52.323 -73.479  0.50 24.27           C
ATOM   5659  CD  LYS a 274     -48.863  52.056 -74.393  0.50 26.13           C
ATOM   5660  CE  LYS a 274     -48.764  50.682 -75.031  0.50 24.31           C
ATOM   5661  NZ  LYS a 274     -50.069  50.263 -75.610  0.50 25.62           N
ATOM   5662  C   LYS a 274     -45.043  51.589 -72.029  0.50 24.17           C
ATOM   5663  O   LYS a 274     -44.499  50.495 -72.123  0.50 25.25           O
ATOM   5664  N   PHE a 275     -45.526  52.080 -70.888  0.50 23.73           N
ATOM   5665  CA  PHE a 275     -45.710  51.273 -69.677  0.50 24.13           C
ATOM   5666  CB  PHE a 275     -45.080  51.956 -68.448  0.50 22.76           C
ATOM   5667  CG  PHE a 275     -43.584  52.060 -68.476  0.50 22.66           C
ATOM   5668  CD1 PHE a 275     -42.964  53.191 -68.990  0.50 20.95           C
ATOM   5669  CE1 PHE a 275     -41.592  53.306 -68.989  0.50 20.90           C
ATOM   5670  CZ  PHE a 275     -40.809  52.301 -68.427  0.50 22.39           C
ATOM   5671  CE2 PHE a 275     -41.415  51.182 -67.898  0.50 21.24           C
ATOM   5672  CD2 PHE a 275     -42.795  51.070 -67.916  0.50 21.35           C
ATOM   5673  C   PHE a 275     -47.191  51.143 -69.377  0.50 23.13           C
ATOM   5674  O   PHE a 275     -47.905  52.146 -69.355  0.50 24.11           O
ATOM   5675  N   ASN a 276     -47.643  49.918 -69.108  0.50 22.43           N
ATOM   5676  CA  ASN a 276     -48.888  49.700 -68.386  0.50 22.44           C
ATOM   5677  CB  ASN a 276     -49.846  48.803 -69.166  0.50 22.77           C
ATOM   5678  CG  ASN a 276     -50.214  49.367 -70.530  0.50 25.45           C
ATOM   5679  OD1 ASN a 276     -49.720  48.890 -71.551  0.50 23.12           O
ATOM   5680  ND2 ASN a 276     -51.114  50.356 -70.555  0.50 24.98           N
ATOM   5681  C   ASN a 276     -48.539  49.003 -67.067  0.50 20.42           C
ATOM   5682  O   ASN a 276     -47.587  48.233 -67.019  0.50 19.14           O
```

Figure 27 (Continued)

```
ATOM   5683  N    TRP a 277     -49.322  49.275 -66.029  0.50 21.23           N
ATOM   5684  CA   TRP a 277     -49.154  48.654 -64.709  0.50 20.67           C
ATOM   5685  CB   TRP a 277     -48.850  49.725 -63.668  0.50 19.83           C
ATOM   5686  CG   TRP a 277     -47.431  50.230 -63.654  0.50 20.16           C
ATOM   5687  CD1  TRP a 277     -46.960  51.388 -64.218  0.50 20.00           C
ATOM   5688  NE1  TRP a 277     -45.619  51.522 -63.973  0.50 21.13           N
ATOM   5689  CE2  TRP a 277     -45.195  50.452 -63.223  0.50 20.44           C
ATOM   5690  CD2  TRP a 277     -46.310  49.615 -63.010  0.50 20.57           C
ATOM   5691  CE3  TRP a 277     -46.144  48.443 -62.256  0.50 21.44           C
ATOM   5692  CZ3  TRP a 277     -44.890  48.137 -61.785  0.50 20.87           C
ATOM   5693  CH2  TRP a 277     -43.801  48.990 -62.006  0.50 19.66           C
ATOM   5694  CZ2  TRP a 277     -43.935  50.154 -62.728  0.50 19.51           C
ATOM   5695  C    TRP a 277     -50.452  47.948 -64.299  0.50 20.87           C
ATOM   5696  O    TRP a 277     -51.555  48.473 -64.527  0.50 20.54           O
ATOM   5697  N    TYR a 278     -50.341  46.781 -63.665  0.50 19.68           N
ATOM   5698  CA   TYR a 278     -51.530  46.037 -63.227  0.50 19.32           C
ATOM   5699  CB   TYR a 278     -51.888  44.891 -64.187  0.50 19.92           C
ATOM   5700  CG   TYR a 278     -51.942  45.316 -65.628  0.50 19.69           C
ATOM   5701  CD1  TYR a 278     -50.779  45.445 -66.361  0.50 19.10           C
ATOM   5702  CE1  TYR a 278     -50.809  45.873 -67.678  0.50 19.20           C
ATOM   5703  CZ   TYR a 278     -52.019  46.140 -68.281  0.50 18.57           C
ATOM   5704  OH   TYR a 278     -52.034  46.550 -69.614  0.50 19.06           O
ATOM   5705  CE2  TYR a 278     -53.191  46.017 -67.575  0.50 19.27           C
ATOM   5706  CD2  TYR a 278     -53.152  45.599 -66.249  0.50 19.75           C
ATOM   5707  C    TYR a 278     -51.310  45.435 -61.852  0.50 19.77           C
ATOM   5708  O    TYR a 278     -50.187  45.112 -61.477  0.50 18.89           O
ATOM   5709  N    VAL a 279     -52.402  45.278 -61.122  0.50 19.89           N
ATOM   5710  CA   VAL a 279     -52.353  44.670 -59.800  0.50 21.35           C
ATOM   5711  CB   VAL a 279     -52.780  45.670 -58.717  0.50 20.67           C
ATOM   5712  CG1  VAL a 279     -52.842  44.993 -57.354  0.50 20.67           C
ATOM   5713  CG2  VAL a 279     -51.798  46.839 -58.660  0.50 19.44           C
ATOM   5714  C    VAL a 279     -53.293  43.469 -59.875  0.50 23.23           C
ATOM   5715  O    VAL a 279     -54.487  43.620 -60.161  0.50 24.33           O
ATOM   5716  N    ASP a 280     -52.752  42.274 -59.693  0.50 24.14           N
ATOM   5717  CA   ASP a 280     -53.558  41.059 -59.843  0.50 25.23           C
ATOM   5718  CB   ASP a 280     -54.561  40.969 -58.695  0.50 26.05           C
ATOM   5719  CG   ASP a 280     -53.891  40.658 -57.372  0.50 26.75           C
ATOM   5720  OD1  ASP a 280     -52.821  40.014 -57.404  0.50 26.33           O
ATOM   5721  OD2  ASP a 280     -54.420  41.054 -56.312  0.50 25.14           O
ATOM   5722  C    ASP a 280     -54.269  41.030 -61.209  0.50 26.18           C
ATOM   5723  O    ASP a 280     -55.392  40.530 -61.340  0.50 24.60           O
ATOM   5724  N    GLY a 281     -53.601  41.566 -62.220  0.50 26.97           N
ATOM   5725  CA   GLY a 281     -54.124  41.538 -63.591  0.50 27.58           C
ATOM   5726  C    GLY a 281     -55.095  42.668 -63.879  0.50 29.34           C
ATOM   5727  O    GLY a 281     -55.524  42.851 -65.028  0.50 30.71           O
ATOM   5728  N    VAL a 282     -55.445  43.431 -62.849  0.50 29.11           N
ATOM   5729  CA   VAL a 282     -56.243  44.639 -63.037  0.50 28.81           C
ATOM   5730  CB   VAL a 282     -57.084  44.973 -61.790  0.50 30.58           C
ATOM   5731  CG1  VAL a 282     -57.862  46.263 -61.999  0.50 33.15           C
ATOM   5732  CG2  VAL a 282     -58.037  43.829 -61.480  0.50 32.66           C
ATOM   5733  C    VAL a 282     -55.325  45.807 -63.363  0.50 26.97           C
ATOM   5734  O    VAL a 282     -54.538  46.247 -62.522  0.50 24.87           O
ATOM   5735  N    GLU a 283     -55.416  46.321 -64.589  0.50 24.43           N
ATOM   5736  CA   GLU a 283     -54.615  47.486 -64.934  0.50 22.89           C
ATOM   5737  CB   GLU a 283     -54.920  47.982 -66.355  0.50 22.30           C
ATOM   5738  CG   GLU a 283     -54.008  49.129 -66.752  0.50 21.70           C
ATOM   5739  CD   GLU a 283     -53.961  49.341 -68.249  0.50 22.08           C
ATOM   5740  OE1  GLU a 283     -53.041  50.041 -68.707  0.50 21.86           O
ATOM   5741  OE2  GLU a 283     -54.850  48.812 -68.949  0.50 22.06           O
ATOM   5742  C    GLU a 283     -54.835  48.627 -63.942  0.50 23.15           C
ATOM   5743  O    GLU a 283     -55.968  48.851 -63.486  0.50 24.26           O
ATOM   5744  N    VAL a 284     -53.760  49.346 -63.627  0.50 22.62           N
ATOM   5745  CA   VAL a 284     -53.797  50.474 -62.700  0.50 21.56           C
ATOM   5746  CB   VAL a 284     -53.161  50.090 -61.347  0.50 20.55           C
```

Figure 27 (Continued)

```
ATOM   5747  CG1 VAL a 284     -53.983  48.976 -60.701  0.50 19.95           C
ATOM   5748  CG2 VAL a 284     -51.710  49.682 -61.540  0.50 21.00           C
ATOM   5749  C   VAL a 284     -53.125  51.714 -63.307  0.50 23.02           C
ATOM   5750  O   VAL a 284     -52.206  51.585 -64.112  0.50 26.31           O
ATOM   5751  N   HIS a 285     -53.594  52.903 -62.928  0.50 26.11           N
ATOM   5752  CA  HIS a 285     -53.324  54.126 -63.701  0.50 26.70           C
ATOM   5753  CB  HIS a 285     -54.643  54.877 -63.981  0.50 25.70           C
ATOM   5754  CG  HIS a 285     -55.795  53.971 -64.276  0.50 27.38           C
ATOM   5755  ND1 HIS a 285     -55.804  53.101 -65.348  0.50 25.13           N
ATOM   5756  CE1 HIS a 285     -56.926  52.403 -65.333  0.50 28.61           C
ATOM   5757  NE2 HIS a 285     -57.643  52.789 -64.291  0.50 27.72           N
ATOM   5758  CD2 HIS a 285     -56.959  53.766 -63.614  0.50 25.63           C
ATOM   5759  C   HIS a 285     -52.354  55.092 -63.054  0.50 28.20           C
ATOM   5760  O   HIS a 285     -51.966  56.075 -63.681  0.50 28.93           O
ATOM   5761  N   ASN a 286     -51.958  54.820 -61.811  0.50 27.50           N
ATOM   5762  CA  ASN a 286     -51.265  55.819 -60.996  0.50 28.20           C
ATOM   5763  CB  ASN a 286     -51.714  55.718 -59.532  0.50 29.65           C
ATOM   5764  CG  ASN a 286     -51.416  54.362 -58.926  0.50 30.39           C
ATOM   5765  OD1 ASN a 286     -51.776  53.325 -59.487  0.50 29.62           O
ATOM   5766  ND2 ASN a 286     -50.766  54.359 -57.767  0.50 31.85           N
ATOM   5767  C   ASN a 286     -49.734  55.846 -61.049  0.50 27.60           C
ATOM   5768  O   ASN a 286     -49.120  56.651 -60.360  0.50 28.05           O
ATOM   5769  N   ALA a 287     -49.112  54.992 -61.853  0.50 25.97           N
ATOM   5770  CA  ALA a 287     -47.650  54.991 -61.922  0.50 25.26           C
ATOM   5771  CB  ALA a 287     -47.146  53.872 -62.820  0.50 25.41           C
ATOM   5772  C   ALA a 287     -47.097  56.342 -62.383  0.50 28.71           C
ATOM   5773  O   ALA a 287     -47.774  57.096 -63.109  0.50 25.88           O
ATOM   5774  N   LYS a 288     -45.879  56.647 -61.943  0.50 26.31           N
ATOM   5775  CA  LYS a 288     -45.214  57.889 -62.305  0.50 29.01           C
ATOM   5776  CB  LYS a 288     -44.809  58.674 -61.058  0.50 30.75           C
ATOM   5777  CG  LYS a 288     -45.906  59.554 -60.461  0.50 33.33           C
ATOM   5778  CD  LYS a 288     -46.999  58.748 -59.775  0.50 35.25           C
ATOM   5779  CE  LYS a 288     -48.220  59.617 -59.492  0.50 34.72           C
ATOM   5780  NZ  LYS a 288     -49.266  58.894 -58.715  0.50 35.57           N
ATOM   5781  C   LYS a 288     -43.986  57.580 -63.137  0.50 27.16           C
ATOM   5782  O   LYS a 288     -42.927  57.219 -62.604  0.50 26.88           O
ATOM   5783  N   THR a 289     -44.119  57.737 -64.451  0.50 26.05           N
ATOM   5784  CA  THR a 289     -43.041  57.429 -65.371  0.50 26.51           C
ATOM   5785  CB  THR a 289     -43.618  56.802 -66.652  0.50 27.44           C
ATOM   5786  OG1 THR a 289     -44.333  55.601 -66.310  0.50 28.39           O
ATOM   5787  CG2 THR a 289     -42.518  56.460 -67.630  0.50 27.49           C
ATOM   5788  C   THR a 289     -42.222  58.682 -65.712  0.50 29.34           C
ATOM   5789  O   THR a 289     -42.787  59.704 -66.115  0.50 25.25           O
ATOM   5790  N   LYS a 290     -40.905  58.613 -65.517  0.50 29.57           N
ATOM   5791  CA  LYS a 290     -40.023  59.746 -65.805  0.50 33.34           C
ATOM   5792  CB  LYS a 290     -38.687  59.595 -65.066  0.50 35.58           C
ATOM   5793  CG  LYS a 290     -38.748  58.859 -63.733  0.50 41.38           C
ATOM   5794  CD  LYS a 290     -38.355  59.761 -62.571  0.50 43.80           C
ATOM   5795  CE  LYS a 290     -38.018  58.960 -61.316  0.50 45.65           C
ATOM   5796  NZ  LYS a 290     -39.217  58.392 -60.630  0.50 46.70           N
ATOM   5797  C   LYS a 290     -39.735  59.807 -67.305  0.50 32.55           C
ATOM   5798  O   LYS a 290     -39.964  58.837 -68.023  0.50 32.58           O
ATOM   5799  N   PRO a 291     -39.234  60.954 -67.789  0.50 33.52           N
ATOM   5800  CA  PRO a 291     -38.758  61.023 -69.175  0.50 34.59           C
ATOM   5801  CB  PRO a 291     -38.513  62.525 -69.391  0.50 35.28           C
ATOM   5802  CG  PRO a 291     -39.311  63.207 -68.321  0.50 35.06           C
ATOM   5803  CD  PRO a 291     -39.250  62.276 -67.145  0.50 34.58           C
ATOM   5804  C   PRO a 291     -37.455  60.235 -69.386  0.50 35.00           C
ATOM   5805  O   PRO a 291     -36.617  60.155 -68.484  0.50 35.64           O
ATOM   5806  N   ARG a 292     -37.295  59.669 -70.576  0.50 35.30           N
ATOM   5807  CA  ARG a 292     -36.115  58.878 -70.913  0.50 36.02           C
ATOM   5808  CB  ARG a 292     -36.191  58.430 -72.373  0.50 38.50           C
ATOM   5809  CG  ARG a 292     -36.611  59.533 -73.336  0.50 40.75           C
ATOM   5810  CD  ARG a 292     -36.849  58.976 -74.733  0.50 40.86           C
```

Figure 27 (Continued)

```
ATOM   5811  NE   ARG a 292     -37.335  59.994 -75.659  0.50 43.63           N
ATOM   5812  CZ   ARG a 292     -38.592  60.092 -76.085  0.50 43.11           C
ATOM   5813  NH1  ARG a 292     -39.513  59.231 -75.671  0.50 38.83           N
ATOM   5814  NH2  ARG a 292     -38.927  61.055 -76.934  0.50 44.98           N
ATOM   5815  C    ARG a 292     -34.796  59.600 -70.627  0.50 36.40           C
ATOM   5816  O    ARG a 292     -34.722  60.832 -70.684  0.50 37.31           O
ATOM   5817  N    GLU a 293     -33.766  58.822 -70.291  0.50 35.77           N
ATOM   5818  CA   GLU a 293     -32.424  59.344 -70.052  0.50 36.43           C
ATOM   5819  CB   GLU a 293     -31.989  59.083 -68.607  0.50 39.48           C
ATOM   5820  CG   GLU a 293     -32.499  60.096 -67.596  0.50 42.21           C
ATOM   5821  CD   GLU a 293     -31.711  60.064 -66.299  0.50 47.31           C
ATOM   5822  OE1  GLU a 293     -31.336  58.957 -65.847  0.50 49.20           O
ATOM   5823  OE2  GLU a 293     -31.461  61.151 -65.731  0.50 49.44           O
ATOM   5824  C    GLU a 293     -31.425  58.670 -70.979  0.50 33.92           C
ATOM   5825  O    GLU a 293     -31.132  57.482 -70.830  0.50 32.13           O
ATOM   5826  N    GLU a 294     -30.873  59.411 -71.936  0.50 32.08           N
ATOM   5827  CA   GLU a 294     -29.816  58.817 -72.740  0.50 26.36           C
ATOM   5828  CB   GLU a 294     -29.376  59.729 -73.895  0.50 26.58           C
ATOM   5829  CG   GLU a 294     -28.358  59.048 -74.793  0.50 27.29           C
ATOM   5830  CD   GLU a 294     -27.826  59.963 -75.880  0.50 27.15           C
ATOM   5831  OE1  GLU a 294     -27.700  59.491 -77.021  0.50 29.36           O
ATOM   5832  OE2  GLU a 294     -27.557  61.147 -75.586  0.50 29.18           O
ATOM   5833  C    GLU a 294     -28.619  58.506 -71.852  0.50 26.64           C
ATOM   5834  O    GLU a 294     -28.270  59.293 -70.987  0.50 24.40           O
ATOM   5835  N    GLN a 295     -28.000  57.354 -72.076  0.50 25.85           N
ATOM   5836  CA   GLN a 295     -26.843  56.912 -71.295  0.50 27.59           C
ATOM   5837  CB   GLN a 295     -26.933  55.403 -71.025  0.50 27.47           C
ATOM   5838  CG   GLN a 295     -28.063  54.984 -70.097  0.50 27.31           C
ATOM   5839  CD   GLN a 295     -28.007  55.699 -68.768  0.50 26.11           C
ATOM   5840  OE1  GLN a 295     -27.146  55.410 -67.922  0.50 26.33           O
ATOM   5841  NE2  GLN a 295     -28.907  56.657 -68.580  0.50 24.60           N
ATOM   5842  C    GLN a 295     -25.537  57.204 -72.033  0.50 28.54           C
ATOM   5843  O    GLN a 295     -25.539  57.436 -73.245  0.50 30.03           O
ATOM   5844  N    TYR a 296     -24.425  57.160 -71.306  0.50 30.21           N
ATOM   5845  CA   TYR a 296     -23.119  57.406 -71.908  0.50 30.59           C
ATOM   5846  CB   TYR a 296     -21.982  57.234 -70.891  0.50 30.64           C
ATOM   5847  CG   TYR a 296     -21.243  58.517 -70.577  0.50 32.63           C
ATOM   5848  CD1  TYR a 296     -21.549  59.268 -69.447  0.50 33.81           C
ATOM   5849  CE1  TYR a 296     -20.874  60.445 -69.168  0.50 35.01           C
ATOM   5850  CZ   TYR a 296     -19.880  60.886 -70.032  0.50 34.83           C
ATOM   5851  OH   TYR a 296     -19.206  62.061 -69.784  0.50 36.28           O
ATOM   5852  CE2  TYR a 296     -19.565  60.158 -71.154  0.50 33.11           C
ATOM   5853  CD2  TYR a 296     -20.246  58.988 -71.426  0.50 32.06           C
ATOM   5854  C    TYR a 296     -22.879  56.509 -73.119  0.50 29.54           C
ATOM   5855  O    TYR a 296     -21.988  56.791 -73.917  0.50 29.09           O
ATOM   5856  N    ASN a 297     -23.664  55.438 -73.249  0.50 30.34           N
ATOM   5857  CA   ASN a 297     -23.479  54.455 -74.328  0.50 30.08           C
ATOM   5858  CB   ASN a 297     -23.427  53.027 -73.760  0.50 30.23           C
ATOM   5859  CG   ASN a 297     -24.795  52.508 -73.345  0.50 30.09           C
ATOM   5860  OD1  ASN a 297     -25.745  53.278 -73.166  0.50 28.04           O
ATOM   5861  ND2  ASN a 297     -24.900  51.186 -73.182  0.50 30.53           N
ATOM   5862  C    ASN a 297     -24.502  54.532 -75.477  0.50 30.77           C
ATOM   5863  O    ASN a 297     -24.626  53.598 -76.263  0.50 33.16           O
ATOM   5864  N    SER a 298     -25.248  55.628 -75.560  0.50 31.60           N
ATOM   5865  CA   SER a 298     -26.106  55.874 -76.724  0.50 30.06           C
ATOM   5866  CB   SER a 298     -25.390  55.436 -78.008  0.50 30.03           C
ATOM   5867  OG   SER a 298     -24.060  55.903 -77.991  0.50 26.60           O
ATOM   5868  C    SER a 298     -27.517  55.282 -76.702  0.50 29.48           C
ATOM   5869  O    SER a 298     -28.394  55.792 -77.393  0.50 28.41           O
ATOM   5870  N    THR a 299     -27.733  54.194 -75.956  0.50 27.46           N
ATOM   5871  CA   THR a 299     -29.092  53.734 -75.695  0.50 27.38           C
ATOM   5872  CB   THR a 299     -29.151  52.239 -75.328  0.50 28.02           C
ATOM   5873  OG1  THR a 299     -28.427  52.021 -74.110  0.50 27.98           O
ATOM   5874  CG2  THR a 299     -28.548  51.384 -76.434  0.50 28.43           C
```

Figure 27 (Continued)

```
ATOM   5875  C    THR a 299     -29.576  54.528 -74.496  0.50 26.16           C
ATOM   5876  O    THR a 299     -28.754  54.982 -73.704  0.50 26.24           O
ATOM   5877  N    TYR a 300     -30.890  54.711 -74.359  0.50 26.34           N
ATOM   5878  CA   TYR a 300     -31.404  55.385 -73.174  0.50 23.90           C
ATOM   5879  CB   TYR a 300     -32.481  56.423 -73.489  0.50 23.52           C
ATOM   5880  CG   TYR a 300     -32.294  57.155 -74.800  0.50 24.00           C
ATOM   5881  CD1  TYR a 300     -32.433  56.481 -76.002  0.50 24.77           C
ATOM   5882  CE1  TYR a 300     -32.276  57.136 -77.209  0.50 26.16           C
ATOM   5883  CZ   TYR a 300     -31.993  58.479 -77.218  0.50 27.03           C
ATOM   5884  OH   TYR a 300     -31.850  59.120 -78.438  0.50 28.48           O
ATOM   5885  CE2  TYR a 300     -31.853  59.176 -76.039  0.50 25.75           C
ATOM   5886  CD2  TYR a 300     -32.006  58.510 -74.830  0.50 25.06           C
ATOM   5887  C    TYR a 300     -32.008  54.385 -72.208  0.50 22.97           C
ATOM   5888  O    TYR a 300     -32.153  53.191 -72.501  0.50 23.15           O
ATOM   5889  N    ARG a 301     -32.402  54.926 -71.067  0.50 24.33           N
ATOM   5890  CA   ARG a 301     -32.966  54.147 -69.969  0.50 23.79           C
ATOM   5891  CB   ARG a 301     -31.885  53.950 -68.893  0.50 25.44           C
ATOM   5892  CG   ARG a 301     -32.307  53.250 -67.604  0.50 25.04           C
ATOM   5893  CD   ARG a 301     -31.142  53.308 -66.624  0.50 26.54           C
ATOM   5894  NE   ARG a 301     -31.413  52.663 -65.339  0.50 27.18           N
ATOM   5895  CZ   ARG a 301     -31.808  53.325 -64.258  0.50 29.31           C
ATOM   5896  NH1  ARG a 301     -31.998  54.635 -64.321  0.50 27.67           N
ATOM   5897  NH2  ARG a 301     -32.020  52.674 -63.121  0.50 30.71           N
ATOM   5898  C    ARG a 301     -34.133  54.971 -69.448  0.50 24.08           C
ATOM   5899  O    ARG a 301     -34.013  56.194 -69.257  0.50 23.67           O
ATOM   5900  N    VAL a 302     -35.277  54.309 -69.267  0.50 23.13           N
ATOM   5901  CA   VAL a 302     -36.483  54.958 -68.771  0.50 22.57           C
ATOM   5902  CB   VAL a 302     -37.580  55.064 -69.863  0.50 22.59           C
ATOM   5903  CG1  VAL a 302     -38.164  53.701 -70.173  0.50 23.79           C
ATOM   5904  CG2  VAL a 302     -38.689  56.019 -69.442  0.50 21.62           C
ATOM   5905  C    VAL a 302     -37.010  54.144 -67.589  0.50 20.62           C
ATOM   5906  O    VAL a 302     -36.778  52.933 -67.508  0.50 20.16           O
ATOM   5907  N    VAL a 303     -37.742  54.820 -66.718  0.50 20.47           N
ATOM   5908  CA   VAL a 303     -38.174  54.244 -65.445  0.50 20.61           C
ATOM   5909  CB   VAL a 303     -37.356  54.832 -64.278  0.50 21.13           C
ATOM   5910  CG1  VAL a 303     -37.865  54.300 -62.935  0.50 22.57           C
ATOM   5911  CG2  VAL a 303     -35.873  54.530 -64.437  0.50 21.31           C
ATOM   5912  C    VAL a 303     -39.634  54.556 -65.206  0.50 20.51           C
ATOM   5913  O    VAL a 303     -40.084  55.698 -65.388  0.50 19.60           O
ATOM   5914  N    SER a 304     -40.383  53.568 -64.729  0.50 19.21           N
ATOM   5915  CA   SER a 304     -41.682  53.889 -64.181  0.50 19.04           C
ATOM   5916  CB   SER a 304     -42.809  53.339 -65.039  0.50 19.02           C
ATOM   5917  OG   SER a 304     -44.039  53.884 -64.607  0.50 18.71           O
ATOM   5918  C    SER a 304     -41.759  53.336 -62.772  0.50 20.19           C
ATOM   5919  O    SER a 304     -41.193  52.287 -62.481  0.50 21.76           O
ATOM   5920  N    VAL a 305     -42.430  54.077 -61.913  0.50 20.55           N
ATOM   5921  CA   VAL a 305     -42.504  53.730 -60.506  0.50 19.70           C
ATOM   5922  CB   VAL a 305     -41.778  54.767 -59.638  0.50 19.98           C
ATOM   5923  CG1  VAL a 305     -41.987  54.453 -58.150  0.50 19.83           C
ATOM   5924  CG2  VAL a 305     -40.298  54.803 -60.009  0.50 20.61           C
ATOM   5925  C    VAL a 305     -43.963  53.674 -60.122  0.50 19.41           C
ATOM   5926  O    VAL a 305     -44.759  54.567 -60.450  0.50 19.34           O
ATOM   5927  N    LEU a 306     -44.317  52.605 -59.423  0.50 18.74           N
ATOM   5928  CA   LEU a 306     -45.663  52.469 -58.925  0.50 18.40           C
ATOM   5929  CB   LEU a 306     -46.300  51.184 -59.448  0.50 18.69           C
ATOM   5930  CG   LEU a 306     -47.726  50.990 -58.935  0.50 17.67           C
ATOM   5931  CD1  LEU a 306     -48.632  52.128 -59.392  0.50 18.38           C
ATOM   5932  CD2  LEU a 306     -48.287  49.670 -59.427  0.50 17.32           C
ATOM   5933  C    LEU a 306     -45.598  52.432 -57.418  0.50 19.18           C
ATOM   5934  O    LEU a 306     -44.877  51.608 -56.851  0.50 21.04           O
ATOM   5935  N    THR a 307     -46.336  53.330 -56.778  0.50 19.66           N
ATOM   5936  CA   THR a 307     -46.439  53.299 -55.332  0.50 20.08           C
ATOM   5937  CB   THR a 307     -46.989  54.600 -54.747  0.50 22.06           C
ATOM   5938  OG1  THR a 307     -46.507  55.703 -55.515  0.50 22.05           O
```

Figure 27 (Continued)

```
ATOM   5939  CG2 THR a 307     -46.511  54.746 -53.311  0.50 20.72           C
ATOM   5940  C   THR a 307     -47.385  52.169 -55.001  0.50 20.36           C
ATOM   5941  O   THR a 307     -48.445  52.046 -55.599  0.50 21.88           O
ATOM   5942  N   VAL a 308     -46.992  51.317 -54.064  0.50 20.38           N
ATOM   5943  CA  VAL a 308     -47.859  50.220 -53.668  0.50 19.97           C
ATOM   5944  CB  VAL a 308     -47.137  48.853 -53.771  0.50 21.25           C
ATOM   5945  CG1 VAL a 308     -46.817  48.519 -55.218  0.50 22.59           C
ATOM   5946  CG2 VAL a 308     -45.857  48.875 -52.961  0.50 18.69           C
ATOM   5947  C   VAL a 308     -48.432  50.455 -52.267  0.50 19.83           C
ATOM   5948  O   VAL a 308     -47.866  51.202 -51.456  0.50 20.18           O
ATOM   5949  N   LEU a 309     -49.613  49.899 -52.020  0.50 18.99           N
ATOM   5950  CA  LEU a 309     -50.220  49.992 -50.704  0.50 18.30           C
ATOM   5951  CB  LEU a 309     -51.726  49.747 -50.789  0.50 19.70           C
ATOM   5952  CG  LEU a 309     -52.441  50.739 -51.728  0.50 20.21           C
ATOM   5953  CD1 LEU a 309     -53.870  50.306 -52.057  0.50 19.97           C
ATOM   5954  CD2 LEU a 309     -52.397  52.147 -51.152  0.50 20.47           C
ATOM   5955  C   LEU a 309     -49.553  48.924 -49.844  0.50 17.19           C
ATOM   5956  O   LEU a 309     -49.423  47.786 -50.271  0.50 18.19           O
ATOM   5957  N   HIS a 310     -49.116  49.296 -48.648  0.50 16.90           N
ATOM   5958  CA  HIS a 310     -48.419  48.339 -47.782  0.50 17.30           C
ATOM   5959  CB  HIS a 310     -48.321  48.915 -46.374  0.50 16.82           C
ATOM   5960  CG  HIS a 310     -47.610  50.226 -46.318  0.50 17.27           C
ATOM   5961  ND1 HIS a 310     -48.188  51.401 -46.754  0.50 17.19           N
ATOM   5962  CE1 HIS a 310     -47.326  52.390 -46.608  0.50 17.35           C
ATOM   5963  NE2 HIS a 310     -46.211  51.901 -46.092  0.50 16.98           N
ATOM   5964  CD2 HIS a 310     -46.361  50.548 -45.903  0.50 16.94           C
ATOM   5965  C   HIS a 310     -49.163  47.006 -47.712  0.50 17.54           C
ATOM   5966  O   HIS a 310     -48.581  45.912 -47.891  0.50 17.08           O
ATOM   5967  N   GLN a 311     -50.455  47.094 -47.412  0.50 18.89           N
ATOM   5968  CA  GLN a 311     -51.222  45.895 -47.166  0.50 20.76           C
ATOM   5969  CB  GLN a 311     -52.615  46.211 -46.601  0.50 22.71           C
ATOM   5970  CG  GLN a 311     -53.383  44.962 -46.148  0.50 26.03           C
ATOM   5971  CD  GLN a 311     -52.891  44.403 -44.813  0.50 28.24           C
ATOM   5972  OE1 GLN a 311     -52.734  45.143 -43.844  0.50 30.91           O
ATOM   5973  NE2 GLN a 311     -52.627  43.093 -44.765  0.50 30.85           N
ATOM   5974  C   GLN a 311     -51.332  45.056 -48.426  0.50 19.76           C
ATOM   5975  O   GLN a 311     -51.392  43.831 -48.348  0.50 20.11           O
ATOM   5976  N   ASP a 312     -51.367  45.702 -49.589  0.50 19.07           N
ATOM   5977  CA  ASP a 312     -51.473  44.952 -50.835  0.50 19.16           C
ATOM   5978  CB  ASP a 312     -51.690  45.884 -52.038  0.50 19.71           C
ATOM   5979  CG  ASP a 312     -53.104  46.497 -52.087  0.50 20.86           C
ATOM   5980  OD1 ASP a 312     -53.995  46.120 -51.288  0.50 19.43           O
ATOM   5981  OD2 ASP a 312     -53.335  47.373 -52.939  0.50 21.60           O
ATOM   5982  C   ASP a 312     -50.217  44.097 -51.049  0.50 17.43           C
ATOM   5983  O   ASP a 312     -50.302  42.945 -51.458  0.50 16.89           O
ATOM   5984  N   TRP a 313     -49.048  44.670 -50.787  0.50 17.04           N
ATOM   5985  CA  TRP a 313     -47.817  43.920 -50.956  0.50 16.83           C
ATOM   5986  CB  TRP a 313     -46.586  44.820 -50.748  0.50 16.56           C
ATOM   5987  CG  TRP a 313     -45.293  44.056 -50.927  0.50 16.56           C
ATOM   5988  CD1 TRP a 313     -44.480  43.548 -49.937  0.50 16.30           C
ATOM   5989  NE1 TRP a 313     -43.408  42.880 -50.507  0.50 15.62           N
ATOM   5990  CE2 TRP a 313     -43.505  42.968 -51.871  0.50 16.32           C
ATOM   5991  CD2 TRP a 313     -44.694  43.673 -52.173  0.50 16.37           C
ATOM   5992  CE3 TRP a 313     -45.016  43.908 -53.515  0.50 16.56           C
ATOM   5993  CZ3 TRP a 313     -44.180  43.378 -54.517  0.50 16.41           C
ATOM   5994  CH2 TRP a 313     -43.015  42.665 -54.183  0.50 17.08           C
ATOM   5995  CZ2 TRP a 313     -42.669  42.437 -52.872  0.50 16.15           C
ATOM   5996  C   TRP a 313     -47.811  42.766 -49.944  0.50 15.84           C
ATOM   5997  O   TRP a 313     -47.474  41.626 -50.278  0.50 17.63           O
ATOM   5998  N   LEU a 314     -48.150  43.082 -48.702  0.50 16.08           N
ATOM   5999  CA  LEU a 314     -48.145  42.068 -47.653  0.50 16.56           C
ATOM   6000  CB  LEU a 314     -48.360  42.692 -46.293  0.50 17.15           C
ATOM   6001  CG  LEU a 314     -47.197  43.540 -45.770  0.50 16.49           C
ATOM   6002  CD1 LEU a 314     -47.594  44.035 -44.381  0.50 17.33           C
```

Figure 27 (Continued)

```
ATOM   6003  CD2 LEU a 314     -45.912  42.734 -45.688  0.50 17.58           C
ATOM   6004  C   LEU a 314     -49.173  40.967 -47.906  0.50 17.65           C
ATOM   6005  O   LEU a 314     -48.958  39.810 -47.515  0.50 19.62           O
ATOM   6006  N   ASN a 315     -50.259  41.327 -48.580  0.50 16.95           N
ATOM   6007  CA  ASN a 315     -51.314  40.368 -48.899  0.50 17.75           C
ATOM   6008  CB  ASN a 315     -52.671  41.085 -49.030  0.50 18.87           C
ATOM   6009  CG  ASN a 315     -53.289  41.404 -47.690  0.50 19.56           C
ATOM   6010  OD1 ASN a 315     -52.867  40.864 -46.663  0.50 20.97           O
ATOM   6011  ND2 ASN a 315     -54.275  42.307 -47.678  0.50 20.15           N
ATOM   6012  C   ASN a 315     -51.052  39.536 -50.140  0.50 18.47           C
ATOM   6013  O   ASN a 315     -51.911  38.735 -50.541  0.50 18.70           O
ATOM   6014  N   GLY a 316     -49.876  39.713 -50.737  0.50 17.80           N
ATOM   6015  CA  GLY a 316     -49.418  38.862 -51.824  0.50 18.69           C
ATOM   6016  C   GLY a 316     -49.929  39.230 -53.204  0.50 19.69           C
ATOM   6017  O   GLY a 316     -49.905  38.401 -54.113  0.50 19.27           O
ATOM   6018  N   LYS a 317     -50.381  40.463 -53.377  0.50 19.30           N
ATOM   6019  CA  LYS a 317     -50.840  40.877 -54.697  0.50 19.41           C
ATOM   6020  CB  LYS a 317     -51.578  42.212 -54.624  0.50 19.51           C
ATOM   6021  CG  LYS a 317     -52.717  42.204 -53.601  0.50 19.99           C
ATOM   6022  CD  LYS a 317     -53.969  42.889 -54.124  0.50 22.04           C
ATOM   6023  CE  LYS a 317     -55.172  42.578 -53.247  0.50 21.89           C
ATOM   6024  NZ  LYS a 317     -55.911  43.832 -52.917  0.50 26.79           N
ATOM   6025  C   LYS a 317     -49.670  40.908 -55.681  0.50 19.83           C
ATOM   6026  O   LYS a 317     -48.545  41.238 -55.298  0.50 19.31           O
ATOM   6027  N   GLU a 318     -49.947  40.538 -56.940  0.50 20.02           N
ATOM   6028  CA  GLU a 318     -48.928  40.477 -57.993  0.50 21.62           C
ATOM   6029  CB  GLU a 318     -49.242  39.347 -58.995  0.50 24.60           C
ATOM   6030  CG  GLU a 318     -48.582  38.003 -58.682  0.50 28.12           C
ATOM   6031  CD  GLU a 318     -48.456  37.098 -59.908  0.50 29.88           C
ATOM   6032  OE1 GLU a 318     -47.466  36.341 -60.005  0.50 33.79           O
ATOM   6033  OE2 GLU a 318     -49.334  37.146 -60.792  0.50 31.22           O
ATOM   6034  C   GLU a 318     -48.890  41.811 -58.731  0.50 20.69           C
ATOM   6035  O   GLU a 318     -49.946  42.402 -59.004  0.50 19.53           O
ATOM   6036  N   TYR a 319     -47.680  42.293 -59.022  0.50 20.69           N
ATOM   6037  CA  TYR a 319     -47.481  43.553 -59.736  0.50 20.91           C
ATOM   6038  CB  TYR a 319     -46.590  44.492 -58.912  0.50 19.46           C
ATOM   6039  CG  TYR a 319     -47.292  44.909 -57.660  0.50 19.65           C
ATOM   6040  CD1 TYR a 319     -47.300  44.075 -56.542  0.50 19.79           C
ATOM   6041  CE1 TYR a 319     -47.969  44.431 -55.394  0.50 19.48           C
ATOM   6042  CZ  TYR a 319     -48.653  45.635 -55.343  0.50 19.61           C
ATOM   6043  OH  TYR a 319     -49.343  45.976 -54.202  0.50 20.52           O
ATOM   6044  CE2 TYR a 319     -48.682  46.468 -56.443  0.50 20.16           C
ATOM   6045  CD2 TYR a 319     -48.005  46.106 -57.593  0.50 18.84           C
ATOM   6046  C   TYR a 319     -46.865  43.257 -61.093  0.50 21.02           C
ATOM   6047  O   TYR a 319     -45.785  42.670 -61.163  0.50 22.74           O
ATOM   6048  N   LYS a 320     -47.561  43.660 -62.157  0.50 21.45           N
ATOM   6049  CA  LYS a 320     -47.113  43.386 -63.525  0.50 21.56           C
ATOM   6050  CB  LYS a 320     -48.225  42.725 -64.338  0.50 23.44           C
ATOM   6051  CG  LYS a 320     -47.958  42.758 -65.839  0.50 24.07           C
ATOM   6052  CD  LYS a 320     -49.194  42.320 -66.606  0.50 26.26           C
ATOM   6053  CE  LYS a 320     -49.285  40.814 -66.658  0.50 25.15           C
ATOM   6054  NZ  LYS a 320     -50.662  40.334 -66.968  0.50 30.17           N
ATOM   6055  C   LYS a 320     -46.695  44.674 -64.202  0.50 20.94           C
ATOM   6056  O   LYS a 320     -47.428  45.657 -64.166  0.50 20.80           O
ATOM   6057  N   CYS a 321     -45.487  44.680 -64.752  0.50 22.65           N
ATOM   6058  CA  CYS a 321     -45.053  45.768 -65.609  0.50 23.99           C
ATOM   6059  CB  CYS a 321     -43.650  46.240 -65.227  0.50 24.88           C
ATOM   6060  SG  CYS a 321     -43.057  47.557 -66.321  0.50 25.65           S
ATOM   6061  C   CYS a 321     -45.053  45.259 -67.040  0.50 24.64           C
ATOM   6062  O   CYS a 321     -44.334  44.316 -67.362  0.50 24.77           O
ATOM   6063  N   LYS a 322     -45.873  45.865 -67.892  0.50 24.82           N
ATOM   6064  CA  LYS a 322     -45.851  45.536 -69.310  0.50 25.32           C
ATOM   6065  CB  LYS a 322     -47.252  45.270 -69.854  0.50 25.93           C
ATOM   6066  CG  LYS a 322     -47.217  44.721 -71.278  0.50 27.44           C
```

Figure 27 (Continued)

```
ATOM   6067  CD   LYS a 322      -48.513  44.943 -72.039  0.50 30.55           C
ATOM   6068  CE   LYS a 322      -49.737  44.845 -71.151  0.50 31.36           C
ATOM   6069  NZ   LYS a 322      -51.002  44.903 -71.952  0.50 34.46           N
ATOM   6070  C    LYS a 322      -45.225  46.689 -70.073  0.50 25.05           C
ATOM   6071  O    LYS a 322      -45.621  47.841 -69.903  0.50 25.28           O
ATOM   6072  N    VAL a 323      -44.212  46.395 -70.875  0.50 24.96           N
ATOM   6073  CA   VAL a 323      -43.455  47.410 -71.597  0.50 25.70           C
ATOM   6074  CB   VAL a 323      -41.970  47.377 -71.215  0.50 24.64           C
ATOM   6075  CG1  VAL a 323      -41.146  48.270 -72.127  0.50 23.64           C
ATOM   6076  CG2  VAL a 323      -41.784  47.740 -69.760  0.50 23.43           C
ATOM   6077  C    VAL a 323      -43.549  47.216 -73.109  0.50 25.46           C
ATOM   6078  O    VAL a 323      -43.284  46.151 -73.608  0.50 26.05           O
ATOM   6079  N    SER a 324      -43.909  48.284 -73.802  0.50 27.75           N
ATOM   6080  CA   SER a 324      -44.084  48.274 -75.247  0.50 27.53           C
ATOM   6081  CB   SER a 324      -45.493  48.720 -75.626  0.50 26.33           C
ATOM   6082  OG   SER a 324      -46.477  47.884 -75.083  0.50 26.99           O
ATOM   6083  C    SER a 324      -43.078  49.214 -75.877  0.50 26.36           C
ATOM   6084  O    SER a 324      -42.856  50.299 -75.392  0.50 25.30           O
ATOM   6085  N    ASN a 325      -42.445  48.740 -76.937  0.50 27.08           N
ATOM   6086  CA   ASN a 325      -41.517  49.519 -77.727  0.50 26.15           C
ATOM   6087  CB   ASN a 325      -40.125  49.371 -77.135  0.50 27.21           C
ATOM   6088  CG   ASN a 325      -39.056  50.099 -77.915  0.50 27.78           C
ATOM   6089  OD1  ASN a 325      -38.289  49.485 -78.621  0.50 28.06           O
ATOM   6090  ND2  ASN a 325      -38.974  51.399 -77.739  0.50 25.95           N
ATOM   6091  C    ASN a 325      -41.577  49.002 -79.162  0.50 26.82           C
ATOM   6092  O    ASN a 325      -41.786  47.828 -79.381  0.50 25.13           O
ATOM   6093  N    LYS a 326      -41.377  49.881 -80.134  0.50 28.12           N
ATOM   6094  CA   LYS a 326      -41.522  49.508 -81.546  0.50 30.34           C
ATOM   6095  CB   LYS a 326      -41.639  50.742 -82.453  0.50 30.05           C
ATOM   6096  CG   LYS a 326      -43.036  51.340 -82.433  0.50 32.21           C
ATOM   6097  CD   LYS a 326      -43.147  52.755 -82.971  0.50 34.10           C
ATOM   6098  CE   LYS a 326      -44.411  53.420 -82.442  0.50 35.95           C
ATOM   6099  NZ   LYS a 326      -44.790  54.728 -83.061  0.50 31.93           N
ATOM   6100  C    LYS a 326      -40.498  48.481 -82.023  0.50 30.49           C
ATOM   6101  O    LYS a 326      -40.727  47.749 -82.958  0.50 30.38           O
ATOM   6102  N    ALA a 327      -39.370  48.439 -81.348  0.50 31.51           N
ATOM   6103  CA   ALA a 327      -38.302  47.520 -81.652  0.50 31.50           C
ATOM   6104  CB   ALA a 327      -36.994  48.065 -81.145  0.50 29.36           C
ATOM   6105  C    ALA a 327      -38.568  46.122 -81.083  0.50 33.86           C
ATOM   6106  O    ALA a 327      -37.762  45.228 -81.228  0.50 32.88           O
ATOM   6107  N    LEU a 328      -39.695  45.974 -80.396  0.50 34.31           N
ATOM   6108  CA   LEU a 328      -40.164  44.683 -79.926  0.50 34.17           C
ATOM   6109  CB   LEU a 328      -40.646  44.798 -78.485  0.50 32.86           C
ATOM   6110  CG   LEU a 328      -39.698  45.245 -77.385  0.50 33.97           C
ATOM   6111  CD1  LEU a 328      -40.500  45.694 -76.187  0.50 31.07           C
ATOM   6112  CD2  LEU a 328      -38.783  44.107 -76.998  0.50 33.54           C
ATOM   6113  C    LEU a 328      -41.328  44.158 -80.767  0.50 34.39           C
ATOM   6114  O    LEU a 328      -42.321  44.827 -80.957  0.50 35.71           O
ATOM   6115  N    PRO a 329      -41.188  42.933 -81.228  0.50 34.54           N
ATOM   6116  CA   PRO a 329      -42.214  42.147 -81.902  0.50 33.67           C
ATOM   6117  CB   PRO a 329      -41.538  40.789 -82.123  0.50 35.46           C
ATOM   6118  CG   PRO a 329      -40.422  40.738 -81.134  0.50 35.69           C
ATOM   6119  CD   PRO a 329      -39.965  42.156 -80.962  0.50 35.03           C
ATOM   6120  C    PRO a 329      -43.418  41.979 -80.987  0.50 33.34           C
ATOM   6121  O    PRO a 329      -44.556  41.983 -81.453  0.50 28.75           O
ATOM   6122  N    ALA a 330      -43.150  41.856 -79.685  0.50 34.11           N
ATOM   6123  CA   ALA a 330      -44.186  41.643 -78.677  0.50 31.17           C
ATOM   6124  CB   ALA a 330      -44.432  40.156 -78.472  0.50 30.28           C
ATOM   6125  C    ALA a 330      -43.770  42.292 -77.357  0.50 30.56           C
ATOM   6126  O    ALA a 330      -42.591  42.263 -76.995  0.50 30.41           O
ATOM   6127  N    PRO a 331      -44.743  42.857 -76.632  0.50 29.36           N
ATOM   6128  CA   PRO a 331      -44.474  43.622 -75.420  0.50 30.48           C
ATOM   6129  CB   PRO a 331      -45.850  44.195 -75.048  0.50 30.60           C
ATOM   6130  CG   PRO a 331      -46.737  43.927 -76.232  0.50 32.18           C
```

Figure 27 (Continued)

```
ATOM   6131  CD   PRO a 331     -46.184  42.682 -76.841  0.50 29.60           C
ATOM   6132  C    PRO a 331     -43.974  42.711 -74.314  0.50 30.55           C
ATOM   6133  O    PRO a 331     -44.521  41.627 -74.120  0.50 32.00           O
ATOM   6134  N    ILE a 332     -42.942  43.168 -73.607  0.50 31.25           N
ATOM   6135  CA   ILE a 332     -42.272  42.396 -72.564  0.50 31.04           C
ATOM   6136  CB   ILE a 332     -40.788  42.781 -72.480  0.50 30.79           C
ATOM   6137  CG1  ILE a 332     -40.044  42.259 -73.711  0.50 29.50           C
ATOM   6138  CD1  ILE a 332     -38.551  42.492 -73.675  0.50 29.63           C
ATOM   6139  CG2  ILE a 332     -40.159  42.255 -71.198  0.50 30.77           C
ATOM   6140  C    ILE a 332     -42.919  42.644 -71.208  0.50 30.66           C
ATOM   6141  O    ILE a 332     -43.090  43.798 -70.798  0.50 28.46           O
ATOM   6142  N    GLU a 333     -43.281  41.559 -70.527  0.50 30.09           N
ATOM   6143  CA   GLU a 333     -43.930  41.649 -69.218  0.50 30.77           C
ATOM   6144  CB   GLU a 333     -45.324  41.020 -69.263  0.50 30.50           C
ATOM   6145  CG   GLU a 333     -46.138  41.340 -70.504  0.50 33.09           C
ATOM   6146  CD   GLU a 333     -47.411  40.518 -70.589  0.50 34.32           C
ATOM   6147  OE1  GLU a 333     -48.294  40.874 -71.399  0.50 34.10           O
ATOM   6148  OE2  GLU a 333     -47.531  39.515 -69.842  0.50 35.69           O
ATOM   6149  C    GLU a 333     -43.109  40.949 -68.135  0.50 28.63           C
ATOM   6150  O    GLU a 333     -42.779  39.768 -68.262  0.50 29.21           O
ATOM   6151  N    LYS a 334     -42.796  41.690 -67.073  0.50 26.71           N
ATOM   6152  CA   LYS a 334     -42.198  41.138 -65.849  0.50 25.42           C
ATOM   6153  CB   LYS a 334     -40.981  41.968 -65.434  0.50 24.95           C
ATOM   6154  CG   LYS a 334     -39.876  42.054 -66.478  0.50 26.14           C
ATOM   6155  CD   LYS a 334     -39.019  40.800 -66.484  0.50 26.36           C
ATOM   6156  CE   LYS a 334     -38.199  40.707 -67.760  0.50 27.57           C
ATOM   6157  NZ   LYS a 334     -37.293  39.528 -67.713  0.50 28.69           N
ATOM   6158  C    LYS a 334     -43.228  41.192 -64.728  0.50 24.32           C
ATOM   6159  O    LYS a 334     -44.043  42.116 -64.668  0.50 25.21           O
ATOM   6160  N    THR a 335     -43.202  40.206 -63.836  0.50 23.97           N
ATOM   6161  CA   THR a 335     -44.132  40.200 -62.704  0.50 22.92           C
ATOM   6162  CB   THR a 335     -45.119  39.018 -62.796  0.50 23.92           C
ATOM   6163  OG1  THR a 335     -45.931  39.158 -63.973  0.50 26.49           O
ATOM   6164  CG2  THR a 335     -46.007  38.962 -61.550  0.50 25.75           C
ATOM   6165  C    THR a 335     -43.361  40.082 -61.402  0.50 21.89           C
ATOM   6166  O    THR a 335     -42.286  39.490 -61.372  0.50 20.08           O
ATOM   6167  N    ILE a 336     -43.909  40.647 -60.325  0.50 20.91           N
ATOM   6168  CA   ILE a 336     -43.257  40.521 -59.025  0.50 20.32           C
ATOM   6169  CB   ILE a 336     -42.200  41.621 -58.790  0.50 19.95           C
ATOM   6170  CG1  ILE a 336     -41.113  41.106 -57.849  0.50 20.04           C
ATOM   6171  CD1  ILE a 336     -39.732  41.644 -58.170  0.50 20.73           C
ATOM   6172  CG2  ILE a 336     -42.853  42.903 -58.273  0.50 21.07           C
ATOM   6173  C    ILE a 336     -44.239  40.524 -57.879  0.50 19.04           C
ATOM   6174  O    ILE a 336     -45.311  41.125 -57.952  0.50 20.77           O
ATOM   6175  N    SER a 337     -43.834  39.883 -56.785  0.50 19.20           N
ATOM   6176  CA   SER a 337     -44.688  39.791 -55.622  0.50 18.06           C
ATOM   6177  CB   SER a 337     -45.772  38.745 -55.862  0.50 19.70           C
ATOM   6178  OG   SER a 337     -45.172  37.487 -56.133  0.50 20.49           O
ATOM   6179  C    SER a 337     -43.855  39.377 -54.413  0.50 17.00           C
ATOM   6180  O    SER a 337     -42.666  39.017 -54.524  0.50 15.63           O
ATOM   6181  N    LYS a 338     -44.496  39.429 -53.258  0.50 17.22           N
ATOM   6182  CA   LYS a 338     -43.831  39.127 -52.009  0.50 17.47           C
ATOM   6183  CB   LYS a 338     -44.716  39.585 -50.850  0.50 17.67           C
ATOM   6184  CG   LYS a 338     -44.007  39.547 -49.500  0.50 18.05           C
ATOM   6185  CD   LYS a 338     -44.985  39.849 -48.363  0.50 19.60           C
ATOM   6186  CE   LYS a 338     -45.829  38.628 -48.042  0.50 19.08           C
ATOM   6187  NZ   LYS a 338     -45.008  37.533 -47.440  0.50 19.28           N
ATOM   6188  C    LYS a 338     -43.606  37.630 -51.919  0.50 17.94           C
ATOM   6189  O    LYS a 338     -44.479  36.837 -52.303  0.50 18.83           O
ATOM   6190  N    ALA a 339     -42.439  37.240 -51.409  0.50 17.19           N
ATOM   6191  CA   ALA a 339     -42.163  35.825 -51.139  0.50 18.49           C
ATOM   6192  CB   ALA a 339     -40.894  35.670 -50.308  0.50 18.80           C
ATOM   6193  C    ALA a 339     -43.336  35.150 -50.441  0.50 18.34           C
ATOM   6194  O    ALA a 339     -43.916  35.697 -49.509  0.50 19.90           O
```

Figure 27 (Continued)

```
ATOM   6195  N    LYS a 340     -43.660  33.940 -50.881  0.50 18.51           N
ATOM   6196  CA   LYS a 340     -44.776  33.185 -50.297  0.50 18.57           C
ATOM   6197  CB   LYS a 340     -45.542  32.423 -51.376  0.50 20.41           C
ATOM   6198  CG   LYS a 340     -46.222  33.297 -52.430  0.50 21.83           C
ATOM   6199  CD   LYS a 340     -46.514  32.453 -53.663  0.50 24.63           C
ATOM   6200  CE   LYS a 340     -46.565  33.292 -54.934  0.50 27.39           C
ATOM   6201  NZ   LYS a 340     -46.140  32.500 -56.122  0.50 29.04           N
ATOM   6202  C    LYS a 340     -44.305  32.185 -49.238  0.50 18.20           C
ATOM   6203  O    LYS a 340     -43.116  31.844 -49.157  0.50 17.86           O
ATOM   6204  N    GLY a 341     -45.270  31.682 -48.461  0.50 18.04           N
ATOM   6205  CA   GLY a 341     -44.986  30.787 -47.335  0.50 18.12           C
ATOM   6206  C    GLY a 341     -45.633  31.359 -46.083  0.50 18.13           C
ATOM   6207  O    GLY a 341     -45.812  32.569 -45.970  0.50 18.66           O
ATOM   6208  N    GLN a 342     -46.042  30.497 -45.150  0.50 19.23           N
ATOM   6209  CA   GLN a 342     -46.772  30.969 -43.975  0.50 18.83           C
ATOM   6210  CB   GLN a 342     -47.372  29.793 -43.199  0.50 21.25           C
ATOM   6211  CG   GLN a 342     -48.630  29.213 -43.851  0.50 22.28           C
ATOM   6212  CD   GLN a 342     -49.904  30.031 -43.577  0.50 24.72           C
ATOM   6213  OE1  GLN a 342     -50.030  30.711 -42.549  0.50 26.34           O
ATOM   6214  NE2  GLN a 342     -50.863  29.953 -44.499  0.50 24.15           N
ATOM   6215  C    GLN a 342     -45.856  31.789 -43.050  0.50 16.87           C
ATOM   6216  O    GLN a 342     -44.770  31.344 -42.725  0.50 15.53           O
ATOM   6217  N    PRO a 343     -46.324  32.969 -42.606  0.50 16.91           N
ATOM   6218  CA   PRO a 343     -45.483  33.804 -41.762  0.50 16.61           C
ATOM   6219  CB   PRO a 343     -46.309  35.098 -41.597  0.50 17.02           C
ATOM   6220  CG   PRO a 343     -47.420  35.016 -42.629  0.50 17.74           C
ATOM   6221  CD   PRO a 343     -47.666  33.549 -42.789  0.50 17.65           C
ATOM   6222  C    PRO a 343     -45.231  33.149 -40.407  0.50 15.68           C
ATOM   6223  O    PRO a 343     -46.101  32.416 -39.891  0.50 16.96           O
ATOM   6224  N    ARG a 344     -44.046  33.376 -39.838  0.50 15.00           N
ATOM   6225  CA   ARG a 344     -43.789  32.966 -38.485  0.50 15.03           C
ATOM   6226  CB   ARG a 344     -42.857  31.751 -38.439  0.50 15.96           C
ATOM   6227  CG   ARG a 344     -43.544  30.459 -38.850  0.50 18.38           C
ATOM   6228  CD   ARG a 344     -42.554  29.335 -39.046  0.50 21.72           C
ATOM   6229  NE   ARG a 344     -41.888  28.935 -37.808  0.50 22.84           N
ATOM   6230  CZ   ARG a 344     -41.055  27.894 -37.710  0.50 22.70           C
ATOM   6231  NH1  ARG a 344     -40.771  27.140 -38.780  0.50 21.39           N
ATOM   6232  NH2  ARG a 344     -40.489  27.625 -36.551  0.50 20.58           N
ATOM   6233  C    ARG a 344     -43.134  34.137 -37.797  0.50 14.53           C
ATOM   6234  O    ARG a 344     -42.257  34.786 -38.369  0.50 12.85           O
ATOM   6235  N    GLU a 345     -43.561  34.374 -36.572  0.50 14.46           N
ATOM   6236  CA   GLU a 345     -43.091  35.498 -35.773  0.50 15.97           C
ATOM   6237  CB   GLU a 345     -44.081  35.702 -34.624  0.50 17.14           C
ATOM   6238  CG   GLU a 345     -43.598  36.764 -33.634  0.50 19.21           C
ATOM   6239  CD   GLU a 345     -44.291  36.730 -32.286  0.50 22.15           C
ATOM   6240  OE1  GLU a 345     -44.558  37.815 -31.731  0.50 24.79           O
ATOM   6241  OE2  GLU a 345     -44.547  35.634 -31.748  0.50 22.05           O
ATOM   6242  C    GLU a 345     -41.730  35.182 -35.147  0.50 15.36           C
ATOM   6243  O    GLU a 345     -41.634  34.180 -34.426  0.50 15.10           O
ATOM   6244  N    PRO a 346     -40.705  36.051 -35.381  0.50 15.08           N
ATOM   6245  CA   PRO a 346     -39.345  35.935 -34.828  0.50 16.60           C
ATOM   6246  CB   PRO a 346     -38.577  37.043 -35.578  0.50 17.24           C
ATOM   6247  CG   PRO a 346     -39.626  38.060 -35.858  0.50 16.62           C
ATOM   6248  CD   PRO a 346     -40.818  37.222 -36.261  0.50 15.55           C
ATOM   6249  C    PRO a 346     -39.316  36.181 -33.311  0.50 18.48           C
ATOM   6250  O    PRO a 346     -40.082  37.016 -32.777  0.50 18.00           O
ATOM   6251  N    GLN a 347     -38.458  35.441 -32.608  0.50 17.34           N
ATOM   6252  CA   GLN a 347     -38.124  35.752 -31.233  0.50 18.35           C
ATOM   6253  CB   GLN a 347     -37.876  34.451 -30.442  0.50 20.94           C
ATOM   6254  CG   GLN a 347     -39.084  33.514 -30.387  0.50 24.65           C
ATOM   6255  CD   GLN a 347     -39.036  32.368 -31.392  0.50 27.47           C
ATOM   6256  OE1  GLN a 347     -38.175  31.490 -31.320  0.50 24.46           O
ATOM   6257  NE2  GLN a 347     -39.998  32.356 -32.317  0.50 31.36           N
ATOM   6258  C    GLN a 347     -36.838  36.589 -31.305  0.50 16.00           C
```

Figure 27 (Continued)

```
ATOM   6259  O    GLN a 347     -35.965  36.295 -32.124  0.50 17.01           O
ATOM   6260  N    VAL a 348     -36.693  37.607 -30.452  0.50 15.39           N
ATOM   6261  CA   VAL a 348     -35.494  38.471 -30.512  0.50 15.10           C
ATOM   6262  CB   VAL a 348     -35.878  39.941 -30.806  0.50 15.27           C
ATOM   6263  CG1  VAL a 348     -34.617  40.823 -30.803  0.50 15.06           C
ATOM   6264  CG2  VAL a 348     -36.657  40.028 -32.127  0.50 15.07           C
ATOM   6265  C    VAL a 348     -34.736  38.466 -29.187  0.50 14.95           C
ATOM   6266  O    VAL a 348     -35.324  38.769 -28.150  0.50 16.58           O
ATOM   6267  N    TYR a 349     -33.445  38.123 -29.221  0.50 14.89           N
ATOM   6268  CA   TYR a 349     -32.638  38.004 -27.999  0.50 15.91           C
ATOM   6269  CB   TYR a 349     -32.350  36.515 -27.698  0.50 16.33           C
ATOM   6270  CG   TYR a 349     -33.586  35.626 -27.678  0.50 16.87           C
ATOM   6271  CD1  TYR a 349     -34.543  35.755 -26.663  0.50 17.40           C
ATOM   6272  CE1  TYR a 349     -35.662  34.937 -26.623  0.50 18.54           C
ATOM   6273  CZ   TYR a 349     -35.828  33.959 -27.580  0.50 17.85           C
ATOM   6274  OH   TYR a 349     -36.947  33.155 -27.557  0.50 19.30           O
ATOM   6275  CE2  TYR a 349     -34.892  33.794 -28.582  0.50 17.63           C
ATOM   6276  CD2  TYR a 349     -33.780  34.630 -28.631  0.50 17.54           C
ATOM   6277  C    TYR a 349     -31.333  38.772 -28.120  0.50 16.39           C
ATOM   6278  O    TYR a 349     -30.540  38.504 -29.026  0.50 15.09           O
ATOM   6279  N    VAL a 350     -31.065  39.701 -27.199  0.50 16.21           N
ATOM   6280  CA   VAL a 350     -29.766  40.380 -27.218  0.50 17.09           C
ATOM   6281  CB   VAL a 350     -29.861  41.929 -27.038  0.50 16.85           C
ATOM   6282  CG1  VAL a 350     -30.576  42.578 -28.238  0.50 16.98           C
ATOM   6283  CG2  VAL a 350     -30.548  42.299 -25.725  0.50 16.99           C
ATOM   6284  C    VAL a 350     -28.772  39.746 -26.233  0.50 17.32           C
ATOM   6285  O    VAL a 350     -29.173  39.193 -25.191  0.50 19.37           O
ATOM   6286  N    TYR a 351     -27.484  39.850 -26.558  0.50 16.82           N
ATOM   6287  CA   TYR a 351     -26.421  39.227 -25.760  0.50 17.33           C
ATOM   6288  CB   TYR a 351     -25.755  38.104 -26.556  0.50 18.46           C
ATOM   6289  CG   TYR a 351     -26.610  36.888 -26.816  0.50 20.47           C
ATOM   6290  CD1  TYR a 351     -26.300  35.662 -26.231  0.50 21.16           C
ATOM   6291  CE1  TYR a 351     -27.063  34.535 -26.489  0.50 22.25           C
ATOM   6292  CZ   TYR a 351     -28.114  34.621 -27.374  0.50 21.87           C
ATOM   6293  OH   TYR a 351     -28.857  33.503 -27.649  0.50 23.52           O
ATOM   6294  CE2  TYR a 351     -28.419  35.817 -27.994  0.50 20.74           C
ATOM   6295  CD2  TYR a 351     -27.660  36.935 -27.720  0.50 19.73           C
ATOM   6296  C    TYR a 351     -25.355  40.244 -25.426  0.50 17.88           C
ATOM   6297  O    TYR a 351     -24.840  40.923 -26.311  0.50 18.38           O
ATOM   6298  N    PRO a 352     -25.006  40.362 -24.148  0.50 19.93           N
ATOM   6299  CA   PRO a 352     -23.894  41.248 -23.808  0.50 20.70           C
ATOM   6300  CB   PRO a 352     -24.060  41.464 -22.299  0.50 20.65           C
ATOM   6301  CG   PRO a 352     -24.818  40.271 -21.821  0.50 21.35           C
ATOM   6302  CD   PRO a 352     -25.681  39.808 -22.965  0.50 20.12           C
ATOM   6303  C    PRO a 352     -22.551  40.586 -24.116  0.50 22.66           C
ATOM   6304  O    PRO a 352     -22.509  39.374 -24.364  0.50 21.94           O
ATOM   6305  N    PRO a 353     -21.466  41.377 -24.111  0.50 22.64           N
ATOM   6306  CA   PRO a 353     -20.132  40.875 -24.425  0.50 22.95           C
ATOM   6307  CB   PRO a 353     -19.215  42.042 -24.059  0.50 23.61           C
ATOM   6308  CG   PRO a 353     -20.081  43.247 -24.168  0.50 23.17           C
ATOM   6309  CD   PRO a 353     -21.448  42.809 -23.756  0.50 24.49           C
ATOM   6310  C    PRO a 353     -19.726  39.643 -23.631  0.50 22.45           C
ATOM   6311  O    PRO a 353     -20.163  39.439 -22.493  0.50 23.26           O
ATOM   6312  N    SER a 354     -18.886  38.835 -24.260  0.50 23.86           N
ATOM   6313  CA   SER a 354     -18.135  37.807 -23.562  0.50 23.56           C
ATOM   6314  CB   SER a 354     -17.202  37.110 -24.550  0.50 20.46           C
ATOM   6315  OG   SER a 354     -16.299  36.267 -23.857  0.50 23.52           O
ATOM   6316  C    SER a 354     -17.281  38.463 -22.477  0.50 25.11           C
ATOM   6317  O    SER a 354     -16.874  39.611 -22.623  0.50 24.61           O
ATOM   6318  N    ARG a 355     -16.982  37.725 -21.411  0.50 28.96           N
ATOM   6319  CA   ARG a 355     -16.007  38.190 -20.418  0.50 32.54           C
ATOM   6320  CB   ARG a 355     -15.834  37.148 -19.315  0.50 37.44           C
ATOM   6321  CG   ARG a 355     -14.620  37.394 -18.433  0.50 42.01           C
ATOM   6322  CD   ARG a 355     -13.952  36.095 -17.988  0.50 47.51           C
```

Figure 27 (Continued)

```
ATOM   6323  NE  ARG a 355     -14.840  35.222 -17.221  0.50 49.12      N
ATOM   6324  CZ  ARG a 355     -15.260  34.026 -17.631  0.50 49.71      C
ATOM   6325  NH1 ARG a 355     -14.879  33.548 -18.811  0.50 47.79      N
ATOM   6326  NH2 ARG a 355     -16.060  33.305 -16.857  0.50 50.08      N
ATOM   6327  C   ARG a 355     -14.650  38.458 -21.080  0.50 31.70      C
ATOM   6328  O   ARG a 355     -13.986  39.465 -20.815  0.50 30.46      O
ATOM   6329  N   ASP a 356     -14.239  37.535 -21.941  0.50 29.93      N
ATOM   6330  CA  ASP a 356     -12.956  37.632 -22.623  0.50 27.26      C
ATOM   6331  CB  ASP a 356     -12.759  36.433 -23.552  0.50 29.93      C
ATOM   6332  CG  ASP a 356     -12.679  35.118 -22.810  0.50 31.56      C
ATOM   6333  OD1 ASP a 356     -13.076  35.048 -21.612  0.50 32.83      O
ATOM   6334  OD2 ASP a 356     -12.215  34.142 -23.430  0.50 30.59      O
ATOM   6335  C   ASP a 356     -12.834  38.917 -23.429  0.50 26.84      C
ATOM   6336  O   ASP a 356     -11.762  39.513 -23.516  0.50 25.01      O
ATOM   6337  N   GLU a 357     -13.925  39.345 -24.055  0.50 24.34      N
ATOM   6338  CA  GLU a 357     -13.849  40.530 -24.877  0.50 24.13      C
ATOM   6339  CB  GLU a 357     -15.087  40.650 -25.765  0.50 21.13      C
ATOM   6340  CG  GLU a 357     -14.835  41.432 -27.036  0.50 22.03      C
ATOM   6341  CD  GLU a 357     -16.070  41.485 -27.915  0.50 20.05      C
ATOM   6342  OE1 GLU a 357     -17.174  41.305 -27.360  0.50 22.28      O
ATOM   6343  OE2 GLU a 357     -15.928  41.698 -29.133  0.50 22.08      O
ATOM   6344  C   GLU a 357     -13.734  41.770 -23.991  0.50 25.19      C
ATOM   6345  O   GLU a 357     -13.277  42.809 -24.445  0.50 25.18      O
ATOM   6346  N   LEU a 358     -14.193  41.661 -22.746  0.50 27.79      N
ATOM   6347  CA  LEU a 358     -14.223  42.820 -21.848  0.50 31.50      C
ATOM   6348  CB  LEU a 358     -15.062  42.538 -20.598  0.50 30.00      C
ATOM   6349  CG  LEU a 358     -16.587  42.524 -20.777  0.50 31.90      C
ATOM   6350  CD1 LEU a 358     -17.282  42.097 -19.494  0.50 30.86      C
ATOM   6351  CD2 LEU a 358     -17.087  43.886 -21.248  0.50 31.34      C
ATOM   6352  C   LEU a 358     -12.815  43.271 -21.465  0.50 33.54      C
ATOM   6353  O   LEU a 358     -12.645  44.168 -20.642  0.50 37.00      O
ATOM   6354  N   THR a 359     -11.815  42.649 -22.088  0.50 37.77      N
ATOM   6355  CA  THR a 359     -10.423  43.063 -21.955  0.50 37.75      C
ATOM   6356  CB  THR a 359      -9.476  41.852 -21.821  0.50 39.83      C
ATOM   6357  OG1 THR a 359      -8.797  41.620 -23.069  0.50 39.52      O
ATOM   6358  CG2 THR a 359     -10.245  40.611 -21.407  0.50 38.84      C
ATOM   6359  C   THR a 359      -9.980  43.859 -23.182  0.50 36.80      C
ATOM   6360  O   THR a 359      -8.964  44.563 -23.137  0.50 34.30      O
ATOM   6361  N   LYS a 360     -10.725  43.726 -24.282  0.50 32.48      N
ATOM   6362  CA  LYS a 360     -10.390  44.430 -25.525  0.50 30.50      C
ATOM   6363  CB  LYS a 360     -11.023  43.747 -26.750  0.50 31.77      C
ATOM   6364  CG  LYS a 360     -10.501  42.347 -27.068  0.50 32.84      C
ATOM   6365  CD  LYS a 360      -9.235  42.366 -27.922  0.50 33.05      C
ATOM   6366  CE  LYS a 360      -8.777  40.948 -28.252  0.50 32.49      C
ATOM   6367  NZ  LYS a 360      -7.465  40.865 -28.959  0.50 30.70      N
ATOM   6368  C   LYS a 360     -10.859  45.879 -25.421  0.50 27.79      C
ATOM   6369  O   LYS a 360     -11.540  46.243 -24.467  0.50 29.80      O
ATOM   6370  N   ASN a 361     -10.485  46.705 -26.390  0.50 27.78      N
ATOM   6371  CA  ASN a 361     -10.841  48.116 -26.357  0.50 25.82      C
ATOM   6372  CB  ASN a 361      -9.898  48.926 -27.243  0.50 30.40      C
ATOM   6373  CG  ASN a 361      -8.446  48.769 -26.832  0.50 33.51      C
ATOM   6374  OD1 ASN a 361      -8.144  48.646 -25.648  0.50 34.81      O
ATOM   6375  ND2 ASN a 361      -7.543  48.775 -27.808  0.50 37.24      N
ATOM   6376  C   ASN a 361     -12.272  48.308 -26.834  0.50 23.73      C
ATOM   6377  O   ASN a 361     -12.841  49.393 -26.694  0.50 21.50      O
ATOM   6378  N   GLN a 362     -12.827  47.244 -27.411  0.50 20.83      N
ATOM   6379  CA  GLN a 362     -14.184  47.262 -27.966  0.50 22.08      C
ATOM   6380  CB  GLN a 362     -14.138  47.415 -29.494  0.50 23.73      C
ATOM   6381  CG  GLN a 362     -13.433  48.685 -29.942  0.50 28.08      C
ATOM   6382  CD  GLN a 362     -13.872  49.197 -31.308  0.50 30.18      C
ATOM   6383  OE1 GLN a 362     -13.608  48.578 -32.344  0.50 30.09      O
ATOM   6384  NE2 GLN a 362     -14.517  50.359 -31.315  0.50 33.10      N
ATOM   6385  C   GLN a 362     -14.896  45.972 -27.579  0.50 20.28      C
ATOM   6386  O   GLN a 362     -14.260  44.925 -27.412  0.50 18.32      O
```

Figure 27 (Continued)

```
ATOM   6387  N    VAL a 363     -16.220  46.031 -27.453  0.50 19.18           N
ATOM   6388  CA   VAL a 363     -16.984  44.829 -27.153  0.50 18.13           C
ATOM   6389  CB   VAL a 363     -17.594  44.878 -25.737  0.50 17.56           C
ATOM   6390  CG1  VAL a 363     -16.502  45.109 -24.685  0.50 18.85           C
ATOM   6391  CG2  VAL a 363     -18.657  45.963 -25.646  0.50 17.44           C
ATOM   6392  C    VAL a 363     -18.073  44.639 -28.201  0.50 18.35           C
ATOM   6393  O    VAL a 363     -18.455  45.582 -28.885  0.50 16.68           O
ATOM   6394  N    SER a 364     -18.535  43.398 -28.336  0.50 17.63           N
ATOM   6395  CA   SER a 364     -19.440  43.006 -29.412  0.50 18.13           C
ATOM   6396  CB   SER a 364     -18.911  41.735 -30.107  0.50 17.16           C
ATOM   6397  OG   SER a 364     -17.582  41.926 -30.556  0.50 18.06           O
ATOM   6398  C    SER a 364     -20.830  42.739 -28.873  0.50 16.75           C
ATOM   6399  O    SER a 364     -21.077  41.715 -28.182  0.50 19.21           O
ATOM   6400  N    LEU a 365     -21.759  43.631 -29.208  0.50 16.97           N
ATOM   6401  CA   LEU a 365     -23.145  43.458 -28.787  0.50 15.06           C
ATOM   6402  CB   LEU a 365     -23.855  44.815 -28.628  0.50 15.19           C
ATOM   6403  CG   LEU a 365     -23.313  45.592 -27.425  0.50 16.75           C
ATOM   6404  CD1  LEU a 365     -24.134  46.874 -27.232  0.50 15.26           C
ATOM   6405  CD2  LEU a 365     -23.324  44.724 -26.174  0.50 16.39           C
ATOM   6406  C    LEU a 365     -23.847  42.622 -29.844  0.50 14.73           C
ATOM   6407  O    LEU a 365     -23.700  42.889 -31.031  0.50 14.92           O
ATOM   6408  N    THR a 366     -24.578  41.609 -29.401  0.50 14.70           N
ATOM   6409  CA   THR a 366     -25.154  40.594 -30.299  0.50 15.47           C
ATOM   6410  CB   THR a 366     -24.606  39.196 -29.943  0.50 14.91           C
ATOM   6411  OG1  THR a 366     -23.164  39.175 -30.017  0.50 13.93           O
ATOM   6412  CG2  THR a 366     -25.221  38.132 -30.837  0.50 15.13           C
ATOM   6413  C    THR a 366     -26.688  40.532 -30.203  0.50 14.72           C
ATOM   6414  O    THR a 366     -27.257  40.388 -29.111  0.50 15.38           O
ATOM   6415  N    CYS a 367     -27.344  40.577 -31.360  0.50 14.95           N
ATOM   6416  CA   CYS a 367     -28.804  40.475 -31.463  0.50 14.60           C
ATOM   6417  CB   CYS a 367     -29.365  41.718 -32.146  0.50 15.83           C
ATOM   6418  SG   CYS a 367     -31.183  41.870 -32.168  0.50 16.36           S
ATOM   6419  C    CYS a 367     -29.097  39.262 -32.333  0.50 14.34           C
ATOM   6420  O    CYS a 367     -28.713  39.234 -33.486  0.50 13.87           O
ATOM   6421  N    LEU a 368     -29.730  38.255 -31.746  0.50 13.72           N
ATOM   6422  CA   LEU a 368     -30.130  37.041 -32.474  0.50 13.77           C
ATOM   6423  CB   LEU a 368     -29.931  35.823 -31.571  0.50 13.96           C
ATOM   6424  CG   LEU a 368     -30.814  34.586 -31.803  0.50 13.68           C
ATOM   6425  CD1  LEU a 368     -30.506  33.884 -33.119  0.50 13.04           C
ATOM   6426  CD2  LEU a 368     -30.648  33.609 -30.630  0.50 13.95           C
ATOM   6427  C    LEU a 368     -31.605  37.147 -32.752  0.50 13.30           C
ATOM   6428  O    LEU a 368     -32.371  37.453 -31.853  0.50 14.54           O
ATOM   6429  N    VAL a 369     -32.005  36.895 -33.991  0.50 13.65           N
ATOM   6430  CA   VAL a 369     -33.408  36.944 -34.345  0.50 13.63           C
ATOM   6431  CB   VAL a 369     -33.668  37.980 -35.448  0.50 13.08           C
ATOM   6432  CG1  VAL a 369     -35.179  38.149 -35.654  0.50 13.92           C
ATOM   6433  CG2  VAL a 369     -33.014  39.320 -35.088  0.50 14.66           C
ATOM   6434  C    VAL a 369     -33.752  35.557 -34.866  0.50 13.83           C
ATOM   6435  O    VAL a 369     -33.182  35.129 -35.857  0.50 14.47           O
ATOM   6436  N    LYS a 370     -34.636  34.848 -34.184  0.50 15.18           N
ATOM   6437  CA   LYS a 370     -34.901  33.465 -34.598  0.50 15.83           C
ATOM   6438  CB   LYS a 370     -34.179  32.451 -33.692  0.50 18.10           C
ATOM   6439  CG   LYS a 370     -34.823  32.291 -32.337  0.50 17.51           C
ATOM   6440  CD   LYS a 370     -34.287  31.132 -31.496  0.50 20.23           C
ATOM   6441  CE   LYS a 370     -34.750  29.802 -32.052  0.50 21.14           C
ATOM   6442  NZ   LYS a 370     -34.633  28.690 -31.074  0.50 21.67           N
ATOM   6443  C    LYS a 370     -36.366  33.085 -34.747  0.50 14.71           C
ATOM   6444  O    LYS a 370     -37.257  33.630 -34.069  0.50 14.43           O
ATOM   6445  N    GLY a 371     -36.594  32.174 -35.690  0.50 13.67           N
ATOM   6446  CA   GLY a 371     -37.896  31.574 -35.909  0.50 14.25           C
ATOM   6447  C    GLY a 371     -38.827  32.382 -36.794  0.50 13.96           C
ATOM   6448  O    GLY a 371     -40.063  32.295 -36.635  0.50 14.16           O
ATOM   6449  N    PHE a 372     -38.261  33.169 -37.712  0.50 13.79           N
ATOM   6450  CA   PHE a 372     -39.083  33.976 -38.629  0.50 13.62           C
```

Figure 27 (Continued)

```
ATOM   6451  CB   PHE a 372    -38.611  35.465 -38.649  0.50 13.52           C
ATOM   6452  CG   PHE a 372    -37.194  35.689 -39.178  0.50 12.94           C
ATOM   6453  CD1  PHE a 372    -36.087  35.629 -38.324  0.50 12.67           C
ATOM   6454  CE1  PHE a 372    -34.800  35.894 -38.792  0.50 12.32           C
ATOM   6455  CZ   PHE a 372    -34.598  36.223 -40.125  0.50 13.10           C
ATOM   6456  CE2  PHE a 372    -35.679  36.312 -40.977  0.50 13.21           C
ATOM   6457  CD2  PHE a 372    -36.971  36.053 -40.512  0.50 13.47           C
ATOM   6458  C    PHE a 372    -39.232  33.414 -40.042  0.50 13.96           C
ATOM   6459  O    PHE a 372    -38.394  32.652 -40.533  0.50 13.89           O
ATOM   6460  N    TYR a 373    -40.290  33.869 -40.705  0.50 13.72           N
ATOM   6461  CA   TYR a 373    -40.585  33.460 -42.071  0.50 15.56           C
ATOM   6462  CB   TYR a 373    -41.216  32.073 -42.123  0.50 15.80           C
ATOM   6463  CG   TYR a 373    -41.026  31.514 -43.498  0.50 17.69           C
ATOM   6464  CD1  TYR a 373    -41.929  31.798 -44.507  0.50 18.19           C
ATOM   6465  CE1  TYR a 373    -41.723  31.325 -45.793  0.50 21.95           C
ATOM   6466  CZ   TYR a 373    -40.596  30.581 -46.068  0.50 21.77           C
ATOM   6467  OH   TYR a 373    -40.411  30.095 -47.354  0.50 28.39           O
ATOM   6468  CE2  TYR a 373    -39.672  30.311 -45.089  0.50 21.00           C
ATOM   6469  CD2  TYR a 373    -39.885  30.783 -43.808  0.50 17.61           C
ATOM   6470  C    TYR a 373    -41.503  34.534 -42.614  0.50 14.97           C
ATOM   6471  O    TYR a 373    -42.432  34.916 -41.910  0.50 14.66           O
ATOM   6472  N    PRO a 374    -41.486  34.686 -43.938  0.50 15.59           N
ATOM   6473  CA   PRO a 374    -40.347  34.796 -44.835  0.50 15.28           C
ATOM   6474  CB   PRO a 374    -40.935  35.444 -46.083  0.50 16.27           C
ATOM   6475  CG   PRO a 374    -41.943  36.382 -45.518  0.50 16.40           C
ATOM   6476  CD   PRO a 374    -42.497  35.707 -44.282  0.50 16.55           C
ATOM   6477  C    PRO a 374    -39.089  35.503 -44.353  0.50 15.15           C
ATOM   6478  O    PRO a 374    -39.062  36.041 -43.250  0.50 15.18           O
ATOM   6479  N    SER a 375    -38.052  35.462 -45.174  0.50 14.77           N
ATOM   6480  CA   SER a 375    -36.752  35.937 -44.730  0.50 14.88           C
ATOM   6481  CB   SER a 375    -35.628  35.333 -45.562  0.50 15.75           C
ATOM   6482  OG   SER a 375    -35.712  35.779 -46.910  0.50 16.46           O
ATOM   6483  C    SER a 375    -36.664  37.461 -44.772  0.50 14.25           C
ATOM   6484  O    SER a 375    -35.717  38.045 -44.240  0.50 14.37           O
ATOM   6485  N    ASP a 376    -37.647  38.103 -45.386  0.50 14.62           N
ATOM   6486  CA   ASP a 376    -37.647  39.558 -45.511  0.50 14.90           C
ATOM   6487  CB   ASP a 376    -38.840  39.994 -46.365  0.50 15.48           C
ATOM   6488  CG   ASP a 376    -38.963  39.165 -47.639  0.50 15.47           C
ATOM   6489  OD1  ASP a 376    -38.506  39.604 -48.684  0.50 18.29           O
ATOM   6490  OD2  ASP a 376    -39.501  38.062 -47.604  0.50 18.64           O
ATOM   6491  C    ASP a 376    -37.711  40.216 -44.132  0.50 14.72           C
ATOM   6492  O    ASP a 376    -38.599  39.908 -43.339  0.50 15.45           O
ATOM   6493  N    ILE a 377    -36.768  41.101 -43.835  0.50 13.84           N
ATOM   6494  CA   ILE a 377    -36.623  41.577 -42.459  0.50 13.19           C
ATOM   6495  CB   ILE a 377    -36.060  40.453 -41.534  0.50 12.58           C
ATOM   6496  CG1  ILE a 377    -36.404  40.748 -40.056  0.50 12.86           C
ATOM   6497  CD1  ILE a 377    -36.435  39.528 -39.149  0.50 11.79           C
ATOM   6498  CG2  ILE a 377    -34.570  40.244 -41.754  0.50 13.64           C
ATOM   6499  C    ILE a 377    -35.673  42.769 -42.465  0.50 13.92           C
ATOM   6500  O    ILE a 377    -34.808  42.858 -43.351  0.50 14.25           O
ATOM   6501  N    ALA a 378    -35.834  43.668 -41.493  0.50 13.07           N
ATOM   6502  CA   ALA a 378    -34.894  44.791 -41.320  0.50 12.54           C
ATOM   6503  CB   ALA a 378    -35.554  46.088 -41.722  0.50 13.81           C
ATOM   6504  C    ALA a 378    -34.456  44.839 -39.848  0.50 12.53           C
ATOM   6505  O    ALA a 378    -35.289  44.708 -38.960  0.50 13.45           O
ATOM   6506  N    VAL a 379    -33.165  45.039 -39.600  0.50 13.25           N
ATOM   6507  CA   VAL a 379    -32.596  44.980 -38.250  0.50 12.49           C
ATOM   6508  CB   VAL a 379    -31.767  43.685 -38.056  0.50 12.53           C
ATOM   6509  CG1  VAL a 379    -30.966  43.747 -36.760  0.50 12.60           C
ATOM   6510  CG2  VAL a 379    -32.700  42.480 -38.052  0.50 11.68           C
ATOM   6511  C    VAL a 379    -31.684  46.196 -38.039  0.50 13.18           C
ATOM   6512  O    VAL a 379    -30.743  46.408 -38.795  0.50 13.63           O
ATOM   6513  N    GLU a 380    -32.020  47.021 -37.052  0.50 13.51           N
ATOM   6514  CA   GLU a 380    -31.324  48.311 -36.857  0.50 13.33           C
```

Figure 27 (Continued)

| | | | | | | | | | |
|---|---|---|---|---|---|---|---|---|---|
| ATOM | 6515 | CB | GLU | a 380 | -32.265 | 49.477 | -37.201 | 0.50 13.47 | C |
| ATOM | 6516 | CG | GLU | a 380 | -32.606 | 49.540 | -38.685 | 0.50 14.68 | C |
| ATOM | 6517 | CD | GLU | a 380 | -33.550 | 50.664 | -39.019 | 0.50 15.57 | C |
| ATOM | 6518 | OE1 | GLU | a 380 | -33.876 | 51.465 | -38.104 | 0.50 15.72 | O |
| ATOM | 6519 | OE2 | GLU | a 380 | -33.964 | 50.728 | -40.191 | 0.50 16.68 | O |
| ATOM | 6520 | C | GLU | a 380 | -30.903 | 48.406 | -35.409 | 0.50 13.25 | C |
| ATOM | 6521 | O | GLU | a 380 | -31.519 | 47.794 | -34.530 | 0.50 13.92 | O |
| ATOM | 6522 | N | TRP | a 381 | -29.867 | 49.199 | -35.130 | 0.50 13.15 | N |
| ATOM | 6523 | CA | TRP | a 381 | -29.510 | 49.462 | -33.736 | 0.50 13.27 | C |
| ATOM | 6524 | CB | TRP | a 381 | -28.078 | 49.042 | -33.454 | 0.50 13.51 | C |
| ATOM | 6525 | CG | TRP | a 381 | -27.784 | 47.525 | -33.478 | 0.50 13.59 | C |
| ATOM | 6526 | CD1 | TRP | a 381 | -27.500 | 46.752 | -34.586 | 0.50 14.22 | C |
| ATOM | 6527 | NE1 | TRP | a 381 | -27.208 | 45.462 | -34.193 | 0.50 14.26 | N |
| ATOM | 6528 | CE2 | TRP | a 381 | -27.322 | 45.377 | -32.830 | 0.50 13.38 | C |
| ATOM | 6529 | CD2 | TRP | a 381 | -27.644 | 46.670 | -32.347 | 0.50 13.61 | C |
| ATOM | 6530 | CE3 | TRP | a 381 | -27.817 | 46.852 | -30.961 | 0.50 13.74 | C |
| ATOM | 6531 | CZ3 | TRP | a 381 | -27.614 | 45.801 | -30.125 | 0.50 15.20 | C |
| ATOM | 6532 | CH2 | TRP | a 381 | -27.272 | 44.516 | -30.635 | 0.50 14.35 | C |
| ATOM | 6533 | CZ2 | TRP | a 381 | -27.119 | 44.304 | -31.978 | 0.50 14.22 | C |
| ATOM | 6534 | C | TRP | a 381 | -29.596 | 50.967 | -33.430 | 0.50 14.10 | C |
| ATOM | 6535 | O | TRP | a 381 | -29.372 | 51.806 | -34.314 | 0.50 15.87 | O |
| ATOM | 6536 | N | GLU | a 382 | -29.854 | 51.285 | -32.165 | 0.50 14.61 | N |
| ATOM | 6537 | CA | GLU | a 382 | -29.846 | 52.680 | -31.722 | 0.50 15.22 | C |
| ATOM | 6538 | CB | GLU | a 382 | -31.199 | 53.358 | -31.996 | 0.50 14.73 | C |
| ATOM | 6539 | CG | GLU | a 382 | -32.368 | 52.705 | -31.287 | 0.50 15.06 | C |
| ATOM | 6540 | CD | GLU | a 382 | -33.165 | 51.774 | -32.181 | 0.50 15.30 | C |
| ATOM | 6541 | OE1 | GLU | a 382 | -33.570 | 52.179 | -33.310 | 0.50 15.97 | O |
| ATOM | 6542 | OE2 | GLU | a 382 | -33.418 | 50.649 | -31.715 | 0.50 15.00 | O |
| ATOM | 6543 | C | GLU | a 382 | -29.472 | 52.810 | -30.258 | 0.50 15.56 | C |
| ATOM | 6544 | O | GLU | a 382 | -29.474 | 51.834 | -29.498 | 0.50 15.06 | O |
| ATOM | 6545 | N | SER | a 383 | -29.122 | 54.037 | -29.870 | 0.50 16.28 | N |
| ATOM | 6546 | CA | SER | a 383 | -28.715 | 54.313 | -28.502 | 0.50 17.70 | C |
| ATOM | 6547 | CB | SER | a 383 | -27.207 | 54.053 | -28.336 | 0.50 18.09 | C |
| ATOM | 6548 | OG | SER | a 383 | -26.750 | 54.440 | -27.040 | 0.50 20.31 | O |
| ATOM | 6549 | C | SER | a 383 | -29.004 | 55.802 | -28.246 | 0.50 18.78 | C |
| ATOM | 6550 | O | SER | a 383 | -28.783 | 56.635 | -29.119 | 0.50 19.56 | O |
| ATOM | 6551 | N | ASN | a 384 | -29.510 | 56.121 | -27.060 | 0.50 21.47 | N |
| ATOM | 6552 | CA | ASN | a 384 | -29.604 | 57.529 | -26.681 | 0.50 24.24 | C |
| ATOM | 6553 | CB | ASN | a 384 | -28.258 | 58.005 | -26.145 | 0.50 26.66 | C |
| ATOM | 6554 | CG | ASN | a 384 | -27.944 | 57.397 | -24.803 | 0.50 29.35 | C |
| ATOM | 6555 | OD1 | ASN | a 384 | -28.855 | 57.166 | -24.006 | 0.50 32.01 | O |
| ATOM | 6556 | ND2 | ASN | a 384 | -26.662 | 57.105 | -24.546 | 0.50 31.49 | N |
| ATOM | 6557 | C | ASN | a 384 | -30.054 | 58.382 | -27.858 | 0.50 24.72 | C |
| ATOM | 6558 | O | ASN | a 384 | -29.503 | 59.459 | -28.123 | 0.50 25.68 | O |
| ATOM | 6559 | N | GLY | a 385 | -31.023 | 57.857 | -28.604 | 0.50 23.74 | N |
| ATOM | 6560 | CA | GLY | a 385 | -31.720 | 58.649 | -29.613 | 0.50 24.48 | C |
| ATOM | 6561 | C | GLY | a 385 | -31.208 | 58.710 | -31.042 | 0.50 23.87 | C |
| ATOM | 6562 | O | GLY | a 385 | -31.783 | 59.421 | -31.857 | 0.50 29.44 | O |
| ATOM | 6563 | N | GLN | a 386 | -30.126 | 58.008 | -31.357 | 0.50 22.49 | N |
| ATOM | 6564 | CA | GLN | a 386 | -29.580 | 58.016 | -32.712 | 0.50 23.22 | C |
| ATOM | 6565 | CB | GLN | a 386 | -28.554 | 59.147 | -32.907 | 0.50 23.59 | C |
| ATOM | 6566 | CG | GLN | a 386 | -27.769 | 59.050 | -34.217 | 0.50 24.92 | C |
| ATOM | 6567 | CD | GLN | a 386 | -26.773 | 60.168 | -34.378 | 0.50 24.97 | C |
| ATOM | 6568 | OE1 | GLN | a 386 | -26.893 | 61.204 | -33.736 | 0.50 24.12 | O |
| ATOM | 6569 | NE2 | GLN | a 386 | -25.785 | 59.970 | -35.255 | 0.50 24.58 | N |
| ATOM | 6570 | C | GLN | a 386 | -28.956 | 56.678 | -33.131 | 0.50 21.19 | C |
| ATOM | 6571 | O | GLN | a 386 | -28.362 | 55.947 | -32.314 | 0.50 18.17 | O |
| ATOM | 6572 | N | PRO | a 387 | -29.054 | 56.382 | -34.432 | 0.50 20.18 | N |
| ATOM | 6573 | CA | PRO | a 387 | -28.506 | 55.182 | -35.046 | 0.50 18.89 | C |
| ATOM | 6574 | CB | PRO | a 387 | -28.705 | 55.439 | -36.543 | 0.50 19.27 | C |
| ATOM | 6575 | CG | PRO | a 387 | -29.877 | 56.371 | -36.610 | 0.50 20.40 | C |
| ATOM | 6576 | CD | PRO | a 387 | -29.710 | 57.262 | -35.416 | 0.50 20.17 | C |
| ATOM | 6577 | C | PRO | a 387 | -27.023 | 54.969 | -34.774 | 0.50 19.24 | C |
| ATOM | 6578 | O | PRO | a 387 | -26.204 | 55.908 | -34.907 | 0.50 17.87 | O |

Figure 27 (Continued)

```
ATOM   6579  N   GLU a 388     -26.664  53.738 -34.399  0.50 16.78           N
ATOM   6580  CA  GLU a 388     -25.253  53.329 -34.344  0.50 18.94           C
ATOM   6581  CB  GLU a 388     -25.092  52.118 -33.434  0.50 19.51           C
ATOM   6582  CG  GLU a 388     -25.527  52.409 -32.011  0.50 20.45           C
ATOM   6583  CD  GLU a 388     -24.400  53.018 -31.186  0.50 21.48           C
ATOM   6584  OE1 GLU a 388     -23.245  52.591 -31.370  0.50 23.65           O
ATOM   6585  OE2 GLU a 388     -24.670  53.921 -30.369  0.50 20.38           O
ATOM   6586  C   GLU a 388     -24.592  53.095 -35.714  0.50 18.68           C
ATOM   6587  O   GLU a 388     -25.197  52.636 -36.648  0.50 18.49           O
ATOM   6588  N   ASN a 389     -23.318  53.423 -35.866  0.50 21.30           N
ATOM   6589  CA  ASN a 389     -22.778  53.220 -37.202  0.50 22.34           C
ATOM   6590  CB  ASN a 389     -21.643  54.204 -37.530  0.50 22.88           C
ATOM   6591  CG  ASN a 389     -21.274  54.196 -39.006  0.50 23.22           C
ATOM   6592  OD1 ASN a 389     -22.142  54.306 -39.881  0.50 26.14           O
ATOM   6593  ND2 ASN a 389     -19.975  54.036 -39.295  0.50 24.69           N
ATOM   6594  C   ASN a 389     -22.370  51.772 -37.441  0.50 23.86           C
ATOM   6595  O   ASN a 389     -22.911  51.092 -38.340  0.50 25.72           O
ATOM   6596  N   ASN a 390     -21.435  51.333 -36.604  0.50 21.55           N
ATOM   6597  CA  ASN a 390     -20.657  50.147 -36.828  0.50 20.84           C
ATOM   6598  CB  ASN a 390     -19.331  50.233 -36.053  0.50 20.93           C
ATOM   6599  CG  ASN a 390     -18.320  49.215 -36.542  0.50 22.13           C
ATOM   6600  OD1 ASN a 390     -18.514  48.604 -37.592  0.50 22.96           O
ATOM   6601  ND2 ASN a 390     -17.229  49.053 -35.811  0.50 25.66           N
ATOM   6602  C   ASN a 390     -21.403  48.906 -36.405  0.50 18.64           C
ATOM   6603  O   ASN a 390     -21.108  48.350 -35.367  0.50 18.28           O
ATOM   6604  N   TYR a 391     -22.370  48.488 -37.206  0.50 18.85           N
ATOM   6605  CA  TYR a 391     -22.951  47.144 -37.027  0.50 17.87           C
ATOM   6606  CB  TYR a 391     -24.350  47.191 -36.366  0.50 17.79           C
ATOM   6607  CG  TYR a 391     -25.494  47.815 -37.159  0.50 18.47           C
ATOM   6608  CD1 TYR a 391     -26.253  47.064 -38.065  0.50 18.05           C
ATOM   6609  CE1 TYR a 391     -27.322  47.631 -38.756  0.50 19.19           C
ATOM   6610  CZ  TYR a 391     -27.663  48.947 -38.509  0.50 18.46           C
ATOM   6611  OH  TYR a 391     -28.739  49.509 -39.174  0.50 21.45           O
ATOM   6612  CE2 TYR a 391     -26.946  49.701 -37.599  0.50 18.42           C
ATOM   6613  CD2 TYR a 391     -25.873  49.137 -36.928  0.50 19.12           C
ATOM   6614  C   TYR a 391     -22.996  46.362 -38.315  0.50 17.86           C
ATOM   6615  O   TYR a 391     -23.083  46.939 -39.398  0.50 19.21           O
ATOM   6616  N   LYS a 392     -22.962  45.034 -38.190  0.50 16.81           N
ATOM   6617  CA  LYS a 392     -22.974  44.162 -39.346  0.50 16.62           C
ATOM   6618  CB  LYS a 392     -21.592  43.535 -39.591  0.50 17.96           C
ATOM   6619  CG  LYS a 392     -20.575  44.454 -40.266  0.50 18.44           C
ATOM   6620  CD  LYS a 392     -20.792  44.548 -41.763  0.50 21.28           C
ATOM   6621  CE  LYS a 392     -19.546  45.086 -42.425  0.50 21.45           C
ATOM   6622  NZ  LYS a 392     -19.333  46.467 -41.929  0.50 23.55           N
ATOM   6623  C   LYS a 392     -23.966  43.069 -39.018  0.50 16.53           C
ATOM   6624  O   LYS a 392     -24.126  42.702 -37.850  0.50 17.59           O
ATOM   6625  N   THR a 393     -24.633  42.562 -40.037  0.50 17.52           N
ATOM   6626  CA  THR a 393     -25.667  41.559 -39.841  0.50 16.36           C
ATOM   6627  CB  THR a 393     -27.050  42.195 -40.034  0.50 17.07           C
ATOM   6628  OG1 THR a 393     -27.147  43.312 -39.149  0.50 16.68           O
ATOM   6629  CG2 THR a 393     -28.148  41.206 -39.697  0.50 17.12           C
ATOM   6630  C   THR a 393     -25.483  40.416 -40.834  0.50 17.36           C
ATOM   6631  O   THR a 393     -25.165  40.640 -42.009  0.50 18.39           O
ATOM   6632  N   THR a 394     -25.666  39.187 -40.368  0.50 16.31           N
ATOM   6633  CA  THR a 394     -25.658  38.032 -41.277  0.50 16.74           C
ATOM   6634  CB  THR a 394     -25.658  36.688 -40.501  0.50 15.87           C
ATOM   6635  OG1 THR a 394     -26.962  36.428 -39.914  0.50 15.04           O
ATOM   6636  CG2 THR a 394     -24.542  36.660 -39.421  0.50 16.41           C
ATOM   6637  C   THR a 394     -26.907  38.102 -42.158  0.50 15.67           C
ATOM   6638  O   THR a 394     -27.976  38.444 -41.675  0.50 17.57           O
ATOM   6639  N   PRO a 395     -26.790  37.792 -43.454  0.50 16.13           N
ATOM   6640  CA  PRO a 395     -28.056  37.520 -44.118  0.50 16.27           C
ATOM   6641  CB  PRO a 395     -27.634  37.132 -45.533  0.50 16.10           C
ATOM   6642  CG  PRO a 395     -26.353  37.846 -45.751  0.50 16.21           C
```

Figure 27 (Continued)

```
ATOM   6643  CD   PRO a 395     -25.677  37.955 -44.411  0.50 16.14           C
ATOM   6644  C    PRO a 395      28.734  36.339  43.432  0.50 16.52           C
ATOM   6645  O    PRO a 395     -28.046  35.489 -42.825  0.50 17.04           O
ATOM   6646  N    PRO a 396     -30.070  36.284 -43.492  0.50 16.57           N
ATOM   6647  CA   PRO a 396     -30.806  35.184 -42.892  0.50 16.09           C
ATOM   6648  CB   PRO a 396     -32.286  35.535 -43.179  0.50 16.54           C
ATOM   6649  CG   PRO a 396     -32.282  36.997 -43.420  0.50 17.33           C
ATOM   6650  CD   PRO a 396     -30.966  37.314 -44.056  0.50 15.85           C
ATOM   6651  C    PRO a 396     -30.455  33.873 -43.578  0.50 17.27           C
ATOM   6652  O    PRO a 396     -30.145  33.861 -44.778  0.50 17.24           O
ATOM   6653  N    VAL a 397     -30.534  32.785 -42.816  0.50 17.74           N
ATOM   6654  CA   VAL a 397     -30.223  31.441 -43.322  0.50 19.27           C
ATOM   6655  CB   VAL a 397     -28.778  31.072 -42.981  0.50 20.15           C
ATOM   6656  CG1  VAL a 397     -27.812  32.017 -43.688  0.50 21.83           C
ATOM   6657  CG2  VAL a 397     -28.583  31.094 -41.465  0.50 22.87           C
ATOM   6658  C    VAL a 397     -31.161  30.466 -42.627  0.50 18.80           C
ATOM   6659  O    VAL a 397     -31.573  30.709 -41.516  0.50 16.72           O
ATOM   6660  N    LEU a 398     -31.542  29.381 -43.299  0.50 19.96           N
ATOM   6661  CA   LEU a 398     -32.509  28.418 -42.740  0.50 19.87           C
ATOM   6662  CB   LEU a 398     -32.909  27.390 -43.821  0.50 20.84           C
ATOM   6663  CG   LEU a 398     -33.594  27.957 -45.056  0.50 23.14           C
ATOM   6664  CD1  LEU a 398     -33.613  26.927 -46.189  0.50 24.07           C
ATOM   6665  CD2  LEU a 398     -35.005  28.362 -44.649  0.50 21.81           C
ATOM   6666  C    LEU a 398     -32.041  27.661 -41.495  0.50 19.67           C
ATOM   6667  O    LEU a 398     -30.903  27.136 -41.434  0.50 20.87           O
ATOM   6668  N    ASP a 399     -32.932  27.582 -40.511  0.50 19.19           N
ATOM   6669  CA   ASP a 399     -32.684  26.823 -39.281  0.50 18.98           C
ATOM   6670  CB   ASP a 399     -33.415  27.479 -38.113  0.50 18.73           C
ATOM   6671  CG   ASP a 399     -32.713  27.274 -36.774  0.50 18.23           C
ATOM   6672  OD1  ASP a 399     -31.996  26.264 -36.591  0.50 18.49           O
ATOM   6673  OD2  ASP a 399     -32.905  28.123 -35.886  0.50 16.48           O
ATOM   6674  C    ASP a 399     -33.181  25.387 -39.479  0.50 20.18           C
ATOM   6675  O    ASP a 399     -33.570  24.998 -40.594  0.50 20.55           O
ATOM   6676  N    SER a 400     -33.171  24.604 -38.408  0.50 20.53           N
ATOM   6677  CA   SER a 400     -33.487  23.178 -38.540  0.50 22.25           C
ATOM   6678  CB   SER a 400     -32.768  22.370 -37.452  0.50 22.93           C
ATOM   6679  OG   SER a 400     -33.190  22.775 -36.159  0.50 24.51           O
ATOM   6680  C    SER a 400     -34.990  22.883 -38.613  0.50 21.80           C
ATOM   6681  O    SER a 400     -35.393  21.755 -38.922  0.50 21.86           O
ATOM   6682  N    ASP a 401     -35.823  23.900 -38.357  0.50 20.62           N
ATOM   6683  CA   ASP a 401     -37.292  23.781 -38.502  0.50 20.59           C
ATOM   6684  CB   ASP a 401     -37.971  24.347 -37.258  0.50 20.53           C
ATOM   6685  CG   ASP a 401     -37.514  25.761 -36.947  0.50 19.11           C
ATOM   6686  OD1  ASP a 401     -36.869  26.372 -37.828  0.50 18.94           O
ATOM   6687  OD2  ASP a 401     -37.784  26.251 -35.835  0.50 20.07           O
ATOM   6688  C    ASP a 401     -37.895  24.443 -39.762  0.50 21.09           C
ATOM   6689  O    ASP a 401     -39.126  24.517 -39.913  0.50 24.23           O
ATOM   6690  N    GLY a 402     -37.049  24.892 -40.678  0.50 19.76           N
ATOM   6691  CA   GLY a 402     -37.518  25.593 -41.878  0.50 19.43           C
ATOM   6692  C    GLY a 402     -37.916  27.050 -41.620  0.50 18.14           C
ATOM   6693  O    GLY a 402     -38.545  27.708 -42.465  0.50 18.37           O
ATOM   6694  N    SER a 403     -37.568  27.550 -40.439  0.50 18.05           N
ATOM   6695  CA   SER a 403     -37.610  29.004 -40.212  0.50 16.80           C
ATOM   6696  CB   SER a 403     -38.141  29.354 -38.810  0.50 16.36           C
ATOM   6697  OG   SER a 403     -37.203  29.042 -37.791  0.50 17.11           O
ATOM   6698  C    SER a 403     -36.205  29.580 -40.408  0.50 16.38           C
ATOM   6699  O    SER a 403     -35.200  28.846 -40.455  0.50 14.87           O
ATOM   6700  N    PHE a 404     -36.137  30.903 -40.519  0.50 14.60           N
ATOM   6701  CA   PHE a 404     -34.856  31.603 -40.685  0.50 14.29           C
ATOM   6702  CB   PHE a 404     -35.018  32.799 -41.633  0.50 14.76           C
ATOM   6703  CG   PHE a 404     -35.159  32.405 -43.057  0.50 15.36           C
ATOM   6704  CD1  PHE a 404     -36.422  32.318 -43.639  0.50 15.84           C
ATOM   6705  CE1  PHE a 404     -36.560  31.915 -44.959  0.50 16.27           C
ATOM   6706  CZ   PHE a 404     -35.428  31.612 -45.706  0.50 15.64           C
```

Figure 27 (Continued)

```
ATOM   6707  CE2 PHE a 404     -34.169  31.710 -45.136  0.50 15.27           C
ATOM   6708  CD2 PHE a 404     -34.042  32.115 -43.814  0.50 15.99           C
ATOM   6709  C   PHE a 404     -34.309  32.150 -39.387  0.50 13.85           C
ATOM   6710  O   PHE a 404     -35.060  32.436 -38.442  0.50 14.21           O
ATOM   6711  N   ALA a 405     -32.987  32.332 -39.379  0.50 13.91           N
ATOM   6712  CA  ALA a 405     -32.326  33.102 -38.338  0.50 14.37           C
ATOM   6713  CB  ALA a 405     -31.766  32.188 -37.265  0.50 15.34           C
ATOM   6714  C   ALA a 405     -31.241  34.012 -38.872  0.50 13.92           C
ATOM   6715  O   ALA a 405     -30.649  33.746 -39.917  0.50 13.84           O
ATOM   6716  N   LEU a 406     -30.963  35.084 -38.132  0.50 13.28           N
ATOM   6717  CA  LEU a 406     -29.734  35.839 -38.336  0.50 13.84           C
ATOM   6718  CB  LEU a 406     -29.896  37.054 -39.260  0.50 14.60           C
ATOM   6719  CG  LEU a 406     -30.867  38.186 -38.896  0.50 13.84           C
ATOM   6720  CD1 LEU a 406     -30.506  39.042 -37.674  0.50 13.59           C
ATOM   6721  CD2 LEU a 406     -31.056  39.091 -40.108  0.50 13.07           C
ATOM   6722  C   LEU a 406     -29.165  36.304 -37.032  0.50 13.36           C
ATOM   6723  O   LEU a 406     -29.792  36.216 -35.968  0.50 14.55           O
ATOM   6724  N   VAL a 407     -27.977  36.857 -37.142  0.50 14.14           N
ATOM   6725  CA  VAL a 407     -27.358  37.507 -36.011  0.50 14.20           C
ATOM   6726  CB  VAL a 407     -26.182  36.675 -35.489  0.50 14.34           C
ATOM   6727  CG1 VAL a 407     -25.644  37.327 -34.232  0.50 14.37           C
ATOM   6728  CG2 VAL a 407     -26.626  35.250 -35.243  0.50 15.44           C
ATOM   6729  C   VAL a 407     -26.816  38.840 -36.496  0.50 14.04           C
ATOM   6730  O   VAL a 407     -26.172  38.906 -37.553  0.50 14.01           O
ATOM   6731  N   SER a 408     -27.090  39.891 -35.725  0.50 14.48           N
ATOM   6732  CA  SER a 408     -26.515  41.212 -35.965  0.50 14.67           C
ATOM   6733  CB  SER a 408     -27.641  42.253 -35.941  0.50 13.61           C
ATOM   6734  OG  SER a 408     -27.159  43.578 -36.122  0.50 13.76           O
ATOM   6735  C   SER a 408     -25.539  41.527 -34.843  0.50 14.05           C
ATOM   6736  O   SER a 408     -25.852  41.315 -33.663  0.50 14.94           O
ATOM   6737  N   LYS a 409     -24.372  42.042 -35.219  0.50 14.55           N
ATOM   6738  CA  LYS a 409     -23.309  42.394 -34.276  0.50 15.26           C
ATOM   6739  CB  LYS a 409     -22.007  41.650 -34.639  0.50 15.53           C
ATOM   6740  CG  LYS a 409     -20.829  41.976 -33.699  0.50 15.90           C
ATOM   6741  CD  LYS a 409     -19.637  41.011 -33.846  0.50 16.41           C
ATOM   6742  CE  LYS a 409     -18.839  41.220 -35.136  0.50 16.55           C
ATOM   6743  NZ  LYS a 409     -18.178  42.572 -35.187  0.50 16.27           N
ATOM   6744  C   LYS a 409     -23.060  43.905 -34.310  0.50 15.42           C
ATOM   6745  O   LYS a 409     -22.747  44.470 -35.357  0.50 16.50           O
ATOM   6746  N   LEU a 410     -23.237  44.559 -33.172  0.50 15.57           N
ATOM   6747  CA  LEU a 410     -22.910  45.981 -33.071  0.50 15.60           C
ATOM   6748  CB  LEU a 410     -24.034  46.730 -32.332  0.50 15.52           C
ATOM   6749  CG  LEU a 410     -23.748  48.191 -31.968  0.50 15.45           C
ATOM   6750  CD1 LEU a 410     -23.517  49.009 -33.230  0.50 15.29           C
ATOM   6751  CD2 LEU a 410     -24.894  48.771 -31.127  0.50 14.39           C
ATOM   6752  C   LEU a 410     -21.571  46.108 -32.343  0.50 17.12           C
ATOM   6753  O   LEU a 410     -21.359  45.486 -31.306  0.50 17.42           O
ATOM   6754  N   THR a 411     -20.666  46.882 -32.942  0.50 16.35           N
ATOM   6755  CA  THR a 411     -19.350  47.159 -32.362  0.50 16.72           C
ATOM   6756  CB  THR a 411     -18.266  47.115 -33.444  0.50 18.09           C
ATOM   6757  OG1 THR a 411     -18.292  45.834 -34.086  0.50 18.30           O
ATOM   6758  CG2 THR a 411     -16.883  47.353 -32.843  0.50 16.43           C
ATOM   6759  C   THR a 411     -19.369  48.550 -31.761  0.50 17.34           C
ATOM   6760  O   THR a 411     -19.708  49.509 -32.432  0.50 16.09           O
ATOM   6761  N   VAL a 412     -19.041  48.644 -30.480  0.50 18.18           N
ATOM   6762  CA  VAL a 412     -18.912  49.937 -29.820  0.50 17.73           C
ATOM   6763  CB  VAL a 412     -20.071  50.157 -28.837  0.50 18.03           C
ATOM   6764  CG1 VAL a 412     -21.403  50.107 -29.599  0.50 17.67           C
ATOM   6765  CG2 VAL a 412     -20.023  49.112 -27.723  0.50 17.96           C
ATOM   6766  C   VAL a 412     -17.577  49.988 -29.063  0.50 18.05           C
ATOM   6767  O   VAL a 412     -17.001  48.955 -28.731  0.50 17.02           O
ATOM   6768  N   ASP a 413     -17.071  51.187 -28.809  0.50 20.50           N
ATOM   6769  CA  ASP a 413     -15.885  51.309 -27.959  0.50 22.02           C
ATOM   6770  CB  ASP a 413     -15.468  52.774 -27.814  0.50 25.39           C
```

Figure 27 (Continued)

```
ATOM   6771  CG   ASP a 413     -15.027  53.403 -29.117  0.50 27.67           C
ATOM   6772  OD1  ASP a 413     -14.621  52.684 -30.053  0.50 29.46           O
ATOM   6773  OD2  ASP a 413     -15.061  54.654 -29.180  0.50 32.54           O
ATOM   6774  C    ASP a 413     -16.195  50.747 -26.572  0.50 21.02           C
ATOM   6775  O    ASP a 413     -17.275  50.967 -26.041  0.50 19.62           O
ATOM   6776  N    LYS a 414     -15.248  50.029 -25.972  0.50 20.61           N
ATOM   6777  CA   LYS a 414     -15.474  49.458 -24.644  0.50 21.41           C
ATOM   6778  CB   LYS a 414     -14.205  48.740 -24.143  0.50 22.06           C
ATOM   6779  CG   LYS a 414     -14.369  47.975 -22.832  0.50 24.20           C
ATOM   6780  CD   LYS a 414     -13.151  47.098 -22.554  0.50 26.92           C
ATOM   6781  CE   LYS a 414     -11.909  47.949 -22.314  0.50 26.95           C
ATOM   6782  NZ   LYS a 414     -10.628  47.185 -22.372  0.50 27.04           N
ATOM   6783  C    LYS a 414     -15.899  50.536 -23.648  0.50 22.75           C
ATOM   6784  O    LYS a 414     -16.642  50.257 -22.710  0.50 21.83           O
ATOM   6785  N    SER a 415     -15.401  51.757 -23.829  0.50 22.64           N
ATOM   6786  CA   SER a 415     -15.657  52.807 -22.862  0.50 24.80           C
ATOM   6787  CB   SER a 415     -14.805  54.061 -23.131  0.50 26.45           C
ATOM   6788  OG   SER a 415     -15.050  54.596 -24.425  0.50 25.34           O
ATOM   6789  C    SER a 415     -17.143  53.144 -22.831  0.50 25.51           C
ATOM   6790  O    SER a 415     -17.706  53.350 -21.759  0.50 23.97           O
ATOM   6791  N    ARG a 416     -17.789  53.150 -23.997  0.50 25.10           N
ATOM   6792  CA   ARG a 416     -19.232  53.422 -24.022  0.50 25.07           C
ATOM   6793  CB   ARG a 416     -19.728  53.670 -25.436  0.50 25.92           C
ATOM   6794  CG   ARG a 416     -19.116  54.885 -26.102  0.50 27.82           C
ATOM   6795  CD   ARG a 416     -19.693  55.051 -27.493  0.50 29.56           C
ATOM   6796  NE   ARG a 416     -21.138  55.232 -27.436  0.50 28.69           N
ATOM   6797  CZ   ARG a 416     -21.973  54.901 -28.420  0.50 29.12           C
ATOM   6798  NH1  ARG a 416     -21.503  54.373 -29.542  0.50 28.48           N
ATOM   6799  NH2  ARG a 416     -23.273  55.119 -28.285  0.50 24.74           N
ATOM   6800  C    ARG a 416     -20.083  52.337 -23.361  0.50 23.92           C
ATOM   6801  O    ARG a 416     -21.144  52.647 -22.812  0.50 21.57           O
ATOM   6802  N    TRP a 417     -19.639  51.076 -23.433  0.50 22.41           N
ATOM   6803  CA   TRP a 417     -20.316  49.985 -22.718  0.50 22.99           C
ATOM   6804  CB   TRP a 417     -19.818  48.604 -23.182  0.50 23.01           C
ATOM   6805  CG   TRP a 417     -20.434  47.447 -22.425  0.50 23.11           C
ATOM   6806  CD1  TRP a 417     -19.822  46.662 -21.492  0.50 23.79           C
ATOM   6807  NE1  TRP a 417     -20.693  45.712 -21.024  0.50 25.15           N
ATOM   6808  CE2  TRP a 417     -21.902  45.867 -21.649  0.50 22.72           C
ATOM   6809  CD2  TRP a 417     -21.774  46.947 -22.547  0.50 23.54           C
ATOM   6810  CE3  TRP a 417     -22.880  47.316 -23.320  0.50 21.91           C
ATOM   6811  CZ3  TRP a 417     -24.052  46.600 -23.177  0.50 20.90           C
ATOM   6812  CH2  TRP a 417     -24.155  45.530 -22.278  0.50 21.26           C
ATOM   6813  CZ2  TRP a 417     -23.090  45.139 -21.510  0.50 23.39           C
ATOM   6814  C    TRP a 417     -20.183  50.105 -21.201  0.50 23.95           C
ATOM   6815  O    TRP a 417     -21.166  50.024 -20.473  0.50 24.85           O
ATOM   6816  N    GLN a 418     -18.961  50.282 -20.703  0.50 26.31           N
ATOM   6817  CA   GLN a 418     -18.821  50.306 -19.254  0.50 25.53           C
ATOM   6818  CB   GLN a 418     -17.415  49.820 -18.798  0.50 29.39           C
ATOM   6819  CG   GLN a 418     -17.406  48.636 -17.793  0.50 30.01           C
ATOM   6820  CD   GLN a 418     -16.943  47.277 -18.360  0.50 28.22           C
ATOM   6821  OE1  GLN a 418     -16.154  47.217 -19.299  0.50 29.74           O
ATOM   6822  NE2  GLN a 418     -17.396  46.181 -17.745  0.50 26.82           N
ATOM   6823  C    GLN a 418     -19.281  51.690 -18.706  0.50 24.90           C
ATOM   6824  O    GLN a 418     -19.599  51.822 -17.524  0.50 24.96           O
ATOM   6825  N    GLN a 419     -19.393  52.703 -19.573  0.50 24.19           N
ATOM   6826  CA   GLN a 419     -20.069  53.966 -19.171  0.50 23.65           C
ATOM   6827  CB   GLN a 419     -19.749  55.116 -20.123  0.50 25.85           C
ATOM   6828  CG   GLN a 419     -18.362  55.701 -19.913  0.50 26.96           C
ATOM   6829  CD   GLN a 419     -18.079  56.855 -20.853  0.50 30.16           C
ATOM   6830  OE1  GLN a 419     -18.212  56.728 -22.071  0.50 29.12           O
ATOM   6831  NE2  GLN a 419     -17.676  57.990 -20.289  0.50 33.29           N
ATOM   6832  C    GLN a 419     -21.596  53.860 -18.996  0.50 22.11           C
ATOM   6833  O    GLN a 419     -22.246  54.815 -18.585  0.50 21.09           O
ATOM   6834  N    GLY a 420     -22.165  52.710 -19.337  0.50 21.36           N
```

Figure 27 (Continued)

```
ATOM   6835  CA   GLY a 420     -23.568  52.447 -19.026  0.50 21.48           C
ATOM   6836  C    GLY a 420     -24.565  52.824 -20.116  0.50 21.60           C
ATOM   6837  O    GLY a 420     -25.764  52.879 -19.869  0.50 20.97           O
ATOM   6838  N    ASN a 421     -24.091  53.111 -21.318  0.50 22.15           N
ATOM   6839  CA   ASN a 421     -25.030  53.415 -22.395  0.50 20.58           C
ATOM   6840  CB   ASN a 421     -24.305  53.948 -23.622  0.50 23.00           C
ATOM   6841  CG   ASN a 421     -23.242  54.973 -23.264  0.50 25.32           C
ATOM   6842  OD1  ASN a 421     -23.010  55.273 -22.079  0.50 26.96           O
ATOM   6843  ND2  ASN a 421     -22.585  55.512 -24.277  0.50 24.19           N
ATOM   6844  C    ASN a 421     -25.876  52.186 -22.739  0.50 20.38           C
ATOM   6845  O    ASN a 421     -25.388  51.050 -22.688  0.50 19.62           O
ATOM   6846  N    VAL a 422     -27.156  52.421 -23.029  0.50 18.60           N
ATOM   6847  CA   VAL a 422     -28.095  51.343 -23.332  0.50 18.33           C
ATOM   6848  CB   VAL a 422     -29.497  51.637 -22.776  0.50 19.16           C
ATOM   6849  CG1  VAL a 422     -30.507  50.605 -23.282  0.50 19.66           C
ATOM   6850  CG2  VAL a 422     -29.464  51.694 -21.247  0.50 20.25           C
ATOM   6851  C    VAL a 422     -28.186  51.307 -24.838  0.50 17.57           C
ATOM   6852  O    VAL a 422     -28.450  52.329 -25.464  0.50 16.44           O
ATOM   6853  N    PHE a 423     -27.984  50.119 -25.410  0.50 16.85           N
ATOM   6854  CA   PHE a 423     -28.004  49.947 -26.866  0.50 16.65           C
ATOM   6855  CB   PHE a 423     -26.680  49.303 -27.344  0.50 17.71           C
ATOM   6856  CG   PHE a 423     -25.482  50.216 -27.170  0.50 16.90           C
ATOM   6857  CD1  PHE a 423     -24.772  50.235 -25.977  0.50 18.41           C
ATOM   6858  CE1  PHE a 423     -23.705  51.101 -25.807  0.50 17.10           C
ATOM   6859  CZ   PHE a 423     -23.335  51.954 -26.832  0.50 17.63           C
ATOM   6860  CE2  PHE a 423     -24.038  51.959 -28.021  0.50 17.68           C
ATOM   6861  CD2  PHE a 423     -25.114  51.096 -28.186  0.50 18.02           C
ATOM   6862  C    PHE a 423     -29.211  49.075 -27.200  0.50 16.31           C
ATOM   6863  O    PHE a 423     -29.543  48.172 -26.441  0.50 15.86           O
ATOM   6864  N    SER a 424     -29.869  49.369 -28.321  0.50 14.80           N
ATOM   6865  CA   SER a 424     -31.147  48.723 -28.646  0.50 14.63           C
ATOM   6866  CB   SER a 424     -32.302  49.743 -28.581  0.50 14.97           C
ATOM   6867  OG   SER a 424     -32.585  50.071 -27.238  0.50 15.85           O
ATOM   6868  C    SER a 424     -31.096  48.138 -30.044  0.50 13.63           C
ATOM   6869  O    SER a 424     -30.586  48.760 -30.977  0.50 14.48           O
ATOM   6870  N    CYS a 425     -31.612  46.923 -30.163  0.50 13.39           N
ATOM   6871  CA   CYS a 425     -31.766  46.250 -31.449  0.50 13.87           C
ATOM   6872  CB   CYS a 425     -31.262  44.808 -31.311  0.50 14.58           C
ATOM   6873  SG   CYS a 425     -31.462  43.834 -32.795  0.50 16.53           S
ATOM   6874  C    CYS a 425     -33.254  46.278 -31.789  0.50 13.66           C
ATOM   6875  O    CYS a 425     -34.080  45.773 -31.018  0.50 14.99           O
ATOM   6876  N    SER a 426     -33.592  46.923 -32.901  0.50 14.06           N
ATOM   6877  CA   SER a 426     -34.974  47.027 -33.391  0.50 13.17           C
ATOM   6878  CB   SER a 426     -35.292  48.434 -33.932  0.50 13.57           C
ATOM   6879  OG   SER a 426     -35.630  49.365 -32.906  0.50 14.44           O
ATOM   6880  C    SER a 426     -35.100  46.025 -34.536  0.50 12.59           C
ATOM   6881  O    SER a 426     -34.181  45.865 -35.334  0.50 12.70           O
ATOM   6882  N    VAL a 427     -36.249  45.377 -34.620  0.50 11.93           N
ATOM   6883  CA   VAL a 427     -36.477  44.318 -35.604  0.50 11.91           C
ATOM   6884  CB   VAL a 427     -36.530  42.943 -34.912  0.50 11.79           C
ATOM   6885  CG1  VAL a 427     -36.923  41.858 -35.910  0.50 12.09           C
ATOM   6886  CG2  VAL a 427     -35.177  42.650 -34.236  0.50 12.68           C
ATOM   6887  C    VAL a 427     -37.815  44.599 -36.260  0.50 11.33           C
ATOM   6888  O    VAL a 427     -38.821  44.718 -35.561  0.50 12.36           O
ATOM   6889  N    MET a 428     -37.826  44.663 -37.589  0.50 12.42           N
ATOM   6890  CA   MET a 428     -39.068  44.894 -38.337  0.50 12.38           C
ATOM   6891  CB   MET a 428     -38.917  46.187 -39.175  0.50 13.85           C
ATOM   6892  CG   MET a 428     -38.854  47.418 -38.279  0.50 14.89           C
ATOM   6893  SD   MET a 428     -37.928  48.785 -39.055  0.50 16.97           S
ATOM   6894  CE   MET a 428     -36.283  48.330 -38.503  0.50 15.67           C
ATOM   6895  C    MET a 428     -39.347  43.692 -39.205  0.50 11.62           C
ATOM   6896  O    MET a 428     -38.481  43.267 -39.972  0.50 10.19           O
ATOM   6897  N    HIS a 429     -40.547  43.124 -39.056  0.50 11.24           N
ATOM   6898  CA   HIS a 429     -40.944  41.910 -39.775  0.50 12.67           C
```

Figure 27 (Continued)

```
ATOM   6899  CB   HIS a 429    -40.385  40.657 -39.054  0.50 12.50           C
ATOM   6900  CG   HIS a 429    -40.578  39.381 -39.822  0.50 12.67           C
ATOM   6901  ND1  HIS a 429    -41.745  38.650 -39.746  0.50 12.72           N
ATOM   6902  CE1  HIS a 429    -41.662  37.604 -40.545  0.50 12.64           C
ATOM   6903  NE2  HIS a 429    -40.469  37.617 -41.123  0.50 13.12           N
ATOM   6904  CD2  HIS a 429    -39.784  38.738 -40.710  0.50 13.21           C
ATOM   6905  C    HIS a 429    -42.462  41.855 -39.838  0.50 12.72           C
ATOM   6906  O    HIS a 429    -43.138  42.282 -38.903  0.50 13.60           O
ATOM   6907  N    GLU a 430    -42.997  41.263 -40.903  0.50 13.67           N
ATOM   6908  CA   GLU a 430    -44.440  41.225 -41.106  0.50 14.14           C
ATOM   6909  CB   GLU a 430    -44.756  40.545 -42.446  0.50 15.91           C
ATOM   6910  CG   GLU a 430    -44.333  39.088 -42.526  0.50 16.68           C
ATOM   6911  CD   GLU a 430    -44.771  38.453 -43.835  0.50 19.31           C
ATOM   6912  OE1  GLU a 430    -44.201  38.804 -44.888  0.50 19.51           O
ATOM   6913  OE2  GLU a 430    -45.704  37.627 -43.808  0.50 19.92           O
ATOM   6914  C    GLU a 430    -45.159  40.505 -39.977  0.50 14.95           C
ATOM   6915  O    GLU a 430    -46.300  40.841 -39.655  0.50 13.68           O
ATOM   6916  N    ALA a 431    -44.487  39.532 -39.356  0.50 13.67           N
ATOM   6917  CA   ALA a 431    -45.169  38.696 -38.384  0.50 14.72           C
ATOM   6918  CB   ALA a 431    -44.694  37.248 -38.506  0.50 13.83           C
ATOM   6919  C    ALA a 431    -45.098  39.175 -36.949  0.50 14.58           C
ATOM   6920  O    ALA a 431    -45.642  38.525 -36.055  0.50 16.69           O
ATOM   6921  N    LEU a 432    -44.459  40.320 -36.728  0.50 13.85           N
ATOM   6922  CA   LEU a 432    -44.447  40.938 -35.422  0.50 13.69           C
ATOM   6923  CB   LEU a 432    -43.195  41.796 -35.283  0.50 13.49           C
ATOM   6924  CG   LEU a 432    -41.911  40.994 -35.057  0.50 13.69           C
ATOM   6925  CD1  LEU a 432    -40.675  41.885 -35.191  0.50 13.71           C
ATOM   6926  CD2  LEU a 432    -41.983  40.405 -33.642  0.50 14.63           C
ATOM   6927  C    LEU a 432    -45.658  41.840 -35.210  0.50 13.49           C
ATOM   6928  O    LEU a 432    -46.158  42.479 -36.159  0.50 14.00           O
ATOM   6929  N    HIS a 433    -46.070  41.966 -33.949  0.50 14.13           N
ATOM   6930  CA   HIS a 433    -47.039  43.004 -33.615  0.50 15.62           C
ATOM   6931  CB   HIS a 433    -47.358  43.019 -32.124  0.50 16.71           C
ATOM   6932  CG   HIS a 433    -48.381  44.050 -31.766  0.50 19.82           C
ATOM   6933  ND1  HIS a 433    -48.081  45.164 -31.018  0.50 21.85           N
ATOM   6934  CE1  HIS a 433    -49.168  45.907 -30.879  0.50 23.47           C
ATOM   6935  NE2  HIS a 433    -50.154  45.334 -31.544  0.50 20.93           N
ATOM   6936  CD2  HIS a 433    -49.688  44.168 -32.109  0.50 21.70           C
ATOM   6937  C    HIS a 433    -46.511  44.355 -34.039  0.50 15.71           C
ATOM   6938  O    HIS a 433    -45.345  44.649 -33.777  0.50 14.97           O
ATOM   6939  N    ASN a 434    -47.355  45.156 -34.706  0.50 15.82           N
ATOM   6940  CA   ASN a 434    -46.978  46.460 -35.258  0.50 15.65           C
ATOM   6941  CB   ASN a 434    -46.639  47.465 -34.147  0.50 17.50           C
ATOM   6942  CG   ASN a 434    -47.839  47.862 -33.325  0.50 18.88           C
ATOM   6943  OD1  ASN a 434    -48.977  47.824 -33.802  0.50 20.13           O
ATOM   6944  ND2  ASN a 434    -47.589  48.280 -32.083  0.50 20.00           N
ATOM   6945  C    ASN a 434    -45.783  46.403 -36.213  0.50 15.01           C
ATOM   6946  O    ASN a 434    -45.163  47.435 -36.493  0.50 14.53           O
ATOM   6947  N    HIS a 435    -45.429  45.189 -36.650  0.50 13.09           N
ATOM   6948  CA   HIS a 435    -44.275  44.941 -37.531  0.50 12.98           C
ATOM   6949  CB   HIS a 435    -44.463  45.584 -38.905  0.50 14.07           C
ATOM   6950  CG   HIS a 435    -45.768  45.224 -39.537  0.50 14.21           C
ATOM   6951  ND1  HIS a 435    -46.342  45.969 -40.542  0.50 15.33           N
ATOM   6952  CE1  HIS a 435    -47.495  45.416 -40.889  0.50 15.28           C
ATOM   6953  NE2  HIS a 435    -47.702  44.362 -40.124  0.50 13.58           N
ATOM   6954  CD2  HIS a 435    -46.648  44.232 -39.250  0.50 15.29           C
ATOM   6955  C    HIS a 435    -42.952  45.356 -36.920  0.50 12.44           C
ATOM   6956  O    HIS a 435    -41.964  45.591 -37.648  0.50 12.40           O
ATOM   6957  N    TYR a 436    -42.922  45.391 -35.592  0.50 12.95           N
ATOM   6958  CA   TYR a 436    -41.771  45.977 -34.891  0.50 12.72           C
ATOM   6959  CB   TYR a 436    -41.930  47.519 -34.853  0.50 13.29           C
ATOM   6960  CG   TYR a 436    -40.823  48.219 -34.112  0.50 13.60           C
ATOM   6961  CD1  TYR a 436    -40.889  48.396 -32.733  0.50 14.53           C
ATOM   6962  CE1  TYR a 436    -39.859  49.036 -32.047  0.50 14.60           C
```

Figure 27 (Continued)

```
ATOM   6963  CZ  TYR a 436     -38.751  49.486 -32.736  0.50 14.36           C
ATOM   6964  OH  TYR a 436     -37.705  50.115 -32.077  0.50 16.67           O
ATOM   6965  CE2 TYR a 436     -38.661  49.323 -34.105  0.50 14.65           C
ATOM   6966  CD2 TYR a 436     -39.698  48.699 -34.791  0.50 13.73           C
ATOM   6967  C   TYR a 436     -41.612  45.459 -33.478  0.50 12.04           C
ATOM   6968  O   TYR a 436     -42.596  45.369 -32.721  0.50 12.55           O
ATOM   6969  N   THR a 437     -40.382  45.119 -33.101  0.50 12.82           N
ATOM   6970  CA  THR a 437     -40.076  44.876 -31.694  0.50 13.33           C
ATOM   6971  CB  THR a 437     -40.351  43.407 -31.258  0.50 14.39           C
ATOM   6972  OG1 THR a 437     -40.538  43.355 -29.836  0.50 14.91           O
ATOM   6973  CG2 THR a 437     -39.191  42.554 -31.613  0.50 14.47           C
ATOM   6974  C   THR a 437     -38.640  45.339 -31.406  0.50 13.98           C
ATOM   6975  O   THR a 437     -37.828  45.472 -32.307  0.50 13.34           O
ATOM   6976  N   GLN a 438     -38.343  45.626 -30.149  0.50 14.10           N
ATOM   6977  CA  GLN a 438     -37.058  46.198 -29.788  0.50 14.82           C
ATOM   6978  CB  GLN a 438     -37.198  47.721 -29.585  0.50 14.91           C
ATOM   6979  CG  GLN a 438     -35.880  48.472 -29.462  0.50 15.51           C
ATOM   6980  CD  GLN a 438     -36.081  49.828 -28.826  0.50 16.60           C
ATOM   6981  OE1 GLN a 438     -36.714  49.938 -27.768  0.50 15.95           O
ATOM   6982  NE2 GLN a 438     -35.534  50.871 -29.452  0.50 15.98           N
ATOM   6983  C   GLN a 438     -36.619  45.550 -28.485  0.50 15.97           C
ATOM   6984  O   GLN a 438     -37.440  45.333 -27.581  0.50 16.89           O
ATOM   6985  N   LYS a 439     -35.350  45.181 -28.408  0.50 15.26           N
ATOM   6986  CA  LYS a 439     -34.780  44.704 -27.140  0.50 16.45           C
ATOM   6987  CB  LYS a 439     -34.441  43.212 -27.195  0.50 17.85           C
ATOM   6988  CG  LYS a 439     -35.593  42.297 -27.616  0.50 19.88           C
ATOM   6989  CD  LYS a 439     -36.711  42.261 -26.583  0.50 21.44           C
ATOM   6990  CE  LYS a 439     -37.619  41.050 -26.788  0.50 23.45           C
ATOM   6991  NZ  LYS a 439     -37.108  39.799 -26.137  0.50 24.81           N
ATOM   6992  C   LYS a 439     -33.516  45.507 -26.869  0.50 16.06           C
ATOM   6993  O   LYS a 439     -32.791  45.848 -27.799  0.50 16.15           O
ATOM   6994  N   SER a 440     -33.228  45.798 -25.600  0.50 15.80           N
ATOM   6995  CA  SER a 440     -32.094  46.672 -25.291  0.50 16.18           C
ATOM   6996  CB  SER a 440     -32.577  48.047 -24.778  0.50 16.34           C
ATOM   6997  OG  SER a 440     -33.169  48.784 -25.833  0.50 16.00           O
ATOM   6998  C   SER a 440     -31.136  46.032 -24.279  0.50 15.86           C
ATOM   6999  O   SER a 440     -31.504  45.094 -23.550  0.50 16.86           O
ATOM   7000  N   LEU a 441     -29.900  46.521 -24.250  0.50 16.97           N
ATOM   7001  CA  LEU a 441     -28.964  46.032 -23.251  0.50 17.65           C
ATOM   7002  CB  LEU a 441     -28.371  44.695 -23.659  0.50 19.51           C
ATOM   7003  CG  LEU a 441     -27.467  44.684 -24.874  0.50 20.11           C
ATOM   7004  CD1 LEU a 441     -28.196  45.160 -26.122  0.50 19.93           C
ATOM   7005  CD2 LEU a 441     -26.956  43.271 -25.084  0.50 21.85           C
ATOM   7006  C   LEU a 441     -27.884  46.989 -22.812  0.50 16.75           C
ATOM   7007  O   LEU a 441     -27.507  47.929 -23.527  0.50 15.76           O
ATOM   7008  N   SER a 442     -27.431  46.776 -21.584  0.50 18.07           N
ATOM   7009  CA  SER a 442     -26.417  47.638 -21.001  0.50 18.58           C
ATOM   7010  CB  SER a 442     -27.029  48.956 -20.505  0.50 19.48           C
ATOM   7011  OG  SER a 442     -27.942  48.706 -19.462  0.50 19.16           O
ATOM   7012  C   SER a 442     -25.824  46.892 -19.822  0.50 20.50           C
ATOM   7013  O   SER a 442     -26.358  45.863 -19.376  0.50 20.50           O
ATOM   7014  N   LEU a 443     -24.744  47.457 -19.298  0.50 23.32           N
ATOM   7015  CA  LEU a 443     -24.003  46.847 -18.202  0.50 25.62           C
ATOM   7016  CB  LEU a 443     -22.985  47.842 -17.655  0.50 24.38           C
ATOM   7017  CG  LEU a 443     -21.779  47.276 -16.894  0.50 27.28           C
ATOM   7018  CD1 LEU a 443     -20.517  47.296 -17.760  0.50 26.80           C
ATOM   7019  CD2 LEU a 443     -22.063  45.881 -16.362  0.50 27.29           C
ATOM   7020  C   LEU a 443     -24.915  46.407 -17.063  0.50 26.98           C
ATOM   7021  O   LEU a 443     -25.803  47.150 -16.631  0.50 27.60           O
ATOM   7022  N   SER a 444     -24.676  45.199 -16.572  0.50 30.75           N
ATOM   7023  CA  SER a 444     -25.295  44.743 -15.339  0.50 34.91           C
ATOM   7024  CB  SER a 444     -26.256  43.591 -15.634  0.50 37.17           C
ATOM   7025  OG  SER a 444     -25.643  42.624 -16.470  0.50 37.76           O
ATOM   7026  C   SER a 444     -24.220  44.298 -14.337  0.50 35.70           C
```

Figure 27 (Continued)

```
ATOM    7027  O    SER a 444     -23.623  43.236 -14.496  0.50 35.38           O
ATOM    7028  N    PRO a 445     -23.970  45.115 -13.299  0.50 37.50           N
ATOM    7029  CA   PRO a 445     -22.999  44.710 -12.286  0.50 37.81           C
ATOM    7030  CB   PRO a 445     -22.932  45.926 -11.359  0.50 36.53           C
ATOM    7031  CG   PRO a 445     -24.267  46.574 -11.502  0.50 37.91           C
ATOM    7032  CD   PRO a 445     -24.667  46.361 -12.937  0.50 36.51           C
ATOM    7033  C    PRO a 445     -23.525  43.501 -11.529  0.50 38.20           C
ATOM    7034  O    PRO a 445     -24.737  43.381 -11.347  0.50 40.33           O
HETATM  7035  C1   NAG a 500     -26.125  50.918 -71.518  0.50 29.77           C
HETATM  7036  C2   NAG a 500     -26.054  49.399 -71.460  0.50 31.36           C
HETATM  7037  N2   NAG a 500     -26.384  48.772 -72.730  0.50 32.38           N
HETATM  7038  C7   NAG a 500     -25.453  48.183 -73.485  0.50 37.35           C
HETATM  7039  O7   NAG a 500     -24.255  48.152 -73.184  0.50 37.70           O
HETATM  7040  C8   NAG a 500     -25.932  47.553 -74.763  0.50 37.28           C
HETATM  7041  C3   NAG a 500     -27.052  48.854 -70.439  0.50 30.97           C
HETATM  7042  O3   NAG a 500     -26.840  47.467 -70.289  0.50 31.64           O
HETATM  7043  C4   NAG a 500     -26.972  49.582 -69.103  0.50 29.91           C
HETATM  7044  O4   NAG a 500     -28.053  49.153 -68.292  0.50 29.69           O
HETATM  7045  C5   NAG a 500     -27.068  51.082 -69.365  0.50 29.61           C
HETATM  7046  C6   NAG a 500     -27.062  51.921 -68.085  0.50 30.24           C
HETATM  7047  O6   NAG a 500     -25.831  51.803 -67.397  0.50 29.52           O
HETATM  7048  O5   NAG a 500     -26.006  51.478 -70.218  0.50 29.13           O
HETATM  7049  C1   FUC a 501     -25.140  52.568 -67.077  0.50 26.65           C
HETATM  7050  C2   FUC a 501     -24.057  52.357 -66.027  0.50 26.44           C
HETATM  7051  O2   FUC a 501     -24.564  51.526 -65.000  0.50 26.80           O
HETATM  7052  C3   FUC a 501     -22.827  51.699 -66.631  0.50 25.99           C
HETATM  7053  O3   FUC a 501     -21.779  51.691 -65.689  0.50 25.16           O
HETATM  7054  C4   FUC a 501     -22.352  52.429 -67.883  0.50 26.54           C
HETATM  7055  O4   FUC a 501     -21.720  53.635 -67.497  0.50 25.51           O
HETATM  7056  C5   FUC a 501     -23.527  52.664 -68.837  0.50 26.66           C
HETATM  7057  C6   FUC a 501     -23.110  53.531 -70.025  0.50 26.37           C
HETATM  7058  O5   FUC a 501     -24.612  53.285 -68.184  0.50 27.59           O
HETATM  7059  C1   NAG a 502     -27.725  48.107 -67.402  0.50 34.06           C
HETATM  7060  C2   NAG a 502     -28.529  48.292 -66.122  0.50 33.09           C
HETATM  7061  N2   NAG a 502     -28.171  49.528 -65.469  0.50 31.57           N
HETATM  7062  C7   NAG a 502     -29.025  50.503 -65.143  0.50 32.12           C
HETATM  7063  O7   NAG a 502     -28.648  51.533 -64.575  0.50 32.38           O
HETATM  7064  C8   NAG a 502     -30.468  50.317 -65.490  0.50 30.76           C
HETATM  7065  C3   NAG a 502     -28.204  47.155 -65.172  0.50 33.61           C
HETATM  7066  O3   NAG a 502     -28.994  47.309 -64.013  0.50 34.02           O
HETATM  7067  C4   NAG a 502     -28.465  45.818 -65.856  0.50 33.33           C
HETATM  7068  O4   NAG a 502     -27.929  44.782 -65.064  0.50 34.61           O
HETATM  7069  C5   NAG a 502     -27.800  45.765 -67.235  0.50 35.02           C
HETATM  7070  C6   NAG a 502     -28.240  44.511 -67.978  0.50 34.81           C
HETATM  7071  O6   NAG a 502     -27.559  44.444 -69.208  0.50 38.35           O
HETATM  7072  O5   NAG a 502     -28.117  46.901 -68.018  0.50 34.45           O
HETATM  7073  C1   BMA a 503     -29.242  43.906 -64.459  0.50 24.82           C
HETATM  7074  O5   BMA a 503     -28.929  44.489 -63.201  0.50 26.27           O
HETATM  7075  C5   BMA a 503     -29.815  43.992 -62.184  0.50 26.49           C
HETATM  7076  C6   BMA a 503     -29.570  44.724 -60.872  0.50 26.64           C
HETATM  7077  O6   BMA a 503     -29.569  46.141 -61.092  0.50 26.83           O
HETATM  7078  C4   BMA a 503     -29.592  42.497 -61.968  0.50 27.34           C
HETATM  7079  O4   BMA a 503     -30.554  41.996 -61.026  0.50 28.09           O
HETATM  7080  C3   BMA a 503     -29.757  41.756 -63.277  0.50 25.78           C
HETATM  7081  O3   BMA a 503     -29.397  40.380 -63.086  0.50 26.68           O
HETATM  7082  C2   BMA a 503     -28.909  42.427 -64.359  0.50 25.80           C
HETATM  7083  O2   BMA a 503     -27.514  42.343 -64.057  0.50 22.99           O
HETATM  7084  C1   MAN a 504     -29.523  46.960 -59.969  0.50 29.66           C
HETATM  7085  C2   MAN a 504     -30.016  48.379 -60.175  0.50 29.77           C
HETATM  7086  O2   MAN a 504     -30.002  49.022 -58.928  0.50 29.61           O
HETATM  7087  C3   MAN a 504     -28.999  49.129 -61.012  0.50 31.42           C
HETATM  7088  O3   MAN a 504     -29.431  50.460 -61.158  0.50 31.29           O
HETATM  7089  C4   MAN a 504     -27.684  49.119 -60.246  0.50 30.99           C
HETATM  7090  O4   MAN a 504     -26.668  49.657 -61.061  0.50 32.90           O
```

Figure 27 (Continued)

```
HETATM 7091  C5  MAN a 504     -27.294  47.707 -59.796  0.50 30.73           C
HETATM 7092  C6  MAN a 504     -26.117  47.752 -58.821  0.50 29.81           C
HETATM 7093  O6  MAN a 504     -25.586  46.450 -58.717  0.50 29.33           O
HETATM 7094  O5  MAN a 504     -28.373  47.051 -59.153  0.50 30.81           O
HETATM 7095  C1  NAG a 505     -31.401  48.752 -58.318  0.50 22.59           C
HETATM 7096  C2  NAG a 505     -31.130  48.972 -56.834  0.50 22.80           C
HETATM 7097  N2  NAG a 505     -30.268  47.903 -56.353  0.50 24.91           N
HETATM 7098  C7  NAG a 505     -29.024  48.154 -55.943  0.50 29.01           C
HETATM 7099  O7  NAG a 505     -28.535  49.279 -55.964  0.50 28.46           O
HETATM 7100  C8  NAG a 505     -28.201  46.987 -55.466  0.50 31.47           C
HETATM 7101  C3  NAG a 505     -32.459  48.948 -56.083  0.50 21.61           C
HETATM 7102  O3  NAG a 505     -32.277  49.253 -54.702  0.50 23.11           O
HETATM 7103  C4  NAG a 505     -33.477  49.887 -56.719  0.50 20.90           C
HETATM 7104  O4  NAG a 505     -34.737  49.640 -56.141  0.50 20.07           O
HETATM 7105  C5  NAG a 505     -33.572  49.604 -58.213  0.50 21.56           C
HETATM 7106  C6  NAG a 505     -34.589  50.495 -58.922  0.50 22.71           C
HETATM 7107  O6  NAG a 505     -34.163  51.838 -58.849  0.50 21.62           O
HETATM 7108  O5  NAG a 505     -32.281  49.764 -58.754  0.50 22.10           O
HETATM 7109  C1  GAL a 506     -35.626  50.463 -55.849  0.50 26.11           C
HETATM 7110  C2  GAL a 506     -36.927  49.957 -55.212  0.50 25.47           C
HETATM 7111  O2  GAL a 506     -37.849  49.377 -56.143  0.50 22.25           O
HETATM 7112  C3  GAL a 506     -37.670  51.114 -54.572  0.50 26.27           C
HETATM 7113  O3  GAL a 506     -38.752  50.600 -53.851  0.50 26.21           O
HETATM 7114  C4  GAL a 506     -36.773  51.899 -53.644  0.50 28.95           C
HETATM 7115  O4  GAL a 506     -36.292  51.040 -52.634  0.50 28.92           O
HETATM 7116  C5  GAL a 506     -35.594  52.415 -54.466  0.50 27.77           C
HETATM 7117  C6  GAL a 506     -34.737  53.336 -53.596  0.50 29.35           C
HETATM 7118  O6  GAL a 506     -33.519  53.620 -54.243  0.50 29.97           O
HETATM 7119  O5  GAL a 506     -34.855  51.314 -54.984  0.50 26.43           O
HETATM 7120  C1  MAN a 507     -30.620  39.734 -63.462  0.50 41.87           C
HETATM 7121  C2  MAN a 507     -30.412  38.409 -62.742  0.50 43.26           C
HETATM 7122  O2  MAN a 507     -31.562  37.616 -62.908  0.50 46.23           O
HETATM 7123  C3  MAN a 507     -29.243  37.645 -63.333  0.50 43.58           C
HETATM 7124  O3  MAN a 507     -29.211  36.369 -62.742  0.50 45.86           O
HETATM 7125  C4  MAN a 507     -29.433  37.515 -64.838  0.50 43.07           C
HETATM 7126  O4  MAN a 507     -28.267  36.966 -65.414  0.50 43.87           O
HETATM 7127  C5  MAN a 507     -29.725  38.885 -65.456  0.50 42.27           C
HETATM 7128  C6  MAN a 507     -30.007  38.779 -66.949  0.50 42.86           C
HETATM 7129  O6  MAN a 507     -29.631  39.990 -67.568  0.50 40.40           O
HETATM 7130  O5  MAN a 507     -30.841  39.486 -64.833  0.50 41.04           O
HETATM 7131  C1  NAG a 508     -32.538  36.860 -62.558  0.50118.54           C
HETATM 7132  C2  NAG a 508     -32.362  37.146 -61.072  0.50117.38           C
HETATM 7133  N2  NAG a 508     -31.197  36.455 -60.554  0.50116.51           N
HETATM 7134  C7  NAG a 508     -30.744  36.687 -59.325  0.50114.72           C
HETATM 7135  O7  NAG a 508     -29.759  36.119 -58.861  0.50115.46           O
HETATM 7136  C8  NAG a 508     -31.500  37.693 -58.508  0.50112.64           C
HETATM 7137  C3  NAG a 508     -33.612  36.749 -60.300  0.50116.92           C
HETATM 7138  O3  NAG a 508     -33.504  37.185 -58.963  0.50115.20           O
HETATM 7139  C4  NAG a 508     -34.839  37.378 -60.947  0.50116.66           C
HETATM 7140  O4  NAG a 508     -36.004  36.851 -60.354  0.50115.18           O
HETATM 7141  C5  NAG a 508     -34.860  37.109 -62.448  0.50117.88           C
HETATM 7142  C6  NAG a 508     -36.041  37.808 -63.108  0.50119.61           C
HETATM 7143  O6  NAG a 508     -36.711  36.897 -63.950  0.50120.08           O
HETATM 7144  O5  NAG a 508     -33.662  37.566 -63.036  0.50117.36           O
HETATM 7145  O2  EDO E   2     -17.966   7.657 -32.334  0.50 23.57           O
HETATM 7146  C2  EDO E   2     -17.778   6.377 -32.974  0.50 26.15           C
HETATM 7147  C1  EDO E   2     -18.118   5.209 -32.053  0.50 24.63           C
HETATM 7148  O1  EDO E   2     -17.987   5.637 -30.698  0.50 29.13           O
HETATM 7149  O2  EDO E   4     -38.223  55.268 -41.840  0.50 37.39           O
HETATM 7150  C2  EDO E   4     -39.525  55.357 -41.242  0.50 33.89           C
HETATM 7151  C1  EDO E   4     -39.503  56.422 -40.155  0.50 35.58           C
HETATM 7152  O1  EDO E   4     -38.147  56.659 -39.734  0.50 37.09           O
HETATM 7153  O2  EDO E   5     -17.869  28.377 -41.533  0.50 32.07           O
HETATM 7154  C2  EDO E   5     -17.337  27.047 -41.611  0.50 28.27           C
```

Figure 27 (Continued)

```
HETATM 7155  C1  EDO E   5     -18.084  26.186 -40.604  0.50 25.89           C
HETATM 7156  O1  EDO E   5     -17.316  25.045 -40.202  0.50 26.14           O
HETATM 7157  O2  EDO E   6     -31.549 -12.603 -20.439  0.50 30.44           O
HETATM 7158  C2  EDO E   6     -31.855 -13.540 -21.477  0.50 28.40           C
HETATM 7159  C1  EDO E   6     -33.242 -13.222 -22.034  0.50 31.20           C
HETATM 7160  O1  EDO E   6     -34.190 -14.203 -21.597  0.50 31.29           O
HETATM 7161  O2  EDO E   7     -15.035   4.512 -26.544  0.50 35.28           O
HETATM 7162  C2  EDO E   7     -14.857   3.768 -27.767  0.50 29.18           C
HETATM 7163  C1  EDO E   7     -15.629   2.448 -27.664  0.50 31.06           C
HETATM 7164  O1  EDO E   7     -15.998   1.999 -28.974  0.50 27.35           O
HETATM 7165  O2  EDO E   8     -14.739 -13.336 -41.142  0.50 54.79           O
HETATM 7166  C2  EDO E   8     -14.331 -13.048 -39.795  0.50 55.26           C
HETATM 7167  C1  EDO E   8     -14.655 -11.600 -39.443  0.50 55.51           C
HETATM 7168  O1  EDO E   8     -15.349 -10.953 -40.521  0.50 55.61           O
HETATM 7169  O2  EDO E   9     -42.267 -23.021   2.226  0.50 37.75           O
HETATM 7170  C2  EDO E   9     -42.662 -23.550   0.956  0.50 34.28           C
HETATM 7171  C1  EDO E   9     -42.199 -24.993   0.819  0.50 34.71           C
HETATM 7172  O1  EDO E   9     -43.284 -25.785   0.302  0.50 35.55           O
HETATM 7173  I   IOD I   1      -5.449  16.287 -35.889  0.50 18.26           I
HETATM 7174  I   IOD I   2     -14.904  18.645 -43.396  0.50 23.27           I
HETATM 7119  O   HOH S   1     -13.913   9.082 -28.579  0.50 19.81           O
HETATM 7120  O   HOH S   2     -10.293   5.502 -23.058  0.50 21.27           O
HETATM 7121  O   HOH S   3     -46.480 -17.795 -37.755  0.50 24.03           O
HETATM 7122  O   HOH S   4      -5.970  -8.558 -32.066  0.50 15.37           O
HETATM 7123  O   HOH S   5     -35.927 -21.809 -38.214  0.50 21.12           O
HETATM 7124  O   HOH S   6     -17.248  15.621 -47.372  0.50 22.91           O
HETATM 7125  O   HOH S   7     -14.452  -7.820 -38.334  0.50 15.32           O
HETATM 7126  O   HOH S   8     -29.898 -11.376 -35.575  0.50 13.53           O
HETATM 7127  O   HOH S   9     -29.456   7.037 -38.415  0.50 17.52           O
HETATM 7128  O   HOH S  10     -30.085 -18.202 -40.245  0.50 14.34           O
HETATM 7129  O   HOH S  11       1.282  10.848 -20.319  0.50 21.84           O
HETATM 7130  O   HOH S  12     -46.281 -24.704 -39.700  0.50 20.26           O
HETATM 7131  O   HOH S  13     -40.198  -1.107 -25.077  0.50 26.57           O
HETATM 7132  O   HOH S  14     -16.042  11.526 -32.165  0.50 20.33           O
HETATM 7133  O   HOH S  15     -33.674 -13.525 -31.596  0.50 20.31           O
HETATM 7134  O   HOH S  16     -38.234 -23.165 -37.083  0.50 17.03           O
HETATM 7135  O   HOH S  17     -42.531 -11.164 -28.887  0.50 21.49           O
HETATM 7136  O   HOH S  18     -19.767 -12.830 -38.259  0.50 16.78           O
HETATM 7137  O   HOH S  19     -17.589  -9.357 -43.018  0.50 18.41           O
HETATM 7138  O   HOH S  20     -35.272   3.464 -36.819  0.50 21.45           O
HETATM 7139  O   HOH S  21      -2.307   3.436 -21.526  0.50 15.76           O
HETATM 7140  O   HOH S  22      -4.842   8.762 -43.300  0.50 19.45           O
HETATM 7141  O   HOH S  23      -6.968   3.144 -29.074  0.50 20.01           O
HETATM 7142  O   HOH S  24     -20.506 -11.182 -40.376  0.50 20.34           O
HETATM 7143  O   HOH S  25     -47.080 -10.197 -22.799  0.50 14.65           O
HETATM 7144  O   HOH S  26     -11.280  -3.771 -26.845  0.50 18.81           O
HETATM 7145  O   HOH S  27     -27.770 -21.491  -6.896  0.50 20.20           O
HETATM 7146  O   HOH S  28     -24.653 -13.693 -56.003  0.50 20.22           O
HETATM 7147  O   HOH S  29     -10.253  14.099 -44.679  0.50 11.60           O
HETATM 7148  O   HOH S  30     -54.401  -8.948 -23.527  0.50 22.43           O
HETATM 7149  O   HOH S  31     -49.998  -1.368 -33.683  0.50 22.81           O
HETATM 7151  O   HOH S  33     -14.717  13.713 -38.730  0.50 17.93           O
HETATM 7152  O   HOH S  34     -32.439   5.793 -41.934  0.50 13.57           O
HETATM 7153  O   HOH S  35      -2.219  10.272 -31.421  0.50 19.54           O
HETATM 7154  O   HOH S  36     -20.105  14.418 -37.632  0.50 16.88           O
HETATM 7155  O   HOH S  37     -41.953  -8.692 -31.768  0.50 16.81           O
HETATM 7156  O   HOH S  38      -8.369   3.298 -31.341  0.50 15.46           O
HETATM 7157  O   HOH S  39     -20.554   7.763 -34.279  0.50 17.16           O
HETATM 7158  O   HOH S  40     -35.098 -11.871  -5.740  0.50 23.82           O
HETATM 7159  O   HOH S  41     -50.291 -18.231 -21.925  0.50 20.87           O
HETATM 7160  O   HOH S  42     -25.908  12.446 -53.460  0.50 19.63           O
HETATM 7161  O   HOH S  43     -35.678 -21.247 -29.028  0.50 13.44           O
HETATM 7162  O   HOH S  44      -8.971   1.908 -23.855  0.50 24.04           O
HETATM 7163  O   HOH S  45     -17.618  17.843 -45.263  0.50 14.72           O
```

Figure 27 (Continued)

```
HETATM 7164  O   HOH S  46      -7.291   5.347 -27.789  0.50 21.37           O
HETATM 7165  O   HOH S  47     -50.074  -6.207 -26.660  0.50 22.08           O
HETATM 7166  O   HOH S  48     -52.063   0.485 -33.319  0.50 19.72           O
HETATM 7167  O   HOH S  49     -26.526  -0.255 -50.900  0.50 24.17           O
HETATM 7168  O   HOH S  50     -15.270   6.913 -28.700  0.50 18.52           O
HETATM 7169  O   HOH S  51     -36.341  14.294 -54.364  0.50 17.89           O
HETATM 7170  O   HOH S  52     -23.544  -1.482 -51.244  0.50 20.73           O
HETATM 7171  O   HOH S  53     -30.131   8.849 -36.240  0.50 27.21           O
HETATM 7172  O   HOH S  54       1.679  14.047  -8.061  0.50 21.86           O
HETATM 7173  O   HOH S  55     -11.917  -5.670 -45.100  0.50 31.49           O
HETATM 7174  O   HOH S  56      -4.774   3.142 -42.767  0.50 23.84           O
HETATM 7175  O   HOH S  57      -4.638  -0.353 -15.359  0.50 22.94           O
HETATM 7176  O   HOH S  58     -41.122 -10.601 -26.464  0.50 19.81           O
HETATM 7177  O   HOH S  59       1.608   4.770 -12.404  0.50 18.83           O
HETATM 7178  O   HOH S  60     -16.967  19.323 -40.902  0.50 22.36           O
HETATM 7179  O   HOH S  61     -25.000  25.575 -40.817  0.50 19.87           O
HETATM 7180  O   HOH S  62     -31.875 -19.891 -39.666  0.50 19.95           O
HETATM 7181  O   HOH S  63     -10.496   1.223 -45.273  0.50 23.76           O
HETATM 7182  O   HOH S  65     -33.909  -3.305 -50.061  0.50 21.34           O
HETATM 7183  O   HOH S  66     -12.975  -9.460 -39.453  0.50 25.15           O
HETATM 7184  O   HOH S  67     -14.308  -8.311 -46.297  0.50 24.96           O
HETATM 7185  O   HOH S  69     -19.068  16.693 -49.105  0.50 15.65           O
HETATM 7186  O   HOH S  70     -26.396 -15.376  -4.804  0.50 57.82           O
HETATM 7187  O   HOH S  71     -38.944  -1.841 -26.842  0.50 23.62           O
HETATM 7188  O   HOH S  72     -37.711   3.145 -44.816  0.50 25.93           O
HETATM 7189  O   HOH S  73     -42.441  -7.135 -17.596  0.50 24.90           O
HETATM 7190  O   HOH S  74       4.917   1.944 -22.771  0.50 18.74           O
HETATM 7191  O   HOH S  75      -7.209  20.442 -27.360  0.50 37.55           O
HETATM 7192  O   HOH S  76     -16.308   2.101 -49.840  0.50 14.53           O
HETATM 7193  O   HOH S  77      -4.136  21.711 -30.063  0.50 24.64           O
HETATM 7194  O   HOH S  78     -54.399  -9.111 -19.974  0.50 27.00           O
HETATM 7195  O   HOH S  79      -1.208  17.679 -16.203  0.50 22.67           O
HETATM 7196  O   HOH S  80     -22.907 -18.759 -43.879  0.50 23.91           O
HETATM 7197  O   HOH S  81     -19.165  -3.968 -48.026  0.50 17.62           O
HETATM 7198  O   HOH S  82      -5.457   5.949 -43.312  0.50 29.19           O
HETATM 7199  O   HOH S  83      -8.716  -7.210 -39.157  0.50 21.90           O
HETATM 7200  O   HOH S  84     -31.446  15.759 -44.021  0.50 26.65           O
HETATM 7201  O   HOH S  85     -28.362 -20.332 -18.352  0.50 28.56           O
HETATM 7202  O   HOH S  86       5.998  15.756 -13.566  0.50 24.19           O
HETATM 7203  O   HOH S  87      -8.874   4.592 -25.143  0.50 22.01           O
HETATM 7204  O   HOH S  88     -54.767 -14.100 -26.310  0.50 20.79           O
HETATM 7205  O   HOH S  89     -24.742 -17.324 -36.207  0.50 19.49           O
HETATM 7206  O   HOH S  90      -7.435   0.829 -27.275  0.50 22.93           O
HETATM 7207  O   HOH S  91      -7.974   0.515 -43.868  0.50 23.26           O
HETATM 7208  O   HOH S  92       1.298  14.513 -27.550  0.50 25.25           O
HETATM 7209  O   HOH S  93       1.247  12.749 -18.155  0.50 37.85           O
HETATM 7210  O   HOH S  94       0.460   6.993 -37.878  0.50 23.01           O
HETATM 7211  O   HOH S  95     -35.417 -10.636 -10.338  0.50 28.23           O
HETATM 7212  O   HOH S  96     -44.411 -26.608 -31.171  0.50 23.87           O
HETATM 7213  O   HOH S  97     -29.392 -18.881 -55.561  0.50 28.61           O
HETATM 7214  O   HOH S  98      -0.902  15.857 -24.149  0.50 29.55           O
HETATM 7215  O   HOH S  99     -23.135 -11.186 -32.380  0.50 33.61           O
HETATM 7216  O   HOH S 100       0.330   5.355 -34.921  0.50 25.45           O
HETATM 7217  O   HOH S 101     -26.628 -24.522 -43.346  0.50 29.97           O
HETATM 7218  O   HOH S 102      -4.858  -2.704 -27.516  0.50 25.22           O
HETATM 7219  O   HOH S 103      -7.272  -4.572 -21.279  0.50 24.44           O
HETATM 7220  O   HOH S 104     -25.385   2.926 -29.979  0.50 22.15           O
HETATM 7221  O   HOH S 106      -3.146   3.000   0.176  0.50 32.73           O
HETATM 7222  O   HOH S 107     -13.772  10.687 -48.364  0.50 23.44           O
HETATM 7223  O   HOH S 108     -19.653 -18.322 -48.035  0.50 29.97           O
HETATM 7224  O   HOH S 109     -39.163  -2.556 -46.291  0.50 32.82           O
HETATM 7225  O   HOH S 110     -46.844 -17.094 -39.422  0.50 25.56           O
HETATM 7226  O   HOH S 111     -21.068  17.633 -52.248  0.50 23.41           O
HETATM 7227  O   HOH S 112      -4.734  19.062 -16.416  0.50 20.84           O
```

Figure 27 (Continued)

```
HETATM 7228  O    HOH S 113     -10.477  17.072 -23.494  0.50 31.99           O
HETATM 7229  O    HOH S 114     -17.399  22.602 -40.046  0.50 21.32           O
HETATM 7230  O    HOH S 116     -11.457  14.642 -47.717  0.50 23.17           O
HETATM 7231  O    HOH S 117     -30.895 -16.982 -13.105  0.50 27.56           O
HETATM 7232  O    HOH S 118     -49.981 -15.339 -32.238  0.50 34.94           O
HETATM 7233  O    HOH S 119     -12.574  20.125  -7.237  0.50 23.82           O
HETATM 7234  O    HOH S 120     -44.735 -13.067 -44.970  0.50 18.88           O
HETATM 7235  O    HOH S 121     -47.898 -22.503 -27.226  0.50 18.90           O
HETATM 7236  O    HOH S 122       6.999   3.623 -18.376  0.50 34.48           O
HETATM 7237  O    HOH S 123     -15.933 -16.232 -41.354  0.50 32.60           O
HETATM 7238  O    HOH S 124     -11.430  16.049 -17.130  0.50 19.40           O
HETATM 7239  O    HOH S 125     -19.202  10.542 -33.085  0.50 17.36           O
HETATM 7240  O    HOH S 126     -24.303  21.450   4.190  0.50 21.34           O
HETATM 7241  O    HOH S 127     -24.592  -8.373 -30.978  0.50 25.21           O
HETATM 7242  O    HOH S 128     -19.559   0.317 -53.984  0.50 34.17           O
HETATM 7243  O    HOH S 129      -4.343  -5.071 -39.142  0.50 21.02           O
HETATM 7244  O    HOH S 130      -2.473  10.709  -1.834  0.50 24.34           O
HETATM 7245  O    HOH S 131      -8.958  15.451   5.172  0.50 21.55           O
HETATM 7246  O    HOH S 132     -40.818  -8.595 -24.467  0.50 32.09           O
HETATM 7247  O    HOH S 133     -24.789  18.687 -54.903  0.50 25.73           O
HETATM 7248  O    HOH S 134       4.898   8.839  -3.630  0.50 31.14           O
HETATM 7249  O    HOH S 135      -9.197  -4.990 -25.437  0.50 15.92           O
HETATM 7250  O    HOH S 136     -18.293   6.601  -0.427  0.50 28.40           O
HETATM 7251  O    HOH S 137     -30.749 -19.070 -15.161  0.50 42.80           O
HETATM 7252  O    HOH S 138     -54.028 -24.458 -15.523  0.50 31.03           O
HETATM 7253  O    HOH S 139     -52.311 -11.980 -30.311  0.50 29.00           O
HETATM 7254  O    HOH S 140     -41.489 -12.296 -47.356  0.50 25.72           O
HETATM 7255  O    HOH S 141     -35.882  -9.212  -5.765  0.50 38.28           O
HETATM 7256  O    HOH S 142     -35.061  -9.320 -29.400  0.50 21.84           O
HETATM 7257  O    HOH S 143     -45.015 -21.249  -4.505  0.50 27.73           O
HETATM 7258  O    HOH S 144     -34.999  17.003 -55.611  0.50 38.16           O
HETATM 7259  O    HOH S 145     -55.806 -15.264 -17.409  0.50 28.53           O
HETATM 7260  O    HOH S 146     -50.595 -11.059 -40.059  0.50 24.53           O
HETATM 7261  O    HOH S 147      -9.604  17.828 -26.533  0.50 19.00           O
HETATM 7262  O    HOH S 148      -1.421  -5.130 -24.525  0.50 17.64           O
HETATM 7263  O    HOH S 150      -6.957 -10.815 -30.802  0.50 24.49           O
HETATM 7264  O    HOH S 151     -45.365  -6.931 -43.635  0.50 28.82           O
HETATM 7265  O    HOH S 152      -2.372  18.536 -27.907  0.50 28.19           O
HETATM 7266  O    HOH S 153     -24.540   7.034 -31.951  0.50 24.69           O
HETATM 7267  O    HOH S 154     -45.950 -25.726 -19.361  0.50 44.67           O
HETATM 7268  O    HOH S 155     -39.711 -27.723  -6.504  0.50 34.81           O
HETATM 7269  O    HOH S 156      -0.339  -0.337 -26.270  0.50 20.97           O
HETATM 7270  O    HOH S 157     -20.992 -17.647 -44.976  0.50 27.49           O
HETATM 7271  O    HOH S 158     -11.860  -1.148 -24.978  0.50 35.76           O
HETATM 7272  O    HOH S 159       4.955   1.087 -19.903  0.50 22.24           O
HETATM 7273  O    HOH S 160      -8.953 -11.573 -28.904  0.50 28.09           O
HETATM 7274  O    HOH S 162      -6.629   6.692 -45.354  0.50 27.51           O
HETATM 7275  O    HOH S 163     -30.314  -4.579 -52.913  0.50 21.50           O
HETATM 7276  O    HOH S 164     -20.223   2.898 -52.059  0.50 27.57           O
HETATM 7277  O    HOH S 165     -14.124  -3.715 -25.442  0.50 26.62           O
HETATM 7278  O    HOH S 166     -28.389  20.507 -52.464  0.50 25.17           O
HETATM 7279  O    HOH S 167     -50.022 -22.557 -10.089  0.50 29.31           O
HETATM 7280  O    HOH S 168     -50.360 -21.070 -29.420  0.50 29.92           O
HETATM 7281  O    HOH S 169      -2.861  -0.765 -22.717  0.50 25.21           O
HETATM 7282  O    HOH S 170     -14.059   7.813 -50.917  0.50 18.36           O
HETATM 7283  O    HOH S 171     -39.593  -1.691 -48.692  0.50 31.37           O
HETATM 7284  O    HOH S 174       5.517   6.335 -24.371  0.50 18.99           O
HETATM 7285  O    HOH S 175     -37.129   5.157 -38.939  0.50 26.93           O
HETATM 7286  O    HOH S 176      -1.465  11.695 -33.601  0.50 29.32           O
HETATM 7287  O    HOH S 177     -20.208 -11.565 -31.305  0.50 17.57           O
HETATM 7288  O    HOH S 178     -48.721  -6.061 -20.224  0.50 24.22           O
HETATM 7289  O    HOH S 179     -37.203 -22.627 -20.246  0.50 23.18           O
HETATM 7290  O    HOH S 180     -50.352 -12.442 -13.429  0.50 25.87           O
HETATM 7291  O    HOH S 181     -38.361   2.858 -25.774  0.50 28.16           O
```

Figure 27 (Continued)

```
HETATM 7292  O   HOH S 182     -49.326  -7.699 -36.592  0.50 30.70           O
HETATM 7293  O   HOH S 183     -20.568 -18.828  -7.131  0.50 31.51           O
HETATM 7294  O   HOH S 185     -36.259  -9.668 -52.074  0.50 29.68           O
HETATM 7295  O   HOH S 186     -31.432 -27.130 -20.547  0.50 20.39           O
HETATM 7296  O   HOH S 187     -22.224  -6.708 -56.771  0.50 24.15           O
HETATM 7297  O   HOH S 189     -54.775 -18.231 -21.203  0.50 32.39           O
HETATM 7298  O   HOH S 190       2.457   0.207 -18.420  0.50 28.68           O
HETATM 7299  O   HOH S 191      -4.390  18.165  -4.247  0.50 31.68           O
HETATM 7300  O   HOH S 192       5.852   9.383 -19.582  0.50 29.06           O
HETATM 7301  O   HOH S 193     -17.748  15.758 -36.799  0.50 22.42           O
HETATM 7302  O   HOH S 194     -48.391  -1.407 -25.253  0.50 43.14           O
HETATM 7303  O   HOH S 195       2.340  11.858 -27.143  0.50 14.01           O
HETATM 7304  O   HOH S 196     -49.178  -4.487 -28.965  0.50 25.63           O
HETATM 7305  O   HOH S 197      -7.280   1.535  -2.594  0.50 26.46           O
HETATM 7306  O   HOH S 198      -3.057  18.202  -6.562  0.50 27.09           O
HETATM 7307  O   HOH S 199       2.025  11.798 -30.285  0.50 39.06           O
HETATM 7308  O   HOH S 200       0.346  16.161 -10.822  0.50 22.08           O
HETATM 7309  O   HOH S 201     -27.656 -18.445 -20.618  0.50 29.36           O
HETATM 7310  O   HOH S 202     -50.373  -1.752 -28.542  0.50 18.44           O
HETATM 7311  O   HOH S 203     -19.703  14.550  -3.144  0.50 22.83           O
HETATM 7312  O   HOH S 204     -25.045  12.219 -33.160  0.50 27.63           O
HETATM 7313  O   HOH S 206     -22.519  15.571 -56.869  0.50 21.47           O
HETATM 7314  O   HOH S 207     -26.837   5.838 -30.704  0.50 30.15           O
HETATM 7315  O   HOH S 208       0.481   1.585 -11.887  0.50 28.75           O
HETATM 7316  O   HOH S 209      -8.991 -11.509 -47.708  0.50 34.34           O
HETATM 7317  O   HOH S 210     -22.467  -4.780 -47.419  0.50 19.94           O
HETATM 7318  O   HOH S 211     -23.105  20.953   6.922  0.50 27.52           O
HETATM 7319  O   HOH S 212      -3.533  22.324  -9.276  0.50 23.93           O
HETATM 7320  O   HOH S 213      -1.038  16.997  -8.287  0.50 27.08           O
HETATM 7321  O   HOH S 214       4.980  11.925 -26.316  0.50 25.12           O
HETATM 7322  O   HOH S 215     -49.432  -9.920 -34.627  0.50 26.56           O
HETATM 7323  O   HOH S 216     -25.551 -20.431 -51.877  0.50 28.58           O
HETATM 7324  O   HOH S 217     -44.337   2.897 -30.614  0.50 23.23           O
HETATM 7325  O   HOH S 218     -25.308 -19.611 -17.155  0.50 25.98           O
HETATM 7326  O   HOH S 219       0.445   9.773 -30.861  0.50 20.64           O
HETATM 7327  O   HOH S 220     -11.133 -10.976 -29.532  0.50 17.85           O
HETATM 7328  O   HOH S 221     -13.630 -16.507 -52.319  0.50 25.46           O
HETATM 7329  O   HOH S 222     -41.838  -8.195 -10.900  0.50 30.60           O
HETATM 7330  O   HOH S 223      -0.674  -5.248 -34.194  0.50 25.70           O
HETATM 7331  O   HOH S 224     -25.085  57.911 -29.238  0.50 25.20           O
HETATM 7332  O   HOH S 226     -35.132 -13.258 -25.306  0.50 26.38           O
HETATM 7333  O   HOH S 227     -44.939  -9.542 -44.471  0.50 27.15           O
HETATM 7334  O   HOH S 228     -25.306  13.935 -34.248  0.50 22.06           O
HETATM 7335  O   HOH S 229     -38.465   5.395 -27.123  0.50 34.34           O
HETATM 7336  O   HOH S 230     -33.004  19.071 -49.992  0.50 31.74           O
HETATM 7337  O   HOH S 231     -50.867 -12.909 -32.528  0.50 26.28           O
HETATM 7338  O   HOH S 232     -10.027   3.427 -21.807  0.50 26.38           O
HETATM 7339  O   HOH S 233       5.030  11.147 -17.658  0.50 32.58           O
HETATM 7340  O   HOH S 234     -34.713 -21.265 -26.114  0.50 24.13           O
HETATM 7341  O   HOH S 235       6.751   7.050 -17.183  0.50 31.02           O
HETATM 7342  O   HOH S 236      -8.506   0.570 -17.135  0.50 21.46           O
HETATM 7343  O   HOH S 237     -27.692  -6.621 -55.234  0.50 37.53           O
HETATM 7344  O   HOH S 238     -43.375 -26.522 -19.499  0.50 27.58           O
HETATM 7345  O   HOH S 239      -2.110  20.150  -7.850  0.50 43.36           O
HETATM 7346  O   HOH S 240     -36.106   5.612 -44.805  0.50 21.27           O
HETATM 7347  O   HOH S 241       2.032  14.086 -16.979  0.50 49.19           O
HETATM 7348  O   HOH S 242      -8.974   2.782 -19.231  0.50 21.31           O
HETATM 7349  O   HOH S 243     -36.140 -11.435 -24.841  0.50 31.53           O
HETATM 7350  O   HOH S 244     -24.744 -21.767 -42.295  0.50 21.53           O
HETATM 7351  O   HOH S 245     -23.728  -3.240 -31.189  0.50 17.75           O
HETATM 7352  O   HOH S 246     -33.602 -26.410 -44.430  0.50 21.85           O
HETATM 7353  O   HOH S 247       8.028   8.231  -7.917  0.50 28.78           O
HETATM 7354  O   HOH S 248     -21.580   4.153 -53.884  0.50 25.47           O
HETATM 7355  O   HOH S 249      -1.337   3.651 -36.819  0.50 25.97           O
```

Figure 27 (Continued)

```
HETATM 7356  O    HOH S 250     -41.859 -10.764  -3.881  0.50 26.38           O
HETATM 7357  O    HOH S 251      -5.048   0.587  -8.265  0.50 27.43           O
HETATM 7358  O    HOH S 252     -38.824 -19.146 -25.892  0.50 13.75           O
HETATM 7359  O    HOH S 253     -35.455 -15.142 -31.081  0.50 11.02           O
HETATM 7360  O    HOH S 254     -16.689  16.725 -39.223  0.50 21.25           O
HETATM 7361  O    HOH S 255     -37.428  -3.704 -48.845  0.50 24.45           O
HETATM 7362  O    HOH S 256     -24.182  22.441  -3.058  0.50 30.92           O
HETATM 7363  O    HOH S 257     -24.575  18.941  -5.943  0.50 19.59           O
HETATM 7364  O    HOH S 258      -5.271   8.820   3.566  0.50 21.63           O
HETATM 7365  O    HOH S 259     -27.567  16.874 -31.883  0.50 23.71           O
HETATM 7366  O    HOH S 260     -50.829   0.026 -28.977  0.50 22.73           O
HETATM 7367  O    HOH S 261     -41.325   8.274 -46.449  0.50 32.44           O
HETATM 7368  O    HOH S 262     -32.938 -19.353 -49.069  0.50 22.88           O
HETATM 7369  O    HOH S 263     -36.530  15.061 -49.452  0.50 37.95           O
HETATM 7370  O    HOH S 264     -35.441 -15.117 -23.825  0.50 16.14           O
HETATM 7371  O    HOH S 265     -13.571   3.144 -25.384  0.50 22.11           O
HETATM 7372  O    HOH S 266     -17.871   3.044 -29.380  0.50 24.60           O
HETATM 7373  O    HOH S 267     -17.445  10.956 -10.386  0.50 23.45           O
HETATM 7374  O    HOH S 268     -10.102  19.926  -0.836  0.50 24.07           O
HETATM 7375  O    HOH S 269     -13.207  15.935 -24.396  0.50 36.09           O
HETATM 7376  O    HOH S 270      -8.972  17.238   6.785  0.50 26.81           O
HETATM 7377  O    HOH S 271     -24.093   5.742 -54.729  0.50 32.96           O
HETATM 7379  O    HOH S 273     -20.130   7.205 -54.534  0.50 19.85           O
HETATM 7380  O    HOH S 274     -39.214 -11.868 -25.792  0.50 32.34           O
HETATM 7381  O    HOH S 275     -39.838 -20.656 -38.962  0.50 48.50           O
HETATM 7382  O    HOH S 276     -12.811   4.340 -22.748  0.50 39.06           O
HETATM 7383  O    HOH S 277     -23.236  35.116 -47.291  0.50 31.38           O
HETATM 7384  O    HOH S 278     -16.003  19.362  -7.503  0.50 29.60           O
HETATM 7385  O    HOH S 279     -15.496   8.039 -19.172  0.50 38.46           O
HETATM 7386  O    HOH S 280     -26.362  -1.690 -29.671  0.50 42.36           O
HETATM 7387  O    HOH S 281      -0.075  -3.617 -34.898  0.50 19.52           O
HETATM 7388  O    HOH S 282     -33.160 -12.201 -29.506  0.50 26.79           O
HETATM 7389  O    HOH S 283     -29.663   6.024 -29.887  0.50 24.06           O
HETATM 7390  O    HOH S 284     -14.505   7.566 -23.242  0.50 27.33           O
HETATM 7391  O    HOH S 285       0.975  10.538  -0.629  0.50 29.94           O
HETATM 7392  O    HOH S 286     -41.242   1.811 -40.060  0.50 35.39           O
HETATM 7393  O    HOH S 287     -24.379  11.620  -9.549  0.50 28.78           O
HETATM 7394  O    HOH S 288     -37.245  17.120 -47.833  0.50 35.52           O
HETATM 7396  O    HOH S 290     -43.150   1.629 -25.017  0.50 21.76           O
HETATM 7397  O    HOH S 291     -31.550 -18.318 -52.371  0.50 27.91           O
HETATM 7398  O    HOH S 292     -25.934  33.772 -46.807  0.50 27.78           O
HETATM 7399  O    HOH S 293     -27.260 -22.109 -47.499  0.50 35.69           O
HETATM 7400  O    HOH S 294     -30.216  14.653 -42.452  0.50 37.54           O
HETATM 7401  O    HOH S 295     -31.127  -2.333 -53.981  0.50 31.43           O
HETATM 7402  O    HOH S 296     -28.723   5.586 -55.404  0.50 28.05           O
HETATM 7403  O    HOH S 297      -1.885  -0.888 -37.850  0.50 29.27           O
HETATM 7404  O    HOH S 298     -18.855  -8.229 -28.226  0.50 21.38           O
HETATM 7405  O    HOH S 299     -10.749 -12.801 -40.442  0.50 41.58           O
HETATM 7406  O    HOH S 300     -12.072  -0.336 -55.345  0.50 30.77           O
HETATM 7407  O    HOH S 301      -0.507  -2.575 -18.074  0.50 42.05           O
HETATM 7408  O    HOH S 302       0.079   3.272 -39.278  0.50 33.55           O
HETATM 7409  O    HOH S 303       6.732   5.970 -28.749  0.50 33.68           O
HETATM 7410  O    HOH S 304     -46.211   0.603 -38.439  0.50 27.32           O
HETATM 7411  O    HOH S 305     -36.845 -12.717 -50.555  0.50 32.19           O
HETATM 7412  O    HOH S 306     -41.692 -28.070  -8.437  0.50 28.74           O
HETATM 7413  O    HOH S 307     -17.459  13.174 -12.389  0.50 27.14           O
HETATM 7414  O    HOH S 308     -10.592   0.085 -48.595  0.50 36.68           O
HETATM 7415  O    HOH S 309     -49.814  -9.984 -37.275  0.50 32.91           O
HETATM 7416  O    HOH S 311     -30.702   6.006 -57.680  0.50 36.16           O
HETATM 7417  O    HOH S 312     -32.556 -27.879 -14.042  0.50 43.50           O
HETATM 7418  O    HOH S 313      -5.759  -2.059 -19.534  0.50 26.69           O
HETATM 7419  O    HOH S 314     -20.311  29.278 -43.036  0.50 37.04           O
HETATM 7420  O    HOH S 315     -44.202 -26.471  -6.948  0.50 31.64           O
HETATM 7421  O    HOH S 316     -31.921  18.046 -43.566  0.50 28.12           O
```

Figure 27 (Continued)

```
HETATM 7422  O   HOH S 317     -40.204  -9.213 -21.577  0.50 28.45           O
HETATM 7423  O   HOH S 318      -6.807  -0.205  -7.422  0.50 31.09           O
HETATM 7424  O   HOH S 319       0.542  17.790 -23.370  0.50 36.52           O
HETATM 7425  O   HOH S 320     -14.105   9.410 -19.390  0.50 28.34           O
HETATM 7426  O   HOH S 321     -43.006  -2.939 -21.010  0.50 32.25           O
HETATM 7427  O   HOH S 322     -36.057 -23.439 -46.186  0.50 34.55           O
HETATM 7428  O   HOH S 323     -55.800  -7.077 -19.619  0.50 33.69           O
HETATM 7429  O   HOH S 324     -32.837 -28.021 -48.982  0.50 38.65           O
HETATM 7430  O   HOH S 325     -56.076 -17.330 -24.747  0.50 37.02           O
HETATM 7431  O   HOH S 326      -2.635  -3.511 -41.033  0.50 28.36           O
HETATM 7433  O   HOH S 328     -33.990 -17.647 -50.255  0.50 29.42           O
HETATM 7434  O   HOH S 329     -37.222 -27.492   2.679  0.50 36.02           O
HETATM 7435  O   HOH S 330     -27.981  -9.114 -31.306  0.50 32.67           O
HETATM 7436  O   HOH S 331     -10.396  -2.291 -47.010  0.50 26.97           O
HETATM 7437  O   HOH S 332      -2.644  -7.943 -18.432  0.50 32.81           O
HETATM 7438  O   HOH S 333     -32.961 -22.105   1.050  0.50 42.46           O
HETATM 7439  O   HOH S 334     -43.487 -13.395 -46.625  0.50 41.08           O
HETATM 7440  O   HOH S 335     -26.258   5.826 -55.716  0.50 30.72           O
HETATM 7441  O   HOH S 336     -48.317  -9.810 -10.926  0.50 50.44           O
HETATM 7443  O   HOH S 339     -21.907  -4.628 -55.253  0.50 35.85           O
HETATM 7444  O   HOH S 340     -22.463  19.166   7.842  0.50 33.23           O
HETATM 7445  O   HOH S 341     -38.845   8.202 -43.640  0.50 22.77           O
HETATM 7446  O   HOH S 342     -27.398  35.026 -48.711  0.50 35.25           O
HETATM 7447  O   HOH S 343     -24.983  18.170 -47.943  0.50 32.55           O
HETATM 7448  O   HOH S 345     -24.471  10.502 -11.684  0.50 30.90           O
HETATM 7449  O   HOH S 346     -24.161  21.113 -52.015  0.50 29.52           O
HETATM 7451  O   HOH S 349     -48.427 -23.407 -30.626  0.50 34.34           O
HETATM 7452  O   HOH S 350     -47.605   1.959 -35.144  0.50 29.86           O
HETATM 7453  O   HOH S 351     -26.813 -22.921 -50.350  0.50 38.57           O
HETATM 7454  O   HOH S 352     -47.653 -25.578  -7.024  0.50 39.03           O
HETATM 7455  O   HOH S 353       7.918   6.061 -24.706  0.50 34.33           O
HETATM 7456  O   HOH S 354     -42.174  -3.942 -44.102  0.50 26.57           O
HETATM 7457  O   HOH S 355     -29.166  -5.382 -54.619  0.50 29.37           O
HETATM 7458  O   HOH S 356      -8.287   0.556  -9.914  0.50 30.18           O
HETATM 7460  O   HOH S 358     -32.412  -8.973 -29.537  0.50 33.21           O
HETATM 7461  O   HOH S 359     -15.937   3.997 -12.719  0.50 12.28           O
HETATM 7462  O   HOH S 360     -47.476 -15.777 -33.190  0.50 12.40           O
HETATM 7463  O   HOH S 361     -17.040  -3.032 -27.471  0.50 40.51           O
HETATM 7464  O   HOH S 362     -30.461 -15.839 -24.110  0.50 20.99           O
HETATM 7465  O   HOH S 363     -11.614  -8.863 -26.939  0.50 19.73           O
HETATM 7466  O   HOH S 364     -15.286  11.655   4.844  0.50 38.71           O
HETATM 7467  O   HOH S 365     -41.716   3.792 -31.801  0.50 32.74           O
HETATM 7468  O   HOH S 366     -56.475 -13.296 -19.019  0.50 41.17           O
HETATM 7469  O   HOH S 367     -48.868 -16.283 -36.339  0.50 35.38           O
HETATM 7470  O   HOH S 368     -35.042   8.856 -38.416  0.50 39.50           O
HETATM 7472  O   HOH S 370     -47.865  -3.811 -39.295  0.50 37.07           O
HETATM 7473  O   HOH S 371     -31.187   2.034 -27.112  0.50 31.19           O
HETATM 7474  O   HOH S 372     -50.208 -10.025 -12.934  0.50 33.53           O
HETATM 7475  O   HOH S 373      -7.105  -1.229 -19.134  0.50 43.74           O
HETATM 7476  O   HOH S 374     -49.580 -13.800 -37.640  0.50 30.23           O
HETATM 7477  O   HOH S 375     -46.588 -24.479 -30.856  0.50 27.07           O
HETATM 7478  O   HOH S 376     -19.634  24.559 -44.691  0.50 24.74           O
HETATM 7479  O   HOH S 377     -29.863   2.665 -28.404  0.50 26.06           O
HETATM 7480  O   HOH S 378     -14.727  20.649  -9.772  0.50 41.20           O
HETATM 7482  O   HOH S 380     -50.160 -15.308 -39.376  0.50 35.55           O
HETATM 7483  O   HOH S 381       0.171  20.639 -10.412  0.50 32.18           O
HETATM 7484  O   HOH S 382     -43.492  -9.534 -46.873  0.50 24.61           O
HETATM 7485  O   HOH S 383     -30.220  -8.176 -55.664  0.50 28.27           O
HETATM 7486  O   HOH S 385     -33.696 -10.125 -14.807  0.50 18.49           O
HETATM 7487  O   HOH S 386     -48.452 -24.216 -13.061  0.50 34.41           O
HETATM 7488  O   HOH S 387      -2.648   9.605   4.433  0.50 33.35           O
HETATM 7489  O   HOH S 388     -14.491   4.476 -15.155  0.50 37.41           O
HETATM 7490  O   HOH S 389     -51.465 -19.340  -3.047  0.50 33.32           O
HETATM 7491  O   HOH S 390     -46.263  -9.382  -7.023  0.50 33.00           O
```

Figure 27 (Continued)

```
HETATM 7492  O   HOH S 391     -50.635 -17.197 -35.908  0.50 29.34           O
HETATM 7493  O   HOH S 392      -0.904   0.664 -10.255  0.50 28.53           O
HETATM 7494  O   HOH S 393     -20.205   3.100 -31.224  0.50 24.84           O
HETATM 7495  O   HOH S 394     -27.451  17.651 -40.386  0.50 23.70           O
HETATM 7496  O   HOH S 395      -0.816  -0.331  -7.593  0.50 45.90           O
HETATM 7498  O   HOH S 397     -38.733 -29.126  -4.506  0.50 36.32           O
HETATM 7499  O   HOH S 398     -36.366  41.154 -63.654  0.50 12.47           O
HETATM 7500  O   HOH S 399     -13.290   4.074  -3.702  0.50 16.59           O
HETATM 7501  O   HOH S 400     -18.337   6.897 -17.387  0.50 14.66           O
HETATM 7502  O   HOH S 401     -11.424 -10.912 -45.537  0.50 15.33           O
HETATM 7503  O   HOH S 402     -32.010 -11.366 -55.749  0.50 33.26           O
HETATM 7504  O   HOH S 403     -14.411 -14.805 -57.286  0.50 25.18           O
HETATM 7505  O   HOH S 404     -35.929 -32.255  -7.915  0.50 39.36           O
HETATM 7506  O   HOH S 405     -30.662  62.553 -71.756  0.50 26.18           O
HETATM 7507  O   HOH S 406     -41.037  47.127 -29.146  0.50 28.23           O
HETATM 7508  O   HOH S 408      -0.722   9.400 -36.136  0.50 28.30           O
HETATM 7509  O   HOH S 409     -33.723  37.645 -47.523  0.50 32.70           O
HETATM 7510  O   HOH S 410     -16.218  46.320 -35.895  0.50 35.63           O
HETATM 7511  O   HOH S 411     -14.245  44.900 -34.570  0.50 42.20           O
HETATM 7512  O   HOH S 412     -17.241  26.348 -18.613  0.50 31.31           O
HETATM 7513  O2  EDO F   2     -31.401  44.622 -42.164  0.50 22.33           O
HETATM 7514  C2  EDO F   2     -30.896  43.278 -42.119  0.50 21.85           C
HETATM 7515  C1  EDO F   2     -29.890  43.134 -43.261  0.50 21.77           C
HETATM 7516  O1  EDO F   2     -30.614  43.220 -44.494  0.50 22.27           O
HETATM 7517  O2  EDO F   5     -30.641  65.118 -32.389  0.50 47.76           O
HETATM 7518  C2  EDO F   5     -31.149  63.787 -32.553  0.50 44.41           C
HETATM 7519  C1  EDO F   5     -31.135  63.432 -34.035  0.50 43.40           C
HETATM 7520  O1  EDO F   5     -32.028  62.339 -34.293  0.50 41.81           O
HETATM 7521  O2  EDO F   6     -18.521  25.631 -54.880  0.50 32.08           O
HETATM 7522  C2  EDO F   6     -18.031  24.654 -53.949  0.50 34.28           C
HETATM 7523  C1  EDO F   6     -16.566  24.364 -54.256  0.50 35.07           C
HETATM 7524  O1  EDO F   6     -15.905  23.844 -53.097  0.50 34.95           O
HETATM 7525  O2  EDO F   7     -33.545  43.130 -47.230  0.50 27.81           O
HETATM 7526  C2  EDO F   7     -34.230  42.622 -46.060  0.50 26.16           C
HETATM 7527  C1  EDO F   7     -34.772  41.212 -46.289  0.50 21.96           C
HETATM 7528  O1  EDO F   7     -34.184  40.277 -45.360  0.50 23.30           O
HETATM 7529  O2  EDO F   8     -35.854  25.891 -32.519  0.50 34.42           O
HETATM 7530  C2  EDO F   8     -34.892  26.542 -33.360  0.50 34.80           C
HETATM 7531  C1  EDO F   8     -34.001  25.488 -34.013  0.50 34.99           C
HETATM 7532  O1  EDO F   8     -32.621  25.853 -33.889  0.50 31.72           O
HETATM 7533  I   IOD i   1      -5.449  16.292 -35.865  0.50 17.86           I
HETATM 7534  I   IOD i   2     -14.800  18.579 -43.479  0.50 23.46           I
HETATM 7535  O   HOH H   1     -35.642  47.163 -45.794  0.50 19.35           O
HETATM 7536  O   HOH H   2     -39.134  43.321 -50.817  0.50 22.40           O
HETATM 7537  O   HOH H   3      -3.033  19.890 -37.621  0.50 18.44           O
HETATM 7538  O   HOH H   4     -43.318  28.866 -43.139  0.50 17.62           O
HETATM 7539  O   HOH H   5     -13.269  15.431 -36.099  0.50 23.85           O
HETATM 7540  O   HOH H   6     -32.173  53.061 -27.106  0.50 22.76           O
HETATM 7541  O   HOH H   7     -34.808  29.861 -36.676  0.50 17.99           O
HETATM 7542  O   HOH H   8     -20.099  25.103 -38.857  0.50 20.78           O
HETATM 7543  O   HOH H   9     -19.902  44.884 -35.290  0.50 15.75           O
HETATM 7544  O   HOH H  10     -20.096  19.220 -34.173  0.50 13.39           O
HETATM 7545  O   HOH H  11     -50.860  48.313 -54.064  0.50 21.15           O
HETATM 7546  O   HOH H  12      -2.998  13.184 -35.049  0.50 19.15           O
HETATM 7547  O   HOH H  13      -8.736  35.990 -49.797  0.50 21.27           O
HETATM 7548  O   HOH H  14     -32.744  48.771 -42.096  0.50 17.64           O
HETATM 7549  O   HOH H  15     -15.251  24.689 -43.601  0.50 18.79           O
HETATM 7550  O   HOH H  16     -10.576  14.512 -37.379  0.50 25.71           O
HETATM 7551  O   HOH H  17      -7.795  26.592 -44.576  0.50 13.85           O
HETATM 7552  O   HOH H  18     -30.093  24.466 -35.277  0.50 19.22           O
HETATM 7553  O   HOH H  19     -31.888  28.193 -31.339  0.50 19.18           O
HETATM 7554  O   HOH H  20     -14.077  41.184 -37.102  0.50 20.13           O
HETATM 7555  O   HOH H  21     -46.785  40.572 -53.060  0.50 14.04           O
HETATM 7556  O   HOH H  22     -43.736  46.097 -30.523  0.50 22.41           O
```

Figure 27 (Continued)

```
HETATM 7557  O   HOH H  23     -42.398  40.509 -45.537  0.50 18.80           O
HETATM 7558  O   HOH H  24     -29.044  26.233 -34.037  0.50 20.21           O
HETATM 7559  O   HOH H  25      -2.373  27.069 -52.323  0.50 15.34           O
HETATM 7560  O   HOH H  26     -38.225  33.830 -47.735  0.50 20.77           O
HETATM 7561  O   HOH H  27     -21.047  15.444 -67.736  0.50 32.49           O
HETATM 7562  O   HOH H  28     -24.602  24.479 -18.154  0.50 20.28           O
HETATM 7563  O   HOH H  29     -38.506  51.569 -30.233  0.50 18.81           O
HETATM 7564  O   HOH H  30       4.735  28.329 -51.670  0.50 19.67           O
HETATM 7565  O   HOH H  31      -0.004  36.474 -40.195  0.50 25.54           O
HETATM 7566  O   HOH H  32     -36.970 -10.957 -12.459  0.50 15.47           O
HETATM 7567  O   HOH H  33     -34.788  51.370 -35.320  0.50 18.72           O
HETATM 7568  O   HOH H  34     -17.035  43.437 -33.250  0.50 12.71           O
HETATM 7569  O   HOH H  35     -47.310  47.287 -43.366  0.50 16.77           O
HETATM 7570  O   HOH H  36     -29.606  51.965 -37.383  0.50 13.48           O
HETATM 7571  O   HOH H  37      -7.889  28.953 -42.033  0.50 12.27           O
HETATM 7572  O   HOH H  38     -41.172  40.756 -43.165  0.50 15.73           O
HETATM 7573  O   HOH H  39     -29.207  44.635 -40.603  0.50 17.53           O
HETATM 7574  O   HOH H  40     -13.995  24.602 -68.793  0.50 25.25           O
HETATM 7575  O   HOH H  41       0.955  19.332 -52.027  0.50 20.59           O
HETATM 7576  O   HOH H  42     -23.982  49.638 -20.608  0.50 20.66           O
HETATM 7577  O   HOH H  43     -13.352  16.018 -46.162  0.50 14.23           O
HETATM 7578  O   HOH H  44     -40.004  38.989 -50.890  0.50 20.39           O
HETATM 7579  O   HOH H  45     -32.080  54.984 -28.225  0.50 14.91           O
HETATM 7580  O   HOH H  46     -42.499  42.441 -47.371  0.50 14.38           O
HETATM 7581  O   HOH H  47       1.048  30.890 -47.132  0.50 20.88           O
HETATM 7582  O   HOH H  48     -23.357  36.953 -23.070  0.50 17.52           O
HETATM 7583  O   HOH H  49      -8.625   9.185 -45.997  0.50 15.06           O
HETATM 7584  O   HOH H  50     -33.976  44.786 -45.117  0.50 21.39           O
HETATM 7585  O   HOH H  51     -25.284  36.331 -23.240  0.50 21.91           O
HETATM 7586  O   HOH H  52     -19.045  46.172 -37.319  0.50 24.62           O
HETATM 7587  O   HOH H  53     -21.765  39.858 -27.672  0.50 19.56           O
HETATM 7588  O   HOH H  54     -51.243  50.846 -66.947  0.50 19.24           O
HETATM 7589  O   HOH H  55     -36.930  31.219 -29.065  0.50 16.52           O
HETATM 7590  O   HOH H  56     -45.327  40.446 -31.853  0.50 23.19           O
HETATM 7591  O   HOH H  57     -45.700  37.115 -58.569  0.50 31.40           O
HETATM 7592  O   HOH H  58      -7.862  26.440 -46.908  0.50 18.46           O
HETATM 7593  O   HOH H  59     -50.487  41.555 -62.311  0.50 20.72           O
HETATM 7594  O   HOH H  60     -32.559  56.197 -33.939  0.50 21.05           O
HETATM 7595  O   HOH H  61     -25.194  63.059 -33.652  0.50 23.27           O
HETATM 7596  O   HOH H  62     -17.641  17.647 -35.053  0.50 19.46           O
HETATM 7597  O   HOH H  63     -38.613  37.999 -28.542  0.50 23.63           O
HETATM 7598  O   HOH H  64     -18.501  38.896 -27.024  0.50 16.25           O
HETATM 7599  O   HOH H  65     -15.990  33.164 -24.153  0.50 20.88           O
HETATM 7600  O   HOH H  66     -36.946  28.274 -34.557  0.50 25.20           O
HETATM 7601  O   HOH H  67     -35.306  29.124 -28.754  0.50 25.52           O
HETATM 7602  O   HOH H  68     -25.380  55.910 -30.951  0.50 22.36           O
HETATM 7603  O   HOH H  69     -30.100  54.187 -25.421  0.50 23.42           O
HETATM 7604  O   HOH H  70     -23.185  22.634 -69.545  0.50 23.71           O
HETATM 7605  O   HOH H  71     -10.947  34.881 -47.886  0.50 19.30           O
HETATM 7606  O   HOH H  72     -11.748  40.883 -30.343  0.50 20.15           O
HETATM 7607  O   HOH H  73      -8.091  29.804 -56.302  0.50 22.61           O
HETATM 7608  O   HOH H  74     -53.824  39.099 -52.452  0.50 17.72           O
HETATM 7609  O   HOH H  75     -43.158  58.362 -46.607  0.50 23.56           O
HETATM 7610  O   HOH H  76     -32.762  38.852 -24.645  0.50 22.13           O
HETATM 7611  O   HOH H  77     -45.311  59.332 -43.791  0.50 23.92           O
HETATM 7612  O   HOH H  78       4.521  29.111 -54.106  0.50 30.57           O
HETATM 7613  O   HOH H  79     -47.403  55.804 -57.868  0.50 22.75           O
HETATM 7614  O   HOH H  80     -26.310  19.013 -30.808  0.50 25.07           O
HETATM 7615  O   HOH H  82     -43.961  42.768 -31.709  0.50 17.58           O
HETATM 7616  O   HOH H  83     -41.316  31.277 -34.121  0.50 34.91           O
HETATM 7617  O   HOH H  84     -18.607  53.177 -30.047  0.50 33.13           O
HETATM 7618  O   HOH H  85     -20.339  17.677 -55.602  0.50 32.59           O
HETATM 7619  O   HOH H  86     -55.080  54.096 -60.535  0.50 29.66           O
HETATM 7620  O   HOH H  87     -41.114  42.217 -48.778  0.50 24.72           O
```

Figure 27 (Continued)

```
HETATM 7621  O    HOH H  88       5.378  24.094 -48.999  0.50 17.06           O
HETATM 7622  O    HOH H  89     -23.789  20.523 -37.874  0.50 25.11           O
HETATM 7623  O    HOH H  90     -41.873  38.710 -47.223  0.50 46.41           O
HETATM 7624  O    HOH H  91     -40.631  38.631 -30.630  0.50 26.18           O
HETATM 7625  O    HOH H  92     -50.435  52.182 -47.939  0.50 21.03           O
HETATM 7626  O    HOH H  93     -50.143  49.895 -56.400  0.50 17.45           O
HETATM 7627  O    HOH H  94     -50.165  44.435 -35.306  0.50 23.04           O
HETATM 7628  O    HOH H  95     -15.906  26.737 -59.893  0.50 31.24           O
HETATM 7629  O    HOH H  96      -5.431  11.385 -43.931  0.50 22.64           O
HETATM 7630  O    HOH H  97     -20.790  17.974 -19.531  0.50 21.35           O
HETATM 7631  O    HOH H  98     -48.293  53.743 -50.036  0.50 21.65           O
HETATM 7632  O    HOH H  99     -26.384  26.494 -43.230  0.50 19.06           O
HETATM 7633  O    HOH H 100     -49.244  42.485 -38.708  0.50 30.25           O
HETATM 7634  O    HOH H 101     -21.661  13.135 -31.118  0.50 27.07           O
HETATM 7635  O    HOH H 102     -45.884  34.986 -47.322  0.50 21.74           O
HETATM 7636  O    HOH H 103     -41.583  32.634 -52.829  0.50 21.65           O
HETATM 7637  O    HOH H 104     -23.565  41.271 -44.344  0.50 23.43           O
HETATM 7638  O    HOH H 105     -16.139  21.192 -39.042  0.50 15.93           O
HETATM 7640  O    HOH H 107     -36.332  47.802 -25.688  0.50 22.39           O
HETATM 7641  O    HOH H 108     -30.494  18.927 -27.090  0.50 25.54           O
HETATM 7642  O    HOH H 109      -9.974  33.798 -28.712  0.50 14.42           O
HETATM 7643  O    HOH H 110      -3.397  20.856 -34.176  0.50 18.76           O
HETATM 7644  O    HOH H 111     -27.959  55.239 -22.885  0.50 17.83           O
HETATM 7645  O    HOH H 112     -45.925  56.224 -58.095  0.50 30.38           O
HETATM 7646  O    HOH H 113     -39.750  55.231 -51.053  0.50 34.31           O
HETATM 7647  O    HOH H 114     -30.883  60.333 -34.746  0.50 31.14           O
HETATM 7648  O    HOH H 115     -19.267  12.073 -61.423  0.50 29.92           O
HETATM 7649  O    HOH H 116     -38.762  51.409 -27.146  0.50 25.49           O
HETATM 7650  O    HOH H 117     -18.743  20.319 -61.388  0.50 29.23           O
HETATM 7651  O    HOH H 118       0.831  22.629 -41.996  0.50 25.57           O
HETATM 7652  O    HOH H 119     -35.943  57.452 -66.818  0.50 19.04           O
HETATM 7653  O    HOH H 120      -4.497  24.396 -29.996  0.50 23.74           O
HETATM 7654  O    HOH H 121      -1.415  14.606 -48.248  0.50 30.78           O
HETATM 7655  O    HOH H 122     -56.454  42.341 -56.137  0.50 27.05           O
HETATM 7656  O    HOH H 123     -33.253  21.746 -32.098  0.50 26.30           O
HETATM 7657  O    HOH H 124     -37.240  53.380 -57.406  0.50 26.75           O
HETATM 7658  O    HOH H 125     -31.419  48.179 -41.994  0.50 26.26           O
HETATM 7659  O    HOH H 126     -25.879  59.405 -78.685  0.50 18.85           O
HETATM 7660  O    HOH H 127     -25.568  28.004 -43.195  0.50 38.71           O
HETATM 7661  O    HOH H 128     -29.427  37.974 -20.465  0.50 22.03           O
HETATM 7662  O    HOH H 129     -46.033  32.749 -35.759  0.50 23.45           O
HETATM 7663  O    HOH H 130     -46.790  48.986 -72.441  0.50 24.80           O
HETATM 7664  O    HOH H 131     -41.663  52.602 -79.703  0.50 25.03           O
HETATM 7665  O    HOH H 132      -9.225  29.350 -50.022  0.50 24.28           O
HETATM 7666  O    HOH H 133     -25.020  55.816 -19.435  0.50 33.12           O
HETATM 7667  O    HOH H 134     -54.435  47.588 -70.509  0.50 32.78           O
HETATM 7668  O    HOH H 135     -40.255  32.405 -48.949  0.50 39.47           O
HETATM 7669  O    HOH H 136     -31.973  44.637 -75.008  0.50 28.77           O
HETATM 7670  O    HOH H 137     -18.682  18.839 -59.092  0.50 37.73           O
HETATM 7671  O    HOH H 138       4.004  11.824 -58.222  0.50 34.62           O
HETATM 7672  O    HOH H 139       2.741  26.313 -43.461  0.50 22.18           O
HETATM 7673  O    HOH H 140      -8.166  26.104 -26.654  0.50 27.05           O
HETATM 7674  O    HOH H 141     -12.957  27.213 -69.287  0.50 40.19           O
HETATM 7675  O    HOH H 142     -15.132  29.653 -44.715  0.50 21.40           O
HETATM 7676  O    HOH H 143      -4.358  17.495 -70.284  0.50 26.13           O
HETATM 7677  O    HOH H 144       6.152  21.516 -56.834  0.50 25.84           O
HETATM 7678  O    HOH H 145       0.694  26.907 -35.525  0.50 28.20           O
HETATM 7679  O    HOH H 146     -40.647  56.592 -47.906  0.50 25.03           O
HETATM 7680  O    HOH H 147     -47.905  32.720 -48.857  0.50 22.86           O
HETATM 7681  O    HOH H 148     -10.544  12.216 -76.178  0.50 30.52           O
HETATM 7682  O    HOH H 149     -15.856  20.118 -31.929  0.50 22.21           O
HETATM 7683  O    HOH H 150      -3.428  31.183 -31.482  0.50 18.17           O
HETATM 7684  O    HOH H 151     -47.042  55.786 -48.089  0.50 38.22           O
HETATM 7685  O    HOH H 152     -24.274  44.088 -42.575  0.50 17.39           O
```

Figure 27 (Continued)

```
HETATM 7686  O   HOH H 153      -2.328  31.352 -51.563  0.50 25.78           O
HETATM 7687  O   HOH H 154      -3.315  11.796 -55.167  0.50 24.60           O
HETATM 7688  O   HOH H 155      -9.696   9.109 -67.630  0.50 30.48           O
HETATM 7689  O   HOH H 156     -50.172  37.734 -47.758  0.50 29.44           O
HETATM 7690  O   HOH H 157     -29.678  19.745 -29.156  0.50 28.69           O
HETATM 7691  O   HOH H 158     -39.759  24.472 -34.438  0.50 29.08           O
HETATM 7692  O   HOH H 159     -37.759  36.376 -48.893  0.50 19.15           O
HETATM 7693  O   HOH H 160     -53.487  38.300 -54.485  0.50 29.90           O
HETATM 7694  O   HOH H 161     -41.120  26.711 -45.722  0.50 27.26           O
HETATM 7695  O   HOH H 162     -55.740  47.672 -57.259  0.50 35.81           O
HETATM 7696  O   HOH H 163     -42.864  44.904 -29.148  0.50 28.80           O
HETATM 7697  O   HOH H 164     -18.308  33.537 -22.167  0.50 23.77           O
HETATM 7698  O   HOH H 165     -30.194  39.675 -22.502  0.50 23.40           O
HETATM 7699  O   HOH H 166     -36.319  32.290 -49.283  0.50 26.11           O
HETATM 7700  O   HOH H 167     -21.161  57.100 -21.115  0.50 32.78           O
HETATM 7701  O   HOH H 168      -0.353  14.237 -64.128  0.50 27.37           O
HETATM 7702  O   HOH H 169       0.228  16.420 -45.712  0.50 29.76           O
HETATM 7703  O   HOH H 170     -47.063  36.502 -51.053  0.50 18.15           O
HETATM 7704  O   HOH H 171     -35.279  44.403 -23.724  0.50 18.57           O
HETATM 7705  O   HOH H 172      -8.526  42.883 -37.299  0.50 27.32           O
HETATM 7706  O   HOH H 173     -18.817  17.623 -51.349  0.50 19.88           O
HETATM 7707  O   HOH H 174     -54.854  44.902 -49.434  0.50 21.13           O
HETATM 7708  O   HOH H 175     -12.018  42.908 -36.360  0.50 22.25           O
HETATM 7709  O   HOH H 176     -47.998  48.911 -40.735  0.50 23.38           O
HETATM 7710  O   HOH H 177     -29.103  26.651 -43.843  0.50 18.65           O
HETATM 7711  O   HOH H 178      -1.147  31.787 -53.206  0.50 26.33           O
HETATM 7712  O   HOH H 179     -13.140  14.871 -54.002  0.50 25.17           O
HETATM 7713  O   HOH H 180       0.890  24.123 -61.146  0.50 21.32           O
HETATM 7714  O   HOH H 181     -11.189  41.220 -47.881  0.50 39.75           O
HETATM 7715  O   HOH H 182      -0.671  28.836 -36.606  0.50 24.05           O
HETATM 7716  O   HOH H 183     -28.696  18.877 -68.108  0.50 37.13           O
HETATM 7717  O   HOH H 185     -13.527  28.833 -22.090  0.50 30.42           O
HETATM 7718  O   HOH H 186     -11.190  10.674 -52.443  0.50 30.65           O
HETATM 7719  O   HOH H 188     -46.321  54.992 -70.385  0.50 18.94           O
HETATM 7720  O   HOH H 189     -54.856  48.209 -55.287  0.50 31.13           O
HETATM 7721  O   HOH H 190     -31.817  53.179 -37.423  0.50 19.89           O
HETATM 7722  O   HOH H 191      -1.415  35.279 -49.758  0.50 15.91           O
HETATM 7723  O   HOH H 192     -51.992  49.685 -46.488  0.50 19.57           O
HETATM 7724  O   HOH H 193     -43.428  39.150 -71.692  0.50 26.51           O
HETATM 7725  O   HOH H 194     -47.586  55.309 -67.251  0.50 32.33           O
HETATM 7726  O   HOH H 195     -52.271  49.536 -44.143  0.50 26.22           O
HETATM 7727  O   HOH H 196       0.308  17.232 -54.437  0.50 22.90           O
HETATM 7728  O   HOH H 197     -49.806  52.848 -64.219  0.50 32.89           O
HETATM 7729  O   HOH H 198     -22.143  18.078 -54.275  0.50 18.77           O
HETATM 7730  O   HOH H 199       1.013  35.550 -46.686  0.50 18.06           O
HETATM 7731  O   HOH H 200     -30.366  51.363 -71.925  0.50 39.71           O
HETATM 7732  O   HOH H 201     -23.215  49.216 -40.962  0.50 35.79           O
HETATM 7733  O   HOH H 202      -7.851  40.517 -36.445  0.50 28.06           O
HETATM 7734  O   HOH H 203     -27.757  51.785 -17.664  0.50 32.33           O
HETATM 7735  O   HOH H 204     -22.770  43.084 -44.759  0.50 25.89           O
HETATM 7736  O   HOH H 205     -50.637  39.340 -62.683  0.50 31.71           O
HETATM 7737  O   HOH H 206     -40.930  26.750 -25.675  0.50 29.89           O
HETATM 7738  O   HOH H 207     -25.863  58.522 -81.146  0.50 28.04           O
HETATM 7739  O   HOH H 208     -46.501  58.739 -65.890  0.50 31.61           O
HETATM 7740  O   HOH H 209     -48.864  53.355 -66.499  0.50 24.95           O
HETATM 7741  O   HOH H 210     -54.831  49.468 -47.035  0.50 34.51           O
HETATM 7742  O   HOH H 211      -0.697  27.831 -40.931  0.50 19.55           O
HETATM 7743  O   HOH H 212     -23.011  16.174 -22.702  0.50 32.86           O
HETATM 7744  O   HOH H 213      -5.096  40.474 -42.774  0.50 27.61           O
HETATM 7745  O   HOH H 214     -23.730  17.307 -57.489  0.50 25.78           O
HETATM 7746  O   HOH H 215     -49.939  47.666 -43.062  0.50 28.96           O
HETATM 7747  O   HOH H 216     -38.055  27.243 -45.773  0.50 22.61           O
HETATM 7748  O   HOH H 217      -8.831  28.613 -63.127  0.50 31.61           O
HETATM 7749  O   HOH H 218     -48.538  31.564 -40.210  0.50 24.87           O
```

Figure 27 (Continued)

```
HETATM 7751  O    HOH H 220     -50.218  44.156 -41.719  0.50 23.11           O
HETATM 7752  O    HOH H 221     -13.946  23.906 -49.372  0.50 17.58           O
HETATM 7753  O    HOH H 222      -4.813  28.390 -30.701  0.50 17.77           O
HETATM 7754  O    HOH H 224     -10.822  42.864 -46.199  0.50 42.59           O
HETATM 7755  O    HOH H 225     -17.419  56.501 -23.670  0.50 27.18           O
HETATM 7756  O    HOH H 226       1.087  24.694 -40.461  0.50 26.11           O
HETATM 7757  O    HOH H 227     -39.437  40.241 -52.531  0.50 60.61           O
HETATM 7758  O    HOH H 228       7.409  25.160 -55.322  0.50 30.02           O
HETATM 7759  O    HOH H 229     -14.702  16.016 -48.070  0.50 32.71           O
HETATM 7760  O    HOH H 230     -56.374  44.489 -58.431  0.50 32.19           O
HETATM 7761  O    HOH H 231     -41.895  37.391 -57.521  0.50 18.11           O
HETATM 7762  O    HOH H 232     -22.975  30.621 -18.933  0.50 24.23           O
HETATM 7763  O    HOH H 233      -5.574  10.898 -54.789  0.50 37.98           O
HETATM 7764  O    HOH H 234     -48.030  58.004 -66.893  0.50 33.16           O
HETATM 7765  O    HOH H 235     -13.606  42.696 -30.315  0.50 21.79           O
HETATM 7766  O    HOH H 236     -52.235  51.690 -57.927  0.50 23.44           O
HETATM 7767  O    HOH H 237     -40.438  40.586 -54.154  0.50 28.38           O
HETATM 7768  O    HOH H 238     -12.495  26.706 -49.008  0.50 32.21           O
HETATM 7769  O    HOH H 239     -23.932  15.273 -31.945  0.50 40.77           O
HETATM 7770  O    HOH H 240     -25.414  34.274 -44.149  0.50 48.28           O
HETATM 7771  O    HOH H 241     -15.156  11.732 -29.828  0.50 21.26           O
HETATM 7772  O    HOH H 242     -58.432  46.242 -65.973  0.50 29.19           O
HETATM 7773  O    HOH H 243     -29.292  41.508 -20.831  0.50 36.45           O
HETATM 7774  O    HOH H 244     -48.531  40.068 -38.378  0.50 18.93           O
HETATM 7775  O    HOH H 245      -7.283  27.714 -69.980  0.50 43.27           O
HETATM 7776  O    HOH H 246     -45.408  38.842 -66.444  0.50 28.87           O
HETATM 7777  O    HOH H 247     -10.063  17.880 -48.898  0.50 11.45           O
HETATM 7778  O    HOH H 248     -13.548  22.190 -43.781  0.50 21.78           O
HETATM 7779  O    HOH H 249     -33.321  54.265 -34.828  0.50 17.44           O
HETATM 7780  O    HOH H 250     -25.039  60.676 -71.005  0.50 33.86           O
HETATM 7781  O    HOH H 251     -24.072  55.610 -68.933  0.50 32.93           O
HETATM 7782  O    HOH H 252     -20.489  16.095 -20.390  0.50 42.65           O
HETATM 7783  O    HOH H 253     -23.248  54.913 -42.141  0.50 35.68           O
HETATM 7784  O    HOH H 254       1.222  38.444 -44.947  0.50 25.80           O
HETATM 7785  O    HOH H 255     -35.877  50.370 -78.953  0.50 20.69           O
HETATM 7786  O    HOH H 256     -17.614  13.592 -56.831  0.50 28.74           O
HETATM 7787  O    HOH H 257     -15.446  18.308 -24.650  0.50 30.14           O
HETATM 7788  O    HOH H 258     -12.715  51.713 -25.059  0.50 32.99           O
HETATM 7789  O    HOH H 259     -14.319  21.951 -51.962  0.50 30.02           O
HETATM 7790  O    HOH H 260     -31.313  40.933 -43.705  0.50 30.53           O
HETATM 7791  O    HOH H 261     -31.737  47.694 -64.732  0.50 28.06           O
HETATM 7792  O    HOH H 262     -39.993  58.409 -72.901  0.50 26.42           O
HETATM 7793  O    HOH H 263     -21.919  36.486 -45.360  0.50 17.35           O
HETATM 7794  O    HOH H 264     -36.486  52.885 -50.121  0.50 20.10           O
HETATM 7795  O    HOH H 265      -0.092  33.201 -46.027  0.50 19.84           O
HETATM 7796  O    HOH H 266      -1.279  20.785 -40.683  0.50  5.36           O
HETATM 7797  O    HOH H 267      -8.938  16.177 -36.396  0.50 19.90           O
HETATM 7798  O    HOH H 268     -42.263  27.234 -44.151  0.50 23.95           O
HETATM 7800  O    HOH H 270     -36.480  42.453 -51.106  0.50 21.56           O
HETATM 7801  O    HOH H 271     -51.441  47.263 -73.336  0.50 35.14           O
HETATM 7802  O    HOH H 272     -15.504  15.792 -30.522  0.50 18.18           O
HETATM 7803  O    HOH H 273     -37.106  28.561 -47.657  0.50 26.89           O
HETATM 7804  O    HOH H 274     -16.098  25.416 -46.188  0.50 36.36           O
HETATM 7805  O    HOH H 276     -19.075  22.625 -71.632  0.50 30.17           O
HETATM 7806  O    HOH H 277     -48.666  35.783 -53.822  0.50 17.48           O
HETATM 7807  O    HOH H 278      -6.860  40.231 -50.287  0.50 45.10           O
HETATM 7808  O    HOH H 279     -41.136  55.547 -80.968  0.50 26.44           O
HETATM 7809  O    HOH H 280     -49.936  34.061 -38.767  0.50 31.99           O
HETATM 7810  O    HOH H 281     -28.594  44.315 -20.466  0.50 27.76           O
HETATM 7811  O    HOH H 282     -23.289  35.324 -43.304  0.50 15.92           O
HETATM 7812  O    HOH H 283     -24.856  48.276 -65.818  0.50 41.46           O
HETATM 7813  O    HOH H 284     -51.657  42.628 -71.440  0.50 39.77           O
HETATM 7814  O    HOH H 285     -20.137  43.769 -19.546  0.50 27.16           O
HETATM 7815  O    HOH H 286     -31.312  47.808 -20.580  0.50 17.75           O
```

Figure 27 (Continued)

```
HETATM 7816  O   HOH H 287     -19.629  43.004 -45.441  0.50 31.77           O
HETATM 7817  O   HOH H 288     -47.478  36.826 -35.596  0.50 25.80           O
HETATM 7818  O   HOH H 289      -8.704  33.187 -29.985  0.50 22.66           O
HETATM 7819  O   HOH H 290     -10.405  25.420 -49.129  0.50 34.85           O
HETATM 7820  O   HOH H 291     -21.120  10.682 -30.881  0.50 26.37           O
HETATM 7821  O   HOH H 292      -7.217  39.678 -35.207  0.50 28.30           O
HETATM 7822  O   HOH H 293     -18.840  52.328 -33.071  0.50 34.97           O
HETATM 7823  O   HOH H 294     -19.487  35.839 -20.401  0.50 32.51           O
HETATM 7824  O   HOH H 295     -18.626  18.840 -22.216  0.50 40.45           O
HETATM 7825  O   HOH H 296      -0.777  14.105 -42.790  0.50 30.76           O
HETATM 7826  O   HOH H 297     -35.518  44.331 -51.835  0.50 27.87           O
HETATM 7827  O   HOH H 298      -5.635  27.827 -28.020  0.50 35.19           O
HETATM 7829  O   HOH H 300     -17.431  55.572 -30.190  0.50 37.47           O
HETATM 7830  O   HOH H 301     -50.025  55.343 -51.683  0.50 26.34           O
HETATM 7831  O   HOH H 302     -28.029  55.833 -82.227  0.50 35.47           O
HETATM 7832  O   HOH H 303     -16.440  20.602 -23.557  0.50 28.32           O
HETATM 7833  O   HOH H 304     -22.361  14.947 -25.828  0.50 24.84           O
HETATM 7834  O   HOH H 305     -39.586  35.591 -26.238  0.50 42.53           O
HETATM 7835  O   HOH H 306     -17.006  10.518 -61.160  0.50 34.81           O
HETATM 7836  O   HOH H 307     -23.923  47.341 -41.816  0.50 38.28           O
HETATM 7837  O   HOH H 308       0.303  34.809 -56.984  0.50 33.63           O
HETATM 7838  O   HOH H 309     -55.525  42.489 -44.879  0.50 29.59           O
HETATM 7839  O   HOH H 310     -12.398  53.660 -25.755  0.50 44.38           O
HETATM 7840  O   HOH H 311     -36.212  37.767 -18.720  0.50 32.90           O
HETATM 7841  O   HOH H 312     -51.713  41.728 -69.270  0.50 33.79           O
HETATM 7842  O   HOH H 313     -26.113  43.238 -20.380  0.50 25.79           O
HETATM 7844  O   HOH H 315      -1.011  20.958 -38.614  0.50 32.30           O
HETATM 7845  O   HOH H 316     -15.948  15.085 -75.438  0.50 30.83           O
HETATM 7846  O   HOH H 317     -32.584  56.769 -66.181  0.50 31.03           O
HETATM 7848  O   HOH H 321     -22.003  25.832 -55.085  0.50 35.72           O
HETATM 7849  O   HOH H 322     -39.536  56.837 -46.773  0.50 32.93           O
HETATM 7850  O   HOH H 323     -23.260  43.084 -17.966  0.50 45.29           O
HETATM 7851  O   HOH H 324     -50.902  31.757 -40.163  0.50 28.67           O
HETATM 7852  O   HOH H 325     -36.392  18.468 -54.271  0.50 35.90           O
HETATM 7853  O   HOH H 326      -7.554  35.157 -52.958  0.50 26.31           O
HETATM 7854  O   HOH H 327     -29.183  56.418 -64.475  0.50 37.29           O
HETATM 7855  O   HOH H 328     -29.585  29.177 -45.026  0.50 28.30           O
HETATM 7856  O   HOH H 329       2.317  20.715 -38.753  0.50 54.22           O
HETATM 7857  O   HOH H 330     -43.267  34.011 -55.079  0.50 50.26           O
HETATM 7858  O   HOH H 331     -41.468  36.332 -55.057  0.50 31.01           O
HETATM 7859  O   HOH H 332     -25.485  46.957 -63.414  0.50 38.29           O
HETATM 7860  O   HOH H 333     -31.771  49.576 -62.879  0.50 32.49           O
HETATM 7861  O   HOH H 334     -49.248  47.909 -75.919  0.50 31.13           O
HETATM 7862  O   HOH H 335      -5.417  10.521 -66.574  0.50 33.36           O
HETATM 7863  O   HOH H 336      -1.437  28.379 -63.382  0.50 33.95           O
HETATM 7864  O   HOH H 337      -2.105  28.105 -66.587  0.50 52.67           O
HETATM 7865  O   HOH H 338     -41.133  58.696 -70.282  0.50 28.17           O
HETATM 7866  O   HOH H 339      -1.298  33.879 -36.455  0.50 28.98           O
HETATM 7867  O   HOH H 340     -22.361  27.086 -42.818  0.50 29.94           O
HETATM 7868  O   HOH H 341     -12.712  25.895 -22.897  0.50 39.15           O
HETATM 7869  O   HOH H 342     -48.474  41.646 -73.541  0.50 32.97           O
HETATM 7870  O   HOH H 343       0.441  14.411 -53.528  0.50 35.29           O
HETATM 7871  O   HOH H 344     -29.069  32.651 -19.292  0.50 31.24           O
HETATM 7872  O   HOH H 345     -17.322  18.327 -20.005  0.50 38.32           O
HETATM 7873  O   HOH H 346       0.010  12.954 -48.944  0.50 35.44           O
HETATM 7874  O   HOH H 347       1.260  22.610 -34.302  0.50 34.28           O
HETATM 7875  O   HOH H 348     -13.727  13.142 -27.596  0.50 25.68           O
HETATM 7876  O   HOH H 349     -47.191  38.043 -68.279  0.50 37.65           O
HETATM 7877  O   HOH H 350     -34.910  58.371 -64.614  0.50 27.77           O
HETATM 7878  O   HOH H 351       7.547  30.455 -54.331  0.50 36.69           O
HETATM 7879  O   HOH H 352     -38.588  37.122 -27.301  0.50 40.94           O
HETATM 7880  O   HOH H 353     -49.845  37.392 -66.080  0.50 30.74           O
HETATM 7881  O   HOH H 356     -58.389  42.542 -57.846  0.50 38.23           O
HETATM 7882  O   HOH H 357      -0.576  23.252 -36.721  0.50 25.39           O
```

Figure 27 (Continued)

```
HETATM 7883  O   HOH H 359      -6.390  23.458 -27.446  0.50 43.34           O
HETATM 7884  O   HOH H 360       6.869  20.711 -50.700  0.50 38.58           O
HETATM 7885  O   HOH H 361     -10.204  28.382 -51.352  0.50 34.05           O
HETATM 7886  O   HOH H 362     -56.341  45.984 -47.877  0.50 33.64           O
HETATM 7887  O   HOH H 363     -18.706  54.442 -41.492  0.50 29.68           O
HETATM 7889  O   HOH H 365       1.766  38.257 -41.076  0.50 16.51           O
HETATM 7890  O   HOH H 366     -32.603  35.537 -48.089  0.50 28.47           O
HETATM 7891  O   HOH H 367      -4.815  27.682 -65.235  0.50 27.04           O
HETATM 7892  O   HOH H 368     -28.451  30.662 -18.070  0.50 25.07           O
HETATM 7893  O   HOH H 369       5.435  20.657 -53.449  0.50 27.34           O
HETATM 7894  O   HOH H 370     -54.530  49.792 -56.051  0.50 43.42           O
HETATM 7895  O   HOH H 372      -6.942  10.164 -67.026  0.50 33.65           O
HETATM 7896  O   HOH H 373     -42.522  37.827 -64.689  0.50 29.56           O
HETATM 7897  O   HOH H 374     -40.115  54.771 -83.685  0.50 30.38           O
HETATM 7898  O   HOH H 375     -19.084  11.092 -23.624  0.50 30.40           O
HETATM 7899  O   HOH H 376     -49.702  32.755 -51.284  0.50 25.05           O
HETATM 7900  O   HOH H 378     -21.884  24.947 -43.414  0.50 30.26           O
HETATM 7901  O   HOH H 380     -22.951  56.756 -31.738  0.50 33.38           O
HETATM 7902  O   HOH H 381     -37.268  41.435 -22.240  0.50 40.44           O
HETATM 7903  O   HOH H 382      -6.220   6.779 -61.811  0.50 33.26           O
HETATM 7904  O   HOH H 383     -29.426  23.392 -38.600  0.50 22.12           O
HETATM 7905  O   HOH H 384      -4.526  10.743 -64.161  0.50 32.17           O
HETATM 7906  O   HOH H 386     -30.390  61.671 -77.862  0.50 31.41           O
HETATM 7907  O   HOH H 387     -13.633  17.612 -34.321  0.50 24.35           O
HETATM 7908  O   HOH H 388     -29.620  24.816 -40.650  0.50 37.83           O
HETATM 7909  O   HOH H 389     -35.597  46.560 -53.549  0.50 23.29           O
HETATM 7910  O   HOH H 390     -33.809  44.943 -55.534  0.50 24.53           O
```

CRYSTAL STRUCTURES OF HETERODIMERIC FC DOMAINS

CROSS REFERENCE TO RELATED APPLICATIONS

This application is a Continuation-in-part of U.S. application Ser. No. 13/668,098, filed Nov. 2, 2012, entitled "Stable Heterodimeric Antibody Design with Mutations in the Fc Domain", and claims priority to U.S. Provisional Application No. 61/813,084, filed Apr. 17, 2013, each of which is hereby incorporated by reference in its entirety.

TECHNICAL FIELD

The present disclosure relates to Fc heterodimer proteins in crystalline form, a cystallizable composition comprising such Fc heterodimer proteins, and methods for identifying mutations which promote heterodimeric Fc chain pair formation.

BACKGROUND

There is a drive in the pharmaceutical industry towards the development of bispecific therapeutics that can concurrently bind two or more distinct targets or epitopes in order to achieve novel mechanisms of action and efficacy. See, Beck et al., 2010, Nature Reviews, Immunology 10: 345-352; Carter, 2011, Experimental Cell Research 317: 1261-1269; Kontermann, 2012, mABs 4: 182-197; and Segal et al., 2001, Journal of Immunology Methods 248:1-6. In recent years, a number of bispecific formats based on either antibody or other protein domains have been designed with the goal of creating a modular molecular scaffold. See, Kontermann, 2012, mABs 4:182-197; and Klein et al., 2012, mABs 27:4(6). From this, it is clear that modular multi-domain, multi-functional monoclonal antibodies, with their intrinsic therapeutically relevant features combined with the experiences gained in the biopharmaceutical development of these molecules as therapeutics, makes this class of molecules an attractive molecular class for pharmaceutical development provided that such molecules do not substantially deviate from their native structural and functional characteristics.

Initial IgG-like bispecific antibody development centered on use of a hybrid hybridoma of two cells that produces two different antibodies of interest. See, Milstein and Cuello, 1983, Nature 305: 537-540. Co-expression of the four different antibody chains (two heavy and two light) in such a fused cell leads to the non-selective formation of up to ten different combinations of heavy and light chain pairs, from which the one correct bispecific molecule is recovered through laborious purification. Improving on this, some workers have used either natural or engineered differences in Protein A binding affinities of the two antibody heavy chains for selective isolation of the heterodimer from the homodimers. See Lindhofer et al., 1995, Journal of Immunology 155: 219-225; Igawa and Tsunoda, 2007, United States Patent Publication No. 2009/0263392 A1; Davis and Smith, 2010, "Readily Isolated Bispecific Antibodies with Native Immunoglobulin Format", United States Patent Publication No. 2010/00331527; and Klein et al., 2012, MAbs. 27:4(6). The bispecific antibody of interest that is obtained in any of these non-selective chain pairing expression strategies appears to be limited to a maximum of 12.5% of the total antibody yield in cases where both light-heavy and heavy-heavy chain pairing is essential or 50% if selective light-heavy chain pairing requirement is abrogated such as by using a common light chain. In either case this approach will significantly impact the cost of goods.

In order to overcome this impact and diminish the formation of unwanted Fc chain pairs, structure guided attempts to engineer mutations resulting in selective pairing of preferred heavy chains when co-expressed in a recombinant manner is desirable. Prominent among these rational design efforts is the knob-into-hole strategy, developed by Presta, Carter and coworkers, which employs steric point mutations in the CH3-CH3 interface to preferentially drive Fc heterodimerisation and prevent formation of homodimers. See, Ridgway and Presta, 1996, Protein Engineering 9: 617-621; Merchant et al. 1998, Nature Biotechnology 17: 677-681; and Atwell et al., 1997, Journal of Molecular Biology 270: 26-35. Such designs have yielded high heterodimer selectivity, but have caused about 11° C. lowering in thermal stability of the CH3 domain relative to the wild type. In contrast to this steric complementarity approach in the knob-into-hole designs, Gunasekaran and coworkers have recently employed electrostatic complementarity design strategy to achieve the selective heterodimerization goal. See, Gunasekaran et al., 2010, The Journal of Biological Chemistry 285: 19637-19646. Davis and coworkers have designed strand exchange engineered domain (SEED) CH3 which is comprised of alternating segments of human IgA and IgG CH3 sequences leading to preferentially associating heterodimers. See Davis et al., 2010, PEDS 23: 195-202. The engineered CH3 domains of both these approaches have melting temperatures of the CH3 domains of ~68° C.

Alternately, an annealing based approach for producing bispecific antibodies by mixing two different antibodies has been pursued in other technologies. See Jackman et al., 2010, J. Biol. Chem 285: 20850-20859; and Strop et al., 2012, J. Mol. Biol. 420, 204-219. These rational engineering approaches favor heterodimer formation by destabilizing the natural homodimer interface and result in antibodies comprising less stable CH3 domains than the parent molecule. A protein with reduced stability of its native folded state is potentially prone to a number of aggregation related challenges in its handling and development. See, Wang, 2005, International Journal of Pharmaceutics 289: 1-30; and Demarest et al., 2008, Current Opinion in Drug Discovery and Development 11: 675-687. Further, the mutations in the IgG Fc region and the reduced stability of the CH3 domain could have an impact on immunogenicity and pharmacokinetic properties, which are important drug like properties that have to be validated for successful design of a modular bispecific scaffold.

Given the above background, there is a need in the art for Fc heterodimer proteins in crystalline form, cystallizable compositions comprising such Fc heterodimer proteins, and methods for identifying mutations which promote heterodimeric Fc chain pair formation. Such articles and methods are needed in order to develop polypeptide constructs that comprise antigen-binding domains that are linked to an Fc heterodimer protein comprising CH3 domains which have been modified to select for heterodimers with favorable drug-like properties such as ease of manufacturing and analytical characterization; formulation and stability of the therapeutic at the requisite drug concentrations; and pharmacokinetic properties, immunogenicity and toxicity that are similar to Fc heterodimer proteins without a modified CH3 domain. An antibody platform that takes into consideration all of these aspects concurrently would significantly empower the drug developer in the design of best-in-class bi- and multi-specific therapeutic candidates.

SUMMARY

The disclosed embodiments address the needs presented in the prior art. Disclosed are the atomic coordinates of compositions comprising Fc heterodimer proteins in crystalline form derived from high resolution x-ray diffraction. Further disclosed are systems and methods for using all or a portion of these atomic coordinates to identify and design improved Fc heterodimer proteins. Further disclosed are compositions comprising a mixture of (i) a solubilized Fc heterodimer protein and (ii) a mother liquor solution. The mother liquor solution comprises between 2% and 10% (v/v) ethylene glycol, between 10% and 25% (w/v) polyethylene glycol having an average molecular weight of between 2000 Daltons and 10000 Daltons, and between 0.05 M and 0.40 M ammonium iodide. Further disclosed are systems and methods of identifying a mutation which promotes heterodimeric Fc chain pair formation in which structure based modeling is performed to identify a candidate mutation to an Fc chain using all or a portion of the disclosed three-dimensional atomic coordinates.

One aspect of the present disclosure provides a composition comprising an Fc heterodimer protein in crystalline form. In this aspect, the Fc heterodimer protein comprises the amino acid sequences set forth in (i) SEQ ID NOS: 2 and 3 or (ii) SEQ ID NOS: 4 and 5 of FIG. 16. The crystal is in space group $P2_12_12_1$ with unit cell dimensions a=49±2 Å, b=75±2 Å, c=149±2 Å, α=β=γ=90°. In some embodiments, the Fc heterodimer protein comprises the amino acid sequences set forth in SEQ ID NOS: 2 and 3 and has a three dimensional structure characterized by the atomic coordinates of (i) chains A and B of FIG. 27 or (ii) chains a and b of FIG. 27. In some embodiments, the Fc heterodimer protein comprises the amino acid sequences set forth in SEQ ID NOS: 4 and 5 and has a three dimensional structure characterized by the atomic coordinates of (i) chains A and B of FIG. 26 or (ii) chains a and b of FIG. 26. In some embodiments, the Fc heterodimer protein comprises the amino acid sequences set forth in SEQ ID NOS: 2 and 3 forming a CH3 domain interface, and the Fc heterodimer protein provides complementary hydrophobic and electrostatic surfaces, created by residues 366, 392, 394 of SEQ ID NO: 2 and residues 351, 405, 407 of SEQ ID NO: 3, at the CH3 domain interface with distinct surface complementarity relative to wild type Fc interface surfaces. In some embodiments, the Fc heterodimer protein comprises the amino acid sequences set forth in SEQ ID NOS: 2 and 3 forming a CH3 domain interface, and the Fc heterodimer protein provides complementary hydrophobic and electrostatic surfaces, created by residues 366, 392, 394 of SEQ ID NO: 3 and residues 351, 405, 407 of SEQ ID NO: 2, at the CH3 domain interface with distinct surface complementarity relative to wild type Fc interface surfaces. In some embodiments, the Fc heterodimer protein comprises the amino acid sequences set forth in SEQ ID NOS: 4 and 5 forming a CH3 domain interface, and the Fc heterodimer protein provides complementary hydrophobic and electrostatic surfaces, created by residues 366, 392, 394 of SEQ ID NO: 4 and residues 351, 405, 407 of SEQ ID NO: 5, at the CH3 domain interface with distinct surface complementarity relative to corresponding wild type Fc interface surfaces. In some embodiments, the Fc heterodimer protein comprises the amino acid sequences set forth in SEQ ID NOS: 4 and 5 forming a CH3 domain interface, and the Fc heterodimer protein provides complementary hydrophobic and electrostatic surfaces, created by residues 366, 392, 394 of SEQ ID NO: 5 and residues 351, 405, 407 of SEQ ID NO: 4, at the CH3 domain interface with distinct surface complementarity relative to corresponding wild type Fc interface surfaces. In some embodiments, the Fc heterodimer protein comprises a D399-K409 salt bridge.

Another aspect provides a method of obtaining the above-identified composition by producing and purifying the Fc heterodimer protein and subjecting the purified Fc heterodimer protein to conditions which promote crystallization, thereby obtaining the Fc heterodimer protein in crystalline form. In some embodiments, the conditions which promote crystallization comprise mixing the purified Fc heterodimer protein with a mother liquor solution. In some embodiments the mother liquor solution comprises between 2% and 10% (v/v) ethylene glycol, between 10% and 25% (w/v) polyethylene glycol having an average molecular weight of between 2000 Daltons and 10000 Daltons, and between 0.05 M and 0.40 M ammonium iodide. In some embodiments, the mother liquor solution comprises 5% (v/v/) ethylene glycol, 18% (w/v) polyethylene glycol having an average molecular weight of 3350 Daltons, and 0.15 M ammonium iodide. In some embodiments, the purified Fc heterodimer protein is mixed with a first aliquot of the mother liquor solution and suspended over a second aliquot of the mother liquor in a hanging drop method. In some embodiments, the purified Fc heterodimer protein is mixed with a first aliquot of the mother liquor solution in a 2:1 ratio, a 1:1 ratio, a 3:1 ratio, or a 0.5:2 ratio. In some embodiments, a sitting drop method rather than a hanging drop method is used. In some embodiments, the purified Fc heterodimer protein is incubated at a temperature of between 15° C. and 25° C. after the mixing.

Another aspect provides a crystallizable composition comprising a mixture of (i) a solubilized Fc heterodimer protein comprising the amino acid sequence set forth in (a) SEQ ID NOS: 2 and 3 or (b) SEQ ID NOS: 3 and 4 of FIG. 16 and (ii) a mother liquor solution. The mother liquor solution comprises between 2% and 10% (v/v) ethylene glycol, between 10% and 25% (w/v) polyethylene glycol having an average molecular weight of between 2000 Daltons and 10000 Daltons, and between 0.05 M and 0.40 M ammonium iodide. In some embodiments, the mother liquor solution comprises 5% (v/v/) ethylene glycol, 18% (w/v) polyethylene glycol having an average molecular weight of 3350 Daltons, and 0.15 M ammonium iodide.

Another aspect provides a method of identifying a mutation which promotes heterodimeric Fc chain pair formation. The method comprises performing structure based modeling, using a suitably programmed computer, to identify a candidate mutation to an Fc chain using a three-dimensional atomic crystal structure of an Fc heterodimer protein which is defined by the atomic coordinates of any combination of chains a, b, A, and B of FIG. 26 or 27 determined from an X-ray diffraction quality crystal of the Fc heterodimer protein. The Fc heterodimer protein comprises the amino acid sequences as set forth in (i) SEQ ID NOS: 2 and 3 or (ii) SEQ ID NOS: 4 and 5, and the X-ray diffraction quality crystal is in an orthorhombic space group. In some embodiments, the orthorhombic space group is $P2_12_12_1$ and has unit cell dimensions a=49±2 Å, b=75±2 Å, c=149±2 Å, α=β=γ=90°. In some embodiments, the structure based modeling comprises (a) identifying a plurality of residues on the three-dimensional structure that influence heterodimeric Fc chain pair formation, (b) modeling a plurality of three-dimensional Fc structures using the three-dimensional atomic crystal structure as a template, wherein each three-dimensional Fc structure in the plurality of three-dimensional Fc structures includes mutations to one or more of the residues in the plurality of residues, (c) comparing each three-dimensional Fc structure in the plurality of three-dimensional Fc structures to the three-dimensional atomic crystal structure, and (d) selecting one of the three-dimensional Fc structure in the plurality of three-dimensional Fc structures based on the comparing (c). In some embodiments, the comparing (c) compares a calculated thermodynamic property of the three-dimensional atomic crystal structure to a calculated thermodynamic property of a three-dimensional Fc structure in the plurality of three-dimensional Fc structures. In some embodiments, the thermodynamic property is entropy, average energy, average enthalpy, free energy or heat capacity. In some embodiments, the comparing (c) compares a physical property of the three-dimensional atomic crystal structure to a calculated thermodynamic property of a three-dimensional Fc structure in the plurality of three-dimensional Fc structures, where the physical property is selected from the group consisting of (i) one or more electrostatic interactions, (ii) one or more polar interactions, (iii) one or more hydrogen-bond interactions, (iv) a comparison of buried versus accessible surface area, (v) accessible surface area, (vi) one or more hydrophobic interactions, and (vii) presence or absence of one or more buried water molecules.

BRIEF DESCRIPTION OF THE FIGURES

FIG. 8 summarizes the backbone RMSD (root mean square deviation) calculations of alignments of respective crystal structures over the dimeric CH3-CH3 domains in accordance with some embodiments of the present disclosure.

FIG. 10 shows the FcgR binding affinities of the disclosed constructs, AZ1 and AZ2, relative to Trastuzumab wild type, in accordance with some embodiments of the present disclosure.

FIG. 14 summarizes FcRn binding affinities for Trastuzumab WT, and trastuzumab-based heterodimeric antibodies anti-her2-AZ1, and anti-her2(Herceptin)-AZ2, in accordance with some embodiments of the present disclosure.

FIG. 16 provides the primary amino acid sequences of AZ1 and AZ2, and the amino acid sequence of the portion of immunoglobulin G 1 (IgG1) isotype that served as the starting point to the derivation of AZ1 and AZ2, in accordance with some embodiments of the present disclosure.

FIG. 24 shows a comparison of wild type IgG1 Fc and ZW1 and illustrates the second shell, distal position of the key stabilizing mutation T350V.

FIG. 25 provides the amino acid numbering used herein according to the EU index as set forth in Kabat for the CH2 and CH3 domains from human IgG1. See, Kabat et al., 1991, NIH Publication 91-3242, National Technical Information Service, Springfield, Va.

FIG. 26 provides the structure coordinates for AZ2 (including SEQ ID NO: 4 and SEQ ID NO.: 5) in accordance with some embodiments of the present disclosure.

FIG. 27 provides the structure coordinates for AZ1 (including SEQ ID NO: 2 and SEQ ID NO.: 3) in accordance with some embodiments of the present disclosure.

DETAILED DESCRIPTION

Figure 1:
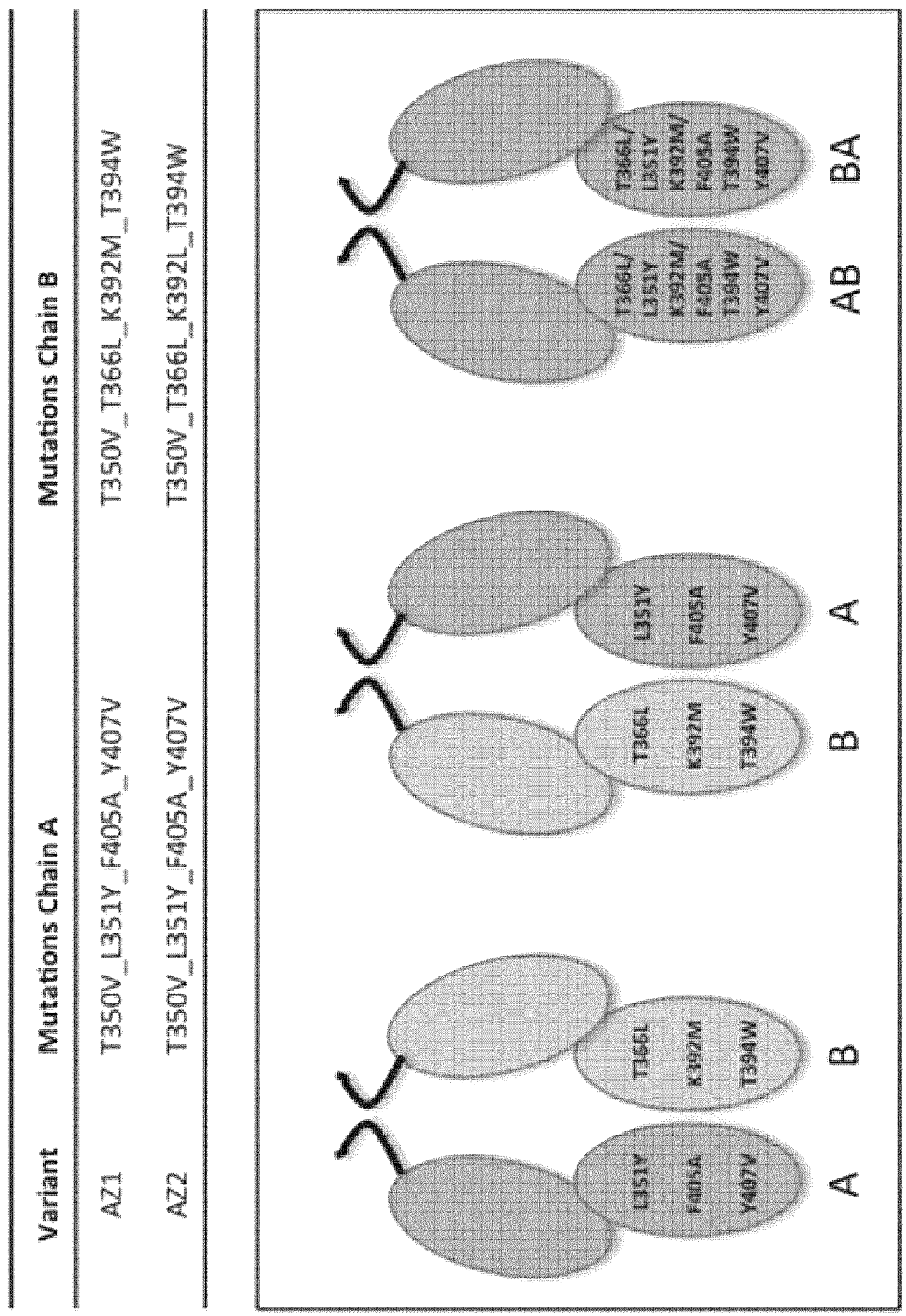
FIG. 1 provides an illustration of the two observed orientations of the Fc heterodimers AZ1 and AZ2, with respect to Chain A and Chain B in the crystal, in accordance with an embodiment of the present disclosure.

A rational structure and computational modeling guided IgG1 Fc engineering effort to preferentially achieve heterodimeric Fc proteins with wild type Fc like stability is disclosed. The engineering approach utilizes distinct mutations at the CH3 interface to preferentially drive heterodimer formation and prevent the formation of homodimers. The designed heterodimer achieves over 99% purity while retaining the wild type Fc like stability, as demonstrated by thermal melting (CH3 Tm of ~82° C.) and accelerated aggregation assessment under forced degradation conditions. Further, validation of the Fc heterodimer protein by stable cell line development and early manufacturability assessment shows no impact of the CH3 mutations on the preferred wild type Fc stability.

Independent of the high specificity and stability of the designed Fc heterodimeric proteins, an additional requirement for the successful design of bispecific heterodimeric antibodies includes one or more of favorable pharmacokinetic properties, Fc effector function and decreased immunogenicity. To ensure these drug-like properties, it is desirable to preserve the wild type Fc surface characteristics and retain the natural symmetry of the wild type Fc. Introduction of asymmetric steric or electrostatic mutations at the CH3 interface as in the case of prior studies, can potentially also induce an asymmetry or shift in the naturally symmetric orientation of the two CH3 domains. This leads to an altered Fc surface area and likely presents a significantly higher risk of immunogenicity and optimal pharmacokinetic properties. In addition, distal CH3 mutations have been shown to alter FcgammaR binding and thus, breaking the natural CH3 symmetry by mutations in the CH3 interface can similarly impact the wild type Fc functionality. See, Shields et al., 2001, Journal of Biological Chemistry 276: 6591-6604. Thus, retaining the natural CH3 symmetry is likely an important consideration to ensure wild type like Fc functionality, optimal pharmacokinetic properties and low immunogenicity.

To investigate the impact of the CH3 interface mutations of the disclosed Fc heterodimeric proteins on the preferred wild type IgG structure and properties and to further validate the disclosed scaffold, the crystal structures of two such Fc heterodimeric proteins along with experimental data to assess Fc effector functionality and pharmacokinetic properties was elucidated and is disclosed herein.

In order that the invention described herein may be more fully understood, the following detailed description is set forth.

Throughout the specification, the word "comprise" or variations such as "comprises" or "comprising" will be understood to imply the inclusion of a stated integer or groups of integers but not the exclusion of any other integer or groups of integers.

The following abbreviations are used throughout the application:

The following abbreviations are used herein for amino acids: A=Ala=alanine; T=Thr=threonine; V=Val=valine; C=Cys=cysteine; L=Leu=leucine; Y=Tyr=tyrosine; I=Ile=isoleucine, N=Asn=asparagine; P=Pro=proline; Q=Gln=glutamine; F=Phe=phenylalanine; D=Asp=aspartic acid; W=Trp=tryptophan; E=Glu=glutamic acid; M=Met=methionine; K=Lys=lysine; G=Gly=glycine; R=Arg=arginine; S=Ser=serine; and H=His=histidine;

As used herein, the following definitions shall apply unless otherwise indicated. Also, combinations of substituents or variables are permissible only if such combinations result in stable compounds.

The term "about" when used in the context of RMSD (root mean square deviation) values takes into consideration the standard error of the RMSD value, which is ±0.1 Å.

The term "aliphatic" refers to straight chain or branched hydrocarbons that are completely saturated or that contain one or more units of unsaturation. For example, aliphatic groups include substituted or unsubstituted linear or branched alkyl, alkenyl and alkynyl groups. Unless indicated otherwise, the term "aliphatic" encompasses both substituted and unsubstituted hydrocarbons. The term "alkyl", used alone or as part of a larger moiety, refers to both straight and branched saturated chains containing one to twelve carbon atoms. The terms "alkenyl" and "alkynyl", used alone or as part of a larger moiety, encompass both straight and branched chains containing two to twelve carbon atoms and at least one unit of unsaturation. An alkenyl group contains at least one carbon-carbon double bond and an alkynyl group contains at least one carbon-carbon triple bond.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of a complex or native macromolecular structure.

The term "CH3-CH3 domain" refers to the pair of CH3 domains that are part of the IgG antibody Fc structure. The CH3 domain in each of the two chains of the Fc interface contact the complementary chain at the CH3 domain interface (also referred to herein as "CH3 interface").

The term "CH2-CH3 domain" refers to the CH2 and CH3 domains present in tandem in each of the two chains of IgG antibody. An Fc structure comprises two CH2-CH3 domains.

The term "Fc heterodimer protein" refers to an Fc structure in which the two chains constituting the Fc structure do not have the same primary protein sequence. The primary protein sequence of both the CH3 domains in a native (wild type) IgG1 antibody is the same leading to the formation of a homodimeric Fc structure. On the other hand, engineering at the CH3-CH3 domain interface is performed to achieve a Fc heterodimer protein wherein the two CH3 domains no longer have the same primary protein sequence.

The term "heterodimeric Fc chain pair" refers to the two polypeptide chains constituting the Fc structure where the two polypeptide chains do not have the same primary protein sequence.

Disclosed is a transferable immunglobulin G-based Fc heterodimeric protein which achieves over 99% heterodimer purity while retaining wild type Fc-like stability. The Fc heterodimeric protein is a scaffold that can be used to prepare bispecific heterodimeric antibodies. The Fc heterodimeric protein has been successfully validated for stable cell line development and early manufacturability assessment using industry standard processes for cell line and downstream process development. Apart from the manufacturability of the bispecific heterodimeric antibodies other additional requirements for successful design of a therapeutic scaffold include favorable pharmacokinetic properties, Fc effector function and low immunogenicity. This is particularly important in the development of bispecific heterodimeric IgG1 like scaffolds, where the introduction of mutations in the IgG constant region and the resulting reduced stability of the CH3 domain, as is observed in a number of other bispecific scaffolds, could have an impact on immunogenicity and the preferred pharmacokinetic properties. To ensure these drug-like properties in the development of a modular scaffold, it is important to also validate that the engineered Fc mutations in the bispecific scaffold preserve the wild type Fc surface characteristics and retain the natural symmetry of the wild type Fc, as these are determinants of immunogenicity and Fc effector function.

Rational Engineering Strategy.

The design of variant Fc heterodimeric proteins from wild type homodimers is illustrated by the concept of positive and negative design in the context of protein engineering by balancing stability vs. specificity, in which mutations are introduced with the goal of driving heterodimer formation over homodimer formation. Negative design strategies focus on maximizing unfavorable interactions for the formation of homodimers, by e.g. introducing mutations that lead to steric clashes or electrostatic repulsion in homodimer formation. In contrast, in positive design approaches, amino acid modifications are introduced into polypeptides to maximize favorable interactions within or between proteins. This strategy assumes that when introducing multiple mutations that specifically stabilize the desired heterodimer while neglecting the effect on the homodimers, the net effect will be a preference for the desired heterodimer interactions over the homodimers and hence a greater heterodimer specificity. It is understood in the context of protein engineering that positive design strategies optimize the stability of the desired protein interactions, but rarely achieve >90% specificity, whereas negative design approaches have successfully been employed to achieve close to 100% specificity, but with significant loss in stability of the desired product.

A challenge in protein-protein engineering for altered specificity and in designing heterodimers from natural homodimers is to achieve close to 100% specificity while maintaining the wild-type complex/homodimer affinity and stability. This is likely more challenging if the natural complex has a high affinity and complex stability, like e.g. the Fc CH3-CH3 domain, which has been reported to have a natural affinity in the pM range.

This challenge is reflected in the Fc heterodimeric protein designs by point mutations in the CH3-CH3 domain, which have achieved high selectivity of >95% heterodimer purity, but with significantly lower stability as indicated by the CH3-CH3 Tm. See Table 1, below. For example, the knobs-into-holes strategy developed by Genentech, or the electrostatic steering strategy developed by Amgen have employed mainly negative design asymmetric point mutations to drive heterodimer formation, which lead to high heterodimer specificity but low stability. In a subsequent development by Genentech the initial knobs-into-holes design was optimized for higher stability by experimental library screening and by disulfide stabilization. While the library approach only gained stabilization by 1-2 deg to ~70° C., the disulfide stabilization was more successful with an increase of CH3 Tm to >77° C. Since the engineered disulfide is partially solvent exposed, it remains questionable whether this stabilization is a viable option to ensure long term stability and in vivo stability. In the disclosed approach, disulfide engineering for heterodimer stabilization is avoided in order to prevent potential complications in manufacturability and formulation.

Figure 17:
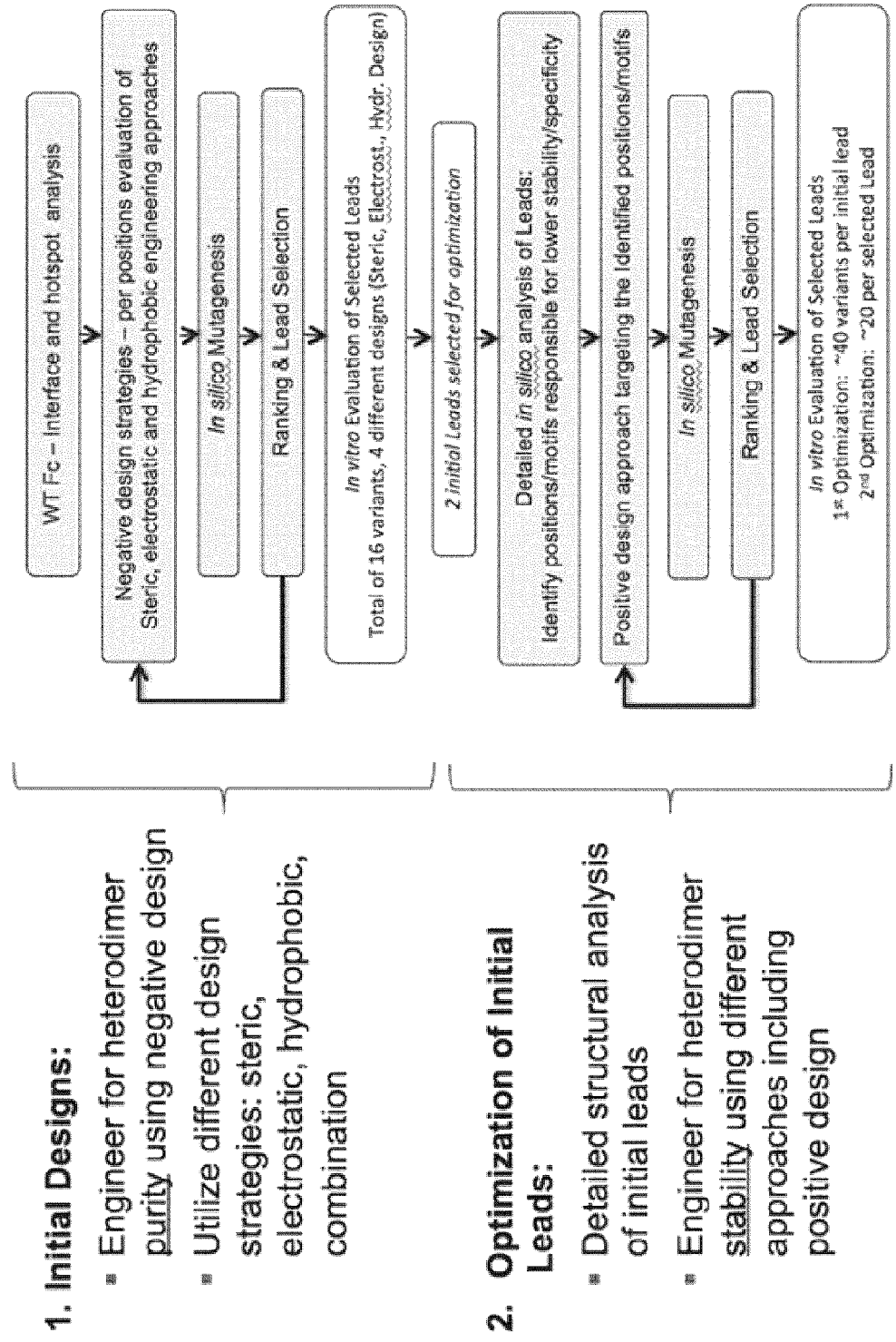
FIG. 17 provides steps in an iterative rational protein engineering strategy in accordance with some embodiments of the present disclosure.
Figure 18:
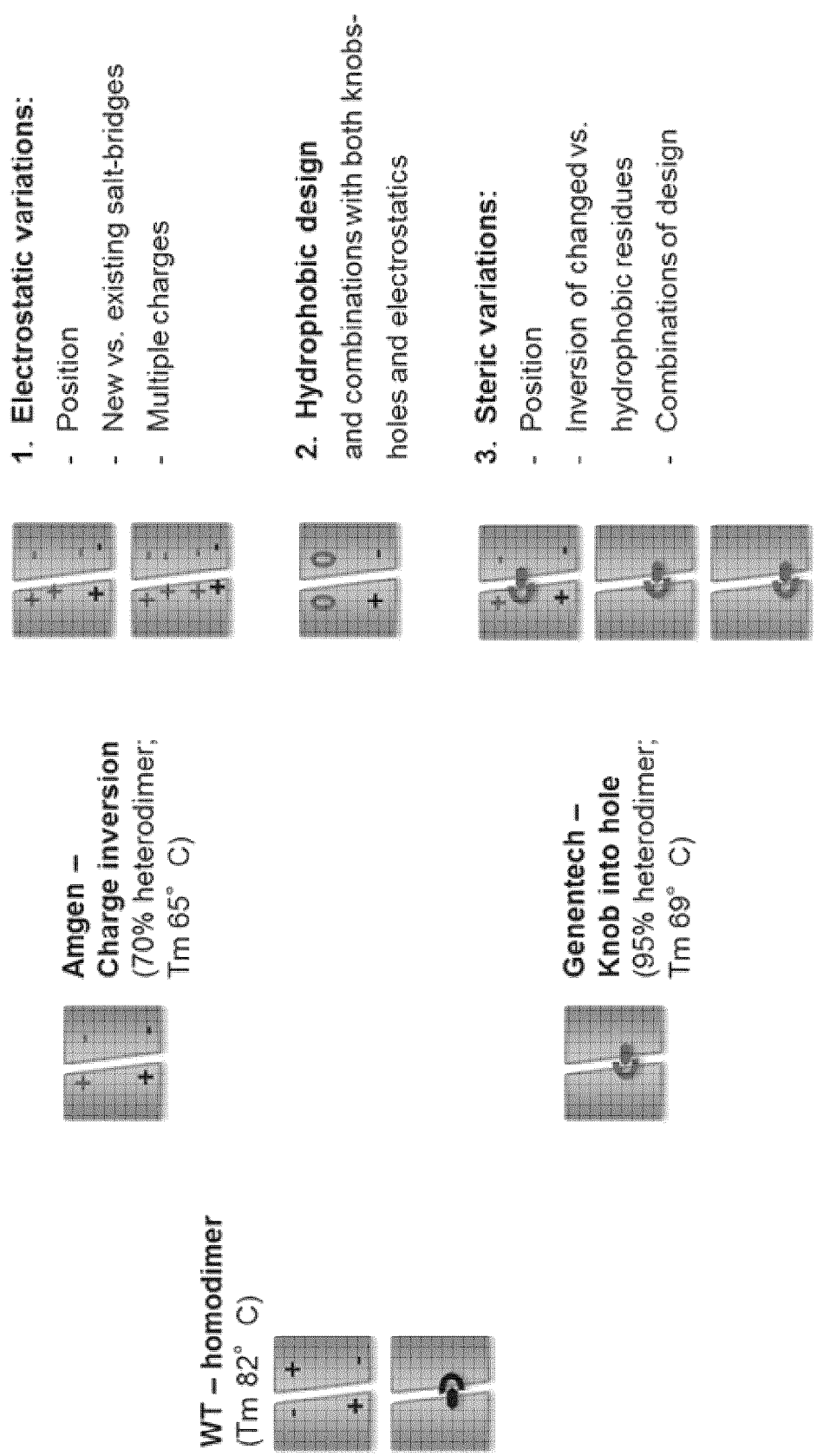
FIG. 18 provides a schematic representation of design space addressed in the current and prior work in order to achieve heterodimer pairing in a mutated Fc in accordance with some embodiments of the present disclosure.

To address the challenges in Fc heterodimeric protein engineering, disclosed is the implementation of a two stage approach that specifically combines negative and positive design strategies to achieve 100% specificity and wild-type like CH3-CH3 stability as summarized in FIG. 17. Specifically, in the initial design phase the core interface positions were computationally screened using different negative design strategies, including steric-, electrostatic- and hydrophobic-design approaches as shown in FIG. 18, and the variants with predicted high heterodimer specificity were tested experimentally for expression and stability as described below. A total of sixteen variants based on four core designs were experimentally characterized in the initial design phase. From this initial set of negative design Fc variant heterodimers, which were expected to have lower stability, the Fc variant heterodimers with greater than 90% purity and a melting temperature of about 68° C. or greater were selected for further development. In the second design phase the selected Fc variant heterodimers were each analyzed with computational methods and comprehensive structure function analysis to identify the structural reasons these Fc variants had a lower stability than the wild-type Fc homodimer, which is 83° C. for IgG1. Following a detailed computational and structural analysis those selected Fc variant heterodimers were further modified to drive both stability and purity using positive design strategies.

TABLE 1

Published Fc Heterodimeric Antibodies.

| | Chains | Engineering Approach | Source | Purity | Tm ° C. |
|---|---|---|---|---|---|
| Wild-Type | — | | | | 83 |
| Control 1 | K409D_K392D D399K_E356K | Electrostatic steering | Gunaskekaran et al, 2010, J. Biol. Chem. 285(25); 19637-19646 | >95% | 67 |

TABLE 1-continued

Published Fc Heterodimeric Antibodies.

| | Chains | Engineering Approach | Source | Purity | Tm ° C. |
|---|---|---|---|---|---|
| Control 2 | K409D_K392D D399K | Electrostatic steering | Gunaskekaran et al, 2010, J. Biol. Chem. 285(25); 19637-19646 | <80% | — |
| Control 3 | T366S_L368A_Y407V T366W | Knobs-into-holes (KH) | Atwell et al., 1997, J. Mol. Biol. 270: 26-35. | >95% | 69 |
| Control 4 | Y349C_T366S_L368A_Y407V S354C_T366W | Knobs-into-holes (KH) plus disulfide | Merchant et al., 1998, Nature Biotechnology 16: 677-681. | >95% | ** |
| Control 5 | IgG-IgA chimera | Strand Exchange | Muda et al., 2011, Protein Engineering, Design and Selection 24: 447-454. | 90% | 68 |

** A Tm greater than 77° C. was observed for control 4 in the assay system used; the Tm for this variant has not been published in the literature.

Computational Engineering Strategy.

Figure 19:
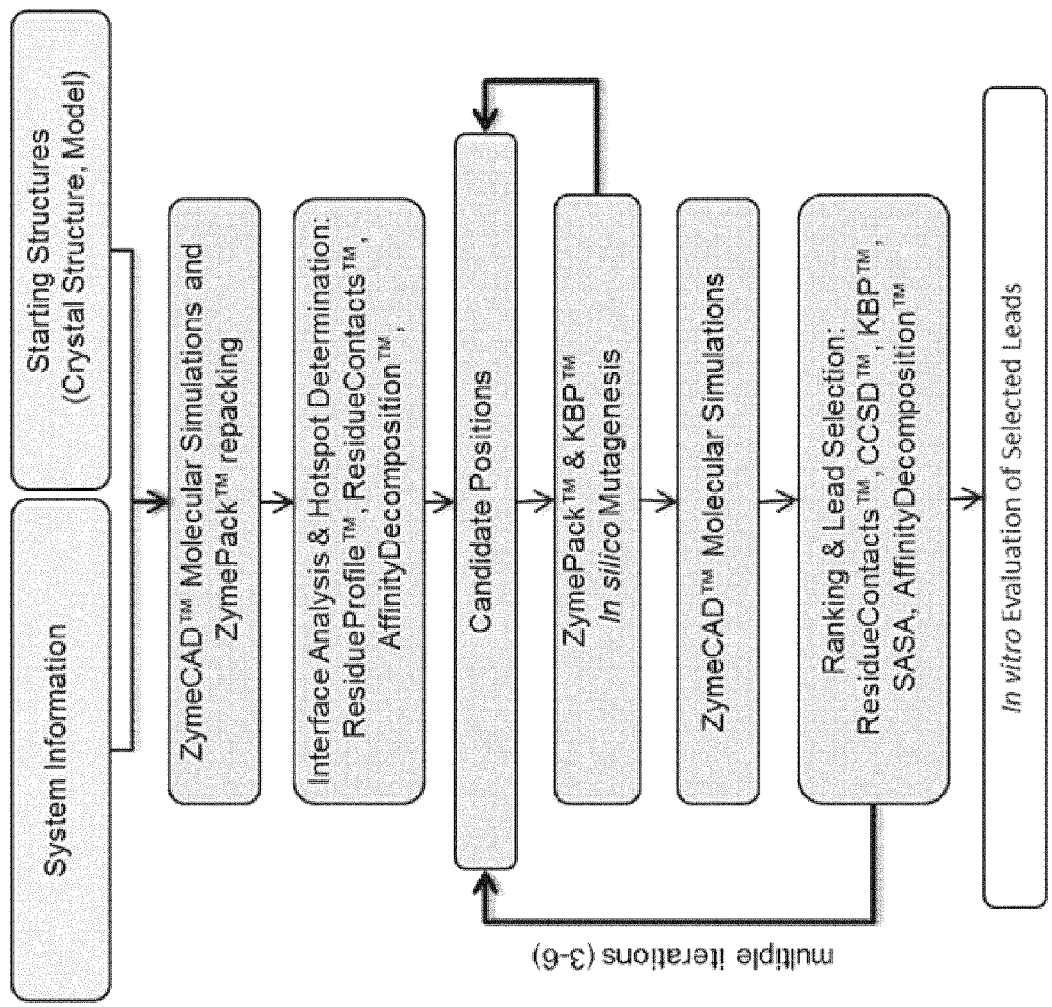
FIG. 19 provides a computational structure function analysis and screening strategy used in accordance with some embodiments of the present disclosure.

The computational tools and structure-function analysis included molecular dynamic (MD) analysis, protein amino acid sidechain/backbone re-packing, bioinformatics sequence and structural database derived statistical potentials (KBP), cavity and (hydrophobic) packing analysis Lennar-Jones interactions, contact density estimates (CCSD), changes in solvent accessibility of different functional groups in the protein (SASA), electrostatic-GB calculations, and coupling analysis as indicated in FIG. 19.

An aspect of the disclosed protein engineering approach relied on combining structural information of the Fc IgG protein derived from X-ray crystallography with computational modeling and simulation of the wild type and variant forms of the CH3 domain. This allowed for gaining novel structural and physico-chemical insights about the potential role of individual amino acids and their cooperative action. These structural and physico-chemical insights, obtained from multiple variant CH3 domains, along with the resulting empirical data pertaining to their stability and purity helped us develop an understanding for the relationship between purity and stability of the Fc heterodimer as compared to the Fc homodimers and the simulated structural models. In order to execute these simulations, complete and realistic models were built and the quality of the wild type Fc structure of an IgG1 antibody was refined. Protein structures derived from X-ray crystallography are lacking in detail regarding certain features of the protein in aqueous medium under physiological condition and the refinement procedures addressed these limitations.

Molecular dynamics (MD) was employed to simulate the protein structure, to evaluate the intrinsic dynamic nature of the Fc homodimer and the variant CH3 domains in an aqueous environment. Molecular dynamics simulations track the dynamic trajectory of a molecule resulting from motions arising out of interactions and transient forces acting between all the atomic entities in the protein and its local environment, in this case the atoms constituting the Fc and its surrounding water molecules.

The impact of mutations on the local environment of the site of mutation was studied in detail. The formation of a well packed core at the CH3 interface between chain A and B is critical for the pairing of the two chains in a stable Fc structure. Good packing is the result of strong structural complementarity between interacting molecular partners coupled with favorable interactions between the contacting groups. The favorable interactions result from either buried hydrophobic contacts well removed from solvent exposure or from the formation of complementary electrostatic contacts between hydrophilic polar groups. These hydrophobic and hydrophilic contacts have entropic and enthalpic contributions to the free energy of dimer formation at the CH3 interface. A variety of algorithms were employed to accurately model the packing at the CH3 interface between chain A and chain B and subsequently evaluate the thermodynamic properties of the interface by scoring a number of relevant physicochemical properties.

Protein-packing methods were employed including mean field and dead-end elimination methods along with flexible backbones to optimize and prepare model structures for the large number of variants being screened computationally. Following packing, a number of features were scored including contact density, clash score, hydrophobicity and electrostatics. Use of the Generalized Born method allowed for the accurate modeling of the effect of solvent environment and to contrast the free energy differences following mutation of specific positions in the protein to alternate residue types. Contact density and clash score provided a measure of complementarity, one aspect of effective protein packing. These screening procedures are based on the application of knowledge-based potentials as well as coupling analysis schemes relying on pair-wise residue interaction energy and entropy computations.

This comprehensive in-silico analysis provided a detailed understanding of the differences of each Fc variant compared to wild-type with respect to interface hotspots, sites of asymmetry, cavities and poorly packed regions, structural dynamics of individual sites and sites of local unfolding. The computational analysis helped identify specific residues, sequence/structural motifs and cavities that were not optimized and in combination were responsible for the lower stability (e.g., Tm of 68° C.) and/or lower specificity of <90% purity. In the second design phase, targeted positive design was used to specifically address these sites with additional point-mutations and tested these by in-silico modeling using the above described methodology and analysis.

Optimization of Initial Variants and Structural Rational.

To improve the initial negative design Fc variants for stability and purity, the structural and computational strategies described above were employed. The in depth structure-function analysis of the initial negative design variant provided a detailed understanding for each of the introduced mutations.

Figure 20:
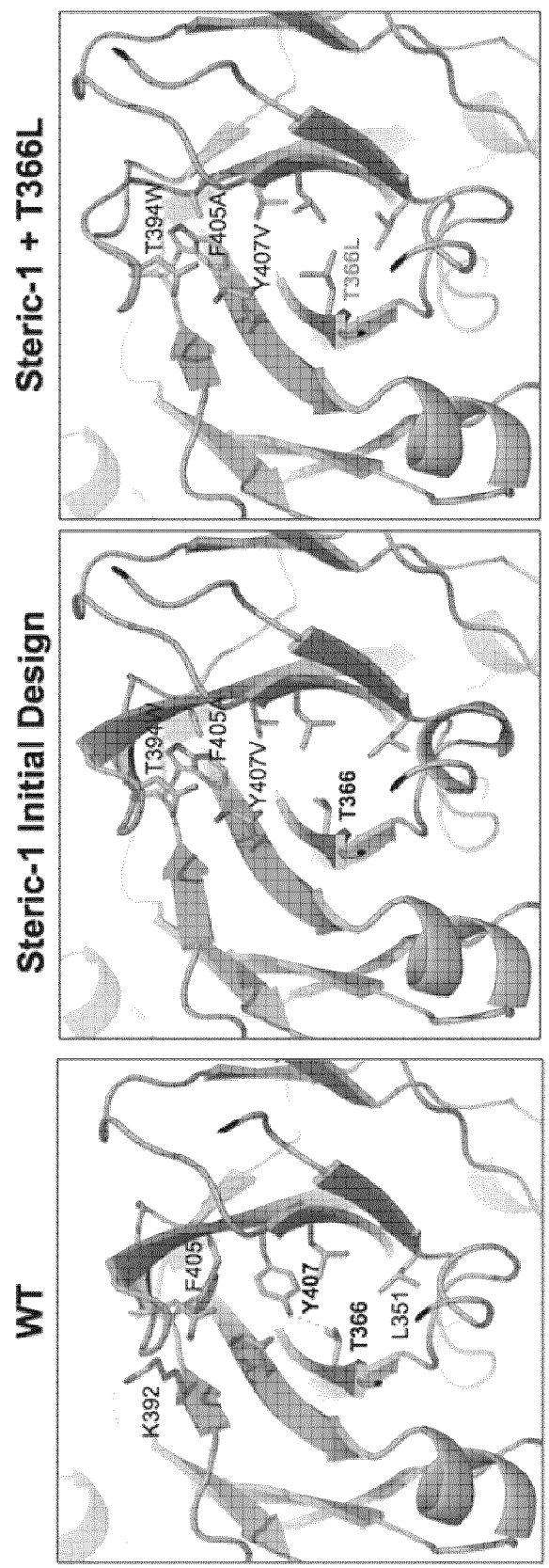
FIG. 20 illustrates the wild type Fc versus an initial heterodimer design and the structural rationale for the key additional swap T366L. T366 is a hotspot in wild type Fc and, while it does not contribute to heterodimer formation, it is still present as a hotspot in the undesired wild type like homodimers. The rationale is supported by the introduced single additional swap T366L which improved the heterodimer purity from ~90 to >95%.

For example, the analysis showed that the important interface hotspots that are lost with respect to wild-type homodimer formation are the interactions of wild-type (chain A) F405-(chain B) K409, (chain A) Y407-(chain B) T366 and the packing of (chain AB) Y407-Y407 and -(chain A) F405 FIG. 20. The analysis revealed in addition that one strong wild-type hotspot (chain A) T366 was affected but not contributing in the heterodimer formation, while likely still being present in the undesired homodimer. As illustrated in FIG. 20, the single amino acid change of (chain B) T366L increased the heterodimer purity of the initial design variants from ~80% to >95%.

Figure 21:
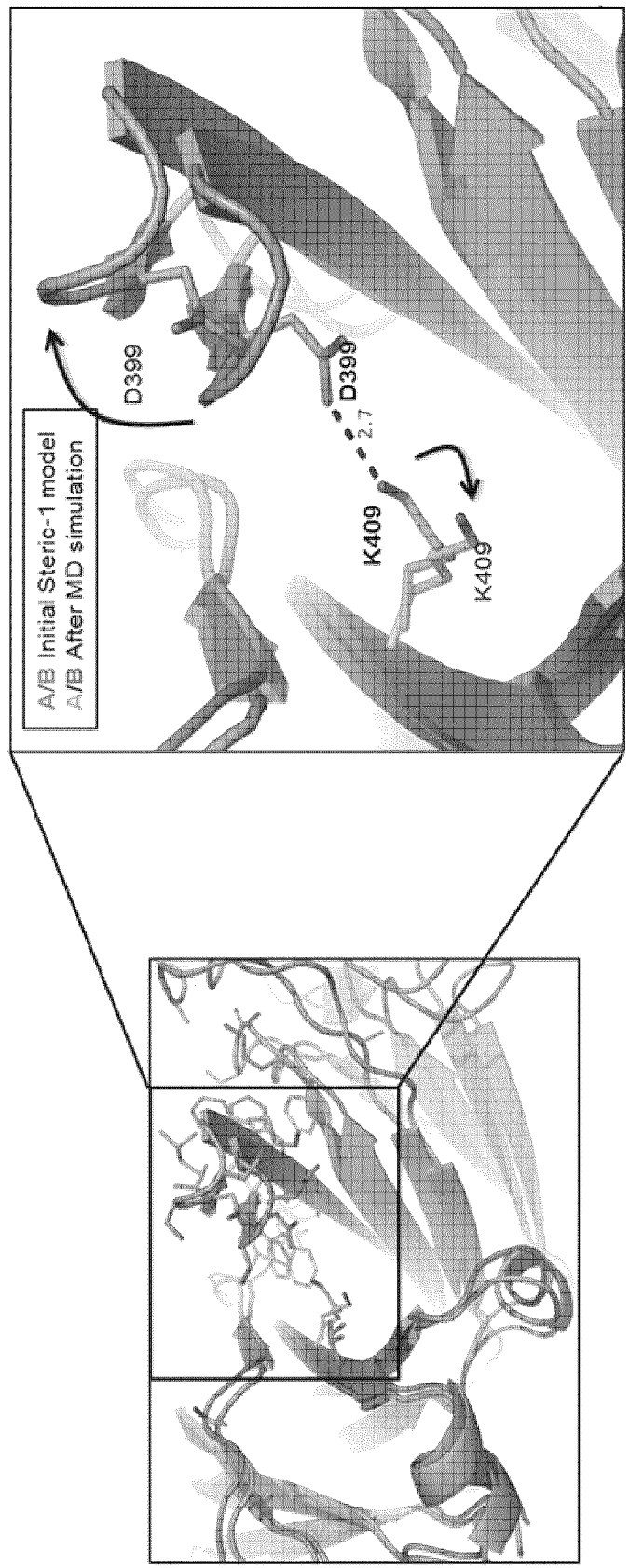
FIG. 21 illustrates the utility and importance of the conformational dynamics analysis of the initial negative design as described in detail herein. The predicted model after in silico mutagenesis (backbone conformation close to WT) is superimposed with a representative structure of a 50 ns Molecular Dynamics simulation analysis. The figure highlights the large conformational difference in the loop region D399-S400 versus wild type, which in turn exposes the hydrophobic core to solvent and causes decreased stability of the initial heterodimer.

The molecular dynamics simulation of the initial heterodimer variant with low stability showed a large conformational difference in the loop region D399-S400-D401 (FIG. 21) and the associated β-sheets at K370. This resulted in the loss of the interchain interactions K409-D399. In the wild type IgG1 CH3 domain these regions tether the interface at the rim and protect the hydrophobic core interactions. This analysis indicated an important factor for the lower stability of the initial heterodimer variant compared to wild type stability.

Figure 22:
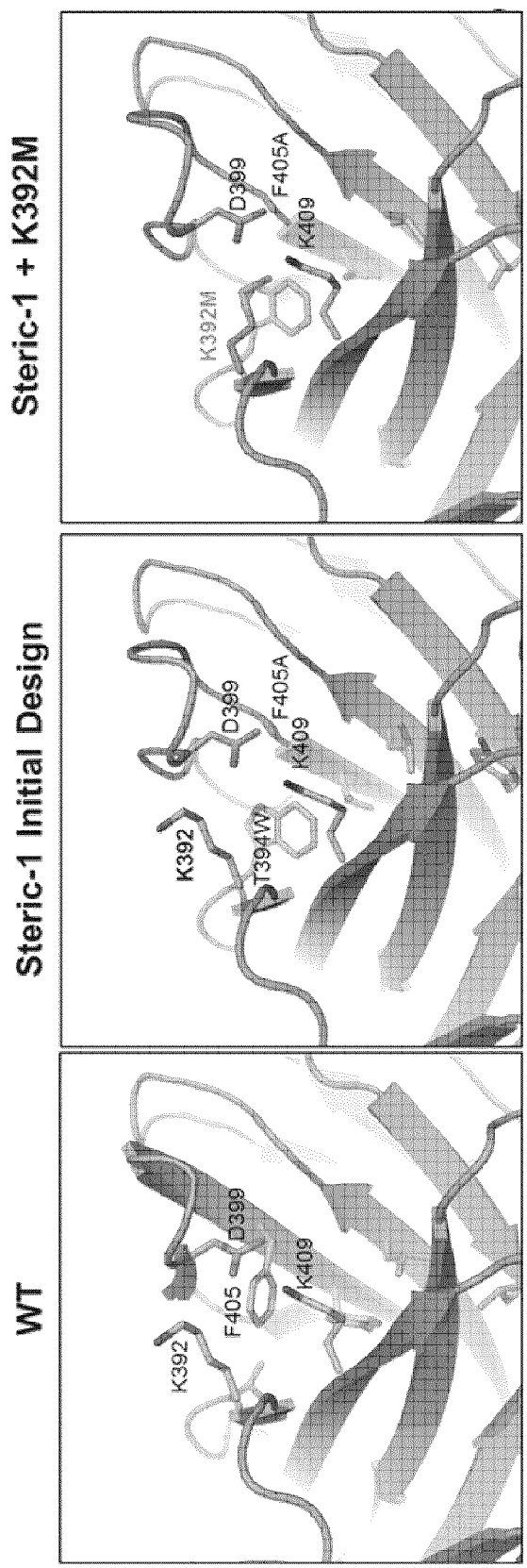
FIG. 22 illustrates how information from the comprehensive in silico analysis disclosed herein and the molecular dynamics simulation was used to identify the key K392M mutation, which stabilized the loop conformation and increased the stability of the initial negative design variant by ~4° C. (CH3-CH3 Tm).

Consequently, residues and sequence motifs responsible for the low stability were identified and the subsequent positive design engineering efforts were therefore specifically focused on stabilizing the loop conformation of positions 399-401 in a more 'closed'—wild-type like conformation. In order to achieve this stabilization of the loop conformation of positions 399-401 the above described computational approach was used to evaluate different targeted design ideas. This strategy identified the single mutation difference K392M/L which leads to an increase in CH3 stability of ~4° C. as illustrated in FIG. 22.

Figure 23:
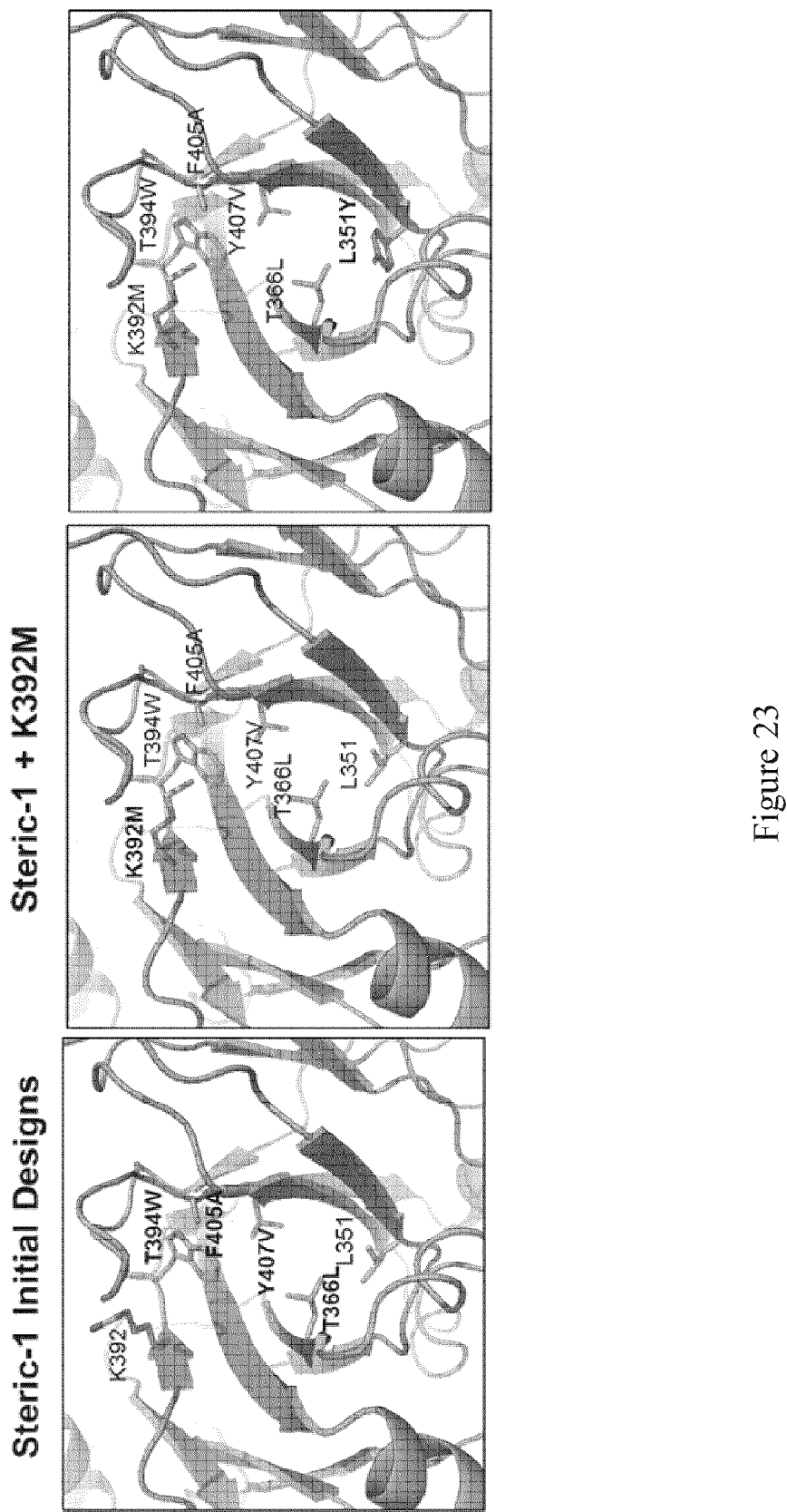
FIG. 23 illustrates how the in silico analysis disclosed herein indicated that one of the reasons for the lower than wild type stability of the initial heterodimer is the loss of the core interaction/packing of Y407 and T366. The initial heterodimer shows non-optimal packing at this hydrophobic core. The figure illustrates how the distal mutation L351Y was able to stabilize the heterodimer by coupling effects and improved hydrophobic packing, without impacting the initial mutations T366L/Y407V, which are essential for heterodimer specificity.

Thirdly, a cavity at the core packing positions T366, T394W and L368 was identified as a reason for the lower than wild-type stability FIG. 23. To improve the core packing, the positions at T366/L368 were computationally screened and, in addition, distal positions were evaluated for stabilization of the core packing. This procedure identified the distal swap L351Y, which as a single mutations does not show any impact, but in combination with T366L and L368 gives an improved CH3 Tm of >5° C., indicating a strong coupling effect of the distal change L351Y.

The employed engineering approach to improve the heterodimer stability is not limited to introducing mutations that increase complementarity across the two chains. Mutations of amino acids that are not directly contacting the complementary chain were evaluated as a means to improve the stability of the Fc heterodimeric protein. As an example, the second shell position T350 in the CH3 domain of IgG1 is buried and the threonine residue facing the interior of the CH3 domain. The distal second shell mutation T350V has been identified by the described computational screening and it improves the stability of the Fc domain by >2° C. Tm. See FIG. 24.

Crystal Structure of Fc Heterodimeric Proteins.

In a direct advancement of this validation, disclosed are the crystal structures of the Fc heterodimeric proteins AZ1 and AZ2, which are based upon the CH2 and CH3 domains of human igG1 Kabat antibody. The primary amino acid sequence of AZ1 and AZ2 and the amino acid sequence of the CH2 and CH3 domains of human igG1 Kabat antibody immunoglobulin are provided in FIG. 16. See, Kabat et al., 1991, NIH Publication 91-3242, National Technical Information Service, Springfield, Va. For convenience, FIG. 25 provides the amino acids numbering used herein according to the EU index as set forth in Kabat for the CH2 and CH3 domains from human IgG1.

Crystals of the Fc heterodimeric proteins in accordance with the present disclosure were obtained in a number of different screening conditions. Using the hanging drop vapor diffusion method, the reservoir conditions refined for data collection and structure solution were ethyleneglycol, polyethylene glycol with an average molecular weight of 3350 Daltons, and ammonium iodide.

Fc heterodimeric protein constructs of AZ1 and AZ2 were transiently expressed in CHO (Chinese hamster ovary) cells and purified to homogeneity by protein A column chromatography and SEC (size exclusion chromatography). The purified Fc heterodimeric proteins were crystallized at 18° C. after ~24 hours of incubation via hanging drop vapor diffusion method at a ratio of 2:1 above a mother liquor solution composed of 5% (v/v) ethylene glycol, 18% (w/v) polyethylene glycol 3350, and 0.15 M ammonium iodide with aid of microseeding. Crystals were cryoprotected by increasing the concentration of ethylene glycol to 30% (v/v) and subsequently flash cooled in liquid nitrogen. Diffraction data from both crystals were collected at 100 K, using 0.5 degree oscillations for 200 degrees total, and processed with XDS. See Kabsch, 2010, Acta crystallography D Biological Crystallography 66: 125-132, which is hereby incorporated by reference in its entirety, for teaching on such processing of diffraction data. The structure of AZ1 was solved via molecular replacement with Phaser using PDBID: 2J6E as a query protein. See, McCoy, 2007, Acta Crystallography D Biological Crystallography 63: 32-41, which is hereby incorporated by reference in its entirety, for teachings on molecular replacement. The structure of AZ1 was then used to solve AZ2 in similar fashion. In order to accommodate the perfect twin reciprocal relationship of the heterodimer present in the crystallographic asymmetric unit (e.g., the occupancy of molecule A can be equally be described by molecule B and vice versa), two possible heterodimer pairs, each with 0.5 atomic occupancies, were modeled with Coot, and refined with Refmac. See, Emsley and Coot, 2004, Acta Crystallography D Biological Crystallography 60, 2126-2132; and Murshudov et al., 1997, Acta Crystallography D Biological Crystallography 53, 240-255, which are hereby incorporated herein by reference in their entirety, respectively, for teaching on Coot and Refmac. Diffraction data processing and structure refinement statistics for AZ1 and AZ2 are presented in Table 2. FIG. 26 provides the structure coordinates for AZ2 (including SEQ ID NO: 4 and SEQ ID NO.: 5). FIG. 27 provides the structure coordinates for AZ1 (including SEQ ID NO: 2 and SEQ ID NO.: 3).

TABLE 2

| Data collection and structural refinement statistics. | | |
|---|---|---|
| | AZ1 | AZ2 |
| Data collection | | |
| Synchrotron | CSLS | CSLS |
| Beam line | CMCF-BM | CMCF-BM |
| Wavelength (Å) | 0.98005 | 0.98005 |
| Space group | $P2_12_12_1$ | $P2_12_12_1$ |

TABLE 2-continued

Data collection and structural refinement statistics.

| | AZ1 | AZ2 |
|---|---|---|
| Cell dimensions | | |
| a, b, c (Å) | 49.54, 74.92, 148.92 | 49.67, 74.72, 148.93 |
| α, β, γ (°) | 90, 90, 90 | 90, 90, 90 |
| Resolution (Å) | 47-1.75 (1.84-1.75)* | 47-2.10 (2.21-2.10) |
| $R_{sym}$ or $R_{merge}$ | 0.043 (0.413) | 0.074 (0.502) |
| I/σI | 26 (3.9) | 15.9 (4.0) |
| Completeness (%) | 100 (100) | 99.9 (99.9) |
| Redundancy | 7.3 (7.4) | 6.8 (7.0) |
| Refinement | | |
| Resolution (Å) | 1.75 | 2.15 |
| No. reflections, free | 53,467 (2,849) | 29,307 (1,557) |
| $R_{work}/R_{free}$ | 17.8/20.8 | 20.0/25.9 |
| No. atoms | | |
| Protein Chains | 6704 | 6704 |
| Carbohydrate/ions | 440/4 | 440/4 |
| Solvent | 802 | 415 |
| B-factors | | |
| Protein Chains | 23.8 | 44.4 |
| Carbohydrate/ions | 54.3/20.7 | 67.0/41.5 |
| Solvent | 27.0 | 40.8 |
| RMS deviations | | |
| Bond lengths (Å) | 0.008 | 0.010 |
| Bond angles (°) | 1.32 | 1.53 |
| Ramachandran Data | | |
| Most favored (%, no.) | 96.8 (805) | 94.5 (786) |
| Additionally allowed (%, no.) | 2.4 (20) | 4.3 (36) |
| Disallowed (%, no.) | 0.8 (7) | 1.2 (10) |

*Values in parentheses are for highest-resolution shell.

Figure 2:
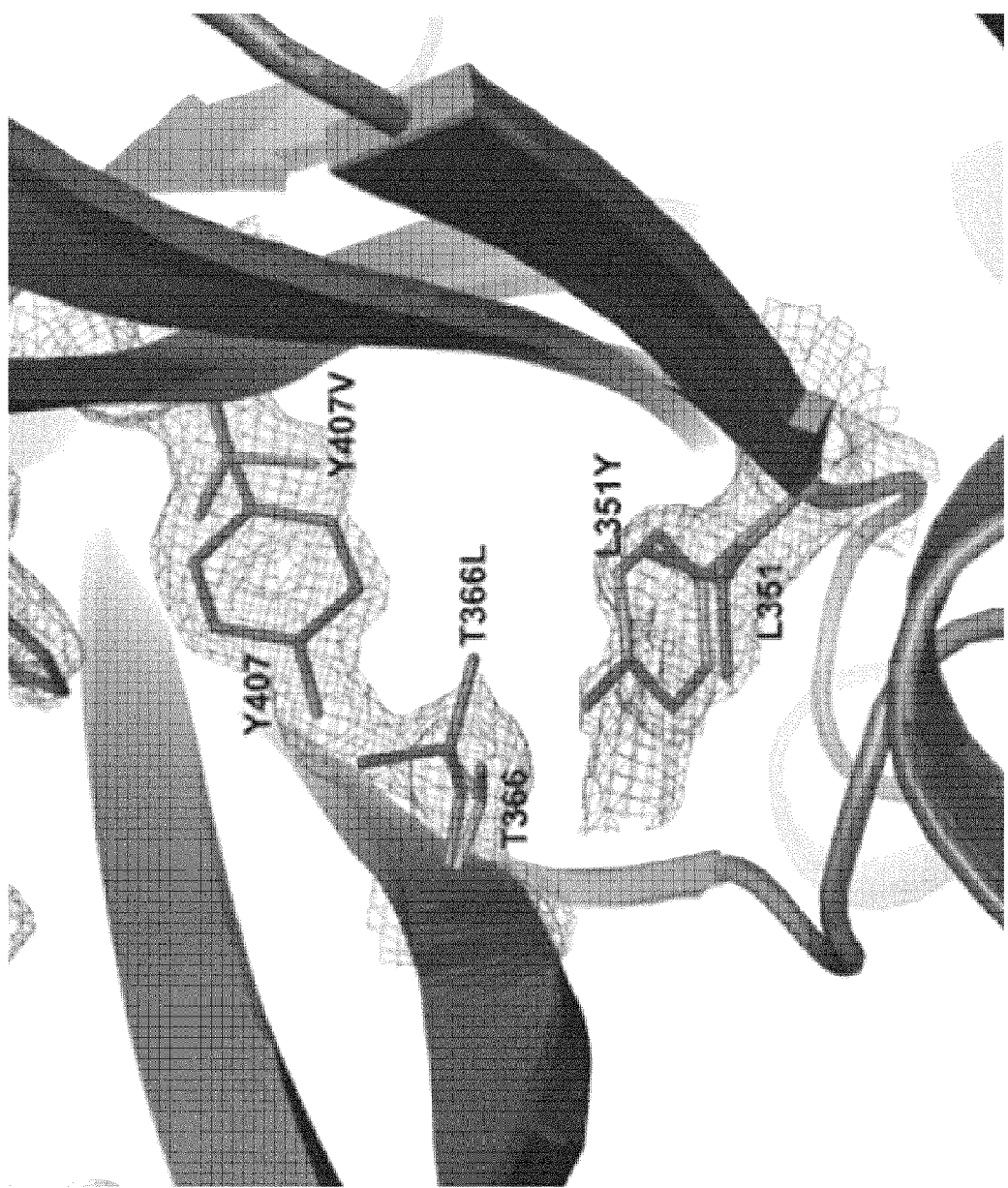
FIG. 2 illustrates electron density at sites of mutation in the disclosed crystallographic structures, in accordance with some embodiments of the present disclosure.
Figure 3:
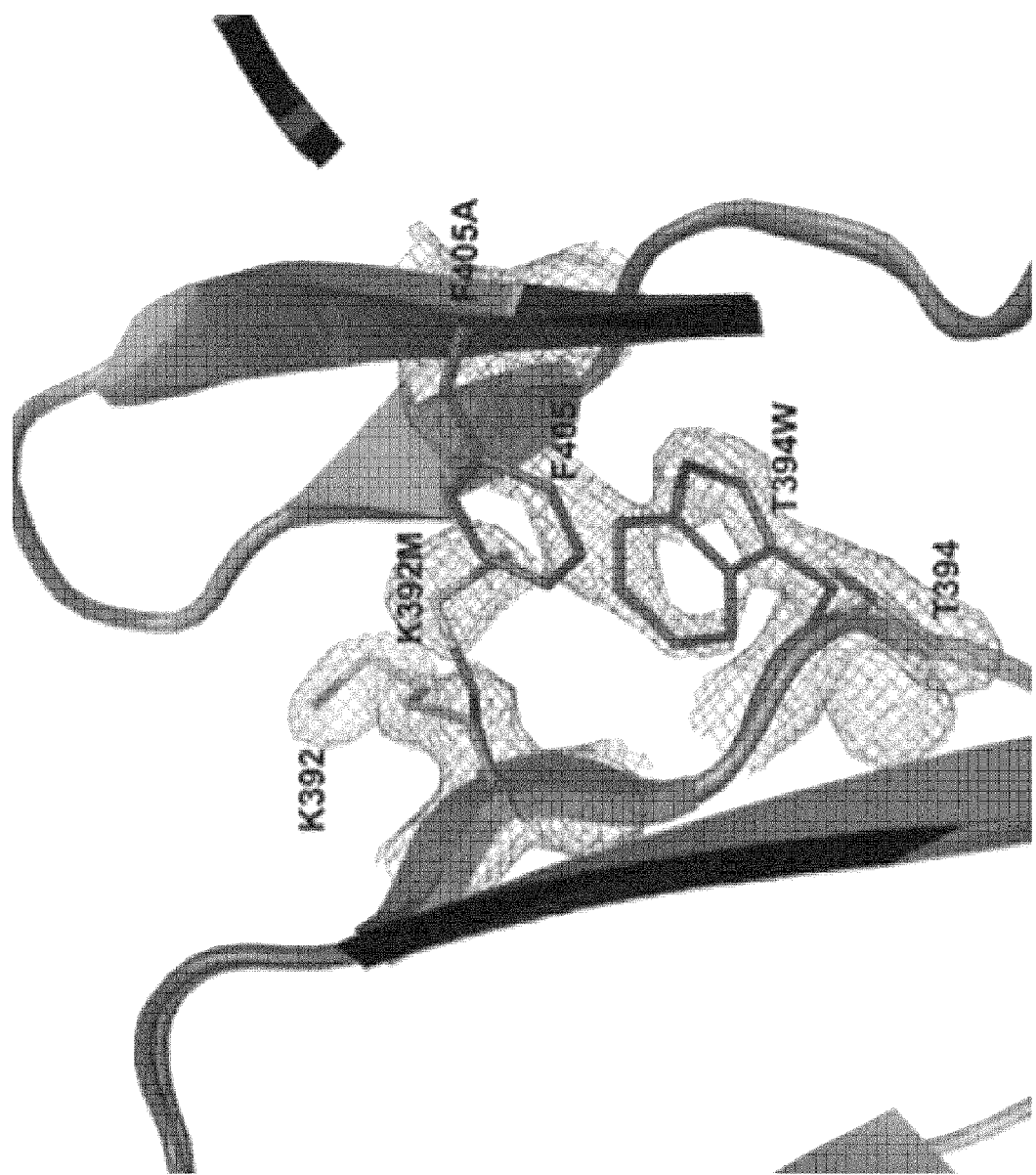
FIG. 3 illustrates electron density at sites of mutation in the disclosed crystallographic structures, in accordance with some embodiments of the present disclosure.
Figure 4:
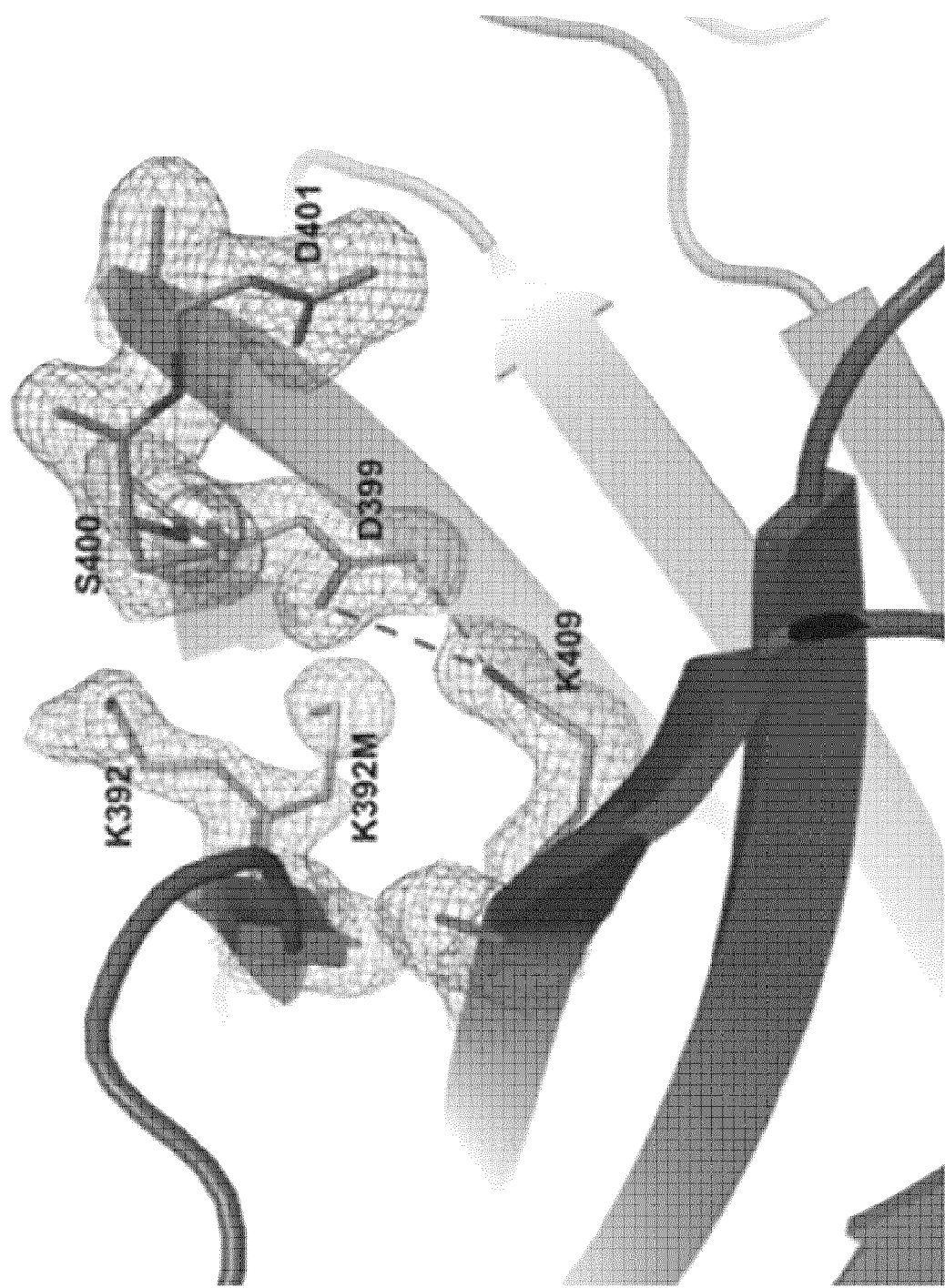
FIG. 4 illustrates electron density at sites of mutation in the disclosed crystallographic structures, in accordance with some embodiments of the present disclosure.

Despite the engineered asymmetry at the heterodimeric interface of the disclosed variant, the overall surface symmetry has been preserved for both AZ1 and AZ2. Crystallographically, this feature manifests in that the heterodimeric asymmetric unit can be oriented in both possible configurations when averaged throughout the crystal lattice. For example, in each asymmetric unit the occupancy of molecule A can be described with equal frequency by molecule B and vice versa when averaged throughout the crystal. See FIG. 1 for a graphical depiction of molecule A and B in AZ1 and AZ2. Use of alternate sidechain conformations is possible when multiple conformations are evident from calculated electron density, but the sequence conflict of two different residues was not tolerated by the available software refinement packages. Similarly, creating alternate overlapping chains at the same position with 0.5 occupancies introduced steric clashes during structural refinement, and therefore did not provide a suitable solution to the duplicity of the designed interface. Therefore, while non-canonical, in order to accommodate the interface residue heterogeneity, two adjacent asymmetric units were modeled: one in which the heterodimer A:B is oriented and the other where the mirrored heterodimer B:A was modeled, and each was assigned 0.5 occupancy. The electron density using such modeling, as illustrated in FIGS. 2 through 4, shows the 50%:50% occupancy of the possible orientations A:B and B:A at the mutated interface residues. Inspection of the difference density at the CH3-CH3 interface showed no significant peaks, thus confirming the two possible orientations. For further validation the B-factors of the mutated interface residues of the two orientations A:B and B:A were compared to high resolution WT Fc structures. The refined B-factors of the mutated residues are very similar to the overall B-factor of the core CH3-CH3 interface residues and are comparable to the B-factors of published WT Fc structures. Further, calculation of OMIT maps at the CH3-CH3 interface did not reveal any errors of the modeled 50%:50% occupancy. This analysis confirms the modeled 50%:50% occupancy of the A:B and B:A orientation.

Comparison of AZ1 and AZ2 Crystal Structures and in Silico Models.

Both the AZ1 and AZ2 crystal structures show overall agreement with wild type Fc structures. Importantly, detailed inspection of the engineered CH3-CH3 domain confirms that all introduced mutations are fully buried and that the wild type surface characteristics of the Fc and the CH3-CH3 domain are maintained. This is further underlined by the fact that both AZ1 and AZ2 constructs crystallized as a 50%:50% mixture of the two possible CH3-CH3 orientations A:B and B:A, and this is only possible when the natural homodimeric surface of the CH3-CH3 domain is not broken by the asymmetric CH3 interface mutations.

Maintaining the wild type Fc surface characteristics is an important aspect in reducing the risk of immunogenicity, since both surface exposed mutations and a shift in the wild type symmetric CH3-CH3 orientation due to the engineered interface mutations potentially creates new B-cell epitopes at the Fc domain which significantly increases the risk of an immunogenic response. Together with maintaining the wild type IgG1 stability, this addresses two fundamental concerns in immunogenicity and further de-risks the development of new bispecific therapeutic molecules based on the disclosed scaffold.

One desired goal in the computational design of the Fc heterodimeric proteins had been to prevent the formation of exposed mutations and exposed altered side chain conformations, which would create new potential surface epitopes. After the final round of design, the in silico model of AZ1 and AZ2 predicted all mutational changes to be buried in the CH3 interface residue, thus not altering the wild type CH3 surface area.

Figure 5:
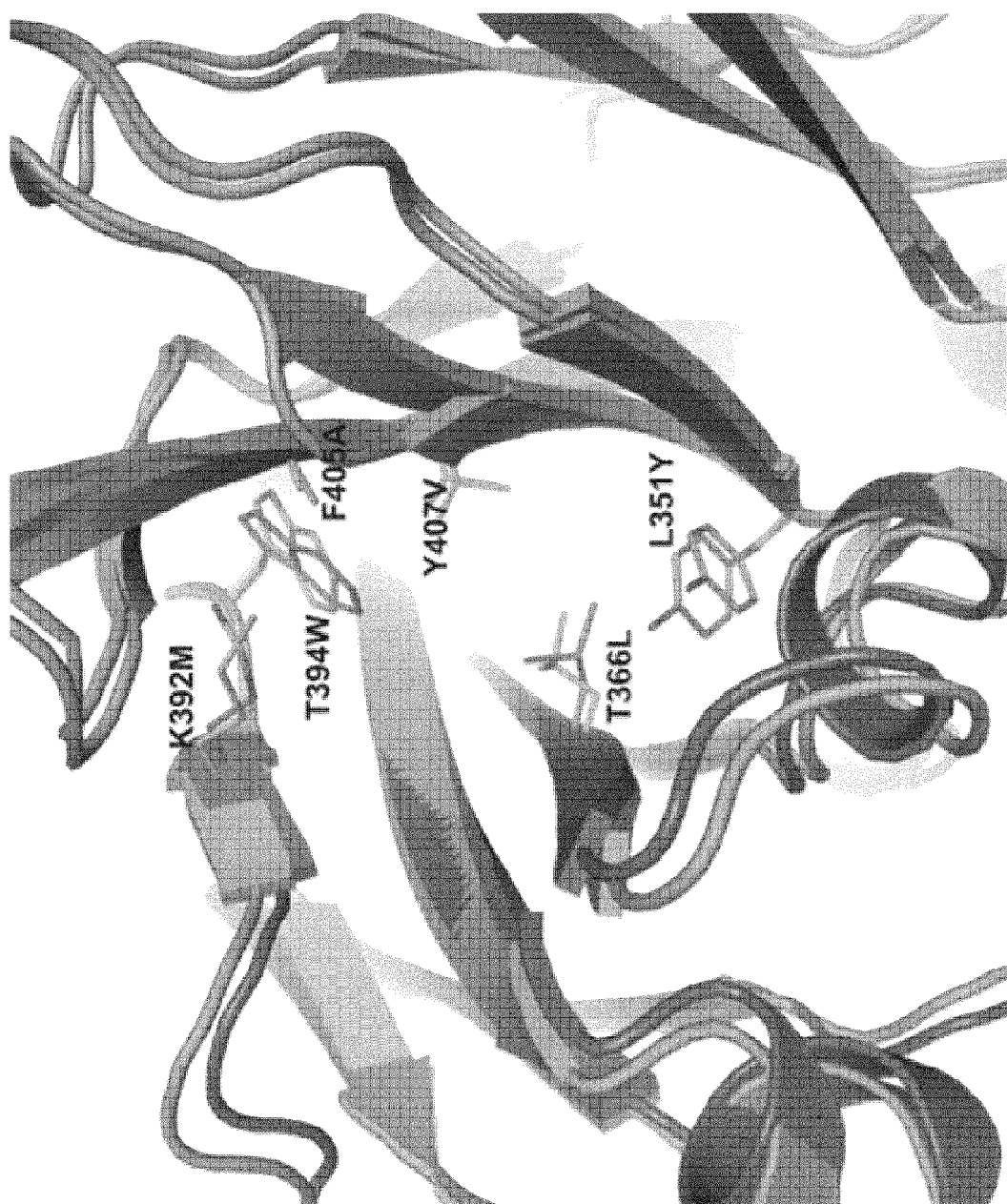
FIG. 5 compares the disclosed crystal structure of AZ1 to the predicted in silico model for AZ1, in accordance with some embodiments of the present disclosure.

To validate the in silico model and the hypothesis that the introduced CH3 mutations do not create newly exposed surface area, the crystal structures of the AZ1 and AZ2 were compared to the predicted in silico models. See FIGS. 5 and 6. The superposition of the heterodimeric CH3 domains shows a agreement of the crystal structures and the in silico models for both variants AZ1 and AZ2 with an all atom RMSD of 0.8 Å and 0.7 Å. Inspection of the mutated and wild type interface residues further shows comparable side chain conformations for the crystal structures and the computational models. The crystal structures of AZ1 and AZ2 thus confirm that all mutated residues are fully buried in the CH3 interface and that the introduced mutations do not lead to altered CH3 surface area.

Figure 6:
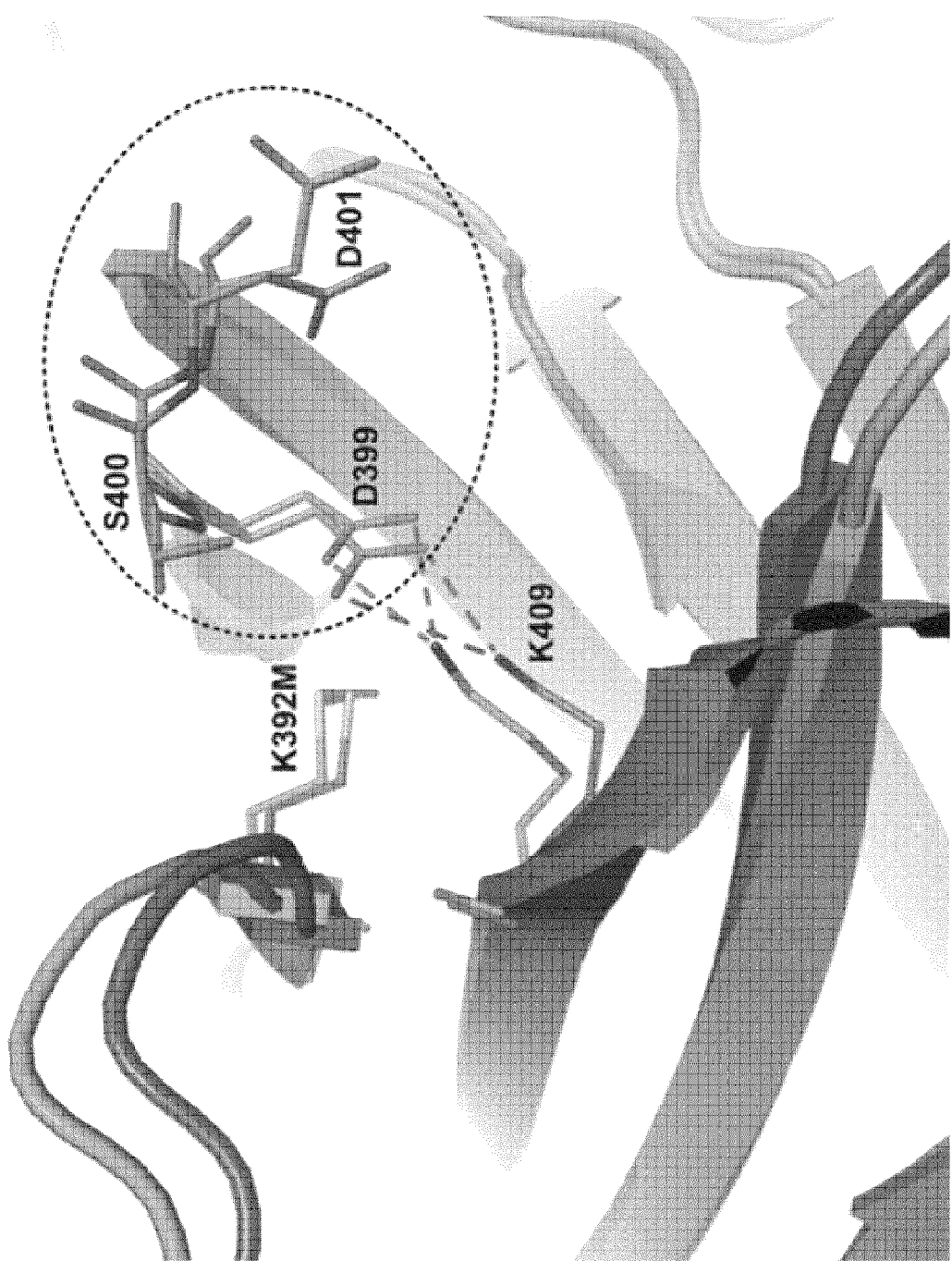
FIG. 6 also compares the disclosed crystal structure of AZ1 to the predicted in silico model for AZ1, in accordance with some embodiments of the present disclosure.

A particular focus in the design of a stable Fc heterodimeric protein was retaining the strong wild type salt bridge interaction at residues K409-D399. This interaction is affected by the neighboring essential heterodimer mutations, but retaining this salt bridge in the heterodimer ensures wild type stability of the CH3 interface. In addition, loss of the K409-D399 salt bridge interaction will likely lead to an altered loop conformation of D399-D401 and in turn newly exposed interface residues. As illustrated in FIG. 6, the wild type Fc salt bridge interaction of K409-D399 and the loop conformation of D399-D401 is maintained in the crystal structures of both AZ1 and AZ2 Fc heterodimeric proteins.

Comparison of the CH3 Domain of the AZ Crystal Structures and High Resolution Wild Type Fc Crystal Structures.

To further evaluate potential negative effects of the heterodimer mutations on the highly conserved homodimeric CH3-CH3 structure, the AZ1 and AZ2 crystal structures were compared to a number of representative wild type Fc crystal structures, crystallized under different conditions and crystal space groups. The respective crystal structures were superimposed over the dimeric CH3-CH3 domains and the backbone RMSD was calculated. The results of this comparison are summarized in FIG. 8. The comparison confirmed good overall agreement of the heterodimer CH3-CH3 domain and wild type CH3-CH3 structures.

Figure 7:
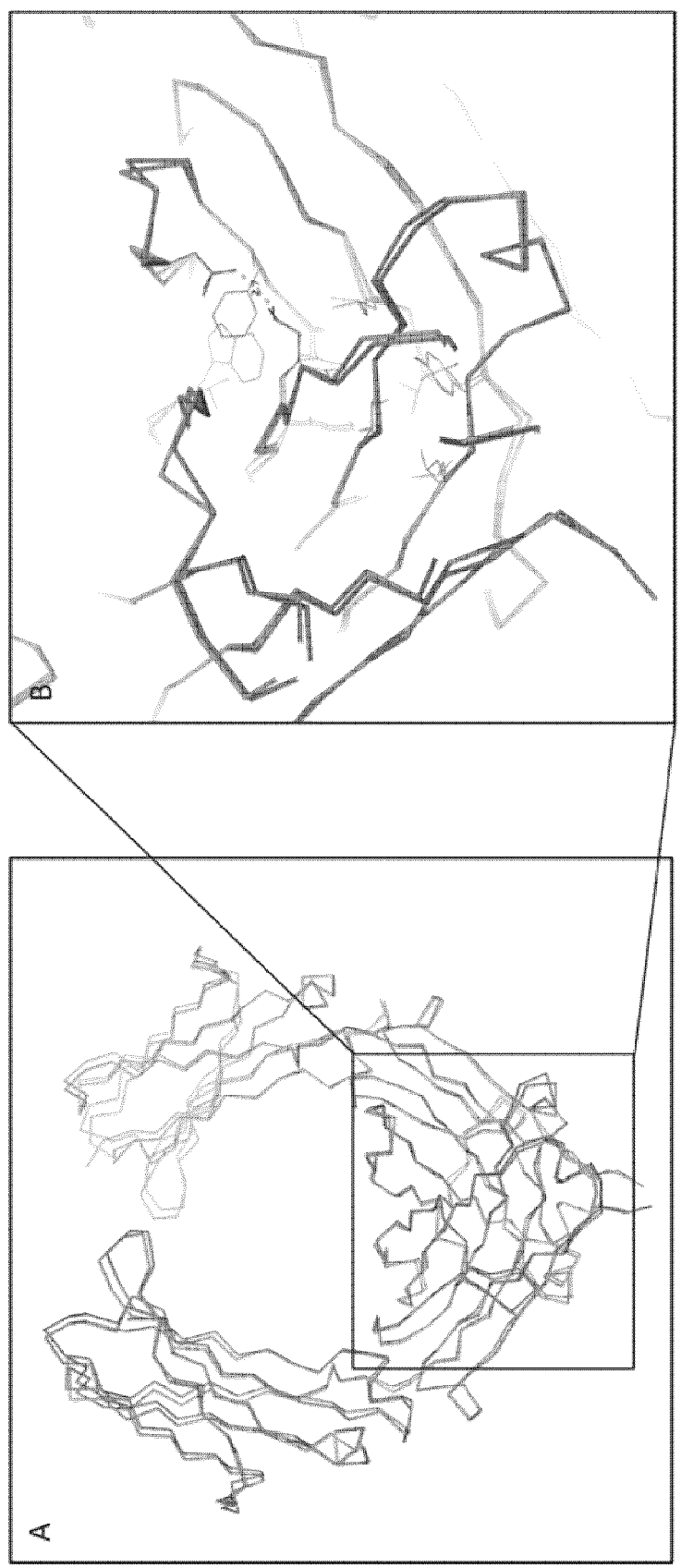
FIG. 7 provides the superposition of CH3-CH3 domain of the disclosed AZ1 heterodimer with high resolution wild-type homodimer Fc crystal structures, in accordance with some embodiments of the present disclosure.

For more detailed analysis of potential effects of the heterodimer mutations on the wild type surface characteristics of the CH3 domain and the homodimeric Fc symmetry, the AZ1 and AZ2 crystal structures were compared to the two published wild type Fc crystal structures with the highest resolution, 1L6x and 3AVE (1.6 Å and 1.9 Å respectively). As illustrated in FIG. 7, the homodimeric CH3-CH3 domains of the two representative high resolution wild type Fc crystal structures were overlaid. Per residue all atom RMSDs calculated across the entire CH3-CH3 domain of the structures showed good agreement between the structures. The per residue RMSDs of the 1L6x to 3AVE comparison was used as a reference for the naturally occurring variation of backbone and sidechain conformations between wild-type Fc structures. To uncover any differences of the heterodimeric CH3-CH3 domain to the wild type homodimeric CH3-CH3 domain apart from the engineered interface residues, the AZ1/AZ2 crystal structures were compared to 1L6x and 3AVE by per residue RMSD calculation in a similarly manner. The comparison of the per residue RMSDs of AZ1:1L6x to the RMSDs of the wild type Fc structures 1L6x:3AVE shows a similar pattern for the engineered heterodimeric CH3-CH3 and the wild type homodimeric CH3-CH3 domain. Further, the same RMSD analysis was done for the two observed heterodimer orientations of A:B and B:A (see FIG. 1 for a description of this nomenclature) and the results are very similar. This analysis highlights that the asymmetric mutations at the CH3 interface do not induce an asymmetry or shift in the naturally symmetric orientation of the two CH3 domains towards each other and that the highly conserved dimeric CH3-CH3 structure is preserved in the engineered heterodimer.

Comparison of the CH2-CH3 Domain Angle and the Crystal Packing of the AZ Crystal Structures and High Resolution Wild Type Fc Crystal Structures.

The AZ1 and AZ2 crystal structures were compared to different Fc crystal structures with focus on the CH3-CH2 interdomain angle and the Fc structural conformations.

Overall, the comparison of wild type Fc structures shows a high identity in the CH3-CH3 domain and a significantly larger variation in the CH3-CH2 interdomain angle and the conformation of the CH2 domains. In deference to the tight dimeric nature of the CH3-CH3 domain, the interaction of the two CH2 domains is mainly mediated by the complex-type glycan attached to the conserved N297. The glycoform of the Fc has been shown to be important for Fc mediated effector function and FcgammaR and C1q binding. For example, mutation of the N297 glycosylation site to prevent N-glycosylation leads to near depletion of all Fc mediated effector functions, like antigen-dependent cellular cytotoxicity (ADCC) and complement-dependent cytotoxicity (CDC), while truncation of the complex-type Fc glycan structure by only the core-fucose moiety displays increased binding to activating Fcgamma receptors and enhanced ADCC. Further, alteration of the complex-type glycan structure to high mannose-type glycans, which also do not contain the core-fucose moiety, has been reported to yield enhanced ADCC activity while C1q mediated complement activation is reduced. The structural reasons for the observed differences in effector function due to altered Fc glycans are potentially of different nature. The recently published crystal structure of a fucosylated Fc in complex with FcgammaRIIIa revealed a unique Fc-FcgammaR carbohydrate-carbohydrate interaction which is only present in the case of a fucosylated Fc and this additional interaction has been proposed to be the reason for the higher affinity to FcgammaRIII. In contrast, complete de-glycosylation at N297 has been shown to lead to a more 'closed' conformation of the CH2 domains and this in turn is thought to prevent efficient binding of FcgammaR, which requires an 'open' CH2 conformation as determined in the Fc-FcgammaR co-complex structures. See, Krapp et al., 2003, Journal of Molecular Biology 325:979-989, which is hereby incorporated by reference herein in its entirety. Based on further comparisons of different glycoform Fc crystal structures and the observed variation in the CH2 conformations it has been proposed that the degree of 'openness' of the CH2 domains is influenced by the Fc glycoform and plays a role in Fc effector function.

The comparison of the AZ1 and AZ2 crystal structures to wild type Fc crystal structures reveals that AZ1 and AZ2 crystallized in an 'open' conformation that resembles the conformation observed in the PDB ID 2WAH. See, Crispin et al., 2009, Journal of Molecular Biology 387:1061:1066, which is hereby incorporated by reference herein in its entirety. The crystal structure 2WAH presents an immature high mannose-type glycan structure and a distinct 'open' conformation of the CH2 domains. In an independent analysis, high mannose-type glycan IgGs have been reported to display enhanced ADCC and based on this result, it has been proposed that the high mannose-type glycan induces the 'open' conformation observed in the 2WAH crystal structure, which in turn is the reason for the enhanced ADCC.

In contrast to the immature high mannose-type glycan of the 2WAH variant, the AZ1 and AZ2 crystal structures clearly show an IgG1 like core complex-type glycan structure that is similar to what has been observed in wild type Fc crystal structures. The carbohydrate-carbohydrate interaction of AZ1, AZ2 was analyzed. The glycan structures were compared by superposition to wild type Fc structures as described and detailed by Nagae and Yamaguchi. See, Nagae and Yamaguchi 2012, Function and 3D Structure of the N-Glycans on Glycoproteins. Int J Mol Sci. 13: 8398-8429, which is hereby incorporated by reference herein in its entirety. Nagae and Yamaguchi categorized the available wild type Fc crystal structures with respect to their carbohydrate-carbohydrate interactions and the distance of the Man-4 moieties. According to this categorization, the AZ glycan structure falls within the complex-type glycan conformations and carbohydrate-carbohydrate interactions naturally observed in wild type Fc crystal structures. This suggests that the 'open' conformation of the CH2 domains in the AZ crystal structures is not a consequence of non-wild type glycan structure, but likely has a different reason.

To further investigate the relevance of the observed 'open' conformation in AZ crystal structures, all available wild type Fc crystal structures were compared and differences in the CH2-CH3 interdomain angle, crystal space group, crystal packing and crystallization conditions were evaluated. FIG. 8 lists a representative subset of Fc crystal structures grouped by distinct crystal contacts and crystal packing. Close inspection of the crystal packing of the wild type Fc structures revealed two distinct possible crystal packing within structures crystallized in the same orthorhombic space group $P2_12_12_1$.

Analysis of the differences in crystal packing, as exemplified by comparison of the AZ1 and 3AVE structures, reveals that the most significant difference in crystal contacts and packing between the 3AVE and AZ1 structure is at the CH2 domain and the hinge, which is close to the interaction region with FcgammaRs. The most prominent crystal contact in 3AVE is affects only one of the CH2 domains, while for AZ1 the adjacent Fc is bound in between two CH2 domains. This difference in crystal contacts and crystal packing is in agreement with the observed differences in 'openness' of the Fc structures.

Furthermore, in the crystal structure of AZ1 and AZ2, two tightly bound iodide ions were found at the CH2-CH3 domain interface. Analysis of the interactions of the CH2-CH3 domain and the iodide ions shows that the tight interactions are only formed in the 'open' conformation with the particular CH2-CH3 interdomain angle, as observed in the AZ1 and AZ2 crystal structures, which suggests that the presence of the iodide in the crystallization conditions might favor the 'open' conformation.

This analysis suggests that the crystallization conditions and the crystal packing might be the main determining factor for the degree of 'openness' of the CH2 conformation and the CH2-CH3 interdomain angle as observed in glycosylated Fc crystal structures.

Analysis of Glycosylation Pattern of Fc Heterodimeric Proteins.

Figure 9:
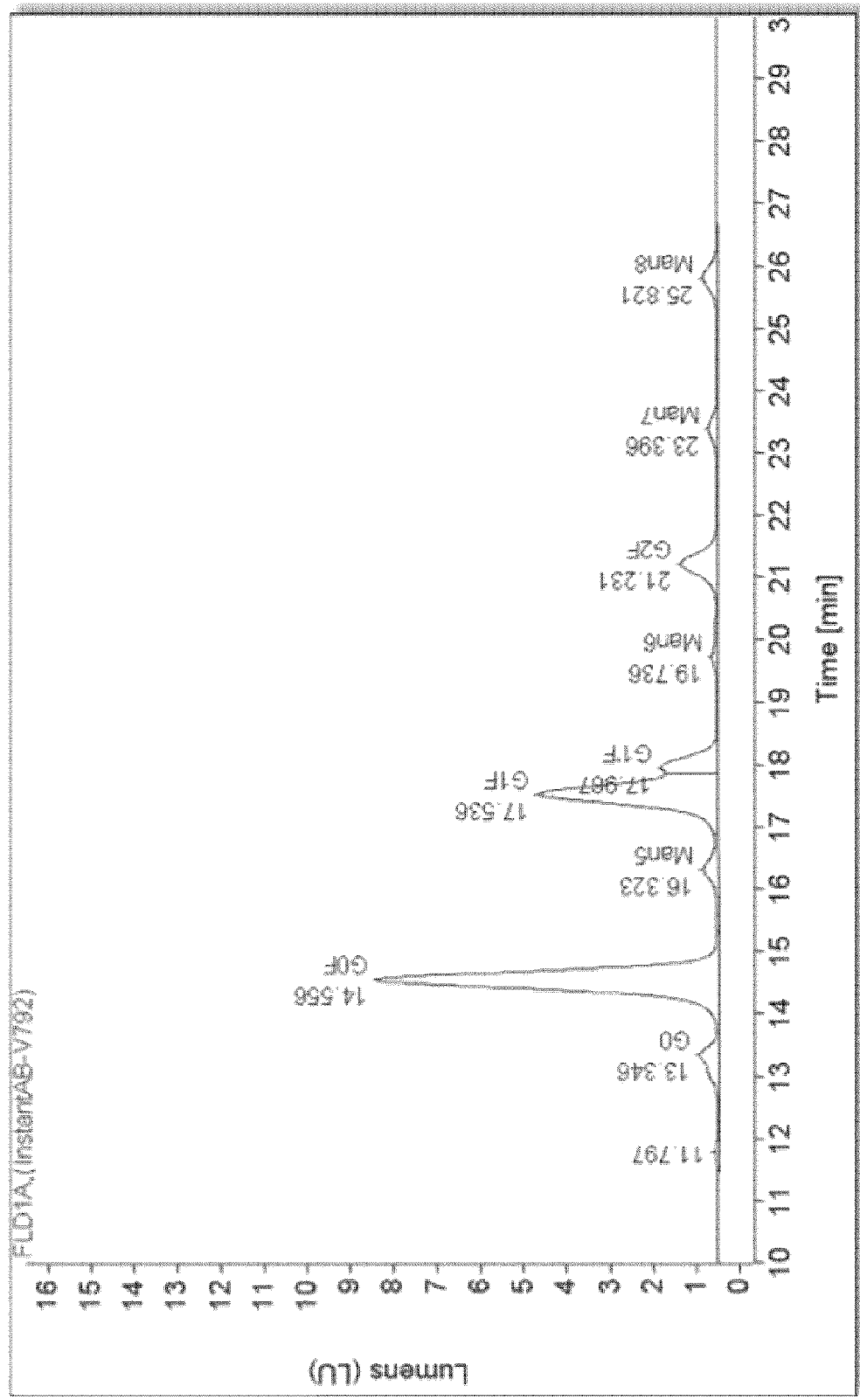
FIG. 9 provides a glycosylation analysis of AZ1, indicating that it has a wild-type glyco-pattern, in accordance with some embodiments of the present disclosure.

As discussed above, the glycosylation observed in the crystal structures of Fc heterodimeric proteins AZ1 and AZ2 resembles the typical wild type like complex-type core-glycan structure. For further validation of the glycoform present in AZ1 and AZ2, the detailed glycosylation profile of full size IgG1 heterodimeric antibody was analyzed. For this analysis two proof of concept molecules were designed that on the commercial anti-HER2 antibody Trastuzumab with two identical Trastuzumab Fabs attached to AZ1 or to AZ2. The bivalent anti-her2-AZ1 heterodimeric antibody was expressed in CHO cells by transient co-expression and the heterodimer purity was confirmed using mass spectrometry. The analysis illustrated in FIG. 9 shows a typical IgG1 like complex-type glycosylation pattern with G0F and G1F being the most prominent glycoforms. This reflects the core complex-type glycosylation observed in the AZ1 and AZ2 crystal structures and confirms the wild type IgG1 glycosylation of the engineered Fc heterodimeric protein. To produce the data for FIG. 9, the Trastuzumab based heterodimeric antibody anti-her2-AZ1 was expressed and purified as described herein. Glycans were analyzed with GLYKO-PREP™ Rapid N-Glycan Preparation with InstantAB (Prozyme) using the standard manufacturer protocol.

FcgammaR Binding and Fc Effector Function of Fc Heterodimeric Proteins.

To confirm that the engineered Fc heterodimeric protein retains all Fc mediated effector functions, the FcgammaR binding affinities were determined by surface plasmon resonance (SPR) and the ADCC and CDC activity were also determined. The SPR and ADCC experiments were performed on the anti-her2-AZ1 heterodimeric antibody, described above, and compared to similarly produced parent Trastuzumab, while the CDC activity was measured using bivalent anti-CD20(Rituximab)-AZ1 heterodimeric antibody and similarly produced parent Rituximab as control.

In the first set of experiments the affinities to the activating FcgammaRIIIa (CD16a(F158)) and the inhibiting FcgammaRIIb (CD32b(Y163)) were determined by SPR. The sensorgrams of the heterodimeric antibodies anti-her2-AZ1, anti-her2-AZ2 and parent Trastuzumab were highly similar, and no significant differences were detected. As detailed in FIG. 10, the calculated FcgammaR affinities for the AZ1 and AZ2-based heterodimeric antibodies are very similar to wild type IgG1 control.

Figure 11:
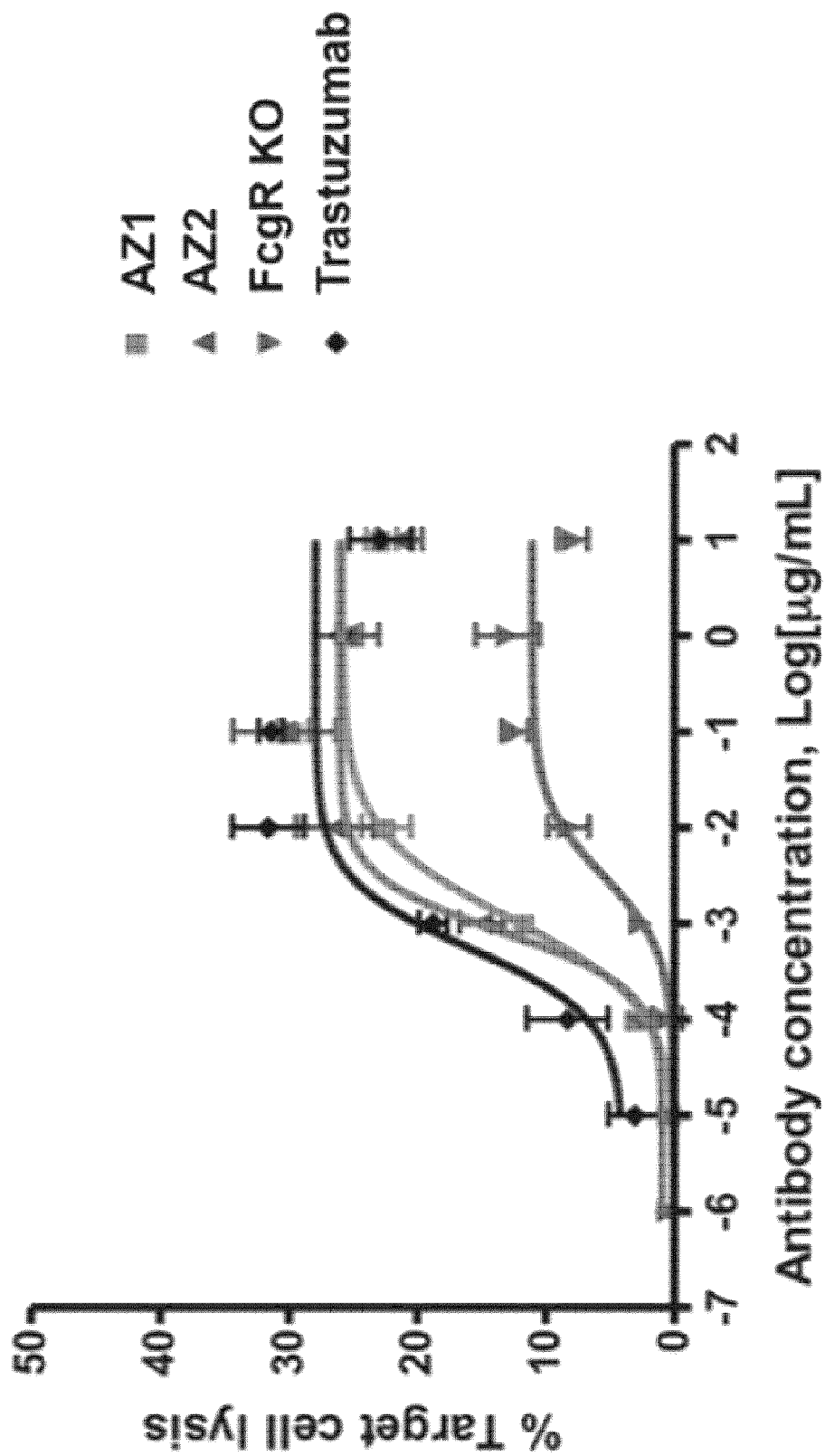
FIG. 11 illustrates the ADCC activity of an anti-Her2 heterodimeric antibody (anti-her2(Herceptin)-AZ1) and parent Trastuzumab against the melanoma cell line SKOV3, measured using human peripheral blood mononuclear cells (PBMC) as effector cells, in accordance with some embodiments of the present disclosure.
Figure 12:
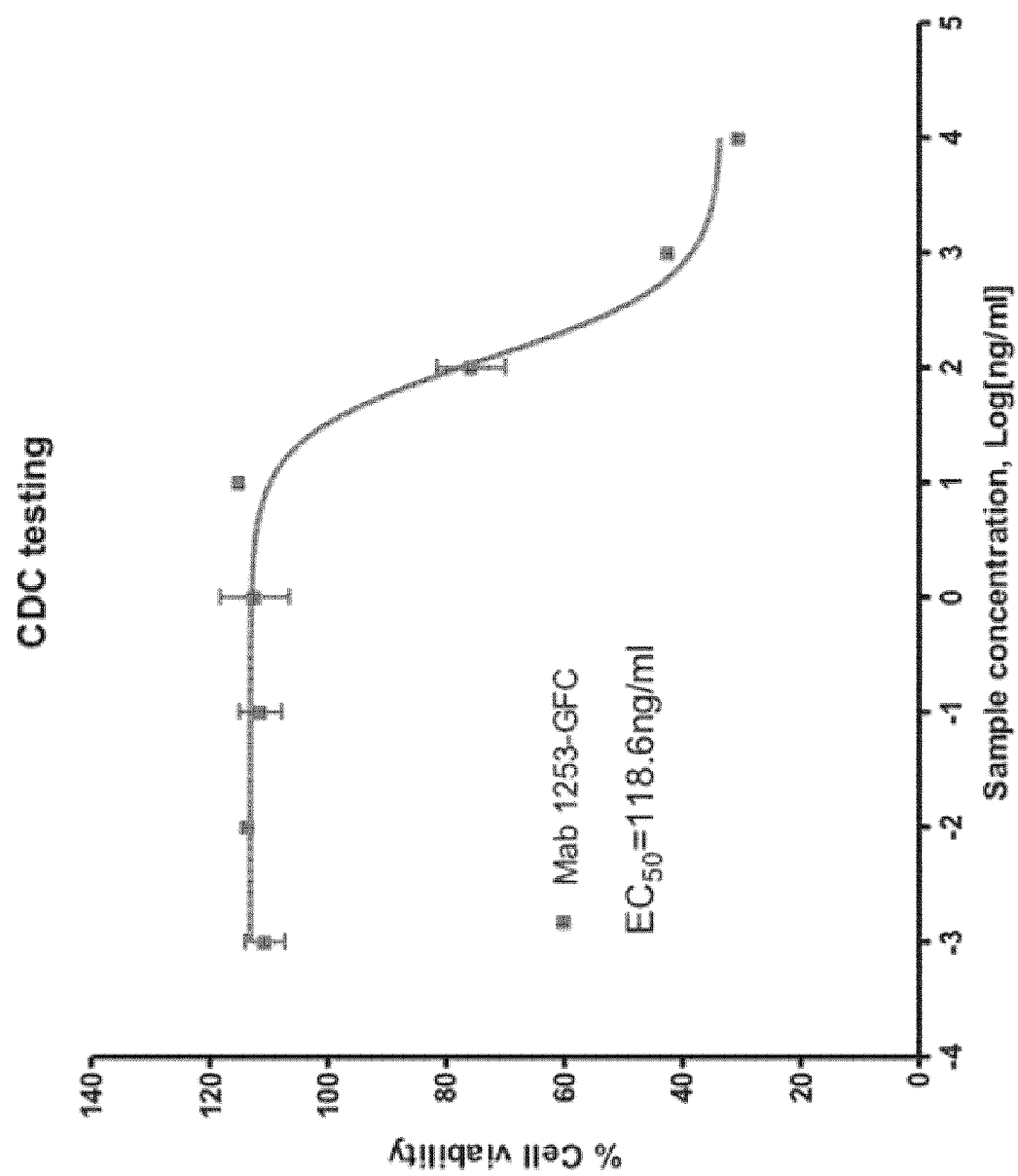
FIGS. 12 and 13 illustrate the CDC activity of an anti-CD20 heterodimeric antibody (anti-CD20(Rituximab)-AZ1) and parent Rituximab as control was determined using human serum as a complement source, against the human CD20 B lymphocyte cell line Raji, in accordance with some embodiments of the present disclosure.
Figure 13:
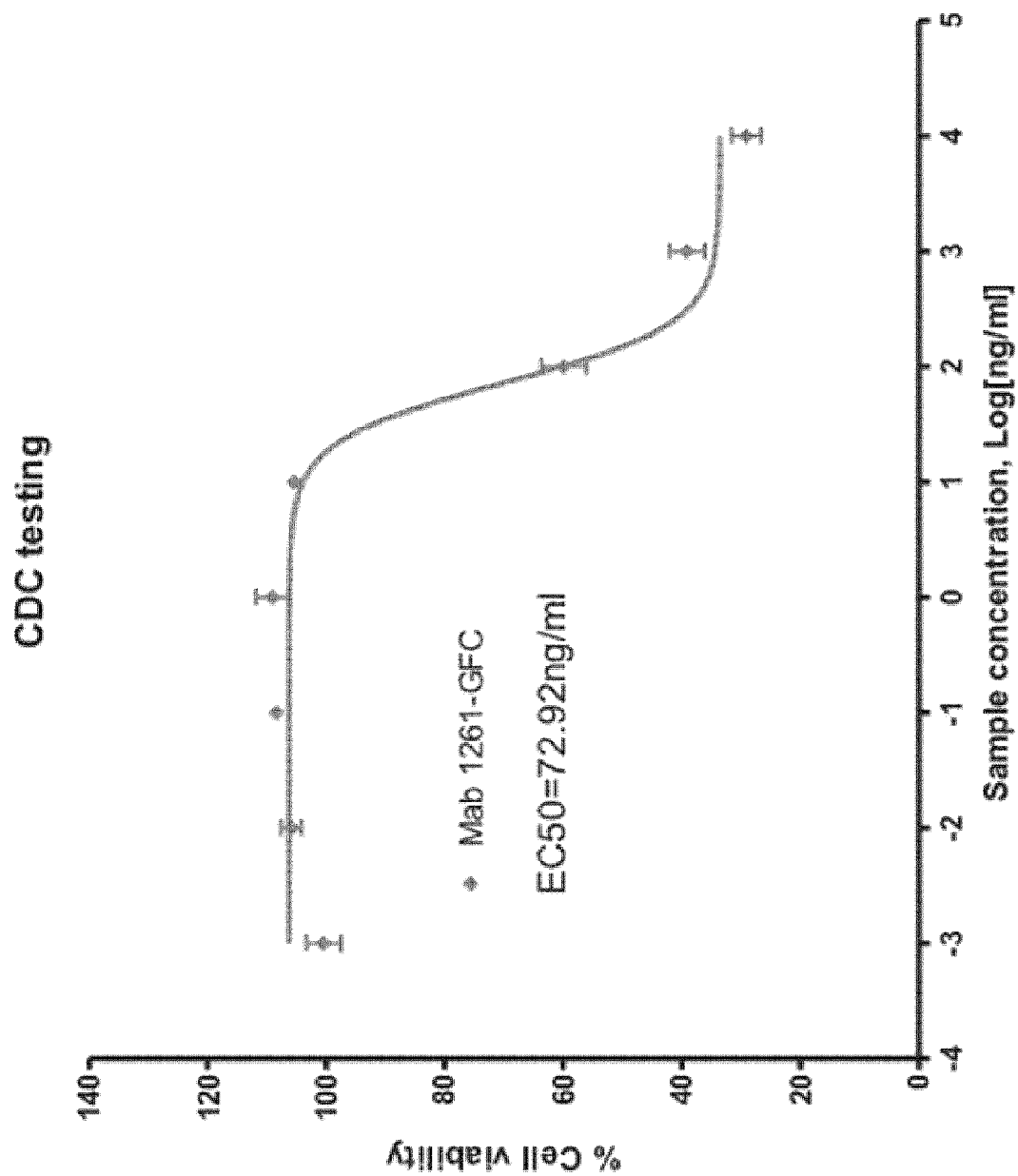

In a second set of experiments, as illustrated in FIG. 11, the ADCC activity of the anti-her2-AZ1 heterodimeric antibody and parent Trastuzumab against the melanoma cell lines SKOV3 was measured using human peripheral blood mononuclear cells (PBMC) as effector cells. No significant difference between the AZ1 heterodimeric antibody and parent Trastuzumab was observed. The CDC activity of anti-CD20(Rituximab)-AZ1 heterodimeric antibody and parent Rituximab as control was determined using human serum as a complement source, against the human CD20 B lymphocyte cell line Raji. As depicted in FIGS. 12 and 13, no significant difference between the Rituximab based AZ1 heterodimeric antibody and parent Rituximab was observed.

Taken together, the results of the ADCC and CDC activity of AZ1-based heterodimeric antibodies compared to the wild type IgG1 controls confirms wild type IgG1 mediated effector function of the engineered heterodimeric antibodies.

FcRn (Neonatal Fc Receptor) Binding and Pharmacokinetic Profile of Trastuzumab-Based AZ1 and AZ2 Heterodimeric Antibodies in Mice.

The human FcRn binding kinetics of the Trastuzumab based AZ1 and AZ2 heterodimer antibodies (anti-her2-AZ1 or anti-her2-AZ2, as described above, and the parent trastuzumab control was estimated by SPR for binding at pH 6.0 and release at pH 7.5. The sensorgrams of the heterodimeric antibodies and parent Trastuzumab were highly similar, and no significant differences were detected. The resulting FcRn affinities for AZ1 and AZ2 anti-her2 heterodimeric antibodies in comparison to parent Trastuzumab are summarized in FIG. 14.

Figure 15:
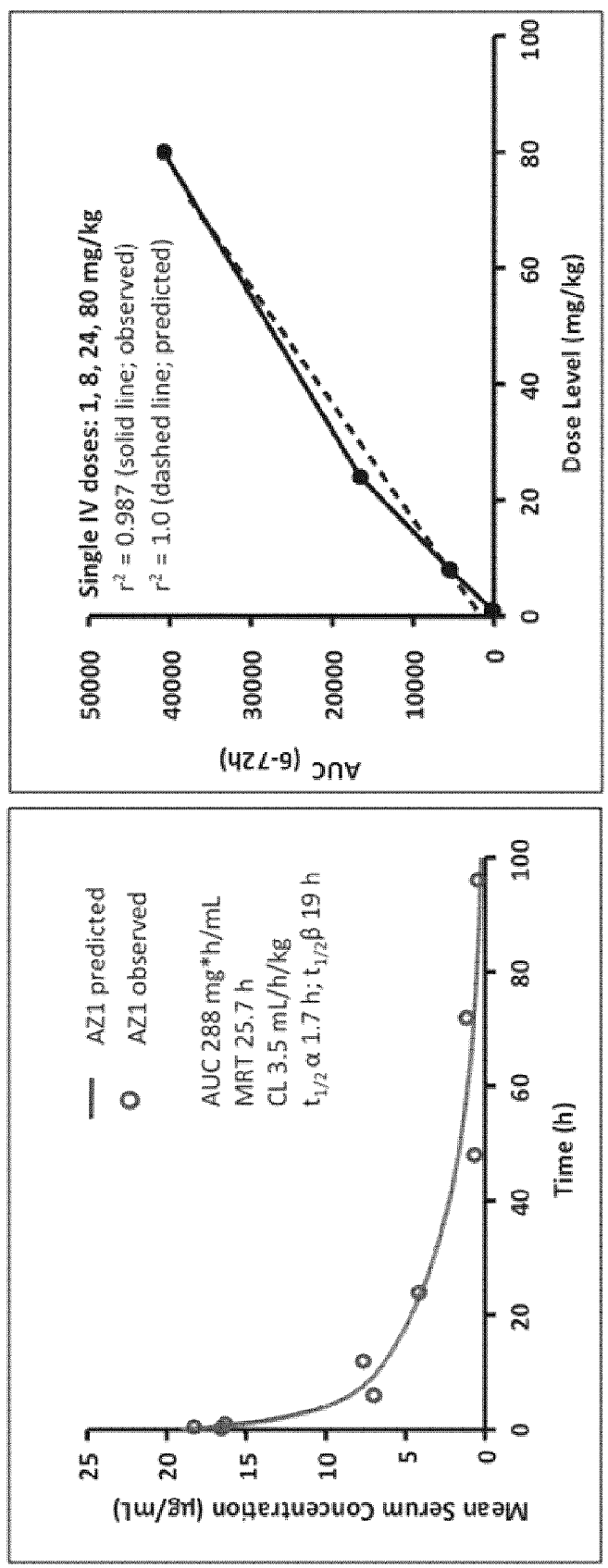
FIG. 15 illustrates a pharmacokinetic (PK) study in which the Trastuzumab based anti-her2 AZ1 heterodimeric antibody (anti-her2(Herceptin)-AZ1) was injected intravenously into nude mice at 4 different dose levels of 1, 8, 24 and 80 mg/kg, and the plasma clearances were monitored by an anti-Trastuzumab specific ELISA, in accordance with some embodiments of the present disclosure.

To assess the in vivo properties of the heterodimeric antibodies, a pharmacokinetic (PK) study was performed using the Trastuzumab based anti-her2 AZ1 heterodimeric antibody (anti-her2-AZ1), described above. Nude mice were injected intravenously at 4 different dose levels of 1, 8, 24 and 80 mg/kg, and the plasma clearances were monitored by an anti-Trastuzumab specific ELISA, as illustrated in FIG. 15. The kinetics of elimination at the different dose levels is linear over the studied dose range and the calculated pharmacokinetic properties are very similar to those published for parent Trastuzumab. The mouse PK analysis verified that the engineered heterodimeric antibody retains the preferred wild type IgG1 like pharmacokinetic properties.

In an additional set of studies, the glycosylation profile of the heterodimeric antibody was analyzed because altered glycosylation can significantly affect the Fc functionality and potentially also immunogenicity. The glycosylation analysis showed a typical IgG1 glycosylation profile for the heterodimeric antibody. Further, more detailed functional validation of heterodimeric antibodies by FcgammaR binding, ADCC and CDC analysis demonstrated that the heterodimeric antibodies retain all wild type Fc mediated effector functions. To assess the in vivo properties of the heterodimeric antibodies, a pharmacokinetic study was performed at different doses, showing no significant differences to wild type IgG1 clearance behavior. All together, the disclosed structural and functional analysis demonstrates preferred IgG1 drug like properties including Fc effector functionality, pharmacokinetics and early immunogenicity analysis, which significantly de-risk the development of bispecific therapeutics based on the Azymetric scaffold.

Despite the wild type IgG1 glycosylation and Fc effector function of the disclosed Fc heterodimeric proteins, as demonstrated here, the crystal structures of the AZ1 and AZ2 Fc heterodimeric proteins surprisingly showed an 'open' conformation of the CH2 domains and the CH2-CH3 interdomain angle. This 'open' conformation of the CH2 domains had previously been suggested to be due to altered glycosylation and has further been implicated to play a role in increased FcgammaR binding and ADCC. Here it is demonstrated that although crystallized in an 'open' conformation, the disclosed Fc heterodimeric protein neither displays altered glycosylation, nor enhanced FcgammaR binding and ADCC, questioning the hypothesized correlation of 'openness' and ADCC activity. Further detailed structural analysis of Fc crystal structures presented here suggests that the 'openness' of the CH2 domains and the CH2-CH3 interdomain angle as observed in crystal structures might in contrast be induced to the crystallization conditions and crystal packing. This observation further questions the relevance of the 'openness' of the CH2 domains in crystal structures and the correlation to function. Nevertheless, IgG1 structures with altered, namely high mannose-type, glycosylation have been reported to display enhanced ADCC activity and reduced C1q dependent CDC. Since specific to ADCC, this might on the other hand also be a consequence of the lack of core fucose in the high mannose-type glycoforms, as recently discussed for non-fucosylated complex-type glycan IgG, rather than the 'openness' of the CH2 domain. This hypothesis is supported by the data on the heterodimeric antibodies showing wild type like Fc effector function and glycosylation.

Expression and Purification of Fc Heterodimeric Proteins for Crystallization.

Using separate plasmids for the two heavy chains and one light chain, CHO cells were transfected in exponential growth phase (1.5 to 2 million cells/mL) with aqueous 1 mg/mL 25 kDa polyethylenimine (PEI, Polysciences) at a PEI:DNA ratio of 2.5:1 (Raymond et al. 2011). For example, the transfection DNA comprised 5% GFP (green fluorescent protein), 45% salmon sperm DNA, 25% light chain and 12.5% of each of the complementary heterodimer heavy chains. At four to 48 hours after transfection in F17 serum-free media (Gibco), TN1 peptone is added to a final concentration of 0.5%. The clarified culture medium was loaded onto a MabSelect SuRe (GE Healthcare) protein-A column and washed with 10 column volumes of PBS buffer at pH 7.2. The antibody was eluted with 10 column volumes of citrate buffer at pH 3.6 with the pooled fractions containing the antibody neutralized with TRIS at pH 11. The antibody was finally desalted using an Econo-Pac 10DG column (Bio-Rad) and subsequently further purified by gel filtration. For gel filtration, 3.5 mg of the purified antibody was concentrated to 1.5 mL and loaded onto a Superdex 200 HiLoad 16/600 200 pg column (GE Healthcare) via an AKTA Express FPLC at a flow-rate of 1 mL/min PBS buffer at pH 7.4 was used at a flow-rate of 1 mL/min.

Binding Analysis to FcgammaR and FcRn by SPR.

All binding experiments disclosed herein (e.g., FIGS. 10 through 13) were carried out using a BioRad ProteOn XPR36 instrument. Briefly, recombinant HER-2/neu (p185, ErbB-2 (eBiosciences, Inc.)) was captured on the activated GLM sensorchip by injecting 4.0 µg/mL in 10 mM NaOAc (pH 4.5) at 25 µL/min until approximately 3000 resonance units (RUs) were immobilized with the remaining active groups quenched. An aliquot of 40 µg/mL of purified anti-HER-2/neu antibodies comprising the modified CH3 domains were indirectly captured on the sensorchip by binding the Her-2/neu protein when injected at 25 µL/min for 240s (resulting in approximately 500 RUs) following a buffer injection to establish a stable baseline. FcgammaR (CD16a(f allotype) and CD32b) concentrations (6000, 2000, 667, 222, and 74.0 nM) were injected at 60 µL/min for 120s with a 180s dissociation phase to obtain a set of binding sensograms. Resultant $K_D$ values were determined from binding isotherms using the Equilibrium Fit model with reported values as the mean of three independent runs.

Binding to FcRn was determined by SPR in two different orientations. First, in the direct capture method, recombinant FcRn was captured on a high density surfaces at approximately 5000 RUs, using standard NHS/EDC coupling and 100 nM of heterodimeric IgG and was injected in triplicate at 50 µL/min for 120 seconds with 600 second dissociation in MES pH 6 running buffer. Second, in the indirect capture experiment, a goat anti-human IgG surface was used to indirectly capture the antibodies (approximately 400 RUs each), followed by an injection of a 3-fold FcRn dilution series (6000 nM high conc). Running buffer was 10 mM MES/150 mM NaCl/3.4 mM EDTA/0.05 Tween20 at pH6. There was no significant binding of FcRn to the goat polyclonal surface. Both the AZ1 and AZ2-based heterodimeric antibodies showed similar to wild type sensograms. FIG. 14 shows the Kd determined by the indirect immobilization method with flowing FcRn.

Analysis of ADCC and CDC Mediated Effector Function.

The ADCC protocol was performed by harvesting SKBR3 target cells (ATCC, Cat# HTB-30) by centrifugation at 800 rpm for three minutes. The cells were washed once with assay medium and centrifuged and the medium above the pellet was completely removed. The cells were gently suspended with assay medium to make single cell solution. The number of SKBR3 cells was adjusted to 4× cell stock (10,000 cells in 50 µl assay medium). The test antibodies were then diluted to the desired concentrations as noted above.

The SKBR3 target cells were seeded in the assay plates as follows. An aliquot of 50 µl of 4× target cell stock and 50 µl of 4× sample diluents was added to wells of a 96-well assay plate and the plate was incubated at room temperature for thirty minutes in cell culture incubator. Effector cells (NK92/FcgammaRIIIa(158VN), 100 µl, E/T=5:1, i.e, 50,000 effector cells per well) were added to initiate the reaction and mixed gently by cross shaking.

Triton X-100 was added to cell controls without effector cells and antibody in a final concentration of 1% to lyse the target cells and these controls served as the maximum lysis controls. ADCC assay buffer (98% Phenol red free MEM medium, 1% Pen/Strep and 1% FBS) was added in to cell controls without effector cells and antibody and it served as the minimum LDH release control. Target cells incubated with effector cells without the presence of antibodies were set as background control of non-specific LDH release when both cells were incubated together. The plate was incubated at 37° C./5% $CO_2$ incubator for 6 hours. Cell viability was assayed with an LDH kit (Roche, cat#11644793001). The absorbance data was read at OD492 nm and OD650 nm. Data analysis and the reported percentages of cell lysis were calculated according the formula below: Cell lysis %=100* (Experimental data−(E+T))/(Maximum release−Minimum release).

The CDC protocol used for the CDC data disclosed herein was performed as follows. Rituximab based proof of concept of the disclosed heterodimers (anti-CD20(Rituximab)-AZ1) were tested for complement-dependent cytotoxicity using Raji cells. Cells were initially incubated for thirty minutes at 37° C. Subsequently, Raji and effector cells were combined and incubated for another two hours using 10% NHS as complement source and 5000 target cells/well. Cell titers were determined by glo cell viability assay using luminescens.

Additional Embodiments.

Those of skill in the art understand that a set of structure coordinates for a protein, a complex of proteins, or a portion thereof, such as AZ1 and AZ2, is a relative set of points that define a shape in three dimensions. Thus, it is possible that an entirely different set of coordinates could define a similar or identical shape. Moreover, slight variations in the individual coordinates will have little effect on overall shape.

The variations in coordinates discussed above may be generated because of mathematical manipulations of the AZ1 and/or AZ2 structure coordinates. For example, the structure coordinates set forth in FIG. 26 or 27 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within a certain root mean square deviation as compared to the original coordinates, the resulting three-dimensional shape is considered encompassed by the present disclosure.

Various computational analyses may be necessary to determine whether a macromolecule or portion thereof is sufficiently similar to AZ1 or AZ2. Such analyses may be carried out using well known software applications, such as the Molecular Similarity application of QUANTA (Molecular Simulations Inc., San Diego, Calif. 1998), CCP4 (Acta Crystallogr., D50, 760-763 (1994)) or ProFit (A. C. R. Martin, ProFit version 1.8, bioinfo.org.uk/software). In particular, the Molecular Similarity software application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure in the comparison is identified by a name. One structure is identified as the target (e.g., the fixed structure); all remaining structures are working structures (e.g., moving structures). Since atom equivalency within QUANTA is defined by user input, for the purpose of the present disclosure, equivalent atoms are considered to be protein backbone atoms N, C, O and $C_a$ for all corresponding amino acids between the two structures being compared. Moreover, the corresponding amino acids may be identified by sequence alignment programs such as the "bestfit" program available from the Genetics Computer Group which uses the local homology algorithm described by Smith and Waterman in Advances in Applied Mathematics 2, 482 (1981), which is incorporated herein by reference. The identification of equivalent residues can also be assisted by secondary structure alignment, for example, aligning secondary structure such as α-helices, β-sheets or hinge regions in the structure when present. For programs that calculate RMSD values of the backbone atoms, an RMSD cutoff value can be used to exclude pairs of equivalent atoms with extreme individual RMSD values, or in situations where the equivalent atom cannot be found in the corresponding structure.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of the present disclosure, any molecule or molecular complex that is within a predetermined root mean square deviation for backbone atoms (C, O, N and $C_a$) when superimposed on the relevant backbone atoms described by structure coordinates listed in any one of FIGS. 26 and 27 are encompassed by the present disclosure. In some embodiments, this RMSD is not greater than about 3.0 Å. In some embodiments, this RMSD is not greater than about 1.0 Å. In some embodiments, this RMSD is not greater than about 0.5 Å. In one embodiment, this RMSD is not greater than about 0.2 Å.

In another embodiment, the root mean square deviation of the backbone atoms between the amino acid residues of a candidate molecular structure and the AZ1 or AZ2 amino acid residues according to FIG. 26 or 27 is not greater than about 0.3 Å, and at least one of the amino acid residues of the candidate molecular structure is not identical to the AZ2 or AZ2 amino acid residue to which it corresponds.

In another embodiment, the root mean square deviation of the backbone atoms between the amino acid residues of a candidate molecular structure and the AZ1 or AZ2 amino acid residues according to FIG. 26 or 27 is not greater than about 0.3 Å, and at least two, at least three, at least four, or at least five of the amino acid residues of the candidate molecular structure is not identical to the AZ2 or AZ2 amino acid residue to which it corresponds. Additionally, in some embodiments, the candidate molecular structure may have additional residues not found in AZ1 or AZ2, or may be missing some terminal residues found in AZ1 or AZ2.

In another embodiment, the root mean square deviation of the backbone atoms between the amino acid residues of a candidate molecular structure and the AZ1 or AZ2 amino acid residues according to FIG. 26 or 27 is not greater than about 0.3 Å, at least one, at least two, at least three, at least four, or at least five of the amino acid residues of the candidate molecular structure is/are not identical to the AZ2 or AZ2 amino acid residue to which it corresponds.

Structure Determination of Other Molecules.

The structure coordinates set forth in FIGS. 26 and 27 can also be used to aid in obtaining structural information about another crystallized molecule or molecular complex. This may be achieved by any of a number of well-known techniques, including molecular replacement.

In one embodiment, a computer is disclosed for determining at least a portion of the structure coordinates corresponding to X-ray diffraction data obtained from a molecule or molecular complex, where the computer comprises: a) a machine-readable data storage medium comprising a data storage material encoded with machine-readable data, where the data comprises at least a portion of the structure coordinates of AZ1 or AZ2 according to FIG. 26 or 27, b) a machine-readable data storage medium comprising a data storage material encoded with machine-readable data, where the data comprises X-ray diffraction data obtained from the molecule or molecular complex; and, c) instructions for performing a Fourier transform of the machine readable data of (a) and for processing the machine readable data of (b) into structure coordinates. For example, the Fourier transform of at least a portion of the structure coordinates set forth in FIG. 26 or 27 may be used to determine at least a portion of the structure coordinates of IgG1 homologs. Therefore, in another embodiment the present disclosure provides a method of utilizing molecular replacement to obtain structural information about a molecule or molecular complex whose structure is unknown comprising the steps of: a) crystallizing the molecule or molecular complex of unknown structure; b) generating an X-ray diffraction pattern from the crystallized molecule or molecular complex; and c) applying at least a portion of the AZ1 or AZ2 structure coordinates set forth in FIG. 26 or 27 to the X-ray diffraction pattern to generate a three-dimensional electron density map of the molecule or molecular complex whose structure is unknown. By using molecular replacement, all or part of the structure coordinates of the AZ1 or AZ2 as provided by the present disclosure (and set forth in FIGS. 26 and 27) can be used to determine the structure of a crystallized molecule or molecular complex whose structure is unknown more quickly and efficiently than attempting to determine such information through more complex techniques such as multiple isomorphous replacement.

Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of AZ1 or AZ2 according to FIG. 26 or 27 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, 1985, "Use of the Rotation and Translation Functions", in Meth. Enzymol. 115: 55-77; Rossmann, ed., 1972, "The Molecular Replacement Method", Int. Sci. Rev. Ser. 13, Gordon & Breach, New York. The structure of any portion of any crystallized molecule or molecular complex that is sufficiently homologous to any portion of the AZ1 or AZ2 can be resolved by this method.

In some embodiments, the method of molecular replacement is utilized to obtain structural information about a immunoglobulin G homologue. The structure coordinates of AZ1 and AZ2 as provided by the present disclosure are particularly useful in solving the structure of other variants of immunoglobulin G or portions thereof. For instance, the structure coordinates of AZ1 and AZ2 as provided by this invention are useful in solving the structure of immunoglobulin G proteins that have amino acid substitutions, additions and/or deletions (referred to collectively as "immunoglobulin G mutants", as compared to naturally occurring immunoglobulins.

All of the macromolecules referred to above may be studied using well-known X-ray diffraction techniques and may be refined against 1.5-3.4 Å resolution X-ray data to an R value of about 0.30 or less using computer software, such as X-PLOR (Yale University, distributed by Molecular Simulations, Inc.; see, e.g., Blundell & Johnson, 1985, Meth. Enzymol., 114 & 115, H. W. Wyckoff et al., eds., Academic Press.

Computer System.

Figure 28:
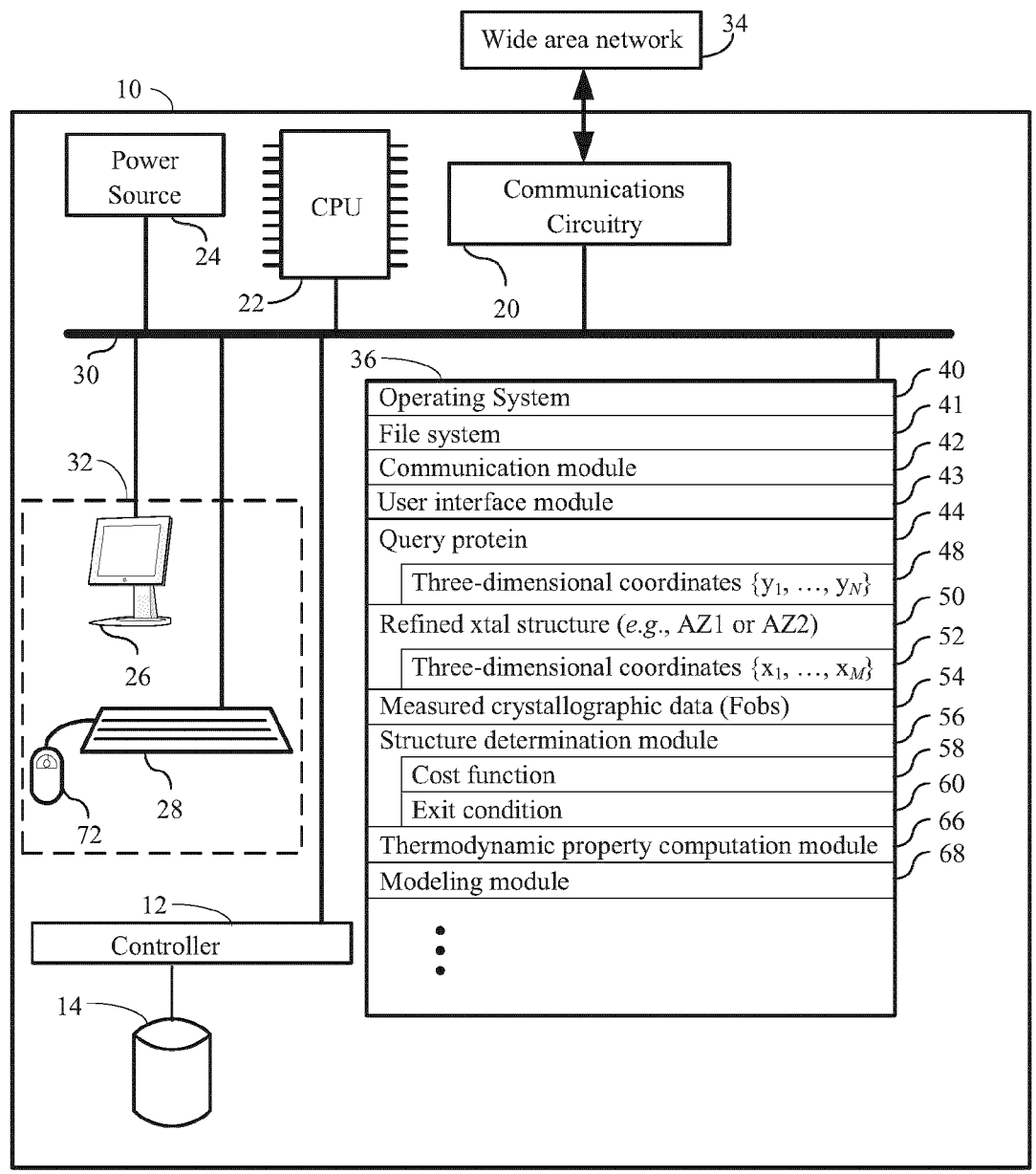
FIG. 28 is a block diagram illustrating a system for performing aspects of the present disclosure.

FIG. 28 is a block diagram illustrating a computer according to some embodiments. The computer 10 typically includes one or more processing units (CPU's, sometimes called processors) 22 for executing programs (e.g., programs stored in memory 36), one or more network or other communications interfaces 20, memory 36, a user interface 32, which includes one or more input devices (such as a keyboard 28, mouse 72, touch screen, keypads, etc.) and one or more output devices such as a display device 26, and one or more communication buses 30 for interconnecting these components. The communication buses 30 may include circuitry (sometimes called a chipset) that interconnects and controls communications between system components.

Memory 36 includes high-speed random access memory, such as DRAM, SRAM, DDR RAM or other random access solid state memory devices; and typically includes non-volatile memory, such as one or more magnetic disk storage devices, optical disk storage devices, flash memory devices, or other non-volatile solid state storage devices. Memory 36 optionally includes one or more storage devices remotely located from the CPU(s) 22. Memory 36, or alternately the non-volatile memory device(s) within memory 36, comprises a non-transitory computer readable storage medium. In some embodiments, the non-volatile components in memory 36 include one or more hard drives 14 controlled by one or more hard drive controllers 12. In some embodiments, memory 36 or the computer readable storage medium of memory 36 stores the following programs, modules and data structures, or a subset thereof:

- an operating system 40 that includes procedures for handling various basic system services and for performing hardware dependent tasks;
- a file system 41 for handling basic file I/O tasks;
- an optional communication module 42 that is used for connecting the computer 10 to other computers via the one or more communication interfaces 20 (wired or wireless) and one or more communication networks 34, such as the Internet, other wide area networks, local area networks, metropolitan area networks, and so on;
- an optional user interface module 43 that receives commands from the user via the input devices 28, 72, etc. and generates user interface objects in the display device 26;
- a query protein 44, including a set of three-dimensional coordinates $\{y_1, \ldots, y_N\}$ 48 for the query protein (e.g., PDBID: 2J6E) to use as a starting bases for obtaining phases for a composition comprising an Fc heterodimer protein 50 in crystal form in accordance with the present disclosure;
- a refined atomic crystal structure of a composition comprising an Fc heterodimer protein 50 in crystal form in accordance with the present disclosure including three-dimensional coordinates {x$_1$, ..., x$_M$} 52 for the Fc heterodimer protein 50 (e.g., those disclosed in FIG. 26 or 27);

measured crystallographic data 54 for the composition comprising an Fc heterodimer protein 50 in crystal form;

a structure determination module 56 for using the three-dimensional coordinates 48 of the query protein 44 and the measured crystallographic data 54 to determine the refined crystal structure comprising an Fc heterodimer protein 50 in accordance with the present disclosure; and a thermodynamic property computation module 66 for computing a thermodynamic property of all or a portion of the refined crystal structure 50.

An aspect of the present disclosure provides a method of identifying a mutation which promotes heterodimeric Fc chain pair formation. In this method, structure based modeling is performed, using a suitably programmed computer, such as computer 10 of FIG. 28. The modeling is performed to identify a candidate mutation to an Fc chain using a three-dimensional atomic crystal structure of an Fc heterodimer protein. In some embodiments this three-dimensional atomic crystal structure is refined crystal structure 50. In some embodiments this three-dimensional atomic crystal structure is all or a portion of the coordinates for AZ1 or AZ2 as set forth in FIGS. 26 and 27. In some embodiments, this three-dimensional atomic crystal structure is defined by the atomic coordinates of any combination of chains a, b, A, and B of FIG. 26 or 27 determined from an X-ray diffraction quality crystal of the Fc heterodimer protein, where the Fc heterodimer protein comprises the amino acid sequences as set forth in (i) SEQ ID NOS: 2 and 3 or (ii) SEQ ID NOS: 4 and 5 of FIG. 16, and the X-ray diffraction quality crystal is in an orthorhombic space group. In some embodiments the orthorhombic space group is P2$_1$2$_1$2$_1$ and has unit cell dimensions a=49±2 Å, b=75±2 Å, c=149±2 Å, $\alpha=\beta=\gamma=90°$. In some embodiments, the structure based modeling is performed by modeling module 68. In some embodiments, the modeling comprises identifying a plurality of residues on the three-dimensional structure that influence heterodimeric Fc chain pair formation, (b) modeling a plurality of three-dimensional Fc structures using the three-dimensional atomic crystal structure as a template, where each three-dimensional Fc structure in the plurality of three-dimensional Fc structures includes mutations to one or more of the residues in the plurality of residues, (c) comparing each three-dimensional Fc structure in the plurality of three-dimensional Fc structures to the three-dimensional atomic crystal structure, and (d) selecting one of the three-dimensional Fc structure in the plurality of three-dimensional Fc structures based on the comparing (c).

In some embodiments the comparing (c) compares a calculated thermodynamic property of the three-dimensional atomic crystal structure to a calculated thermodynamic property of a three-dimensional Fc structure in the plurality of three-dimensional Fc structures. In some embodiments the thermodynamic property is entropy, average energy, average enthalpy, free energy or heat capacity. In some embodiments the modeling, including the calculation of the thermodynamic property, is performed using the techniques disclosed in U.S. Provisional Patent Application No. 61/793,203, entitled "Systems and Methods for Identifying Thermodynamic Effects of Atomic Changes to Polymers", filed Mar. 15, 2013, which is hereby incorporated by reference herein in its entirety.

In some embodiments, the comparing (c) compares a physical property of the three-dimensional atomic crystal structure to a calculated thermodynamic property of a three-dimensional Fc structure in the plurality of three-dimensional Fc structures, where the physical property is selected from the group consisting of (i) one or more electrostatic interactions, (ii) one or more polar interactions, (iii) one or more hydrogen-bond interactions, (iv) a comparison of buried versus accessible surface area, (v) accessible surface area, (vi) one or more hydrophobic interactions, and (vii) presence or absence of one or more buried water molecules.

In some embodiments, the modeling is performed using the techniques disclosed in U.S. Provisional Patent Application No. 61/662,549, entitled "Systems and Methods for Identifying Thermodynamically Relevant Polymer Conformations", filed Jun. 21, 2012, which is hereby incorporated by reference herein in its entirety. In some embodiments, such modeling is facilitated using the techniques disclosed in U.S. Provisional Patent Application No. 61/613,711, entitled "Systems and Methods for Making Two Dimensional Graphs of Complex Molecules", filed Mar. 31, 2013, which is hereby incorporated by reference herein in its entirety. In some embodiments, such modeling is facilitated using the techniques disclosed in U.S. patent application Ser. No. 13/822,258, entitled "System for Molecular Packing Calculations", filed Mar. 11, 2013, claiming priority to International Application PCT/CA11/01061, which is hereby incorporated by reference herein in its entirety. In some embodiments, such modeling is facilitated using the techniques disclosed in U.S. patent application Ser. No. 13/822,231, entitled "Simplifying Residue Relationships in Protein Design", filed Mar. 11, 2013, claiming priority to International Application PCT/CA11/01103, which is hereby incorporated by reference herein in its entirety. In some embodiments, such modeling is facilitated using the techniques disclosed in International Application No. PCT/CA2010/001923, entitled "Combined On-Lattice/Off-Lattice Optimization Method for Rigid Body Docking", filed Dec. 2, 2010, which is hereby incorporated by reference herein in its entirety. In some embodiments, such modeling is facilitated using the techniques disclosed in U.S. Provisional Patent Application No. 61/684,236, entitled "Methods for Sampling and Analysis of Protein Conformational Dynamics", filed Aug. 17, 2012, which is hereby incorporated by reference herein in its entirety. In some embodiments, such modeling is facilitated using the techniques disclosed in U.S. patent application Ser. No. 11/441,526, entitled "System and Method for Modeling Interactions", filed May 26, 2006, which is hereby incorporated by reference herein in its entirety. In some embodiments, such modeling is facilitated using the techniques disclosed in U.S. patent application Ser. No. 11/581,075, entitled "System and Method for Simulating the Time-Dependent Behaviour of Atomic and/or Molecular Systems Subject to Static or Dynamic Fields", filed Oct. 16, 2006, which is hereby incorporated by reference herein in its entirety. In some embodiments, such modeling is facilitated using the techniques disclosed in U.S. patent application Ser. No. 12/866,437, entitled "Methods for Determining Correlated Residues in a Protein or other Biopolymer Using Molecular Dynamics", filed Oct. 11, 2010, which is hereby incorporated by reference herein in its entirety.

In some embodiments modeling module 68, in fact, represents one or more programs. In some embodiments, modeling module 68 comprises any or a portion of the techniques disclosed or incorporated in QUANTA (Molecular Simulations Inc., San Diego, Calif. 1998), CCP4 (Acta Crystallogr., D50, 760-763 (1994)), ProFit (A. C. R. Martin, ProFit version 1.8, bioinfo.org.uk/software); Cohen et al., 1990, "Molecular Modeling Software and Methods for Medicinal Chemistry", Journal of Medicinal Chemistry 33: 883-894; Navia and Murcko, 1992, "The Use of Structural Information in Drug Design", Current Opinions in Structural Biology 2: 202-210 (1992); Balbes et al., 1994, "A Perspective of Modern Methods in Computer-Aided Drug Design", in Reviews in Computational Chemistry 5, Lipkowitz and Boyd, Eds., VCH, New York, pp. 337-380; Guida, 1994, "Software For Structure-Based Drug Design", Current Opinion in Structural Biology 4: 777-781, Bohacek et al., 1996, "The art and practice of structure-based drug design: A molecular modeling perspective", Medicinal Research Reviews 16: 3-50; Leach, 2001, "Molecular Modelling, Principles and Applications", Second Edition, Prentice Hall, Upper Saddle River, N.J.; and Cramer, 2004, "Essentials of Computational Chemistry: Theories and Models", Wiley, Hoboken, N.J., each of which is hereby incorporated by reference, to name a few representative samples.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present disclosure can be implemented as a computer program product that comprises a computer program mechanism embedded in a non-transitory computer readable storage medium such as CD-ROM, DVD, magnetic disk storage product, and the like.

Many modifications and variations of the present disclosure can be made without departing from its spirit and scope, as will be apparent to those skilled in the art. The specific embodiments described herein are offered by way of example only. The present disclosure is to be limited only by the terms of the appended claims, along with the full scope of equivalents to which such claims are entitled.

What is claimed:

1. A composition comprising an Fc heterodimer protein in crystalline form, wherein:
    said Fc heterodimer protein comprises the amino acid sequences set forth in (i) SEQ ID NOS:2 and 3 or (ii) SEQ ID NOS:4 and 5;
    said crystal is in space group $P2_12_12_1$; and
    said crystal has unit cell dimensions a=49±2 Å, b=75±2 Å, c=149±2 Å, α=β=γ=90°.

2. The composition of claim 1, wherein said Fc heterodimer protein comprises the amino acid sequences set forth in SEQ ID NOS:2 and 3 and has a three dimensional structure characterized by the atomic coordinates of (i) chains A and B of FIG. 27 or (ii) chains a and b of FIG. 27.

3. The composition of claim 1, wherein said Fc heterodimer protein comprises the amino acid sequences set forth in SEQ ID NOS:4 and 5 and has a three dimensional structure characterized by the atomic coordinates of (i) chains A and B of FIG. 26 or (ii) chains a and b of FIG. 26.

4. The composition of claim 1, wherein said Fc heterodimer protein comprises the amino acid sequences set forth in SEQ ID NOS: 2 and 3 forming a CH3 domain interface, and wherein the Fc heterodimer protein provides complementary hydrophobic and electrostatic surfaces, created by residues 366, 392, 394 of SEQ ID NO: 2 and residues 351, 405, 407 of SEQ ID NO: 3, at the CH3 domain interface with opposite surface complementarity to corresponding wild type Fc interface surfaces.

5. The composition of claim 1, wherein said Fc heterodimer protein comprises the amino acid sequences set forth in SEQ ID NOS: 4 and 5 forming a CH3 domain interface, and wherein the Fc heterodimer protein provides complementary hydrophobic and electrostatic surfaces, created by residues 366, 392, 394 of SEQ ID NO: 4 and residues 351, 405, 407 of SEQ ID NO: 5, at the CH3 domain interface with distinct surface complementarity relative to the corresponding wild type Fc interface surfaces.

6. The composition of claim 1, wherein said Fc heterodimer protein comprises a D399-K409 salt bridge.

7. The composition of claim 4, wherein said CH3 domain interface is formed in two orientations and said crystalline form of said Fc heterodimer protein comprises a 50:50 mixture of the two orientations.

8. A method of obtaining the composition of claim 1, comprising the steps of:
    a) producing and purifying said Fc heterodimer protein; and
    b) subjecting the purified Fc heterodimer protein of step a) to conditions which promote crystallization, thereby obtaining the Fc heterodimer protein in crystalline form.

9. The method of claim 8, wherein the conditions which promote crystallization comprise mixing the purified Fc heterodimer protein with a mother liquor solution, wherein the mother liquor solution comprises between 2% and 10% (v/v) ethylene glycol, between 10% and 25% (w/v) polyethylene glycol having an average molecular weight of between 2000 Daltons and 10000 Daltons, and between 0.05 M and 0.40 M ammonium iodide.

10. The method of claim 9, wherein the mother liquor solution comprises 5% (v/v) ethylene glycol, 18% (w/v) polyethylene glycol having an average molecular weight of 3350 Daltons, and 0.15 M ammonium iodide.

11. The method of claim 9, wherein the purified Fc heterodimer protein is mixed with a first aliquot of the mother liquor solution and suspended over a second aliquot of the mother liquor in a hanging drop method.

12. The method of claim 11, wherein the purified Fc heterodimer protein is mixed with a first aliquot of the mother liquor solution in a 2:1 ratio.

13. The method of claim 11, wherein the purified Fc heterodimer protein is incubated at a temperature of between 15° C. and 25° C. after the mixing.

14. A crystallizable composition comprising a mixture of (i) a solubilized Fc heterodimer protein comprising the amino acid sequence set forth in (a) SEQ ID NOS: 2 and 3 or (b) SEQ ID NOS: 4 and 5 and (ii) a mother liquor solution, wherein the mother liquor solution comprises between 2% and 10% (v/v) ethylene glycol, between 10% and 25% (w/v) polyethylene glycol having an average molecular weight of between 2000 Daltons and 10000 Daltons, and between 0.05 M and 0.40 M ammonium iodide.

15. The crystallizable composition of claim 14, wherein the mother liquor solution comprises 5% (v/v) ethylene glycol, 18% (w/v) polyethylene glycol having an average molecular weight of 3350 Daltons, and 0.15 M ammonium iodide.

* * * * *

SEQUENCE LISTING

<160> NUMBER OF SEQ ID NOS: 5

<210> SEQ ID NO 1
<211> LENGTH: 226
<212> TYPE: PRT
<213> ORGANISM: Homo sapiens

<400> SEQUENCE: 1

```
Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
```

<210> SEQ ID NO 2
<211> LENGTH: 226
<212> TYPE: PRT
<213> ORGANISM: Artificial Sequence
<220> FEATURE:
<223> OTHER INFORMATION: Mutated form of Human IgG1 Fc germaline sequence 231-447 (AZ1 heterodimer)

<400> SEQUENCE: 2

```
Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Val Leu Pro Pro Ser Arg Asp Glu Leu Thr Lys Asn Gln Val Ser Leu
130                 135                 140

Leu Cys Leu Val Lys Gly Phe Tyr Pro Ser Asp Ile Ala Val Glu Trp
145                 150                 155                 160

Glu Ser Asn Gly Gln Pro Glu Asn Asn Tyr Leu Thr Trp Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225
```

<210> SEQ ID NO 3
<211> LENGTH: 226
<212> TYPE: PRT
<213> ORGANISM: Artificial Sequence
<220> FEATURE:
<223> OTHER INFORMATION: Mutated form of Human IgG1 Fc germline sequence 231-447 (AZ1 heterodimer)

<400> SEQUENCE: 3

```
Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Asp Val Ser His Glu
        35                  40                  45

Asp Pro Glu Val Lys Phe Asn Trp Tyr Val Asp Gly Val Glu Val His
```

```
                50                  55                  60
Asn Ala Lys Thr Lys Pro Arg Glu Glu Gln Tyr Asn Ser Thr Tyr Arg
 65                  70                  75                  80

Val Val Ser Val Leu Thr Val Leu His Gln Asp Trp Leu Asn Gly Lys
                 85                  90                  95

Glu Tyr Lys Cys Lys Val Ser Asn Lys Ala Leu Pro Ala Pro Ile Glu
                100                 105                 110

Lys Thr Ile Ser Lys Ala Lys Gly Gln Pro Arg Glu Pro Gln Val Tyr
                115                 120                 125

Val Tyr Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Ala Leu Val Ser Lys Leu Thr Val Asp
                180                 185                 190

Lys Ser Arg Trp Gln Gln Gly Asn Val Phe Ser Cys Ser Val Met His
                195                 200                 205

Glu Ala Leu His Asn His Tyr Thr Gln Lys Ser Leu Ser Leu Ser Pro
    210                 215                 220

Gly Lys
225

<210> SEQ ID NO 4
<211> LENGTH: 226
<212> TYPE: PRT
<213> ORGANISM: Artificial Sequence
<220> FEATURE:
<223> OTHER INFORMATION: Mutated form of Human IgG1 Fc germline sequence
      231-447 (AZ2 heterodimer)

<400> SEQUENCE: 4

Lys Thr His Thr Cys Pro Pro Cys Pro Ala Pro Glu Leu Leu Gly Gly
  1               5                  10                  15

Pro Ser Val Phe Leu Phe Pro Pro Lys Pro Lys Asp Thr Leu Met Ile
                 20                  25                  30

Ser Arg Thr Pro Glu Val Thr Cys Val Val Val Asp Val Ser His Glu
             35                  40                  45

Asp Pro Glu Val Lys Phe Asn Trp Tyr Val Asp Gly Val Glu Val His
     50                  55                  60

Asn Ala Lys Thr Lys Pro Arg Glu Glu Gln Tyr Asn Ser Thr Tyr Arg
 65                  70                  75                  80

Val Val Ser Val Leu Thr Val Leu His Gln Asp Trp Leu Asn Gly Lys
                 85                  90                  95

Glu Tyr Lys Cys Lys Val Ser Asn Lys Ala Leu Pro Ala Pro Ile Glu
                100                 105                 110

Lys Thr Ile Ser Lys Ala Lys Gly Gln Pro Arg Glu Pro Gln Val Tyr
                115                 120                 125

Val Leu Pro Pro Ser Arg Asp Glu Leu Thr Lys Asn Gln Val Ser Leu
    130                 135                 140

Leu Cys Leu Val Lys Gly Phe Tyr Pro Ser Asp Ile Ala Val Glu Trp
145                 150                 155                 160

Glu Ser Asn Gly Gln Pro Glu Asn Asn Tyr Met Thr Trp Pro Pro Val
                165                 170                 175
```

-continued

```
Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
        210                 215                 220

Gly Lys
225

<210> SEQ ID NO 5
<211> LENGTH: 226
<212> TYPE: PRT
<213> ORGANISM: Artificial Sequence
<220> FEATURE:
<223> OTHER INFORMATION: Mutated form of Human IgG1 Fc germline sequence
      231-447 (AZ2 heterodimer)

<400> SEQUENCE: 5

Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
            85                  90                  95

Glu Tyr Lys Cys Lys Val Ser Asn Lys Ala Leu Pro Ala Pro Ile Glu
        100                 105                 110

Lys Thr Ile Ser Lys Ala Lys Gly Gln Pro Arg Glu Pro Gln Val Tyr
            115                 120                 125

Val Tyr Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
            165                 170                 175

Leu Asp Ser Asp Gly Ser Phe Ala Leu Val Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
        210                 215                 220

Gly Lys
225
```